US011607443B2

(12) United States Patent
Combier et al.

(10) Patent No.: US 11,607,443 B2
(45) Date of Patent: Mar. 21, 2023

(54) THERAPEUTIC PEPTIDES

(71) Applicants: UNIVERSITE TOULOUSE III-PAUL SABATIER, Toulouse (FR); CENTRE NATIONAL DE LA RECHERCHE SCIENTIFIQUE, Paris (FR); INSERM (INSTITUT NATIONAL DE LA SANTE ET DE LA RECHERCHE MEDICALE), Paris (FR); ETABLISSEMENT FRANÇAIS DU SANG, La Plaine Saint Denis (FR)

(72) Inventors: Jean-Philippe Combier, Castanet Tolosan (FR); Anne Prel, Toulouse (FR); Frédéric Deschaseaux, Toulouse (FR)

(73) Assignees: UNIVERSITE TOULOUSE III-PAUL SABATIER, Toulouse (FR); CENTRE NATIONAL DE LA RECHERCHE SCIENTIFIQUE, Paris (FR); INSERM (INSTITUT NATIONAL DE LA SANTE ET DE LA RECHERCHE MEDICALE), Paris (FR); ETABLISSEMENT FRANÇAIS DU SANG, La Plaine Saint Denis (FR)

( * ) Notice: Subject to any disclaimer, the term of this patent is extended or adjusted under 35 U.S.C. 154(b) by 143 days.

(21) Appl. No.: 16/481,111

(22) PCT Filed: Dec. 22, 2017

(86) PCT No.: PCT/FR2017/000259
§ 371 (c)(1),
(2) Date: Jul. 26, 2019

(87) PCT Pub. No.: WO2018/115602
PCT Pub. Date: Jun. 28, 2018

(65) Prior Publication Data
US 2020/0000878 A1    Jan. 2, 2020

(30) Foreign Application Priority Data

Dec. 22, 2016 (FR) ..................... 16/63245

(51) Int. Cl.
| | | |
|---|---|---|
| *A61K 38/17* | (2006.01) | |
| *A61P 9/10* | (2006.01) | |
| *A61P 31/14* | (2006.01) | |
| *A61P 11/00* | (2006.01) | |
| *A61P 19/08* | (2006.01) | |
| *A61P 35/00* | (2006.01) | |
| *C12Q 1/6883* | (2018.01) | |

(52) U.S. Cl.
CPC ............ *A61K 38/1709* (2013.01); *A61P 9/10* (2018.01); *A61P 11/00* (2018.01); *A61P 19/08* (2018.01); *A61P 31/14* (2018.01); *A61P 35/00* (2018.01); *C12Q 1/6883* (2013.01); *C12Q 2600/178* (2013.01)

(58) Field of Classification Search
None
See application file for complete search history.

(56) References Cited

U.S. PATENT DOCUMENTS 5,403,824 A * 4/1995 D'Souza ............... A61K 31/00
514/16.9

FOREIGN PATENT DOCUMENTS

| WO | WO 2004/083241 | * | 9/2004 |
| WO | 2015/063431 A1 | | 5/2015 |
| WO | WO 2015/063431 | * | 5/2015 |

OTHER PUBLICATIONS

Couzigou et al. (RNA Biol. Nov. 2015; 12(11): 1178-1180) (Year: 2015).*
Preliminary Research Report dated Aug. 1, 2017 in corresponding French application No. 1663245; 6 pages.
International Search Report and Written Opinion of the International Searching Authority dated Apr. 18, 2018 in corresponding International application No. PCT/FR2017/000259; 32 pages.
Database EMBI, "Human DNA sequence from clone RP11-2B6 on chromosome 9q22.2-31.1", Database accession No. AL158152; 22 pages.
Nelson et al., "A peptide encoded by a transcript annotated as long noncoding RNA enhances SERCA activity in muscle", Science, Jan. 2016, p. 271-275; 6 pages.
Anderson et al., "A Micropeptide Encoded by a Putative Long Noncoding RNA Regulates Muscle Performance", CELL, Feb. 2015, p. 595-606; 14 pages.
Kim et al., "Long noncoding RNAs in diseases of aging", Biochimica Et Biophysica Acta. Gene Regulatory Mechanisms, Jul. 2015, p. 209-221; 14 pages.
Makarewich et al., "Mining for Micropeptides", Trends in Cell Biology, May 2017, p. 1-12; 12 pages.
Andrews et al. "Emerging evidence for functional peptides encoded by short open reading frames", Nature Reviews Genetics, Feb. 2014, p. 193-204; 12 pages.
Tonkin et al., One Small Step for Muscle: A New Micropeptide Regulates Performance, Cell Metabolism, Apr. 2015, p. 515-516; 2 pages.
Dhgushi et al., "Marrow cell induced osteogenesis in porous hydroxyapatite and tricalcium phosphate: A comparative histomorphometric study of ectopic bone formation", Journal of Biomedical Materials Research, 1990, p. 1563-1570; 8 pages.
Wang et al., "Bone tissue engineering via human induced pluripotent, umbilical cord and bone marrow mesenchymal stem cells in rat cranium", Acta Biomaterialia, 2015, p. 236-248; 14 pages.

(Continued)

*Primary Examiner* — Sergio Coffa
(74) *Attorney, Agent, or Firm* — Maier & Maier, PLLC

(57) ABSTRACT

Compositions containing micropeptides capable of modulating the accumulation of miRs involved in certain pathologies, and the use of these micropeptides for treating the certain pathologies. Also, methods of identifying these micropeptides modulating the accumulation of miRs involved in pathologies. Further, nuclei acids encoding those micropeptides that modulate the accumulation of miRs involved in pathologies.

9 Claims, 380 Drawing Sheets
Specification includes a Sequence Listing.

(56) References Cited

OTHER PUBLICATIONS

Mok et al., "microRNAs in skeletal muscle development", Seminars in Cell & Developmental Biology, 2017, p. 67-76; 10 pages.
Alexander et al., "Skeletal Muscle MicroRNAs: Their Diagnostic and Therapeutic Potential in Human Muscle Diseases", Journal of Neuromuscular Diseases, 2015, p. 1-11; 12 pages.
Chiellini et al., "Stathmin-like 2, a developmentally-associated neuronal marker, is expressed and modulated during osteogenesis of human mesenchymal stem cells", Biochemical and Biophysical Research Communications, 2008, p. 64-68; 5 pages.
Cordonnier et al., "Consistent Osteoblastic Differentiation of Human Mesenchymal Stem Cells with Bone Morphogenetic Protein 4 and Low Serum", Tissue Engineering, 2011, p. 249-259; 12 pages.
Esquela-Kerscher et al., "The let-7 microRNA reduces tumor growth in mouse models of lung cancer", Cell Cycle, 2008, p. 759-764; 7 pages.
Guttman et al., "Modular regulatory principles of large non-coding RNAs", Nature, 2012, p. 339-346; 8 pages.
Ingolia et al., "Ribosome Profiling of Mouse Embryonic Stem Cells Reveals the Complexity and Dynamics of Mammalian Proteomes", Cell, 2011, p. 789-802; 14 pages.
Lauressergues et al., "Primary transcripts of microRNAs encode regulatory peptides", Nature, 2015, p. 90-104; 15 pages.
Li et al., "MicroRNA-7a/b Protects against Cardiac Myocyte Injury in Ischemia/Reperfusion by Targeting Poly(ADP-Ribose) Polymerase", PLoS One, 2014, p. 1-9; 9 pages.
Montgomery et al., "MicroRNA mimicry blocks pulmonary fibrosis", EMBO Molecular Medicine, 2014, p. 1347-1356; 10 pages.
Mukherjee et al., "Transcriptional Suppression of miR-181c by Hepatitis C Virus Enhances Homeobox A1 Expression", Journal of Virology, 2014, p. 7929-7940; 12 pages.
International Preliminary Report on Patentability (Chapter 1) dated Jun. 25, 2019, in corresponding International application No. PCT/FR2017/000259; 9 pages.

\* cited by examiner

Figure 1

| miR | order | mPEP | mPEP SEQ ID | miORF | miORF SEQ ID |
|---|---|---|---|---|---|
| hsa-let-7a-1 | 1 | MADAAASAGPSPFYFAETRGSGWAEWESRAPARACPANAGWDWWGGLPPPAGGWPRGAGGLLAEVAGARGTGEGCRVAAAGPAPTPSASRPAPHRQGGGGGVILHPYPALPPASIKLGAGGRPAFRPAPVGRRRL* | 1 | ATGGCGGACGCGGCAGCGAGCGGGTCCGTCGCAGCCATTTTATTCGCGGAGACTCGCGGCAGCGGGTGGCAGAATGGAGAGCGGTGCCGCCGTCTCCGGCTAACGCGGGCTGGGACTGTGGAGCCGGCTGCCCCTCCAGCGGGCGGTGCCCGGGGGCCGTGCGGCTGCTAGCGAGAAGTCGCGGGGCTCGGGGCACGGCGGAGGGTGCCGGTGCCCCGCGCCGGGGGCCGCTCCAACCCCTCCGCTTCCGCGCCAGCTCTCACCGACAGGGCGGGGAGGGGGGTCATTCTTCACATTCCTACCCCGCCCTTCCCCCGGCTTCAATCAAACTTGGGGCGGGGGCGGAAGGCCCGCCCTTCCGGCCGGCCGCTGTTGGCCGGCGCCGCCTCTGA | 2 |
| | 2 | MGEPCAGPRLSG* | 3 | ATGGGAGAGCCGTGCGCCGGCCCCGCGCCTGTCCGGCTAA | 4 |
| | 3 | MKEGR* | 5 | ATGAAGGAGGGAAGTAG | 6 |
| | 4 | MPLLPAAKCSLPS* | 7 | ATGCCTCTGCTCCCCGCGGCCAAGTGCAGCCTCCCTTCCTGA | 8 |
| hsa-let-7a-2 | 1 | MRETIRKTEKL* | 9 | ATGAGAGAACGATCAGAAAACTGAAAGCTGTAG | 10 |
| | 2 | MSPWIQCSSPQGIKTQINFPFCKQLHCEEAFH* | 11 | ATGTCACCATGGATTCAGTGTTCAAGTCCACAGCCAGGCAAAACTCAATAAATATTTCCTTTTGCAAGTCCACTGTGCACTGTGCCTTCCATTAG | 12 |
| | 3 | MDSYFKSTARQNSNKFSFLQAAAL* | 13 | ATGGATTCAGTGTTCAAGTCCACAGCCAGGCAAAACTCAAATAAATTTTCCTTTTGCAAGCAGCTGCACTGTGA | 14 |
| | 4 | MKGRRTPRPKHGQ* | 15 | ATGAAGGAAGGCGAACCCCGGTCAAAACATGGCAATGA | 16 |
| hsa-let-7c | 1 | MYKYIHLGFLIFFISVAPGVQVVIGYMDELYSGEV* | 17 | ATGTATAAGTACATACATTTGGGGTTTTTAATTTTATTCAGTAGCTTTGGGTACAAGTTGGTTATTGGTACATGGAGATGAATTGTATAGTGGTGAAGTCTGA | 18 |
| | 2 | MNCLVVKSEILVHSSPT* | 19 | ATGAATTGTATAGTGGTGAAGTCTGAGATTTAGTGCACTGTCACCTACCTGA | 20 |
| | 3 | MLSSV* | 21 | ATGCTTTCAAGTGTCTAA | 22 |
| | 4 | MKRKFFDRFYDNSFFFSS* | 23 | ATGAAGAGAAAATTTGATCGCTTTTATGATAATAGTTTTTTTTCTCTTCCTAA | 24 |
| hsa-let-7d | 1 | MADAAASAGPSPFYFAETRGSGWAEWESRAPARACPANAGWDWWGGLPPPAGGWPRGAGGLLAEVAGARGTGEGCRVAAAGPAPTPSASRPAPHRQGGGGGVILHPYPALPPASIKLGAGGRPAFRPAPVGRRRL* | 25 | ATGGCGGACGCGGCAGCGAGCGGGTCCGGTCCGTCGCCATTTTATTCGCGGAGACTCGCGGCAGCGGGTGGGCAGAATGGGAGAGCGGTGCCGCCGTCCGGCTAACGCGGGCTGTGGGACTGTGGCCGCTGCCCCTCCAGCGGGCGGTGCCCGGGGCCGTGCGGCTGCTAGCGGAAGTCGCGGGGGCTCGGGCACGGGGGAGGGGTGCCGGTGCCCCCGCGCCCAACCCCTCGCTTCCGCTTCCGCCCAGCTCTCACCGACAGGCGGGGAGGGGGGTCATTCTTCACATTCCTACCCCGCCCTTCCCCCGCTTCAATCAAACTTGGGGCGGGGAAGGCCCGCCCTTCCGGCCGGCCGCTGTTGGCCGGCGCCGCCTCTGA | 26 |
| | 2 | MGEPCAGPRLSG* | 27 | ATGGGAGAGCCGTGCGCCGGCCCCGCGCCTGTCCGGCTAA | 28 |
| | 3 | MKEGR* | 29 | ATGAAGGAGGGAAGTAG | 30 |
| | 4 | MPLLPAAKCSLPS* | 31 | ATGCCCCTGCTCCCCGCGGCCAAGTGCAGCCTCCCTTCCTGA | 32 |

Figure 1 (Continued)

| | | | | |
|---|---|---|---|---|
| hsa-let-7e | 1 | MGHDTENAFQAEKEDUDRERAKGRTDVQRQKGGQTER DTERQQKQPRMTGAERRRERGRERERERREGGREG ERERESTHRARRRRREEGGRPARDRTGRRGGGELGKA GEERDWPRRRAGERERPRRLPASFVPSLLCVRLLWPG LPLPLPPPPRGWMEFFPLDLGQLRGRGEARPDWAGRW GGRAGGPLORGLVRRPRSRRGPGRGSPGPQSRGGGD GRRESGRREGGWRGRREEGERPPCGEGGERMESARRR WGPACCPGAAEKTPSLRRGSRGSRESAFREGGGLGPAL LGP* | 33 | ATGGGAGACACAGATAATGCCCACAGGCAGAGACCAGGAAAGAGGGAGATGAGATAGGAGA GGGCGAAGGAGAGCAGATGTCAGAGACAGGAGGACAGACGGAAAGAGA CACAGAGAGAGTCAGCAGAAGAGAAGCAACAAGAATGACAGTAGCAGAGGAGAAGAGA AGAGGGAGAGAGCGAGAGAGCACTGCACAGAGGCGAGGAGGAGGCGCAGAGAGAGAAGAG GAGAGAGAGCGAGGCCAGCAGGACAGACTGGCCGAGAGACTGGCGGAGGAGAGCTAGGG AAAGCCGGGAGGAGGAGCGAGACTCCCGGCCTCTTTGTCCCTCTCCCTCCCGGGCTGGATGGAATTTTTCCC GGCCCGGCCTCCCCCCCGGCCTCCCGCTCCCGCCCGGGCTGGATGGAATTTTTCCC CTGGACCTGGGCCAGCTCCGGGCCAGTGGGGGGAAGCCAGGCCGGACTGGGCTGGGC GGGGGAGGGGCGGGGTCCAGGGAGGGAGCTCCTCGGAGAGGATCGGGGAGGGACGGCGGG GCGCAGCCGGCGGCGGAGTCCGCGCCGGGCGCCCGGAGTCGGGGAGGGGCGGGACCCGCC GGTGACGGCGGAGGGGCGGAGTGAGAGAAGGGAAGGAGGATGGGCGGGAGACGGCGCGG AGGAAGGGATGGGGAGGGCGCTGGCCGCGCCGGGCGCGCCGGAGAAGACCCTTCCCTGC GACGGCGGAGCGGCGGAGCCGGAGTCTGCGAGTGCGAAGGGAGGGTTGGGGGCTGGG GCCGGCACTCGGTCCCTGA | 34 |
| | 2 | MPHRQRKRMEIGRGRKEGQMCRDRREDRRKETQRGSK SNQE* | 35 | ATGCCCCACAGCAGACAGAAGAGAGGATGGAGATAGGGAGGAGGGCGAAAGGAAGGAC AGATGTCAGAGACAGAAGGGAGGACAGACGGAAAAGAGACACAGAGAGGCAGCAA AAGCAACCAAGAATGA | 36 |
| | 3 | MAGTAGGRGEAAVRRRGEDGERSAAVGPGLRARGG GEDPFFATREPREP* | 37 | ATGGCGGGAGGCGCTCGGGGAGAAGGGAGAGGCCGCGTGCGCGAAGGCGGGAG AGGATGGGAGGCGCTCGGCGCGCGGACGGGCGGCGCGCTGCGGCCCCGGAGCCGTGA AGAAGACCCTTCGGCGCTGGGCTGGTAGATGTGCTGGAAGAGACTAG | 38 |
| | 4 | MGAGAGRIVAGRD* | 39 | ATGGGGCTGGGCTGGTAGATGTGCTGGAAGAGACTAG | 40 |
| hsa-let-7f-1 | 1 | MADAASSAGPSPFYAETRGSGWAEWESRAPAKACPA NAGWDWWGGLPPPAGGWPRGAGGLLAEYAGARGTGE GCRVAAAGPAPTPSASRPAPHRQGGGGVLLHPYPALP PASIKLGAGGRPAFRPAPVGRRRL* | 41 | ATGGCCGGACGCGGCAGCGAGCGCGGCGGTCCGTCGCGCCATTTTATTTCGCGGAGACTCG CCGCAGCGGCGGTGGGCAGCAAGGGAGAGCCGTGGGCGGCGGCTCTTCGGGTACGGGCCA ACGCGGGCTGGCCGCCGGGCGCGGCTCAGGGAAGTGCAGCGCCCCGGCGCTTCCGCCCCGCCAGCTCCTC GCCGTGGCCGCCGCGGAGCCGCGCGCCTCCAACCCCCTCCGCGGGCACGGGAGGGT ACCGACAGGGCGGGGAGGGGGTCAATTCAAACTTGGGGGGCGAAGGCCCGCTTCCGGCCGGCCTTCCC GCCGGCGCGCGCTGA | 42 |
| | 2 | MGEPCAGPRLSG* | 43 | ATGGGAGAGCCGTGCGCGGCCGGCCGTCCGGCTAA | 44 |
| | 3 | MKEGR* | 45 | ATGAAGGAGGGAAGGTAG | 46 |
| | 4 | MPLLPAAKCSLFS* | 47 | ATGCCCCTGCTCCCGGCCGGGCAGCTGCAGCCTCCCTTCCTGA | 48 |
| hsa-let-7i | 1 | MYKYIHILGFLIFFISVAFGVQVVIGYMDELYSGEV* | 49 | ATGTATAAGTACATACATCAGTTTTGGCGTTTTTTAATTTATTCAGTAGCTTTG GGGTACAAGTGGTTATTGGTTACATGGATGAATTGTATAGTGGTGAAGTCTGA | 50 |
| | 2 | MNCIVVKSEILVHSSPT* | 51 | ATGAATTGTATATGTGGTGAAGTCTGAGATTTTAGTGCACTCGTCACTTACCTGA | 52 |
| | 3 | MLSSV* | 53 | ATGCTTTCAAGTGTCTAA | 54 |
| | 4 | MKRKFDRFYDNSFFFSS* | 55 | ATGAAGAGAAACATCAGAAAATGCTTATGATATAGTTTTTTCTTCCTAA | 56 |
| hsa-mir-100 | 1 | MRETIR&TEKL* | 57 | ATGAGAGAAACGATCAGAAAACTGAAAAGCTGTAG | 58 |
| | 2 | MSPWFQCSSPQPGKTQNFPCKQLHCEFAFH* | 59 | ATGTCACCATGGTTCAGTGTTCAAGTCCACAGCCACGGCAAAACTCAAATAAATTTT CCTTTTGCAAGGATTCAGTGTTCAAGTCCACTGTGAGTGCGCTTCCATTAG | 60 |
| | 3 | MDSVFKSTARQNSMKFSFLQAAAL* | 61 | ATGGATTCAGTGTTCAAGTCCACAGCCAGGCAAAACTCAAATAAATTTCCTTTTG CAAGCAGCTGCACTGTGA | 62 |
| | 4 | MKGRRFPRPKHGQ* | 63 | ATGAAGCGAACGCGAACCCCGCGTCCAAACATGGCAATGA | 64 |

Figure 1 (Continued)

| | | | | | |
|---|---|---|---|---|---|
| hsa-mir-101-1 | 1 | MRVCFFY* | 65 | ATGAGAGTCTGTTCTTTATTAG | 66 |
| | 2 | MSVPSPPPPRQVVICRCFGIFSSLWTCPPPTSK* | 67 | ATGTCTGTCCCAGCCCCTTTCCCCCCGGCAAGTTGTGATCTGCAGATGTTTGGG ATTTTCTCTTCCCTGGACCTGTCCCCGCCCCACCAACCAGCAAATAG | 68 |
| | 3 | MFWDELFPLDLSPTNQQIAPGPRLREREK* | 69 | ATGTTTTGGGATTTCTCTTCCCTGGACCTGTCCCCACCAACCAGCAAATAGCTC CTGGGCCTAGGTTGAGGGAGAGAAGTGA | 70 |
| | 4 | MESAVPP* | 71 | ATGGAATCTGCTGTCCCCGTAG | 72 |
| hsa-mir-103-1 | 1 | MKSAASSRGGGGGGGRGGGGWGSWWGGGRGGGCGAGK GGGGDGGOGGKGGFGARARGFGGGRGRGRGGDG KDRGGGGQORRGGVAKSKSRRRKGAMVVSVEPHRHEG GGCTTCGGCGGCGCGGCCCGGGGGCCGGGGCGCGGCGGCGACGGCAAGGATC GCGGCGGCGGTGGACAGCGGCGCGGGCGGCTGGGGCCAAGAGCAAGAGCCGCCCAG GAAGGGCGCCATGGTGGTCGTGGGGGCGTCCGAGCCGCAGCCGGCAGCACTGGTGCCGGTCTTCATCT ACCGCGGCGGAGGACGCCGTCACCGTGACAGCGGAACCGCTGAACATTGGTCCGGCCAGTCTGTG VFTYRGAEDALVTLNMVPGQSYYGERRVTVTEGGVRKQ TACGGCGAGGCGGAGGACGCGGCTGGAACATTGGTCCCGGCCAGTCTGTG EYRTWNPFRSKLAAAILGGVDQIHKPKSKVLYLGAASG GTGAACCCGTTCTCGTCCTTAAGCTGGCCGCGGCGATCCTGGGCGGGTGGACCAG TVSHVSDHGPDGLYVAVEFSHRAGRDLYNVAKKRTNI TCCACATCAAGCCAAGTCAAAGTCCTGTACCTGGGCGCCGCCAGTGGCACCACCG BPVLEDARHPLKYRMLIGMVDVIFADVAQPDQSRIVALN TCTCCCCATGTCTCCGACATCATTGGCCCAGACGGCCTGTCCAGCGTCGAGTCT AHTFLRNGGHFLJSIKANCJDSTASAEAVFASEVRKLQQ CCACGGCCGGCCTGGAGACGCCGGGCACCATCGGCCGTCGAGCGCCAATGCT ENLKPQEQLTLEPYERDHAVVGVYRPLPKSSSSSK* GACTCCACCGCCATCCGGCGCGAGGGTGTGTTGCTTGAGGGGAGTTGCAG | 73 | ATGAAGTCGGCCGCCGAGTCTCGCGGGGGCGGTGGGGGCGGCCGGGGGGCCG GCTGGGGCAGCTGGGGGTCGGGGGCGTCGAGCCGTGGGCAGCAAGGGCCGG GCGGCGGCGACGGCGGCGGCGAGCGGCGCTTCGGGCGCGGCGGCGCGC GGCTTCGGCGGCGCGGCCCGGGGGCCGGGGCGCGGCGGCGACGGCAAGGATC GCGGCGGCGGTGGACAGCGGCGCGGGCGGCTGGGGCCAAGAGCAAGAGCCGCCCAG GAAGGGCGCCATGGTGGTCGTGAGCGTGGAGCCGCACCGGCACGAGGGCGTCTTCATCT ACCGCGGCGGAGGACGCCGTCACCGTGACAGCGGAACCGCTGAACATTGGTCCGGCCAGTCTGTG TACGGCGAGGCGGAGGACGCGGCTGGAACATTGGTCCCGGCCAGTCTGTG GTGAACCCGTTCTCGTCCTTAAGCTGGCCGCGGCGATCCTGGGCGGGTGGACCAG TCCACATCAAGCCAAGTCAAAGTCCTGTACCTGGGCGCCGCCAGTGGCACCACCG TCTCCCCATGTCTCCGACATCATTGGCCCAGACGGCCTGTCCAGCGTCGAGTCT CCACGGCCGGCCTGGAGACGCCGGGCACCATCGGCCGTCGAGCGCCAATGCT GACTCCACCGCCATCCGGCGCGAGGGTGTGTTGCTTGAGGGGAGTTGCAG CAGGAGAACTTGAAGCCTCAAGAGCAGCAGCTTGACCTGGAGCCTATGAGCGGAGACCA CGCTGTGGTGGGTCGGGGTCTACAGACCGCTTCCCAAGAGCAGCAGCAAATAG | 74 |
| | 2 | MSPTSLAQTAWSTPSSSPTAPAAIWSTWPPRSAPTSFRSW RTRGTRSSTACSSGWWT* | 75 | ATGTCTCCGACACATTGGCCCAGACTGCCTGGTCTACGCCGTCGAGTTCTCCACC GCGCCGCCGGATCTGGTCAAGTGCCAAGAAGCCACCAACATCATTCCGGTC CTGGAGGACGCGCCACCGCTCAAGTACCGCATGCTCATCGGGATGGTGGACGT GA | 76 |
| | 3 | MGATFSSRPTASTPPHPPRLCLLLR* | 77 | ATGGGGGCCACTTTCTCATCTCAAGCCATGCAACTGCATCGACTCCACCGCATCCG CCGAGGCTGTGTTGCTTCTGAGGTGA | 78 |
| | 4 | MSGTTLWWSGSTDLFPRAAANSTQLRLACHLPKAALCL LLFSVCFLCECPVLFFY* | 79 | ATGAGCGGGACCACGCTGTGGTGGTCGGGGTCTACGGACCTCTTCCCAAGAGCAGC AGCAAATAGCACCCAGCTCCGCCTGGCCATCCTCCCCAAGGCTGCTTGTGTTT GCTATTATTTCTGTGTTTCTTTGTGAGTGTTTGTTTCTATTAA | 80 |
| hsa-mir-103-2 | 1 | MATSGGQTERDSC* | 81 | ATGGCCACTAGTGGAGGCCAGAGTTTAGGGAGACTGAAAGGACAGTGCTAA | 82 |
| | 2 | MVTAEFMGTSQPEGGETAVSWDEDYGTAAQRSTNAER RQCLGAGAQR* | 83 | ATGGTAACAGCAGAGTTTATGGGCACTCTCACAACCTGAAGGTGGTGAGACGGCAGT AAGCTGGGATGAGGATGTGGGCACTGCTGCACAGAGATCAACAAATGCAGAGAA GGCAGTGTTGCAGTGGAGCTCAGAGGTAA | 84 |
| hsa-mir-103-2 | 3 | MRMWALLHRDQQMQREGSVSGLELRGKGWLKCSLEIS QKDANDCLGRPRTEAEDSHS* | 85 | ATGAGAATGTGGGCACTGCTGCACAGAGATCAACAAATGCAGAGAAGGCAGTGT CTGGGGCTGGAGCTCAGAGGTAAGGGTGGTGTTGAAGTGTTCCCTGAAATCAGTC AAGGTGATGCTAATGACTGCTTGGGAGACCCAGGACTGAGGCTGAGGACAGCCAC AGCTAA | 86 |
| | 4 | MLMTAWGDPGLRLRTATANCQQRMNQNISSLGGRTGK RALLSEN* | 87 | ATGCTAATGACTGCTTGGGGAGACCCAGGACTGAGGCTGAGGACAGCCACAGCTAA CTGTCAGCAGAGAATGAACCAGAACATTAGCTCAGGAGGCAGGACAAGA GGGCTCTGCTGAGTGAGAACTGA | 88 |

Figure 1 (Continued)

| | | | | |
|---|---|---|---|---|
| hsa-mir-106a | 1 | MKKGRKPTCAEDSRWRNDCCBRCIHR* | 89 | ATGAAAAAGGGAGGAAGCCACCTGTGCGACTGACTCGCGGTGAGAAATGATTG TGGTTTTCGTTGCATCCACCGGCTGA | 90 |
| | 2 | MIVVFVASTADS* | 91 | ATGATTGTTGTTTTCGTTGCATCACCGCTGACTCCTGA | 92 |
| | 3 | MAPLSSSGLWAATITLVTMVEREGSGFILHPFPPSLPPAC LPGLSSSDPACSLVSDL* | 93 | ATGGCGCCCTTGCTCTCTGGCTTTGGGCTGCCAACTACCCTGGTAACAATG GTGGAAAGGAGGGGTCCGGCTTCATTTGCACCCCTCCTCCTGCCCC GCTTGCCTTCCAGGCGTTTCCTCCTCCGACCCAGCTGGTGCTCACTGGTCTCTGATTTGT AA | 94 |
| | 4 | MLNSILIYRLKLRLHHFILQSAVGLWP* | 95 | ATGCTTAATTGCATTTGATTGTGCGTCTAAACTAAGACATCATTTATTCTACAGA GCGCTGTCGGGCTTTGGCCTTGA | 96 |
| hsa-mir-122 | 1 | MTGGC* | 97 | ATGACGGGAGGCTGCTGA | 98 |
| | 2 | MPPSA* | 99 | ATGCCACCAGCGCTGA | 100 |
| | 3 | MHLFPQKA* | 101 | ATGATTATTCTGTTTCCTCAGAAAGCTTGA | 102 |
| | 4 | MVSV* | 103 | ATGGTTTCCGTTTAA | 104 |
| hsa-mir-124-1 | 1 | MAIHWGIRFSFMLFP* | 105 | ATGGCTATTCACTGGGGCATCAGGTTTCTTTCATGCTATTCCTGA | 106 |
| | 2 | MVHMYGTYFTFEQQYLQSCECNN* | 107 | ATGGTACACATGTATGGCACTTACATTTCACTGAGCAGCAATACTTGCAAAGCTGT GAGTGCAATAACTAA | 108 |
| | 3 | MALTFSLSSSNTCKAVSAITKQIMVFSSGKGSEITYSTPLF HRRGF* | 109 | ATGGCACTTACATTTCTCACTGAGCAGCAATACTTGCAAAGCTGTGAGTGCAATAACT AAACAGATCATGGTGTTTCAAGCGGGATTACCGGAGCGCAATCACGTATTCAACCCCC TTGTTTCACAGAAGAGGATTCTGA | 110 |
| | 4 | MGEQ* | 111 | ATGGGTGAGCAGTGA | 112 |
| hsa-mir-124-2 | 1 | MKIFIPLPHSTRLQDSCFRSFSPVHDV* | 113 | ATGAAAATCTTCATCCCCCCTCCATTCTACTAGGCTACAAGATTCTGTTTCGTT CCTTCTCACCGGTTGGAAGATGTGTAA | 114 |
| | 2 | MCKIKDVEVCSDFFKSQLTTARTATRITRAHAGCKYBP FLR* | 115 | ATGTGTAAAATCAAAGATGTGAAAGATCCTCAAGCCAACTAACC ACGCACGGACTGCGACGCGGATTACCGGAGCGCAACGCTGTAAGTACCATCC TTCCTGCGGTAG | 116 |
| | 3 | MLESRRLSSGL* | 117 | ATGCTTGAGAGGCGCCGCCTCAGCTGCGGGCTGTAA | 118 |
| | 4 | MDGNQVTEIPKLARLSDTLGRQNGIGRRDLKRREEGIRV PPPRA* | 119 | ATGGATGGAAATCAGGTCACAGAATCCTAAGCTTGCCAGGCTCTCAGACACGCTT GGGAGACAGAATGGAATTGGAAGGAGGGATCTGAAGAGGAGGAGGAATCCGTG TTCCCCACCCCCGGGCCTAG | 120 |
| | 1 | MSIQLRHAVNAKRGASSAAPPSWKWPASPSGPAPLPREE GEPGPRRPFAPRTNPANNAPAQSAAQLPGRGSGRGTQR GPHASGVAGRVGAAEGKRGGSLRPGPGCGPAPGHVC PQRGAPRRPQRAAGPGRQREGPRGAAGGCVGRRARVR RCPRCWRRGGPRGTGRPSAALAPTAGALDSCHGNVG GGGAGSEVTAKSSALPRAAAPRGGAEAALAVAPEQPPQP RTRLAWGRGSASASRVQTRAVDTPDRIPPPKSPALGCAG PGT* | 121 | ATGTCTATACAATTAAGCACGGCGGTGAATGCCAAGAGAGGCGCCTCCGCCGCTCCT TTCTCATGGAAATGGCCGGCGTCCCCAAGCGGCCCTCCCCGGGAGGA AGGGCGAGCCCGGGCCCCAGAGTGCGGCCATTCGCGGGAACATCTGGCGAACAATG AGGGGGAGGCCGGGGAGCCTCGGCCTGCCGCAGGCTGCGCGCAGCCCGGCCACGTG GAGGGGAGCCGGCCAGCCCCAGCTGCGCCAAGGCGCGGGCGGCCCGGAGAGC TGCGCGCCGAGGGGTCCACGGAGGCGGCGCCCCGGACGGGAGGCGGG AAAGGAGGCTCGCGGGCGGGGACGCCCGCCCTGGACAGTTGCCACGCAACGT CCAAGTGCGGCCCGGCCAGGCTTGCATGGGCGACACGCGGGGTCTGCGTCGTCGT GGGAGGAGTGGGGCAGGGTGGGGTGGAGGTGACGCCTAAGTCGCCCCTTCCGGGCCG CTGCGCCAGGACCAGCCGGCGGAGCGTCCGGTGATGGACACGCGGGGTGTCGTCGTC AACGAGGGCCGGTGGACACGCCCATCCGCCCACCTAAGCTCGCCCTTCTGGGCGG GTGCAGGACCAGGCACGTGA | 122 |

Figure 1 (Continued)

| | | | |
|---|---|---|---|
| hsa-mir-124-3 | 2 | MPREAPPLLSHGNGNGPRARPAQRPSRGRKASPAPGGHS RRGQIRRTMRPPRVRPSCRAGDLAAGHKCARTPLASRG GWGRPRAAEGGACGRGQAAASRPPATCVRSAERPGAR RGBRGPGDKGRVHGERRAGAWGGGLGCGAVRGAGGG AAPAGREGGQVRPSPPQRAPWTVATATWEEVGQGLRS PLSLPFLGPLRRGAGRRRSLWPQSSPRSPGPLHGDGG LRPRPGSKRGRWTRRTASRPQSRLWAVQDQARETPQPR EKMTNPSPAAICSRSDTHSGLLQGFFFCPRKPAPPADAR HRLCAASPAFIPGPGWAVMPR* | 123 | ATGCCAAGAGAGGCGCCTCCGCGCCTCCTTCTCATGGAAATGCCCGCGAGCCGT CCGGCCCAGCGCCCTCCGCGGAGGAAGGCGAGCCCGGCCCCGGCGGCCATTC GCGCCGCGGGACAAATCGCGCCGAACAATGCGCCCGCCCAGAGTGCGCCCAGCTGCC GGCCCGCGGGGATCTGGCCGCGCGGGACACAAAGGCCCGAACACAAGGCCGACCTCGGCCGCCTCTGCGTGCGCG GGCGGTGGGGCTGCCGGCTCCGGCGCAGGGGAGCCTTGCGGCCGCGGGGCCAGG CTGCCGGTGGCCCAGGGGGCGTCGGGCGCCCGAGGGGACGGCGGTGTCCGCAGCAAAGGAGGTCCACGGAGACGCGCGG CGCAGAGGGCGGTCGGGACGGGAGAGGGCGCGCAAGTGCGGCGCCTCGGCCCCACAGCGCGCC GGGGCCCCGCGGCGGGGACAGTTGCCACGGCAACGTGGGAGGAGGTGGGGCAGGGTCTGAGGTCAC GGCCTAAGTCTGCCCTTCCTGCGCGCCCTGCCGCCCGGGGCGGGGCGGGGAGGCGGCGC GCTGTGTGCCCCAGACAGCAGCCCCAGGACCCAGGCTGCATGGGGACGG TTGCTCTGCCCCAAAGACAAATGACAAATCCTCCCGCCCATCTGCACGCCAGTGACACC GGGTCTGCGTCCAGGTCCAAACGAGGCGGTGGACACGGCAGCAGCCACTGCTCCGAG CCCAGGGAGAAAATGACAAATCCTCTGCAGGACCAGGGCGTCAATCGCCAT CACTCGGGTTTGCTGCAGGGGTTTTTCTGCGCCTCCTGCGCTTCTGCAATCGCCAGCCCCGGCTGG GACCCCGCGCACCGCGCTCTGCGCCTCGCGCTCTGTCCCCGACCGCCCATCCCAGCCTCCGGCTGG GCTGTGATGCCCGGTAA |
| | 3 | MEMAIREPVRPSAPPAGGRRARPPAAIRAADKSGEQCAR PECGPAAGPGIWPRDTKCPARLWRRGACGRGRPRG EPAAGARLRPAGPRPRVSAARSAQAPAEGGGARETKGG STGSGRVRGAAG* | 125 | ATGGAAATGCTGCCCGGCCGTCGAGCGCTCCGCGGCCCAGCCTCCGGAGGAAGGCG AGCCCGGCCCCGATTGCGGCCCAGCTGCCGGCGCGACAAATCCGGGAACAATGCGCC CCCGCAAGTGCGGCCGCCAGCTGCGCGGGAGCTCGCCGGGAGGGGTGGACGAGGGCGCG GGAGGCCTGGCACGCTCTGCGCCGGCGTTGCGCGGCCAGGCTGCGCGCGACAGGGCTGCAGG CCGCACGCCTGGGCGAGCGCCAGGCGCCCGCAGAGGGCGCGGAGGGCGCGGGACAAAGG GAGGGTCAGCGGGAGCGGCGCGTGGGGCGGTCGTTGCAGGCTAG |
| | 4 | MGTCVCVRYVQGPNEGGHAGPHPAPKAGSGLCRTRFV RLRSPGRK* | 127 | ATGGGGACGTGGGTTGCTGCGTCGCGCCTCAGGCCTCCCAAACGAGGCGGGTGACACGC CGGACCCGATCCGCCTCGCCCCAAAGCGGGCTCTGGGCGGTGTGCAGGACCAGGCACGTGA GAGCTCCGCAGCCCAGGCCCCAGGGAGAAAATGA |
| hsa-mir-125a | 1 | MGDTNAPQAEKEDGDREAKGCRTDVQRQKGGQTER DTERQKQKPRMTGAERRRERGRERERERGGREGG ERERESTHRARRRRRRREGGRPARDRTGRGGGELGKA GEERDWPRRAGERERRPRRLPASFVPSLLCVRLLWPG LPLPLPPPRGWMEFFPLDLGQLRGRGEARPWAGRW GGAGGGPLGRGLVRRPRSRRGPGRGSRGGDSRPQGCRQGGD GRRRESGRREGWRGRRREEGERPPCGEGGEPMESARRR WGPACGPGAAEKTPSLRRGSRGSRESAEREGGGLPAL LGP* | 129 | ATGGGAGACACAGATAATGCCCACCAGGCAGAGAAAGAGGATGCGAGATAGGAGA GGGCGAAAGGAGGCAGCAGATGTGCAGAGACAGAGGGGAAAAGACCAGACAGAGGAAAGAGG CACAAGAGGAGGCAGCAAAACCAAGAGAATGACAGGAGCAGGAGAAAGAGGAGGAGGAAGAGGGA AGAGAGGAGAGCCAGGAGGACCAGGAGACACGGAGGCGAGCAGCAGAGAGAAGAGAG GAGAGGAGGCCAGGAGGCCAGGAGGCAGGACTGGCAGAGAGGCGCAGGAGAGGGAGCTAGG AAAGCGCGGTAGCGACGTCCCCGGACCTCTGTCCCTGCTTGTCCTCCTCTCCCTGGTCCAGGCTTCTCTG GCCCCGCGCCTCCCGCGACCTTCCCGGCTGTTGATGGAATTTCCCAGGCTTCTCTG CTGGAACCTGGGCTCCGGGCTGATGGGCTGATGGGCTGATGGACTGGCTGGGC GGTGACGGGCGGAGGGGCGGCCAGGGAGGGCGGAGGGAAGGCCAGCCAGCAGGCCAGGCGGCC GCGAGGGCCTGAGGAGGCCCGCGCCTTGCCGGCCAGGAGGCGGAAGGGCGGAGGGAAGGCGCTCG AGGAAGGGAGAGGCCCGCCTTGCCGGGCCTGCGGGCCCGGAGCCGTGAGTTCGGGAGCCGTGAGGAGGGA GCGGCGGAGGGCCGGAGGCCGGAGCCGTGAGTTCGCGGAAAGGGAGGGTGGGGGCTCCCTGA GCCCCGCACTCCCTGGGTCCCTGA |

Figure 1 (Continued)

| | | | | | |
|---|---|---|---|---|---|
| | 2 | | MPHRQRKRMEHGRGRKEGQMCRDRRREDRRKETQRGSK SNQE* | 131 | ATGCCCCACAGGCAGAGACAGAGAAAGAGGATGGAGATAGGGAGAGGCGAAAGGAAGGAC AGATGTGCAGAGACAGAAGGGAGGAAGACAGAGGCGAAAGAGAGGCAGCAA AAGCAACCAAGAATGA | 132 |
| | 3 | | MAGTAGGGRGEAAVRRRRGEDGERSAAVGPGLRARGG GEDPFPATREPREP* | 133 | ATGGCGGGGACGGCGGGAGGAAGGGAGAGGGAGAGGCCCGCCGTGCGGCGAAAGGCGGGAG AGGATGGAGAGGCGTCGCGCGGTTGGGGCCTCTCGGCCTCGGGCCCGGGGGCCGCGG AGAAGACCCCTTCCTGCGACGCGGGAGCCGCGGAGCGTGA | 134 |
| | 4 | | MGAGAGRIVAGRD* | 135 | ATGGGCGCTGAGGCTGTAGGATCGTGGCTGGAAAGCTGTAG | 136 |
| | 1 | | MREIIRKTEKL* | 137 | ATGAGAGAAACGATCAGAAAAACTGAAAAGCTGTAG | 138 |
| hsa-mir-125b-1 | 2 | | MSPWIQCSSPQPGKTQINPFCKQLRCEFAFH* | 139 | ATGTCACCATGGATTCAGTGTTCAAGTCCATGCCAGCAACCTCAAAACTCAATAAATTTT CCTTTTTGCAAGCAGTCACTGTCAGTTCGCTTCCATTAG | 140 |
| | 3 | | MDSVFKSTARQNSNKFSFLQAAAL* | 141 | ATGGATTCAGTGTTCAAGTCCACAGCCAGGCAAAACTCAATAAATTTTCCTTTTTG CAAGCAGTCACTGTGA | 142 |
| | 4 | | MKGRRTPRPKHGQ* | 143 | ATGAAGGGAAGGCAAGGCCCGTCCAAAACATGGCCAATGA | 144 |
| | 1 | | MRRAL* | 145 | ATGAGGAGGGCATTGTAG | 146 |
| hsa-mir-127 | 2 | | MRVIDPGCRSPKE* | 147 | ATGAGGGTCATTGATCCTGGGTGCAGATCTCCAAAGAATGA | 148 |
| | 3 | | MTERKRIEWWKETIGWEKMKIEKRK* | 149 | ATGACAGAAAGAAAGAGGAGAATTGGGGAGAAGAGATAGGATGGGAAAAAATGA AAATAGAAAAGGAAGTGA | 150 |
| | 4 | | MGKNENRKKEVKEHN* | 151 | ATGGGAAAAATGAAATAGAAAAAAGGAAGTGAAAGATAATAATAATTAG | 152 |
| hsa-mir-129-1 | 1 | | MLGVWARHEGPSLAGPDGSSTPSGKARDKPLHAELCRE LEADTHSANLQW* | 153 | ATGTTGGGAGTCTGGGCAAGGCACGAGGCCCCTCTTAGCAGGTCCGATGGCTC CTCCACACTTCAGGAAAAGCAAGACAGAGATAAACCATTGCATGCTGAGCTCTGCAGGG AACTGGAGGCGGACACTGGCAATGTCAT | 154 |
| hsa-mir-129-1 | 2 | | MAPPHLQEKQEINHCMLSSAGNWRRTPSILQTCNGDTS GISLPLPGLQPLRQVRPRPGWLRDLCVALLTSCYGSRRP L* | 155 | ATGGCTCCTCCACACTTGCAGGAGAAGCAAGAGATAAACCATTGCATGCTGAGCTCT CCAGGGAACTGGAGGCGGACACCTGAGGCACCATCTGCAAACCTGCAATGGTGACACTTCT GGAATCTCCTTGCTCTTCCAGGCTCTAAGGCAGTTAAGACCCAGGCCA GGTTGGGCTCAGGGACCCTCGTGACCTCGTAGCATTGCTGACCTCATGTTATGAAGCAGGAGG CCACTGTGA | 156 |
| hsa-mir-129-1 | 3 | | MVTLLESPCLFQGCSL* | 157 | ATGGTGACACTTCTGGAATCTCCTTGCTGCAGGGCTGCAGCCTCTAA | 158 |
| hsa-mir-129-1 | 4 | | MLWKQEATVRCGA* | 159 | ATGTTATGAAGCAGGAGGCCACTGTGAGATGCGGGGCTTAG | 160 |
| hsa-mir-129-2 | 1 | | MKTAARGAFELRRLLSRCPLSAPRTSLPLPAGARSGAPA RSPAKRRVFNKLEEGRNAGVKLGKPQLPRS* | 161 | ATGAAAACCGCTGCCAGGGGGCATTGAACTCGGCGTTGCTTGCTGTCGTCTGCGCCT CTCTCTGCCGCTCCCGCTAAGCGACGAGTCTTCAACAAGTTGAGGAAGGCAGGAACGC AGGGGTTAAGCTCGGAAAGCGCAATTACCAAGATCGTGA | 162 |
| hsa-mir-129-2 | 2 | | MPWEGEWVAELQEGDGWAKGVGRQGLEDSASTVERR FLRACWARVGVCVRARAPARTSIPGCQRTNMATFPPSS CNVCSSNPSWVRFPPLGDYTAREGDSQDVY* | 163 | ATGCCGTGGAGGGTGAGTGGGTCGCGAGCTCGAGGAGGGTGATGGATGGCGA AGGGGTGGGTCGACAGGACTTGAAGACAGTGCCTCCACCGTGCAGGACGTTTT CTCCGGGCTGTGTGGGCGAGGGTGCCAAAGAACAAATATGCAACTTCCCCCAAGTTCTTG CACGTGGATTGCAGTAACCACCTCTGGTGAGGTTTCCCCACGTCAGGGGACTATACTGC TAGGGAGGGAGATAGTCAGGACGTCCCTTAG | 164 |
| hsa-mir-129-2 | 3 | | MDGRRGWYDRDLKTVPPPSRDVFSGRAGRGWECVCA RARPARRFQGAKEQIWQLSPQVLAMFAVTHPG* | 165 | ATGGATGGGCGAAGGGGGTGGGTCGACAGGACTTGAAGACAGTGCTCCACGTC GAGAGACGTTTCTCCGGGCTGTGTGGGCGAGGGTGGGAGGTGTGAGTTGTGTGCGCGCG CGGCCCCGCCGCAGTTCCAGATTCCAGGGTGCCAAAGAACAAATATGGGAACTTCCCC CCAAGTTCTTGCAATGTTTGCAGTAACCATCCTGGGTGA | 166 |
| | 4 | | MGEGGGSTGT* | 167 | ATGGGCGAAGGGGGTGGGTCACAGGGACTTGA | 168 |
| | 1 | | MCRYRELPEG* | 169 | ATGTGTAGGTATCGAGAGCTCCCGAAGGGTAA | 170 |

Figure 1 (Continued)

| | | | | |
|---|---|---|---|---|
| hsa-mir-130a | 2 | MCGGSAGHGRAGPSVSTWVCEGVECSEGDRGPKGWSRAGSSAPPEVVG* | 171 | ATGGGGGCTCCGCTGGGCACGGCGGCCGAGCTGGGCGTCCACCTGGGTGTGTGGAGGGCGTGGAGGTGTCCGAGGGGGAACCGGGGCCGAAGGGCTGGAGCAGGGCAGGGAGTTCTGCACCTCCAGAAGTTGTAGGGGTGA | 172 |
| | 3 | MCVGGRALTQFLLEGCVMRAELCSKYG* | 173 | ATGTGTGTGTGGGGGGGCGTGCAGTCCAGCAAGTATGCTGA | 174 |
| | 4 | MAESLCVCYCVCVCVTCACVVQPRGCVVRGEHSWVLKESAPHPPLPSCLSHPHRTWLSGPSWSPPPVAMAARRGWEETVGASPLPLLQLIIPHLPFLSLSQAGFHPLLLWGQGPEDGGQ* | 175 | ATGGCTGAGAGTTGTGTGTGTGTGTGTGTGTGTGTGTGTACGTGCGGCCTGTGTGGTCCAGCCCCTCACCCCTGTCGGGGGAGCACAGTTGGGTGTTGAAGGAGAGCGCCCCCACTTCCAGGTGCTCTCATCCATTCACAGAACATGGCTTTCAGGACCTCGTGCCATGGCTGCGAGGAGGGGTGGGAGAGACAGTTGCGCGCCAGCCCTGCGCCAGCTAACCCCACCTGCCCTTCTCCCTTTCACAGCTGGGCCCATCCCGCTGCTCTGCCCAGCGCCAAGATGTGGCCAATGA | 176 |
| | 1 | MITSHKKPLVRWLLSCSSSCLEWPGASIVSSIVCPAHSPAGTHTGRVRAVRRPGRLAPARHFSPPLPLPSAERGHQPCGLGTGEGPAALWSGSPGRPARTRRRSRR* | 177 | ATGATCACGTCGCACAAGAAGCCCTTGGTGCGCTGGCTGCTCCAGCAGCACTCTCCTTGCGGGACACACACCTCCATCGTGTCCAGCACGTCTGCCCAGCCACCTCTGCTGCGGGACACACACCCGGCGGCCTCGGTGAGAGCCGTGCGGCCCGCTTCCTCAGTGCGGGGGCATCACCCAGCGCCGCCTGGGCACCGGCGAAGGACCGGCTGCCCTGCGCCTGCGCCTCAGTGCGGGGGCATCAGCGCCGCCGCCGCCGCCGCCCGCCCGAGGAAAGTCATTCAGGCGGAGAACTTTACCAAAGTAGGGAGAAGGAAAATGA | 178 |
| | 2 | MSASGKVIQGGELYPSREKGSRGTSASRLGRSCPSWGK* | 179 | ATGTCCGCTTCAGGAAAAGTCATTCAGGGCGGAGAACTTTACCCAAGTAGGGAGAAGGGAAGTTGCCCAGTTGGGGGAAGTGA | 180 |
| | 3 | MPHPPLPGPELCCQGSAPASPARQLPFPSLPLASPAHVRAEPAPGR* | 181 | CCGCCCCACCCGCCGCTGCCAGCCCGCCCTTCCCTCCCTGCCCAGCCCATGTGCGGGCAGAGCCGGCCCCCGGGCCGCTGA | 182 |
| hsa-mir-132 | 4 | MCGQSRPRAADPAVNPARSRGPVYLSPKGTTPGALNASRQPRWGTRARRCTRGGRRTRTGLSRVPRPSRSPARGPTWGACRKPRARLTADPGGTWLRCPPPAGFPVGLSCWSVLPASWSRLSPAALSAHSYLERPGPAGAAAAMAPPKGRAGLCAAGRCLPPAHLSWRRTDAEPAGRGPPYPQVRPPTCTHLGPRPRTRESOKPWGFELSAPMYVFLGTQPQPFGKVLPASTGLGWWGRGYPAQE* | 183 | ATGTGCGGGCAGAGCCGGCCGGCCGCCGACCCGGCCGTTGAACCCGCCGCCGCCGGAGGCAGAGGCCAGGCCGGCCGTGCGGCCCGGGGACGCCCCTGAAGCCGGACACCGGACCCTGAACCCAGGGCCGCAGCGCTCAGAGAGATGCACCGAGGCGGCCGACGCACGAGGAACCGGGGCCATGTCGAAGCCCCGGGCGCGCCGCCGCTAGACTCCCGGGGCCGGGGACCCTGGGACCCTGCGACGGACGCGGCGGTCGCGCTTTGCTGTCCGCACACTCTTATCTGGAGCGCCGGGGACCTGCAGCCCCGCGGTCGCTCAGCCGCCGCTATGCGCGCCACCCTGCGGGGGCAGATGCCTGAGCGCGGACAGGGCCTGCGCAGCCCTGCGCAGCCCTGCGCCATGTACGTATTTCTAGGCACACAGCCAGCCCCAGTTGCGGAGAAAAGTCCTGCCCGAGCGGAGCGCCCGGAGCCTGGAGGTTATCCGCGCAGGAGTAG | 184 |
| | 1 | MLLTLWERFINERNVSLFQVCAFDIVYIGKGHNAVLVCEMK* | 185 | ATGCTATTGACATTATGGGAAAGATTTATCAATGAGAAATGTCTCTTTTCAGGTATGTGCTTTTGATATAGTTTACATTGGAAAGGGTCATAATGCTGTTTTAGTTGTGAAATAAGTAA | 186 |
| hsa-mir-133a-1 | 2 | MGKIYQ* | 187 | ATGGGAAAGATTTATCAATGA | 188 |
| | 3 | MREMCLFRYVLLJ* | 189 | ATGAGAGAAATGTGTCTCTTTTCAGGTATGTGCTTTTGATATAG | 190 |
| | 4 | MLFP* | 191 | ATGCTTTTCCCATGA | 192 |

Figure 1 (Continued)

| | | | | | |
|---|---|---|---|---|---|
| hsa-mir-133b | 1 | MELKNEGEMGGQGTNWGMTAYSVRIGNAHKGQMKMISLCVIRRIAITKIRVKGEGGKGKRE* | 193 | ATGGAACTAAAGAATGAAGGAGAAATGGGTGACAGGCACAAATTGGGAATGACAGCCTATTCAGTGAGGATAGGAAATGCACATAAAGGACAGATGAAGATGATTCTCTGTGTTGATTAGAAGGATAGCAATTACAAAGATAAGAGTGAAAGGAGAGGGAGGAAAGGGAAAAGGGAATAA | 194 |
| | 2 | MKEKWVDRAQIGE* | 195 | ATGAAGGAGAAATGGTTGACAGGCACACGCACAAATTGGGAATGA | 196 |
| | 3 | MHHKDR* | 197 | ATGCACATAAAGGACAGATGA | 198 |
| | 4 | MLRKSPGC* | 199 | ATGCTTAGAAAATCACCAGGCTGTTAG | 200 |
| hsa-mir-134 | 1 | MPNKPGSMMTTGGV* | 201 | ATGCCCAATCTGGATCGATGATGACCACTGGTGGCGTATGA | 202 |
| | 2 | MSHT* | 203 | ATGAGTCATACATGA | 204 |
| | 3 | MMNMCLEL* | 205 | ATGATGAATATGTGTCTGGAACTCTGA | 206 |
| | 4 | MHSYVIIMIGSMKE* | 207 | ATGCATTCTTATGTTATTATTATGATTGGTCAATGAAGAATGA | 208 |
| hsa-mir-135a-2 | 1 | MMKMEYKAIPSLLSLTNLYQFSE* | 209 | ATGATGAAAATGAAATATAAAGCAATATTTCTCTGTTGAGTCTAACTAATCTTTATCAGTTTTCAAGATAA | 210 |
| | 2 | MGHLYCVALDLFCSTM* | 211 | ATGGGACATTTATATTGTGTAGCGTTGGGATTTATTTGCTCAACAATGTAA | 212 |
| | 3 | MLKGKLRS* | 213 | ATGCTCAAAGGAAAGCTAAGGTCTGA | 214 |
| | 4 | MFYFPGPVWS* | 215 | ATGTTCTATTTTCCAGGCCAGTCTGGTCATAG | 216 |
| hsa-mir-136 | 1 | MRRAL* | 217 | ATGAGGAGGCATTGAG | 218 |
| | 2 | MRVIDPGCRSPKE* | 219 | ATGAGGGTCATTGATCCTGGGTGCAGATCCAAAGAATGA | 220 |
| | 3 | MTERKREWWKETIGWEKMKIEKRK* | 221 | ATGACAGAAGAAAGAGGGAGTGTGAAAACAATAGGATGGGAAAAATGAAATAGAAAAAAGGAAGTGA | 222 |
| | 4 | MGKNENRKKEFVKEHNN* | 223 | ATGGGAAAAATGAAAATGAAAGAAGTGAAAGATAATAATAATTAG | 224 |
| hsa-mir-138-2 | 1 | MLLCALSGVSGPQ* | 225 | ATGCTTCTCCTGTGTGCCCTCTGCCTTTGCTTCGTGCTGATCTGCCACAGTAG | 226 |
| | 2 | MSRCFALSSCARLLPTSSGSAPKA* | 227 | ATGAGCAGATGCGTTTGTCTTGTCCTCGTGCCAGGCTCCTCCCCACATCCTCTGGATCAGTCCACGTGCTAG | 228 |
| | 3 | MLCFVLLCQAPPHLWISSTCLDSDSVIHRGGP* | 229 | ATGCTTTGCTTTGTCCTTGTCCTGTGCCAGGCTCCTCCCCACATCCTCTGGATCAGTCCACGTGCTAGATTCAGACTCCGTGATTCAACCGTGGGGCCTTAA | 230 |
| | 4 | MSPRIK* | 231 | ATGTCTCCCAGGATCAAATGA | 232 |
| hsa-mir-141 | 1 | MGAALRGGRRRRRRGGD* | 233 | ATGGGGGCCGCCTCCGGGGAGAGGAGGCGCCGCGCGCGTCGTCGCGGGGGGGACTGA | 234 |
| | 2 | MDRRIDGSEVGHEASRKKLQRTRTRVPEPGVGGFRNRREVGNGKGVW* | 235 | ATGGATAGGAGAGATGGCAGCGAGGTGGGGCATGAAGCCTCCAGGAAAAGCTCCAAGGACCAGACGGTTCCGGAGCCTGGGGTTGGGGCTTAGGAATAGACGGGAAGTGGGAAACGGGAAAGGGGTGTGTAG | 236 |
| | 3 | MAARWGMKPPGKSSKGPEHGFRSLGLGALGHDGKWETGKGCGRWKEGLWLMNLGETEAWAKRGPFLRRAGGFPAWKREGHVFYTVFIPLLQYTSDPVFPTPDIVISWKGHWGPVVWVIPKLVRRKIGTQKGELGRKGFWEDGNGELSNLTGTPGKLRPPPSTLQFPERPLPLEL* | 237 | ATGGCAGCGAGGTGGGGCATGAAGCCTCCAGGAAAAAGCTCCAAGGGAAGTGGGGAGACCGGGTTCGGAGCCTGGGAGATGGCAGCGAGGGATTGTGCTGATAGAGCCTGATGAACCTGGGCGAGACGAAGGCTTGGGCAAAGAGGTCATTTTGACAGGTTTCATTCCCTACTGCAGTCACCTCTGACCCTGTTTCCCTATCCCACACATAGTTATTTCTTGGAGAGGACCTGGGGCACAGTAGTGTGGGTTATCCCAAAACTAGTGAGGAATGGAAAACAGGAACACAGAAGGGGGAGTTGGGAAGGAAAAGGGGTTCTGGGAGGATGGAATTGAGCAACCTTACAGGCACTCCAGGCAAGTTGCGACCTCCACCCTCCAATTTCCGGAGCGTCCGCTGCCCCTGGAGCTGTGA | 238 |
| | 4 | MEMEN* | 239 | ATGGAAATGGAAATTGA | 240 |
| | 1 | MREFAQGKAP* | 241 | ATGCCGGAAGCTCAGGCAAAGGCCCTTGA | 242 |

Figure 1 (Continued)

| | | | | | |
|---|---|---|---|---|---|
| hsa-mir-142 | 2 | MAPGPQAGKFVSKEEGWRVRRGWQRVRRG* | 243 | ATGGCTCCGGGACCCCAGGCGGGGACGGGGAAAGAGGTGTCCAAGGAGGAGGGCTGGAGAG TAAGGCGGGGATGGCAGAGGGTACGCAGAGGCTGA | 244 |
| | 3 | MAEGTQRLRSGTSVSRGASLFLRPTWPPFLLG* | 245 | ATGGCAGAGGGTACGCAGAGGCTGAGAAGTGGGACCAGTGTCTCAAGGGGCGGCCAG CCTCTTCCTCCGCCACATGGCCACCATTTTGTTGGGATAG | 246 |
| | 4 | MATIFVGHALGSCQGWSRAVRESGLWAGGEAENQGSGE SGLWGWWSGWGLRPWGVRTLGCYGGWD* | 247 | ATGGCCACCATTTTGTTGGGATAGCCTTGGGCTCCTGCCAGGGAACAGCAGGGCA GTGAGGGAGTTCAGGACTTTGGGCTGGTGGGAGGCCGAGAATCAAGGCTCTGGGGA GTCAGGACTTTGGGCTGGTGGGAGGCTGGGGACTGAGGCCTGGGGGTCAGGA CCTTGGGCTGCTATGGAGGCTGGGACTGA | 248 |
| | 1 | MPLWQRGAPEAGSN* | 249 | ATGCCCTGTGGCAGCGAGGCGGGACGCAGAGGCTGGGTCTAATTAG | 250 |
| | 2 | MLHLGVLLSC* | 251 | ATGCTCGATCTGGGGGTCTTGTCTGTCTGCTAA | 252 |
| | 3 | MISKHPSS* | 253 | ATGATCTCTAAGCATCCATCCAGCTGA | 254 |
| hsa-mir-143 | 4 | MVLLASRIPCCCSQLGHEGAEGGVHRVNILSAQASPRHPS LRQSPWLLHRQCFFLIVWGHDFVIPRAWGSWQGKWFSN NGFFEKQSWGRGNVSSGSGRQAEHLGRLGADCTWSNGK GCW* | 255 | ATGGTTCTGTTGGCTTCGAGGATTCCTGTTGTTGTAGTCAATTGGGGAAGAAGGT GCAGAGGAGTGCAGTCTCCTGGCTTCAAGAGCTCAGGCCAGTGCTTCAGCCACCCG AGTCTCAGGCAGTCCCTGGCTTCAAGAGCTCAGGCCAGTGCTTCTTCCATTGTGTG GGCTTTGATTTGTAATTCCAAGAGCCTGGGCTCCTGGCAAGGAAACAAAGCTGGGGCTCTGG AATAATGGTTTCGAGAAACAACTGGGGAAGGCAATGTAAGCTCAGGCTCTGG CAGGCAGGCAGAGATCCTGGGAAGGCTGGGTGCTGACTGCACATGGAGCAATGGGA AGGGATGCTGGTGA | 256 |
| hsa-mir-144 | 1 | MGGGSRSPGGQVPVWGGALKQRSFLGTVRPVNSKQAG ACWGLPALPAQETRMRPLQVGKPGSGQCSLGLQNAAS SRISJ* | 257 | ATGGGGGCGGGTCGCCAGAGGTCGTTTCTGGCACAGGCACGACCCGTAATTCAAGCAGGCTGGGG GAAACAGAGGTCGTTTCTGGCACAGGCACGACCCGTAATTCAAGCAGGCTGGGG CTTGTTCGGGGATTACCGRACTGCGCCAGGAGACGCGATGCGRCCTCTACAG GTGGGAAACCCGGTTCTGGGCAGTTGGGATTGCAAAATGCTGCAAGTTCC AGAATTCTATCTAG | 258 |
| | 2 | MGRGPETEVVSRHSQTR* | 259 | ATGGGGGAGGGGCCTGAAACAGAGGTCGTTTCTCGGCACAGTCAGACCCGTTAA | 260 |
| | 3 | MLQVPEFLSRWGMGTAVLGKRNCY* | 261 | ATGCTTCAAGCTCACTTGGATCTCAAATCAATCTCCACTGGGACATCCCTAG GAAAAGGAACTCTATTGA | 262 |
| | 4 | MASGSLWISKSISPLGHPQCVGDKYPTPLKTRNSLEDRR ETPREH* | 263 | TGTGTGGGAGGATAATACCTACCCCCTGAAGACCAGAAATAGCCTTGAGGACAG AAGGGAGACTCCCAGAGAACACTAA | 264 |
| | 1 | MPLWQRGAPEAGSN* | 265 | ATGCCCTGTGGCAGCGAGGCGCACCAGAGGCTGGGTCTAATTAG | 266 |
| | 2 | MLHLGVLLSC* | 267 | ATGCTCGATCTGGGGGTCTTGTCTGTCTAA | 268 |
| | 3 | MISKHPSS* | 269 | ATGATCTCTAAGCATCCATCCAGCTGA | 270 |
| hsa-mir-145 | 4 | MVLLASRIPCCCSQLGEEGAEGGVHRVNILSAQASPRHPS LRQSPWLLHRQCFFLIVWGHDFVIPRAWGSWQCKWFSN NGFFEKQSWGRGNVSSGSGRQAEHLGRLGADCTWSNGK GCW* | 271 | ATGGTTCTCGTTGGCTTCGAGGATTCCTTGTTGTTGTAGTCAATTGGGGAAGAAGGT GCAGAGGAGTGCAGTCTCCTGGCTTCAAGAGTTAACATCCTATCAGGCAGTCGGCACCCT AGTCTCAGGCAGTCCCTGGCTTCAAGAGCTCAGGCCAGTGCTTCTTCCATTGTGTGG GGCTTTGATTTGTAATTCCAAGAGAACAAAGCTGGGGCTCCTGGCAAGGAAATGGTTTCA AATAATGGTTTCGAGAAAACAAAGCTGGGGCAAGGCAATGTAAGCTCAGGCTCTGG CAGGCAGCAGAGATCCTGGGAAGGCTGGGTGCTGACTGCACATGGAGCAATGGGA AGGGATGCTGGTGA | 272 |
| | 1 | MLFLQDA* | 273 | ATGCTCTTTCTCCAAGACGCTTGA | 274 |
| hsa-mir-146a | 2 | MAPAGPIGVVNPGPEGMPKGGQDGQETVAQRGGGEQR LNWK* | 275 | ATGGCCACCAGCAGGGCCGATTGGAGTGGTAAACCTGGGCCGGAAGGCATGCCAAA GGGTGGACAGGATGGACAGGAACAGTAGCAACGACGAGGAGGGGGAGAACAGCGG CTGAATTGGAAATGA | 276 |
| | 3 | MDRRQ* | 277 | ATGGACAGGAGACAGTAG | 278 |
| | 4 | MSWEKHHAS* | 279 | ATGAGCTGGGAAAAACATCATTGCAAGCTGA | 280 |

Figure 1 (Continued)

| | | | | |
|---|---|---|---|---|
| hsa-mir-146b | 1 | MSGFSIPVWLDSGQGASSPGPREFHL* | 281 | ATGTCTGGGTTCTCTATTCCGTCTGCCTTGATTCTGGACAAGGGGCTTCCTCTCCAG GGCCTCGGTTTCCCCATCTTTAA | 282 |
| | 2 | MRSGFRCDEPAEAVAPERQTYSGAVALASFTSPHTHPV DDGGRHYSWGSPKRILGLLGPGDAVRGSPEAESRGLGRH CPRADPAPDPTTKPKASREALPLAG* | 283 | ATGAGAAGTGGTTTCGTTCGTGATGAGCAGCTGAAGCGGTTGCACCGGAGCGCA GACCGTCAGCGGTGCAGTGCCTCTCCGGTCTTCACATCCCACCCCATCCGT GGATGATGGGGAAGGCACTACTCCTGGAGGTTCCCGAAGCGGATCCTGGGACTGG GACCTTGGGACGCCGGTGAGAGGCAGCCCTGAAGCTGAGTCCAGAGTTCTGGGGCCT CATTGTCCCAGGCGACCGACCCAGCCCAGGCGACCCTACAACTAAGCCAAGCCTAAGCCG AGAAGCACTACCACTRGCGRGCTGA | 284 |
| | 3 | MSQLKRLHRSARPSAVQWLSRPSHPPTPIPWMMGEGTT PGVPRSGGSWDWDLGTR* | 285 | ATGAGCCAGCTGAAGCGGTTGCATCGGAGCGCATCCGTGAGCGGTCAGCGGTCAGTGGCT CTCGTCTTCACATCCCCACACCATCCGTGGATGATGGGGAAGGCACTAC TCCTGGGGTTCCCCGAAGCGGATCCTGGGACTGGGACCTGGGAGCGGGTGA | 286 |
| | 4 | MKGTQLEJ* | 287 | ATGAAAGGGACCCAGTTGGAAATATAG | 288 |
| hsa-mir-147a | 1 | MHRKPKTVYLIVFLSDTFFSAPLFFSILLRPHRSHDHMVI SWSSILLTTPS* | 289 | ATGCACAGAAAACAAAGACCGTGTATCTCATTGTATTCTTCTGACACTTTCTTT CAGCCCCCCTCTTTTTTCCATCCTTTTGAGACCCACAGTCACATGATCATATGGT CATTTCATGGTCTTCAACTCTTCAGACCCCTTCATAG | 290 |
| | 2 | MHWSFHGLQLLRPLHSTDFTISF* | 291 | ATGATCATATGGTCTTCAACTCTTCATGGTCTCAACTCTTCAGACCCCTTCATAGTACGGACT TCACCATTTCCTTTTAA | 292 |
| | 3 | MVFNSYDPFIVRTSPFPENFLVS* | 293 | ATGGTTCTCAACTCTTACGACCCCTTCATAGTACGGACTTCACCATTTCCTTTTAATT TCCTAGTGAGTTAA | 294 |
| | 4 | MKWSLF* | 295 | ATGAAATGGAGCCTTTCTGA | 296 |
| | 1 | MERWRGVWGKMGKHFPDLLHARNSCSGAVCGGRGSA RMGDRVVAYAAGKRGCREGEKSSLGDCVQKCARTGS AGSTA* | 297 | ATGGAACGGTGGCGAGGGGTTTGCGCGGAAGATGGAAAGCACTTTCCAGACCTGTT GCACGCGCCAACAGTTGGTCGTTATGCTGCAGGGAGAATGGAAGATGGAAGATCGAAGCGTGGGCGGTCTGCTAGGA TGGGGGACGAGCAGTCTTGGGACTGTGTGCAAGGTTGTGCGCAACGGGGTCCGCGGGAA GCACTGCCTAA | 298 |
| | 2 | MWGEGVC* | 299 | ATGTGGGAGGAGGGCGTCTGCTAG | 300 |
| | 3 | MLQCKGAGRGRRAVLGTVCKVVRERGPREALPNGA GRIPKSGWVERRGWDIFDPSSRGWARAAGRPGHEYWE WLGKGVSGEAPQSGSFLGRPILGAFFPGPVFVPHRLTLSA PNIRPRAAPPPPAFQMGR* | 301 | ATGCTCTCAAGGGAGAAAAGGGGTGCCGGGAGGGGAGAAGAGCAGTCTTGGGGACTG TGTGTGCAAGGTTGTGCGCGAACAGCGGGTCCCGGGAGAAGCACTGCCTAATGGGGCAGGG AGAATCCAAAGAGTGGGTTGGCCGGCGCGGCTGGAAGCAGGGGATGGCAGACGACTTTGACCCGA GTTCCCGGGCTGGGCTGGAGCCTGGAAGACCGGAAGAGTACTGGGAATGG CTGGGGAAGGGGGGTCTCAGGGAGGCCTGATTTGTTCCCACCGGTTAAACTCTTTCAGT CATCTTTAGGGCGTGCGTTAGCCGGCCTGGCAGCGCGCCAGCTTCCCAGATGGGAAGGTAA CCGAATATTGCGTTCCCTCGTGCAGCGCGCCAGCTTCCAGATGGGAAGGTAA | 302 |
| | 4 | MGQGESQRVGGWNGGDGTTSTRVPGAGRGRLEDRE* | 303 | ATGGGGCAGGGAGGAGAATTCCCAGGGAGTTCCCAGGGAAGAGGAGATCCAAAGAGTGGGTTGGGGATGGGGACGA CTTCGACCCGAGTTCTCACCTGGGGAAGGACAAGGACAAGCAGGTCTCAGTGAGATGAGCTTTAATGAGG | 304 |
| hsa-mir-148a | 1 | MKJFFTWGRTGLSEMSFNGGNAKQVKTKTK* | 305 | ATGAAATTCTTCACCTGGGGAAGGACAAGCAGTCTCAGTGAGATGAGCTTTAATGCGGCAAT AAACGCAAGCAGGTTAAAACAAAGACAAGTAA | 306 |
| | 2 | MEETPSRLKQRQSKSYWGTKISVELISIYQ* | 307 | ATGGAGGAAAACTCCAGCCGACTTAAGCAGAGGCAGTCTAAGACAAAGAATTCCTAGGGGTAC AAAGATTTCTGTGGAGTTAATAAATCTACTGGGGTAC | 308 |
| | 3 | MQWLFPVIAALWEAEAGKRSLEVRSLRPAWPTWRNPIST RKILSRAWWGTPVIPATRESEAQESREPRKRRLP* | 309 | ATGCAGTGGCTCACGCCTGTAATAGCAGCACTTTGGAGGCTGAAGCTGGCAGATC ACTTGAGGTCATGAGGTTAGCCGGCCATGTTGGGCACGCTGTAATCCAGCTACTCGG CAAAAAATATTAGCCGGGGCATGTTGGGCACGCTGTAATCCAGCTACTCGGG AGTCTGAGGCACAAGAGTGATTGAACCCAGGAGGCGGAGGTTGCCGTGA | 310 |
| | 4 | MAKPHLYQKNT* | 311 | ATGGCGAAACCCCATCTTACCAAAAAATACTTAG | 312 |
| hsa-mir-150 | 1 | MPPPGSMMTTGGV* | 313 | ATGCCAATCCTGATGATGACCGGTGGCGTATGA | 314 |

Figure 1 (Continued)

| | | | | | |
|---|---|---|---|---|---|
| hsa-mir-154 | 2 | MSHT* | 315 | ATGAGTCATACAATGA | 316 |
| | 3 | MMNMCLEL* | 317 | ATGATGAATATGTGTCTGGAACTCTGA | 318 |
| | 4 | MHSYVHMIGSMKE* | 319 | ATGCATTCTATGTTATTATGGTCAATGAAAGAATGA | 320 |
| | 1 | MPSRGGDARWGAWGQRRPDRPTPDRARGGHGPGRRR ALFLGARGGWGARKSNARREYGPARARS* | 321 | ATGCCCTCGCTGGGGGGGGACGCTGCCGGCGGAGTACCGGCCGGACACCTGACCGGCGCGGGAGGCCACGGGCGGCGGCGGGCTGTTCTTGGGTGCGCGGGGCTGGGGGCGCGGGGCCGGCTCGGAAATGCCAGAAGAGAGAGTACGGCCCGGCGCGGCGCGCGTTCGTGA | 322 |
| | 2 | MGGVGTAAPRPPDT* | 323 | ATGGGGGGCGTGGGGACAGCGGCGCCGCCGACCGCCGACACCTGA | 324 |
| hsa-mir-181c | 3 | MPEESTARRARVREGCSGQVHGRSGLRRPILAGAPLRP GRGLGVLQPRHLRKPWRPARAAPPACHYRQQLQGIYW GQGLRTGTRPPKLAIKRENGPESHCRGALLKLQGAFHG DLPWRAGWGWGGGKDTSLADRD* | 325 | ATGCCAGAAGAGAGTACGGCGCCCGCGCGGCGGCGTTCGTGAAGGCTGCTCCGGCCAAGTTCATGGGCGTCGGGCCTGGGAGACCGATCGGCACCTCCGGGGTGCTGCAGCCGCGCCACCTCCGGAAGCCCTGGCGCCTGTGGCGCGCCGCCCCCTCGGGGTGCTGCAGCCGCGCCACCTCCGGCAGCTGCAGGGTATTTACTGGGGCCAAGGTTTGCGAACAGGAACCCGCCTCCAAAACTGGCCATAAAAAGGAAAATGGCCCCGAATCCCACTGCCGGGAGCCTGGAGGCCTTTAAGCTACAGGGGCCTTTCACGGCGACCTGCCTTGGAGGGCAGGCTGGGGGTGGAAAAGACACCTCATTGGCTGATAGGGACTGA | 326 |
| | 4 | MGARACGDRSWRGPRSGLAAGWGCCSRATSGSPGALR GPPLRPVITGSSCRVFTGAKVCEQEPALQNWP* | 327 | ATGGGCGCTCTGGGCTGCGGAGACCGATCCTGGCGGGGACCGCGGAGCGGGGTGCTGCAGCCGCGCCACCTCCGGAAGCCCTGGCGCCTGCGCGGGCCGCCCCTCCGGAACAGGAACCCGCCTCCAAAACTGGCCATAA | 328 |
| | 1 | MPSRGGDARWGAWGQRRPDRPTPDRARGGHGPGRRR ALFLGARGGWGARKSNARREYGPARARS* | 329 | ATGCCCTCGCTGGGGGGGGACGCTGCCGGCGGAGTACCGGCCGGACACCTGACCGGCGCGGGAGGCCACGGGCGGCGGCGGGCTGTTCTTGGGTGCGCGGGGCTGGGGGCGCGGGGCCGGCTCGGAAATGCCAGAAGAGA | 330 |
| | 2 | MGGVGTAAPRPPDT* | 331 | ATGGGGGGCGTGGGGACAGCGGCGCCGCCGACCGCCGACACCTGA | 332 |
| hsa-mir-181d | 3 | MPEESTARRARVREGCSGQVHGRSGLRRPILAGAPLRP GRGLGVLQPRHLRKPWRPARAAPPACHYRQQLQGIYW GQGLRTGTRPPKLAIKRENGPESHCRGALLKLQGAFHG DLPWRAGWGWGGGKDTSLADRD* | 333 | ATGCCAGAAGAGAGTACGGCGCCCGCGCGGCGGCGTTCGTGAAGGCTGCTCCGGCCAAGTTCATGGGCGTCGGGCCTGGGAGACCGATCGGCACCTCCGGGGTGCTGCAGCCGCGCCACCTCCGGAAGCCCTGGCGCCTGTGGCGCGCCGCCCCCTCGGGGTGCTGCAGCCGCGCCACCTCCGGCAGCTGCAGGGTATTTACTGGGGCCAAGGTTTGCGAACAGGAACCCGCCTCCAAAACTGCCCATAAAAAGGAAAATGGCCCCGAATCCCACTGCCGGGAGCCTGGAGGCCTTTAAGCTACAGGGGCCTTTCACGGCGACCTGCCTTGGAGGGCAGGCTGGGGGTGGAAAAGACACCTCATTGGCTGATAGGGACTGA | 334 |
| | 4 | MGARACGDRSWRGPRSGLAAGWGCCSRATSGSPGALR GPPLRPVITGSSCRVFTGAKVCEQEPALQNWP* | 335 | ATGGGCGCTCTGGGCCTGCGGAGACCGATCCTGGCGGGGACCGCGGAGCGGGGTGCTGCAGCCGCGCCACCTCCGGAAGCCCTGGCGCCTGCGCGGGCCGCCCCTCCGGAACAGGAACCCGCCTCCAAAACTGGCCATAA | 336 |
| | 1 | MRLFPNRGRFCLASLVWTPRGAERRLCAQPGAGAGECL GPGAGGRAGRSQSGAQ* | 337 | ATGCGGCTCTTTCCAAACCGGGGCCGTTTTGCTGCTTCTCTGGTGTGGACTCCGCGGGAGCTGAGCGCTGAGAGGCGCCTGCAGCCTGGGGCTGGGGCTGTGCGCCTGACCGGCGGCGGCTGAGCGGGCCCGGGGCGGGAGCCGGGGGCGGAGCCGCAGAGCGGGGCTGAGTGTCTAGTAG | 338 |

Figure 1 (Continued)

| | | | | |
|---|---|---|---|---|
| hsa-mir-182 | 2 | MTRQCLLALPRLQAEAPTGRLGPGSASGVCPAPSAVPG RGRGRERLRSECGRCLRGAYPRGVWLGSGCVSPPWA QAEAPGWEGAAESAGAPELAPPASCQGCAAGSRLLPWP GAAPPSLWGKAALRPPVCLHFAATHPGNPGARE* | 339 | ATGACGCGGCAGTGCCTACTGCTCTTCCCGCCTTCAGGCGGAGGCGCCACGGG GCGGCTGGGTCCCGGAACGGCTCCGCCAGTGGGTCCGCCAGCGCTGTCCCGG GCCTACCCGCGAGGAGTTTGGCTGGGGTCGCGTTTGGCCGCCTGGTGGCT CAGGCCGAAGCGCCCAGGCTGAGGCGCCGGGGCCCCGGGAGC TGGCCCCCTCCAGCGTCTTGTCAGGCGGCTGCGCGGCTCGGTTCCGTCGGC CCGAGCCGCCCCCCAGTCTCTGGGGAAAGCGGCTCTCAGACCTCCGGTGCC TCCACTTCGCTGCGGCCACTCATCCCGGAACCCCGCGCGACGGGAATGA |
| | 3 | MRHRSPPSTAPFLLIALVAPRFPALPQDRRLDGLPLAPH RSAHPRTMGSEGVTRGQGSPDSTYSSRLSHSFALPTRAP GHRVQ* | 341 | ATGAGACACCGTTCCCAGCCCTTCCCAACTGCCCATTCCTGTAATAGCGCTAGTGGCA CCCAGGTTCCAGCCCTTCCCAAGATCGGCGCTGGACGGCTTGCCTTCTGGCGCCT CACCGGTCAGGCGCATCCAGGACTATGGGACAGTGAGGGTGTCACCGGGGTCAGGG GTGCCCGATTCCACGGTGTCCCAGGCTGAGCGCATTCGTTTGCTCTCTCCAACCCG GGCTCCGGACACCGGTGACAGTAA |
| | 4 | MGTESADL* | 343 | ATGRGCACCGAGTCGGATCTCTGA |
| | 1 | MRLFPNRGRPFCLASLVVTPRGAERRLCAQPGAGAGECL GFGAGGRAGRSQSGAQ* | 345 | ATGCGGCTCTTTCCAAACCGGGGCCGTTTTCTGCCTGGCTTCTCTGGTGGTGGACTCCG CGGGAGCTGAGAGCGGCTGTGCGCCCAGCCTGGAGCCGGCGCAGGTGAGTGTCT GGGGCCGGGCTGAGGACGGGCCGGCAGGGAGGGCCGGGGCTCAGTAG |
| | 2 | MTRQCLLALPRLQAEAPTGRLGPGSASGVCPAPSAVPG RGRGRERLRSECGRCLRGAYPRGVWLGSGCVSPPWA QAEAPGWEGAAESAGAPELAPPASCQGCAAGSRLLPWP GAAPPSLWGKAALRPPVCLHFAATHPGNPGARE* | 347 | ATGACGCGGCAGTGCCTACTGCTCTTCCCGCCTTCAGGCGGAGGCGCCACGGG GCGGCTGGGTCCCGGAACGGCTCCGCCAGTGGGTCCGCCAGCGCTGTCCCGG GCCTACCCGCGAGGAGTTTGGCTGGGGTCGCGTTTGGCCGCCTGGTGGCT CAGGCCGAAGCGCCCAGGCTGAGGCGCCGGGGCCCCGGGAGC TGGCCCCCTCCAGCGTCTTGTCAGGCGGCTGCGCGGCTCGGTTCCGTCGGC CCGAGCCGCCCCCCAGTCTCTGGGGAAAGCGGCTCTCAGACCTCCGGTGCC TCCACTTCGCTGCGGCCACTCATCCCGGAACCCCGCGCGACGGGAATGA |
| hsa-mir-183 | 3 | MRHRSPPSTAPFLLIALVAPRFPALPQDRRLDGLPLAPH RSAHPRTMGSEGVTRGQGSPDSTYSSRLSHSFALPTRAP GHRVQ* | 349 | ATGAGACACCGTTCCCAGCCCTTCCCAACTGCCCATTCCTGTAATAGCGCTAGTGGCA CCCAGGTTCCAGCCCTTCCCAAGATCGGCGCTGGACGGCTTGCCTTCTGGCGCCT CACCGGTCAGGCGCATCCAGGACTATGGGACAGTGAGGGTGTCACCGGGGTCAGGG GTGCCCGATTCCACGGTGTCCCAGGCTGAGCGCATTCGTTTGCTCTCTCCAACCCG GGCTCCGGACACCGGTGACAGTAA |
| | 4 | MGTESADL* | 351 | ATGRGCACCGAGTCGGATCTCTGA |
| | 1 | MVGLQRCLHLV* | 353 | ATGGTGGATTACAAAGGTGCTTAATTTGGTTGA |
| | 2 | MNAAQHILC* | 355 | ATGAATGCGTCAGCATATTTATGTTAA |
| hsa-mir-184 | 3 | MLLSIFYVKMLFLCLKIFRKGK* | 357 | ATGCTGCTCAAGCATATTTATGTTAAAAATTTGTTTTATGTTTAAAAATTTTAGAA AAGGTAAATAA |
| | 4 | MLKICFYV* | 359 | ATGTAAAATTTGTTTTTATGTTTAA |
| | 1 | MKKGRKPPTCASDSRWRNDCGFRCHIE* | 361 | ATGAAAAAGGGAGGAAGCCCACCTGTGCAGTGACTGCGCGTTGGAGAAAATGATTG TGGTTTCGTTGCATCCACCGCTGA |
| hsa-mir-18b | 2 | MIVVPVASSTADS* | 363 | ATGATTGTGGTTTCGTTGCATCCACCGCTGACTCTGA |
| | 3 | MAPLSSSGLWAATITLVTMVEREGSGFILHPFPPSLPPAC LPGLSSSDPACSLVSDL* | 365 | ATGGCCGCCTTGCCTTCCTCTTCCGGGCTTTGGGCTGCACAATCACCGTGTAACAATG GTGGAAAGGGACGGGAGGGTCCAGGCTTTCCTCCTTCTTGCCCCCC GCTTGCCCTTGCAGGACTTTCCTCCTCCGACCCAGCGTGCTCACTGGTCTCTGATTTGT AA |

Figure 1 (Continued)

| | | | | | |
|---|---|---|---|---|---|
| | 4 | MLNSILFVRLKLRHHFILQSAVGLWP* | 367 | ATGCTTAATTCCATTTGATTGTGGTCTTAAACTAAGACATCATTTTATTCTACAGAGCGCTGTCGGGCTTTGGCCTTGA | 368 |
| hsa-mir-190b | 1 | MAPFYNPVCHLFLTYHSTQNFMV* | 369 | ATGGCCCCATTCTATAATCCTGTGTCATCTACTTTTCTCACTTATCACTCTACCCAAAATTTCATGTATAA | 370 |
| | 2 | MIQVVKVYP* | 371 | ATGATCCAGGTGGTAAAGTTTATCCCTAA | 372 |
| | 3 | MSPKSPYLSDQSRNHSDHFG* | 373 | ATGAGCCCTAAGTCCCCATATCTTTCGACCAGTCTAGAAATCATTCTGATCATTTTGGTTAA | 374 |
| | 4 | MKLTPFLEQKTFLLAYQSHLKKE* | 375 | ATGAAACTTACCCATTCCTTGAGCAGAAAAACTTCCTCCTCGCCTACCAGAGCCACCTAAAGAAGAATGA | 376 |
| hsa-mir-192 | 1 | MCPDLLTPRS* | 377 | ATGTGCCCTGACCTCCTGACCCCACGGTCTGA | 378 |
| | 2 | MCMSTTASYRQYQC* | 379 | ATGTGTATGTCAACAACGGGTCAGTACGTCAGTACCAGTGTTGA | 380 |
| | 3 | MGQVGV* | 381 | ATGGGCCAAGTGGGTGTCTAG | 382 |
| | 4 | MAPTYISHRPPRLSVPAWREALEERWGDLASSREEAKGDAREAKRCKVRGLRLGTVRSPDSQLS* | 383 | ATGGCCCCCACTTACATCTCCCACGACCCCCCGGCTCAGTGTCCTCAGTCTGCTCCGGAGGGAGGGCCTGAGGAAAGTGGGGAGATCTGGCTTCAAGCCGGAGGAGGCCAAGGGAGATGCTAGGAGGAGCCAAGAGGTGTAAGGTCAGAGGCTTGAAGGCTGGGAACGGTGAGGAGCCCTGACTCACAGCTCAGCTGA | 384 |
| | 1 | MGTLRSRWPAGTRVPPDLRVLWRGNFPERVPEFPERWFLDCSLEGELCRPCALPVFLSTKQTRLFNWWVLLFQSW* | 385 | ATGGGGACACTAAGGTCAGTGCCGCGGGGACTCGGGTCCGCGATTGCGAGTGTTATGCGGGGCAACTTCAGAGAGGTGCCTGAGTTTCCGAACGGTGTTTCTGGATTGTTCTTTGGAAGGTGAATTATGCAGGCATGCGACCTGTCTCCTGTCTACAAAGCAAACCAGATTGTTCAACTGGTGCGTGCTTCTTTCCAGTCCTGGTGA | 386 |
| hsa-mir-193a | 2 | MACQLSREGA* | 387 | ATGGCGCGAAACTTTCCAGAGAGGGTGCCTGA | 388 |
| | 3 | MQAMRTACLPVYKANQVQLVGASPPVLVN* | 389 | ATGCAGGCCATGCGCACTGCGCTGTCTCCTGTCTACAAAGCAAACCAGATTGTTCAACTGGTGGGTGCCTCTTTTCCAGTCCTGGTGAACTGA | 390 |
| | 4 | MTLPTSSLG* | 391 | ATGACACTCCCACATCATCTCTAGGATAA | 392 |
| hsa-mir-193b | 1 | MGTGEGRWRRGSARFSRDSARDACLGCDCRRRCRHPGSPSDPSPAPQRGV* | 393 | ATGGGAACGGAGAGGGGAGGTGGCGCGGGGGAGCGCGGCGTTCTCGGGACTCGGCGCGAGACCCTTGCTCGGCTCGATTGCCGCGCTGCCGCCACCCGGCTCCCCCTCGGACCCCTTCCCGCTCCCAGAGRGGCGTGTGA | 394 |
| | 2 | MPRAEQAGRARRSTCARAPLAWAAAPAGAGPPRGSRTSREPPSESYRRPLKLSAPSPREAGSPGALALASAGRGQKN* | 395 | ATGCCGCGCGCAGAAGCAGCTGGCAGGGCGCGCCGCTGCGCTCCACGCGTCGCTCCACGCGTCGCGCGAGCGCGCTGCCATGCGGGAGGGCGCCTGCGGGGCGCCGCGATCGCCGGATCAGCCGGGAACCACCGTGCGTCCCAGAGAGTTACCCGGCGCCCCCTAAAGTTGTCAGTCCCTCCCCGAAGGCAGGGCGCGTTAGCTCTGCAGGACGGGGGCAAAAAACTAG | 396 |
| | 3 | MCGGACGGGRAPGIPD* | 397 | ATGCGCGGCGCGGCTGCGGGCCGGGCCCGGGGATCCCGGACTAG | 398 |
| | 4 | MRRLCPLRTHPYL* | 399 | ATGCGCCGCTTATGTCCTCTGAGGACACATCATATTATAA | 400 |
| hsa-mir-196a-2 | 1 | MPGLDGVGTGHLECCKFSVSSPNFFSIFF* | 401 | ATGCCTGGCTTGGATGGTGTTGGAACAGGGCATTGGAATGTTGTAAGTTTTGTTTCCTCTTTAATTTTTCTTTCCATTTTTCTAG | 402 |
| | 2 | MALEEQGIWNVVSFLPLLIFSFPFFSS* | 403 | ATGGCTTGGAACAGGGACATTGGAATGTTGTAAGTTTCGTTCCTCTCTTTAATTTTTCTTTCTCATTTTTCCATTTTTCTAGTTAA | 404 |
| | 3 | MSGWEISVCVARGFLLKGNVALVGFHCNFG* | 405 | ATGAGTGGCTTTGGGAAATTTCTGTGTCGCGGCAAGAGGTTTTCTCCTGAAAGGGAATGTGGCTTTGGTTGGATTCACTGTAATTTGGTTGA | 406 |
| | 4 | MWLWLDFTVILVERKPSQSSSSGFKJHFCCRSWGPSGSFSDTWGKNVEETGAGEEKLRGTTFPEKL* | 407 | ATGTGGCTTTGGTTGGATTCACTGTAATTCTTGTCTGTAGGAGCTGGGAGCTGGGGGCCTTCAGGATCTTTCTCTGATACTTGGGGAAGAATGTGGAAGAAACCGGGAGCAGGGAGGCAGGGGAGGAAAAGCTGAGGGGAACGACTTTCCTGAAAAGTGTAG | 408 |

Figure 1 (Continued)

| | | | | | |
|---|---|---|---|---|---|
| hsa-mir-197 | 1 | MGDLAPQN* | 409 | ATGGGAGACTTGGCACCACAAATTAG | 410 |
| | 2 | MAFYYKQVKEERHLLWLGSESVPTHKFPLCKGLALIAS* | 411 | ATGGCATTTTATTATAAGCAAGTGAAGGAGGAGAGACATCTGTTGTTGGCTGGGTCTGAATCTGTTCCAACTCATAAGGGCTTGGCACTGATAGCCAGCTAG | 412 |
| | 3 | MQPALCVWAALWTSLVTLLPDHSSRLCTEREG* | 413 | ATGCAGCCAGCTCTGTGTCTGGGCCGCACTATGGACTTCACTAGTAACCCTTTGCCAGATCACAGTAGTAGACTTTGTATAGAAGAGAAGGTTGA | 414 |
| | 4 | MDFTSNPFARSQ* | 415 | ATGGACTTCACTAGTAACCCTTTTGCCAGATCACAGTAG | 416 |
| hsa-mir-199a-1 | 1 | MFQARACSMRHHQPRGLLNAGRCCI* | 417 | ATGTTCCAGGCCAGAGGTGTAGCATGCGCCACCAGCCCACCAGCCCCGGGGCTTCTCAATGCTGTGTCGTGCTGTATGA | 418 |
| | 2 | MLVAAVYEPHCRPPVVRHSVPATLPSMMLPEYPTWVPTPGPSEDRATA* | 419 | ATGCTGGTGGCTGCTGTGTATATGAGCCCATCTGCCGGCCCTTCCCGTCCGTCACTCTGTCCCAGCCACGCTGCCTCCCTGAGTGTCCCTGAGTATCCACCTGGTTCCTACCCCAGGGCCTTCGGACGACCGGGTACTGCCTGA | 420 |
| | 3 | MSPSAGPSPSVTLSQPRCPP* | 421 | ATGAGCCCATCTGCCGGCCCTTCCCGTCCACTCTGTCCCAGCCACGCTGCCTCCCATGA | 422 |
| | 4 | MAPSCPNSTRTLPTSILLFPHTTRHVSCAC* | 423 | ATGGCTCCTCCTGCCTGCAACTCTACCCGACATCCTCCCAACTCTACCGTCACGTTCTGCCTTGTTGA | 424 |
| hsa-mir-199b | 1 | MWPQPRLPPRPAMSEETRQSKLAAAKKKVKCTGSRPPDPAPAPLRWQDHGQSLCHS* | 425 | ATGTGGCCCCAAGCCCGCCTCCTGCCGCCCAGCCCAGCCCGCCAGCGAGGAAACCCGACAGAGCAAAGTTGGCCGCAGGAAGAAGGTAAAGTGCACCGGTCGCCCCCCGACCCCAGCCCCAGCTCACTCCGATGGCAGGACCATGGGCAGAGTCTCTGCCACTCCTGA | 426 |
| | 2 | MAGPWPESLPLLRHTGLGSPRRVRAPSTKVLSASPAPSAAQPPPSPVAPG* | 427 | ATGGCAGGACCATGGCTCAGAGTCTCTGCCACTCCTGAGGCACACCGGGCTGGCTCCCGCTCAGCCTCGCCCAGCCACACCAAAGTGTGCTGAGCAAGTCTGTCCAGCCTGCTCCTGCGGCCGCCCCGGAGCCCAGCCCAGCCCGGCCACTCGCTCCAAGCCCCTGGGCAGTCTTTGAGCTGGCCTCCCAAGGAACTAGGACCCCAGCAATTCAGCGCTGCCCCTGCCAGTGACTTTGGGCCCGTGA | 428 |
| | 3 | MARVSATPEAHRAGLPTARPGSLHQSLVSQPRPLSRPAPALASRPRVTLGWCSRGSPLQTRPSPPAPRSPTSLGSLGWRLQGPRTPAIQPLPSPVTLGP* | 429 | ATGGCTAGGGTGTCTGCCACTCCTGAGGCACACCGGGCTGGCCTCCCACTCCGCCCGGGGCTCCCCAGCCAAGCCCAGGGAGTCTGAAGGGCACGGGTTCCCGCTCGGGTTGCACCAGCCTCGCCCCAGCCCAGCAGTCGCCCCGGGGTCACTTTGGGCTGTGTCGCGGCCTCCGGCAGCCTGCCTTCCCCCAGAAGTGCACTGGCCAGCCAATCCACGCCAAGCTCCCAAGGAACTAAGGACCCCAAGGAACTGGAAGCCTCCACATCATTGGAATCTCCAGTGATGTGGCCTCTGGG | 430 |
| | 4 | MFPLGVECSDYTIPLGTVISCARPVFDLRTQSPKCSRPASGSSGHSINFQLEGDWGLWPLCGRGFRLPYTLMIDIDSVKSLHFTRELKTLAVSLGGNVRTGLVWFSPRLLLSRETLTFFSDFSTSYSNSPWFWDQSALQWSLE* | 431 | ATGTTCCCCCTAGGAGTGGAAGTAGTAGACTTTGATCTTAGGACCCAGTCACAATCCCCCTGCGACTCACTGCAACCGTAATTAGGTCGCGAACAGCCAGCTCTTTGTCACGATCAAGTGCCAGCTCTGTTCCTCCTGGTTCCTCTGGTCACAGGATAAATTCCAGCTGGAAGGGGATTGGGGACTATGGACCTAGGAGGGAGCTTCAGCTGCTTCTTACAGCATAACATAGACATTGACAGTGTTGAAAAGCTCCAGGACTTCACCCTTGCCATTTGCACCCTTGCACCCTTGCACCCTCCGGACCCTTGCCATTTTGCACCCTGCTTACCATTGGCAGTATCTCTGGCTACTCTCCAGAGAGGCCAATGTGAGAACCTACACTTTCACCCTGCAGGTTCCATTGGTTTCTCCACCTATATTCCAATTCTCCAAGTTCTGGAAATTCCAAGTTCTGGAATGA | 432 |
| hsa-mir-19b-2 | 1 | MKKGRKPTCASDSRWRNDCGFRCHHR* | 433 | ATGAAAAAGGGAGGAAGCCCACCTGTGCGAGTGACTCGGTGAGAAATGATTGTGGTTTCGTTGCATCCACCGGTGA | 434 |
| | 2 | MIVVFVASTADS* | 435 | ATGATTGTTGTTTCGTTGCATCCACCGGTGACTCCTGA | 436 |
| | 3 | MAPLSSSGLWAATFLVTMVEREGSGFILHPFPPSLPPACLPGLSSSDPACSLVSDL* | 437 | ATGGCGCCTTGTCCTCTTCTGGCTTTGGCCTGCCACATCACCCTGGTAACAATGGTGGAAAGGGAGGGGTCCGGCTTCATTTGCACCCTTCCTCCTTCCCCTCGCTTGCCTTGCCTTGCACCCTCCAGGCTTCTCTCGACCCAGCGTGCTCACTGGTCTCTGATTTGTAA | 438 |
| | 4 | MLNSLIVRLKLRHHFLQSAVGLWP* | 439 | ATGCTTAATTCCATTTGATTGTGGTCTTAAACTAAGACATCATTTTATTCTACAGAGCGCGTCTGGCGCTTTGGCCTTGA | 440 |

Figure 1 (Continued)

| | | | | | |
|---|---|---|---|---|---|
| hsa-mir-200a | 1 | MGCRQPGQRPGELRSLQTQAGAGPSPPQGKVGPCADA AGFRVWSHLGPTGCVFRARAQCVGSRHGVPSGQGLGR GQAPRGVTFLPPT* | 441 | ATGGGCTGTCGCCAGCCTGGCCAGCCTCCCAGGGAGCTCCGGTCACTGCAGACACA GGCTGGACGCGGTCCTTCCCCCCCAGGGAAAGGTTGGGCCCTGCTGCAGATGCGG CTGGGTTCGGGTGTGAGCCATCTTGGACCCAGGCTGCGTCTTCCGGGCACGGG CACAGTGTGTGGGCTCCAGGCATGGGGTGCCCAGGGCAGGGCCTGGGCAGAGGG CAGGCTCCGAGAGGGCTCACGTTCTTGCCGCTACCTGA | 442 |
| | 2 | MRLGFGCGAILDPRAASSGHGHSVWAPGMGCPQGRAW AEGRLREGSRSCRLPDSRPSRKFSPEAATAVLRHFVRRR EAVASEVGA* | 443 | ATGCGCCTGGGTTCGGGTGTGAGCCATCTTGGACCCACGGGCTGCGTCTTCCGGG CACGGGCACAGTGTGTGGGCTCCAGGCATGGGGTGCCCAGGGCAGGGCCTGGGC AGAGGGCAGGCTCCGAGAGGGTCACGTTCTTGCCGCTACCTGACAGCAGGCCTT CTAGAAAGTTCTCTCCAGAAGCAGCCACCGCCGTCCTGAGGGCACTTTGTGCGGAGAC GGGAAGCTGTCGCCTCAGAGGTGCGTGCGTAG | 444 |
| | 3 | MTASPLGSGVCGGKGLVSAPSGQRPAEPMGGEVGAWG RGWSGTGGAQPGEAGAGSQAPRYDWGGGNVSREVFY LNVKRLSTVAAAGNKVRPTEAQP* | 445 | ATGACCGCGTCTCCTTGGGCTCTGGAGTCTGCGGTGGAAGGGCTTGGTTTCAGCA CCCTCTGGTCAGGAGCCCGGCCGAGCCATGGGCGGTGAGGTTGGTGCCTGGGTCG TGGAAGCTGGTACAGGTGGGGCTCAGCCGAGAAGCTGGAGCGGTTCCCAGG CCCGGCGCTATGACTGGGGTGGGGGCAACGTGTCTCGTGAGGTTTTTACTTAAATG TGAAACGGCTCAGTACGGTGGCCGCAGCCGGCGGGAACAAGGTCGCACCCGGAGGCC CAGCCTTGA | 446 |
| | 4 | MTGVGATSLVRFFT* | 447 | ATGACTGGGGTGGGGGCAACGTCTCGTGAGGTTTTTACTTAA | 448 |
| hsa-mir-200b | 1 | MGCRQPGQRPGELRSLQTQAGAGPSPPQGKVGPCADA AGFRVWSHLGPTGCVFRARAQCVGSRHGVPSGQGLGR GQAPRGVTFLPPT* | 449 | ATGGGCTGTCGCCAGCCTGGCCAGCCTCCCAGGGAGCTCCGGTCACTGCAGACACA GGCTGGACGCGGTCCTTCCCCCCCAGGGAAACCGGTTGGCCCCTGCTGCAGATGCGG CTGGGTTCGGGTGTGAGCCATCTTGGAGCCCAGGCTGCGTCTTCCGCGCACGGG CACAGTGTGTGGGCTCCAGGCATGGGGTGTCCCAGGGCAGGGCCTGGGCAGAGGG CAGGCTCCGAGAGGGTCACGTTCTTGCCGCTACCTGA | 450 |
| | 2 | MRLGFGCGAILDPRAASSGHGHSVWAPGMGCPQGRAW AEGRLREGSRSCRLPDSRPSRKFSPEAATAVLRHFVRRR EAVASEVGA* | 451 | ATGCGCCTGGGTTTCGGGTGTGAGCCATCTGTGAGCTCCAGCCATGGGGTGCCCGG AGAGGCACAGTGTGGTGGCTCCAGGGGTCACGTTCTTGCCCGCTACCTGACAGCAGGCCT AGAGGCAGGCTCCGAGAGGGTCACGTTCTTGCCCGCTACCTGACAGCAGGCCTT CTAGAAAGTTCTCTCCAGAAGCAGCCACCGCCGTCCTGAGGGCACTTTGTGCGGAGAC GGGAAGCTGTCGCCTCAGAGGTGCGTGCGTAG | 452 |
| | 3 | MTASPLGSGVCGGKGLVSAPSGQRPAEPMGGEVGAWG RGWSGTGGAQPGEAGAGSQAPRYDWGGGNVSREVFY LNVKRLSTVAAAGNKVRPTEAQP* | 453 | ATGCGCGGTCTCCTTGGGCTCCTTGGAGTCTGCGGTGGGAAGGCTTGGTTCAGCA CCCTCTGGTCAGGAGCCCGGCCGAGCCATGGGCGGTGAGGTTGGTGCCTGGGTCG TGGCTGGTCTGGTACAGGTGGGGCTCAGGGCTCAGCCGGAGAAGCTGGAGCGGTTCCAGG CCCGGCGCTATGACTGGGGTGGGGGCAACGTCTCGTGAGGTTTTTACTTAAATG TGAAACGGCTCAGTACGGTGGCCAGCCGGCGGGAACAAGGTCGCGACCCACCGGAGGCC CAGCCTTGA | 454 |
| | 4 | MTGVGATSLVRFFT* | 455 | ATGACTGGGGTGGGGGCAACGTCTCTGTGAGGTTTTACTTAA | 456 |
| | 1 | MGAALRGGRGRRRRRRGGD* | 457 | ATGGGGGCCGCCCTCCGGGGTCGGGCCGGCCGCGTCGTCGGGGCGCGGA CTGA | 458 |
| | 2 | MDRRDGSEVGHEASRKKLQRTRTRVPEPGVGGFRNRR EVGNGKGVW* | 459 | ATGGATAGGAGAGATGGCAGCGAGGTGGGGCATGAAGCCTCCAGGAAAAAGCTCCA AAGGACCAGAACACCGGGTTCCGAGCCTGGGGCATGAAGCCTCCAGGAAAAAGCTCCA AAGTGGGAAACGGGAAAGGGAGGGTGGGTAG | 460 |

Figure 1 (Continued)

| | | | | |
|---|---|---|---|---|
| hsa-mir-200c | 3 | MAARWGMKPPGKSSKGPEHGFRSLGLGALGHDGKWET GKGCGRWKEGLWLMNLGETEAWAKRGPPLRRAGGFP AWKREGHVFVTVFIPLLQVTSDPVFPIPDIVISWRGHWG PVVWVIPKLVRRKTGTQKGELGRKGFWEDGNGELSNL TGTPGKLRPPPSTLQFPERPLPLEL* | 461 | ATGGCAGGCGAGGTGGGGCATGGCAGGCTCCAAGAAAAGCTCAAGGACCAGAACA CGGGTTCCGGAGCCTGGGGTTGGGGGCTTAGGAGTGAATAGACGGGAAGTGGAAGCGG GAAAGGGTGTGTAGGTGAAAGAGAGGTCCATTTGTGAAGAGGATTGTGGCTGATGAACCGGAGTTTCCAGGT GGAAGAGGGAAGGCCATGTCTTTGTGACGGTTTCATTCCCTACTGCAGGTCACCT CTGACCCTGTTTCCCTATCCCAGACATAGTTATTTCTTGGAGAGGGCACTGGGCC CAGTAGTGTGGGTTATCCCAAAACTAGTGAGGAGGAAAACAGGAACACAGAAGGGG GAGTTGGGAAGAAGGCTTCTGGAGGATGAAATGGAGAATTGAGCAACCTTAC AGGCACTCCAGGCAAGTTGCAGCCTCCACCCTCCAATTTCCGGAGCGTCC GCTGCCCCTGGAGCTGTGA | 462 |
| | 4 | MEMEN* | 463 | ATGGAAATGGAGAATTGA | 464 |
| | 1 | MRARGCGGMGVGAAEPQRCLCPQARCPWPRRSRPWW RTCCTCWWAAWTGGTSVLSPWLGGRAGPSSWTPTWTC PSGSWCTGSSQWPPATPL* | 465 | ATGAGGGCACGTGCTGTGGGGCATGGAGTGGAGGCTGCAGAGCCACAGCGCTG TCTGTGCCCGACGCTGTGTGGCGTGGAGCGGAGCCGCGGCCGGCGGCCGTGGTGGAGGA CCTGCTGTACGTGCTGCAGGCACGTCGTGGCGTGGCGTGGCAGGAGTACGTCAGTCAGCGCCTGG CTGGGGAGGCAGAGCCGGACCTGCACAGGATCCTCCAGTGGCCGCGAGCCAGTACTCGCTGTA GAGCTGGTGCACAGGATCCTCCAGTGGCCGCAGTACTCGCTGTGA | 466 |
| hsa-mir-202 | 2 | MTMGTSASLLKRAPALVTTPCPTQFWRVCESPSRVLTH LLLGQKFPSGMWGSSESFASCLG* | 467 | ATGACCATGGGGACGTCTGCATGCGCTTCTAAAGAGAGCGCCGCTTGGTGACAACT CCGTTGCCAACTCAGTTTGAGGGTCTGTGAGTCACCATCCAGGTCCTGACTCAT CTCCTCCTGGGGACAAAAGTTCCCCTGGGATGTGGGGTTCAAGTGAGTCATTTGCT TCCTGTTTGGGATGA | 468 |
| | 3 | MRLRISDIVCACSLPF* | 469 | ATGAGACTCAGAATATCGACATTGTATGTGCCTGCAGCTTGCCTTTTGA | 470 |
| | 4 | MCLQLAPLRKSDSPSSRFIEEKSSPEYGQVNHALAAAMR TLVKEHLILVSQLEQLHRQGLLSLQELWFVIQPAMRTM DILASLGACPPGGHGAVVGGRC* | 471 | ATGTGCCTGCAGCTGGCCCTGCTTCGTAAGAGTGACAGTCCTTCCAGTTCATTG AAGAGAAGTCTTCCTGTGAAGGAGCACCTGAATCGGCAGGTGAACCACCGCTGGCCGTCGCATG CGCACCCTGGTGAAGGAACACCTGATTCTGGTGTCACAGCTGGAGCAGCTGCACAG GCAGGGCCTCCTTCGCTGCAGAAGCTCTGGTTCTACATCCAGCCAGCCATGCGCAC CATGGACATCCTGGCCAGCCTCGGGGCCCCCGGGGGACATGGGGCAGTGTGG TGGGTGGCAGGTGTTGA | 472 |
| hsa-mir-203 | 1 | MARAVGPERRLLAVYTGGTIGMRSELGGESETLGGVG LWTWPRPGASDPPAFTGVVGESNPRLLDGGCGLRSLSSG SGHRRPHAWSPDLDRGHGCGGFPSPRSCSRERPATLGPGP LCCRCAPEGQRPEVLEYGAGGPQGIGLPLLLWTQKA* | 473 | ATGGCGCGCGTGGGTGGGGGCCGAGCGGGAGGCTGCTGGCCGTGTACACCGGCGGCCAC CATTGGCATGCGGAGTGAGCTCGGGGAGGTGAGCCGGAGACCCTGGGCGTCGGCGGGGTAGGCC CTGACCTGCGCCGACCCGGCCGGAGCCTCGCGGAGCTGAGGGCGTGCGGCGGTGTTG GGGAGTCAAATCGCGCCTGCCGGTGATGGGGGTGCGGTCGGAGGAGATTGCGG TCCGGCCACCGGGCCTCGCCGTCCGCCATGGAAGGCTTCCGGGAACGCCTGAGCCGGCCAGCCGG TGGGTTCTGCGCTGCCGCTGCGCGGCCCAGCGTCCGCCATTGGCCTGCGCTCGAAGTCTGGACAGAAGGCTAG GGGAGGGCCCCAGGGCATTGGCCTGCCGCTCCTGCTCTGGACAGAAGGCTAG | 474 |
| | 2 | MGGAG* | 475 | ATGGGCGCGGGCTGA | 476 |
| | 3 | MEPRPGQRRLRWVLAVLPGAPCDPGARPPVLRPF* | 477 | ATGGAGCCCGACCTGGACAGAGGAGGATTGCGGTGGTTCTCGCCGTCGCGGTGCT CCCGGGAGCGCCCTGCGACCTGGGGGCCAGGCGCCGGCCCCCTGTGCCGCTGCGCCCTG A | 478 |
| | 4 | MGREGPRALACRSCSGHRRLRRLPWRRLRRLRGPLNCD TQHGVPVPWGPGQAAVVGTILGLPGICGDARVHTRGGL RALLPLCGPG* | 479 | ATGGGGGAGGGCCCGAGGGCGCTGGCCTGCCGCTCGTGCTCTGGACACAGAAG GCTTAGGAGGCTGCCCTGGAAGGCTTAGGAGGCTGCCCTGGAAGGCTTAGAGCGTCGAGAGGACCCTCAACTGCG ACACCCAGCACGGGGTGCCCGTACCTGGCATCTGGGGGTCCAGGTCAGGCAGCAGTGGTTGGC ACGATACTGGGGCTACCTGGCATCTGGGGGACGACGCACGTGTTCACACCCGAGGTGG CCTCAGAGCCCTGCTTCCTGCCCCTGTGTTGA | 480 |

Figure 1 (Continued)

| | | | | | |
|---|---|---|---|---|---|
| hsa-mir-206 | 1 | MELKNEGEMGGQGTNWGMTAYSVRIGNAHKGQMKM BSLCYIRRLAHTKIRVKGEGGKGKRE* | 481 | ATGGAACTAAAGAATGAAGGAGAAATGGGTGGACAGGGCACAAATTGGTGAATGA CAGCCTATTCAGTGAGGATAGGAAATGCACATAAAGGACAGATGAAGATGATTTCT CTGTGTTGATTAGAAGGATAGCAATTACAAAGATAAGAGTGAAGGGAGGGGAGG AAAGGGAAAAGGGAATAA | 482 |
| | 2 | MKEKWVDRAQKGE* | 483 | ATGAAGGAGAAATGGTTGGACAGGGCACAAATTGGGAATGA | 484 |
| | 3 | MHIKLDR* | 485 | ATGCACATAAAGGACAGAATGA | 486 |
| | 4 | MLRKSPGC* | 487 | ATGCTTAGAAATCACCAGGCTGTTAG | 488 |
| hsa-mir-20b | 1 | MKKGRKPTCASDSRWRNDCGFRCIHR* | 489 | ATGAAAAAGGGGAGGAAGCCCACCTGTGCGAGTGACTCGGCTTGGAGAAATGATTG TGGTTTTCGTTGCATCCACCGTGA | 490 |
| | 2 | MIVVFVASTADS* | 491 | ATGATTGTGGTTTTCGTTGCATCACCGCTGACTCCTGA | 492 |
| | 3 | MAPLSSSGLWAATHLVTMVEREGSGFILHPFPPSLPPAC LPGLSSSDPACSLVSDL* | 493 | ATGGCGCCTGTCCTCTTCTGGGCTTTGGCTGCCACAATCACCCTGGTAACAATG GTGGAAAGGGAGGGGTCCGGCTTCATTTTGCACCCTTCCCCTCCCTTCCTTGCCCCC GCTTGCCTTCCAGGGCTTCCTCCTCCAGCCCCAGCGTGCTCACTGGTCTCTGATTTGT AA | 494 |
| | 4 | MLNSILIVRLKLRHHFILQSAVGLWP* | 495 | ATGCTTAATTCCATTTTGATTGTGCGTCTTAAACTAAGACATCATTTATTCTACAGA GCGCTGTCCGGCTTTGGCTTGA | 496 |
| hsa-mir-21 | 1 | MLVGEILVFKGLLDGVNFLFFFH* | 497 | ATGTTGGTTGGGGAGATTTTGGTTTTAAGGGTTGTTAGATGAGTAAATTTCTT TTTTTTTTTTAA | 498 |
| | 2 | MCLFLWATVPCFQCCPRHRSISAEAISGVPGGSTAEASP QKRNGHTTGKTLIRFLLPSGKFRAEITFTALTHIFRQISEV GLPVFLDRS* | 499 | ATGTGTCTTTTCTTTGGCTACTGTACCCTGCTTCCAGTGCTTCTCCCCGCATAGGT CCATTCTGCAGAAAGCCATTTCAGGAGTACCTGGAGGCTCAACGGCAGAAGCTTCAC CACAAAAGCGAAATGGCACACCACAGGTAGAGACTTTAAGATCCGGTTTCTTCTCCCT CTGGAAGTTTCGGGCTGAAATTACATTCACAGCTCTCACTCACATTTTTAGGCAAA TAAGTGAAGTTGGTTTGCCAGTGTTCCTTGACAGAAGTTGA | 500 |
| | 3 | MGITPQVRL* | 501 | ATGGGCACACACCAGGTAAGACTTTAA | 502 |
| | 4 | MLYWEICLCLRLESVTSVHLLLKTRVEPMESNGSVT* | 503 | TTCTCCTAAAAGAAATTTGTCTTTGTCTTAGACTAGAAAGTTAACTTCTGTTACAATC TTCTCCTACTGGGAAATTTGTCTTTGTCTTAGACTAGAAAGTAACTTCTGTTACATAG | 504 |
| hsa-mir-210 | 1 | MRVGRGGRRRRRGSAELRTGRGGHEGAKRHCLGPAF PGIA* | 505 | ATGAGGGTGCGGCGGGGACGGGGTGGGGGATCGGAGGAGGTGCGAAGCGCGGGT TCCGCGGAGCCTGA | 506 |
| | 2 | MCARRPHLQSHL* | 507 | ATGTGTGCCGCGCCGGCTACACCTGCAGTCACACCTGTAG | 508 |
| | 3 | MALAPER* | 509 | ATGGCCTTGGCTCCTGAGAGCGTAA | 510 |
| | 4 | MPVPERPAAGPDSPRPGTRRAAPRVLFGEWLLGEISSGC YEGLQWLDEARTCFRVPWKHFARKDLSEADARIFKVG TPAPPRPCGWESPPRTPRARHTCSVPLFRPGLWPAAGGRL AAGEVARPPRLRLRSAPAGKPTSAAHCAARVAS* | 511 | ATGCCAGTCCCCGAGCGCCCGGCCGGCTCCGCGCCGGCACCCGC AGGGCAGCCGGGCCCCGGAGATCAGCAGGCGG CTGCTATGAGGGGCTGCCAGTGCTGGACTGGAGACGAGGCCCGACCTGTTCCGCTGCCTG GAAGCACTTCGGCGTGCGCAAGGACCTGAGCGAGGCCGACGCGCGATCTTCAAGGTGG GACACCGCAGCCGCCTCGTCTCCCCCCCTGCAGCCTGGGCTGGCCCCGGCAGGTGGCC CGCCTAGCAGCAGGGAGGGCCCGCCCCCCGCACTGCGCAGCCAGCCGCGAGCGCCGCC GGCTGGAAAACCAACTTCGCTGCGACTCGGCAGGAGCACGCGTCGCTTCGTGA | 512 |
| | 1 | MTSHKPLVRWLLSCSSSCLEWPGASIVSSIVCPAHSPA GTHTGRVRAVRRPGRLAPARHFSPPLPLPSAERGHQPC GLGTGEGPAALWSGSPGRPARTRRRSRR* | 513 | ATGATCACGTCCACAAGAAGCCTTGGTGCCGTTGTTGAGCTGCAGCAGC TGCCTGCGGAGTGCCGCGGCGGCTCCAGCATCGTCGTCCAGCATCGTCGTCCAGCACACTCT CCTGCGGTGGACACACACCGCCGGTGACGCCCGTGACGCTGCTGAGGCCCTGGCC CCAGCCCCGGACACTTCTCCCCCACTTCCTCCCCAAGGAACCTGCCCTCGAGCATCA GCCCTGCGGCCTGGCCTGGCCCCTGAGCGCACCCTGCCCTCCGTCCGGGAGCGCCGG GCCGGCCCGCCCCCGGACCCAGGGAGGAGGGAGCAGGGAGGGGTGA | 514 |

Figure 1 (Continued)

| | | | | | |
|---|---|---|---|---|---|
| | 2 | MSASGKVIQGIGELYPSREKGSRGTSASRLGRSCPSWGK* | 515 | ATGTCTGCTTCAGGAAAAGTCATTCAGGGCGGAGAACTTTACCCAAGTAGGGAGAAAGGGAGCCGAGGAAACCAGCGCCTCCGCCTCCGGCCTCGGGAGAACTTGCCCAGTTGGGGGAAGTGA | 516 |
| hsa-mir-212 | 3 | MPHPPLPGPELCQGSAPASPARQLPPPSLPLASPAHVRAEPAPGR* | 517 | ATGCCCCACCCGCCAGTCCCCTTCCCTGCCCTGAGCTGTGCCAGGCAGCGCCCCTGCCAGCCCCGCGCCCAGTCCCCTTCCCTTGCCTCTCCAGCCCATGTGCGGCGAGAGCCGGCCCGGGCGCTGA | 518 |
| | 4 | MCGQSRPRAADPAVNPARSRGPVVYLSPKGTTPGALNASRQPRWGTRARRCTRGGCRRTRTGLSRVPRPSRSPARGPTWGACRKPRARLTADPGGTWLRCPFPAGFPVGLSCWSVLPASWSRLSPAALSAHSYLERPGPAGAAAAMAPPRGRAGLCAAGRCLPPAHLSWRRTDAEPAGRGPPYPQVRPPTCTHLGPRPRTRESQKPWGFELSAPMYVFLGTQPQFGKVLPASTGLGWWGRGYPAQE* | 519 | ATGTGCGGCCAGAGTCCGCCGGCGGCTGCTGACCCGCCGTGAACCCGGCGCGAGCCGGGGCCCGTGCTCCTGAGTCCGAAAGGACGACACCGGAGACCGGAACGCACGCCGCAGTCCCTTCCCTGCCTCGATGGGCACCCAGAGATGCCCAGAGAACGGGGCACCTGGGGGCATGTGACCCGCCCCGGGATCCGAAGGCGGATCCAGGGGGACACCTGGGGGCGCTGTCGCTGCCTCCCGCGGTCTCTGCCCGCACCCGGGGCGCGTCGGTCCGGCCCGCCCGAGGGTCTGTCCTGTCTGGTCCGTCCCCGCCGCCCGAGCCGCCCTCAGCCCGCCGCCTTCGCCACACTCTTATCTGGAGCGGCCGGCGCTGCTGCGGCGTATGCGCCACCTGCGGGCGCGGGAAGGGCTCTGCTGCGGCGGGCCGGCCGTCGCGGCGCGAGGGCCCACCCGAGTCCCCACCTCGAGCTGAGGCAGCAGATGCTGAGCGCCCCATGTACGTATTCTAGGCACACGCGAGTCCCAGAAACCTGGGGGCGCAGAAAGTCGTACCCACTGGGCGCTCCCATGTACGTATTCTAGGCACACGCGAGTCCCAGAAACCTGGGGTTTCTGCCCGAGCACGGACCTCGGGTGGTGGGGAGAGGTTATCCTGCGCAGGAGTAG | 520 |
| | 1 | MSNYTILGQYCVPLVLCFLRSPTYWNFDYLDIFVFKRGGEFA* | 521 | ATGTCTAATTATACAAATCCTTGGACAATACTGTTTTTTGGTGTCTGTGTTTTTAAGAAGTCCTACTTACTGGAATTTGACTATTTGGATATTTTGTTTTTAAAAGGGGAGGGGAATTTGCTTAA | 522 |
| hsa-mir-214 | 2 | MNLPFLPFLKYFVTILH* | 523 | ATGAATTTGCCTTTCTGCCTTTCTTAAATAGGTTCCTGTTGTTCACATATAA | 524 |
| | 3 | MRHLNRFLLFH* | 525 | ATGAGACATTTAAATAGGTTCCTGTTGTTCACATATAA | 526 |
| | 4 | MHFPPMDKVMVLIY* | 527 | ATGATAATTTTCTTTTCATGGACAAGGTTATGGTACTTATTACTAA | 528 |
| | 1 | MRLQLLTAVGALAGTIACALLTEGGAVGSELAGGAGPGWVLPFTAGGFHYVATVSYVLPELLREASPLQSLLEVLGLLGGVIMMVLIAHLE* | 529 | ATGAGGCTCTGCAACTACTGCAGCAGTAGGGGCACTGCAGGCACAGCCTGTGCCCTTCTCACTGAGGAGGAGGAGCAGTGGCAGTGAAAATTGCAGGTGCAGTCCTGGCTGGGTCTGCCATTACTGCAGGGGTCTTATCTACGGAGGTGGTGTCGTGTCAACAGTGTCGTGTGCCGAGCTGCTGAAGGAGGAGCATTCAATCATTGTGCTGATTGCCACCTTGAGCTGA | 530 |
| | 2 | MVTLALGPSRAGSLTEAGAVRMRGQRDHSVGHCLTMLHLEG* | 531 | ATGGTTACTTTGGCATTAGGGCCTTCAAGGGCTGGCAGTCTTACAGAGGCTGGAGCGGTGAGAATGAGAGCCAGAGGGACCATAGTGTTGGCGACTGTCGACCATGTTGCATTTGGAAGGCTAA | 532 |
| hsa-mir-219-1 | 3 | MKKAGRDRG* | 533 | ATGAAGAAGCTGGAAGGGACAGGGGGTGA | 534 |
| | 4 | MAAYLVSPTPPVLGEPSCYTGSSPRSSFLSPTSWWRLLQGRPESWTERVTGGVGDKHQTSIVCPDLGVIGGMGWERVSWYSHGLIFFVSIPFISLCLNRGGGVVTGNKDLRSSAPHAVFVFLGKMGPLVFSTPGAPKQQCRATFPRWEVGLRWWPQMA* | 535 | ATGGCAGCCTACCTGGTGTCCCCACCGCCACCTGTTCTGGGAGAACAAGTTGCTACACAGGAAGTTCTCCAGTTCTCTCCACCAGTTGGTGGAGGCTTCAGGGAAGACCAGAGTTCTGACAGAGACCCTGAACAGGAGGAGTCGGGATAAACATCAACATCAATCGTGTTCTCATGCCGATTTTTTTGTCTGAATTTTTTTGTCTATCCTTTTCATTCTATATCACTGTGGTTCGGAATCCAGGGTAGGGAGGGGTGTAACCGAAATAAACGACCTCGCTGCCCCACATCAGGTAGCTTCTTTTGGGGGAATGGCGCCCCTTCCACGCCACGCCGGTGGCCGGCCAGTAGTTGCGCCACGCCACGCCACACCCCGGGCCCTAAGCAAGCAAGGTTGCGGCAGCAATCCCTCAAGGTCAGGCGCCATTATCACCCGCCACCTGCGGGCGCCGGCTTGAGAGGCACCACCCCGGGCCTAA | 536 |
| | 1 | MPARSQAPCLPKAPHSPPSSPRSGPEQWDFYYLHPPDEETEAENKEVI* | 537 | ATGCCTGCCCGTAGCCAGGCCCCTGCCTGCTGCCCCAAGCACCTTGCTGCCCAAAGCACCTCACTCCCCGCCATCTAGTCCCTGCAGCGCCCTGAGCAGTGAGACTCTACTACCTCCATTTCCAGATGAGGAAACAGAGAGCTGAGAACAAGGAAGTCATTTGA | 538 |

Figure 1 (Continued)

| | | | | |
|---|---|---|---|---|
| hsa-mir-219-2 | 2 | MRKQRLRTRKSFD* | 539 | ATGAGGAAACAGAGGCTGAGAACAAGGAAGTCATTGATTAA | 540 |
| | 3 | MQPSAVAHAYNPSTLGSRDGRIT* | 541 | ATGCAGCCAGCGCAGTGGCTCATATGCCTATAATCCAGCACTTTGGGAAGCCGAGA CGGGCGGATCACCTGA | 542 |
| | 4 | MPRPALWEAETGGSPEVGSSRLA* | 543 | ATGCCTATAATCCCAGCACTTTGGGAAGCCGAGACGGGCGGATCACCTGAAGTCGG GAGTTCAAGACTAGCCTGA | 544 |
| hsa-mir-220 | 1 | MLFFPPPKVVFP* | 545 | ATGCTGTTCTTTCCGCCATTCCCAAAAGTTGTTTCCCTTAA | 546 |
| | 2 | MKTFHQGECSLTTFSLNDRNIK* | 547 | ATGAAGACTTTCCATCAAGGTGAGTGTTCTCTCACCACCTTTTCACTTAATGATAGA AACATAAAATGA | 548 |
| | 3 | MIET* | 549 | ATGATAGAAACATAA | 550 |
| | 4 | MSSDNVEKLDAFYKLQLLVFFT* | 551 | ATGAGTTCTGATAATGTTGAAAAACTAGATGCATTTTACAAGCTACAACTACTGTT TTTTCACCTAA | 552 |
| hsa-mir-220b | 1 | MGALAPVVSPVGLRRGPHPDPNAWASPSPVPRCPVAGA PGRRCGRRGEREKPLPRRCQPATQPMANPGLGLLLALG LPFLLARWGRAWGQSRYQLRALGGRGLDSWISAGDVA * | 553 | ATGGGTGCCTGGCGCAGCCTGTTCTCTCGTGGCCTGGCGCGGAGCTGCGCCACCCC GATCCCAACGCCTGGCCTCCGCGTAGGAGGCGGCAGCGGAGAAGCCCCTTCCTGGCGCTG CCAACCCGCCACCCAGCCATGGCGAACCCTGGGCTGCTCCTCTGGCGCTGG CCTGCGGTCCTGCGCCGCTGGGCCGAGCCTGGGGCCAAGTAGGTACCAG CTGAGAGCGCTGGGGGAGAGGGTCTGGATTCCTGGATCTCTGCTGGGGAACGTGCC TTAG | 554 |
| | 2 | MKGRV* | 555 | ATGAAAGGCAGAGTTGA | 556 |
| | 3 | MPKAGADGRGWERKMETELFSAFTLHSTDHFCK* | 557 | ATGCCCAAAGCAGGTGCAGATGGCGGGATGGGCGTGGAGAGAAAGATGGAGACTGAGT TATTCTCTGCCTTCACCCTGCATAGCACCGATCACTTCTGCAAATGA | 558 |
| | 4 | MGGDCRERWRLSYSLPSPSTVQITSANENSTVLPSSTSS SSDGNLVSWRYMWEDGSKDVI* | 559 | ATGGGCGGGGATGGAGAGAGATGGAGACTGAGTTATTCTCGCTTCACCCTC CACAGTACAGACCACTTCTGCAAATGAAAATGAGAATAGCACTGTTTGCTTCATCCACCAG CTCCAGCTCCGATGCAACCTGGTAGTGAGTTGGAGGTATATGTGGGAAGATGGCAGCA AGATGTTATCTAG | 560 |
| | 1 | MIEGDHNVPGVAAHVDHLCADGEERGEGVRHRQDPSP* | 561 | ATGATAGAGGGAGACCACAACGTCCCGGGGTTGCGGCCCATGTAGATCACCTGTG TGCGGATGGTGAGGAGGAGGGGAAGGCGTCAGACACAGGCAAGACCAGGCCCCCT GA | 562 |
| hsa-mir-220c | 2 | MVRRGEKASDTGKTPAPEASCPGDPSLLTLKQEGLRAD SFFFAMESDSVSPRLECSGAISAHCNLCLLGSGDSPVSAS * | 563 | ATGGTGAGGAGAGGGGAGAAGGCGTCAGACACAGGCAAGACCCCAGCCCTGAGG CCTCCGCCTGAGAACCCCTCTTCTGACCTGCACCCTCTTAAGCAGGACTCAGGCGAG ACTCTTTTTTGCGATGGAGTCTGACTCTGTTTGCCCAGCTGGAGTGCAGTGG CGCCATCTCAGCTCATTGCAACCTCCTGCGTCAGCGGTTCAGCGATTCTCCTGTGTCA GCCTCCTGA | 564 |
| | 3 | MFSRDGVLPCWLLTD* | 565 | ATGTTTAGTAGAGATGGGGTTTTACCATGTTGGTTACTCACAGATTGA | 566 |
| | 4 | MGFYHVGYSQIEEPLEDRQGLTRS* | 567 | ATGGGGTTTTACCATGTTGGTTACTCACAGATTGAGGAACCCCTTGAGGACAGGCAG GGTCTTTACAGTTCCTAG | 568 |
| hsa-mir-221 | 1 | MQSKHLHFMNYLQFK* | 569 | ATGCAAAGTAAACATCTGCATTTATGAACTACTTCAATTAAATAG | 570 |
| | 2 | MTCFGSKIC* | 571 | ATGACATGTTTTGGGAGTAAGACCTGTTAA | 572 |
| | 3 | MFWE* | 573 | ATGTTTTGGGAGTAA | 574 |
| | 4 | MWLKKCHLVDLFSLA* | 575 | ATGTGGTTATGTAAATGCATCATTTAGTTGATCTTTTTCTTAGCCTAG | 576 |
| hsa-mir-222 | 1 | MQSKHLHFMNYLQFK* | 577 | ATGCAAAGTAAACATTTGCATTTTATGAACTACTTCAATTAAATAG | 578 |
| | 2 | MTCFGSKTC* | 579 | ATGACATGTTTTGGGAGTAAGACCTGTTAA | 580 |
| | 3 | MFWE* | 581 | ATGTTTTGGGAGTAA | 582 |
| | 4 | MWLCKCHLVDLFSLA* | 583 | ATGTGGTTATGTAAATGCATCATTTAGTTGATCTTTTTCTTAGCCTAG | 584 |
| | 1 | MTKAPLH* | 585 | ATGACCAAAGCACCACTCCACTGA | 586 |

Figure 1 (Continued)

| | | | | | |
|---|---|---|---|---|---|
| hsa-mir-223 | 2 | MVSICPLFLDSQAGAESMAAKGGLDLPIPPSSDPPQGLR SKVGGRRLPLAFYPRGSNGGEKGIGYPLSNQDV* | 587 | ATGGTATCCATTGCCCTCTCTTGGATTCTCAAGCTGGGCAGAGTCCATGGCA GCCAAGGGTGGCTTGGATCTGCCCATTCCATTCTCTTCAGACCCTCCAGGGATTA AGGTCAAAGGTGGGAGGAAGAAGGCTTCCATTGACCTTTATCCTAGAGGTTCTAAT GGAGGGCAAAAGGCGATAGGCTATAGGGATATTTTCTATCCAATCAGGATGTTTAG | 588 |
| | 3 | MEGKRG* | 589 | ATGGAGGGGAAAAGGGGATAG | 590 |
| | 4 | MFRR* | 591 | ATGTTTAGGAGATAG | 592 |
| hsa-mir-23a | 1 | MSHRAQPEIHFF* | 593 | ATGAGCCACGCGCTCAGCCTGAAATTATTTCTTTTTAA | 594 |
| | 2 | MVIDHGSLKLLGSSSPPTSAA* | 595 | ATGGTCATAGATCACGGCAGCCTCAAACTCCTGGGCTCAAGCAGTCCTCCCACCTCA GCCGCCTGA | 596 |
| | 3 | MCTTTPG* | 597 | ATGTGTACCACCACTCCTGCTGA | 598 |
| | 4 | MAKPHLYKN* | 599 | ATGGCAAAACCCCATCTCTACAAAATTAG | 600 |
| hsa-mir-23b | 1 | MSHRAQPEIHFF* | 601 | ATGAGCCACGGCGCTCAGCCTGAAATTATTTCTTTTTAA | 602 |
| | 2 | MVIDHGSLKLLGSSSPPTSAA* | 603 | ATGGTCATAGATCACGGCAGCCTCAAACTCCTGGGCTCAAGCAGTCCTCCCACCTCA GCCGCCTGA | 604 |
| | 3 | MCTTTPG* | 605 | ATGTGTACCACCACTCCTGCTGA | 606 |
| | 4 | MAKPHLYKN* | 607 | ATGGCAAAACCCCATCTCTACAAAATTAG | 608 |
| hsa-mir-27a | 1 | MNLGTVISPS* | 609 | ATGAATCTGGGCACTGTAATCAGTCCATCCTGA | 610 |
| | 2 | MRSCLVLVLGCVDFLGLSQVCVGLIWTS* | 611 | ATGAGGTCCTGCCTCGTCGTCTGGTGTTAGGATGTGTGGACCCCTTAGGTCTCAGTCAG GTGTGTGTGGGGTTGATCTGGACGAGTTGA | 612 |
| | 3 | MCGPLRSQSGVCGVDLDELIRSVP* | 613 | ATGTGTGGACCCCTTAGGTCTCAGTCAGGTCAGGTGTGTGGGGTTGATCTGGACGAGTTG ATAATCAGATCAGTGCCTAG | 614 |
| | 4 | MRTLRCWMGWSTRSPPLLG* | 615 | ATGAGAACCCTGAGGTGTTGGATGGTTGGTCTACAAGGTCACCTCCACTGCTAGGA TGA | 616 |
| hsa-mir-27b | 1 | MNLGTVISPS* | 617 | ATGAATCTGGGCACTGTAATCAGTCCATCCTGA | 618 |
| | 2 | MRSCLVLVLGCVDFLGLSQVCVGLIWTS* | 619 | ATGAGGTCCTGCCTCGTCGTCTGGTGTTAGGATGTGTGGACCCCTTAGGTCTCAGTCAG GTGTGTGTGGGGTTGATCTGGACGAGTTGA | 620 |
| | 3 | MCGPLRSQSGVCGVDLDELIRSVP* | 621 | ATGTGTGGACCCCTTAGGTCTCAGTCAGGTCAGGTGTGTGGGGTTGATCTGGACGAGTTG ATAATCAGATCAGTGCCTAG | 622 |
| | 4 | MRTLRCWMGWSTRSPPLLG* | 623 | ATGAGAACCCTGAGGTGTTGGATGGTTGGTCTACAAGGTCACCTCCACTGCTAGGA TGA | 624 |
| hsa-mir-298 | 1 | MPNPGSMMTTGGV* | 625 | ATGCCCAATCTGGATCGATGATGACCACTGGTGGCGTATGA | 626 |
| | 2 | MSHT* | 627 | ATGAGTCATACATGA | 628 |
| | 3 | MMNMCLEL* | 629 | ATGATGAATATGTCTGGAACTCTGA | 630 |
| | 4 | MHSYVIBMIGSMKE* | 631 | ATGCATTCTTATGTTATTATTGGTCAATGAAGAATGA | 632 |
| hsa-mir-299 | 1 | MSWGKGAPAFGVSTCLFS* | 633 | ATGTCGGGAAAGGGAGCACCAGCATTGGTGTTTCACTTGCCTCTTTTCTGA | 634 |
| | 2 | MESNPLLPGQVLRLGILCTPVHW* | 635 | ATGGAATCCAATCCTCTGCTTCCAGGACAAGTCCTGCGCTTGGGGATCCTCTGTACG CCCGTTCACTGGTGA | 636 |
| | 3 | MYDSNF* | 637 | ATGTATGACAGCAATTTCTGA | 638 |
| | 4 | MTAISDFTSSCP* | 639 | ATGACAGCAATTTCTGATTTCACTAGTTCTTGCTTCTAA | 640 |
| hsa-mir-29a | 1 | MSWGKGAPAFGVSTCLFS* | 641 | ATGTCGGGAAAGGGAGCACCAGCATTGGTGTTTCACTTGCCTCTTTTCTGA | 642 |
| | 2 | MESNPLLPGQVLRLGILCTPVHW* | 643 | ATGGAATCCAATCCTCTGCTTCCAGGACAAGTCCTGCGCTTGGGGATCCTCTGTACG CCCGTTCACTGGTGA | 644 |
| hsa-mir-29b-1 | 3 | MYDSNF* | 645 | ATGTATGACAGCAATTTCTGA | 646 |
| | 4 | MTAISDFTSSCP* | 647 | ATGACAGCAATTTCTGATTTCACTAGTTCTTGCTTCTAA | 648 |

Figure 1 (Continued)

| | | | | | |
|---|---|---|---|---|---|
| hsa-mir-29b-2 | 1 | MGPNSGTFGTAAPYGGTKIWVCAGGDGWSDGLQDLMA* | 649 | ATGGGACCAACAAATTCTGAACATTCGGACTGCGGCACCTTACGCGCGGGACCAAGAT TTGGGTCTGCCGCAGGCGGCGGATGGGTGGTCCGACGGGCTTCAGGACTTGATGGCGT AA | 650 |
| | 2 | MGGPTGPRT* | 651 | ATGGGTGGTCCGACGGGCTTCAGGACTTGA | 652 |
| | 3 | MYLLGSGALSLCMWVLCLSHLLSRFLLFISLREGFPPL* | 653 | ATGTATTTGCTGGGATCAGGGGCGCTGTCTCTGTGTATGTGGGTGCTCTGTCTTCTC ACCTTCTTCTCGATTTTTGCTATTTATTTCTCTGAGGGAGGGTTTTTTCCACTTTAA | 654 |
| | 4 | MWKVRE* | 655 | ATGTGGAAGGTAAGGGAGTGA | 656 |
| hsa-mir-29c | 1 | MGPNSGTFGTAAPYGGTKIWVCAGGDGWSDGLQDLMA* | 657 | ATGGGACCAACAAATTCTGAACATTCGGACTGCGGCACCTTACGCGCGGGACCAAGAT TTGGGTCTGCCGCAGGCGGCGGATGGGTGGTCCGACGGGCTTCAGGACTTGATGGCGT AA | 658 |
| | 2 | MGGPTGPRT* | 659 | ATGGGTGGTCCGACGGGCTTCAGGACTTGA | 660 |
| | 3 | MYLLGSGALSLCMWVLCLSHLLSRFLLFISLREGFPPL* | 661 | ATGTATTTGCTGGGATCAGGGGCGCTGTCTCTGTGTATGTGGGTGCTCTGTCTTCTC ACCTTCTTCTCGATTTTTGCTATTTATTTCTCTGAGGGAGGGTTTTTTCCACTTTAA | 662 |
| | 4 | MWKVRE* | 663 | ATGTGGAAGGTAAGGGAGTGA | 664 |
| hsa-mir-300 | 1 | MPNPGSMMTTGGV* | 665 | ATGCCAATCTGATCGATGATGATCCACTGGTGGCGTATGA | 666 |
| | 2 | MSHT* | 667 | ATGAGTCATACATGA | 668 |
| | 3 | MMNMCLEL* | 669 | ATGATGAATATGTGTCTGGAACTTGA | 670 |
| | 4 | MHSYVHMGSMKE* | 671 | ATGCATTCTTATGTTATTATGGTCAATGAAAGAATGA | 672 |
| hsa-mir-30b | 1 | MTDAAEAAFSVRTPPIPSSRRAPCPPPLARPSPWRWRVP APSPPAAPGAPRARGAGRWEREGGRGGPAASSPDPRP RAR* | 673 | ATGACGGACGCGGCGGAGGCGGCTTTCTCAGTTCGGACGCCGCCGATCCCCAGCTCT CGCCGCCGCCCTGCCCGCCCGCCCCTCACCCTGCGCTGCCGCCGGGCG CCCGGAGCGGGAGGGTGGAGGCGGTGGGGCGCGCGTGGGGCTCGGCTCGGCGCGGGGCG CTGGAGCGGGAGGGTGGAGGCGGCGGCAAGCTGGGCCCCTCCGCCGACCCCC GACCCCGGGCCAGGTGA | 674 |
| | 2 | MGRAAGGRWAPPRGS* | 675 | ATGGGCGCGGCGGCGGGAGGCGCAAGCTGGGCCCCTCCGGGCTCGTGA | 676 |
| | 3 | MFIRQLQETLPSGRGALLFAGASESGGPHSKTRVKPGW TGRE* | 677 | ATGTTTATCCGGCAGTTGCAAGAACTCTGCCTGCCGGGACGAGGCGCCTTGCTTTT GGCGGGGCAGCGAAAGTGGCGAGATTTCACAGCAAAACTCGGGTGAAGCCAGGCTG GACCGGCGGGAGTGA | 678 |
| | 4 | MGTRDERIRLCVAPGHDVCTLLCQCLMFVAYGYFRTK* | 679 | ATGGGGACCAGAGAGATGAACGAATCCGCTCGTGTGTAGCACCAGGCATGATGTGTG CACGTTGCTATGCCAGTGTTAATGTTGTGTGCTTATGGTTATTTAGGACTAAGA | 680 |
| | 1 | MTDAAEAAFSVRTPPIPSSRRAPCPPPLARPSPWRWRVP APSPPAAPGAPRARGAGRWEREGGGRGGPAASSPDPRP RAR* | 681 | ATGACGGACGCGGCGGAGGCGGCTTTCTCAGTCGGACGCCGCCGATCCCCAGCTCT CGCCGCCGCCCTGCCCGCCCGCCCCTCACCCTGCGCTGCCGCCGTC CCCGGAGCGGGAGGGTGGAGGCGGTGGGGGCGCGCGGTGGGGCTCGGCGCGGGGCG CTGGAGCGGGAGGGTGGGCGGCGGCAAGCTGGGCCCCTCCGCCGCCGACCCCC GACCCCGGGCCAGGTGA | 682 |
| hsa-mir-30d | 2 | MGRAAGGRWAPPRGS* | 683 | ATGGGCGCGGCGGCGGGAGGCGCAAGCTGGGCCCCTCCGCCGGGCTCGTGA | 684 |
| | 3 | MFIRQLQETLPSGRGALLFAGASESGGPHSKTRVKPGW TGRE* | 685 | ATGTTTATCCGGCAGTTGCAAGAACTCTGCCTGTCCGGGACGAGGCGCCTTGCTTTT GCCGGGGCCAGCGAGTTGCAAAGTGGCGGAATTTCACAGCAAAACTCGGGTGAAGCCAGGCTG GACCGGCGGGAGTGA | 686 |
| | 4 | MGTRDERIRLCVAPGHDVCTLLCQCLMFVAYGYFRTK* | 687 | ATGGGGACCAGAGAGATGAACGAATCCGCTCGTGTAGCACCAGGCATGATGTGTG CACGTTGCTATGCCAGTGTTGTTGTTGCTTATGGTTATTTAGGACTAAGTGA | 688 |
| | 1 | MSHRAQPEHFF* | 689 | ATGAGCCACCGCGCCTCAGCCTGAAATTATTTCTTTTTAA | 690 |

Figure 1 (Continued)

| | | | | |
|---|---|---|---|---|
| hsa-mir-32 | 2 | MVDHGSLKLLGSSSPPTSAA* | 691 | ATGGTCATAGATCACGGCAGCCTCAAACTCTGGGCTCAAGCAGTCCTCCACCCTCAGCCGCCTGA | 692 |
| | 3 | MCTTTPG* | 693 | ATGTGTACCACCACTCCTGGCTGA | 694 |
| | 4 | MAKPHLYKN* | 695 | ATGCAAAACCCATCTCTACAAAAATTAG | 696 |
| hsa-mir-320 | 1 | MLPGREGATRSPEGTDTRTLAEPHPLAFRSPSRCVPPVASQLLPSHVARLPGPPR* | 697 | ATGTTGCCTGGGAGAGAAGGGGACGAGATCACCAGAGGGGACTGACACGCGGACCCTGGCGGAACCCCACCCCCTGGCTTTCGGTTCCGGTCGCGTCCTCCAGTGGCCCTCAGCTCGCCCCCACGTGGCCAAGTCCCGGAACCACCCAGGTGA | 698 |
| | 2 | MLRRSGYLASGRWRGGAKIRVPGFVGHHAAM* | 699 | ATGCTGCGCGCGCTCGGGGGGTCTTGGCCTCCGGCGGTGCGTGGAGGCGCCAAGATCAGGGTCCGGGTTTTGTCGCCACCAGCCCGCAATGTGA | 700 |
| | 3 | MCRGARRGAESFTWT* | 701 | ATGCGCCGAGCGGCGCGGCGGGCGCAGAGTTGAGACCTGAACTAA | 702 |
| | 4 | MVTLEWSLPPGSDLARFRGPLCAPGGVLG* | 703 | ATGGTTGACCTTGGAGTGGTCATTACCTCCGGGCAAGGACCTTGCCCACTTTCGGGACCCCTTCCGCTGTCCTGGTGGAGTCCTGGGTGA | 704 |
| hsa-mir-320-d | 1 | MESRSVAQAEVQWHNLSSLQPPPPWFK* | 705 | ATGGAGTCTCGTCTGTCGCCAGGCTGAAGTGCAGTGGCACAATCTCAGCTCACTGCAACCTCCGCCTCCTTGGTTCAAGTGA | 706 |
| | 2 | MRFHHVGQAGLKLLTS* | 707 | ATGAGGTTTCACCATGTTGGTCAGGCTGGTCAAACTCCTGACCTCGTGA | 708 |
| | 3 | MLVRLVSNS* | 709 | ATGTTGGTCAGGCTGGTCAAACTCCTGA | 710 |
| | 4 | MNGLIHSLRQRPHYPTTS* | 711 | ATGAATCGATTAATCATTCATTGAGGCAGAGACCTCATTACCCAATCACTTCTTAA | 712 |
| hsa-mir-323 | 1 | MPNFGSMMTTGGV* | 713 | ATGCCCAATCTGGATCCTGAATGATGACCACTGGTGGCGTATGA | 714 |
| | 2 | MSHT* | 715 | ATGAGTCATACATGA | 716 |
| | 3 | MMNMCLEL* | 717 | ATGATGAATATGTCTGAACTCTGA | 718 |
| | 4 | MHSYVIMIGSMKE* | 719 | ATGCATTCTTATGTTATTATAGGTCAATGAAAGAATGA | 720 |
| hsa-mir-324 | 1 | MPFLNCVALHVIHISFLSATRETAENN* | 721 | ATGCCATTCTTAAACTGTGTGGCTTTGCATGTGATCCATATCTCCTTCTTTCAGCCACCAGAGAAACGGCCGGAGAACAATTGA | 722 |
| | 2 | MLVTFPLAKR* | 723 | ATGCTGGTTACATTCCCTTAGCAAAGAGGTAG | 724 |
| | 3 | MRGVDGRDS* | 725 | ATGCGCGGAGTGGATGGGCGGGATAGCTAG | 726 |
| | 4 | MAGIASLNSSEEGGFGVAG* | 727 | ATGGCCGGGATAGCTAGCTTGAACAGCAGTGAAAGGAAGGGGATTTGGAGTCGGCTGGTTGA | 728 |
| hsa-mir-328 | 1 | MRWSRCPWR* | 729 | ATGCGATGGCGAGTCGCTGCCCTGAGGTCCCCTGAGGTGA | 730 |
| | 2 | MAESLPLEYRGSRPQA* | 731 | ATGGCGGAGTCGCTGCCCTGAGGTGAGGAAGCCGCCTCAGGCTAG | 732 |
| | 3 | MSAPSRRPEG* | 733 | ATGTCCGCTCCATCTCATCGTCCGAAGGTAA | 734 |
| | 4 | MSPPPTETAAPSPWQWETDCSLPLMCNDL* | 735 | ATGATCTCTCCATTTCCTACAGAGACGGCCGCCCCTTCTCCCTGGCAGTGGGAAACAGAGTGCCGTCCAATCTGCATGATGAACTGCAATGATCTGA | 736 |
| hsa-mir-329-1 | 1 | MPNPGSMMTTGGV* | 737 | ATGCCCAATCCTGGATGATGATGACCACTGGTGGCGTATGA | 738 |
| | 2 | MSHT* | 739 | ATGAGTCATACATGA | 740 |
| | 3 | MMNMCLEL* | 741 | ATGATGAATATGTCTGAACTCTGA | 742 |
| | 4 | MHSYVIMIGSMKE* | 743 | ATGCATTCTTATGTTATTATAGGTCAATGAAAGAATGA | 744 |
| hsa-mir-329-2 | 1 | MPNPGSMMTTGGV* | 745 | ATGCCCAATCCTGGATGATGATGACCACTGGTGGTGTATGA | 746 |
| | 2 | MSHT* | 747 | ATGAGTCATACATGA | 748 |
| | 3 | MMNMCLEL* | 749 | ATGATGAATATGTCTGGAACTCTGA | 750 |
| | 4 | MHSYVIMIGSMKE* | 751 | ATGCATTCTTATGTTATTATAGGTCAATGAAAGAATGA | 752 |

Figure 1 (Continued)

| | | | | | |
|---|---|---|---|---|---|
| hsa-mir-331 | 1 | MLLTLWERFINERNVSLFQVCAFDIVYIGKGHNAVLVCENK* | 753 | ATGCTATTGACATTATGGGAAAGATTTATCAATGAGAGAAATGTGTCTCTTTTCAGGTATGTGCTTTTGATATAGTTTACATTGGAAAGGTCATAATGCGTGTTTAGTTTGTGAAAATAAGTAA | 754 |
| | 2 | MGKIYQ* | 755 | ATGGGAAAGATTTATCAATGA | 756 |
| | 3 | MREMCLFPRYYLLI* | 757 | ATGAGAGAAATGTGTCTCTTTTCAGGTATGTGCTTTTGATATAG | 758 |
| | 4 | MLFP* | 759 | ATGCTTTTCCATGA | 760 |
| hsa-mir-345 | 1 | MRLTEKSSIT* | 761 | ATGAGACTAACAGAAAAATCAAGTATCACATAG | 762 |
| | 2 | MLKMNNRSRLHLVSRSLPCNDCALASPSCSLSAFLMWRFEM* | 763 | ATGTTAAAAATGAACAATGGAGCAGGCTACATTTAGTTTCACGGTCTCTTCCCTGTAATGACTGTGCACTAGCAAGTCCTTCCTGTTCTTGTCAGCGTTCTTGATGTGGCGATTTGAAATGTAA | 764 |
| | 3 | MTVR* | 765 | ATGACTGTGCACTAG | 766 |
| | 4 | MPSL* | 767 | ATGCCATCCCTTTAG | 768 |
| hsa-mir-34a | 1 | MRRPCTTAPGGARVPTATSWRLRAAGAEHQTDARC* | 769 | ATGCGGAGACCTGCACCACTGCTCCGGGCGGCGCTCCGGTCCGACGGCACCTCCTGGCGGCTGCGCGCAAGCGCCAGGATCCAGACGGACGCACGGTGCTGA | 770 |
| | 2 | MTNGECCF* | 771 | ATGACAAATGGGAGTGCTGCTTTTAG | 772 |
| | 3 | MGSAASRCSYQLASCVLGWAVFTCASGLSAHQVWRALLGNSVEDQDGPLEG* | 773 | ATGGGGAGTGCTGCTTCTAGGTGCTCTGTACCAACTGGCTTCGTGGTCTCGGATGGGCGGTGTTCACAGGCGCTTCGGGCTGAGCGCCACTCAAGTGTGGCGCGCTTTGGAAACTCCGTGAAGACCAGGACGGACCCTGAGGGTTAG | 774 |
| | 4 | MGGVHRRFGAERPPSVARAFGKLRGRPGRTPGGLGRL* | 775 | ATGGGCGGTGTTCACAGGCGCTTCGGGCTGAGCGCCACTCAAGTGTGGCGCGCTTTTGCGGAAACTCCGTGAAGACCAGGACGGACCCTGAGGGTTAGGAAGACTTTGA | 776 |
| hsa-mir-34b | 1 | MGVGARLPAWEGAGPPRQRRPLAQLRVLCAARPAGVPLGPGVSSGAACAQPW* | 777 | ATGGGGGTCGGGGCGCGGCTCCCGGCCTGGGAGGGCGCGGGTCCTCCCCGGCCTAGGCGCCGGTGGTCGGAGGGCCGGGGGGTCCCGCCATGGTAG | 778 |
| | 2 | MVGRPPVKWGPRRAPTPRRRCGPSGSCSRGCPVLGL* | 779 | ATGGTAGGGCGTCCCCCGGTGAAATGGGGTCCGAGGCGGGCAGCTGCGCGCTGCGACCGTCGGTTGTAG | 780 |
| | 3 | MGSEAGPDPASALRTVRELQPRVPGARFVGSVIS* | 781 | ATGGGTCCGAGGCGGCCGGGCCCGGTGCTGGCGTCGGACCGTCGGAGCTGCAGCCGCGGGTGCCGGTGCCGGTGCTGCCGGTTGTAGCACGTCATTAGCTGA | 782 |
| | 4 | MPEKRGVGVGPAQPAPRAPAASARKPAVSPDTVKLLALSRSHRR* | 783 | ATGCCTGAGAAGCGCGGCGTGGGCGTGGGTCCTGCGAGCGCCGGAGCGCCCGGCAAGTGCGAGGAAACCGCGGGTTCTCCAGATACAGTTAAACTGTTAGCTCTCTCTAGGAGTCACAGAAGATGA | 784 |
| hsa-mir-34c | 1 | MGVGARLPAWEGAGPPRQRRPLAQLRVLCAARPAGVPLGPGVSSGAACAQPW* | 785 | ATGGGGGTCGGGGCGCGGCTCCCGGCCTGGGAGGGCGCGGGTCCTCCCCGGCCGGAGGCGGGGGTCCCGCCAGCCATGGTAG | 786 |
| | 2 | MVGRPPVKWGPRRAPTPRRRCGPGSCSRGCPVLGL* | 787 | ATGGTAGGGCGTCCCCCGGTGAAATGGGGTCCGAGGCGGGCAGCTGCGCGGACCGTCGGGCCGGTGTCTCGGTTTGTAG | 788 |
| | 3 | MGSEAGPDPASALRTVRELQPRVPGARFVGSVIS* | 789 | ATGGGTCGCGAGGCGGGCCCGGTGCTGGCGTCGGACCGTCGGAGCTGCAGCCGCGGGTGCCGGTGCTGCCGGTTGTAGCACGTCATTAGCTGA | 790 |
| | 4 | MPEKRGVGPAQPAPRAPAASARKPAVSPDTVKLLALSRSHRR* | 791 | ATGCCTGCAAGTGCGAGGAAACGCGGGTTCTCCAGATACAGTTAAACTGTTAGCTCTCTCTAGGAGTCACAGAAGATGA | 792 |
| | 1 | MKKGRKPTCASDSRWRNDCGPRCIHR* | 793 | ATGAAAAAGGGGAGGAAGCCCACCTGTGCGAGTGACCTGCGGTTGCCGTTGGAGAAATGATTG | 794 |

Figure 1 (Continued)

| | | | | |
|---|---|---|---|---|
| hsa-mir-363 | 2 | MIVVFVASTADS* | 795 | ATGATTGTGTTTGTTCTTCTGTGCATCCACGCTGACTCCTGA |
| | 3 | MAFLSSSGLWAATTLVTMVEREGSGFILHPFPPSLPPAC LPGLSSSDPACSLVSDL* | 797 | ATGGCGCCTTGTCCTTCTGGCTTTGGGCTGCCACAATCACCCTGGTAACAATG GTGGAAAGGAGGGGTCCGGCTTCATTTTGCACCCCTTCCCTCCTTCCTGCCCCG GCTTGCCTTCCAGGGCTTTCCTCTCCGACCCAGGCTGCTCACTGGTCTCTGATTTGT AA |
| hsa-mir-365-1 | 4 | MLNSILIVRLKLRLHHFILQSAVGLWP* | 799 | ATGCTTAATTCATTTGATTGTGCGTCTTAAACTAAGACATCATTTATTCTACAGA GCGCTGTCGGGCTTTGGCCTTGA |
| | 1 | MGTGEGRWRRGSARFSRDSARDACLGCDCRRCGRHPGS PSDPSPAPQRGV* | 801 | ATGGGAACGGGAGAGGGAGGTGGTCGGCGGGGAGCGCGCGGTTCTCTGGGACT CGGCGCGAGAGACCCTGTCTGGGCTGCATTGCCGGCCGCGGCCACCCGGCTCCC CCTCCGACCCGTCTCCCGCTCCCCAGAGGGGCGTGTGA |
| | 2 | MPRAEQAGRARRSTCARAPLAWAAAPAGAGPRGSRTS REPPSPESYRRPLKLSAPSPREAGSPGALALASAGRGQK N* | 803 | ATGCCCCGCGCGGAGCAGGCGGGACGCGCCCGCTCCACGTGCGCCCGAGCCC GCTGGCATGGCCGGCGCGGCCCTGGCGGCGGCGCCCGCGGGATCCCGGACTAGCC GGAACCACCGTCCCCAGAGAGTTACCGCTCGCCCCTAAAGTTGTCAGCTCCTCCC CCGAGAAGCAGGCAGCCCTGGCGCGTTGGCTTAGCTTCTACGAGGACGGGGCAA AAAAACTAG |
| | 3 | MGGGACGGRAPGIPD* | 805 | ATGGGCGGCGGCGCCTGCGGGGACGGGCCCGGGATCCCGGACTAG |
| | 4 | MRRLLPLRTHPYL* | 807 | ATGCGCCGCTTATGTCCTCTGAGACACATCATTTATAA |
| hsa-mir-369 | 1 | MPNPGSMMTTGGV* | 809 | ATGCCCAATCCTGGATCGATGATGACCACTGGTGCGTATGA |
| | 2 | MSHT* | 811 | ATGAGTCATACATGA |
| | 3 | MMNMCLEL* | 813 | ATGATGAATATGTGTCTGGAACTCTGA |
| | 4 | MHSYVIRMGSMKE* | 815 | ATGCATTCTTATGTTATTATTCGGTCAATGAAAGAATGA |
| hsa-mir-370 | 1 | MRRAL* | 817 | ATGAGGAGGGCATTGTAG |
| | 2 | MRVIDPGCRSPKE* | 819 | ATGAGGGTCATTGATCCTGGGTGCAGATCTCCAAAAGAATGA |
| | 3 | MTERKREWWKETGWEKMKHEKRK* | 821 | ATGACAGAAAGAAAAGAGGAGTGGTGGAAAAAGGAAGTGAAAAGAATGGAAGATGAAGTA AAATAGAAAAGAAGTGA |
| | 4 | MGKNENRKEVKEHNN* | 823 | ATGGGAAAAAATGAAAATAGAAAAGAAGTGAAAGATAATAATAATTAG |
| hsa-mir-371 | 1 | METLYRVPFLALECPNLKLKKPPWLHMPLAMTMYALV VVSYFLITRGIVYDVTVEPPGVGSMTDEQGHQRPVAFL AYRVSGQYYYGRTWIQLPVYNGRFRFHNPGPIECTKYP KTQ* | 825 | ATGGAGACGCTTGTACCGTGTCCGTTCTTAGCGCTTGAATGTCCAACCTGAAGCTG AAGAAGCGCCTCCAATGCTGCACGATGTACGCGCTGGTCATGACTATGTATGCTGCGTGTG GTGTCTTACTTCGGCTCTATGACTGATGAACAAGGCATCAGAGGCAGTAGCTTCTTGGCC TACAGAGTGGCTCTATGACTGATGAACAATATTATATGGAAGGACTTGATCCAGTCCTGTTTAC AATGGAGAGTTTAGGTTTCATAATCCTGGACCGATCGAATGCACCAAATATCCCAAA ACTCAATAG |
| | 2 | MSQPEAEEAALAAHAVGHDYVCSGGGVLLPHHQRNRL* | 827 | ATGTCCCAACCTGAAGCTGAAGAAGCCGCCCTGGCTGCACATGCCGTTGGCCATGAC TATGTATGCTCTGGTGGGGGTGTTACTTCCTCATCACCAGAGGAAATCGTTTATGA |
| | 3 | MLWWCLTSSSPEESFMMLRLNRQVLAL* | 829 | ATGCTCTGGTGGTTGTCTTACTTCCTCATCACCAGAGGAAATCGTTTATGATGTTA CGGTTGAACCGGCAGTGTTGGCTCTATGA |
| | 4 | MNKGIRGQ* | 831 | ATGAACAAGGCATCAGAGGCCAGTAG |
| hsa-mir-372 | 1 | METLYRVPFLALECPNLKLKKPPWLHMPLAMTMYALV VVSYFLITRGIVYDVTVEPPGVGSMTDEQGHQRPVAFL AYRVSGQYYYGRTWIQLPVYNGRFRFHNPGPIECTKYP KTQ* | 833 | ATGGAGACTTGTACCGTGTCCGTTCTTAGCGCTTGAATGTCCAACCTGAAGCTG AAGAAGCGCCTCCAATGCTGCACGATGTGCGTTGGCCATGCTATGTATGCTGCGTGTG GTGTTGAACCGGCAGTGTTGGCTCTACTTCCTCATCACCAGAGGAAATCGTTTATGATGTTA CGGTTGAACCGGCAGTGTTGGCTCTATGACTGATGAACAAGGCATCAGAGGCCAGTAG GGTGTTGGCTCTATGACTGATGAACAAGGCATCAGAGGCCAGTAGCTTCTTGGCC TACAGAGTAAGTGGACAATATTATTATGGAAGGACTTGGATCCAGTCCTGTTTAC AATGGGAGGTTTAGGTTTCATAATCCTGGACCGATCGAATGCACCAAATATCCCAAA ACTCAATAG |

| | |
|---|---|
| | 796 |
| | 798 |
| | 800 |
| | 802 |
| | 804 |
| | 806 |
| | 808 |
| | 810 |
| | 812 |
| | 814 |
| | 816 |
| | 818 |
| | 820 |
| | 822 |
| | 824 |
| | 826 |
| | 828 |
| | 830 |
| | 832 |
| | 834 |

Figure 1 (Continued)

| | | | | |
|---|---|---|---|---|
| | 2 | MSQPEAEEAALAARAVGHDYVCSGGGVLLPHHQRNRL* | 835 | ATGTCCCAACTGAAGCTGAAGAAGCTGCCCTGGCTGCTGCCCTGGCCAATGAC TATGTTATGCTCTGGTGGTGGTGGTGTCTTACTTCCTCATCACCAGAGGAATCGTTTATGATGTTA | 836 |
| hsa-mir-374b | 3 | MLWWCLTSSSPEESFMMLRLNRQYLAL* | 837 | ATGCTCTGGTGGTGGTGTCTTACTTCCTCATCACCAGAGGAATCGTTTATGATGTTA CGGTTGAACCGCCAGGTGTTGGCTCTATGA | 838 |
| | 4 | MNKGHRGQ* | 839 | ATGAACAAGGGCATCAGAGGCCAGTAG | 840 |
| hsa-mir-375 | 1 | MHEGITNCTLSTREGINTFCYLGVWVGFVDTPLWFTI SMP* | 841 | ATGCATGAGGGAATCACAAACTGCACACTTTCCACAAGGGAGGAATAAATACTTTT TTCTGTGTCCTTGGAGTGGTGGGATTCGTGGATACATTTCTGTTTCACTATTT CAATGATATGA | 842 |
| | 2 | MRELQTAHFPQGRE* | 843 | ATGAGAGAACTACAAACTGCACACTTTCCACAAGGGAGGGAATAA | 844 |
| | 3 | MKEPHVAAQKIFHRWKLRLVHLH* | 845 | ATGAAGGAGCCTCATGTTGCAGCACAGAAGATTTTTCATCGTTGGAAGTTAAGGTTA GTTCACCTTCATTGA | 846 |
| | 4 | MLQHRRFFIVGS* | 847 | ATGTTGCAGCACAGAAGATTTTTCATCGTTGGAAGTTAA | 848 |
| | 1 | MRSGEGGG* | 849 | ATGCGTTCAGGTGAGGGCGGAGGCTAG | 850 |
| | 2 | MALGKSPFGLLVFPFAQ* | 851 | ATGGCCCTTGGGCAAGTCATTTCCGGCCTCTTGGTTTTCCATTGTCAGTGA | 852 |
| hsa-mir-375 | 3 | MLGKMQALTELEPRLRCGKSGRGKLRATMEPQHSSDL CGAADILRCHSLILPWSLFQSKNV* | 853 | ATGCTGGGAAGATGCAGGCCTTACGGAGTTGGAGCCAAGGCTGAGGTTGGAAA ATCTGGGCGGGGAAAGCTGAGGGCCACCATGGAGCCTCAAATCCACTCTGGATC TCTGTGTGCGGCTGACATCCTGAGATGTCACTCCTCCTTGGTCCTCTT TCAGTCTAAAAACGTCTGA | 854 |
| | 4 | MSLPDTPLVPLSV* | 855 | ATGTCACTCCCTGACACTCCTTGTCCTCTTTCAGTCTAA | 856 |
| | 1 | MPNPGSSMMTTGGV* | 857 | ATGCCCAATCCTGGATCGATGATGACCACTGGTGGCGTATGA | 858 |
| hsa-mir-376a-1 | 2 | MSHT* | 859 | ATGAGTCATACATGA | 860 |
| | 3 | MMNMCLEL* | 861 | ATGATGAATATGTGTCTGGAACTCTGA | 862 |
| | 4 | MHSYVIMIGSMKE* | 863 | ATGCATTCTTATGTTATTATGGGTCAATGAAGGAATGA | 864 |
| | 1 | MPNPGSMMTTGGV* | 865 | ATGCCCAATCCTGGATCGATGATGACCACTGGTGGCGTATGA | 866 |
| hsa-mir-376a-2 | 2 | MSHT* | 867 | ATGAGTCATACATGA | 868 |
| | 3 | MMNMCLEL* | 869 | ATGATGAATATGTGTCTGGAACTCTGA | 870 |
| | 4 | MHSYVIMIGSMKE* | 871 | ATGCATTCTTATGTTATTATGGGTCAATGAAGGAATGA | 872 |
| | 1 | MPNPGSSMMTTGGV* | 873 | ATGCCCAATCCTGGATCGATGATGACCACTGGTGGCGTATGA | 874 |
| hsa-mir-376c | 2 | MSHT* | 875 | ATGAGTCATACATGA | 876 |
| | 3 | MMNMCLEL* | 877 | ATGATGAATATGTGTCTGGAACTCTGA | 878 |
| | 4 | MHSYVIMIGSMKE* | 879 | ATGCATTCTTATGTTATTATGGGTCAATGAAGGAATGA | 880 |
| | 1 | MPNPGSMMTTGGV* | 881 | ATGCCCAATCCTGGATCGATGATGACCACTGGTGGCGTATGA | 882 |
| hsa-mir-376b | 2 | MSHT* | 883 | ATGAGTCATACATGA | 884 |
| | 3 | MMNMCLEL* | 885 | ATGATGAATATGTGTCTGGAACTCTGA | 886 |
| | 4 | MHSYVIMIGSMKE* | 887 | ATGCATTCTTATGTTATTATGGGTCAATGAAGAAGAATGA | 888 |
| hsa-mir-377 | 1 | MPNPGSSMMTTGGV* | 889 | ATGCCCAATCCTGGATCGATGATGACCACTGGTGGCGTATGA | 890 |
| | 2 | MSHT* | 891 | ATGAGTCATACATGA | 892 |
| | 3 | MMNMCLEL* | 893 | ATGATGAATATGTGTCTGGAACTCTGA | 894 |
| | 4 | MHSYVIMIGSMKE* | 895 | ATGCATTCTTATGTTATTATGGGTCAATGAAGAAGAATGA | 896 |
| | 1 | MPLH* | 897 | ATGCCACTGCACTAA | 898 |
| hsa-mir-378 | 2 | MGEFCDKELRRFPCKINLSL* | 899 | ATGGGAGAATTTGTGATAAAGAGACTTAGAAGATTTGTAAATAAACTTATCTTTATAA | 900 |
| | 3 | MFLIA* | 901 | ATGTTTTAATAGCATGA | 902 |

Figure 1 (Continued)

| | | | | | |
|---|---|---|---|---|---|
| hsa-mir-379 | 4 | MNFQISE* | 903 | ATGAACTTTCAAATTTCAGAATAA | 904 |
| | 1 | MPNPGSMMTTGGV* | 905 | ATGCCCAATCTGGATCGATGATGACCACTGGTGGCGTATGA | 906 |
| | 2 | MSHT* | 907 | ATGAGTCATACATGA | 908 |
| | 3 | MMNMCLEL* | 909 | ATGATGAATATGTCTGGAACTCTGA | 910 |
| | 4 | MHSYVIIMIGSMKE* | 911 | ATGCATTCTTATGTTATTATGATTGGGTCAATGAAAGAATGA | 912 |
| hsa-mir-380 | 1 | MPNPGSMMTTGGV* | 913 | ATGCCCAATCTGGATGATGATGACCACTGGTGGCGTATGA | 914 |
| | 2 | MSHT* | 915 | ATGAGTCATACATGA | 916 |
| | 3 | MMNMCLEL* | 917 | ATGATGAATATGTCTGGAACTCTGA | 918 |
| | 4 | MHSYVIIMIGSMKE* | 919 | ATGCATTCTTATGTTATTATGATTGGGTCAATGAAAGAATGA | 920 |
| hsa-mir-381 | 1 | MPNPGSMMTTGGV* | 921 | ATGCCCAATCTGGATCGATGATGACCACTGGTGGCGTATGA | 922 |
| | 2 | MSHT* | 923 | ATGAGTCATACATGA | 924 |
| | 3 | MMNMCLEL* | 925 | ATGATGAATATGTCTGGAACTCTGA | 926 |
| | 4 | MHSYVIIMIGSMKE* | 927 | ATGCATTCTTATGTTATTATGATTGGGTCAATGAAAGAATGA | 928 |
| hsa-mir-382 | 1 | MPNPGSMMTTGGV* | 929 | ATGCCCAATCTGGATCGATGATGACCACTGGTGGCGTATGA | 930 |
| | 2 | MSHT* | 931 | ATGAGTCATACATGA | 932 |
| | 3 | MMNMCLEL* | 933 | ATGATGAATATGTCTGGAACTCTGA | 934 |
| | 4 | MHSYVIIMIGSMKE* | 935 | ATGCATTCTTATGTTATTATGATTGGGTCAATGAAAGAATGA | 936 |
| hsa-mir-409 | 1 | MPNPGSMMTTGGV* | 937 | ATGCCCAATCTGGATCGATGATGACCACTGGTGGCGTATGA | 938 |
| | 2 | MSHT* | 939 | ATGAGTCATACATGA | 940 |
| | 3 | MMNMCLEL* | 941 | ATGATGAATATGTCTGGAACTCTGA | 942 |
| | 4 | MHSYVIIMIGSMKE* | 943 | ATGCATTCTTATGTTATTATGATTGGGTCAATGAAAGAATGA | 944 |
| hsa-mir-410 | 1 | MPNPGSMMTTGGV* | 945 | ATGCCCAATCTGGATCGATGATGACCACTGGTGGCGTATGA | 946 |
| | 2 | MSHT* | 947 | ATGAGTCATACATGA | 948 |
| | 3 | MMNMCLEL* | 949 | ATGATGAATATGTCTGGAACTCTGA | 950 |
| | 4 | MHSYVIIMIGSMKE* | 951 | ATGCATTCTTATGTTATTATGATTGGGTCAATGAAAGAATGA | 952 |
| hsa-mir-411 | 1 | MPNPGSMMTTGGV* | 953 | ATGCCCAATCTGGATCGATGATGACCACTGGTGGCGTATGA | 954 |
| | 2 | MSHT* | 955 | ATGAGTCATACATGA | 956 |
| | 3 | MMNMCLEL* | 957 | ATGATGAATATGTCTGGAACTCTGA | 958 |
| | 4 | MHSYVIIMIGSMKE* | 959 | ATGCATTCTTATGTTATTATGATTGGGTCAATGAAAGAATGA | 960 |
| hsa-mir-412 | 1 | MPNPGSMMTTGGV* | 961 | ATGCCCAATCTGGATCGATGATGACCACTGGTGGCGTATGA | 962 |
| | 2 | MSHT* | 963 | ATGAGTCATACATGA | 964 |
| | 3 | MMNMCLEL* | 965 | ATGATGAATATGTCTGGAACTCTGA | 966 |
| | 4 | MHSYVIIMIGSMKE* | 967 | ATGCATTCTTATGTTATTATGATTGGGTCAATGAAAGAATGA | 968 |
| hsa-mir-421 | 1 | MLFCVLDLNFKMCKLVIYLYYYNFIVYIFISSVSMLCLK LKISQHLFLTAFNM* | 969 | ATGTTATTTTGTGTTGATCTAAATTTAAGATGTGTAAGCTAGTATATATTTAT ATTTATTATATAAATTTATTGTATATATATTCATAAGCTCGTCAGTATGTATGCTT AAAGCTTAAAATAAGCAAATCATTCTTTCCTGACTGCTTTAACATGTAG | 970 |
| | 2 | MLKA* | 971 | ATGCTTAAAGCTTAA | 972 |
| | 3 | MLGPEPYSAKKAFRALKTKYNKHRIQSKDRYPNIEY* | 973 | ATGTTGGGATTTGAACCAGTAAGTGCAAAGAAAGCTTTCAGGGCCCTAAAACTAA GTACAATAAGCACCGCATACAGAGACCAGATATACTTCAATATAGAGTACTGA | 974 |
| | 4 | MFVGITELFWLHVPQAKGTTTIRLJPPPSESTGILCCLH* | 975 | ATGTTTGTTGTTGCGCATCACCAGGCTCATTCCTCCTCCCAGTGAAAGCACAGTCTCTTTGGCTACATGGACCAGTGAAAGCACAGTATTCTTTGTTGTCTTCACTGA | 976 |

Figure 1 (Continued)

| | | | | | |
|---|---|---|---|---|---|
| hsa-mir-422a | 1 | MAGAESLSPRLLGWNGFHRFPNIRWGGVRRAFARWS TPGRAPLVREGFQQDIDGKRTSGNEHRLSIYMHPAWGRH WRIFCRRIFLPLRSPSWERTCGYSACP* | 977 | ATGGCAGGGGCAGAAAGCCTCAGTCCCAGGCTTCTCTTGGTTGGAATGGGTTTCACAG GTTCTTTCCTAATATCAGATGGGAGGGTGAGGAGGGTGAGGAGGGCATTTGCCCGCTGGAGCA CACCTGGGAGAGCACCACTTGTGAGGGAAGGGTTCCAGCAGGACATCGATGGGAAA CGCACATCAGGAATGAACATCTGAGCATTTACATGCACCAGCATGGGGAAGGCA CTGGAGAATATTCTGCAGGAGGATATTCCTGTTCCTAAGGAGCCCGAGCTGGGAGC GCACCTGTGGATATTCAGCTTGCCCATAG | 973 |
| | 2 | MGFTGSFLISDGEG* | 979 | ATGGGTTTCACAGGTCTTTCTTCCTAATATCAGATGGGAGGGTGA | 980 |
| | 3 | MGRGEEGICPLEHTWESTICEGRVPAGHRWETTHIRK* | 981 | ATGGGGAGGGGTGAGGAGGGCATTTGCCCGCTGGAGCACACCTGGAGCACCAC TTGTGAGGGAAGGTTCCAGCAGGACATCGATGGGAAACGCACATCAGGAAATGA | 982 |
| | 4 | MGNAHQEMNI* | 983 | ATGGGAAACGCACATCAGGAAATGAACATCTGA | 984 |
| hsa-mir-429 | 1 | MGCCRQPGQRPGELRSLQTQAGAGPSPPQGKVGPCADA AGFRVWSHLGPTGCVFRARAQCVGSRHGVPSCQGLGR GQAPRGVTFLPPT* | 985 | ATGGGCTGCGAGCCAGGCCAGGCGACCCAGGGAGGAGCTCCGTGCACTGCAGACACA GCCTGGAGCGGTCCTTCCCCAGCCCCAGGGAAGGTTGGGCCTCGGCAGATGCGG CTGGGTTTCGGGTGTGGGCTCATCTGAGCCACCGGGCTGCGTCTCCGGCACGGG CACAGTGTGTGGGCTCAGGCATGCGGGGCCTCAGGRCAGGGCTGGGCAGAGGG CAGGGCTCCGAGAGGGTTACGTTCTTGCCGCTACCTGA | 986 |
| | 2 | MRLGFGCGAILDPRAASSGHGHSVWAPGMGGCPQGRAW AEGRLREGSRSCRLPDSRPSRKFSPEAATAVLRHFVRRR EAVASEVGA* | 987 | ATGCGCCTGGGTTCGGGTGTGGGCGCCATCTTGGACCCACGGGCTGCGTCTTCCGG CACGGGCACAGTGTGTGGGCTCCAGRCATGCGGGGCCTCAGGRCAGGGCTGGGC AGAGGGCAGGGCTCCGAGAGCAGGTCACGTTCTGCCGCCTACCTGAGCGACCAGGCCTT CTAGAAAGTTCTCTGCCCTCAGGGTCGCTAG GGGAAGCTGTGCGTCAGGAGTGTGGTCGTAG | 988 |
| | 3 | MTASPLGSGVCGGKGLVSAPSGQRPAEPMGGEVGAWG RGWSGTGAQPGEAGAGSQAPRYDWGGGNVSREVPY LNVKRLSTVAAAGNKVRPTEAQP* | 989 | ATGACCGCGTCTCTTGGGCTCTGGAGTCTGCGGTGGAAGGCTTGGTTCAGCA CCCTTGCAGAGCCGGACCAGGCCCAGCGGCCGAGATGGTGAGCTGGGCCGGGTCG TGGCTGGTCAGTGTACAGGTGGGGCTCAGCCCAGCAACGTCTCTGTGAGGTTTTACTTAAATG CCCGCTATGACTGGGGGAGGAGGGAAGGTCTGGAGGTTTTTACTTAAATG TGAAACGGCTCAGTAGGGTCAGTGGCCGCACCGCCGGAACAAGGTCCGACCACCGAGGCC CAGCCTTGA | 990 |
| | 4 | MTGVGATSLVRFFT* | 991 | ATGACTGGGGTGGGCACGTCTCGTGAGTTTTTACTTAA | 992 |
| hsa-mir-431 | 1 | MRRAL* | 993 | ATGAGGAGGGCATTGTAG | 994 |
| | 2 | MRVIDPGCRSPKE* | 995 | ATGAGGGTCATTGATCCTGGGTGCAGATCTCCAAAGAATGA | 996 |
| | 3 | MTERKREWWKETIGWEKMKIEKRK* | 997 | ATGACAGAAGAAATGGAGTGGTGGAAAGAAACAATAGGATGGGAAAAATGA AAATAGAAAAGGAAGTTGA | 998 |
| | 4 | MGKNENRKKEVKEIHNN* | 999 | ATGGGAAAGAATGAAATAGAAAAGGAAGATAATAAATAATTAG | 1000 |
| hsa-mir-432 | 1 | MRRAL* | 1001 | ATGAGGAGGGCATTGTAG | 1002 |
| | 2 | MRVIDPGCRSPKE* | 1003 | ATGAGGGTCATTGATCCTGGGTGCAGATCTCCAAAGAATGA | 1004 |
| | 3 | MTERKREWWKETIGWEKMKIEKRK* | 1005 | ATGACAGAAGAAATGGAGTGGTGGAAAGAAACAATAGGATGGGAAAAATGA AAATAGAAAAGGAAGTTGA | 1006 |
| | 4 | MGKNENRKKEVKEIHNN* | 1007 | ATGGGAAAGAATAGAAAAGGAAGTGAAAATAAGGAAGATAATAAATAATTAG | 1008 |
| hsa-mir-433 | 1 | MRRAL* | 1009 | ATGAGGAGGGCATTGTAG | 1010 |
| | 2 | MRVIDPGCRSPKE* | 1011 | ATGAGGGTCATTGATCCTGGTGCAGATCTCCAAAGAATGA | 1012 |
| | 3 | MTERKREWWKETIGWERMKIEKRK* | 1013 | ATGACAGAAGAAATGGAGTGGTGAAAGAAACAATAGGATGTGAAAAACAATAGGAAGAATGA | 1014 |
| | 4 | MGKNENRKKEVKEIHNN* | 1015 | ATGGGAAAGAATGAAATAGAAAAGGAAGTGAAAGAATAATAAATAATTAG | 1016 |

Figure 1 (Continued)

| | | | | |
|---|---|---|---|---|
| hsa-mir-451 | 1 | MGRGGSRSPGGQYPVWGGALKQRSFLGTVRPVNSKQAG ACWGLPALPAQETRMRPLQVGKPGSGQCSLGLQNAAS SRISI* | 1017 | ATGGGGGGCGGGTCGCGCAGCCCTGGAGGGCAGGTGCCTGTATGGGGAGGGCCCT GAAACAGAGGTCGTTTCTGGCACAGTCAGACCCGTTAATTCCAAGCAGGCTGGGG CTTGTTGGGGATTACCGGCACTGCCCGCCAGGAGACGCGGATGCGGCCTCTACAG GTTGGGAAACCCGGTTCGGGCAGTGCAGTTTGGGATTGCAAAATGCTGCAAGTTCC AGAATTTCTATCTAG | 1018 |
| | 2 | MGRGPETEVVSRUSQTR* | 1019 | ATGCGGGAGGGGCCCTGAAACAGAGGTCGTTTCTCGCACAGTCAGACCCGTTAA | 1020 |
| | 3 | MLQVPEFLSRWGMGTAVLGKRNCY* | 1021 | ATGCTGCAAGTTCCAGAATTTCTATCTAGGTGGGGCATGGGGACTGCGGTACTGGG GAAAAGGAACTGCTATTGA | 1022 |
| | 4 | MASGSLWISKSISPLGHPQCVGDKYPTPLKTRNSLEDRR ETPREH* | 1023 | ATGGCTTCAGGTCTCACTTTGGATCCAAAATCTCTCCACTGGGACATCCCAG TGTGTGGGAGTAAGTACCCTACCCCCTGAAGACCAGAAATAGCTTGAGGACAG AGGGAGACTCCCAGAGAACACTAA | 1024 |
| hsa-mir-485 | 1 | MPNPGSMMTTGGV* | 1025 | ATGCCCAATCTGGATCGATGATGACCACTGGTGGCGTATGA | 1026 |
| | 2 | MSHT* | 1027 | ATGAGTCATACATGA | 1028 |
| | 3 | MMNMCLEL* | 1029 | ATGATGAATATGTCTGGAACTCTGA | 1030 |
| | 4 | MHSYVIMGSMKE* | 1031 | ATGCATTCTTATGTTATTATGGTCAATGAAAGAATGA | 1032 |
| hsa-mir-487a | 1 | MPNPGSMMTTGGV* | 1033 | ATGCCCAATCTGGATCGATGATGACCACTGGTGGCGTATGA | 1034 |
| | 2 | MSHT* | 1035 | ATGAGTCATACATGA | 1036 |
| | 3 | MMNMCLEL* | 1037 | ATGATGAATATGTCTGGAACTCTGA | 1038 |
| | 4 | MHSYVIMGSMKE* | 1039 | ATGCATTCTTATGTTATTATGATTGGTCAATGAAAGAATGA | 1040 |
| hsa-mir-487b | 1 | MPNPGSMMTTGGV* | 1041 | ATGCCCAATCCTGGATCGATGATGACCACTGGTGGCGTATGA | 1042 |
| | 2 | MSHT* | 1043 | ATGAGTCATACATGA | 1044 |
| | 3 | MMNMCLEL* | 1045 | ATGATGAATATGTCTGGAACTCTGA | 1046 |
| | 4 | MHSYVIMGSMKE* | 1047 | ATGCATTCTTATGTTATTATGATTGGTCAATGAAAGAATGA | 1048 |
| hsa-mir-493 | 1 | MRRAL* | 1049 | ATGAGGAGGCATTGTAG | 1050 |
| | 2 | MRVIDPGCRSPKE* | 1051 | ATGAGGGTCATTGATCCTGGGTGCAGATCTCCAAAGAATGA | 1052 |
| | 3 | MTERKREWWKETIGWEKMKIEKRK* | 1053 | ATGACAGAAAGAAAGAGAGGAGTGGTGGAAAGAAACAATAGGATGGGAAAAATGA AAATAGAAAAGGAAGTGA | 1054 |
| | 4 | MCKNENRRKEVKEHPN* | 1055 | ATGGGAAAAATGAAAATAGAAAAGGAAGTGAAAGATATAATAATTAG | 1056 |
| hsa-mir-494 | 1 | MPNPGSMMTTGGV* | 1057 | ATGCCCAATCTGGATCGATGATGACCACTGGTGGCGTATGA | 1058 |
| | 2 | MSHT* | 1059 | ATGAGTCATACATGA | 1060 |
| | 3 | MMNMCLEL* | 1061 | ATGATGAATATGTCTGCTGGAACTCTGA | 1062 |
| | 4 | MHSYVIMGSMKE* | 1063 | ATGCATTCTTATGTTATTATGGTCAATGAAAGAATGA | 1064 |
| hsa-mir-495 | 1 | MPNPGSMMTTGGV* | 1065 | ATGCCCAATCTGGATCGATGATGACCACTGTGGCGTATGA | 1066 |
| | 2 | MSHT* | 1067 | ATGAGTCATACATGA | 1068 |
| | 3 | MMNMCLEL* | 1069 | ATGATGAATATGTCTGGAACTCTGA | 1070 |
| | 4 | MHSYVIMGSMKE* | 1071 | ATGCATTCTTATGTTATTATGGTCAATGAAAGAATGA | 1072 |
| hsa-mir-496 | 1 | MPNPGSMMTTGGV* | 1073 | ATGCCCAATCTGGATCGATGATGACCACTGGTGGCGTATGA | 1074 |
| | 2 | MSHT* | 1075 | ATGAGTCATACATGA | 1076 |
| | 3 | MMNMCLEL* | 1077 | ATGATGAATATGTCTGGAACTCTGA | 1078 |
| | 4 | MHSYVIMGSMKE* | 1079 | ATGCATTCTTATGTTATTATGATTGGTCAATGAAAGAATGA | 1080 |

Figure 1 (Continued)

| | | | | |
|---|---|---|---|---|
| hsa-mir-498 | 1 | METLYRVPFLALECPNLKLEKPPWLHMPLAMTMYALV VVSYFLTRGIVYDVTYEPPGVGSMTDEQGHQRPVAFL AYRVSGQYYYGRTWIQLPVYNGRFRFHNPGPIECTKYP KTQ* | 1081 | ATGGAGACTTTGTACCGTGTCCCGTTCTTAGCGCTTGAATGTCCCAACCTGAAGCTG AAGAAGCCCCCTGGCTGCACATCGTTGGCCATGACATGTATGCTCTGGTTGGTG GTGTCTTACTTCGTCTGGTCTTCCTCATCACCAGAGGAATCGTTTATGATGTTACG GTGTTGGCTCTATGACTGACAATATTATTGGAAGGACTTGGATCCAGCTTCTTGCC TACAGAGTAAGTGGACAATATTATTGGAAGGACTTGGATCCAGCTTCTCGTTTAC AATGGGAGGTTTAGGTTTCATAATCCTGACCGATGAATGCACCAAATATCCCAAA ACTCAATAG | 1082 |
| | 2 | MSQPEAEEAALAAHAVGHDYVCSGQGVLLPHHQRNRL* | 1083 | ATGTCCCAACCTGAAGCTGAAGAAGCCGCCCTGGCTGCACATGCCGTTGGCCATGAC TATGTATGCTCTGGTCAGGGAGTTCTTCCTCATCACCAGAGGAATCGTTTATGA | 1084 |
| | 3 | MLWWWCLTSSSPEESFMMLRLMRQYLAL* | 1085 | ATGCTCTGGTGGTGTGTCTTACTTCCTCATCACCAGAGGAGTTCTTCCTCTATGA CGGTTGAACCGCCACGGTTTGGCTCTATGA | 1086 |
| | 4 | MNKGIRGQ* | 1087 | ATGAACAAGGGCATCAGAGGCCAGTAG | 1088 |
| hsa-mir-506 | 1 | MPATWLPIKPEVL* | 1089 | ATGCCAGCAACATGGCTTCCTATAAAGCCTGAGGTCCTGTGA | 1090 |
| | 2 | MASYKA* | 1091 | ATGGCTTCCTATAAGCTGA | 1092 |
| | 3 | MQKWPNTKNWYQ* | 1093 | ATGCAAAAATGGCCTAATACAAAAATTGGTACCAGTAG | 1094 |
| | 4 | MRKQLWNQVMSRVWKSLEGSEADMKIKESLDFLQDC* | 1095 | ATGAGGAAGCAACTTTGAACCAGGTAATGAGCAGAGAGTTTGGAAGAGTTGGAGGG GTCAGACAGACATGAAGATAAAGGAAAGTTTAGATTTCTTCAAGACTGCTGA | 1096 |
| hsa-mir-507 | 1 | MPATWLPIKPEVL* | 1097 | ATGCCAGCAACATGGCTTCCTATAAAGCCTGAGGTCCTGA | 1098 |
| | 2 | MASYKA* | 1099 | ATGGCTTCCTATAAAGCCTGA | 1100 |
| | 3 | MQKWPNTKNWYQ* | 1101 | ATGCAAAAATGCCTAATACAAAAATTGGTACCAGTAG | 1102 |
| | 4 | MRKQLWNQVMSRVWKSLEGSEADMKIKESLDFLQDC* | 1103 | ATGAGGAAGCAACTTTGGAACCAGGTAATGAGCAGAGTTTGGAAGAGTTGGAGGG GTCAGACAGACATGAAGATAAAGGAAAGTTTAGATTTCTTCAAGACTGCTGA | 1104 |
| hsa-mir-508 | 1 | MPATWLPIKPEVL* | 1105 | ATGCCAGCAACATGGCTTCCTATAAAGCCTGAGGTCCTGA | 1106 |
| | 2 | MASYKA* | 1107 | ATGGCTTCCTATAAAGCCTGA | 1108 |
| | 3 | MQKWPNTKNWYQ* | 1109 | ATGCAAAAATGCCTAATACAAAAATTGGTACCAGTAG | 1110 |
| | 4 | MRKQLWNQVMSRVWKSLEGSEADMKIKESLDFLQDC* | 1111 | ATGAGGAAGCAACTTTGGAACCAGGTAATGAGCAGAGTTTGAAGAGTTGGAGGG GTCAGACAGACATGAAGATAAAGGAAAGTTTAGATTTCTTCAAGACTGCTGA | 1112 |
| hsa-mir-509-1 | 1 | MPATWLPIKPEVL* | 1113 | ATGCCAGCAACATGGCTTCCTATAAAGCCTGAGGTCCTGTGA | 1114 |
| | 2 | MASYKA* | 1115 | ATGGCTTCCTATAAAGCCTGA | 1116 |
| | 3 | MQKWPNTKNWYQ* | 1117 | ATGCAAAAATGCCTAATACAAAAATTGGTACCAGTAG | 1118 |
| | 4 | MRKQLWNQVMSRVWKSLEGSEADMKIKESLDFLQDC* | 1119 | ATGAGGAAGCAACTTTGGAACCAGGTAATAGCAGAGCAGAGTTTGGAAGAGTTGGAGGG GTCAGAAGCAGACATGAAGATAAAGGAAAGTTTAGATTTCTTCAAGACTGCTGA | 1120 |
| hsa-mir-510 | 1 | MPATWLPIKPEVL* | 1121 | ATGCCAGCAACATGGCTTCCTATAAAGCCTGAGGTCCTGA | 1122 |
| | 2 | MASYKA* | 1123 | ATGGCTTCCTATAAAGCCTGA | 1124 |
| | 3 | MQKWPNTKNWYQ* | 1125 | ATGCAAAAATGGCCTAATACAAAAATTGGTACCAGTAG | 1126 |
| | 4 | MRKQLWNQVMSRVWKSLEGSEADMKIKESLDFLQDC* | 1127 | ATGAGGAAGCAACTTTGGAACCAGGTAATAGCAGAGTTGGAAGAGTTGGAGGG GTCAGAAGCAGACATGAAGATAAAGGAAAGTTTAGATTCTTCAAGACGCTGA | 1128 |
| hsa-mir-512-1 | 1 | METLYRVPFLALECPNLKLEKPPWLHMPLAMTMYALV VVSYFLTRGIVYDVTYEPPGVGSMTDEQGHQRPVAFL AYRVSGQYYYGRTWIQLPVYNGRFRFHNPGPIECTKYP KTQ* | 1129 | ATGGAGACTTTGTACCGTGTCCCGTTCTTAGCGCTTGAATGTCCCAACCTGAAGCTG AAGAAGCCCCCTGGCTGCACATGCCGTTGGCCATGACATGTATGCTCTGGTTGGTG GTGTCTTACTTCGTCTGGTCTTCCTCATCACCAGAGGAGTTCATCTATGATGTTACG GTGTTGGCTCTATGACTGACAATATTATTGGAAGGACTTGGATCCAGCTTCTTGCC TACAGAGTAAGTGGACAATATTATTGGAAGGACTTGGATCCAGCTTCTCGTTTAC AATGGGAGGTTTAGGTTTCATAATCCTGACCGATGAATGCACCAAATATCCCAAA ACTCAATAG | 1130 |

Figure 1 (Continued)

| | | | | | |
|---|---|---|---|---|---|
| hsa-mir-512-2 | 2 | MSQPEAEEAALAAHAVGHDYVCSGGVLLPHHQRNRL* | 1131 | ATGTCCCAACCTGAAGCTGAAGAAGCCGCCCTGGCTGCACATGCCGTTGGCCATGAC TATGTATGCTCTGGTGGTGTTACTTCCTCATCACCAGAGGAATCGTTTATGATGTTA | 1132 |
| | 3 | MLWWWCLTSSSPEESFMMLRLNRQVLAL* | 1133 | ATGCTCTGGTGGTGGTGTCTTACTTCCTCATCACCAGAGGAATCGTTTATGATGTTA CGGTTGAACCGCCAGGTGTTGCTCTGA | 1134 |
| | 4 | MNKGIRGQ* | 1135 | ATGAACAAGGGCATCAGAGGCCAGTAG | 1136 |
| | 1 | METLYRVPPLALECPNLKLKKPPWLHMPLAMTMYALV VSSYPLJTRGIVYDVTVEPPGVGSMTDEQGHQRPVAFL AYRVSGQYYYGRTWIQLPVYNGRFRFHNPGPIECTKYP KTQ* | 1137 | ATGGAGACTTTGTACCGTGTCCGTTCTTAGCGTTGCACATGCCGTTGAATGTCCAACCTGAAGCTG AAGAAGCCGCCCTGGCTGCACATGCCGTTGAATGTTATGATGTATGCTCGGTGGTG GGTTCTTACTTCCTCATCACCAGAGGAATCGTTTATGATGTTACGGTTGAACCGCCA GGTGTTGGCTCTATGACTGATGAACAAGGCCATCAGAGGCCAGTAGCTTTCTGGCC TACAGAGTAAGTGACAATATTATTATGGAAGGACTGGATCCAGTTCCTCGTTTAC AATGGGAGGTTTAGGTTTCATAAATCCTGGACCGATCGAATGCACCAAATATCCAAA ACTCAATAG | 1138 |
| | 2 | MSQPEAEEAALAAHAVGHDYVCSGGVLLPHHQRNRL* | 1139 | ATGTCCCAACCTGAAGCTGAAGAAGCCGCCCTGGCTGCACATGCCGTTGGCCATGAC TATGTATGCTCTGGTGGTGTTACTTCCTCATCACCAGAGGAATCGTTTATGA | 1140 |
| | 3 | MLWWWCLTSSSPEESFMMLRLNRQVLAL* | 1141 | ATGCTCTGGTGGTGGTGTCTTACTTCCTCATCACCAGAGGAATCGTTTATGATGTTA CGGTTGAACCGCCAGGTGTTGCTCTATGA | 1142 |
| | 4 | MNKGIRGQ* | 1143 | ATGAACAAGGGCATCAGAGGCCAGTAG | 1144 |
| hsa-mir-514-1 | 1 | MPATWLPIKPEVL* | 1145 | ATGCCAGCAACATGCTTCCTATAAAGCCTGAGGTCCTGA | 1146 |
| | 2 | MASYKA* | 1147 | ATGGCTTCCTATAAAGCCTGA | 1148 |
| | 3 | MQKWPNTKNWYQ* | 1149 | ATGCAAAAATGGCTAATACAAAAATTGGTACCAGTAG | 1150 |
| | 4 | MRKQLWNQVMSRVWKSLEGSEADMKIKESLDFLQDC* | 1151 | ATGAGGAAGCAACTTTGGAACCAGGTAATGAGCAGAGTTTGGAAGAGTTTGGAGGG GTCAGAAGCAGACATGAAGATAAAGGAAAGTTTAGATTTCTTCAAGACTGCTGA | 1152 |
| hsa-mir-514-2 | 1 | MPATWLPIKPEVL* | 1153 | ATGCCAGCAACATGCTTCCTATAAAGCCTGA | 1154 |
| | 2 | MASYKA* | 1155 | ATGGCTTCCTATAAAGCCTGA | 1156 |
| | 3 | MQKWPNTKNWYQ* | 1157 | ATGCAAAAATGGCCTAATACAAAAATTGGTACCAGTAG | 1158 |
| | 4 | MRKQLWNQVMSRVWKSLEGSEADMKIKESLDFLQDC* | 1159 | ATGAGGAAGCAACTTTGGAACCAGGTAATGAGCAGAGTTTGGAAGAGTTTGGAGGG GTCAGAAGCAGACATGAAGATAAAGGAAAGTTTAGATTTCTTCAAGACTGCTGA | 1160 |
| hsa-mir-514-3 | 1 | MPATWLPIKPEVL* | 1161 | ATGCCAGCAACATGCTTCCTATAAAGCCTGA | 1162 |
| | 2 | MASYKA* | 1163 | ATGGCTTCCTATAAAGCCTGA | 1164 |
| | 3 | MQKWPNTKNWYQ* | 1165 | ATGCAAAAATGGCCTAATACAAAAATTGGTACCAGTAG | 1166 |
| | 4 | MRKQLWNQVMSRVWKSLEGSEADMKIKESLDFLQDC* | 1167 | ATGAGGAAGCAACTTTGGAACCAGGTAATGAGCAGAGTTTGGAAGAGTTTGGAGGG GTCAGAAGCAGACATGAAGATAAAGGAAAGTTTAGATTTCTTCAAGACTGCTGA | 1168 |
| hsa-mir-515-1 | 1 | METLYRVPPLALECPNLKLKKPPWLHMPLAMTMYALV VSSYPLJTRGIVYDVTVEPPGVGSMTDEQGHQRPVAFL AYRVSGQYYYGRTWIQLPVYNGRFRFHNPGPIECTKYP KTQ* | 1169 | ATGGAGACTTTGTACCGTGTCCGTTCTTAGCGTTGCACATGCCGTTGAATGTCCAACCTGAAGCTG AAGAAGCCGCCCTGGCTGCACATGCCGTTGAATGTTATGATGTATGCTCGGTGGTG GGTTCTTACTTCCTCATCACCAGAGGAATCGTTTATGATGTTACGGTTGAACCGCCA GGTGTTGGCTCTATGACTGATGAACAAGGCCATCAGAGGCCAGTAGCTTTCTGGCC TACAGAGTAAGTGACAATATTATTATGGAAGGACTGGATCCAGTTCCTCGTTTAC AATGGGAGGTTTAGGTTTCATAAATCCTGGACCGATCGAATGCACCAAATATCCAAA ACTCAATAG | 1170 |
| hsa-mir-515-1 | 2 | MSQPEAEEAALAAHAVGHDYVCSGGVLLPHHQRNRL* | 1171 | ATGTCCCAACCTGAAGCTGAAGAAGCCGCCCTGGCTGCACATGCCGTTGGCCATGAC TATGTATGCTCTGGTGGTGTTACTTCCTCATCACCAGAGGAATCGTTTATGA | 1172 |

Figure 1 (Continued)

| | | | | |
|---|---|---|---|---|
| hsa-mir-515-2 | 3 | MLWWWCLTSSPEESPMMLRLNRQVLAL* | 1173 | ATGCTCTGGTGGTGGTGTCTTACTTCCTCATCACCAGAGGAATCGTTTATGATGTTA | 1174 |
| | 4 | MNKGIRGQ* | 1175 | ATGAACAAGGGCATCAGAGGCCAGTAG | 1176 |
| | 1 | METLYRVPFLALECPNLKLKKPPWLHMPLAMTMYALV VVSYFLITRGIVYDVTVEPPGVGSMTIDEQGHQRPVAFL AYRVSGQYYYGRTWIQLPVYNGRFHNPGPIECTKYP KTQ* | 1177 | ATGGAGACTTTGTACCGTGCCGTTCTTAGCGTTGCCATGCGTTGGCTGAATGCTGAAGCTG AAGAAGCCGCCCTGGCTGCACATCGCTGGCCATGACTATGTTACGGTTGAACCGCCA GTGTCTTACTTCCTCATCACCAGAGGAATCGTTTATGATGTTACGGTTGAACCGCCA GGTGTTGGCTCTATGACTGATGAACAAGGCCATCAGAGGACTTGGATCGAGCTTCTTGGCC TACAGAGTAAGTGGACAATATTATTATGGAAGGACTTGGATCGAGCTTCTTGTTAC AATGGGAGGTTTAGGTTTCATAATCCTGGACCGATCGAATGCACCAAATATCCAAA ACTCAATAG | 1178 |
| | 2 | MSQPEAEEAALAAHAVGHDYYCSGGGVLLPHHQRNRL* | 1179 | ATGTCCCAACTGAAGCTGAAGAAGCCGCCCTGGCTGCACATGCCGTTGGCCATGAC TATGTATGCTCTGGTGGTGGTGTCTTACTTCCTCATCACCAGAGGAATCGTTTATGATGTTA | 1180 |
| | 3 | MLWWWCLTSSPEESPMMLRLNRQVLAL* | 1181 | ATGCTCTGGTGGTGGTGTCTTACTTCCTCATCACCAGAGGAATCGTTTATGATGTTA CGGTTGAACAAGGGCCAGTAG | 1182 |
| | 4 | MNKGIRGQ* | 1183 | ATGAACAAGGGCATCAGAGGCCAGTAG | 1184 |
| hsa-mir-516a-1 | 1 | METLYRVPFLALECPNLKLKKPPWLHMPLAMTMYALV VVSYFLITRGIVYDVTVEPPGVGSMTIDEQGHQRPVAFL AYRVSGQYYYGRTWIQLPVYNGRFHNPGPIECTKYP KTQ* | 1185 | ATGGAGACTTTGTACCGTGCCGTTCTTAGCGTTGCCATGCGTTGGCTGAATGCTGAAGCTG AAGAAGCCGCCCTGGCTCTTCCTCATCACCAGAGGAATCGTTTATGATGTTACGGTTGAACCGCCA GTGTCTTACTTCCTCATCACCAGAGGAATCGTTTATGATGTTACGGTTGAACCGCCA GGTGTTGGCTCTATGACTGATGAACAAGGCCATCAGAGGACTTGGATCGAGCTTCTTGGCC TACAGAGTAAGTGGACAATATTATTATGGAAGGACTTGGATCGAGCTTCTTGTTAC AATGGGAGGTTTAGGTTTCATAATCCTGGACCGATCGAATGCACCAAATATCCAAA ACTCAATAG | 1186 |
| | 2 | MSQPEAEEAALAAHAVGHDYYCSGGGVLLPHHQRNRL* | 1187 | ATGTCCCAACTGAAGCTGAAGAAGCCGCCCTGGCTGCACATGCCGTTGGCCATGAC TATGTATGCTCTGGTGGTGGTGTCTTACTTCCTCATCACCAGAGGAATCGTTTATGATGTTA | 1188 |
| | 3 | MLWWWCLTSSPEESPMMLRLNRQVLAL* | 1189 | ATGCTCTGGTGGTGGTGTCTTACTTCCTCATCACCAGAGGAATCGTTTATGATGTTA CGGTTGAACCAGGGCCAGGTGTTGGCTCAGTAG | 1190 |
| | 4 | MNKGIRGQ* | 1191 | ATGAACAAGGGCATCAGAGGCCAGTAG | 1192 |
| hsa-mir-516a-2 | 1 | METLYRVPFLALECPNLKLKKPPWLHMPLAMTMYALV VVSYFLITRGIVYDVTVEPPGVGSMTIDEQGHQRPVAFL AYRVSGQYYYGRTWIQLPVYNGRFHNPGPIECTKYP KTQ* | 1193 | ATGGAGACTTTGTACCGTGCCGTTCTTAGCGTTGCCATGCGTTGGCTGAATGCTGAAGCTG AAGAAGCCGCCCTGGCTGCACATCGCTGGCCATGACTATGTTACGGTTGAACCGCCA GTGTCTTACTTCCTCATCACCAGAGGAATCGTTTATGATGTTACGGTTGAACCGCCA GGTGTTGGCTCTATGACTGATGAACAAGGCCATCAGAGGACTTGGATCGAGCTTCTTGGCC TACAGAGTAAGTGGACAATATTATTATGGAAGGACTTGGATCGAGCTTCTTGTTAC AATGGGAGGTTTAGGTTTCATAAJCCTGGACCGATCGAATGCACCAAATATCCAAA ACTCAATAG | 1194 |
| | 2 | MSQPEAEEAALAAHAVGHDYYCSGGGVLLPHHQRNRL* | 1195 | ATGTCCCAACTGAAGCTGAAGAAGCCGCCCTGGCCTGCACATGCCGTTGGCCATGAC TATGTATGCTCTGGTGGTGGTGTCTTACTTCCTCATCACCAGAGGAATCGTTTATGATGTTA | 1196 |
| | 3 | MLWWWCLTSSPEESPMMLRLNRQVLAL* | 1197 | ATGCTCTGGTGGTGGTGTCTTACTTCCTCATCACCAGAGGAATCGTTTATGATGTTA CGGTTGAACAAGGGCATCAGAGGCCAGTAG | 1198 |
| | 4 | MNKGIRGQ* | 1199 | ATGAACAAGGGCATCAGAGGCCAGTAG | 1200 |

Figure 1 (Continued)

| | | | | |
|---|---|---|---|---|
| hsa-mir-516b-1 | 1 | METLYRVPFLALECPNLKLKKPPWLHMPLAMTMYALV VVSYFLITRGIVYDVTVEPPGVGSMTDEQGHQRPVAFL AYRVSGQYYYGRTWIQLPVVNGRFRFHNPGPIECTKYP KTQ* | 1201 | ATGGAGACTTTGTACCGTGTCCCGTTCTTAGCGCTTGAAGCTG AAGAAGCCGCCCTGGCTGCACATGCCGTTGGCCATGACTATGTATGCTCTGGTGGTG GTGTCTTACTTCCTCATCACCAGAGGAATCGTTTATGATGTTACGGTTGAACCGCCA GGTGTTGGCTCTATGACTGATGAACAAGGGCATCAGAGGCCAGTAGCTTTCTTGCC TACAGAGTAAGTGGACAATATTATTATGGAAGGACTTGGATCGAGTCCTGTTTAC AATGGGAGGTTTAGGTTTCATAATCCTGGACCGATCGAATGCACCAAATATCCCAAA ACTCAATAG | 1202 |
| | 2 | MSQPEAEEAALAAHAVGHDYYCSGGGVLLPHHQRNRL* | 1203 | ATGTCCCAACTGAAGCTGAAGAAGCCGCCCTGGCTGCACATGCCGTTGGCCATGAC TATGTATGCTCTGGTGGTGTCGTTACTTCCTCATCACCAGAGGAATCGTTTATGA | 1204 |
| | 3 | MLWWWCLTSSSPEESFMMLRLNRQVLAL* | 1205 | ATGCTCTGGTGGTGGTGTCTTACTTCCTCATCACCAGAGGAATCGTTTATGATGTTA CGGTTGAACCGCCAGGTGTTGGCTCTATGA | 1206 |
| | 4 | MNKGIRGQ* | 1207 | ATGAACAAGGGCATCAGAGGCCAGTAG | 1208 |
| hsa-mir-516b-2 | 1 | METLYRVPFLALECPNLKLKKPPWLHMPLAMTMYALV VVSYFLITRGIVYDVTVEPPGVGSMTDEQGHQRPVAFL AYRVSGQYYYGRTWIQLPVVNGRFRFHNPGPIECTKYP KTQ* | 1209 | ATGGAGACTTTGTACCGTGTCCCGTTCTTAGCGCTTGAAGCTG AAGAAGCCGCCCTGGCTGCACATGCCGTTGGCCATGACTATGTATGCTCTGGTG GTGTCTTACTTCCTCATCACCAGAGGAATCGTTTATGATGTTACGGTTGAACCGCCA GGTGTTGGCTCTATGACTGATGAACAAGGGCATCAGAGGCCAGTAGCTTTCTTGCC TACAGAGTAAGTGGACAATATTATTATGGAAGGACTTGGATCCAGCTTCCTGTTTAC AATGGGAGGTTTAGGTTTCATAATCCTGGACCGATCGAATGCACCAAATATCCCAAA ACTCAATAG | 1210 |
| | 2 | MSQPEAEEAALAAHAVGHDYYCSGGGVLLPHHQRNRL* | 1211 | ATGTCCCAACTGAAGCTGAAGAAGCCGCCCTGGCTGCACATGCCGTTGGCCATGAC TATGTATGCTCTGGTGGTGTCGTTACTTCCTCATCACCAGAGGAATCGTTTATGA | 1212 |
| | 3 | MLWWWCLTSSSPEESFMMLRLNRQVLAL* | 1213 | ATGCTCTGGTGGTGTCGTCTTACTTCCTCATCACCAGAGGAATCGTTTATGATGTTA CGGTTGAACCGCCAGGTGTTGGCTCTATGA | 1214 |
| | 4 | MNKGIRGQ* | 1215 | ATGAACAAGGGCATCAGAGGCCAGTAG | 1216 |
| hsa-mir-517a-1 | 1 | METLYRVPFLALECPNLKLKKPPWLHMPLAMTMYALV VVSYFLITRGIVYDVTVEPPGVGSMTDEQGHQRPVAFL AYRVSGQYYYGRTWIQLPVVNGRFRFHNPGPIECTKYP KTQ* | 1217 | ATGGAGACTTTGTACCGTGTCCCGTTCTTAGCGCTTGAAGCTG AAGAAGCCGCCCTGGCTGCACATGCCGTTGGCCATGACTATGTATGCTCTGGTGGTG GTGTCTTACTTCCTCATCACCAGAGGAATCGTTTATGATGTTACGGTTGAACCGCCA GGTGTTGGCTCTATGACTGATGAACAAGGGCATCAGAGGCCAGTAGCTTTCTTGCC TACAGAGTAAGTGGACAATATTATTATGGAAGGACTTGGATCCAGCTTCCTGTTTAC AATGGGAGGTTTAGGTTTCATAATCCTGGACCGATCGAATGCACCAAATATCCCAAA ACTCAATAG | 1218 |
| | 2 | MSQPEAEEAALAAHAVGHDYYCSGGGVLLPHHQRNRL* | 1219 | ATGTCCCAACTGAAGCTGAAGAAGCCGCCCTGGCTGCACATGCCGTTGGCCATGAC TATGTATGCTCTGGTGGTGTCGTTACTTCCTCATCACCAGAGGAATCGTTTATGA | 1220 |
| | 3 | MLWWWCLTSSSPEESFMMLRLNRQVLAL* | 1221 | ATGCTCTGGTGGTGTCGTCTTACTTCCTCATCACCAGAGGAATCGTTTATGATGTTA CGGTTGAACCGCCAGGTGTTGGCTCTATGA | 1222 |
| | 4 | MNKGIRGQ* | 1223 | ATGAACAAGGGCATCAGAGGCCAGTAG | 1224 |
| hsa-mir-517a-2 | 1 | METLYRVPFLALECPNLKLKKPPWLIRMPLAMTMYALV VVSYFLITRGIVYDVTVEPPGVGSMTDEQGHQRPVAFL AYRVSGQYYYGRTWIQLPVVNGRFRFHNPGPIECTKYP KTQ* | 1225 | ATGGAGACTTTGTACCGTGTCCCGTTCTTAGCGCTTGAAGCTG AAGAAGCCGCCCTGGCTGCACATGCCGTTGGCCATGACTATGTATGCTCTGGTGGTG GTGTCTTACTTCCTCATCACCAGAGGAATCGTTTATGATGTTACGGTTGAACCGCCA GGTGTTGGCTCTATGACTGATGAACAAGGGCATCAGAGGCCAGTAGCTTTCTTGCC TACAGAGTAAGTGGAGGTTTAGGTTTCATAATCCTGGACCGATCGAATGCACCAAATATCCCAAA ACTCAATAG | 1226 |

Figure 1 (Continued)

| | | | | |
|---|---|---|---|---|
| | 2 | MSQPEAEEAALAAHAVGHDYVCSGGGVLLPHHQRNRL* | 1227 | ATGTCCCAACCTGAAGCTGAAGAAGCCGCCCTGGCTGCACATGCCGTTGGCCATGAC TATGTATGCTCTGGTGGTGTCTTACTTCCTCATCACCAGAGGAATCGTTTATGATGAC | 1228 |
| | 3 | MLWWWCLTSSSPEESFMMLRLNRQVLAL* | 1229 | ATGCTCTGGTGGTGGTGTCTTACTTCCTCATCACCAGAGGAATCGTTTATGATGTTA CGGTTGAACCGCCAGGTGTTGGCTCTATAG | 1230 |
| | 4 | MNKGIRGQ* | 1231 | ATGAACAAGGGCATCAGAGGCCAGTAG | 1232 |
| hsa-mir-517c | 1 | METLYRVPFLALECPNLKLKKPPWLHMPLAMTMYALV VVSYFLITRGIVYDVTVEPPGVGSMTDEQGHQRPVAFL AYRVSGQYYYGRTWIQLPVYNGRFFHNPGPIECTKYP KTQ* | 1233 | ATGGAGACTTTGTACCGTGTCCCGTTCTTAGCGCTTGAATGTCCAACCTGAAGCTG AAGAAGCCGCCCTGGCTGCACATGCCGTTGGCCATGACTATGTATGCTCTGGTGGTG GTGTCTTACTTCCTCATCACTGACTGATGAACAAGGCATCAGAGGCCAGTAGTTTG TAGGTGTCTATGATGAACAAGGCATCAGAGGCATCAGAGGACTTGGATCCAGTTCTTGGCC TACAGAGTAAGTGGACAATATTATTACGAAGGACTTGGATCCAGTCCAGTTCTGTTTAC AATGGGAGGTTTAGGTTTCATAATCCTGGACCGATCGAATGCACCAAATATCCCAAA ACTCAATAG | 1234 |
| | 2 | MSQPEAEEAALAAHAVGHDYVCSGGGVLLPHHQRNRL* | 1235 | ATGTCCCAACCTGAAGCTGAAGAAGCCGCCCTGGCTGCACATGCCGTTGGCCATGAC TATGTATGCTCTGGTGGTGTCTTACTTCCTCATCACCAGAGGAATCGTTTATGATGA | 1236 |
| | 3 | MLWWWCLTSSSPEESFMMLRLNRQVLAL* | 1237 | ATGCTCTGGTGGTGGTGTCTTACTTCCTCATCACCAGAGGAATCGTTTATGATGTTA CGGTTGAACCGCCAGGTGTTGGCTCTATAG | 1238 |
| | 4 | MNKGIRGQ* | 1239 | ATGAACAAGGGCATCAGAGGCCAGTAG | 1240 |
| hsa-mir-518a-1 | 1 | METLYRVPFLALECPNLKLKKPPWLHMPLAMTMYALV VVSYFLITRGIVYDVTVEPPGVGSMTDEQGHQRPVAFL AYRVSGQYYYGRTWIQLPVYNGRFFHNPGPIECTKYP KTQ* | 1241 | ATGGAGACTTTGTACCGTGTCCCGTTCTTAGCGCTTGAATGTCCAACCTGAAGCTG AAGAAGCCGCCCTGGCTGCACATGCCGTTGGCCATGACTATGTATGCTCTGGTGGTG GTGTCTTACTTCCTCATGACTGATGAACAAGGCATCAGAGGCCAGTAGTTCTTGGCC TACAGAGTAAGTGGACAATATTATTAATCCTGAAGGACTTGGATCCAGTCCAGTTCTGTTTAC AATGGGAGGTTTAGGTTTCATAATCCTGGACCGATCGAATGCACCAAATATCCCAAA ACTCAATAG | 1242 |
| | 2 | MSQPEAEEAALAAHAVGHDYVCSGGGVLLPHHQRNRL* | 1243 | ATGTCCCAACCTGAAGCTGAAGAAGCCGCCCTGGCTGCACATGCCGTTGGCCATGAC TATGTATGCTCTGGTGGTGTCTTACTTCCTCATCACCAGAGGAATCGTTTATGA | 1244 |
| | 3 | MLWWWCLTSSSPEESFMMLRLNRQVLAL* | 1245 | ATGCTCTGGTGGTGGTGTCTTACTTCCTCATCACCAGAGGAATCGTTTATGATGTTA CGGTTGAACCGCCAGGTGTTGGCTCTATAG | 1246 |
| | 4 | MNKGIRGQ* | 1247 | ATGAACAAGGGCATCAGAGGCCAGTAG | 1248 |
| hsa-mir-518a-2 | 1 | METLYRVPFLALECPNLKLKKPPWLHMPLAMTMYALV VVSYFLITRGIVYDVTVEPPGVGSMTDEQGHQRPVAFL AYRVSGQYYYGRTWIQLPVYNGRFFHNPGPIECTKYP KTQ* | 1249 | ATGGAGACTTTGTACCGTGTCCCGTTCTTAGCGCTTGAATGTCCAACCTGAAGCTG AAGAAGCCGCCCTGGCTGCACATGCCGTTGGCCATGACTATGTATGCTCTGGTGGTG GTGTCTTGGCTCTATGACTGATGAACAAGGCATCAGAGGCCAGTAGTTCTTGGCC GGTGTTAAGTGGACAATATATTATTAATCCTGAAGGACTTGGATCCAGTCAGTTTCTGTTTAC TACAGAGTAAGTGGACAATATATTATTAATCCTGGACCGATCGAATGCACCAAATATCCCAAA ACTCAATAG | 1250 |
| | 2 | MSQPEAEEAALAAHAVGHDYVCSGGGVLLPHHQRNRL* | 1251 | ATGTCCCAACCTGAAGCTGAAGAAGCCGCCCTGGCTGCACATGCCGTTGGCCATGAC TATGTATGCTCTGGTGGTGTCTTACTTCCTCATCACCAGAGGAATCGTTTATGATGAC | 1252 |
| | 3 | MLWWWCLTSSSPEESFMMLRLNRQVLAL* | 1253 | ATGCTCTGGTGGTGGTGTCTTACTTCCTCATCACCAGAGGAATCGTTTATGATGTTA CGGTTGAACCGCCAGGTGTTGGCTCTATAG | 1254 |
| | 4 | MNKGIRGQ* | 1255 | ATGAACAAGGGCATCAGAGGCCAGTAG | 1256 |

Figure 1 (Continued)

| | | | | | |
|---|---|---|---|---|---|
| hsa-mir-518b | 1 | METLYRVPFLALECPNLKLKKPPWLHMPLAMTMYALV VVSYFLITRGIVYDVTVEPPGVGSMTDEQGHQRPVAFL AYRVSGQYYYGRTWIQLPVVNGRFRFHNPGPIECTKYP KTQ* | 1257 | ATGGAGACTTTGTACCGTGTCCCGTTCTTAGCGCTTGAATGTCCCAACCTGAAGCTG AAGAAGCCGCCCTGGCTGCACATGCCGTTGGCCATGACTATGTATGCTCTGGTGGTG GTGTCTTACTTCCTCATCACCAGAGGAATCGTTTATGATGTTACGGTTGAACCGCCA GGTGTTGGCTCTATGACTGATGAACAAGGGCATCAGAGGCCAGTAGCTTTCTTGGCC TACAGAGTAAGTGGACAATATTATTATGGAAGACTTGGATCGAATCCAGTTCCTGTTTAC AATGGGAGGTTTAGGTTTCATAATCCTGGACCGATCGAATGCACCAAATATCCCAAA ACTCAATAG |
| | 2 | MSQPEAEEAALAAHAVGHDYYCSGGGVLLPHHQRNRL* | 1259 | ATGTCCCAACCTGAAGCTGAAGAAGCCGCCCTGGCTGCACATGCCGTTGGCCATGAC TATGTATGCTCTGGTGGTGGTGTCTTACTTCCTCATCACCAGAGGAATCGTTTATGA |
| | 3 | MLWWWCLTSSSPEESFMMLRLNRQVLAL* | 1261 | ATGCTCTGGTGGTGGTGTCTTACTTCCTCATCACCAGAGGAATCGTTTATGATGTTA CGGTTGAACCGCCAGGTGTTGGCTCTATGA |
| | 4 | MNKGIRGQ* | 1263 | ATGAACAAGGGCATCAGAGGCCAGTAG |
| hsa-mir-518c | 1 | METLYRVPFLALECPNLKLKKPPWLHMPLAMTMYALV VVSYFLITRGIVYDVTVEPPGVGSMTDEQGHQRPVAFL AYRVSGQYYYGRTWIQLPVVNGRFRFHNPGPIECTKYP KTQ* | 1265 | ATGGAGACTTTGTACCGTGTCCCGTTCTTAGCGCTTGAATGTCCCAACCTGAAGCTG AAGAAGCCGCCCTGGCTGCACATGCCGTTGGCCATGACTATGTATGCTCTGGTGGTG GTGTCTTACTTCCTCATCACCAGAGGAATCGTTTATGATGTTACGGTTGAACCGCCA GGTGTTGGCTCTATGACTGATGAACAAGGGCATCAGAGGCCAGTAGCTTTCTTGGCC TACAGAGTAAGTGGACAATATTATTATGGAAGACTTGGATCAGCTTCCTGTTTAC AATGGGAGGTTTAGGTTTCATAATCCTGGACCGATCGAATGCACCAAATATCCCAAA ACTCAATAG |
| | 2 | MSQPEAEEAALAAHAVGHDYYCSGGGVLLPHHQRNRL* | 1267 | ATGTCCCAACCTGAAGCTGAAGAAGCCGCCCTGGCTGCACATGCCGTTGGCCATGAC TATGTATGCTCTGGTGGTGGTGTCTTACTTCCTCATCACCAGAGGAATCGTTTATGA |
| | 3 | MLWWWCLTSSSPEESFMMLRLNRQVLAL* | 1269 | ATGCTCTGGTGGTGGTGTCTTACTTCCTCATCACCAGAGGAATCGTTTATGATGTTA CGGTTGAACCGCCAGGTGTTGGCTCTATGA |
| | 4 | MNKGIRGQ* | 1271 | ATGAACAAGGGCATCAGAGGCCAGTAG |
| hsa-mir-518d | 1 | METLYRVPFLALECPNLKLKKPPWLHMPLAMTMYALV VVSYFLITRGIVYDVTVEPPGVGSMTDEQGHQRPVAFL AYRVSGQYYYGRTWIQLPVVNGRFRFHNPGPIECTKYP KTQ* | 1273 | ATGGAGACTTTGTACCGTGTCCCGTTCTTAGCGCTTGAATGTCCAACCTGAAGCTG AAGAAGCCGCCCTGGCTGCACATGCCGTTGGCCATGACTATGTATGCTCTGGTGGTG GTGTCTTACTTCCTCATCACCAGAGGAATCGTTTATGATGTTACGGTTGAACCGCCA GGTGTTGGCTCTATGACTGATGAACAAGGGCATCAGAGGCCAGTAGCTTTCTTGGCC TACAGAGTAAGTGGACAATATTATTATGGAAGACTTGGATCCGAATCCAGTTCCTGTTTAC AATGGGAGGTTTAGGTTTCATAATCCTGGACCGATCGAATGCACCAAATATCCCAAA ACTCAATAG |
| | 2 | MSQPEAEEAALAAHAVGHDYYCSGGGVLLPHHQRNRL* | 1275 | ATGTCCCAACCTGAAGCTGAAGAAGCCGCCCTGGCTGCACATGCCGTTGGCCATGAC TATGTATGCTCTGGTGGTGGTGTCTTACTTCCTCATCACCAGAGGAATCGTTTATGA |
| | 3 | MLWWWCLTSSSPEESFMMLRLNRQVLAL* | 1277 | ATGCTCTGGTGGTGGTGTCTTACTTCCTCATCACCAGAGGAATCGTTTATGATGTTA CGGTTGAACCGCCAGGTGTTGGCTCTATGA |
| | 4 | MNKGIRGQ* | 1279 | ATGAACAAGGGCATCAGAGGCCAGTAG |
| hsa-mir-518e | 1 | METLYRVPFLALECPNLKLKKPPWLIRMPLAMTMYALV VVSYFLITRGIVYDVTVEPPGVGSMTDEQGHQRPVAFL AYRVSGQYYYGRTWIQLPVVNGRFRFHNPGPIECTKYP KTQ* | 1281 | ATGGAGACTTTGTACCGTGTCCCGTTCTTAGCGCTTGAATGTCCCAACCTGAAGCTG AAGAAGCCGCCCTGGCTGCACATGCCGTTGGCCATGACTATGTATGCTCTGGTGGTG GTGTCTTACTTCCTCATCACCAGAGGAATCGTTTATGATGTTACGGTTGAACCGCCA GGTGTTGGCTCTATGACTGATGAACAAGGGCATCAGAGCCCAGTAGCTTTCTTGGCC TACAGAGTAAGTGGACAATATTATTATGGAAGACTTGGATCGAATCCAGCTTCCTGTTTAC AATGGGAGGTTTAGGTTTCATAATCCTGGACCGATCGAATGCACCAAATATCCCAAA ACTCAATAG | 1282 |

Figure 1 (Continued)

| | | | | |
|---|---|---|---|---|
| | 2 | MSQPEAEEAALAAHAVGHDYVCSGGGVLLPHHQRNRL* | 1283 | ATGTCCCAACCTGAAGCTGAAGAAGCGGCCCTGGCTGCACATGCCGTTGGCCATGAC TATGTATGCTCTGGTGGTGTCTTACTTCCTCATCACCAGAGGAATCGTTTATGATGAC | 1284 |
| hsa-mir-518f | 3 | MLWWWCLTSSSPEESFMMLRLNRQVLAL* | 1285 | ATGCTCTGGTGGTGGTGTCTTACTTCCTCATCACCAGAGGAATCGTTTATGATGTTA CGGTTGAACCGCCAGGTGTTGGCTCTAGAGGCCAGTAG | 1286 |
| | 4 | MNKGIRGQ* | 1287 | ATGAACAAGGGCATCAGAGGCCAGTAG | 1288 |
| | 1 | METLYRVPFLALECPNLKLKKPPWLHMPLAMTMYALV VVSYFLITRGIVYDVTVEPPGVGSMTDEQGHQRPVAFL AYRVSGQYYYGRTWIQLPVYNGRFRFHNPGPIECTKYP KTQ* | 1289 | ATGGAGACTTTGTACCGTGCCCGTTCTAGCGCTTGAATGTCCAACCTGAAGCTG AAGAAGCCGCCCTGGCTGCACATGCCGTTGGCCATGACTATGTATGCTCTGGTGGTG GTGTCTTACTTCCTCATCACCAGAGGAATCGTTTATGATGACGTTACGGTTGAACCGCCA GGTGTGTCCTATGACTGGACACATATTATTATCCGGACCGATCAGAGGACTTGGATCAGCTTCTGGCC TACAGAGTAAGTGGACAATATTATTATCCGGACCGATCGAATGCACCAAATATCCCAAA AATGGGAGGTTTAGGTTTCATAATCCTGGACCGATCGAATGCACCAAATATCCCAAA ACTCAATAG | 1290 |
| | 2 | MSQPEAEEAALAAHAVGHDYVCSGGGVLLPHHQRNRL* | 1291 | ATGTCCCAACCTGAAGCTGAAGAAGCCGCCCTGGCTGCACATGCCGTTGGCCATGAC TATGTATGCTCTGGTGGTGGTGTCTTACTTCCTCATCACCAGAGGAATCGTTTATGA | 1292 |
| | 3 | MLWWWCLTSSSPEESFMMLRLNRQVLAL* | 1293 | ATGCTCTGGTGGTGGTGTCTTACTTCCTCATCACCAGAGGAATCGTTTATGATGTTA CGGTTGAACCGCCAGGTGTTGGCTCTAG | 1294 |
| | 4 | MNKGIRGQ* | 1295 | ATGAACAAGGGCATCAGAGGCCAGTAG | 1296 |
| hsa-mir-519a-1 | 1 | METLYRVPFLALECPNLKLKKPPWLHMPLAMTMYALV VVSYFLITRGIVYDVTVEPPGVGSMTDEQGHQRPVAFL AYRVSGQYYYGRTWIQLPVYNGRFRFHNPGPIECTKYP KTQ* | 1297 | ATGGAGACTTTGTACCGTGCCCGTTCTAGCGCTTGAATGTCCAACCTGAAGCTG AAGAAGCCGCCCTGGCTGCACATGCCGTTGGCCATGACTATGTATGCTCTGGTGGTG GTGTCTTACTTCCTCATGACTGATGAACAAGGCATCAGAGGCCAGTAGCTTCTTGGCC ACAGAGTAAGTGGACAATATTATTATCCGGACCGATCGAATGCACCAAATATCCCAAA AATGGGAGGTTTAGGTTTCATAATCCTGGACCGATCGAATGCACCAAATATCCCAAA ACTCAATAG | 1298 |
| | 2 | MSQPEAEEAALAAHAVGHDYVCSGGGVLLPHHQRNRL* | 1299 | ATGTCCCAACCTGAAGCTGAAGAAGCCGCCCTGGCTGCACATGCCGTTGGCCATGAC TATGTATGCTCTGGTGGTGGTGTCTTACTTCCTCATCACCAGAGGAATCGTTTATGA | 1300 |
| | 3 | MLWWWCLTSSSPEESFMMLRLNRQVLAL* | 1301 | ATGCTCTGGTGGTGGTGTCTTACTTCCTCATCACCAGAGGAATCGTTTATGATGTTA CGGTTGAACCGCCAGGTGTTGGCTCAGTAG | 1302 |
| | 4 | MNKGIRGQ* | 1303 | ATGAACAAGGGCATCAGAGGCCAGTAG | 1304 |
| hsa-mir-519a-2 | 1 | METLYRVPFLALECPNLKLKKPPWLHMPLAMTMYALV VVSYFLITRGIVYDVTVEPPGVGSMTDEQGHQRPVAFL AYRVSGQYYYGRTWIQLPVYNGRFRFHNPGPIECTKYP KTQ* | 1305 | ATGGAGACTTTGTACCGTGCCCGTTCTAGCGCTTGAATGTCCAACCTGAAGCTG AAGAAGCCGCCCTGGCTGCACATGCCGTTGGCCATGACTATGTATGCTCTGGTGGTG GTGTCTTACTTCCTCATGACTGATGAACAAGGCATCAGAGGCCAGTAGCTTCTTGGCC GGTGTGCCTATGACTGATGAACAAGGGCATCAGAGGCCAGTAGCTTCTTGGCC ACAGAGTAAGTGGACAATATTATTATCCGGACCGATCGAATGCACCAAATATCCCAAA AATGGGAGGTTTAGGTTTCATAATCCTGGACCGATCGAATGCACCAAATATCCCAAA ACTCAATAG | 1306 |
| | 2 | MSQPEAEEAALAAHAVGHDYVCSGGGVLLPHHQRNRL* | 1307 | ATGTCCCAACCTGAAGCTGAAGAAGCCGCCCTGGCTGCACATGCCGTTGGCCATGAC TATGTATGCTCTGGTGGTGGTGTCTTACTTCCTCATCACCAGAGGAATCGTTTATGA | 1308 |
| | 3 | MLWWWCLTSSSPEESFMMLRLNRQVLAL* | 1309 | ATGCTCTGGTGGTGGTGTCTTACTTCCTCATCACCAGAGGAATCGTTTATGATGTTA CGGTTGAACCGCCAGGTGTTGGCTCAGTAG | 1310 |
| | 4 | MNKGIRGQ* | 1311 | ATGAACAAGGGCATCAGAGGCCAGTAG | 1312 |

Figure 1 (Continued)

| | | | | |
|---|---|---|---|---|
| hsa-mir-519c | 1 | METLYRVPFLALECPNLKLKKPPWLHMPLAMTMYALV VVSYFLITRGIVYDVTVEPPGVGSMTDEQGHQRPVAFL AYRVSGQYYYGRTWIQLPVYNGRFRFHNPGPIECTKYP KTQ* | 1313 | ATGGAGACTTTGTACCGTGTCCCGTTCTTAGCGCTTGAAATGTCCCAACCTGAAGCTG AAGAAGCCGCCCTGGCTGCACATGCCGTTGGCCATGACTATGTATGCTCTGGTGGTG GTGTCTTACTTCCTCATCACCAGAGGAATCGTTTATGATGTTACGGTTGAACCGCCA GGTGTTGGCTCTATGACTGATGAACAAGGGCATCAGAGGCCAGTAGCTTTCTTGGCC TACAGAGTAAGTGGACAATATTATTACGGATCCAGTTGGATCCAGCTTCCTGTTTAC AATGGGAGGTTTAGGTTTCATAATCCTGGACCGATCGAATGCACCAAATATCCCAAA ACTCAATAG | 1314 |
| | 2 | MSQPEAEEAALAAHAVGHDYYCSGGGVLLPHHQRNRL* | 1315 | ATGTCCCAACCTGAAGCTGAAGAAGCCGCCCTGGCTGCACATGCCGTTGGCCATGAC TATGTATGCTCTGGTGGTGTCTTACTTCCTCATCACCAGAGGAATCGTTTATGA | 1316 |
| | 3 | MLWWWCLTSSSPEESFMMLRLNRQVLAL* | 1317 | ATGCTCTGGTGGTGTCTTACTTCCTCATCACCAGAGGAATCGTTTATGATGTTA CGGTTGAACCGCCAGGTGTTGGCTCTATGA | 1318 |
| | 4 | MNKGIRGQ* | 1319 | ATGAACAAGGGCATCAGAGGCCAGTAG | 1320 |
| hsa-mir-519d | 1 | METLYRVPFLALECPNLKLKKPPWLHMPLAMTMYALV VVSYFLITRGIVYDVTVEPPGVGSMTDEQGHQRPVAFL AYRVSGQYYYGRTWIQLPVYNGRFRFHNPGPIECTKYP KTQ* | 1321 | ATGGAGACTTTGTACCGTGTCCCGTTCTTAGCGCTTGAAATGTCCCAACCTGAAGCTG AAGAAGCCGCCCTGGCTGCACATGCCGTTGGCCATGACTATGTATGCTCTGGTG GTGTCTTACTTCCTCATCACCAGAGGAATCGTTTATGATGTTACGGTTGAACCGCCA GGTGTTGGCTCTATGACTGATGAACAAGGGCATCAGAGGCCAGTAGCTTTCTTGGCC TACAGAGTAAGTGGACAATATTATTATGGAAGGACTTGGATCCAGCTTCCTGTTTAC AATGGGAGGTTTAGGTTTCATAATCCTGGACCGATCGAATGCACCAAATATCCCAAA ACTCAATAG | 1322 |
| | 2 | MSQPEAEEAALAAHAVGHDYYCSGGGVLLPHHQRNRL* | 1323 | ATGTCCCAACCTGAAGCTGAAGAAGCCGCCCTGGCTGCACATGCCGTTGGCCATGAC TATGTATGCTCTGGTGGTGTCTTACTTCCTCATCACCAGAGGAATCGTTTATGA | 1324 |
| | 3 | MLWWWCLTSSSPEESFMMLRLNRQVLAL* | 1325 | ATGCTCTGGTGGTGTCTTACTTCCTCATCACCAGAGGAATCGTTTATGATGTTA CGGTTGAACCAGGTGTTGGCTCTATGA | 1326 |
| | 4 | MNKGIRGQ* | 1327 | ATGAACAAGGCATCAGAGGCCAGTAG | 1328 |
| hsa-mir-519e | 1 | METLYRVPFLALECPNLKLKKPPWLHMPLAMTMYALV VVSYFLITRGIVYDVTVEPPGVGSMTDEQGHQRPVAFL AYRVSGQYYYGRTWIQLPVYNGRFRFHNPGPIECTKYP KTQ* | 1329 | ATGGAGACTTTGTACCGTGTCCCGTTCTTAGCGCTTGAAATGTCCCAACCTGAAGCTG AAGAAGCCGCCCTGGCTGCACATGCCGTTGGCCATGACTATGTATGCTCTGGTGGTG GTGTCTTACTTCCTCATCACCAGAGGAATCGTTTATGATGTTACGGTTGAACCGCCA GGTGTTGGCTCTATGACTGATGAACAAGGGCATCAGAGGCCAGTAGCTTTCTTGGCC TACAGAGTAAGTGGACAATATTATTATGGAAGGACTTGGATCCAGCTTCCTGTTTAC AATGGGAGGTTTAGGTTTCATAATCCTGGACCGATCGAATGCACCAAATATCCCAAA ACTCAATAG | 1330 |
| | 2 | MSQPEAEEAALAAHAVGHDYYCSGGGVLLPHHQRNRL* | 1331 | ATGTCCCAACCTGAAGCTGAAGAAGCCGCCCTGGCTGCACATGCCGTTGGCCATGAC TATGTATGCTCTGGTGGTGTCTTACTTCCTCATCACCAGAGGAATCGTTTATGA | 1332 |
| | 3 | MLWWWCLTSSSPEESFMMLRLNRQVLAL* | 1333 | ATGCTCTGGTGGTGTCTTACTTCCTCATCACCAGAGGAATCGTTTATGATGTTA CGGTTGAACCAGGTGTTGGCTCTATGA | 1334 |
| | 4 | MNKGIRGQ* | 1335 | ATGAACAAGGGCATCAGAGGCCAGTAG | 1336 |
| hsa-mir-520c-1 | 1 | METLYRVPFLALECPNLKLKKPPWLRMPLAMTMYALV VVSYFLITRGIVYDVTVEPPGVGSMTDEQGHQRPVAFL AYRVSGQYYYGRTWIQLPVYNGRFRFHNPGPIECTKYP KTQ* | 1337 | ATGGAGACTTTGTACCGTGTCCCGTTCTTAGCGCTTGAAATGTCCCAACCTGAAGCTG AAGAAGCCGCCCTGGCTGCACATGCCGTTGGCCATGACTATGTATGCTCTGGTGGTG GTGTCTTACTTCCTCATCACCAGAGGAATCGTTTATGATGTTACGGTTGAACCGCCA GGTGTTGGCTCTATGACTGATGAACAAGGGCATCAGAGGCCAGTAGCTTTCTTGGCC TACAGAGTAAGTGGACAATATTATTATGGAAGGACTTGGATCCAGCTTCCTGTTTAC AATGGGAGGTTTAGGTTTCATAATCCTGGACCGATCGAATGCACCAAATATCCCAAA ACTCAATAG | 1338 |

Figure 1 (Continued)

| | | | | |
|---|---|---|---|---|
| hsa-mir-520c-2 | 2 | MSQPEAEEAALAAHAVGHDYVCSGGGVLLPHHQRNRL* | 1339 | ATGTCCCAACCTGAAGCTGAAGAAGCCGCCCTGGCTGCACATGCCGTTGGCCATGAC TATGTATGCTCTGGTGGTGTCTTACTTCCTCATCACCAGAGGAATCGTTTATGATGAC | 1340 |
| | 3 | MLWWWCLTSSSPEESFMMLRLNRQVLAL* | 1341 | ATGCTCTGGTGGTGGTGTCTTACTTCCTCATCACCAGAGGAATCGTTTATGATGTTA CGGTTGAACCGCCAGGTGTTGGCTCTATAG | 1342 |
| | 4 | MNKGIRGQ* | 1343 | ATGAACAAGGGCATCAGAGGCCAGTAG | 1344 |
| | 1 | METLYRVPFLALECPNLKLKKPPWLHMPLAMTMYALV VVSYFLITRGIVYDVTVEPPGVGSMTDEQGHQRPVAFL AYRVSGQYYYGRTWIQLPVYNGRFFHNPGPIECTKYP KTQ* | 1345 | ATGGAGACTTTGTACCGTGCCGTTCCGTTCTTAGCGCTTGAATGTCCCAACCTGAAGCTG AAGAAGCCGCCCTGGCTGCACATGCCGTTGGCCATGACTATGTATGCTCTGGTGGTG GTGTCTTACTTCCTCATCACTGACTGATGAACAAGGCATCAGAGGCCAGTAGTTCTTGCC TACAGAGTAAGTGGACAATATTATTATCCTGGACCGATCGAATGCACCAAATATCCCAAA ACTCAATAG | 1346 |
| | 2 | MSQPEAEEAALAAHAVGHDYVCSGGGVLLPHHQRNRL* | 1347 | ATGTCCCAACCTGAAGCTGAAGAAGCCGCCCTGGCTGCACATGCCGTTGGCCATGAC TATGTATGCTCTGGTGGTGTCTTACTTCCTCATCACCAGAGGAATCGTTTATGATGTTA | 1348 |
| | 3 | MLWWWCLTSSSPEESFMMLRLNRQVLAL* | 1349 | ATGCTCTGGTGGTGGTGTCTTACTTCCTCATCACCAGAGGAATCGTTTATGATGTTA CGGTTGAACCGCCAGGTGTTGGCTCTATGA | 1350 |
| | 4 | MNKGIRGQ* | 1351 | ATGAACAAGGGCATCAGAGGCCAGTAG | 1352 |
| hsa-mir-520d | 1 | METLYRVPFLALECPNLKLKKPPWLHMPLAMTMYALV VVSYFLITRGIVYDVTVEPPGVGSMTDEQGHQRPVAFL AYRVSGQYYYGRTWIQLPVYNGRFFHNPGPIECTKYP KTQ* | 1353 | ATGGAGACTTTGTACCGTGCCGTTCCGTTCTTAGCGCTTGAATGTCCCAACCTGAAGCTG AAGAAGCCGCCCTGGCTGCACATGCCGTTGGCCATGACTATGTATGCTCTGGTGGTG GTGTCTTACTTCCTCATCACTGACTGATGAACAAGGCATCAGAGGCCAGTAGTTCTTGCC TACAGAGTAAGTGGACAATATTATTATCCTGGACCGATCGAATGCACCAAATATCCCAAA ACTCAATAG | 1354 |
| | 2 | MSQPEAEEAALAAHAVGHDYVCSGGGVLLPHHQRNRL* | 1355 | ATGTCCCAACCTGAAGCTGAAGAAGCCGCCCTGGCTGCACATGCCGTTGGCCATGAC TATGTATGCTCTGGTGGTGTCTTACTTCCTCATCACCAGAGGAATCGTTTATGATGAC | 1356 |
| | 3 | MLWWWCLTSSSPEESFMMLRLNRQVLAL* | 1357 | ATGCTCTGGTGGTGGTGTCTTACTTCCTCATCACCAGAGGAATCGTTTATGATGTTA CGGTTGAACCGCCAGGTGTTGGCTCTATGA | 1358 |
| | 4 | MNKGIRGQ* | 1359 | ATGAACAAGGGCATCAGAGGCCAGTAG | 1360 |
| hsa-mir-520e | 1 | METLYRVPFLALECPNLKLKKPPWLHMPLAMTMYALV VVSYFLITRGIVYDVTVEPPGVGSMTDEQGHQRPVAFL AYRVSGQYYYGRTWIQLPVYNGRFFHNPGPIECTKYP KTQ* | 1361 | ATGGAGACTTTGTACCGTGCCGTTCCGTTCTTAGCGCTTGAATGTCCCAACCTGAAGCTG AAGAAGCCGCCCTGGCTGCACATGCCGTTGGCCATGACTATGTATGCTCTGGTGGTG GTGTCTTACTTCCTCATCACTGACTGATGAACAAGGCATCAGAGGCCAGTAGTTCTTGCC TACAGAGTAAGTGGACAATATTATTATCCTGGACCGATCGAATGCACCAAATATCCCAAA ACTCAATAG | 1362 |
| | 2 | MSQPEAEEAALAAHAVGHDYVCSGGGVLLPHHQRNRL* | 1363 | ATGTCCCAACCTGAAGCTGAAGAAGCCGCCCTGGCTGCACATGCCGTTGGCCATGAC TATGTATGCTCTGGTGGTGTCTTACTTCCTCATCACCAGAGGAATCGTTTATGATGAC | 1364 |
| | 3 | MLWWWCLTSSSPEESFMMLRLNRQVLAL* | 1365 | ATGCTCTGGTGGTGGTGTCTTACTTCCTCATCACCAGAGGAATCGTTTATGATGTTA CGGTTGAACCGCCAGGTGTTGGCTCTATGA | 1366 |
| | 4 | MNKGIRGQ* | 1367 | ATGAACAAGGGCATCAGAGGCCAGTAG | 1368 |

Figure 1 (Continued)

| | | | | |
|---|---|---|---|---|
| hsa-mir-520f | 1 | METLYRVPFLALECPNLKLKKPPWLHMPLAMTMYALVVVSYFLITRGIVYDVTVEPPGVGSMTDEQGHQRPVAFLAYRVSGQYYYGRTWIQLPVVNGRFRFHNPGPIECTKYPKTQ* | 1369 | ATGGAGACTTTGTACCGTGTCCGTTCTTAGCGCTTGAATGTCCAACCTGAAGCTGAAGAAGCCGCCCTTCCTCATCACCAGAGGAATGTCTTGGTGGTGGTGTCTTACTTCCTCATCACCAGAGGAATCGTTTATGATGTTACGGTTGAACCGCAGTAGCTTTCTTGGCCGGTGTTGGCTCTATGACTGATGAACAAGGGCATCAGAGGCCAGTAGCTTTCTTGGCCTACAGAGTAAGTGGACAATATTATTAGGAAGGACTTGGATCCAGCTTCCTGTTTACAATGGGAGGTTTAGGTTTCATAATCCTGGACCGATCGAATGCACCAAATATCCCAAAACTCAATAG | 1370 |
| | 2 | MSQPEAEEAALAAHAVGHDYVCSGGGVLLPHHQRNRL* | 1371 | ATGTCCCAACCTGAAGCTGAAGAAGCCGCCCTGGCTGCACATGCCGTTGGCCATGACTATGTATCTCTGGTGGTGTCTTACTTCCTCATCACCAGAGGAATCGTTTATGA | 1372 |
| | 3 | MLWWWCLTSSSPEESFMMLRLNRQVLAL* | 1373 | ATGCTCTGGTGGTGGTGTCTTACTTCCTCATCACCAGAGGAATCGTTTATGATGTTACGGTTGAACCGCCAGGTGTTGGCTCTATGA | 1374 |
| | 4 | MNKGIRGQ* | 1375 | ATGAACAAGGGCATCAGAGGCCAGTAG | 1376 |
| hsa-mir-520g | 1 | METLYRVPFLALECPNLKLKKPPWLHMPLAMTMYALVVVSYFLITRGIVYDVTVEPPGVGSMTDEQGHQRPVAFLAYRVSGQYYYGRTWIQLPVVNGRFRFHNPGPIECTKYPKTQ* | 1377 | ATGGAGACTTTGTACCGTGTCCGTTCTTAGCGCTTGAATGTCCAACCTGAAGCTGAAGAAGCCGCCCTTCCTCATCACCAGAGGAATGTCTTGGTGGTGTCTTACTTCCTCATCACCAGAGGAATCGTTTATGATGTTACGGTTGAACCGCAGTAGCTTTCTTGGCCGGTGTTGGCTCTATGACTGATGAACAAGGGCATCAGAGGCCAGTAGCTTTCTTGGCCTACAGAGTAAGTGGACAATATTATTAGGAAGGACTTGGATCCAGCTTCCTGTTTACAATGGGAGGTTTAGGTTTCATAATCCTGGACCGATCGAATGCACCAAATATCCCAAAACTCAATAG | 1378 |
| | 2 | MSQPEAEEAALAAHAVGHDYVCSGGGVLLPHHQRNRL* | 1379 | ATGTCCCAACCTGAAGCTGAAGAAGCCGCCCTGGCTGCACATGCCGTTGGCCATGACTATGTATCTCTGGTGGTGTCTTACTTCCTCATCACCAGAGGAATCGTTTATGA | 1380 |
| | 3 | MLWWWCLTSSSPEESFMMLRLNRQVLAL* | 1381 | ATGCTCTGGTGGTGTCTTACTTCCTCATCACCAGAGGAATCGTTTATGATGTTACGGTTGAACCGCCAGGTGTTGGCTCTATGA | 1382 |
| | 4 | MNKGIRGQ* | 1383 | ATGAACAAGGGCATCAGAGGCCAGTAG | 1384 |
| hsa-mir-520h | 1 | METLYRVPFLALECPNLKLKKPPWLHMPLAMTMYALVVVSYFLITRGIVYDVTVEPPGVGSMTDEQGHQRPVAFLAYRVSGQYYYGRTWIQLPVVNGRFRFHNPGPIECTKYPKTQ* | 1385 | ATGGAGACTTTGTACCGTGTCCGTTCTTAGCGCTTGAATGTCCAACCTGAAGCTGAAGAAGCCGCCCTTCCTCATCACCAGAGGAATGTCTTGGTGGTGTCTTACTTCCTCATCACCAGAGGAATCGTTTATGATGTTACGGTTGAACCGCAGTAGCTTTCTTGGCCGGTGTTGGCTCTATGACTGATGAACAAGGGCATCAGAGGCCAGTAGCTTTCTTGGCCTACAGAGTAAGTGGACAATATTATTAGGAAGGACTTGGATCCAGCTTCCTGTTTACAATGGGAGGTTTAGGTTTCATAATCCTGGACCGATCGAATGCACCAAATATCCCAAAACTCAATAG | 1386 |
| | 2 | MSQPEAEEAALAAHAVGHDYVCSGGGVLLPHHQRNRL* | 1387 | ATGTCCCAACCTGAAGCTGAAGAAGCCGCCCTGGCTGCACATGCCGTTGGCCATGACTATGTATCTCTGGTGGTGTCTTACTTCCTCATCACCAGAGGAATCGTTTATGA | 1388 |
| | 3 | MLWWWCLTSSSPEESFMMLRLNRQVLAL* | 1389 | ATGCTCTGGTGGTGTCTTACTTCCTCATCACCAGAGGAATCGTTTATGATGTTACGGTTGAACCGCCAGGTGTTGGCTCTATGA | 1390 |
| | 4 | MNKGIRGQ* | 1391 | ATGAACAAGGGCATCAGAGGCCAGTAG | 1392 |
| hsa-mir-521-1 | 1 | METLYRVPFLALECPNLKLRMPLAMTMYALVVVSYFLITRGIVYDVTVEPPGVGSMTDEQGHQRPVAFLAYRVSGQYYYGRTWIQLPVVNGRFRFHNPGPIECTKYPKTQ* | 1393 | ATGGAGACTTTGTACCGTGTCCGTTCTTAGCGCTTGAATGTCCAACCTGAAGCTGAAGAAGCCGCCCTTCCTCATCACCAGAGGAATGTCTTGGTGGTGGTGTCTTACTTCCTCATCACCAGAGGAATCGTTTATGATGTTACGGTTGAACCGCCAGGTGTTGGCTCTATGACTGATGAACAAGGCCATCAGAGGCCATCAGAGCCAGTAGCTTTCTTGGCCTACAGAGTAAGTGGACAATATTATTAGGAAGGACTTGGATCCAGCTTCCTGTTTACAATGGGAGGTTTAGGTTTCATAATCCTGGACCGATCGAATGCACCAAATATCCCAAAACTCAATAG | 1394 |

Figure 1 (Continued)

| | | | | |
|---|---|---|---|---|
| hsa-mir-521-2 | 2 | MSQPEAEEAALAAHAVGHDYVCSGGGVLLPHHQRNRL* | 1395 | ATGTCCCAACCTGAAGCTGAAGAAGCCGCCCTGGCTGCACATGCCGTTGGCCATGAC TATGTATGCTCTGGTGGTGGTCTTACTTCCTCATCACCAGAGGAATCGTTTATGATGAC | 1396 |
| | 3 | MLWWWCLTSSSPEESFMMLRLNRQVLAL* | 1397 | ATGCTCTGGTGGTGGTGGTGTCTTACTTCCTCATCACCAGAGGAATCGTTTATGATGTTA CGGTTGAACCGCCAGGTGTTGGCTCAGTCTTATAG | 1398 |
| | 4 | MNKGIRGQ* | 1399 | ATGAACAAGGGCATCAGAGGCCAGTAG | 1400 |
| | 1 | METLYRVPFLALECPNLKLKKPPWLHMPLAMTMYALV VVSYFLITRGIVYDVTVEPPGVGSMTDEQGHQRPVAFL AYRVSGQYYYGRTWIQLPVYNGRFRFHNPGPIECTKYP KTQ* | 1401 | ATGGAGACTTTGTACCGTGTCCCGTTCTTAGCGCTTGAATGTCCCAACCTGAAGCTG AAGAAGCCGCCCTGGCTGCACATGCCGTTGGCCATGACTATGTATGCTCTGGTGGTG GTGTCTTACTTCCTCATCACTGACTAATGAACAAGGGCATCAGAGGCCAGTGAACCGCCA GGTGTTGGCTCTATGATGGACAAGTAAGTGGACAATATTATTATGGAAGGACTTGGATCGACTTCTTGGCC TACAGAGTAAGTGGACAATATTAGGTTTCATAATCCTGGACCGATCGAATGCACCAGCTCCTGTTTAC AATGGGAGGTTTAGGTTTCATAATCCTGGACCGATCGAATGCACCAAATATCCCAAA ACTCAATAG | 1402 |
| | 2 | MSQPEAEEAALAAHAVGHDYVCSGGGVLLPHHQRNRL* | 1403 | ATGTCCCAACCTGAAGCTGAAGAAGCCGCCCTGGCTGCACATGCCGTTGGCCATGAC TATGTATGCTCTGGTGGTGGTGTCTTACTTCCTCATCACCAGAGGAATCGTTTATGATGA | 1404 |
| | 3 | MLWWWCLTSSSPEESFMMLRLNRQVLAL* | 1405 | ATGCTCTGGTGGTGGTGTCTTACTTCCTCATCACCAGAGGAATCGTTTATGATGTTA CGGTTGAACCGCCAGGTGTTGGCTCAGTGA | 1406 |
| | 4 | MNKGIRGQ* | 1407 | ATGAACAAGGGCATCAGAGGCCAGTAG | 1408 |
| hsa-mir-522 | 1 | METLYRVPFLALECPNLKLKKPPWLHMPLAMTMYALV VVSYFLITRGIVYDVTVEPPGVGSMTDEQGHQRPVAFL AYRVSGQYYYGRTWIQLPVYNGRFRFHNPGPIECTKYP KTQ* | 1409 | ATGGAGACTTTGTACCGTGTCCCGTTCTTAGCGCTTGAATGTCCCAACCTGAAGCTG AAGAAGCCGCCCTGGCTGCACATGCCGTTGGCCATGACTATGTATGCTCTGGTGGTG GTGTCTTACTTCCTCATGACTGATGAACAAGGGCATCAGAGGCCAGTGAACCGCCA GGTGTTGGCTCTATGATGGACAAGTAAGTGGACAATATTATTATGGAAGGACTTGGATCGACTTCTTGGCC TACAGAGTAAGTGGACAATATTATTATGGAAGGACTTGGATCAGCTTCCTGTTTAC AATGGGAGGTTTAGGTTTCATAATCCTGGACCGATCGAATGCACCAAATATCCCAAA ACTCAATAG | 1410 |
| | 2 | MSQPEAEEAALAAHAVGHDYVCSGGGVLLPHHQRNRL* | 1411 | ATGTCCCAACCTGAAGCTGAAGAAGCCGCCTTGGCTGCACATGCCGTTGGCCATGAC TATGTATGCTCTGTGGTGGTGTCTTACTTCCTCATCACCAGAGGAATCGTTTATGA | 1412 |
| | 3 | MLWWWCLTSSSPEESFMMLRLNRQVLAL* | 1413 | ATGCTCTGGTGGTGGTGTCTTACTTCCTCATCACCAGAGGAATCGTTTATGATGTTA CGGTTGAACCGCCAGGTGTTGGCTCAGTAG | 1414 |
| | 4 | MNKGIRGQ* | 1415 | ATGAACAAGGGCATCAGAGGCCAGTAG | 1416 |
| hsa-mir-524 | 1 | METLYRVPFLALECPNLKLKKPPWLHMPLAMTMYALV VVSYFLITRGIVYDVTVEPPGVGSMTDEQGHQRPVAFL AYRVSGQYYYGRTWIQLPVYNGRFRFHNPGPIECTKYP KTQ* | 1417 | ATGGAGACTTTGTACCGTGTCCCGTTCTTAGCGCTTGAATGTCCCAACCTGAAGCTG AAGAAGCCGCCCTGGCTGCACATGCCGTTGGCCATGACTATGTATGCTCTGGTGGTG GTGTCTTGGCTCTATGATGACAAGGGCATCAGAGCCAGTGAACCGCCAGGTGTTGGCC GGTGTTGGCTCTATGATGGACAAGTAAGTGGACATTATATTATGGAAGGACTTGGATCAGCTTCTTGGCC TACAGAGTAAGTGGACAATATTATTATGGAAGGACTTGGATCAGCTTCCTGTTTAC AATGGGAGGTTTAGGTTTCATAATCCTGGACCGATCGAATGCACCAAATATCCAAA ACTCAATAG | 1418 |
| | 2 | MSQPEAEEAALAAHAVGHDYVCSGGGVLLPHHQRNRL* | 1419 | ATGTCCCAACCTGAAGCTGAAGAAGCCGCCCTGGCTGCACATGCCGTTGGCCATGAC TATGTATGCTCTGGTGGTGGTGTCTTACTTCCTCATCACCAGAGGAATCGTTTATGATGAC | 1420 |
| | 3 | MLWWWCLTSSPEESFMMLRLNRQVLAL* | 1421 | ATGCTCTGGTCGTGGTGTCTTACTTCCTCATCACCAGAGGAATCGTTTATGATGTTA CGGTTGAACCGCCAGGTGTTGGCTCAGTAG | 1422 |
| | 4 | MNKGIRGQ* | 1423 | ATGAACAAGGGCATCAGAGGCCAGTAG | 1424 |

Figure 1 (Continued)

| | | | | | | |
|---|---|---|---|---|---|---|
| hsa-mir-526a-1 | 1 | METLYRVPFLALECPNLKLKKPPWLHMPLAMTMYALV VVSYFLJTRGIVYDVTVEPPGVGSMTDEQGHQRPVAFL AYRVSGQYYYGRTWIQLPVYNGRFRFHNPGIIECTKYP KTQ* | 1425 | ATGGAGACTTTGTACCGTGTCCGTTCTTAGCGCTTGAATGTCCAACCTGAAGCTG AAGAAGCCGCCCTGGCTGCACATGCCGTTGGCCATGACTATGTATGCTCTGGTGGTG GTGTCTTACTTCTGTTCTGGTGGTGTCTTACTTCCTCATCACCAGAGGAATCGTTTATGATGTTA GGTTGTTGGCTCTATGACTGGACAATATTATTGAAGGACTTGATCCAGCTTCTGTTAC ACAGAGTAAGTGGACAATATTCATAATCCTGACCGATCGAATGCACCAAATATCCCAAA ACTCAATAG | 1426 |
| | 2 | MSQPEAEEAALAAHAVGHDYVCSGGGVLLPHFQRNRL* | 1427 | ATGTCCCAACCTGAAGCTGAAGAAGCCGCCCTGGCTGCACATGCCGTTGGCCATGAC TATGTATGCTCTGGTGGTGTCTTACTTCCTCATCACCAGAGGAATCGTTTATGA | 1428 |
| | 3 | MLWWWCLTSSSPEESFMMLRLNRQVLAL* | 1429 | ATGCTCTGGTGGTGTCTTACTTCCTCATCACCAGAGGAATCGTTTATGATGTTA CGGTTGAACCGCCAGGTGTTGGCTCTATGA | 1430 |
| | 4 | MNKGIRGQ* | 1431 | ATGAACAAGGCATCAGAGGCCAGTAG | 1432 |
| hsa-mir-526a-2 | 1 | METLYRVPFLALECPNLKLKKPPWLHMPLAMTMYALV VVSYFLJTRGIVYDVTVEPPGVGSMTDEQGHQRPVAFL AYRVSGQYYYGRTWIQLPVYNGRFRFHNPGIIECTKYP KTQ* | 1433 | ATGGAGACTTTGTACCGTGTCCGTTCTTAGCGCTTGAATGTCCAACCTGAAGCTG AAGAAGCCGCCCTGGCTGCACATGCCGTTGGCCATGACTATGTATGCTCTGGTGGTG GTGTCTTACTTCCTCATCACCAGAGGAATCGTTTATGATGTTACGGTTGAACCGCCA GGTGTTGGCTCTATGACTGGACAATATTATTGAAGGACTTGATCCAGCTTCTGTTAC ACAGAGTAAGTGGACAATATTCATAATCCTGACCGATCGAATGCACCAAATATCCCAAA ACTCAATAG | 1434 |
| | 2 | MSQPEAEEAALAAHAVGHDYVCSGGGVLLPHFQRNRL* | 1435 | ATGTCCCAACCTGAAGCTGAAGAAGCCGCCCTGGCTGCACATGCCGTTGGCCATGAC TATGTATGCTCTGGTGGTGTCTTACTTCCTCATCACCAGAGGAATCGTTTATGA | 1436 |
| | 3 | MLWWWCLTSSSPEESFMMLRLNRQVLAL* | 1437 | ATGCTCTGGTGGTGTCTTACTTCCTCATCACCAGAGGAATCGTTTATGATGTTA CGGTTGAACCGCCAGGTGTTGGCTCTATGA | 1438 |
| | 4 | MNKGIRGQ* | 1439 | ATGAACAAGGCATCAGAGGCCAGTAG | 1440 |
| hsa-mir-527 | 1 | METLYRVPFLALECPNLKLKKPPWLHMPLAMTMYALV VVSYFLJTRGIVYDVTVEPPGVGSMTDEQGHQRPVAFL AYRVSGQYYYGRTWIQLPVYNGRFRFHNPGIIECTKYP KTQ* | 1441 | ATGGAGACTTTGTACCGTGTCCGTTCTTAGCGCTTGAATGTCCAACCTGAAGCTG AAGAAGCCGCCCTGGCTGCACATGCCGTTGGCCATGACTATGTATGCTCTGGTGGTG GTGTCTTACTTCCTCATCACCAGAGGAATCGTTTATGATGTTACGGTTGAACCGCCA GGTGTTGGCTCTATGACTGGACAATATTATTGAAGGACTTGATCCAGCTTCTGTTAC ACAGAGTAAGTGGACAATATTCATAATCCTGACCGATCGAATGCACCAAATATCCCAAA ACTCAATAG | 1442 |
| | 2 | MSQPEAEEAALAAHAVGHDYVCSGGGVLLPHFQRNRL* | 1443 | ATGTCCCAACCTGAAGCTGAAGAAGCCGCCCTGGCTGCACATGCCGTTGGCCATGAC TATGTATGCTCTGGTGGTGTCTTACTTCCTCATCACCAGAGGAATCGTTTATGA | 1444 |
| | 3 | MLWWWCLTSSSPEESFMMLRLNRQVLAL* | 1445 | ATGCTCTGGTGGTGTCTTACTTCCTCATCACCAGAGGAATCGTTTATGATGTTA CGGTTGAACCGCCAGGTGTTGGCTCTATGA | 1446 |
| | 4 | MNKGIRGQ* | 1447 | ATGAACAAGGCATCAGAGGCCAGTAG | 1448 |
| hsa-mir-539 | 1 | MFPNPGSMMTTGGV* | 1449 | ATGCCCAATCTGGATCGATGATGACCACTGGTGCGTATGA | 1450 |
| | 2 | MSIIT* | 1451 | ATGAGTCATACATGA | 1452 |
| | 3 | MMNMCLEL* | 1453 | ATGATGAATATGTCTGGAACTCTGA | 1454 |
| | 4 | MHSYVIIMIGSMKE* | 1455 | ATGCATTCTTATGTTATTATTGGTCAATGAAAGAATGA | 1456 |
| hsa-mir-541 | 1 | MFPNPGSMMTTGGV* | 1457 | ATGCCCAATCTGGATCGATGATGACCACTGGTGCGTATGA | 1458 |
| | 2 | MSIIT* | 1459 | ATGAGTCATACATGA | 1460 |
| | 3 | MMNMCLEL* | 1461 | ATGATGAATATGTCTGGAACTCTGA | 1462 |

Figure 1 (Continued)

| | | | | | |
|---|---|---|---|---|---|
| hsa-mir-543 | 4 | MHSYVIEMIGSMKE* | 1463 | ATGCATTCTTATGTTATTATATGATTGGTCAATGAAAGAATGA | 1464 |
| | 1 | MPNFGSMMTTGGV* | 1465 | ATGCCCAATCTGGATCGGATGATGACCACTGGTGGCGTATGA | 1466 |
| | 2 | MSHT* | 1467 | ATGAGTCATACATGA | 1468 |
| | 3 | MMNMCLEL* | 1469 | ATGATGAATATGTCTTGAACTGA | 1470 |
| | 4 | MHSYVIEMIGSMKE* | 1471 | ATGCATTCTTATGTTATTATATGATTGGGTCAATGAAAGAATGA | 1472 |
| hsa-mir-544 | 1 | MPNFGSMMTTGGV* | 1473 | ATGCCCAATCTGGATGGATGATGACCACTGGTGCGTATGA | 1474 |
| | 2 | MSHT* | 1475 | ATGAGTCATACATGA | 1476 |
| | 3 | MMNMCLEL* | 1477 | ATGATGAATATGTCTGGAACTGA | 1478 |
| | 4 | MHSYVIEMIGSMKE* | 1479 | ATGCATTCTTATGTTATTATATGGTCAATGAAAGAATGA | 1480 |
| hsa-mir-548a-2 | 1 | MARFRLTATSASRVQAILLPQSPEKLGLQAPATTPS* | 1481 | ATGGCACGATTCGGTCACTGCAACCTCTGCCTCCGGGTTCAAGCGATTCCTG CCTCAGTTCCCGAGAAGCTGGGATTACAGGCACCGCACCCGCCAGCTAA | 1482 |
| | 2 | MLVRLVLNS* | 1483 | ATGTTGGTCAGGCTGGTCTTGAACTCTGA | 1484 |
| | 3 | MSTGKQRHKEA* | 1485 | ATGTCAACTGGAAAACAGAGGCACAAGAGGCTTAG | 1486 |
| | 4 | MVLGWNSEGLVLNSLLFTIFCQ* | 1487 | ATGGTGCTGGGTTGGAACTCAGAAGGTCTTGTTCTAAATTCCTACTTTTCACCATTT TTTGCCAATAA | 1488 |
| | 1 | MQPRIPELE* | 1489 | ATGCAGCCTCGAATTCCTGAGTCGAGTGA | 1490 |
| | 2 | MFSRDGVSPCWPDWS* | 1491 | ATGTTTAGHAGAGATGGGGTTTCACCATGTGCCGGACTGGTCTTGA | 1492 |
| hsa-mir-548a-3 | 3 | MGFFHHVGRTGLELLTSGDPACLGLPKCWDDTCEPLCPA KKKKNSFFRDRVFLYCPDWS* | 1493 | ATGGGGTTTCACCATGTTGGCCGGACTGGTCTTGGCCCTGAACTCTGGACCTCAGGTGATCCT GCCTGCCTGCGCTCCCAAAGTGCTGGGATGATACATGTGAGCCACTGTGCCCAGCC AAAAAAAAAAAATTCTTTTTAGAGATAGAGTCTTCCGTATTGCCCAGAC TGGTCTTAA | 1494 |
| | 4 | MLAGLVLNS* | 1495 | ATGTTGCCGGACTGGTCTTGAACTCTGA | 1496 |
| | 1 | MVFHQRGFVVENGREGMNKQPRLLVSRKEVEQGLLCL F* | 1497 | ATGGTCTTTCATCAAAGGGGTTGTTGTTGAAAACGGCAGAGAAGGGATGAATAA GCAGCCAAGGCTCTTGGTTTCCGAAAAGAGGTTGAACAGGACTGCTGTGTCTCTT TTAG | 1498 |
| hsa-mir-548d-2 | 2 | MKVQI* | 1499 | ATGAAAGTACAGATTTAG | 1500 |
| | 3 | MKPVSNTKGCPEAHTAPISFQYSKSNIY* | 1501 | ATGAAGCCTGTTTCTAACACCAAAGGCTGCCCAGAGGCCACACAGCCTTCATTTCA TTCCAATATTCCAAATCCAAACATCTACTGA | 1502 |
| | 4 | MPSLSTGRTQRQPTGLTW* | 1503 | ATGCCATCACTCTCAACAGGAAGGACCCAGAGGACCAGCCCAGGCCTGACTTGGTGA | 1504 |
| | 1 | MWRIDYFAFPSAMIVVYLGQHQPS* | 1505 | ATGTGGAGGATAGTGTTTGCTTTCCCTTCTGCCATGATTGTAGTTACCTGGGACAA CACCAGCCATCCTGA | 1506 |
| hsa-mir-548m | 2 | MCLLSLLP* | 1507 | ATGTGTTTGCTTCCCTCTGCCATGA | 1508 |
| | 3 | MSLLAM* | 1509 | ATGTCTTTATTAGCAATGTGA | 1510 |
| | 4 | MWKQIWK* | 1511 | ATGTGGAAGCAAATTTGGAAGTGA | 1512 |
| | 1 | MAPEELR* | 1513 | ATGGCTCCGGAGGAGCTGAGGTAG | 1514 |
| hsa-mir-548h-2 | 2 | MGYGRVFFLMSFAVDHS* | 1515 | ATGGGCTACGGCCGTGTTTTCTTTTTGATGTCCTTTGCAGTGGATCACAGCTAG | 1516 |
| | 3 | MALCTCTVAKAYLLSV* | 1517 | ATGGCTTTATGTACATGCACAGTAGCAAAGGCGTACTTGCTGTCAGTGTAA | 1518 |
| | 4 | MYMHSSKGVLAVSVNVNTFTLYRRA* | 1519 | ATGTACATGCACAGTAGCAAGGCGTACTTGCTGTCAGTGTAAATGTTAATACGTTT ACTCTTTATCGGAGAGGCCTGA | 1520 |
| | 1 | MGAAHQHVTCIHM* | 1521 | ATGGGTGCAGCACACCAACAGTGCACATGTCAATGTATACATATGTAA | 1522 |
| hsa-mir-548i-4 | 2 | MSHVYICNRKPACHAHVP* | 1523 | ATGTCACATGTATACATATGTAACAACCTGCATGTCATGCACATGTGCCTAG | 1524 |
| | 3 | MYTYVTNLHVMHMCPRT* | 1525 | ATGTATACATATGTAACAAACCTGCATGCACATGTGCCTAGAACTAAGTGTATAA | 1526 |
| | 4 | MSCTCALELNV* | 1527 | ATGTCATGCACATGTGCCTAGAACTAAGTGTATAA | 1528 |

Figure 1 (Continued)

| | | | | |
|---|---|---|---|---|
| hsa-mir-548q | 1 | MHSKGLLPELMAPVFLSSLQFCNIQEGLRVAVLGLAWEPVKYHLHRVLCRIGESHCS* | 1529 | ATGCACAGCAAAGGCCTTCTCCATTCTTATGGCCCCGTGTCCTGTCTCACTACAGTTCTGCAACATACAAGGAGGGCTGAGAGTAGCAGTCCTGGGGTTGGCATGGAACCAGTGAAGTATCATTTGCAGTGTTTTATGTAGAATTGGGAATCTCATTGTTCCTAG | 1530 |
| | 2 | MGTSEVSFASCFM* | 1531 | ATGGAACCAGTGAAGTATCATTTGCATCGTGTTTATGTAG | 1532 |
| | 3 | MEAEKLQPWTCPCTAAWALNTKRSLHFPFSEELLDLMTPGFHMVTIYHGGRRCQGLSSLLLSRNVHPPG* | 1533 | ATGGAGGCTGAGAAGCTACAGCCTTGGTCCTTGCACTGCCTGCGTGGGCCTTGAACACAAAGAGGAGCCTACATTTTTTTTTCTGAAGAGCTGCTGGACTTGATGACTCCTGGGATTCATCATCATGGGATTTATCACGGGGAGACTGTCAAGGACTGTCATCTCTGCTGTTGTCCAGGAATGTCCACCCTCCAGGATAA | 1534 |
| | 4 | MSRTVISAVVQECPPSRIILTQ* | 1535 | ATGTCAAGGACTGTCATCTCTGCTGTTGTCCAGGAATGTCCACCTCCAGGATAATCCTCACCCAGTGA | 1536 |
| hsa-mir-549_os | 1 | MGHTPLPAYLSPRLTGKSKCLJ* | 1537 | ATGGGAACAATAACACCACTCCCTGCTATCTCTCACCAAGGCTTACTGGGAAGAGTAAATGCTTGATTTGA | 1538 |
| | 2 | MLDLSHFSAPGRQNNDLEIKPG* | 1539 | ATGCTTGATTGAGCCATTTCTCTGCCCCTGGTAGACAAAATAATGATCTTGAAATCAAGCCTGGGTGA | 1540 |
| | 3 | MILKSSLGELGEGGQESPSPSSFLVVREASMPPPSFVT* | 1541 | ATGATCTTGAAATCAAGCCTGGGTGAGCTTGGGGAGCTGGAAGGTGGGCAAGAATCCCTCCAGCTTCTGTGGTGTCAGGAGAAGCTTCTATGTTCCCCCTTCCTTGTGACCTAG | 1542 |
| | 4 | MPWLLEDWIACTGSTIKILFWLRTQKSIFVDTRNHRNRKAELRGLVPMGQKSSLTNCIDAETLL* | 1543 | ATGCCGTGCTCCTGGAGGACTGGATTGCCTGCACAGGGTCCACTAAGATCCTTTCTGGCTAAGGACCCAAAGTCTATCTTTGTGGACCACCAGAACCACAGAAACAGGAAGCAGAGCTCAGAGTTCTGTTCCATGGGACAGAAATCTTCCCTGACAAATTGTGATGCAGAAACCCTTCTCGA | 1544 |
| | 1 | MHAACLPSLLWL* | 1545 | ATGCACGCAGCATGCCTTCCCAGCCTCGTGGTTGTAG | 1546 |
| | 2 | MPSQPVVVECIEGSWITMDSG* | 1547 | ATGCCTTCCCAGCCTCGTGGTTGTAGAGGTGTATAGAAGGCAGTTGGATCACTATGGACAGCGGGTAA | 1548 |
| hsa-mir-552 | 3 | MEDPEGJKKGLLLVGSPVKSTYKLIRHNAISR* | 1549 | ATGGAGGACCCTGAAGGTAAGAAGGTCTTACTTGTTGTGAGCCTAGTTAAATCCACTTACAAATTAATTAGACACAATGCCATTTCCAGATGA | 1550 |
| | 4 | MPPPDESSGKATVVRACSRSS* | 1551 | ATGCCCCATTTCCAGAATGAGAGTTCTGAAGGCTACTGTCGTGGTTAGGGCTTGTGTTCTCGTTCCTCCTAG | 1552 |
| | 1 | MELGELLYNKSFYIKTASGNKVSLQSVLCGSQNHLLNRKTMW* | 1553 | ATGGAGTTAGGTGAGCTGCTCTACAACAAGTCTGAGTATATCAAGACGGCATCGGGAACAAAGTCAGTCTCCAGTGAGTTGTGTGGAAGCCAGAACATACTTCTCAATCGCAAGACCATGTGGTGA | 1554 |
| hsa-mir-557 | 2 | MTVLSEGIWKT* | 1555 | ATGACTGTATTATCTGAGGGGATCTGGAAAACATAA | 1556 |
| | 3 | MDSIVL* | 1557 | ATGGACTCCATTGTGTTGTGA | 1558 |
| | 4 | MSLLRKSVWSTQLRLVLAPMLARTA* | 1559 | ATGTCTTTATTGAGGAAGAGTGTGGTCAACGCAGCTCAGATTGGTTCTTGCATTCATGTTGGCAAGAACTGCGTGA | 1560 |
| | 1 | MGEPDLHVEKA* | 1561 | ATGGGCGAGCCGGACTTGCACGTGGAGAAAGCGTGA | 1562 |
| hsa-mir-563 | 2 | MCPWVWGGWGAKEWDERWSRNGGRCCPPRGLQAETG* | 1563 | ATGTGCCCCTGGGTTTGGGGAGGCTGGGGAGCCAAGGAGTGGGATGAGAGGTGGTCACGGAATGGGGGGCGCTGCTGTCCTCCCGGGGCTGCAGGCCGAGACGGGTGA | 1564 |
| | 3 | MRGGHGMGGAAVLPGGCRPRPGEGRG* | 1565 | ATGAGAGGTGGTCACGGAATGGGGGGCGCTGCACGGAGGGCGGGGCTGA | 1566 |
| | 4 | MLALWTEGRRLRSRTGCGRPIVFLPVVPIRS* | 1567 | ATGCTGGCACTCTGGACCGAAGGGCGTCGTCTTCGCAGCGAACAGGTTGTGGACGCCAATCGTTTTCTGCCCGTAGTCCAATCCGAAGCTAA | 1568 |
| | 1 | MPPEPAVHEESA* | 1569 | ATGCCTCCTGAGCTGCAGTGCATGAAGAGAGTGCTTGA | 1570 |

Figure 1 (Continued)

| | | | | |
|---|---|---|---|---|
| hsa-mir-568 | 2 | MKRVLELTQPPGLLGLDITSHWNSSSLFPLFVFS* | 1571 | ATGAAGAGAGTGCTGGAGCTGACCCAGCCACCAGGCCTTCTGGGGCTAGACATAAC TTCCCACTGGAACAGCAGCAGCCTCTTCCCCTCTTTGTTTTCAATGA | 1572 |
| | 3 | MKKTAVLLGSQEIDYMGQTFKSMLYPGAQATYRGIRKG ARKSPCS* | 1573 | ATGAAGAAAACGGCTGTTCTTCTAGGTAGCCAGGAAATAGATTACATGGGGCAAAC TTTCAAAAGCAATCTCTACCCTGGTGCTCAGGCTACATACAGAGGCAGAAAAGGGG CACGGAAGAGCCCTTGCTCTGA | 1574 |
| | 4 | MWKLLIQSHSSTEYQDDQPDQNIAKSPLSL* | 1575 | ATGTGGAAACTACTAATCCAAAGCATCATTTCTAGCACTGAGTATCAAGACGATCAG CCTGACCAAAATATTGCAAAGAGTTTCTAAGTCTCTGA | 1576 |
| hsa-mir-572 | 1 | MRWKVG* | 1577 | ATGCGGTGGAAGGTCGGCTGA | 1578 |
| | 2 | MIDRARWPSSV* | 1579 | ATGGACCGAGCACGGTGGCCGAGCTCAGTTGA | 1580 |
| | 3 | MGYPRGADTGRLRLLEEKRGVGFLS* | 1581 | ATGGGTTACCCAGAGGGGCGGATACGGGAAGATTAAGGTTGTTGGAGGAGAAACG TGGAGTAGGCTTTTTGTCTGA | 1582 |
| | 4 | MNCA* | 1583 | ATGAACTGTGCCTGA | 1584 |
| hsa-mir-573 | 1 | MRKNILRRSMLSTNLKFSYKPGL* | 1585 | ATGAGGAAGAACATTCTGAGGCGCAGCATGTTAAGCACAAATTTAAAGTTTCATAC AAGCCTGGCTATAG | 1586 |
| | 2 | MKNRFYNLIVVLIKNSLLNMLQH* | 1587 | ATGAAAAATAGAITTTATAACTTGATTGTGGTACATAATAAAAACAGCCTTTTAAAC ATGTTACAGCACTAA | 1588 |
| | 3 | MVNDFKFLAIKKG* | 1589 | ATGGTTGAACGATTTCAAGTTTTTAGCAATCAAGAAGGTTGA | 1590 |
| | 4 | MQHFI* | 1591 | ATGCAACATATATTATATGA | 1592 |
| hsa-mir-583 | 1 | MCSHCSTPTYE* | 1593 | ATGTGTTCTCATTGTTCAACTCCACTTATGAGTGA | 1594 |
| | 2 | MSENMRCLLF* | 1595 | ATGAGTGAGAACATGCGTGTTTGCTTTTCTGA | 1596 |
| | 3 | MVSSFHVPAKDMNSSFFMAA* | 1597 | ATGGTTTCCAGCTTCATCATTGTCCCTGCAAAGGACATGAACTCATCCTTTTTTATGG CTGCATAG | 1598 |
| | 4 | MSLQRT* | 1599 | ATGTCCCTGCAAAGGACATGA | 1600 |
| hsa-mir-587 | 1 | MQRQMQEECDLYYNESKNIFK* | 1601 | ATGCAGCGACAGATGCAAGAATGTGACTTATATTATAATGAAAGCAAAAATAT TTTCAAATAG | 1602 |
| | 2 | MKAKIFSNRFRGLJNRRSGYECQPKGEQRKRS* | 1603 | ATGAAAGCAAAAATATTTCAAATAGATTCAGGGGGTAATAAACAGAAGGTTCTGG CTATAGTGTCAGCCTAAAGGAGAGCAGAAGAAAAGATCCTAG | 1604 |
| | 3 | MSVSLKESREKDPRVLSQAR* | 1605 | ATGAGTGTCAGCCTAAAGGAGAGCAGAGAGAAAAGATCCTAGAGTTCTCAGCCAGGC AAGATGA | 1606 |
| | 4 | MIAYNTQLSYRE* | 1607 | ATGACTGCTTACAATACACAGTTTCATATAGGGAGTGA | 1608 |
| hsa-mir-596 | 1 | MAAAALRRPTRPIPGCCLGHCPCVFLFYFRTLIKTQTDE* | 1609 | ATGGCAGCTGCTGTTGTTCCGCCTCGAGGCTGCCTGGGCCATCCTGGGTGTCTAGGT CACTGTCCTTGTGTTTTACTTTAGAACTCTTATAAAGACACAAAACGGATG AGTAG | 1610 |
| | 2 | MSRDKLTLGNGLGVVCKAGSAVCVRNPLSSGSVLGCFL GQRPQPSYLQSILLSWRASAMAPRLYCSL* | 1611 | ATGAGTAGAGACAAACTCACACTAGGAAATGGACTGGGTGTGGTTTGCAAAGCGGG GAGCGCGGTCTGTGTCCGGAACCCTCTGTCTAGCGGCAGCGTCCTGGGCTGTTTCCT GGGGCAGCGGCCGCCACAGCCGTCTACTCTGCAGAGCATCGTCTGTTTCTCAGCCAG GCTGCGATGGCCCCAGGCTGTACTGTTCCCTAA | 1612 |
| | 3 | MDWVWFAKRGARSVSGTL* | 1613 | ATGGACTGGGTGTGGTTTGCAAAGCGGGGAGCCGGGTCTGTGTCCGGAACCCTCTGA | 1614 |
| | 4 | MCCPREPGRVMPRGDWGRQEGGEGRARSSEVGSFFPA LVDTPASSATSGVA* | 1615 | ATGTGTTGCCCAGGAGCCCGGCCGGGTGATGCCTCCGGGTGACTGGGGACGGCA GGAGGGAGGGGAAGGGGAAGGCAGGGCGCGGAGCCAGTGAGGTCGGCAGCCTTCCCAGCG CTCGTCGACACTCCAGCCTCTTCAGCCGCCACGTCTGGGGTTCGTGA | 1616 |

Figure 1 (Continued)

| | | Protein Sequence | SEQ ID | Nucleotide Sequence | SEQ ID |
|---|---|---|---|---|---|
| hsa-mir-607 | 1 | MSLWRHESSSCRKPRLSTEHCCRLHTLAIFCRPPGPASA AAPRTPSRVARGRARTRGPGVAPPAGGGAGPASPHR GPGVARGRPGPAHPPRAPPAGLRSRRPSTRLJPPPLAARD GAFPQPEVSPAGPAPPSHCPPRPRLPPPSPGLFVFYASPIY HFQPAYRPAPTVASSVJTAAMNFSVETAPPQSLFKKQK* | 1 | ATGAGCTTGTGGCGCCACGAATCCAGTTCTTGCCGAAAGCCGCGTCTCTCAACGGAG CATTGCTGCCGCCTACACAACCCTCGCCATTCTGCCGCCTACACAACCTCGCGCCAGCTCC CCCGGGCGTCGCCCCCGCACGCCAGCCCTGCAGCCTTGGCGTGCGGGGCGGCCGGCACCGCGG ACCGTGGCCCGGCTGGCGGTGCGCTCTGGACGCGCTGGCCGGCCGGCTCGTCACCGGCG CGCCCCGTCCGGCTGGTGCGATCGCGCTCCTTCTACGGGGCCTCTGGCC GCCGGACGGCGCCTCCCACAGCCGGAAGTCAGTCGCGCCCTCCGGAGTCAGAGGCCGCT TGCACTGTCCCCAAGGCACGGCTGCCCCCGCACCTGCCCCCGGGCTTTTTGTTTTT ACGCCAGCCCATTTATCACTTCCAACCTGCTATGCGGCCTATGCGGCCACCAACTGTTGCAA GTTCCGTAATAACTGCTGTAACTTCTCCGTTGAAAACTGCTCTCCCCAGAGCC TGTTTAAGAAGCAGAAATAA | 1617 1618 |
| | 2 | MPVDALTSKIFKGEVDTRY* | 1619 | ATGCCGGTTGGATGCACTGACCTCTAAGGATTTTCAAAGGTGAAGTGGATACACGTTAT TAA | 1620 |
| | 3 | MSKPLGHESP* | 1621 | ATGAGCAAGCCTCTTGAATAATTGAATCACCTTAA | 1622 |
| | 4 | MGNERRKGKEMGWKEKSRDRPIPVGLVP* | 1623 | ATGGGAAACGCAAGAGGAGAAAGGGAAAGAAATGGGTGAAAGAAAAAGCAGAA GAGATCGCCCTATACCAGTAGGCCTAGTACCCTAG | 1624 |
| hsa-mir-610 | 1 | MSKGPKKNVPMVVFCMTHPEYAL* | 1625 | ATGTCGAAGGGACCAAAAAAAAAATGTGTTATGGTGGTTTCTGTATGACACATCCT GAATATGCTCTATAA | 1626 |
| | 2 | MCLWWFSV* | 1627 | ATGTGTTTATGGTGGTTTTCTGTATGA | 1628 |
| | 3 | MLYKYGHTSVRAERDLKDYSHTLPARF* | 1629 | ATGCTCTATAAATATGGAATCACCAGTGTCAGAGCTGAAAGGGACCTGAAAGATTAT TCTCACACTCTCCAGCCAGATTTAA | 1630 |
| | 4 | MESPVSELKGTSKIHLTLSQPDFKWINLIS* | 1631 | ATGGAATCACCAGTGTCAGAGCTGAAAGGGACCTCAAAGATTCATTCTCACACTCTCC CAGCCAGATTTAAGTGGATAAACTGATAACTGATTAGCTGA | 1632 |
| hsa-mir-612 | 1 | MAVPAHANPFASLCIDLNSDFVNFQRCG* | 1633 | ATGGCAGTGCCAGCAATTATTGCTAATCCGTTTGCATCCTATGCATAGATCGAAT TCAGACTTTGTGAATTTCCAGAGGTGTGGGTAA | 1634 |
| | 2 | MHRSEJFRLCEFPEVWVJ* | 1635 | ATGCATAGATCTGAATTTGAATTCAGACTTTGTGAATTCCAGAGTGTGGGTAATATAA | 1636 |
| | 3 | MADLVQIKSYGA* | 1637 | ATGGCTGATCTTGTGCAAATTAAAAGTTATGGGGCATAA | 1638 |
| | 4 | MGHKNSKS* | 1639 | ATGGGGCATAAGAATAGCAAAAGTTGA | 1640 |
| hsa-mir-614 | 1 | MPAIADNRRAPGIAAREMEQGEPFSLKEFFPALPVYVYR VTPYLLITASFVLLWVRLKVFVCFFWFYWHRKL* | 1641 | ATGCCTGCAATTGCTGATAATAGACGTGCCCAGGAATCGCTGCAAGGAAATGGA GCAAGGTGAGCCATTCTTCTTTGAAGGAGTTTTTCCAGCTCCACCGGTTATGTGTAT AGGGTCACACCTCACCTCTTCTATAACTGCCATTATTTGTTCTCTTTGGGTCAGGCTGA AAGTGTTGTTGTCGTTTTTCGGTTTATTGGCATAGAAAACTCTAG | 1642 |
| | 2 | MCIGSHPTFL* | 1643 | ATGTGTATAGGTCACACCTCACCTCTATAA | 1644 |
| | 3 | MASAFLEGAG* | 1645 | ATGGCATCTGCATTCCTGGAAGGTGCAGGCTGA | 1646 |
| | 4 | MGGAEEF* | 1647 | ATGGGTGGAGCGGAGGAGTTTTGA | 1648 |
| | 1 | MAAAPALKHWRTTLERVEKFVSPLYFTDCNLRGRCCGP WSPAAGRPQPCASSFPSGEKPKLQPPGPRDKVPAAGRA GAGEEGVGNGLCRGAARQPSWRRIOQGHKCGPTGQLAPR RKRGGLQHVPTGPSHAGFLGPAALWLCSPAS* | 1649 | ATGGCGGCTGCGCCGCCGCCCTTGAAGCACTGGCGCACCACGCTGGAGCGGGTGGAGAA GTTCGTGTCGCCGCTGTACTTTACCGACTGTAACCTCCGCGCAGGTGTGGGCCCTG GTCCCCGAGCCGGCGCTGGCGACCGCCAACCGTGCGCCTCAAGTGCCGCCGCAGCCAG ACCTAAGCTGCAGCCACCGGCGCCGGGACAAAGTCCGGGGGCCGCCAGCAGCAG GGGCCGGGGAGGGAATGGACTGTGCCGCGGAAGCGCCACCGGCCAGCTGGCCCAGCC CTCTTGCGGAGGAATCCAGCATGTCGGCCGCCACCGGCCGGCCGCTGGCCCCAGGC GGAAACGGGCGGCGCGGCTCCAGCATGCCGCCGCCGCGTGCCGCCGTCCAGCTTCCGGCC GGGCCAGCTGCCCGTGCGTGCTCTCCAGCTTCCTGA | 1650 |

Figure 1 (Continued)

| | | | | |
|---|---|---|---|---|
| hsa-mir-631 | 2 | MDCAAERPGSPLGGSRESAAPPASWPPGGNGAASSM CPPARPTQAFWGQLPCGCALQLPDAGETSLPGGSPAGL PPRAGRRQLRTHVGNAQRVGGATGLGEVPTQLPATPSL SALCRRQLRGHEQHPLLGAAPSAGNSSLVPGSSGDGFHS HVAASGHPLGRAP* | 1651 | ATGGACTGTGCCGCGGAGCGGCCAGGAGGTGGTCCAGGAGGATCCAGGGAAAG TGCGGGCCCAGCCAGTGGCCCAGGTGGCCAAACGGCGCGCTCCAGCATGT GCCCACCGGCCCGTCCACCGAGGTCTTTGGGGCCAGCTGCCCTGTCTGCTC TCCAATGCCTTCCTGACGCCGGAGAGACTTCCTACCAGGAGACTTCAGCGGACTTC CGCCCCGCGCAGGTCGCGCGACAGCTTCGGACCGCACGTAGGCCCAGGGGTG GGCGGGGCACAGGCTAGGGGAAGTCCAACCAGCTCCAGCCACACCTTCGTT AGCACCTCTGCCTGCTGGAACAGCTCTGGGATCGGAGCAGCACCCCTGCTGGAGC TTCCCACGTGGCGCGCTCCTTAGGAAGGGCACCCTAG | 1652 |
| | 3 | MVFIPTWPPLDIP* | 1653 | ATGGTTTCATTCCACGTGGCCGCCTCTGGACATCCCTTAG | 1654 |
| | 4 | MLGFFQAPADTLSKEGYQDRTSTSRPITTALLQMVDLL VPGGADHPRGMGGPGSSPLLGK* | 1655 | ATGCTTGGAGAGTTTCAAGCCTGCGACACTTTATCCAAGGAAGGATATCAGGAT AGGACTTCTACCTCTAGGCCTATCACAACAGCTCTCTTGCAGATGGTGGACCTGCTG GTTCCGGGTGAGCTGACCATCCCAGAGGCATGGGTGGCCCAGGAAGTTCACCTTT GCTGGGAAAGTGA | 1656 |
| hsa-mir-633 | 1 | MLSSLJSHQ* | 1657 | ATGCTCTCGAGTCTCATTCCACCAGTGA | 1658 |
| | 2 | MCQKIKSGNLALWSLCSLQKFSEY* | 1659 | ATGTGCCAGAAGAAATAAAAGTGGAAATCTTGCTTTGTGGTCTCTTTGCTCGCTGCAA AAATTTTCTGAGTACTAA | 1660 |
| | 3 | MNRVNQILIEF* | 1661 | ATGAATCGTGTAAATCAAATCTTATTAATTGAATCTAA | 1662 |
| | 4 | MEENASSV* | 1663 | ATGGAGAAAATGCTTCATCAGTGTGA | 1664 |
| hsa-mir-645 | 1 | MSFWGTVEGVRGSTWGHQ* | 1665 | ATGTCATTCTGGGAACAGTGGAGGAGTGCGGCAGCACCTGGGGGCACCAGTGA | 1666 |
| | 2 | MWSGAPGLCGWGGICFWVTPCLPFSSTTF* | 1667 | ATGTGGAGTGGGAGGCTCCAGGCTGTGTGGCTGGGATCTGCTTCTGGGTTAC CCCATGCTCCCCTTCCAAGTACTACTTTTAA | 1668 |
| | 3 | MPPLLKYYFLHMAPAIHFIVDVSQYRWLTSLIPALGEAE ARRITRGQEFKTSLGNIYRPPSLQKNKNS* | 1669 | ATGCCTCCCCTTCTCAAGTACTACTTTTTAATCATCATGGCTCCTGCCATTCATTCA HAGTTGATGTAAGCCAGTGCCAGTGCGTGGCTCACGTCTTAATCCAGCACTTGGGAGG CTGAGGCCAGGAGGATCACTTGAGGCCAGGAGTTCAAGACCAGCTGGGCAACATA GTGAGACCCCGTCTCTACAAAAAACAAAAACAGTTAG | 1670 |
| | 4 | MLAPLHSSLGBDRARPCLKNK* | 1671 | ATGCTTGCACCACTGCACCTCTAGCCTGGGTGACAGAGCAAGACCCTGTCTCAAAAT AAATAA | 1672 |
| hsa-mir-654 | 1 | MPNPGSMMTTGGV* | 1673 | ATGCCCAATCCTGGATCGATGATGACCACTGGTGGCGTATGA | 1674 |
| | 2 | MSHT* | 1675 | ATGAGTCATACATGA | 1676 |
| | 3 | MMNMCLEL* | 1677 | ATGATGAATATGTGTCTGGAACTCTGA | 1678 |
| | 4 | MHSYVHMIGSMKE* | 1679 | ATGCATTCTTATGTTATTATGATTGGTCAATGAAAGAATGA | 1680 |
| hsa-mir-655 | 1 | MPNPGSMMTTGGV* | 1681 | ATGCCCAATCCTGGATCGATGATGACCACTGGTGGCGTATGA | 1682 |
| | 2 | MSHT* | 1683 | ATGAGTCATACATGA | 1684 |
| | 3 | MMNMCLEL* | 1685 | ATGATGAATATGTGTCTGGAACTCTGA | 1686 |
| | 4 | MHSYVHMIGSMKE* | 1687 | ATGCATTCTTATGTTATTATGATTGGTCAATGAAAGAATGA | 1688 |
| hsa-mir-656 | 1 | MPNPGSMMTTGGV* | 1689 | ATGCCCAATCCTGGATCGATGATGACCACTGGTGGCGTATGA | 1690 |
| | 2 | MSHT* | 1691 | ATGAGTCATACATGA | 1692 |
| | 3 | MMNMCLEL* | 1693 | ATGATGAATATGTGTCTGGAACTCTGA | 1694 |
| | 4 | MHSYVHMIGSMKE* | 1695 | ATGCATTCTTATGTTATTATGATTGGTCAATGAAAGAATGA | 1696 |
| hsa-mir-668 | 1 | MPNPGSMMTTGGV* | 1697 | ATGCCCAATCCTGGATCGATGATGACCACTGGTGGCGTATGA | 1698 |
| | 2 | MSHT* | 1699 | ATGAGTCATACATGA | 1700 |
| | 3 | MMNMCLEL* | 1701 | ATGATGAATATGTGTCTGGAACTCTGA | 1702 |

Figure 1 (Continued)

| | | | | | |
|---|---|---|---|---|---|
| | 4 | MHSYVIMGSMKE* | 1703 | ATGCATTCTTATGTTATTATGATTGGGTCAATGAAAGAATGA | 1704 |
| hsa-mir-659 | 1 | MLSSIRMGYIVRAMSSACICSPCLLIWGWGGEWYWVK* | 1705 | ATGCTCTCATCCATTCCATTCTGCTTGTTACATCGTGAGGCAATGGCCAGCGCATGCATCTGCTCATTCTGCTTGTAATCTGGGATGGGGTGGAGAGTGGTACTGGGTCAAATGA | 1706 |
| | 2 | MBLLLLVNLGMGWRVVLGQMRRTS* | 1707 | ATGCATCTGCTCATTCTGCTTGTTAATCTGGGATGGGGTGGAGAGTGGTACTGGGH CAAATGAGACGGACTTCCTGA | 1708 |
| | 3 | MTTEI* | 1709 | ATGACGACAGAAATATAG | 1710 |
| | 4 | MCRATAFQSTTGHGPHRGW* | 1711 | ATGTGCCGTGCAACAGCGTTTCAGTGACAACAGGCCATGGCCACATATAGGAATGGTGA | 1712 |
| | 1 | MGAASATHSSPCLAGHSRLL* | 1713 | ATGGGGCGTGCCAGCGCACGCACGCACTCCTTTCTGCCTGGCCGGCCACTCCCGTCTGCTGTGA | 1714 |
| | 2 | MESAPSIWRTGAAPGRASSTRAMVRLQLDADFTPQGTRRPICLEAAVLRQCRCLHGPSPALLQV* | 1715 | ATGGAATCTGCACCTTCCATCTGAGAACTGGGCGCCGCCCCAGGCGGGCGGGCTTCCAGCACCAGAGCGATGGTCAGCTTCAGCTGGACGCAGATTCACCCGCAGGGCACACGCAGACCCCATTTGTTTGGAAGCGGCAGTCTAAGGCAGTGCAGGTGCCTCACGCGCCCAGCCCAGCTCCTGCAGGTGTAA | 1716 |
| hsa-mir-662 | 3 | MQIPGHPMACRGPSEGCGPGSRGAPHGAEVLGSHGAGVGSAQVPCDPMATFFSWLHAPQGLGVPLTARFLAVGGVCFLPPSGGVQSLRGLPTSSGAWGSRVGHPEAVCLPATFPSGRADQAGSACGWGC* | 1717 | ATGCAGATTCCAGGGCGCCCCATGGCCTGCAGAGGGCCCTCAGAGCAAGGAAGGGCCGGGCTCTGGGGAGCCCTCAGCATCCCAGGTGCTGAGGTCCTTGGGTCACATGGAGCTGGGGTGGGGAGTGCGCCAGGTCCCCATTTCTGGGAGCTGTCTCCTGGCTTCGCCACCCCAAGGGCTGGGGTCCGGGGTCTCAGAGCCTCACTGCCCATTTCTGGCTGTGGGGAGGGGTGTGTTTTCTTGCACCCTAACCTCTAGAGTCTGTTCACCCGGAGGCTGTTGCCTGCCCCGGACAATTCCCCAGTGCCTGTGGGGAGTAGAGTTCGTCAGCAGGCAGGCTCTGCCTGTGGGATGGGGTGTAA | 1718 |
| | 4 | MELGWGVPRSPVIRWPRFPPGFTHPKGWGSHSLPIFWLWGGSVFFHLLKVFRASGASPLPLGPGGVESVTRRLCASPRHSPVAGPTRQALPVDGAAEHERYTPISELWVDPPGLGQGHQEAALPYSAMYASLKGVSVEASSLFCEPHPYPRRTILYQGGSSPHPLPHPTYAHRPHPREYKGLPRLLTGPAPPHLDCT* | 1719 | ATGGAGCTGGGTTGGGGTGCCCGAGCTCCCGTGATCCGATGGCCACGTTTCCCTCCTGGGCTTCACGCACCCCAAGGGCTGGGGGTCCCAACTCCCTGCCCATTTTCTGGCTGGGGAGTGGCGAGCTCAGCCTCAGGGGCTCTCCACTTCTCTGGGGCTGGGGGGAGTAGAGCTGCGCGAGCTCAGCTGGTCGTGGCCTCCCGACATTCCCCAAGTGCCCACGTGCCGGGCAACCCTGGGAGTCGTCCAGTGCAGGCTCTGCCTGTGATGGGCTGCTGAGCATGATAGCCTGTGATCGCCGTCTTGAGCGGTCAGGACCGGGGCTCCAAGGTTTCAGGAGGCAGCTCTATTCTACTCGCATGATGGCCCTGCTGAAAGGGTGAGTGTAGAAGCCAGTCCCTCTTCTGGAGCCGCATTGCATGGGGCGGCCATCTACCCCAGGAGGACAATTCTGTTCAGGGAGGAGGTACCAAGGGGCTCCCCAGCCGAGTCTCCGACCACCACTGGCCCGGGCCACGCGCCCCACCTGACTGCACCTGA | 1720 |
| | 1 | MRRAL* | 1721 | ATGAGGAGGGCATTGTAG | 1722 |
| | 2 | MRVIDPICRSPLE* | 1723 | ATGAGGGTCATTGATCCTCGGTGCAGATCTCAAAGAATGA | 1724 |
| hsa-mir-665 | 3 | MTERKREWWKETGWEKMKIERRK* | 1725 | ATGACAGAAGAAAGAGAAGGAGTGGTTGGAAAGAACAATAGGATTGGAAAATGA | 1726 |
| | 4 | MGKNENRKKEVKHPN* | 1727 | ATGGGAAAAAATGAAAATAGAAAAAAGAAGTGAAAGATAATAAATAG | 1728 |
| hsa-mir-758 | 1 | MPNPGSMMTTGGV* | 1729 | ATGCCCAATCTGGATCGATGATGACCACTGGTGGTGTATGA | 1730 |
| | 2 | MSHT* | 1731 | ATGAGTCATACATGA | 1732 |
| | 3 | MMNMCLEL* | 1733 | ATGATGAATATGTGTCTGGAACTCTGA | 1734 |
| | 4 | MHSYVIMGSMKE* | 1735 | ATGCATTCTTATGTTATTATGGGTCAATGAAAGAATGA | 1736 |
| hsa-mir-759 | 1 | MVKPRLY* | 1737 | ATGGTGAAACCCGTCTACTAA | 1738 |
| | 2 | MVACACSPSYLGG* | 1739 | ATGGTGGCGTGTGCGTGTAGTCCCAGCTATTTGGGAGGCTGA | 1740 |
| | 3 | MFFLHSV* | 1741 | ATGATCACCACCTGCACTCTGCTCTAG | 1742 |

Figure 1 (Continued)

| | | | | | |
|---|---|---|---|---|---|
| | 4 | MVKPGLY* | 1743 | ATGGTGAAACCTGGTCTCTACTAA | 1744 |
| hsa-mir-760 | 1 | MCAGKCCKIYFLYVGIKISLKVINLINVCKEERKVKNRVLGFLNI* | 1745 | ATGTGTGCTGGGAAATGCTGCAAATATATTTTATAGTGGGATCAAATAAGTTTGAAAGTTCATAAACCTAATAAATGTAGCAAAGAAGAGGAAGGTCAAGAACAGAGTGCTAGGGTTTCTAAATATTGA | 1746 |
| | 2 | MLQNIFFICRJDQNKFESHKPNKCMQRREEGQEQSARVSKYLSLGS* | 1747 | ATGCTGCAAATAATATTTTTATGTATGCAAAGAAGAGGAAAGGTCAAGAACAGAGTGCTAGGGTTTCCTAATAAATGTATGCAAAGAAGAGGAAAGGTCAAGAACAGAGTGCTAGGGTTGA | 1748 |
| | 3 | MYAKKRGRSRTEC* | 1749 | ATGTATGCAAAGAAGAGGAAGTCAAGAACAGAGTGCTAG | 1750 |
| | 4 | MAKKNQPRGRKRTKKPSPGNQVKKCSMKESMVRRVNCVSNYYCI* | 1751 | ATGGCAAAGAAGAATCAGCCCAGAGGTAGGAAGGAGAAGACCAAGAAACCAAGCCCTGGCAACCAGGTTAAAAAGTGTTCTATGAAGGAAAAGCAATGTCCGTAGGGTCAACTGTGTGTCCAATTACTACTGTATTTAG | 1752 |
| hsa-mir-802 | 1 | MSYFFLJSFPLJGSLCYAQVGVHNHSSLQSQTCGLK* | 1753 | ATGTCCTATTTCTTCCTTTTCTTTTTCTTATAGGTTCTCTGTGTTGCACAGGTTGGAGTGCACAATCATAGCTCATTGCAGTCTCAGACTTGTGGCTCAAGTGA | 1754 |
| | 2 | MPPCQAEF* | 1755 | ATGCCACCATGCCAGGCTGAATTTTAA | 1756 |
| | 3 | MLSSRPPKLLGL* | 1757 | ATGCTCTCATCTGGCCTCCAAATTGCTGGGTTATAG | 1758 |
| | 4 | MKCCVNTRRKVSPQRCLSLSRMSNIWADNKTLNSHEVWQYHLMNWQYYKCLRHKMLRFHLFSRTLRSCVGF* | 1759 | ATGAAATGTGTTGTGAACACAAGAAGAAGGTTAGCCCACAGAGATGTCTCTCACTTTCCAAGAATGTCAAATATTTGGGCTGAACAAAACTTTGAACAGTCATGAAGTATGGCAATATCATCATCTAATGAACTCTAATATATAAATGTCTAAGAATCATAAAATGTTAAGCTCAGAAGCTGTGTTGAATTCTAA | 1760 |
| | 1 | MPNPGSMMTTGGV* | 1761 | ATGCCCAATCTGGATCGATGATGACCACTGGTGGCGTATGA | 1762 |
| | 2 | MSHT* | 1763 | ATGAGTCATACATGA | 1764 |
| | 3 | MMNMCLEL* | 1765 | ATGATGAATATGTGTCTGGAACTCTGA | 1766 |
| | 4 | MHSYVIEMGSMKE* | 1767 | ATGCATTCTTATGTTATTATGGTCAATGAAAGAATGA | 1768 |
| hsa-mir-889 | 1 | MLLGHHLPGPPSR* | 1769 | ATGCTTCTGGCCACCATTGCCAGGGCTCCGCTGAGGTAA | 1770 |
| | 2 | MGTLTWAIQMIKMERGWDAGEGVLQPEGRGPRG* | 1771 | ATGGGCACCCTTACCTGGGCTATTCAAATGATCAAAATGGAACGGGGATGGGATGGAGGTGAGGGAGTGCTCCAGCGGAGGCCCGGAGGGCCCAGAGGATGA | 1772 |
| | 3 | MGCG* | 1773 | ATGGGATGCGGTGA | 1774 |
| | 4 | MRVRECSSRRARGHEDDVRLEAWTPGSCPWAPCASSQGSERLRGAPAIRFPFLSRAFDSSLLYTPACK* | 1775 | ATGCGGGTGAGGGAGTGCTCCAGCCGGAGGGCCCGGGGCCACGTTGCCTCCAGCGAAGGCCTTCCGAGCGACTGCGTGCGGGCTCCAGCTATCCGATTCCCTTCCTAAGTCGCGCGTTCGACAGCTCCTCCTTTACACACCGCGTGCAAATGA | 1776 |
| hsa-mir-9-2 | 1 | MKKGRKPTCASDSRWRNDCCHFRCHR* | 1777 | ATGAAAAAGGGAGGAAGCCACTGTGCGAGGACTGCGTTGGAGAAATGATTGTGGTTTCGTTGCATCCACCGCTGA | 1778 |
| | 2 | MIVVFYASTADS* | 1779 | ATGATTGTGGTTTTCGTTTGCATCCACCGCTGA | 1780 |
| | 3 | MAPLSSSGLWAAITTLVTMVEREGSGFILRPFPPSLPPACLPGLSSSDPACSLVSDL* | 1781 | ATGGCGCCCTTCTCTTCGGGCTTCTGGGCTGCCAAATCACCCTGGTAACAATGGTGGAAAGGAAGGGGTCCGGCTTCATTTGCACCCCTTCCTCCTTGCCCCCGCTTGGCCTTCCAGGGCTTTCCTCCGACCCAGCGTGCCTCACTGGTCTCTGATTTGTAA | 1782 |
| | 4 | MLNSILIVRLKLRHHFILQSAVGLWP* | 1783 | ATGCTTAATTCGATTTGATTGTCGTCTTAAACTAAGACATCATTTATTCTACAGAGCGCTGTCGGGCTTGGCCTTGA | 1784 |
| hsa-mir-92b | 1 | MAMCCHLSWG* | 1785 | ATGGCAATGTGTGTCATCTTCCTGGGGTTAG | 1786 |
| | 2 | MDPKAKGSKILNSESGGLLLTPFPGAAASGMAQSPQALCLKKGK* | 1787 | ATGGACCCCAAGGCCAAAGGGTCAAAATTCTGAATTCTGAATTCTGAATCGTGTGGCCTCCTCCTCACACCCTTCCCCGAGCAGCTGCCCGGAATGCCTCAAAGTGCTCAAAGTCCTCAGGCACTGTGTCTGAAGAGGGAAATAA | 1788 |
| | 3 | MRWLSHKA* | 1789 | ATGTGGCTCTCCCACAAGGCATGA | 1790 |

Figure 1 (Continued)

| | | | | |
|---|---|---|---|---|
| hsa-mir-920 | 4 | MFSWEKQNTPRRPPRMDVSMITPESATSWGPS* | 1791 | ATGTTTTCTTGGGAGAAGCAGAATACACCAAGACGCCCCCTCGCATGGATGTGTCA ATGATCACCCCAGAATCCGCCACAAGCTGGGGTCCCTCATAG | 1792 |
| | 1 | MTGRVSQDNQKGEFNLIFKNK* | 1793 | ATGACTGGGAGAGTCAGTCAAGTAATCAGAAGGAGAATTAACCTTATCTTTAAG AATAAGTAG | 1794 |
| | 2 | MVKS* | 1795 | ATGGTTAAGTCATAA | 1796 |
| | 3 | MSKLEKNLHEC* | 1797 | ATGAGTAAAATTAGAGAAGAACCTACACGAATCTGA | 1798 |
| | 4 | MLRNCSEENGKSSKPLHKPQS* | 1799 | ATGCTGAGAAATTGTTCTGAAGAAATGGAAAGTCATCAAAGCCTTTACACAAGCCA CAATCTTAA | 1800 |
| hsa-mir-924 | 1 | MKLIRLG* | 1801 | ATGAAGCTGATTAGGTTGGGGTAG | 1802 |
| | 2 | MERARMQ* | 1803 | ATGGAGAGGGCAAGGATGCAGTAA | 1804 |
| | 3 | MFKFGVLKREKIRIYELKNHMI* | 1805 | ATGTTTAAATTTGTGTTCTGAAAAGAGAAAATTAGGATATATGAGTTGAAGAAT CACAATATATAG | 1806 |
| | 4 | MLFKAMGLDDVEGKGKSMLREEMGIYIHL* | 1807 | ATGCTCTTTTAAAGCAATGGACTAGATGATGTGGAGGGTAAGGGAAAGAGCATGTT GAGGGAAGAGATGGGAATCTACATTCATTTATAA | 1808 |
| hsa-mir-9-3 | 1 | MRSPGQGRPEGG* | 1809 | ATGCGCTCGCCCGGGCAGGGCAGGGCCTGGAGGGGCGGCTAG | 1810 |
| | 2 | MRGALPLRVGGRTQSSRAKGCGAVGSAQR* | 1811 | ATGAGAGGTGCGCTCCACTGCGGGTGGGAGGCAGGACTCAGTCATCCGGGCAAA GGGTTGTGGGCAGTGGGAAGCGCCAGAGTGA | 1812 |
| | 3 | MHHTAPALDKIYDVFPPLKWEVVGKSYSLCSPLRAPEQ ASLICLWASLQPPPA* | 1813 | TGCACCACACAGCACCGCTCTAGACAAGATTTATGCGTTTTCCCCTCTGAAA TGGAAAGTTGTTGGAAATCCTATTCACCTCCGTGCCCAGAACAG GCCTCTTGATCTGTCTGTGGCGTCTTGCAGCTCCTCCAGCCTAG | 1814 |
| | 4 | MTPFPL* | 1815 | ATGACGTTTTCCCCTCTGA | 1816 |
| | 1 | MRLFPNRGRFCLASLVWTPRGAERRLCAQPGAGAGECL GPGAGGRAGRSQSGAQ* | 1817 | ATGCGGCTCTTTCCAAACCGGGGCCGTTTTGCCTGGCTTCTCGTGTGGACTCCG CGCGGGAGCTGAGAGCGCGCTGTGCGCCAGCCTGGAGCCGCGCAGTGAGTGTCT GGGCGGGAGCGGGGGGCGGCCGGAGCGAGGCCAGAGGGGTCAGTAG | 1818 |
| hsa-mir-96 | 2 | MTRQCLLALPRLQAEAPTGRLGPGSASGVCPAPSAVPG RGRGREKLRSECGRCLRGAYPRGVWLGSGCVSPPWWA QAEAPGWEGAAAESAGAPELAPPASCQGCAAGSRLLFWP GAAPPSLWGKAALRPPVCLHFAATHPGNPGARE* | 1819 | ATGACGCGGCAGTGCCTACTGCGCCTTCCGCGCCTTGCCCAGGCGGAGGCGCCCACGGG GCCCTGGGTCCCGGGTCCGCGAGCGGGCCCAGCCTGCCCAGGCCCAGCCCGTGTCCGG GCGGGGGCGCGGGGCGGAGGAGTTTGGCTGCGGTCCAGTGCGGCCTGCGCCTTGCGAGTT GCCTACCCGGAAGCGCCAGCTCGGAGGCCTGCGAGGGCTGCGGCCTGGTCGAGAGCGCCGAGC CAGGGGGCCCTGCAGCGTCTGTCAGGGCTGCGCCAGGGCTGGTTCGAGGCTGCTTCCGTGGC TGGCCCCGCGCCCCAGTCTCTGGCGAACCCCGGCGCACGGAATGA TCCACTTCGCGGCCACTCATCCGGGAACCCCGGCGCACGGAATGA | 1820 |
| | 3 | MRHRSPPSTAPFLLIALVAPRFPALPQDRRLDGLPLAPH RSAHPRTMGSEGVTRGQGSPDSTVSSRLSHSFALPTRAP GHRVQ* | 1821 | ATGAGACACCGTTCCCCGCTCAACTGCCCTCAATGCCCCATTCCTGTTAATAGCGCTAGTGGCA CCCAGGTTCCCAGCCGCATCCCAGGACTATGGCAGTGAGGGTGTCACCCGGGGTCAGGG CACCGGTCAGCGCATCCAGGACTATGGCAGTGAGGGTGTCACCCGGGGTCAGGG GTCGCCCGATTCCTCCAGGCTGAGCCATTCGTTTGCTCTTCCAACCCG GGCTCCCGGACACCGTGTACAGTAA | 1822 |
| | 4 | MGTESADL* | 1823 | ATGGGCACCGAGTCGGCGGATCTCTGA | 1824 |

Figure 1 (Continued)

| | | | | |
|---|---|---|---|---|
| hsa-mir-99b | 1 | MGIDTDNAPQAEKEDGDRERAKGRTDVQRQKGGQTER DTERQQKQPRMTGAERRRERGRERERERERGGREG ERERESTHRARRRRREEGGRPARDRTGRRGGGELGKA GEERDWFPRRRAGHERERPRRLPASFVPSLLCVRLLWPG LPLPLPPPPRGWMEFFPLDLGQLRGRGEARPDWAGRW GGAGAGGPLLGRGLVRRPRSRRGPGRGSPGPQSRGGGD GRRESGRREGGWRGRREEGERPPCGEGGERMESARRR WGPACGPGAAEKTPSLRRGSRGSRESAEREGGGLGPAL LGP* | 1825 | ATGGGAGACACAGATAATGCCCACAGGCAGAGAAAGAGGATGGAGATAGGGAGA GGGCGAAAGGAAGGCAGACAGATGTGCAGAGACAGAAGGGAGGACAGAGAGGAAAAGAGA CACAGAGAGAGGCAGCAAAAGCAACCAAGAATGACAGGAGCAGGAGACGAGAGGGAA AGAGGGAGAGAGCGAGAGAGCACGCACGAGAGAGGAGAGGAGAGGAGAGAGAGAG GGAGAGGAGGCCAGCGAGGCCAGGGCCAGGGCGGAGGAGGAGGCGCAGGAGAAGAGAG AAAGCCGGGAGGAGAGCGAAGACGGGGAGCGGCCGAGGGGAGGGAGGGGAGCTAGGG GCCCCGCGGCCTCCCCCTCCGGCTCCTTTGTCCCTCCTCCCCGGGCTGATGGAATTTTTCCC CTGGACCTGGGCAGCTCCGGGCAGTCCGGGCAGGGGGGAAGCCAGGCCGGACTGGCCTGGCC GCGCCAGCCGGCGGGTCAGHAGGGGGTCAAGHAGGGGGAAGGGGAAGGGGAAGGGGAAGGAGGATCGGCGCGAGGACGGCGGG GGTGACGGGCCGGAGGGAGAGGCCGGTGCGGGCAGAAGGGAGAAGGGGAAGGATGCGGGGACGGCGCTCG GCGCGGTGGGCCCGGCTGCGGGCCCGGGCCCGGCGGAGAAGGACCCCTTCCCCTGC GCGCGGAGGCCGCGAGGCCGTGAGTCGGGAGCCGGGAAAGGAGGGTGGGGGCTGGG GCCCGCACTCCTGGGTCCCTGA | 1826 |
| | 2 | MPHRQRKRMEIGRGRKEGQMCRDRREDRRKFTQRGSK SNQE* | 1827 | ATGCCCCACAGGCAGAGAAGAGGATGGAGATAGGGAGAAAGAGGAAAGGAAGGAC AGATGTGCAGAGACAGAAGGGAGGACAGAGACGAAAGAGAACACAGAGAGGCAGCAA AAGCAACCAAGAATGA | 1828 |
| | 3 | MAGTAGGRGEAAVRRRGHEDGERSAAVGPGLRARGG GEDFPATREPREP* | 1829 | ATGGCGGGGACGGCGGGAGAAGGGGAGAAGGGGAGAAGGGGCGCCGTGCGGCGGAGGGGAGAG AGGATGGAGAGCGCTCCGGCTGCGACGGAGGCCCCGCGGCCCGGGAGCCGTGA AGAAGACCCCTTCCCTGCGACGGAGAGCCCGCGGGAGCCGTGA | 1830 |
| | 4 | MGAGAGRIVAGRD* | 1831 | ATGGGGCTGGAGCTGGTAGGATCGGCTGAAGAGACTAG | 1832 |
| hsa-mir-940 | 1 | MGCNGGPLRGGDTFAAEFTRMEGRARRGNSRRRGSLEAAG KGGPGTGSQARASFAAAARSY* | 1833 | ATGGGGTGCAACGGCGGCCTCTCCGGGAGGTGACACTGCCGCTGAGACCGGAAT GGAAGGCGCGCCCGGGGGAACAGCAGGCGGCGAGGTTCGTGGAAGCAGGG AAGGGAGGCCCGGTACCGGCTCGCAGCGCCGCGAGCTTCGCGCAGCGGCACG GAGCGTGTGA | 1834 |
| | 2 | MLARLVEMS* | 1835 | ATGTTGGCCAGATGGTCGAGAACTCCTGA | 1836 |
| | 3 | MTWRL* | 1837 | ATGACTTGGAGACTTTAG | 1838 |
| | 4 | MSEQRTGCSLVTRSGWVGEWMDR* | 1839 | ATGTCAAGAGCAAAGGACAGGGTGCAGCTTGGTGACCGGAGTGGGTGGGGTGA ATGGATGGATAGATAG | 1840 |
| hsa-mir-1184-3 | 1 | MVSCRTR* | 1841 | ATGGTTTCTTGCAGAAACGAGGTGA | 1842 |
| | 2 | MASVSFSWVAMTKDWSSRKSSSGSWPLLSCPWLSKAS QEYSRVWACSGSSLAGGGCRRSSSSTRIDTSQRTSTSEK APRAAGHGAAEPEFGGSSAAGRAGVAPGPGWGAGGGG GGSDCTGWLPCSRARRCMRVKTARAPV* | 1843 | ATGGCTTCCGGTCCTGTCCTTTCGTGGGTAGCCATGACCAAAGACTGGAGCAGCAGAAAG AGCTCCTCGGGAAGCTGGCCCTGCCTCTCGGCCCGTGCCTGCAGCAGCTTGGCGCGGTTGTG GAGTACTTCTCCAGGGTCTGGGCGTGCAGCGGCAGCACTTCGCAGCCAGCACGTCCGAGA CAGGAGGAGCAGCAGCAGCACGGGAGAAGTGCGCCCAGGTTCGAGGAAGCAG AGGCGGCCAGGTGCGGGAGCAGTCGCCCGGTCGCCCCGGGTGGGGTGCCGGCGGGG GCGGCGGCAGTGACTGCACCGGGTGCTGCACGGGGCCTGCTCCTCCGCCAGCGCTGCAT CGCGCGTGAAGACGGCCAGGGGCCGGTGTAG | 1844 |
| | 3 | MLAAPSTSRRAAAAGRAGAGRRALRPPRRAAVPAP APQPEPAPCPGEVQRAGSEAGPGRAVSGVCKSRVSGMR HQDPGKVRGAWRGTSCC* | 1845 | ATGCTCGCCGCCCCAAGCACTTCCGACGCGCCGCCGCCGGCTGGCGGCGGGGGCCGT GCGGGGCGACGTGCCCTGCCCCTGCCCCTGCCCTGCCCTGTCGCGCCGCTGCCGCCGCCGCCGCCG CTCCCCAGCCGCCCAACCCTGCCCTTGCCCCTGTGAGCGCGGATGCAAGAGCGGGATCGGAG GATCCAAGACCCTGCGAAGGTACGCGGGCTGGCGGGCGGGGCCGGGCACCAGCTGCTGTAG | 1846 |

Figure 1 (Continued)

| | | | | |
|---|---|---|---|---|
| | 4 | MQIEGLGIDADPRPWEGTRGLAGHQLLLARLQCKWSRL LKASHSLSI* | 1847 | ATGCAAATCGAGGGTCTCGGGATCGGAATCCAAGACCCTGGGAAGGTACGCGGGG CCTGGCGGGCACCAGCTGCTGCTAGCTCGGCTGCAATGCAAGTGGTCTAGGTTGCT AAAGGCATCCCACAGCCTCTCCATCTGA | 1848 |
| hsa-mir-1302-8 | 1 | MGLTLLPNSSTPAHYFLQHLEQLLFLALDTHSVRPYPSG LSQALPQ* | 1849 | ATGGGGCTCACCCTGCTCCTCCAAACAGTTCAACTCCTGCACATTATTTCTTCAACATC TGGAGCAGTTACTTTTTTATTGCCCTAGACACACTCTGTCCGCCATATCCTTCAGG CCTTTCTCAAGCATTACCCTTTCAATGA | 1850 |
| | 2 | MTVDTYSNMSTSFLDFPYPHSQPYPSLAPI* | 1851 | ATGACAGTGGACACAGTCTCAACATGTCAACCTCCTTCCTTGACTTCCCTATCCCC ATTCTCAACCTTATTTCTTCCTTAGCACCTATCTAG | 1852 |
| | 3 | MYFTYAFIVCYPSKIKAL* | 1853 | ATGTATTTTTACTTATGCTTTTATTGTCTGTATCCTTCTAAAATTAAAGCTCTGTGA | 1854 |
| | 4 | MLLLSAILLKLKLCEHHKDFCLVP* | 1855 | ATGCTTTTATTGTCTGCTATCTTCTAAAATTAAAGCTCTGTGAGCACAAGGATTTTT GTTTGGTTCCTTAA | 1856 |
| | 1 | MQGCEGGGWEGWGEAGSAEMWGAQRWGGSAGPPGT AQPRALCPGPRGLTREGDARPCCSAAARAPPAAILIGPT EARPQKPLPQ* | 1857 | ATGCAAGGTTGTGAGGGTTGTGATGGAGGGCTGGGGCGAGGCGGGCGGTCCGCAG AGATGTGGGGGGCGCAGAGATGGGGGGAGCTGGGGCCCCCGGGGACGCGCA GCCTCCGGCTCGTGTCCCGGGCCGCGGGTTAACTAGAGAAGGTGACGCGCGCC CCTGTCCTGCTCAGCCGCGCGTGCCTCCGGCGCGGATCCTAATTGGCCGACAG AAGCCGCCCCAGAAGCCCTCCACAGTAG | 1858 |
| | 2 | MGGLGRGGVRRIDVGGAEMGGVRGPAGDRAASGSVPG AARYN* | 1859 | ATGGGAGGGCTGGGGCGAGGCGGGGTCCGCAGAGATGTGGGGGGCGCAGAGATGG GGGGGGTCCGCGCCGGGGACCGTGCGCGGAGCTCCGGCTCGTGTCCCGGGGCC GCGCGGGGTTAACTAG | 1860 |
| hsa-mir-3178 | 3 | MTVSRAHAPNAVSGLIDVLGAHEVQRLGRRKG#G* | 1861 | ATGACGGTCTCCGTGCCCAGCCCAAAGGCAGTTCTGCCTGGATGTGCTGGA GCCAGCGAGGTGCAGAGGCTCGAGAGACTCGGCGAAAGGACCTGGCTGA | 1862 |
| | 4 | MCSEPTRCRGSDGERDLAEIWVLNRGLGPASRQRAPTS DTRPGAVCGLAGAGSHLQFTHGTKRAJPTSSESMHLQL HPSPHARPPNP* | 1863 | ATGTGCTCTGGAGCCCACGAGGTGCAGAGGCTCGAGAGGGACCTGGCTGA GATCTGGGTTCTTAAACCGCGGACTGGGCCGCGGCCAGCGCCTCCCACA GTGACACCGCGGCCGGTCTGCGGGATCTCGCAGGCGCGGGTCTCATCTCCAG TTCAACACACGGACGAAAACGGGCACCTACCAGTCTGAGAGCATGCAACCTCCAA CTCCATCCCTCCCCACATGCCACCACCCCCCCAAACCGTAA | 1864 |
| | 1 | MVTHDKEGQSCHLSREDCASF* | 1865 | ATGGTGACCATGATAAGGAAGGACAGTCATGTCATTCCGGGAAGACTGTGCC AGTTTTTAA | 1866 |
| | 2 | MIRKDSHVIFPGKTVFVFNFAT* | 1867 | ATGATAAGGAAGGACAGTCATGTCATTCCGGGAAGACTGTGCCAGTTTTTAAC TTTGCAACTTGA | 1868 |
| hsa-mir-3179-2 | 3 | MSSFPGRLCQFLTLQLECQDFCSFYLY* | 1869 | ATGTCATCTTTCCCGGGAAGACTGTGCCAGTTTTTAACTTTGCAACTTGAATGTCAA GATTTTTGTTCCTTTATCTGTATTAA | 1870 |
| | 4 | MSRFLFLSVLMFLRFQKYY* | 1871 | ATGTCAAGATTTTTGTTCCTTTATCGTATTAATGTTTCTAGAATTCAGAAATACA TATATTGA | 1872 |
| | 1 | MVTHDKEGQSCHLSREDCASF* | 1873 | ATGGTGACCATGATAAGGAAGGACAGTCATGTCATTCCGGGAAGACTGTGCC AGTTTTTAA | 1874 |
| | 2 | MIRKDSHVIFPGKTVFVFNFAT* | 1875 | ATGATAAGGAAGGACAGTCATGTCATTCCGGGAAGACTGTGCCAGTTTTTAAC TTTGCAACTTGA | 1876 |
| hsa-mir-3180-2 | 3 | MSSFPGRLCQFLTLQLECQDFCSFYLY* | 1877 | ATGTCATCTTTCCCGGGAAGACTGTGCCAGTTTTTAACTTGCAACTTGAATGTCAA GATTTTTGTTCCTTTATCTGTATTAA | 1878 |
| | 4 | MSRFLFLSVLMFLRFQKYY* | 1879 | ATGTCAAGATTTTTGTTCCTTTATCGTATTAATGTTCTTAGAATTCAGAAATACA TATATTGA | 1880 |
| | 1 | MFPRVSTFLFLRPLSRHPLSSGSPETSAAAIMLLTVRHGT VRYRSSALLAR* | 1881 | ATGTTTCCTAGAGTCTGGACGTTCCTACCTCTTCGCCCCTTTCCGCACCCTTGT CCTCTGGAAGCCCGGAGACATCAGCGGCTGCGATTATGCTACTCACTGTTCGGCACG GAACAGTCAGGTTACCGCAGTTCAGCGCTGTCCGGTCTTAG | 1882 |
| hsa-mir-3204-1 | 2 | MLPPAGS* | 1883 | ATGTTACCACCTGCTGGGTCTTAG | 1884 |

Figure 1 (Continued)

| | | | | | |
|---|---|---|---|---|---|
| | 3 | MTCPRS* | 1885 | ATGACTTGCCCAAGGTCATAG | 1886 |
| | 4 | MNEYLLG* | 1887 | ATGAATGAGTACTTGCTGGGATAG | 1888 |
| hsa-mir-769 | 1 | MGHSSCQVLRSRSLECSFFFPFETEFRSCSPGWSAMAR3WLTETSTSQRGNYRRPPHPANCLYF* | 1889 | ATGGGACATTCATCCTGCCAGGTACTTGCTCTTGAGACAGAGTTCGCTCTTGTAGCCCAGGCTGGAGTGCAATGCGCGATCTTGCCTCACTGCAGATCCTCACTTCCCAGATTCAAGGAATTACAGGCGCCCGCCACCACCCAGCTAATTGTTTGTATTTTTAG | 1890 |
| | 2 | MLARLVLNS* | 1891 | ATGTTGGCCAGGTTGGTCTGAACTGTGA | 1892 |
| | 3 | MPHQLLCYHSGLSLSPALTWFVAVAFQVGSLPLTVRGILVEQKSGQVVSPFKPSPGSSHITLQKSSPYPRGPMLLGSSSSLPSTPITSLIPLAHSAAATLASPLSFEHSEHRAISGPLYSLSLNALPPQGLCTRCPVLLDQVFSGVCVASSTPLSGLRSDVSFTTRHLLKYYSS* | 1893 | ATGCCTCACCAGCTCCTTGCTACCACTCGGCCTCAGTTGTCTCCTGCTCTTACTGTTTGTTGCAGATCTCCAGGTGGGCTCCTGCTCCTCACTGTTAGGGRGATACTAGTAGAACAGAAGTCAGGTCAGTTGTTCTCCTTCAAACCCTCCTGCGCTCCCACATTACACTGCAAAAGTCTTCACCATATCCACGAGGCCCAACCTATTGGGTTCCTCCTCCTCCACTCCAACTCCCATCACTTCTCTACTTCCTGGTCACTCTGCTGCAGCCACCCTGGCTCCCCGCTGCTCCGTCATTTGAACATAGCGAACACATTGCCATCTCAGGGCCTTTGTACTCGCTCCCTGAACGCCACCTCAGGGCTGTGTGGCTTTCTTCCACACCTCTTCTGTCCTTGGATCAGGTCTTTCAGGTGTCTAGGTGTCAGTGAGCCACCTCTTTCAGGTCTCCGCTCAGCGTCAGCTTCACAACCAGCATTTGCTAAAGTACTACTCAAGCTAA | 1894 |
| | 4 | MALHLALFFFITPLPDIDYYYFF* | 1895 | ATGGCCCTTCACTTGGCTTTATTTTTCATAAACACCACTACCTGATATAGATTATTATTATTATTTTGA | 1896 |
| | 1 | MTVPLFSGGEQNICLLS* | 1897 | ATGACAGTCCACTTTCAGTGGAGAGAACAAATATCTGTCTACTCTCTTGA | 1898 |
| | 2 | MQADECHSCN* | 1899 | ATGCAGGCAGATGAGTGTCACAGTCGTAACTGA | 1900 |
| hsa-mir-1251 | 3 | MSVTAVTEAQSSTHSGADFRDGERGHRR* | 1901 | ATGAGTGTCACAGCTGTAACTGAGGCACAGAGCAGTACACAGTGGAGCCGATTTCGGCGATGGCGAGAGGGGCACCGGAGGTGA | 1902 |
| | 4 | MARGGTGGDNNNNKTVLRTSFR* | 1903 | ATGGCGAGAGGGGCACCGGAGGTGACAACAATAACAAGAGACTGTCCTTGGACAAGTTTTAGGTAA | 1904 |
| | 1 | MSDTGTTLPSQSPFQCWGSSVFSRPFPGFNASSRQRDGILGEC* | 1905 | ATGTCTGACACTGGCACCACTCTGCCATCCAGAGTCCATTCCAGTTCATTCAATGCTGGGGGTCATCCGGTTTCAGCAGGTTCTTCCCTGGGTTCAACGCGTCTTCCCGCCAGAGGGATGGAATCTTGGGTGAGTGTTGA | 1906 |
| | 2 | MLGVIGFQQVLPWVQRVFPPEGWNLG* | 1907 | ATGCTGGGGGTCATCGGTTTCAGCAGGTTCTTCCTGTGGGTTCAACGCGTCTTCCCGCCAGAGGGATGGAATCTTGGGTGA | 1908 |
| | 3 | MESWVSVEMRQKQKRKVELEHVTDLGPEVACEALEETPPCELMVTQLEDHKAQARESHPQS* | 1909 | ATGGAATCTTGGGTGAGTGTTGAAATGCGTCAGAAGCAAAAGCGAAAGTGGAACTGGAGCACGTCACAGACCTTGGACCAGAAGTGGCCTGTGAGGCACTGGAAGAGACGCCACCGTGCAGCTGATGGTCACAGCAGCTTGAGGAGACCACAAAGCCCAAGGCAAGAGAGAGCACCCCCAAAGCTAA | 1910 |
| | 4 | MQQSEAITGQGIDALKREEQPGPPAAV* | 1911 | ATGCAGCAGAGCGAGGCCATAACTGGCCAGGGAGACGGCACTCAAGAGAGAGAACAGCCAGGGCCGCCAGCAGCCGTCGGGGTCTAG | 1912 |
| hsa-mir-3179-3 | 1 | MMNVSLGLSEPLVICGLLIDRLLILLIDHVSGS* | 1913 | ATGATGAATGTTCTCTTGGGTCTGAGTCTGAACCCTGTCATTTGTGGGCTGCTAGATCGATTATTAATATTGCTGATTGATCATGTTAGTGGTTCTTAG | 1914 |
| | 2 | MPFLLVCLNPLSFVGC* | 1915 | ATGTTTCTTCTGGTCTGCCTGAACCCTTGTCATTTGTGGCTGCTAG | 1916 |
| | 3 | MLVVLSD* | 1917 | ATGTTAGTGGTTCTTAGTGATTAA | 1918 |
| | 4 | MWRLPDLTSQWSMTA* | 1919 | ATGTGGCGCCTTCCAGACTTGACTTCACAGTGGAGCATGACAGCTTGA | 1920 |
| hsa-mir-3180-3 | 1 | MMNVSLGLSEPLVICGLLDRLLILLIDHVSGS* | 1921 | ATGATGAATGTTTCTCTTGGTCTGTCTGAACCCTGTCATTTGTGGGCTGCTAGATCGATTATTAATATTGCTGATTGATCATGTTAGTGGTTCTTAG | 1922 |
| | 2 | MFLLVCLNPLSFVGC* | 1923 | ATGTTTCTTCTGGTCTGTCTGAACCCTTGTCATTTGTGGGCTGCTAG | 1924 |
| | 3 | MLVVLSD* | 1925 | ATGTTAGTGGTTCTTAGTGATTAA | 1926 |

Figure 1 (Continued)

| | | | | | |
|---|---|---|---|---|---|
| | 4 | MWRLPDLTSQWSMTA* | 1927 | ATGTGGCGCCTTCCAGACTTGACTTCACAGTGAGCATGACAGGTTGA | 1928 |
| | 1 | MWSECKKTSILK* | 1929 | ATGTGGGTCAGAGTTGAAGAAACTTGAAGAAAACTAGTAATCTTAAGGTAG | 1930 |
| hsa-mir-3159 | 2 | MVGRLHFLPSYQFCPFSHVYCVRESCDKIKSTVLHGEITRVH* | 1931 | ATTGTGGGAAGACTTCATTTTTACCCTGTACAGTTTTGTTTTTCAGTCATGTTATTGTGTTAAGAGAAAGTTGTGACAGTTGTATCAAAATAAAAAGTACTGTGTTAATAATTATAGGCGAAATTACAAGAGTCCATTGA | 1932 |
| | 3 | MFIV* | 1933 | ATGTTTATTGTGTAA | 1934 |
| | 4 | MKTWGKIIL* | 1935 | ATGAAGACTTGGGGAAAAATAATTCTGTAA | 1936 |
| | 1 | MKRHIATRATEHKKERGQRREARWHLLPAGGGASEERLPGLSGTPILTLHLRKGRLWRK* | 1937 | ATGAAAATAAAACACATGCAACCAGAGCACTGAACACTGAAAAGGAGGAGGACAGAGAAGAGAGGGAGGTGGCATCTGCTCCGGCTGCCGGCGCTTCGGAGAGGCTCCCCTGGCTGCGGCGGACCCGCATTTGACCCTGCATTTGAGGAAGGGCGACTGTGGAGAAATGA | 1938 |
| hsa-mir-4323 | 2 | MRREGVRAGGGSACFFFFLSLSLFLEVWGPV* | 1939 | ATGAGGCGAGAGGGGGTCAGGGCTGTGGGGGTCCGCCTGTTTTTTCTCTCTTCCTGGAGGTGTGGGGGCCGGTTAG | 1940 |
| | 3 | MMVRLVGDAV* | 1941 | ATGATGGTGAGGATATTGGTCGTGATGCTGTCTGA | 1942 |
| | 4 | MLSEAPKQAGCNGGGEVRGHRERERAGWWE* | 1943 | ATGCTCTGTCTGAAGCTCCCGAAGCAAGCAGGGTGCAATGCGGGGGAGAGGTAAGAGGCACAGGGGAACGAGAAAGGGCTGGGTGGGTGGGAATGA | 1944 |
| | 1 | MGDPHRLESQGLLSSAVKGLSLAGTGLNRREMHYLVSCDLGQQLGRVIWDAGSFPLSPPFHSSRFTTAQ* | 1945 | ATGGGCGACCGCACAGACTTGAATCCAGGGCTCCTCAGCAGTCTGTGAAGGGCTGTCCGCTGGACTGGCTTAACAGAAGGGAAATGCACTATCTCGTGTCTGCGATCTGGGTCAGCTCGTCCTTCATCGGATGCAGCCAGCCTCCCTTCCTCTTCCTCCTCCATTCATAGCTCCAGTTCACCACTGCACAGTAA | 1946 |
| hsa-mir-4267 | 2 | MQAPFLFLLLHFIAPGSPLHSNGQSKKGTIVPCAPFSGTR* | 1947 | ATGCAGGCTCCTTCCCTCTTTCCTCTTCCTCTCTATAGCTCCAGTTCACCACTGCACAGTAATGGCCAGAGCAAGAAAGGGACCATTGTGCCCTGTGCCCCTTCTCAGGCACCAGGTAGCCAGGTAG | 1948 |
| | 3 | MARARKGPLCPVPPSQAPGRLSLCLVDQD* | 1949 | ATGGCCAGAGCAAGAAAGGGACCATTGTGCCCTGTGCCCCTTCTCAGGCACCAGGTAGACTTTCCCTCGTCTCGTTGACCAGGACTAA | 1950 |
| | 4 | MSLMAWAVTSPYW* | 1951 | ATGAGCCTAATGGCATGGCAGTGGACATCCCTTACTGGTGA | 1952 |
| | 1 | MWISKREYESSPSAVRCKCL* | 1953 | ATGTGGATCAGCAGCGAATACGAGTCCAGCCGTCCGTGTCCGCTGCAAATGCCTCTAG | 1954 |
| | 2 | MPLGRLLSCVIPFLAKTYLWAKMKIGKAFVLFCFWIDSGFKKTRPMKVTAVSWSEHPPKPCNVSEDFD* | 1955 | ATGCCTCTAGGCAGCTGTTACTTAGTTGCGTATACGCTTCTTGCCAAAACCTATCTATGGCAAAAACAAGATTGGCAAGGCTTTGTTTTGTTTTTGGATTGACTCAGGATTTAAAAAACCGATGAAGGTGACAGTCAGTTGGAGTGAGCATCCCCAAAGTTCTGCAATGTCTGTGAGGACTTTGATTAA | 1956 |
| hsa-mir-1246 | 3 | MGKKQDWQQGFCFVLFLD* | 1957 | ATGGGCAAAAAGCAAGATTGGCAAGGCTTTTTTTAAGTCATTCAAATATCGTGAGATGCATTGTTACAGGAGACGCTTGCCATCCGAATGA | 1958 |
| | 4 | MCLRLTLINLFLSHSKYREMHCYRKTLAIPKTPLLSKENGPVLSRVPHMGGIDSSAFNVMKVM* | 1959 | ATGTGTCTGAGGACTTTGATTAACTTTTTTAAGTCATTCAAATATCGTGAGATGCATTGTTACAGGAAGACGCTTGCCATCCCAAAACCACCCCACTTCTCTTAAGCAGGACCCAGTCCTCTCCGAGTCCCACACATGGAGGTGATAGCAGTGTTTCAATGTAAATAAGGTAATGTAA | 1960 |
| | 1 | MIGLRPRHARRTVFVY* | 1961 | ATGATTGGTCTAAGGCCCCGGCACCGTCGGCGCACAGTATTCGTGGTGGTGTAG | 1962 |
| | 2 | MLTIEN* | 1963 | ATGTTGACAATTGAGAATTGA | 1964 |
| | 3 | MDFLLSAL* | 1965 | ATGGACCTCCTCCTCCTCAGCATTATAG | 1966 |
| hsa-mir-1274b | 4 | MEEGVGHASFYPYSNWISIDLKSDKKHLQSISLKLATCRLHLYDKTWYSNQGDH* | 1967 | ATGGAAGAAGGGGTTGGACATGCCAGTTTTTACCCTTACCCCTACAGCAATAACATCAGATAGGACCTTAAGTCTGATAAGAAACATTTACAATCTATTTCTGAAACTTGCTACCTGCAGGCTTCATCTGTATGATAAACCTGGGTCTCCAACCAAGGTGATCATAA | 1968 |
| | 1 | MGAERLGVRGNSLTRGALAGPAAASETF* | 1969 | ATGGGTGCTGAAGCGTTTAGGGGTGCGGGCAACTCCCTAACTCGTGGGGCCCTGGCCGGCCCCTGCCGCGGCGTCGGAGACCTTCTGA | 1970 |

Figure 1 (Continued)

| | | | | | |
|---|---|---|---|---|---|
| hsa-mir-1247 | 2 | MRRWPLFSISQSRDFSAVWGRGAHPRNLLRRGKPAWSLPLASVLLSCPSPLWVGGVFQVG* | 1971 | ATGAGAAGGTGGCCCTCCTTCTCCAATCTCCAGTCAGGCGATTTCTCTGCTGTGGGGCAGGGGCGCACACCCAGGAACTTACTACGTAGAGGGAAGCCAGCCTGGTCTCTCCCCCTTGCGTCAGTGCTCCTAAGCTGCCCCTCACCACTCTGGGTAGGGGTCTTTCAGGTGGGCTAG | 1972 |
| | 3 | MGWFPKPFSHS* | 1973 | ATGGGATGGTTCCCAAGCCCTTTCCACAGCCCTTTCCACAGTAG | 1974 |
| | 4 | MVPQALFPQLVSENA* | 1975 | ATGGTTCCCAAGCCCTTTCCACAGTTAGTTCAGAAAATGCATAA | 1976 |
| hsa-mir-1253 | 1 | MRAALDGRHCQAGLVQTPRFFLGPLPTLCSGAAALTWATRSKP* | 1977 | ATGAGGGCTGCGTTAGATGGGAGACACTGCCAGGCTGGGCTGTGCAAACCCCAGATTCTTCCTGGGCCCCCTGCCAGGCAGCCCTAACCTGGGCCACAAGGAGCAAACCCTGA | 1978 |
| | 2 | MGDTARLGSCKPPDSSWAPCQRSAQEQP* | 1979 | ATGGGAGACACTGCCAGGCTGGCTCGTGCAAACCCCAGATTCTTCCTGGGCCCCCTGCCAACGCTCTGCTCAGGAGCAGCCCTAA | 1980 |
| | 3 | MMPQGDDAAGR* | 1981 | ATGATGCCGCAGGGCGATGATGCCGCAGGCAGATGA | 1982 |
| | 4 | MMPQADEQ* | 1983 | ATGATGCCGCAGGCAGATGAACAGTGA | 1984 |
| hsa-mir-3158-2 | 1 | MEAWPLLHHFLHNGNNNTYLVGSL* | 1985 | ATGGAAGCTTGGCCTTCATATTCACTTTCTGCACAATGGAATAATAATATCTATCTTGTBGCTCATTGTGA | 1986 |
| | 2 | MGHISLWAHCEM* | 1987 | ATGGGAATAATAATATCTATCTTGTGGGCTCATTGTGAGATGTGA | 1988 |
| | 3 | MCARPF* | 1989 | ATGTGCGCACGCCCTTTCTAA | 1990 |
| | 4 | MTMGIREWGGGQEWLQVVGSS* | 1991 | ATGACCATGGGAATAAGGAGTGGGGGTGGGGGCAGGCGCGGGGTCGCATGGCTGA | 1992 |
| | | | | GGAGTAGTTGA | |
| hsa-mir-1285-2 | 1 | MGAGAERRGAARGRHG* | 1993 | ATGGGCGCGGCGGCGAGGCGAGCAGCGGAGCAGGAGGCGGTGAGTCCATGTGAAGAG | 1994 |
| | 2 | MAELQQLRVQEAVESMVKSLERENIRKMQVAGLGPNQDPLLSGWVPGPSLSHHATPCTAAASPQTGCGRPWGRRGGLGQDFGSFGGSDEIRVFLPCARLFSAPSSPGQERPRKQVGSPWWQALAPPPSFLTRPLPQVSGPRPSRGAANVKDQKGEDFRPPRWPGHACPSCAQPRFTQRGFLHCSSLSPAMPLCVSVLLSRSSMRFPDSAP* | 1995 | ATGGCTGAGCTGCAGCAGCTCCGGGTGCAGGAGGCGGTGGAGTCCATGTGAAGAGTCTGAAAGAGAGAAACATCCGGAAGATGCAGGTAGCGGGGCTGGGGCCGAACCAGGACCCCCTTCTCAGCGGATGGGTTCCCAGCCGGTCCCTGAGCCATCATGCCACACCGACGCCTTGCACTGCAGCGCTGCAGCAGACGTTTGGCGGATCCGGGAAGATCCGTGTGCCCTTCGGCCTGCGCGAGGCTGTTTCGGCCCCTTCCAGCCGGGCAGGAGCTCCTGGCGGGCGGTGGGAAGCCCCCGTGGCCAAGCCCTTACGGGGCCCGCTGGCGGCCAGGCGCTCCAGGCCCTGCCTCTTACGCGGGTTTCCTCTCAGATAGCAGGAGTATGCGTTTCCAGATAGTGCCCCTTGA | 1996 |
| | 3 | MKSVCPCRARGCPPPLPARGRSVLGGRWEAPGGRRSPHHLPLLRGPFRR* | 1997 | ATGAAATCGGTGTGCCCGTGCCGTGCGCGGGGCTGTTTTCCGCCCCTTCCAGCCGGGGCAGGAGCGTCCTCGGCGGCAGGTGGAAGCCCCTGGTGGCCAGGCGCTCGCCCA | 1998 |
| | 4 | MPASLAPNLASHSAGFYTVLL* | 1999 | ATGCCTGCTTCTCTTGCGCCCAACCTGCTTCACACAGCGCGGGTTTCACACTGTTCTTCTCTGA | 2000 |
| hsa-mir-1285-2 | 1 | MGSCCCLFGDAAILASAREG* | 2001 | ATGGGCTGCGTGCCTGCGTGTGTCTTCGGAGACGCTGCTATCTTAGCGTCAGCGAGGGAAGGTTGA | 2002 |

Figure 1 (Continued)

| | | | | |
|---|---|---|---|---|
| hsa-mir-3168 | 2 | MQSREDAPRSRRLASPRGGKRPKKJHKPTVSAFFTCGPEE LKDTAHSAALLAQLKSFYDARLLCDVTIEVVTPGSGPG TGRLPPCNRNYLAAACPYFKSMFTGRMYESQQASVFM HDVDAESFEVLVDYCYTGRVSLSEANVERLYAASDML QLEYVREACASFLARRLELTNCTAILKFADAFGHRKLRS QAQSYIAQNFKQLSHMGSIREETLADLTLAQLLAVLRL DSLDYESEQTVCHVAVQWLEAAPKERGPSAAEVFKCV RWMHFTEEDQDYLEGLLTKPIVKKYCLDVIEGALQMR YGDLLYKSLVPVPNSSSSSSNSLVSAAENPPQRLGMC AKEMVIFFGHPRDPFLCCDPYSGDLYKVPSPLTCLAHTR TVTTLAVCTSPHDIYLAAQPRTDLWVYKPAQNSWQL ADRLLCREGMDVAYLNGYIYILGGRDPITGVKLKEVEC YNVKIRNQWALVAPLPHSFLSFDLMVIRDYLYALNSKR MFCYDPFSHNMWLKCVSLKRNDFQEACVFNEERYCICDI PVMKVYNPVRAEWRQMNNIPLYSETNNYRIKHGQKLL LIFTSRITPQWKKNRVTVYEYDIRGDQWINGTTLLGLLQFD SNFFCLSARVYPSCLEPGQSPLTBEEIPSESSTEWDLGG FSEPDSESGSSSSLSDDDFWVRVAPQ* | 2003 | | 2004 |
| | 3 | MRGCCVM* | 2005 | ATGCGCGCTGCTGTGTGATGTGA | 2006 |
| | 4 | MCWPRHVPTSRACSQVACTRASRPA* | 2007 | ATGTGCTGGCTGCTGGCATGTCCTACTTCAAGAGCATGTTCACAGGTGGCATGTACG AGAGCCAGCAGGCCAGCGTGA | 2008 |
| hsa-mir-1973 | 1 | MLSPKL* | 2009 | ATGCTTAGCCCTAAACTCTAA | 2010 |
| | 2 | MRWQEMGYIFYIRQSQQPL* | 2011 | ATGAGGTGGCAAGAATGGGCTACATTTTCTATATCCGGCAAATCTCACAACAACCT TTATGA | 2012 |
| | 3 | MKSKGSRRI* | 2013 | ATGAAAATCAAGGGCTCAAGGAGGATTTAG | 2014 |
| | 4 | MKHAHTAHHPPQLL* | 2015 | ATGAAGCATGCACACGCTCATCACCTCTCAAATATTACTCTAG | 2016 |
| | 1 | MFAYTLAPGRR* | 2017 | ATGTTTGCTTACACGTTAGCTCCTGGAGGAGATAG | 2018 |

Figure 1 (Continued)

| | | Protein | SEQ ID | Nucleotide | SEQ ID |
|---|---|---|---|---|---|
| hsa-mir-4309 | 2 | MKRVLPSHFPAGHKLLQFSKVSKPRQSQA* | 2019 | ATGAAGCGGGTACTGCCATCCACTTTCAGCAGGCACAAGCTCTCCAATTCTCCAAGGTCAGCAAGCCACGGCAGAGCCAGGCCTAG | 2020 |
| | 3 | MPCAGTRGAPGGLRKVRPHVTGQSHGRGS* | 2021 | ATGCCCTGTGCGCTGGCACGCGTGGGGCGCCGGGGCGCTCGGGCGCGGTTACGTAAAGTTCGGCCTCCCCACGTCACCGGGCAGAGTCACCGCCGCGGCTCGTGA | 2022 |
| | 4 | MGGGAGATGCRASPPLPRTGARAVPRGRIAGRRCRRRRRAAGGGRRAGATAARARRSRALSRRGRIAGRRCRRRRRAAGGGRRAAQCGPGQAGQRDRPPPPLARAAGPRHHPLAAALJHCYVTGRRAGRTAGPAENFGET* | 2023 | ATGGGGGGCGGGGGCGCACAAGCCGGGGCCGTCCCGCCCGCTGCCGCCGGACCGGAGCGGGCGCGTCCCCGCGGCGAGCGGGCCAAAGGTCCCACGACGACGCACGGAGGGACCACCGCGGCGCCGCCGCCGCGCGTGGGCGGCAAGCCCATCCCGAGCGGCCGGGGAGCGGCGGCGGCACCGCGGGGCAAGGAACGGCAACGCACCCAGCTGCGCGCCGCCCCATTGGTACGTCTGGCCCGGCCGCCACCACGCTGAACGCTGGAAAACCTTGTGAGAAACTGA | 2024 |
| | 1 | MGTRGLPGSRAGAAPGGFAGRASLGRGGSPLQKGRVPPSASCARPSLGJGSGRGWRCFAFPPFS* | 2025 | ATGGGGAGGGCCTTCCCGGCTCTCGGGAGAGGCCTCCCGGCTCTCCCTGGGAGTGAGCCCCTCTGGGAATAGGAAGCCGGAGAGGCTGGAGATGTTCGCAATTCTTTCCGTTTTCCTGA | 2026 |
| | 2 | MFRILSVFLRSFSWVQSLLKVC* | 2027 | ATGTTTCGCATTCTTTCCGTTTTCCGTTGGTCCGTTAAAGTCTGTAA | 2028 |
| | 3 | MRAGRWVLQTARRGLPALGPSTAGSGAAHSPPGVRQEARRLPFRRTLRVT* | 2029 | ATGCGTGCGGGCAGGTGGGTCTGCAGATCGCGGCGCCCTGCCTCCGAGTGAGGCAGGAGGCACTTAG | 2030 |
| | 4 | MGVSLSWNVWGLVQRWGLGSCWEGGAPKDNGGPFSSCSQVDGSLPCPSELSLAGPRAAARGSPAEVAAAGTYGLSWPGDSWVLLLLSCHQANVVSFLSLYSIVPDIAVGTKVGTSHFASP* | 2031 | ATGGGGGTGCTTGGAGGGAGGCAAAGGACAATGGTGGCCCCTTCAAGTTGCAGTCAAGTGACGGCTCACTTCCTGCCAGGGCTGGCAAGTGGCCTGTGCAGCAGAGGCAGCCTGGGCTGCAGCTGCAGGGACCTGCAGGGAGGCCACCAGCTAACGTTGTCTCCTTCTTTCTCCTCTACAGCATTGTCCCCAGATAGCCGTTGGTACAAGGTAGGCACTTTAA | 2032 |
| hsa-mir-3187 | 1 | MPHSKEKKTCKKCKNDNRKTILFRAPQ* | 2033 | ATGTTCATTATAATCTCAAAGGAGAAAAAAACTTGTAAAAATGCAAAATGACAACAGAAAAACCATCTTATTCGAGCATTCCAGTAA | 2034 |
| | 2 | MTTIEKPSYSEHSSMPFVYVLSCTISSSWFV* | 2035 | ATGACAACAGAAAAACCATCTTATTCGAGCATTCCAGCATTCCAGTAACTTTTGTGTATGTACTTAGCTGTACTATAAGTAGTTGTTTGTATGA | 2036 |
| | 3 | MYLAVL* | 2037 | ATGTACTTAGCTGTACTATAA | 2038 |
| | 4 | MRWLKRPKIKGFFFLFCL* | 2039 | ATGAGATGGTTAAAAGGCCAAAGATAAAAGGTTCTTTTTCTTTTGTCTATGA | 2040 |
| hsa-mir-1244-3 | 1 | MAPPALRAGELGRERGGERDTRAGTKPCYRVVGQAGWLASLVSIGERPPAVAPTCESAGAGMVLGVMAAGWGSRCPPCRSRRPALSHQLGPIPPAPVGAGRVPIAAAAAILASATPRHRARPCGPLALSSLPARASRG* | 2041 | ATGGCCCCGCCTGCCTGAGAGCTGGAGAACTCGGGAGGGAGGAGGAGAGAGAGACACGCGTGCGGGGACGAAACTTGTTCGTCGTCATGGGGGCAGGCTGGATGGCTCGGCCAGCCTGGTGGATATGCGGGACGTATCGGAGGAGCGCCCCTGCCGTTGGAGCGTCTCCGGCGATGTCTCGGCATGCGGGGCCTACCGCGCATCCGCCCTGCTGCCTGCCGGCGAGCCGTCGTCCGCCTCGTCCACCAGCTCGGCGCTGCCCCATCCTTGCCTTGCCACACCGGCACCGCGCACCGAGCGTCCTGCGCCGCCTGCCGTCTCCAGCCTTCTCCGCGTAGGCGGTCTCGAGGGTAG | 2042 |
| hsa-mir-1826 | 2 | MARQPGEYRGAPPCRGPYM* | 2043 | ATGGCTCGCCAGCTCGGTGAGTATCGGGGAGTATCGGGGAGCGCCCCTGCCGTGGCCCCTACATGPGA | 2044 |

Figure 1 (Continued)

| | | | | |
|---|---|---|---|---|
| | 3 | MGRVRWARGGVRSGGARPSLASPADSIPSASRGRASLSSRR* | 2045 | ATGGGTCTGGTGCGGTGGCCCGCGTGGCCCGACTCCATCCCTTCGGTTCGGAGGGCCCGCCCTCCCTCCCCTCCCGCCGACTCCATCCCTTCGGCCAGCCGGGGCGCTGCCTCACTTTCAAGTCGCTGCTGA | 2046 |
| | 4 | MACAPCCGGGNPRAPYGCCQCSPSAPVVDTASLCCETFLPLSGVWSRCCLTGFHEGNPLADVLCQEGLLVLGAPFLPNPPCMTFSGGSLGFCVDEERS* | 2047 | ATGGCCTGTGCACCTGCCTGCCCGGGAATCCCGGCGCCCGTGGGTGCTGCTACCCCCTCTCTGGAGTCTGTTGCCCCCGTGGTCTGTTGCTGTTGACTGGCGCCTCCTGTGTGTGAAACCTTCCTACCCCTCTCTGGAGTCTGTTGCCCCCGTGGTTGTGACTGGCGCCTCCTGTGAAGGAAACCCTTGGCCGACCTGCTGTGCCAGGAGGCCTCTGGTTGGAGCGCCCTTGCCAAATCCACCTTGTATGACTTTAGCGGTGAGTCACTGGCGTTCTGTGTCGATGAAGAACGCAGCTAG | 2048 |
| | 1 | MSLPGEHSSLRPHSQKLCLDSPGVGELAARIPKRYRGDVRASGCKPQARRALARSTGSLGSALQGG* | 2049 | ATGTCACTGCCTGGTGAGCACTCTTCCTCAGACCCATTCCAGAAGCTCTGCCTGATTCCCCAGGGTAGCGAGCTGGCTGCCAGGATTCCTAAGCGTACCGGGGAGAGTGTGAAGGGCTCCGGCGGCTGGGAAACCCTAGGCCAGCGCTGCCTGCGCTCGACGGGTCTCCGGGAGTGCTTTGCAGGCGGATGA | 2050 |
| hsa-mir-3149 | 2 | MTTDGPATCLPEPAEINSLSSLCTQAPRAGRSPSAAQLPQARRSHLPEGSLPTRPSLSRSSSDSHQGTPEARRLAATRRRLPEALRDVRKQRKPCPPKPRLPLGPSTLYVVSSLAAPDPGLTGS* | 2051 | ATGACTGACGGCCAGCTACCGCTCCTTCCTGAGCCTGCAGAGATAAACAGCCTATCCTCCCTGTGCACACAGGCCCGGAGGGCGGAGTCTCAAGCGCAGCACAACTGCCCAGGCCCGACGCAGCCAGGTCCCCGAGGGCTCCACCCAGGCCATCCCTCAGCCGGTCCCTCGGACAGCGAACAAGGAACCCGGAGGCGCCGAGGCGTCTGCCGCACACCGTGGCGGCTGCCCCAGAGGCCCTTCGCGATGTCGGAAGCAGAGAAAGCCCGGCCCTGTCAAGCCCGGCTCCCTAGGCCCTCGACGTGTAGTGCCTCACTTGCCCTTGACCCGCGGGCTGACCGCGGTTCGTGA | 2052 |
| | 3 | MSASRESPALPSPGFP* | 2053 | ATGTCCGCAAGCAGAGAAAGTACGGAGCCTGCCTTCCCAAGCCCTGCCTAG | 2054 |
| | 4 | MFQRKLRGAWAFRRLRSVSALESRSANPRSCFQLGGRGVSRPCNCRRLLPPCLLASCLPGKGKSKLLNFGKGSEANLNS* | 2055 | ATGTTTCAGAGAAAGTTACGTGGAGCGTGGGCGTTTCGCAGACTCTCAGGTCAGTGTCTGCCCTAGAGAGCCGGAGTGCAAACCCGGAGTGCAAACCCCGAGTCCTGTGCACTGGCTCCCTGGCGTGGAGGTCGTGGAGTTTCACGACCTTGTAATTGTGCCGCGGTTGCTTTTTCCCGTGTTATTGGCTTCCTGTCCCCTGAAAAGGCAAATCAAGCTGCTGAATTTGGGAAAGGCAGTGAAGCAAACCTAAACTCCTAA | 2056 |
| | 1 | MWPQRLPPRPAMSEETRQSKLAAAKKKVKCTGSRPPDPAPAPLRWQDHGQSLCHS* | 2057 | ATGTGGCCCCAACTCCGCTCCCCGCCCGGATTCGGAAGAAAACCCGACAGAGCAAATTGGCCGCAGCGAAAGAAAAAGTAAAGTGCACTGGGCTCGCGGTCCGCACCTCTGCCACTCCTGA | 2058 |
| | 2 | MAGPWPESLPLLRHTGLGSPRRVRAPSTKVLSASPAPSAAQPPPSPVAPG* | 2059 | ATGGCAGGACCATGGCCAGAGTCTGCAGAGTCCTGCACTCCTGAGGCACACCGGGCTGGGTCCCCACGGCGCGTCCGGGCTCCCAGCACCAAAGTGTTGTCAGCCAGCCCGCCCCCCCTCAGCCGCCCAGCCCTGCGCTGGCGCCCCGGGTGA | 2060 |
| | 3 | MARVSATPEAHRAGLPTARPGSLHQSLVSQPRRLSRPAPALASRPRVTLGWCSRGSPLQTRPSPPAPRSPTSLGSLGWRLQGPRTPAIQPLPSPVTLGP* | 2061 | ATGGCCAGAGTCAGTGCTCCACTCGAGGCACACAGGGCTGGCTTCCCACGGCGCGTCGGGGCTCCCTCCACCAAAGCCCAGCCGGCCTCAGCGCCCCGCCCGGGGCCAGTTTCCAGGGCGCCCGACTTTGGGGCTGTCCCCCGAAGTCGACTTCCCCGGAAGTCCAGACTGCTCAAGACTGCGAAGCCCTGCTCCAAGGACGTCCAAGGAGCTCCAAGGACCTAGGAACCCAGCAATTCAGCGCCTCAGCCCCTCGCCAGTGACTTTGGCCCCTGA | 2062 |
| hsa-mir-3154 | 4 | MPPLGVFCSDVTIPLGTVISCARPVFDLRTQSPKCSHPASGSSGHSINFQLEGDWGLWDLCGRGFRLPYTLNIDIDSVKSLHFTRELKTLAVSLGGNVRTGLVWFSPRLLLSRETLTFFSDFSTSYSNSPWFWDQSALQWSLE* | 2063 | ATGTTCCCCCTAGGAGTGGAATGGAATGTAGTGACGTCACAATTCCCGTGACTTCACAATTCCCGTGAACCGTAATTAGTTGCGGAGACCAGTCTTGATCTTAGGACCGCAGTCCTTAGGCGCCAGTCCCTAAGTGCTTCTCATCCTTCCTGGTTTCCTTCGGTCACAGCATAAATTCAGCAGGGATTGGGTACTAGGGACTATGGGACCTTAGGAGGAGGAGGTTTCACCCTGCCTTAACACATAGACATTGACAGTGTGAAAAGCCTACACTTCACCCTGAACTGAAAACATTGGCAAGTATCTCTGGGTGGCAATGTGAGAACGGGATTGGTTTGGTTTTCCCCAGGTTTCTACTCTCCAGAGAGACTTTAACATTTTTTCGACTTCTGACTTCTGCACTCTATTCGAATTCGAATTCGAATTCTACGAATTCGAAT CCATATTCGAATTCGAATTCGAAGATTCGAATATTCGAATTCGACATATTCGAATTCGAATTCGAATTCGAAGCCCCCAAAGCAAATTCGCAAATTCGCAAAGCCAAAGGTCTCCAATTCGAAGCAGGTTCAGGTTCTACTCCTCCAGAGAGACTTTAACATTTTTTCGACTTCTGACTTCTGCACTCTATTCGAATTCGAATTCTACTCCTCCATGGTCTCGGAATGA | 2064 |

Figure 1 (Continued)

| | | | | |
|---|---|---|---|---|
| hsa-mir-1184-2 | 1 | MAAVGITKRRSGNDVPLFLPRRKRGCMRFGNRQSHLV NVTDAKSPGLGKKKSLGEWDGSDSLS* | 2065 | ATGGCGGCAGTAGGAATAACAAAACGCAGAAGCGGGAACGATGTCTTTTATTCCT CCCAGACGCAAACGTGGATGCATGAGGTTTGGTAACAGGCAAAGTCATCTGGTTA ACGTGACTGATGCAAAAAGTCCCGGCCTGGGCAAAAGAAGTCACTGGGTGAATGG GATGGATCAGACTCCCTGTCCTGA | 2066 |
| | 2 | MSPYSSPDANVDA* | 2067 | ATGTCTTTTATTCCTCCCAGACGCAAACGTGGATGCATGA | 2068 |
| | 3 | MHEVW* | 2069 | ATGCATGAGGTTTGGTAA | 2070 |
| | 4 | MQKYPAWAKRSHWVNGMDQTPCPEGEMVSCRTR* | 2071 | ATGCAAAAAGTCCCGGCCTGGGCAAAAGAAGTCACTGGTGAATGGGATGGATCA GACTCCCTGTCCTGAGGGGGAGATGGTTCTGCAGAACGAGGTGA | 2072 |
| hsa-mir-1827 | 1 | MVSFVEFVYYCLFVLRWSPAPSPRWKCSVMISAHCNL GLPGSSDSPASAS* | 2073 | ATGGTCTCATTTGTTTTTTGTTTGTTTGTTTGTTGTTTGAGATGGAGTCC AGCTCCGTCACCTAGGTGGAAATGCAGTGTCAGTGATCTCAGCTCACTGCAACCTCGG CCTCCCAGGTTCAAGCGATTCTCCTGCCTCAGCCTCCTGA | 2074 |
| | 2 | MESSSVT* | 2075 | ATGGAGTCCAGCTCCGTCACCTAG | 2076 |
| | 3 | MQCHDLSSLQPRPPRFKRFSCLSLLSSWNLQVPTTTPS* | 2077 | ATGCAGTGTCATGATCTCAGCTCCGTCACCTGCAACCTCGGCCTCCCAGGTTCAAGCGATTC TCCTGCCTCAGCCTCCTGAGTAGCTGGAATTACAGGTGCCCACCACCACCCAGC TAA | 2078 |
| | 4 | MIRPPRPPKVRD5KYEPPRPVSLICF* | 2079 | ATGATTCGCCCGCCTAGGCCTCCCAAAGTGCGGGATTCCAAGTATGAGCCACCGCGC CCAGTCAGTCTCATTTGTTTTTAA | 2080 |
| hsa-mir-4283-2 | 1 | MITPS* | 2081 | ATGACACCCTGTGA | 2082 |
| | 2 | MVMRGAGARVVACAGSSTNGSGAGQLVKAGGAGLGC GSARRTLGALARLSTGSGGLFLEPGVLLGSRAKGVLGT SSVGFPSSRVAALSAKQNR* | 2083 | ATGGTGATGAGGGGTGCTGGGGCCAGGGTGGTGCAGGAGAGCTGCAGCTCCACAAA TGGCTCGGGGCGCTGGGCAGCTGGTGAAAGGCGGGGTGGTGCGGGACTGGCTGCGGCA GTGCCCGGCGCACCTGGGGGCCTTGACTCGCTTGTCCACAGCCTCTGGGGGCTCT TCTTGGAACCTGGAGGTGCTGCTCGGGCTCCAGGGTACGGGGTACTGGGGACTTCG TCTGTTTGGGTTCCCTTCCTCCAGGGTAGCAGCTCTGTCTGCAAAACAAACAGATGA | 2084 |
| | 3 | MARVLGSW* | 2085 | ATGGCTCGGGTCCGGGTCTGGGCAGCTGGTGA | 2086 |
| | 4 | MRGWGGGFLAEMSCGPHQKGLLL* | 2087 | ATGAGAGGCTGGGGCGGGGGCTTCCTGGCAGAGATGAGCTGTGGCTTTCATCAGAA AGGCCTGCTTCTGTGTA | 2088 |

Figure 1 (Continued)

| | | | |
|---|---|---|---|
| hsa-mir-3195 | 1 | MLMLAAVLAGPLAARVCAAGGAACTTLLGDSALTPGA GAAAJAAPGPGWPLTPAGPPAAGAGAGAGAAPALPPFWAA AGGTAGAAVGPAGWPGGRARVAGAGGGGGAAA GAAGAGAAGGEGAAGAGGAAAAPTKGGYWMTVPGAA GLGSGSSAAGPLLTRLTAGAAAWCEFSSAALPFKVCAA PGFAGLPGPGPGPGPGQAQGPGPARAASAAGPAGLAGP AGAGSGPAATAAAAGTIGAQDPALPSGGGLSFAAGGAG PAGTRGRGREGGPGRCGPPPPGRALPAGGGSGAAPGAP SAGAAGPAPAAPAGLPLTTWFPSAPAAAARTSGVRGAR WWWWAALAASCDSSEPTRSLTTFSSTSLLKKTSSSRSEP AAIFFPRPPPPPLGPSAPGRGGGSDWGGRWAGGGRRA AGGGRGRAAGGRGSGGGPAQARRPRAPGDWLRRAL KRRGQWLRALEAGARAVGRGAAAAGSAGAQGRG RRGGGRGGGRRAAGRGMRERCAGPGRGGRGAATGPR SLSRLAPKWLRRR* | ATGACCATGCTGGCCGCCGTGCTGGCCGGCCCTGGCCGCCGGCCGC CGGGGGCCGCCCCTGCTACCACCCTCTTGGGCGACTTGGGGCGG CCGCGGCAGCCGTCCGCGGACCCGGAGTTGCCCCGTGCCGGC CGGGCCGGCGGACGGCGGCGGCGGCGGGCCGGGAGGTGGCTGGGGCCG GGGGCCAGAGTGCGTCAGTGGCGGCCGTCTGAATACAGTGCCGGAG GGCCACGAGCAGCGGCGGCTCGGGCCGTCTGACCAGCTGGGCAGC GGCAGCAGCGCGGCGGCGGCCGTCGATGGCCCGGCAGGTGCGGCGCCCC CCGCGCGCGCTGGGCCTGCCGAAGCCTCCTGGCCTTGCCCGGGCCGCGG CCGGCGGCAGCAAGCCCGGCGGCGCCGACTGCGAGCGGGCCGCGG GGGACAAGGCGGCGGCTCTACCTGCGGGGGCCGCTCGACGCCCCCTTCG CCGGCCGCGGTCGGCCGTCCTCGCGCCCGCAGCCGCCGCCGCTCACAACATG GCGGGGGGCTCGAGCGCGGCCGCCGCCGCACCTCGAGCGTCGTGCGGCGAGT GTTCCGAGCGCTGGCCGCGAGCTGCTGACCTGCGACTCGAGAAGACCTCGTCCAGCAGGGAGCCCACCAGGTTCG GGTGGTGGTGGGCCCGGGCCCGGCCGCGCCGGGCGCGCCCGGGAGGCGCTACCAGTATCGAG CGCGCGCCGCATCTTTTTCCTGGGCGGCCAGGAGGGCCGAGCTCAGCGGAG CCTGGGCTGCAGGAGGGTTCCCGACCGGACTGGGAGAAGCGCTGAGCGTGGGGAC CGGGGTGCGGGAGCAGCAGCGCGGACGGGGAGGGCGCGCGCCGGCGTGAGCTCAGGGGCGCGGCC ACGGTGCTGGGCCGTGGCGGACGGCGGAGGCCGAGGCGGCGACGGGACCTCGCTT TGTCTCGGCTCGCTCCAAATGGCTGCGGCGGCTGA | 2089, 2090 |
| | 2 | MVPERAGGRGPHLGRARREVVVGRAGRQLRLQRAH QVAHHFLVHLAVEEDLVQQIRARRHLFSSAAAAAARA ERAWARRRFRLGRALGGRGAARGRRGAGARGRGAGE RGWRPCAGAETAGARRLAAARA* | ATGGTTCCCGAGCGCGCCGGCCGCGGCCGCACCTGGGCGTGCGCGGCGA GGTGGTGGTGGGCCGCGCTGCGCTGCAGCTGCGACTCAGCGAGCCCAGG TCGCTCAACCACTTTCTGCTTGAAGAGAGACCTCGTCAGAGATCC GAGCCCGCCGCCATCTTTTTCCTGCCGCCGCCCTGGGCCGAGC GCCCTGGGCGAGGAGGAGGTTCCGACTGGGCGCGCCGCTGGCGCTGCGGGCGGC GGCGCGGGAGCGCGGCCGGCGGCGCCGGCGCCGGCGGAGCGGGG GTGGCGGGCCGGGACCGGAGAGACCGCGGGACCGCGGGATTGGCTGCCGGCC GCGCTTAA | 2091, 2092 |

Figure 1 (Continued)

| | | | | | |
|---|---|---|---|---|---|
| | 3 | MAASARGRGAGGRPGCGSSGGKRGGWSSGARAPGRW RTGRGPPGGGARDAGTVRWAGPRRARGIDGASLFVSAR SKMAAAALTGAPGGRRARWQRRRKRARPRPGEQRAGM PGRRRAARRPW8GWAWEAGNGNGEGTVAARPGDGDRR PAPPSRRGEAGSASGSAGPGRWGGVLRARLFSPSNRDH PWPFPFLNKPSRPGLTVPAPSCLGDRSVV* | 2093 | ATGGCTGCGAGCGCTAGAGGGCGCGGGGCGCCGGGGGCGCGGGGCGGGTCGCGGGGGTGCGGCAGCA GCGGCGGGAAGCGCGGGGCGCCCGGAGCTGGAGCTCAAGGGGCGCTGAAGGCCGTAGGCGGTGGCG GACGGGGAGGGGGGCGCCCCGGCGGGATGCGGGAAGCGGTGCGCTGGGCG GGGCCGAGGGCGGCGGCGCGCGGGAGGCGGACGGGAGCGCCTCGCTCTTTGTCTCGGCTCGCTC CAAATGGCTGCCGGCGCTGACGGGAGCCCGGGAGCCGGGAACAGCGCGCTGCCGCGTGG AGCGGCGGCGCAGGGCCCTGCGAGCGCAGGATGGGATGGGCGGGGATGCCGGG ACCGGCGGAGGAGGACTGTCGCAGAGCTGTGTCGCCTCTGCTCAGCCGTCGGGCGGT GGGGAGGGGTCCTGCGCGAGGRTCCTGCGACTCTCTTCTGGTACCAGTGTACCACCCTCTGC TCCCCTGCCATTTTAATCAATAAACCAGCGCCCGGGCTGACTGTCCCGACCC CAGCTGCCTTGGAGACAGGAGTGTCGTATAA | 2094 |
| | 4 | MGLGGGRERGGDCRSAPWGRGPAPGPSKPPRGSWVRL WLSRSRAVGRGPARTALLALQS* | 2095 | ATGGGCTGGAGAGGCGGGGCGGGAACGGGAGGGGACTGTCGCAGCGGGACCTGGG GACGGGGACCGGCGGCGCCCGCCCTCCAAGCCGCGCGGGAAGCTGGGTCGCCTC TGGCTCAGCGCGGTCCGGGGCCGGTGGGGAGGGGCTCTGCGCGCACGGCTCTCTGCG CCTCCAATGTGTGA | 2096 |
| hsa-mir-1538 | 1 | MGLASCRRKGPGCCS* | 2097 | ATGGGCCTGCTTCTGCGGCGCCGGGCTGCTGTCCGA | 2098 |
| | 2 | MANRIPKTSSY* | 2099 | ATGGCAAACCGTATCCCAAAACCTGAGTATTGA | 2100 |
| | 3 | MEEERI* | 2101 | ATGGAGGAAGAACGCATTTAA | 2102 |
| | 4 | MPVATWAWFLSYSNGFVFYLQG* | 2103 | ATGCCAGTAGCCACGTGGGCATGTTTTAAGCTATTCGAATGGTTTCGTTTTTATC TACAAGGATAG | 2104 |
| hsa-mir-4283-1 | 1 | MRKRRRRRKRRRKTKRKRRRRRRRGRRRPVRPPW SWQRCSYGPRRHGPRRRSPRPRSCRLPPPLLSPSHCCCC CCSRTLRPRPAQPGPCPGSWGSQSPRT* | 2105 | AGGAAGAGAAGAGGAAGAGGAAGAGGAAGACGAAGACGAAGACGAAGAGGAGG AGGAGGAGGAGGAAGGAGGAGGCCAGGGTGGCCTGTGGAAGGCCGTGAAGGCCGCCT GGAGCTGGGCAGCGCTGCAGTTACGGCCCGTCCCCGAGCCGCCGAGC CCCGTTCCCGTCGTTCTTGCCTTCCTCCTTCTCGGCCCGTCTCCGAGCCACTGCTGCT GCTGCTGCTCTCCGGCGACTCTTCCGGCCCGCCCGTTGTCCGGCCCTCCAGCCTGGGGCCTGTCCGG GCTCTTTGGGGTTCCAGAGTCCTCGAAGCGTGA | 2106 |
| | 2 | MTPP* | 2107 | ATGACACCACCCCGTGA | 2108 |
| | 3 | MVMRGAGARVVAGAGSSTNGSGAGQLVKAGGAGLGC GSARRTLGALARLSTGSGGLFLEPGVLLGSRAKGVLGT SSVGFPSSRVEALSAKQNR* | 2109 | ATGGTTGATGAGGGGTGCTGCGGCCAGGGTGGTGGCAGGAGCTGGCAGTCCACAAA TGGGCTGCTCTGGGCAGGCCAGTCTGGTGAAGGCGGGTGGTGGCCTGGGGCTGCGCA GTGCCGGCGGCACCTTGGGAGCCTTGGCGCTCTTGGCTCCAGGCTCTGAGGCGGCTCT TCTTGGAACCTGGGGTGCTCTTCCGCAGGGCGTAAGGCGGTACTGGGACTTCGT CTGTTGGGTTCCCTTCCTCCAGGGTAGAAGCTCTGCTGCAAAACAGATGA | 2110 |
| | 4 | MARVLGSW* | 2111 | ATGGCTCGGGTGCTGGGCAGCTGGTGA | 2112 |
| hsa-mir-4256 | 1 | MGDGQAGGAGRGCGHFPPVPnLQ* | 2113 | ATGGGTGACGCCAGGCTGGCGACGAGCGGGAAGGGAATGCGGGCACTTCCCTCCTGT CCCAACCTACAGTGA | 2114 |
| | 2 | MRALPSCPQPFTVTPALSTEDALISSILALL* | 2115 | ATGCGGGCACTTCCCTCCTGTCCCAACCTACAGTGACACCGGCGCTGAGCACGGAG GATGCCACTCATTTCCTCCATCCTTGCGCTTCGTGAAATGGTAGAGTCCCTGCCACC TGCGCTTCTGTGA | 2116 |
| | 3 | MHSFPPSLRFCEMGRVPATGSWRS* | 2117 | ATGCACTCATTTCCTCCATCCTTGCGCTTCGTGAAATGGTAGAGTCCCTGCCACC GGGAGTTGGAGGTCTTAA | 2118 |
| | 4 | MLSARAHRPCFF* | 2119 | ATGCTTTCAGCTAGAGCTCATGCCCCTGCTTCTCTGA | 2120 |
| | 1 | MAGERPR* | 2121 | ATGGCCGGTGAAAGGCCGTTGA | 2122 |
| | 2 | MNGNADL* | 2123 | ATGAATGGCAATGCTGACCTCTGA | 2124 |

Figure 1 (Continued)

| | | | | | |
|---|---|---|---|---|---|
| hsa-mir-3166 | 3 | MAMLTSEQLGGGNTEHFHTHSTGNQLTRRTTGPKMPR ALVTFSLFPYPKNSELHRKTVLHGQHTNNNGKHLLST RYMPEGL* | 2125 | ATGGCAATGCTGACCTCTGAGCAGCTTGGAGGTTGGGAACACTGAGCACTTTCACACC CATTCAACTGGTAATCAGTTAACAAGGAGGACAACTGGTCGAAAATGCCAAGGGC ACTGGTGACTTTTAGCCTCTTCCCATATCCTAAAAACTCAAAAATCAGAGCTGCACAGAAAGAC AGTTTTAACAATGGTCAGATTATTACAAATAATAATAATGGCAAACATTTATTGAG CACTCGCTATATGCCAGAGGGTTTATAA | 2126 |
| | 4 | MANIY* | 2127 | ATGGCAAACATTTATTGA | 2128 |
| | 1 | MSLASQ* | 2129 | ATGTCTTGGCTTCAGTGA | 2130 |
| | 2 | MVVGHGGATCPITPA* | 2131 | ATGGTGGTAGGTCACGtAGGCGCCACTGCCCATGCCTCCTAG | 2132 |
| | 3 | MLHSWEFPSPPTEPGRRR* | 2133 | ATGCTTCACTCCTGGGAATTCCCGtCACCTCTCACCTGAGCCCGGGCGCCCGCAGGTAG | 2134 |
| hsa-mir-320b-1 | 4 | MRVARGTGPGGQGWRVGRAARQVNQGFTPRLRGRRR DVQALPKAQLATHNLGSRRHRSSSFLLEIKTKPFGDLN LFTKWNPILHFTLG* | 2135 | ATGAGGGTGGCCCGGAGTGGCCGGGCAGGACTGGGCAGGACTCCGGGCGCCGGCGAGAT CAGCCCCGGCAAGTTAATCAGGGCTTCACACCCAGACTTCACGGGGCCGCCGGCGAGAT GTACAGGCCCTTCCCAAAGCCAGCTGGCCACCCATAACCTGGGAAGCCGGCGCA CAGAAGCTCGTCTTCCTCCTCTGAAACAAAACAAAAGCCCTTTGGAGACTTGAATCT GTTTCACGAAGTGAACCCCATATTGCACTTCACTCTGATAA | 2136 |
| | 1 | METLYRVPFLALECPNLKLKKPPWLHMPLAMTMYALV VVSYFLJJTRGHVYDYVTVEPPGVGSMTDEQGHQRPVAFL AYRVSGQYYYGRTWIQLPVYNGRFRHNPGPIECTKYP KTQ* | 2137 | ATGGAGACTTTGTACCGTGTCCCGTTCTTAGCCCTTGAATGTCCAACCTGAAGCTG AAGAAGCCGCCTGGCTGCACATGCCGTTGGCCATGACTATGTATGCTTGGTTGGTG GTGTCTTACTTCCTCATCACCAGAGAATCGTTATGGTTACGTTACGGTTGAACCGCCA GGTGTTGGCTCTATGATGACAATATTATGGAAGGACTTGATCCAGCTTGCTGTTTAC ATGAATGGGAGGTTTAGGTTCATAATCGTGGACCGATCGAATGCACCAAATATCCCAAA ACTCAATAG | 2138 |
| | 2 | MSQPEAEEAALAAHAVGHDYVCSGGGVLLPHHQRNRL* | 2139 | ATGTCCCAACCTGAAGCTGAAGAAGCCGCCCTGGCTGCACATGCCGTTGGCCATGAC TATGTATGCTCTGGTGGTGGTGTCTTACTTCCTCATCACCAGAGGAATCGTTATGA TGTTA | 2140 |
| | 3 | MLWWWCLTSSSPEESFMMLRLNRQVLAL* | 2141 | ATGCTCTGGTGGTGGTGGTGTCTTACTTCCTCATCACCAGAGGAATCGTTATGATGTTA CGGTTGAACCGCCAGGTGTTGGCTCTATGA | 2142 |
| hsa-mir-1283-1 | 4 | MNKGHRGQ* | 2143 | ATGAACAAGGGCATCAGAGGCCAGTAG | 2144 |
| | 1 | METLYRVPFLALECPNLKLKKPPWLHMPLAMTMYALV VVSYFLJJTRGHVYDYVTVEPPGVGSMTDEQGHQRPVAFL AYRVSGQYYYGRTWIQLPVYNGRFRHNPGPIECTKYP KTQ* | 2145 | ATGGAGACTTTGTACCGTGTCCCGTTCTTAGCCCTTGAATGTCCAACCTGAAGCTG AAGAAGCCGCCTGGCTGCACATGCCGTTGCCATGACTATGTATGCTCTGGTGGTG GTGTCTTACTTCCTCATCACTGATGAACAACGGCCATGCGTTATGCGGTTGAACCGCCA GGGTGTTGGCTCTATGATGACAATATTATGGAAGGACTTGATCCAGCTTGCTGTTTAC AATGGAGGGTTTAGGTTCATAATCGTGGACCGATCGAATGCACCAAATATCCCAAA ACTCAATAG | 2146 |
| hsa-mir-520-b | 2 | MSQPEAEEAALAAHAVGHDYVCSGGGVLLPHHQRNRL* | 2147 | ATGTCCCAACCTGAAGCTGAAGAAGCCGCCCTGGCTGCACATGCCGTTGGCCATGAC TATGTATGCTCTGGTGGTGGTGTCTTACTTCCTCATCACCAGAGGAATCGTTATGA | 2148 |
| | 3 | MLWWWCLTSSSPEESFMMLRLNRQVLAL* | 2149 | ATGCTCTGGTGGTGGTGTCTTACTTCCTCATCACCAGAGGAATCGTTATGATGTTA CGGTTGAACCGCCAGGTGTTGGCTCTATGA | 2150 |
| | 4 | MNKGHRGQ* | 2151 | ATGAACAAGGGCATCAGAGGCCAGTAG | 2152 |

Figure 1 (Continued)

| | | | | | |
|---|---|---|---|---|---|
| hsa-mir-1283-2 | 1 | METLYRVPFLALECPNLKLKKPPWLHMPLAMTMYALV VSYFLTRGIVYDVTVEPPGVGSMTDEQGHQRPVAFL AYRVSGQYYYGRTWIQLPVYMGRFHNPGPHECTKYP KTQ* | 2153 | ATGGAGACTTTGTACGTGCCGTGTCCGTTCTTAGCGCTGAATGTCCAACCTGAAGCTG AAGAAGCCGCCGCCTGGCTGCACATGCCGTTGGCCATGGCCATGACTATGTATGCCCTGGTG GTGTCTTACTTCCTCATCACGAGGAATCGTTTATGATGTTACGGTTGAACCGGCA GGTGTTGGCTCATGATGAACAAGGGCATCAGAGGCCATCAGAGGCCAGTAGCTTTCTTGGCC TACAGAGTAAGTGGACAATATTATTATGAAGGACTTGGATCCAGTTCCAGTCGTTTAC AATGGGAGGTTTAGGTTTCATAATCCTGGACCGATCGAATGCACCAAATATCCCAAA ACTCAATAG | 2154 |
| | 2 | MSQPEAEEAALAAHAVGHDYVCSGGGVLLPHHQRNRL* | 2155 | ATGTCCCAACCTGAAGCTGAAGAAGCCGCCCTGGCTGCACATGCCGTTGGCCATGAC TATGTATGCTCTGGTGGTGGTCTTACTTCCTCATCACCAGAGGAATCGTTTATGA | 2156 |
| | 3 | MLWWWCLTSSSPEESPMMLRLMRQVLAL* | 2157 | ATGCTCTGGTGGTGGTGGTGCTTACTTCCTCATCACCAGAGGAATCGTTTATGATGTTA CGGTTGAACCGCCAGGTGTTGGCTCTATGA | 2158 |
| | 4 | MNKGIRGQ* | 2159 | ATGAACAAGGGCATCAGAGGCCAGTAG | 2160 |
| | 1 | MSHHQCVLGLLPWLPNYLPHSHVLIIPKGSRITSLLCSAP SCGSHVTQSQRQDLGSYPKSRVYVCPHSAFLTSSLQPH WLPPSSWNISGTRQPQGLCTCCSLFRLCALREPQASLS HLLQVFPSFSFPPFSFFFSFFSLSFCCFFFFFFFLIHQAGVQW HDLGSLQSPPPGFK* | 2161 | ATGAGCCACCAACCAGTGTGTGCTTGGAATTGTTGCCATGGCTTCCAAACTATCTCCC CATTCTATCATTGTCTGTGCCATGTCCCATGCAAGGAGTCGGATCACCGTCTCTGCTCA GCACCTCTGCTGGCTCCCATGTCACCAGAGTCAAAGACAAGATCTGGACAGTGC CCTAAATCCGTGCTGCTGTCCTGGTTGTATGCCGCACTCTGCCATCTCCGCTCCAGC CACACTGCTTGCTGTCCTGTTCCCTCTCCTGAGACATATCAGGCACCAAGCCTGC TTTGCACTTGCTGTCCTGTTCCCTCTCCTGAGACTCTGTGCCTGAGAGAACACACAAGCCTG CTCTCTCACCTCGCATGATGCTTGGCTGCTGCAATCCTCCGCCTCCTGGGTTCAAGTA TGGAGTGCAGTGGCATGATGCTTGGCTGCTGCAATCCTCCGCCTCCTGGGTTCAAGTA A | 2162 |
| hsa-mir-3147 | 2 | MASKLSPFFYHCLLDTQRKSDHVSALLSTLLWLPCHPES KTRSWQCP* | 2163 | ATGGCTTCCAAACTATCTCCCATTCTATCATTGTCTTGATACCCAAAGGAAGTCG GATCACCGTCTCTGCTCTGCTCACCGTCCCTGTGGCTCCCATGTCACCAGAGTCA AAGACAAGATCTGGACAGTGCCCTAA | 2164 |
| | 3 | MSPRVKDKILAVSLNPVWLYAPTLPF* | 2165 | ATGTCACCCAGAGTCAAAGACAAGATCTGGACAGTGTCCCTAAATCCGTGTGGTTG TATGCCCCACTCTGCCTTTCTGA | 2166 |
| | 4 | MPPLCLSDIFPPATLASSLLEHRHTAASGPLHLLFPLPE TLCPERTTSLPLSPPPGLSLIFFESFFLFPSFFLLFFFFFF FPDTPGWSAVA* | 2167 | ATGCCCCCACTCTGCCTTTCTGACATTTCCCAGCCACACTGGCTTCCTCCTCC TCCTGGAACATATCAAGGCACACAGCCGCAGCTCAGGCTCCTCCAGGCCTCCTCCCTC TTCCTGAGACTCTGTGCCCTGAGAGAACACACAAGCCTCCCACTCGTGTGTCCTC GTCTTTCCCCTCATTTCTTTCTTTCTTTTTCTGATACACAGGCTGGAGTGCAGTGGCATGA GTTTTTTTTTTTTTTTTTTCTGATACACAGGCTGGAGTGCAGTGGCATGA | 2168 |
| hsa-mir-1268 | 1 | MVNGSRNSSPVRPSLSCSP* | 2169 | ATGGTGAACGGCAGCCGGAACTCATGCGCCGTGCGGCCTCGTTGAGCTGCAGCC GTAG | 2170 |
| | 2 | MMESRA* | 2171 | ATGATGGAGTCACGTGCGTGA | 2172 |
| | 3 | MHRSSRPHRNSTR* | 2173 | ATGCACCGGTCCAGCAGGCCGCATAGGAACTCCACGCGCTGA | 2174 |
| | 4 | MPVPSSGR* | 2175 | ATGCCCGTGCCCAGCAGCGGCGGGTGA | 2176 |
| hsa-mir-4316 | 1 | MRMPPHSLLQMVTKLPAQLTSAEPVTRPALLQFRMWY SHPVWGWNC* | 2177 | ATGAGGATGCCGCCGCACAGCCTACTCAAATGTCACTAAGTTGCCTGCACAGCTA ACATCTGCCGAGCCTGTGACACGACCAGCTTGCTTCAATTTCGAATGTGGTACTCC CACCCAGTTTGGGGTGGAACTGTTAG | 2178 |
| | 2 | MVEPAPGSLCQLGLPGHRPREALSKAGPVFIPCFLASVPP KALERPWSQRSG* | 2179 | ATGGTTGAACCTGCACCAGGGTCACTGTGCCAGCTGGGCCTGCCAGGCCACCGTCCC CGAGCTCTGTCCAAGGCAGGGCCAGTGTTCATACCTTGCTTCCTTGCCAGTGTCCCA CCCAAGGCCCTGGAAAGCCCTGGAGTCAGAGATCCGGCTAA | 2180 |

Figure 1 (Continued)

| | | | | | |
|---|---|---|---|---|---|
| hsa-mir-1302-1 | 3 | MPHTCCVTMGQRLSLSVPPGLL* | 2181 | ATGCCCCATACCTGCTGTGTGACTATGGGCCAGCGACTCAGCCTCTCTGTGCCTCCGGGTTGCTGTGA | 2182 |
| | 4 | MHRGP* | 2183 | ATGCACAGAGGCCTGA | 2184 |
| | 1 | MRVPVASYPHQHWILIICFQKPSQWEYMSLISYYFYKYSL* | 2185 | ATGAGAGTTCCAGTGGCTTCATATCCTCACCAGCATTGGATATTAATTATCTGTTTTCAAAAGCCATCTCAGTGGGAATATGTCACTTATCAGCTATGTGTTTACAAATATAGTCTTTAA | 2186 |
| hsa-mir-1302-1 | 2 | MCFTNIVFKSVACHHFLNSVFQSIEVLHFYKVKFHHLWFKKPSQWEYMSLISYYFYKYSL* | 2187 | ATGTGTTTTACAAATATAGTCTTTAAGTCTGTGGCTTGTCATCATTTTCTTAACAGTGTCTTTCAAAGTATAGAAGTTCTACATTTTATAAGTCAAATTTATCATATTTATGGTTTAAAAAGCCATCTCAGTGGGAATATGTCACTTATCAGCTATGTGTTTACAAATATAGTCTTTAA | 2188 |
| | 3 | MCFTNIVFKSVACHHFLNSVFQSIEVLHFYEVKFHHLWFMLPCLS* | 2189 | ATGTGTTTTACAAATATAGTCTTTAAGTCTGTGGCTTGTCATCATTTTCTTAACAGTGTCTTTCAAAGTATAGAAGTTCTACATTTTATGAGGTCATCAAATTTATCATATTTATGGTTTATGCTTTTTAGCTAA | 2190 |
| | 4 | MRSNLSLFYGLCFFVLAKKSLSNSRSQRPFSFY* | 2191 | ATGAGGTCAAATTTATCATTATTTATGGTTTATGCTTTTGTCTTAGCTAAGAAATCTTTGTCTAACTCAAGGTCACAAAGATTTTCTCCTTTTTTATTAG | 2192 |
| hsa-mir-1979 | 1 | MCAGKCCKIYFLYVGIKISLKVINLINVCKEERKVKMRVLGFLNI* | 2193 | ATGTGTGCTGGGAAATGCTGCAAATATCTGTTTCTATATGGGATCAAAATAAGTTTGAAAGTCATAAACCTAATAAACCTAATAAATGTATGCAAAGAAGAGGAAGGTCAAGAACAGAGTGCTAGGGTTTC | 2194 |
| | 2 | MLQNFFHCRDQNKFESHKPNKCMQRREEGEQEQSARVSKYLSLCGS* | 2195 | ATGCTGCAAAATATATTTTTCATGTAGGGATCAAAATAAGTTTGAAAGTCATAAACCTAATAATATTGAGTTTGGGAAGTGA | 2196 |
| | 3 | MYAKKRGRSRTEC* | 2197 | ATGTATGCAAAGAAGAGGAAGGTCAAGACAGAGTGCTAG | 2198 |
| | 4 | MAKKNQPRGRKRTKKPSPGNQVKKCSMKESMVRRVNCVSNYYCI* | 2199 | ATGGCAAAGAAGAATCAGCCAGGAGTAGGAAGGAAGAGAACCAAGAACCAAGAACCCTGGCAACCAGGTTAAAGAGTGTGTTCTATGAAGGAAAGCATGGTCCGTAGGGTCAACTGTGTCCAATTCACTACTGTATTTAG | 2200 |
| | 1 | MHSR* | 2201 | ATGCATAATCTCAGATAA | 2202 |
| | 2 | MVSIW* | 2203 | ATGGTTTCTATATGGTAA | 2204 |
| hsa-mir-2052 | 3 | MYKCRVSLCLYMSFPSVFDFKQPILRHLDLTNYSCGHYCVWSLVSYGN* | 2205 | ATGTTAAAATGCCGTGTAAGTCTTGTTGTTATAACATTTCTTTCCAAGTGTTTTCGATTTAAACAACCCATACTACGAATAATACTGATTAACTATAGTTGTGAATATATTGTGTTTGGTCTTTGGTTAGCTATGGTAACTAA | 2206 |
| | 4 | MPCKSLFY* | 2207 | ATGCCCTGCAAGTCTACTGTATTAG | 2208 |
| | 1 | MATYVAHLQS* | 2209 | ATGGCAACTTATGTTGCACACCTGCAATCCTGA | 2210 |
| | 2 | MLHTCNFESLGIQKEPFPE* | 2211 | ATGTTGCACACCTGCAATCCTGAGTTCCTGAGGGATACAGAAGGAGCCCCATTTCCTGAGTGA | 2212 |
| hsa-mir-4311 | 3 | SMHLI* | 2213 | ATGCACATTCTAATCTAA | 2214 |
| | 4 | MILLKEKEKKDTQGPYNSSDCIGSI* | 2215 | ATGATTCTTTGAAGGAGAAAAGAAGGACACCAAGGCCGTATAATAGTGGGGACTGTATAGGAAGCATATAG | 2216 |
| hsa-mir-3118-6 | 1 | MQGELKLCHPGRKPSDLASFGASLGDSLQLSFNTFQQFCVLYYHKNSPCIFYPLSNRNLNMHME* | 2217 | CTTTGGCGCCGAGCTGGTCGTCAGTCGTCAGCCCAGGAAAACCAAGGAAACCCTCCGACTTGCCAGGCAAAGGCAAAGCAAAGGACAACCTGCAGCCTCAGCTCAACCTTTCAACAGTCTGTGTTCTCTATTCATCACAAGAATTCATCTGTATTCTATCCTTTATATCTTAAAATAGGAATTTAAATATGCATATGGAGTGA | 2218 |
| | 2 | MCLFCLMYNFLRSKJMTLLQF* | 2219 | ATGTGTCTTTTTGTTAATGTATAATTTCTAAGAAGTAAATTATGACTCTACTGCAAATATAA | 2220 |
| | 3 | MFFNSISDEGSSNRFKSLQGTLKELYSQC* | 2221 | ATGTTTTTCAACTCAATAAGCGATGAGGGTTCCAGTAACAGGTTCAAATCATTGCAAGGAACATTAAAGGAGCTTTACAGCCAATGTTAA | 2222 |

Figure 1 (Continued)

| | | | | | |
|---|---|---|---|---|---|
| | 4 | MRVPVTGSNHCKEH* | 2223 | ATGAGGGTTCCAGTAACAGGTTCAAATCATTGCAAGGAACATTAA | 2224 |
| hsa-mir-3118-4 | 1 | MLHGTSWSAIFLVTLRLHQID* | 2225 | ATGTTAATAGGTACCTCTTGGAGTGCCATTTTCCTTGTAACCCTTAGATTAATTCAGATTGACTGA | 2226 |
| | 2 | MLLCI* | 2227 | ATGCTTGCTTTGCATCTAG | 2228 |
| | 3 | MFRK* | 2229 | ATGTTTAGAAAATAG | 2230 |
| | 4 | MSPLLSASALGKFPRTSLLCLLKYEMKINVAQQARESLL* | 2231 | ATGTCACCACTTGTCAGCATCTGCATTGGRCAAATTTCTAGGACCTCCCTCTGTGTCTTTTAAAATATGAAAACAAAATCAATGTAGCGCAGCAAGCCAGGGAAAGTCTGCTTTGA | 2232 |
| hsa-mir-297 | 1 | MPHLARRVLRPRSRADCYHSCLRSNCKAAARLGRGRPPLPRLA* | 2233 | AGCTGTCTGAGATCAAACTGCAAGGCGGCAGGAGACGCAGCGAGACTGGGGAGGGGGCGCCACCATTGCCCAGGCTTGCTTAG | 2234 |
| | 2 | MSLSDSFEESSGSPSTQLEI* | 2235 | ATGTCCCTGTCTGACAGCTTTGAAGAGAGCAGCAGTGGTTCTCCCAGCACACAGCTGGAGATCTGA | 2236 |
| | 3 | MDRLPPQVGF* | 2237 | ATGGACAGACTGCCTCCCCAAGTGGGTCCTGA | 2238 |
| | 4 | MCTSPSSKTKSR* | 2239 | ATGTGCACATCACCATCATCAAGCAAGACCAAAAGTAGATAA | 2240 |
| hsa-mir-1471 | 1 | MQHSRRHVGSREQTLRQWTCWQLTLELLNLQNSEKINFCSL* | 2241 | ATGCAGCATTCAAGGCGCCATGTTGGAAGGCAGAGAGCAGACCCTCACCAGACAATGGACTTGCTGGCAACTTCTCAGAACTCTGAGAAAATAATTTCTGTTCTTTATAA | 2242 |
| | 2 | MLEAESRPSPDNGLAGNSLLNFSTSRTLRK* | 2243 | CTTGAACTTCTCAACCTGCAACCAGCAGAGAGCAGACCAGAATGGACTGTGCTGGCAACTCACT | 2244 |
| | 3 | MDLLATHS* | 2245 | ATGGACTTGCTGGCAACTCACTTGA | 2246 |
| | 4 | MASSWTYG* | 2247 | ATGGCCTCCTCCTGGACGTACGGTGA | 2248 |
| hsa-mir-514b | 1 | MPATWLPIKPEVL* | 2249 | ATGCCAGCAACATGGCTTCCTATAAGCCTGAGGTCCTGTGA | 2250 |
| | 2 | MASYKA* | 2251 | ATGGCTTCCTATAAGCCTGA | 2252 |
| | 3 | MQKWPNTKNWYQ* | 2253 | ATGCAAAAATGGCCTAATACAAAAATTGGTACCAGTAG | 2254 |
| | 4 | MRKQLWNQVMSRVWKSLEGSEADMKIKESLDFLQIDC* | 2255 | ATGAGGAAGCAACTTGGAACCAGGTAATGAGCAGGTAAGGAAGATAAAGGAAGTTTAGATTTCTTCAAGACTGCTGA | 2256 |
| hsa-mir-513a-1 | 1 | MPATWLPIKPEVL* | 2257 | ATGCCAGCAGCAACATGGCTTCCTATAAAGCCTGAGGTCCTGTGA | 2258 |
| | 2 | MASYKA* | 2259 | ATGGCTTCCTATAAAGCCTGA | 2260 |
| | 3 | MQKWPNTKNWYQ* | 2261 | ATGCAAAAATGGCCTAATACAAAAATTGGTACCAGTAG | 2262 |
| | 4 | MRKQLWNQVMSRVWKSLEGSEADMKIKESLDFLQDC* | 2263 | ATGAGGAAGCAACTTGGAACCAGGTAATGAGCAGGTAAAGGAAGATAAAGGAAAGTTTAGATTTCTTCAAGACTGCTGA | 2264 |
| hsa-mir-513a-2 | 1 | MPATWLPIKPEVL* | 2265 | ATGCCAGCAGCAACATGGCCTTCCTATAAAGCCTGAGGTCCTGTGA | 2266 |
| | 2 | MASYKA* | 2267 | ATGGCTTCCTATAAAGCCTGA | 2268 |
| | 3 | MQKWPNTKNWYQ* | 2269 | ATGCAAAAATGGCCTAATACAAAAATTGGTACCAGTAG | 2270 |
| | 4 | MRKQLWNQVMSRVWKSLEGSEADMKIKESLDFLQDC* | 2271 | ATGAGGAAGCAACTTGGAACCAGGTAATGAGCAGGTAAAGGAAGATAAAGGAAGTTTAGATTTCTTCAAGACTGCTGA | 2272 |
| hsa-mir-513b | 1 | MPATWLPIKPEVL* | 2273 | ATGCCAGCAGCAACATGGCTTCCTATAAAGCCTGAGGTCCTGTGA | 2274 |
| | 2 | MASYKA* | 2275 | ATGGCTTCCTATAAAGCCTGA | 2276 |
| | 3 | MQKWPNTKNWYQ* | 2277 | ATGCAAAAATGGCCTAATACAAAAATTGGTACCAGTAG | 2278 |
| | 4 | MRKQLWNQVMSRVWKSLEGSEADMKIKESLDFLQDC* | 2279 | ATGAGGAAGCAACTTGGAACCAGGTAATGAGCAGGTAAAGGAAGATAAAGGAAGTTTAGATTTCTTCAAGACTGCTGA | 2280 |
| hsa-mir-513c | 1 | MPATWLPIKPEVL* | 2281 | ATGCCAGCAGCAACATGGCTTCCTATAAAGCCTGTGA | 2282 |
| | 2 | MASYKA* | 2283 | ATGGCTTCCTATAAAGCCTGA | 2284 |

Figure 1 (Continued)

| | | | | | |
|---|---|---|---|---|---|
| hsa-mir-513c | 3 | MQKWPNTKNWYQ* | 2285 | ATGCAAAAATGGCCTAATACAAAAAATTGGTACCAGTAG | 2285 |
| | 4 | MRKQLWNQVMSRVWKSLEGSEADMKIKESLDFLQDC* | 2287 | ATGAGGAAGCAACTTGGAACCAGGTAATGAGCAGAGTTTGGAAGAGTTTGGAGGG GTCAGAAGCAGACATGAAGATAAAGGAAAGTTTAGATTTTCTTCAAGACTGCTGA | 2288 |
| hsa-mir-4277 | 1 | MGGGEGRAEWESSRPWGVGRGGW* | 2289 | ATGGGTCAAGGCCGTGAGGGTGGAGAAGGAGGGCAGAGTGGAGTCAAGGCCAT GGGGGGTGGGAGGGAGGGGTGGTGA | 2290 |
| | 2 | MGGGEGRVVRPGVRAMGPVPEARNLDLS* | 2291 | ATGGGGGGTGGGAGGCAAGGAGTGGTGAGGCCATGGGGTCAGGGCCATGGGACCAG TGCCCGAGGCAAGGAACCTGGATTGTCCTGA | 2292 |
| | 3 | MGAPAEPSEGVYSPAWVSHHPSGCCRMRWAGSGRR* | 2293 | ATGGGTGCCCCTGCAGAGCCCAGCGAGGAGTGGTGAGTCCTGCCTGGGTTCCA CCATCCCTCCGGCTGCTGCAGGATGAGATGGGCAGGTAGCGGCAGGAGGTGA | 2294 |
| | 4 | MKAGRGAQLVKGEGPMAAGWGWGAVIDYLWSRLQLL S* | 2295 | ATGAAGGCTGGAAGGGGTGCTCAGCTGGTTAAGGAGGAGGGTCCCATGGCAGCTGG CTGGGGGTGGGGGCTGTGATAGATTATCTGTGGTCCAGACTGCAGCTGCTCTCTG A | 2296 |
| | 1 | MPRLMKFMVNCNTLMEGKKSPCFNMFQTFHLTKVFNS VLIL* | 2297 | ATGTTCAGGTTAAGGAAATTATGGTTAACACACTCGATGGAGGGAAAGAAA TCTTTTGTTGTTCAACATGTTCAAACCTTTCACCTTACTAAAGTGTTAACTCTGTCCT CATACTTTAG | 2298 |
| hsa-mir-320c-2 | 2 | MNKIKYFFHKILGTLSPIEVGGSCNCTTDLECVKDHSRP CWEENWE* | 2299 | ATGAACAAAATTAAATATTTCTTCACAAGATCTAGTACTTTAAGTCCATTGAA GTTGGTGAGCTGTAATTGCACTACAGACCTAGAATGTGTTAAAGACCATTCCAGG CCATGCTGGGAAAATTGGGAATGA | 2300 |
| | 3 | MLGKLGMNVSEVSWHLCPHCYFIVLIN* | 2301 | ATGCTGGAAAATTGGGAATGTCAGTGAGGTTCATGGCATCTTTGTTTCAT TGTTATTTATTGTATTAATTAA | 2302 |
| | 4 | MSVRPHGIFYFIVILY* | 2303 | ATGTCAGTGAGGTTTCATGGCATCTTTGTTTCATTGTATTTTATTGTATTAA | 2304 |
| | 1 | MKKQLPASPQRPVHISALQFS* | 2305 | ATGAAAAAACAACTCCTGCCAGCCCCCAGAGACCTGTTATCATAATTTCTGCCTTG CAATTTTCCTAA | 2306 |
| hsa-mir-4305 | 2 | MNRSTMF* | 2307 | ATGAACAGAAGCACAATGTTCTAA | 2308 |
| | 3 | MLFQFYVPFLTL* | 2309 | ATGCTTATTTTCAGTTTATGTTCCTTTCCTAACATTATAG | 2310 |
| | 4 | MFLS* | 2311 | ATGTTCCTTTCCTAA | 2312 |
| | 1 | MTLGPTILEATRISTAKAITQEMERNSWPGAVAHTCSPST LGGQGGQITRSGDRDHPG* | 2313 | ATGACCTTGGGACCCACTCTGGAAGCCACGCGCATTTCCACTGCCAAAGCAATAACA CAGGAGATGGAAAGAAATTCTTGGCCAGGCGCGGTGGCCCACGCTGTAGTCCCAG CACTTTGGGAGGCCAAGGCGGGCAGATCACGAGGTCAGGAGATCGAGACCATCCTG GCTAG | 2314 |
| | 2 | MKMWQRCGGVSVWQRGGVSVWWCVRVAECLCGAM SMWWCVHVSAW* | 2315 | ATGAAAATGTGGCAACGATGTGGTGGTGTCTCTGTGTGGCAGCGTGTGTGGTGTGTCT GTGTGGCAGTGTCTCGTGTGCAGTGTCTATGTCCATGTGCTATGTCCATGGTTGG TGTGTTCATGTGCATCTGCATGGTGA | 2316 |
| hsa-mir-3118-5 | 3 | MWWCLCVAAWCVCVVPCGRVSVWCVHVVCS CICMVMSPCDSVCIHVTMSVCPCVHMAVSVWCLTV WRCVHVTVWRCVCVCWQCPCGSVFVCSCDGVSM* | 2317 | ATGTGGTGGTGTCTCTGTGTGGCAGCGTGGTGTGTCTGTGTGGTGGTGTGTCCG TGTGGCAGTGTCTGTGTGTCCGTGTGGACAGTGTCTGTGGACAGTGTCATGTCGC ATGTGGTGATCTGTGTGGGAGGTCTGAGTGTCGACAATGTCTGTGGTCCT TGTGTCCACATGGCAGTGTCTGTGGACAGTGTCTGAGGGTGTGTCCAT GTGACAGTGTGGCGGTGTGCGTGTGCTGGCAGTGTCCATGTGGACAGTGTTTGTG GTTCCTGTGTGATGGTGTGCATGTGA | 2318 |
| | 4 | MYLHGDVSY* | 2319 | ATGTATCTGCATGGTGATGTCTCGTGTGA | 2320 |
| | 1 | MLRT* | 2321 | ATGCTAAGAACGTGA | 2322 |
| | 2 | MRIDSQYCPRSTLR* | 2323 | ATGAGAGATTCCAAGTATGTCCACGTCAACCTTCGGTAA | 2324 |
| | 3 | MSTVNLAVSLCARRNPG* | 2325 | ATGTCCACGTTCAACTTGCGGTAAGCTTGTGTCTCGGAGGAATCCAGGGTAA | 2326 |

Figure 1 (Continued)

| | | | | |
|---|---|---|---|---|
| hsa-mir-3141 | 4 | MGQAESKYASYLSPIKHLRRGGVKASTENLIMLFQTIEQ FCTWFPEQGTLYLKDWEKIGKELKQASREGKHPLTVW NDWAHKATLEPFQIEEDSVSVSDAPESCVIDCEEEAGTE FKKGMESSHCKNVAESVMARSMQNC* | 2327 | ATGGGGCAAGCTGAAAGTAAATAGCTCTTATCTCAGCTTCATTAAAATTATCTTA AGAAGAGGGGAGTTAAAGCTTCCAGAACCAGGAACTTCTACAGAAAAATCTAATTATGCTATTTCAAACAATA GAACAATTCTGCCCATGGTTCCCATGGTTCCAGAACCAGGAACTTTATATTTAAAAGATTGGGAA AAAATTGGCAAGAATTAAAACAAGCAAGTAGGGAAGGTAAAATCATCCACTTAC AGTATGGAATGACTGGGCCATTATTAAAGCAACTTTAGAAGCTTTCAAATAGAAGA AGATAGTTGTTTCAGTTTCTGATCCCTGAGAGCTGTGTAATAGATTGTGAAGAAGA GGCAGGAACAGAGTTCAAGAAGGAATGGAAAGTTCACATTGTAAAAATGTAGCAG AGTCTGTAATGCTCGGTCAATGCAAAATTGTTGA | 2328 |
| hsa-mir-4266 | 1 | MPPSRQRWECLFCRHLQAAVPKVSCSRQDTNTRIDGE PLLSHL* | 2329 | ATGCCCCCATCTAGGCAGAGATGGAGTGCTCTTCTGCAGACACCTACAAGCAGCT GCTGTCCCTAAAGTGAGCTGTTCCAGGCAGGATACAAACACCAGGATCGATGGAGA GCCACTCCTTCCCATCTGTAA | 2330 |
| | 2 | MGVPLLQTPTSSCCP* | 2331 | ATGGGAGTGCCTCTTCTGCAGACACTCAAGCAGCTGCTGTCCCTAA | 2332 |
| | 3 | MESHSPICNPS* | 2333 | ATGGAGAGCCACTCCTTTCCCATCTGTAATCCAGTTAG | 2334 |
| | 4 | MFSGKL* | 2335 | ATGTTCTCAGGGAAGTTATGA | 2336 |
| | 1 | MHDSK | 2337 | ATGCATGATTCAAAATGA | 2338 |
| hsa-mir-4280 | 2 | MIQNDHFIWMKIKLQRGKLRRGETS* | 2339 | ATGATTCAAAATGATCACATTTCATCTGGATGAAGATTAAATTGCAGAGGGGCAAA CTTAGAAGAGGAGACAAGTTAG | 2340 |
| | 3 | MITESSCG* | 2341 | ATGATCACATTTCATCTGGATGA | 2342 |
| | 4 | MVVRLAW* | 2343 | ATGGTGGTTAGACATTAGCATGGTAG | 2344 |
| | 1 | MCLTPFLS* | 2345 | ATGTGTTTGACTCCTTTCTGTCATGA | 2346 |
| hsa-mir-548g | 2 | MIYSFLRPQPSGTVSQLNLFSL* | 2347 | ATGATTGTAAGTTCCTGAGGCCTCCCCAGCCATCCGAACTGTAAGTCAATTAAAC CTCTTTTCTTTATAA | 2348 |
| | 3 | MLYMSLI* | 2349 | ATGCTATACATGTCACTCATTTAA | 2350 |
| | 4 | MYIQCFLLYAQNFALLLKSKFRIFIHHLKKIPHTH* | 2351 | ATGTATATATAATTCAATGCTTTTTATCATGCACAGAATTTGCACTATTGCTAAAAT CTAAGTTTAGAATATTTCATCCATGTTCCAGAACAAAGATACCTCATACCCATTAG | 2352 |
| hsa-mir-1302-10 | 1 | MLARPGWRRGAGAERRAAPAQAQRHMLPRPGVEAWR RREEAHRAGAGAETHASASRGGGVAQAQRRKPTGGG WGGVCCRSKVARRRAGAGGGWRRARAEIHVTVARRR DG* | 2353 | ATGCTAGCGCGTCCGGGTGAGGCGTGGCGCAGGGGCGTGGCGCAGGAGGGCGCCGCGCC GCGCAGGCGCAGAGAGGCGCACCGGCGTCCAGGGTGGAGGCGTGGCGCAGGC AGAGAGGCGCAGGCGTGGCCAGGCGCAGGCGCAGAGACACATGCTAGCGCGTCCAGG GGTGGAGGCGTGGCGCAGGAGGCGCAGAGACGCCAAGCGCGACGCCGGGCGCGGTGGCGGG GCGTGTGTGCCACGCGGAGCAAGTGCACGACGCCGGTGGCGCGGGGGCGGGTG GCGGTGTGCCACGCGGAGCAAGTGCACGACGCCGGTGGCGCGGGGGCGGGTG | 2354 |
| hsa-mir-1302-10 | 2 | MLARPGVEAWRRPRDASLRAGVGGACVAGAKSHGAG LGRGEGGAVHAQKLTSRWRGAETGRTSVIRKAGHDRPL LAAGHYRTRLLTVLCQGAPCWRLGQLQGSLA* | 2355 | ATGCTAGCGCGTCCAGGGTTGGAGCGTGGCGCAGGGGCGTGGCGCAAGCGCTACG GCGGGGGTTGGGGGGGCGTGTGTGCAGGAGCAAAGTGCACGCGACGCGTG GGCAGAGACGGGTTAGAAGCGTGCAGAGCGCAGAAACTGCCAGAAACTGGCGCG CTTGCAGCGCGGCACTACAGACCGCCGTTGCTCACGTGCTGTGCCAGGCGCCCCTTG CTTGCAGCGCGGCACTACAGACCGCCGTTGCTCACGTGCTGTGCCAGGCGCCCTCTCTTCTAG TGCTGGCGACTAGGGCAACTGCAGGCGCCTCTCTTTCTAG | 2356 |
| | 3 | MLFGLSRLLNMGFLGLKVKNKYV* | 2357 | ATGCTGTTTGGTCTCAGTAGACTCCTAAATATGGGATTCCTGGGTTTAAAGTAAAA AATAAATATGTTTAA | 2358 |
| | 4 | MFNL* | 2359 | ATGTTTAATTTGTGA | 2360 |
| | 1 | MYIRCPDSLTH* | 2361 | ATGTACATTCGGTGTCCAGATTCATTAACTCATTAA | 2362 |
| hsa-mir-3197 | 2 | MATF* | 2363 | ATGCAACATTCTAA | 2364 |
| | 3 | MLDPFFFTSF* | 2365 | ATGCTTGATCCCTTCCTTTCTTTCTTTACCAGCTTTTAA | 2366 |
| | 4 | MSWAS* | 2367 | ATGAGTTGGGCTTCTAG | 2368 |

Figure 1 (Continued)

| | | | | |
|---|---|---|---|---|
| hsa-mir-1197 | 1 | MPNPGSMMTTGGV* | 2369 | ATGCCAATCTGGATCGATGATGACCACTGGTGGCGTATGA | 2370 |
| | 2 | MSHT* | 2371 | ATGAGTCATACATGA | 2372 |
| hsa-mir-1197 | 3 | MMNMCLEL* | 2373 | ATGATGAATATGTGTCTGGAACTCTGA | 2374 |
| | 4 | MHSYVIRMIGSMKE* | 2375 | ATGCATTCTTATGTTATTATTATGATTGGTCAATGAAAGAATGA | 2376 |
| hsa-mir-1193 | 1 | MPNPGSMMTTGGV* | 2377 | ATGCCCAATCTGGATCGATGATGACCACTGGTGGCGTATGA | 2378 |
| | 2 | MSHT* | 2379 | ATGAGTCATACATGA | 2380 |
| | 3 | MMNMCLEL* | 2381 | ATGATGAATATGTGTCTGGAACTCTGA | 2382 |
| | 4 | MHSYVIRMIGSMKE* | 2383 | ATGCATTCTTATGTTATTATTATGATTGGTCAATGAAAGAATGA | 2384 |
| hsa-mir-1185-1 | 1 | MPNPGSMMTTGGV* | 2385 | ATGCCCAATCTGGATCGATGATGACCACTGGTGGCGTATGA | 2386 |
| | 2 | MSHT* | 2387 | ATGAGTCATACATGA | 2388 |
| | 3 | MMNMCLEL* | 2389 | ATGATGAATATGTGTCTGGAACTCTGA | 2390 |
| | 4 | MHSYVIRMIGSMKE* | 2391 | ATGCATTCTTATGTTATTATTATGATTGGTCAATGAAAGAATGA | 2392 |
| hsa-mir-1185-2 | 1 | MPNPGSMMTTGGV* | 2393 | ATGCCAATCTGGATCGATGATGACCACTGGTGGCGTATGA | 2394 |
| | 2 | MSHT* | 2395 | ATGAGTCATACATGA | 2396 |
| | 3 | MMNMCLEL* | 2397 | ATGATGAATATGTGTCTGGAACTCTGA | 2398 |
| | 4 | MHSYVIRMIGSMKE* | 2399 | ATGCATTCTTATGTTATTATTATGATTGGTCAATGAAAGAATGA | 2400 |
| hsa-mir-4278 | 1 | MQNENWSLLFKNYEEFQVSKD* | 2401 | ATGCAAAATGAAAATTGGAGCCTCTTATTCAAAAATTATGAAGAATTCAAGTTAGCAAAGACTAA | 2402 |
| | 2 | MKIGASYSKIMKNFKLAKTKCGLGPLNRSPK* | 2403 | ATGAAAATTGGAGCCTCTTATTCAAAAATTATGAAGAATTCAAGTTAGCAAAGACTAAATGTGGCTTGGCCCTTTGAACAGGAGCCCTAA | 2404 |
| | 3 | MWLGPFEQEP* | 2405 | ATGTGGCTTGGGCCCTTTGAACAGGAGCCCTAA | 2406 |
| | 4 | MKTEVQFISGHRALPSLPAKMRGPHGRTAPQREDPHVLRHLKQDKYVHVRITGSMSH* | 2407 | ATGAAGACAGAAGTGCAGTTCATCAGCGGCACAGGGCCCTTCCTTCCCTTCCAGCCAAAATGAGGGGCCCAGAATCGGCAGAACAGTCTCAAAGAGAAGATCCCATGTCCTGAGACAAATATGTTCATGTCCGATTACTGGGTCTATGTCTCATTGA | 2408 |
| | 1 | MTENHYH* | 2409 | ATGACAGAAAATCACTACTCATTATGA | 2410 |
| hsa-mir-3116-2 | 2 | MLKILCESYFPFVAIVRILRYYRACMFKKHEEFFWLSPNTDKSEQEGGHI* | 2411 | ATGCTTAAAAATTCTTTGCGAGTCCTATTTGCCATTGTGGCTATTGTAGGATTCTGCGTTACTACCGGTGCATGCATGTTCAAGAAGCATGAGGAATTTTTTGGCTTTCCCCAAATACAGACAAATCAGAGCAACAAGAGAAGGGGTCACATTGA | 2412 |
| | 3 | MHVQEA* | 2413 | ATGCATGTTCAAGAAGCATGA | 2414 |
| | 4 | MRNFGPQIQTNQSNKKGVTFDY* | 2415 | ATGAGGAATTTTTTGGCTTTCCCCAAATACAGACAAATCAGAGCAACAAGAAGGG GGTCACATTGATTATTAA | 2416 |
| hsa-mir-1324 | 1 | MELLGFCPHHHEERGGCLWYPCFYCNL* | 2417 | ATGGAGCTACTTGGCTTTTGCTTTCATCACACATGAGGAAAAGAGGATGTGCTTATGGTACCCCTGTTTTTACTGCAACCTGTAA | 2418 |
| | 2 | MVPLFLLQPVIDEMLPVAESKTLN* | 2419 | ATGTACCCCTGTTTTACTGCAACTGTAACTGAAATAGATGAGAACCTCCTGTTGCAGAGAGCAAAACACTGAACTAA | 2420 |
| | 3 | MRTSLLQRAKH* | 2421 | ATGAGAACCTCCCGTTGCAGAGAGCAAAACACTGA | 2422 |
| | 4 | MQFLASLHSDRDNCLGSCSLYERQLTKSQLLRYLNNFIL* | 2423 | ATGCAAAACGTTGCAAGTTGCACAGTGACAGAGACAAATTGTTGGGCAGCTGTCTCTATAATGAAAGGCAATTGACCAAAAGTCAGTTACTGAGATATCTCAATAATTTCATTTTATTTTAA | 2424 |
| hsa-mir-2117 | 1 | MRPHCMNVPSLN* | 2425 | ATGAGATTCCATTGTATGAATGTACCATCATTAATTAA | 2426 |
| | 2 | MYHH* | 2427 | ATGTACCATCATTAA | 2428 |
| | 3 | MVLLAYIPGTLGEAFP* | 2429 | ATGTCCTCCTTGCATATATATTTTTGGTACACTTGGGAAGKYTTCCCATAA | 2430 |
| | 4 | MYLKLS* | 2431 | ATGTATTTAAGTGTCATAG | 2432 |

Figure 1 (Continued)

| | | | | | |
|---|---|---|---|---|---|
| hsa-mir-2114 | 1 | MEHLPGTTPTVC* | 2433 | ATGGAGCACCTACCAGGTACCACCTACGTGTCTAG | 2434 |
| | 2 | MGQRVQGCAMPCALM* | 2435 | ATGGGACAGAGGGTACAGGGTTGTCCATGCCTGTGCTCTGATGTGA | 2436 |
| | 3 | MGVFGHCSR* | 2437 | ATGGGTGTATTTGGCCATTGCAAAAGATAA | 2438 |
| | 4 | MHRTALSTTGPAFNSKYSHSQVCVPSSLIWCD* | 2439 | ATGCATAGAACAGGTTTGCCCTCGAGTTTAATATGGTGTGATTGA | 2440 |
| hsa-mir-3119-1 | 1 | MLASLVWNS* | 2441 | ATGTTGGCCAGCCTGGTCTGGAACTCCTGA | 2442 |
| | 2 | MGLQV* | 2443 | ATGGGATTACAGGTGTGA | 2444 |
| | 3 | MPCLYL* | 2445 | ATGCCATGTTTATACTTATGA | 2446 |
| | 4 | MFILMNPYKLVKHY* | 2447 | ATGTTTATACTTATGAATCCATATAAACTAGTAAAACACTATTAG | 2448 |
| hsa-let-7a-1 | 1 | MKHR* | 2449 | ATGAAGCACAGATAG | 2450 |
| | 2 | MYYICTFANSPRSFR* | 2451 | ATGTATGTTCATATGCACTTTTGCAAACTCACCAAGAAGTTTCGATGA | 2452 |
| | 3 | MSYALLQTHQEVSDEHMKKMSEGLIVL* | 2453 | ATGTCATATGCACTTTTGCAAACTCACCAAGAAGTTTCGATGAACATATGAAGAAA | 2454 |
| | 4 | MHFCKLTKKFPMNI* | 2455 | ATGTCAGAAGGGCTCATAGTGCTATAA | 2456 |
| hsa-let-7a-2 | 1 | MSPGKTRKPV* | 2457 | ATGAGCCCAGGCAAGACCAGAACCTGTGTAA | 2458 |
| | 2 | MHLLYATEAL* | 2459 | ATGCATTTATTGTATGCCACTGAGGCTTTGTAG | 2460 |
| | 3 | MPLRLCSVYYAAFFCDNAAFFVTTWCLLCSIFVTMDT* | 2461 | ATGCCACTGAGGCTTTGTAGTGTTTATTATGCAGCATTTTTGTGACAATGCTGCATTTTTTGTGACAATTTTGGTGTTTATTATGCAGCATTTTTGTGACAATGGACACCTGA | 2462 |
| | 4 | MQHFFVTMLHFL* | 2463 | ATGCAGCATTTTTTGTGACAATGCTGCATTTTGTGA | 2464 |
| hsa-let-7a-3 | 1 | MHLPFQ* | 2465 | ATGCACCTGCCTTCCAGTAG | 2466 |
| | 2 | MLGVGRGGQLCPWPGGEGAGGPCGSPVGALWGWPHI GSCYPCNKIPWRAVCLLEEGRRNHHVKQRMAFDECVL FLGVDAGPLGSMGWCRVDPTVACVRHVAVGQFLAGG DPSPDTCRAPSQTLEAWEGLWMPPYTPPRLLSLWFLDR TFRHHETKFAQALPSPWENPAGHGKEECPPARPDQSR PTCQARPASSWGTREPQASRQEKPPTAEGLVSGGELL GGVTTGRGSGWGIFNDVVASGHRPLPPPHLSCPPHLVTQ TVA* | 2467 | ATGCTGGGTGTTGGCCGTGGAGGACAATTGTGCCCTGGCCAGGCGGGAGGGGGC AGGTGGACCCTGTGGGAGCCCTGTGGGAGCCCTGTGGGGAGCCAGTGTGGGGACAG CCTGCTATCCTTGCAACAAGATCCCTGGGAGCCCTGTGGGAGCCAGTGTGCTCTAGAAGAGCA GGAGAAATCACGCAGGTCCTCTGGCAGCCATGGGCGTTTGAGAGTGCGTTGAGAGTGCTTTTTCTAG GGTCGACGCAGGTCCTCTGGCAGCCATGGGCGTTGAGAGTGCGTGGGACCCCACGGTG CCTGTGTTCGCCGGGCACCCAGCCAAACCTTGAGGCCTGGGAGAGGTCTGGATGCC GACACCTGCCGGGGCACCCAGCCAAACCTTGAGGCCTGGGAAGGTCTGGATGCC ACCCTACACCCGCCGGGCACCCAGCCAAACCTTGAGGCCTGGGAAGGTCTGGATGCC CAGGGCCAGGCCGCATCCTGCCGGGACCACCAGCGGGAGCCCAGGCTGCGCCACATGC CCAGGGCCAGGCCGCATCCTGCCGGGACCACCAGCGGGAGCCCAGGCTGCGCCACATGC AAAGCCCCCAGCCCCTGCCACCGCAGAAGGGCTGGTTCTGTGGGGAGTTGCTGCTGGGTGGG TGACCGCCCCTGCCACCGCCAGGTTCAGCCTGGGTATTTTTAATGATTAGTTGCATCTGTC ACCGGCCCGCCCTGCCACCGCCAGATTCTTCTGCCCTCCACCTTGTGACCCAGAGTCT GGCTTGA | 2468 |
| | 3 | MSYCFF* | 2469 | ATGAGTGTGTGCTTTCTAG | 2470 |
| | 4 | MGRRNAARLPAQTRVAPHARPGPHPPGAHGSPRLPGRK SPPPQKGWSLVGSCCWVG* | 2471 | ATGGGAAGGAGAAATGCTGCGCGCTTCGCCGCAGACCAGAGTCGCCCACATGC CAGGCCAGGCCGCATCCTCCTGGGCACACGGGAGCCCAGGCTTCCGGCAGGA AAAGCCCCCCAGGGGCTGGTCTCTGGGGTCTGTGGGAGTTGCTGCTGGGTGGGG TGA | 2472 |
| | 1 | MHLPFQ* | 2473 | ATGCACCTGCCTTCCAGTAG | 2474 |

Figure 1 (Continued)

| | | Protein | SEQ ID | Nucleotide | SEQ ID |
|---|---|---|---|---|---|
| hsa-let-7b | 1 | | | ATGCTCGGTGTTGGCCGTGGAGGACAATGTGCCCTGCCAGCGGGAGGGGGCAGGTGGACCCTGTGGAGGCCCTGTGGGGGTGGCCACACAGAAGGGCACTGCTCATCCTTGCAACAAGATCCCCTGAGGGCAGTGCTGCTCCTAGAAGAAGGCAGGAAATACCACCAGGTGAAGCAGAGAATGGCGTTGATGAGTGTGCTTTTCTAGGGTCGACGCAGGTCCTCTGTGGCAGGTGGCCATGGGGTGTCCGGGTGACCCTGCGGTGGCCTGTGTTCGCCACGTGACCACCGCCAGCTCCTTGGAGGCCTGGAAGTCTCTGGATGCCGACACCTGCTCGGCGACCCGCCAGACTCCTTGTCCCAGGAAACATTCGTCACCAGAAACGAAGTTTGCCCAGACCCTCCAGGCCCCTCACCCTGGCCCCGCCTGCCGCCTGAGGACAGGAACCCAGCCGGGCCCACGARPASSWGTREPQASRQEKPPTAEGLVSGGELLCCAGGAGGAGGAATGCTGCCGGCCATCTCTGAGGACCAGGAGCCCAGGAGCCAGGAGCCTTCGCCAGGAAAAGCCAGGCCCCACCCTGCCACCACGGGTGGTCTCTGGTGGGAGGTTGTCTGGGTGGGGTGACCAGGAGGTCGGGGTTTAATGATGTAGTTGCATCTGGCACCGCCCCTGCCACCCCGATCTTTCCTGCGGTATTTTAAAGCCCCACCTTGTGACCCAGACTGTGGCTTGA | 2476 |
| | 2 | MLGVGRGGQLCPWPGGEGAARGPCGSPVGALWGWPHGSCYPCNKIPWRAVCLLEEGRRNHRYKQRMAFDECVLPLGVDAGPLGSMGWCRVDPTVACVRHVAVGQFLAGGDFSPDTCRAPSQTLEAWEGLWMPPYTPPRLLSLWFLDRTFRHHETKFAQALPSPWENPAGHGKEECPPARPDQSRPTCQARPASSWGTREPQASRQEKPPTAEGLVSGGELLGGVTTGRGSGWGHFNDVVASGHRPLPPPHLSCPPHLVTQTVA* | 2475 | | |
| hsa-let-7c | 3 | MSVCFF* | 2477 | ATGAGTGTGTGCTTTTCTAG | 2478 |
| | 4 | MGRRNAARLPAQTRVAPHARPGPHPPGAHGSPRLPGRKSPPPQKGWSLVGSCCWVG* | 2479 | ATGGGAAGGAGGAATGCTGCCCGCTGCCCGGAGACCAGAGTCGCCCCACATGCCAGGCCAGGCCCGCATCCTCCTGGGCACACGGGAGCCCAGGCTTCCCGGCAGGAAAAGCCCCCACCGCAGAAGGCTGGTCTCTGGTGGGAGTTGCTGCTGGGTGGGGTGA | 2480 |
| hsa-let-7d | 1 | MGVTSVSFIDVLLCCLSEGLAHTRT* | 2481 | ATGGGAGTCACATCAGTTCTTTCACTGATGTTCTCCTATGCCGAGAGGCCTG | 2482 |
| | 2 | MFSYAYQKAWHILGLNK* | 2483 | ATGTTCTCCTATCAGAAGGCTTGGCACATACTAGGACTTAA | 2484 |
| | 3 | MPIRRPGTY* | 2485 | ATGCCTATCAGAAGGCCTGCACATACTAG | 2486 |
| | 4 | MRTGNLNFYVNECVIGFLVLLNHGA* | 2487 | ATGAGAACTGGAAATTTAAACTTTTATGTCAATGAATGTGTCATCGGCTTTCTGTGTTTTGCTGAATCATGGGCTTAA | 2488 |
| hsa-let-7e | 1 | MKHR* | 2489 | ATGAAGCACAGATAG | 2490 |
| | 2 | MYVICTFANSPRSFR* | 2491 | ATGTATGTCATATGCACTTTTGCAAACTCACCAAGAAGTTCCGATGA | 2492 |
| | 3 | MSYALLQTHQEVSDEHMKKMSEGLIVL* | 2493 | ATGTCATATGCACTTTTGCAAACTCACCAAGAAGTTCCGATGAACATATGAAGAAA | 2494 |
| | 4 | MHFCKLTKKFPMNI* | 2495 | ATGCACTTTTGCAAACTCACCAAGAAGTTCCGATGAACATATGA | 2496 |
| hsa-let-7f | 1 | MPLHSSLGNPSQK* | 2497 | ATGCCACTGCACTCCAGCCTGGGCAATCCGTCTCAAAAATAA | 2498 |
| | 2 | MHNH* | 2499 | ATGCATAACCATTAG | 2500 |
| | 3 | MNTMEYYHKMNEEVL* | 2501 | ATGAATATGGAGTATTATCACTATTAAAATGAATGAGGAGGTTCTATAA | 2502 |
| | 4 | MRRFYKPRYGRIFGYHVKKKKKTKVQNNVLSGDRKEEGGIYVHRCIKNLWKDT* | 2503 | ATGAGGAGGTTCTATAAGCCTAGATATGGGAGGATCTTTGGATATCATGTAAAAAAAAAAAAAACCAAGGTGCAGAATAAATGTGCATAGATGTATAAAATTCCTCTGGAAAGATACATAA | 2504 |
| hsa-let-7g | 1 | MKHR* | 2505 | ATGAAGCACAGATAG | 2506 |
| | 2 | MYVICTFANSPRSFR* | 2507 | ATGTATGTCATATGCACTTTTGCAAACTCACCAAGAAGTTCCGATGA | 2508 |
| | 3 | MSYALLQTHQEVSDEHMKKMSEGLIVL* | 2509 | ATGTCATATGCACTTTTGCAAACTCACCAAGAAGTTCCGATGAACATATGAAGAAA | 2510 |
| | 4 | MHFCKLTKKFPMNI* | 2511 | ATGCACTTTTGCAAACTCACCAAGAAGTTCCGATGAACATATGA | 2512 |
| hsa-let-7i | 1 | MMGTGTMILEHNKELKIL* | 2513 | ATGATGGGCACTGGGACAATGATACTTGAACATAACAAGAACTAAAGAACTGTGA | 2514 |
| | 2 | MTLKVALGFYYWSRFKIFYLFKTYVVCFKKLCYK* | 2515 | ATGACCTTGAAAGTTGCATTGGGTTTTTATTATTGGTCCAGTTTAAAACATTTTATCTATTTAAAACATATGTTGTGTTTTAAGAAGTATGTTATAAATA | 2516 |

Figure 1 (Continued)

| | | | | |
|---|---|---|---|---|
| | 3 | MLCVLRSYVFNNSIVVKSPESSGARLLRCKSQLCYFTKCV TLGKLINLFWCPPL* | 2517 | ATGTTGTGTTTAAGAAGTTATGTTATAAATAACAGCATTGTGGTTAAGAGCCCA GAGTCTGGGGCAGGCTTCTTAGAATGCAAATCCCAACTCTGTTATTTTACTAAATGT GTGACCTTGGGCAAGTTAATTAACCTGTTTTGGTGTCCTCCTGTGA | 2518 |
| | 4 | MQIFLLFY* | 2519 | ATGCAAATCCAACTCTGTTATTTTACTAA | 2520 |
| | 1 | MSPGKTRKPV* | 2521 | ATGAGCCCAGGCAAGACCAGAAAACCTGTGTAA | 2522 |
| | 2 | MHLLYATEAL* | 2523 | ATGCATTTTATTGTATGCCACTGAGGCTTTGTAG | 2524 |
| hsa-mir-100 | 3 | MPRLRLCSVYYAAFFCDNAAFFVTWCLLCSIFVTMDT* | 2525 | ATGCCACTGAGGCTTTGTAGTGTTTATTATGCAGCATTTTTGTGACAATGCTGCAT TTTTTGTGACAATTTGGTGTTTATTATGCAGCATTTTTGTGACAATGGACACCTGA | 2526 |
| | 4 | MQHFFVTMLHFL* | 2527 | ATGCAGCATTTTTTGTGACAATGCTGCATTTTTGTGA | 2528 |
| | 1 | MQGIS* | 2529 | ATGCAAGGAATTTCCTAG | 2530 |
| | 2 | MELWKRSSSGLHLLHC* | 2531 | ATGGAATTATGGAAAAGATCTCTTCAGGCCTTCATTGCTCATTGCTAG | 2532 |
| hsa-mir-101-1 | 3 | MEKILFRPSFAHSLLVMVLNMGDIK* | 2533 | ATGGAAAAGATCCTTCAGGCCTTCATTTGCTCATTCATAGTCATGGTGCTAA ATATGGGAGATATAAAATGA | 2534 |
| | 4 | MSMAWPWPQSLP* | 2535 | ATGAGTATGGCATGGCCGTGGCCTCAAAGCTTACCCTAG | 2536 |
| | 1 | MCFLNAVLAAVNFVWNPVSVVWKCIDFWQCALF* | 2537 | ATGTGTTTCCTTAATGCTGTATTGGCGGCCGTGAACTTGTTTGGAATCCAGTCTCTG TAGTCTGGAAATGTGATTTCTGCAGTGTGCTCTGTTTGA | 2538 |
| hsa-mir-101-2 | 2 | MLYWRP* | 2539 | ATGCTGTATTGGCGGCCGTGA | 2540 |
| | 3 | MGPITVGSPLPSLGVQMVVSFDDAGKWGRAFQGRT* | 2541 | ATGGGTTTCATCACAGTGGGGTCCCCTCTTGTTCTCTCGGGTGTGCAGATGGTCGTG TCCTTTGATGATGATGCTGGGAAATGCGAAGGCTTTCAGGGAGAACATAA | 2542 |
| | 4 | MMMLGNGEGLSRGEHKS* | 2543 | ATGATGATGCTGGGAAATGCGGAAGGCTTTCAGGGAGAACATAAAAGTTAA | 2544 |
| | 1 | MFDLKKKIKGLLMFLGCSILGS* | 2545 | ATGTTTGATTTAAAAAAAATTAAAGGGCTGTTAATGTTTTAGGGTGTTCCATA CTAGGAAGTTAG | 2546 |
| | 2 | MEGLLFCGRFLL* | 2547 | ATGGAAGGTCTTATCCTTTTGTGGGAAGGTTTTTACTTTGA | 2548 |
| | 3 | MLGPQI* | 2549 | ATGCTAGGACCACAGATATAG | 2550 |
| | 4 | MGVVYTHDFPTLRFSILMLIT* | 2551 | ATGGGTGTGTTTATACACATGACTTCCAACTGCATTTCAGTATCCTTATCGTGA TAACTTGA | 2552 |
| | 1 | MHSLQYPLASPPRKQFPVCEAALWTASPLVDPG* | 2553 | ATGCACTCCTCTCAGTATCCTCTCGCCCGAAAACAGTTCCAGTTCCGCG AGGCCCCTCTGCCTCTTCCCCTAGTGGATCCGGGCTGA | 2554 |
| hsa-mir-107 | 2 | MHLGRKGTSQAPDHFALPKDEPGQLERWGVRTERHT* | 2555 | ATGCATCTAGGGAGGAAAAGGTACCTCGCAGGCCCCAGACCATTTGCCTTACCAAAA GATGACCCAGGCCAGTTGGAAAGGTGGGGAGTTCAGGAGTCAGGACGGCACACCTAG | 2556 |
| | 3 | MTQASWKGGESGRKGTPRGEVEGKCQPVWGVAS* | 2557 | ATGACCCAGGCCAGGCAGTTGGAAAGGTGGGGAGTCGGAGGACGGAAAGGCACACCTAGGG GAGAGTGGAGGGGAAAGTGCCAGCGTGTGTGGGCGGCGTCGCCTCTTGA | 2558 |
| | 4 | MIEDTLFRGSCRLVLRCMHLSNSFSPLFSESQGIPRREKG NPSQGEVGVWEAIFGRKGNRKRTGCPHRRCSGPEAEAV TSRSCQ* | 2559 | ATGATAGAGGATACCCTATTCGCGGCTCTGCAGCTTGTCCTTAGGCATGCAT CTCTCTAATTCGTTTCTGTTTCGTGTTTCTGAAATCCAAGGGATCCAAGGAGGAGA AGGAAATCCTTCCCAGGGAGAGGTGGGGGTCTGGAAATCCAAGGGATCCCAAGGAGG GAAAAACCGAAAGCGACAGCCGGTTGTCCGACACCCGCGTCCTCTGACCAGAGGACAGA GGCTGTAACATCCGGAGCTGCCAGTAG | 2560 |
| hsa-mir-10a | 1 | MPAPKAHFWHSWSTLEKLQ* | 2561 | ATGCCAGCTCCAAGGCCCACTTTGGCACTCCTGGGCACTCTGGAAAGTCCAG TAG | 2562 |
| | 2 | MAGLSLASQP* | 2563 | ATGGCAGGGCTGTCTCTGGCTTCCCAGCCATAG | 2564 |
| hsa-mir-122 | 3 | MVTQASSWLSQCPSSMACPHMDPRFRGSASIRLKARCL PF* | 2565 | ATGGTCACACAAGCTTCCTCTTGGCTCTCAATGCCCTTCTCCATGGCGTGCCCTC ATATGGACCCTCGATTCCGCGGCATCAGGCATCAGGCTCAAGGCGCCGTTGTCTCC CCTTCTAG | 2566 |

Figure 1 (Continued)

| | | | | | |
|---|---|---|---|---|---|
| | 4 | MPFFHGVPSYGPSIPRLSEHQAEGPLSPLLASSTSDSPGS LSHPPT* | 2567 | ATGCCCTTCCATGGCGTGCCCTCATATGGACCCTCGATTCCGCGGCTCAGCGAG CATCAGGCTGAAGGCCCGTTGTCTCCCCTTGTAGCAAGCTCCACAAGTGACTCTCCA GGATCCTTTCCCATCCACCTACATGA | 2568 |
| hsa-mir-125a | 1 | MPLHSSLGNPSQK* | 2569 | ATGCCACTCACTCCAHCCTGGGCAATCCTGCGTCTCAAAAATAA | 2570 |
| | 2 | MHNH* | 2571 | ATGCATAACCATTAG | 2572 |
| | 3 | MNTMEYTITIKMNEEVL* | 2573 | ATGAATACAATGGAATATTATCACTATTAAAATGAATGAGGAGGTTCTATAA | 2574 |
| | 4 | MRRFYKPRYGRIFGYHVKKKKKJKVQNNVLSGDRKEE GGHYVHRCIKFLWKDT* | 2575 | ATGAGGAGGTTCTATAAGCCTAGATATGGAGGATCTTTGGATATCATGTAAAAAA AAAAAAAAACCAAGGTGCAGAATAATTGTGATCCTATCAGGGACAGAAAAGAGG AGGGTGGTATATATGTGCATAGAHGTATAAAATTCCTCTGGAAAGATACATAA | 2576 |
| | 1 | MPSVKLRPVCVYISVCNREIAWIRGKKSCICICCF* | 2577 | ATGCCTTCTGTAAAGTTAAGGCTGTGTGTGTATATCTCTGTATGTAATAGAGAG ATAGCAGTCCACAGAGCTGGAATATCAGTAGGCAGTTGCTGTA | 2578 |
| hsa-mir-125b-2 | 2 | MWSPQSWNSRQLL* | 2579 | ATGTGGAGTCCACAGAGCTGGAATATCAGTAGGCAGTTGCTGTAA | 2580 |
| | 3 | MFNY* | 2581 | ATGTTCAATTATTAA | 2582 |
| | 4 | MSDSHSEVMTLYPKYCGGLSRKINSIKDTDARELKKKK KKRWY* | 2583 | ATGTCTGATAGCCATAGGAGTCATGACATTAATTTATCCAAAGTATTGTGGCAA CTGTCTAGAAAAATAAATAGCATAAAGGACACAGAGCTAATTATCCAGAGAACTAAAAAAGAA AAAAAAAAAAGGTGGGTCTGA | 2584 |
| | 1 | MNQQGPLCALHPVPLGGRGTPMPCSGLWEEGEG* | 2585 | ATGAACCAACAGGGACCTCTCTGCCCCTTCACCGGTTCTCTGGGAGGAGGGG AACGCCAATGCCGGGACGGCTTGGGAGGAGGGGAAGGCTAA | 2586 |
| hsa-mir-129-1 | 2 | MPSQMLFPASRIYSGV* | 2587 | ATGCCCTCTCAAATGCTCTTCCCTGCTTCCGCCATCTACTCAGGTGTGTGA | 2588 |
| | 3 | MCYYFGRASVSRGNLMTQ* | 2589 | ATGTGTTACTATTTCGGGGAGGCAGTGTTTCCAGGGAACCTAATGACGCAATGA | 2590 |
| | 4 | MTSMQVSSRLSGRAGGLPAPGLGAVCGREGAGEVARA AGAGAREPRLSPGTGGRPLPAPEPRQLPAARAGVSP* | 2591 | ATGACGTCAATGCAGGTCAGCAGCAGGTCTCCGGGAGGCCTCCCGGAGGGCCGGCGGAGGCGCGGCTCCGGCC TTTCGGCCTCGGCGCAGTCTGCGGGGAGCCCCGGCGGAGGGCGCGGCGAGGTTGCGCGAGGGCGG CTGGCCGCGGGGGCCGAACCCAGGCAACTCCGCCGCCGGGCAGGAGTTTCTCCGTAG | 2592 |
| | 1 | MLWEQIRLFQAECRTRPKIKTVVAAELTFSEHLLNARC WANNLHSHSFAAGNSQPYGAGLIAISILQEGNRGS* | 2593 | ATGCTGTGGGAGCAGATAAGATTGTTCCAGCAGATGTGCAGGACAAGGCAAAGAT AAAAACTGTAGTGGCAGCAGAACTCACTTCAGTGAACACTTACTAAATGCCAGGTG CTGGCCAACAATTTACACAGACATCTCATTTGCTGCTGGCAACAGCCAGCCTATGG GGCAGGTTTGATTGCCATTCAATTTGCAAGAAGGCAACAGGGGTTCATAA | 2594 |
| hsa-mir-130b | 2 | MQDKAKNKNCSGSRTHFQ* | 2595 | ATGCAGGACAAGGCTGCTGGGCAACAATTTACACAGACATCTAGTGCAGCGAGAACTCACTTTCAGTGA | 2596 |
| | 3 | MPGAGPTIYTASHLLLATASPMCGQV* | 2597 | ATGCCAGGTGCTGGGCCAACAATTTACACAGCATCTCATTGCTGCTGGCAACAGCC AGCCCTATGGGGCAGGTTTGA | 2598 |
| | 4 | MNASPQSGSQSRRNQSLHFKSPYLPQIQKITGPRPRSP* | 2599 | ATGAATGCTTCTCCCCAAAGTGGATCACATACACAATGGACCACAAACCAAAGCTTACACTTC CGTTCCACCATATCTCCACAGATCAAAGACCACGGGGCCACGGGCCAGGACCCGGTCTCCA TAG | 2600 |
| hsa-mir-133a | 1 | MLFIFSVRRLR* | 2601 | ATGTTGTTCATTTTTCTGTGAGAAGGCTAAGATGA | 2602 |
| | 2 | MRGKRDILGGVMEIGYWNCTGDWIPGPYP* | 2603 | ATGAGGGGCAAGAGAGACATACTGGGGGAGTTATGGAGTTGGGTATTGGAACTG TACTGGAAGATTGGATACCTGGACCATATCCCTGA | 2604 |
| | 3 | MIKLMHGPEDAKAVHPESNHYVNHPASLSRLSLM* | 2605 | ATGATAAAGTTGAACCATGGCCCAGAAGATGCAAAAGCAGTCAAAAGCCAA CCACTATGTGAATCACCCAGCCAGTCTTAGCAGGCTGTCCTGATGTGA | 2606 |
| | 4 | MAQKMQKQCIRKATTM* | 2607 | ATGCCCAGAAGATGCAAAAGCAGTGCATCCGGAAAAGCCAACCACTATGTGA | 2608 |
| hsa-mir-133b | 1 | MPLRK* | 2609 | ATGCCACTCAGGAAGTGA | 2610 |

Figure 1 (Continued)

| | | | | |
|---|---|---|---|---|
| hsa-mir-138-2 | 2 | MLNAESENEPLGWRVDPGLTKSWQSPH* | 2611 | ATGCTGAATGCTGAGTCAGAGAAATGAACCCTGGGCTGGCGGGTTGACCCAGGCCT GACAAAGTCTTGCAGTCCCACACTGA | 2612 |
| | 3 | MLSQKMNPWAGGLTQA* | 2613 | ATGCTGAGTCAGAAATGAACCCTGGCTGGCTGGCGGTTGACCCAGGCCTGA | 2614 |
| | 4 | MEMCVLYQN* | 2615 | ATGGAAATGTGTGTTTTATATCAGAATTGA | 2616 |
| hsa-mir-141 | 1 | MDRLTT* | 2617 | ATGGACAGACTCACAACTGA | 2618 |
| | 2 | MAASPPPLPDPVYSPARPQAGPTLLLL* | 2619 | ATGGCTGCATCCCCCACCTTCCTGACCCTGTATAGCCAGCCAGGCCAGCCCTTAG GCAGGGCCAACCTTCTCCTCTGTAA | 2620 |
| | 3 | MGNCVCLRACLA* | 2621 | ATGGGTAACTGTGTGCTCGGCTGCCTCCGGTTA | 2622 |
| | 4 | MEGDHNRVVVKSTEMTADDKTGTVTHHTLAMCPGTK RLHTLVQSRHFCHSHFTVAETEGQKN* | 2623 | ATGGAGGGCGATCATAACAGGGTGGTGGTGAAAAGCACCGAGATGACGGCTGACGA TAAGACGGGCACAGTGACTCATCACACGCTGGCCATGTGCCCAGGCACTAAAAGACT ACACACGTTAGTCAGTCTAGGCACTTCTAGCACTTCTGTCATTCTCATTTTACCGTGGCGGAAAACT GAGGGACAGAAAACTAA | 2624 |
| | 1 | MAKFSIVYFYLT* | 2625 | ATGGCAAAGTTTCCATTGTATATTTTATTTGACCTAA | 2626 |
| | 2 | MPCIQ* | 2627 | ATGCCCTTGTATTCAGTGA | 2628 |
| | 3 | MFKRLITFIQMFL* | 2629 | ATGTTTAAGCGTTTGATCACTTTTATTCAAATGTTCCTATGA | 2630 |
| hsa-mir-181a-1 | 4 | MITRRYCAFSYYFNAPMYTAGLNNHKSNVCLESDWFV YLHCCRKSH* | 2631 | ATGATAACCAGAAGATACTGTGCATTCTCATATATTTAATGCTCAATGTATACTG CAGGCTTAAATAACCATAAAGTAATGTTTGTTTAGAAAGTGACTGGTTTGTTTACC TTCACTGCTGCAGAAAATCTCACTAG | 2632 |
| | 1 | MSQMTVLYNDLVSQWLRKMENKPQGP* | 2633 | ATGTCACAAATGACAGTCCTGTATAATGACCTGGTTCCCAGTGGCTCAGAAAGATG GAAAATAAACCCCAAGGACCCTAG | 2634 |
| hsa-mir-181a-2 | 2 | MTWFPSGSERWKINPKDPSSDRLKRADRGCLA* | 2635 | ATGACCTGGTTCCAGTGGCTCAGAAAGATGGAAAATAAACCCAAGGACCCTAG TTCAGACAGACTGAAGAGACGAGACCGTTGCTGTCTTGCATGA | 2636 |
| | 3 | MIKGYVTAQ* | 2637 | ATGATTAAAGGCTATGTCACAGCTCAGTAG | 2638 |
| | 4 | MSQLSRVHAFIASPPQQPLM* | 2639 | ATGTCACAGCTCAGTGAGGTCCATGGGTCCATGCTTTCATAGCTTCCCCCCAGACAACCCTA ATGTGA | 2640 |
| hsa-mir-181b-1 | 1 | MAKFSIVYFYLT* | 2641 | ATGGCAAAGTTTTCCATTGTATATTTTATTTGACCTAA | 2642 |
| | 2 | MPCJQ* | 2643 | ATGCCTTGTATTCAGTGA | 2644 |
| | 3 | MFKRLITFIQMFL* | 2645 | ATGTTTAAGCGTTTGATCACTTTTATTCAAATGTTCCTATGA | 2646 |
| | 4 | MITRRYCAFSYYFNAPMYTAGLNNHKSNVCLESDWFV YLHCCRKSH* | 2647 | ATGATAACCAGAAGATACTGTGCATTCTCATATATTTAATGCTCAATGTATACTG CAGGCTTAAATAACCATAAAGTAATGTTTGTTTAGAAAGTGACTGGTTTGTTTACC TTCACTGCTGCAGAAAATCTCACTAG | 2648 |
| hsa-mir-181b-2 | 1 | MSQMTVLYNDLVSQWLRKMENKPQGP* | 2649 | ATGTCACAAATGACAGTCCTGTATAATGACCTGGTTCCCAGTGGCTCAGAAAGATG GAAAATAAACCCAAGGACCCTAG | 2650 |
| | 2 | MTWFPSGSERWKINPKDPSSDRLKRADRGCLA* | 2651 | ATGACCTGGTTCCAGTGGCTCAGAAAGATGGAAAATAAACCCAAGGACCCTAG TTCAGACAGACTGAAGAGACGAGACCGTGGCTGTCTTGCATGA | 2652 |
| | 3 | MIKGYVTAQ* | 2653 | ATGATTAAAGGCTATGTCACAGCTCAGTAG | 2654 |
| | 4 | MSQLSRVHAFIASPPQQPLM* | 2655 | ATGTCACAGCTCAGTAGGTCCATGCTTTCATAGCTTCCCCCCAGCAACCCTA ATGTGA | 2656 |
| hsa-mir-181c | 1 | MPVIPAL* | 2657 | ATGCCTGTAATCCCAGCACTTTAA | 2658 |
| | 2 | MGGWLESGRRRIQ* | 2659 | ATGGGAGGATGGCTTGAATCCGGAGCGGAGGATACAGTGA | 2660 |
| | 3 | MGCIC* | 2661 | ATGGGTTGCATCTGTTAA | 2662 |
| | 4 | MELPFPETGKMAGDRLQLRK* | 2663 | ATGGAGCTGCCATTTCCGGAGACCGGGAAGATGGCGGGAGACCGTTTGCAGTTGAG GAAATGA | 2664 |
| | 1 | MPVIPAL* | 2665 | ATGCCTGTAATCCCAGCACTTTAA | 2666 |
| | 2 | MGGWLESGRRRIQ* | 2667 | ATGGGAGGATGGCTTGAATCCGGAGCGGAGGATACAGTGA | 2668 |

Figure 1 (Continued)

| | | | | |
|---|---|---|---|---|
| hsa-mir-181d | 3 | MGFFC* | 2669 | ATGGGTTGCATCTGTTAA |
| | 4 | MELPFPETGKMAGIDRLQLRK* | 2671 | ATGGAGCTGCCATTTCCGGAGACCGGGAAGATGGCGGGAGACCGTTTGCAGTTGAAGGAAATGA | 2670, 2672 |
| | 1 | MALREGRAGPGAGGGKTLLESFSVHSVEPPRSRAGAAGPPFSSRAVRAARAPCSSGPRAQVPHLWTSPACSAEAAAPLQVAGPGPSPADLSPDTQEARGRVPAPLCSPAGLGAPAPPPLAGQRRFGPGPGALQAPSMRLFPNRGRFCLASLVWTPRGAERRLCAQPGAGAGECLGPGAGGRAGRSQSGAQ* | 2673 | ATGGCGCTGCGCGAGGGTCGGGCGGGCCCGGGCGCGGGGGGCGGGAAGACCCTCCTGGAGTCATTCTCGTTCGTCCACTCCGTGGAGCCGCCGCGCAGCCGCGCGGGAGCCGCAGCCCCGTTCTTCCGGTCCTCAGCGAGTCCCGGGGCCGGGCCGGGTACCCCGTCTGGACCTCCCCCGGCCAGCCGCGGAGGCGGCTCCTTCAGGTGGCCGGGCCGGGTCCCGGCTCCCCGTTGTCCCGGCGCTGGGCTCCGGCGCCCAGGAAGCGGCGGCCCGGGTCCCCGGGGCACGGAGTTTGGCGCGGACCGCGTTTGCCGGCGCGCTGCAGGCCGAGCTCGGGGTCATGCCGCGAGCTTTCCAAACCGGGAGGTCTCTCTGAGGCCGCGCTGGCGAGGCGCGTGAGTTGGGGGAGCTGAGAGCGCGCTGTGCGCCCAGCCTGGCGCGCCAGGTGAGTCAGCCTCCTGCCAGGGCGGGGGCGGGGGCTCAGTAG | 2674 |
| hsa-mir-182 | 2 | MIRQCLLALPRLQAEAPTGRLGPGSASGVCPAPSAVPGRGRGRERLRSECGRCLRGAYPRGVWLGSGCVSPPWWAQAEAPGWEGAAESAGAPELAPPASCGCAAGSRLLPWPGAAPPSLWGKAALRPPVCLHFAATHPGNPGARE* | 2675 | ATGACGCGGCAGTGCCTACTGGCTCTTCCGCGCCTTCAGGCGGAGGCGCCCACGGGCGCCCTGGGTCCGGGCAGTGCGAGCGTCTGCCCAGCGCCCAGCGCTGTTCCGGGCCTACCCGCGAGGCGGTTGGCCTGGGAGCGGCTGCGGGGAGCGCGTTGCGCCTGGTGGGCTCAGGCGGAAGCGCCAGGTCTTGTCAGGGCTGCGGCCTGGTTCGGAGGCCCCGGAGCTGGCCCCTCCAGCCGCCCCGCCCAGTCTCTGGGGAAAGCGGCTCTCAGACTCCGTGCCCTTCCACTTCGCGGCACTCATCCCGGGAACCCGGCGCACGCGAATGA | 2676 |
| | 3 | MRHRSPPSTAPFLLIALVAPRFPALPQDRRLDGLPLAPHRSAHPKTMGSEGVTRGQGSPDSTVSSRLSHSFALPTRAPGHRVQ* | 2677 | ATGAGACACCGTTCCCGCCCAGGTTCCACCCCCGACGCCCTCCCAACTGCCCGCCCATTCTGTTAATAGCGCTAGTGGCACCCAGGTTCAGCGCATCCCAAGATGGGGCTGACCGCTTGCCTCTGCGCCCTCACCGGTGTCAGTGAGGGTGTCACCGGGGTCAGGGGTGCCCGATTCTCAGGGTCTCCAGGCTGAGCCATTCGTTGCTCTTCCAACCCGGGGCTCCGGACACGTGTACAGTAA | 2678 |
| | 4 | MGTESADL* | 2679 | ATGGGCACGGAGTCGGCGGATCTCTGA | 2680 |
| | 1 | MALREGRAGPGAGGGKTLLESFSVHSVEPPRSRAGAAGPPFSSRAVRAARAPCSSGPRAQVPHLWTSPACSAEAAAPLQVAGPGPSPADLSPDTQEARGRVPAPLCSPAGLGAPAPPPLAGQRRFGPGPGALQAPSMRLFPNRGRFCLASLVWTPRGAERRLCAQPGAGAGECLGPGAGGRAGRSQSGAQ* | 2681 | ATGGCGCTGCGCGAGGGTCGGGCGGGCCCGGGCGCGGGGGGCGGGAAGACCCTCCTGGAGTCATTCTCGTTCGTCCACTCCGTGGAGCCGCCGCGCAGCCGCGCGGGAGCCGCAGCCCCGTTCTTCCGGTCCTCAGCGAGTGGCCGGGCCGGGTACCCCGTCTGACCTCCCCGGCCAGCCGCGGAGGCGGCTCCTTCACCGACGCCAGGAAGCGGTGGCCGGGTCCCCGGGGCCGGGGGTCCCGGCTCCCCGTTGTTCCCGGCGCTGGGCTCCGGCGCCCAGGAAGCGGCGGCCCGGGAGGTTTGGCCCGGCGCTTTGCCCAGCCGCGGAGCTCGGGGCACTCAAACCGGGAGCTCTCTCTGAGGCCGCAGCCTGGCGCCGCTGAGCGGCCGCTGCGCAGGTGAGTGTCTGGGGCGCAGGGGAGCTGAGAGCGCGGAGGCCAGGAGGCGGGGGCTCAGTAG | 2682 |

Figure 1 (Continued)

| | | | | |
|---|---|---|---|---|
| hsa-mir-183 | 2 | MTRQCLLALPRLQAEAPTGRLGPGSASGVCPAFSAVPG RGRGRERLRSECGRCLRGAYPRGVWLGSGCYSPPWWA QAEAPGWEGAAESAGAPELAPPASCQGCAAGSRLLPWP GAAPPSLWGKAALRPPVCLHFAATHPGNPGARE* | 2683 | ATGACGCGGCAGTGCTACTCGCTCTTCCGGCCTCTTCAGGGCTGGAGGCCCCACGGG GGGCCTGGTCCTGGGTCCGGCCCAGTGCCGGTCTGCCCAGCGCCAGCGCTGTTCCGG GCGGGGGCGCGGGCGAGGAGTTTGCTCGGCAGCCTGCGGTCGCGGAGTCCGCCCTGGTGGGCT GCCTACCCGCGAGGAGTTTGCTCGAGGGTGCTGCGTTTGCCGCCTGGTGGGCT CAGGCGGAAGCGCCAGGCTGGGAGGGGCTGCGCAAGGGGCTGCGGAAGCTGCTTCCGTGCC TGGCCCTCCAGCGTCTGTCAGGGCTGCGGCGCTGCGGCGCTGCGAGGCTGCTTCCGTGCC CCGGAGCGCCCCCGCCCAGTCTCTGGGCGAAAGCGGCTCTCAGACCTCCGTGTGCC TCCACTTCGCGGCCACTCATCCCGGAACCCGGCGCACGCAGCGAATGA | 2684 |
| | 3 | MRHRSPPSTAPFLLJALVAPRFPALPQDRRLDGLPLAPH RSAHPRTMGSEGVTRGQCGSPDSTVSSRLSHSFALPTRAP GHRVQ* | 2685 | ATGAGACACCGTTCCGCCGCCTCAACTGCCTCCCATTCTGTTAATAGCGCTAGTGGCA CCCAGGTTCCGACCTTCCCAGCTCCCAAGATGCGGCGTTGGACGGCTTGCCTCTGGCGCCT CACCGGCGCATCCAGACTATGGGCAGTGAGGGTGTCACCCGGGGTCAGGG GTGCGCGGATTCCACGGTGTCCTCCAGGCTGAGCCATTCGTTTGCTCTCCAACCCG GGCTCCCGGACACCGTGTACAGTAA | 2686 |
| | 4 | MGTESADL* | 2687 | ATGGGCACCGAGTCTGCGGATCTCTGA | 2688 |
| hsa-mir-190 | 1 | MAETWA* | 2689 | ATGGCTGAGACTTGGGCATGA | 2690 |
| | 2 | MRTEEQRKERK* | 2691 | ATGAGGACAGAGGAGCAAAGGAAGGAGAAGAAAATGA | 2692 |
| | 3 | MKRRGKQGICS* | 2693 | ATGAAAAGACGCGGGAAACGCAAGCAAGGAATTGTAGTTAA | 2694 |
| | 4 | MRLSDFKL* | 2695 | ATGAGATTATCTGATGAAATCAAGTTATAA | 2696 |
| hsa-mir-192 | 1 | MGKPRLGLGIREPSPC* | 2697 | ATGGGGAAACCAAGGCTCGGGTTGGGAATCAGGGAACCTCACTTGCTAG | 2698 |
| | 2 | MPPGEADGAQPDASWTRPTLPGHSPGLPALRTALVISID GGGHINHHQGLGQRLKRPWAQGVPTSSLCPEGQPGTQ VRGFLSGRTPAALPVLGGS* | 2699 | ATGCCACCCGGAGAGGCAGATGGGGCCAGTCCAGGGCTTCCTGCCCTTGAACGCACTGCCGGCCCAC CCTGCCCGGGCACAGTCCAGGGCTTCCTGCCCTTGAACGCACTGTGATCAGTAT TGACGGTGGTGGGAGATAATCATTAACCACCAGGGGCTGGGTCAACGGCTCAAAA GGGGCCTGGGCCAGGGTGTCCCACTTCCTCGAGTGGTAGGACCCTCCGCGCCTCCGGCA CTCAGGTAAGAGGCTCCGAGTGGTAGGACCCCTCCTGCGCCTCCGGCA GCTCCTGA | 2700 |
| | 3 | MGPSLMLPGPAPPCPGTVQGFLPFEPHL* | 2701 | ATGGGCCCCAGCCTGATGCTTCCTGGACCCGCCCCACCCTGCCCGGGCACAGTCCAG GGCTTCCTGCCCTTCGAACCGCACTTGTGA | 2702 |
| | 4 | MGWPGRAPSSLCLGFHCGHGP* | 2703 | ATGGGGTGGCCGGGACGAGCCCTTCCTCTGTGCCTTGGTTCCACTGTGGATA AGGGGGCCTTAG | 2704 |
| | 1 | MVAHACNPSYS&G* | 2705 | ATGGTGGCATGCCTGTAATCACTGTACTCTGAGGCTGA | 2706 |
| | 2 | MPVIPVTLEAEAGESPTPGR* | 2707 | ATGCCTGTAATCCAGTTACTCTGAGGCTGAGGCAGGAGAATCGCTTACACCTGGG AGATAG | 2708 |
| | 3 | MERAGTPQAEGEEASSLPLAGVPGTSSVASGLPAKLGG VFYERDLCWPTEDSKHPL* | 2709 | ATGGAGAGGGCAGGGACACCACAGGCAAGGAGGAAGGAGGAGGCAGCTCGCCCCTT GGCTGGGGTCCCTGGGACCTCCTCTGTGGCATCAGGACTGCCGCTAAGTGGGTGG TGTGTTTTATGAGCGTGACCTGTGTTGCCAACAGAGGACAGGCAAAATACATTTTT ATGA | 2710 |

Figure 1 (Continued)

| | | | | |
|---|---|---|---|---|
| hsa-mir-193b | 4 | MSVTCVGQQRTAKYIFYDPGRFRPVTFSRREAGRWRGT SHVSVMWILFAKEGPLLQWIWGSLGRGVGEDFRKG MSCWGGASPLLREFMKSITAMAGESVSTRGQIFARWRG HPCALPPSSSTSPRALSPGSSNKVTLDWGGSTTLFSGP KLGWYLGEFLGTQCVCAISTLGDPGDSSHSRGGERPSW GGCKRLGEPA* | 2711 | ATGAGCGTGACCTGTGTTGCCAACAGAGGAACAGCAAATACATTTTTATGATCCT GGGAGGTTCAGGCAGTCAGTTATGTGGATTTCGCGCAGAGGACGTGGCGGTGGAGAGGGAC AAGTCATGTCTCAGTTGTCCTGGGCAGGGGTCCAGGGGTCCTGAAAGAGGGGCCACTCTGCAATG GATTTGGGGGTCCCTGGGCAGGGGTCCTGCAGGGGGTCCAGGGGGAAGATTTTAGGAAGGGGA TGAGCTGCTGGGGGGGCATCTCCCTTACTGCGGGAAATGAAAGTATTACAGCT ATGGCTGGTGAGTGTCAGCAGGCCAGATCTTTGCCAGGTGGAGGGGACA CCCTTGTGCCCTACCCCAAGTTCCAGCACCTCTCCAAGAGCCCTTAGCCCGGAAG CAGCAACAAAGTGACATTGGGAGACTGGGGAGGAGGAAGGCAACAACTTTATTTCTGGCC CGAAGCTGGGTTGGTATTTGGGAGGGACTTCAGCCATTCCAGAGGAGGTGAAGAGACCGTCA CAACCCTGGGGGATCCAGGGGACTCTGGGAGCCTTCGRGRGAACCTGCCTGA | 2712 |
| | 1 | MGKPRLGLGIREPSPC* | 2713 | ATGGGGAAACCAAGGCTCGGGTTGGAATCAGGGAACCCTCACCTTGCTAG | 2714 |
| | 2 | MPPGEADGAQPDASWTRPTLPGHSPGLPALRTALVISHD GGGHINHHQGLGQRLKRPWAQGVPTSSLCPEGQPGTQ VRGFLSGRTPAALPVLGGS* | 2715 | ATGCCACCCGGGGCAGAGGCAGATGGCCCAGCTGATGCTTCGGACCCGCCCAC CCTGCCCGGGGCACAGTCCAAGGCTCCTGCCTCGAACGCACTTGTGATCAGTAT TGACGGTGGTGGGATAATCATTAACCACCACCACGCGGCTTGGGCTCAAGCGCTCAAAG GCCCCTGGGCCCAGGGTGTCCCAGGTGTCCAAGGCCAGCAGCCCGGCA CTCAGGTAAGAGAGGCTTCCTGGTAGGACCCCTGCCCGCCCTCCTGTCCTAGGAG GCTCCTGA | 2716 |
| | 3 | MGPSLMLPGPAPPCPGTVQGFLPFEPHL* | 2717 | ATGGGGCCCAGCTGATGCTTCCTGATGCTCCTGAACCGCACTTGTGA | 2718 |
| | 4 | MGWPGRAPSSLCLGFHCGIRGP* | 2719 | ATGGGGTGGCCGGGACGAGCCCTTCCTCTCTGTGCCTTGGTTCCACTGTGGATA AGGGGCCCTAG | 2720 |
| hsa-mir-194-2 | 1 | MDTQEAFSPGEKQGEGREDRRKLKFWGVLILGVFCHSGC FW* | 2721 | ATGGATACCAAGAAGCTTTTCCCAGGGAGAAACAAGGTGAGGCCGAGGA CAGGAGACTAAAGTTCTGGGGTGTTCTTATTTGGGGGTGTTTGTCACTCGGCTG CTTTTGGTGA | 2722 |
| | 2 | MSFAYSALSPQHLEVSLVNPQISPGFEGRNLERVWYLLL LLCGLREKRGRKGGFRL* | 2723 | ATGTCTTTTGCTTATAGTGCCCTCCACCCCAGATTCTAGAAGTTTCTTTAGTGAACC CCCAAATAAGCCCAGGATTTGAAGGAGAAACTTGAAAGGGTGTGGTATCTCCTTT TATTATTATGTGGCTTGAGCGGAGAAGAGAGAGAGAAAGGCCGTTTCAGACTCTGA | 2724 |
| | 3 | MWLEGEEREKRRFQTLNPNFLREHPLVWGKLEKNGVS LGQVGTPDQCSAVGTYARRGAGGVQGGDSCTLIF* | 2725 | ATGTGGCTTGAGGGAGGAGCACCCTTAGTTTGGGGGAAGTTGGAGAAAAATGGGTGTCCCT TGGCCAAGTGGAGCACCCCTGACCAGGGCAGTGCTGTTGGAACTGTGGCAAGGAGGG GTGCTGGTGGGGTACAAGGAGGTGATTCTTGCACCCGATTTTCTAG | 2726 |
| | 4 | MGTPLAKWAPLTRAVLLELWQGGVLVGYKEVILAP* | 2727 | ATGGGCTGTCCCTTGGCCAAGTGGCACCCTGACCAGGCAGTGCTGTTGGAACT GTGGCAAGGAGGGGTCTGGTGGGGTACAAGGAGGTGATTCTTGCACCCTGA | 2728 |
| hsa-mir-195 | 1 | MKHRK* | 2729 | ATGAAGCACCGAAAATGA | 2730 |
| | 2 | MIELKGEMDKSTHVRYFNSSHLVKSLVKSLCPFYRGKT EA* | 2731 | ATGATAGAATTGAAAGGAGAGATGGACAAATCCACAATTATAGTAAGATATTTCAA CAGTTCTCACTTGGTAAAAATCACTTGTAAAATCACTCTGCCCATTTTACAGAGGAAA AACTGAGGCCTAA | 2732 |
| | 3 | MPPGQPPAGRDWIVRGCPQSHAG* | 2733 | ATGCCCCCTGGACAACCACCACCTGCAGGAAGGCGACTGGATTGTGAGGGGTGTCCCA GTCCCATGCAGGGTGA | 2734 |
| | 4 | MQVEEAGSQG* | 2735 | ATGCAGGTTGAGGAGGAAGCAGGGTCTCAGGGTGA | 2736 |
| hsa-mir-196a-1 | 1 | MRQRRRAAVAVAGV* | 2737 | ATGAGGCAGCGTCGTCGGGCAGCTGTGGCGGTGGCGGGGGTCTAG | 2738 |

Figure 1 (Continued)

| | | | | |
|---|---|---|---|---|
| hsa-mir-196b | 2 | MEPPDGPFPPPQQQPPPPQPPQPQPAPQATSCSFAQNIKEE SSYCLYDSADKCPKVSATAAELAPFFRGPPFDGCALGTS SGVPVPGYFRLSQAYGTAKGYGSGGGAQQLGAGPFP AQPFGKGFDLPPALASGSADAARKERALDSPPPPTLACG SGGGSQGDEEAHASSSAAEELSPAPSESSKASPEKDSLG KQGCRGLQSGGQTGRHKEEKDQKTRSPRSSRPALAQA AGRLTL* | 2739 | ATGGAGCCGCCTGACGGCCCGCCGCCGCCGCCCCAGCAGCAGCCGCCGCCCCCGCC GCAACCACCCAGCCGCCTCAGCGCAGCAGCCCTCGTGCTCTTTGCGCAGAACATCAA AGAAGAGAGCTCCTACTGCCTCTACGACTCTGCTGACAAGTGCCCAAAGTCTGGC CACTGCGCCGCCTCCAAGGGCTCCATCGCCGCCGCTCCCGCCGCTGGCCGCCCT GGGCACCTCCAGGGACTTGGCTCCCAGTGCCAGCTGCGCGGCGCCACTCGGGCTACGG CACCGCCCAAGGGCTATGGAGCCCCCGGGGTCGCGGTTTCGATCTCCGCGCTAGCCTCCG GCTTCCCCGCGATGGCCGGGAGCGAAGAGCCGCGCGCCCACG CTGGCTTGCTGGCAGCGCGGGGAGCTCGAGGCGAGCGGCGCACCGTGTC CTGGCCGGGAGAGCTCTCCCGGCCCCTTGCGAGCAGCAGCCTGCGGG AGAAGGATTCCCTTGGGTAAGCAGGGCTGCAGAGGGCTGCAGTCAGGCGCAGAGACA GGCAGACACAAGGAGGAGAAGGATCAGAAAACTAGGAGCCCGCAGCAGCCGGC CGGCCTTGCCCAAGCTGCAGGCAGCCGCTGACCTTGTGA | 2740 |
| | 3 | MPQSLGHRRRTGSLPAGPAARRLRPGHLQRGASAWLLP PPSGLRHRQGLWQRRRRSAATRGWPVPRAAPGARFRSP ARASLRLGRCGPEGASPRFAAAPHAGLRQRRGLAGRRG GARVVLGRGGALPGPFREQQSLAGEGFPG* | 2741 | ATGCCCCAAAGTTCTGGCCACCGGCGCCGCAACTGCTCTCCGCGGGCCCTGC CCCGACGGCCACCGTGGGCACTGCCAGGCTATGGCAGGGCTGGCTACTTCCG CCTTTCTCAGGGCTACGGCACCGCCGTTCCCGGCCGCAGCCCCGGGCGCGGTTCGATCTCC AGCAACTCGGGGCTGGCCGTTCCCGGCCCGTCGCGGCGGGAGCGAAGGAGCGAGCCCTGAT CGCCCGCTAGCCTCGGCTCGGGCCGATGCGCCCGGAAGGAGGAAGGAGCCTCGAT TCGCGCCGCACGTCGGCTTGCGCCAGCGTGGGCGGGGCTCGCAGGGCACGA GGAGGCGCACGGTCGCGTCCTCGCCGCGAGGAGCTCTCCCCGGCCCCTTCGGAGA GCAGCAAAGCTCGCGGAAGGATTCCCGGTAA | 2742 |
| | 4 | MAAAAAARSNSGLARSPRSPRGAVSISRFR* | 2743 | ATGGCGGCCGCAGCGCGGCGGCGTTTCGATCTCCCGCCGCTAG CCCCGGGGCGCGGTTTCGATCTCCCGCCGCTAG | 2744 |
| | 1 | MVGSPALSGSMVEGHGLGGEHWALESRSRGKGSRWIQ RALGTAAPPPAHPSRPQFTHPFAHPSHPRHPRHPRHPR HPRHPRHPRHPRHPR2POLRPSPAPPSPPRPQPRPSPASHR PGGSLAFLPGWKRVKSATGVRVEQEGGRRRGGKDRWAP RGGGAACRGLPPPLDPV* | 2745 | ATGGTTGGGTCACTGCCTTGTCTGGCAGCATGGTGAGAAGGCATGGCTGGGCGG GGAGCACTGGGGACTGCAAGTCAAGTCGCAGCCCACCTCCCGCCCGCCATCCCG AGCCCCTACGCCCCATCCCGCCATCCCGCATCCCGCCATCCCCGCCATCCCGC CCCAGCCCAGCCCTCCATCCCGCCAGCCCAGCCCTCCAGCCCTCCGC CATCGCCTCGGAAGCTCCCATCCTGCCGGGTGGAAACGGTGTGTCTGCTACC GCGGTTCGTGTGGAACGCGGAAGGCAGAAGGCGGACGAGGTGAAAGAGGCTGGG CGCCCCGAGGAGCGGGAGCCCTCCGAAGGCCCTCAAGTTCAGAGGCAAAGGCAGC AGGTGGATCCAGCGAGCCCTAG | 2746 |
| | 2 | MAWAGSTGPWNQGPEAK AAGGSSEP* | 2747 | ATGACAATGTCTACCCAGCAGGAGGAGCCAGCAGGAGCCAGCAGCCACAGT TCCTGGAGATTCCGACACCAAGTGCAGCCACTGTCGCGGGCGTGAGTGC CCCACACGACCAGCTCCACGCGACCCAGCTGGCCACAGCCACTGGCCCCCTCCGTGAGG AGGAGAGAGGGCTTCGGGCAGCCTGAGGGCCTCACTCACTTCCTTGGT AGGTGGGGATGCCGCGGCCTCCGAGACTTGA | 2748 |
| hsa-mir-200a | 3 | MTMSYPAGGPGRNLWQPPVPGDSDTKCSHCAGPGVE WPHTDQLTPAGRATGPPPWRRREASGATRCAPGPLTSL VGGGCRPGPPET* | 2749 | ATGCCGGCCTCCAGGGACCTGTCCAGCGCTCCGCCCTGCCCCTGCAGCTCAGCGAGAG CGGGGGCCCTGCTGTCACGCCAGAGCGGCATCAGCCCTCACGGGCCACTCCGTTAGCAAT CCTCCCCCAGCTCGGGCTTAGGAGCTGCCAGCTCACGAGGACTCTCCAGCAGGCACCTGA GGGCCTGGGGCTTGGGGCCTGGGTAGGGACTGCCGTGGTCTCCCAGCAGCTACC CAGGTTCATCCAGGATGAAAGCAGGGAGTGGGAACCACGTGA | 2750 |
| | 4 | MPAWASRDLSPAPALAPRETCASERPRPPLPEPCTRAVR GPCCTPERASALSHSVSNPPPSSGPQNWPSTEL RGTRGP WGLGRDWPARGPPAAIPRFIQDESRAVGIT* | 2751 | ATGCCGGCCTGGGCCTCCAGGGACCTGTCCGCGCCGGCTCTCGCCCCTCGCGAGACTTGC GCTAGTGAGCGCCCTCGCCCACCCCTAGAGCCATGCACAGCCCTCAGCCACTCCGTTAGCAAT CCTCCCCCCAGCTCAGGGCCTAGGAACTGCCAGCACTGCAAACTCACGAGGCACCTGA GGGCCTGGGGCTTGGGGCCTGGGTAGGGACGCAAGGGCAGTGGGAACCACGTGA | 2752 |

Figure 1 (Continued)

| | | | | |
|---|---|---|---|---|
| | 1 | MVGSPALSGSMVEGHGLGGEHWALESRSRGKGSRWIQ RALGTAAPPPAHPSRPQPTHPIPAHPSHPRHPRHPRHPR HPRHPRHPRHPRHPRPQLRPSPAPPSPPRPQPRPSPASHR PGGSLAFLPGWKRVSATGVRVEQEGGRRGGKDRWAP RGGGAAGRGLPPPDPV* | 2753 | ATGGTGGGGTCACCTGCCTTGTCTGGCAGCATGGTAGAAGGGCATGGCCTGGGCGG GGAGCACTGGGCCTGGAATCAAGGTCAGAGGCAAAGGCAGCAGGTGGATCCAGC AGCCCTAGGGACTGCAGCCCCCACCCATCCCGCCCCATCCCGCCCATCCCG CCATCCCGCCATCCCGCCATCCCGCCATCCCGCCCATCCCGCCATCCCGCCATCCCG CCCAGCCCAGCCTCCATCCCGCCCCGCCGCCCCGCCCCGCCGCCCAGCTCGCC CATCGGCCTGGAGGCCTCCTGCGGCCTTCTGCCGGGGTGGAAACGGGTGTCTGCTACC GGGGTTCGTGTGAGCAGGAAGGGGAAGGCGACGAGGTGAAAGACCGCTGG CGCCCCGAGGAGCGGAGCTGCTGGGAGGGGCTCCCTCCCGCCGATCCTGTTTAA | 2754 |
| hsa-mir-200b | 2 | MAWAGSTGPWNQGPEAKAAGGSSEP* | 2755 | ATGGCCTGGGCGGGAGCACTGGGCCTGGAATCAAGGTCAGAGCAAAGGCAGC AGGTGGATCCAGCGAGCCCTAG | 2756 |
| | 3 | MTMSYPAGGPGRNLWQPPVPGDSDTKCSHCAGPGVE WPHTDQLTPAGRATGPPPWRRREASGATRCAPGPLTSL VGGGCRPGPPET* | 2757 | ATGACAATGTCTACCGAGGAGGACCAGGCCGAACCTTTGCAGCCACCAGT TCCTGAAGATTCCGACACCAAGTGCAGCCACTGTGCGGGCGGGTGTGGAGTGGC CCCACACCGACCAGCTCACGCCAGTGGCAGAGCCACTGGCCCCTCCGTGGAGG AGGAGAGAGCGCTCGGGCCACGTGCCTGGCCTGCCCAGGCCACTCACTTCCTTGGT AGGTGGGGGATGCCGGCCTGGCCTCCGAGACTGA | 2758 |
| | 4 | MPAWASRDLSPAPALAPRETCASERFRPLPEPCTRAVR GPCCTPERASALSHSVSNPPPSSGPQNWPSTELRGTRGP WGLGRDWPARGPPAAIPRFIQDESRAVGTT* | 2759 | ATGCCGGCCTGGGCCTCCCGGGACCTGAGCCCTGCCCTGCCCTGCCCTGAGAG ACCTGTGCCAGGAGCGTCCAGGCTCCCCTGAGCCTTGCACCCGGCGGTG CGGGGCCCTGCTGCACCCAGAGCGGGCATCAGCCCAGCCACTCCGTTAGCAAT CCTCCCCCCCAGCCTGGGCCTCAGAACTGGCCATCCACGGAGCTCAGAGGCACCGA GGGCCCTGGGCCTCGGGATAGGACTGGCCAGGGTCTCTCCAGCAGCCATACC CAGGTTCATCCAGATGAAAGCAGGGCAGTGGGAACCACGTGA | 2760 |
| | 1 | MDRLTT* | 2761 | ATGAGACAGACTCACAACGTGA | 2762 |
| | 2 | MAASPPPLPDPVVSPARPQAGPTLLLL* | 2763 | ATGGCCTGCATCCCCCCACTCTCCTGACCCTGTATAGCCCAGCCAGGCCCAG GCAGGCCAACCCTTCTCCTCTTGTAA | 2764 |
| | 3 | MGNCVCLRACLA* | 2765 | ATGGGTAACTGTGTGTGCCTCCGCGTGCCTCCGTGA | 2766 |
| hsa-mir-208c | 4 | MEGDHNRVVVKSTEMTADDKTGTVTHHTLAMCPGTK RLHTLVQSRHFCHSHFTVAETEGQKN* | 2767 | ATGGAGGGCGATCATAACAGGGTTGGTTGTGAAAAGCACCGAGATGACGGCTGACGA TAAGACGGGCACAGTTAGTTCAGTTCAGTTCAGGACGTTGCATGCCAGGCACTAAAAGACT ACACACGTTAGTTCAGTTCAGTTCAGGCACTTCGTCATTTCACCGTTGGCGAAACT GAGGGACAGAAAAACTAA | 2768 |
| | 1 | MHGGARATPAPPRLRAMARPRPRPVSRQRPRPRAHSV SSPGNGPARAPPIPSRLPATAPARAPPIPSRLLATAPPLPA PCPCPGHCPAPPPPCWARPRRPRAASTPGWTRSRSATHAP PGPGPQLWRWARVREVVESEGPPRQGPAPSAQEKRRM ARGAPPGCSLTPPFKSLGLRTPLRLCCIRLSLSDL* | 2769 | ATGCACGGAGGAGCCGCTACCCCGCCCGCCCGTCCTCCGGCAATGCCCG CCCGCCCCGCCCCGTCCTGGAGGGGCCCGCAACGGCCCGCCTCGTCTGCGGC AACGACGCGCCGGCCAAGCCCCCATCCCGTCTGCTGCCGCACCCGGCAGAACC TCTTCCGACCCGCCATGCCCCGGCCTCCGCGCCCCACCCGCCTGCTCAGC GGCTCGACCCGCCCCCGGCCCCCCGGGAACCCGCTGCTGCCGCTATGCCCCGG CACCCACGGCGCCGGCCTCGAGGGCCCCGAGGGCCTCGGCCCCCCGAGGAG AAGTCGTGAGTCGAGCGTGAGGGCTGCGCCTCCAGGCCCCAAGG AAGCGGCGAATGGCCCGCGTTGCCTCCGAACCCGCCTTCGCATCCGTCAGCT AGTCTGGGGCTGCGAACCCGCTTCGCATGCTGCTTCGCATCGGCCTTTCAGAT CTGTAG | 2770 |

Figure 1 (Continued)

| | | | | | |
|---|---|---|---|---|---|
| hsa-mir-202 | 2 | MPLSGPLPRTPPAMLGSTPAPRGLHAWLDALPLSHPRAAWPGTSAMAVGARPRSRGVRGAPAAGACALGPGEAANGPRRPSRLLADPPAQESGAANPASPLLHPTQPFFRSVGSGTPVSDYRAGLTAHTRRSTPPDAHVPSGHPLGASPWCQAGALASEEVASALGT* | 2771 | ATGCCCTTGTCCGGGCCACTGCCCGCCACCCCCCCGCCATGCTGGGCTCTGACCCCGGCCCCGCGCCCGCTCTCACGGCCTGTCGGACGGCCTCCCGCTCAGCCACCAACGGCCGCCTGGCCCGGACCTGCAGCTATGGCGGTGGGCGCGTCCGGAAGTCTGGAGTCCGAGGGGCCCCCGACCCCGGTTGCTCGCTGATCCGAACTCCGACTCAGCTTTCAGATCTGAGGATCCGCGAACCCCGCTTCGCCTTGCCATCGGACGGCGGGCTCACGGCCACACGCGCGCAGTACCCGACTCCAGTGTCCGACGTTCCCTCTGGCCACCCCTGGGAGCGTCCCCGTGGTGCCAGGCTGGGCGCGCTGCCGCGCTGGCCTGCTGCTCTGCTCTAGGCACCTGA | 2772 |
| | 3 | MRTPPLGTPWERPRGARLARWPLRRWLLL* | 2773 | ATGCGCACGTTCCCTCTGGGCACCCCTGGGAGCGTCCCCGTGGTGCCAGGCTGGCGCGCTGGCCTGCTGCTCTGCTCTAG | 2774 |
| | 4 | MGAASGWLLRGRALS* | 2775 | ATGGGTGCTGCCTCCGGGTGGCTGCTGCGAGGCGAGAGCCCTGAGCTGA | 2776 |
| hsa-mir-204 | 1 | MQRHFKNRRVFLLSLFQ* | 2777 | ATGCAGAGGCACTTAAGAACACGAGAGTCTTTCTGCTGAGCTCTTTCAATAA | 2778 |
| | 2 | MNVL* | 2779 | ATGAATGTTTTATGA | 2780 |
| | 3 | MFYDKKQVATKWKF* | 2781 | ATGTTTTATGATAAAAAAACAAGTAGCAACAAAATGAAAATTTTAA | 2782 |
| | 4 | MIKNK* | 2783 | ATGATAAAAAACAAGTAG | 2784 |
| hsa-mir-206 | 1 | MLFHFSVRRLR* | 2785 | ATGTTGTTCATTTTTCTGTGAGAAGCTAAGATGA | 2786 |
| | 2 | MRGKRDILGGVMEIGYWNCTGDWIPGPYP* | 2787 | ATGAGGGGCAAGAGAGACATACTGGGGGGAGTTATGGAGATTGGGTATTGGAACTGTACTGGAGATTGGATACCTGGACCATATCCTGA | 2788 |
| | 3 | MIKLMHGPEDAKAVHPESSNHYVNHPASLSRLSLM* | 2789 | ATGATAAAGTTGAACCATGGCCCAGAAGATGCAAAAGCCGTGCATCCTGAAAGTAACCACTATGTGAATCACCCAGCCAGTCTTAGCAAGGCTGTCCTGATGTGA | 2790 |
| | 4 | MAQKMQKQCIRKATTM* | 2791 | ATGGCCCAGAAGATGCAAAAGCAGTGCATCCGAAAGCAACCACTATGTGA | 2792 |
| hsa-mir-21 | 1 | MAWSQLTATSTSWVQAILRPQPPE* | 2793 | ATGGCGTGGTCTCAGCTCACTGCAACCTCCACTTCCTGGGTTCAAGCGATTCTTCCGGCCTCAGCCTCCCGAGTAG | 2794 |
| | 2 | MRRKVLNMQFFVFFFETEHSRCPGWSAMA* | 2795 | ATGAGAAGGAAAGTTCTTATAAATATGCAGTTTTTTGTTTTTTGAGACAGAGTTTCAACTCTGTTGCCCAGGCTGGAGTGCAATGGCATGA | 2796 |
| | 3 | MISAHCNLCLPGSSDSPASASLVVGHCMCHBAWLILYF* | 2797 | ATGATCTCGGCTCACTGCAACCTCTGCCTCCCAGGTTCAAGCGATTCTCCTGCCTCAGCCTCACTAGTGGGGATTCTGTGCATGTGCCACCACCTGGCTAATTTTGTATTTTAG | 2798 |
| | 4 | MSHCSRPHKFAVFKVALFVHHFIYTKHHFNYIYLIY* | 2799 | ATGAGCCACTGCTCCGGCCACATAAATTGCAGTTTCAGTTTCAAGGTCAACCTTTTGTCATATATTGTATACACAAAATACATATTTAATTATATATTAA | 2800 |
| hsa-mir-210 | 1 | MISFQDVSLNDICKDAFSR* | 2801 | ATGATCTCGTTTCAAGATGTTTCCCTTAATGACATCTGCAAAGATGCTTTCTCCCGATGA | 2802 |
| | 2 | MPPLMTSAKMLSPDEGTIFRKPGY* | 2803 | ATGTTTCCCTTAATGACATCTGCAAAGATGCTTTCTCCCGATGAGGGCACATTTAGGAAGCCTGGGTATTAG | 2804 |
| | 3 | MRAHLGSLGIRMWIYLLFGGGTIPLTTDAEKRCL* | 2805 | ATGAGGGCACATTTAGGAAGCCTGGGTATTAGGATGTGGATATCTTCTTTTTGGCGGAGGGCACCATCCACTCACTAGACAGATGCTGAGAAAAGGTGCTGTGA | 2806 |
| | 4 | MLRKGACEIGRTGRSGPTSAGHDRNTELPCPLAPSCPLV* | 2807 | ATGCTGAGAAAGGGCACGTGCCTGTGAAATTGGCAGGACTGGGGCAGGAGTGGGTTCACGTCAGCAGGCACGACAGGAACACAGAGCTGCCCTGTCCTTGCCCCTTCTTGTCCCCTAGTCTGA | 2808 |
| | 1 | MVAGACSPSYSGG* | 2809 | ATGGTTGCGGGTGCCTGTAGTCCAGCTACTCAGGAGCTGA | 2810 |
| hsa-mir-216a | 2 | MYSTREGRSKLIQPLQLQFHGADQWLMSLKLHMSLYCRKSTSKIFFFYEREVGHSLVLRIATQLHIGSPQ* | 2811 | ATGTACTCTACCAGAGAGGTAGGTCAAGCTGATTCAGCATTCAACTTCAATTCCATGGAGCAGATCAGTGGCTCATGTCACTGAAGTTAATTATTATGTCTCGTCTGCAAGAAAGAGCACCTCCAAAATTTCTTTTTTTATGAAAGAAGAAGTGGCATAAGTTTAGTTGTTAAGGATTGCAACCCAATTACATATAGGCAGCCCCAATGA | 2812 |

Figure 1 (Continued)

| | | | | |
|---|---|---|---|---|
| hsa-mir-217 | 3 | MFQJSGSCH* | 2813 | ATGGAGCAGATCAGHGGCTCATGTCACTGA | 2814 |
| | 4 | MKEKLA* | 2815 | ATGAAAGAGAAGTTGGCATAA | 2816 |
| | 1 | MVAGACSPSYSGG* | 2817 | ATGGTTGCGGGTGCCTGTAGTCAAGTGTCCAGCTACTCAGGAGCTGA | 2818 |
| | 2 | MYSTREGRSKLIQPLQLQFHGADQWLMSLKLHHMSLVCRKSTSKHFPFYEREVGISLVLRIATQLHGSPQ* | 2819 | ATGTACTTCACCAGAGAAGGTAGGTCAAGCTGATTCAGCGATTCAGCTTCAATTCCATGGAGCAGATCAGTGCTCATGCACTGCAAGTCACTGAAGTTAATTATTATGTCTCTGTCTGCAGAAAGAGCACCTCCAAAATTTCTTTTTTATGAAAGAGAAGTTGGCATAAGTTTAGTCTTAAGGATTGCAACCCAATTACATAT AGCCAGCCCCCAATGA | 2820 |
| | 3 | MFQJSGSCH* | 2821 | ATGGAGCAGATCAGHGGCTCATGTCACTGA | 2822 |
| | 4 | MKEKLA* | 2823 | ATGAAAGAGAAGTTGGCATAA | 2824 |
| | 1 | MLWDLE* | 2825 | ATGCTGTGGGACCTGGAGTAA | 2826 |
| hsa-mir-221 | 2 | MVLNTLAFPSKIPLGTDFPSLVLKPVDPC* | 2827 | ATGGTGCTTAACACACTTGCATTCCTTCCAAAATCCCTTTAGGAACAGAGACTTCTTCAGTTTAGTCCTAAAGCCTGTAGATCCATGCTAA | 2828 |
| | 3 | MLSDMTFFHIRLSKTLMMAVTVAYCAVTMFWTGTVVRALPASTHFSS* | 2829 | ATGCTAAGTGATATGACTTTTTTCACATCAGATTAAGCAAAACACTGATGATGGTGACTGTGCTTATTGTGCAGTTACCATGTTCTGGACAGGCACTGTGTAAGGGCTCTACCTGCATCGACCCATTTTTCCTCATGA | 2830 |
| | 4 | MTNYWCNYHAHFIDEHTEAQRGRGTYLGPLCHGTRJ* | 2831 | ATGACAAACTATTGGTGCAATTATCATGCCCATTTCATAGATGAACACACAGAGGCACAGAGAGGTAAAGGAACTTACTTAGGCCACTCATCGTCATGAACCAGAATCTA | 2832 |
| | 1 | MRACYPSPWVQSAWKSL* | 2833 | ATGAGAGCATGTATCTCAGCCGTGGGTTCAGATGCTGGAAGTCTTTAA | 2834 |
| hsa-mir-222 | 2 | MPAPILSPVCSFLHLSILSHKSFNIYLQIGERKDGSESPSGDGRGEAINSLYVPFTSLTASCI* | 2835 | ATGCCGGCCTTCAAACATCTACCTGCAAATAGGTGAAAGAAGATGGGAGTGAGAGTCCATCAGGGGACGGGAGGACCTGGAGGAGAAGCAATAAACTCACTCTATGTCCTTTCACCTCACTGACTGCATCTTGTATCTGA | 2836 |
| | 3 | MGVRVHQGTGEEKQ* | 2837 | ATGGGAGTGAGTCCATCAGGGACGGGAGGAGAAGCAATAA | 2838 |
| | 4 | MFLSPH* | 2839 | ATGTTCCTTTCACCTCACTGA | 2840 |
| | 1 | MAPFGLPRAQ* | 2841 | ATGGCCCCATTTGGCCTGCCCCAGGGCTCAATGA | 2842 |
| hsa-mir-23a | 2 | MRGELGHASCCSLLVPHGPSRYLCLSSPGAGTHGTARLQLPVWWLLHMRKELPCDQRKHLGTWRGGVPKSHYLLCSLSLSPLQVPASGPARCTPHPCATAGWGSWGWDLLPVTNHIARDFQPTLSSATEDAARGRGGREAPKPVPGLRSRA* | 2843 | ATGAGGGGAGAAGCTTGGCCATGCAAGTTGCTGTAGCCTCCTTGTCCCGCATGGCCCTCCAGTTATCTCCGTGGTGGCTCTGGGCTCTGGGCCTGGAACGAGGGCACAGTAGGCTCCAGCTCCGTGGTGGCTCTGGTCCTGCATATGAGAAAAGAGCTTCCTTGTGATCAAAGGAAGCATCGGGAGCCTGGGACCTGGAGGGGAGGGTGTCCCAAATCCATTACCTCTCTTGCTCTCTCTCTTCTTTCTCCCGGCACCCTCCAGGTGCAGCTCTGGGCCCCTCGAGGTGCCCCCTCACCACATTGCCAGGATTTCCAACCGACCTCGGATTCCTCCCTGTCCAGGGATTCGTCACCAAATCGACGGGGTGGCAGGAGACCTGTGGCCTGCGACCCTGGAGGAGCAGGGCTTAG | 2844 |
| | 3 | MQVAVASLSRMGPLGHSASPVLGLERRAQLGSSSPCGGSCI* | 2845 | ATGCAAGTTGCTGTAGCCTCCCTCGCATGGGCCTCTAGGTATCTCCGTGGTGGCTCTGGAAACGGAGGGCACAGTAGCTAGGCTCCAGCTCCGTGGTGGTGCCTCCTGCATATGA | 2846 |
| | 4 | MGFASCHKSHCQGPPTDPELCHRGCCPGTGWQRGPEACAWPEEGQLAACEQGPHQVFVTVAKPRPGPHLLWPCRLSPAAACLPAIHLPGLPGLCLPCLLS* | 2847 | ATGGGATTTGCTTCCTGTCACAAATCACATTGCCAGGGATTTCCAACCGACCTCGGCTCTGCCCTGAGGATGCTGCCGGGACAGGGTCAGAGAGGCCAGAGGCTGCTACCAAGCCTGTGCTTCACAGTCGCTAAGTTCGGCCCGCAGGGCCCTCCATCCGGCCTTGGCCCGCCTTGTTCACAGTGCTAAGTTCGCCCCGCAGGGCCCTCACTCGTCATCCGGCCATCCTGGCCTCTGCCGCTGTCCCTGTGCTGCCTACTGA | 2848 |
| hsa-mir-23b | 1 | MGTNGNLDPATRRLR* | 2849 | ATGGCACAAATGGAAACTTAGATCCTGCTACAAGAAGGTTACATTAA | 2850 |
| | 2 | MQVGVGVRGD* | 2851 | ATGCAGGTTGGCGGTGGGAGTGGGAGTTGGGGATTAA | 2852 |

Figure 1 (Continued)

| | | | | | |
|---|---|---|---|---|---|
| | 3 | MGASCAAALR* | 2853 | ATGGGAGCATCATGCGCAGCAGCACTCCGATAA | 2854 |
| | 4 | MRSSTPHLLYGRIA* | 2855 | ATGCGCAGCAGCACTCCGATAATTCTGTTGTATGGCAGAATAGCGTAA | 2856 |
| hsa-mir-24-1 | 1 | MGTNGNLDPATRRLH* | 2857 | ATGGGCACAAATGAAACTTAGATCCTGCTACAAGAAGGTTACATTAA | 2858 |
| | 2 | MQVGVGVRGD* | 2859 | ATGCAGGTGGGCGTGGAGTGAGGGGGATTAA | 2860 |
| | 3 | MGASCAAALR* | 2861 | ATGGGAGCATCATGCGCAGCAGCACTCCGATAA | 2862 |
| | 4 | MRSSTPHLLYGRIA* | 2863 | ATGCGCAGCAGCACTCCGATAATTCTGTTGTATGGCAGAATAGCGTAA | 2864 |
| | 1 | MAPFGLPRAQ* | 2865 | ATGGCCCCATTTGGCCTGCCCAGGGCTCAATGA | 2866 |
| | 2 | MRGFELGHASCCSLLVPHGPSRYLCLSSPGAGTHGTARLQLPVWWLLHMRKELPCDQRKHLGTWRGGVPKSHYLLCSLSLSPLQVPASGPARCPPHPCATAGWGSWGWDLLPVHMHARDFQPTLSSATEDAARGRGGREAPKPVPGLRSRA* | 2867 | ATGAGGGGGAGCTTGGCATGCAAGTTGCTGTAGCCTCCTTGTCCCGCATGGGCCCTCTAGGTATCCTGCCCTTCCAGTCCGTGTCTCAGGGCTCCTCAGTGCCAGCCCGTGTGGTGCTCTGCCATATGAAGGGCCGAGCTAGCCTCCCTGTTGGCATATGAGAACGGAGGCACAGCTAGGCTCAGTGATCAAAGGAAGCATCTGGGAGCCTGGAGGGAAGGGTCCCCAAATCTCATTACTCCTTTGCTCTCTCTCTTTCTCCCCCTCCAGGTGCAGCCTCTGCCCTCCAGCCTCTGCCCCCTCAACCCCTGTGCCACGGCCGGCTGGGGTTCCTGGGATGGAGTTGCTTCCTGTACAAATCACATTGCCAGGGATTTCCAACCGACCCTGAGCTGCCTGGCCTGCCACCGAGAGCGGCACCGGCTAGGGACGGGATGGGTCCACCAGAGGCCCGGGGCACGAGAGCGGCGGAGCTGCCTGAGAGGTGGCCCTGGACGCCGAGAGCGGCCCGAAGCCTGGTGTTGTGAGGAGGGATGTGGTGGGGTTGGCTGGCCAGCCCGTGATCCGAACCTCTGCAACCTGGGGACCCCGCATGGCCACAGCTCAGGCTGGGCTGTGGTGCCAGCATAG | 2868 |
| hsa-mir-24-2 | 3 | MQVAVASLSRMGPLGISASPVLGLERRAQLGSSSPCGGSCT* | 2869 | ATGCAAGTTGCTGGGGCTGGAAACGGACCTGAGCCTCCTCTGTCCCGCATGGGCCCTCTAGGTATCTGCCTCTCCAGTCCTGGGGCTGGAAACGGAGCACAGCTAGGCTCAGTGACCTCCCCGTGTGGTGGCTCCTGCATATGA | 2870 |
| | 4 | MGFASCHKSHCQGFPTDPELCHRGCCPGTGWQRGPEACAWPEEQGLAACEQGPHQVVFTVAKPRPGPHLLWPCRLSPAAACLPAHLPGLPGLCLPCLLS* | 2871 | ATGGGATTGCTTCTGTCACAAATCACATTGCCAGGGATTTCCAACCGACCCTGAGCTGCCTGGCCTGCCACCGAGGATGCTGCCCGGGGACGGGTGGCAGAGGGCCCGAAGCCTGGCACCAAGTCGTGCCAGGAGGTCCACCAAGTCGTGCCCTCGGCCTCCTGCCTCTGCCTGGCCTGCCGCCTCCCTGCTGCCTCCTGGGCTCTGCCTCCCGTGCTACTGAGCTGA | 2872 |
| | 1 | MLPGDGVAERPRSLCLA* | 2873 | ATGCTCCCGGGGACGGGGGTGGCAGAGAGGCCCGAAGCCTGTGCCTGGCCTGA | 2874 |
| | 2 | MLGAEMRTQNQTCVWRRDVVGGVGWAQMCAAGPDPQLCNWGPLHGHSSGWAVVPA* | 2875 | ATGCTTGAGCAGAGATGAGGACTCAGAATCAGACTGCGTGTGTGGAGGAGGGATGTGGTGGGGTTGGCTGGCCAGCCCGTGATCCGAACCTCTGCAACTGGGGACCCCTGCATGGCCACAGCTCAGGCTGGGCTGTGGTGCCAGCATAG | 2876 |
| hsa-mir-24-2 | 3 | MWWVGLAGPKCVLQALIPNSATGDPCMATAQAGLWCQHR* | 2877 | ATGTGGTGGGTGGGGTTGGCGGTTGGCTGGGCCAAATGTGTCTGCAGGCCTGATCCAACCTCTGCAACTGGGGACCCCTGCATGGCCACAGCTCAGGCTGGCTGTGGTGCCAGCATAGATAG | 2878 |
| | 4 | MPTPGFRYQAGLT* | 2879 | ATGCCAACTCCTGGCTTCCGGTATCAGGCTGGGTTGACCTGA | 2880 |
| | 1 | MRFVNYRDLQGWPLVNSDYYLFPHCHLGGPHAWRSQWPGLA* | 2881 | ATGAGGTTTGTGAACTATCGGGACCTACAGGGTTGGCCCTTGGTAAACAGTGATTATTATCTCTTCCCACACTGCCATCTTAGGTGGCCCTGCATGCCTGGCGGTCCCAATGGCCTGGTCTGGCCTGA | 2882 |
| hsa-mir-26a-1 | 2 | MPGGPNGLVWPDLPLK* | 2883 | ATGCCTGGCGGTCCCAATGGCCTGGTCTGGCCTGACCTGCCCTTTGAA | 2884 |
| | 3 | MAWSGLTCL* | 2885 | ATGGCCTGGTCTGGCCTGACCTGCCTTTGA | 2886 |
| | 4 | MRRLK* | 2887 | ATGAGAGCGCTGAAATGA | 2888 |
| | 1 | MAPFGLPRAQ* | 2889 | ATGGCCCCATTTGGCCTGCCCAGGGCTCAATGA | 2890 |

Figure 1 (Continued)

| | | | | | |
|---|---|---|---|---|---|
| hsa-mir-27a | 2 | MRGELGHASCCSLLVPHGPSRYLCLSSPGAGTEGTARL QLPVWWLLHMRKELPCDQRKHLGTWRGGVPKSHYLL CSLSLSPLQVPASGFARCPPHPCATAGWGSWGWDLLPV TNHIARDFQPTLSSATEDAARGRGREAPKPVPGLRSRA * | 2891 | ATGAGGGGGGAGCTTGGCCATGCAAGTTGCTGTAGCCTCCTTGTCCGCATGGCCC TCTAGGTATCTTGCCTCTCCAGTTGCTGGGCTGGCCTCCTCCGGGCTGGAACCGAGGGCACAGCTAGGCTC CAGCTCCCCGTGTGGTGGCTCCTGCATATGAAGAAAAGAGCTTCCCTGTGATCAAAGG AAGCATCTGGGGACTTGGACGGGAGGGTGTCCCAAATCTCATTACCTCCTTTGCTCT CCTCTCTTTTCTCCCCCAGGTGCCAGCCTGGGCCCCAGCCGGTGCCCCCTCACC CCTGTGCCACGCCGCCGCTGGGGTTCCTGGGATGGATTTGCTTCTGTCACAAATC ACATTGCCAGGGATTTCCAACGACCCTGAGCTCTGCACCTGAGCTGCCTGCCCCGG GACGGGGTTGCAGAGAGGCCCGAAGCCTGTCGTCCGCCTGAGGAGCAGGGCTTAG | 2892 |
| | 3 | MQVAVASLSRMGPLGISASPVLGLERRAQLGSSSPCGG SCI* | 2893 | ATGCAAGTTGCTGTAGCCTCCTTGTCCCGCATGGGCCCTCTAGGTATCTCTGCCTCTC CAGTTGCTGGGCTGGAACGGAGGGCACAGCTAGGCTCCCAGCTCCCAGCTCCCCGTGTGGTGGC TCCTGCATATGA | 2894 |
| | 4 | MGIASCHKSHCQGFFTBPELCHRGCCPGTGWQRGPEA CAWPEEQGLAACEQGPHQVVFFTVAKFRPPGPHLLWPC RLSPAAACLPAILLPGLPGLCLPCLLS* | 2895 | ATGGGATTGCTTCTGTCACAAATCACATTGCCAGGGATTTCCAACGACCCTGAG CTCTGCCACCGAGGATGCTGCCCGGGACGGGGTGGCAGAGGAGGGCCTGTGGCAGCCTG TGCCTGGCTGAGGAGCAGGGCTTAGCTGCTGTGAGGACCCTCACCAACAAGTCG CCAGGACAGGGGTCCCACTGGCCCCAGGTCCTCGGCCCTCCTGCCTTGCCGCCT GTCCCCTGCTGCCGCCTGTCTGCCATCCTGCTGCCTGCTGCCCCTGGGCTCTGC CTCCCGTGCTACTGAGCTGA | 2896 |
| | 1 | MGTNGNLDPATKRLH* | 2897 | ATGGGCACAAATTGAGATCTGCTACAAGAAGTTACATTAA | 2898 |
| | 2 | MQYGVGVRGD* | 2899 | ATGCAGTTGGGAGTGGGAGTGGAGTGAGTGGGATTAA | 2900 |
| | 3 | MGASCAAALR* | 2901 | ATGGGAGCATCATGCCAGCAGCACTCGATAA | 2902 |
| | 4 | MRSSTPHLLYGRIA* | 2903 | ATGCGCAGCAGCACTCCGATAATTCTGTTGTATGCAGAATAGCGTAA | 2904 |
| hsa-mir-27b | 1 | MWAPPPHACCPVISDPWRWDVYHGSAQSPTVFTPATS GMILPSPS* | 2905 | ATGTGGGCTCCACCCCACGCCTGCATCTCGATCCTGGCGGTGG GATGTCTACCATGGCTCTGCCACATGTCTTCACCCCTGCCACATCTGGCA TGATTTTACCGTCCCTTCCTAG | 2906 |
| | 2 | MSTMALPNPPLSSPLPHLA* | 2907 | ATGTCTACCATGGCTCTGCCAATCCTCCGCCACTGTCTTCACCCCTGCCACATCTGGCAT GA | 2908 |
| | 3 | MKFLLNNPSACPELIQSPMTIVLSTSRTHRSTFSVPENW TPFHS* | 2909 | ATGAAGCCTCTGAATAATCCATCAGCCTGCCCTGAGCTCATCCAGTCTCCAATG ACGATTGTGCTCCTGACCCACGAGCCACCGAGCACTTCTGTCCCTGAGAAT TGGACTCCATTCCACAGTTAG | 2910 |
| | 4 | MILRGLS* | 2911 | ATGATTTTAAGAGGTCTGTCTTGA | 2912 |
| hsa-mir-29b-1 | 1 | MWAPPPHACCPVISDPWRWDVYHGSAQSPTVFTPATS GMILPSPS* | 2913 | ATGTGGGCTCCACCCCACGCCTGCATCTCGATCCTGGCGGTGG GATGTCTACCATGGCTCTGCCACATGTCTTCACCCCTGCCACATCTGGCA TGATTTTACCGTCCCTTCCTAG | 2914 |
| | 2 | MSTMALPNPPLSSPLPHLA* | 2915 | ATGTCTACCATGGCTCTGCCAATCCTCCGCCACTGTCTTCACCCCTGCCACATCTGGCAT GA | 2916 |
| | 3 | MKFLLNNPSACPELIQSPMTIVLSTSRTHRSTFSVPENW TPFHS* | 2917 | ATGAAGCCTCTGAATAATCCATCAGCCTGCCCTGAGCTCATCCAGTCTCCAATG ACGATTGTGCTCCTGACCCACGAGCCACCGAGCACTTCTGTCCCTGAGAAT TGGACTCCATTCCACAGTTAG | 2918 |
| | 4 | MILRGLS* | 2919 | ATGATTTTAAGAGGTCTGTCTTGA | 2920 |
| hsa-mir-30b | 1 | MLWEQIRLFQAECRTRPKIKTVVAAELTFSEHLLNARC WANNLHSISFAAGNSQPYGAGLIAISHLQEGNRGS* | 2921 | ATGCTGTGGGAGCAGATAAGATTGTTCCAGGCAGAATGCAGGACAAGGCCAAAAT AAAAACTGTAGTGGCAGCAGAACTCACTTTCAGTGAACACTTACTAAATGCCAGCTG CTGGGCCAACAATTTACACAGCATCTCAATTTGCTGCAACAGCCAGCCTATGG GGCAGGTTTGATTGCAATCTCAATTTTGCAAGAAGGCAACAGGGGTTCATAA | 2922 |
| | 2 | MQDKAKNKNCSGSKTHFQ* | 2923 | ATGCAGGACAAGGCCAAGAACAAAATGTAGTGGCAGCAGAACTCACTTTCAGTGA | 2924 |

Figure 1 (Continued)

| | | | | |
|---|---|---|---|---|
| | 3 | MPGAGPTTYTASHLLATASPMGQV* | 2925 | ATGCCAGGTGCTGGCCAACAGCATTACACAGCATTCATTGCGCTGGCAACAGCCAGCCCTATGGGGCAGGTTGA | 2926 |
| | 4 | MNASPQSGSQSRRNQSLHFRSPYLPQHQKTTGPRTRSP* | 2927 | ATGAATGCTTCCCATATCTCCCACAGATCCAAAGTGGATCACAATCACGAAGAAACCAAAGCTTACACTTCCGTTCCCCATATCTCCCACAGATCCAAAGACCACGGGGCCCAGGAGCCCGGTCTCCATAG | 2928 |
| hsa-mir-30a | 1 | MCHRARLIFLFLFL* | 2929 | ATGTGCCACCGTGCCAGGCTAATATTTTATTTTATTTGTAA | 2930 |
| | 2 | MGSHFWAQAIPPQPPKVLGL* | 2931 | ATGGGGGTCTCACTCTGGCTCAAGCAATCTTCCTCAGCCTCCCAAAGTGCTGGGATTATAG | 2932 |
| | 3 | MGKGI* | 2933 | ATGGGTAAGGTATATGA | 2934 |
| | 4 | MNLFYFAACNPIPMPNPICIQYTNNGDKFFYRKLHKPVTDYCVCKYTQTIL* | 2935 | ATGAATCTCTTTATTTGCTTGCTGCAACCCAATTCCCATGCCAAACCCAATTGTATCCAAACAAACATATTGGAGACAAGTTCTATAGAAAGTTCATAAGCCAGTTACTGACTACTGTGTCTGTAAATATACTCAAACTATTTTGTAG | 2936 |
| hsa-mir-30b | 1 | MPLHL* | 2937 | ATGCCCCTAATAATTTTATAA | 2938 |
| | 2 | MNSQLIHEC* | 2939 | ATGAACAGCCAACTCATACATGAATGTTAG | 2940 |
| | 3 | MNVRETFCR* | 2941 | ATGAATGTTAGAGAAACTTTTGAGGTGA | 2942 |
| | 4 | MLFKLFVGDNMHK* | 2943 | ATGTTAGAGAAACTTTTGTAGGTGATAATATGCATAAATAG | 2944 |
| hsa-mir-30d | 1 | MPLHL* | 2945 | ATGCCCTAATAATTTTATAA | 2946 |
| | 2 | MNSQLIHEC* | 2947 | ATGAACAGCCAACTCATACATGAATGTTAG | 2948 |
| | 3 | MNVRETFCR* | 2949 | ATGAATGTTAGAGAAACTTTTGTAGGTGA | 2950 |
| | 4 | MLEKLFVGDNMHK* | 2951 | ATGTTAGAGAAACTTTTGTAGGTGATAATATGCATAAATAG | 2952 |
| hsa-mir-32 | 1 | MSQRAGLAEKCLSGLRHLPRSFTDTLPGVWDKLVNT* | 2953 | ATGAGCCAGCGTGCTGGCCTTGCTGAGAAATGTTGAGTGGACTGAGGCATTGCCAAGAAGTTCACAGATACTTATTTGAGTGGACTGAGGCAAACTGGTTAATACTTAA | 2954 |
| | 2 | MFEWTEAFAKKFHRYFIWSVGQITG* | 2955 | ATGTTTGAATGGACTGAGGCATTTGCCAAGAAGTTCACAGATACTTATTTGGAGTGTGGACAAACTGGTTAA | 2956 |
| | 3 | MTLWLSVATDFLFMTIFLIHST* | 2957 | ATGACTTTGTGGCTGTCAGTGGCAACTGACTTCTCTCTTTATGACCATCTTCTCTATACACAGCACATAA | 2958 |
| | 4 | MLHI* | 2959 | ATGTTGCACATTTGA | 2960 |
| hsa-mir-34a | 1 | MQNQTRNSPDLTRLIQHRGKF* | 2961 | ATGCAAAATCAAACAAGAAACTCCCCAGACCTCACTAGACTACATCAGACTACATAGAGG | 2962 |
| | 2 | MKAKCFITDAT* | 2963 | ATGAAAGCAAAGTGCTTTATCACTGATGCTACCTAA | 2964 |
| | 3 | MLPNSCHSTLLPGLCTFSNYFISCVYQVGPNIRAIHDEEPKPGKEVLPPN* | 2965 | ATGCTACCTAATAGTTGCCACAGCACCCTGCTCCCTGGTTTATGCACATTCTCGAATTATTTATCTCATGCGTCTACCAAGTTCCTAACATAAGGGCAATTTTATAGATGAGGAACCAAAGCCAAGGTCCAGGAAGTCCTATTTCCAAATTAG | 2966 |
| | 4 | MHILELFYLMRLPSRS* | 2967 | ATGCACATTCTGAATTATTTTATCCATGGTCTACCAAGTAGGTCCTAA | 2968 |
| hsa-mir-379 | 1 | MHREK* | 2969 | ATGCATAGAGAAAATAG | 2970 |
| | 2 | MNTCLEL* | 2971 | ATGAATACATGTCTGGAACTCTGA | 2972 |
| | 3 | MSGTLRPIRKSISSVSHDSIGRCQEYRLSLF* | 2973 | ATGTCTGGAACTCTGAGGCCCATCAGAAAGTCAATTCCTCTGTTCACATGATTCTATAGGTAGAATGTCAGGAATACAGACTCAGTTGTTTAG | 2974 |
| | 4 | MSGHQTQFVLGLCVLCIYILFYNWISENQ* | 2975 | ATGTCAGGAATACAGACTCAGTTTGTTCTTGGTGTGTTATGCATTTATATTTATTTTATAATTGGATCAGTGAGAATCAATAA | 2976 |
| hsa-mir-410 | 1 | MHREK* | 2977 | ATGCATAGAGAAAATAG | 2978 |
| | 2 | MNTCLEL* | 2979 | ATGAATACATGTCTGGAACTCTGA | 2980 |
| | 3 | MSGTLRPIRKSISSVSHDSIGRCQEYRLSLF* | 2981 | ATGTCTGGAACTCTGAGGCCCATCAGAAAGTCAATTCCTCTGTTCACATGATTCTATAGGTAGAATACAGACTCAGTTGTTTAG | 2982 |

Figure 1 (Continued)

| | | | | | |
|---|---|---|---|---|---|
| | 4 | MSGHQTQFVLGLCVLCTYLFYNWISENQ* | 2983 | ATGTCAGGAATACAGACTCAGTTGTTTGTGTCTTGTGTTATGCATTTATATTT TATTTTATAATTGGATCAGTGAGAATCAATAA | 2984 |
| hsa-mir-411 | 1 | MHRFK* | 2985 | ATGCATAGAATACATGTCTGAAACTCTGA | 2986 |
| | 2 | MNTCLEL* | 2987 | ATGAATACATGTCTGAACTCTGA | 2988 |
| | 3 | MSGTLRPIRKSISSVSHDSIGRCQEYRLSLF* | 2989 | ATGTCTGGAACTCTGAGGCCCATCGAGAAAGTCAATTTCCTGTTCACATGATTCT ATAGGTAGAATGTCAGGAATACAGAACTCAGTTGTTTAG | 2990 |
| | 4 | MSGHQTQFVLGLCVLCTYLFYNWISENQ* | 2991 | ATGTCAGGAATACAGACTCAGTTGTTTGTTAGGTCTTGTGTGTTATGCATTTATATTT TATTTTATAATTGGATCAGTGAGAATCAATAA | 2992 |
| hsa-mir-429 | 1 | MVGSPALSGSMVEGHGLLGGEHWALESRSRGKGSRWIQ RALGTIAAPPPAHPSRPQPTHPIPAHPSHPRHPRHPHPRHP HPRHPRHPRHPRHPRPQLRPSPAPPSSPPRPQPRPSPASHR PGGSLAFLPGWKRVSATGVRVEQEGGRRRGGKDRWAP RGGGAASGRGLPPPDPV* | 2993 | ATGGTGGGGTCACTTGCCTTGTCTGGCAGCATGGTAGAAGGGCATGGCCTGGGCGG GGAGCACTGGGCCTTGGAATCAAGGTCCAGAGGCCACACCGACCAGGCAGCCACC GAGCCCTAGGGACTGCAGCCCCTGCAGCCCATCCCGCAGCCCATCCCGCAGCCACC ATCCATCCCGCCCACCATCCCGCCCATCCCGCCATCCCGCCATCCCGCAGTCCGC CCATCCCGCCACCAGCCCTCCATCCCGGCCTTCCTGCCGCCGGCCAGCCCCTGCCTCC CATCCGGCCTCGAGGCTCCCTGGCTTGGAAACGGTGTCTGCTACC GGGTTCGTGTGAAGCACGAAGGGGAAGGCGACGAGGTGGAAAGACCGCTGGG CCCCCGAGGAGGCGGAGCTGCTGGGAGCGGGGCCTCCCTCCCCGATCCTGTTTAA | 2994 |
| | 2 | MAWAGSTGPWNQGPEAKAAGGSSEP* | 2995 | ATGGCCTGGGCTGGCGGAGCACTGCGCCCTGGAATCAAGGTCCAGAGGCAAAGGCAGC AGGTGGATCCAGCGAGCCCTAG | 2996 |
| | 3 | MTMSYPACGPGRNLWQPPYPGDSDTKCSHCAGPGVE WPHTDQLTPAGRATGPPPWRREASGATRCAPGPLTSL VGGGCRPGPPET* | 2997 | ATGACAATGTCCTACCCAGCAGGAGGACCAGGCCGGAACCTTGGCAGCCACCAGT TCCTGGAGATTCCGAACACCAAGTGCAGCCACTGTGCGGGGCCGGTGTGGAGTGGG CCCACCACCGACCAGCTCACGCCAGCTGGCAGAGCACTGGGCCCCTCCTGGAGG AGGAGAGAGGCCTGCAGCCGGCTGGGCCTCCGGGACTTGCT AGGTGGGGGATGCCGGGCCTGGGCCTCCGAGACTGA | 2998 |
| | 4 | MPAWASRDLSPAPALAPRETCASERPRPPLPEPCTRAVR GPCCTPERASALSHSVSNPPSSGPQNWPSTELRGTRGP WGLGRDWPARGPPAAIPRFIQDESRAVGTT* | 2999 | ATGCCGGCTGGGCTCGGAGCTCCAGCGCCTGAGCCTGCCCTTGCCCTGCCCAGAGAG ACCTGTGCAGCGAGCGTCCCAGAGCCTCCCTCCCTGAGCCTGCACCGGGCGGTG CGGGGCCCTGCCTGCAGGCTCAGCATCCAGCCCTCAGCCACTCCGTTAGCAAT CCTCCCCCAGAGCCTCCCAGGGCTCCAGCACTCAGCCCTCAGCGACCGTCAGAGGCACCCGA GGGCCCTGGGCTGGCTGGTAGGGACTGGCCAGCTCGGGGTCCTCCAGCAGCCATACC CAGGTTCATCATACTATAGAATAATATTATAA | 3000 |
| | 1 | MIYTHYL* | 3001 | ATGATATATACTCATTATAGAATAATATTATAA | 3002 |
| | 2 | MAFCFRSSFPC* | 3003 | ATGGCATTCTGCTTTATAAGCATTCTTTTCCCTGCTAA | 3004 |
| | 3 | MYYV* | 3005 | ATGTATTATGTTTAG | 3006 |
| hsa-mir-448 | 4 | MFRRAEVLFG* | 3007 | ATGTTTAGAAGGGCTGAAGTGTTATTTGGATGA | 3008 |
| | 1 | MHRN* | 3009 | ATGCATCGAAATTGA | 3010 |
| | 2 | MPFSDLKHSLYLYLHDPSCSVPRFSSKDKNVNKAIF* | 3011 | ATGCCTTTCTGACTTAAAACATTCCTGTACCTTATTACACGATCCAAGTTGCA GTGTCCTAGATTTTCCTCAAGGACAAAAATGTGAATAAAGCAATATTTAG | 3012 |
| hsa-mir-450a-1 | 3 | MCHMCGRLV* | 3013 | ATGTGCATCATGTGTGGGAGACTGTATAA | 3014 |
| | 4 | MLPPPRRHLSTIFSFFPQHMLFVSEEAACTWHCIKPIRQT WPLN* | 3015 | ATGTTACCACCTCCAAGGAGGACACCTTCCACTATTTTCTCCAACACA TGTTATTGTTAGTGAGGAAGCTGCGTGCACGTGGCATTGTATAAGTTATTAGAC AGACCTGGCCCTTAAACTAG | 3016 |
| | 1 | MHRN* | 3017 | ATGCATCGAAATTGA | 3018 |
| hsa-mir-450a-2 | 2 | MPFSDLKHSLYLYLHDPSCSVPRFSSKDKNVNKAIF* | 3019 | ATGCCCTTTCTGACTTAAAACATTCCTGTACCTTATTACACGATCCAAGTTGCA GTGTCCTAGATTTTCCTCAAGGACAAAAATGTGAATAAAGCAATATTTAG | 3020 |
| | 3 | MCHMCGRLV* | 3021 | ATGTGCATCATAATGTGTGGGAGACTGTATAA | 3022 |

Figure 1 (Continued)

| | | | | | |
|---|---|---|---|---|---|
| | 4 | MLPPPRRHLSTFSFFPQHMLFVSEEAACTWHCIKFIRQTWPLN* | 3023 | ATGTTACCACCTCCAAGGAGGCACCTTTCCACTATTTTCTCATTTTTCCCAACACATGTTATTTGTTAGTGAGGAAGCTGCGTGCACGTGGCATTGTATAAAGTTTATTAGACAGACGTGGCCCTTAAACTAG | 3024 |
| hsa-mir-450b | 1 | MHRN* | 3025 | ATGCATCGAAATTGA | 3026 |
| | 2 | MPFSDLKHSLYLYLHDPSCSVPRFSSK.DKNVNKAIF* | 3027 | ATGCCCTTTCTGACTTAAAACATTCCTTGTACCTTATTTACACGATCCAAGTTGCAGTGTGCCTAGATTTTCCTCCAAGGACAAAATGTGAATAAAGCAATATTTTAG | 3028 |
| | 3 | MCHMCGRLV* | 3029 | ATGTGCATCATAATGTGTGCGGAGACTTGTATAA | 3030 |
| | 4 | MLPPPRRHLSTFSFFPQHMLFVSEEAACTWHCIKFIRQTWPLN* | 3031 | ATGTTACCACCTCCAAGGAGGCACCTTTCCACTATTTTCTCCAACACATGTTATTTGTTAGTGAGGAAGCTGCGTGCACGTGGCATTGTATAAAGTTTATTAGACAGACGTGGCCCTTAAACTAG | 3032 |
| | 1 | MRFTFTSRCLALFLLLNVSKTKVFKAMLMKNAE* | 3033 | ATGAGGTTCACATTTACAAGCCGGTGCTTGGCACTGTTCTTCTTCTAAATGTAAGTAAAACAAAAGTATTCAAAGCCATGCTAATGAAGAATGCTGAATAA | 3034 |
| hsa-mir-489 | 2 | MLNKEECFECDLISICKGRHWSPEAETKFLKAHLLNILLTNLSSELSLI* | 3035 | ATGCTGAATAAGGAGGAATGTTTTGAGTGTGATTTAATTAGTATTTGCAAGGTAGGCATTGGTCTCCAGAAGCCGAAACTAGTTCCTCAAAGCCATTATTTTGTTAATATTTTGTTAACAAATCTCCCTGAACTGTCTAATTTAA | 3036 |
| | 3 | MFSC* | 3037 | ATGTTTTCATGTGA | 3038 |
| | 4 | MLKKLCFES* | 3039 | ATGTTGAAAAAACTATGTTTGAATCTAG | 3040 |
| | 1 | MGNQILPTNEKQNFLSTH* | 3041 | ATGGGGAACCAAATTCTTCCTACAAATGAAGAAAACAGAACTTCTTGTCTACACATTAA | 3042 |
| | 2 | MRNRTSCLHKMTLET* | 3043 | ATGAGAAACAGAACTTCTTGTCTCAGCAGACTTTTTAATGACTTCAACCAAGTGA | 3044 |
| | 3 | MSRSGSRPFSTK* | 3045 | ATGTCAAGATCTGGCAGCAGACTTTTCTACACCTTAG | 3046 |
| hsa-mir-491 | 4 | MRPRHLFPYPYFFLRVPQGILETTKSDIFRVICLNSFILRKISILSSTTGHPLRFTSLSSPFSAGSFQRVSSWLLSVCYSLLTWEPLPRPTRKYMPIQ* | 3047 | ATGAGGCCCAGGCACTGTTTCTGTTTTTGATATTTTAGAGTATAATTGTCTTAACTTGTCTTAAAATTCCAACAACTAAGTCAGATATTTTCCTAAGGGTGCCCAGGTTAAAATTCCATTCTGTCATCCAACGGAATTCCACTCCGTCATCCAGTCTCCTGTTTTTTTTCGCTGGCTGTTCATCGTGGCTGCTGTCTGTCTGTTACAGCCTTCTCACGTGGCGAGCCCTGCCCCGCCCCACAGAAAATACATGTTTATCATTCAGTAA | 3048 |
| | 1 | MDTQEAFSPGFKQGEGREDRRLKFWGVLILGVFCHSGCFW* | 3049 | ATGGATACCCAAGAAGCTTTTTCCCAGGGGAGAAACAAGGTGAGGRCCGTGAGGACAGGAGACTAAAGTTCTGGGGTGTCTTATTTGGGGGTGTTTTGTCACTCTGGCTGCTTTTTGGTGA | 3050 |
| hsa-mir-497 | 2 | MSPAYSALSPQJLEVSLVMPQISPGFEGRNLERVWYLLLLCGLREKRGRKGGFRL* | 3051 | ATGTCTTTTTGCTTATAGTGCCCTCTCACCCGACAGATTCTCAAGGGAGAAACTTGAAGGGAGAAGGTGTAGTCTCCTTTTATTATTATGTGGCTTGAGGGAGAGAGAGGGAGAAAAGGCGGTTTCAGACTCTGA | 3052 |
| | 3 | MWLEGEEREKRFQTLNPNFLREHPLVWGKLEKNGVSLGQVGTPDQGSAVGTYARRGAGVQGGIDSCTLIF* | 3053 | ATGTGGCTTGAGGGAGAAGAGAGAGGGAGAAAAGGCGGTTTCAGACTCTGAATCCAATTTCTTAAGGGAGGAACCCTTAGTTTGGGAAGTTGGAAGTTGAGAAAAATGGGGTGTCCTTGGCCAAGTGGGCACCCCTGCCAAGGCCAGTCTGTTGGAACTGTGCCAAGGAGGGGTGTCGGTGGGGTACAAGGAGGTGATTCTTGCACCCTGATTTCTAG | 3054 |
| | 4 | MGCPLAKWAPLTRAVLLELWQQGVLVGYKEVILAP* | 3055 | ATGGGGTGTCCTTGGCCAAGTGGGCACCCTGACCAGGGTGCTGTTGGAACTGTGGCAAGGAGGGTGCTGGTGGGGTACAAGGAGGTGATTCTTGCACCCTGA | 3056 |
| | 1 | MGFSLJAE* | 3057 | ATGGGCTCTCGTTGATCGCAGAATGA | 3058 |
| hsa-mir-505 | 2 | MKPKLRNMPLKSFRP* | 3059 | ATGAAGTTCAAACTTGTAACATGTTTTGAAGATTTAGATTTTAG | 3060 |
| | 3 | MQCRSPLFL* | 3061 | ATGCAATGCGCTCTCCCTATTTCTCTAG | 3062 |
| | 4 | MSLSPISLAL* | 3063 | ATGTCGCTCTCCCTATTTCTCTAGCACTTTGA | 3064 |
| | 1 | MHRN* | 3065 | ATGCATCGAAATTGA | 3066 |

Figure 1 (Continued)

| | | | | | |
|---|---|---|---|---|---|
| hsa-mir-542 | 2 | MPFSDLKHSLYLYLHDPSCSVPRFSSKDKNVNKAH* | 3067 | ATGCCCTTTCTGACTTAAAACATTCTGACCTTTATTACACGATCCAAGTTGCAGTGTGCCTAGATTTCCTCAAGGACAAAAATGTGAATAAAGCAATATTTTAG | 3068 |
| | 3 | MCHMCGRLY* | 3069 | ATGTGCATCATATGTGTGGGAGACTTGTATA | 3070 |
| | 4 | MLPPPRRHLSTHFSFFPQHMLFVSEEAACTWHCIKFIRQTWPLN* | 3071 | ATGTTACCACCTCCAAGGAGGCACCTTCCACTATTTCTCACTATTTTCCCAACACATGTTATTTGTTAGTGAGGAAGCTGCTGCCACGTGGCATTGTATAAAGTTTATTAGACAGACGTGGCCCTTAAACTAG | 3072 |
| hsa-mir-653 | 1 | MRFTFTSRCLALFLLNVSKTKVFKAMLMKNAE* | 3073 | ATGAGGTTCACAATTTCAAGCACGGTTGCTTGGCACTGTTCTTCTTCTCTAAATGTAAGTAAAACAAAAGTATTCAAAGCCATGCTAATGAAGAATGCTGAATAA | 3074 |
| | 2 | MLNKEECFECDLISICKGRHWSPEAETKFLKAHLNHLLTNLSSHLSLI* | 3075 | ATGCTGAATAAGGAAGAATGTTTTGAGTGTGATTTAATTAGTATTTGCAAGGTAGGCATTGGTCTCCAGAAGCCGAAACTAAGTTCCTCAAAGCCATTATTTTGCTTAATATTTTGTTAACAAATCTCCTCTGAACTGTCTCTAATTTAA | 3076 |
| | 3 | MFSC* | 3077 | ATGTTTTCATGTTGA | 3078 |
| | 4 | MLKKLCFES* | 3079 | ATGTTGAAAAACTATGTTTGAATCTTAG | 3080 |
| hsa-mir-656 | 1 | MHREK* | 3081 | ATGCATAGAGAAAAATAG | 3082 |
| | 2 | MNTCLEL* | 3083 | ATGAATACATGTCTGAACTCTGA | 3084 |
| | 3 | MSGTLRPHRKSISSVSHDSIGRCQEYRLSLF* | 3085 | ATGTCTGGAACTCTGAGGCCCATCAGAAAGTCAATTCCTCTGTTCACATGATTCTATAGGTAGATGTCAGGAATACAGACTCAGTTTGTTTAG | 3086 |
| | 4 | MSCIQTQFVLGLCVLCTYILFPYNWISENQ* | 3087 | ATGTCAGGAATACAGACTCAGTTTGTTTAGGTCTTTGTGTTATGCATTTATATTTTATTTTATAATTGGATCAGTGAGAATCAATAA | 3088 |
| hsa-mir-7-1 | 1 | MNLLLH* | 3089 | ATGAACTTACTGCTCATTATTAA | 3090 |
| | 2 | MCGVVAHMVILVDLLLHK* | 3091 | ATGCAGGGGGTCGTGGCTCATATGGTCGATCTTGGTGGACCTATTATTACTACAAGTAA | 3092 |
| | 3 | MIBPPCIFPNSEGFNKNTHLGLRLC* | 3093 | ATGATTATTCCTCCTTTCTGTATATTTTTAATTCAGAAGGTTTTAACAAAATACACATTTAGGATTGAGGTTATGTTATA | 3094 |
| | 4 | MLMGHFSELGFQLFESCQVISAINKSS* | 3095 | ATGTTAAATGGCTTTAGTGAGCTGGGTTTCAGCTGTTTGAGTCTGTCAAGTGATCAGTGCTATTAATAAAAGTAGTTAA | 3096 |
| hsa-mir-96 | 1 | MALREGRAGPGAGGGKITLLESFSVHSVEPPRSRAGAAGPPSSRAVRAARAPCSSGPRAQVPLWTSPACSAEAAPLQVAGPGPSPADLSPDTQEARGRVPAPLCSPAGLGAPAPPPLAGQRRFGPGPGALQAPSMRLFPNRGRFCLASLVWTPRGAERRLCAQPGAGAGECLGPGAGGRAGRSQSGAQ* | 3097 | ATGGCGCTGCGTGCGAGGGAGGGCGTGCAGGTCCATTCTCGTGCACTCGTCGAGCCCGAGCGTCGGAGCGAGGGCCCCCCGTCTTCCGGTCCTCGGGCCCAGTACCCCTCTGACCTCCCCGGCAGCCCCGGCCAGACCTGCACCCAGGAAGCGAGGCCCGGGGCTCGCCGGGTCCGCGGGTCCCCCCTTGTTCCCGGCTCGGCTCGGCCCCGGCTCGGCGCGTCCTGCGCGGGCCTCGGGTGGGCCCCGGGCAGCCCCGGCCCGCCGCTTCCCCCCTTTGCCTGGCCGTTTTGCCTGCCCTTGGCCCTCCAAGCTCGGTCCATGCCCCGCTCTTCCAACCGGGCGTTTTGCCTGGCCGCCTCAGGCCGCGGGCTCCTCGGTGTGACTCCGGCGCCGCGCTGACTCCAAGGCCGTGGCTGAGCGCAGTGAGTGTCTGGGCGCGGAGCGGCGCGCGCGCCCGAGCCAGAGCGGGGGCTCAGTAG | 3098 |
| | 2 | MTRQCLLALPRLQAEAPTGRLGPGSASGVCPAPSAVPGRGRGRERLRSEGRCLRGAYPRGVWLGSGCVSPPWWAQAEAPGWEGAAESAGAPELAPPASCQGCAAGSRLLFWPGAAPPSLWGKAALRPPVCLHFAATHPGNPGARE* | 3099 | ATGACGCAGTGCCTACTGGCTGCCCCTTCCGCGCCTCCAGCGCGAGGCGCCACCGGGCGGCCTGGGTCCGGGCTCGCCAGTGCGTCTGCCCAGCGCCTCTCCCGGAGTGCGGGGCGCGGGGAGCGCGGAGCGCGGGAGCCCTGAGTGCCGCTACCGCGCGGAGGAGTTGCGCTGGGAGGAGGCGCAGGTCGCAGGGTCAGCTCGGGTCGGGGAGCCCGAGCCAGGCGGAAGCGCCAGGCGCGGGACCCTCCTCCGGAAGCGGCAAGCTCGCAGGGGAGGGAGCCCACCGAGGGCGCCCCCACCGGCCGGGGGAAGCGCGGGTCCAGAGCCCCACTTCGCCGCCGCACCCACCCCCGGGAAGCGGCAAGCGCCAAGCCAAAGCGGGCCGTTGCGCTGTCTGCCTAAGCGGGGCCGCGGGGAAGCGCGACCCCGGCCGCACGGCGAATGA | 3100 |

Figure 1 (Continued)

| | | Protein | | Nucleotide | |
|---|---|---|---|---|---|
| | 3 | MRHRSPPSTAPPLLIALVAPRFPALPQDRRLDGLPLAPH RSAHPRTMGSEGVTRGQGSPDSTVSSRLSHSFALPTRAP GHRVQ* | 3101 | ATGAGAGACACCGTTCCCGCCCTCAACTGCCCATTCCTGTTAATAGCGCTAGTGGCA CCCAGGTTCCCAGCCCTTCCCAGACCTTCCCAAGATCGGGCGGTCTTGCCGGGCCT CACCGGTCAGCGCCATCCAGGAGTATGGGCAGTGAGGCAGTGAGGCAGTGAGGCAGTGGTGTCACCGGGTCAGGG GTCGCCCGATTCCACGGTGTCCTCCAGGCTGAGCCAATCGTTTGCTCTTCCAACCCG GCTCCCGGACACGTGTACAGTAA | 3102 |
| | 4 | MGHESADL* | 3103 | ATGGGACACGAGTCGGCGATCTGA | 3104 |
| hsa-mir-99a | 1 | MGYTSVSFTDVLLCLSEGLAHTRT* | 3105 | ATGGGAGTCACATCAGTTTCTTTCACTGATGTTCTCCTATGCCTATCAGAAGGCCTG GCACATACTAGACTTAA | 3106 |
| | 2 | MFSYAYQKAWHILGLNK* | 3107 | ATGTTCTCCTATGCCTATCAGAAGGCCTGGCACATACTAGGACTTAATAAATAA | 3108 |
| | 3 | MPHRRPGTY* | 3109 | ATGCCTATCAGAAGGCCTGGCACATACTAG | 3110 |
| | 4 | MRTGNLNFYVNECVICFLVLLNHGA* | 3111 | ATGAGAACTGGAAATTTAAATTTTATGTCAATGAATGTCATCTGCTTCTTTGTT TGCTGAATCATGGGCTTAA | 3112 |
| hsa-mir-99b | 1 | MPLHSSLGNPSQK* | 3113 | ATGCCACTGCACTCCAGCCTGGCAATCCGTCTCAAAATAA | 3114 |
| | 2 | MHNH* | 3115 | ATGCATAACCATTAG | 3116 |
| | 3 | MNTMEYYHTKMNEEVL* | 3117 | ATGAATACAATGGAATATTATCACTATTAAAATGAATGAGGAGGTTCTATAA | 3118 |
| | 4 | MRRFYKPRYGRIFGYHVKKKKKTKVQNNVILSGDRKEE GGIYVHRCIKFLWKDT* | 3119 | ATGAGGAGGTTCTATAAGCCTAGATATGGGAGGATCTTTGGATATCATGTAAAAAA AAAAAAAAAACCAAGGTGCAGAATAATGTGATCCTATCAGGGGACAAGAAAGAGG AGGTGGTATATATGTGCATAGATGTATAAAATTCCTCTGGAAAGATACATAA | 3120 |
| | 1 | ATGCTCCCAGGTGA | 3121 | ATGCTCCCAGGTGA | 3122 |
| hsa-let-7a-2 | 2 | MVRTIMPPGLFSL* | 3123 | ATGGTTGAGAACGATCATGAATTCTCCAGGCTTTCTCCTATGA | 3124 |
| | 3 | MKGKIGVDYFMVF* | 3125 | ATGAAAGGTAAGATTGGGTACGATTATTTATGGTATTTAG | 3126 |
| | 4 | MLYFHILFPRVRFCFFKNVRL* | 3127 | ATGCTGTATTTTCATATTCTGTTTCCTCGGGTTAGATTTGTTTAAGAAAATGTGA GGCTTTTA | 3128 |
| | 1 | MFLNKCKNNF* | 3129 | ATGTTTCTAAACAAGTGTAAAATAATTTTAA | 3130 |
| hsa-let-7c | 2 | MLLKNSASNENYNLFHTKN* | 3131 | ATGCTTTTGAAAAATTCAGCAAGTATCATGAAAACTATAATTGCATACTAAGAAT TGA | 3132 |
| | 3 | MKTHCLRIDVHR* | 3133 | ATGAAAACTCATAATTGCATACTAAGAATTGACGTTATAATATTCGTAA | 3134 |
| | 4 | MLLKSYFLHLQCRVNREKCRTD* | 3135 | ATGCTTTTAAAATCATATTTCTTATTACAATATGTAGGTAAACAATGAAAAA TGTAGAAACTGATTAA | 3136 |
| hsa-let-7f-2 | 1 | MEYKCMSLKMWRNWNLRTLLARKQTGAAIVEKVGWPF KKLNEILLYNPAMSTLRYMSPKTESRGSTICTLMFIAALF TIAKRWKQSKVPLTDEWINKRWYIHTMEYH* | 3137 | ATGGAATATAAATGTATGTCGTTGAAGATGTGGAGAAATTGGAACCTTGGTTCTTCCTG GCAAGAAAGCAACATAGAATTACTGTATAATCCAGCAAATTCCACTCTTACGTATATGTCCCC CAAAACTGAAAGCAGGGGCTCAACTATTTGTACACTCATGTTTATAGCAGCATTATT CACAATAGCCAAAAGGTGGAAACAATCTAAATATCCGCTAACAGATGAATGGATAA ACAAAGGTGGTATATACATAACGATGGAATATCATTGA | 3138 |
| | 2 | MDKQKVVYTYDGISLSSKTE* | 3139 | ATGGATAAACAAAGGTGGTATATACATAACGATGGAATATCATTGAGCAGCAAAAC AGAATGA | 3140 |
| | 3 | MLQHG* | 3141 | ATGCTACAACATGGATGA | 3142 |
| | 4 | MDEGQRHCAN* | 3143 | ATGGATGAAGGTCAAGACATTGTCTAACTGA | 3144 |
| | 1 | MLSL* | 3145 | ATGCTTTCTTTGA | 3146 |
| hsa-let-7i | 2 | MNLISYYF* | 3147 | ATGAATTAATTAATCTCAGTTATTTTAA | 3148 |
| | 3 | MGSLELCAVC* | 3149 | ATGGGTAGCCTTGAATTATGTGCCGTTTGTGA | 3150 |
| | 4 | MCRLLKGL* | 3151 | ATGTGCCGTTTGCTGAAAGGTCTTTAG | 3152 |
| | 1 | MYVCVCVCVCVRERERERDRERERKS* | 3153 | ATGTATGTGTGTGTGTGTGTGTGTGTGTGAGAGAGAGAGAGAGAGAGA GAGAGACAGAGAGAGAGAGAGAAGAGTTAG | 3154 |

Figure 1 (Continued)

| | | | | | |
|---|---|---|---|---|---|
| hsa-mir-100 | 2 | MYVCVCVCV* | 3155 | ATGTATGTGTGTGTGTGTGTGTGTGTGTGA | 3156 |
| | 3 | MCVCVCVCVCERERERERQREREKELGG* | 3157 | ATGTGTGTGTGTGTGTGTGTGTGTGTGAGAGAGAGAGAGAGAGAGACA GAGAGAGAGAGAAAGAGAGTTAGGAGGTTGA | 3158 |
| | 4 | MWKSIDMESPRWRNADLLGEMQRDRGV* | 3159 | ATGTGGAAATCAATAGACATGGAGAGCCCTAGGTGGAGAAACGTGACCTGCTGGG TGAAATGCAGAGAGACAGGGGTGTGTGA | 3160 |
| hsa-mir-10b | 1 | MIQI* | 3161 | ATGATCCAGATCTAA | 3162 |
| | 2 | MCDNFFTQNVKAHFHYP* | 3163 | ATGTGTGACAATTTTTCATTACCCAGAATGTAAAGCAATCATATATTTCATTATC CTTAA | 3164 |
| | 3 | MLKQS* | 3165 | ATGTTAAAGCAATCATAA | 3166 |
| | 4 | MKIRGTIGK* | 3167 | ATGAAAATAAGAGGGACTATATAGGAAAATGA | 3168 |
| hsa-mir-1-1 | 1 | MDTGSREAAFTRDLPRKPADAQVSPQDTSRVSGLQFLV WPQEQGVVQLPEKEEAGPASSGVLGRAPPKVPLSTQPSL GLAGMR* | 3169 | ATGGATACGGGGTCCCGGGAGGCAGCCTTCACCAGGGACCTGCCCAGGAAACCAGC AGATGCCCAGGTAAGCCCCAGGACCACTCTCGGTCTCGTCTGCAGTTCCTCGT CTGGCCTCAGGAGCAAGGAGTTGTCCAGCTCCCGGAGAGGAGGAGGCTGGTCTG CGAGTGGGGTGTCTGGGCAGGGCGCCCCCAAGGTTCCTCTCCACCCAGCCTCTC TGGGCTTGGCTGGGATGAGGTGA | 3170 |
| | 2 | MEDASLLWGEGGGAACLFHGRKTELLLGPGTGARDFL GLTVHFCLSGSCECVRQTERIDGFRIDGGAPRSEGGRESW APGGGWTPGSSGRKAVLLTQRGLRQ* | 3171 | ATGGATGATGCCTCCCTGCTCTGGGGTGAGGGTGGAGGGGCAGCCTGTCTCTTCAT GGACGCAAAACCGAGCTACTGCTGGGGCCAGGGACAGGGCGCTCGAGACTTTCTGGG GCTCACTGTCCACTTCTGCCTTTCTGATCCTGTGTGAGACAGAGAG AGATGGATTCAGGATATGAGAGGATCGCCAGGGGGTCAGAGGGGCAGGGAGTCCTGG GCCCCTGGGGGTGGCTGGCACCAGGCAGGAAGGCTGTCCTGCTCAC ACAGAGAGGGCTCCGGCAGTGA | 3172 |
| | 3 | MMPPCSGVRVEGQPVSSMDAKPSYCWGQQALETFW GSLSTSAFLDRVSV* | 3173 | ATGATGCCTCCCCTGCTCTGGGGTGAGGGTCAGGACGACAGGCGCTCGAGACTTTCTGGG GCAAAACCGAGCTACTGCTGGGGCCAGGACAGGCGCTCGAGACTTTCTGGGGCTC ACTGTCCACTTCTGCCTTTCTGATCGTGTGAGTGTGA | 3174 |
| | 4 | MDSEMEGRRGQKGAGSPGPLGVAGHQAAVAGRL8C3 HREGSGSRLQGRSYTASELPSLHRSGVSFYRGGYPGSW NCMQTACLGNILLYMPIWTC* | 3175 | ATGGATTCAGGATGGAGGCGCAGGGTCAGAAGGGGCAGGAGTCCTGGC CCTGGGCTGGCTGGACACCAGGCACAGTGGCAGGACAACTGCCTCTGAGCTGCC AGAGAGGGTCCGGCAGTAGACTCCAGGGAAGAAGTTACACTGCTCCTGGGGTTGAA CTGCATGCAGACTGCCTGCTGGGAAACATACTTCTTTATAGGCCATATGACCTG CTAA | 3176 |
| hsa-mir-1-2 | 1 | MWKS* | 3177 | ATGTGGAAGTCCTGA | 3178 |
| | 2 | MQTIS* | 3179 | ATGCAGACTATTTCCTAA | 3180 |
| | 3 | MYSGGQRKTG* | 3181 | ATGTATTCTGAGGGCAAAGAAAACAGGGTGA | 3182 |
| | 4 | MFTYIWGF* | 3183 | ATGTTTACAGTTATTTGGGGGAGTAA | 3184 |
| hsa-mir-124-2 | 1 | MCLLAYFT* | 3185 | ATGTGTCTTTAGCTTATTTCATAACCTGA | 3186 |
| | 2 | MQVRRIKIVHN* | 3187 | ATGCAGGTTAGAAGAATAAAAATAGTTCATAATTAA | 3188 |
| | 3 | MKLQFFECAGCWN* | 3189 | ATGAAACTGCAGTTCTTTGAATGTGCAGTTGCTGRAATTAG | 3190 |
| | 4 | MCRLLELDATYILNTHTYFNILVLDNVFKVLEKNMQ* | 3191 | ATGTGCAGGTTGCTGGAGTTAGATGCTACATATTTTGAACACACATACTTATTTT AATATTTTAGTTTTAGTTAGACAACGTATTCAAAGTACTTGAGAAGAATATGCAATGA | 3192 |
| hsa-mir-124-2 | 1 | MQAARSLVPQWVPWCPGKA* | 3193 | ATGCAGGCAGCAGCCAGGTCGCTGTCCCACAGTTGGTCCTTGGTGCCCTGCAAGGC CTGA | 3194 |
| | 2 | MVQLPPLDSYQLATTGLADTHLGMDLTPGSI* | 3195 | ATGGTCCAGTTACCCCCTTGACAGTTACCAACTAGCAGCAGACCAACAGGCCTGCCTGAC ACACATCTGGCAATGCCTCACAACCCTGGTGCTCTGAC | 3196 |

Figure 1 (Continued)

| | | | | | |
|---|---|---|---|---|---|
| hsa-mir-124-3 | 3 | MTSQPLGASRHNQFCGWRLEKAGGQPRAAGSPSPSWALQQFLIYCSGVLARAVRKREGGTARFLHVTPGVQAGAGTPALPEPGG* | 3197 | ATGACCTCACAACCCTGGGAGCATCTAGGCACAACCAGTTTGTGGTGGCGGTGGAGAAGCTGGGCGCCAGTGGGGCCAGGGGCAGGATCTCCTTCTGGCTCTGCAGCAGTTTCTCATCTACTGCAGTGGGGTTCTGCCAGAGCAGTCAGAAAGCATGAAGGAGGCACTGCTGCTGCTTCCTCCACGTGACTCTGGGGTTGCAAGCTGGGCAGGGACCCCGGCTCTGCCAGAACCCCACCAGGGGCTAG | 3198 |
| | 4 | MKEALLASST* | 3199 | ATGGTAAAAGAGAAAGGAGAAGGAGTTGAGCGAGCGAGAGAAGCTAGGTGTGATGAGACAGACTAG | 3200 |
| hsa-mir-125b-1 | 1 | MVKEKRREVERAREKLGVMMTD* | 3201 | ATGATTCCATTTTAAAGGAGGGAGGGGAGAGTCTAG | 3202 |
| | 2 | MIPFLKEGRGRV* | 3203 | ATGGAAATATCTAAAAAATATTTACTAAGTGGTTGAGGCCTCTCCAGTGTCCTCCTGGCTGTGGCTGCTTGTCATTCTCTTTGA | 3204 |
| | 3 | MEISKKIPSIFTKCVEASPVSSWLWLLCHSL* | 3205 | | 3206 |
| | 4 | MKNRKKKEKKHL* | 3207 | ATGAAAAACAGAAACAGGAGAAAGGAGAGAAACATTTGTAA | 3208 |
| hsa-mir-125b-2 | 1 | MLPFHSNVPFMTHPQKYYCQKLYSKVITQLH* | 3209 | ATGCTTTTCTTTATCATCAGCAACGTTTTCACCATGACCATCCCAAAAATACTATTGTCAGAAACTGTACTCTAAGTGATTACACAGTTGCACTGA | 3210 |
| | 2 | MLLLVHFKVASIRGYLFS* | 3211 | ATGCTTCTTTTGGTGCATTTTAAGGTGCCTAGTATAAGAGGATATCTTCAGTTAA | 3212 |
| | 3 | MKRGDYIYNFSYALKYIH* | 3213 | ATGAAGAGAGGAGATTATATTTATAACTTTTCATATGCATTGAAATATACATTAG | 3214 |
| | 4 | MPPYNYGSDYVIYSYKHA* | 3215 | ATGCCTCCATATAACTATGCTCAGACTATGTCATATACAGCTATAAGCATGCTTGA | 3216 |
| hsa-mir-128a | 1 | MLQTLQKVLGKQ* | 3217 | ATGCTTCAGACACTACAGAAGGTATTGGGTAAACAATGA | 3218 |
| | 2 | MMMLCHCSLTISKPRGNDSCKQHNTMR* | 3219 | ATGATGAATTTGTGCCATTGTAGCCTCACATCCAAGCCAGGGAAATGACAGCTGTAAACAACAACAGCGATAA | 3220 |
| | 3 | MTAVNNTTQCDKCYENRIYIRHYT* | 3221 | ATGACAGCTGTAAACAACAACAATGCGATAAGTGTATGAAATAGAATATATATATAAGGCACTACACATAA | 3222 |
| | 4 | MKJEYI* | 3223 | ATGAAAATAGAATATATATAA | 3224 |
| hsa-mir-129-2 | 1 | MSCACRRL* | 3225 | ATGTCATGTGCATGCGCAGACTGTGA | 3226 |
| | 2 | MCMPQTVSMS* | 3227 | ATGTGCATGCCAGACTGTGAGTATGAGCTGA | 3228 |
| | 3 | MLRGSPLAAFFAPSKEDSGTD* | 3229 | ATGCTCCGGGTTCTTTTTGCCTGCCTTTTTGCCCCTTCTAAAGAGGATAGTGGGAATTCTTGC | 3230 |
| | 4 | MCIMNLGLHAKKPREGILAEPGITLTML* | 3231 | ATGTGTATAATGAATTTGGGCTGCATGCAAAGAACCGAGAGAGAGGGAATTCTTGCAGAGCCGAGAATCACCCTGACGAATCTCTGA | 3232 |
| hsa-mir-133a-1 | 1 | MWKS* | 3233 | ATGTGGAAGTTCCTGA | 3234 |
| | 2 | MQTIS* | 3235 | ATGCAGACTATTCCTAA | 3236 |
| | 3 | MYSGGQRKTG* | 3237 | ATGTATTCTGGAGGGCAAAGAAAAACAGGTGA | 3238 |
| | 4 | MFTVIWGE* | 3239 | ATGTTTACAGTTATTTGGGGGAGTAA | 3240 |
| hsa-mir-133a-2 | 1 | MRKPQWQLAPEKARQGWPSPTERRLLEPSGPGDLRPQELGAVAVVRKGWVLAGRQPMPGRREAAQLSLGKASSKAGERGVRGSRKGELCEAPDL* | 3241 | ATGAGGAAACCAGTGGTGCTGCCAGAGAAGGCAGGCAGGCTGGCCCTCCCTACCCGGAGGCTGCTGGAGCCCTCGGGGCCCGGGGATCTGAGGCCCCAGGAGCTAGGGGCAGTGGTCGTCGTGTGGTGAGGCAGATGGGTCTTGGCAGGAAGGCAGCCATGCCTGGGAGGCGGGAAGGCAGCACAGCTCAGTTTGGGAAGGCAAGTCCAAGGCCGGAGAGCGTGGGGTGGGGGTCTAGGAAGGGTGAGCTCTGTGAAGCACCTGACCTTTGA | 3242 |
| | 2 | MGLGRKAAHAWEAGGSTAQPGEGKLQGRRAWGAGV* | 3243 | ATGGGTCTTGGCAGGAAGGCAGCTCATCCTGGGAGGCGGAGCAGCAGCAGTCAGTTCGGGAAGGCAAGTCCAAGGCCGGAGAGCGTGGGGTCTAG | 3244 |
| | 3 | MGPLGRFWGLWGVGFLAFLERKEKNTYKEVEEPQGPPLSALAPCW* | 3245 | ATGGGGCCCTTGGGACGCTTCTGGGGACTTTTGGGGCGTTGGGCGTTGGTTCTTGGCTTTTAGAGAGAAAAAGAAAAATACTTACAAGGAAGTTGAGGAGCCTCAGGGACCTCCCTTGTCAGCCCTGCCCCATGCTGGTGA | 3246 |

Figure 1 (Continued)

| | | | | |
|---|---|---|---|---|
| | 4 | MLVRPQESEGKGLEDLPVSGSCCLREQSRTGGCPGPQGSPTSCPEDGPSSGTSQEHELWACSFTFARKGVDHTLGKE* | 3247 | ATGCTGGTGAGACCCCAGGTTCAGAGGGAAGGGCTAGAGGAATCTGCCAGTGAGTGGGAGCTGCTGCCTGAGGGAGCAGAGCAGAAACAGGGCGGTCCCGGTCCACAGGGGTCCCCGACGTCCTGCCCGAAGGATGACCTAGTTCCGGCACGTCCAAGAACACGAATTGTGGGCTGTTCCTTCACATTGCAAGAAAAGGTTGATCACACCCTTGGCAAAGAATGA | 3248 |
| hsa-mir-135a-2 | 1 | MAKLLCLY* | 3249 | ATGGCGAAACTCTGTCTCTACTAA | 3250 |
| | 2 | MEVAMSQDCALAPQPGQQNETLSQKIR* | 3251 | ATGGAGGTTGCAATGAGCCAAGATTGTGCCCTCCCAGCCTGGGCAACAGAATGAGACTCTTTCTCAAAAATAAATAA | 3252 |
| | 3 | MRLFLKK* | 3253 | ATGAGACTCTTTCTCAAAAATAA | 3254 |
| | 4 | MISSSRLHPQDARLVQHMHNKRNPLHKQSQ* | 3255 | ATGATCTCATCAAGTCGCTTCATCCCCAAGATGCAAGGCTGGTTCAACATATGCATATCAATAAACGTAATCCATTACATAAACAGAGCTCAATGA | 3256 |
| hsa-mir-137 | 1 | MIHRYFYECKLKHPSA* | 3257 | ATGATAACCATTAGATATTTTACGAGTGTAAACTGAAGCATCCTCTGCCTAG | 3258 |
| | 2 | MWSYGLFN* | 3259 | ATGTGGTCCTACGGTCTTCCAAATTAA | 3260 |
| | 3 | MHQSQ* | 3261 | ATGCACCAGAGTCAATGA | 3262 |
| | 4 | MKRVSCYSQYSSTPFQVDVKPLLVRT* | 3263 | ATGAAGAGAGTCAGCTGCTACTCCCAGTATTCTTCCACTCCTTTCCAAGTAGATGTAAGTTCCTTTGGTGAGGACCTAA | 3264 |
| hsa-mir-138-1 | 1 | MPTHCMLY* | 3265 | ATGCCTACAATAACATGTATGCTTTACTGA | 3266 |
| | 2 | MYALLTM* | 3267 | ATGTATGCTTTACTGACCATGTAG | 3268 |
| | 3 | MILIPQMLEAKRSSI* | 3269 | ATGATCTAATACCTCAGAATTTGAAGCCAAAAGGTCCTCCATTTAG | 3270 |
| | 4 | MKKQ* | 3271 | ATGAAAAAGCAGTGA | 3272 |
| hsa-mir-138-2 | 1 | MHPGK* | 3273 | ATGCACCCTGTAAATAG | 3274 |
| | 2 | MLQCL* | 3275 | ATGTTGTTGCAGTGCCTCTGA | 3276 |
| | 3 | MYWVGQNLLKEYLNSWLLGFL* | 3277 | ATGTATTGGGTGGGGCAGAATTTGCTTAAATATTTAAATAGTTGGTTATTGGATTTTTGTGA | 3278 |
| | 4 | MRWNMKHEFLFTKTRSFFGIAGESE* | 3279 | ATGAGGTGGAATATGAAATAGAAATTTATTTTATTTACTAAAACCAGATCCTCTTTGGGATTGCAGGTGAGAGTGAGTGA | 3280 |
| hsa-mir-144 | 1 | MLPFLALFLFCFK* | 3281 | ATGTTGCCTTTTTAGCCCTTTTATTTCTTTGTTTAAGTGA | 3282 |
| | 2 | MTDTEQIKFMVRSYVGMSHYHSQDTFAQEGTPSQLVKLLGQK* | 3283 | ATGACTGATACTGAGCAAATTAAGTTTATGGTCAGAAGTTATGTAGGAAACTCCATTACCAATTCCCAAGATACTTTTGCCCAGGAGGGCACCCATCCAGCTTGTAAAATTGCTGGGACAAAAATGA | 3284 |
| | 3 | MHVEVLLLALKFL* | 3285 | ATGATTATCGTAGAGGAAGTTTTGCTGCTTTAAAATTTATTATGA | 3286 |
| | 4 | MYTRTEL* | 3287 | ATGTATACCAGGACTGAGTTGTAG | 3288 |
| hsa-mir-145 | 1 | MLRLGVLLSC* | 3289 | ATGCTGCATCTGGGGTCTTGCTGTCTTGCTAA | 3290 |
| | 2 | MISKHPSS* | 3291 | ATGATCTCTAAGCATCCATCCAGCTGA | 3292 |
| | 3 | MVLLASRIPCCCSQLGEREGAEGYHRVNILSAQASPRHPSLRQSPWLLHRQCFFLJVWGFDFVIPRAWGSWQGKWFSNNGFEKQSWGRGNVSSGSGRQAEILGRLLGADCTWSNGKGCW* | 3293 | ATGGTCCTGTTGGCTTCTAGGATTCCTTGTTGTTGTAGTCAATGGGGAAGAAGGTGCAGAGGAGTGCACAGAGTTAACATCCATCAGCCAAGCTTCACCTCGGCAACCGAGTCTCAGGCAGTGCCTTGGCTTCTACATAGGCAGCAGTGCTTCTTCCATTGTGTGGGGCTTTGATTTTGTAATTCCAAGAGCCTGGGCTCTGGCAAGGAAAATGGTTTTCAATAATGGTTTCGAGAAACAAAGCTGGGAAGAATCCTCGGAAGGGTGCAATGTAAGCTAAGCCAAGTGTAAGCTCAGGCTCTGGCAGGCAGGCAGAGAATCCTCGGAAGCTGGGTGCTGACTGCACATGAGCAATGGGAAGGGATGCTGGTGA | 3294 |
| | 4 | MVFK* | 3295 | ATGGTTTTCAAATAA | 3296 |
| | 1 | MESCSRPVARAGGQW* | 3297 | ATGGAGTCTTGCTCCCGGCCTGTGCCCGGGCTGGAGGGCAGTGGTAA | 3298 |
| | 2 | MRATMPG* | 3299 | ATGCGCGCCACAAATGCCTGGCTAA | 3300 |

Figure 1 (Continued)

| | | | | |
|---|---|---|---|---|
| hsa-mir-146a | 3 | MGFWTELASLYLLFLKSYCCPYAWYSLEQISSHTRSSLRERRWTLGVYPVVWSCWTVSLWSG* | 3301 | ATGGGTTTTTGGACAGAACTGGCTTCTCTTTATTGTGTTTTAAAATCATACTGCTGTCCTTATGCATGGTACTCCTTGGAACAGATAAGCAGCATAAGAAGCTCTTGAGAGAGAAGGTGACTCTGGGGGTGCTGCCGGTTGTTTGGAGTGTTGGACTGTTAGCTTGTGGAGTGGGTGA | 3302 |
| | 4 | MHGTPWNR* | 3303 | ATGCATGGTACTCCTTGGAACAGATAA | 3304 |
| | 1 | MGTHFPNAVFPGRAGAFLLYS* | 3305 | ATGGGCACTCACTTCCCAATGCAGTGTTTCCTGGGAGAGCAGGAGCATTCTTACTGCTGTATCGTGA | 3306 |
| | 2 | MQCPLGFQEHSYCCIREHSYCRV* | 3307 | ATGCAGTGTTTCCTGGGAGAGCAGGAGCATTCTTACTGCTGTATCGTGAGCATTCTTACTGTCAGGGTGTGA | 3308 |
| hsa-mir-153-2 | 3 | MAVSLIVKPRCQEEQGNPSPLFRSFRGPLKLVGSKDKSGFRRS* | 3309 | ATGGCAGTCAGTCTCATTGTAAAACCAAGATGCCAGGAGGAGCAGGAGGAAACCCTCCTTCTTGTTCAGAAGCTCGTGTGTCCCGTTAAATTGGTAGGGTCAAGGATAAATCTGGTACAAGGCGTTCATAA | 3310 |
| | 4 | MPGGTGKPLLLVQKLPWSP* | 3311 | ATGCCAGGAGGAACAGGGAAACCCTCCTTCTTGTTCAGAAGCTCCCGTTGGTCCCCT TAA | 3312 |
| hsa-mir-15b | 1 | MQYRSILSE* | 3313 | ATGCAGTATCGGTCTATATTGAGTGAATAG | 3314 |
| | 2 | MISFSFYL* | 3315 | ATGATTTCCTTTTCATTTTATTTGTAG | 3316 |
| | 3 | MLHAYIYHWINTRKSLNKGIFF* | 3317 | ATGCTCCATGCTTACATATATCACTGGATCAATACAAGAAAAAGTTTAAATAAAGGCATTTTTTAA | 3318 |
| | 4 | MLTYITGSIQEKV* | 3319 | ATGCTTACATATATCACTGGATCAATACAAGAAAAGTTTAA | 3320 |
| hsa-mir-16-2 | 1 | MQYRSILSE* | 3321 | ATGCAGTATCGGTCTATATTGAGTGAATAG | 3322 |
| | 2 | MISFSFYL* | 3323 | ATGATTTCCTTTTCATTTGTTATTGTAG | 3324 |
| | 3 | MLHAYIYHWINTRKSLNKGIFF* | 3325 | ATGCTCCATGCTTACATATATCACTGGATCAATACAAGAAAAAGTTTAAATAAAGGCATTTTTTAA | 3326 |
| | 4 | MLTYITGSIQEKV* | 3327 | ATGCTTACATATATCACTGGATCAATACAAGAAAAAGTTTAA | 3328 |
| hsa-mir-181a-1 | 1 | MCQH* | 3329 | ATGTGCCAGCATTAG | 3330 |
| | 2 | MECP* | 3331 | ATGGAATGTCCTTAA | 3332 |
| | 3 | MSLNSMGGAE* | 3333 | ATGTCCTTAAATTCTAATGGAGGAGCTGAGTGA | 3334 |
| | 4 | MEELSEQIHHMWVRVKC* | 3335 | ATGGAGGAGCTGAGTGAACAAATACATCATATAATGTGGTCAGGGTTAAATGCTAG | 3336 |
| | 1 | MCQH* | 3337 | ATGTGCCAGCATTAG | 3338 |
| | 2 | MECP* | 3339 | ATGGAATGTCCTTAA | 3340 |
| hsa-mir-181b-1 | 3 | MSLNSNGGAE* | 3341 | ATGTCCTTAAATTCTAATGGAGGAGCTGAGTGA | 3342 |
| | 4 | MEELSEQIHHMWVRVKC* | 3343 | ATGGAGGAGCTGAGTGAACAAATACATCATATAATGGGTCAGGGTTAAATGCTAG | 3344 |
| | 1 | MNCN* | 3345 | ATGATAAACTGTAATTAG | 3346 |
| | 2 | MWTVKYLRAKPLTSLSISIRLAAHLEHRSSMLPRAGLLAHHSQDSSGQGLC* | 3347 | ATGTGGACAGTGAAGTATTTGCGTGCAAAGCCCTCACCTCTGAGCATTCCATCAGGCTCGTGCTGTCACCTGGAGCACAGGTCATCTATGCCCGGGCAGGACTCCTCGCCATCACAGCCAGCCAAGACTCCTCAGTCAAGGCCTCTGCTGA | 3348 |
| | 3 | MLTSVLLQLPHRDAQQVGFPKQKLGSPPGRGKGQAGAAGRAHHDTV* | 3349 | ATGCTGACCTCTGTTCTTTACAGCTTCTCATCGGGATGCAAGCAGCCAGGTGCTGA | 3350 |

Figure 1 (Continued)

| | | | | |
|---|---|---|---|---|
| hsa-mir-187 | 4 | MHSKSDSPSRSWAAHLEEEARQVLQVGLTMTQCETSG YNTGPQRCSDFSCLVLQPEGRRSAAEPAPLVLRDSTQG TAQRPWESPGSGQVGGVLGERPTRTTPGVTHSAPFFV LVSSLRTQLGSPLAQCR* | 3351 | ATGCACAGCAAGTCGGATTCCCAAGCAGCAAGCTGGGCAGCCACCTGGAAGAGGA GGCCAGGCAGGTGCTGCAGGTGGGCCTCACCATGACACAGTGTGAGACCTGGGCT ACAACACAGGACCGGGGCGCTGCTCCTGGACCCTCGTGTCTTGTTGTTGCAGCCGGAGG GACGGCAGGTCCGCAGAGACCATGGGAACCCTGTCCTGAGGGACTGCGACACAGGGG ACTGCACAGAGACCAGAGTCCAGGCTCAGGTGGGCCAGGTGGGTGGGTGTT GGGAGAGAGGCCGACCGGACCCAGTGTCACCCATTCAGCCCCCTTTTTGT CCTAGTTTCGTCCTCCTCGTACACAGCTTGGCTCACCTCTGGCCCAGTGCAGGTAG | 3352 |
| | 1 | MILPQYPE* | 3353 | ATGATTCTCCACCTCAGTATCTGAGTAG | 3354 |
| hsa-mir-18b | 2 | MLPNLALNSQPQANLPPCSPKVLGLQV* | 3355 | ATGTTGCCAAACTGGCCTTGAACTCCAGCCTCAAGCAAACCTCCACCTTGTTCTC CCAAAGTGCTGGGACTACAAGGTGTGA | 3356 |
| | 3 | MQRYK* | 3357 | ATGCAAAGATATAAATAG | 3358 |
| | 4 | MILPDKIDYKTMSHREKEEYFTIKRRSIYQKEM* | 3359 | ATGATATTACCAGACAAAATAGACTATAAGAGACAATGAGTATTATCAGAGAGAAAGA AGAATATTTCACCATAAAAAGGAGGTCAATATATCAGAAAGAAATGTAG | 3360 |
| hsa-mir-191 | 1 | MGGGCQLIHRPWFGGAQEHSSLFLLGC* | 3361 | ATGGGTGGGCAAGGCAACTGATACAAGACCATGGTTTGGCGGTGGTGCTCAAGA ACATAGCTCCCTCTTCCTTCTGGGGTGCTGA | 3362 |
| | 2 | MVWGWCSRT* | 3363 | ATGGTTTGGGGGTGGTGCTCAAGAACATAG | 3364 |
| | 3 | MCLRLPWALHFCTCTCGGE* | 3365 | ATGTGCCTGAGGCTGCCCTGGGCACTGCACATGCACGTGCACATGTGGGGGTGA GTAG | 3366 |
| | 4 | MHVHMWG* | 3367 | ATGCACGTGCACATGTGGGGTGA | 3368 |
| hsa-mir-194-1 | 1 | MLKLGWKNSKTTDALQKAYRGISSLQINNLP* | 3369 | ATGTTAAAACTTGGGTGGAAAATAGTAAAATCACTGATGCTTTACAAAAAGCTTAC AGAGGCATAAGTAGTTTACAAATAAATAACTTGTTTAA | 3370 |
| | 2 | MLYKKLTEA* | 3371 | ATGCTTTACAAAAGCTTACAGAGAGGCATAA | 3372 |
| | 3 | MRQC* | 3373 | ATGAGACAAATGTGA | 3374 |
| | 4 | MLKIKPIAADHPH* | 3375 | ATGTTGAAGATAAAGCCATAGCAGCAGACCATCCACATTGA | 3376 |
| hsa-mir-196a-2 | 1 | MSPSERGVPKEQYYSGGADHFPPHPGGARLEGREEKE GEGGKYQLRNYPRIRFSPCDG* | 3377 | ATGTCATTTCAAGAGAGGAGTGTTTAAGGAGCAATACTACAGCCGGAGGAGCTGA CATCTCTTTTTTTTTTCCCATCCGGAGCGGGAGCGGGCCGCGGTTGGAGRGGAGGAAA AAGAAGGCATGAAGGAGGGGGAAAATATCAGCTCCGTAATTATCCGCCATTCCGGTTCTCA CCATGTGACGGCTAG | 3378 |
| | 2 | MGFENGLDDSDGRDVSGVKLSAGGARRVE* | 3379 | ATGGGATTTGAAAATGGCTTGATGATTCAGACGGCCGTGACGTCAGCGGGGTCAA GTTGTCGGCAGGCGGAGCGGAGCGGCAGAGTGGAGTAA | 3380 |
| | 3 | MALMIQTAVTSAGSSCRQAERAEWSNSAI* | 3381 | ATGGCCTTGATGATTCAGACGGCCGTGACGTCAGCGGGGTCAAGTTGTCGGCAGGC GGAGCGCGAGAGTGGAGTAACAGCGGCCATCTAG | 3382 |
| | 4 | MRERGKERGNPGLKTVKFLKLKGRDTNQVLLPTLHLPFP YPRTRLPLLILGMGVG* | 3383 | ATGCGGGAGAGAGGGAGAGGGAACCCGGGACTCAAGGTCAAGTTTCAAGTTTAAGCTCTCAAATTCA AATTAAAAAGGTCGAGACAACGTAGGTACTACTCTCCCACTCTTCATCTCCCTTCC ATATCCCCGACCCTCTTACCTTGCGGATGGGAGTGGGGTGA | 3384 |
| hsa-mir-196b | 1 | MINPCINFAFFSKIPYK* | 3385 | ATGATTAATCCATGTATAAATTTCGCTTTTTTTTCTAAATTTTCTACAAATAA | 3386 |
| | 2 | MYKFRFF* | 3387 | ATGTATAAATTTCGCTTTTTTTTCTAA | 3388 |
| | 3 | MAIANIC* | 3389 | ATGGCAATTGCTAATATTTGTGA | 3390 |
| | 4 | MSQALC* | 3391 | ATGAGCCAGGCATTATGCTAA | 3392 |
| hsa-mir-194-2 | 1 | MKSLSMPMS* | 3393 | ATGAAGTCTTTGTCATGCCATGTCCTGA | 3394 |
| | 2 | MVLPRFSSRVFMVLVLHLSLNPS* | 3395 | ATGGTATTGCCTAGGTTTTCTTCTAGGGTTTTATGGTTTAGTCTTACATTTAAGTC TTAATCCATCTTGA | 3396 |
| | 3 | MASQFSQHRLLNKGSFPHFLFLSGLSKIRWL* | 3397 | ATGGCTAGCCAGTTTTCCCAACACCGTTTATTAAATAAGGGATCTTTCCCCATTTCT TGTTTTTGTCAGTTTGTCAAAGATCAGATAGGTTGTAG | 3398 |

Figure 1 (Continued)

| | | | | | |
|---|---|---|---|---|---|
| | 4 | MVVDVWCYF* | 3399 | ATGGTTGATGTGTGGTGTTATTCTGA | 3400 |
| | 1 | MILPPQYPE* | 3401 | ATGATCCTCCCAACTGGCTACCTGAGTAG | 3402 |
| hsa-mir-19b-2 | 2 | MLPNLALNSQPQANLPPCSPKVLGLQV* | 3403 | ATGTTGCCCAACTGGCCTTGAACTCCCAGCCTCAAGCAAACCTCCCACCTGTTCTCCAAAGTGCTGGGACTACAGGTGTGA | 3404 |
| | 3 | MQRYK* | 3405 | ATGCAAAAGATATAATAG | 3406 |
| | 4 | MILPDKIDYKTMSHREKEEYFTIKRRSIYQKEM* | 3407 | ATGATATTACCAGACAAAATAGACTATAAGACAATGAGTATTATCAGAGAAAGAAGAATATTTCACCATAAAAGGAGGTCAATATATCAGAAGAAATGTAG | 3408 |
| | 1 | MFYICFDFPCTVHELEMIWQ* | 3409 | ATGTTTTACATCTGCTTTGATTTTCCCTGTACAGTACATGAACTAGAGATGATATGGCAATAA | 3410 |
| hsa-mir-205 | 2 | MAINFPVNTH* | 3411 | ATGGCAATAAATTTCCTGTGAATACACACTAA | 3412 |
| | 3 | MRQHIS* | 3413 | ATGAGGCAACACATTAGTTGA | 3414 |
| | 4 | MSSNPDISDSLQNIDS* | 3415 | ATGTCAAGCAATCCAGATATTTCTGATTCCCTCCAAAACATAGACTCTGA | 3416 |
| | 1 | MILPPQYPE* | 3417 | ATGATCCTCCCACCTCAGTATCCTGAGTAG | 3418 |
| hsa-mir-20b | 2 | MLPNLALNSQPQANLPPCSPKVLGLQV* | 3419 | ATGTTGCCCAACTGGCCTTGAACCTCCCAGCCTCAAGCAACCTCCCACCTGTCTCCAAAGTGCTGGGACTACAGGTGTGA | 3420 |
| | 3 | MQRYK* | 3421 | ATGCAAAGATATAATAG | 3422 |
| | 4 | MILPDKIDYKTMSHREKEEYFTIKRRSIYQKEM* | 3423 | ATGATATTACCAGACAAAATAGACAATAAGACATATAGACTATAAGGAGTAAGAATGAGTATTATCAGAGAGAAAGAAGAATATTTCACCATAAAAGGAGGTCAATATATCAGAAGAAATGTAG | 3424 |
| | 1 | MAQRIK* | 3425 | ATGGCACAAGAATAAATTGA | 3426 |
| hsa-mir-21 | 2 | MNDFSEVPHLSPLVPVRTGLNQLIRK* | 3427 | ATGAATGACTTCTCAGAAGTCCCACATTTATCACCACTAGTTCCTGTAAGAACTGGTTTGAACCAATTAATAAGGAAATGA | 3428 |
| | 3 | MITSQKSHIYHH* | 3429 | ATGACTTCTCAGAAGTCCCACATTATCACCACTAG | 3430 |
| | 4 | MTYACVIPS* | 3431 | ATGACTTATGTTGTGTCATTCCTAGTTAA | 3432 |
| | 1 | MGVHYFILLNCRD* | 3433 | ATGGGTGTTCACTATTTCATTCTTCTCAACGTAGAGATTAG | 3434 |
| | 2 | MNHLTQYSAYNRLSNNKM* | 3435 | ATGAATCACTTAACACAGTACTCAGCATATAATAGGCTTCAAACAACAAGATGTAG | 3436 |
| hsa-mir-214 | 3 | MTQSMKYRNMAGCGGSCL* | 3437 | ATGACTCAGTCTATGAAGTATCGAAATATGGCAGGGTGTGGTCATGCCTGTAA | 3438 |
| | 4 | MPVILALWEAKAGGSPDIMSSRPACPTWCNPISTKKLQKLARRGDYCL* | 3439 | ATGCCTGTAATCCTAGCACTTTGGGAAGCCAAGGCGGGTGGATCACCTGATATCATGAGTTCGAGACCAGCCTGCCCAACATGGTGTAACCCCATCCTCTACTAAAAATTACAAAAATTAGCCAAGGCGTGGTGATGTGCCTGTAA | 3440 |
| | 1 | MLKLGWKNSKITDALQKAYRGISSLQIMMLF* | 3441 | ATGTTAAAACTTGGGTGGAAAATAGTAAATCACTGATGCTTTACAAAAGCTTACAGAGGCATAAAAGCTTACAGAGGCATAA | 3442 |
| hsa-mir-215 | 2 | MLYKKLTEA* | 3443 | ATGCTTTACAAAAGCTTACAGAGGCATAA | 3444 |
| | 3 | MRQC* | 3445 | ATGAGACAATGTGA | 3446 |
| | 4 | MLKIPIAADHPH* | 3447 | ATGTTGAAGATAAAGCCATAGCAGAGACCATCCACATTGA | 3448 |
| | 1 | MVGFSFVPDLFLGAVFSFIQRGFSPFCALGSSYLPLKCRPNDLSPLTSYQNPTGPLRTLCPYKTLFKSLYNHICHTVEIYLFHCLSPSLDQELTEDQYQAALMYLSLNEWNYECTLLS* | 3449 | ATGGTGGGCTTTCATTCCTTCGTCCCAGATTTATTCCTTGGGAGCAGTGTTTCTTTTATCCAAAGAGGCTTTCTCCCTTTCTGTGCCTTGGGAAGCCAAGGCTCTACCTACCTTTAAAGTGCCGCCCAAATGACCTGTCCTTCTTACCTCTTATCAGAATCCTGTAATCCTGTGATCATTGAGGTATTTGCCACATTGTTGAAATTTATCTTTTCACTGTGTCTCCATGCTAAGATTTAAATAACTTGTTTAACCATGTGTCCTAGCCTCAGAATCAACAGAGCTCACAGAGGCACCAGTACCAGGCAGCAGCCTCAGTGATCCGCAGCTGAATGAATTATGACCATGAATGCACCCTGCCTCTCTTGTTCTTAA | 3450 |

Figure 1 (Continued)

| | | | | |
|---|---|---|---|---|
| hsa-mir-216a | 2 | MTCPFLPLIRIQQGSSTLCAPTRLCSNPCHTFATLLKFIPF TVCLHR* | 3451 | ATGACCTGTCTGTTCTTCTTACCTCTTATCCAGAATCCAACAGGGTTCCTCCACACTCTGTG CCCCTACAAGACTTGTTCAAATCCCTGTCTCTTGTCTCTTGTCTTGTCTTGTATAATCACATTGCCACATTGTTGAAATT TATCTTTTCACTGTCTGTCTCCATCGCTAG | 3452 |
| | 3 | MNGHMNAPCSLCLNPTQGSRPGSVPSPFPGLSQPLTPGY ECLPSLK* | 3453 | ATGAATGGAATTATGAATGCACCCTGCTCTTGTCTTAATCCTACCCAAGGTTCCA GGCCTGGCTCAGTCCGAGCCCTTCTCCGGACTTTCTCAGCCACTCACTCCAGGCT ATGAGTGTCTCCTTCTCTGAAATGA | 3454 |
| | 4 | MHPALFVLILPKVPGLAQSRAPSLDFLSHSLQAMSVSLL* | 3455 | ATGCACCCTGCTCTCTTTGTCTTAATCCTACCCAAGGTTCCAGGTTCCAGTCC GAGCCCCTTCTCCGGACTTTCTCAGCCACTCACTCCAGCTATGAGTGTCTCCTTCT CTGA | 3456 |
| | 1 | MVGFSFVPDLFLGAVFSFIQRGFSPFCALGSSYLPLKCRP NDLSFLTSYQNPTGFLHTLCPYKTLFKSLYNHCHIVEIY LPHCLSPSLDQELTEDQYQAALMYLSLNEWNYECTLLS LS* | 3457 | ATGGTGGGCTTCTCATTCGTTCCAGATTTATTCCTGGGAGCAGTGTTTTCTTTTATCC AAAGAGGCTTTTCTCCCTTTCTGTGCCCTGAGCTCTACCTACCTTAAAGTGCC GCCAAATGACCTGTCCTTTCTTACCTCTTATCAGAATCCAACAGGGTTCCTCCACAC TCTGTGCCCCTACAAGACTTTGTTCAAATCCCTGTATAATCACATTGCCACATTGTT GAAATTTATCTTTTCACTGCTCTACCTATCTCAGTCTGAATGAGCTCAGAGAGAC CAGTACCAGGACAGCACTCCAATGTATCTCAGTCTGAATGAATGATTATGAATGCACC CTGCTCTCTTGTCTTAA | 3458 |
| hsa-mir-216b | 2 | MTCPFLPLIRIQQGSSTLCAPTRLCSNPCHTFATLLKFIPF TVCLHR* | 3459 | ATGACCTGTCTGTTCTTCTTACCTCTTATCCAGAATCCAACAGGGTTCCTCCACACTCTG CCCCTACAAGACTTGTTCAAATCCCTGTATAATCACATTGCCACATTGTTGAAATT TATCTTTTCACTGTCTGTCTCCATCGCTAG | 3460 |
| | 3 | MNGHMNAPCSLCLNPTQGSRPGSVPSPFPGLSQPLTPGY ECLPSLK* | 3461 | ATGAATGGAATTATGAATGCACCCTGCTCTCTTGTCTTAATCCTACCCAAGGTTCCA GGCCTGGCTCAGTCCGAGCCCTTCTCCGGACTTTCTCAGCCACTCACTCCAGGCT ATGAGTGTCTCCTTCTCTGAAATGA | 3462 |
| | 4 | MHPALFVLILPKVPGLAQSRAPSLDFLSHSLQAMSVSLL* | 3463 | ATGCACCCTGCTCTCTTTGTCTTAATCCTACCCAAGGTTCCAGGCTGCTCAGTCC GAGCCCCTTCTCCGGACTTTCTCAGCCACTCACTCCAGCTATGAGTGTCTCCTTCT CTGA | 3464 |
| | 1 | MVGRSFVPLFLGAVFSFIQRGFSPFCALGSSYYLPLKCRP NDLSFLTSYQNPTGFLHTLCPYKTLFKSLYNHCHIVEIY LFHCLSSPSLDQELTEDQYQAALMYLSLNEWNYECTLLS LS* | 3465 | ATGGTGGGCTTCTCATTCGTTCCAGATTTATTCCTGGAGCAGTGTTTTCTTTTATCC AAAGAGGCTTTTCTCCCTTTCTGTGCCCTGAGCTCTACCTACCTTAAAGTGC GCCAAATGACCTGTCCTTCTTACCTCTTATCAGAATCCAACAGGGTTCCTCCACAC TCTGTGCCCCTACAAGACTTTGTTCAAATCCCTATAATCACATTGCCACATTGTT GAAATTTATCTTTTCACTGCTCTACCTATCTCAGTCGAATGAGCTCAGAGGAC CAGTACCAGGACAGCACTCCAATGTATCTCAGTCTGAATGAATGATTATGAATGCACC CTGCTCTCTTGTCTTAA | 3466 |
| hsa-mir-217 | 2 | MTCPFLPLIRIQQGSSTLCAPTRLCSNPCHTFATLLKFIPF TVCLHR* | 3467 | ATGACCTGTCTGTTCTTCTTACCTCTTATCCAGAATCCAACAGGGTTCCTCCACACTCTGTG CCCCTACAAGACTTGTTCAAATCCCTGTATAATCACATTGCCACATTGTTGAAATT TATCTTTTCACTGTCTGTCTCCATCGCTAG | 3468 |
| | 3 | MNGHMNAPCSLCLNPTQGSRPGSVPSPFPGLSQPLTPGY ECLPSLK* | 3469 | ATGAATGGAATTATGAATGCACCCTGCTCTCTTGTCTTAATCCTACCCAAGGTTCCA GGCCTGGCTCAGTCCGAGCCCTTCTCCGGACTTTCTCAGCCACTCACTCCAGGCT ATGAGTGTCTCCTTCTCTGAAATGA | 3470 |
| | 4 | MHPALFVLILPKVPGLAQSRAPSLDFLSHSLQAMSVSLL* | 3471 | ATGCACCCTGCTCTCTTTGTCTTAATCCTACCCAAGGTTCCAGGCTGCTCAGTCC GAGCCCCTTCTCCGGACTTTCTCAGCCACTCACTCCAGCTATGAGTGTCTCCTTCT CTGA | 3472 |
| hsa-mir-218-1 | 1 | MCSLEVSSCSINVSPEYYLLSVVNCILFHTSICGILQLLS VSY* | 3473 | ATGTGTTCCCTGGAAGTTAGTAGTTGCTCAATAAATGTTAGCTTTGAGTATTACCTTA TTTATCAGTTGTAAATTGCATACTTTTCACACTTCCATCGTGGAATTTTACAGTT ATTGTCAGTAAGTTATTGA | 3474 |
| | 2 | MLALSITLFYQL* | 3475 | ATGTTAGCTTTGAGTATTACCTTATTTATCAGTTGTAA | 3476 |
| | 3 | MKEIITVFNKTVAEN* | 3477 | ATGAAAGAGATTATTATTACTGTTGTTCAACAAAACTGTTGCTGAGAACTAG | 3478 |

Figure 1 (Continued)

| | | | | | |
|---|---|---|---|---|---|
| | 4 | MHINQEATVKVVIKTYPERNRHKQ* | 3479 | ATGCATATAAATCAAGAAGCAACAGTCAAGGTGGTGATAAAAACATACCTGAAAG AAACAGAATTATCATAAAGCAATGA | 3480 |
| hsa-mir-218-2 | 1 | MGRRRRLQGRQDPGSSVSPRAKEKVGLGRPLHMCLLQ AKIYIFRFQSVLPKGQVEKY1* | 3481 | ATGGGGAGGAGGAGGACGGTTCGAGGGGAGACAGGACCCAGGCAGCAGCGTCTC CAAGAGCTAAGGAGAAGGTGGGCTGGGGCGGCCTTTGCACATGTGCCTGTTACAG GCTAAGATTTTATATTTTCGTTTCCAAAGTGTGCTCCCAAAGGGCAAGTAGAGAAA TACATATAG | 3482 |
| | 2 | MVQPFDHSML* | 3483 | ATGGTACAGCCCTTTGACCACAGTATGTTATAG | 3484 |
| | 3 | MPTKNTFTSLAPPSLITVF* | 3485 | ATGTTCACGAAAAACACTTTCACTAGCTTCACCTCCTCCATCCCTGATTACTGTGTTCTGA | 3486 |
| | 4 | MGENSRGHLSLSWKEK* | 3487 | ATGGGGAAAACAGCAGGGGAATTCTCAGCTATCTTGGAAGAAGAAGTAG | 3488 |
| hsa-mir-221 | 1 | MQSIKVSLQGPSQGKK* | 3489 | ATGCAGTCCATAAAGGTTAGTCTCCAGGGCCAGTCAGGGCAAAAATGA | 3490 |
| | 2 | MRGKICACTCTCVRACAHVFVEGSKEQMEKKQLD* | 3491 | ATGAGAGGGAAGATCTGTGCGTGTACGTGTACATGTGTGCGTGCATGTGCACATGTC TTTGTTGAGGGAAGCAAGGAACAAATGGAGAAAAAACAGTTGTGA | 3492 |
| | 3 | MCACMCTCLC* | 3493 | ATGTGTGCGTGCATGTGCACATGTCTTGTGA | 3494 |
| | 4 | MSLLREARNKWRKNSLTDKYSQ* | 3495 | ATGTCTTTGTTGAGGGAAGCAAGGAACAAATGGAGAAAAACAGCTTGACTGACAA ATATAGCCAATAA | 3496 |
| hsa-mir-222 | 1 | MQSIKVSLQGPSQGKK* | 3497 | ATGCAGTCCATAAAGGTTAGTCTCCAGGGCCAGTTCAGGGCAAAAATGA | 3498 |
| | 2 | MRGKICACTCTCVRACAHVFVEGSKEQMEKKQLD* | 3499 | ATGAGAGGGAAGATCTGTGCGTGTACGTGTACATGTGTCGTGTGCATGTGCACATGTC TTTGTTGAGGGAAGCAAGGAACAAATGGAGAAAAACAGTCTTGTTGA | 3500 |
| | 3 | MCACMCTCLC* | 3501 | ATGTGTGCGTGCATGTGCACATGTCTTGTGA | 3502 |
| | 4 | MSLLREARNKWRKNSLIDKYSQ* | 3503 | ATGTCTTTGTTGAGGGAAGCAAGGAACAAATGGAGAAAAAACAGTTGACTGACAA ATATAGCCAATAA | 3504 |
| hsa-mir-23b | 1 | MPYLCNHKFICHAGHSILRSHINLHKVNSLQCIVLWILT NGWARCSGSGL* | 3505 | ATGCCATACCTTTGTAATAATAATTAAGTTCATTGTCATGCGGCCATTCTATCCTAA GATCCCACATTAATTGCATAAAGTTAACTCTCTGCAGTGTATTGTTCTGTGGATTTT GACAAGATGGGGCCAGGTGCAGTGGCTCAGGCCTGTAATCCCAGCACTTTGGGAGGTCG | 3506 |
| | 2 | MPAILS* | 3507 | ATGCCGGCCATTCTATCCTAA | 3508 |
| | 3 | MDGRPGAVAQACNPSTLGGRGGRIT* | 3509 | ATGGATGGGCCAGGTGCAGTGGCTCAGGCCTGTAATCCCAGCACTTGGGAGGTCG AGGTGGGAGGATCACTTGA | 3510 |
| | 4 | MGGYQWLRPVIPALWEVEVGGSLETRTSREIGSYASTA TRP* | 3511 | ATGGGCCAGGTCAGTGGCTCAGGACCAGGACTTCAAGAGACTTCATCAGGAGGTCGAGGT GGGAGGATCACTTGAGACCAGGAGTTCAAGAGAAATAGGTAGTTATGCATCTACTG CCACAAGACCCTAA | 3512 |
| hsa-mir-24-1 | 1 | MPYLCNHKFICHAGHSILRSHINLHKVNSLQCIVLWILT NGWARCSGSGL* | 3513 | ATGCCATACCTTTGTAATAATAATTAAGTTCATTGTCATGCGGCCATTCTATCCTAA GATCCCACATTAATTGCATAAAGTTAACTCTCTGCAGTGTATTGTTCTGTGGATTTT GACAAGATGGGGCCAGGTGCAGTGGCTCAGGCCTGTAA | 3514 |
| | 2 | MPAILS* | 3515 | ATGCCGGCCATTCTATCCTAA | 3516 |
| | 3 | MDGRPGAVAQACNPSTLGGRGGRIT* | 3517 | ATGGATGGGCCAGGTGCAGTGGCTCAGGCCTGTAATCCCAGCACTTTGGGAGGTCG AGGTGGGAGGATCACTGA | 3518 |
| | 4 | MGGYQWLRPVIPALWEVEVGGSLETRTSREIGSYASTA TRP* | 3519 | ATGGGCCAGGTGCAGTGGCTCAGGCCTGTAATCCCAGCACTTTGGGAGGTCGAGGT GGGAGGATCACTTGAGACCAGGAGTTCAAGAGACCAGCAGTGCCAGTGCAGTGCAGTGCATTATGCATCTACTG CCACAAGACCCTAA | 3520 |
| hsa-mir-24-2 | 1 | MPYLCNHKFICHAGHSILRSHINLHKVNSLQCIVLWILT NGWARCSGSGL* | 3521 | ATGCCATACCTTTGTAATAATAATTAAGTTCATTGTCATGCGGCCATTCTATCCTAA GATCCCACATTAATTGCATAAAGTTAACTCTCTGCAGTGTATTGTTCTGTGGATTTT GACAAATGGATGGGGCCAGGTGCAGTGGCTCAGGCCTGTAA | 3522 |
| | 2 | MPAILS* | 3523 | ATGCCGGCCATTCTATCCTAA | 3524 |

Figure 1 (Continued)

| | | | | |
|---|---|---|---|---|
| hsa-mir-27b | 3 | MDGFGAVAQACNPSTLGGRGGRIT* | 3525 | ATGGATGGGCCAGGTGCAGTGCAGTGGCTCAGGCCTGTAATCCCAGCACTTTGGGAGGTCG AGGTGGGAGGATCACTTGA | 3526 |
| | 4 | MGQYQWLRPVIPALWEVEVGGSLETRTSREIGSYASTA TRP* | 3527 | ATGGGCCAGGTGCAGTGGCTCAGGCCTGTAATCCCAGCACTTTGGGAGGTCGAGGT GGGAGGATCACTTGAGACCAGGAGTTCAAGAGAATAGGTAGTTATGCATCTACTG CCACAAGACCCTAA | 3528 |
| | 1 | MRKK* | 3529 | ATGAGGAAGAAATAA | 3530 |
| | 2 | MRKFITTRQS* | 3531 | ATGAGGAAATTCATCACTACTAGACAGTCTAG | 3532 |
| hsa-mir-29b-2 | 3 | MFDQGSPTSGNKKMHTIMKTHKIMNSLID* | 3533 | ATGTTCGATCAAGGTAGTCCTACATCTGAAAACAAAAGATGATAATCACTATCATG AAAACACATAAAATTATGAACTCATTGATAGACTAG | 3534 |
| | 4 | MENKKYDPTICCLK* | 3535 | ATGGAGAATAAGAAATATGACCAACTATATGCTGTCTTAAATAA | 3536 |
| | 1 | MRKK* | 3537 | ATGAGGAAGAAATAA | 3538 |
| | 2 | MRKFITTRQS* | 3539 | ATGAGGAAATTCATCACTACTAGACAGTCTAG | 3540 |
| hsa-mir-29c | 3 | MFDQGSPTSGNKKMHTIMKTHKIMNSLID* | 3541 | ATGTTCGATCAAGGTAGTCCTACATCTGAAAACAAAAGATGATAATCACTATCATG AAAACACATAAAATTATGAACTCATTGATAGACTAG | 3542 |
| | 4 | MENKKYDPTICCLK* | 3543 | ATGGAGAATAAGAAATATGACCAACTATATGCTGTCTTAAATAA | 3544 |
| | 1 | MGICIISALMWPEIGGLVSPSLLLVAKQQS* | 3545 | ATGGGTATTTGCATAATCAGTGCTTTGATGTGGCCAGAAATCGGAGGTTTGGTCTCC CCAAGTCTGCTATTAAGGAATGTCAAAAAGGAGGGATG | 3546 |
| | 2 | MIKLKECPKKEG* | 3547 | ATGATTAAACTTAAGGAATGTCCAAAAAGGAGGGATGA | 3548 |
| hsa-mir-302a | 3 | MSKKGGMKDQLSHHSTDTPRPPPPPCFLLFSAVSFPKR LVWGMVHLPWGRPTWHRVGKGRGPLGPRRGQVCRSGS PCPQRVFSPV* | 3549 | ATGTCCAAAAAGGAGGGATGAAAGACCAGCTTCTCATCACTCCACGGACACC CGCCCCCCCGCCCCCTGCCTTTCTATTATTCTCTGCAGTTCTTCTTTCCAAAG CGCTTGGTTTGGGGGATGGTGCATCCACGTGGCACCGAGTG GGCATCGGACAGGGTCCCTAGGGCGGGCAAGGTCTGCAGGAGCGGTTC TCCTTGCCCCCAACGCGTTTTTCCTTCCCCAGTTGA | 3550 |
| | 4 | MLLIILCSFFSKALGLGDGASPLGPPHVAPSGHRQGSPR AKEGPGLQERFSLPPTRFSFPSLIFPAGMGFILWRTLK* | 3551 | ATGCTTCTTATTATTCTCTGCAGTTCTTTCCAAAGCGCTTGGTTTGGGGATGGTG CATCCACGTGGCACCGAGTGGCATCGGACAGGCGTTCCTCTTGCCAACGCGTTTT CCTTCCCCAGTTGATTTGCAGCCGGGATGCGGTTCATCTTATGGAGGACGTTGA AGTGA | 3552 |
| | 1 | MGICIISALMWPEIGGLVSPSLLLVAKQQS* | 3553 | ATGGGTATTTGCATAATCAGTGCTTTGATGTGGCCAGAAATCGGAGGTTTGGTCTCC CCAAGTCTGCTATTAAGGAATGTCAAAAAGGAGGGATG | 3554 |
| | 2 | MIKLKECPKKEG* | 3555 | ATGATTAAACTTAAGGAATGTCCAAAAAGGAGGGATGA | 3556 |
| hsa-mir-302b | 3 | MSKKGGMKDQLSHHSTDTPRPPPPPCFLLFSAVSFPKR LVWGMVHLPWGRPTWHRVGKGRGPLGPRRGQVCRSGS PCPQRVFSPV* | 3557 | ATGTCCAAAAAGGAGGGATGAAAGACCAGCTTCTCATCACTCCACGGACACC CGCCCCCCCGCCCCCTGCCTTTCTATTATTCTCTGCAGTTCTTCTTTCCAAAG CGCTTGGTTTGGGGGATGGTGCATCCACGTGGCACCGAGTG GGCATCGGACAGGGTCCCTAGGGCGGGCAAGGTCTGCAGGAGCGGTTC TCCTTGCCCCCAACGCGTTTTTCCTTCCCCAGTTGA | 3558 |
| | 4 | MLLIILCSFFSKALGLGDGASPLGPPHVAPSGHRQGSPR AKEGPGLQERFSLPPTRFSFPSLIFPAGMGFILWRTLK* | 3559 | ATGCTTCTTATTATTCTCTGCAGTTCTTTCCAAAGCGCTTGGTTTGGGGATGGTG CATCCACGTGGCACCGAGTGGCATCGGACAGGCGTTCCTCTTGCCAACGCGTTTT CCTTCCCCAGTTGATTTGCAGCCGGGATGCGGTTCATCTTATGGAGGACGTTGA AGTGA | 3560 |
| | 1 | MGICIISALMWPEIGGLVSPSLLLVAKQQS* | 3561 | ATGGGTATTTGCATAATCAGTGCTTTGATGTGGCCAGAAATCGGAGGTTTGGTCTCC CCAAGTCTGCTATTAAGGAATGTCAAAAAGGAGGGATG | 3562 |
| | 2 | MIKLKECPKKEG* | 3563 | ATGATTAAACTTAAGGAATGTCCAAAAAGGAGGGATGA | 3564 |

Figure 1 (Continued)

| | | | | |
|---|---|---|---|---|
| hsa-mir-302c | 3 | MSKKGGMKDQLSHHSTDTTRPPHPPPCFLLFSAVSFPKR LVWGMVHLPWGRPTWHRVGIGRGPLGPRRGQVCRSGS PCPQRVFFSPV* | 3565 | ATGTCAAAAAGGAGGATGAAAGACCAGTTCTCATCACTCACGGACACC CGGCCCCCGCCCCCCCATGGTGCATCCCTTGtGCGCCGCCCACGTGGCACCGAGTG CGCTTGGTTGGGGATGGTCCCTAGGGCAAGGAGGGCATCGGCAGGtGTCCCTA TCCTTGCCGCCAACGCGTTTTCCTTGCCCAGTTGA | 3566 |
| | 4 | MLLHLCSFFSKALGLGDGASPLGPPHVAPSGHRQGSPR AKEGPGLQERFSLPPTRFSFPSLIFPAGMGFHLWRTLK* | 3567 | ATGCTTCTTATTCTCTGCAGTTCTTTTTCCAAAGGCGCTTGGTTGGGGATGGTG CATCTCCTTGGGGCCCGCCACGTGGCACCGAGTGCGCATCGGCAGGGGTCCCTA GGGCCAAGGAGGGGCCAGGTCTGCAGGAGCGGTTCCTTGCCCAACGCGTTTT CTTCCCCAGTTGATTTTCCAGCCGGATGGGGATTCATCTTATGAGGACGTTGA AGTGA | 3568 |
| | 1 | MGHCHSALMWPEIGGLVSPSLLLVAKQQS* | 3569 | ATGGGTATTTGCATAATCAGIGCTTTGATGGTGGCCAGAAATCGGAGGTTGGTCTCC CAAGTTGCTATTGGTAGCGAAGCAACAAAGCTAG | 3570 |
| | 2 | MIKLKECPKKEG* | 3571 | ATGATTAAACTTAAGGAATGTCCAAAAAGGAGGGATGA | 3572 |
| hsa-mir-302d | 3 | MSKKGGMKDQLSHHSTDTTRPPPPPPPCFLLFSAVSFPKR LVWGMVHLPWGRPTWHRVGIGRGPLGPRRGQVCRSGS PCPQRVFPSPV* | 3573 | ATGTCAAAAAGGAGGGGATGAAAGACCAGCTTCTCATCACTCACGGACACC CCGCCCCCGCCCCCCCATGCTTCTATTCTCTGCAGTTCTCTTTTCCAAAG CGCTTGGTTGGGGGATGGTGCATCTCCTTGGGGCCGCCCACGTGGCACCGAGTG GGCATCGGCAGGGGTCCCTAGGGCCAAGGAGGCGCCAGGTCTGCAGGAGCGGTTC TCCTTGCCCCCAACGCGTTTTTCCTTCCCCAGTTGA | 3574 |
| | 4 | MLLHLCSFFSKALGLGDGASPLGPPHVAPSGHRQGSPR AKEGPGLQERFSLPPTRFSFPSLIFPAGMGFHLWRTLK* | 3575 | ATGCTTCTTATTCTCTGCAGTTCTCTTTTCCAAAGGCGCTTGGTTGGGGATGGTG CATCTCCTTGGGGCCGCCCACGTGGCACCGAGTGGGCATGGCAGGGGTCCCTA GGGCCAAGGAGGCGCCAGGTCTGCAGGAGCGGTTCTCCTTGCCCCCAACGCGTTTTT CCTTCCCCAGTTTGATTTTCCAGCCGGATGGGGTTCATCTTATGAGGACGTTGA AGTGA | 3576 |
| | 1 | MLNVRFTLLR* | 3577 | ATGTTAAATGTACGCTTTACGCTGTTAA | 3578 |
| | 2 | MYALRC* | 3579 | ATGTACGCTTTACGCTGTTAA | 3580 |
| hsa-mir-30a | 3 | MHVEIHLSNLATCLFTSCG* | 3581 | ATGCATGTTGAAATCATATAAGTAACCTGGCCACTTGCCTATTTACTTCTTGTGGCTAA | 3582 |
| | 4 | MLKSY* | 3583 | ATGTTGAAATCATATTAA | 3584 |
| | 1 | MYPNKVL* | 3585 | ATGTATTTAATAAAGTTTATAA | 3586 |
| hsa-mir-32 | 2 | MGQAQWLMPVIPALCEAKVGRSLEPRSSKPAWPKW* | 3587 | ATGGGCCAGGCACAGTGGCTCATGCCTGTAATCCCAGCACTCTGTGAGGCCAAGGT GGGCAGATCACTGAGGTTCAAAACCAGCCTGGCCAAAATGGTAA | 3588 |
| | 3 | MVKPRLY* | 3589 | ATGGTAAAACCCGTCTCTACTAA | 3590 |
| | 4 | MPVIPATQEAEAGE* | 3591 | ATGCCTGTAATCCCAGCTACTCAGGAGGCTGAGGCAGGAGGAATGA | 3592 |
| hsa-mir-328 | 1 | MMWPGRGTVDGGGGESQANILDFYKRETFILSAPSSPP SPQFVSSSRQGCYPVWGHAGPPGQACLDPGS* | 3593 | ATGATGTGGCCAGGACGAGGAACTGTAGATGGAGGAGGGGAAAGCCAGCCA ATATTTTGGATTTTTACAAAAGGGAAACTTTCATATTAAGTGCTCCTCTCACCTCC AAGCCACAATTCGTCTCCAGCAGCAGGAGGTCTGTTACCCAGTCTGGGGCCACGC AGGACCCTGCAGGGCAGGCTGGATTTTGGATTTTTACAAAAGGGAAACT | 3594 |
| | 2 | MEEEGKARPIFWIFTKGKLSY* | 3595 | ATGGAGGAGGAGGAGCCTCTCTGTTAAACAGGCTGTCCCTGGGTCCATTTAACAGCC TTCATATTAA | 3596 |
| | 3 | MQGGASSVKQSCPWVHLTAKK* | 3597 | ATGCAGGGAGGAGCCTCTCTGTTAAACAGGCTGTCCCTGGGTCCATTTAACAGCC AAAAATAG | 3598 |
| | 4 | MLFSPAAYNFLLPKIWGTKFKLYYYHLAASNIY* | 3599 | ATGTTGTTTCACCAGCTGCTATAACTTCTTATTACCAAAATTGGGGACAAAG TTTAAGCTGTATTACTATCATTTAGCAGCATCCAACATTTATGA | 3600 |
| | 1 | MGHCHSALMWPEIGGLVSPSLLLVAKQQS* | 3601 | ATGGGTCATTGCATAATCAGTGCTTTGATGTGGCCAGAAATCGGAGGACAAAGCTAG | 3602 |
| | 2 | MIKLKECPKKEG* | 3603 | ATGATTAAACTTAAGGAATGTCCAAAAAAGGAGGGATGA | 3604 |

Figure 1 (Continued)

| | | | | |
|---|---|---|---|---|
| hsa-mir-367 | 3 | MSKKGGMKDQLSHHSTDTPRPPPPPCFLLLFSAVSFPKRLVWGMVHLPWGRPTWEHRVGJGRGPLGPRRGQVCRSGSPCPQRVFFSPV* | ATGTCAAAAAAGGAGGAATGAAAGACCAGCTTCTCATCACTCCACGACACCCCGCCCCCCGCCCCCCCCATGCTTCTTATTATTCTCTGCAGTTCTTTCCAAAGCGCTTGGTTTGGGGATGGTGCATCTCCTGGGGCGCCAGGGGTCCCCATGGCATCGCAGGGGGTTCCCCTAGGGCCAAGGAGGGGCCAGTTCGCAGGTCGCAGGAGGCGGTTCTCCTTGCCGCCCAACGCGTTTTCCTTCCCCAGTTGA | 3605 / 3606 |
| | 4 | MLLHLCSFFSKALGLGDGASPLGPPHVAPSGHRQGSPRAKEGPGLQERFSLPPTRFSFPSLIFPAGMGFILWRTLK* | ATGCTTCTTATTATTCTCTGCAGTTCTTTTCCAAAGCGCTTGGTTTGGGGATGGTGCATCTCCTGGGGCGCCAGGGGTCCCCATCGGCAGGGGGTCCCTAGGGCCAAGGAGGGGCCAGTTCGCAGGTCTGCAGGAGGCGGTTCCTTGCCCCAACGCGTTTTTCTTCCCCAGTTGATTGATTTTCCAGCGGGATGGGGTTCATCTTATGGAGGACGTTGAAGTGA | 3607 / 3608 |
| hsa-mir-451 | 1 | MLPFLALFLFCFK* | ATGTTGCCTTTTTTAGCCCTCTTTTTATTTGTTTAAGTGA | 3609 / 3610 |
| | 2 | MTDTEQKFMVRSYVGNSHYHSQDTFAQEGTPSQLVKLLGGK* | ATGACTGATACTGAGCAAGATACTTTTGCCCAGGAGCGGCACCCCATCCCAGCTTGTAAAATTGCTGGGACAAAATGA | 3611 / 3612 |
| | 3 | MRVEEVLLLALKFLL* | ATGATTATCGTAGAGGAAGTTTTGCTCTGCTGGCTTTAAAATTTTTATTATGA | 3613 / 3614 |
| | 4 | MYTRTEL* | ATGTATACCAGGACTGAGTTGTAG | 3615 / 3616 |
| | 1 | MFFG* | ATGTTCATTGGATGA | 3617 / 3618 |
| hsa-mir-455 | 2 | MSQASSPGALTSCVRHLAFHRSQHFQEYLPSGSGTVAHACIPSTLGAQGWMFT* | ATGAGCCAAGCATCAAGTCCAGGAGCACTCACCTCTGTGTGAGGCATCTTGCTTTTCACAGATCTCAGCATTTTCAAGAATATTTACCTTCTCGGGTCAGGACACAGTTGCCTCACGCCTGTATTCCCAGCACTTTGGAGCCCAAGCTGGATGATCACTTGA | 3619 / 3620 |
| | 3 | MPSP* | ATGCCATCTCCTTAA | 3621 / 3622 |
| | 4 | MLFQYL* | ATGCTTTTTCAGTACTTATAG | 3623 / 3624 |
| | 1 | MGLMREPRNKPMHLWSHQHRCQDHTVGKRQFLQ* | ATGGGACTGAATAGAGAACCCAGAAACCCACACAGATGTGGAAAAAGACAGTTCAACAACAGCCAAGATCACCAGAATGTGGGAAAAAGACAGTTTCTTCAATAA | 3625 / 3626 |
| hsa-mir-499 | 2 | MVNYYSTQMPRSHSGKKTVSSINYFSETKNPHVEE* | ATGGTCAATTATTATTATTTCAACACAGATGCCAAGATCACACAGTGGGAAAAGACAGTTTCTTCAATAAATTATTTTCACACTAGAAGAATGA | 3627 / 3628 |
| | 3 | MRPSFRTVPKNQHTHKN* | ATGAGACCCTCATTTCGTACTGTACCCAAAAATCAACACACACAAATTAA | 3629 / 3630 |
| | 4 | MTLVWAKIFYMTLKAWTNT* | ATGACATTGTTTGGGCAAAGATTTTATATGACTCTGAAAGCATGGATAACAAACACATAA | 3631 / 3632 |
| hsa-mir-499 | 1 | MGGRESSESGVEEALVFEGVHVCWALTQGRGJGSQRESPSIWSCGLGJDRALVQLPCRCHLPVPAALGRLEPPGFPAPPPSPQCHCHDGCE* | ATGGGTGCCGCGGAGTTCTCGAATCTGGAGTGGAGGAAGCCCTGTGTTTGAGGGTCGTGCATGTATGTTGGGCACTCACCCAAGGAGCTGCATTGGAGCCAGAGGAGTCGGCTATATCTGGTCTTGGTCTTGTGGGTTGGGGATCTGGGGGTGCCTTGGGCGCCTGTCAGTTCAGGTTTCCAGACTGCCATCTTCCTCCACCCGAGTGCCACTGATGATGTGAGTGACTCCTCCTCCTCCTCCTCACCCGGCACTCACCAAGGAGGCTGCATTGGGAGCTGCATTGGGAGGATGGGGAGTCGCCTAG | 3633 / 3634 |
| | 2 | MYAGHSPKEAALGARGSRLVSGLVGWGIVP* | ATGTATGGTGGCACTCACCAAGGAGGCTGCATTGGGAGCCAGAGGAGTCGCCTAG | 3635 / 3636 |
| | 3 | MLGTHPRRLHWEPEGVA* | ATGCTGGGCACTCACCAAGGAGGCTGCATTGGGAGCCAGAGGAGTCGCCTAG | 3637 / 3638 |
| | 4 | MMDVSELGESARYLRQCYQEMTKVHTIPWDGKWRQRGRGHSHRDALMDSDQELGGVAPAQG* | ATGATGGATGTGAGTGAACTGGGAGAGTCTGCCCGCTACCTCCGCCAGGCTACCAAGAATGACGAAGGTGCACACTATCCATGGGACGGTAAGTGGAGACAGAGGGGGAGGGCGTCATAGCCACGAGAGATGCCCTTATGGACTCAGACCTCAGAGAATTGGGAGAGGGGGGGCACCAGCTCAGGGCTGA | 3639 / 3640 |
| hsa-mir-551b | 1 | MKFLFNLANK* | ATGAAATTTTTATTCAACCTGGCAAATAAATGA | 3641 / 3642 |
| | 2 | MMTPMFLSRIKCWKNEQLHLMTSFAIVPNQSDFGLSQA* | ATGATGACATTCATGTTCTTAAGTCGTATAAAATGCTGGAAAAATGAATAAATCTGGAAATAGAATAAAAAATCTGGAAATTGCTTAAGCCAAGCTTAA | 3643 / 3644 |
| | 3 | MLEK* | ATGCTGGAAAAATGA | 3645 / 3646 |

Figure 1 (Continued)

| | | | | | |
|---|---|---|---|---|---|
| | 4 | MNSSTL* | 3647 | ATGAACAGCTCCACCTTATGA | 3648 |
| hsa-mir-555 | 1 | MSRMVSVWPQHQNVFSKKRCAEYPLIVGPAVGEEVTK MGNNKPLP* | 3649 | ATGAGCAGGATGGTGTCTGTATGGCCCAGCACCAAAATGTGTTAGCAAGAAGCG ATGTGCTGAATACCCACTCATAGTGGTCCTGCAGTGGGTGAAGAAGTCACAAAGA TGGGCAATAACAAGCCCTGCCCTGA | 3650 |
| | 2 | MAPAPKCV* | 3651 | ATGGCCCCAGCACCAAAATGTGTTTAG | 3652 |
| | 3 | MCLARSDVLNTHS* | 3653 | ATGTGTTTAGCAAGAAGCGATGTGCTGAATACCCACTCATAG | 3654 |
| | 4 | MLSAGREDM* | 3655 | ATGCTGTCTGCTGGGAGGAGAAGACATGTAG | 3656 |
| | 1 | MLSSITND* | 3657 | ATGCTGAGTTCCATCACCAACGATTAG | 3658 |
| hsa-mir-559 | 2 | MIQKVWTRLRNMPSPPFI* | 3659 | ATGATTCAGAAGGTCTGGACTAGGCTGAGGAACATGCCCTCTTTCCTTTTTATCTAA | 3660 |
| | 3 | MYLCYLNQGEHR* | 3661 | ATGTATCTCTGCTATCTGAACCAAGGTGAGCACAGATAA | 3662 |
| | 4 | MFIVHYFLKVKFYLIF* | 3663 | ATGTTCATAGTACATTACTTTTAAAGTCAAGTTCTACTTAATTTCTAA | 3664 |
| hsa-mir-568 | 1 | MTQPGSASLSQHAFLGTGGQPDAKRGIKVVSLRVEVSR SKM* | 3665 | ATGACACAGCCGGGCTCTGCCTCTCTATCTCAAATCATTGCTCTTAGGACTGGG GGCCAACTTGATGCAAAGAAGAGGCATAAAGGTGGTGAGCCTGAGGTTGAGGTCTC ACGAAGTAAAATGTGA | 3666 |
| | 2 | MQREA* | 3667 | ATGCAAAGAGAGGCATAA | 3668 |
| | 3 | MRLPREHTANTA* | 3669 | ATGAGGCTGCCAAGAGAGCACACTGCTAACACTGCCTGA | 3670 |
| | 4 | MDGSRGAGTQRREMAVGGVKAPQPSGRWGKRPLSTR DLAHLLFDSVDYPSKCSL* | 3671 | ATGGATGGGAGCAGGGGGCAGGGACCCAAAGGAGGGAAATGGCTGTGGGTGGTG TGAAGGCCCCCCAGCCTCAGGAAGGTGGGCAAGAGACCACTGAGCACAAGGGAT CTTGCCCAACTCTCTTTTGACTCTGTGGATTATTCCATCTCACTGTGA | 3672 |
| hsa-mir-615 | 1 | MFQRRTASGPEPVTRATRLWNSRKNSTLTATSLAAGA* | 3673 | ATGTTCCAAGAGACGGACGGCAAGGTGACCAGATGGCTTAACGCTGAACGGCTACCAGACT CTGAACCTGAGAAGAATTCCACTTTAACCGCTACCTCACTGGCGCAGGCGCATA G | 3674 |
| | 2 | MRDRSRSGSRTAG* | 3675 | ATGAGAGACAGATCAAGATCTGGTTCAGAACCGCACGATGA | 3676 |
| | 3 | MKWLKDSKMKSKEAL* | 3677 | ATGAAGTGGAAGAAGATTCCAAAATGAAAAGCAAAGAGGCTCTTTAG | 3678 |
| | 4 | MNDLHMKGEHRPRAPTVALCFPNLISTTSSPQNPGTSPA CACCMPSQAGSPSLLASSTSGVSWHWTPASGPRGPLLS HSPCREFLCPPFDFLLLSNYLLTLGFS* | 3679 | ATGAATGATTTGCATATGAAAGGAGAGCATCGCCTAGGGCCCACAGTTGCTCTA TGCTTTCCAAACCTTATCTCACTACATCTTCCCCTCAAAACCCGGGAACCTCCCAG CCTGCGCCCTGCTGCATGCCCTCAGGCGGCAGCCCAGCTGTCCAA CTAGTGGGGTTTCCTGGCACTGGACCCCAGGAAGTGTCCTTAGAGGCCCTTTGCGT CCTATAAGTCCATGCCCGCAATTTCTGTGCCCTCTGACCCATTGCTGTTGTCCAACTA TTTATTGACTCTGGGCTCCTTCTGA | 3680 |
| | 1 | MGTFCPQSSSHSNCFVGLAKPQRERKQRHSP* | 3681 | ATGGGCACCTTCTGTCCCCAGTCCTCTCCCAGTCACATCAAATGCTTTGTGGGACTGGCTA AGTTTCAAAGGGAAAGAAAACAAAGGCACAGTCATAG | 3682 |
| | 2 | MCVCVVCLWACMYYVRGLSYFTRVFTRVCMCACGVCV HTRVSCMCMWSVCAYACVCTQVCGVGAVSPHSLL* | 3683 | ATGTGTGTCTGCGTGGTATGTTTGTGGCATGCATGTACGTGCGTGGCGTGTGTG TTCACACGTGTGTTCACACGTGTTCATGTGTGTCCTGTGGGGTGTGCGTTCACACG CGGTATCATGCATGCATGTGGAGTGTGTCTCGCGCCTATGCCTGTGTGCACACAG GTGTGTGAGGGTGGGAGCTGTCTCGCACTCTCCTTTAG | 3684 |
| hsa-mir-671 | 3 | MFVGMHYRAWLVCVHTCVHTCVHVCLWGVRSHARIM HVHVECVVRLCLCVHTGVWGGSCLSALSPLAFLTLCQDT LRSHSPGRTALRPYRIPQGANPGNPATPGVRTAVTWEG SAAFLPPPSSTSLHLASGLSMPALVPLSLVT* | 3685 | ATGTTTGTGGGCATGCATGCATGTACGTGCGTGGCTTGTCGTGTTCACACGTGTTCAC CATGTGTGTGGCATGTGCGTCTGCGTTCACACGCGTATCATGCATGTG CTGTCTCCGAGTGTTGTGCGCTATCCTGTGGGCGTCGTTCCTGACTCTGTGCCAGGAGTAC CCGGCTGTGCAGCTCCAGGACACCCTAGGC TCCAACTCTCCAGGAATGCTGCCACCCGTCAGCACCAGCTGTCAACTGGAGGCCAGTG CTGCTTTTTCTCCCCCCTCGGTTCTTCTTCCACTGGTGACATGA | 3686 |

Figure 1 (Continued)

| | | | | | |
|---|---|---|---|---|---|
| | 4 | MPVCAHRCVGWELSLRTLSFSLPDSLPGHPTLPLSRKNS TETLQNTPGSEPGESCHPWSEDSCHLGGQCCFSPPSVQH QPPPGQWPFYACAGSSFTGDMRASHQLRLGQASQRTP GPFPSQPPALASSEHRHEPGRGGLSLTPYCFPRNCLAGK RPRMPPALYESRATSADSHGNPGRLEELLSPPASDK* | 3687 | ATGCCTGTGTGTGCACAGGTGTGTGGGGTGGAGTGTCTCCGCACTCTCC TTTAGCCTTCCTGACTCTGCAGAACCACCTACGCTCCCACTCTCCAGGAAGAAC AGCACTGAGACCCTACAGAGATACCCACCTGGGAGGAGGGCAGTCCTGCCACCG CTGGAGTGAGGACAGCCTCCACCTGGCCAGTGGCCTTTCTATGCCTGCGCTGGTTCCTTCTC CAGCACCAGCCTCCACTGGCCAGTGGGCTTTCTATGCCTGCGCTGGTTCCTTCTC ACTGGTGACATGAGGGCGAGTCACCAGCTCCATCTGGGACAGGCCTCCCAGCGAAC TCCTGGCCCCTTCCCCTCCAACCCCTGCCTGGCAGTCAGCAGAGCACAGACATGA GCCAGGTAGGGGGGGTCTCAGCTCACTCTTTACCAGTCTACCAAGTGCCACTGGC AGGAAAAGGACGCCTGCCGATGCCCCCAGCTCTTTACCAGTCTACCAAGTGCTGA CTCTCACGGGAACCCTGGGAGACTAGAAGAGTGTTATCACCACCAGCATTGACAA GTAA | 3688 |
| hsa-mir-7-1 | 1 | MFLTVIQHCLSSTYALASHLSYINDNPVFFLHTLFPLSFF FPNYFSLCLSYRDFFSL VILG* | 3689 | ATGTTCTTACTGTAATACAACACTGCTGTCTTCCACATATGCATTAGCTTCTCATC TCTCATATATTAATGATAATTTGTCTTCTTCCTGCATACTTTATTTCCTCTAAGTTTT TTTTTTTTCCTAATTATTTCAGTCTCTCTGTCTTCATAGAGATTTCTTCAGTCTGGT GATTCTTGGCTAG | 3690 |
| | 2 | MHLSSSCLYFL* | 3691 | ATGATAATTTGTCTTCCTGCATACTTTATTTCCTCTAA | 3692 |
| | 3 | MGFQRVIDLRLCAHDRGLSNVRFTAGRASWTT* | 3693 | ATGGGGTTCCAAAGAGTGGATCTAAGGCTCTGTGCTCATGATAGGGGTTTGTCAAAT GTTCGCTTCACTGCTGGGAGAGCCAGCTGGACCACTTAG | 3694 |
| | 4 | MGVCQMFASLLGEPAGPLSQ* | 3695 | ATGATAGGGGTTTGTCAAAGTTCGCTTCACTGCTGGGAGAGCCAGCTGGACCACTT AGTCAGTGA | 3696 |
| hsa-mir-875 | 1 | MLSSITND* | 3697 | ATGCTGAGTTCCATCACCAACGATTAG | 3698 |
| | 2 | MIQKVWTFLRNMPSFPFFI* | 3699 | ATGATTCAGAAGGTCTGGACTAGGCTGAGGAACATGCCTCTTTCCCTTTTTATCTAA | 3700 |
| | 3 | MYLCYLNQGEHR* | 3701 | ATGTATCTCTGTATCTGAACCAAGGTGAGCAGATAA | 3702 |
| | 4 | MFIVHYFLKVKFYLIF* | 3703 | ATGTTCATAGTACATTACTTTTTAAAGTCAAGTTCTACTTAATTTCTAA | 3704 |
| hsa-mir-9-1 | 1 | MVSIS* | 3705 | ATGGTCTCCGATCTCCTGA | 3706 |
| | 2 | MSHCAQPRHFLTTHGTPTKTNHHLGHKENY* | 3707 | ATGAGCCAACTGCGCCCAGCTCGCCCAGAATTCACTTCTTTTAACTACTCATGGAACCCT ACAAAACACTAACCATATTTAGTCACAAAGAAAATGTTAA | 3708 |
| | 3 | MEHLQKLTIF* | 3709 | ATGGAACACTTACAAAAACTAACCATATTTTAG | 3710 |
| | 4 | MFKNHKCNEFFKSQN* | 3711 | ATGTTTAAAAATGCAATGCAATGAAGTCAATTTTTAAATCACAAAATTAG | 3712 |
| hsa-mir-9-2 | 1 | MSVLVFHKLDNRK* | 3713 | ATGAGTGTATTGTTCTTCATAAAGCTTAGATAACCGAAAGTAA | 3714 |
| | 2 | MKDYSRETVKTRKVRMTY* | 3715 | ATGAAAGACTACAGCCGAGAGACAGTAAAACCAGAAAGGTCAGGAATACTTATTGA | 3716 |
| | 3 | MIKGGMREN* | 3717 | ATGATTAAAGGTGCGATGCGATGAGAGAAATTAA | 3718 |
| | 4 | MTHTC* | 3719 | ATGACACACATGCTAA | 3720 |
| hsa-mir-99a | 1 | MFLNKCKNNF* | 3721 | ATGTTTCTAAACAAGTGTAAAATAATTTTAA | 3722 |
| | 2 | MLLKNSASINENYNLHTKN* | 3723 | ATGCTTTTGAAAATTCAGCAAGTATCAATGAAGTATCAAGAATTTGCATACTAAGAAT TGA | 3724 |
| | 3 | MKTHCILRIDVHFR* | 3725 | ATGAAAACTATAATTGCATACTAAGAATTGACGTTATATATTCGGTAA | 3726 |
| | 4 | MLLKSYFLILQICRVNNEKCRTD* | 3727 | ATGCTTTTAAAATCATATTTCTTATATTACAAATGTAGGGTAAACAATGAAATGAAAAA TGTAGAACTGATTAA | 3728 |

Figure 1 (Continued)

| | | | | | |
|---|---|---|---|---|---|
| hsa-let-7a-1 | 1 | MGLRAFRGARPCIGLPATALLSLRPPRRPPAPPSGSWR GALPAATGARAGAFPRPRRFPSPRARGGYGGRGSERGSV AILFRGDSRQRYVGRMGEPCAGPRLSG* | 3729 | ATGGGCTTGCGGGCTTTCGCGCGCGCCGCCCTGCATCGGCCTCCGGCGACCGCG CTGCTTTCCGCTCAGCCCCGGCACGCCGGCAAGCGACGGGCGCGGCCATTCCACGGCCGCG CGGGGTGCTCCCGGACGGCGAGGTGGTATGGCGAGCGCGGGCAGCGAGCGCGGGT ACGGGGCCTGCCGAGCGGAGGTGGTATGGCGAGCGCGGGCAGCGAGCGCGGGT CCGTGCGCCATTTATTTCGCGGAGACTCGCGCAGCGGGTGCGCAGAATGGGAGAG CCGTGCGCCGGCCGCCGGCCGCCGGCCTGCCGGCTAA | 3730 |
| | 2 | MADAAASAGPSPFYFAETRGSGWAEWESRAPARACPA NAGWDWWGGLPPPAGGWPRGAGGHLLAEVAGARGTGE GCRVAAAGPAPTPSASRPAPHRQGGGGVILHIPYPALP PASIKLGAGGRPAFRPAPVGRRRL* | 3731 | ATGGCCGACGGCAGCGCAGCCGTAGCAGAATGGCAGAAGCGCGGTCCGTGCGCCATTTATTTCGCGGAGACTCG CGCAGCGGACTGTGTGGGCGCGCCTGCCCCTCCAGCGGCGGTGGCCCGG GGGGCCGGCCGGGCCGCGTGCTAGCGAAGTCGCGGCGCGCGGGCGGCGAGGGGT GCCGGTGGCGCGCCAGGGGCCCGGGGCTCAAACCCCCCGGCCGCCCAGTTCTC ACCGACAGGGCGGGGAGGGGGGGGGGTCATTCTTCACATCTTACCCGGCCTTCCC GCTTCAATCAAACTTGGGGCGGCGGAAGGCCGGGCCGGCCGGCGCCGTTTG GCCGCGCCGCTCTGA | 3732 |
| | 3 | MKEGR* | 3733 | ATGAAGGAGGAAGGTAG | 3734 |
| | 4 | MPLLPAAKCSLPS* | 3735 | ATGCCCCTGCTCCCGGCGCCAAGTGCAGCCTCCCTTCCTGA | 3736 |
| hsa-let-7a-2 | 1 | MGPLIQGFHRPAGADGVRDLTMAPARSCCVLSEA* | 3737 | ATGGGACCCTTGATACAAGGCTTTCATAGACCAGCCGGTGCTGATGGGGTCCGGGA CTTGACGATGGCCCGTGCTCGTTCCTGTGTTCTATCTGAGGCATGA | 3738 |
| | 2 | MGSGT* | 3739 | ATGGGGTCGGGACTTGA | 3740 |
| | 3 | MIPPRFWEVESTGQRLHLTH* | 3741 | ATGATTTTCTTTCGTTTTTGGGAGGTAGAGAGCACGGGCAGAGTTGCACTGACA CATTAG | 3742 |
| | 4 | MGVTVPPCLPLYLDKDLLYPDF* | 3743 | ATGGGGTTACTGTGCCCCCTGTCTACCCTGCTTTATCTGATAAGGACTTGCTTT ATCCTGATTTCTAA | 3744 |
| hsa-let-7a-3 | 1 | MPGTVAAPLSFLIEGQLLLGPGVVDSALDLSQGTGLPS WLGRRITGGHLNKPLPLSGSQFTHL* | 3745 | ATGCCCGGCACCGTGGCTGCTCCCCTGTCCTTCCTGATCGAAGGCCAGCTGCTG GTCCTCGGTGTCGTGGACTCAGCCCTGGATCTGAGTCAGGGCACTGGGCTCCCATCC TGGCTCGGGCGTAGAATCACTGGTGGGCACTTGAATAAGCCCCTTCCTCTCTCCGGG TCTCAGTTTACCCATCTGTAA | 3746 |
| | 2 | MKSSIYFLSSLQCREERKTKRK* | 3747 | ATGAAAAGCTCCATCTATTCTTGAGTTCCTTGCAATGCCGAGAAAAGACAAAG AGAAAATGA | 3748 |
| | 3 | MPRKKDKEKMKPQYTVAAGFSRLGFLFAFKEGFPPLGK ESWNLTRDDCLRGGEPARAHGHAAWKV* | 3749 | ATGCCCAGAAAGAAGGATAAAGAAATGAAGCCACAGTACACTGTTGCTGCCGG GTTCTCAGAACTGGGATTTCTTGTTTGCTTTCAAAGAGGGTTTTTTCCTCTAGGGAAA GAGTCATGGAATTTGACCAGAGATCACTGGTGAGCGGCCAAGAGCCAGCCAGAGC CCACGGACATTGAGCATGAGAGGTGAA | 3750 |
| | 4 | MEFDQR* | 3751 | ATGGAATTTGACCAGAGATGA | 3752 |
| hsa-let-7b | 1 | MPGTVAAPLSFLIEGQLLLGPGVVDSALDLSQGTGLPS WLGRRITGGHLNKPLPLSGSQFTHL* | 3753 | ATGCCCGGCACCGTGGCTGCTCCCCTGTCCTTCCTGATGAAGGCCAGCTGCTG TGGCTCGGGCGTGGAACTCAGCCCTGGATCTGAGTCAGGGCACTGGGCTCCCATCC TGGCTCGGGCGTAGAATCACTGGTGGGCACTTGAATAAGCCCCTTCCTCTCTCCGGG TCTCAGTTTACCCATCTGTAA | 3754 |
| | 2 | MKSSIYFLSSLQCREERKTKRK* | 3755 | ATGAAAAGCTCCATCTATTCTTCTGAGTTCCTTGCAATGCCGAGAAAAGACAAAG AGAAAATGA | 3756 |
| | 3 | MPRKKDKEKMKPQYTVAAGFSRLGFLFAFKEGFPPLGK ESWNLTRDDCLRGGEPARAHGHAAWKV* | 3757 | ATGCCCAGAAAGAAGGATAAAGAAATGAAGCCACAGTACACTGTTGCTGCCGG GTTCTCAGAACTGGGATTTCTTGTTTGCTTTCAAAGAGGTTTTTTTCTAGGGAAA GAGTCATGGAATTTGACCAGAGATGATTGTTTGAGGGGCCAAGAGCCAGCCAGAGC CCACGGACATGAGCAGCAGAGATGA | 3758 |
| | 4 | MEFDQR* | 3759 | ATGGAATTTGACCAGAGATGA | 3760 |

Figure 1 (Continued)

| | | | | |
|---|---|---|---|---|
| hsa-let-7c | 1 | MRLLCPCCRKEPADWPLSAAHSTGWL* | 3761 | ATGCACCTATTGTGTCCCTGCTGCAGAAAGGAGAGCCTGCCGATTGGCCACTGTCTGCAGCACATAGCACTGGCTGGTTATAA | 3762 |
| | 2 | MTAFFLQGGWRESGEGGGVSSTVKAAQIFFLSLSLPLHRLFLPHALSHFA* | 3763 | ATGACTGCATTCTTTTGCAAGGGGGTGGAGGGAAGGGAAGGAGGGGTGTCAGCTCAACTGTAAAAGCTGCACAGATTTTTCTTCTCTCTCCATCAGATTGTTTCTGTTTCATTCGCTGTCTCATTCGCATAG | 3764 |
| | 3 | MPCLISHS* | 3765 | ATGCCCTGTCTCATTCGCATAGCTAA | 3766 |
| | 4 | MLIKIPCLNLKNNDSAVIRNLYRV* | 3767 | ATGCTAATTAAGATCCCTTGTCTTAACCTGAAAAATAATGACTCGGCTGTAATTAGAAATCTGGTGAGAGTTTAA | 3768 |
| hsa-let-7c | 1 | MVCERISVCLGRKLFDLQKSQKTSR* | 3769 | ATGGTTTGTGAAAGATATCGTGTGCTTAGGGAGGAAACTTTTTGATCTGCAGAAAAGCCAGAAGACATCTAGGTAA | 3770 |
| | 2 | MFTFVEVQNVLTIVCLFFVCLFKS* | 3771 | ATGTTCACTTTTGTAGAAGTCAAATGTACTGACGATTGTTGCTTATTTTTGTTGTTTGTTAAATCTTAA | 3772 |
| | 3 | MLLWKEY* | 3773 | ATGTTGCTTTGGAAGGAATATTAA | 3774 |
| | 4 | MRPLCT* | 3775 | ATGAGGCCCTTGCACATGA | 3776 |
| hsa-let-7c | 1 | MLLLDSSCLIFLLLWLF* | 3777 | ATGCTTCCTAGACAGCAGTTGTCTGATATTTCTCCTTTGTGGTTGTTTTAG | 3778 |
| | 2 | MDMKSEESDHRRKPFQVKIK.NKEQIRFTVFKEKQHSFDCVLL* | 3779 | ATGGATATGAAAAGTGAAGAAAGTGATCATAGGAGAAAGCCATTTCAGGTAAAAAATAAAAAACAAAGAGCAAATAAGATTTACTGTTTTAAAGAAAAACAACATTCTTTTGACTGTGTTTGTTATAA | 3780 |
| | 3 | MSVTVEHLMVFI* | 3781 | ATGAGTGTAACTGTGGAAATTTTATTGATGGTTTTCATTTGA | 3782 |
| | 4 | MCAMTYLCEKFLVVNWAVCVPLNICLCIHTLKIGAIRFTRKLYRKRKKLYPLICCTI* | 3783 | ATGTGTGCTATGACCTACCTTTGTGAAAATTTCTTGGTCAATTGGGCAGTTTGTGTCCCATTGAATATATGTCTGTGTATCCATACGCTTAAGATAGGTGCAATACGGTTACTAGAAAAGCTTTATAGGAAAAGAAAAAATTATATTTCTTATTTGTTGTACCATATAA | 3784 |
| hsa-let-7d | 1 | MGLRAPRGARPCJGLPATALLSLRPPRRRPPAPPSGSWRGALPAATGARAGAFPRPRRPSPRARGGYGRGSERGSVAILFRGDSRQRVGRMGEPCAGPRLSG* | 3785 | ATGGGCTTGCGCGCTTTCCGGGCAAGGCCTTCCCTCAGGCGCCGGCGCCATCGGGTCTGGCTGCTTCGCTGTCTCCGCGGCGACGGGCGCTGCAGGGCGCTCCATCCCACGGCGCGCGGGTGTCCCTCGCGAGCGCGAGCGGGTGGTATGCGGACGGCAGCGAGCGCGGGTCCGTGCCGCCTCGCCAGCGGAGACTGGCGCCAGCGGTGGGCAGAATGGGAGAGCCGTGCGCGCCGCGCTGTCCGGGCTAA | 3786 |
| hsa-let-7d | 2 | MADAAASAGPSPFYFAETRGSGWAEWESRAPARACJPANAGWDWWGGLPPPAGGWPRGAGGLLAEVAGARGTGEGCRVAAAGPAPTPSASRPAPHRQGGGGGVILHPYPALPPASJKLGAGGRPAFRPAPVGRRRL* | 3787 | ATGGCGGACGGCGGCGGCAGCGGCGTCGTGCCATTTTATTTCGCGGAGACTCGCGGCAGCGGGTGGGCAGAATGGGAGAGCCGTGCGCCGCGTGCCTGTCCGGCTAACGCGGGCCGGAGACTGGTGGGACTGTGGCTAGCGGAAGTCGCGGCAGGTTGGCCGGGGCACGCCGGGGTGCCGGTGCCGCCCGGGGCGCCGGAGCGCGGAGGGGGAGGGGGGGTCCAACCCCTCGCGCTCGCAACCCCTCGCCTCCTCACATTCTTCACGCTCCTACCGCGCCTCCCCACCGACAGGCGGCGGGAGGCGGCCCAATCAAACTTGGGCGGCGGGAAGGCCGCCTTCCGGCCCGGCCGCCTGTTGGCCGGCGCCGGCCTCTGA | 3788 |
| | 3 | MKEGR* | 3789 | ATGAAGGAGGAAGTAG | 3790 |
| | 4 | MPLLPAAKCSLPS* | 3791 | ATGCCCCTCCTCCCGCGCCAAGTGCAGCCTCCCTTCTGA | 3792 |

Figure 1 (Continued)

| | | | | |
|---|---|---|---|---|
| hsa-let-7e | 1 | MGDTDNAPQAEKEDGDRERAKGRTDVQRQKGGQTER DTERQQKQPRMTGAERRRERGRERERERERECGREG ERERESTHRARRRRREEGGRPARDRTGRRGGGELGKA GEERFWPRRAGERERRPRRLPASFVPSLLCVRLLWPG LPLPLPPPRGWAMEFPPLDIGQLRCRGEARPDWAGRW GEAGAGGPLLGRGLVRRPRSRRGPGRGSPGPQSRGGGD GRREESGRREGGWRGRREEGERPPCGEGGERMESARRR WGPACGPGAAEKTPSLRRGSRGSRESAEREGGGLGPAL LGP* | 3793 | ATGGGAGACACAGATAATGCCCACAGGCAGAGAAAGAGGATGGAGATAGGGAGA GGGCGAAAGAGAGGCAGCAAAAGAGAACCAAGAGAATGACGAGGACCAGAGGAGGAGGAGGAGGAGGAGAGGAGGAGAGAGGAGGAGAGGAGGAGAGGAAGAG GAGAGGCAGCCAGTGAGGCGAGGGGTCGGAGGAGGCGAGGAGCTAGGGG AAAGCCGGGGAGGAGAGCCGAGACTGGCCGAGGAGGGGCCGGCGAGCGAGCGCC GCCCCGGGCCTCCGGCTCTTTGTCCCTCTCCCGGCCTCCTCGTCAGGCTTCTCTG GCCGAGGCCCTCCCCCTGCCTGCCTGCCGGAGGAAGCCAGGCGGGAGCCGGCTGGC CTGGACCTGGGCAAGGCTCCGGCAGGGGTGAAGCCAGGCCGGGACTGGCTGGC GCGCAGCGCGGCGGGTCCAGGAGGGGAGCCCGGGCGGCGGAGCCGCAGAGCCGGAGGA GGTGACGGCGGAGGCCGCGCGCGTCGCGAAGGCCCGGGAGGATGCGGGGACGGCGG AGGAAGGGAGAGAGGCCGCGCGTCGCGAAGGCGGAGAAGGATGGAGAGCGCTCG GCGCGGGTGGGCCTCGGGGAGCGCGTGAGTCTGCGAAAGGGAGGTTGGGGTGGG GCCGCACTCCTGGGTCCCTGA | 3794 |
| | 2 | MPHRQRKRMEIGRGRKEGQMCRDRREDRRKETQRGSK SNQE* | 3795 | ATGCCCACAGGCAGAGAAAGAGGATGGAGATAGGGAGAGGCGAAAGGAAGGAC AGATATGCAGAGAGAAGGGAGGACAGGACGGAAAAGAGACACGAGAGGCAGCAA AAGCAACCAAGAATGA | 3796 |
| | 3 | MAGTAGRGEAAVRRRGEIDGERSAAVGPGLRARGG GEDPFPATREPREP* | 3797 | ATGGCGGGGACGGCGGGGAGGGGAGAGGCGCCGTGCGAAGGCGGGGGCGG AGGATGGAGAGCGTTCCCTGCGACGCGTGGGCCGGGCCCGGCCTGCGGCGGGCGG AGAAGACCCCTTCCCCGACGACGCGACCGAGCCGCGGAGCCGTGA | 3798 |
| | 4 | MGAGAGRIVAGRD* | 3799 | ATGGGGCTGGGCTGGTAGGATCGTGGCTGGAAGAGACTAG | 3800 |
| hsa-let-7f-1 | 1 | MGLRAFRGARPCIGLPATALLSLRPPRRPAPPSGSWR GALPAAYTGARAGAFPRPRRPSPRARGGYGGRGSERGSY AILPRGDSRQRYVGRMGEPCACGPRLSG* | 3801 | ATGGGGCTGCGGGCCTTCCGCGGTGCGCGCCCCTGCATCGGCCTCCCGGCCACCGCGCTG CTGTCGCTCTCCCGGCCACGGCGCCGCGCCCACCGCGTCGAGGCCGGCGAGCATTCCACGCGCGCG CCGGGCCCTTCTCCGGAGCGCGGAGTCGGCGCAGCCGAGCGCGGAGGGCGGGGTG CCGTCGCCATTTATTTCCGCGCGCCTGTCCGGCTAA | 3802 |
| | 2 | MADAAASAGPSFYFAETRGSGWAEWESRAPARACPA NAGWDWWGGLPHPAGOWPRGAGLLAEVAGARGTGE GCRVAAAGPAPTPSASRPAPHRQGGGGGGVILHIPYPALP PASIKLLGAGGRPAFRPAPVGRRRL* | 3803 | ATGGCGGACGCGGCAGCGAGCGGGGTTCGGTCGGCCATTTTATTTCGCGGAGACTCG ACCGCGCGGTGGGCAGATGGTGGGCGCAGAATGGGTCGGCCGGTGCCCGGCTA CGCCGCGGGGCGAGTGCTGCTAGCGCAAGTCGCGGAGCGGCCGGGCACGGGGAGGGGT GGGGGCCGGCGGCTGCTGTCGCGCGCCGGGCGGCTCGGCGCTTCCCGGCAGTCTC GCCGCGTGGCCGCGGGGGGGCGGAGGGGGGTCATCCCATCCCGGAGGCCCCCCC CGCTTCAATCAAACTTGGGGCGCGGGCGAAGGCCCGGCTCGGCCTGCGCCGTTG GCCGGCGCCCCTGA | 3804 |
| | 3 | MKEGR* | 3805 | ATGAAGGAGGGAAGTAG | 3806 |
| | 4 | MPLLPAAKCSLPS* | 3807 | ATGCCCTGCTCCCCGGCGGCCAAGTGCAGCCTCCTTCCTGA | 3808 |
| hsa-let-7f-2 | 1 | MKVDRTKLKKTPEAVSIQKFTLLIFSSLKNKKIFVNSSSS MLFKSHHPYTQKAVKQQLV* | 3809 | ATGAAAGTTACTTGCTTATTTTTCTCATTCATTAAACTGAAGAACAACCACTGAGGCTGAAGTATCCA AAAGTTTACTTGCTTATTTTCTCATCAAATCTCATCACCCATATATACAAAAGGCAGTAAAACAACAA CTTGTCTAG | 3810 |
| | 2 | MDSQETSGK* | 3811 | ATGGATAGCCAAGAGACCAGTGGAAAGTGA | 3812 |
| | 3 | MQKGCVV* | 3813 | ATGCAGAAAGGATGTGTGGTATAA | 3814 |
| | 4 | MCGHMERADMGSDF* | 3815 | ATGTGTGGTCATATGGAAAGAGCAGATATGGGTTCAGATTTTTAA | 3816 |

Figure 1 (Continued)

| | | | | | |
|---|---|---|---|---|---|
| hsa-let-7g | 1 | MKLTDSVLRSFRVAKVFRENSDKINCTDFSPNGETVISS SDDDISIVLYIDCQEGK* | 3817 | ATGAAGCTGACCGACAGCGTGTTGCGGAGCTTCCGCGTTGCTTAAGGTGTTCCGGA AAACTCGGACAAGATTAACTGCTTCAGATTTCAGCCCAACGGCGAGAGGGCAAGTGA GAGTAGCGACGACGACTCCATCGTGCTCTATGACTGCCAGGAGGGCAAGTGA | 3818 |
| | 2 | MTARRASECCGCGPGPESQCLPPVAQHRSLGLPSVPTSAP SLFCTRSCQGRLHPAAVQETYFFLLKKR* | 3819 | ATGACTGCCAGGAGCGCCGGTGCCCAGCACAGTCCCCTGCCCGTGGCCCAGCACCGG CCCTCCCTCCGGTGCCCAGCACAGTCCCCTGCCCGTGGCCCGAGTTCAGG CCCAGCTCTATTGCACGGTTCTGCCAGGGCGCTCACCCGGCAGCCGTCCA GGAGACCTTTTATTTTTTCTTCTTAAAAAAAAGATAA | 3820 |
| | 3 | MSSVSPERYASLAKPHLDLDL* | 3821 | ATGTCTTCGGTCCTTGAGCGCTATGCATCACTTGCCAAACCCCACTTGACCTTG ACCTTTAA | 3822 |
| | 4 | MHHLPAFTLTLTFKRPVRPPWAHQVAFSAPQAVKGAGL LRPRRTAGAAFLPPSAASALSCALSTVTSIPPWHSAHPL PLSFRPPFCRQTAWVALLSCQDLPVVPL* | 3823 | ATGCATCACTTGCCAAACCCCACCTTGACCTTGACCTTTAAACGCCCGGTCAGGCCCA CCCTGGGCCACCAGGTAGCGTTTTCAGCTCCAGCTGTCAAAGGTGCTGGTCTG CTCTGGAGGCAGGACTGCAGGGGCTGCTTTCCTCAGCACTGCACCTGCAGCGTA GCTCTCTGTGTCTCAGCTGCCTCCTGCGCCTTCTGCGTGACACTGGCTGTGGGTTGCACTTCT CCCGGCCCCCAGCTTCTGCGTCAGATTATTGTTTGTGCGCCCTTTA TAGCTGTCAGGATTATTGTTTGTGCCCCTTTGA | 3824 |
| | 1 | MAARGAAWRGGHYVRSSARASLSDL* | 3825 | ATGGCGGCGCGGGCGCGTGGCGGCGGTCAGTGTGGCGAGTAGCGCGC GAGCCCTTCCTTAAGTGAATCTCTAA | 3826 |
| | 2 | MPWLLPGGAGGSLCGMPAGDYRRRERAGGGFDSAAR VGARVPDSAAAQPPPGTRSREGRERRSSGRGGSS* | 3827 | ATGCCCTTGGCTGCTGTTTGGCGGAGCCGGCGGAGCCTCCGCGATGCCGCCGG CGATTACGGCGCCGAGAGCGGGCGCCGGTGGACAGCGCCGGCGCGGTGG CCCCGCAGTACCGGACTCGGCGCAGCGGGACGTGGGAGCAGG GAGGCGCCGAGCGCCAGCCGGTGAGCAGTCCTAG | 3828 |
| | 3 | MALAEVYYCAVGRVVTLPAVETTAQATALLVLVMLSA AEDNGWESPLFSGALPGDSPRSLGARPARPPRKPLVSHF PRRN* | 3829 | ATGGCCCTGGCTGAGGTAGTAGTTGTGTGTGCTGAGTAGTCTTGTGACATTGCCGCT GTGGAGATAACTGCTGCAAGTAACTGCCTAGTGGTGATGCTGCTAGGCGCCG GAGGCAATGGCTGCGAATCCCCTTGTTTTCCGGGCGCTGGCTAGTCAGGGGACAGCC GCGAAGCCTCGGCGCCGCCGGCCACCACGGAAACCGTTAGTTTTCACATTT TCCTAGAAGGAATGA | 3830 |
| | 4 | MAGNPLCFPGRCLGTAREASAPGRRGHHGNR* | 3831 | ATGGCTGGGAATCCCCTTGCTGTTTTCCGGGGCGCTGCCTGGGGACAGCCCCGGAAGCC TCGGCGCCGGCCGGCCACCACGGAAACCGTTAG | 3832 |
| hsa-mir-100 | 1 | MGPLIQGFHRPAGADGVRDLTMAPARSCCVLSEA* | 3833 | ATGGGACCCCTTGATACAAGGCTTTCATAGACCAGCCGGTGCTGATGGGGTCCGGGA CTTGAGAGATGGCGCCGTCGGACTTGA | 3834 |
| | 2 | MGSGT* | 3835 | ATGGGGTCGYGGACTTGA | 3836 |
| | 3 | MIFFRFWEVESTCQRLHLTH* | 3837 | ATGATTTTCTTCGTTTTGGGAGGTAGAGAGCACGGGCAGAGGTTGCACCTGACA CATTAG | 3838 |
| | 4 | MGVTVPPCLPLLYLIDKIDLLYPDF* | 3839 | ATGGGGGTTACTGTGCCCCGTGCTACCGCTCTTATCTTGATAAGGACTTGCTTT ATCCTGATTTCTAA | 3840 |
| | 1 | MTQASRGRGAHAAARPSPHRHSSMV* | 3841 | ATGACGCAGGCCTCGCTGCGGGAGCACATGCACATCTTCCCTCCACATCGT CACTCTTCTATGGTTTAG | 3842 |
| hsa-mir-10087-1 | 2 | MQPVPLHIVTLLWFRSFSRTLLPGSELAQAVTSSCRTFY LSISVLGPETRGCLLTLCNKPGHCHSEGFVIFYPF* | 3843 | ATGCAGCCGTCCTCCTCACATGTCACTCTTCTATGGTTTAGAAGTTTCAGTCGCA CACTCCTACCCGGGTCGGAGTTAGCTCAAGCGGTTACCTCCTATGCCGGACTTCT ATCTGTCCATCTCGTGCTTGGGTTCGAGACCCGGCTTACTGACCCTTTAT GCAATAAATTCGGTATAATCGGTATAATCGTCACTCTGAAGGCTTTGTTATTTTTATCCCTTTTA | 3844 |
| | 3 | MPDFLSVHLCAGVRDPRVLTDPFMQ* | 3845 | ATGCCGGACTTTCTATCTGTCCATCTCGTGCTTGGGTTCGAGACCCGGGTGCTT ACTGACCCTTTATGCAATAA | 3846 |

Figure 1 (Continued)

| | | | | |
|---|---|---|---|---|
| | 4 | MEAGHWSYRACVTSLYCQYGRMGTKKCLCSSRDTPGS SETPQLRTAECVMDFVPSRTEV* | 3847 | ATGGAGGCTGGCCACTGTTCTTACAGGGCGTGCGTGACCAGCCTGTACTGCCAGGT AGGACGCATGGGACAAAAATGCTTGTCAGTTCACGAGACACACTGGAAGCT CCGAGACCCACAACTTCGGACCGCGAGTGCGTTATGAGTTCGTCCAAGTAGGA CGGAAGTTTAA | 3848 |
| hsa-mir-101-1 | 1 | MRPGSFFFFFP* | 3849 | ATGAGACCGGAAGTTTTTTTTTTTTAA | 3850 |
| | 2 | MAEIE* | 3851 | ATGGCAGAGATAGAATAA | 3852 |
| | 3 | MATYTLWRALLRH* | 3853 | ATGGCGACGGTCATGTTGTGGCGAGCCTTGCTGCGTCATTAG | 3854 |
| | 4 | MQJAGRTKEGEPGTPGGAGGCGGGGRARGRRGARGRA PAGGGLRGACGRARLGAQSVDVRVRARAPPWSAGCCA PGPVSRRVGAGLGTREAVGRTERLRRGWPRRTRTRSRG ARPARHPHWGLGAGQAAPGAEGAPLPSA* | 3855 | ATGCAAATAGCGGGAAGAACAAAGGAAGGAGGCGGGGACCCGCGGGGGCGCAG GTGGTGTGGGGCGGGGCGGGCGGGGCGCGCGGGGCGCGCGGGGGCCGAG AGTGTGGACGTTCCGAGTTCGCGCCGTGCGCCGCCCGTGCGCCGAGGCGCTGCTGCGC TCCCGGACCCCCTCGCGGCGCGTCGGAGCCGGCGTGGGGACGGGGAAGCCGTGG GGCGCACAGAGCGGCCGTAGCATCGGCGAGCACTGGGGTCTGGGGACGCAGCCGT GGGGCTCGGCCGTGGCCACTGCGCCCAGCGCCTAG | 3856 |
| hsa-mir-101-2 | 1 | MATJAHSLSYAGCNFLRQRLVLSTLSGRPVKIRKRARD DNPGLRGMLVWAARGVGAGAEGRPS* | 3857 | ATGGCGACTCAGGCGCCACTCCTCAGCTACGCAGGGTCAACTTCTTGCCCAACGT CTGGTCCTGTCTACCCTGAGCGGGCGCCCCGTCAAAATCGAAAGATTYGGCCAGA GACGACAACCCGGGACCTCCGAGTTAACTTGTGTGGCGGCGGCGTGGGCGC GGGGGCTGAGGIGAGACCGAGCTGA | 3858 |
| | 2 | MPWGPARCWLGGSASGERVGEGRWRVASKAGGAGTV GEAGSGPEGSAQLQAALGYSSGALVYNSCTESSFTCSNK SLASPLRVPSAPLALAINLSKEKNSLLDRNMVNEPGEKH WERKVPWVGSLPCLKAVLRSSCPLGHRLFLSP* | 3859 | ATGCCGGTGGGGGCCCGCGGTGTTGGTTGGCCGGCTCGGCGTCGGCGAGCGCGT GGGGGAGGGCAGGTGGCGGCGTCGCTCCAAAGCCGGAGGGGCAGGCACAGTGGG GAGGCGGCTGGTAGTAAACAGTCGACGTTCCACGTTTACGTGAGCCTCGGCGTCTC CTCGGCGCGTCGGCGTCGCCCTTGCGCCCTTGCCCTGCCATAAACCTCA AGGAGAGAAAACAGTTGTTGACCGAAATATGGTGAATAGCGGGGGAGAGACA TTGGGAGAGCTGCCCCCCTTGGACACCCGGCTGTTCCTGTCCAAGCAGTTCTCAG AAGCAGCTGCGGGGGAGAGACATTGGGAGGAAGACATTGGGAGAAGTACCTTGGGTTGGTTCTCTGCCC | 3860 |
| | 3 | MSRGRDIGREKYLGLVLCPVSKQPSEAAAPLDTGCSCR HDFSAALTLYLGCG* | 3861 | ATGTCTCAAAGCAGTTCTCAGAAGCAGCTGCCCGTGAGCAAACAGCCGTCTTCCTGTCG CCATATTCTCGGCCGCTGCCCCACACTTGTCCTTGGGTGTGATAAAGAAATTTTAAA | 3862 |
| | 4 | MISRLPSHLSLGVDKEIFKILCLFSAVTYIDVRRTGALR* | 3863 | ATGATTTCTGTGTTTGTTTCAGCCGTGACTGATGATGTGCGCAGGACAGGAGCTTTG AGATAG | 3864 |
| hsa-mir-101-2 | 1 | MLFLHFFSSKYIAIS* | 3865 | ATGTTATTTCTCCATTTTTAGTTCAAATATAGCCATCTTGA | 3866 |
| | 2 | MCGWGMPASVIKSSFRQ* | 3867 | ATGTGTCGTTGGGAATGCCAGCTTCGTTGTATAAAGTCTAGTTTAGGCAATAA | 3868 |
| | 3 | MRKTFLYIYK* | 3869 | ATGAGAAAACCTTTTTATATTTATAAATAG | 3870 |
| | 4 | MFFH* | 3871 | ATGTTCTTTCACTGA | 3872 |
| hsa-mir-103-1 | 1 | MHRGPSSEAPQLPQHASEWSQREEGWVLVTPARRRPMAV TEMGVLGKSGSDLSRSRREGGMNSSRGLSWLFGHSQIS P* | 3873 | ATGCATCGGGGCCCCTCCTCCGAGGCCCCTCAGCTTCCGCAGATGGCCCAGAGTGG GACTGAGATGGGAAGAAGAGGGTCTTAGTCACGCAGGAGGAGCTCAGCAATGGT AAGGGGGAATGAACTCTTCGAGAGGACTGTTCATGGCTGTTGCCATTCTCAGATTT CCCCTTGA | 3874 |
| | 2 | MAVRPFSDFFLRQESWSSGHGKRYNQGSRAVLKIDP* | 3875 | ATGGCTGTTCGCCATTCTCAGATTTCCCTTGAGACAGGAAAGCTGGTCGTCAGGC CATGGAAAGCGCTACAATCAGGGCTGTGCTTAAGATAGACCCTTGA | 3876 |
| | 3 | MESATIRALELCLR* | 3877 | ATGGAAAGCGCTACAATCAGGGCTCTAGAGGCTGTGCTTAAGATAG | 3878 |
| | 4 | MLGSE* | 3879 | ATGTTAGGGGTCGGAATGA | 3880 |

Figure 1 (Continued)

| | | | | |
|---|---|---|---|---|
| hsa-mir-103-2 | 1 | MFGLSRLLSACVGERGTRRNERTGACLHGN* | 3881 | ATGTTTGGGCTAAGCGCCGCTCCTTTCCGCCTGCGTTGGAGAGAGAGGTACCAGAAGG AATGAAAGGACTGGGGCTTGTCTGCCATGGCAACTGA | 3882 |
| | 2 | MKGLGLVSMATERKRWVINPSPPSCGEGGEVGAGK* | 3883 | ATGAAAGGACTGGGGCTTGTGTCTGCAACTGA AGAAAGAGGTGGGTTATAAA TCCTTCGCCACCTCCTGTGGCGAAGGAGGGAAGTGGGAAGTGGGAAGTAG | 3884 |
| | 3 | MHWGP* | 3885 | ATCCATTGGGGGCCATAG | 3886 |
| | 4 | MDFFFNHLPFSFGEKNWSPPGLRP* | 3887 | ATGGATTTTTTTTTAATCATCTTCCTTCTCTTTTGGAGAGAAAAATTGGTCACCTC CAGGACTGAGACCCTGA | 3888 |
| hsa-mir-105-1 | 1 | MFLLPPPPSSGLL* | 3889 | ATGTTCCTTCCCCCCTCCCCAAGCTCAGGTCTCCTTTAG | 3890 |
| | 2 | MLCSCDAILGSPVGLVEAQRRHLSRETLG* | 3891 | ATGCTCTGCAGCTGTGATGCTATCCTGGGTTCCCAGTGGGCTGGTGGAAGCCCAG AGGCGGCATCTGAGCAGGAGACACTGGGGTAA | 3892 |
| | 3 | MLSWVPQWGWWKPRGGI* | 3893 | ATGCTATCTGTGGTTCCCCAGTGGGGCTGGTGGAAGCCCAGAGGCGGCATCTGA | 3894 |
| | 4 | MWYMRDLLHCQ* | 3895 | ATGTGGTATATGCGTGATTTGCTTCATTGTCAGTGA | 3896 |
| hsa-mir-105-2 | 1 | MFLLPPPPSSGLL* | 3897 | ATGTTCCTTCCCCCCTCCCCAAGCTCAGGTCTCTTTAG | 3898 |
| | 2 | MLCSCDAILGSPVGLVEAQRRHLSRETLG* | 3899 | ATGCTCTGCAGCTGTGATGCTATCCTGGGTTCCCAGTGGGGCTGGTGGAAGCCCAG AGGCGGCATCTGAGCAGGAGACACTGGGGTAA | 3900 |
| | 3 | MLSWVPQWGWWKPRGGI* | 3901 | ATGCTATCTGTGGTTCCCCAGTGGGGCTGGTGGAAGCCCAGAGGCGGCATCTGA | 3902 |
| | 4 | MWYMRDLLHCQ* | 3903 | ATGTGGTATATGCGTGATTTGCTTCATTGTCAGTGA | 3904 |
| hsa-mir-106a | 1 | MGGGE* | 3905 | ATGGGGGGTGGCGAATAG | 3906 |
| | 2 | MSCLMNC* | 3907 | ATGTCTTGTTTAATGAACTGCTAA | 3908 |
| | 3 | MSLLGSYPYLFPLIG* | 3909 | ATGTCACTCTTGGGAGTTACTTCTACTTGTTCCTTTAATAGGATGA | 3910 |
| | 4 | MFSSPTFFCLSNQDT* | 3911 | ATGATTTCATCTTTTCATCTTTTCAACCTTCTGTCTCTCCAACCAAGACACATAG | 3912 |
| hsa-mir-106b | 1 | MSGSFPLEDRMENWEIMAVLESRQEDGESRAACPALRPR NKRTRYRWPFFKSDSPPPAPARTAGNPAPALPRPEIPFKRP HRLPVTHSRPAR* | 3913 | ATGAGCGGGTCCCCCTTGGAGGACAGAAGTGAAGAATTGAAGAATCATGGCCGTTCT GGAGAGTAGACAAGAAGACGGCGAAAGTCGGACTGCCCGCCCTGCCGCCCTCCGGA ACAAAAGAACGCGTGTGCGCTGKGCCTTTAAGAGCGATTCTCTCCGCCGCCGCCAG GTCGGACCGCGGAAAACCGCGCTGCACTACCCGCCCGGAGATTCCCTTCCGAC GCCGGACCGCCACCGCCCGTCCGTCACTCATTCTAGGCGCCGCACGGTGA | 3914 |
| | 2 | MALKDYALEKGTGLRAREGVLRGEPPGEHLLV* | 3915 | ATGGCACTGAAGGACTACGCGCTAGAGAAGGGTACGGGTCTACGAGCCCGGGAGGG CGTCCTGCGCGGGAGGGAGCCTCCCGGGGAAACACTGTTGGTGTGA | 3916 |
| | 3 | MLKKS* | 3917 | ATGTTGAAGAAAAGTAG | 3918 |
| | 4 | MANGWIGSRPGRRNPEL* | 3919 | ATGGCCAATGCTGGACTGGCTCCCGCCTGGCGGAGGAATCCGAGCTGTGA | 3920 |
| | 1 | MTILQRYLAHWGQD* | 3921 | ATGACCCTTGCAAAGGTATCTTGCTCAGGATCTGGGGACAGGATTAG | 3922 |

Figure 1 (Continued)

| | | | | | |
|---|---|---|---|---|---|
| hsa-mir-107 | 2 | MLKLVGGGGQDWACSVAGTSLGGEEAAPEVARPGD QGKAGGGSPGWGCAGIPDSAPGAGVLQAGAVGPARGG QGAEEVGGESAGGGEERRVRHPQAPALRLLNRKPQGGS GEJKTPENDLQRGRLSRGPRTAPPAPGMGJDRSGQQERS VPHSPGAPVGTSAAAVNGLLHNGFHPPPVQPPHVCSRG PVGGSDAAPQRLPLLPEIQPQPLLPQHDSPAKKCRLRRR MDSGRKNRPRKSRWEGSAGARQTQRAGPGTGSG* | 3923 | ATGTTGAAACTCGTCGGTGGCGGTGGCGGGCAGGACTGGGCATGCTCAGTGGCGGG GACCAGTCGGGAGGTCTGGGAGGCGAGGAAGCCGCGTTTGAAGTCGCGCGGGATCCAGG GGAAGGCGGGCGGCCGRGAGCCCCGGCTCGGGGTCCGCGGGGATCCCGATTCCGCG CCCGGGGCTGGCCTGCTGCCCAGGCCGGCCGTGGGGCCGGCCGGGGCGGGCAGG GCGCAGGAGGAGGTGGGGAGTCGGCAGGAGGTGGCCAGGAGGGGAGGAGGCGCCGGTTCGCCA TCCCCAGGCGCCGGGCTCTGCGGCTGCTGAATCGGAAGCCGGCAGGGAGGATCGGGG AAATAAAGAGCCGAGAATTGACCTTCAGGGAGGCCCTGAGCCGGGCCCCGCG ACAGACCTCAGGCCATGGCGCTCCCGTGGCACCGGCAGGGAGCCAGCAGAGGCGCCCGT CCCGACACTCTCCAGGGCCCCCTGGGCACCGGCACCAGCCGCCGCCGCCGTTGAACGGGCTGC TGCACAACGGCTTCCATCCGCGCACAGTTCAGCCGTCAGCCAGGTC CAGTGGGGCAGCGGCAGGAGGCGCGCCCAGCGCCCAGCATGACCTCCCGGCCTGCTGCCAG CGCAGCCACTGCTCCCTCAGCACGTCCCGGGCCAGAAATGCCGCTGCGGAG GAGGATGGACTCGGGAGAAGAACAGCCGCCCTGGTGGGGAGAAGTCCCGCTGGGAGGGGAGC GCGGGCAGCCAAGGCAGGCCAGCGTGCGGGGCCGGGACTGGGAGCGGGTGA | 3924 |
| | 3 | MLSGGDQSGRRGSRV* | 3925 | ATGCTCAGTGCCGGGGACCAGTCTGGCAGGCGAGGCGAGAAGCCGGTTTGA | 3926 |
| | 4 | MTSSEAA* | 3927 | ATGACCTCCAGCACGAGCGCCCTGA | 3928 |
| hsa-mir-10a | 1 | MIPSGLGTPGRRRVAGRGEVTLATCGCQEKAAGKPRKID PGAQGRWLSSRAAPALILLCVLLFVSFWAVKGRGSLPL R* | 3929 | ATGATTCCTAGCGCTAGCAACCTGTGGCTGACGCCTGGACGCTGGAGGTGGCTGGGAGGGCGA GGTCACGCTAGCAACCTGTGCAGGAGAAGGGCGGCTGGGAAGCCACGGAAAG ACCCGGAGCGCAGCGGAGGTGCTGGTCGCCGCCGCAGCCCTGCTCTTATTTTAC TATTAGTCGTGTTGCTGTTCGTATCCTTCGGGGCGTGAAGGGAGAGGCAGCCTCC CGCTCCGGTGA | 3930 |
| | 2 | MRVAVRILLGGEGERQPPAPVKPVLGVAHKPCSPSQAA GGVRGVRRLGGHGRW* | 3931 | ATGCGTGTTGCTGTTCGTATCCTTCTGGGCGGTGAAGGGAGAGGCAGCCTCCGCT CCGGTGAAACCCGTTCCTGGAGTCGCGCCATAAACCCTGTTCCATTCCAGRCGGCT GGAGGGGTGAGGGGTGCGGCGCCCTTGGTGAGTCGGTTCCTGGGAGACCGTAA | 3932 |
| | 3 | MPTGWTGFRELAS* | 3933 | ATGCCGACGGGTTGGACGGGTTGGACGCCTGAGTTGA | 3934 |
| | 4 | MGWGRGLDRWSGSWRP* | 3935 | ATGGGGTGGCGGGAGGGCCTGACGTTGGAGTGGTCCTGGAGACCCTAA | 3936 |
| hsa-mir-10b | 1 | MSGSLRPRVSAAGQRLVDYSRRPDRPPPVARQPSGKNR PLPAPQHATKKPGAPTPLGSSVRLLPYISRGSGGRSLSKPL PPITSFLGRPLGPGVESGWVQKSKGAVLFQKF* | 3937 | ATGAGCGGGTCTCTGCGTCCCAGAGTGAGCGCAGCGCCTAGTGGATTA CAGCAGACGCCCGGACGCCCGCGTTAGCTCGGCAGCCTTCGGCGTAAGAATC CAGCCCTGCCGCTGTCCCAGCATGCACCAAGAAGCTGGGGCGCCGACCCCTTGG GCAGCTCAGTCGGTGCTCCCACATTCCAGGAGGCGTCCTCGTGTCTA AGCCCCTTGCCCAATCACTTCGTTCTAAGGGGCAGTATTATTTCAAAAATTCTGA | 3938 |
| | 2 | MPPRSLGRRPPWAAQSGCSPTFPGEVGGRCLSPFPQSLR S* | 3939 | ATGCCACCAAGAAGCTGGGCGCCGACTCCCTTGGCAGCTCAGTCGGCTCC CCTACATTTCCGGGGAAGTGGGGGTCGCTGCCTCTAAGCCCTTCTGCCAATCACTT CGTTCCTAG | 3940 |
| | 3 | MESPSILP* | 3941 | ATGGAGAGCCCCTCAATCTACCCTAG | 3942 |
| | 4 | MCLVFESRL* | 3943 | ATGTCTTGTGTTTGAATCTAGCCTTTAG | 3944 |
| | 1 | MVRERSPRGPLGQGRVFGMLGRVYKNCKGEAGS* | 3945 | ATGGTTCAGGGAGCGCAGCCGAGGGCCACTGGCCAGGGCGCGTTTGGGAT GCTTGGCCGGGTATATAAGAACTGCAAAGGTGAGGGGCCTGA | 3946 |

Figure 1 (Continued)

| | | | | |
|---|---|---|---|---|
| hsa-mir-1-1 | 2 | MAWGLRGIWAGGAIHLPLRNKAPAAGRGAKLTLNLQYPPLRCWWGAGHPELSGGEAAPGIRDSALLQLSQPRQCQEAFTGAGRGGGRGAHVGGD* | 3947 | ATGGCATGGGRGCTTCGGGCTRGGCTGGAGGCGGATTCACCTGCGCTCCGCAACAAAGCCCCGGCCAGCCGGCCGTGGGGGCTAAACTTACCTTGAACTTGCAGTATCCCCACTGAGGTGCTGCTGCGGCAGGATTCCGAGCTCCGAGCTGAGCGCGCGCGAGGCTGCGCCGGCCGGAGGACTCGCACTTCTGCAGCTCTCCCAGCCACGCAGGTGCAGGAGGCGCAGGGGCGGGACTCCGGAGGGGCAGGGCGAGGGCGAGGTGGGGGCACATGTGGCGGAGACTTTACACAGRGGCAGGGCGGCGAGGTGGGGGCGGATTCACCTGCCGCTCCGCAACAAAGAG | 3948 |
| | 3 | MGASGLGWGRDSPAAPQQSPGSRAWG* | 3949 | ATGGGGCTTCCGGGCTGGCTGGGCGGGRDSPAAPQQSPGSRGGGCTAA | 3950 |
| | 4 | MWAETRGASGRAALVVGVCAGPCWGA* | 3951 | ATGTGGGCGGAGACTAGGGAGGGGTTCGGGGAGAGCAGCCCTGGTGTGGGTCAGCCTGTG | 3952 |
| hsa-mir-122 | 1 | MAVFP* | 3953 | ATGGCAGTCTTCCGTGA | 3954 |
| | 2 | MYSLGDLSSLPRWPPWLPAGRTPPLSRGMDFPILLSVFDQRWC* | 3955 | ATGTATTCACTAGGTGACCTGTCTTCTCTGCCTCGGTGGCCTCCATGGCCTGCTGCTGGCCGCACACCCCACTCAGCAGAGAATGGACTTTCCAATCTGCTGAGTGTGTTTGACCAAAGGTGGTGCTGA | 3956 |
| | 3 | MAACWPHTPTQQRNGLSNLAECV* | 3957 | ATGGCTGCCTGCCTGCCGCACACCCCACTCAGCAGGAATGGACTTTCCAATCTTGCTGAGTGTGTTGA | 3958 |
| | 4 | MRLIRKRKNCLLLNPGSHKGRGERPKATEAVEGAILPATGRALD* | 3959 | ATGCGACTTATCAGAAAGAGAAAGAATGTTTACTTTTAAACCTGGATCCATAAGGGAGAGGGGAGAGGCCTAAAGCCACAGAAGCTGTGAAAGGCGCCATCCTGCCTGCCACAGGAAGGGCCTTGGACTGA | 3960 |
| hsa-mir-124-1 | 1 | MVGVLNQATASVVFPQCKYPSLREETLSEW* | 3961 | ATGGTGGGAGTCTTGAACCAAGCCACTGCCAGTGTAGTTTTTCCACCACAAAAGTATTTTAGTTTGAGGGAAACGTTATCAGAATGGTAA | 3962 |
| | 2 | MVSFSLKDSPNDGFPQSGMVFRN* | 3963 | ATGGTAAGTTTTCCCTGAAAGACAGCCCAAATGATGGCTTTCCAATCAGGCATGGTCTTCAGAAATTAA | 3964 |
| | 3 | MMAFSNQAWSSERKHQLQAMVYFLRFFFFRLLLLLFPLLLLFLFPPSLSD* | 3965 | ATGATGGCTTTTTCCAATCAGGCATGGTCTTCAGAAATTAAACATCAGTTGCAGGCAATGGTTTATTTCTCCTTATTTTCTTTCCTCTCCTCTTCCCCTCCTCCTCCTCTGATTAA | 3966 |
| | 4 | MASKREGPRPGHPSCSHSCWVGASAATLAGCVVSAGLLLAGGACSPHL* | 3967 | ATGGCCTCGAAGGAGAGGCCTCGCCGGGTACCTCTTGTGCAGCCACTCTGCTGGGTCGGGGCGTGTGTGCAGGGGCTGCTTTAGCTGGCGCAGGGCTTGTTCTCCCCATCTCTAG | 3968 |
| | | MTTGLTPHPSAGCPEQSWTVFLAPSPEGRPSWETGFSSNSN* | 3969 | ATGACGACTGGCCTGCCTGACACCTCATCCATCAGCAGGGTGCCAGCAGGGTGCCAGAGAGTTGGACAGTTCCTTGCTGCATCTCCAGAGGGGAGGCCAGTTGGGAAACAGGATTCTCTTCCAATAGCAATTAG | 3970 |
| | 2 | MRRRNPGLRGLIRNFVVSNKLWPLEESTPWLLWL* | 3971 | ATGAGGAGAAATCAGGTCTCCGTGGCTGATTAGAAACTTGTTGTGTCAAATAAACTTTGCCACTGGAGGAAAAGTACCCATGGTTGCTCTGGCTTTAG | 3972 |
| | 3 | MYALALERSVQGFSIFFSPLSLSLPLSLSLPSSLVSKGASGQR* | 3973 | ATGGTTGCTCTGGCTTTAGAAAGATCTGCCAGGCTTCCAATCTTCTTTTCACCCTCTCTCTGCCACTTTCCCCGACATTTTCCCTCCTGCCATTTAAACAGCGCTGA | 3974 |
| hsa-mir-124-2 | 4 | MAGDPVRTKPCAGLLWQAEKGALGPGPQALTRTHPADRLFIRTALQSPRLPLFAEQWRFRRESKALFRFLSDVLHLGKHRPPLFPPTFSLLAPKAVRFRGNFCEFRACSTNTSVRRRRDRWKKESPRDPCVCVCVCVCVCVCVMHLEDGSCL* | 3975 | ATGGCCGGTGACCCAGTAAGGACTAAACTTGCGCTGGTTATTGTGGCAAGCTGAGAAAGGGCTTTAGGCCCGGACCCCAGTGCCCAGCCACTGACCGCACATCCCGGGATCGCCTATTCATTCGCACAGCCCGGACCCCAGTCGCCCAGCCACTGACCGCACCATTGTTGCTGAGCAACAATGGAGATTTCGCAGGGAAAAGTAAACTCTTTCAGATTTCCCGACATTTTCCCTCCTGCCATTTAAAGCTGTTCGTTTTGGGGAAACCTTCGTGAGTTGCGCCTTGTTGACCAACACAGTGTAGGAGAGGGCGAGACCGGTGTGTGTGAAAAGAGAGAGCCCAGAGATTTCCGTGTGTGTGTGTGTGTGTGTGAATGCATTTAGAGGACGGGAGCTGCCTCTAG | 3976 |

Figure 1 (Continued)

| | | | | | |
|---|---|---|---|---|---|
| hsa-mir-124-3 | 1 | MADKREGEGVGVGVSARVSSPPPAPAPAGAT* | 3977 | ATGGCGGACAAGAGAGGAGGGGAGGGGTGGGGGTCTCGGCCCGTGTTCTCCCC TCCTCCGCTCCCGCCCGCCGGAGCCAACCTGA | 3978 |
| | 2 | MKPTKLAGPPKRSPPERTLRGGRGRGCRRAPLPARLLP AGSAPKPWTALPPARLAGGRCTPGVEVGSRGPRSSLLRT PRGAGPP* | 3979 | ATGAAACCTACGAAGCTCGCGGGCTCACCGAAAAGTTCCCAACTGGAGCGGACTCT GGGGGGCCGGGGCAGAGGCTGCAGGCGGGCCTTCCCCTTCCGCGCGGCTCCTAC CGGCTGGCTCCGCCCCAAGCCTGACGGCGCCCTTCCCAGCCGCTGGCTGGGG GCGCTGCACCACGGGTGAATTGRAGCCGGGGACCCGATCGCTACTCAGG ACTTCAAGAGGGGCCGGTTCTTCTAG | 3980 |
| | 3 | MYKNLG* | 3981 | ATGTACAAAAATCTAGGGTGA | 3982 |
| | 4 | MCGAKESFPLEWEQAPRSWNPEASWTRPGS* | 3983 | ATGGGGGGTGCTAAGGAGTCTTTCCCCTTAGAATGGGAACAAGCTCAAGGAGCTG GAATCCTGAGGCGTCCTGAATCCGTCCAGGAAGCTAA | 3984 |
| hsa-mir-124-3 | 1 | MAQGLGWP* | 3985 | ATGGCGCAGGGCTGGTTGGCCTAG | 3986 |
| | 2 | MGTEACRPRRPALLAV* | 3987 | ATGGGGAACAGAGATGCCTCGCGGCCGCGGCCTGGCTCTTGCAGTCTAA | 3988 |
| | 3 | MGAGKDIL* | 3989 | ATGGGGGCGGGAAGCGACGACCTTTAA | 3990 |
| | 4 | MCSWRGCARGCRRAM* | 3991 | ATGTGCAGCTGGAGGGCTGCGTGCGTCAGGAGGGCCATGTGA | 3992 |
| hsa-mir-125a | 1 | MGIDTFNAPOAEKELDGDRERAKGRTDVQRQKGGQTER DTERQQKQPRMTGAERRRERGRERERREGGREG ERERESTHRARRRRREEGGRPARDRTGRRGGEGELGKA GEERDWPRRAGERERRPRRLPASFVPSLLCVRLLWPG LPLPLPPPRGWMEFFPLDLGQLRGRGEARPDWAGIRW GGAGACGPLGRGLVRRPRSRRGPGRGSPGPQSRGGGID GRRESGRREEGWRGRREEGERPPCGEGGERMESARRE WGPACCGPGAAEKTPSLRRGSRGSRRESAEREGGGHLGPAL LGP* | 3993 | ATGGGAGACACAGATAATGCCCACAGGCAGAGAAAGAGGATGGAGATAGGGAGA GGGCGAAAGAGAGGAGCAGATGTGCAGAGACAGAAGGGAGGACAGACGAAAGAGA CACAGAGGAGCAGCAAACCAAGAGAGAGCAGAAGAATGACAGGAGCAGAGGAGGAGGAA GAGAGAGGAGAGAGGAGAGAGCAGAGGCGCACAGACGAGAGGAGCGCAGAAGAAGAGG GGAGGGAGGAGGCCAGCGAGGGACAGAGGGTCGGAGGCCGAGAGGGAGCTAGG AAAGCCGGGAGGAGCGAGACTGGCCGAGAGTCCTTTGTCCCTTCCGGCCTCTGTGCTCAGGCTTCTCTG GCCCCGGCCCTCTCGGCCTCGGCCTTTGTCCCCTCTCCGGGCGTGGATGGAATTTTTTCCC CTGGACTTGGGGCAGTCTCCGGGCCAGGGCAGGGAAGCCAGGCCGACTGGGCTGGGCG GGTGGGGAGGGCCGGTCCAGGGAGTCCGGGGCGGAGGTCCAAGGGCGGCTGGCTGTCCGACGCC GCGCAGCGCGGGCGGGGTCCAGGGAGTCCAGGGGCGCGAAGGGCCGGCGGGAGGCCCGAGAGC CGGAGGA AGGAAGGGAGAGGGCCGCCTGGCCGTCCGGAGGGCCGAAGAGGATGGAGAGCGCTCG GCCGGTTGGGCCTCCGCCCGGGAGCCGTGAGTCGGAAAAGGAGGGTGGGGGCTGG GCCGCCACTCCTGGGTCCGTGA | 3994 |
| | 2 | MPHRQRKRMEJGRGRKEGQMCRDRREDRRKETQRGSK SNQE* | 3995 | ATGCCCCACAGCCAGAGACAGAAGGCAGAAAGAGGATGGAGAGGGCGAAAGGAAGGAC AGATGTGCAGAGACAGAGGGAGGACAGACAGAGGGCGAAAAGAGACACAGAGAGGCAGCAA AAGCAACCAAGAATGA | 3996 |
| | 3 | MAAGTAGGGEAAVRRRGEDGERSAAVGPGLRARGG GEDPFPATREPREP* | 3997 | ATGGCGGGGACGGCGGGAGGGGAGGAAGGGGAGGCCGCCGTGCGCGGAAGGCGGGGAG AGGATGGAGAGCGCTCGGCGGCTGCGAGCCGGGAGCCGCGCGGAGCCGTGA AGAAGACCCCTTCCCTGCAGCGGACGCGCGGAGCCGCGGGAGCCGTGA | 3998 |
| | 4 | MGAGAGRIVAGRLD* | 3999 | ATGGGAGCTGGCGCTGGTAGGATTGTGGCTGGAAGAGACTAG | 4000 |
| hsa-mir-125b-1 | 1 | MVPQEAVRAPLRFEWVSSERYSSLHFYSLRILLLGLLI* | 4001 | ATGGTGCCACAGGAGGCTGTGCGGGCCCCGCTCGCTTCGAATGGGTGAGTTCAGA ACGCTATTCGTCTTTACACTTCGTCTATAGCCTCCGAATCCTACTTCTTGGTCTTCTCCTTT GA | 4002 |
| | 2 | MGFRTLFVFILL* | 4003 | ATGGGTGAGTTCAGAACGCTATTCGTCTTTTATACTTCTATAG | 4004 |
| | 3 | MFPACGILALGERDASYFLFSHLC* | 4005 | ATGATTTTTGCATGGGCATACTTGCCCTGGGGAAAGAGATGCCTCCTATTTTCTC | 4006 |
| | 4 | MRHTCPGGKRCLLFSLQSFVLVVN* | 4007 | ATGCGGCATACTTGCCCTGGGGGAAAAGGATGCCTCCTATTTCTCTTCAGTCATTT GTGCTAGTCGTAAATTAA | 4008 |

Figure 1 (Continued)

| | | | | | |
|---|---|---|---|---|---|
| hsa-mir-125b-1 | 1 | MGPLKQGFHRPAGADGVRDLTMAPARSCCVLSEA* | 4009 | ATGGGACCCTTGATACAAGGCTTTCATAGACCAGCCGGTGCTGATGGGTCCGGGACTTGACGATGGCGCCGCTGCCTCGTTCCTGTTGTCTATCTGAGGCATGA | 4010 |
| | 2 | MGSGT* | 4011 | ATGGGGTCCGGACTTGA | 4012 |
| | 3 | MIFPRFWEVESTGQRLHLTH* | 4013 | ATGATTTTTCTTCGTTTTTGGGAGGTAGAGAGCACGGGGCAGAGGTTGCACCTGACACATTAG | 4014 |
| | 4 | MGVTVPPCLPLLYLDKDLLYPDF* | 4015 | ATGGGGGTTACTGTGCCCCCGTCACCCCTGCTTATCTGATAAGGACTTGCTTTATCCTGATTTCTAA | 4016 |
| | 1 | MHLLCPCCRKEPADWPLSAAHSTGWL* | 4017 | ATGCACCTATTGTGTCCCTGCTGCAGAAAGGAGCCTGCCGATTGGCCACTGTCTGCAGCACATAGCACTGGCTGTATAA | 4018 |
| hsa-mir-125b-2 | 2 | MITAFFLQGGWRESGEGRGGVSSTVKAAQIFFLSLSLPLHRLFLFHALSHFA* | 4019 | ATGACTGCATTCTTTTTGCAAGGTGGGTGGAGGGAGAGCGGGAAGGAGGGGTGTCAGCTCAACTGTACACAGATGTGCCATCTCTCTGCCTCTCCATAGATTGTTTCTGTTTCATGCCCTGTCTCATTCGCATAG | 4020 |
| | 3 | MPCLISHS* | 4021 | ATGCCCTGTCTCATTCGCATAGCTAA | 4022 |
| | 4 | MLKIPCLNL KNMDSAVIRNLVRV* | 4023 | ATGCTAATTAAGATCCCTTGTCTTAACCTGAAAATAATGACTCGGCTGTAATTAGAAATCTCGTGAGAGTTTAA | 4024 |
| hsa-mir-125b-2 | 1 | MVCERISVCLGRKLFDLQKSQKTSR* | 4025 | ATGGTTTGTGAAAGAATATCTGTGTGCTTAGGGAGGAAAACTTTTTGATCTGCAGAAAAGCCAGAAGACATCTAGGTAA | 4026 |
| | 2 | MFTFVFVEVQNVLJTVCLFFVCLFKS* | 4027 | ATGTTCACTTTTGTAGAAGTTCAAAATGTACTGACGATTGTTTGCTTATTTTTGTTTGTTTGTTTAAAATCTTAA | 4028 |
| | 3 | MLLWKEY* | 4029 | ATGTTGCTTGGAAGGAATATTAA | 4030 |
| | 4 | MRPLCT* | 4031 | ATGAGGCCCTTGCACATGA | 4032 |
| | 1 | MLLLDSSCLIFLLLWLF* | 4033 | ATGCTCCTAGACAGCAGTTGTCTGATATTTCTCTTTGTGTTGTTTAG | 4034 |
| hsa-mir-125b-2 | 2 | MDMKSEESDHRRKPQVKIKNKEQRFTVFKEKQHSFDCVLL* | 4035 | ATGGATATGAAAAGTGAAGAAAGTGATCATAGGAGAAAACCATTCAGGTAAAAATAAAAAACAAAGAGCAAATAAGATTTACTGTTTTAAAGAAAAACAACATTCTTTGACTGTGTTTGTTATAA | 4036 |
| | 3 | MSVTVEILLMVFI* | 4037 | ATGAGTGTAACTGTTGAAATTTTATTGATGTTTTCATTTGA | 4038 |
| | 4 | MCAMTYLCEKFLVVNWAVCVPLNICLCIHTLKIGAIRFTRKLYRERKKLYFLICCTI* | 4039 | ATGTGTGCTATGACCTACCTTTGTGAAAATTCTTGTGGTCAATTGGGCAGTTGTGTCCCATTGAAAATATGTCTGTGTATCCATACGCTAAGATAGTGCAATACGTTTACTAGAAAAGCTTTATATGGAAAAGAAAAAATTATTCTTATTGTGTACCATAA | 4040 |
| hsa-mir-125b-2 | 1 | MLCLASRCVSVCLCARACSLGHPCLAEGRGWRVSAWRVKASQSVRSKGTLESN* | 4041 | ATGCTTTGCCTCGCCTCGCTGTCTATCGTGAGGGGAGGGGTGGCGTGAGTGCCGTGGAGGGTATCGGGCATCCGTGTCTAGCGCAGGGAGAAGCAAAGTACGTTGGAGAGCAACTAA | 4042 |
| | 2 | MPVCARVLARASVSSRGEGVACECVEGKSQSVSEKQRYVGEQLKSD* | 4043 | ATGCCTGTGTGCGCGCGTGTTAGCCGCGTGGAGTGCGTGGAGGGTAAAAGCCAGTCAGTCAGTGAGAAGCAAAGGTACGTTGGAGCAACTAAATCTGACTGA | 4044 |
| | 3 | MYSLRRMGLRDGGHMLMSFLWRGEIFHSDNWLNAMVKNCKAIFSFREKHGLRSKGCFIFSLFVSAAFLFFWFLFFNYLF* | 4045 | ATGTATTCCTAAGGAGGATGGGATGGTTCCGTGATGGCGGTGTATAATTATGTAAATGTCATTTTATGGAGGGTGAGATTTTCATTCTGTCGATAATTGGTCAATAAGTCAAAAATTGTAAAGCCATATTCAGTTTAGGAAAGCATGGACTAGACTAAGGGCTGTTTATTTTTCGCTGTTTTGAGTGCTGCTTTTTGTTTTTGTTTGTTTTAACTATTATTTAA | 4046 |
| | 4 | MGV* | 4047 | ATGGGGTGGTATAA | 4048 |

Figure 1 (Continued)

| | | | | |
|---|---|---|---|---|
| hsa-mir-125 | 1 | MSGEGDTQMQSRWGPAKKPAHKAMDSSTPSAGAVGSPRKGDSCGQGKGEGSPGRPPRLRRPDSSPGPPFSTLEQAASTCEPAASSENGSPSTQRVSLWDVGQGPEQAGRGERKGWGPSLLPAQTLAREQTAPLPAGTPAWQLPPAPVGSGTSSDGKVPPHPWLTEPARPRPGGARGKQEAPSLPHSASLPPPAPPAARLPRPRLVPLCLAPPEMPRLASARGLVCPLLGLQRPKAPW* | 4049 | ATGTCAGGAGAGAAGGGGACAACTCAGATGCAAAGCCGGTGGGGACCTGCCAAGAAGCCAGCCCACAAGGCCATGGACTGCTCCACGCATCAGCTGGAGCAGTGGGGCAGCCCAGGAAGGGAGAGCCATGGAGCGGGAAGGCGAGGGCTCCCGGGACCCCCGAGGGCTCAGGGCCCGGACTTCAGGGAGCCCCTGAGCCCCTGAGCTCCAGTCTGCCTCCTGTTTCCACCCTGAACAAGCGGCTTCCACCTGTGAGCCAGGCAGCTGCTCTCTGAAATGAAGCCCTCAACTCAGAGGGTGTGCTCCTCGGGACCCTCACTCTCCCTGCCACTTCCCTGCCCAAACCCTCGCTGGGAGCCAGGCAGACGGCTAAAGGCTGGGACCTGTGGTCAGGGCGACCCTCAAACCCTCCTCAGCTCCCAAGGCTGGGGACCACCCTGCCCCCGGTCTGGGACCCCTGCCAGCCCCCATCGGTGCTGACAGAGCCCAGTCCGAGGCTGGACCAGCCAGCCCACCCATCCTCCTGTCCACCACATCGTGGTGAGAGCCAGCCCGTCCGAGGCAGCCCTGATGGGAAGGTTCCACCACATCGTGGTGAGAGCCCATCCTCCTGCCCTGATGCCTCTGAGCCCCGGCCTCCGACCCGGCCGCCTCCAGGGGCTTAGTCTGCCCTCTGTCTCGCCCACCTGAGATGCCCCAGCTGCCTCTGCCCGCCAGGGGCTTAGTTCTGCCCTCTCCCTGGGCGCTTCAGAGGCCAAAGCCACCCTGGTGA |
| | 2 | MEAPQLRGCRSGTWVRGRSRQGEVRGKAGDPHFSLPKPSLGSRRLLCPQAPLPGSSLQPPSGPGRPLMGRFHHIRG*PSLGSRRLLCPQAPLPGSSLQPPSGPGRPLMGRFHHIRG* | 4051 | ATGGAAGCCCCTCAACTCAGAGGCTGTCGCTCTGGGACCTGGGTCAGGGGTCGCGGAGCCAGGCAGGAGAGGTGAGAGGAAAGGCTGGGGACCCCCACTTCTCCCTGCCAAACCCTCGCTCGGGAGCAGGCGACTGGGGACCTGGGTGCGGGAGCCAGGCAGGAGAGAGGTGAGAGGAAAGGGCTGGGACCCCACTTCTCCCTGCCAAACCCTCGCTCGGGAGCAGGCGACTGGGTCCGGGACTTCCTGGGACTTCCCTGCCCTGCTGCAGGCACCCTGCTCTGCCAGCTCCCTCCAGCCCCGTGGGGTCGGGACTTCCTGGGAGTCCAATGGGAACCAGGACAATGGGAAACTGAGGCCTGTGTGGGGCACAAAGCTGGTGA |
| | 3 | MALLTRETMGKLRPVWGTKLGPELQLPAPAGPPPLTPPQAG* | 4053 | ATGGCCCTGACCAGAGAAACAATGGGAAACTGAGGCCTGTGTGGGGCACAAAGCTGGGACCAGAGTTCCTGCCTCGGCACCGCCCTCCACCTCTGACACCACCCCAGGCAGGGTGA |
| | 4 | MRKTGAGLGVATILSHQVSPSVLGP* | 4055 | ATGAGGACAAGGCGCAGGCCTTGGGGTTGCCACACTCTCCCACCAGGTCTCCCCCTCTGTGCTGGGCCCCTGA |
| | 1 | MGAGRGRQVGRGRGRGGGAGLGAPTARARAAVAAARARPGSGCECGASGARRGRGPVAARACSRACGPAEPPGAGNLAARGAGHGSGTRQRDRWGRGRSGPGRPRLGRAGPGEWAQRPREPAPPAGGGRAGGAAGRAGVAAAPRPTRDSAPRGPACAACSAPREPRSQQRGWEGAAGRSVSLRLCALPRGPRGPQPCSRREGSASACGAARPLPLRTRPLAGGGCGAAAGGQVGREPVGAGGTGTGLLVHLAPPPPRPAPLGRGRGPPRGNGACSTGSESTTGFLWPRENMTFKN* | 4057 | ATGGGGGCCGGGCGCGGCCGCCAGGTGGGCCGCGGCCGCGGGGGCGGCGGCGGGGCCCTGGGGCTCGGGGCCCCCACGGCGCGGGCGCGCGTGGCGGCCGCGCCCGGATCCGGCTGTGCGGCGTGAGTGCGAAGCCGGGAGCCGGAGCGCCCGGGGCGGGGAACCTGCCCGCGGCGGGGAGCCCGGGAGGCGGCGTCCGGGACGCAGAGGCAGGCCGACGCTGGGGAGGGCGGGGTGAGCGCCGGTCGGGCGTCGGGCGGAGAATGGCGGGCCCAGCGGCCCGAGCCCGCCACCGGCCGGGGCGGACTCAGCGGGCGCGCCCGGCCTCGGGGCCCCAGCGGAGAACCCCGGCCCCAGAACCCCGAGCGCCGACTCAGGCGGCTCGGGGAGGGCCCAGCGAGGGCCCGAGCCCCAGGCCAGCCCGCGGAGCCCCAGTGCTCTCGCGGGACCAGCCAGGCCGCTGTCTCCGCGGTGGGGGCTCGGGGGGCGGCGCCGAACCCCGGAGCCTGGGAGGAGCCCGGTGGCGCTGGGAGCAGGGCTGACCGGACTGTGCTGCCACTGGTGGGGAAATGCCGGAGCCCGGCCGCCAGTGCCCGCCCTCGGGGCCCCCCGAGGGGTTCCGCGGTGGGGCTCACGGGGGCTTCCCCAGCCGGGAAAATGGCGCTGGGACGCCACCCCTGGGCGGCGGCCGGGTCCTGGGGCACGGGTCGGGACTGTGCTCGGTCACCTCGCTGTCCTTGCAGCACCGGCTCGGAGAGCACCCACGGGGCTTCCTCTGGCCTCGGGAAAACATGACTTTCAAAAATTGA |

Figure 1 (Continued)

| | | | | | |
|---|---|---|---|---|---|
| hsa-mir-126 | 2 | MGPAAPGTGSPCRRRAGGRRGGEGERGRRGPSSDPARLS ASGPSLCRLLRPPRTPEPAARLGGGGQVRLAPPLRPPS WAPRSPALLPPRGVRQCLRRSQAPPSADPASRGWGLRG CCRAGGEGAARGRWGHGDRTACiPPGAAAPSPPGTPGSR PWPPPGKWGHQHRLGEHHGLPLASGKHDFQKLSLHLAP LPVQATLRNCGGELCQYVWGAMRSGRFAYPQARPGIP LPTSSRRAAALPLPSRVPLPNVPRLRVLP* | 4059 | ATGGGCCCAGCGGCCCCCGGAACCGGCTCCCCCTGCCAGCGGGGGGCGGCCGGGCG GCGCGCCGGGGAGRGCCGGGGTCCGCCCCCTTCGCGCCCCCGACCGGGCGACTCA GCGCCTGCGGGGCCTGTGCCCCTGCTCCGCCTCCGCGGAACCCCGGAGCCAG CAGCCGCGGTGGGGGGGGCCGGTCCCGGCCAGCCTCTGGGGCGGCAGCCTGGGGGCT CCCTCGTGGGCCCGGCGGCCCAGCCCTGTGCGGGACCCGGCTCTGGCGGTGGGGCT CTGCCGCAGCCAGGCCTGCCGGCCAGGTGGGAGGGAGCCCGTGGCGCTGGGGCACGGG GCGGGGGCTGCTGCCTGGTCCACCTGGCCCGCCCCCCTCCGGCACCCCTGG GACCGGACTGCTGGTCCACCTGGCCGCCCCTCCCGCCCGCCCGGCACCCCTGG CCAGGGCCGTTCCCTCGTGCAGGCGACTCTGGAGAATGGGCTTGCAGCACCGCTGTGCAAT AGCACCGCCTTCCTGTGCAGGCGACTCTGGAGATTTCAAAATTGAGTCTCCACTT ATGTGGGGGGCCCACATCAAGCGCGCGGAGCCGGCGCTGCCCTGCCCCTACCCCCGCCCTGGC ATCCCCCTGCCCACATCAAGCGCGCGGAGCGCGCTGCCCTGCCGCCCTTCCTTCCCGGGTC CCACTCCCCAATGTCCCCGACTTCGAGTCTTGCCTGA | 4060 |
| | 3 | MGLAAPARRAPRASSGLGKT* | 4061 | ATGGGGCTTGCAGCACCGGCTCGGAGAGCACCACGGGTCTTCCTCTGGCCTCGGGAA AACATGA | 4062 |
| | 4 | MCGGQ* | 4063 | ATGTGTGGGGGCAATGA | 4064 |
| hsa-mir-127 | 1 | MVNPILCT* | 4065 | ATGTTAATCAATTCTGTGCACTGA | 4066 |
| | 2 | MTERMNGHMND* | 4067 | ATGACAGAAAGAATGAATGGACACATGAACGACTGA | 4068 |
| | 3 | MEMPGTARKELPMGLSFISLWAPEVHKREKRQEEKCQ GVKDRAKERQK* | 4069 | ATGGAAATGCCTGGCACAGCCAGGAAGGAGCTGCCCATGGGATTGTCATTCATCTCA CTCTGGGCACCTGAGTCCATAAGCGTGAAAAGGGCAGGAAGAGAAGTGTCAGGG AGTTCAAAGATAGAGCTAAGGAAAGGCAAAATGA | 4070 |
| | 4 | MKLNFSERENKFKPIKKRTNTWVYL* | 4071 | ATGAAACTAAACTTCGAAAGCGAAAATGAAAAGCCAAAATAAAGAAAACCAATAAAAAGAGAA CGAATACGTGGGTGTATCTGTAA | 4072 |
| hsa-mir-128a | 1 | MSLRGRTTYE* | 4073 | ATGTCACTCCGGGACGTACAACCTATGAATAG | 4074 |
| | 2 | MNSRLPLKENEEAGLVRGGKGRDSASRGCRWSRCPGW* | 4075 | ATGAATAGTCGGCTGCCGCTCAAAGAACGAAGAGGCGGGGCTAGTGCGTGGG GAAGGGGCGGGATTCTGCCAGCGGCGGAGCCGGTGCCGGAGGCCGGTGTCCGGGCTGGT GA | 4076 |
| | 3 | MGLIPFRKTLTCTHPAPPSPRRAALQPPPPQ* | 4077 | ATGGGGTTAATTCCCTTTCGTAAGACTCTTACTTGCACCCACCCAGCCCGCCGTCG CCCGCCGCCGCCGCCTGCCCCTAACGCGCCTTGCTCCTCCTCAGTAA | 4078 |
| | 4 | MPFPPPSSSPGITRLAFLPRPPTGSANGEGGRQGRDVVC GKVAFPAGSSALQPGRPSDVPLLPARR* | 4079 | ATGCCCCTCCAACCGCTAGCGCTAACGGAGAAGGAGAGGCAGGGGGAGAGATGTGT GTGTGGAAAGGTGGCCTTCCAGCCGGTCGTTCAGCCAGGGAGAGATGTGT CGTCCGGCTGCTAGCCAGCCGGCGTTCAGCCAGGGAGCCTTCAGCTATTGA | 4080 |
| hsa-mir-128b | 1 | MFMHRNIAEVDVVAVSYSGLLPDHLLKM* | 4081 | ATGTTTATGCATAGAAATATAGCTGAGGTGGATGTGGTTGCTGTCAGCTATTCAGGT TTGCTACCTGATCACCTCTGAAGATGTAG | 4082 |
| | 2 | MWLLSAFQVCYLITS* | 4083 | ATGTGGTTGCTGTCAGTACAGATATTCATTTAA | 4084 |
| | 3 | MCLEYRYSF* | 4085 | ATGTGTTTAGAGTACAGATATTCATTTTAA | 4086 |
| | 4 | MFDFLPV* | 4087 | ATGTTTGATTTTCTACCAGTATGA | 4088 |

Figure 1 (Continued)

| | | | | |
|---|---|---|---|---|
| hsa-mir-129-1 | 1 | MLHMIQPPRSTPVAALRPRRRDPSPCLPDDLCLTPSCLL LYSHKFAASSPTSVLRGQPPSTSQQHCEASVPSPTCSSLS LLQSNSQYFPKTFRDCPLPVEEKQALRLARTTKVCLNRLS HLFSHFSPSCAYKSAPLCMSRP* | 4089 | ATGCTGCATATGATCCAGCCACCTCGCTCTACTCCTGTGGCTGCCTTCGTCCTCGTC GCCGGGACCCCTCTCCCTGCCTCCCAGACGACCTGTCGTTCCACCCCTTCGTCTCTT ATATTCTAACTCTCAGCAGCATTGCGAAGCCTCGTTTTCTCCCGACTTGCAGCAGCC TCCATTACCTCCTCCAGTCAATTTGCAGGTTTTTCCGCACACCTTCAGAGACTGCCCATT GCCTGTAGAGGAAAGCAGGCTCTTGCCTGCACGACCACCAAGGTTTGCCTGA ACATCCTTTCCCACCTTTCTGCTCACTTCTCCCCTTCCTGTGCCTACAAATCAGCCCCT CTGTGTATGTCTCGGCCTTGA | 4090 |
| | 2 | MDADFAPSLFVLVPWEEAAQEKDQAPGEADALASGCL VGRAPGTQGEMSTLPF* | 4091 | ATGGATGCTGATTTGCCCCATCATTATTGTGTTGTTCATGGAAGAAGCGGCC CAGGAGAAAGATCAGGCTCCGGGACACCCAAGGAGAAGGCTGATGGCTTGCTTCGGATGTTTAGT TGGAAGGGCTCCGGCACCCAAGGAGAAATGTCCACACTTCCTCTAA | 4092 |
| | 3 | MLLLPHHYLCWCHGKKRPRRKIRLQERLMRLLRDV* | 4093 | ATGCTGATTTTGCCCCATCATTATTTGTGCTGGTGCATGGAAGAAGCGGCCCAGG AGAAAGATCAGGCTCCAGGAGAGGCTGATGCGCTTGCTTCGGGATGTTTAG | 4094 |
| | 4 | MGRSGPGERSGSRRG* | 4095 | ATGGGAAGAAGCGGCCCAGGAGCGACGAAGATCAGGTCCAGGAGAGGCTGA | 4096 |
| hsa-mir-129-2 | 1 | MRAGCVMALVTVHSELRRNRDFAWRRPLHGRWGAGG HQESGDGGGGEDLSNENRCQGGI* | 4097 | ATGCGCGCTGGCTGCGTCATGGCTCTAGTCACAGTTCATTCCGAACTGAGAAGGAAT CGTGACTTCGCCTGGAGACGTCCCTACATGGAGATGCGGGGGAGCACCA AATCAGTGGGACGGGGCGTGCGGGAAGACCTATCCAATGAAAACCGCTGCCAGG GGGCATTGA | 4098 |
| | 2 | MGDGRGGTKSVGTGVGGKTYPMKTAARGAFELRRL LSRCPLSAPRTSLPLPAGARSGPAPARSPAKRRVFNKLEE GRNAGVKLGKPQLPRS* | 4099 | ATGGGAGATGGGCGGGGAACCAAGTCAGTGGGGACGGGGACCTGAACTGCCTGTGT AGACCTATCCAATGAAAACCGTGCCAGGGGAGCCATTGAACTCCGTCTGCT CTCGCTGCCCCTCTCCCCGCCACCTGCCTCGCCGCTCCACCAAACGTCGAGCGGCTCGCA GTGGCGCGCATGCAGGGTTAAGCTCGGAAAGCGCAATTACCAAGATCGTGA GCAGGAACGCAGGGGTTAAGCTCGGAAAGCGCAATTACCAAGATCGTGA | 4100 |
| | 3 | MCKGGGAPNQWGRGWCGRPIQ* | 4101 | ATGGGGGGCGGGGCGCCGAACCAGTGGGACGGGGCGTGGGGCGGCCTAG TCCAATGA | 4102 |
| | 4 | MPWEGEWVAELQEGDGWAKGVGRQGLEDSASTVERR FLRACWARVGVCVRARAPARTSIPGCQRINMATFFPSS CNVCSNPSWVRFPPLGDYTAREGDSQDVP* | 4103 | ATGCCGTGGAGGGTGAGTGGGTCGCGAGCTGCAGGAGGCTGATGGATGCGGA ACGGGGTGGGTCGACAGGGACTTGAAGACAGTGCCTCCACCGTCGAGACGTTT CTCCGCGCCGTCTGCGCGAGGTGCCAAAGAACAACAATATGGCAACTTTCCCCAAGTTCTTG CACGTCGATTCCAGGTCCAGGGTCCAAAGAACAACAATATGGCAACTTTCCCCAAGTTCTTG CAATGTTTGCAGTAACCCATCCTGGGTGAGTTTCCCACTGGGGACTATACTGC TAGGGAGGGAGATAGTCAGGACGTCCTTAG | 4104 |
| hsa-mir-130a | 1 | MGAWGSGSCSLHSRIPSIQDGRQGVWKEKGGEGGRAR SAEERVSAAHRPRNLGPGRRVAGRPLGIQOARPGRGAGG VREGVSEGERGQGGEPRGREGQRKSPGRRRWQAEDPN EEHQCVGIESPPKGNDTDFRPYSLLGKGGGRSGLFLSSSFP PPHESPLVGHFSIFSFGNTVTGKHQACLSEVASLSFSSGGR GGYGMGGSAGHGRAGPSVSTWVVCEGVECSEGDRGP KGWSRAGSSAPPEVVG* | 4105 | ATGGGAGCCTGGAGGGAGTGGGGAGCGGATCGTGCTCACTCAGTCAAGAATCCAAGTATTCAA GATGACGTGGAGTGTGAAGGAGAAAAKGGGGAGGGGAGAAGGAGCGAGAT CGGCAGAGGAGAGGGCTCGGGGACGCGCCAAGCCGGGATCCAAGCCTCCGCCTGGG CGGGTGGCGAGAGGGCAGAGAAGGCGTGAGCGAGGGAGCCAGGAGGGAGCCAAGAGG GAGGAAGGGCAGAGAAGAGCCCGGAAGAAGAGCTTCCGAAGGTAACGACACCGATTT AACGAAGAGCAATGTGTAGGTATCGGGAAGGAGGGGGCATCTTTCTATTTTTCTTTGAA TTCCTTTTTCCTTATTCCTCATTCCTCACTGTGGCAGGCGTGTCTTCTGAGGTGGCCTCACTGTCATTT ACACTGTAACTGTCCCCGTGCGGGCAGTAGGAATGGGGCCTCCGGAGTGTTCCGAGGGGAA GGGCCATCTGTCTCCACCTGTCGGGGTGTGTGCGAGGGTAGGATGGGGCCTCCGGAGTGTTCCGAGGGGAA GGGGGCGAAGGCTGGAGGCTGGAGCAGGGCAGGGAGTTCTGCACCTCCAGAGAAGTGTGTAG GGTGA | 4106 |

Figure 1 (Continued)

| | | | | |
|---|---|---|---|---|
| | 2 | MDGRECGRRKGARGEERDRQRRGSPRPTGLATSVPAG GWRGGRWGSKPGPGEGLAGCERA* | 4107 | ATGGACGGCAGGGAGTGTGGAAGGAGAAAGGGGCGAGGGGGAAGAGCGAGATC GGCAGAGGAGAGGGGCTTCCGCGACCGGCCTCGCAACCTGCGGTCCCGGCCGGC GGGTGGCGGGGCGCTGGCGCTGGGGATCCAAGCCCGGGAGAGGGCTGGCGG GGTGCGAGAGGGCCTGA | 4108 |
| | 3 | MCRYRELPEG* | 4109 | ATGTGTAGGTATCGAGAGCTTCCCGAAGGGTGA | 4110 |
| | 4 | MCVCGGRALTLQFLLFGCVMRAELCSKYG* | 4111 | ATGTGTGTGTGTGGGGGGCGGTGCGCCAACTCCAGTTCTTGTTGTTTGGGTGTGTA ATGAGGGCTGAGTTGTGCCAGCAAGTATGGCTGA | 4112 |
| | 1 | MPGAGPTTYTASHLLLATASPMGQV* | 4113 | ATGCCAGGTGCTGGGCAACAATTTACACAGCATTCATTTGCTGCTGGCAACAGCC AGCCCTATGGGGCAGGTTTGA | 4114 |
| | 2 | MNASPQSGSQSRRNQSLHFRSPYLPQIQKTTGPRTRSP* | 4115 | ATGAATGCTTCTCCGCAAAGTGGATACAATCCACAGATAACGAAGAAACAAAGCTTACACTTC CGTTCCCCATATCTCCCACAGATCCAAAAGACCACGGGGCCAGGACCGGTCTCA TAG | 4116 |
| hsa-mir-139b | 3 | MLLRKVDHNHEETKAYTSVPHISHRSKRPRGPGPGLHS PAIPGGFQESLTRVLPGDPQWLSWEGGYPSL.* | 4117 | ATGCTTCTCCGCAAAGTGGATCACAATCCACGAAGAAACCAAAGCTTACACTTCCGTT CCCATATCTCCACAGATCCCAAAGACCACGGGGCCAGGACCCGGTCTCCATAGC CAGCCATACCCGGGGTTTTCAGGAAAGTCCTCACTCGGTCCTGCCGGCGATCCG GGGTGGTTGAGTGGGAGGGGGCTACCCAGTTGTAA | 4118 |
| | 4 | MHNKAARGRVHSRLGGSGISTGSRPPPLWARAWRPSP GFQALLSVSLENSQRLLERKGGQSSF* | 4119 | ATGCATAACAAAGCAGCCTGCGTTCACAGCAGGCTTGGCGGGAGGGGTTCGGG AATTTCCACAGGGTCTCGGCCTCCCAAGTGTGGGCTCGCCTGGCGCCCCTCACC GGGCTTCCAAGCGCTCTTGTGTGCTAGAAAACTCGCAGAGATTGGAGCTGA GAAAAGCGCGGCAAAGTTCTTTTGA | 4120 |
| | 1 | MNEPPHEYYARL* | 4121 | ATGAATGAGCCGCCACACGAGTACTACGCGCTATAA | 4122 |
| | 2 | MSRRTSTTRAYKSRRAGQAAGGDRAVATRPAR* | 4123 | ATGAGCCGCCGCACCGACCGGGCAGTGCGACGGCCAGTGCGCCGCCAGGTAA | 4124 |
| hsa-mir-132 | 3 | MCGHGREDEEGTGRRRVGRPLRGGIDGGGRGAPGSPRG CGAGARDDTSPRSTCRRPMDTQLLRRSIEWRTDLGDPP PAFLGLLRHSPRKVRRRCWRPRRAPSSPSLRRGDSASL PGPAERGCRRETDAHPRFPGIPPGTPAPHGVGRPFPAGPV QRVPRRFRLPASASGAVLSGPGGRGLPGPAPFPRPRRKC PLWDIFDVTAL* | 4125 | ATGTGCGGACGGGACGAGGAGGAGGGGACGGGACGGCGCCGGCGGGTGGGC GGCCCCTCCCGGGGCGGAGGATGGGGGGACGAGGCCCGGGCAGCAACCCGCCCGGCGCCGAT TGCGAGCGGAGCCGGAGCCAGCTACTTCGGAGGACACGGACCATCGAGTGGAGGACCCCCGCC CCCCGGCTTCTTGCGGCGTCTGCGCCATTCTCCCAGGAAAGTGAGGCGAAGGTGCT GGCGCCCAGGAGACGCGCCCGCCTCCTCTGCGGCGTGACTCAGCCT CCCCCGGGCCGGCCCCGGGCCTGACTGAGAGGACCCGCGCTCGCCAGCT CCCCCGGCCCGGCCCCTGAGCCTGCATGGCGCTCGGCCGCCCTTTCCGGCA GGTCCGTCCAGCAGGCGCAGCAAGCCCCACGAGTGCCAGGGCCCCAGCCCCGCGGAGCT GTCCTCTCAGACGCGGGGAGGCCCCCCTGGGACATCTTTGACGTCACGGCCTCACGGCCCGA | 4126 |
| | 4 | MGADGGHRGPLAAAEPGPETTRAPAAPAGARWTRSYF GGASSGGPTSETPPRLSWJSSCAILPGK* | 4127 | ATGGGGGGCGGACGGGGGACGCAGGGCACTGCGCCGCAGGACGACCAGCAGCTACTTC GAGGAGGACATCGAGTGAAGGACGACGCACCCTGGAGACCCCCGGCTTTCTTGGGG CTCTGCGCCATTCTGCCATTCTCCCAGGAAAGTGA | 4128 |
| | 1 | MVRERSPRGPLGQGRVFGMLGRVYKNCKGEAGS* | 4129 | ATGGTCAGGAGGCGCAGCCCAGCCCACTGGCACGAGGGCCACTTGGCCCTCGCGTGTTTGGGAT GCTTTGGCGGGTATAAGAACTGCAAAGGTGAGGCGGCTCCTGA | 4130 |

Figure 1 (Continued)

| | | | | |
|---|---|---|---|---|
| hsa-mir-133a-2 | 2 | MAWGLRGWAGGAHLPLRNKAPAAGRGAKLTLNLQYF PLRCWWGAGIPELSGGEAAPGRDSALLQLSQPRQGQEA FTGAGRRGGCRGAHVGGD* | 4131 | ATGGCATGGGGCTTCGGGGCTGGGGCTGGAGCTGGGGGCCTGGGGGCCGATTCACCTGCCGCTCCGCAA CAAAGCCCCGGCAGCCGGGCGTGGGCTGGAGCTAAACTTACCTTGAACTTGCAGTATCCCC ACTGAGGTGCTGTGGGGGCAGGATTCGGAGGCTTCGGAGCTGAGGCGACTGGGAGCTGCC CCGCCGGGACTCGGCACTTCTGCAGCTCTCCAGCCACGTCAGGTCAGGAGGCG TTTACAGRGGCAGGGCGCGAGGTRGHGGCGGGGGGCACATGTGGGGGGAGACT AG | 4132 |
| | 3 | MGASGLGWGRDSPAAPQGSPGSRAWG* | 4133 | ATGGGGGCTTCGGGGCTGGCTGGCGCGGCGCGATTCACCTGCCGCTCCGGAACAAAG CCCCGCAGCCGGGCGTGGGCTAA | 4134 |
| | 4 | MWAETRGASGRAALVVGVCAGPCWGA* | 4135 | ATGTGGGCGGAGACTAGGGGCGCTTCGGGAGGCAGCCCTGGTGGTCGCGTCTG TGCAGGTCCCTGCTGGGGAGCTTGA | 4136 |
| hsa-mir-133b | 1 | MVQSRPANFLYF* | 4137 | ATGGTGCAATCTCGTCCGGCTAATTTTCTGTATTTTAG | 4138 |
| | 2 | MEFHHVVQAFLELLTSGDPAALASQSVGITGVSHRARPI STYYIR* | 4139 | ATGGAGTTTCACCATGTGTCCAGGTTTCTTGAACTCCTGACCTCAGGTGATCCA GCTGCTCTGGCCTCCAAAGTGTGGGATTACAGGCGTGAGCCACCGCCCGGCC CATAAGTACCATATATATAAGATGA | 4140 |
| | 3 | MLSRLFLNS* | 4141 | ATGTTGTCTCCAGCTTTTCTTGAACTCCTGA | 4142 |
| | 4 | MRASPPLRNL* | 4143 | ATGAGAGCTTCCCACCCTAAGAAACTTGTAG | 4144 |
| hsa-mir-134 | 1 | MDQGVEGGCGPGVGRQSACSL* | 4145 | ATGGACCAGGGGTAGAGGGGTGGGTGTGACCTGGGGTCGGGCGCAGTCAG CTTGCAGCCTATGA | 4146 |
| | 2 | MKIDGKEGYRIDRGRVGLRIARAAWHTVLG* | 4147 | ATGAAGGACGGGAAAGGAAGGAGGCTACAGAGATAGGGAAGAGTGGGGCTGAGGATAG CCAGAGCCGGTTGGCACAGTTTAGGGTAA | 4148 |
| | 3 | MTEPVTPGSSFKACLMGDSVVPVTKLGPESQGRAHQV AALP* | 4149 | ATGACTGAGCCGTCACTCCAGGTCTTCCTCAAAGCGTGTCTAATGGAGACAGC GTTGTCCCAGTAACCAAATTGGACCAGAGTCCCAGGGAAGGCTCATCAGGTGGC CGCTCTGCCTTGA | 4150 |
| | 4 | MILFPLDPAPL VPFSL * | 4151 | ATGATTCTTCCCTCTGATCCAGCCCTAGTTCCCTTTCACTTTGA | 4152 |
| hsa-mir-135a-1 | 1 | MGWPEPWGAGRWGECFSAPGSGEQQWTASFRSPGGQ QEWEAEGWPVSREGQGWPGAGRLRSCLGAWLLWVAL G* | 4153 | ATGGGGTGGCCGGAGCCCTGGGGGGCAGGCAGATGGGGAGAATGCTTCTTGCCC AGGCAGTGGGGAGCAGCAGTGACTGAACTTCAGCTTCCCCGGGGGTCAGCAGG AGTGGGAGGCAGCAGCGGTGACCAGTTAGCCGCAGTTAGCCGGACAAGGCTGGCGGGAGC TGGCAGGCCTCCGTTCTGCCTGGGTGCCCAGGCAGTGGGGACGCAGTGGACTGGACTGCCAGCT TCAGGTCCCGGGCTCAGGGGGTCAGAGAGTGGAGGCAGAGGGCGTGGCCAGTAG | 4154 |
| | 2 | MGRMLLCPRQWGAAVDCQLQVPRGSAGVGGRGVAS* | 4155 | ATGGGGAGAATGCTTCTCTGAGTCCAGGCAGTCTGACTTGGGGACCGTGACTGGCTGCTGCTATG CAGGTCCAGTGCTGGTACAGGGGGTTGGCCAGCAGGGCCACGTTGCGCCCTCACAAGTGC | 4156 |
| | 3 | MPSPGVQGSDPTSDWAAAMGLLGASSGTVQGTVTLTS ACASRGVGGWLECAGATPTAQVESLSGGRDLPPAIGSQ VLLQATDPQTHRPTW* | 4157 | ATGCCCAGTCCTGGGGTTCAGGGGTCAGATCCTAGTGACTGGGCCGCCGCAATGC GGGTTGCTGGCTAGCAGGGGGTTGGCCGCTGGCCAACGTTGCCCTGGGAATGTGCTGGGGACTGTGCTGCTGGAACCCCCACTG CTCCTGGAGAGTCTGAGTGGAGGAGAATCTCCCGTGCCGCCATAAGGCTCACAG GTTTTACTCAAGCTACTGATCCCAGACCCATAGACCCACATGGTAA | 4158 |
| | 4 | MCWGYSHCPGGESEWRERSSPCHRLTGFTPSY* | 4159 | ATGTGTGGGGCTACTGCCACTGCCAGGTGAGAGTCTGAGTGGAGGGAGAGATC TTCCCCTTCCATAGGCTCACAGTTTTACTCCAAGCTACTGA | 4160 |
| hsa-mir-135a-2 | 1 | MVKFRNQKS* | 4161 | ATGGTTAAATTCAGAAATCAGAAGAGTTGA | 4162 |
| | 2 | MWKKNCFY* | 4163 | ATGTGGAAAAAAAATGTTTTATTGA | 4164 |
| | 3 | MSNVFFKFNFSVMSLK* | 4165 | ATGTCCAATGTCTTCTTCAAATTTAATTTAGTGTCATGTCTAAAGTAA | 4166 |
| | 4 | MSSNLILVSCL* | 4167 | ATGTCTTCTTAATTTAATTTAGTGTCATGTCTAA | 4168 |
| | 1 | MALCRAWVWGSGGP* | 4169 | ATGGCTTTATGCAGGGCTGGGTCTGGGTTCTGGGGGCCATGA | 4170 |

Figure 1 (Continued)

| | | | | |
|---|---|---|---|---|
| hsa-mir-135b | 2 | MQGLGLGFWGPMREEGKENQRGLGLGQMAQSSGGRP QDAWLFGPEGWACLECVEGRAVLCCVLCCAVV GECRIPVQ* | 4171 | ATGCAGGGCCTGGGTCTGGGTTCTGGGGCCCATGAGAGAGGAAGGAAAGGAGA ACCAGAGGGGTTGAGCTGGGGCAGAATGGCCCAAAGTTCAGTGGGAGGCCGCA GGATGCCTGGTTGTTTGGCCCTGAAGGTTGGGCATGTCTGAGTGTGTGGAGGGGC GTCGTGTCGTGCTGTCGTGCTGTGTGCTGCTGTCGTGTGTTGTGGAGGATTCCTGTCAGTGA | 4172 |
| | 3 | MPGCLALKVGHVVWSVWRGVLCCAVCCVLCCAVLLLG NAGFLSSENRLLLPGLCREPASVALGLRVQLGWERQLL PGJKGRA* | 4173 | ATGCCTGGTTGTTTGGCCCTGAAGGTTGGGCATGTCTGAGTGTGTGGAGGGGCGT GCTGTGCTGTCGTGCTGTGTGCTGTGTGCTGTGTGGCGGTAGTGCTGTTGGGAATGC AGGATTCCTGTCCAGTGAAAACAGGTTGCTTCTACCAGGGTTGTGCAGGAGCCAGC AAGTGTTGTCCCTGGGCTGAGGGTACAGTGGGGTGGGAGAGGCAGCTACTCCCTG GCAGAGGCAGGCCTGA | 4174 |
| | 4 | MSGYVCGGACCAVLCAVCCAVLCCCWGMQDSCPVKTG CFYQGCAGSQQVLPWG* | 4175 | ATGTCTGGAGTGTGTTGTTGAGGGGCTGCTCTGCTGTGTCGTGTGTCTGCT GTGCTGCTGTTGTCAGGGAGCCAGCAAGTGTTGCCCTGGGGCTGA TACCAGGGTTGTGCACGAGGAATGCAGGATTCTGTCCAGTGAAAACAGGTTGCTTC | 4176 |
| | 1 | MVNPLCT* | 4177 | ATGGTTAATCAATTCGTGCACCTGA | 4178 |
| | 2 | MTERMNGHMND* | 4179 | ATGACAGAAAGAATGAATGGACACATGAACGACTGA | 4180 |
| hsa-mir-136 | 3 | MEMPGTARKELPMGLSFISLWAPEVHKREKRQEEKCQ GVKDRAKERQK* | 4181 | ATGGAAATGCCTGGCACAGCCAGGAAGGAGCTGCCCATGGGATTGTCATTCATCTCA CTCTGGCACCTGAGTTCCATAAGCCTGAAAAGAGGCAGGAAGAGAAGTGTCAGGG AGTCAAAGATAGAGCTAAGGAACGACAAAATGA | 4182 |
| | 4 | MKLNESERENKEKPKKKRINTWVYL* | 4183 | ATGAAACTAAATGAAAGTGAAAGGGAAAACCAATAAAAACCAATAAAAGAGAA CGAATACGTGGGGTATCTGTAA | 4184 |
| | 1 | MDLWSRSSSAHPQAGAGSASSKSSGGGGSSSGGGSGSS GSGSSGSGSLVL* | 4185 | ATGGATTATGTCCGGTCAAGCTCAGCCCATCCAGGCAGGGCGCGGCTCAGC GAGCAGCAAGAGTTCTGGTAGCAGCGGCGGCGGAGGGCAGTAGCAGCGGCAGTAGC AGCGGCAGCGGTAGCAGCGGTAGCAGCGGCAGCGGCAGCTTGGTCCTCTGA | 4186 |
| hsa-mir-137 | 2 | MVPVKLSPSPGRGGLSEQQEFWWRRRQ* | 4187 | ATGGTCCCGGTCAAGCTCAGCCCATCCCAGGCAGGGGCGCGGGCTCAGGAGCAGCA AGAGTTCTGGTCGCAGGGCGGCGGAGTAG | 4188 |
| | 3 | MGSSRGRGAR* | 4189 | ATGGGTTCGCAGCGGCGGGCGGCGAGGTGA | 4190 |
| | 4 | MGGERKGVRPEPAGRFGVPSPLLSSPRWGAAGGRDA DGAIF* | 4191 | ATGGGCGGGGAGTCGAAGGGTCCGTTTCCCGAGTCCGTTCCCGAGGCTGCGGGGGTT TCCCAGTTGCGCGCTCCTCTCCCCACGGTGGGTGCGGCTGGAGGGAGAGACGCGG ACGGGGCGATTTTCTAA | 4192 |
| | 1 | MGGCDPLLPCSGPYTYTPPTTCRALRPTARPAGLTWCLR VLLASWGCGNQPWAAFALHEETMRLS* | 4193 | ATGGGTGGGTGTGATCTCCCTCCGTTCCCTGCTGCCGCGGCCCTACACCTCCACC ACCTGCTAGAGCTCCAGCTGGGGCTCTGCCAGCCACGCGTGGGCTCGTCGTCCTCC GTTTTGCTTGCCAGCGAGGAACCAGCCGTGGGCTGCTTTGCCCTACAC GAGGAGCGATGAGAGAGAGAACTGA | 4194 |
| | 2 | MRKVLAKRLRKFATEAHGEEWAQSTSGRQHLFSSTHSP SSP* | 4195 | ATGAGAAAAGTGCTTGCAAAAGCTAAGGCTGCGAAATTGCAAACAGGAGCTCACGGGGA AGAGTGGGCTCAAAGCACCAGTGGCAGGCAGCACCATTCTCATCTACACAGCCC CTCCAGTCCTAG | 4196 |
| | 3 | MPRPLWSWVSLWQKLGFAEPAAF* | 4197 | ATGCCCGTCCTTGTTGGAGCTGGTATCGTTGTGGCAGAAGTTGGGAATTTTTGCA GAGCCTGCTTTTGA | 4198 |
| | 4 | MWVHQ* | 4199 | ATGTGGGTTCACCAGTGA | 4200 |
| hsa-mir-138-1 | 1 | MRIDLLEEQKKPNMEGESLGLIKQGALLEQPPPTELSCCGGAS R* | 4201 | ATGCGTGACTATTAGAGGAGCAAAAGAAGCGAATATGAAGGGAAAGCCTTGG CCTGATCCAGGGTGCTCTAGAACAAATTCCTCCACTGAACTGTCCTGCTGTGGGGC AAGCAGGTGA | 4202 |
| hsa-mir-138-2 | 2 | MHWQQQGDGDSRCGDLEHPHAHLHGETLTDTYLQAR LKKHLGGAG* | 4203 | ATGCACTGGCAACAGCAGGGGGATGGTGACAGCAGGTGTGGGATCTGGAGCACCC ACACGCCCACATCCTCATCGTCATGCCATGTGAGACCCTTACTGACACCTATTTACAAGCAAGGCT TAAAAGAAGCATCTGGGGGGCCGGGTGA | 4204 |

Figure 1 (Continued)

| | | Protein Sequence | SEQ ID | Nucleotide Sequence | SEQ ID |
|---|---|---|---|---|---|
| | 3 | MVTAGVGIWSTHTPTSCMVRPLLTPIYKQGLKRSIWGA PGEGKSSGLSDQTGRFGVGEAGSRK* | 4205 | ATGGTTGACAGCCGGTGTGGGGATCTGGAGCACCCACACGCCACATCCTGCATGT GAGACCCTTACTGACACCTATTTACAAGCAAGGCTTAAAAGAAGCATCTGGGGGG TGCCGGGGTGAAGGCAAATCTTCAGGGCTCTCGGATCAAACTGGGAGATTTGTGGGTT GGAGAAGCAGGCAGCAGGAAATGA | 4206 |
| | 4 | MNLSSVHIWLQSSQTLKLRLQLDVE* | 4207 | ATGAATCTGTCTTCTGTTCATATCTGGCTGCAAAGTCACTAAACGTCAAGCTCAGG CTGCAGCTGGATGTGGAATGA | 4208 |
| hsa-mir-139 | 1 | MRSDGAGMRPLHPLQEPAVPGSATG* | 4209 | ATGAGGAGTGATGGGGCAGGCATGGCCCCACTCCATCCTCTGCAGGAGCCAGCAGT ACCCGGCAGCGCGACCGGCTGA | 4210 |
| | 2 | MGQACGHSILCRSQQYPAARPAEP* | 4211 | ATGGGGCAGGCATGCGGCCACTCCATCCTCTGCAGGAGCCAGCAGTACCCGGCAGC GCGACCGGCTGACCGTGA | 4212 |
| | 3 | MELSHVEGSILFLGTPPPRVARLQPGVGAGYL* | 4213 | ATGGAGCTGAGCCACGTGGAAGGATCGATCCTGTTCCTGGCCACCCCTCCTCCCGC GTTGCCAGACTGCAGCCTGGGGTGGCCAGGTTACCTCTGA | 4214 |
| | 4 | MRVSNVNLVGDEAGVPWKGLLVGGGADNEPEPYLQG LRVYVGRGRSAK* | 4215 | ATGAGGGTGTCTAACGTCAACCTAGTAGGTGATGAGGCTGGGGTTCCATGGAAGGG GCTGCTGTTGGAGGAGGGCGACTGGAAATGAACCTGAACCGGTTCTTCAAGGGCTGA GGGTGTATGTGGGGAGGGGAGGTCTGCCAAGTAG | 4216 |
| hsa-mir-140 | 1 | MGAPAAKGAAGASPPGRGEELRPPGMERSDLCGGHGTR GRGDLELSWKGYPENGPMAWSQREKDAAWTPSESLSL PSCLEMIVTRDFIDGPIQFLNFRRDHRLIJVLLPSRPLSPA WVGHPLLGSLALQLIFL* | 4217 | ATGGGTGCTCCGGCCGCCAAGGGTGCAGCTGGAGCGAGTCCTCCGGAAGGGGAGA GGAGCTAGGTTCCAGGATGGAGCGATCTTTGTGCAGCAGGGCGGACCA GGGGAAGGCGGCGACTTGGAACTGAGCTGGAAGGGGGTCCCTGAAATGGGGTTATG CGGTGGAGCCAGAGGAAATGATTGTTACCCGAGACTTGATGACGGTCCATTCAGTTTT CCTTCCTGTTTGGAAATGATTGTTACCCGAGACTTGATGACGGTCCATTCAGTTTT TAAACTTCAGGAGGCGATCACAGAATCTTGATCGTCTTGCTTCCTCGCGCCACTTA GTCCTGCGTGGGTAGGGTTTCCACTTCTTGGGAGCCTAGCCCTTCAGCTCATTTTCT TTGA | 4218 |
| | 2 | MGLWRGARGKKMLPGPPLRVSPPLPVWK* | 4219 | ATGGGTTTATGGCGTGGAGCGTGGAGGAAAAGATGCTGCCTGACCCCCTCTGAG AGTCTCTCCCTTCCATTCAGTTTTAA | 4220 |
| | 3 | MTVPFSF* | 4221 | ATGACGGTTCCCATTCAGTTTTAA | 4222 |
| | 4 | MAPSLHC* | 4223 | ATGGCTTTTAGCTTACACTGTTGA | 4224 |
| hsa-mir-141 | 1 | MAGGHTCAQGGRRGPGKEPALAARQAEKEGGRAEAR AGSRPWNLGP* | 4225 | ATGGCAGGAGGACACCACCTGTGCGCAGGGTGGCAGGGGAGGCGGGGCCAGGTAACGAGC TGCCGCTGGCCTGCCGGCCAGGCGGAGAAGGAAGGAGGGAAGAGCGGAGGCCAGGGC GGGGCTCTAGGCCGTGAATCTGGGGCCTTAA | 4226 |
| | 2 | MRVGKSVCVAGRERLPGVGEGGSEAACRRKSRGFGGPA WTATWAS* | 4227 | ATGAGGGTGGTGGTAAATCGTGTGTGCGGTCGGGAACGGGGAACTGTCCGCGGGTAGG GGAAGGTGGCTCAGAGCGCGGCCGGCGAAGGTCGAGGGCCTTCGGAGGGCCTGCTT GGACTGCAACCTGGGCTCGTGA | 4228 |
| | 3 | MGIARDLQLFRRDPGPEAA* | 4229 | ATGGGGAGCCAGGGATCTCCAGCTTTTCCGCAGGGATCTGGGCCTGAACCTGCCTGA | 4230 |
| | 4 | MMEAPVPVSATSHASGPQPLAGGSPLPTSHAPRKPLVLS* | 4231 | ATGATGGAGGCCCCTGTCCCTGTGTCAGCAACATCCATGCCTCAGCTCCCAGCCC TTAGTTGGCTGCTGCAGCCCTCCTCCCACTTGCACGCACGCTGGAAGCCCTCGTCTTTG AGCTGA | 4232 |
| | 1 | MTGFLLCPSHYYYTVRFIHYHTSVTQILGKYSVPRFFSP* | 4233 | ATGACTGGATTCTTACTGTGCTTCAGTCATTATTATACTGTTCACTTCACACATT ATCATACTTCAGTGACTCAGGACCTTGGGCAAATACTCGTGCCTCGCTTTTCAGTCC ATAA | 4234 |
| hsa-mir-142 | 2 | MGLLNSCCRTYMR* | 4235 | ATGGGCCTACTTAATAGTTGTTGCAGGACTTACATGAGATAA | 4236 |
| | 3 | MFQSGKFYSVIENQTCHRAHLNTAWDRQQEESPPGSSS RRLLGWNDSAAGPETYIPKLLSDKHK* | 4237 | ATGTTCCAAAGTGGAAAGTTTTATTCAGTGATAGAAAACCAAACCTGTCACAGA GCCCATCTGAACACAGCATGGACCTGCCAACAAGAAGAAAGCCCGGAAGCAG CTCAATCAGGAGGGCTGGGCTGGAATACAGCCAGCGGGCAGGGGCTGAAACTATTTATA TCCCAAAGCTCCTCTCAGATAAACACAAATGA | 4238 |

Figure 1 (Continued)

| | | | | | |
|---|---|---|---|---|---|
| | 4 | | MGPPTRRKPARKQLNQEAGLE* | 4239 | ATGGGACCGCCAACAAGAGAAAAGCCCGCCGGAAGCAGCTCAATCAGGAGGCTGG GCTGGAATGA | 4240 |
| hsa-mir-143 | 1 | | MKMGVYPSFSPF* | 4241 | ATGAAAATGGGAGTTTATCCCTCCTTTCTCCTTCTGA | 4242 |
| | 2 | | MKPSPAFWFLGSRKQRY* | 4243 | ATGAAACCTTCTCCCGCTTTTGTTTTTAGGAAGCAGAAAGCAGAGATATTAA | 4244 |
| | 3 | | MNEVASYHPGRMLGQQFPALADTAKGFPYLIRWLQPP RKVEQDSSSVL* | 4245 | ATGAATGAGGTAGCGTCTTACCACCCTGGCCGCATGCTTGGTCAGCAATTTCCAGCA CTTGCAGACACTGCAAAAGGCTTCCCTATCTCATAAGATGGTTACAACCACCTAGA AAGGTGAGCAGGATTCTTCGTCTGTGTATAA | 4246 |
| | 4 | | MVTT* | 4247 | ATGGTTACAACCACCTAG | 4248 |
| hsa-mir-144 | 1 | | MLYGAGNLAVSASCCCYPWEPGNVALGQGPA* | 4249 | ATGCTTGGTAGGGGCGGGTAATCTGGCAGTTCAGCTTGCTGTTGTTGCTACCCTTGG GAACCTGGCAATGTTGCCCTTGGCCAAGGCCAGCTTGA | 4250 |
| | 2 | | MLPLAKAQLELWQPAPQAKE* | 4251 | ATGTTGCCCTTGGCCAAGGCCCAGCTTGAGCTGTGGCAGCCTGCTCCCCAAGCCAAA GAATAA | 4252 |
| | 3 | | MPVIPALWAPKAGRSPEVRSSRPARPTWRNPISTNNLKI SQTWWWLPVIPATWEAEAGESLESGRRKLH* | 4253 | ATGCCTGTAATCCAGCACTTGGGCACCTAAGGCAGGCAGATCACCTGAGGTCAGG AGTTCGAGACACTGCAAAAGGCTCCTGTCTGCCAACATGGCGAAACCCATCTCTACTAACAATTTAAAA ATTAGCCAGACGACGTGGTGGTGCCTGTACCCAGCCACTTGGGAGGCTGAGGC AGGAGAATCACTTGAACTGGGAGGCGGAAGTTGCATTGA | 4254 |
| | 4 | | MAKPHLY* | 4255 | ATGGCGAAACCCATCTCTACTAA | 4256 |
| hsa-mir-145 | 1 | | MKMGVYPSFSPP* | 4257 | ATGAAAATGGGAGTTTATCCCTCCTTTCTCCTTCTGA | 4258 |
| | 2 | | MKPSPAFWFLGSRKQRY* | 4259 | ATGAAACCTTCTCCCGCTTTTGTTTTTAGGAAGCAGAAAGCAGAGATATTAA | 4260 |
| | 3 | | MNEVASYHPGRMLGQQFPALADTAKGFPYLIRWLQPP RKVEQDSSSVL* | 4261 | ATGAATGAGGTAGCGTCTTACCACCCTGGCCGCATGCTTGGTCAGCAATTTCCAGCA CTTGCAGACACTGCAAAAGGCTTCCCTATCTCATAAGATGGTTACAACCACCTAGA AAGGTGAGCAGGATTCTTCGTCTGTGTATAA | 4262 |
| | 4 | | MVTT* | 4263 | ATGGTTACAACCACCTAG | 4264 |
| hsa-mir-146a | 1 | | MNSVWCHTAQ* | 4265 | ATGAACACAGTGTCTGGTGTATAACATTGTCAATAA | 4266 |
| | 2 | | METLTNCVTLGKSP* | 4267 | ATGGAAACACTTACTAATTGTGTAACTTAGGAAGTCCCCTAA | 4268 |
| | 3 | | MSKRGSQNGDNNSSGYLLWMIAVGLGKMMHVIHLAEC LVPSRCPLKFSYDCSL* | 4269 | ATGAGTAAAAGGGGATCACAAAATGGAGATAATAATTCGGGCTACCTGCTATGAT GATTGCTGTGGGATTAGGGAAGATGATGCACGTGATACATTTAGCAGAGTGCCTGG TGCCTAGTAGTGCCCATTAAAATTTAGCTATGACTGTTCTCTTTAG | 4270 |
| | 4 | | MEHHRATCYG* | 4271 | ATGGAGCATCATAGAGCAACATGCTATGGATAA | 4272 |
| hsa-mir-146a | 1 | | MQGLSCLPLPQQIRVSPERCSFSKTLDRSSFPGWHQQG RLEW* | 4273 | ATGCAAATGCCTTAGCTGCCTTCCTACCCAGCAAATAAGAGTCTCTCCAGAA AGATGCTCTTTCCAAGACGCTTGACGGCTCTCCTTTCCTGGATGGACAGCAG GGCCGATTGGAAGTGGTAA | 4274 |
| | 2 | | MLFLQDA* | 4275 | ATGCTCTTTCTCAAGACGCTTGA | 4276 |
| | 3 | | MAPAGPHGVVNPGPEGMPKGGQDGQETVAQRGGGEQR LNWK* | 4277 | ATGGCACCAGCAGGTCCACATGGAGTGGTAAACCCTGGCCGGAAGGCATGCCAAA GGGTGGACAGGATGGACAGGAGACAGTAGCACAGGAGGGGAGAACAGCGG CTGAATTGGAAATGA | 4278 |
| | 4 | | MDRRQ* | 4279 | ATGACAGGAGACAGTAG | 4280 |
| hsa-mir-146b | 1 | | MGTDSPLPEGTA* | 4281 | ATGGGAACAGACTCCCCACTGCCCTTGGTACTGCTTGA | 4282 |
| | 2 | | MPFHRHSFQ* | 4283 | ATGCCTTTTCACCGCCATTCTTCCAGTGA | 4284 |
| | 3 | | MRNWT* | 4285 | ATGAGAAACTGGACTTGA | 4286 |
| | 4 | | MAGAGSRSGLRLERALWAGPLALPHLPPFSEEPAWGGG GRRLGRGWGPYLRSTG* | 4287 | ATGGCGGGGCGGGTCCGTCTGGCTTGAGGTTAGAAGGGCTCTGGGCAGG GTTCCTGCGCCCTCCACACTTCCTCCTTTCAGAAGAGCCAGCAGCATGCCGGCAGG CGGGAGGCGCTGGGGCGGGCGGGCCTTATTAAGGAGCACCGGCTGA | 4288 |
| | 1 | | MPPAKIL* | 4289 | ATGCCCCAGCCAAAACACTTTAG | 4290 |

Figure 1 (Continued)

| | | | | |
|---|---|---|---|---|
| hsa-mir-147a | 2 | MLLPPFLFLVSFEWSFRNIFSALGEASPDPILGEMPHLCS RSPHITVQIL* | 4291 | ATGCTCCTCCCACCCTTTCTTTTTCTAGTAGTTTGAATGGTCCTTTGAAATATT TTTCTGCCCTTGGGAAGCCTCCTCCTGACCGATACTAGGTGAAATGCCCACCTCT GCTCCTGCAGCCCTCCAGTCCAGCCACCACTGTGCAAATCCTGA | 4292 |
| | 3 | MELPAPEDLAPSSPDTMVRGGDGIALAGSVGCSSPGWES GEWPHATLPVSPSIKRGAEEVGSTDPFCGSCHLCSS* | 4293 | ATGGAATTGCCAGCACTGCAGCCCTCCTCTCCAGACACGATGGTGAGGGG AGGAGACGGGATTGCACTTGCTCTGAAGCGTAGGGTGCAGCAGCCCGGCTGGGAGT CCGGGGAGTGGCCTCATGCCACTTTGCCTGTCCCCATCCATTAAGAGAGGGGCGG AGGAAGTGGGCAGTGACCCTTCCTGCTTCGGTTCTGCCTGTCCATCTGTGCTCTCCT GA | 4294 |
| | 4 | MPLCLSPHPLREGRRKWAVQTLSASYPARCALPEKYLH RCTSVEYVPVCENSD* | 4295 | ATGCCACTTTGCCTGTCCCATCCATTAAGAGAGGGGGCGGAGGAAGTGGGCAGT ACAGACCCTTTCTGCTTCGTCCGCATCTGCCATCTGTGCTCTCCTGAGAATATTGCAC AGGTGTACCTCGGTAGAATACGTACCAGTGTGAAAACTCAAGATTGA | 4296 |
| | 1 | MRAICFRPASSVFRFPLWAGWVS* | 4297 | ATGCGCGCAATCTGCTTCCGGCCTGCGAGCTCGGTTTTCGCTTTTGGGCCGGG TGGGTTTCCTAA | 4298 |
| hsa-mir-147b | 2 | MAPDSDPPFGPLLKLLPLDARDRGTQRCRLGPAALHA LGARLGSAVKISLPDGGSCLCTAWPRRDGADGFVQLDP LCASPGAAVGASRSRSSLSNRLLVPCJPLRRYAVWP VLRERACIAPGARNTAAVLEAAQELLRNRPISLGHVVVA PPGAPGLVAALHVUGGTPSPDPAGLYTPRTRVSLGGEHP SEAQFOPEVPLGLSEAADSLRELLKLPLRYPRALTALG LAVPRGVLLAGPPGVGKTQLVRAVAREACAELLAVSAP ALQGSRPGETEENVRRVFQRARELASRGPSLLFLDEMD ALCPQRGSRAPESRVVAQVLTLLDGASGDREVVVGA TNRPDALDPALRRPGRFDREVNGLGGFAHCRWNLGRF WRHLAAPEAFAS* | 4299 | ATGGCTCCGACTCGATCCTCCCTCGAAGGTCGTCTACCCTTA GACGCTAGAGACCGGGCGCGCCCTGAGCCTCCCGCTGGGCCCGGCCCCCCCACGC CCTGGCCGCAGCTTGGCTCGGCAGTGAAGATCTCGCTACCCGACGGGCGTCCT GCTCCTGAACTGCCGGCCTCGGGCGGCGGGACGGAGCGGAGCGGACTCGTCTGAC CGCTCTGCCGCAGCCCTCCGGCGCCTCGGCGGCGGAGTCCCGGGTGCCGGAGTCC CGGCTCCGAATCGCCTGAAGCCTCCGCCGCCGGTCGCCGGGAAGCCGCGGCCGCGCCT GGAGGGCGGCACAGAGCTGCTCGAGAAACGACGATCTCCTGGGCCACGTGGTG GTGCGCGCCGGCAGGGCCCAGGCCGCACCCTCGCTCCTCGGCCCCAGTCCCGGCGACG CCCAGTCCCGATCCGGAGCCCGGAGTTGCCCCAGAGCCCCTGGGAGGCTTCGGA GAGCCTCCGTCGGAAGCCGGACTCGGAAGCTCCCGCTCGGTCCCCGGGAG GCGGCGACTCGCTAGCGGTGGTGCGGCCGGCCAGGGTTCCGGCTGCAGGGTCAGCCAGCTGCTG GACCCGGGGAAGACCCAGCTCGTTGCCGGCCCGTGCCGGGGAGACAGAACGT GCAGTCAGCGCCGCTTCCAGCGCGCGCCAGCCGCCGCCAGCCTCCTCTT GGGGGCGAAGATGGCCCAGGTTGTTGACGTCTGAGCGTCTGGGAGGTGCTG CCTGGACGAGATTGACGAAGGTGAATGCCTTGGCGGTTGCCCACTGCGGTGA ACCTCGGCGCGCTTCTGCCGCCATTGCTGCCGCCAGAGCCCGAGAGCC GTGGTTGTGGGAGCACTAAGGCCCTAGCCAGCCTGGTGCTGGCCGAGGTC GAGGAGAGATTGACCGAAGAGGTGAATCGCCTTGGCGGTTGCCCACTGCCGTGGA ACCTCGGCGCGCTTCTGCCGCCATTGCTGCCGCCAGAGCCGGCCTCTCTAG | 4300 |
| | 3 | MGLAGLPTVGGTSAASGAIWLPRRRLPLRFEHR* | 4301 | ATGGGCTTGGCGGGTTTGCCACTGTCGGTGGTGGAAACCTCGGCGCGTTCTGCGCGCCATT TGGCCTCGCCCCGGAGCGTTCTGCCTCTTAGGTTGAGCATCGTGA | 4302 |
| | 4 | MQRTRSLPFYDL* | 4303 | ATGCAGAGAACACGTTCTCTGCCGATATGATCGTGA | 4304 |
| | 1 | MSFFQLLMKRKIEVSFKNQ* | 4305 | ATGAGCTTTTTTCCAACTCCTGATGAAAAGGAAAGGAAGTAAGTTTTAAAAACAATTGA | 4306 |
| | 2 | MKRWHRF* | 4307 | ATGAAAAGATGGCACAGATTTTGA | 4308 |
| hsa-mir-147b | 3 | MAQILNKV* | 4309 | ATGCAACAGATTTTGAACAAAGTATAA | 4310 |
| | 4 | MPHIEVSKCVPSTCYLLAHSLGGVHDCGGGWSLIPRCV PSLENRCDVSRSQFIKTPLAVPG* | 4311 | ATGTTTCATATTGAAGTGTCAAATGTCCCTCCACCTGTTATTGTTAGCTCATT CCCTTGGTGGTTCATGACTGTCATGGATGTGGATGTAAGTAGGTTCCAATTTATAAAACGTTTTGA | 4312 |
| | 1 | MVHTQSYFCF* | 4313 | ATGGTACACACTCAATGCTATTTTGTTTTGA | 4314 |

Figure 1 (Continued)

| | | | | | |
|---|---|---|---|---|---|
| hsa-mir-148a | 2 | MRLAPKLGPLLIFPLKSCETTSLVLLIRSIF* | 4315 | ATGAGGCTAGCCCCAAGTTGGGACCATTATTAATTTTCCCCTCAAGTCATGCGAAACATCTCTTGTCCTTTAATCAGAAGCATATTTAG | 4316 |
| | 3 | MRNISCPFNQKHLGAAE* | 4317 | ATGCGAAACATCTCTTGTCCTTTAATCAGAAGCATATTTAGGGCGTGCGGAATAA | 4318 |
| | 4 | MADNSPPPPVFY* | 4319 | ATGGCAGACAATAACTCCCCAGTCCCCCAGTATTTTATTAA | 4320 |
| hsa-mir-148b | 1 | MWFLPTPRPHLAPGQRGHTWLQASPSPPFQPRSPARSAFLPCI* | 4321 | ATGTGGTTTCTGCCCACACCCCGCCCACACCCTTGCTCCTGGCCAGCCCTTCAGCCAGGAGTCAGCAGTCAGGTCTGCGTTTCTCCCATGCATTTGA | 4322 |
| | 2 | MAPSLSQPSFSAQESSQVCVSPMHLTNSNLMVHSNVTFKLYTGCRRLVSPRLS* | 4323 | ATGGCTCCAAGCCTCTCCCAGCCTCTTTAGCCCAGGAGTCAGGAGTCCAGCCAGGTCTGCGTTTCTCCCATGCAATTGACGAATTCAACCTGATGGTCACTCGAATGTGACCTTTAAACTTTATACAGGTCGTCGTGCCCACGCTCTCTAG | 4324 |
| | 3 | MCPFTCSLLPSPLSLRSPRTKDSFLARFLSVCEGS* | 4325 | ATGTGTCCCTTTCACCTGTAGCCTTCTCTCCCCCCCTCAGCCTCAGAAGTCCAAGGACAAAGGATTCTTTCTTGGCCAGTTGTTCAGTGTGTGAAGGAGTTAG | 4326 |
| | 4 | MAPNSVRPVSTLIHLFFFPERGSLCLPGWSAVV* | 4327 | ATGGCACCCAACTCTGTTAGGCCAGTAAGTACCCTTATTCATCTTTTTTTTTTTTCCAGAGAGGGGCTCACTCTGTCTCCCAGGCTGGAGTGCAGTGGTGTGA | 4328 |
| hsa-mir-148b | 1 | MLGGGGRGVWDQGIARPLLAGGPGHRGSDGGLDPLKHITHCSLCSSLGKDRI* | 4329 | ATGCTTGGGGGAGGTGGTATACACAGAGGCTCAGTTGGGACTAGATTTCTGAAGCATATAACTCATTGTTCCTTGTTCCAGTTGGGTAAGGATAGGATTTAA | 4330 |
| | 2 | MPFSRA* | 4331 | ATGCCCTTTAGCAGAGCCTAG | 4332 |
| | 3 | MDEG* | 4333 | ATGGATGAAGGCTGA | 4334 |
| | 4 | MKADR* | 4335 | ATGAAGGCTGATAGATAA | 4336 |
| hsa-mir-148b | 1 | MILJLGGA* | 4337 | ATGATCTTATCCTAGGCGGGGCCTAA | 4338 |
| | 2 | MGTYGQSAAAFLLRLHVGTSCGARWRR* | 4339 | ATGGGAACGTATGGCCAATCAGCGCGCCAATGTGAGGGGCTGA | 4340 |
| | 3 | MANQRRIRFFCGSTSAPAAGQDGCADFCGRSWRGSRIDAVVSTGAGSQGSARVGDGEREFRVILGD* | 4341 | ATGGCCAATCAGAGGCGGCTGATTTGGTAGGAGGGCTCCACGTGCGGCACCAGCTGCGGGGCAAGATGCTGTGTGTCCACAGGGCGCCGGGAGTCAGGGTTCAGCCCGAGTGGAGAACGGGGAAAGAGAGTTCCGGGTAATTCTTGGGACTGA | 4342 |
| | 4 | MEALILVGAGGAAEMLWCPQGPGVRVQPEWETGKESSG* | 4343 | ATGGAGGCGCTGATTTTGGTAGGAGCTGGAGHGGCAGCAGAGATGCTGTGGTGTCCACAGGGGCCGGGAGTCAGCCGGGTTCAGCGGGTCGGGGAGACGGGGAAAGAGAGTTCGGGTAA | 4344 |
| hsa-mir-148b | 1 | MELRARGWWLLCAAAALVACARGDPASKSRSCGEVRQIYGAKGFSLSDVPQAEISGE* | 4345 | ATGGAGCTCCGGGCGGGGTGGTGGCTGCTATGTGCGGCCGCAGCGGCCTGCGCCGAGCTACGGAGCCAGCGAGCGGCAGCGAGCCCGCCAGATCTACGGAGCCAAGGGGTTCAGCCTGTCGGAGATCTCGGGTGAGTGA | 4346 |
| | 2 | MCGRSAGRLRPRGPGQQEPELRRGPPDLRSQGLQPERRAPGGDLG* | 4347 | ATGTGTGGCCGGAGCGCTGGCCGCCTGCGCCCGCGGGAGCCCGGCCAGCAAGAGCCGGAGCTCCGGAGATCTCGGGAGATCCAGAGATCCAGATCTCAGCCTGCAGCCCGAGCGGACGTCCCCCAGGCGGGAGATCTGGGTAA | 4348 |
| hsa-mir-149 | 3 | MAPCAAAPLQPHGPRLQAPRRTPSPGSPFPRSVVLRPSPPPARRLLPCGADLAGLRARGAPPGPRLELGYFCPPLGPARLQAGSPSPGAGCRGAVGLGVAGLSGRR* | 4349 | ATGGCTCCCTGCGCTGCGGCTCCTGCGCCCCCAACCCCAGGGCCTCCAAGCCGCGCCCGACTCCCTCCCCAGGGTCTGCCGCGCTTCTTCCCGCCGGAGCTGGCGTGCTGATCTCGGGGGCCGCGCCGGCGGCCTCCCCGCCCCCCGACGCCCCCCCCGCAGCCGCCCGGGAGCTCCCAGGGCGGCTCCCCGCGCCTCCGGAGGCTCGGGGCTGCTCGGGGGCGTGGGGGCCGGCCGGCCGGCGTGCGGGGCCGGCCGGGGCTCGGGCGTCGGGGGGGCGCGTGTGGGCTCGGGCGCGTCGGGGCTGCGGGGGCGCCGGCTGA | 4350 |

Figure 1 (Continued)

| | | | | |
|---|---|---|---|---|
| | 4 | MGTQRRNAHGPGDSEQEGSVHLGEGGLWPCLAAGGG VVGGGSRALLDPCPSRRNRTHRQPLALGGSPDAPSLRFL* | 4351 | ATGGGGACTCAGCGCAGAAATGCCCATGTCCTGCGATTCTGAGCAAGAAGGATC CGTGCATCTGGGTGAGGGGTCTGGGTGCCATGCCTCTGACCCTTGCCGCGGGGGGCGAGTGG TGGGAGGAGGCAGTCCGGCCCTTGGTCGCGGGCTCTGAGGCCCTCTGGATCTCCCGATGCCCCAGCCTGAGGTTCTTGTAA AGACAGCCCCTTGCCTGCCCTTGGTGATCTCCCGATGCCCCAGCCTGAGGTTCTTGTAA |
| | 1 | MVAGGLRADGRGVGRGGKHDGVSLGAVDAVDEELRC RGRSTSQVGPRLPLAQTSGAQADRDWPGAQAS* | 4353 | ATGGTGGGGGGGGGCTTCGGGCAGACGCGCAGGGGTGTGGGGAGGGCAGGGAAGC ACGATGGGGTGAGTCGGAGCTGTGGGGATGCGGTCCAAGGCTGACGAGGAGGATGCCGT GGCCGGTCCACCTCGCAGGTGGGCCAAGGTGCTGCCCTCTGGCTCAGACGTCAGGAGC CCAGGGCGGAGCGGAGGACTGGCCAAGGGCGCAGGCTTCTTAG |
| hsa-mir-149 | 2 | MPLTRS* | 4355 | ATGCCGTTGACGAGGAGCTGA |
| | 3 | MPWPVHLAGGAKAASGSDVRSPGGQGLARGAGFLEDG AKVRKRSSAAWAVGGPQETPWVVCPVPHPRRLLDVP EDATATGAGWGPRADGPGAGAGFEKRVRAWGKPSQPS ASQEGPVAGCRAE* | 4357 | ATGCCGTGGCCGGTCCACCTCGCAGGTGGGCCAAGGCTGCCCTCTGGCTCAGACGTC AGGAGCCCAGCCGGACGGAGGACTGTCGCCAGGGCGCAGGCTTCTTAGAGGATGGGG CAAAGTGAGGAAAAGATCCTCGCAGTCGCACCCTCAGTGGGCTGTCCCCAGGAAACC CCTGGGTCGTTTGTCAGTCGACCTCACCCAGCGAGCTGGCTGGACGCTGCCGGAG GATGCCACAGCACCGGAGTCTGGTTGGGGTCGGAGCCAGAGATGGGCCAGGGGCTGG GCCAGGCTTCGAGAAGAGGGTTCGGGCTTGGGGAAAGCCTTCGCAGCCATCGGCCA GCCAGGCCCCGTTGCCGGGTGCAGAGCTGAGTAG |
| | 4 | MGQK* | 4359 | ATGGGGCAAAAGTGA |
| | 1 | MTAGILGHIALHSERPQPLAFPQEGACFAALQGDSAEPAS AISCPGQPVAPACAGPELRRRKPAGGLLPLTAVRPACS GPQGAASIQPARGSQAFARLASSLPGAPRPAPELWLRVF HPVLVRGGREGRGLLCWGSWNNAGRRAGWASWPGGAE GSAGEAEARGPVRGREGV* | 4361 | ATGACAGCTGGTTCTTGGGCACATTGCCTCTCTCATTCAGAAAAGGCCCCCAGCCCTTGCCA TTCTTCCAAGGAGGGGGCTGCTTCCAGGGGCAGGCCACTCCAGAGAGCTCCAGCCGAG TCTGCCCATCTCATGTCCAGAAAGCCACCAACGGAGGCCTCGATCCAGCCTCTCCAGCC CTCGCAGAGGGGCTCAGGGGCGCCGCCCTTTGACTGCCGTGCCGTCCAGCG TGCAGCGGGGCTCAGGGGCGCCGCTGCCCGCTCGATCCAGCGTGCCGCCGAGCCTGCGCT GCCCGCCTTGCCTGCAGCCTGCCGTGCTTGTCACTCCCGTGCTTGTCGAGGAGGGCGGTAGGGCGGGAGGGGACGGGGGCTGTGCTG CGGTCTTCACTCCCGTGCTTGTCGAGGAGGGCGGTGGCCGGGGCCGGGAGTTGCCGGGCGG GCTGAGGGGTCGGCGGGGAGGTGAGGGCCGGGGCGGCGGGGCGGGTGAGG |
| hsa-mir-149 | 2 | MSRTTTCGPCLRRAGAPQKEASGRPPAFDCRASSLQRA SGGRLDPACPRLPGLRPPCVQPAGGSQAGARALAPCLH SRACPRREGGTGAVLGQLEQRRSPGRLGELAGRG* | 4363 | ATGTCAGGAGGACCACAACCTGTGCCGGCCTGCCTGCGCGGCCGGAGCTCCGCAGAA GAAGCCAGCCAGGGCCGGAAGGCCTCGATCCAGCGTGTCCTCGTGCCTCAAGCTGCAGCGGG CCTCAGGGACCCGAGCCCGCCCGCTTTGACTGCCGAGCCCGCCTTGCCGCCTCGCCCGCCTT GGGTCGAGCCTGCCGCGGGGCTCCCGCCCGCCTCGCCGCCGCCCGCGCCTTGCCGCCTCGCTCTTC ACTCCCGTGCTTGTCGAGGAGGGCGGTGGCCGGGGGCCGGGGCGGCGGGGAGTTGGCTGGGGCTG GAACAACCAGGTGCGCCAGGTGCCGGCTGGGCGGCCGAGTTGGCCGGGCGGGCTGA |
| | 3 | MPLVSLSRLRGGWVGPREGGAQEEPAGDATHP PP* | 4365 | ATGCCTCTCGTCAGCCTCTCGCGTCTCCGGGGATGGGTGGGACCGCGGAGGAGGGCGGCTGGGGCG GGACCTGCGAGGGCACGAGCGGCACAGGAGAGCCGGGGCACGGGGACGCCACCCTCCTCCTAG |
| | 4 | MCPADLCSPGLGSLDGCTGPHHSPHPRRDAS* | 4367 | ATGTGCCCTGCCGACTGCAGCCCGACCTGGGGCTGTCGGCAGCCTGGATGGGTGCACGGGGCCCCTGA |
| hsa-mir-149 | 1 | MALSPNPCTSAGLRPWYRPGGQQPGDPGTGRPQGVR* | 4369 | ATGGCCCTGTCTCCAAACCCTTGTACCAGTGCTGGCTCAGACCCTGGTACAGGCCT GGGGACAGGACCCTGGGACAGCCCCAAGGGTGAGGTGA |

Figure 1 (Continued)

| | | | | | |
|---|---|---|---|---|---|
| hsa-mir-150 | 2 | MRLSPSGPTYPLVRSCLIAPTPCLSSPPLCDAQSTPVSIV PASRGGLCSPQLCKTPPHVPQPWATVCPVLFLSRPPSL RPVCIGFSPDASCPLPSQQPGPRYH* | 4371 | ATGCGTCTCTCCCTTCGGGTCCCCACATATCTCTGGTGCGTCCTGCCTCACCGCC CCACCCCATGCCTCTGTCCCCACTCTGTCGTGATGCAAGTACACCTGTTTCTAT TGTACCTGCCACAACCCTGGGCACCGTGGTCTGTGTCCTCCCCAGCTGTCCTCCC CATGTGCCACAACCCTGGGCACCGTGGCTCGTGCCTGTCCGTTCCTCTCAAGGCCCCA TCTCTGCGCCTGTGTATTGGCCGTCTCCGGACGCTTCCTGCCCACTTCCTTCCC AGCAGCCTGGCCCCGGTACCACTGA | 4372 |
| | 3 | MPVVPTSV* | 4373 | ATGCCTGTCGTCCCCACCTCTGTGTGA | 4374 |
| | 4 | MRKVHLFLLYLPLAVVCCALPSSAKPLLPMCHNPGPPCV LSCSSQGPHLCGLCVLGRLRTLPAHFLPSSLGPGTTEQA PGEPHDATCPHRQFPYCDFEAAGAEEVSRI* | 4375 | ATGCGCAAAGTACACCTGTTTCTATTGTACCTGCCTCTCCGGGTGGTCTGTGCTCTCC CCAGCTGTCGAAAACCCTCCTCCAGGCCTGCACAACCCTGGCCACCGTGTCC TGTCCTGTTCTCAAGGCCCCATTCTGCCGGCTGTGTATTGGCCGTCTCCG GACGCTTCCTGCCACTCTCCAGCAGCTGGGCCGTACCACTGAACAGGC TCCAGGGAGCCTCATGATGCCACTCGCCACCACCACCAATTCCTTACTGCGATTT TGAGGCAGCTGGCGCAGAGGAAGTTTCTAGAATCTGA | 4376 |
| hsa-mir-151 | 1 | MRRRPAPPAPPARVLGGGEAGGREEVGGPRGGREA* | 4377 | ATGCGGCGGGAGACCGGCCCCTCGCCGCCCGGCCCTGGGTTCGGGAGGAGGGGA GGCCGGTGGCCGTGAGGAGGTTGGGGGCCCTGCGGAGGCCGAGAGGCTTAA | 4378 |
| | 2 | MPEKQKCRGRRRKREIAGTSAGFARTREGGSRRPDLRP PGAASRAAKGGLRAALCRCPSPKPAVSPNANPQVW* | 4379 | ATGCCTGAAAAACAAAAGGGAGAGGCAGGAGGAGGAGGAAATCGCAGGGA CGTCGGCAGGGTTCGCCGACTTCCGT CCCCGGGCGGCCGTGCGGCCTGCGAGGAGGCAGCCAGGCGCCCGACCTCCGT CCGAGCCCCAAGCCGCCGTGTCCCGAACGCAAACCCTCAAGTTTGGTAG | 4380 |
| | 3 | MRLR* | 4381 | ATGAGACTAAGATAA | 4382 |
| | 4 | MGTGYTFKLKAEGSARVWGFVFKT* | 4383 | ATGGGAACTGGTTATACATTCAAGCTGAAGGCAGTGCAAGAGTTTGGGG ATTTGTATTTAAGACTTAA | 4384 |
| | 1 | MQRPEAGHVRTRGRGPRRQAGGRRRLLEPGSPRGCGY GAGGRGDPGRRELGRDRAGLGGAANSELARPAAGNPV SPLTGPRTREEKFVPAPTGEEACPESVGAGLKFWVRLE WGWRVSCDSAGRVRSGLSVPDSAPITGG* | 4385 | ATGCAGCGGCCGGAGGCTGGGCACGTCCGCACCCGCGGCCGGGGACCCCGCGGCGGCA GGCGGCCGGGGGAGGCGGCGGCGCCCTGCTCGAGCCGGGAGCCCCTGGCTGCCGGGTACG GAGCGGGCGGGGAGGCGGGGATCCAGCAGCTCAGCAGACTCGCGCCCGGCGCGGGAGCTGCGACAGAGCAGG GTTAGGGGGAGCAGCAGCCCAACTCAGAAACTCGCGCCCGGCGCTGGGAACTTGT CACCCGGACTGGGCGTGTCTGAGTCGTCTGGGCGGGGGGAAAAGTTCGTCCAGCGCCGACCGGA GAGGGGCCGTGTCTGAGTCCAGGCGGCTGGGGGCCTGAAGTTCTGGGTCCGTTTGAA TGGGGGGTGCGGTGGTGAGTTGCCATTCGCGGGAGGGGTAAGGAGTGGCTTGCGCCGTGCCG TCCCAGACTCGGCTCCATCACGGTGGTGA | 4386 |
| hsa-mir-152 | 2 | MGMLLESTRARAWGRADSAGPARPGISWKKEARPAVP PGFGSVIHSDSGSGAVSA* | 4387 | ATGGGCATGCTTCTGGAGTCTACCCGGCAGGCCTGGGGCCGCGCTGATAGCGC AGGTCCAGCCCGGCCAGGGATCAGCTGGAAGAAGGCTCGGCCCGTGTCCCC CCGGCCCAGGTCTGTGATACACTCCGGGCTCTGGAGCAGTCAGTGCATGA | 4388 |
| | 3 | MTELGPGRTFCTQRAQRPLGACSGTSAWEWSGHLGWP MWHRAGQNQLWTLRTGVAGA* | 4389 | ATGACAGAACTTGGGCCCGGAAGGACCTTCTGCACCCAACGGGCACAGCGCCACT CGGGCCCTGCAGTGGAACATCTGCTGGAGTGGAGTGGCACTTGGGTTGGCCCA TGTGGCACAGGGCTGGGCAGAACCAGCTGTGGGACCTTGAGGACTGTGCTGGGG GCCTGA | 4390 |
| | 4 | MYPRASRSHRHRVSTSSQGPNGTLLSGVSCRNLPSTPSR LPSS* | 4391 | ATGTATCCTAGGGCCAGCAGATCCATAGACACAGGGTGTCCACCTCGAGTCAGGG GCCAAACGGGAACTCTCCTCCTGGGTGTCAGTTGCAGGAACCTTCCCTCTACACCATC AAGGCTGTTTTCATCCTAG | 4392 |

Figure 1 (Continued)

| | | | | |
|---|---|---|---|---|
| hsa-mir-153-1 | 1 | MGGGGAGVRPPLGLEFRVGPGASASDFWPPAPDPTLPPLKAGLRLRLCPSPSLHHPRGPAPRRPLLLCSLPLTLPGLAPSPPPASSRGPSAFCLPFSLSRTPASPLLPVPSCPAVSRPCTALPCCPLRLSLPPFARLPSFIPLRFSFIPLRLFASFFCVFHSFSFPLSSSSLSPSLSHSVSASPFFSLSISPSPRFSSFLSALSPVFLHLLPLSASFSLLLCPSLPLPPAACLSSLCPSLSLLPSFSLSLTAASVIFVICS* | 4393 | ATGGGCGGGGGCGGAGCCGGAGCCCTGGAGCCCGGGTCGGGCCTGGAGCCTCCGGCCTGACTTCCGGCCGCCGCTGGCCTGGAGCCCCGGCTGTGG... (sequence) | 4394 |
| | 2 | MDRQDMWPGDHPELGARGTGKRQRLSKGVVWEDLWILGGSVEQVGTRQGLPEGLTLPQH* | 4395 | ATGGATAGACAGGACATGTGGCCCGGGGACCACCCGAGCTGGGAGCAAGGGTAC... (sequence) | 4396 |
| | 3 | MSLGTGQRSRAGGGDMGHVSEPQDSSF* | 4397 | ATGTCTCTAGGTACTGGACAGAGGAGCAGAGCTGGGGTGGGGACATGGGTATAGTTTCTGAACCTCAGGACAGCAGTTTCTAA | 4398 |
| | 4 | MDLF* | 4399 | ATGGATCTGTTTTAA | 4400 |
| hsa-mir-153-1 | 1 | MRRPRRPGGLGGSGGLRLLLCLLLSSRPGGCSAVSAHGQEETWAGGWWGAGSSLGPJAKLGGGEGEMS* | 4401 | ATGCGGGGCCCGCGCGGCCTGGGGCTCCGGGGATCCGGGGGTCTCCGGCTGCT... (sequence) | 4402 |
| | 2 | MKLGENMGWGRHAR* | 4403 | ATGAAGCTCGGGGAGAATATTGGTTGGGAGGCATCGAGATGA | 4404 |
| | 3 | MRDEEGERASRRKGA* | 4405 | ATGCGAGATTAGGAAGGTGAGAGGCGTTCGGAGGAAAGGGCGTAG | 4406 |
| | 4 | MRKVRGRLGGKGRRPGGGAGNTGAGPKRIGLWGKLQVREKDTGCMWAEGLRDRLRDHRRSHLLRGAWEVVTGAEEWEGEVAGRMRER* | 4407 | ATGAGGAAGGTGAGAGGGTCTCGAGGAATACGGGGGGGACTCTAAGAGAATTGGGCTCTGGGGAAAATTGCAGTT... (sequence) | 4408 |
| hsa-mir-153-1 | 1 | MSTPVSVPSLRSSLPGEPGLRAHLV* | 4409 | ATGTCCACACTGTCTCTGTCCTCTGTCCTCCAGGTGAACCTGGTC | 4410 |
| | 2 | MTEESLPPQGPSWTSAGMTRGPPAGQCALSARHRGARLRCS* | 4411 | ATGACCGAGGAGTCCCTCCCTCCTCAAGGTCCCTCCTGGACTTCCGCAGGTATGACGCTCGGTGCTCTGA | 4412 |
| hsa-mir-153-2 | 3 | MCHRILMHKARMPSWILIWLHGMKEVASAGPDTTLRDLLAGKPGDT* | 4413 | ATGTGCCACAGGATATTGATGCATAAAGCTCGAATGCCAGTTCAGTTGGATTCATCTGG... (sequence) | 4414 |
| | 4 | MLDSVLQEEIDNEKKAAFKTTALYVNSRSALARWWCLVNKPPQGK* | 4415 | ATGCTAGACTCTGTCTTACGAGGAAGAAATTGACAATGAAAAAGCAGCATTAA... (sequence) | 4416 |

Figure 1 (Continued)

| | | | | |
|---|---|---|---|---|
| hsa-mir-153-2 | 1 | MGPPLPLLLLLLLPPRVLPAAPSSVPRGRQLPGRLGE WGAPGEGRLNELVGGVVRGAPP* | 4417 | ATGGGGCCGCCGCTCCCGCTGCTGCTGCTACTGCTGCTGCTGCTCCGCCACGCGTC CTGCCTGCCGCGCCCTTCGTCCGTCCCGCGGTGCCGGCAGTCCCGGGGTCTGGGT GAGTGGGGGAGGGGGGGAGGGGCGCCTCAATGAATTAGTTGGGGGGGTTGTGAG AGGGGCGCCTCCGTGA | 4418 |
| | 2 | MQGRRLNK* | 4419 | ATGCAGGGAAGGCGCCTCAATAAATGA | 4420 |
| | 3 | MSEGVGEGAPLRGSGGGTPQ* | 4421 | ATGAGTGGGGGCGTTGGGGAGGGGCGTTCTGGGGAGGGACGC CTCAATGA | 4422 |
| | 4 | MNERGAWGEGRLNECGAWGKGRLNE* | 4423 | ATGAATGAGAGGGGGCGTGGGGAGGGCCGCCTCTGAGAGGTTCGGGGAGGGGCGTGGG GAAAGGGCGCCTCAATGAATGA | 4424 |
| hsa-mir-154 | 1 | MDQGVEGCGCGPGVGRQSACSL* | 4425 | ATGGACCAGGGGGTAGAGGGGAGGTGGGTGTGGACCTGGGGCTCGGGGCCCAGTCAG CTTTGCAGCCTATGA | 4426 |
| | 2 | MKDGKEGYRDRGRVGLRIARAAWHTVLG* | 4427 | ATGAAGGACGGAAAGGAGGGCTACAGAGATAGGGGAAGAGTGGGCGCTGAGGATAG CCAGAGCGGCTTGGCACACAGTTTAGGGTAA | 4428 |
| | 3 | MTEPVTPGSSFKACLMGDSVVPVTKLGPESQGRAHQV AALP* | 4429 | ATGACTGAGCCGGTCACTCCAGGGTCTTCCTTCAAAGCGTGTCTAATGCGAGACAGCC GTTGTCCCAGTAACCAAATTGGGACCAGAGTCCCAGGGAAGGGCTCATCAGGTGGC CGCTCTGCCTTGA | 4430 |
| | 4 | MILFPLDPAPLVPFSL* | 4431 | ATGATTCTCTTCCCTCCTCGGATCCAGCCTCTTAGTTCCTTTTCACTTTGA | 4432 |
| hsa-mir-155 | 1 | MSHK* | 4433 | ATGAGTCACAAGTGA | 4434 |
| | 2 | MDSRGRQREGGVFET* | 4435 | ATGGATTCCCGGGGACAGAGGCAGGGGAAGGAGGGGTGTTCGAAACCTAA | 4436 |
| | 3 | MVGDVPV* | 4437 | ATGGTTGGGGACGTACCTGTATAA | 4438 |
| | 4 | MALDQLPCWSGQRSV* | 4439 | ATGGCCCTGGACCAGTTCCCTGTTGGAGTGGCAGAGAAGTGTGTAA | 4440 |
| hsa-mir-155 | 1 | MKYKSEKKKTVLCQNASFPLCILAFENSEERFLFI* | 4441 | ATGAAGTACAAATCAGAAAAGAAAACTGTACTGTGTCAGAATGCAAGCTTTCCT CTTTGCATTTGAATTCCGAAGAGCGTTTTTGTTTATTAA | 4442 |
| | 2 | MQAFLFAFWHLKTPKSGFCFLFKEDDTYVYPIQN* | 4443 | ATGCAAGCTTTCTTTTGCATTTGGCATTTGAAACTCCGAAGAGCGGTTTTTGTT TTTATTTAAAGAAGATGATACATATGTACCGATTCAAAACTAGAGAATAG | 4444 |
| | 3 | MHHMCTRFKTRE* | 4445 | ATGATACATATGTGTACCGATCAACAATGTCATCTTTAA | 4446 |
| | 4 | MPKGNNVIF* | 4447 | ATGCCTAAAGGTAACAATGTCATCTTTAA | 4448 |
| hsa-mir-15a | 1 | MRSLSAFGAIFE* | 4449 | ATGAGGAGCTCAGCGTTTCGGCGCCATTTCGAGTGA | 4450 |
| | 2 | MPDLINLAGETG* | 4451 | ATGCCTGATCTCATCAATCTAGCGGGAGAGACAGGATAA | 4452 |
| | 3 | MTPPEKLL* | 4453 | ATGACTCCGCCGGAAAAATTACTTTAA | 4454 |
| | 4 | MWREGRCETGLWGEGCSLSGTRTGCCGEAAAQRICQQ DPPPGTGACDGALRGLCRRPLLDRRTGRAPLPHFRTGPP FLAVFSTR* | 4455 | ATGTGGCGGGAGCGGTGCGAGACGGGACTGTGGGAGGGAGGGAGTGCAGTTGA GGGGGAGAGCGGCCCGCCGGGACGGGAGACGCCCGCCGGGGATCTGTCAGCAA GACCCCCCCCCCGGACAGGGACCGCCGGGCGCGGAGGCCCTGAGCGCCTCCAGGCG GCGGTCCTTGACAGGAGGACGGCCGCTGAACCCGGCGGGCCCCATTTCCGAACCGGGCC GCTTTTCTGCGCCGTTTTCTGACCCGGTGA | 4456 |
| hsa-mir-15a | 1 | MLTQSINSGTKGPTSSELC* | 4457 | ATGTTGACGCAATCTATAAATAGTGGAACAAAAGGACCAACTTCCTCGGAGCTTTGC TGA | 4458 |
| | 2 | MGRGALRRGRGRABRRGPRRAGGTPG* | 4459 | ATGGGCCGGGGCGCTGCGCCGGGAGGGCGGCGGCGGAGGGCGGGCGCCGCGCCC GCCGAGGGGGACACCTGGTGA | 4460 |
| | 3 | MAGACAAAKIDGILACATRAVGRAEARAALLGSRRGSR LLLSPVGRPPEATRQGPEAAACASLPPSSDPAPQLRPLT AVGGWSREALSLHAAVPPGSGAHAASKH* | 4461 | ATGGCCGGTGCCTGCCAGCCAAAGATCGACGGCCTCGCCTGCACCCGAGCCGTGGGCCGGGCC GGTAGGAGGAGGCGGAGGCGCGGAGGCCGCGGCCGCCCTGCTGGGTCGACGCTACGCCGGAGGGCTCCGG CTGCTTCTCTCGCCCGTGGGCCGCCCTCCTGAGACTCGGACCGGGAGCTCCGGAGCTTCGTCGTCCTCTA ACTGCTGTGGGAGGATGAGCAGAGAAGCGCTGTCGCTGCACCGCCAGTTCGTCGTCCTCTA TGGCTCTGGTGCCCACGCAGCCAAGCACTGA | 4462 |

Figure 1 (Continued)

| | | | | | |
|---|---|---|---|---|---|
| | 4 | MRLAPSELGPGASASSSNCCGRMEQRSAVAARRRAPW LWCPRSQQALSWGAGWNRGTLASRSLGPERERPPRRR GGSTGRGEGAELALLTAVPERGGRKLGRGGGEVGVG AGGESARAGFGGERGAGSCDVQTPPLQAGCRGDVTTL DCRGWHFRSLPSCSPAPGTAGWSPFAV* | 4463 | ATGGCGCTCGCTCCTCCCGAGCTCGGACCCGGGCGCTCAGCTTCGTCCTCTAACTGC TGTGGGAGGATGGAGCAGCAGAGAAGCCGTGTCGCTGAGCTGGCGGGGCCGGGGCA CTGGTGCCCACCGCCAGCCAGCAAGCACTGAGCTGCGGAGCCAGGTGGAACCGGGGCA CGCTGCTTCTCGGAGCCTCGGACCTGAGCGCGAGCTCGGGAGCTGGGAGCTGCCGTGC GGTTCCACAGGCGCAAAGTTGGGAGGGCGGCGGAGCCGGAGCGGAGCGGAGGAGCGGG TGGGGAGGGCGAGAGAGCGCGCGACTTCGGCCGGGGAGGGTGCAGGGTGCACCCTTGACT ATGTACAGACACACCCCGCTACAGCTGGCTGCAGGGTGCAGGGGTGACGTCACCCTTGACT GCAGGGGTGCACTTCGCTCCCCAGCCGTGCTCCCAGCTGCTCCCAGCCCTGGCACCGCCG GCTGGAGCCCTTTCGCAGTTTGA | 4464 |
| | 1 | MAVHAALFFKLVDPRNHCAHL* | 4465 | ATGGCGGTGATAATCGCCGCACTTTTTCAAATTAGTCGATCCCAGAAATCATTGC GCGCATTTGTAA | 4466 |
| hsa-mir-15b | 2 | MSRGGPEPRRSFL* | 4467 | ATGTCTCGGGGAGGCCTCGAGCCTCGCAGATCTTTCTTTAA | 4468 |
| | 3 | MYYCPTGLRLGSWRDKLLPLQN* | 4469 | ATGTTTACTGTCAACGGACTCGCGCTGGGGAGTCGAGAGACAAACTCTTGCCA CTCAAAATTAG | 4470 |
| | 4 | MPRAYNGARS* | 4471 | ATGCCCCGGGCGTCAACGGCGCCAGGAGCTAA | 4472 |
| | 1 | MRSLSAFGAIFE* | 4473 | ATGAGGAGCCTCAGTGCTTTCGGCGCCATTTGAGTGA | 4474 |
| | 2 | MPDLINLAGETG* | 4475 | ATGCCTGATCTCATCAATCTAGCGGGAGAGACAGGATAA | 4476 |
| | 3 | MTPPEKLL* | 4477 | ATGACTCCGCCGGAAAATTACTTTAA | 4478 |
| hsa-mir-16-1 | 4 | MWRERGETGLWGEGSCSLSGTRTGCGGAAAAQRICQQ DPPRGTGAGDGALRGLCRRPLLDRRTGRAPLPHERTGPP FLAVFSTR* | 4479 | ATGTGGCGGGAGCGCGGAGAGACGGGCTGTGGGGGGAGGGAGCTGCAGTTGA GCGGGACGCGGACCGGTGCGGTCGGAGCAGCCGCCGCCAGCGGATCGTCAGCAA GACCCCCGCCGGACCGGAGCCGGGACACGGCACTGCGGGGTCTCTGCAGGCG CTGCTCCGTTGACAGGAGGATGGAGCAGAGACAGGATAACCGGGCCTCCCCCATTCCGAACCGGGCC GCCTTTTCTGCGGTTTTCTGACCCGGTGA | 4480 |
| | 1 | MLTQSINSGGTKGPTSSELC* | 4481 | ATGTTGACGCAAATCTATAAATAGTGGAACAAAAGGACCAACTTCCTCGGAGCTTTGC TGA | 4482 |
| | 2 | MGRGALRRGRGRARRGPRRGGTPG* | 4483 | ATGGGGCGGGGAGCGCTGCGCGGAGCGCTGCGCGGGGGAGGGGCGGGCGCGCGCGGGGCCC GCCGAGGGGGGACACCTGGCTGA | 4484 |
| hsa-mir-16-1 | 3 | MAGACAAAKIDGGLACATRAVGRAEARAALLGSRRGSR LLLSPVGRPPEATRIQGPEAAACASLPPSSDPAPQLRPLT AVGGWSREALSLHAAVPPGSGAHAASKH* | 4485 | ATGGCGGGTGTTGCCTTCGCGCACAGCAGCAAAGACGGAGGACTGGCGTGCACCGGC GTAGGAGAGCGGAGCCGCGACCGCCTGCTGGGAGGCTACGCGCTCAGGCCCGAGGCC CTGCTTCTCTCGCCCGTGGGCCGCCTCGCTCCTCCGAGCTCGGCGCCTCAGCTTCGTCCTCTA ACTGCTGTGGGGAGGATGGAGCAGAGAAGCAGAGAAGCAGAGCCGTGCTGCTGACGCCAAGCACTGA TGGCCTCTGGTGCCCACGCAGCCAGCAAGCACTGA | 4486 |
| | 4 | MRLAPSELGPGASASSSNCCGRMEQRSAVAARRRAPW LWCPRSQQALSWGAGWNRGTLASRSLGPERERPPRRR GGSTGRGEGAELALLTAVPERGGRKLGRGGGEVGVG AGGESARAGFGGERGAGSCDVQTPPLQAGCRGDVTTL DCRGWHFRSLPSCSPAPGTAGWSPFAV* | 4487 | ATGCGCCTCGCTCCTCCCGAGCTCGGACCCGGGCGCTCAGCTTCGTCCTCTAACTGC TGTGGGAGGATGGAGCAGCAGAGAAGCCGTGTCGCTGCAGCGCTGGCGGGGCCGGGGCT CTGGTGCCCAGGCCAGCCAGCAAGCACTGAGCTGGGAGCCAGGTGGAACCGGGGGCAGCA CGCTGCTTCTCGGAGCCTCGGACCTGAGCGCGAGCTGGCGCTGACGCCAAGCACCGGGCT GGTTCCACAGGCGCGAAAGTTGGGAGGGCGGCGGAGCCGGAGCGTGGGAGCTGCCGGA GGGGGAGAGGAGCGCGCCGACTTCGGCGGGAGGCTGCAGCGCGAGGAGCGGCCCGGCGG AGGTACGACAGACACCCCGCTACAGCTGGCTGCAGGGGTGACGTCACCCTTGACTGCTG TGGCAGGGGTGCACTTCCGCTCCTCCCAGCCGTGCTCCCAGCTGCTCCCAGCCCTGTGCCGG GCTGGAGCCCTTTCGCAGTTTGA | 4488 |
| | 1 | MAVHAALFFKLVDPRNHCAHL* | 4489 | ATGGCGGTGATAATCGCCGCACTTTTTTCAAATTAGTGGATCCCAGAAATCATTGTAA | 4490 |

Figure 1 (Continued)

| | | | | |
|---|---|---|---|---|
| hsa-mir-16-2 | 2 | MSRGGPEPRRSFL* | 4491 | ATGTCTCGGGAGGCCCTGAGCCTGGAGATCTTTCTTTAA | 4492 |
| | 3 | MVYCPTGLRLGSWRDKLLPLQN* | 4493 | ATGGTTTACTGCCAACGGGACTCCGCTGGGGAGCTGGAGAGACAAACTCTTGCA CTCCAAAATTAG | 4494 |
| | 4 | MPRAVNGARS* | 4495 | ATGCCCCGGGCCGTCAACGGTGCCAGGAGCTAA | 4496 |
| hsa-mir-17 | 1 | MVAATPPGESARPSGDGGKPVVCGPGLAGGAERPGAD WPGAAWRRRGRGGSRPLAAPACGSRIWLPPRSPAGRR RGIAGPGREGGRGRRARGGRARDPFRRPCLGRPEGGWAD GEHNGPSCRGRGRARPVPSPGPARAGRGIVSG* | 4497 | ATGGTGGCGGCTACTCCTCCTGGTGAGTCGCCGCCCCTCCGGCGACGGAGGGAA ACCTGTTGTGTGCGGCCCCGGGTCTGGCGGCGGAGCGGCCTGGGGCCGGACT GCCCCGGCGTGTGCCAGCGCCATCTGGCTGCCCCTCGCTGCCCTGCCATTGGCC GAGGGGGCGCAGAGCCGGGGCGGCGGACCCCTGCCTGGGGGAGAGGACGTGCGGCC GCGCCCCGGGACCTGCCGCCAGAACCCTTCCGGCGAGAGAGGACGTGCGAGCGCGGGA GGHNGCGCTGCCGGGCTGTGGGGTCTGGGTAG | 4498 |
| | 2 | MAPRGEDVRGPCLLRGPGRARGVGSLGRKVSPEGES* | 4499 | ATGGCCCCTCGCGGAGAGGACGTGCGAGGGCCCGTGCCTTCTCGGGGCCCGGGGCG CCGCGGGCGTGGGTCTGGGTAGGAAAGTTCTCCGAGGGCGAGAGTTAA | 4500 |
| | 3 | MGPAAGREGARPRGTCAPAGGVAWAGARGSPNFVRA RVGGGAPRSARPGRHPRSAWALLARVGSLGAGPATSPP WPSEEAAVGLSRGVEPPAPGRLLGVWRGRASPARRERR PRRHVPAGRAARG* | 4501 | ATGGGCCCAGCGGCCGGCCGTGCGAGGGGAGCCGCAGCGGTCCGATCGGCCGAGG GTGGGGGCAGGGGCCGGAGACGGAGGGCTGGGCCGATCGGGCTCAGCCGCCTCCCGCGTG GGCTTTGTTAGCGCCGGAGCTGGGGCAGTCGGCGTCAGCGAGGCCAGCGCGTCGGCCGTG GCCGCTTGCTGGAGGAGGCGTCAGCGTCAGCCAGCCAGCCTCGGCGGAGGCGCGT CCCGGCGCCATGTGCCTGGGCCGCCGCCGGCCGCTGACGGGGTGA | 4502 |
| | 4 | MPLRGGLHGGEGGGHGGDCAPPPIVPGLGLGPRATGTA AAEPPLWAGLGGAGGHKGGAARPRPRTRASAPPVA ARLPPGNGLGGLPRPAGPDSDPPPPGGYAENRRAALPL VRHVLPARAP* | 4503 | ATGTTCCTGCGGGGCGGGCTGCACGGCGGGGAGGGCGGGGACATGGCGGCGACTG CGCTCCGCGCCGAGCCCCCGATGTTCCGGCTTAGGCCTTGGGCCGGAGGGAGGACACCG GGAGGGCGCGGTCGCTCCGCGGCCCTCTGGGCCGCCACTCGGGGCTCGGCGGCCTCGC GGAGGGGCGGTTGCGGCGAAACGTGTTGGGCGGCGTGGGGGCCTCGAGGCCGCGT ACTCTGACGCACATGTGCCTGGGCCGCCATCGGAACATCGCAGGGCCGCTGACGCCTG TGTGCGACATGTGCCTGGGCCGCCGGGCTCCATGA | 4504 |
| | 1 | MSLSVKTKKKLDTGTQARRGIEPRQISLQPCLLSSH* | 4505 | ATGAGTTGCAGTTAAACAAAAAAATTAGATACTGAACCGAGGTAGACG AGGTATTGAACCCGCAGATCCTTGCAGCCCTCTCGTCTCAGCTCGCATTGA | 4506 |
| hsa-mir-181a-1 | 2 | MTQMMDRSTFSHVHTGRKRICWSLAVQGFVF* | 4507 | ATGACCCAGATGATGGACAGAAGCACATTTAGTCATGTGCACACTGGAAGAAGCG GATTTGCTGGTCCCTGGAAGAAAGCGGATTTGCTGGTCCCTGGCAGTGCAGGGGTTTGTCT TCTGA | 4508 |
| | 3 | MCTLEESGFAGPWQCRGLSSDWAVF* | 4509 | ATGTGCACACTGGAAGAAAGCGGATTTGCTGGTCCCTGGCAGTGCAGGGGTTTGTCT TCTGATTGGGCTGTGCCCTGA | 4510 |
| | 4 | MKIG* | 4511 | ATGAAAATTGGATAG | 4512 |
| hsa-mir-181a-2 | 1 | MPIRK VESAS* | 4513 | ATGCCGAGGAAGGAAGGTAGAAAGTGCTTCATAA | 4514 |
| | 2 | MCGRMFTVGFYSDRIS* | 4515 | ATGTGTGGAAGAATGACTGTAGGATTTTACAGTGACAGAATTAGTTAA | 4516 |
| | 3 | MPVFFSPFS* | 4517 | ATGTTTTTTGTTATTTTTCCCCTTCAGTTAA | 4518 |
| | 4 | MTHFQILFLHLQRLYCSSKLN* | 4519 | ATGACGCATTTTCAATTTTATTTTACATTACAGAGACTTTATTGTAGTTCTAAAC TAATAAACTAA | 4520 |
| hsa-mir-181b-1 | 1 | MSLWPHG* | 4521 | ATGTCTCTTTGTGGCCAATAGGATAG | 4522 |
| | 2 | MTHCFPCLSHGL* | 4523 | ATGACTCACTGCCCTGTCTTTCACATGGCTGTAA | 4524 |
| | 3 | MGCNLVQFRTADSTASTGARDV* | 4525 | ATGGGCTGTAATTTAGTTCAATTCAGAACTGCAGATAGTACAGCTTCCACAGGAGCA AGGGATGTCTGA | 4526 |
| | 4 | MSEHKWLSSE* | 4527 | ATGTCTGAGCACAAGTGGCTGAGTTCCGAGTGA | 4528 |

Figure 1 (Continued)

| | | | | | |
|---|---|---|---|---|---|
| hsa-mir-181b-2 | 1 | MTKCASVHHLGH* | 4529 | ATGACTAAATGTGCTTCTGTCCATCATCTGGGTCATATATAG | 4530 |
| | 2 | MCFCPSSGSYIVQCELSRQGCKEIWRGSIPRLAWVPVSN FFFVLTDKLISLLGQDAVLAGSSISTARHLSGNTEVVL* | 4531 | ATGTGCTTCTGTCCATCATCTGGGTCATATATAGTTCAATGCGAGCTGAGCAGACAG GGCTGCAAGGAAATCTGGCCGCGGTTCAATAACCTCGTCTAGCCTGGTTCCAGTATCT AATTTTTTTGTTTGATACCAAACTCCATTTCTACTGGACAAGGATGCTGTGC TGGCTGGAAGTTCCATTTCTACAGCAAGAATCTACTCTGGAAACACAGAAGTGTCC TCTAG | 4532 |
| | 3 | MRAEQTGLQGNLARFNTSSSLGSSI* | 4533 | ATGCGAGCTGAGCAGACAGGGCTGAAGTTCCATTCTACAGCAAGAATCTGGCGCGGTTCAATACCTCGTC TAGCCTGGGTTCCAGTATCTAA | 4534 |
| | 4 | MLCWLEVPPLQQESYLETQKLSSSHSSSNFFDCRCCFLP SPPSPFDKDPTVKSLT* | 4535 | ATGTGTCTGGCTGGAAGTTCCATTTCTACAGCAAGAATCCTATCGCAAGAACACAG AAGTTGTCCTCTAGCCACAGCAGCTCGAACTTTTTGATTGTCGTTGCTTTCTCC CATCACCCCCATCCCCTTTGACAAAGATCCAACTGTAAAAAGTCTTACGTAA | 4536 |
| hsa-mir-181c | 1 | MPVIPALWEAQELETNLANIVKPCLYSKYKN* | 4537 | ATGCCTGTAATCCCAGCACTTGGGAGGCCGAGGAGTTGGAGACCAACCTGGCCAA CATAGTGAAACCCTGTCTCTACTCAAAATACAAAATTAG | 4538 |
| | 2 | MGVSLCFPG* | 4539 | ATGGGGTCTCACTGTGTTTTCCAGGCTAG | 4540 |
| | 3 | MGISCSQRDECSVIISNVHNTCAPNSLSFPSPRRSPP* | 4541 | ATGGGTATATCCTGCTCACAGCGTGATGAATGTAGCGTTATCATCAGTAATGTAATT ATTAACACCTGTGCTCCCAACTCACTCTCCTTCCCAAGTCCTAGGCGTTCTCCTCCTT AG | 4542 |
| | 4 | MNVALSSVM* | 4543 | ATGAATGTAGCGTTATCATCAGTAATGTAA | 4544 |
| hsa-mir-181d | 1 | MPVIPALWEAQELETNLANIVKPCLYSKYKN* | 4545 | ATGCCTGTAATCCCAGCACTTGGGAGGCCCAGGAGTTGGAGACCAACCTGCCAA CATAGTGAAACCCTGTCTCTACTCAAAATACAAAATTAG | 4546 |
| | 2 | MGVSLCFPG* | 4547 | ATGGGGTCTCACTGTGTTTTCCAGGCTAG | 4548 |
| | 3 | MGISCSQRDECSVIISNVIRNTCAPNSLSFPSPRRSPP* | 4549 | ATGGGTATATCCTGCTCACAGCGTGATGAATGTAGCGTTATCATCAGTAATGTAATT ATTAACACCTGTGCTCCCAACTCACTCTCCTTCCCAAGTCCTAGGCGTTCCTCCCTT AG | 4550 |
| | 4 | MNVALSSVM* | 4551 | ATGAATGTAGCGTTATCATCAGTAATGTAA | 4552 |
| hsa-mir-182 | 1 | MCIFFHPRGASHSAHFANGKLRLREVK* | 4553 | ATGTGCATTTTCTTCCATCCCCAGAGGTGCGAGTCATTTCTGCCCATTTTGCAAATGGG AAACTGAGGCTTAGAGAGGTGAAGTGA | 4554 |
| | 2 | MPWGQG* | 4555 | ATGCCATGGGGCCAGGGTTAG | 4556 |
| | 3 | MGPGLAGEPHHSERGQWQNHGRISGSA* | 4557 | ATGGGGCCAGGGTTAGCAGGAGAAGAACCTCACCATTCGGAGAGGCGCAATGGCAGAA CCAACGGCCGCATCAGTGGGGTCTGCGTGA | 4558 |
| | 4 | MAEPRPHQWCVRGLYPGHLSP* | 4559 | ATGGCAGAACCACGGCCGCATCAGTGGGTCTGCGTGAGGGGCTTGTATCCGGGCA CCTTTCCCCCTAG | 4560 |
| hsa-mir-183 | 1 | MCIFFHPRGASHSAHFANGKLRLREVK* | 4561 | ATGTGCATTTTCTTCATCCCAGAGGTGCGAGTCATTCTGCCCATTTTGCAAATGGG AAACTGAGGCTTAGAGAGGTGAAGTGA | 4562 |
| | 2 | MPWGQG* | 4563 | ATGCCATGGCGCCAGGGTTAG | 4564 |
| | 3 | MGPGLAGEPHHSERGQWQNHGRISGSA* | 4565 | ATGGGGCCAGGGTTAGCAGGAGAACCTCACCATTCGGAGAGGCGCAATGCAGAA CCAACGGCCGCATCAGTGGGGTCTGCGTGA | 4566 |
| | 4 | MAEPRPHQWCVRGLYPGHLSP* | 4567 | ATGGCAGAACCACGGCCGCATCAGTGGGTCTGCGTGAGGGGCTTGTATCCGGGCA CCTTTCCCCCTAG | 4568 |
| hsa-mir-184 | 1 | MGKTWRSRSGCPRTAGDSRRRPWA* | 4569 | ATGGGGAAAACCTGGCGTCCCGCTCGGGGTGCCCGAGGACAGCAGGGATCCAG GAGGAGACCTTGGGCATAG | 4570 |
| | 2 | MRPLPEDAGVAFVFCQ* | 4571 | ATGCGCCCCTGCCTGAGGATGCTGGGGTAGCCTTTGTTTGTCAGTGA | 4572 |
| | 3 | MCSLRLGLGSPLEKSGWVVGEGRGLIPQTSL* | 4573 | ATGTGCTCTCTGCGACTGGGTTAGGTGTCTCCCCTTGAGAAAAGCGGTTGGGTGGTT GGTGAGGGAAGGGGGCTTATTCCACAGACTTCTTTATAA | 4574 |
| | 4 | MLLSFSYVRNHVLRQKVS* | 4575 | ATGCTTTTGTCTTTTCGGTTTATAGGAACCATGTGCTGAAGACAGAAGGTTTCATGA | 4576 |

Figure 1 (Continued)

| | | | | | |
|---|---|---|---|---|---|
| hsa-mir-185 | 1 | MPKSQAGGANLGWESSRADCHPPQLPQAQLGVIRHTVT MDFFKTGPSTSEGGTLGATPGP* | 4577 | ATGCCAAAAAGCCAAGCTGGGAGCAAACTTGGGTGGAGACAGGCTGACTG TCATCCACCTCAGCTTCCCAAGCTTGGGGTCATCAGACACACTGTGACCAT GGATTTCCAAAAACTGGTCCCTCCACCTGAGGGCCAGACCTGGGGGCCACACC AGGGCCGTAG | 4578 |
| | 2 | MPPPTISMLRGGSRFP* | 4579 | ATGCCCTCCCCACCTCAATGTGAGAGGGGAGGATCCCGTTTCCTTAG | 4580 |
| | 3 | MGSRDPAARPAYPGAPRSRHPPGPGPSLTQPSQGRKTI AASGQRLRGTKAGPPGQADAPPSASDPGPGSPQANFPP TCLSSAGIGPGLGGRWPAAGEAVAGPGSAPAPRPLGLR LGGLAPRGGGSGGHGEQPTGRGRAQVGRGGRGGRG GRGAGNYPSRPPETGGGALQPRVAPCPPTSRHLPPPTA GLDPCSLPLPAAGVSLSRRKTLAKSFPGLGLASVYDHTS VRLQRGKQFRQGRCPCCDAQSTRPPSLAQTWLRLSFTC HEMGADFTVVTAL* | 4581 | ATGGGGCTCCAGAGACCCTGCGCGCCCTGCATACCCGGGGGCACCGCTCACA CCGCACCCGCCGGCCCTGGCCTGCAGCGGCCCCAGCCAGGAGGGCAAGA CAATAGCTGCCTCGGCCAGCAGCGTACTCCTGACCCGGCCAGGGTCCTCCGGGCAG CCTCCAACCTGTCTGAGTTGGCACGCCAAGGGTCCACCAAGCAACTTC AGCAGCAGGGGAGGCGGTGCCTGGACCAGCTCGGCTCCTCCGGCCCTCG GCCTCAGGCTCGGTGGACTCGGGGCGCGCGGCGGCGATGTGGGCGGTTCACGGG GAGCAGCAATCGGGCGGCGGCGGCCAGGTGGCGTGCGGCGGACAGGGTG GCGTGGCGGGCGGGCGGGCAATGTGAGGTCCGCCCCCAGAGACAGGGGG CGGGGGCCTGCAGACTTTGCAAGTCTTCCTCCCCCCAGACTCGTTTGGCCTGGTTTA TGACCACACTTCAGTCGCCTGCAAAGGGGAAACAGTTCCGGCAGGCAGGTGCC CGTGCTGCGATGCACAGAGCACAAGGCTCCTCACTGGCACAAACTGGCTGCGA CTCAGTTTCACCTGCCATGAAATGGGGCCGATGAGACAGTAG | 4582 |
| | 4 | MTTLQSACKGGNSSGRAGARAAMHRAQGLPHWHKPG CDSVSPAMKWGPMRQ* | 4583 | ATGACCACACTTCAGTCGCCTGCAAAGGGGAAACAGTTCCGGCAGGCAGGTGCC CGTGCTGCGATGCACAGAGCACAAGGCTCCTCACTGGCACAAACCTGGCTGCG ACTCAGTTTCACCTGCCATTGGCCTTCAGTCCCGGGATGA | 4584 |
| hsa-mir-185 | 1 | MRGEDGLPLGLRDVSPGG* | 4585 | ATGCGCGGAGATGACGGCTTGCCATTGGGCCTCCGGGGATGTCAGTCCCGGGATGA | 4586 |
| | 2 | MTACHWASGMSVPADDRPPRGGAAAPHLPEPLRRWQ GTRDRSLPADLREHPPTIQPRAGTGRAGAPSPDSGRVAS ATTPSSQVSPFSACYSLRAARRSLLSTSNCILHASREREF CCYPHFTVGKQPQRGSHLLEHSRLILGPGGSLILTPLGP RSGETMEVGAAVFPRAGRDPLGKPGIAHLPHQAWM* | 4587 | ATGACGGCTTGCCATTGGGCCTCCGGGATGTCAGTCCCGGCGGATGACCGGCCCCCT CGCGGAGGGGCAGCCGCTCCTCCCCAGCCGACTTACGAGAACATCCCGACCATCCAGCC TACGGAGCAGGGACTGGCAGAGACCCGGAGCCAGGTTCACAGAGGCCGCAGGTATCCCCCAGACTCTTCAGCGCCTACTCGCTCGGCG CTGCGCGCCTCGCGCTCTGTCTCCATGGAATTGGAAACAGCCTCAGAGGTTCTC AGCTTGCTTGAAACACAGTGCTTGCCTGGGCCTGGGGAAGCAGGAGAGTGAGTATTTCGAGG CCCTGGGTCCCCGCAGCGGGGACGATGGGAAGCCTCGGTAAACCAGGGGCTCAGTATTTCCGAGG GCAGGAAGGAGACCCCTCGGTAAACCAGGGCTCACCTCCCCCACCAGGCCTGGAT GTAG | 4588 |
| | 3 | MTGPLAEGPRPRTCPNLCGGGGVRGTAPSQPTYENIP RPSSPEQGLAEPAPLPRTLAA* | 4589 | ATGACCGGCCTGGCCGAGGGCCGGCCCCGCACCTGCCCGAACCTCTGCGG CGGCGGTGGCAGGTACGGCGGGACCGCTCCCCAGCCGACTTACGAGAACATCC CGCGGTCCATCCAGCCCCGAGCAGGGACTGGCAGAGCCGGCGCCTTCCCCGGACT CTGGCCGCGGTAG | 4590 |
| | 4 | MGPFLTSSWHSHSPTALRLGRQSCAFMPAPRTTVPFSS PYLESGRNGASLPVEJHVGYISLPD* | 4591 | ATGGGGCCAGCAGAGTTGTGCGTTTAGCTGCCGCACCCGTACTACTTGTCCATTTCTT CACCCTACCTGGAGTCAGGAAGAAACCGGTTCGCTTCACTGCCTGTTGAGATTCACGTAG GTTACATTCCTTGCCAGATTAA | 4592 |
| | 1 | MVNAPASGWAVLGWLRWRAGAAPGSRRRWRR* | 4593 | ATGGTGAACGCGCCGGCTTCGGCTGGGCGGTACTGGCTTGCCTGCGGTGGCGGCGC GGGCGCGGCACCGGAAGTCGGCGGCCGGTGGCGGAGGCGGTGA | 4594 |

Figure 1 (Continued)

| | | | | | |
|---|---|---|---|---|---|
| hsa-mir-185 | 1 | MPRALLEGVFDNPRWHGMRGTLAGGTRLAAGRLRSAGLGAAWSLQGVWAARPWPASGTALAPGHSAPYPRPAAGQQGDS* | 4595 | ATGCCCCGCGCGTTACTGGAAGGTGTTTTGATAATCCCGCTGGCACTGGATGCGAGGGACTCTGGCAGGTGGGACCAGAACTCGCTGCGGGAGGCTGAGATCGGCAGGGTTGGGAGCTGCCGTGGTCCCTGCAGGCGTGTGGCTGCTGGCCAGCATCAGGGACAGCTCTGGCGCCCGGTCACTCTGCCCCTACCCGCGGCCTGCTGCGGCCAGCAGGGTGACAGCTAA | 4596 |
| | 3 | MRPSWGGLGS* | 4597 | ATGCGGCCTTCCTGGGGAGGTTTGGGTAGTTAG | 4598 |
| | 4 | MSHALPWPGLFALSCGSRPADHCFAATLGTVPSSMRQM* | 4599 | ATGTCACATGCCCTGGCCAGGCCTGTTTGCACTGTGTGGCTCTAGACCTGCTGACCACTGTTTTGCTGCCACAGTGCCCTCTCCATGAGGCAGATGTGA | 4600 |
| | 1 | MSTKMFRVSDGDWICPDKK* | 4601 | ATGTCGACCAAGAATTTCCGAGTCAGTGACGGGGACTGGATTTGCCTGACAAAAGTGA | 4602 |
| hsa-mir-186 | 2 | MIFCALRRVEAANRQPPGGKKAPNLLTREVFPGAFVLDMSSAFPRHYLRKVASLFRVRDGLPFCHPPPPRPGFSDRKPLQSGQLGVGSPPRDFSLQNFFLVHGKYCFLAIVLLPLIVHLVLYFYSNFSSILFSPPPEALPSSVWEILTFSLWHSPQELGFSPP* | 4603 | ATGATTTTCTGTGCCTTAAGACGGGTTGAGGCGGCGAACCGCCAGTTCCTGGCGGGAAGAAGGCTCCCAATCTCCTCGACATTACCTCCGAGAGAGTCTTTCCGGGAGCCTCTCTTTTAGAGTGCATGTCTTCAGCGTTCCTCCGACATTACCTCCGACATTACCTCCGAGAGAGTCTTTCCGGAGCCTCTCTTTTAGAGTGCGAGATGGCCTACCTTTTGCCCCCACCCCCGCCCCGGCCAGGTTTAGCGATAGGAAACCTCTCCAGTCAGCAGGCCAGCTGGTTGATCTCCCCACGCTGCTGCTTACTCTGTTCACGGAAAATATTGCTTCCGACTGTCGTCCTTTTGCCTGCAGAAACTTACTCTGTTCACGGAAATATATTGCTTTCTCAACTTGACATTTTCTTGTGGATCATTTCTCCACAAGAATTGGGCTTTTCGCCCTCTAG | 4604 |
| | 3 | MAYLFAPTPLPRPGQVLAIGMLSSQASLVLDLPHVTFLCRTLLLFTENLAFSHSSFCLL* | 4605 | ATGGCCTACCTTTTGCCCCCACCCCCGCCCCGGCCAGGTTTTAGCGATAGGAAACCTCTCCAGTCAGCAGGCCAGCTGGTTGATCTCCCCACGCTGCTGCTTACTCTGTTCACGGAAAATATTGCTTCTCAACTTGACATTTTCTTGTGGATCATTTCTCCACAAGAATTGGGCTTTTCGCCCTCTAG | 4606 |
| | 4 | MPAAEKHVC* | 4607 | ATGCCTGCAGCAGAGAAGCACGTTGTTGTGA | 4608 |
| | 1 | MSCYLLM* | 4609 | ATGAGTTGCTATCTCTTAATGTGA | 4610 |
| hsa-mir-187 | 2 | MGEERPQASLLRGKESLLTG* | 4611 | ATGGGGGAGGAAAAGACCCCAAGCTTCTCTCCTTAGAGGGAAGGAATCCTTACTTACAGGTTAG | 4612 |
| | 3 | MDPCAPLPIPQAKGSEGRARSPRLAFGGTGLEGPLGAQRPREIEYLYAQQPSLSRRTE* | 4613 | ATGGATCCTGCGCCTGCACTTCCAATTCCCAAGCAAAGGGAAGGGAGCGGGAGAGCGCGGAGCCCCGGATTAGCGTTCGGAGAACTGGCCTAGCAGGGCCACTCGAGGCGCAAAGGCCCCCGCGAAATAGAATATCTATAGCCAGCAACCTCCCTTTCGAGGCGCACGGAATAA | 4614 |
| | 4 | MSVRPSPRGTR* | 4615 | ATGAGCGTACGCCGCCGCGCTTGCTCCCCGGTACCAGGTGA | 4616 |
| | 1 | MSRAPASLPLLPGWAV* | 4617 | ATGAGCCGCGCGCGTTGCTCCCCGGTCGGCTGTGTGA | 4618 |
| hsa-mir-188 | 2 | MKLCRLRGALTQLGVLDARADRARCPPAADTGSAAPDLGDR* | 4619 | ATGAAGCTCTGCCGCTACGTGGGGCGCTCACTCAACTTGGTGTCTGGACGCCAGAGCGACCGAGCGCGTGCCGCCACGGCGCCGGACACGGGCTCCGCCGCTCCGGACCTCGGCGACAGGTAA | 4620 |
| | 3 | MGLPRARRWQPGA* | 4621 | ATGGGGCTTCCCCGCGCCCGGCGTTGGCAGCCGGCGCTTAG | 4622 |
| | 4 | MVPGLPERSFLAERRQARPAFESECLAACVPPPGLG* | 4623 | ATGGTCCCTGGGTTGCCCGAGCAAGTTTCCTTGGAGCGGCGCCAAGCCGCCCCGCTTTTTGAATCGGAGTGTTTAGCCGCTGCCTGCGTCCCTTTCCGGACTGGGGTAG | 4624 |

Figure 1 (Continued)

| | | | | | |
|---|---|---|---|---|---|
| hsa-mir-18a | 1 | MVAATPPGESARPSGDGGKPVVCGPGLAGGAERPGAD WPGAAWRRRGRGESRPLAAPACGSRIWLPFRSPAGRR RGAGPGREGGRGRRARGGRARDPRRPCLGRPEGGWAD GEHWGPSGRGRARPYPSPGPGARAGRGVSG* | 4625 | ATGGTGGCGGCTACTCCTCCTGGTGAGTCTGCCCGCCCTCCGGCGACGAGGGAA ACCTGTGTGTCGCAGCCCGGGTCTGCGGGGCGGAGCGCTCCGGGGCGGACT GGCCCGGGGCAGCGTGGCGGCGGCGTGGCCGGGGCCTGGGGGCGGTTGGCC CCCCGCTGTTGGCAGCCGCATTGGCTGCCCCTCGCTGCCCGGGCGGTCGGCG GAGGGGGCAGGGCGGGCGGCGAGGTGGAGGCGGCGAAGCGGCGGGCGGC CCGGCCCGGACCGGCTGCCTGCCGCAGACCCGGGGCGGCCGGCGTCGGCGA CGGCGAACACAATGGCCCCTCGGGAGGACGTGCGAGGCCGTGCTTCTCCGG GCCCCGGGCGCGCGGGGCGTGGGGTCTCTGGGTAG | 4626 |
| | 2 | MAPRGEDVRGPCLLRGPGRARGVGSLGRKVSPEGES* | 4627 | ATGGCCCCTCGGGAGGACGTGCGAGGCCGTGCCTTCTCGGGGCCCGGGGCG CGCGGGGCGTGGGGTCTCTGGCTAGGAGAAGTTCTCCGAGGGCGAAGTTAA | 4628 |
| hsa-mir-18a | 3 | MGQAAGREGARPRGTCAPAGGVAWAGARCGSPMFVRA RVGGGAPRSARPGRHPRSAWALLARVGSLGAGPATSPP WPSEEAAVGLSRGVEEPAPGRLLGVWRGRASPARRERR PRRHVPAGRAARG* | 4629 | ATGGGGCAGGCCGCGGCGTGGAGCGGGCGGCGCCACGAGGTACCTGCGCAG GTGGGCGAGGGCGCCGAGATCGGAGCCCCGGTTCGTACGCCGGAGG CGCTTGTTAGCCCGCTGGCAGCCTCGCGCCGCAACTTCCCCCGCCGTG CCCTCGAGGAGGCCGCAGTCGGCCTCAGCGGCGGAGTCGCTGCCC GCGCTTGCTGGGAGTGTGCGCGGGAGGGCCAGGCGGCTCCGCGGAGCGGCGT CCCGGCCCATGTTCCTGCGGGGCGGGCTGCACGGGGTGA | 4630 |
| hsa-mir-18a | 4 | MFLRGGLHGGEFGGGRGGDCAPPIYPGLGLGPRATGTA AAEPPLWAGLGGAGGHKGGAARPRPRTRASAPPVA ARLPPGNGLLGGLPRPAGPDSDPPPGGYAENRRAALPL VRHVLPARAP* | 4631 | ATGTTCCTGCGGGGCGGCTCACGGCGGTGAGGCGGGACATGGCGGCGACTG CGGCCGCCGCCGATTGTTCCCGCTTAGGCTCGGCCGGTGCGACGGGCACCG CGGGCCGGAGCTCCCCGCCCCTCGTGGGGGGCGTGGGGAACAAA GGAGGGGCGGCTGCCGCCGGAAACGGGTTGGGCTACGTGGAGAATGGGAGAATCGCAGG GCCCGCGGCCGTCCGTCCCGCCGGCCTG ACTCTTACCGCCGCCGCCGCCGTGCTGGCGCTACGTGGAGAATGCAGGGCCGCGCTCTCCC TTGTGTCGACATGTCTGCCGCGCCCGGGGTCCATGA | 4632 |
| | 1 | MGGGH* | 4633 | ATGGGCGGTGGTGGCGAATAG | 4634 |
| | 2 | MSCLMNC* | 4635 | ATGTCTTGTTTAATGAACTGCTAA | 4636 |
| | 3 | MSLLGSYFYLFPLIG* | 4637 | ATGTCACTCTTGGGAGTTACTTCACTTGTTCCTTAATAGGATGA | 4638 |
| | 4 | MISSFPITFCLSMQDT* | 4639 | ATGATTTCATCTTTCCAACCTTCTTCGTCTCTCAACCAAGACACATAG | 4640 |
| hsa-mir-19c | 1 | MVALSLKHCVRHCNVVKTMQFEPSTAVYDACRVIRERV PEAQTGQGRSWVIYWLLKTCLHVFHFFAKETEAPSGTQ AY* | 4641 | ATGGTGGCCCTGTCCTTAAAGCATTGTGTGCGCCACTGCAACGTGGTGAAGACCATG CAGTTTGAACCATCTACAGCTGTGTACGATGCGTGTCGAGTCATTCGGGAACGGGTG CCTGAGGCACAAACTGGCCAAGGTAGGTCATGGTTATTTACTGCTTCTTAAAACG TGTTTGCATGTTTTCACTTTTTGCTAAAGAGACAGAGCTCCAAGTGGTACACAA GCTATTAG | 4642 |
| hsa-mir-19c | 2 | MRVESFGNGCLRHKLLGKVGHGLFTGFLKRVCMFFTFLL KRQRLQVVHKPISAYVSNEIPS* | 4643 | ATGCGTGTCGAGTCATTCGGGAACGGGTGCCTGAGGCACAAACTGGGCAAGGTAGG TCATGGGTTATTTACTGGCTTCTTAAAACGTGTTTGCATGTTTTCACTTTTTGCTA AAGAGACAGAGCTCCAAGTGGTACACAAGCCTATTAGTGCATATGTTTCAAATGA AATACCTTCTTAG | 4644 |
| | 3 | MGYLLAS* | 4645 | ATGGGTTATTTACTGGCTTCTTAA | 4646 |
| | 4 | MFQMKYLLRSDTTCFLCETCDYSDHAHC* | 4647 | ATGTTTCAAATGAAATACCTTCTTAGATCAGACACTACCTGCTTCCTCTGTGAGACTT GTGATTACAGTGACCATGCCCACTGCTGA | 4648 |
| hsa-mir-19b | 1 | MTMGHHEAIINTFALTRR* | 4649 | ATGACAATGGGAATTCATGAAGCTATAACCAACACTTTTGCACTAACAAGACGATAG | 4650 |
| hsa-mir-19b | 2 | MPEFLFTKNKLFNFCHLTCQR* | 4651 | ATGCCTGAATTTCTATTCACAAACTAAAAAACAAACTTTTCAACTTCTGCCATCTTACCT GCCAAAGATAA | 4652 |
| | 3 | MNEEQF* | 4653 | ATGAATGAAGAACAGTTCTAA | 4654 |

Figure 1 (Continued)

| | | | | |
|---|---|---|---|---|
| hsa-mir-191 | 4 | MKNSSNASEV* | 4655 | ATGAAGAACAGTTCTAATGCCTCCGAAGTATAG | 4656 |
| | 1 | MGEVYKLLC* | 4657 | ATGGGAGAAGTGTATAAATTATTATGTTGA | 4658 |
| | 2 | MLISKISAKG* | 4659 | ATGTTGATAAGCAAGATAAGTGCCAAAGGGTAG | 4660 |
| | 3 | MRAAPVTRPS* | 4661 | ATGAGAGCAGCTCCAGTTACTCGGCTTCATGA | 4662 |
| | 4 | MTQEVEGGTGTGIGLQRKGQHQPV* | 4663 | ATGACACAGGAAGTTGAAGGTGGCACAGGCATTGGGCTGCAAAGAAAAGGCCAGCATCAGCCTGTCTAG | 4664 |
| hsa-mir-191 | 1 | MGSQGSRVGRAGWVPEAEAQCTSGAQRAAMLEQRRRRRGASWVPAAAPVGWSRGPSRAAEGRPARRQGGRASGQLFPDPRPPPAWPRPPTPPPPRAQRPHPGAVRSR* | 4665 | ATGGGGTCTCAGGGGTCAAGGGTCGGTAGGGCGGGCTGGGCTGGGAAGCGGAAGCGCAGTTGCACTTCAGGCGCAGCGGGGGTCGGGGCGGCCATGTTGGAGCAGCAGCGGAGGCGCGCGAGGGCCGGTCGCCGTCTTGGGCTCCGCAGCGGCGACGCCGAGTTGGAGCCGGGGCCTAGCCGGCGCCGGGGCGGCCGGCGGCCGCGGAGGCGCTCGCAGGGCGGCCAACGGCCAACTCTCCCGGACCCGCCGCTCCCCCGGCCTGCCGAGACCCCGCCACCCCACCCCCACCCGCCGACCCAGCGACCTGGGGCTGTGCGGTCCGGTAG | 4666 |
| hsa-mir-191 | 2 | MCKDCAWRTVSGEGKCPRHLRIQECFQTKSPRAFPPGYSEDPFCCIRAVGRNYTDGPHGPRDLPDPG* | 4667 | ATGTGCAAGGATTGTGCTTGGAGAACAGTTCTGGGAGGGAAGTGCCCAAGACACCTGAGGATCCAAGAATGTTTCCAAACAAGAGCCTAGGGCATTTCTCCAGGGTATTTCTGAAGACTTCATCTGCTGCATTAGAGCCGGTGGGAAGAAACTACACAGACGGGCTCATGCTCGAGGGACCTGCCTGATCGTCCTGA | 4668 |
| | 3 | MFPNKEP* | 4669 | ATGTTTCCAAACAAGAGCCCTAG | 4670 |
| | 4 | MARGTCLILADLLMLWCSWGAASCFWEPSVLGWVLDVSYD* | 4671 | ATGGCCCGAGGAACCTGCCTGATCTTGGCTGATCTTTTAATGCTCTGGTGCAGCTGGGGAGCTGCCTCTTCTTCTGGGAACCTGAAGTGTTGGGTTGGGTTAGATGTTAGTTATGATTGA | 4672 |
| hsa-mir-192 | 1 | MGKPRLGLGHREPSPC* | 4673 | ATGGGGAAACCAAGGCTCGGTTGGGAATCAGGGAACCCTCACCTGCTAG | 4674 |
| | 2 | MFPGEADGAQPDASWTRPTLPGHSPGLFALRTALVISIDGGGHHNHHQGLGQRLKRPWAQGVPTSSLCPEGQPGTQVRGFLSGRTPAALPVLGGS* | 4675 | ATGCCACCCGGAGAGGCAGATGGGGCCCAGCCTGATGCTTCCTGGACCCGCCCACCCTGCCCGGCACAGTCCAGGGCTTCCTGCCCTCGAACCCGCACTGTGATCAGTATTGAGCAGGTGGTGGGATAATCATTAACCACCACCAGGGGCTCAAAAGGCCCTGGGCCAGGGGTGCTCCTGCCCCACTTCTCCTTGTCCCGAAGGCCAGCCGGCCAGGCTTCAGTGAAGAGAGCTTCCTGAGACTGGTAGGACCCTGCGCCTCCTGTCCTAGGAGGCTCCTGA | 4676 |
| | 3 | MGPSLMLPGPAPPCPGTVQGFLPEPHL* | 4677 | ATGGGGCCCAGCCTGATGCTTCCTGGACCGCTCCTGCCCCACCCTGCCCGGCACAGTCCAGGGCTTCCTGCCCTTCGCCTTCGAACCGCACTGTGA | 4678 |
| | 4 | MGWPGRAPSSLCLGFHCGIRGP* | 4679 | ATGGGCTGTCCGGGTCGCGCCTTCGGGACGAGCCCCTTCCTCTCTGCCTTGGTTTCCACTGTGGGATAAGGGCCCTAG | 4680 |
| hsa-mir-1932 | 1 | MGKLRPAAGALHRAGARPCSGAAGRGLPAPVSAGGSAGSCSDGSKEEKGKLLGSGAGRTA* | 4681 | ATGGGGAAGTTGAGGCCGGCGGCCGGGGCCCTGCACCGGGCCGGCGCGCGGCCCTGCAGCGGCGCCGCCGGGGCGGGCCTCCCGGCGCCCGTCTCGGCTGGAGGAAGGCGCTGGGGAAGCCTCCGGGGCGGCAGGGAAAATTACTGGGCTCCGGGCGGGAAGGACTGCGTGA | 4682 |
| | 2 | MCRQHVEPGRAAASKPTPPTFEGSRRPAPLLPASSGSLS* | 4683 | ATGTGTCGCCAGCACGTGGAGCCTGGCCGCGGCGGAGCAAGCCGCGACCCCCAACTTTCGAGGGTCTCGGCGGCCCCGGCTCCTCCGGGCTCGCTCGTC | 4684 |
| | 3 | MAPVPRQRCGLGLAGGCGLLREVGHRGSCPAPRAPRPRS* | 4685 | ATGGCCCCCGTGCCCAGGCAGCGGTGCGGCCTCGGCCTCCGGGGCTGCGGAGGGTGCGGCCTGCTCGAGAGGTTGGCCACGAGGTCGTGCCCGGCGCCGCGGCCACGGCCGTCCGCCGCTCCTCCTCTCCAGGTTCGA | 4686 |
| | 4 | MGAEGWVFAGEMRVSDQLAYKVPVLGPRDQRLLPGPRPRPASSRAGVRSGQAASQVHAGEGVVRCARPGCVR* | 4687 | ATGGGAGCTGAGGGCTGGGTCTTTGCGGGCGAGATGAGGGTGTCTGACCAGCTCGCCTACAAAGTCCCAGTTCTGGGCCCCAGGGACCAGCGTCTTCTCCCCGGGCCAGGCCCCGGCCCGGCCAGCTCCTCGGGCTGCGTCCGGCAGGCGGCGAGCCAGGTGCACGCGGGCGAGGGTGTGGTCCGCTGCGCTCCCGGCTGCGTGCGGTGA | 4688 |

Figure 1 (Continued)

| | | | | |
|---|---|---|---|---|
| hsa-mir-193a | 1 | MCHQHVEPGRAAASKPTPPTFEGSRRPAPLPASSGSLS* | 4689 | ATGTGTCACCAGCAGCACGTGGAGCCAGGTCGGAGCCAAGCCGACCCCCCC AACTTTCGAGGGTTCGAGTCGAGCCTCCTCCGCTCGTCCCCGGAGCAAGGCGGCCT CTAG | 4690 |
| | 2 | MAPVPRQRCGLGLAGGCGLLREVGHGSCPAFRAPRPPS* | 4691 | GCTGCGAGAGGTCGGCCAGCAGCGGCTCCCTGCCCGCGCCTCGCCTTGCGCGAGAGGTGCGGCCT GCTGA | 4692 |
| | 3 | MGAEGWVFAGEMRVSDQLAYKVPVLGPRDQRLLPGPR PRPASSRAGVRSGQAASQVHAGEGVVRCARPGCVR* | 4693 | ATGGGAGCTGAGGGCTGGGTCTTTGCGGCGAGATGAGGGTCGGATCAACTGGC CTACAAAGTCCAGTTCCTCCGGCCCGGGACCAGCGTCTCCCGGTCCTCGCC CAGGCCGGCTTCCCGGCTGGCGTCCGGAGGTGCTCTCAGGTTCA CGCTGGAGAAGGAGTGGTGAGGTGCGCTGCCGTGCGGTGA | 4694 |
| | 4 | MGQALPLTEACPAVLSRAATLSLGVGRTGPDF* | 4695 | ATGGGCCAAGCCTGCCACTTACCGAGGCCTGCCTGCTGTGCTTCCAGGGGCGGCA ACCTTGAGCTTGGGGGTGGGAGAACGGGCCTGACTTCTAG | 4696 |
| hsa-mir-193b | 1 | MGTTGEGRWRRGSARFSRDSARDACLGCDCRRCRHPGS PSDPSPAPQRGV* | 4697 | CGGCGGCGAGAGCGTTGTCTGGCGCTGCGATTGCGCGCGCCTGCCACCCGGTCCC CCTCGACCCCTCGCCTGCCAGAGGCGGTGA | 4698 |
| | 2 | MPRAEQAGRARRSTCARAPLAWAAAPAGAGPRGSRTS REPPSESYRRPLKLSAPSPREAGSPGALALASAGRGQK N* | 4699 | ATGCCGCGCGCGGAGCAGGCGGCAGGCGCGCGCCGGCCTGCCCGCCGAGCCC GCTGGCATGGCGCGGCGGCGCCTCCCAGAGAGTTACCGCCGCCCCTAAAGTTGTCAGCTGCCTCC GGGAACCACCCGTCCCCGGATCCCGGGACCTAGCC CCCGAGAAGCAGGCAGCCTGGCGCGTTGGCTTAGCTCTGCAAGGACGGGGGCAA AAAACTAG | 4700 |
| | 3 | MCGGACCGRAPGIPD* | 4701 | ATGGGCGGCGGCGCTGCGGGGCCCGGGACTAG | 4702 |
| | 4 | MRRLCPLRTHPYL* | 4703 | ATGCGCCGCTTATGTCCTCTGACACATCCATATTTATA | 4704 |
| hsa-mir-194-1 | 1 | MSTGLTEMNALDPHLPFICSCALFSYKVDGLFREPLGN V* | 4705 | ATGTCCACGGGCCTGACAGAAATGAATGCTCTGACCCCATCCACTTGCCTTTCATT TGTTCCTGTGCCCTTTCATACAAAGTGGATGGCTCTTTAGGTTCCTTTAGGAA ATGTGTAA | 4706 |
| | 2 | MLWTPSTCLSFVPVPFFHTKWMASLGFL* | 4707 | ATGCTCTGGACCCCATCCACTTGCCTTTCATTGTTCCTGTGCCTTTTTCATACAA AGTGGATGGCCTCTTTAGGTTCCTTAG | 4708 |
| | 3 | MCKCLQAFVLTLK* | 4709 | ATGTGTAAGTGCCTTCAGGCCTTTGTGCTCACATTAAATAA | 4710 |
| | 4 | MAFVTRQMNNVKYFQK* | 4711 | ATGGCATTTGTGACTATCCAAATGAACAATGTAAAGTACTTTCAAAATAG | 4712 |
| hsa-mir-194-2 | 1 | MGKPRLGLGHREPSPC* | 4713 | ATGGGGAAACCAAGGCTCGGGTTGGGACATCGGGAACCCTCACTTGCTAG | 4714 |
| | 2 | MPPGEADGAQPPDASWTRPTLPGHSPGLPALRTALVISID GGGHHNHHQGLGQRLKRPWAQGVPTSSLCPEGQPGTQ VRGFLSGRTPAALPVLGGS* | 4715 | ATGCCACCCGGAGAGGCAGATGGGGCAGTCCAGGCTCCTGCCCTTGAACCGACCTGCCGCCCAC CCTGCCGGGCACAGTCCAGGGATAATCATTAACCACCAGGGCGTGGGTCAACGGCTCAAAA GGCCCTGGCGTGGTGGGAGCCCAGGTGTCCCACTTCCTCGTGCCGAAGGCAGCCCGGCA CTCAGTAAGGAGGCTTCCTGAGGTGGTAGAACCCCTGCCGCCCTCCCTGTCCTAGGAG GCTCCTGA | 4716 |
| | 3 | MGPSLMLPGRAPPCPGTVQGFLPFEPHL* | 4717 | ATGGGGCCCAGCTGCTTCCTGATGCTTCCTGGACCCGCCCACCCTGCCCGGGCACAGTCCAG GGCTTCCTGCCCTTCGAACCGCACTGTGA | 4718 |
| | 4 | MGWPGRAPSSLCLGFHCGHRGP* | 4719 | ATGGGGTGGCCCGGGACGAGCGAGCCCCTTCCTCTCTGTGCTTGGTTCCACTGTGGGGATA AGGGGCCTTAG | 4720 |
| | 1 | MGWDGFWGGVPNSDWEWRNPS* | 4721 | ATGGGCTGGGACGGCTTTTGGGGCGGTGTCCCCAATTCTGACTGGGAGTGGAGGAA CCCCTCCTGA | 4722 |
| | 2 | MRLGRLLSPAPQM* | 4723 | ATGCGACTGGGCGGCTCCTTTCTCCTGCACCCAAATGTGA | 4724 |

Figure 1 (Continued)

| | | | | | |
|---|---|---|---|---|---|
| hsa-mir-195 | 3 | MHPKFCSFQNRGPGSQGRVAEVSGEGSVLCFQERRGG WGGGLEVRAGVGLALSVLELGG* | 4725 | ATGCACCCTAAATTTGCTCTTTCAAAATAGGGACCAGGATCTCAGGGGAGAGTAGCTGAGGTAAGTGGGGAGGGAAGGGAAGTGTCCTCTGTTTCAGGAGACGTGGCGGTTGGGGGGGAGGTTGGAGAGTGCGTGCTGGGTGGGGTTGGCTTTGTCAGTCTTTGAATTGGGGGATGA | 4726 |
| | 4 | MIGEAFSYTPKLQPPRRKPKAETREPPNIPSR* | 4727 | ATGATTGGAGAGGCTTTCTTCTATACCCTAAACTGCAGCCCCCAGACCGGAAACCAAAGGCTGAGACCAGAGAGCCCCCAACATCCCCAGCCGTTAG | 4728 |
| | 1 | MGAGVSVSTCEQAGVWRGREEERAR* | 4729 | ATGGGTGCGGGTGTGAGCGTGAGCACCTGTGAGCAGGTGGGTGTCTGGAGAGGCAGAGGTGAGGAGGCGGCACGTTAG | 4730 |
| hsa-mir-196a-1 | 2 | MNCLTWGSSASAEPGPWDLGRYPSQQLFRSTGPPLQIPFFLCLFPRIPETF* | 4731 | ATGAATTGTCTTACCTGGGGCAGCTGGCTCTGCAGAGCCAGGCCCTGGGACATTTGGGCAGGTGCCTTCAGACAACTGTCAGATCAACCGGCTTCCCCTCCAAATCCCATTCTTCCTCTGTTTGTTCCTAGAATTCCGAAACTTCTGA | 4732 |
| | 3 | MHLRICLKLRILFICGDLQLG* | 4733 | ATGCACCTTCGTATCTGTTTGAAGTTGAGAATTCTTTTATCTGTGGAGACCTCCAGCTGGGCTGA | 4734 |
| | 4 | MSLESELSGPAPKWFYLESWVQFFRCVV* | 4735 | ATGTCTCTGGAATCTGAGCTATCAGGACCGGCTCCAAATGGTTTTACCTAGAGTCCTGGGTTCAGTTCTTCCGATGTGTTTAG | 4736 |
| hsa-mir-196a-2 | 1 | MIKRGRDGNGRPKGAESLLCGSSGWGKSWGPRTGTTAVASGHRSWNKVPPLS* | 4737 | ATGATTAAGAGAGGAAGAGATGGCAATGGAAGACCTAAGGGAGAGCAGAGTCACTCTGTGGCAGCTCAGGTTGGGGTAAGAGCTGGGGGATGGGGGAAAGCTGGGGGTCAAGGTCATGGACCACTGCAGTGGCCTCTGGCCACAGATCCTGGAACATCTGGAACAAAGTCCCTCACTGAGTTGA | 4738 |
| | 2 | MAMGDLREQSHSVAAQVGVRAGGPGQPLQWPLATDPGTKSLH* | 4739 | ATGGCAATGGGAGACCTAAGCGAGCAGAGTCACTCGTGGCAGCTCAGTTGGGTAAGGGAGACCCCAGGACAGGGTCAGTGGCCTCTGGCCACAGATCCTGGAACAAAGTCCCTCACTGA | 4740 |
| | 3 | MLPHLVGFFQSWNGTERRGDLARPEESARVSQLGESQGTQDLLD* | 4741 | ATGCTTTTCCATCTGGTTGGATTTTTCCAGAGCTGGAATGGAACAGAGAGAAGGGGGGATCTGGCAAGGTTTAGGAATCTGCCAGGTCAGGTCAGCAGCGGCGGAGCGGCGGCGGAGGCGGCGGCGTACTCAGGATCTTTTAGATTAA | 4742 |
| | 4 | MEQREGGIWQGLGNLPCGASWGKARVLRIF* | 4743 | ATGGAACAGAGAGAAGGGGGATCTGGCAAGGTTTAGGGAATCTGCCAGGGTCAGCCAGTGTGGTTGA | 4744 |
| hsa-mir-196b | 1 | MAGFSPWRRRQRRRRRRRARQPFAGSTRTGR* | 4745 | ATGGCAGGTTCTCTCCTTGCGCGGCGCGGCAGCGGCGGAGCGGCGGAGCGCGGCGCGGGCGGCGAGGGAGGCAGCCTTCGCCCTGTCGCTAACGGCTGGTCGGTGA | 4746 |
| | 2 | MTTGWRQPCVSSPVANG* | 4747 | ATGATCACGACCGGATGCGCGATGTCTTGCGTTCTTCGCTGTCGCTAA | 4748 |
| | 3 | MAAALRFFACR* | 4749 | ATGGCGCAGCAGCTTCGGTTCTTCGCTGTCGCTAA | 4750 |
| | 4 | MFHTAPLCSWVLEKGTLPRASMF* | 4751 | ATGTTCCATACAGCACCTTGTGCAGCTGGGTCTGGAGAAGGGGGACCCTTCCAAGAGCCAGTATGTTTTAA | 4752 |
| | 1 | MRRYKPGWGFAAIS* | 4753 | ATGCGCGCTATAAACCGGCTGGGGTTTTGCAGCGGATTCTTAG | 4754 |
| | 2 | MRSQ* | 4755 | ATGAGATCTCAATAG | 4756 |
| hsa-mir-196b | 3 | MAHFRSMSKPPGSREPQHDSWPLFASDTKSSTVHYFTCPAPLHFRKRGLTLKK* | 4757 | ATGGCCCACTTCCGATCAATGTCAAAGCCGCCGGGAGCCGGAGAACCCCAGCATGATTCTTGGCCTTTTGCCTCAGACACTAAGAGCAGCACGTACATTATTTCACTTGTCCGCTCCCTTGTCATAACGGCATTCGTAGGCCTCGGAGCCTCGGAGCGTCCGCCGCGGACTCACCCTCAAGAAGTGA | 4758 |
| | 4 | MILGLCSLLILRAARYIISLVPLPFITEKGDSPSRSDWYGNLKQRAFARPRERRRAEKPAVPWQ* | 4759 | ATGATTCTTGGCCTTTGCTCCCTTCTCATAACGCTCCGGGCCGCTCAGCAGCCGCACCGTACATTATTTCACTTGTCCGCTCCCTTGTCATAACGCACCGGCATTCGTCTAGGCTCCGCAGAAAAGGGGACTCACCCTCAAGAAGTGGTATGGTAATTTAAAGCAACGGCATTCGCTAGGCCTCGGAGCGTCCGCCGCGGAGCATTCAGCTCCAAGAAGTGAAGCCAGCTGTCCCTTGGCAGTGA | 4760 |
| | 1 | MLIYILQGYPSRGGHPGD* | 4761 | ATGCTGATTTACATCCTCCAGGGATACCCTCCAGGGAGGCCATCAGGAGACTGA | 4762 |

Figure 1 (Continued)

| | | | | | |
|---|---|---|---|---|---|
| hsa-mir-197 | 2 | MWVRADHLPGAQKPQGPLTSYLWIPKESPRVLGLEVCPSLQPMGIRVGGCYF* | 4763 | ATGTGGGTGAGGGCTGACCACTCCCGGGGCGCTCAGAAACCCAGGGGCCACTCACAAGCTATCTGAACCAATGGGATCCCCAAGAGTCCCCAGAGTTCTAGGTCTGGAAGTCTGTCCCTCCCTTCAACCAATGGGCATAAGAGTCGGGGGGTGCTATTTTAG | 4764 |
| | 3 | MSGKEVTGPVSLCSVVSSLDREESGSLGLSRGWLG* | 4765 | ATGTCTGGGAAAGAGGTCACAGGAGTCAGGTTCCTTGGCTGACTGCAGGCCAGGTGCTCAGTGCTCAGTGGTGTCCAGCTGGACAAGGAAGAGTCAGGTTCCTTGGCTGACTGCAGGGGTTGGCTTGGCTGA | 4766 |
| | 4 | MRWLGATDPET* | 4767 | ATGAGATGGTTAGGGCGACTGACCCAGAGACATAG | 4768 |
| hsa-mir-198 | 1 | MGRSWGGROAGKERS* | 4769 | ATGGGAGGAGAGCTGGGGGGCAGGCAGGCGGGAAGAGAAGAGTCTTAA | 4770 |
| | 2 | MWKRWLALALALVAVAWVRAEVGEGPRSPNSVPGASWVCALGGWARVLGMLSRGGAGSFGPWGVLGWSWGSNAAYET* | 4771 | ATGTGGAAACGCTGGCTCGCGCTCGCGCTGGCTGGTGGCGGCTGCTGGGTCCGCGCCGAGTTAGGCGAGGGCGCCGAGGGCGGAACTCGGACTCGGACTCGGACTCGGACTCGGACTCGGACTCGGACTCGGTCCGCGTGCTCCCGGGGCGCTCTTGGGTCTCGCCGCTGGGGCGGCGAGTCGGAGTCCCGGGCGCCGAGGGCGCCGAGGGCGGAAGGAAGGAAGGACCAGTGGGGAGTTCGGGGGAGAGCAATGCTGGCAGTAATGCTGCTTACGAAACTTAA | 4772 |
| | 3 | MLLTKLKSLKQEK* | 4773 | ATGCTGCTTACGAAACTTAAATCTTAAAGCAGGAAAGTAG | 4774 |
| | 4 | MEGERGGGEGTGWADGDEAATGAAAASSKRRLSSVLHFRGD* | 4775 | ATGGAGGGAGAGGCGGGAGGAGAGGCAGCAGCGAGTTCAAAAAGGCGCCTCAGTTCCGTCCGTCCTTCACTTCAGAGGAGACTGA | 4776 |
| | 1 | MPHLELFTVRFRREISGRLPGAAGTHACARAHTHTHTCVCAPPPHPRPPKSQTFLLSPEATIPNPASCSASPTL* | 4777 | ATGCCACATCTGAAACTGTTTACAGTGCGATTCCGCCGAGAAATCAGTGGCGCGCTTCCTGGTCTGCGCCCCCTCCTCCCCACGCGTCGCGCGCACCCCGACCCCAAAGAGTCAGACATTCCTCCTGAGTGTGTCGCGCCCCCTCCTCCCCACGCGTCGCGCGCACCCCGACCCCAAAGAGTCAGACATTCCTCCTGAGCCAGAAGCCACGACCACGAGCCTCTGCTCCCCCACTCTTTAG | 4778 |
| hsa-mir-199a-1 | 2 | MRAGPSLATSEGTERIVSGRVVVSLAAQRC* | 4779 | ATGCGAGCGGCGCCTTGCCTGTTCCTTGGCGCTGCTCAGAGGTGCTGAAAGAGTGTGGTTCCTTGGCGCTGCTCAGAGGTGCTGA | 4780 |
| | 3 | MDSRPRQPSVQTTCSGGSQCVQ* | 4781 | ATGGATAGCGGCCGCCAGCCCAGCGTGTTCAGACTACCGTTCAGGAGGCTCTCAATGTGTACAGTAG | 4782 |
| | 4 | MCTYVCTLVRLGLGERLVETGPPNSPAGECHFPPPRFPLWQSLA* | 4783 | ATGTGTACAGTAGTCTGCACATTGGTAGGCTGGGCTTGGTGAGCGGCTCGTCGAGACAGGCCCCCAAACTCGCCGGCAGGTGAGTGCATTTCCACCACCCGTTCCCACTGTGGCAGAGCCTCGCATAG | 4784 |
| | 1 | MHRKEGSYHFQGIALIARYI* | 4785 | ATGCATAAAGAAGGTAGTGTAATCTTTCAGGGAATTGCCCTAATAGCAAGATATATATAG | 4786 |
| hsa-mir-199a-2 | 2 | MCVCVCVCVCV* | 4787 | ATGTGTGTGTGTGTGTGTGTGTGTGTGTGTAA | 4788 |
| | 3 | MKSSGLDIFVLVFI* | 4789 | ATGAAGAGTTCAGGCTGGACATATTGGTTTCTTGTTTCATCTGA | 4790 |
| | 4 | MVEKHLYFKRCFAKPLMLSKLLYEK* | 4791 | ATGGTGGAGAAGCATCTTATTTTAAAAGATGTTTGCAAAGCCTCTTATGCTTTCAAAATTACTATATGAAAAGTGA | 4792 |
| hsa-mir-199b | 1 | MGLKRPPDGQTLLPGWTRGHLHSVYPVFRLSVQDSQIVQ* | 4793 | ATGGGCTGAAGCGCCACCGGATGGACAGAGACATCTGCTGCTGGATGGACCAGAGGACACCTCCACTCCGTCCGTTCAGGACTCCCAAATTGTACAGTAGTCTGCACATTGGTTAG | 4794 |
| | 2 | MDRHCCLDGPEDTSTPSTQCLDYLRTPKLYSSLHIG* | 4795 | ATGGACAGACACTGCTGCCTGGATGGACCAGAGGACACCTCCACTCCGTCCGTTCAGGACTCCCAAATTGTACAGTAGTCTGCACATTGGTTAG | 4796 |
| | 3 | MDQRTPPLRLPSV* | 4797 | ATGGACCAGAGGACACCTCCACTCCGTCACCAGTGTTTAG | 4798 |
| | 4 | MDGGATLCGTGWG* | 4799 | ATGGATGGGGGTGCTACCCTGTGTGGGACTGGTTGGGGTAG | 4800 |

| | | | | |
|---|---|---|---|---|
| | 4 | MFLRGGLHGGEGGGHGKDCAPPPIVPGLGLGPRATGTAAAEPPPLWAGLGGAGGHKGGAARPRPRTRASAPPVAARLPPGNGLGGLPRPAGPDSDPPPPGGYAENRRAALPLVRHVLPARAP* | 4815 | ATGTTCCTGCGGGCGGGCTGCGGGGGTGAGGGCGGGACATGGCGGCGACTGCGGCGCGCCGCCGATTGTCCGCCCCTCTGGGCGGGCCTCCGGCCTGAGGCTGCGACGGGCACCGCGGAGGGCGGCGGCCGCCCGAGCCCGCTCCCCGCACTCGGGCTCCGGGGGCTGCCTCGGCGCCGCCGCGTCCGCGCGAGGCGGCTGCCGCCGGGGAAACGGGTTGGGGGGGTTGCCGCGGTCCGGCGGGGCTGACTCTGACCGACATGTGCTGCCGCCCCGGACTCGTAGTGCGGACATGTGCGAATAG | 4816 |
| | 1 | MGGGE* | 4817 | ATGGGGGGTGGCGAATAG | 4818 |
| hsa-mir-19b-2 | 2 | MSCLMNC* | 4819 | ATGTCTTGTTTAATGAACTGCTAA | 4820 |
| | 3 | MSLLGSYFYLFPLIG* | 4821 | ATGTCACTCTTGCAACCTTCTTTCCTGTCTCTCTGCCTTCCAACCAAGACACATAG | 4822 |
| | 4 | MISSFPTFPCLSNQDT* | 4823 | ATGATTTCATCTTTTCCAACCTTCTTCGTCTCTCTGCCAACCAAGACACATAG | 4824 |
| | 1 | MGCRQPGQRPGELRSLQTQAGAGPSPPQCKVGPCADAAGFRVWSHLGPTGCVFRARAQCVGSRHGVPSGQGLGRGQAPRGVTFLPPT* | 4825 | ATGGGCTGTCGCCAGCCTGGCCAGCGTCCAGGGAGCTCCGGTCACTGCAGACACAGGCTGAGCGGGTCCTTCCCCCCCAGGGAAAGGTGGGCCCTGCGCAGATGCGGCTGGGTTTCGAGCGGTGTGGAGCTCAGGATGGGACCACGGGACCGCTGTCCGGGCAGGAATGTGTGCGAGAGGGTCACGTTCTTGCCGCCTACCTGA | 4826 |
| | 2 | MRLGFGCGAILDPRAASSGHGHSVWAPGMGCPQGRAWAEGRLREGSRSCRLPDSRPSRKFSPEAATAVLRHFVRRREAVASEVGA* | 4827 | ATGCGCGGCTGGGTTTCGGGTGTGGAGCCATCTTGACCCACCAGGGCTGCGTCTCCGGGACGGGCACAGTGTGTGGGGTCAGCATGGGGTGCCCTCAGGGCAGGGCCTGGGCTAGAAAGTTCTCTCCAGAAGCAGCAGCAGCACCGCCGTCTGAGGCACTTGTCGGAGACCTAGAAAGTTCTCTCCAGAAGCAGCAGCAGCCCGCGTCGACGTGGCGTAG | 4828 |
| hsa-mir-200a | 3 | MTASPLGSGVCGGKGLVSAPSGQRPAEPMGGEVGAWGRGWSGTGGAQPGEAGAGSQAPRYDWGGGNVSREVFYLNVKRLSTVAAAGNKVRPTEAQP* | 4829 | ATGACCGCGCTCCTTGGCTCTGGAGTCTGCGGTGGAAGGGCTTGGTTTCAGCACCCTCTCCTTGGCGCCTCATGGGACCACGGGGCAGGTTCTGCAGGCCCTCTGCTGACTGGGGTGGGCAACGTCTCTCGTGAGGTTTTTACTTAAATGAAAACGGTCCGGGAAACAAGGTCCGACCACCCCAAGGCCCAGCCTTGA | 4830 |
| | 4 | MTGVGATSLVRFFT* | 4831 | ATGACTGGGGTGGGCGCAACGTCTCTGAGGTTTTACTTAA | 4832 |
| | 1 | MGCRQPGQRPGELRSLQTQAGAGPSPPQCKVGPCADAAGFRVWSHLGPTGCVFRARAQCVGSRHGVPSGQGLGRGQAPRGVTFLPPT* | 4833 | ATGGGCTGTCGCCAGCCTGGCCAGCGTCCAGGGAGCTCCGGTCACTGCAGACACAGGCTGAGCGGGTCCTTCCCCCCCAGGGAAAGGTGGGCCCTGCGCAGATGCGGCTGGGTTTCGAGCGGTGTGGAGCTCAGGATGGGACCACGGGACCGCTGTCCGGGCAGGAATGTGTGCGAGAGGGTCACGTTCTTGCCGCCTACCTGA | 4834 |
| | 2 | MRLGFGCGAILDPRAASSGHGHSVWAPGMGCPQGRAWAEGRLREGSRSCRLPDSRPSRKFSPEAATAVLRHFVRRREAVASEVGA* | 4835 | ATGCGCGGCTGGGTTTCGGGTGTGGAGCCATCTTGACCCACCAGGGCTGCGTCTCCGGGACGGGCACAGTGTGTGGGGTCAGCATGGGGTGCCCTCAGGGCAGGGCCTGGGCTAGAAAGTTCTCTCCAGAAGCAGCAGCAGCACCGCCGTCTGAGGCACTTGTCGGAGAC | 4836 |
| hsa-mir-200b | 3 | MTASPLGSGVCGGKGLVSAPSGQRPAEPMGGEVGAWGRGWSGTGGAQPGEAGAGSQAPRYDWGGGNVSREVFYLNVKRLSTVAAAGNKVRPTEAQP* | 4837 | ATGACCGCGCTCCTTGGCTCTGGAGTCTGCGGTGGAAGGGCTTGGTTTCAGCACCCTCTGTTGCAGGCCGGCCAGCCATGGGCGGTGCCCATGGGGCGTGGGGCTCAGCGCGGGGCAACGTGGAGAAGCTGAGCCGGTTCCCAGGTGAAACGGTCTCTGTGAGGTTTTTTACTTAAATGTGAAACGGCTCAGTACGGTGAGCGCAGCGGGAACAAAGGTCCGACCACCAGCAGAGGCCCAGCCTTGA | 4838 |
| | 4 | MTGVGATSLVRFFT* | 4839 | ATGACTGGGGTGGGCGCAACGTCTCTGAGGTTTTACTTAA | 4840 |

Figure 1 (Continued)

| | | | | |
|---|---|---|---|---|
| hsa-mir-200c | 1 | MAGGHTCAQGGRRGPGKEPALAARQAEKEGGRAEAR AGSRPWNLGP* | 4841 | ATGGCAGGAGGACACACCTGTGCGCAGGGTGCAGGCGGGGCCAGGTAAGGAGC CTGCGCTGGCTGCCGGCCAGGCGGGAGAAGGAAGGAGGAAGCGGAAGCGGAAGGCCAGGGC GGGCTCTAGGCCGTGGAATCTGGGCCTTAA | 4842 |
| | 2 | MRVGKSVCVAGRERLPGVGEGGSEAAGRRSRGFGGPA WTATWAS* | 4843 | ATGAGGGTGGGTAAATCGGTGTGTGCCGGGTGCGGGTTGGGAGAAGCTGCCRGGGGTAGG GGAAGGTGGCTCAGAGGCGGCGGGCCGACGGTCGGAGGGGCTTCGGAGRGCCTGCTT GGACTGCAACCTGGGCCTCGTGA | 4844 |
| | 3 | MGARDLQLFRRDPGREAA* | 4845 | ATGGGAGCCAGGGATCTGCAGCTTTCCCAGGGATCCTGGTCCTGAAGCTGCCTGA | 4846 |
| | 4 | MMEAPVPVSATSIASGPQPLAGCSPLPTSHAPRRPLVLS* | 4847 | ATGATGGAGGCCCCTGTCCTGTCAGCAACCATCATGCGCTCAGTGCCCAGCCC TTAGCTGGCTGCAGCGCCCCCCACTCCCACGCACCCTCGTCTG AGCTGA | 4848 |
| hsa-mir-202 | 1 | MRAPLGGGLHFSAGRWWVPLTSPGVYFCMCEP* | 4849 | ATGAGGGCTCCCCTTGGGGCGGCTGCATTTCTCAGCGGGAAGGTGGGTGGGT GCCCCTCACATCCACCTGCGTTTATTTTGCATGTGTGAAATATAA | 4850 |
| | 2 | MGTYGPKLTAE* | 4851 | ATGGGAACATATGGTCCGAAACTCACTGCTGAATAA | 4852 |
| | 3 | MVRNSLLNNVLS* | 4853 | ATGGTCCGAAACTCACTGCTGAATAATGTGCTGTCATGA | 4854 |
| | 4 | MCCHEIYFKMPLIEYNLG* | 4855 | ATGTGCTGTCATGAAATTTACTTCAAAACCCCTCACGGAGTACAAATCTGGGTAG | 4856 |
| hsa-mir-203 | 1 | MQRWQGLSSLLYHQELCMPQKSLSLPERQFPQLQNENN KTFLIPFPGWLRWLSHTRPMWKCLGGPSDLVAVFWSG AHLGS* | 4857 | ATGCAGCGATGGCAAGGCCTGTCATCCCTTCTCTACCACCAAGAGCTGTGCAATCCC CAGAAGTCACTGTCCGTGCCTGAGCCTGAGTTCCCAACTGCAAATGAAAATAAC AAAACCTTTCTGATTCCTTTCCCTTCCAGGGTGGCTGCGTGGTTGAGCCACGGGCCC ATGTGGAAATGTCTGGGGGTCCCAGATCGTGGTGTTCTGGTCTGGGGCT CACCTTGGCTCCTGA | 4858 |
| | 2 | MARPVIPSLPPRAVQSPEVTVPP* | 4859 | ATGGCAAGGCCTGTCATCCCTTCTACCACCAAGAGCTGTGCAATCCCCAGAAGTC ACTGTCCCTCCCTGA | 4860 |
| | 3 | MKJTKPF* | 4861 | ATGAAAATAACAAAACCTTTCTGA | 4862 |
| | 4 | MSGGSLRSGGCVLVWGSPWLLSTWLLAGWAGGGMAC HRPALE* | 4863 | ATGTCTGGGGGTCCTCCAGATCTGGTGGCTGTTCTGGTCTGGGGCTCACCTTGG CTCCTGAGCACTTGGCTGGCTGGGCGGTGCGTGGGATGGCGTGTCACGGC CCTGCACTGAATGA | 4864 |
| hsa-mir-204 | 1 | MGKKWRDAAEMERGCSDREDMAESRRRSRSASRGRFA ESWKRLSSKQGSTKRSGLPSQQTPVSGRGRAPVFAPFSP FARDLSPFHGAELASLRVRARELVAPLLMK* | 4865 | ATGGGAAGAAGTGGAGGATGGCGGCGAAATGGAGCGCGGCTGCTCGACCGCG AGGACAACGCGGAGATGGAGCGCGGCTGCAGCGACCGGGAGGACATGGCAGAGTCTCGGCC GAGTCGTGGAAAAGGTTAAGTTCCAAGCAGGGTTCCACCAAACGCTCGGGACTCC GTCGCAGCAGACCAGCCGGTGAGTGAGCGCGACTTGAGCCTTTCATGTGTGCTGAACTTGCTCCTAAGGGT TCCCTTCGCACGGAACTGTGGCGCGCTTCTAATGAAATAG | 4866 |
| | 2 | MRRKWSGAAPTARTTRRAADAAGAPAGAGLPSRGKG* | 4867 | ATGCGGGCGGAAATGGAGCGGGCGGGGCTGCTCGACCGCGAGGACAACGCGGAGAGCCG CAGAGCGCAGCCGGGAGCCGACGCCGGGCAGGTTTGCCGAGTCGTGGAAAAGGTTAA | 4868 |
| | 3 | MVLNLPP* | 4869 | ATGGTCTGAACTTGCCTCCTAA | 4870 |
| | 4 | MFERRGGSLLDHKSFAVNRACETLSSVL* | 4871 | ATGTTCGAGAGGCGAGGGGGCTCGCTGTTAGATCATAAGAGTTTTGCAGTTAACAG AGCGTGTGAGACGTTGTCGAGTGTATTGTGA | 4872 |
| hsa-mir-205 | 1 | MLPRLVLNS* | 4873 | ATGTTGCCCAGACTGGTCTTGAACTCCTGA | 4874 |
| | 2 | MFFFIKERNQLPRTGPHLSSGVISVPHRPAELGALYRVS VSHFLFPVLKP* | 4875 | ATGTTCTTTTTCATTAAAGAGAAATCAACTATTCAGGACCGGCCCCCACCTTCT CAGGAGTCATTTCTGTTCCGCACAGGCCTGCTGAACTGGTGCTTTATATAGGGTAA GTGTTTCTCATTTTTGTTCCCTGTCTTCAAGCCTTAG | 4876 |
| | 3 | MAVAISLFCHL* | 4877 | ATGGCTGTAGCCATCTCTCTGTTCTGCATTATCTTAAGA | 4878 |

Figure 1 (Continued)

| | | | | | |
|---|---|---|---|---|---|
| | 4 | MTKKKNSYFRANSKLGPDVSRHRYYSYLKVSLKSVDLG NFGKTKMSQ* | 4879 | ATGACAAAAAAGAAAATTCTATTTGAAGCAAACTCAAACTAGTCCTGATGTC TCAAGGCACAGGTACTCGTACTTAAAGGTGAGTCTGAAATCTGGATTGGGGAAC TTTGGAAAAACAAAGATGAGTGGCTAG | 4880 |
| hsa-mir-206 | 1 | MLHFSLRS* | 4881 | ATGCTAATAATATTTCCCTGAGAAGCTGA | 4882 |
| | 2 | MKGPCTWGRVGISYCSTGFCCKH* | 4883 | ATGAAAGGCTTTGTATTGGGGGAGGTGGAATTTCTACTGTTCAACAGGTTTT TGTTGTAAACATTAA | 4884 |
| | 3 | MWEGVPLLSQEGGQAPGSLRSPFS* | 4885 | ATGTGGGAGGGAGTGCCACTTCTGTCCAGGAGGAGGCCAGGCACCAGGCAGCCT GCATTCACCATTCTCCTGA | 4886 |
| | 4 | MWGPPSQFSFK* | 4887 | ATGTGGGGACCTCCCTCCAATTCTCCTTCAAATGA | 4888 |
| | 1 | MPCSPSTEPPP* | 4889 | ATGCCCTGCAGCCGTCCAGAGCCCCACCGTGA | 4890 |
| | 2 | MLSPSFHLPSSPGWLPSLDPGFILPLGLHRHLSQSCPFVS LPCPSFLARVLTSLPLCF* | 4891 | ATGTTGTCTCCATCTTTCCATCTTCCTCTCTTTGGATGGCTTCCTTCCCTTGATCC TGGTTTAPCTTGCCTCTTGGTCTTCATGACACTTGTCACAATCATGCTTCTTGTC TTCTCCCTTGTCCTTGTCCTTCTTGGCACGTGTTCACCTCCGTCCTCTGCTTCTA A | 4892 |
| hsa-mir-208 | 3 | MASFP* | 4893 | ATGGCTTCCTTCCCTGA | 4894 |
| | 4 | MLLCLSPLSFLLGTCSHLPASLLLTLFPHPVPRTHIDSVPF LFCLCVFPPLTPWSVLPVCALGLPPSPGGLPLLFFTLLICS SLCPALPLLFLAPPTVQILQDSP* | 4895 | ATGCTCTGTGCTCTCCCCTGTCCTTCCTTCTGGCACGTGTTCACCTCCGTCC CCTTTCTTTTCTGGGCTCCTCTAACCTGTTCCACACCCGTCCCTCCACTAATGACTCGGTC CCCTTTCTTTTCTGCCTCTGCGTCTTTCCGTCTTCTGACTCCCTGGTCTGTCTGCCTGT CTGGCGCTCGGGCCTGCCTCCATCCCCCGGGTGGCCTCGGTCCTGTGTTCTTCACTCTC CTCATCTGTTCTTCTCTGCCCGGCTCTACCTCTTGTTCCTGCTCCACCCACGG TCCAGATTCTTCAGGATTCTCCGTGA | 4896 |
| | 1 | MNPMPGRRGKGWGGVGVG* | 4897 | ATGAATCCATGCAGGGAGGCACTGTGCAGCGACTGCAGCGATGCTTCTGCAACC CCCAGTCCCAATCATTAA | 4898 |
| | 2 | MAVGTVPATAQPSAMPSATSAISPCHLQPPTCTPAPQP PVPNH* | 4899 | ATGGCGGTGGCACTGTGCCAGCACTGCCAGCCAGCGATGCCTCTGCAACC CCCAGTCCTATTTCCCCTGCAGAGAGTTCCTAAGGAGCCAGTCGATGGCTTCTGCAACC CCCAGTCCCAATCATTAA | 4900 |
| hsa-mir-208 | 3 | MLINPTGQAARLGVQRGCEEK* | 4901 | ATGCTAATTAACATTCCTACAGGGCAGGCTGCCAGGCTGCAGAGGCGATG TGAAGAGAAGTAG | 4902 |
| | 4 | MGEEGEPVFLEEQRGGKENPKEG* | 4903 | ATGGGGGAGGAGGAAGAGAGCCAGTCTTCTAGAAGAACAGCGGGAGGGGAAAG AGAACCCAAAAGAAGGATGA | 4904 |
| | 1 | MQDPMQSTRSSHWAHMCRSKHCRMQHRSS* | 4905 | ATGCAGGACTTCATGCAGGTACAGAGTACCAGGAGCACACATGCAGGTCT AAACATGGCGTATGTGCCACAGGAGTTCCTAG | 4906 |
| | 2 | MGVCATGVPRGRYLHLSIWDQYALQGVCVCVCVCVC VDKPA* | 4907 | ATGGGCGTATGTGCCACAGGAGTTCCTAGGGAGAGATATCTGCATCTGAGCATATG GACCAATATGCATTACAGGGTGTGTGTGTGTGTGTGTGTGTGTGTGGA CAAGCCTGCATAG | 4908 |
| hsa-mir-208b | 3 | MGPICITGCVCVCVCVCVCGQACIV* | 4909 | ATGGGACCAATATGCATTACAGGGTGTGTGTGTGTGTGTGTGTGGACAAGCCTGCATAGTCTGA | 4910 |
| | 4 | MHYRVCVCVCVCVCVCVWTSLHSLNVRKGMYLTD* | 4911 | ATGCATTACAGGGTGTGTGTGTGTGTGTGTGTGGGACAAGCCTG CATAGTCTGAAATGCAGAAAAGGTATGTACTCACTGACTGA | 4912 |
| | 1 | MNPMPGRRGKGWGGVGVG* | 4913 | ATGAATCCATGCAGGGAGGCACTGTGCAGCGACTGCAGCGATGCTTCTGCAACC CCCAGTCCCAATCATTAA | 4914 |
| | 2 | MAVGTVPATAQPSAMPSATSAISPCHLQPPTCTPAPQP PVPNH* | 4915 | ATGGCGGTGGCACTGTGCCAGCACTGCCAGCGATGCCTCTGCAACC CCCAGTCCCAATCATTAA | 4916 |
| hsa-mir-208b | 3 | MLINPTGQAARLGVQRGCEEK* | 4917 | ATGCTAATTAACATTCCTACAGGGCAGGCTGCCAGGCTGCAGAGGCGATG TGAAGAGAAGTAG | 4918 |
| | 4 | MGEEGEPVFLEEQRGGKENPKEG* | 4919 | ATGGGGGAGGAGGAAGAGAGCCAGTCTTCTAGAAGAACAGCGGGAGGGGAAAG AGAACCCAAAAGAAGGATGA | 4920 |

Figure 1 (Continued)

| | | | | | |
|---|---|---|---|---|---|
| hsa-mir-20a | 1 | MVAATPQESARPSGDGGKPVVCGPGLAGGAERPGAD WPGAAWRRRGRGGSRPLAAPACGSRIWLPPRSPAGRR RGACPGREGGKGRRARGRARDPRRPCLGRPEGGWAD GEHNGPSGRGRARPVPSPGPGARAGRGVSG* | 4921 | ATGGTGGCGGCTACTCCTCCTGGTGAGTCTGCCGCCCTCCGGCGACGGAGGGAA ACCTGTTGTGCGGCCCGGGTTGCGGCGGCCGGGTTGGCGGGGCTGCCGGGCGACT GGCCCGGGGCAGCGTGCTGGCGGCGGCGGCTGCCGGGGCGGTTCTGGCGTTGCC CCCCGGCGTGTGGCAGCCGCATCTGCTGCCCCTGCTCGCCCGCGGGCCGGCG GAGGGGCAGRCCGGGGCAGAGCGTGCAGTGCGGAAGGGGCGCAGGTGCCGGCGC CGCCCCGGACCCGGCAGCCTGCCTGGCGCAGATCCTGGCGAGAGGACCTGCCCCG CGGCGAACACAATGGCCCTCGGCGGGGCGTGCGAGGGCCCGTGCCTTCTCCGG GGCCCCGGGCGCGCGCGGGGCGTGGGGTCTCTGGGTAG | 4922 |
| | 2 | MAPRGHEDYRGPCLLRGPGRARGVGSLGRKVSPEGES* | 4923 | ATGGCCCCTCGGGGAGAGGACTTGCGAGGCCGTGCCTTCTCCGGGGCCCGGGCG CGCGGGGCGTGGGGTCTCTGGGTAGGAAAGTTCTCCGAGGGCGAGAGTTAA | 4924 |
| | 3 | MGQAAGREGARPKGTCAPAGGVAWAGARGSPNFVRA RVGGGAPRSARPGRHPRSAWALLARVGSLGAGPATSPP WPSEEAAVGLSRGVEPPAPGRLLGVWRGRASPARRERR PRRHVPAGRAARG* | 4925 | ATGGGGCAGGCCGCGGGCCGGGAGGGGCCGCGCCCACGAGGTACCTGCGCGCAG CGGGGCGTGGCGTGGGCGGGAGCCCGGTTCCCAAACTTGTACGCGGAGG GTGGCGCCCAGGGGCCCCCGTGGCGAGATCGGGGCCGCCACCCCGGCTCCCGCGTG GGCTTTGTTAGCCCGGCGAGTCGCAGCCTCAGCCGCGGCGTGAGCCTCGCGCCCG GCCCTGGAGGAGGCCGCGAGTGCAGCGCTCAGCCGCGGCGTGAGCCTCGCGCCCG GCCGCTTGCTGGGAGTGTGGCGCGGAAGGCCAGCCGCTGCGCGGGAGGCGCGT CCCCGCGCCATGTTCTGCCGGGGCTGCACCGGGGTGA | 4926 |
| | 4 | MFLRGGLHGGEGGGHGGDCAPPPIVPGLGLGPRATGTA AAEPPLWAGLGGAGGHKGGAARPRPRRTRASAPPVA ARLPFGNGLGGLPRPAGPDSDPFPPGGYAENRRAALPL VRHVLPARAP* | 4927 | ATGTTCTGCGGCGGGCTGCACGGGGGTGAGGGCGGGGACATGGCGGCGACTG CGGCCGGGGAGCCCCTGGGCTGGGCGGGACTAAGGCGCGGCCTCGGGAGGGCGGC CGGCGGGCGCGCGCGGAGCCCCGCCCCGGCTCTCCGGGCTCGCACTCGGCCGCCGTCCC GGAGGGCGCGGCGGCTCCGCGAATCGGGTTGGGGGGTTGCCGCTCCGGCGGGCTG ACTCTGACCGCACATGTGCTGCCGGCCCGGGCTGCCATGA TGTGCGACATGTCGTGGGGCTCCATGA | 4928 |
| | 1 | MGGGE* | 4929 | ATGGGGGGTGGCGAATAG | 4930 |
| hsa-mir-20b | 2 | MSCLMNC* | 4931 | ATGTCTTGTTTAATGAACTGCTAA | 4932 |
| | 3 | MSLLGSYFYLFPLIG* | 4933 | ATGTCACTCTTGGGAGTTACTTCTACTTGTTCCTTTAATAGGATGA | 4934 |
| | 4 | MISSPTFFCLSWQDT* | 4935 | ATGATTTCATCTTTCAACCTTCTCTGTCTCTCAACCAAGACACATAG | 4936 |
| | 1 | MTAEQNKYIL* | 4937 | ATGACAGCAGCAGAACAAATAAGTAAGTACATCCTATAA | 4938 |
| | 2 | MLHPLIFF* | 4939 | ATGCTCCACCCGTTAATCTTTTTTAA | 4940 |
| hsa-mir-21 | 3 | MWPFMWPRLFSNSWAQAHLSQPPKVLDYKLSHRAGS AVYNRKKQTNLSQHFSDP* | 4941 | ATGGCCCCCTATGTGGCCAGGCTGTTCTCAAACTCCTGGGCTCAAGCAATCCTC CTGTCTCAGCCTCCAAAGTGTTGGATTACAGGTGGATTACAGGCTGAGCC GTTTACAACGGAAAAAAACAAAACTTTCCCAAATCTTCTCTGACCCTTAA | 4942 |
| | 4 | MVPGVCQ* | 4943 | ATGGTGCCTGGGGTATGTCAGTAA | 4944 |

Figure 1 (Continued)

| | | Protein | SEQ ID | Nucleotide | SEQ ID |
|---|---|---|---|---|---|
| hsa-mir-210 | 1 | MDGVCLSGQQGRRVGVSEIRGLCCPLGGAEAGPDTLLEGTFPSLCCVQGTSVRSSCCQAEGGPGGAQVWSYLQPTGPSSGGPPLGTSYGKRVTDLVLLCVSAASVGPLRETAGGSSSSLSAFPAFSSLLLKSGPGRVRAYRPCLRSPGLQELRAAPARWRGRGRFSGRLAWTRTGLWKLPALTGLPVTTAK* | 4945 | ATGGACGGGGTGTGCCTCTCTGGCCAGCAGGAGCGGGGGTGGGGTAAGCGAAATCATTCGGGGGGCTTTGCTGCCCCTCGGTTGTGTCCAGGGACGGGGGGCTGAGGCTGGGCCAGATACCCTCTTGGAGGGAACTTCTTTCTTGTCGTCCAGGGCACAGGTGTGGTCATATCTCAGCCAACTTGCCAAGCTGAAGGTGGCCCTGGCAGGCACAGGTGTGGTCATATCTCAGCCAACAGGACCATCTCCGGAGGGCCACCTCTGAGGACTTCTACGGGAAGAGAGTGACAGATTTGGTGCTTCTGTGTTCTGCCGCCTTCAGTGGCCGTCCGGGAGACAGCCGGGTGATCCTCCAGCAGCCTGTCTGCTGCTGAGCCTGTCTGAGCCTCTCAAGTCTACTGTTAAATCAGGACCGGGTCGTGTCCGAGCCTACAGGCCCTGTCTCCGCTCCCCAGCCTGCAGGAGTTGAGGGTGCACCTGCTGCGTGGAGAGGGAGGCAGATTTAGTGGACGCCTGTGCATGGACTCGGACTGGCCTTTGGAAGCTCCCTGACGGGGTTGCCTGTCACCACACTGCGAAGTGA | 4946 |
| | 2 | MDSDWPLEAPCPDGVACHHCEVRLGRTCT* | 4947 | ATGGACTCGGACTGGCCTTTGGAAGCTCCCTGACGGGGTTGCCTGTCACCACACTGCGAAGTGA | 4948 |
| | 3 | MSRNSGRGGSQRRPSIQPGSALCPYLHQVGSLPCIAWGLAGLGPALLWNWMFSGSPAFPHVATVHNIVFKVQFKTQK* | 4949 | ATGAGTAGGAACTCTGGCCGAGGAGGGTCCAGCGCCGCGCCCCTCGATACAGCCTGGCTCTCTGCCCCTCTGGCGTACTTACACCAGGTGGGATCCCTGCCTGCATTGCCTGGGGAGTTGGCTGGGCTTGGGCCCGCCTGGGAACTGGATGTTTCAGGAGCCCAGCCTTTCCTCATGTCAACACAGTTCACAATATAGTTTCAAAGTACAGTTTAAAACTCAAAAGTAA | 4950 |
| | 4 | MSTQFTT* | 4951 | ATGTCAACACAGTTCACAATATAG | 4952 |
| hsa-mir-211 | 1 | MRAQAQVLTCSSWGLLLLLKGGPSSPSSLPWPRRRLKEPELCPLHSTAVAGKLRCG* | 4953 | ATGAGGGCCCAGGCGCCAAGTGCTCACATGTCTCCTCATGGGGACTGCTCCTCTTAAAGGGTGGCCCCTGCTCACCAGCTCCTGCCCTGCCAAGGAGGAGGCTGAAGAGCCTGAGCTGCCCCTTCCAATTCCACTGCTGGCAGGTAAGCTCAGATGCGGGTAA | 4954 |
| | 2 | MLLMGTAPLKGWALLTQLPALAKEEAERA* | 4955 | ATGCTCCTCATGGGGACTGCTCTCTTAAAGGGTGGGCCCTCCTCACCCAGCTCCCTGCCCTGGCCAAGGAGTAAGCACAGGTGAAGGAGGTCAGGTGCAGGTATCCTCAGGTGTGGGTAA | 4956 |
| | 3 | MRVSTGEGRSGAGHLRCG* | 4957 | ATGCGGGTAAGCACAGGTGAAGGAGGTCAGGTGCAGGTATCCTCAGGTGTGGGTAA | 4958 |
| | 4 | MQLSSGVGNLRCR* | 4959 | ATGCAGTTAAGCTCAGTGTTGGTAACCTCAGGTGCAGGTAG | 4960 |
| hsa-mir-211 | 1 | MHPCMLVCAQNCTHAPINNGCLEYGVRRKCEYPCPPVIDLFVNYCNFLHQALTLVDRWVGNR* | 4961 | ATGCATCCGTGCATGTTGGTATGTGCCAGAACTGTACACGCACCATTAACAATGGCTGCCTGAAGTGCCGGAAGGTAAGAAGGGTAAGAAGTGTGAGTATCCATGTCCCTTTGTGATAGATTTATTTGTGAATTACTGTAACTTCCTACATCAGGCACTGACACTTGTGGACAGGTGGGTAGGTAATAGGTAG | 4962 |
| | 2 | MCPELYTRTH* | 4963 | ATGTGTCCAGAACTGTACACGACGACCATTAA | 4964 |
| | 3 | MAAWK* | 4965 | ATGGCTGCCTGGAAGTAG | 4966 |
| | 4 | MSLCDRFICELL* | 4967 | ATGTCCCTTTGTGATAGATTTATTTGTGAATTACTGTAA | 4968 |
| | 1 | MNEPPHEYYARL* | 4969 | ATGAATGAGCCGCCACGAGTACTACCGAGTACTACGCGCGCTATAA | 4970 |
| | 2 | MSRRTSTTRAYKSRRAGGAAGGDRAVATRPAR* | 4971 | ATGAGCCGCCGCACGAGTACGGGCAGTGGGACGGGGAGGCGGCCGCCATAAAAGCGCCGCGGCCAGGC | 4972 |

Figure 1 (Continued)

| | | | | |
|---|---|---|---|---|
| hsa-mir-212 | 3 | MCGHGREDEEGTGRRRVGRPLRGGDGGRGAPGSPRG CGAGARDDTSPRSTCRRPMDTQLLRRSIEWRTDLGDPP PAFLGLLRHSPRKVRRRCWRPRRRAPSSPSLRRGHDSASL PGPAERGCRRETDAHPRFPGSPPGTPAPHGVGRPFPAGPV QRYPRRPRLPASASGAVLSGPGGRGLPGPAPPPRPRRKC PLWDFDVTAL* | 4973 | ATGTGCGGACACGGACGGAGGAGGACGAGGAGGGACGGGCAGGCGGCGGGTGGGGC GCCCCCTCCGGGGTGGCGGGATGGGGGCGGACGGCAGGGCCACCGGCGTCCCTCGCGGC TGCGGAGCCGGACCCAGAGACGGACGACAGCCGCGCAGCAGCCGCGCACCTGCCGGCGCCGAT GGACACGCAGCTACTTCGGAGGAGCATCGAGTGGAGGACCGACCTGGGAGACCCC CCCCGGCTTTCTTGGGGCTCCTGCGCCATTCTCCGGCCCCTCCTGCCTCCAGGAAAGTGAGGCGAAGTGCT GGCGCCCAAGGAGACCGGCCGCCCCTCCTCCCTGCCGCGGTGACGGCGGGTGACTCAGCCT CGTGCCCGGCGCGCGGCTGAGCGGGGTGCAGGCAGGGAGAGACGGACGCCACCCCGC GTCCCGGACCCTCCTGGGACCCCGCATGGCGTCGGGCGTCGGGCGCCCCTTCCGGCA GTCCTCCAGCGCGGGGCGGTCCTCCAGCGACCTCCCGCTTCCGGCTGGAGGGAGCT GTCGTCCAGGGACGCGGGCGGGCGGGGCCTCCAGGACATCTTTGACGTCACGGCCCTGA CCGCCGAAGTGCCCCTCTGGGACACTCTTTGACGTCACGGCCCTCTGA | 4974 |
| | 4 | MGADGGHRGPLAAAEPGHETTRARAAPAGARWTRSYF GGASSGGPTSETPPRLSWGSCAHPGR* | 4975 | ATGGGGGCGGACGGGCGGCACCGGGGGCCTCCCTGCGGCTGCCGAGCCGGGACCCAG AGACGACAGCCACGAGCCAGCACCTCGAGGAGGACAGCACCGGCGGGCCAGCTACTTC GGAGGAGCATCGAGTGGAGGACCGACCTCGGAGACCCCTCGGCTTTCTTGGGGG CTCCTGCTGCGCCATTCTCCCAGGAAAGTGA | 4976 |
| | 1 | MHKEGSYIFQGIALLARYI* | 4977 | ATGCATAAAGAAGGTAGTGTAATCTTTCAGGGAATTGCCTAATAGCAAGATATATATAG | 4978 |
| hsa-mir-214 | 2 | MCVCVCVCVCVCV* | 4979 | ATGTGTGTGTGTGTGTGTGTGTGTGTGTAA | 4980 |
| | 3 | MKSSGLDIFVFLVFI* | 4981 | ATGAAGAGTTCAGGCTGGACATCTTTATTTGTTTCTTGTTTCATCTGA | 4982 |
| | 4 | MVEKHLYFKRCFAKPLMLSKLLYEK* | 4983 | ATGGTGGAGAAGCATCTTATTTTAAAGATGTTTTGCAAAGCCTCTTATGCTTTCA AAATTACTATATGAAAAGTGA | 4984 |
| | 1 | MSTGLTEMNALDPIHLPFICSCALFSYKVDGLFRPPLGN Y* | 4985 | ATGTCTCACGGCTCACAGAAATGAATGCTCTGACCCATCACTTGCTTCATT TGTTCCTGTGCCCTTTTTCATACAAAGTGGATGGCCTCTTAGGTTTCCTTTAGGAA ATGTGTAA | 4986 |
| hsa-mir-215 | 2 | MLWTPSTCLSFVPFFHTKWMASLGFL* | 4987 | ATGCTCTGGACCCCATCCACTTGCTTCTGTTTCCTGTCCCTTTTTTTCATACAA AGTGGATGGCTAAGTGCCTCTTTAGGTTTCTTTAG | 4988 |
| | 3 | MCKCLQAFVLTLK* | 4989 | ATGTGTAAGTGCCTACAGGCCTTTGTCCTCACATTAAAATAA | 4990 |
| | 4 | MAFVTIQMNNVKYFQK* | 4991 | ATGGCATTTGTGACTATCCAAATGAACAATGTAAAGTACTTTCAAAATAG | 4992 |
| | 1 | MLTLKLITSGNNGKKEKLLGCICLENAM* | 4993 | ATGCTGACTTTAAAATTGATAACATCTGGAAATAATGGCAAAAAGGAAAAACTGTTG GGCTGCATCTGTCTTGAAAATGCTATGTAA | 4994 |
| hsa-mir-216a | 2 | MAKRKNCWAASVLKMLCNKIYLIYLKKEKCFVPQFVA TSESSRGYDPSLRKHLPPPANTPGKAVGNNKTRAS* | 4995 | ATGGCAAAAAGGAAAAACTGTTGGGCTGCATCTGTCTTGAAAATGCTATGTAATAAG ATTTACTTACTAATATATTGAAAAGGAAAAATGTTGTCCCAATTTGTTGCAACAT CTGAAAGTTCACGAGGTTATGACCCCCTCTTAAGAAAGCATCTCCACCACCTGCAA ATACCCCAGGAAAAGCAGTTGGAAACATAAAACACGTGCTAGTTAA | 4996 |
| | 3 | MFCSPICCNI* | 4997 | ATGTTTTGTTCCCAATTGTTGTCAACATCTGA | 4998 |
| | 4 | MTPL* | 4999 | ATGACCCCTCTTAA | 5000 |
| | 1 | MLTLKLITSGNNGKKEKLLGCICLENAM* | 5001 | ATGCTGACTTTAAAATTGATAACATCTGGAAATAATGGCAAAAAGGAAAAACTGTTG GGCTGCATCTGTCTTGAAAATGCTATGTAA | 5002 |
| hsa-mir-216b | 2 | MAKRKNCWAASVLKMLCNKIYLIYLKKEKCFVPQFVA TSESSRGYDPSLRKHLPPANTPGKAVGNNKTRAS* | 5003 | ATGGCAAAAAGGAAAAACTGTTGGGCTGCATCTGTCTTGAAAATGCTATGTAATAAG ATTTACTTACTAATATATTGAAAAGGAAAAATGTTTGTTCCCAATTTGTTGCAACAT CTGAAAGTTCACGAGGTTATGACCCCTCTTAAGAAAGCATCTCCACCACCTGCAA ATACCCCAGGAAAAGCAGTTGGAAACAATAAAACACGTGCTAGTTAA | 5004 |
| | 3 | MFCSPICCNI* | 5005 | ATGTTTTGTTCCCAATTGTTGTCAACATCTGA | 5006 |
| | 4 | MTPL* | 5007 | ATGACCCCTCTTAA | 5008 |

Figure 1 (Continued)

| | | | | | |
|---|---|---|---|---|---|
| hsa-mir-217 | 1 | MLTLKLIJTSGMNGRKEKLLGCICLENAM* | 5009 | ATGCTGACTTTAAAATTGATAACATCTGGAAATAATGGCAAAAGGAAAAACTGTTG GGCTGCATCTGTCTTGAAAATGCTATGTAA | 5010 |
| | 2 | MAKRKNCWAASVLKMLCNKIYLIYLKKEKCFVPQFVA TSESSRGYDPSLRKHLPPPANTPGKAVGNNKTRAS* | 5011 | ATGGCAAAAGGAAAAACTGTTGGGCTGCATCTGTCTTGAAAATGCTATGTAATAAG ATTTACTTAATATATTTGAAAAGGAAAAATGTTTTGTTCCCAAATTTGTTGCAACAT CTGAAAGTTCACGAGGTTATGACCCCTCTTTAAGAAAGCATCTCCACCACCTGCAA ATACCCCAGGAAAGCAGTTGGAAACAATAAAACACGTGCTAGTTAA | 5012 |
| | 3 | MFCSPICCNI* | 5013 | ATGTTTTGTTCCCAATTTGTTGCAACATCTGA | 5014 |
| | 4 | MITPL* | 5015 | ATGACCCCTCTTTAA | 5016 |
| hsa-mir-218-1 | 1 | MPSCPARSATGPLGFRAF* | 5017 | ATGCCCAGTTGCCCGCGCTCTGCTACGGGCCCCTGGGCTTCCGGCCTCTAG | 5018 |
| | 2 | MRGVGWQMLSLSLGLVLAHLNKVAPQACPAQCSCSGS TVDCHGLALRSVPRNIFRNTERL* | 5019 | ATGCGCGGCGTTGGCTGGCAGAATGCTGTCCTGTCGTCGGGGTTAGTGCTGGCGATC CTGAACAAGGTGGCACCGCAGGCGTGCCCGGCGCAGTGCTCTTGCTGGGCAGCAC AGTGGACTGTCACGGCTGGGCTGCGCAGGCGTGCCCAGGAATATCCCCGCAACA CCGAGAGACTGTGA | 5020 |
| | 3 | MRSSSSPLPIRAAHPCLHWRNLSAQGPVPGAALASSPPC TSWG* | 5021 | ATGCGCTCTTCGTCTCCCCTCTCCCCATCCGGCCGCTGCACCCTGCCTCCACTGGA GGAACCTGTCAGCTCAGGGTTCCGTTGCCTGGGGCAGCCCTCGCTAGCTCTCCCCAT GCACATCCTGGGGTTGA | 5022 |
| | 4 | MHHLGLSSPGGHWPGKGLCPRRGGSAGSCASSPSPALVP PLAAPCWLVLWGWGAGR* | 5023 | TCCACATCCTGGGGTTGAGCTCTCCGGCGCGCTCTGCTCCGCTCCGATGGAGCTGTG CCCGGCCACTGCAGCTCCTGCTTGCTGCTAGTTCTCGGGGCTGGGGAGCGGGTAGATA G | 5024 |
| | 1 | MRSGAAPAPPMELLLLPPPPPGAPRSARAPCA* | 5025 | ATGCGCAGCGGGGCAGCGCCGCCCCGCGCCGCGATGGAGCTGCTGTTGCTGCCGCC GCCGCCGGAGCCGGAGCCCCCGTGCCCGTGCGCTGA | 5026 |
| | 2 | MAPGWAGVGAAVRARLALALASVLSGPPAVACPTK CTCSAASVDCHGLGLRAVPRGHPRNAERL* | 5027 | ATGGCCCCCGGGTGGGCAGGGGTCGGAGCGGTCCGAGCGCTGGCGCTGGCGCTGAC CTTGCGCTGGCGAGCGCCGCCACCAAGTG TACCTGCTCGCTGCAGCTCCAGCGTGCACAGCGGCGCGAGCCGCCGGTTCCTCG GGGCATCCCGGCAACGCGAGCGCCGTGTGA | 5028 |
| hsa-mir-218-2 | 3 | MQSLFSSLPGYDPSLSELGVCRLGQJWKERSRNPQRWA KSSASPGVRVPDAGPADSFQGVAEERRGEARALQPQGL RVRVRGLRSLKRGAGEGESYRMMGRQGAEAGERARD C* | 5029 | ATGCAGTCTCTATTCTCATCCCTTCCTGGATACGATCCGTCACTTCTCCGAGCTGGGG TCTGTTAGGCTTGGTCAGATCGGAAAGAGAGTCTCCAGACGGATGGCA AAGAGCAGTGCCTCTCCAGGGGTGAGGGTTCCAGACGCAGTGCAGCT CCAAGGAGTAGCTGCAGGCGGAGGGAGGCAAGGAGCACTGCAGCTCAAGGT CTTAGGGTGAGGTCAGGGTCGCGCGTCGCTCAAGGCGGCGGAAGGAGA AAGCTATAGGAGATGGAGATGGGCCGTCAAGGCGCGGAGGCGGGAGAGAGGGCCGAGAC TGTTGA | 5030 |
| | 4 | MGKEQCLSRGFGSRRRAR* | 5031 | ATGGGCAAAGAGCAGTGCCTCTCCAGGGGGTGAGGTTCCAGACGCAGGGCCCGCTGA | 5032 |
| | 1 | MNQPMKGAGESRREGAGKRRRKGRGVCANRLWRPHK DWPRTEGEDREVGGNWGGGRGHPLLPCPRDRPPPGSR SPSPGASARAGTRCPSGSLTAPHPLALYPSHSLHSMGHA LPLPLLFPPHPLRLL* | 5033 | ATGAACCAGCCGATGAAAGGGCTGAGAGAGCAGGAGGAGGGCTGGAAGA GGAGGAGGAAGGGAGGGGGGTCTGCGTAATCGACTCGGCGCCACATAAGGAC TGGCCACGGACTGAAGGAGGAAGTAGGCGGAGCTGGGGTGGGGGC GAGGGCACCCACTGCGTCCTGTTCGCAGGAGGCGGGACAGGAGCAGGGCAGC CCAAGTCGGGAGCCTCAGCTGCGGCGGGGACAAGATGCCCATCAGGGTCTCTAAC TGCCCCCCACCCGTCGCCCGCCCGTATCCCTCATTCCTACACTCCTACTCAAGGTCTCTAAC CTGCCCCTTCCTCTTCTCCCCATCCCCTTCGTTACTCTAG | 5034 |

Figure 1 (Continued)

| | | | | |
|---|---|---|---|---|
| hsa-mir-219-1 | 2 | MPIRVSNCPPPRPVSLSFPTLNGDRSAPSSSLSSPSPSFT LESSKRLLPTSHSRHSAPVYPTHTRTPPSQWELHLVYVP VSAWCLRSPFPPVRLPPFPAPG3RGS* | 5035 | ATGCCCATCAGGGTCTCTAACTGCCCCCCCACCCCTGCCCCTGTATCCCTCATTCCC CTACACTCAAATGGAGATCGCTCTGCCCCTTCCTCTCTTTCCTCCATCCCTTC GTTTACTCTAGAGTCCTGAAGAGGCTTCTGCCACTTCCACTCCAGACATTCTGCC CCTGTATCCCCACCACACGCCGTGTCTCCAACCCCTCCAATGGAGCTCCATCTGT TATGTCCCTGTTTCCGCGTGGTTCCGTGGTCCTCCCGTGCGGCTCTCGA | 5036 |
| | 3 | MGAPSCVCPCFRVVSPFPLSSRAPPSLPRPGPRLLIVQTQ FSSLWLRPRVESGRPEPPPNLERESGSEGLGRAKAEGG GSPQGGKGNPGHGT* | 5037 | ATGGGAGCTCCATCTTGTGTATGTCCCGTTCCGTGGTGTCTCCATTCCCTT CCTTCCGTGCCGTCCCGTTCCCGCCGCCGGAGTCCTCGATTGTCAAA CGCAATTCTGAGTCTATGCCTCCGCCGGAGTTGAGTTGAGTCGCGAGCCGC CGCCCCAAACCTCGAGCGGGAGAGCGGCGTCTAGGGAGCAGCCAAAGCA GAGGGTGAGGGAGTCCCAGGGTGGTAAGGGGAATCCCGGGCACATCGGGACCTA G | 5038 |
| | 4 | MSLFPRGVSIPPLPCASLPSPPRAAAPDCPNAILESMAP AES* | 5039 | ATGTCCCTGTTTCCGCGTGGTCTCTCCATTCCCCTTTCCTCCCGTGCGCCTCCTCC CTTCCCCCCCGGCCCGGCCGCCTCCTGATTGTCCAAACGCAATTCTGAGTCTATGG CTCCGGCCGAGAGTTGA | 5040 |
| | 1 | MLVPGPGEGRGRWAKGSGRGSRRGIGS* | 5041 | ATGCTGGTTCCTGGCCAGGAGAAGGGAGCGGGTCATTCGGGAGTTGA | 5042 |
| | 2 | MGKGVRPREQAGHRELRVPSGGGRTRGPAGAEGEAAP GEGHAMSLRAA* | 5043 | ATGGGCAAAGGGGTCAGGCCAGGGAGGAGCAGGGCATCGGGAGTTGAGGGTGC CGAGTGGGGGGTCGGGGATCAGAGGGTCGGTGCAGAGGGGGAGGCGGCCCCC CGGGGGAGGGGCACGCTATGTCTTAAGAGCTGCCTGA | 5044 |
| hsa-mir-219-2 | 3 | MTIDGPVALFKSSTNCSRAPESAPGPYCWSGPLKARPGP EPPEAPARVQPCASAARRLPVRLHGRCR* | 5045 | ATGACACATTGATGGCCCGTGGCCAGGCCCGTATTGTTGGAGCGGCCCACTAAATCAGTACCAATTGCAGCCGAGC CCCGAGCCGCCAGAGGCGCTCCACGGCGCTCAGCCTGCGCCTCGGCACCCCGG GCTCCCAGTCGGCTCGCTCCACGGCGCTGCAGGTGA | 5046 |
| | 4 | MAPWRYSNPVPLAAEPLSPRQARIVGAAH* | 5047 | ATGGCCCCGTGGCGTTATTCAAATCCAGTACCAATTGCAGCCGAGCCCTTCTCCG CGCCAGGCCGTATTGTTGGAGCGGCCCACTAA | 5048 |
| | 1 | MEGESGVRAATPSPSGRRRGGGRGASGRGAWTGRVS VSGATRKESGTGVVAEGLAEWRGAGGEPRGRRAGGGS PGGPRSEDTGAGHLAWGGSGPPERAARRCFASAGVHW VRASSAPWQGRGRWAGRPLLSFSPGDVM* | 5049 | ATGGAGGGGTGAAAGTGGGGTCCGGCGGCACACCAGCCTTCCGGAGGAGAAG CTGAGGCCTGAACTGGCGGGTTAGT GTGTCAGGAGCTACGAGAAAGAGTCTGGAGTCTGGGAGTCTGCGAAGGCTGG CGAGTGGCGGGGGTCGGGGGAGCAGGTCTGGGAGGGGGCGGAGCCGGCGCTC ACCCGGCGGCCGGCCCGGTCTGAGGATACAGGGGCGGCATCTAGCTGGGAGGGT CTGACCCCCCGAGCGGGCAGTTCAGCGCCTGGCAGGGAAGGGTGCTTTGCCTCG GTCAGGGCGCAGTTCAGCGCCTGGCAGGGAAGGGTGCGTGGCGGGCGGGCCCT CCTCTCGTCTCTCCAGGGATGTTATGTAA | 5050 |
| | 2 | MLCKGGGERSRGRRCRGLMQPKG* | 5051 | ATGTTATGTAAGGGGGGGAGGGGAGCGCGGGTGTCCGGTGCCGGGGCCTTA TGCAACCAAAGGTTAG | 5052 |
| | 3 | MASGEAVTPTSLRPWFQPPTPLACHPGCQIGLGAVRVP EG* | 5053 | ATGGCCTCCGGCGAGGCTGTCACCCCACCTCACTCCTGCGCCTGGTTCCAGCTCCA ACTCCTTTGCCTGTCATCCTGGCTGTCAGATTGGGCTGTCAGAGTGCCA GAGGGTTGA | 5054 |
| hsa-mir-22 | 4 | MEQLVRGSVPWAHPALQPRAPAWHRLSAAAESSGLNR AISDRGRSDGVGLVTQGKEDTQSSCLPRGFRNLNRTPY PPIFLTL* | 5055 | ATGGAGCAGCTGGTCAGAGGGTCAGTGCCCTGGGCCCACCCGCGCTGCAGCCAAG GGCACTCCGCTTGGCACAGAGGAAGACTCTCAGCAGCGTGGACAGAGC TATCTCAGACAGAGGAAGGTCGACGAGTTGAACTGGTCACCCAGGGAAGGAAGC ATACACAAAGTTCATGCTCCCAAGAGGGTTTCGGAATTTGAACCGCACCCGTATC CCCAATCTTTCTTACCCTCTGA | 5056 |
| | 1 | MSGVLETRIC* | 5057 | ATGTCTGGTGTCCTAGAAACAAGAATATGCTAA | 5058 |

Figure 1 (Continued)

| | | | | |
|---|---|---|---|---|
| hsa-mir-220 | 2 | MLTFEERTFCVIEDISQRDLSCNFSLIHLESVY* | 5059 | ATGCTAACCTTTGAAGAAAGAACATTTGTTAATAGAAGACATCAGCCAGAGAGACCTTTCATGTAATCCTTCTAATCATTTAGAATCAGTATTAA | 5060 |
| | 3 | MVHRNISRATSHCSLQDMSRGHTLPTG* | 5061 | ATGGTCATTAGGAATATTTCAAGGCTACATCCATTGCTCCCTGCAGGATATGTCCAGGGGAATTCTGACTTTGCTACTCTGCTCTGA | 5062 |
| | 4 | MSNMHSLPL* | 5063 | ATGTCCAACATGCACTCTGCCTCTGA | 5064 |
| hsa-mir-220b | 1 | MQTLQKTPPTPTFPRCLCCSVSGCRIGSTNEKCS* | 5065 | ATGCAGACGCTGCAAAAACCCCTCAACCCTACATTTCCAGATGCCTTTGCTGCTCCGTTTCTGATGCAGAATTGGTTCTACCAATGA | 5066 |
| | 2 | MPLLLRFWMQNWFYQ* | 5067 | ATGCCTTTGCTGCTCCGTTTCTGGATGCAGAATTAGAAAATGTCATGA | 5068 |
| | 3 | MRNAHERFRKWK* | 5069 | ATGAGAAATGCTCATGAGAGATTTAGAAAGTGGAAGTGA | 5070 |
| | 4 | MLMRDLESGSEAVWACVYILLRSRVVELYHLFS* | 5071 | ATGCTCATGAGAAGCAGGGTTGTGGAGCTATAGATTTATTTCATGA | 5072 |
| hsa-mir-220c | 1 | MGRRRARVFLPRLLPSLLPPPVAPP* | 5073 | ATGGGCCGCCGCAGAGCCCGTGTCTTCCTCCCGCCTGTCCTCCCCTCCCCTGA | 5074 |
| | 2 | MLFL* | 5075 | ATGCTCTTCCTCTAG | 5076 |
| | 3 | MYYIHLFYVHC* | 5077 | ATGTATTATATTATGTTAACATATAAATATATAAATATTAA | 5078 |
| | 4 | MLLYVKHNIKYN* | 5079 | ATGTTATTATATGTTAACATATAAATATTAAATATAATTAA | 5080 |
| hsa-mir-221 | 1 | MRGFCYSFLSENDSHSILPFTLHQVSPSHTHTHTHTH TPFSCPP* | 5081 | ATGAGAGGGTTTTGCTATTCCTTTTGAGTGAAAACGACTCCATAGCATATGCCATTCACACTCCACCACCATTCTCCCTTCACACACCACACACACATTTTTTCACACACCACCATTCTGTCCTCCCTGA | 5082 |
| | 2 | MNNLRFVMDSGCSPFLTFFLNLQELLLSLLPFPTFWFSLP GKLLILPS* | 5083 | ATGAATAATCTTCGCTTGTCATGATGGCCGGATGCTCACCTTTTCTAACATTTTTTAAACCTCCAAGAGTTACTCTCAGCCTCTCCCCACCTTCTGGTTTTCCCTACCTGGTAAACTTCTATTCTACCTAGTAA | 5084 |
| | 3 | MLTFSNIFFKPPRVTPQPPSLPHLLVFPTW* | 5085 | ATGCTCACCTTTTCTAACATTTTTTAAACCTCCAAGAGTTACTCCTCAGCCTCTTCCCCACCTTCTGGTTTTCCCTACCTGGTAA | 5086 |
| | 4 | MKLLPH* | 5087 | ATGAAGCTCTTGCCTCATTGA | 5088 |
| hsa-mir-222 | 1 | MRGFCYSFLSENDSHSILPFTLHQVSPSHTHTHTHTH TPFSCPP* | 5089 | ATGAGAGGGTTTTGCTATTCCTTTTGAGTGAAAACGACTCCATAGCATATGCCATTCACACTCCACCACCATTCTCCCTTCACACACCACACACACATTTTTTCACACACCACCATTCTGTCCTCCCTGA | 5090 |
| | 2 | MNNLRFVMDSGCSPFLTFFLNLQELLLSLLPFPTFWFSLP GKLLILPS* | 5091 | ATGAATAATCTTCGCTTGTCATGATGGCCGGATGCTCACCTTTTCTAACATTTTTTAAACCTCCAAGAGTTACTCTCAGCCTCTTCCCCACCTTCTGGTTTTCCCTACCTGGTAAACTTCTATTCTACCTAGTAA | 5092 |
| | 3 | MLTFSNIFFKPPRVTPQPPSLPHLLVFPTW* | 5093 | ATGCTCACCTTTTCTAACATTTTTTAAACCTCCAAGAGTTACTCCTCAGCCTCTTCCCCACCTTCTGGTTTTCCCTACCTGGTAA | 5094 |
| | 4 | MKLLPH* | 5095 | ATGAAGCTCTTGCCTCATTGA | 5096 |
| hsa-mir-223 | 1 | MGRLRPSPPPLAPSLAPYSASLSSSPLPQQWRGDTEQAE ATSPRAHPPAPRPCSARARSCATPQPPRCLRLR* | 5097 | ATGGGGCGCCTCCGCCCCTCCGCCTCTGCCTTCGCTTGGCGCCTACTCTGCCTCGGCTCAGCAGCAGCCCCTCCGCCAACAATGCGCGGGACACTGAGCAAGCAGAGGCCACCTGCCAGGCTCACCGCCCGCCTCCCTTCCCGATGCTCACCTTTTCTAACATTTTTTCCCTCTGGTCCTGCCGCCACCCAGCCGCCACGCGCATCCTGCCTCCCGCCTGCCTCGCCTGCTCGCCCAGGGCTCGGTCCGCCGCCACAGGGACACTGA | 5098 |
| | 2 | MARGH* | 5099 | ATGGCGCGGGGACACTGA | 5100 |
| | 3 | MHVYIHPSTHHNTKDMEST* | 5101 | ATGCATGTGTATATTCACCCCAGCACTATTCACAATACCAAAGACATGGAATCAACCTAA | 5102 |
| | 4 | MCIFTPALFTIPKTWNQPKCCPSMTDCIKKMYI* | 5103 | ATGTGTATATTCACCCCAGCACTATTCACAATACCAAAGACATGGAATCAACCTAAAGCCCATCAATGACAGACTGCATAAAGAAATGTACATATAA | 5104 |

Figure 1 (Continued)

| | | | | |
|---|---|---|---|---|
| hsa-mir-224 | 1 | 5105 | MLSKVLPVLLGLLLILQSR* | 5106 ATGTTGTCCAAAGTTCTCCAGTCCTTCTAGGCATCTTATTGATCCTCCAGTCGAGGTGA |
| | 2 | 5107 | MRAGLGPPHCRMGSRGP* | 5108 ATGCGCGCGCTCGGCCTCCGCCCTCACGTAGGATGGGCTCCCGGGTCCTTGA |
| | 3 | 5109 | MCECCLVCSLLTFPLRVPTEFQALRQATLTLLASHAAA PVGASLRHELWESLRYPAPAMPPLHR* | 5110 ATGTGTGAGTGTCTCAGGCACTGCGCTCTGTGTTCTCTGCTGCCAGGCAACTGACATTACTTGCTTCCATGCCGCTG CTCTGTTGGTGCCAGTTCGCAGGCACGAGCTTTGTTTAGTCTAAGGAGTGCTCCGCTCA CAGCTATGCCCCCTCTCCACCGCTGA |
| | 4 | 5111 | MPLLLLVPVSGTSFGLV* | 5112 ATGCCGCTGCTCGTTGGTGCCAGTCCTCAGGCACGAGCTTTGGTTTAGTCTAA |
| hsa-mir-23a | 1 | 5113 | MAPFGLFRAQ* | 5114 ATGGCCCCATTTGGCCTGCCAGGGCTCAATGA |
| | 2 | 5115 | MRGELGHASCCSLLVPHGPSRYLCLSSPGAGTEGTARL QLPVWWLLHMRKELPCDQRKHLGTWRGGVPKSHYLL CSLSLSPLQVPASGPARCPPHPCATAGWGSWGWDLLPV TNHIARDFQPTLSSAIEDAARGRGGREAPKPVPGLRSRA* | 5116 ATGAGGGGGAGCTTGGCATGCAAGTTGCTGTAGCCTCCATGCCTCTGTCCGCATGGGCC TCTAGGTATCTCCAGTCCTTGCTCTCCAGTGGGCTGAACGAGGCACAGCTAGGCTC AGCTCCCGTGTGGTCGGAACCTGGAGCCTCATATGAGAAGAGAGCTTCCTGTGATCAAAGG AAGCATCTGGGGACCTGGAGAGTGTCTCAAATCTCATTACCTCCTTTGCTCT CTCTCTCTTCCCCCTCCAGGTGCCAGGTCCAGCAGGCCCTGGGGTTCTGGGAATGGATGGATTTGCTCTGTCACAAATC CCTGCACGGCCGGCTGGGGCCGGCTGGGTAACCGACCCTGAGCTCTGCCACCGAGGATGTGCCGGG ACGGGGCGTGGCAGAGAGGCCTGTGCTGGCCTGGCCTGAAGAGCAGGAGTTAG * |
| | 3 | 5117 | MQVAVASLSRMGPLGISASPVLGLERRAQLGSSSPCGG SCI* | 5118 ATGCAAGTTGCTGTAGCCTCCCTCCTCCGAACGGCATGGGCCTCAGCTCCCGTGGTGG CAGTCCTGGGGCTGGAACGGAGGGCACAGCTAGGCTCCAGCTCCCCGTGTGGTGGC TCCTGCATATGA |
| | 4 | 5119 | MGFASCHKSHCQGPPTDPELCHRGCCPCTGWQRGPEA CAWPEEGLAACEQGPHQVVFTVAKFRPPGPHLLWPC RLSPAAACLPAILLPGLPGLCLPCLLS* | 5120 ATGGGATTTGCTTCCTGTCACAAATCACATTGCCAGGATTCCAACCGACCCTGAG CTCTGCCACCGAGGATGCTGCCCGGACCTTAGCTGCGGGTTGCAGAGAGCCCGAAGCTG TGCCTGGCCTGAGGAGCAGGGCCTTAGTGCTGCCCCAGGCCTCCCTGCCTTGCCCCTT GTTCACAGTTGCTAAGTTCCGCCCCCCAGGCCCCCATCCTCTGCCCCCATCCTCGTCCTGGGCTCTGC CTCCCGTGCCTACTGAGCTGA |
| | 1 | 5121 | MVPWVPGDPAKGLSHGMRFSPPAQPRLCGTPTCPPPA RTARHWEGREAASGGLLSRLRLGLALLQACRIRRLRRR QGEGAGYFYLPPGSRGDRK* | 5122 ATGGTTCCCTGGGTTCCTGGTGACCAGTAAGGGCTTTTCTAGTGGATGCGTTC CCCAGTGCCCAGCCAGCCTAGGGCTGTCGCACCCTACTTGCCTCCCCTCCTGCC AGACAGGAGCGAGCACTGAGGAGGGACGGGAGGGCCTCTCTCCCTCCCG GCTGAGGTCGGCTGCGCCCCTCCAGGATCGGCCGTCTGCGCCGCGG GCAGGGGGAGGGGCGGCGGGTTATTTTACCTCCCTCCAGGCAGGCGGGGGCGACAGGA AGTGA |
| hsa-mir-23a | 2 | 5123 | MGCASPVPQRSLGSVAPLLAPLLPGGQRGTGRDGRRPQG ASSPQ* | 5124 ATGGGATGCGCTTCCGTTCCCCAGTCCAGGACAGCTAGGCTCTGTGGCACCCTACTT GGCCTCCCCTCCTGCCAGGGAGGAGGACGGGAGGCGGCCTCAGGG GCCCTCCTCCCGGCTGA |
| | 3 | 5125 | MWGARELGTATAGLAAGRERG* | 5126 ATGTGGGAGCCAGGGAGCTGGAACAGCCACAGCTGACTGGCGGCGGCCGGGGGG AGCGGGGTTAG |
| | 4 | 5127 | MWVVASLSLIWAPIPSLARGLSDPGQGGGPCPSPQGPPG PSRVGGKRGRRPLAGPACHRHCLPVGCLLGNLTRJPR* | 5128 ATGTGGGTCGTGGCCTCGCTCTCGCTCATCTGGGCGCCAATCCCTCGCTGGCTCGA GGGCTCTCAGATCCTGGGCAGGGAGGGGGGTAAGAGGGGCACCCCGCCTT AGTTCCAGCAGAGTCGGGAGTCGGGCTGCCTCGGACGGGGAAAAGGGGCCGCCGCCT GCCACGGCCATTGTTTACCCGTCGCTGCCTCCTAGGAAACTTAACCCGCCGCCGCGGT AA |
| | 1 | 5129 | MRPKARVDDVTRRVPG* | 5130 ATGCCGGCCCCGGCGCGCGTGTGGATGACGTCACCCGGCCGTGCCGGGTAG |
| | 2 | 5131 | MTSPGACRGSP* | 5132 ATGACGTCACCCGGCGCGTGCCGGGGTAGCCCGTAG |

Figure 1 (Continued)

| | | | | |
|---|---|---|---|---|
| hsa-mir-23b | 3 | MAAGTASPRSEGDGEPSLLTLTFARPARTRIPSSVLPDSWG* | 5133 | ATGGCGGCGGGACAGCATCATTCCGTTCTGAAGGCGACGGGAGAACCCTCCTTAC CCTCACTTTTGCTCGACCAGGCGAGGACCCCTCCTGTTCTCCAGACTCC TGGGGCTGA | 5134 |
| | 4 | MNACMGGEGVAQ* | 5135 | ATGAACGCATGCATGGCGGGGAAGGGGTGGCACAGTAA | 5136 |
| hsa-mir-23b | 1 | MPARAGGRPAGGGAAAIPLRQAPPLGARPPARAAAQAPRPPPAPRLR* | 5137 | ATGCCGGCGGGGAGGCGACCTGCGGGGAGGCGACCTGCGGCGGCCGCTATACCTTT AAGGCAGGCGCCCCCGCGCCCCTCGGGCCGCGCCCCGCCCAGG CCCCGCGCGCCCGCCCGCCCCTGAGGTGA | 5138 |
| hsa-mir-23b | 2 | MRITPGGRRARAPAPPLRPPRPRARYGAGTPS* | 5139 | ATGCGGACCCCTGGAGGGCGCAAGGCGCGGGCTCCGGCGCGCGTGCGTCCTCC CCGGCCGCGGGAGGTACGGGGCGCACGCCGAGTTAG | 5140 |
| | 3 | MAVRTLSPSLKCCGF* | 5141 | ATGGCCGTCAGGACCCTGTCGCCTCTTGAAATGCTGTGGTTTTGA | 5142 |
| | 4 | MLWFLNLRSRNGLE* | 5143 | ATGCTGTGGTTTTTGAACCTCAGTGCAGTCACGAAATGGATTGGAGTGA | 5144 |
| | 1 | MRPRARVDDVTRRVPG* | 5145 | ATGCGGCCCGGGCGGTGGATGACGTCACCCGCGCGTCCGGGTAG | 5146 |
| | 2 | MTSPGACRGSP* | 5147 | ATGACGTCACCCGCGCGTGCCGGGTAGCCCGTAG | 5148 |
| hsa-mir-24-1 | 3 | MAAGTASPRSEGDGEPSLLTLTFARPARTRIPSSVLPDSWG* | 5149 | ATGGCGGCGGGACAGCATCATTCCGTTCTGAAGGCGACGGGGAACCCTCCTTAC CCTCACTTTTGCTCGACCAGGCGAGGACCCCTCCCTGTTCTCCAGACTCC TGGGGCTGA | 5150 |
| | 4 | MNACMGGEGVAQ* | 5151 | ATGAACGCATGCATGGCGGGGAAGGGGTGGCACAGTAA | 5152 |
| hsa-mir-24-1 | 1 | MPARAGGRPAGGGAAAIPLRQAPPLGARPPARAAAQAPRPPPAPRLR* | 5153 | ATGCCGGCGGGGAGGCGACCTGCGGGAGACGCGGCGGCCGCTATACCTTT AAGGCAGGCGCCCCCGCGCCCCTCGGGCCGCGCCCCGCCCAGG CCCCGCGCGCCCGCCCGCCCCTGAGGTGA | 5154 |
| hsa-mir-24-1 | 2 | MRITPGGRRARAPAPPLRPPRPRARYGAGTPS* | 5155 | ATGCGGACCCCTGGAGGGCGCAAGGCGCGGGCTCCGGCGCGCGTGCGTCCTCC CCGGCCGCGGGAGGTACGGGGCGCACGCCGAGTTAG | 5156 |
| | 3 | MAVRTLSPSLKCCGF* | 5157 | ATGGCCGTCAGGACCCTGTCGCCTCTTGAAATGCTGTGGTTTTGA | 5158 |
| | 4 | MLWFLNLRSRNGLE* | 5159 | ATGCTGTGGTTTTTGAACCTCAGTGCAGTCACGAAATGGATTGGAGTGA | 5160 |
| | 1 | MAPFGLPRAQ* | 5161 | ATGGCCCCATTTGGCCTGCCAGGGGCTCAATGA | 5162 |
| hsa-mir-24-2 | 2 | MRGELGHASCCSLLVPHGPSRYLCLSSPGAGTEGTARLQLPVWWLLFMRKELPCDQRKHLGTWRGGVPKSHYLLCSLSLSPLQVPASGPARCFPHPCATAGWGSWGWDLLPVTNHIARDFQPTLSSATEDAARGRGREAPKPVPGLRSRA* | 5163 | ATGAGGGGGGAGCTTGGCCATGCAGTGCTGTAGCCTCTTGTCCGCATGGCCC TCTAGGTATCTCTGCCTCTCCATTGGGTCTGGAGCGCACAGCTAGGCTC CAGCTCCCGTGTGGAACCTGCTCTGCATATGAGGAAAAGAGCTTCCCTGTGATCAAAGG AAGCATTCTGGGACCTGAGGAGGTGTCCCAAATCTCATTACTCTCTTTGCTCT CTCTCTTTTCTGCCAGGTCCAGGTGGCCAGTCTCTGTGCCGCCGGTTGCTTCTGTCACAAATC ACATTGCCAGGGATTTCAACGACCCAGCCAGCAGAGATGCTGCCGG GACGGGGGTGGCAGAGAGCCGTGCCTGGCCTGGCGAGGAGCAGGGCTAG | 5164 |
| | 3 | MQVAVASLSRMGPLGSASPVLGLERRAQLGSSSPCGGSCI* | 5165 | ATGCAAGTTGCTGTAGCCTCCTGTCCGCATGGGCCCTCTAGGTATCTCTGCCTCTC CAGTCTCTGGGGCTGGAACGGCAGGCACAGCTAGGCTCCCAGCTCCCGTGTGGTGGC TCCTGCATATGA | 5166 |
| | 4 | MGFASCHKSHCQGFPTDPELCHRGCCPGTGWQRGPEACAWPEEQGLAACEOQGPHQVVFTVAKFRPPGPHLLWPCRLSPAAACLPAILLPGLLPGLCLPCLLS* | 5167 | ATGGGATTTGCTTCCTGTCACAAATCACATTGCCAGGATTTCAACGACCCTGAG CTCTGCCACCGAGGATGCTGCCCGGGACCGGCTTAGCTGTTGAGCAGGGTCACACAAGTCG TGCCTGGCCTGAGGAGCAGGGTTAGCGCCCCCAGGTTCCGCCCATCCTGGCTTGCGCT TGTTCACAGTGGCTAAGTTGCCCAGGCCTGCCATCCTGCCTGCCTGCCTGGGCCT CTCCCGTGCCTACTGAGCTGA | 5168 |

Figure 1 (Continued)

| | | | | |
|---|---|---|---|---|
| hsa-mir-24-2 | 1 | MVPWVPGDPAKGLSHGMRFPSPPAQPRLCGTPTCPPPARTARHWEGREAASCGLLSRLRLGLALLQAGRIRRLRRRQGEUAGYFYLPPFGSRGDRK* | 5169 | ATGGTTCCCTGGGTTCCTGGTGACCCAGCTAAGGGCCTTCTCATGGGATGCGCTTCCCCAGTCCCCAGCGCAGGCCACTGGGAGGGACGGAGGCGGGGCCTCAGGGGCCCTCTCTCCCGGCTGAGGCTCGGCCTCGCCTTCTCCAGCTGGGAGGGATCCGCCGTCTGCCGCCGGCAGGGGAGGGGCTCGGGGCTCGGTTATTTTTACCTCCTCCAGGCAGCCGAGGGACCAGAAGTGA | 5170 |
| | 2 | MGCASPVPQRSLGSVAPLLAPLLPGQRGTGRDGRRPQGASSPG* | 5171 | ATGGGATGCGCTTCCCCAGTCCCCAGTCCAGTCTAGGCTCTGTGGCACCCTACTTGCCCCCTCTGCCAGGACAGCGAGGCACTGGAGGCACTGGAGGCGGCCTCAGGGGGCCTCCTCTCCCGGCTGA | 5172 |
| | 3 | MWGARELGTATAGLAAGRERG* | 5173 | ATGTGGGGAGCCAGGGAGCTGGGAACAGCCACAGCTGGACTGGCGGCTGGCGCTGGGAGCGGGGTTAG | 5174 |
| | 4 | MWVVASLSLIWAPIPSLARGLSDPGQGGGPCPSPQGPPGPSRVGGKRGRRPLAGRACHRHCLPVGCLLGMLTRPR* | 5175 | ATGTGGGTCGTGGCCTCCCTGTCCTCATCTGGGCGCCAATCCCTCGCTGGCTCGAGGGCTCTCAGATCTGGGCAGGGAGGGGACCCTTCGCCTCGCGCCAGGGACCCCCAGTCCCAGCAGAGTCGGGGTAAGAGGGTGGAGGGGCCTCCGGCCCCGCCTGCCACCGCCATTGTTTACCCGGCGTGCCTCCTAGGAAACTTAACCCGCCGCGGT | 5176 |
| hsa-mir-25 | 1 | MSGSPLEDRMKNWEIMAVLESRQEDGEESRACPALRFRNKRTRVRWPFKSDSPPPAPARTAGNPAPALFRFEIFFRRPHRLPVTHSRPAR* | 5177 | ATGAGCGGGTCCCCCTTGGAGGACAGAATGAAGAATTGGAAATCATGGCCGTTCTGGAGAGTAGACAAGAAGACGGAAAGTCGGCCTGCCCGGCCCTGCCCCGCCCTGCGCCCTGCGGCAGACAAAAGAACGCGTGTCGCCTGGCCTTTAAGAGCGATTCTCCCCCCGCCCAGCTCGGACCGGGAAACCCGGGCTGCACTACCCCGCGAGATTCCCTTCCGACGCCCGCACCGGCTCTCCGTCCACTCATTCTAGGCCCGCACGGTGA | 5178 |
| | 2 | MALEKDYALEKGTGLRAREGVLRGEPPGEHLLV* | 5179 | CGTCCTGCCGGAAGGACTACGGCGCTAGAGAAGGGACTACGAGCGCCGGGAGGGTCTAGGAGCCCGGGAGGGCGTTGGTGTGA | 5180 |
| | 3 | MLKKS* | 5181 | ATGTTGAAGAAAAGKTAG | 5182 |
| | 4 | MANGWTGSRPGRRNPEL* | 5183 | ATGGCCAATGCTGGACTGGTCTCCGCCCTGGTCGGAGGAATCCGAGCTGTGA | 5184 |
| hsa-mir-26a-1 | 1 | MVTRRPLEPSGGGGGSWGAGPGRLSQSAGPGGGRAQAAAASAPPRRAPPAPPRRPRAALGLRGAGPAGGRRAAHPWTARPSSPR* | 5185 | ATGGTGACGAGGCGGCCGCTGGAGCCGTCGGGGGAGGCGGCGGCTGGGGAGCTGGGCAGCGCTGGCAGCGCCGGGCCCGCCGCGCGCCGCGGGCCCGCCCGCCGCGGCCCGGCGCTGGCCTTGCGGGGAGCAGGGCCGGGAGGACGCGGGCCGCCGCGCGCGCCGCCACCCATGACGGCCCGGCCCATCATCACCAGGTGA | 5186 |
| | 2 | MDGPAHTQVTNPKEDEGRLPGAGEKGEEGRRRPAGGERJTPRAAGVHCRAPAWAWGRGAQGPEGAWVWGAPGGERGCQSACAD* | 5187 | ATGGACGGACCGGCCCATACCCAGGTGACCAACCCAAAGGAGGACGAGGGCCGCGTTGCCGGCGCGGCGGAGAAAGGTGAGGAGCGGCGACGCCCAGCGCCGGGCCGCATGGGCCTGGGGAGCGAGGCGCACCCGCGGCTCACTGCCGAGCGCGCCGGGAGTCGTGGGTGGGGGTGCGCGGGAGGAGAGCGAGGTGCTGCCGACTGA | 5188 |
| | 3 | MGLGEGCTGPGGCVGVGCARRRARLPECVCRLSQCECAGAGGETGSECVCI* | 5189 | ATGGGCCTGGGAGGAGGGTGCACAGGGCCTGGTGGCGGGTGCGTGGGTGTCGTCGCAGAGTGCGTGTGCCGACTGAGCCAGTGTGAGTGTGCCGGAGAGCAGGGGGCTGGCGGAGACTGGGAGCGAGGTGCTGCATCTGA | 5190 |
| | 4 | MCVCTRGQSDCKDMCAPHREVVRL* | 5191 | ATGTGTGTGTGCACACGGACAGCGGACAGCAGCGAGTGATTGTAAGGATATGTGTGCACCTCACAG | 5192 |
| hsa-mir-26a-1 | 1 | MERNVWSLF* | 5193 | ATGGAAAGAAATGTGGTCATTGATTAG | 5194 |
| | 2 | MCGH* | 5195 | ATGTGTGGTCATTGA | 5196 |
| | 3 | MKHWCTVRLR* | 5197 | ATGAAACATTGGTGCACAGTTCGTTTAAGGTAA | 5198 |
| | 4 | MIFVI* | 5199 | ATGATCTTTGTGATTGA | 5200 |
| | 1 | MLDPN* | 5201 | ATGTTGGACCCAAACTGA | 5202 |

Figure 1 (Continued)

| | | | | |
|---|---|---|---|---|
| hsa-mir-26a-2 | 2 | MEHGSHTQARREDALVLTKQGRGSNFPKLCYAPGRGG G* | 5203 | ATGGAACACGGCTCCATCATCACCAGGCGCGAGGAGAAGACGCCTGTGCTCAC CAAGCAAGGTAGGCGGCAGCAGCTTCCCAAAACTTTGCGTCGCCCCCGGCGCGGAG GGGGCTAG | 5204 |
| | 3 | MASDPAWF* | 5205 | ATGGCATCAGACCCGGCGTGGTTCTGA | 5206 |
| | 4 | MCPK* | 5207 | ATGTGTCCAAAATAG | 5208 |
| | 1 | MFASASREGNSML* | 5209 | ATGTTTGCATCGCCTCGCCGGAAGGAAACTCCATGTGTAA | 5210 |
| | 2 | MDSSAVITQISKEEARGPLRGRGKGTGAAGRGPKPGRRGR.REGAGHPRGAAAAAPGGRLSCARSSQPEREQGESLNSEAQRGAGPGAFGALFFARGEFETEAGHERELFGGFLAGIAWCMGAPPPLAPMGLGDGGAEEGAYGPPAETPPHPPPPPPRAAVR* | 5211 | ATGGACAGTCCGGCCGTCATTACTGAGATCAGCAAGGAGGAGGCTCGGGGCCCGCT GCGGGGCAAAGGTACCGGGGCTGCGGGAGGGGCCGAAGCGGGGCCCCTTGGG GCGAGAGAAAGGCCCCGGGATCTTCCCCAGGCGAGCAGGGAGCAGGGAGAGTTGA CCGCCTTAGCTGTGCCCGAAGCTCCAGTCCAGCAAGGAGGGCCTGCGCCCTGCGGCCGG ACTCAGAGAGCCTCAGAGACGCGCGGCGGGAGACCTGAGGCCTTTGGGGCCTCTG TTCGCTCGAGGTGAGGAAACTGAGGCAGGAATAGAGAGGAACTCTTCGGGGGTTT CCTGGCAGGCATTGCTGTGCAGGAGCGCCTATGGGCCTCGCCAATGGGGCT GGAGATGGGGAGCTGAGGAGGGCGCTATGGCCACCGCCTGCTGAGACTCCGCCCC ACCCCACCCCACCCCCGGGCTGCGGTCCGGTAG | 5212 |
| hsa-mir-26b | 2 | MGELRRAPMCHPLRLRPTPHPPPGLRSGRVLGGAEV TAGWGGLEGSPANTQLRSPQTSRHAWRRRPPRRHRED GRHFQESLGARGESRAPSGHAPPRKASPRRGCVPQRG WAGYCGGSVFSFSPCGPQDLDAAPRSAHPRLGLAAPELR ARWKG* | 5213 | ATGGGGGGAGCTGAAGAGGAGGGCGCCTATGGCCCACCGCTGAGACTCCGCCCACCGC CACCCCACCCCCGGGCTGCGGTCCGGTAGGGTCTTGGAGGGGGCGCGAGG CACAGAACTTCGCGTCACGCCTGGGAGTCGTTGGAGGAGATCTCCGCCAACACAGCTACGTTCC CGGCCGCACTTCAAGAGTCGCTTGGGGAGGGCTTGCGGGACCCTCGAGGCACAGAGGA GGCACGCACCACCGCAAAGCCTCGCGCGCCCGACGAGCCTGCGTCCCCAGCGT GGCTGGGCTGCCGGGTGGGGGTCTGCTCCTTTCCCGGTGTCTGGCTCTGCCCCAGCGCAGGAT CTGAGCGCTGCCCCCAGGTCGGAAAGGCTAG AGGGCAAGGTGGAAAGGCTAG | 5214 |
| | 4 | MATGHWFQAAGLHPCLWAQPQ* | 5215 | ATGGCCACTGGACACTGGCCCCAGGCTGCACCGTGCACCCTGCCCCCAGGGCCCA GCCGCAGTGA | 5216 |
| | 1 | MAPFGLFRAQ* | 5217 | ATGGCCCCATTTGGCCTGCCCAGGGCTCAATGA | 5218 |
| | 2 | MRGEIGHASCCSLLVPHGPSRYLCLSSPGAGTEGTARL QLPVWLLHMRKELPCDQRKHLGTWRGGVPKSHYLLCSLSLSPLQVPASGFPARCPPHPCATAGWGSWGWDLLPV TNHIARDFQPTLSSATEDAARGRGREAFKPVPGLRSRA * | 5219 | ATGAGGGGGGAGCTTGGCCATGCAAGTGTGTAGCCTCCTTGTCCGCATGGGCCC TCTAGGTATCTCCCGTGGTGGACTTGGCCTCTCCAGTCGAAGGAAAAGAGCTTCCTGTGATCAAAGG CAGCTCCACGTGTGGTGCCTCTGCATATGAGAAAAAGAGCTTCCTGTGATCAAAGG AAGCATTCTGGGGACCTGAGGGAGGTGTCCCCAAATCTCATTACCTCCTTTGCTCT CTCTCTTTTCTCCCCCTGAGTGGCCAGCCTGCCCGTGCCCCCTCACC CCTGTCCCACGGGCCGGGGATTTGCCAACGACCTGCAGAGCCTCTGCTGTCACCCTGTCACCAATC ACATTGCCAGGGATTCAACGACCTGCAGAGCCTCTGTCACAAATC GACGGGGTGGGGCAGAGAGGATTCAACGACCTGCAGAGCCTCTGTGCCGGG TCCTCGCATATGA | 5220 |
| hsa-mir-27a | 3 | MQVAVASLSRMGPLGISSASPVLGLERRAQLGSSSSPCGG SCI* | 5221 | ATGCAAGTTGCTGTAGCCTCGTTGTCCGCAATGGCCCTCTAGGTATCTCTGCCTC CAGTCGTGGGAACGGAGGGCACAGCTAGGCTCCAGCTTCCAGTCTGTGGTGGC | 5222 |
| | 4 | MGFASCHKSRCQGPTIDPELCHRGCCPGTGWQRGFEA CAWPEEQGLAACEQGPHQVVFTVAKFRPPGPHLLWPC RLSPAAACLPAILLPGLPGLCLPCLLS* | 5223 | ATGGGATTTGCTTCCTGCCACAAATCACATTGCCAGGGATTCCAACCGACCCTGA CTCTGCCACTGAGGATGTCTGCCGGGACAGGGCTGTCGTTGTGAGCAGGGTCCACCAAGTCG TGCCTGGCCTAGTGCAGGAGCAGGGCTTAGTGCTTGTGAGCAGGGTCCACCAAGTCG TGTTCACAGTGGCTAAGTTCCGCCGCCCCAGGCCTCACCCTCGTGCTGCCCTTGCCGCCTT GTCCCCTGCTGCCGCTGTCTGCCATCCTGCCCTGGCGTCTGCCCTGGCCCTGC CTCCCGTGCCTACTGAGCTGA | 5224 |

Figure 1 (Continued)

| | | | | |
|---|---|---|---|---|
| hsa-mir-27a | 1 | MVPWVPGDPAKGLSHGMRFPSPAAQPRLCGTPTCPPPABTARHWEGREAASGGLLSRLRLGLALLQAGRBRRLRRRQGEGAGYYPYLPPGSRGDRK* | 5225 | ATGGTTCCCTGGGTTCCTGGGTGACCCAGCTAAGGGCTTTCTCATGGGATGCGCTTCCCCAGTGCCCCAGCGCCAGCCTAGGCTCTGTGGCACCCTACTTGCCCCCTGCCAGGACAGCGAGGCACTGGAGGGACGGGAGGGGAGGGCGGCCTCAGGGGCCTCTCTCCCGGCTGAGGCTTGGCCCCTGCCGCCCTCTCCGCCCTCAGGGAGGATCGCGGAGGCTTGCGCGCCGCAGGAGGGAGGTGGCCGGTTATTTTACCTCCCTCCAGGCAGCCAGGGGCGACAGGAAGTGA | 5226 |
| | 2 | MGCASPVPQRSLGSVAPLLAPLLPGQRGTTGRDGRRPQGASSPG* | 5227 | ATGGGATGCGCTTCCCAGTGCCTTCCTGCAGGACAGCGAGGCACTGGAGGGACGGGAGGGGACCGGGGCCTCAGGGGCCTCTCCCGGCTGA | 5228 |
| | 3 | MWGARELGTATAGLAAGRERG* | 5229 | ATGTGGGGAGCCAGGGAGCTGGGAACAGCCACAGCTGGACTGGCGGCCGGCCGGGAGCGGGGTTAG | 5230 |
| | 4 | MWVVASLSLIWAPIPSLARGLSDPGQGGGPCPSPQGGPPGPSRVGGKRGRRPLAGPACHRHCLPVGCLLGNLTRPR* | 5231 | ATGTGGGTGGTGGCCTCGCTGTCCTCATCTGGCGCAATCCCCTCGCTGGCTCGAGGGCTCAGATCCTGGGCAGGGCTAGGCTCGACCCCCAGGGAGCCCCAGGGGACCCCAGGTCCAGGAGGTAAGGAGGGGAGCGGCCTCTGCCGCCGCCCCTGCCACCGCCATTGTTTACCCGTCGGCTGCCTCCTAGGAAACTTAACCCGCCGCCGCGGGTAA | 5232 |
| hsa-mir-27b | 1 | MRPRARVDDYTRRVPG* | 5233 | ATGCGCCCCGCGCGTGTGATGACTACACCCGGCGTCCGGCGTAG | 5234 |
| | 2 | MTSRPGACRGSP* | 5235 | ATGACGTCACCCGGCCCGGCTGTGCCGGGTAGCCCGTAG | 5236 |
| | 3 | MAAGTASFRSEGDGEPSLTLTFARPARTRIPSSVLPDSWG* | 5237 | ATGGCGGCGGGGACCAGCATCATTCCGTTCTGAAGGCGACGGGAACCCTCCCTTACCCTCACTTTGTCTCGACCAGCGAGGACCCGCATCCCTCCAGTTCTCCCAGACTCCTGGGCTGA | 5238 |
| | 4 | MNACMGGEGVAQ* | 5239 | ATGAACGCCATGCATGGCGCGGAGGGTGCACAGTAA | 5240 |
| hsa-mir-27b | 1 | MPARAGGRPAGGGAAAPLRQAPPLGARPPARAAAQAPRPPAPRLR* | 5241 | ATGCCGGCCAGGGCCGGAGGGCGACCTGCGGAGGCGGCGGCCGCTATACCTTTAAGGCAGGCCCCCCGCCCCTCGGTGCCGCCCCGCCGCCGCGCCCCAGGCCCCGCCCCGCGCCCGCCGCGCCCCAGGCCCCGCCCCGCGCCCGCCGCCTGAGGTGA | 5242 |
| | 2 | MRTPGGRRARAPAPPLRPPPRARYGAGTPS* | 5243 | ATGCGGACCCCTGGGCGGCGCCGCCGCCTGCCGCCGCCGCCGCCGCCGCCGCCGCCGCCGCCGCCGCCGCCGCCGCCGCCGCCGCCGAGGTACGGGGCGGCACGCCGAGGTAG | 5244 |
| | 3 | MAVRTLSPSLKCCGF* | 5245 | ATGGCCGTCAGGACCCTGCCCTCTTGAAATGCTGTGGTTTTGA | 5246 |
| | 4 | MLWFLNLRSRNGLE* | 5247 | ATGCTGTGGTTTTTGAACCTCAGGTCACGAAATGGATTGGAGTGA | 5248 |
| hsa-mir-28 | 1 | MVMGHVAGSAGHFYLGVWTAAFPGEFYPLQWDFKTRSA* | 5249 | ATGGTGATGGGACACGTTGCTGGGAGTGCTGGTCACTTTTATTTGGGGTGTGGACAGCTGCTTTCCCAGGGAGTACTTCTTACAGTGGGATTTCAAGACAAGATCGGCCTGA | 5250 |
| | 2 | MIKAKATSWKGCRDVCGHVGRGSFSLKTVMVGFKSMQNVDV* | 5251 | ATGATTAAGGCTAAAGCAACAAGCTGGAAGGGATGTCGGGATGTCTGTGGACATGTAGGGAGGGGTAGTTTAGCTTGAAAACAGTTATGGTGGGATTTAAGAGTATGCAAAATGTTGATGTGTAG | 5252 |
| | 3 | MSGCLWTCREG* | 5253 | ATGTCGGGATGTCTGTGGACATGTAGGGAGGGGTAG | 5254 |
| | 4 | MSVDM* | 5255 | ATGTCTGTGGACATGTAG | 5256 |
| hsa-mir-296 | 1 | MIGLPRALR* | 5257 | ATGATTGGCTTACCTCGGCTCTTGCCTAG | 5258 |
| | 2 | MRSEETLSAKGKREKDIQKQGYAEAGEKRPFAPPGQGPRLEPGRPREHLPRVSSAPLAAEFPGAGTTRVCEQRRKFFARAMAQITTQPVPKYKYTVGG* | 5259 | ATGAGAAGTGAGGAAACGCTTAGCGCAAAAGGGAAAAGAGAGAAAGACATACAGAAACAAGGTTACGCGGAGGCGGTGAAAAGCCCGCCTTCCCCGCGTTCCTGCCCAAGGGCCCGCTTATTTCCGGGAGGCCCGCGGAGCGACCTCCTGTCCTCCGCACCGCTTGCGCGCAGAGGCGCCGGGCGCAGTTACCACCAGAGTGTGAACAGGCGAAAGTTTTTTGCCCGGGCATGGCGCAAACCACACAGCCGTTCCAAGTACAAGTACACAGTCGCGGGGTAA | 5260 |
| | 3 | MHRRITQNMDTNTHQRQAV* | 5261 | ATGCACAGGCGCAACACAGAATATGGACACCAACACACCAACGACAAGCTGTCTGA | 5262 |

Figure 1 (Continued)

| | | | | |
|---|---|---|---|---|
| | 4 | MTPAHRGPHQPSQGSPGAPGPLPGSSWLT* | 5263 | ATGACCCCAGTCCACCGTGGACCCCACCAGCTAGCCAGGGGAGTCCGGGGCCCC GGGGCCCCTCCCCGGTCCAGTTCCTGGCTCACCTGA | 5264 |
| | 1 | MIGLPRALR* | 5265 | ATGATTGGCTTACCTCGGGCTCTTCGCTAG | 5266 |
| hsa-mir-298 | 2 | MRSEETLSAKGKREKDIQKQGYAEAGEKRFPAPPGQGP RLFPGRPRHLJPRVSSAPLAAERPGAGTTRVCEQRKFFAR AMAQITTQPVPKYKYTVGG* | 5267 | ATGAGAAGTGAGGAAACGCTTAGCGCAAAAGGAAAAAGAGAGAAAGATACAGA AACAAGGTTACGCGGAGGCGGCGAAAAGGGATTCCCGCTCCCCAGGCCAAGGG CCCGCTTATTTCCCGGGAGGCCCCGCACTTCCCGCGTGTTCCTCCGACCGCTT GCCGCAGAGCGCATGCGCAAACCACAACAGCCCGTTCCAAGTGCCAACAGCGAAAGTTTT TGCCCGGCCATGGCGCAAACCACAACAGCCCGTTCCAAGTACAAGTACACAG TCGGCGGGTAA | 5268 |
| | 3 | MHRRTQNMDTNTHQRQAV* | 5269 | ATGCACAGGCGAAACACAGAATATGGACACCAACACCACCAACGACAAGCTGTCTGA | 5270 |
| | 4 | MTPAHRGPHQPSQGSPGAPGPLPGSSWLT* | 5271 | ATGACCCCAGCCACCGTGGACCCCACCAGCTAGCCAGGGAGTCCGGGGCCCC GGGGCCCCTCCCCGGTCAGTTCCTGGCTCACCTGA | 5272 |
| | 1 | MDQGVEGGGCGPGVGRQSACSL* | 5273 | ATGGACCAGGGGGTAGAGGGGGTGGGTGGGACCTGGGGTCGGGCGCCAGTCAG CTTGCACGCTATGA | 5274 |
| hsa-mir-299 | 2 | MKDGKEGYRDRGRVGLRIARAAWHTVLG* | 5275 | ATGAAGGACGGAAAGGAGGGCTACAGAGATAGGGAGAGTGGGGCTGAGGATAG CCAGAGGGGCTTGGCACCAGTTTAGGGTAA | 5276 |
| | 3 | MTEPVTPGSSFKACLMGDSVVPVTKLGPESQGRAHQV AALP* | 5277 | ATGACTGAGCCGGTCACTCCAGGGTCTCCTTCAAAGCGTGTCTAATGGAGACAGC GTTGTCCCAGTAACCAAATTGGGACCAGAGTCCCAGGGAAGGGCTCATCAGGTGGC CGCTCTGCCTTGA | 5278 |
| | 4 | MILFPLDPAPLVPFSL* | 5279 | ATGATTCTCTTCCCTCGATCAGCGCCTCTAGTTCCTTTCACTTTGA | 5280 |
| | 1 | MCHTVFCNSSPCPSSLACIDPLKAMIRAGRRGSRL* | 5281 | ATGTGTCATACTGTGTTCTGTAATTCCTCTTTTGTCCATCTTCCCTGGCTTGCATTG ACCCCTTAAAAGCCATGATTAGGGCCGGGGCCGTGGCCTGAGAGAATAA | 5282 |
| hsa-mir-29a | 2 | MISVYFWINTRTHDRE* | 5283 | ATGATCAGTGTTTACTTTTGGATAAACACCTGACACATGATAGAGAATAA | 5284 |
| | 3 | MIENKCLRERMDLLGNTKN* | 5285 | ATGATAGAGAATAAATGTTTGAGAGAGAACCTGACAAATGACCTACTGGGTAACACCAAAAA CTAA | 5286 |
| | 4 | MFEREK* | 5287 | ATGTTTGAGAGAGAGAAATGA | 5288 |
| | 1 | MCHTVFCNSSPCPSSLACIDPLKAMIRAGRRGSRL* | 5289 | ATGTGTCATACTGTGTTCTGTAATTCCTCTTTTGTCCATCTTCCCTGCTTGCATTG ACCCCTTAAAAGCCATGGCCGGGGCCGTGGCCTCACGCCTGTAA | 5290 |
| hsa-mir-29b-1 | 2 | MISVYFWINTRTHDRE* | 5291 | ATGATCAGTGTTTACTTTTGGATAAACACCTGACACATGATAGAGAATAA | 5292 |
| | 3 | MIENKCLRERMDLLGNTKN* | 5293 | ATGATAGAGAATAAATGTTTGAGAGAGAAATGACCTACTGGGTAACACCAAAAA CTAA | 5294 |
| | 4 | MFEREK* | 5295 | ATGTTTGAGAGAGAGAAATGA | 5296 |
| | 1 | MVTLALGAFLHTSPTQFPQRLL* | 5297 | ATGGTAACTCTGGCTCTAGGAGCATTCCTTCATACCTCCCCGACACAGTTCCCAG AGGCTGTATAA | 5298 |
| hsa-mir-29b-2 | 2 | MVLNLC* | 5299 | ATGGTCTTAAACTTATGTTGA | 5300 |
| | 3 | MLRQLH* | 5301 | ATGTTGAGACAACTGCACTGA | 5302 |
| | 4 | MAGAV* | 5303 | ATGGCAGGCGCTGTGTGA | 5304 |
| | 1 | MVTLALGAFLHTSPTQFPQRLL* | 5305 | ATGGTAACTCTGGCTCTAGGAGCATTCCTTCATACCTCCCCGACACAGTTCCCAG AGGCTGTATAA | 5306 |
| hsa-mir-29c | 2 | MVLNLC* | 5307 | ATGGTCTTAAACTTATGTTGA | 5308 |
| | 3 | MLRQLH* | 5309 | ATGTTGAGACAACTGCACTGA | 5310 |
| | 4 | MAGAV* | 5311 | ATGGCAGGCGCTGTGTGA | 5312 |
| | 1 | MDQGVEGGGCGPGVGRQSACSL* | 5313 | ATGGACCAGGGGGTAGAGGGAGGTGGGTGGGACCTGGGGTCGGGCCAGTCAG CTTTGCACGCTATGA | 5314 |

Figure 1 (Continued)

| | | | | | |
|---|---|---|---|---|---|
| hsa-mir-300 | 2 | MKDGKEGYRDRGRVGLRIARAAWHTVLG* | 5315 | ATGAAGGACGGAAAGGAGGGCTACAGAGATAGGGAAGAGTGGGCTGAGGATAG CCAGAGCGGCTTGGCACACAGTTTTAGGGTAA | 5316 |
| | 3 | MTEPVTPGSSFKACLMGDSVVPVTKLGPESQGRAHQV AALP* | 5317 | ATGACTGAGCCGGTCACTCCAGGGTCTTCCTTCAAAGCGTGTCTAATGGAGAGACGC GTTGTCCCAGTAACCAAATTGGGACCAGAGTCCCAGGGAAGGGCTCATCAGTGBGC CGCTCTGCCTTGA | 5318 |
| | 4 | MILFHLDPAPLVPFSL* | 5319 | ATGATTCTTCTCCTCTGGATCCAGCCGCCCCTCTAGTCCTTTCACTTTGA | 5320 |
| | 1 | MGGSRWNGGANECEMLSDSCPMEALRASTACGHLSAAA VCGMSTHQHGGGGR* | 5321 | ATGGGCAGGAGCCGGTGGAACGGGGCTAATGAGTCGAGATGTTGAGTGACA GCTGTCCCAATGGAGCGCCCTCCGTGCAATGACACTGCGGCTTGCGCCGCCGCGG TCTGCGGAATGTCAACTATTCAACATGGAGGCGGAGGTCGATAA | 5322 |
| hsa-mir-301a | 2 | MSARC* | 5323 | ATGAGTGCGAGATGTTGA | 5324 |
| | 3 | MEAEVDKLELMVSAK* | 5325 | ATGGAGCGCGAGGTCGATAAGCTGGAACTGATGGTGAGTGCAAAGTGA | 5326 |
| | 4 | MASEVGHMLESPETPGGGGWTRVEFPPPAPKGAATVW CLNRLG* | 5327 | ATGGCCTCTGAGGTGGGCACATTTGGAGTCGCCGGAAACTCCGGCGGCGGAGG CTGACCAGAGTCCAGTTCCCTCCTCGCCAAAGGGAGCGCCCACCGTCTGGTG TCTAAACCGCTCGGGTAA | 5328 |
| | 1 | MPGAGPTIYTASHLLLATASPMGQV* | 5329 | ATGCCAGGTGCTGGCCAACAATTTACACCAGCATCTCATTGCTGCAACAGCC AGCCCTATGGGGCAGGTTGA | 5330 |
| | 2 | MNASPQSGSQSRRNQSLHFRSPYLPQIQKTTGPRTRSP* | 5331 | ATGAATGCTTCTCCGCAAAGTGGATCAATCACGACGAAGAAACCAAAGTTACACTTC CGTTCCCCATATCTCCCACAGATCCAAAAGACCACGGGGCCAGGACCCGGTCTCCA TAG | 5332 |
| hsa-mir-301b | 3 | MLLRKVDHNHEETKAYTSVPHSHRSKRPRGPGPGLHS PAIPGGFQESLTRVLPGDPGWLSWEGGYPSL* | 5333 | ATGCTTCTCGCAAGTGGATCACAATCACGAAGAAACCAAAGTTACACTTCCGTT CCCCATATCTCCCACAGATCCAAAAGACCACAGGGGCCCAGGACCCGGTCTCCATAGC CCAGCCCATACCCGGGGGTTTCAGGAGAGTCGCTCACTGGGTCCTGCCGGGCGATCCG GGGTGGTTGGAGGGGGCTACCCCAGTTGTAA | 5334 |
| | 4 | MHXKAARGRVHSRLGGGSGISTCGSRPPPLWARAWRPSP GPQALLSVSLENSQRLERKGQSSF* | 5335 | ATGCATAACAAAGCAGCGCGGCAGCGTCCACTGTGGGCCTGCGGCCTGCCCCTCACC GGGCTTCCAAGCGCTCTGTCGGTGCTAGAAAACTCGAGAGATTGGAGCTGA GAAAAGGCGGCAAAGTTCTTTGA | 5336 |
| | 1 | MVLAVNIDICHLQKKKKGSRPTQDHTFPES* | 5337 | ATGGTTTTAGCTGTTAACATCGATATGTATACTTCAAAAAAAAAAGGATCC AGACCCACCCAGGATCATACATTCCCTGAGAGCTGA | 5338 |
| hsa-mir-302a | 2 | MPFCFLSPQL* | 5339 | ATGCCATTTTGTTTCTTCTGA | 5340 |
| | 3 | MLGGLPSTLTWKCFL* | 5341 | ATGTTCGGTGGGCTCCCTCAACTTAAACATGGAAGTGCTTCTGTTTAG | 5342 |
| | 4 | MEVLSVTLKVSASMF* | 5343 | ATGGAAGTGCTTCTGTGATCTTAAACATGAAGTGCTTCCATGTTTAG | 5344 |
| | 1 | MVLAVNIDICHLQKKKKKGSRPTQDHTFPES* | 5345 | ATGGTTTTAGCTGTTAACATCGATACATTCCTATACTTCAAAAAAAAAAAGGATCC AGACCCACCCAGGATCATACATTCCCTGAGAGCTGA | 5346 |
| hsa-mir-302b | 2 | MPFCFLSPQL* | 5347 | ATGCCATTTTGTTTCTTCTCCTCAGTCTAA | 5348 |
| | 3 | MLGGLPSTLTWKCFL* | 5349 | ATGTTCGGTGGGCTCCCTCAACTTAACATGAAGTGCTTCTGTGA | 5350 |
| | 4 | MEVLSVTLKVSASMF* | 5351 | ATGGAAGTGCTTCTGTGACTTAAACATGAAGTGCTTCCATGTTTAG | 5352 |
| | 1 | MVLAVNIDICHLQKKKKGSRPTQDHTFPES* | 5353 | ATGGTTTTAGCTGTTAACATTGACATCGTATACTTCAAAAAAAAAAGGATCC AGACCCACCCAGGATCATACATTCCCTGAGAGCTGA | 5354 |
| hsa-mir-302c | 2 | MPFCFLSPQL* | 5355 | ATGCCATTTTGTTTCTTCTCCTCAGCTCTAA | 5356 |
| | 3 | MLGGLPSTLTWKCFL* | 5357 | ATGTTGGGTGGGCTCCCTCAACTTTAACATGAAGTGCTTCTGTGA | 5358 |
| | 4 | MEVLSVTLKVSASMF* | 5359 | ATGGAAGTGCTTCTGTGACTTTAAACATGAAGTGCTTCCATGTTTAG | 5360 |
| hsa-mir-302d | 1 | MVLAVNIDICHLQKKKKGSRPTQDHTFPES* | 5361 | ATGGTTTTAGCTGTTAACATTGACATCGTATACTTCAAAAAAAAAAAGGATCC AGACCCACCCAGGATCATACATTCCCTGAGAGCTGA | 5362 |
| | 2 | MPFCFLSPQL* | 5363 | ATGCCATTTTGTTTCTTCTCCTCAGTCTGA | 5364 |

Figure 1 (Continued)

| | | | | | |
|---|---|---|---|---|---|
| | 3 | MLRGLPSTLTWKCFL* | 5365 | ATGTTGGTGGGCTCCCTTCAACTTTAACATGGAAGTGTTTCTGTGA | 5366 |
| | 4 | MEVLSVTLKVSASMF* | 5367 | ATGGAAGTGCTTTCTGTGACTTTAAAAGTAAGTGCTTCATGTTTAG | 5368 |
| hsa-mir-30a | 1 | MSSDFSCTDGEAVLSYGQPPALCGYEAFKCGKSRLRSAEAPSTHWI* | 5369 | ATGTCAAGTGACTTTAGCTGCACAGATGGTGAAGCTGTGCTTCTGTGGGCAGCCACCAGCCCTGTGCTATGGCTATGAAGCATGAAGCATTTAGTACACATTGGATTTAA | 5370 |
| | 2 | MVKLCFLWGSHQPCVAMKHLNVASPD* | 5371 | ATGGTGAAGCTGTGCTTTCTGTGGGGCAGCCACCAGCCCTGTGCTATGAAGCATTTAAATGCACAAGTCCAGATTGA | 5372 |
| | 3 | MWQVQHICRSI* | 5373 | ATGTGGCAAGTCCAAGTTGAGATCTCAGAAGCATTTAG | 5374 |
| | 4 | MKKYKISH* | 5375 | ATGAAAAATACAAAATATCTCATTAA | 5376 |
| | 1 | MYTRAHSRSPSDTLEGKVKLKAREQRDRREPLPPPRAMTDAAEAAFSVRTPFPSSRRAPCPPPLARPSPWRWRVPAPSPPAAPGAPRARGAGRWEREGGRGRGPAASSPDPRPRAR* | 5377 | ATGTACACGCGCGCGCACGCACTGGAGGGAAAGGTCAAACTAAAGGCGAGCGGAGAGACCGGAGGAGCCTGCGCCGCGGATCCCAGCTCTCGCCCGACGCGCCCCTGCCCCCCGCCGGGCTTCTCAGTGCGACGCGCGACCATCCCAGTCTCGCGCGCCCCCCTCTCCCCGGCCGCTCAGCGCGCCTCAGCCCCGGCCTCCGGCGCCGGCGCCTGGGAGGAGCGTGGGGCGCGGCCGCCCGGCCTCCTCCGCCCGACCCCCGACCCCGGGCCAGGTGA | 5378 |
| hsa-mir-30b | 2 | MGRAAGIRWAPPRGS* | 5379 | ATGGGCGGCGCCGGGATCCGCAGGTGGCCCCTCCCGGGCTCGTGA | 5380 |
| | 3 | MFIRQLQETLPSGRGALLFAGASESCGPHSKTRVKPGWTGRE* | 5381 | ATGTTTATCCGGCAGTTGCAAGAAACTCTGCCCTCGGACGAGGGCGCTTGCTTTTTGCCGGGCGCGAAAGTGCGGATTTGCACAGCAAAACTCGGGTGAAGCCAGGGCTGGACCGGCGGGAGTGA | 5382 |
| | 4 | MGTRDERIRLCVAPGHDVCTLLCQCLMFVAYGYPRTK* | 5383 | ATGGGGACCAGAGATGAACGAATCCGCCTGTGTGCCCCTGGTCATGATGTGTGCACGTTGCTATGCAGTGTTTAATGTTTGCTTATGGTTATTTAGGACTAAATGA | 5384 |
| | 1 | MLCSCLARCCRRRARGVRVPRPGPRAPSHWRKATAGGLARDWSVAGRPRTWHLIGRASSGLGGDEGI* | 5385 | ATGTTGTGTCTCTGCCTGGCCCGCTGTTGCCGCCGCCGCGCTCGTGGGGTCGTGTCCTCCGGCCCGCCGATTGCCCATTGGCCGCCGCGGGACGCCTCCAGCCTCGTGTGAGTCCGTCAGGCCTCGGATTGCGTGATGCCGGGCAGCCCGCGCTCCGTTCTAGGGGTGATGAAGGAATCTGA | 5386 |
| | 2 | MKESEAAGMRASWARAAGAMTPCGAGVGLRREGEPRGFKGEERVMAWQVLWG* | 5387 | ATGAAGGAATCTGAGGCTGCAGGCATGCGCGCGTCCTGGGCTAGGGCGGGCGCAATGACCCCCTGCGGCGCAGGCGTGGGGTTGCGGCGAGAGGGCGAGCCTAGAGGCTTTAAGGGCGAAGAGAGGGTGATGGCCTGGCAGGTACTTTGGGGTAG | 5388 |
| hsa-mir-30c-1 | 3 | MAWEWGTLTFRGAFPGTCMAAQDWGVQALRVPGLETPKPK* | 5389 | ATGGCCTGGGAATGGGGCACTCTGACTTTCAGAGGTGCTTTCCTGGCACATGCATGGCCGCCCAAGATTGGGGTGTGCAGGCCCTCAGGTTCCAGGCTTGGAAACACCGAAACCCAAGTGA | 5390 |
| | 4 | MGDTHFQRCFSWYMHGPRLGCAGPQGSRLGNTETQVTG* | 5391 | ATGGGGGACACTCACTTTCAGAGGTGCTTTTCCTGGTACATGCATGGCCCAAGATTGGGTGTGCAGGCCCTCAGGGTTCCAGGCTTGGAAACACCGAAACCCAAGTGACAGGCTGA | 5392 |
| | 1 | MANSLLGKGRTAVRVFSGVDIPDSCFCISCCLLPPPSFGG* | 5393 | ATGGCGAATAGTTGTTGGGGGAAAGGGACGACAGCTGTTCGGGTTTTCAGTGAGTGGACATTCCAGACTCATGTTTCGTGCATCTCCTGTCCCTTTGTTTCCTCCGTCCTTTGGGGGGTAGGGGTATAG | 5394 |
| hsa-mir-30c-1 | 2 | MFLHLLPFVSSVLWGVGIGVT* | 5395 | ATGTTTCTGCATCTCCTGCCTTTGTTTCCGTCCTTGGGGGTAGGGATAGGAGTGACTTAA | 5396 |
| | 3 | MQFPVSLILCFVLK* | 5397 | ATGCAGTTCCCGGTAAGTTTAATTCTTGTTTGTTGAAATGA | 5398 |
| | 4 | MIETV* | 5399 | ATGATAGAAACTGTTTAG | 5400 |
| | 1 | MSSDFSCTDGEAVLSYGQPPALCGYEAFKCGKSRLRSAEAPSTHWI* | 5401 | ATGTCAAGTGACTTTAGCTGCACAGATGGTGAAGCTGTGCTTTCTGTGGGCAGCCACCAGCCCTGTGCTATGGCTATGAAGCATTTAAATGCACAAGTCCAGATTGA... GAAGCATTTAAATGCACAAGTCCAGATTGA | 5402 |

Figure 1 (Continued)

| | | | | | |
|---|---|---|---|---|---|
| hsa-mir-30c-2 | 2 | MVKLCFLWG3HQPCVAMKHLNVASPD* | 5403 | ATGGTGAAGCTGTGCTTTCTGTGGGGCAGCCACCAGCCCTGTGTGGCTATGAAGCATTTAAATGTGGCAAGTCCAGATTGA | 5404 |
| | 3 | MWQVQHEICRSI* | 5405 | ATGTGGCAAGTCCAGATTGAGATCTGCAGAAGCATTTAG | 5406 |
| | 4 | MKKYKISH* | 5407 | ATGAAAAATACAAAATATCTCATTAA | 5408 |
| | 1 | MAYTRAHSRSPSDTLEGKVKLKAREQRDRREPLPPPRAMTDAAEAAFSVRTPFIPSSRRAPCPPPLARPSPWRWRVPAPSPPAAPGAPRARGAGRWEREGGRKGGPAASSPDPRPRAR* | 5409 | ATGTACACGCGCGGCGAGGAGCGAGGAGAGACCCTCCTCAGACACACTGGAGGGAAAGGTCAAACTAAAGGCGAGGAGGCGGCGGACCGGAGGAGGCCTGCCCGCCGCGATCCCAGCTCTATGACGGACGGCGACGGCGGCGCTGCTCGTCAGTGCGAGCACCCTTCACCTGGCGCTGGCGCTGCGCCCGCGCCCCTCGCCCGCCGCCTCCAGCGCGCGTCGGCGGCCGGGCGGCCGGCCCCTCTCCCCCGCCGACCGGCCCCTCGCGGGCGTGGGGGCCTGGGAGCGGGAGGTGGGGGCCGCCGGCGCCTCCTCGCCCGACCCCGACCCCGGGCCAGGTGA | 5410 |
| | 2 | MGRAAGGRWAPPRGS* | 5411 | ATGGGCGCGGCGGGCGGAGGCAGGTGGCCCCTCCCGGGCTGTGA | 5412 |
| | 3 | MFIRQLQFTLPSGRGALLFAGASESGGFHSKTRVKPGWTGRE* | 5413 | ATGTTTATCCGCAGTTGCAAGAAACTCTGCCTCTCGGAACGGAGCGCCTTGCTTTTGCCGGGGCCAGCGAAAGTGGCGAGTTCACAGCAAAACTCGGTGAAGCCAGGCTGAGCGGCCGGAGTGA | 5414 |
| | 4 | MGTRIDERJRLLCYAPGHDVCTLLCQCLMFVAYGYPRTK* | 5415 | ATGGGGACCAGAGATGAACAGAATCCGCCTGTGTGTAGCACCAGGCATGATGTGTGCACGTTGCTATGCCAGTGTTTAATGTTTGCTTATGGTATTTTAGGACTAAATGA | 5416 |
| hsa-mir-30d | 1 | MLCSCLARCCRRRARGVRVPRRPGPRAFSHWRKATAGGLARDWSVAGRPRJWHLIGRASSGLGGDEGI* | 5417 | ATGTTGTGCTCTTGCCTGGCCCGCTGCTGTCGCCGCCGCGCTCGTGTGGTCCGTGTCCTCGCGGCCGTCCCCATTGGCGAAGCGACGGCGGGGGGGCTCGCTCTGATTGGTCGTGATGCGCCGGACCTGGCACCTTATTGGACGCGCCAGTCCGGTCTAGGGGGTGATGAAGGAATCTGA | 5418 |
| | 2 | MKRESEAAGMRASWARAAGAMTPCGAGVGLRREGEPRGFKGEERVMAWQVLWG* | 5419 | ATGAAGGAATCTGAGGCTGCGGGCATGCGGAGCTGGGCCAGGGCGGCTGCGGGAGCTAGGGCGGAGCCTAGAGGCTGGGTTCGGGAATGGGAGGAATGGAAAGGGGGAGGGGTTGAATGGCCTGGCAGGTGATGGCCTGGCAGGGTACTTTGGGGGTAG | 5420 |
| | 3 | MAWEWGTLTFRGAFPGTCMAQDWGVQALRVPGLETPKPK* | 5421 | ATGGCCTGGGAATGGGGGACACTCACTTTCAGAGGTGCTTTTCTGGTACATGCAAGATTGTGCCCAAGATGGGGGTGTGCAGGCTTCAGGGTTCAGGGCTTGAAAACACCGAAACCCAAGTGA | 5422 |
| | 4 | MGDTHFQRCFSWYMHGPRLGCAGPQGSRLGNTETQVTG* | 5423 | ATGGGGACTCACTTTCAGAGATGCTTTTCCTGGTACATGCACGGCCCAAGATTGGGGTGTGCAGGCCCTGCAGGTTCAGGGTTCAGGGCTTGGTACATGCAATGGCATGCGGAAACACCCAAGTGACAGGCTGA | 5424 |
| hsa-mir-30e | 1 | MAANSLLGGGRTAVRVFSGVDIPDSCFCISCCLLFPPSFGG* | 5425 | ATGGCGAATAGTTCCTGCATCCTCCGCTGCCTTGTTTCCGTCTTGGAGGACAGCTGTTCGGGTTTCAGTGGAGTGGACATTCCAGACTCATGTTTCTGCATCCTGCCTTTGTTTCCGTCCGTCCTTTGGGGGTAG | 5426 |
| | 2 | MFLHLLLPFVSSVLWGVGIGVT* | 5427 | ATGTTTCTGCATCCTGCCTTTGTCCGTCCTTGGGGTAGGGATAGGAGTGACTTAA | 5428 |
| | 3 | MQFPVSLILCFVLK* | 5429 | ATGCAGTTCCGGTAAGTTAATTCTTGTTTTGTGTGTTGAAATGA | 5430 |
| | 4 | MIETV* | 5431 | ATGATAGAAACTGTTTAG | 5432 |
| hsa-mir-31 | 1 | MGRKCGNVHSRAPLSGTRAASQEELGEQLRPVHMLGRRQGLAGSTSGAWRRKTRVPGRGAEAGWGTAWSRARAGRRCSVSRLVWGAGGGKRPLRVRLGEAGRRFCPPTRTR* | 5433 | ATGGGGCGAAGGTGCGGGAACGTCACTCCCGCGAGCCGCCCCTCTGGGAGACCAGGGCCGCCAGGGAGGCAGCTGGGCTGGGAGGGCGCTGGGCCCAGGGCTCGCAGTGGGAGCTCGCACTGGGAGGAGAAGGAAGAGCGCGTGCCCGCCGCCGCCGGACCCGCCGAGCTGGAGGCGGGTTCCGTGACGTGGGCCTGGGGGCCGGGAAGCGGCCCCTTCGTGTGCGCTTGGGGCAGGGCCGAGGGCGGCCCGACCCGACCCGGAGGTAA | 5434 |

Figure 1 (Continued)

| | | | | |
|---|---|---|---|---|
| | 2 | MRRGVRRIPERRPPLALRGTAASSCPNLRSSSWPEVTGS LSVPKPRGRSCVCP* | 5435 | ATGCGCCGCGGGGTCCGGCGCATCCCGGAGCGCCGGCCGCCTTGGCTCTTCCGG AACCGCCGCCTCTGTCCCTAAACTCGAGGAAGGAGTTGTGTGTCAGTGA | 5436 |
| | 3 | MSYLAFSAFIQRCLS* | 5437 | ATGAGCGTGTTGGCGAGAGCGCTTTACCACTAAATTACTGTCACTTTGA | 5438 |
| | 4 | MFELSSFYHLKLLSL* | 5439 | ATGTTTGAGTTGAGCTCATTTTACCACTAAATTACTGTCACTTTAA | 5440 |
| hsa-mir-32 | 1 | MADGGGPKDAPSLRSSPGPAPRVPRAVGPSGGGETPR TAALALRFDKPIKQAFYNTGAVLPVCLCCGAAVLVYFL EAFLRPLLWAVLCGTFLHPFKSSLTRLGRHWQRLJ3RA HTPIVLAALLPLCFVDYGVEALGEQALRRRLLLLGA GGPLLYGLYCLGSYLGVQVLLVHAATLICRGLDYFSSL WVSERQSSAPYPRPWSRRSGVQSCSCSSRCRGDEGPHLC CSDRPSPLSFSHLRNLADILPKRGRA* | 5441 | ATGGCCGACGGCGGGCCCAAGGACGCGCCCTAAGGACCTGCGAGCTCTCCGGGCC GGGCCGCCGGGGTCCGCGGAGCCAGTGCGCGCGGCCCAGTGCGGGAGACCCGC GAACCGGCGGCGCTGGCGCTGCGCTTCGACAAGCCCATTAAGCAGGCCTTCTACAACA CCGGGGCCGTGCTGCCGGTGTGCCTGTGCTGCGGGGCGGCCGTGCTCGTGTACTTCA TCCTGGAGGCCTTCAAGAGCTCCTGCGGCTTTGGGCTGTCCGTGCTGTGTCGGGCCACTTTCTGC ACCCCTTCAAGAGCTCGACGGCCTGACGCGCCTCGGCCGCACTGGCCAGCGCGTGCACC GCGCACACGCCATCCGCCGCGGCAGTCGCCGCGTGCTGCCGCGCGTCCGTGACT CTCGGCCGCGAGGCCTGGAGTGCGTACGGCCTACGCCTCGCAGCTACTTGGG GTGCAGGTGCTGCTGGTGCACGCTCATCTGCGCCGGGGCTGGACTACTTC AGCAGCCTGTGTGGGGTGCAATCCTGCAGCTGTTCCTCCGCCCGTTCCTTCCACCTCAGGAATTT CACACCTGTGTCTGAGAGCTGGACGTGCTGGCGAGGGCGACGGCGCG GGGCGGACATTCTTCAAAAGGGGCGCGGCGTGA | 5442 |
| | 2 | MRHFSAPLQELADAPGPPLAAAPRAHRPGRAAPA ALL.RRL RRGPGRAGAAPPPAPAARRRRRPAPVRPLLPR QLLGRAGAAGARCHAHLPRAGLLQQPVGE* | 5443 | ATGGGCACTTTTCTGCACCGCGGCTGCTGACGCGCCTCGGCCGCGACTG GCTCAGGCCTCGTCGTCCTGACTACGGCGTTGGAGGCTGCTGCGGCCGGGAGGAAGCCGGCCGGCGCCGG GCTCTGCTTCGTCGCTCCTCGCCGCCGGCGCGGGCCGGGGCGCGCTGGCGGCGCCGAG GCCGCAGCTACTGGGCGGCAGGGCGCTGGTGCAGGCCTCGTACGGCCTCTACGCC TCGGCAGCTACTGGACTACTTCAGCAGCCTGGGTGAGTGA | 5444 |
| | 3 | MAVGLGFTSGWRGRGCGHPQFCASECQSWKGP* | 5445 | ATGGCAGTGGGGCTTGGTTTACTTCTGGTTGGAGAGGGCGGGGTGCTTCGRGCCA CCCTCAGTTCTGCCATCTGAATGTCAGAGCTGGAAGGGACTTAG | 5446 |
| | 4 | MSELEGTLEILGQLAHLQIGKVTSYQARAT* | 5447 | GGAAAGGTGACCTCTTACCAGGCTAGGCTACTTAG | 5448 |
| hsa-mir-320 | 1 | MGEQL* | 5449 | ATGGGGGAACAGCTTAG | 5450 |
| | 2 | MDCHHNFPRQS* | 5451 | ATGGACTGTCACCACAATTTCCAAGGCAAGTTAG | 5452 |
| | 3 | MAGRCGSCL* | 5453 | ATGGCTGGCGCTTGTGGCTCATGCGTAA | 5454 |
| | 4 | MPVIPALWEAKVGGSRGQEFKISLAKMVKPVSTKNYKK* | 5455 | ATGCCTGTAATCCAGCACTTGGAGGCCAAGGTGGGTGGATCACGAGGTCAGGA GTTCAAGATCAGCTGCCAAGATGGTGAAACCGTCTACTAAAACTACAAAAA GTAA | 5456 |
| hsa-mir-322 | 1 | MRQMSNCLYLTLFVYLQK* | 5457 | ATGATTCAGATGTCAATTGCCTACCTTATTGTCTACTTGCAGAAGTAA | 5458 |
| | 2 | MVKL* | 5459 | ATGGTGAAGTTATAA | 5460 |
| | 3 | MVQNVRRCYTPSWGR* | 5461 | ATGGTTCAAAACGTGAGGCGCTGCTATACCCCTCGTGGGAAGGTAG | 5462 |
| | 4 | MMLHFGTPPPCSGRM* | 5463 | ATGATGCTTCATTTTGGCACCCCTTCCTGCTCAGGTAGAATGTAA | 5464 |
| hsa-mir-323 | 1 | MDQGIVEGGGGCGPGVGRQSACSL* | 5465 | ATGGACCAGGGGGTAGAGGGGTGGGTCCAGGAGGGCGGGCCCAGTCAG CTTGCAGCCTATGA | 5466 |
| | 2 | MKDGKEGYRIDRGRVGLRIARAAWHTVLG* | 5467 | ATGAAGGACGGAAAGGAGGGCTACAGAGATAGGGGAAGAGTGGGGCTGAGGATAG CCAGAGCGGCTGGCACACAGTTTAGGGTAA | 5468 |

Figure 1 (Continued)

| | | Protein | SEQ ID | Nucleotide | SEQ ID |
|---|---|---|---|---|---|
| | 3 | MTEPVTPGSSFKACLMGDSVVPVTKLGPESQGRAHQVAALP* | 5469 | ATGACTGAGCCGGTCACTCCAGGGTCTTCCTTCAAAGGCGTGTAATGGGAGACAGCGTTGTCCCAGTAACCAAATTGGGACCCAAGGAAGGGCTCATCAGGTGGCCGCTCTGCCTTGA | 5470 |
| | 4 | MILFPLDPAPLVPFSL* | 5471 | ATGATTCTCTTCCCTCTGGATCCAGCCCCTAGTTCCTTTCACTTGA | 5472 |
| | 1 | MAAQRWSTRAWPSEEGKQKGDDSHSPLLFLIISAAVCTDSLRVVNKAEWALLCL* | 5473 | ATGGCAGTCAAAGGTGGAGTACTAGAGCCTGGCAAGTGAGGAAGGAAAGCAGAAAGGTGACGATTCTCACTCACTCTTGTTTTTAATAATCGCCGCTGTTTGTACAGACAGGCCTGCGTGTTGTAAATAAAGCAGAAGTGGGCTCTTTGTTTTATAG | 5474 |
| | 2 | MVRFLKAQASLAWVLRGPRLGYTPGGWETVAEGSDHVAGALGGVRRSRDWEGIT* | 5475 | ATGGTTCGTTTCCTGAAGGCACAGGCCAGTCTAGCTGGGTGCTCAGGTGCTCAGAGGACCTCGGCTGGGGGTACAGTTTGGCGGCTGGGAGACCGTTGCTGGAGACGTTCACGTGATGGAGGGGATCACGTGA | 5476 |
| hsa-mir-324 | 3 | MWRGH* | 5477 | ATGTGGCGGGGCACTAG | 5478 |
| | 4 | MRRGGRVPGGSSRRRWRWRAAAAETGALSRTPRPAPRRHPRRSVLFPLCFSPVLGQSCPRSRVGLRVCAGAAGAISFLGGRWSPGARGRDHGG* | 5479 | ATGAGGAGAGGTGGGGCGGGTACCTGGAGGAAAGCTCGCGGCGTCCGGTGGCGGTGGCGGCGCGGGCGCTGAGACCGGTGAGACCGTGCAGATCCGCGCACCCGTGCTTTGAGTCGCACCCGGCGGCTGAGACCGCCCCACCCTGCGCGCTCGCTCCGGTCGTTTGCGGGTGTGCGCAGGCGCGGCAGGGCATTAGCCCTTTGGGGTGGGCGGTGGAGCGCCGGAGACCATGGCGGTAG | 5480 |
| | 1 | MGDKGTR* | 5481 | ATGGCGGACAAAGGGACCCGTG | 5482 |
| | 2 | MWAAAPGPDTQLADTQHWPAAAETHGGRLTHNTRTGTLTRGTGMLAHTLATASTRSSHAVARRHTRLGQHILADSLVGMRSSQSNTHQF* | 5483 | ATGTGGGCCGGCAAACCCGGCCCCGACACCCAGCTCGCTGACACCCAGCATTGGCCGGCAGCCGCAGAGACGCACGGGCGGGAGACGCCATTGACACACTACGGACACGGACACCGGCACGCTGCCGTCAGTACACCCGGTGCACACGCCATGGCCGGTCACACGCTCGGTGCACAGCTCAACACACCAATTCTAG | 5484 |
| hsa-mir-326 | 3 | MSHQHSGAQGHTNTDHRHNQTDALKDWHPTGTSC* | 5485 | ATGTCTCACCAACACAGCGGAGCCCAAGGCACACACACTGACCCCCACAGACACAATCAGACTGATGCCCTCAAAGACTGGCACCCGACTGGCACGAGCTGCTAG | 5486 |
| | 4 | MPSKTGTPQARAASPRPADTHASGPTWPFEVETHTSHRVERPPPPAWGKQJAFHPNRSHPSTLPPFPLTS* | 5487 | ATGCCCTCAAAGACGTTCAGGCCCAGCGGCACTAGCCCAAGGCACGAGGCTGCTACCCACGGCTGGGAAACACACGGAGAAGTGGAAAACACACATCCATCCACACAGGTAGAGCCGCCCCCCGCCACCCGACGCTGGGGAAAACAGATGCATTCATCCAAATATGATCCCATCATCTACTCTGTTCCCTTCCTGACCTCGA | 5488 |
| | 1 | MACKQSQDQVGVRSYLQTMGLPQL* | 5489 | ATGGCTGCAAGCAATCACAGGATCAGGTTGGGGTCAGAAGTTACCTCCAAACCAT | 5490 |
| | 2 | MIRR* | 5491 | ATGATCCGCAGGTAG | 5492 |
| | 3 | MMRCRQEATVLLILPFSLVSYRAPSATQPGPRSAET* | 5493 | ATGATGAGATCCGTCAGGAGGCCACGGTCCTCCTCCTCTCCCCACCAGCCTGGTGAGCTATAGAGAGCTCCATCCGAACTCAGTCAGTTCCGTTAGTGCAGAAACCTAG | 5494 |
| hsa-mir-328 | 4 | MPSGGJHGPPHSPHQPGEL* | 5495 | ATGCCGTCAGGAGGCCACGGTCCTCCCATTCTCCCACCAGCCTGGTGAGCTATAG | 5496 |
| | 1 | MDQGVEGGGCGPGVGRQSACSL* | 5497 | ATGGACCAGGGGGTGGAGGCGGAGGGCTACAGAATAGGGAAGACCTGGGGTCGGCGGCCAGTCAGTTTGCAAGCCTATGA | 5498 |
| | 2 | MKDGKEGYRIDRGRVGLRIARAAWHTVLG* | 5499 | ATGAAGGACGGGAAAGGGGAATATCGGATAGACAGAGGGCGGGTAGGGCTTAGACAGTTTAGGGTAA | 5500 |
| hsa-mir-329-1 | 3 | MTEPVTPGSSFKACLMGDSVVPVTKLGPESQGRAHQVAALP* | 5501 | ATGACTGAGCCGGTCACTCCAGTAACCAAATTGGGACCTGAGTCTCAAAGGCGTCTAATGGGAGACAGCGTTGTCCCAGGACCCAAGGAAGGGCTCATCAGGTGGCCGCTCTGCCTTGA | 5502 |
| | 4 | MILFPLDPAPLVPFSL* | 5503 | ATGATTCTCTTCCCTCTGGATCCAGCCCCTAGTTCCTTTCACTTGA | 5504 |

Figure 1 (Continued)

| | | | | | |
|---|---|---|---|---|---|
| hsa-mir-329-2 | 1 | MDQGVEGGCGPGVGRQSACSL* | 5505 | ATGGACCAGGGGTAGAGGGAGGTGGGTGTGACCTGGGCGGCCAGTCAGCTTGCAGCCTATGA | 5506 |
| | 2 | MKIDGKEGYRDRGRVGLRIARAAWHTVLG* | 5507 | ATGAAGGACGGAAAGGAGGAGGCTACAGATAGGGGAAGAGTGGGGCTGAGGATAGCCAGAGCGGCTTGGCACACAGTTTAGGGTAA | 5508 |
| | 3 | MTEPVTPGSSFKACLMGDSVVPVTKLGPESQGRAHQVAALP* | 5509 | ATGACTGAGCGGTCACTCAGGGTCTTCCTTCAAAGCGTGTCTAATGGAGACAGCGTTGTCCCAGTAACCAAATTGGGACCAGAGTCCCAGGGGAAGGGCTCATCAGGTGGCCGCTCTGCCTTGA | 5510 |
| | 4 | MHLFPLDPAPLVPFSL* | 5511 | ATGATTCTTCTCCCTGGATCGCAGCCCCTCCAGTTCCCTTTCACTTTGA | 5512 |
| | 1 | MSSFGAG* | 5513 | ATGAGTAGCTTTGGAGCTGGGTGA | 5514 |
| | 2 | MVSPLF* | 5515 | ATGGTTTCTCCCCTTTCTGA | 5516 |
| | 3 | MGKGSVEACLLG* | 5517 | ATGGGGAAGGGCTCGGTGGAAGCTTGCTTGTGGGGTGA | 5518 |
| hsa-mir-330 | 4 | MGLVSVPDLWGCPGRGWLRENVPEGPPCAHDDPRRAGTHLQPGHTLGAAFLPAQAGVGVSFCWNLLGAFPPGGNRKAVKAAQACNLSTLGGSFEAKSLRPAWATHKTSTARSRAMWPEWDWCI* | 5519 | ATGGGGCTGGTGTCAGTGCCTGACCTCTGGGGTGTCCTGGCAGAGGATGGCTCGTGAAAATGTTCCTGAGCGGCCATGATGATCCAGAGCGAGCTGGGACCACCTACAGCCTGGACCTGCAGACACGCTCGGAGCTGCCTTGTGCGGCTCAAGCTGGAGTGGGTGTATCCTTTTGCTGGAATCTCCTTGTGCTCCCATCCCCAGGAGGAAATAGAAAGGCAGTCAAGGCAGTCTAGGCCTGTAATCTCAGCCTGGGAACAGCTTGGGAGATCGTTTGAGGCCAAGAGTTTGAGACCTGGCTGGGGCAACATACAAAACAAGCACGCACGTTCAAGGGCTATGTGTGCCCAGATGGGATTGGGATTCATAA | 5520 |
| | 1 | MAAGASSTPCPRLSYHLYFHQAGNQGFLCGCQQ* | 5521 | ATGGCAGGGCGAGCTCCACACCTGCCCCGTCTAAGCTACCACCTTTACTTCCACCAGGCTGGAACCAGGGTTCCTTGGGTTGTCAGCAATGA | 5522 |
| | 2 | MSLGMSLREKGERGHFGLRPSHPGKMSGVGGATRGVILAAPIGWRAKSGARGTEAK* | 5523 | ATGAGTCTGGGTATGAGTATTCTCGGGAAAATGAGCGGGGAGCGAGGGCACTTCGGTCTCCGCCCCTCCACTTGGGAAATGAGCGGGTTGGGGGGCGACTCGGGAGTCAATTTGGCTGCACCCATAGCTGGAAGCCAAATCGGGGCGCGGGTACAGAGCCGAAATAA | 5524 |
| hsa-mir-330 | 3 | MPAGEEFGCQSGLLHLPWFWVCHALPATPKSAARGRRSSVLAAGSRVEPQGEERRGNGEARHDLLAWKVLETVKRRWYS* | 5525 | ATGCCTGCTGGGGAAGAGTTTGGTTGTCATCCGGTCTGCATCTCCTTGGGCTTCTGGGTGCCATGCGTCCTGCAACCCCAAGTCGGCCAGGRGCGCCAAGCGGCGCCCGAAGCTCTGTCCTTGCAGGTTGGCTGGCTCTAGGGGTGCAACCCCAGGGTGCAACCCCAGGGTGAAGGAGGGGAAACGGGAGGCTAGGCATGACATGACCTTTTGCCTTTGAAAGTCTTAGAAACAGTGAAGAAGACGTTGGTATTCATAA | 5526 |
| | 4 | MRCLQPPSPPPGAAEALSLQLALGSNPRVRRGGETGRLGMTFWLGKS* | 5527 | ATGCGCTGCCTGCAACCCCAAGTCGCCGCCAGGGCCCGCCGAAGCTCTGTCTTGCAGCTGGCCCTAGGCAGCAACCCAGGGTGAGGAGGGGAAACGGGAGGCTAGGCATGACATTTTGGCTTTGGAAAGTCTTAG | 5528 |
| | 1 | MFIISETFQGRGLITILPKCQNNPEWLTVALPTKLPLRTRSGD* | 5529 | ATGTTTATTATATCTGAAACATTTCAAGGAAGACATTTCTCATAACTATACTCCCAAAATGTCAGAATAATTCCAGTTGGCTCACAGTTGCACTTGCCACAAACAAAACTGCCTCTAGAAACCCGGAGCGGTGACTAA | 5530 |
| hsa-mir-331 | 2 | MMTYLEHLKLWPLQPWELPPQSPSSSGLAVRPFSSSGVSQCHSLBPHPVSSSGFFYSLCQQASETQLAE* | 5531 | ATGATGACCTATCTGGAACACTTAAAGCTATGGTTTCTCAGCATGGAACTTCCCTTCCAGTCTGGAACCTCTTCCATCTTCCAGGTTTGGCGTTGTCGTCTCTGGTTTCTCTACTCACTCTGAGTGCCACTCCTTACACCTGCCATCAGTTTGGCTGGCATGACAACCTCAATTAGCGAATGA | 5532 |
| hsa-mir-331 | 3 | MVYSPAMGTSLPVSFHFGCSSFLLWGFSVPLLTPSSSSLLWFLLTLPGIRMSISRMMQLAKENGEGKREGIGRRKGGRETHCLLIPSHYFLPPYHS* | 5533 | ATGGTTTCTCCAGCCATGGGAACTTCCCTTCCAGTCTCCTTCCACTTCGGTTGTTCCAGCTTTCTCCTTCTGGGTTCTTCAGTCCGCACTCTCCTTCTCAGGGAAGCCACATGTCAGGAATGATGCAGCTAGCAGAAAATGGAGAAGGGAAAAGAGAGAAAGGGATTGGAATAAGAAGGGGGAGGAGAAAGAGAAAAGAGAGAAAGGGATTGGAATAAGAAGGGGAGGAGGATTGGAATAAGAACCACTACCTGACAGTCAGAGATAA | 5534 |
| | 4 | MHAHTHTHHSQR* | 5535 | ATGCACGCGCACACACACATACACAGTCAGAGATAA | 5536 |

Figure 1 (Continued)

| | | | | |
|---|---|---|---|---|
| hsa-mir-335 | 1 | MPEAIVEATACHFPEAIGGADAWQCEGGSTCWARGR WACARTWRKSSPEPRIRGRVLPGNRVKAENLWPQEAH AQPVLRMMESCRQGLT* | 5537 | ATGCCGGAGGCTATTGTGTGCAGGAGCCACGCGCTGCATTCATACCCTTTGCAATAGT GGCATGACGCCTGACAGGCGCAGGAAGCGGCAAGCACATGCTGGGCTCGGGGCGATG GGCTTGTGCGCGGACCTGGCGACGCTCTAGCCGCGACCGGTATCGTGCCGATG CCTCCCTGGGAACAGGGTGAAGCCCGAGAACCTCTGCCTCAGGAAGCGCATGCGCT AACCGGTTCTCCGAAACATGGAGTCCTGTAGGCAAGGTCTTACCTGA | 5538 |
| | 2 | MLGSGAMGLCADLATL* | 5539 | ATGCTGGGCTCGGGCGCGATGGGCTTGTGCGCGGACCTGGCGACGCTCTAG | 5540 |
| | 3 | MRNRFSETWSPVGKVLPESGKRRAGKEWSLPVHPRSPL QEWD* | 5541 | ATGCGCAACCGGTTCTCCGAAACATGGAGTCCTGTAGGCAAGGTTCTTACCTGAATCA GGTAAGAGAGGCGGGCGGGGAAGGAGTGGAGCCTCCCGTGCACCCTGCAGGCCGCT CCAGGAGTGGGACTAG | 5542 |
| | 4 | MWEGSNRKKKKRERATVPVLKPFPPPSSQAARKLPV* | 5543 | ATGTGGGAAGGTAGTAACAGGAAAAAAAAAGCGAGAAAGAGCGACTGTG CTGTGCTGAAGCCCTTTCCTCCGTCCAGGCAGCTAGAAATTGCCTGTCT GA | 5544 |
| hsa-mir-335 | 1 | MVRRDRLRR* | 5545 | ATGGTGCGCCGAGATCGCCTCCGCAGGTGA | 5546 |
| | 2 | MECSERGTSLG* | 5547 | ATGGAATGTTCAGAACGCGGACCTCCTTGGGTTAG | 5548 |
| | 3 | MFRTRDLLGLGFLDPGVVVRFRISGPRHLDMT* | 5549 | ATGTTCAGAACGCGGGACCTCCTTGGGTTAGGATTTCTAGACCCCGGGATCGTCGTG GTGAGATTTAGGATTTCTGGACCCCAGGCGTCATCTGATATGACTTAG | 5550 |
| | 4 | MTLVSP* | 5551 | ATGACCCTGTCTCACCCTGA | 5552 |
| hsa-mir-335 | 1 | MVNPILCT* | 5553 | ATGGTTAATCAATTCTGTGCACCTGA | 5554 |
| | 2 | MFTERMNGHMND* | 5555 | ATGACAGAAAGAATGAATGGACACATGAACGACTGA | 5556 |
| | 3 | MEMPGTARKELPMGLSFISLWAPEVHKREKRQEEKCQ GVKDRAKERQK* | 5557 | ATGGAAATGCCTGGCACCAGCCAAGGAGGCTGCCCATGGGATTGTCATTCATCTCA CCTCTGGGACTTCTGAGGTCCATAAGCGTGAAAAGAGGCAGGAAGAAGTGTCAGGG AGTCAAAGATAGAGCTAAGGAAAGGCAAAATGA | 5558 |
| | 4 | MKLNESERENKEKPKKRTNTWVYL* | 5559 | ATGAAACTAAATGAAAGGAAAACATAAAGAAAATAAAGAAAACCAATAAAAAGAGAA CGAATACGTGGGTGTATCTGTAA | 5560 |
| | 1 | MGDPGRNIGEGMAPQRPGQPAALSTWYSPRQYETQPG SSPMAVAARYRSRPVCKASHPHSTSTGATQRAWGGGA AASRLETCK* | 5561 | ATGGGGGATCCTGGGAGAAACATAGGGGAAGGGATGGCCCTCCAGCGCCCAGGCCA ACCTGCTCCCTAAGCACCTGTACAGTCCACGGCAGGTGGAGACTCAGCCAGGTTC TTCCTTCATGGCTGTTCGCAGCACGAGGTACCAGGGAGCAGGCCTGTGCAAAGCCAGCCA CCCCACTCCACCAGCACCAGGTTCCACCAAAGGGCATGGGTGGGGGGCGGCTG CCAGCGCCCTCGAAACCTGCAAGTGA | 5562 |
| | 2 | MGWGGGCQPPRNLQVRRGPLSTKTRPGCAPGFPHLSP* | 5563 | ATGGGCTGTGGGGGCGGCTGCCAGCCGCGCTGCCAAGCTCCAGCCTGCGAAACCTGC AAGTGAGGCGGAGGAGGCC CCTGAGCACCAAGACCCCTGGGTGTCCTCCCGGGTTCCCCCCCACTCCTCCCCTG A | 5564 |
| hsa-mir-338 | 3 | MPPLRVPPPSPLLCPPLRAPLCLPLRVPLSVLPPCHPGRG GPPPPRRSARAPARVFGLHQRSPAAPGPGGAPRLSPPPP PVRALRLRRGARGAGALRTCGGRWVMRRLGPGPRAS* | 5565 | ATGCCTCCCCTCCGTGTCCCGTGTCCCCTCCCCCCTCCAAGCCCCTTCTGTCCCCACTCCGTCTC CCCTCTGTTCCCGCCCCCCCCCGTCCCGTCCTCCGGCCCCCATGCCACCCGCCGG CGGAGGAGCCCCCCAGGGGCCGGGAGCCCCTCCAGGCCGGGGAGCGCCTCGTCTGCGC ACTGCACCGCCCCCACCGGTGCGCCACCGGCTGCGCGGCGCGGGGGCCCGGCCCCGGCGG GCCGGGGGGCTCGGA | 5566 |

| | | | | |
|---|---|---|---|---|
| | 4 | MSGHGHAGHDVNHV* | 5591 | ATGTCTGGAATTGGACAGGGGGACAGATGTTAACCATGTTTAA | 5592 |
| | 1 | MGGGSALLKAGLTLTWGAGPCRKAASAATQLEFTLRWAJTW AQVGAGRRVGRRGGRRVRAPGDPEPRGGLPRGSAPS TWVRGGPARRDRAAALGSAVLGRLVRPVRPVRPGAGS DTRTRLWVNSARASGRDSAGS* | 5593 | ATGGGAGGCTCCGCACTTCTGCGGCACTGGGCGCGGGCTCC CTGCCGGAAGGCTCCGCGTCGGACGCAGCTGTTCACGCTTAGGTGGCGACGTGGG CGCAGGTGGGCGACGCAGTAGGCCGTGGGGCCGGCGGGTGGCCGGCGGTCAG GCGCCAAGGAGACCCAGAGCCCGGAGGCCCGGCCTCCCGGGGCTCCGCCCCCTCA GGCGGTGCGCGAGGGCCGGGCCGGTGGCGCGGCGGCGGCGGTCCGA GTGCTGGGGGAGGCTCGTGCGGCAGGCCCGGGCGCGCGGCCGGGCTCCGA CACCCGCACCCGCCCTCGGGTTAACTCAGCGGCGAGTGGAAGGCGACTCAGCTG GCTCCTAG | 5594 |
| hsa-mir-339 | 2 | MRAPPHPDNP* | 5595 | ATGCGCGCCACCACCACCCGGATAATTTTAA | 5596 |
| | 3 | MFFVEMGSHHVTQAGLEFLGSSDGSSCLGLPKCWDYR SEPTRLASLSHSMLSVSFLPSPHSFLKNVHWVPPALPGA LGYSCQQVETSL* | 5597 | ATGTTTTTTGTAGAAATGGGGTCTCTGCCTGCGTCACCAGCTGGTCTCGAATTCTTG GAGCCAAGCGATGATCCTCTGCTCACTTCCATCATAAGCATGCTTTCGTTTCCTTCCTTC CGTCATTCATTCATTCATTTAAAAAACGTTCAATGGTTCCTCCTGCACTGTTCGG GGCATTGGGCTACACGTTGTCAACAAGTGGAGCAACAGTCGTGA | 5598 |
| | 4 | MLPRLVSNSWAQAMDPPASASASQSAGUGYSQRAWPHFP S* | 5599 | ATGTTACCCAGCTCGTCTCGAATTCTTCTGGGCTCAAGGATGATCCTCCTGCCTCG GCCTCCAAAGTCTCGGATTACAGGAGTGAGCAACGCGCTTGGCCTCACTTTCCA TCATAA | 5600 |
| | 1 | MSLVPLTTNRGARGLEAGPQGARAGAGESRPALSYRRP GATQTWRRVAPVGEAVPGGGCRVSWAVATAPPPRLPE RDGRGGFCAEPGDGRQRRAGWSGDHGDPHGAGRRAD PGRHRR* | 5601 | ATGAGCCTGGTCCATTGACAACAACAGGGGGCGCGGCGGCTGGAGGCGGGGCC GCAGGGGGCAACGCAAACATGGGCGGCAGCGTCGGTGGCACCGTCGGTGCCGGGC CGGGGCAAGCAAACATGGGCGGCAGCGTCGGTGGCACCGTCGGTGGCGTGCCGGGC CGGGGTGTCGGGGTGCATGGCGGCTTCGCGGAGCCGGGCGATGGACGAGGGGGA GCTGGTGGCTCTGAGACCATGAGAGACCCTCACGGAGCTGGGCGACGAGCTGACCC TGGGAGACATCGACGGTGA | 5602 |
| | 2 | MAAGGTRR* | 5603 | ATGCGCGCGGTGCCACCCGTCGGTGA | 5604 |
| | 3 | MGKGDKHTAPASP* | 5605 | ATGGKGGGTTGKGGTCATGGCATCGCCCCGGTCTCCTGA | 5606 |
| hsa-mir-33a | 4 | MDDSGELGGLETMETLTELGDELTLGDIDGEWVGGS AGAARGRGYGGAPGCACAHPPTAPVRAGRTPCARCP RRSSTLPALRA* | 5607 | ATGGACGACAGCAGCGGCGAGCTGACCCTGGAGACATGCAGCGTGACCCTCACGGAGCT GGGCGACGAGCCGCGCGGCGGGAGCAGGGCGTTACGCGCGGCGCCGGTTGGCGTGGCG CCACCCCCGACCAGTCCGTTCGCGCGGGAAGAACCCGGTTGCGCACGGTGCCGCC GGGCGGTCCTCAACCCTTCCGGCGCTGCGAGCGTGA | 5608 |
| | 1 | MDCTFEGIFCGLPTSPLYNASVSCRFSWGGRACGLRNL SRKEEPLPEGEGYTVTSSLGKWRATSNQISVPCNSRGKGL LRDPKAASRPKRVWRERVVFSTFSAPALGDQEEAGRR ARCPSATASALFSTPAYCGHLRLFRKTVGALDCQNCOF FFQASVSPTYRRGSHGLG* | 5609 | ATGGATTGCACTTTCGAAGGTATTTTGAGGCTCCGCACCCAGCCCTTTATACAAT GCCTCCGCTCCTCGCCCCAGTCCCCGCTGGGTGGGCGGCATGCGGCGCTACGCAACTTG AGCAGGAAAAGAGCCCCCTGCTACCCTCCGAGGAGAAGGTGACAGTTGACAGCTGCTGG GAAGTGGAGGCTACCTCCAACCAAATTAGCTTCCCTGCAACTCAAGGGAAGG GTTGCTTAGAGACCCAAAGCAGCTCCACCTTTGACACCAGGTTGAGGGAGCAGG GTGGTCTTCTGTACATTCTTGCACCCGCTTGGGACAGACGTCTGCCATTCAGCAGGG AGGAGGGCGGTTGTTGCCTCTGCCAGAGACGTTTGTCAAATTCTATCTAT TGTGGGCATCTTAGACTTTCAGAAGACAGTGGAGCCTAGAGTTGCCAAATTGT CAGTTTTCTTCTTCAGGCCTCAGTTTCCCCATCTATGAAGAGGCTCACACGGACTG GGGTAA | 5610 |
| hsa-mir-33b | 2 | MPPSPAGSPGVGGHAGYAT* | 5611 | ATGCCTCCGTCTTCTGCAGGTCTCTGGGTGGCGGGCATGCGGGCTACGCAACT TGA | 5612 |
| | 3 | MRATQLEQERAPSRGRRCDSYQLAGEVEGYLQPN* | 5613 | ATGCGGGCTACGCAACTTGAGCAGGAAAGAGCCCCTGCTGCGGAGGAGAAGGTGTGA CAGTTACCAGCTCGCTGGCGAAGTGGAAGGCTACCTCCAACCAAATTAG | 5614 |

Figure 1 (Continued)

| | | | | |
|---|---|---|---|---|
| | 4 | MGNPAVESPL* | 5615 | ATGGGAAACCCTGCAGTTGAAAGTCCATTATGA | 5616 |
| hsa-mir-33b | 1 | MDEPPSEAALEQALGEPCDLDAALLTDEGASGRAGLE AAPGGASRGRAGVSLAFVSPTGASSVLCSRGTSRCL* | 5617 | ATGGACGAGCCACCTTCAGCGAGGCGGCTTTGGAGCAGGCGCTGGGCGAGCCGTG CGATCTGGACGCTGGCGCTGCTGACCGACGATGAAGGTGCGTCAGGCGGGGCAGGGC TTGAAGCTGCGGCAGCGGGTGGGCGAGTAGGGGCGCAGGGTCTCCTGGCCTTT GTCTCTCCCACGGCGCTCCAGCTCCGTGCTGTGCTGCGCGGGACTTCCCGGTGTCTC TGA | 5618 |
| | 2 | MATAEAGDPGVAEAPPQRQP* | 5619 | ATGGCTACGGCTGAAGCTGGGGACCCAGGCGTTGGGGACCCAGGCCTCTGCCTGCCCAGCCCA GCCGTGA | 5620 |
| | 3 | MRMGAASRPSPASGCRVLPVCDGHRSLRTHSLTSTECCQAP S* | 5621 | ATGCGCATGGGAGCTGCTCGCCGCCTTCCCGCCTCCGCTTCTCCCGTC TGCGACGGGCACAGCCTCCGCACTCATTGACATCCACTGACATCACCTGACATCACCCGCCCG TCTTAG | 5622 |
| | 4 | MPGPVLGTEGHLQTDLGTPSFREHKNLPGNQTGH* | 5623 | ATGCCAGGCCCCGTCTTAGGCACCGAGGGTTTACAGACAGACCTGGGTACCCCTCT TTTAGGGAAACACAAAATCTCCGGGAAACCAACCGGTATTTAG | 5624 |
| hsa-mir-340 | 1 | MRSGRDCALGLRVAARPAGGRGGGHAPQAAAAREG LCVPLTLLGALPPVPFPSPAASLRGASHSVGPTRGDGG GTLLQPSWDPEETPACDLRRRPRRGPMGASPQAGSGRE GGERRGRGVQEGRARARPRAGRARALPPPGPRPPRL* | 5625 | ATGCGCTCGGGCGGGACTGCGCCTTAGGCTGCGCGTTGCCGCTAGACCAGCAGCGGG TGTGTTCCCGTGACCTCTGCGAGGCGCCTCCATTCGGTGGGACCGACCACCGGGGGATGGAGGG GGCACGGCTTCTACAACCCTCGGGACCCGAAGAGACGCCCGCGTGCGACCTGAG ACCGCCGCCTCCCGAGGAGCCATGGCGTCCCACAGCGGCAGTGGACGTG AGGGGCGCGCAGGCGCGAGCCGCGCGGCTCCGCCGGCCGCCCGCC GGERRGRGVQEGRARARPRAGRARALPPPGPRPPRL*TCTTAG | 5626 |
| | 2 | MEGARFYNPPCGTPKRRPRAT* | 5627 | ATGGAGGGGCACGCTCTACAACCTCTGGGACCCGAAGAGACGCCGCGTGC GACCTGA | 5628 |
| | 3 | MSCAGRAGPARLAALALLTCSLWPARADNASQEYYTA LINVTVQEPGRGRAPLTPFRJDRGRYGLDSPKAEVRGQVL APLPLHGGECRPGGGRGRWSLHPA* | 5629 | ATGAGCTGCGGCGGGCCGGGCCGGCCGGCACGGCTAGCCGGCCTGCGCCCGCCTGCTGAC CTGCAGCTGGGCGGCCGGCACGGCAGACAACCGGAGCCGAGCCAGGAGTACTACACGGCGC TCATCAACGTGACAGTTCAGGAGCCTGGCGTGCAGGAGCCTGCTCACGTTTCGCATCG ACCGGGGCGGCTACGGGCTTGACTCCCCCAAGCCGAGGTCGCGGCCAGGTGCTG GTGCGCCGCCCCTCACGGAGGTGAGTGCCGGCCGGGAGGGGCGGCCGGCGGCCGTGGTC GCTGCATCCCGCGTAG | 5630 |
| | 4 | MGRTSQPVFWKRQVPQFTDLRLR* | 5631 | ATGGGGAGGACGTCAGCTCAGCTGTCAGTTGGAAGCGGCAGGTTCCTCAATCACGAC TTAAGGCTGCGCTAG | 5632 |
| hsa-mir-342 | 1 | MAGAGAQLSVAAAALPRS* | 5633 | ATGGCAGGGGCCGGGGCCCGGGCCCCCGCCAGCTGTCAGTTGCCGCCCCTTCCCCGCAG CTAG | 5634 |
| | 2 | MSPRCPPQPSQTRSRRARCRLPR* | 5635 | ATGAGCCCCCGCTGCCCGCCGCAGCGCAGCGCGGACGCGGAGCCGCGCGCCGGGG CCGGGCTCCCCGCTAG | 5636 |
| | 3 | MASREPWGRLESREGLQGLWGAVPFCKGQAALALAACG VLLGSGPAAAWEADPRGQVWPCPDRARTEVGGSPCA VPSSPEEAGLKPPGVAEASPCQRPEPRLGFYRCSFPSTW SPSTPSSPNSQPFFFFLHASKVQGPQMYRSLMYHPARE PADYQAKK* | 5637 | ATGGCTTCGCAGAGCCGTGGGGGCGTTGCAGGGTGCGGGGTCTGCAGGCGTT GTGGGGGCAGTGTTCGGGGGCGTCTGCAAGGGCCTGCGCCGGACGGCAGACCCCGCCGGCAG GTGGGCCGTTGTCGACGGGCGAGGAGCCGAAGTTGCGGAAGCCTCGTGCGTT GCCTTCCAGCCCGGAGGAGGCTGCGTTGGCTTTACAGGGTAGTTCCCCGACTT CCTGCCAGCCGTCAACCCTCAGAGCCGGCTTCGTCTCCTAATTCTCAACCCCGTCGACTT GGAGCCCGTCAAAGTGCAAGCCCCCAAATGTACCGCGCGTTGATGTATCACCAGCTCG GGAGCTGCTGATTATCAGGCCAAGAAATAA | 5638 |
| | 4 | MTMK* | 5639 | ATGACAATGAAATAA | 5640 |

Figure 1 (Continued)

| | | | | | |
|---|---|---|---|---|---|
| hsa-mir-342 | 1 | MAIR* | 5641 | ATGGCCACAAGGTGA | 5642 |
| | 2 | MSRGNLES* | 5643 | ATGTCAACAGGAAACCTAGAATCTTAA | 5644 |
| | 3 | MGCRNYLRSP* | 5645 | ATGGGCTGTAGAAATTATCTCAGTTCCCTTAG | 5646 |
| | 4 | MTRGQGAYMRLHSRLVTVCSLSSRWSFHYTGLCLLMP VTENGF* | 5647 | ATGACCAGAGGACAGGGGCTTACATGAGGTTACACAGAGTTAGTGACAGTTG CTCCCTCTCTAGCCGCTGGTCTCTTACATTACACAGGGCTGTGTCTTGATGCTGTG ACCTTTAATGCTTCTGA | 5648 |
| hsa-mir-345 | 1 | MDMISPRWAYEDGQRRTFQARRLRERRAEETTDYFGG AKQACFQVKCSCPKPRCFQEGSTDGSATAEGTLPRGK NFHSPKPGRRCWPGDSPSPPPAGADSGWGARVEQTARS EAGGEGENGIRRGHAPSVSRAPSD* | 5649 | ATGGATATGATGATCTCTCCCAGGTGGGCTATGAGGATGGGCAGGAAGGACATTCCA GGCAAGCAGGCCTGCTTCAGGTGAAGTGTTCCGCCCCAAACCGGGTGTTCCAG GAGGGCAGCACAGACGGTAGCGCCACTGCAGAAGGAACTCTCCCATCCGGCGAAA GAATCCCCACTCCCCAAAGCTGGAAGCTGATAGTGGTGGGAGCAAGGTTGGCTGGACAGCCTTACC CCCACCCGTGAGCTGATATGTGGTGGGAGCAAGGTGGAGCAAACAGCGAGAT CAGAAGCGGGAGGGAAGTGGAAATGGAATCGCAGAGGAACACGCCCCTCTGTC TCCAAGGCACCCAGCGATTAG | 5650 |
| | 2 | MRMGSEGHSRQGGCASDVQRRPQMCREAPSRPAFR* | 5651 | ATGAGGATGGGCAGCGAAGGACATTCCAGGCAAGGAGGCTGCGCGAGCGACGTGCA GAGGAGCACAGATGTGCAGAGGCCAAGCAGGCCTGCTTTCAGGTGA | 5652 |
| | 3 | MESAEDTPLSPGHPAISSKFWALCPAASHWVTDREVL TPLSAQHLPNTLPFQRVSPPRSRLRRHRPNT* | 5653 | ATGGAATCGCAGAGAGACACGCCCCTGTCTCCAGGGCACCCAGCGATTAGCAG CAAATTCTGGGCTTTGTGCCCCGCACACAGCCCTCACTGGGTAACCGACCGGAAGTTCT AACTCCCCTCAGCGCACAACACCTCCCAACACACTCCTTTCAACGAGTCTCTCC CCAAGAAGCAGGCTCCGACGCCACAGATTTAATACTTAA | 5654 |
| | 4 | MKRR* | 5655 | ATGAAGAGGCGGTGA | 5656 |
| hsa-mir-346 | 1 | MTSCRARRSPTPSRSSRPTTHSRLCRKVSDRCAQGPLGH GLRGVAAVGTGGVGTSWAAQGTLCSSAAAVPCAVARL PRPT* | 5657 | ATGACATCTCGCAGAGGCGAGAAGATCACCTACTCATCAAGGTCATCGAGGCAAC AACCCATTCCAGGTGTCAGGTGTCAGAGGAAGGTGAGTGACCGTCTGTCCCAGGGCCCACTGG GACACGGCTGCGAGGGCCTCGGAGGCCACCCTCTGTTCCTCGCAGCCGCGGTTGGACGAGCTGG GCTGCGCAGGGCACCCTCTGTTCCTCGCAGCCGCGGTTGGACGAGCTGG CCTTCCCGGCCGCCACCTAG | 5658 |
| | 2 | MRGGAPSPAHLGSAGAGTALRCGPARRACERGELVFLRV AWRPSGCVGAGVRPALAAQACVARGSLCFSVFGGCRV CVPGTCIGRTSPDLSGPVFSSLRGEERPAAGARPVSFSRA* | 5659 | ATGCGCGGTGGCGCCCTTCCGGGCGTCCTCACGGAGAGCCTGGCGCCGGAGCTGCT TGGCGTGGCGCCCTTCCGGGCGTCCTCACGGAGAGCCTGTGTGGGCGCGCGTGTGCGCG CAGGGCGTGCGTCCGGCAGTCTTTGTTCTCGGTGTTGGGGCGTGTC TGCCTGCTTCGAGGTACCTGTATCGGAGGACGCCAGCGGCTGCAGTCCAGTCCAGTGCCCGGTGGCGCGGTC TCCTGCTTCGAGGTGGAAGAGCGTCCAGCGGCGCCGAGCGGCTGCCGCCGGTGTTT CGGGCATAA | 5660 |
| | 3 | MGTLGPAPLSAGAS* | 5661 | ATGGGGACTCTGGGGCCAGCGCCCTCAGTGTGCTGGGGCAAGTTAG | 5662 |
| | 4 | MQGFLAGGTGREV* | 5663 | ATGCAGGGATTCCTTGCTGGAGGAACTGGTAGAGAAGTGTAG | 5664 |
| hsa-mir-346 | 1 | MSRAPGGHGSADAVASPLDMPVRVGAGRLHHPHR* | 5665 | ATGAGCCGGCCCCCGGGGGACATGGAAGCGTGACGCTGTGGCTTCTCCCCTGGA TATGCCAGTGCGTGCTGTCGGTGCGGGGCCGGGCCGGGCCGAGGTAG | 5666 |
| | 2 | MEALTLWLLPWICQCVSVRADSHHHGKRGWRPGRGWA EAPTGQGVRGVQTWRFPGPRGSACGAPPKGRAAPPGG GAVHRRPRRAPAGCLPLPGAPISARGPAAASTDT* | 5667 | ATGGAAGCGCTGACGCTGTGGCTTCTCCCCTGGATATGCCAGTGCGTGCTCGGTGCGG GCCGACTGCACATCCACATCGTTAAGGCAGCGGTGCGGGGGCCGTCAAACTGGCGTTCCTGGGC GGGGGCCCAACGGGGCAGGGTGGGTCGTCCTCGAAGGGCCGCCGCCGCGCCGGGA CGAGCTGTGCACCCCGGCCACCCGCTGCTTGCCGCCGCCCGCCCCGGCT CCGATCTCCGCCGCGCGGTCGAGACCCGCCCCTTAG | 5668 |
| | 3 | MBARRDPRP* | 5669 | ATGGACGGCGGCGTCGAGACCCGCCCCTTAG | 5670 |
| | 4 | MCVGACCQRVSLCAPGTVSVLL* | 5671 | ATGTGTGTGGGGTGCCGTGTTGTCAGCGTGTGCTGTTGCGCCTGGCACGGTGTCG GTGTTACTGTGA | 5672 |

Figure 1 (Continued)

| | | | | |
|---|---|---|---|---|
| hsa-mir-346 | 1 | MLAAAGPLWLPSCPGAWPGAPPRSLFLLPPRSHSTRNGLFRPGT* | 5673 | ATGCTTGCGGCGGCCGGCCCGGTCCCCTGGCTCCCCAGCTGTCCTGGGCCTGGCCCGGCGCCCCGCCCCGGTCTCTCTTGTTCCTCCCCAGGTCCCACTCCACGAGGAACGGTCTGTTTCGGCCGGGGACATGA 5674 |
| | 2 | MTRDARLLRSPGRFGSPSRAVSGRPSSILPPLANRRRRPEPSELGAPQPRPVPAAVPVSERFPSRERGAPGAPSEPRAGESRAARLRLRSHVVERRAEGREAGREGSKAEGEGEGRGRPPFQFAPRRGSDTQPAQSRHAGPAAATASASPEAALAAGSAAATAAGRPRRAGLGSSCQHRRSRHRSRSGSPTALGWAGLGWGGRRAQGRARGRRTGGLGSPGERPGTAPGPAPPRFALPSASPRARVDEPRARGTWKR* | 5675 | ATGACCCGAGACGCGCGGCTGCTGAGGTCGCCAGGTGCCTTCGGAGCCCCTGAGGCCAGTTAGCGCGGCCGGCCTCTCCATTCTCCCGCCCTGGCCCGGGAACCGGAGAAGGTAGGCCCCGAACCGTCAGAGCTCCCGAGCCAGGGCGCTGTGCCCGGTGTTCGGGAGCGTCCGCGAGCGCCGGCCAGCGCGGTGGAGCAACCGGCCGCCTCGAGGAGGCGGGAGGGGAGGGAGGAGGCGGCAGGGAGGGAGGGAGCTGAGGGAGGGGGAGGGGAGGGGGAGGTCGCTCCTCGCCGGGGCTCAGACACAGCCAGCCAGAGCCCAGAGCGCTTAGGCCCGGAAGCGCTGCTGCCACGCGCGGGCCAGCCTCCCCGAAGCCGCTTAGCGCGTGGGAAGCGCTGCAGCGCGCTGGCCTCAAGCTGCCAGCACGCGGCAGCCTCCCGAGCGGAGCGGCGCCCGACGCAGGACGCCAGGGAGCGGTGCGCGGGAGAACGCCTGCACCGGCACGGGCGGCTCGGCTCTCCCGGGGAGCGGCCGCCCGGGGCCGGCGGACTGCACCCGGGGAAGAACGCCACGCGCTCCCGCGCTCGCGCTGCCCTCGGGCGGGCCGGCCGCTTGATGAGCGCGCGCATGGAAGCGCTGA 5676 |
| | 3 | MSBRAPGGHGSADAVASPLDMPVRVGAGRLHHPHR* | 5677 | ATGAGCCGTGCGCCGGGACATGAAGCGCTGACGCTGTGGCTTCTCCCTGATATGCCAGTGCGTGTCGGTGCGGTATGCCAGTGCGTGTCGGTGTCGGATATGCCGACTCCATCATCCACATCGGTAA |
| | 4 | MEALTLWLLPWICQCVSVRADSHHGKRGWRPGRGWAGAPTGQGVRGYVQTWRFPGRGSAGGAPPKGRAAPPGGGAVHRPRRAPAGCLPLPGAPISARGPAASTDT* | 5679 | ATGGAAGCGCTGACGCTGTGGCTTCTCCCTGGATATGCCAGTGCGTGTCGGTGCGGGGGCGACTCCATCATCCAACGGGCAGGAGGGTCGCGACGGTCTGGAGCGGGCCGTGGAGCTGAGGGCTGGACGGTCCCGCGGGCAGCGAGCAAAACTTGACGTTTCCTGGGCGGGGCCTCGGCGGCGGCCCGCGGCCCCCGAAGGGCCGCCGCTCCGGGGGCCGAGGCCGCAACGCCGCCTGAGCAAGCTCCGGGCAGGAGAGGGGAGCCTGGAAGCCTGCACCTGCTCGCCCCCGTCCACCGACACTTAG |
| | 1 | MRPAWPPGPLSFSGGGDAAVPSVWGQPSSPDPGLERRVAAPGGTSRKEDPAAGSAWACLGLPRAGLLGHDHADRGHLEHLRESCSQAPGQERPGSLHYLLAPSQHAPR* | 5681 | ATGCGCCCTGCCTGGCCCCGATCCCCAGCTTGTCTCTTTCTTCAGGTGGAGAGATGCCGCTGTCCCGCTGCCCGGAGGCTGCGGGAACCAGCCAGCCTCCCGGATCCGGGCTGGAGCAGAGGTGGCACCGGCGGCAGGACTCCGGCGTGGACTGCCCGCCTGGGACTCCCGGCCAGGTGATCGGGGGCATTGAGATTGCGGAGCCTCTGCAGCAAGCTCCGGGCAGGAGACCCCCCGTCGCGGCCCTGCGGGCCTGAGGAGCTGGAAGCCTGCAGCTCCCCCCGTCCGACCCGTTCTCCGCCCCGTCCAGCATGCACCCAGGTAA |
| hsa-mir-34a | 2 | MPLSRRSGDSPAPRIPGWRDASRPRGLVARAGRTRRRALPGLAWACSEPGCPSVFTQIGGIWRFCGSPAAKLRCRRGLEACTTCSFRPSMHPGKRLCFSVRAKVCKEGGGN* | 5683 | ATGCCGCTGTCCCGTCCGCGGTCCGGTGACTCCCCGGCACCAGCCCCAGCTCCGGATCCGGGCTGGAGAGACGCGTCCCGCCTGGGAAGAAAGGAGGAACCCGGACGGCGGCTCTGCCAGGTCGAGGGATGAGCCGGCTCCGAGGAGCCCTCGAGGAGCCCGACCCGGAGGAGTCGGCAGGTTTGGGAGGATTTGGGGCATTGGGAGCGGCCTGGAGCATTTGGAGATTTGCGGGCATTGGGAGCCCTCGAGGAGCCCGACCCAGGAGAGCCTTGTGTTTCTCAGTCGCTGCGAAAGTTTGCAAAGAGGAGGCGGGAACTAG |
| | 3 | MKTLFNCVASVRGRISKKQQNVL* | 5685 | ATGAAAACCCTGTTCAATTGTGTAGCCTCGTAAGGGAAGAATTCCAAGAAGCAACAAAATGTTCTTTGA |
| | 4 | MFFDFIISGEKGFLFWGFARLVLSSLLYLQRGARKADWPMGGKWGPWLSCAAGHGDIAANAQPPQFLSSP* | 5687 | ATGTTCTTTGATTCATAATCTCTGGGAGAAAGGATTCCTTTTTGGGGTTTGCTCGGCTAGTTCTTCTTCCCTCCTCATCTCCAGCGTGGGCGTGGAAGGCGACTGGTTCATGGGTGGCAAATGGGGACCCTGCTCTTGCTGCTGCCACCGTGATATTGCAGCAAAATGCTAACCTCCCCAGTTCCTCTCTCACCTTGA |

Figure 1 (Continued)

| | | | | | |
|---|---|---|---|---|---|
| hsa-mir-34b | 1 | MGVGARLPAWEGAGPPRQRRPLAQLRVLCAARPAGVPLGPGVSSGAACAQPW* | 5689 | ATGGGGTCGGGGCGGCCGGCTCCCGGCCTGGGAGGGCGGGTCCTCCCCGGCAGCGCCGGCCGCTGGCCCAGTACGCTGTGTGCGCTGCGAGGCGCGGGTCCTGCGAGCGCGGGGTCCCGCTGGGCCCGGAGGGTCTCCTCGGGATGTCCACCCCAGCCATGGTAG | 5690 |
| | 2 | MVGRPPVKWGPRRAPTPRRCGPSGSCSRGCPVLGL* | 5691 | ATGGTAGGGCGTTCCCGAGGCGTGAAATGGGGTCGAGGCGGGCCCGACCCCGGTCGGCGCTGCGGACCGTCCGGGAGCTGCAGCCGCGGGTCCCGGTGCTCGGTTTGTAG | 5692 |
| | 3 | MGSEAGPDPASALRTVRELQPRVPGARFVGSVIS* | 5693 | ATGGGTCCGAGGCGGGGCCCGGACCCTGCGGCGTCGGCTCGGCGCTGCGGCTGGCGAGCGCGGGTCGGTTTGTAGGCAGTGTCATTAGCTGA | 5694 |
| | 4 | MPEKRGVGVGPAQPAPRAPAASARKPAVSPDTVKLLLALSRSHRR* | 5695 | ATGCCTGAGAAGCGCGGGGTCGGGGTGGGTCCTGCGCAGCCTGCGCCGGCGAGCGCTGCAAGTGCGAGGAAACCCGGTTTCTCCAGATACAGTTAAACTGTTAGCTCTCTCTAGGAGTCACAGAAGATGA | 5696 |
| hsa-mir-34c | 1 | MGVGARLPAWEGAGPPRQRRPLAQLRVLCAARPAGVPLGPGVSSGAACAQPW* | 5697 | ATGGGGTCGGGGCGGCCGGCTCCCGGCCTGGGAGGGCGGGTCCTCCCCGGCAGCGCCGCCGCTGGCCCAGTACGCTGTGTGCGCTGCGAGGCGCGGGTCCTGCGAGGGCCGGGAGGGTCCCGCTGGCCCAGCCATGGTAG | 5698 |
| | 2 | MVGRPPVKWGPRRAPTPRRCGPSGSCSRGCPVLGL* | 5699 | ATGGTAGGGCGTCCCGAGGCGTGAAATGGGGTCGAGGCGGGCCCGACCCCGGTCGGCGCTGCGGACCGTCCGGGAGCTGCAGCCGCGGGTCCCGGTGCTCGGTTTGTAG | 5700 |
| | 3 | MGSEAGPDPASALRTVRELQPRVPGARFVGSVIS* | 5701 | ATGGGGTCCGAGGCGGCCCGGACCGTGCCGGTCGGCTCGGCGCGTCGCTGCGGACCGTCCGGAGCTGCAAGTGCAGTGTCATTAGCTGA | 5702 |
| | 4 | MPEKRGVGVGPAQPAPRAPAASARKPAVSPDTVKLLLALSRSHRR* | 5703 | ATGCCTGAGAAGCGCGGGGTCGGGGTGGGGTCCTGCGCAGCCTGCGCCGGCGAGCGCTGCAAGTGCAAGGAAACCCGGTTTCTCCAGATACAGTTAAACTGTTAGCTCTCTCTAGGAGTCACAGAAGATGA | 5704 |
| hsa-mir-361 | 1 | MHCFLFRLPRRECLT* | 5705 | ATGCACTGTTTCTTTCGCTTCACGAGGAATGCTAACTGA | 5706 |
| | 2 | MPNLISFPQVIVT* | 5707 | ATGCCTAACTTGATCTCATTTCCACAAGTAATAGTCACATGA | 5708 |
| | 3 | MTRFPSRWRILSLRSLM* | 5709 | ATGACACGTTTCCGTCAGATGGCGAATACTCTCCTTTCGAGTTTGATGTGA | 5710 |
| | 4 | MADTLPSEFDVTVTGTGMCSLVLPGQSLGRLSCFCFFCQWRVLGQTSWVESGREN* | 5711 | ATGGCGGATACTCTCCCTTCGGAGTTTGATGTGATATAGGACGGTATGTGTAGCCTGGTTGCTGCGTGACAAAGTTTAGGAAGACTGTCTTGTTTTCTGTCAGTGGCGAGTTTGGGACAAACATCGTGGGTCGAGAGTGGGAGGGAGAACTGA | 5712 |
| | 1 | MSRAPASLPLLPGWAV* | 5713 | ATGAGCCGCGCCGCCAGCCTCCCGCTCCTGCCTGGCTGGGCTGTGTGA | 5714 |
| hsa-mir-362 | 2 | MKLCRLRGALTQLGVLDARADRARCPPAADTGSAAPDLGDR* | 5715 | ATGAAGCTCTGCCGCTACGGCGGGGCGCTCACTGTGCTCGGCGTCCTGGATGCTCGAGACGCCAGAGGGCGCCCGCTCCGGACCTCGGCGACAGGTAA | 5716 |
| | 3 | MGLPRARRWQPGA* | 5717 | ATGGGGCTTCCCCGGGCCCGGCGTTGGCAGCCTGGCGCTAG | 5718 |
| | 4 | MVPGLPERSFLAERRQARPAFESECLAACVPPPGLG* | 5719 | ATGGTCCTGGGTTCCTGGCCGAGCGAAGTTTCCTTGCGGAGCGGCGCCAAGCGCCCGCTTTTGAATCGGAGTGTTTAGCGCCTGCTGTCCCTTTCCGGACTGGGTAG | 5720 |
| | 1 | MGKGF* | 5721 | ATGGGGAAGGGGTGGCGAATAG | 5722 |
| hsa-mir-363 | 2 | MSCLMNC* | 5723 | ATGTCTTGTTTAATGAACTGCTAA | 5724 |
| | 3 | MSLLGSYFYLFPLIG* | 5725 | ATGTCACTCTTGGGAAGTTACTTCACTTGTTCCTTTAATAGGATGA | 5726 |
| | 4 | MISSFPTFFCLSNQDT* | 5727 | ATGATTTCATCTTTTCCAACCTTTTCCTGTCTCTCCAACCAAGACACATAG | 5728 |
| | 1 | MGTGEGRWRRGSARFSRDSARDACLGCDCRRCRHPGSPSDPSPAPQRGV* | 5729 | ATGGGAACCGGGGAGGGAGGTGGCGGCGCGGGAGGCGCGCGCGGTTCTCTGGACTCGGCCGAGACCCTGTCTGGCTGCGATTGCCGCCGCTGCCGCCACCCGGGCTCCCCCTCGGACCCCGGAGCCCTCCCCAGAGGGGCGTGTGA | 5730 |

Figure 1 (Continued)

| | | | | |
|---|---|---|---|---|
| hsa-mir-365-1 | 1 | MPRAEQAGRARRSTCARAPLAWAAAPAGAGPRGSRTS REPPSPFSYRRPLKLSAPSPREAGSPGALALASAGRGQK N* | ATGCCGCGGCGGAGCAGCCGGCCGCCGGCCCGCTCACGTGCGCCGAGCCC GCTGGCATGGGCGGGGCGGCCTGCGGGGCCGGGCCGGGATCCCGGACTAGCC GGGAACCACCGTCCCAGAGAGTTACCGCKGCCGCCTAAAGTTGTCAGTCTCCCC CCGAGAAGCAGGCAGCCTGGCGCGTTGGCTTTAGCTCTCCAGGACGGGGGCAA AAAAACTAG | 5732 |
| | 2 | MGKGACGGRAPGPD* | ATGGGCGGCGGCGCTCGTGCCGGGCCCCGGAGATCCGGACTAG | 5734 |
| | | MRRLCPLRTHPYL* | ATGCGCGCGCTTATGTCCTGAGGACACATCCATATTTATAA | 5736 |
| | 4 | MALKGPDPAPVGHAVFSPRFTRRIF* | ATGGCGTTAAAAGGTCCAGACCCGGCACCTGTAGCCGTATTAGCCCTAGG TTCACCCGGAGAATATTTTAG | 5738 |
| hsa-mir-365-1 | 1 | MPYLALGSPGEYFRCYLKEEIWALVAGCHMARVESLPH RPGRDGRVLTGTGAQSPCQSFGAMRRVPRSQLATGASV LCGDAFSPRSQSEGSESTSIHRTHRGLSSLRWPSVISQAA * | ATGCCGTATTTAGCCCTAGGTTCACCCGGAGAATATTTTAGTGTCTACTTGAAAGAA GAGATCTGGGCCTAGTTGCCGGCTGTCACATGGCAAGGTAGAATCGTCCCTCAC AGCCTGCCCGAGATGGCCGGGTGCTACTGGTACACAGGTGCCAGAGTCCCTGCCA GAGCTTCGGGGCCATGCAGCGGGGTGCCAAGGAGCCAGTAGCCAGCTGGGGTCGG TTCTGTGTGGGGATGCCTTTCACCCGGTTCTCAATCTGAAAGCAGTGAATCCATTC CATTCACAGAACTCACAGAGGCCTCTCCTCTCTGAGATGGCCCAGTGTGATATCCCA GGCTGCGTAG | 5740 |
| | 3 | MAGGCSLVQVPRVPARASGPCDGCQGAS* | ATGGCCGGGTGCTCACTGGTACAGGTGCCCAGAGTCCCTGCCAGAGTCCGGGGCC ATGGACGGGTGCCAAGGAGCAGTAG | 5742 |
| | 4 | MPFHPVLNLKAVNPLPFTELTEASPL* | ATGCCCTTTTCACCCGGTTCTCAATCTGAAGGCAGTGAATCCACTTCCATTCACAGAA CTCACAGAGGCCTCTCCTCTGA | 5744 |
| hsa-mir-365-1 | 1 | MPWGRHPELLSPQILVAEPRDGTWDLSSKTRPLFPETVS YSYAQAGVQW* | ATGCCTTGGGGAAGACACCCTGAACTCTTAGTCCTCAGATCTTAGTGGCTGAACCA AGAGATGCACTGGGACTTAGCAGTAAAACCGTCCCGTTCTTTTTTGAGACAGTG TCTTACTCGTTGCCCAGGCTGGAGTGCAGTGGTGA | 5746 |
| | 2 | MAPGTLAVKPVPFFLRQCLTLLPRLECSGEHSSLQPELP RLKPHPPE* | ATGGCACCTGGGACCTTAGCAGTAAACGTCATCTAGCACCTGAGCTGAACTT CCTAGGCTCAAGCCTCATCCTCCTGAGTGA | 5748 |
| | 3 | MRVWNSHLKFGGNVTSPMMRLALGMMPCIHFGNLLW DSRSVYF* | ATGAGGGTCTGGAACAGTCATCTGAAGTTTGGGGGAAACGTCACGTCTCTATGATG CGCTGGCTTTAGGGAATAATCCTTGTATCCATTTGGAACCTGCTCTCTGGGATTCC AGATCTGTGGTTTTCGTGA | 5750 |
| | 4 | MRSLS* | ATGAGGTCCTTTCGTGA | 5752 |
| hsa-mir-365-2 | 1 | MGKLRPAAGALHRAGARPGSGAAGRGLPAPVSAGSA GSCSDGSKEEKGKLLGSGAGRTA* | ATGGGGAAGTTGAGGCCGGCCGGCGGCGGGGCCCGG GGAGCGGGAGCGGCCGGCAGGGGCGCTCCCGCGCCGGTCTCCGCGGGAGGAAGCGCT GGACAGCTGCTCGGACGGGTCAAACGGAGGAAAATTACTGCGCTCCGGGGC GGGAAGGACTGCGTGA | 5754 |
| | 2 | MCHQHVEPGRAAASKPTPPTFEGSRRPAPLPASSGSLS* | ATGTGTCACCAGCAGGTGGAGCCAGGTCGGCGCAGCAAGCCACCCCC AACTTTCGAGGGGTCCGCCGGCCCCCGGCTTCGTGGGCTCGCTCTC CTAG | 5756 |
| | 3 | MAPVPRQRCGLGLAGGCGLLREVGHGSCPAPRAPPS* | ATGGCCCCCGTGCCCAGGCAGCGGTGCGGCCTGGGTCTGGCGGGAGGGTGCGGCCT GCTGCGAGAGGTCGGCCACGGTCCTGCCCGCCCCGCCCCTCCGCCCGA GCTGA | 5758 |
| | 4 | MGAEGWVFAGEMRVSDQLAYKYPVLGPRDQRLLPGPR PRPASSRAGVRSGQAASQVHAGEGVVRCARPGCVR* | ATGGGAGCTGAGGGCTGGGTCTTTGCGGCGAAGATGAGGGTCGATCAACTGGC CTACAAAGTCCCAGTTCTCGGGCCTCGGGACCAGCGCTTCTTCCCGGTCCCCGGCCC CAGGCCGGCTTCCTCCGGGCTGGCGTCCGGCGCTGCCTCTCAGGTTCA CGCTGGAGAAGGAGTTGGTGAAGGCGTGAGATGAAGTGAGATGAGGTGCTGGTGCCTGCTCAGGTGCTGGTGCCTCGGTGA | 5760 |

Figure 1 (Continued)

| | | | | |
|---|---|---|---|---|
| hsa-mir-365-2 | 1 | MCHQHVEPGRAAASKPTPPTFEGSRRPAPLPASSGSLS* | 5761 | ATGTGTCACCAGCACGTGGAGCCAGGTCGGCTCGCCGCGGCGAGCAAGCCGACCCCC AACTTTCGAGGGGTCTCGCCGCTCTCCCGGCTTCGGTCGGCTCGGCCTCGCTCTC CTAG | 5762 |
| | 2 | MAPVPRQRCGLLAGGCGLLREYGHGSCPARPRPPS* | 5763 | ATGGCCCCCGTGCCAGGCAGCAGGGGTGCGAGCTCGGCTTGCCGGAGGGTGCGGCCT GCTRCGAGAGGTGCGGCCACGGCTCCTGCCGCCCCCCCCCCTCGCCGCCCCGA GCTGA | 5764 |
| | 3 | MGAEGWVFAGEMRVSDQLAYKVPVLGPRDQRLLPGPR PRPASSRAGVRSGQAASQVHAGEGVYRCARPGCVR* | 5765 | ATGGGAGCTGAGGGCTGGGTCTTCGCGGAGATGCGGGTCGGATCAACTGGC CTACAAAGTCCCAGTTCTCGCCGCCGGACCAGCGTCTTCCGCCGTCCTCGCCC CAGGCCGCCGCAGCTCGTCGCGGCAGCTGCCTCGCCGCCAGGTCCA CGCTGGAGAAGGAGGTGTGAGGTGCGCTCGCCCCGGCCTGGCTGCGGTGA | 5766 |
| | 4 | MGQALPLTEACPAVLSRAATLSLGVRTGHPDF* | 5767 | ATGGGCCAAGCCCTGCCACTTACCGAGCCTGCCTGCCTGTGCTTTCCAGGGCGGCA ACCTTGAGCTTGGGGGTGGGAGAACGCGGCCTGACTTCTAG | 5768 |
| hsa-mir-367 | 1 | MVLAVNIDCILQKKKKGSRPTQDHTPPES* | 5769 | ATGGTTTTAGCTGTTAACATTGACATCTGTATACTTCAAAAAAAAAAGGATCC AGACCCACCCAGGATCATACATTCCTGAGAGCTGA | 5770 |
| | 2 | MPFCFLSRQL* | 5771 | ATGCCATTTGTTTCTTCTTTCCTCAGCTCTA | 5772 |
| | 3 | MLGGLPSTLTWKCFL* | 5773 | ATGTTGGGTGGCTCCTTCAACATGAAGTGCTTTCTGTGA | 5774 |
| | 4 | MEVLSVTLKVSASMF* | 5775 | ATGGAAGTGCTTTCTGTGACTTTAAAAGTAAGTCTTCCATGTTTTAG | 5776 |
| hsa-mir-368 | 1 | MDQVEGGGCGPGVGRQSACSL* | 5777 | ATGGACCAGGAGGGGTAGAGGGAAGGCTACAGAGATGGGAAGAGTGGGCAGTCAG CTTGCAGCCTATGA | 5778 |
| | 2 | MKDGKEGYRDRGRVGLRLARAAWHTVLG* | 5779 | ATGAAGGACGGAAAGGAAGGCTACAGAGATAGGGAGTGGCACACAGAGCGT GTTGTCCCAGTCCGGTCACTCCAGGGTCTTCCTTCAAAGCGTGTCTAATGGGAGACAGC CAGAGCGGGCTTGGCACACAGTTTAGGGTAA | 5780 |
| | 3 | MTEPVTPGSSFKACLMGDSVVPVTKLGPESQGRAHQV AALP* | 5781 | ATGACTGAGCCCGGTCACTCCAGGGTCTTCCTTCAAAGCGTGTCTAATGGGAGACAGC GTTGTCCCAGTAACCAAATTGGGACCAGAGTCCATCAGGGCTCATCAGGTGGC CGCTCTGCCTTGA | 5782 |
| | 4 | MILFPLDPAPLVPFSL* | 5783 | ATGATTCTCTTCCCTCTGAATCCAGCCCTGCCTTGA | 5784 |
| hsa-mir-369 | 1 | MDQVEGGGCGPGVGRQSACSL* | 5785 | ATGGACCAGGAGGGGTAGAGGGAAGGCTACAGAGATGGGAAGAGTGGGCAGTCAG CTTGCAGCCTATGA | 5786 |
| | 2 | MKDGKEGYRDRGRVGLRLARAAWHTVLG* | 5787 | ATGAAGGACGGAAAGGAAGGCTACAGAGATAGGGAGTGGCACACAGAGCGT CCAGAGCGGGCTTGGCACACAGTTTAGGGTAA | 5788 |
| | 3 | MTEPVTPGSSFKACLMGDSVVPVTKLGPESQGRAHQV AALP* | 5789 | ATGACTGAGCCCGGTCACTCCAGGGTCTTCCTTCAAAGCGTGTCTAATGGGAGACAGC GTTGTCCCAGTAACCAAATTGGGACCAGAGTCCATCAGGGCTCATCAGGTGGC CGCTCTGCCTTGA | 5790 |
| | 4 | MILFPLDPAPLVPFSL* | 5791 | ATGATTCTCTTCCCTCTGAATCCAGCCCTGCCTTGA | 5792 |
| hsa-mir-370 | 1 | MDQGVEGGGCGPGVGRQSACSL* | 5793 | ATGGACCAGGGGGTAGAGGGGTGGGACCTGGGCGCCAGTCAG CTTGCAGCCTATGA | 5794 |
| | 2 | MKDGKEGYRDRGRVGLRLARAAWHTVLG* | 5795 | ATGAAGGACGGGAAGGAAGGCTACAGAGATAGGGAGTGGCGGGCTGAGGATAG CCAGAGGCGGCTTGGCACACAGTTTAGGGTAA | 5796 |
| | 3 | MTEPVTPGSSPKACLMGDSVVPVTKLGPESQGRAHQV AALP* | 5797 | ATGACTGAGCCGGTCACTCCAGGGTCTTCTTCAAAGCGTGTCAATGGAGACAGC GTTGTCCCAGTAACCAGAGTCCCAGGGAAGGGCTCATCAGGTGGC CGCTCTGCCTTGA | 5798 |
| | 4 | MILFPLDPAPLVPFSL* | 5799 | ATGATTCTCTTCCCTCTGGATCCAGCCCTGCCTTGA | 5800 |
| | 1 | MAEL* | 5801 | ATGGCTGAGCTGTAA | 5802 |
| | 2 | MESGSTQAGVQWRDVSSLQPLPPGF* | 5803 | ATGGAGTCTGGCTCTATCACCAGGCTGGAGTGCAGTGGCGTGATGAGCTCACTG CAACCTCTGCCTCCTGGGTTCAA | 5804 |

Figure 1 (Continued)

| | | | | | |
|---|---|---|---|---|---|
| hsa-mir-371 | 3 | MLFAVSFLSLAHLCSKCCTFSLMKELGLTRKVEHVLPQLARITNGKETLASWGPKSSPSLSHSLP* | 5805 | ATGCTATTTGCTGTCTCATTTCTATCTCTGCCATCCTTTGCAGCAAATGCTGTACATTTTCATTGATGAAGGAACTAGGTTTAATCCATCAGAAAGGTTGAGCACGTACTCCGCAGCTGGCTAGGATTACAACGCAGCTGAAGGAAAGGAAACCCTGGCCTCCTGGGTTAACCAGAAAGGTTGACTTCCTTGAGTCATTTCATTATTTGA | 5806 |
| | 4 | MLYFIDEGTRFNQKG* | 5807 | ATGCTGTACATTTTCATTGATGAAGGAACTAGGTTTAATCAAAGGTTGA | 5808 |
| | 1 | MRGWEGVGFNPIKVEWALTLYKNAAAVNLVLSGRPEVWTYHWPL* | 5809 | ATGAGAGGGTGGGAAGGTGCAGCTGAGTGGGCTCTCACCCTATATAAGAACGCAGCTGCAGTGCAGTGCACGTACTCCGCAGCTGAGGTTGTCTTTCTGCAGACCTGAGGTGTGGACGTATCATTGGCCTCTGTGA | 5810 |
| hsa-mir-371 | 2 | MLFYPLSFYFF* | 5811 | ATGTTATTTATTTCTTCATTTACTTATTTTAG | 5812 |
| | 3 | MKCTGRMMAPCSLDLLGLTLLASSSWDHRRAPPFPCAFFCPFFFFFRRDGVFYVIQAGLELLGSRAILPP* | 5813 | ATGAAGTGCACAGTAGGATCATGGCGCTTGCAGCTCCTGGACTCACCCTTTTAGCCTCCAGTAGCTGGGACCACAGGCGCGCACCATTCCCATGTGCGTTTTCGCTTTTTTTTTTTTTTAGGAGAAGATGGGGTTTTCTAJGTTATCCAAGCTGGTCTCGAACCTCTGGGCTCAAGAGCAATCCTACCACCGTAG | 5814 |
| | 4 | MCVFLLFFFFF* | 5815 | GTCTGCGTTTCGCTTGGCTGAACTGTAA | 5816 |
| | 1 | MAEL* | 5817 | ATGGCTGAGCTGTAA | 5818 |
| hsa-mir-372 | 2 | MESGSITQAGVQWRDVSSLQPLPPGF* | 5819 | ATGGAGTCTGGCTCTATCACCCAGGCTGGAGTGCAGTGGCGTGATGTGAGCTCACTGCAACCTCTGCCTCCCTGGGTTCTAG | 5820 |
| | 3 | MLFAVSFLSLAHLCSKCCTFSLMKELGLTRKVEHVLPQLARITNGKETLASWGPKSSPSLSHSLF* | 5821 | ATGCTATTTGCTGTCTCATTTCTATCTCTGCCATCCTTTGCAGCAAATGCTGTACATTTTCATTGATGAATACAAAGGTTAACCAGAACGTACTCCGCAGCTGGCTAGGATTACAAATGGAAGGAAACCTGGCCTCCTGGGCCCCAAGTCTTCCCCTTCCTTGAGTCATTTCATTATTTTAG | 5822 |
| | 4 | MLYFIDEGTRFNQKG* | 5823 | ATGCTGTACATTTCATTTGATGAAGAACTAGGTTTAATCCAGAAAGGTTGA | 5824 |
| | 1 | MRGWEGVGFNPIKVEWALTLYKNAAAVNLVLSGRPEVWTYHWPL* | 5825 | ATGAGAGGGTGGGAAGGGGTGGGCTTTAAATCCATCAAAGTTGAGTGGGCTCTCACCCTATATAAGAACGCAGCTGCAGTGGCAGTGGCGTGATGTGAGTTGAGACCTGAGGTGTGGACGTATCATTGGCTCTGTGA | 5826 |
| hsa-mir-372 | 2 | MLFYFLSFYIF* | 5827 | ATGTTATTATTCTCTCATTTACTTATTTAG | 5828 |
| | 3 | MKCTGRMMAPCSLDLLGLTLLASSSWDHRRAPPFPCAFFCFFFFFRRDGVFYVIQAGLELLGSRAILPP* | 5829 | ATGAAGTGCACAGTAGGATCATGGCGCTTGCAGCTCCTGGACTCACCCTTCTAGCTCCAGTAGCTGGGACTACAGGCGCGCACCACCATTCCCATGTGCGTTTTCTGCTTTTTTTTTTTAGTAGAGATGGGGTTTCTATGTTATCCAAGCTGGTCTCGAACCTCTGGCCTCAAGAGCAATCCTACCACCGTAG | 5830 |
| | 4 | MCVFLLFFFFF* | 5831 | ATGTGCGTTTCGCTTGCTTGCTGAGCTGTAA | 5832 |
| | 1 | MAEL* | 5833 | ATGGCTGAGCTGTAA | 5834 |
| hsa-mir-373 | 2 | MESGSITQAGVQWRDVSSLQPLPPGP* | 5835 | ATGGAGTCTGGCTCTATCACCCAGGCTGGAGTGCAGTGGCGTGATGTGAGCTCACTGCAACCTCTGCCTCCCTGGGTTCTAG | 5836 |
| | 3 | MLFAVSFLSLAHLCSKCCTFSLMKELGLTRKVEHVLPQLARITNGKETLASWGPKSSPSLSHSLF* | 5837 | ATGCTATTTGCTGTCTCATTTCTATCTCTGCCATCCTTTGCAGCAAATGCTGTACATTTTCATTGATGAATACAAAGGTTAACCAGAACGTACTCCGCAGCTGGCTAGGATTACAAATGGAAGGAAACCCTGGCCTCCTGGGCCCCAAGTCTTCCCCTTCCTTGAGTCATTTCATTATTTTAG | 5838 |
| | 4 | MLYFIDEGTRFNQKG* | 5839 | ATGCTGTACATTTCATTGATGAAGAACTAGGTTTAACCAGAAAGGTTGA | 5840 |
| | 1 | MRGWEGVGFNPIKVEWALTLYKNAAAVNLVLSGRPEVWTYHWPL* | 5841 | ATGAGAGGGTGGGAAGGGGTGGGCTTAATCCATCAAAGTTGAGTGGGCTCTCACCCTATATAAGAACGCAGTGCAGTGGCGTGATGTGAGACCTGAGGTGTGGACGTATCATTGGCTCTGTGA | 5842 |
| | 2 | MLFYFLSFYIF* | 5843 | ATGTTTATTTTCTTCATTTACTTATTTTAG | 5844 |

Figure 1 (Continued)

| | | | | |
|---|---|---|---|---|
| hsa-mir-373 | 3 | MKCTGRMMAPCSLDLLGLTLLASSSWDHRRAPPEPCAF FCFFFFRRDGVFYVIQAGLELLGSRAILPP* | 5845 | ATGAAGTGCACAGGTAGGATGATGGCGCCTTGCAGCTGACCTCCTGGACTCACC CTTTTAGCCTCCAGTAGCTGGGACCTGGGACCACAGGCGCGCACCACCATTCCATGTGCGTTT TTCTGCTTTTTTTTTTCTTCGTCGTTTTAGGAGAGATGGGGTTTCTATGTTATCCAAGCTG GTCTCGAACTCCTGGCCTCAAGCAATCCTACCACCGTAG | 5846 |
| | 4 | MCVELLFFFF* | 5847 | ATGTGCGTTTCTGCTTTCTTTTTTTTTTTAG | 5848 |
| hsa-mir-374a | 1 | MCGNIFFLFLRWGLTLLPRLATS* | 5849 | ATGTGTGGAAATATTTTTTCTTTTTGAGATGGGGTCTCACTCTGTTGCCCAGGC TGGCAACATCATAG | 5850 |
| | 2 | MGSHSVAQAGNIIAHCSLDFLGSSDSSTSAF* | 5851 | ATGGGGTCTCACTCTGTTGCCAGGCTGGCAACATCATAGCTGGCACAATCATAGCT CACTGTAGCCTCTGACTTCCTGGGCTCGAGTGATTCTTCCACCTCAGCCTTCTGA | 5852 |
| | 3 | MSPELVSNS* | 5853 | ATGTCACCCGAGCTGGTCTCGAACTCTGA | 5854 |
| | 4 | MGEGLTKEVWAEGGMMVEASVTEGRGKVEEAEWDSV LGKK* | 5855 | ATGGGAGAGGGATTGACGAAAGAAGTATGGCTGAGGAGGAGGATGGTGGAGG CCAGTGTGACCGAGGGAGGGGAAGAAGGTGGAAGAAGCAGAGTGGGATAGCGGTCCT GGGAAAGAAGTGA | 5856 |
| hsa-mir-374b | 1 | MCGNIFFLFLRWGLTLLPRLATS* | 5857 | ATGTGTGGAAATATTTTTCTTTTTGAGATGGGGTCTCACTCTGTTGCCCAGGC TGGCAACATCATAG | 5858 |
| | 2 | MGSHSVAQAGNIIAHCSLDFLGSSDSSTSAF* | 5859 | ATGGGGTCTCACTCTGTTGCCCAGCTGGCAACATCATAGCTGGCACAATCATAGCT CACTGTAGCCCTCGACTTCCTGGGCTCGAGTGATTCTTCCACCTCAGCCTTCTGA | 5860 |
| | 3 | MSPELVSNS* | 5861 | ATGTCACCCGAGCTGGTCTGAACTCTGA | 5862 |
| | 4 | MGEGLTKEVWAEGGMMVEASVTEGRGKVEEAEWDSV LGKK* | 5863 | ATGGGAGAGGGATTGACGAAAGAAGTATGGCTGAGGAGGAGGATGATGGTGGAGG CCAGTGTGACCGAGGGAGGGGAAGAAGGTGGAAGAAGCAGAGTGGGATAGCGGTCCT GGGAAAGAAGTGA | 5864 |
| hsa-mir-375 | 1 | MHQNILVEASRGEVVLTSRPRVIALPPFCVPR* | 5865 | ATGATCCAGAACATCCTGGTCGAGGCGAGCCGCGGCGAGGTGGTACTCACCTCCG GCCACCGGTCATCGCCGTTCTGCCTGCCCAGGTAA | 5866 |
| | 2 | MPAPSLSIDMPLGVTPGPLSTASKSI* | 5867 | ATGCCCGCGCCAGCCTCCGACATGCCGCTAGGGGTCACGCCTGGGCCTCTCTCC ACCGCCAGTAAAAGCATCTAG | 5868 |
| | 3 | MAGSSPGGLQRRGGNLGPGRMHLSAHTAAGLRPGR* | 5869 | ATGGCAGGGAGCAGCCCCGGCGGACTGCAGAGGCGCGGCGGGAACTTAGGGCCG GGAGGATGCACCTCCGCGCCACACTGGACTGAGACCTGGCGGCGCTAG | 5870 |
| | 4 | MDFHLSVPPNRPGASVLCFSAPPSQRQVGGKVTSGVV PEAPRVPSTLPSAPATKASEKLRSQSPGGGGGSAPPP* | 5871 | ATGGATACCCACCACCTCTCGGTTCCTCCCAGATCCAGGTGGGTGAAAAGTGACATCTGGTGTTGTTC CAGAGGCGCCCAGGGTCCCCAGGGTCCCCCAGCACGCCCCGCCCCCGCCACCAAGGCCTCGG AGAAGCTCCGGCTCCAGAGCCCCGGCGGCGAGGGGGAGCGCTCCGCCTCCATGA | 5872 |
| hsa-mir-376a-1 | 1 | MDQGVEGGGCGPGVGRQSACSL* | 5873 | ATGGACCAGGGGGTAGACGGAGGGGTGGGTGTGGACCTGGGGTCGGGCGCCATGGCAG CTTGCAGCCTATGA | 5874 |
| | 2 | MKDGKEGYRDRGRVGLRIARAAWHTVLG* | 5875 | ATGAAGGACGGAAAGGAGGGCTACAGAGATAGGGGAAGAGTGGGGCTGAGGATAG CCAGAGGGCTTGGCACACAGTTTTAGGGTAA | 5876 |
| hsa-mir-376a-2 | 3 | MTEPVTPGSSFKACLMGDSVPVPVTKLGPESQGRAHQV AALP* | 5877 | ATGACTGAGCGGTCACTCAGGGTCTTCCTTCAAAGCGTGTCTAATGAGAGACAGC GTTGTCCCAGTAACCAAATTGGGACCAGAGTCCCAGGGAAGGGCTCATCAGGTGGC CGCTCTGCCTTGA | 5878 |
| | 4 | MILFFLFDPAPLVPFSL* | 5879 | ATGATTCTCTTCCTCTGATCCAGCCCTCAGTTCCTTTCACTTTGA | 5880 |
| hsa-mir-376a-2 | 1 | MDQGVEGGGCGPGVGRQSACSL* | 5881 | ATGGACCAGGGGGTAGAGGAGGGGTGGGTGTGGACCTGGGGTCGGGCGCCAGTCAG CTTGCAGCCTATGA | 5882 |
| | 2 | MKDGKEGYRDRGRVGLRIARAAWHTVLG* | 5883 | ATGAAGGACGGAAAGGAGGGCTACAGAGGCTACAGAGATAGGGGAAGAGTGGGCTGAGGATAG CCAGAGGGCTTGGCACACAGTTTAGGGTAA | 5884 |

Figure 1 (Continued)

| | | | | |
|---|---|---|---|---|
| hsa-mir-376b | 3 | MTEPVTPGSSFKACLMGDSVVPVTKLGPESQGRAHQVAALP* | 5885 | ATGACTGAGCGGTCACTCCAGGGTCTTCCTTCAAAGCGTGTCTAATGGGAGACAGCGTTGTCCCAGTAACCAAATTGGGACCCAGGGAAGGGCTCATCAGGTGGCCGCTCTGCCTTGA | 5886 |
| | 4 | MILFPLDPAPLVPFSL* | 5887 | ATGATTCTCTTCCCTCTGGATCCAGCCCCTCTAGTTCCCTTTCACTTTGA | 5888 |
| | 1 | MDQGVEGGCGPGVGRQSACSL* | 5889 | ATGGACCAGGGGGTAGAGGGGGAGGTGGGTGGACCTGGGGTCGGGCGCCAGTCAGCTTGCAGCCTATGA | 5890 |
| | 2 | MKDGKEGYRDRGRVGLRIARAAWHTVLG* | 5891 | ATGAAGGACGGAAAGGAGGGCTACAGAGATAGGGGAAGAGTGGGGCTGAGGATAGCCAGAGCGGCTTGGCACACAGTTTAGGGTAA | 5892 |
| | 3 | MTEPVTPGSSFKACLMGDSVVPVTKLGPESQGRAHQVAALP* | 5893 | ATGACTGAGCGGTCACTCCAGGGTCTTCCTTCAAAGCGTGTCTAATGGGAGACAGCGTTGTCCCAGTAACCAAATTGGGACCCAGAGTCCAGGAAGGGCTCATCAGGTGGCCGCTCTGCCTTGA | 5894 |
| | 4 | MILFPLDPAPLVPFSL* | 5895 | ATGATTCTCTTCCCTCTGGATCCAGCCCCTCTAGTTCCCTTTCACTTTGA | 5896 |
| hsa-mir-377 | 1 | MDQGVEGGCGPGVGRQSACSL* | 5897 | ATGGACCAGGGGGTAGAGGGAGGTGGGTGGACCTGGGTCGGGCCAGTCAGCTTGCAGCCTATGA | 5898 |
| | 2 | MKDGKEGYRDRGRVGLRIARAAWHTVLG* | 5899 | ATGAAGGACGGAAAGGAGGGCTACAGAGATAGGGAAGAGTGGGGCTGAGGATAGCCAGAGCGGGCTTGGCACACAGTTTAGGGTAA | 5900 |
| | 3 | MTEPVTPGSSFKACLMGDSVVPVTKLGPESQGRAHQVAALP* | 5901 | ATGACTGAGCGGTCACTCCAGGGTCTTCCTTCAAAGCGTGTCTAATGGGAGACAGCGTTGTCCCAGTAACCAAATTGGGACCCAGAGTCCCAGGAAGGGCTCATCAGGTGGCCGCTCTGCCTTGA | 5902 |
| | 4 | MILFPLDPAPLVPFSL* | 5903 | ATGATTCTCTTCCCTCTGGATCCAGCCCCTCTAGTTCCCTTTCACTTTGA | 5904 |
| | 1 | MAGNDCGALLDEELSSFFLNYLADITQYRPAGAAGPGPGVLSCGGRSCSRGGREAAVGALG* | 5905 | AACTATCTCGCTACAACGGACTCGCGCGCAAGAGCTCTCTCCTTCCTCGGTGCTGAGCGTGCGGGGGCCCAGCGCGGGAGCCGGGACGCAGCGGTGGGAGCCCTGGGGTAA | 5906 |
| | 2 | MRSVTGAGSRRSPGACRSAGGATAAGEGLALAAWSLPPRGQNWGGYPRFLWEVEARHGVGYPQAGAGCWRRAVSARHLLPYFHVDLWPRHGCMPGSPESPSPPGCSPQSAVAGPPRLSTRARSAEFPASCRLKA* | 5907 | ATGCGCTCTGTTACCGGAGCCAGGAGCCGGAGGTCTCCGGCCGCGCTGGAGTCTGCCACCCCGGCGGGCAAAACTGGGGGGTACCGGCCTTCCTTTGGAGGCGGTCTAGCCTTGCGCAGAGCCGGCGACCACGGTGTGGGGGTACCCTCAGGCTGGGTGCAAGCCCGCCTGGGTGCTGGGACTTGTGACCTTGAGTTGTGGACGGCTCATGCCGGGCACTTGCTGGCGGATCTCCAGTTCTAGTCGCAGCGCGCTGTGTGCCGAGCCCCGGGGCGGGGAAGCCGGGAGCCAGGGGGAAGGCCGGAGCCGCCCCCCTGGCATAA | 5908 |
| hsa-mir-378 | 3 | MRAETASSWFRYRAEPPGGKSQAGWGRKDCLGAPGSPCGARPRCALHDAGGREGEAESQALAEPGSPTGDTRVTGEGALVCRGAGERGSWWLGDWERGAAGTSSHQKCQHEACAAPTPSPIFPTQELLQA* | 5909 | ATGCGGGCGGAGACAGCGTCTCCTGGTTCGCTATCGGCGGGACCCCTGGGGGGAAGCCAGGCTGGATGGGCGGAAGGACTGTCTGGGGCGCCCCCTGCGGTGCGCCAGGCACTGGCCCCACGATGGCAGGGGAGGCAGGAAGGAAGCGAGGCGGGTGCGGCCAGGCACTGGCCGAGCCCGGAGCGGCGCACGCGCGTGACAGGAGAGGGTGCTCTGGTGTGGGGAGCCGGGGAGCGGGGGGAAGCTGGTGCTTGGAGAGTGGGAGCGGCTGCTGTGGGAGCAAGCAGCCACCAACAAATTGCCCCACCCAATGCCTGTTGCAAGCATAA | 5910 |
| | 4 | MGAEGLSGGAWVPLRCAAPVRAPRCRGKGRRGGYVPGTG* | 5911 | ATGGGGCGGAGGCGCTCACGATGCAGGGGAAGGGAAGGGAGGCCGGAGTCCAGGCACT | 5912 |
| | 1 | MDQGVEGGCGPGVGRQSACSL* | 5913 | ATGGACCAGGGGGTAGAGGGAGGTGGGTGGACCTGGGTCGGGCGCCAGTCAGCTTGCAGCCTGA | 5914 |

Figure 1 (Continued)

| | | | | |
|---|---|---|---|---|
| hsa-mir-379 | 2 | MKDGKEGYRDRGRVGLRLARAAWHTVLG* | 5915 | ATGAAGGACGGAAAGGAGGGCTACAGAGATAGGGGAAGAGTGGGGCTGAGGATAG CCAGAGGCGGCTTGGCACACAGTTTAGGGTAA | 5916 |
| | 3 | MTEPVTPGSSFKACLMGDSVVPVTKLLGPESQGRAHQV AALP* | 5917 | ATGACTGAGCCGGTCACTCCAGGGTCTTCCTTCAAAGCGTGTCTAATGGGAGACAGC GTTGTTCCCAGTAACCAAATTGGGACCAGAGTCCCAGGGAAGGCGTCATCAGGTGGC CGCTCTGCCTTGA | 5918 |
| | 4 | MILFPLDPAPLVPFSL* | 5919 | ATGATTCTCTTCCCTCTGGATCCAGCCCCTCTAGTTCCCTTTCACTTTGA | 5920 |
| hsa-mir-380 | 1 | MDQGVEGGGCGPGVGRQSACSL* | 5921 | ATGGACCAGGGGGTAGAGGGAGGGCTGCAGAGATAGGGAAGAGTGGGGCTGAGGATAG CTTGCAGCCTATGA | 5922 |
| | 2 | MKDGKEGYRDRGRVGLRLARAAWHTVLG* | 5923 | ATGAAGGACGGAAAGGAGGGCTACAGAGATAGGGGAAGAGTGGGGCTGAGGATAG CCAGAGCGGCTTGGCACACAGTTTAGGGTAA | 5924 |
| | 3 | MTEPVTPGSSFKACLMGDSVVPVTKLLGPESQGRAHQV AALP* | 5925 | ATGACTGAGCCGGTCACTCCAGGGTCTTCCTTCAAAGCGTGTCTAATGGGAGACAGC GTTGTCCCAGTAACCAAATTGGGACCAGAGTCCCAGGGAAGGCTCATCAGGTGGC CGCTCTGCCTTGA | 5926 |
| | 4 | MILFPLDPAPLVPFSL* | 5927 | ATGATTCTCTTCCCTCTGGATCCAGCCCCTCTAGTTCCCTTTCACTTTGA | 5928 |
| hsa-mir-381 | 1 | MDQGVEGGGCGPGVGRQSACSL* | 5929 | ATGGACCAGGGGGTAGAGGGGTGTGGAAGAGTGGGGCTGGGTCGGGCGCCAGTCAG CTTGCAGCCTATGA | 5930 |
| | 2 | MKDGKEGYRDRGRVGLRLARAAWHTVLG* | 5931 | ATGAAGGACGGAAAGGAGGGCTACAGAGATAGGGCAAGAGTTGGGCTGAGGATAG CCAGAGCCGGCTTGGCACACAGTTTAGGGTAA | 5932 |
| | 3 | MTEPVTPGSSFKACLMGDSVVPVTKLLGPESQGRAHQV AALP* | 5933 | ATGACTGAGCCGGTCACTCCAGGGTCTTCCTTCAAAGCGTGTCTAATGGGAGACAGC GTTGTCCCAGTAACCAAATTGGGACCAGAGTCCCAGGGAAGGCTCATCAGGTGGC CGCTCTGCCTTGA | 5934 |
| | 4 | MILFPLDPAPLVPFSL* | 5935 | ATGATTCTCTTCCCTCTGGATCCAGCCCCTCTAGTTCCCTTTCACTTTGA | 5936 |
| hsa-mir-382 | 1 | MDQGVEGGGCGPGVGRQSACSL* | 5937 | ATGGACCAGGGGGTAGAGGGGTGTGGAACCTGGGGTCGGGCGCCAGTCAG CTTGCAGCCTATGA | 5938 |
| | 2 | MKDGKEGYRDRGRVGLRLARAAWHTVLG* | 5939 | ATGAAGGACGGAAAGGAGGGCTACAGAGATAGGGGAAGAGTGGGGCTGAGGATAG CCAGAGCGGCTTGGCACACAGTTTAGGGTAA | 5940 |
| | 3 | MTEPVTPGSSFKACLMGDSVVPVTKLLGPESQGRAHQV AALP* | 5941 | ATGACTGAGCCGGTCACTCCAGGGTCTTCCTTCAAAGCGTGTCTAATGGGAGACAGC GTTGTCCCAGTAACCAAATTGGGACCAGAGTCCCAGGGAAGGCTCATCAGGTGGCC CGCTCTGCCTTGA | 5942 |
| | 4 | MILFPLDPAPLVPFSL* | 5943 | ATGATTCTCTTCCCTCTGGATCCAGCCCCTCTAGTTCCCTTTCACTTTGA | 5944 |
| hsa-mir-383 | 1 | MRDKEGGRYIKHYTCAWQYRITSSPGLFLIIVSRKDPLA YLSPSLQDGPESSHLFIECSRRWNSYCKRKYTTPGESIVL VFQDCFRLIWILIY* | 5945 | ATGAGGGACAAAGAGGGAGGAGGTATATCAAAAACATTATACATGTCTTGGCAATA CAGAACTTCATCATTTGTTTCCGTAAAGACCCCTCTGCC TATCTTTCATTTCTCTGCCAAGATGGACCTAGAGTGACCTAGCCATTTATTATTGAATGTT CCAGAAGATGGAATTCATATGCAAAAGAAATACACTACCCCTGGAGAGAGTATA GTTTTTAGATATTTGAGACTCATTGGATCCGATTCTGATTTATTGA | 5946 |
| | 2 | MCLAIQNFIIWFVPTYCFP* | 5947 | ATGTGCTTGGCAATACAGAACTTCATTTGTTCCTACTTATTGTTCCCGTAA | 5948 |
| | 3 | MDLRVAIYLLNVPEDGIIHLAKENTLPLERV* | 5949 | ATGGACCTGAGAGTAGCCATTTATTTATTGAATGTTCCAGAAGATGGAATTCATATT GCAAAAGAAATACACTACCCCTGGAGAGAGTATAG | 5950 |
| | 4 | MFQKMEFILQKKIHYPWREYSFSISGLF* | 5951 | ATGTTCCAGAAAATGGAATTCATATTGCAAAAGAAAATACACTACCCTGGAGAGA GTATAGTTTTTAGATATTTGGAGATTGTTTTAG | 5952 |
| hsa-mir-409 | 1 | MDQGVEGGGCGPGVGRQSACSL* | 5953 | ATGGACCAGGGGGTAGAGGGAGGTGTGGACCTGGGGTCGGGCGCCAGTCAG CTTGCAGCCTATGA | 5954 |
| | 2 | MKDGKEGYRDRGRVGLRLARAAWHTVLG* | 5955 | ATGAAGGACGGAAAGGAGGGCTACAGAGATAGGGGAAGAGTGGGGCTGAGGATAG CCAGAGCGGCTTGGCACACAGTTTAGGGTAA | 5956 |

Figure 1 (Continued)

| | | | | | |
|---|---|---|---|---|---|
| hsa-mir-410 | 3 | MTEPVTPGSSFKACLMGDSVVPVTKLGPESQGRAHQVAALP* | 5957 | ATGACTGAGCCGGTCACTCCAGGGTCTTCCTTCAAAGCGTGTCTAATGGGAGACAGCGTTGTCCCAGTAACCAAATTGGGACCAGAGTCCCAGGGAAGGGCTCATCAGGTGGCCGCTCTGCCTTGA | 5958 |
| | 4 | MILFPLDPAPLVPFSL* | 5959 | ATGATTCTCTTCCCTCTGGATCCAGCCCCTCAGTTCCTTTCACTTTGA | 5960 |
| | 1 | MDQGVEGGGCGPGVGRQSACSL* | 5961 | ATGGACCAGGGGGTAGAGGGGGGCTACAGAGGAGGGCTGGGGTCGGGCGCCAGTCAGCTTGCAGCCTATGA | 5962 |
| | 2 | MKDGKEGYRDRGRVGLRIARAAWHTVLG* | 5963 | ATGAAGGACGGAAAGGAGGGCTACAGAGATAGGGGAAGAGTGGGGCTGAGGATAGCCAGAGCGGCTTGCACAGTTTAGGGTAA | 5964 |
| hsa-mir-411 | 3 | MTEPVTPGSSFKACLMGDSVVPVTKLGPESQGRAHQVAALP* | 5965 | ATGACTGAGCCGGTCACTCCAGTAACCAAATTGGGACCAGAGTCCCAGGGAAGGCTCATCAGGTGGCCGCTCTGCCTTGA | 5966 |
| | 4 | MILFPLDPAPLVPFSL* | 5967 | ATGATTCTCTTCCCTCTGGATCCAGCCCCTCAGTCCTTTCACTTTGA | 5968 |
| | 1 | MDQGVEGGGCGPGVGRQSACSL* | 5969 | ATGGACCAGGGGGTAGAGGGAGGTGGTGTGGACCTGGGGTCGGGCGCCAGTCAGCTTGCAGCCTATGA | 5970 |
| | 2 | MKDGKEGYRDRGRVGLRIARAAWHTVLG* | 5971 | ATGAAGGACGGAAAGGAGGGCTACAGAGATAGGGGAAGAGTGGGGCTGAGGATAGCCAGAGCGGGCTTGCACACAGTTTAGGGTAA | 5972 |
| hsa-mir-412 | 3 | MTEPVTPGSSFKACLMGDSVVPVTKLGPESQGRAHQV AALP* | 5973 | ATGACTGAGCCGGTCACTCCAtGGGTCTTCCTTCAAAGCGTGTCTAATGGAGACAGCGTTGTCCCAGTAACCAAATTGGGACCAGAGTCCCAGGGAAGGCTCATCAGGTGGCCGCTCTGCCTTGA | 5974 |
| | 4 | MILFPLDPAPLVPFSL* | 5975 | ATGATTCTCTTCCCTCTGGATCCAGCCCCTCAGTTCCTTTCACTTTGA | 5976 |
| | 1 | MDQGVEGGGCGPGVGRQSACSL* | 5977 | ATGGACCAGGGGGTAGAGGGGTAGAGGAGGGCTACAGAGGAGGTGGGGTCGGGCGCCAGTCAGCTTGCAGCCTATGA | 5978 |
| | 2 | MKDGKEGYRDRGRVGLRIARAAWHTVLG* | 5979 | ATGAAGGACGGAAAGGAGGGCTACAGAGATAGGGGAAGAGTGGGGCTGAGGATAGCCAGAGCGGGCTTGCACACAGTTTAGGGTAA | 5980 |
| | 3 | MTEPVTPGSSFKACLMGDSVVPVTKLGPESQGRAHQV AALP* | 5981 | ATGACTGAGCCGGTCACTCCAGGGTCTTCCTTCAAAGCGTGTCTAATGCAGACAGCGTTGTCCCAGTAACCAAATTGGGACCAGAGTCCCAGGGAAGGCTCATCAGGTGGCCGCTCTGCCTTGA | 5982 |
| | 4 | MILFPLDPAPLVPFSL* | 5983 | ATGATTCTCTTCCCTCTGGATCCAGCCCCTCAGTTCCTTTCACTTTGA | 5984 |
| hsa-mir-421 | 1 | MTITKNV* | 5985 | ATGACAATTAACATGACATGCATGTTTATAA | 5986 |
| | 2 | MFNMDMRML* | 5987 | ATGTTTAACATGGACATGCATGTTATAA | 5988 |
| | 3 | MLKTKHNK* | 5989 | ATGTTAAAAACAAAACACAATATAAAATAG | 5990 |
| | 4 | MQRMK* | 5991 | ATGCAGAGAATGAAGTGA | 5992 |
| | 1 | MVYGRGAHKYHFLRIYPDHVIRISSFKSISR* | 5993 | ATGGTGTGGGAGAGGAGCACACAAGTACCACATTTCTGAGGATTGTGCCAGACCATGTCATACGTATAAGCTCATTCAAATCGATTTCCAGATAA | 5994 |
| | 2 | MSYV* | 5995 | ATGTCATACGTATAA | 5996 |
| hsa-mir-422a | 3 | MCAVEPVGTRRGSCYRLSPLSRESGSPEVSPTRPGSWAL APGLSGGJSSRGRPEPRPGQPGAAPPAGAWDGAGRSAPS APRLLGGRVPGALGGEDCRAEPSAPRRVPPRSRRARRARRARRSRRAACRGRDRGSSASRRE* | 5997 | ATGTGCGCGGTAGAGCCCGGTAGGAGCCGCAGAGGGTCTTGCTACCGACTCTCCCGCTCTCCGGAGAGTCTGGGAGCCCTGAGGTCCCTACCGGCCGGGAAGCTGGGACCCGGGACTGTCCGGAGGGCTCAGCAGGGGCGCCGAGCCCGTCCGGGCAGCCGGCCCTCAGCTGGTCTGGGCGGGGCGCGCTGGGACGGCCTGCGGCCACCCCCTCCGGCTCCTAGCTGCTCGCGGGGACCCAGCGACCCGCGGGGCTCCCGTTCCGCGAGAGGACTGCAGGGCCGGACCGGGCACCCAGCCTCAGCCTGAGGTAG | 5998 |
| | 4 | MGGTGRAA* | 5999 | ATGGCGGGACCGGGCGCGGCAGGCAGTGA | 6000 |
| | 1 | MAPGRQ* | 6001 | ATGGCGATTCCGGGCAGGCAGTGA | 6002 |

Figure 1 (Continued)

| | | | | | |
|---|---|---|---|---|---|
| hsa-mir-423 | 2 | MRNYGDCIFGRGVLNALEVKGLCRQG* | 6003 | ATGAGAAACTACGGTGACTGTATCTTTGGCCGAGGAGTTTAAATGGCTGGAAGTG AAGGGACTGTGTCGAAGTGA | 6004 |
| | 3 | MRWK* | 6005 | ATGCGCTGGAAGTGA | 6006 |
| | 4 | MEARSLREKLVRK* | 6007 | ATGGAAGCCGAAGTTTGAGCGAGAAAACTTGTGAGGAAATAA | 6008 |
| hsa-mir-424 | 1 | MIQMSNCLYLTLFVYLQK* | 6009 | ATGATCCAGATGTCAATGCCTCTTAACCTTATTCGTCTACCTTCAGAAGTAA | 6010 |
| | 2 | MVKL* | 6011 | ATGGTCAAGTTATAA | 6012 |
| | 3 | MVQNVRRCYTFSWGR* | 6013 | ATGGTTCAAAACGTGAGGCGCTGTATACCCCCTGTGGGAAGGTAG | 6014 |
| | 4 | MMLHFGTPFPCSGRM* | 6015 | ATGATGCTTCATTTTGGCACCCCTTTCCTGCTCAGGTAGAATGTAA | 6016 |
| | 1 | MGEVYKLLC* | 6017 | ATGGGAGAAGTGTATAAATTATTGTGA | 6018 |
| | 2 | MLISKISAKG* | 6019 | ATGTTGATAAGCAAGATAAGTTGCCAAAGGGTAG | 6020 |
| hsa-mir-425 | 3 | MRAAPVTRPS* | 6021 | ATGAGAGCAGCTCCAGTTACTCGGCCTTCATGA | 6022 |
| | 4 | MTQEVEGGTCRGLQRKGQHQPV* | 6023 | ATGACACAGAAGTTGAAGGTGCACAGGCATTGGGCTGCAAAGAAAAGGCCAGCA TCAGCCTGTCTAG | 6024 |
| hsa-mir-425 | 1 | MGSQGSRVGRAGWVPEAEAQCTSGAQRAAMLEQRRR RRGASWVPAAAPVCGWSRGHPSRAAEGRPARRQCGRASG QLFDPRPPAWPRPTPPPPRAQRPHPGAVRSR* | 6025 | ATGGGGTCTCAGGGTCAAGGGTCGTTAGGGTGGTATGGCGTGGCTGGTTCCGGAAGCGGAAGC GCAGTGCACTTCCGGCGCGTCTTGGGTCCCGGCGCAGCGGAGCGGAGGCGGCGCA GAGGCGCGTCTTGGGTCCCGCGGCGGCGCCATGTTGGAGCAGCGGAGGCGGCGCA GCGCGCGAGAGGCGCCGTGAGGCGGCAAGGGCAAGCGGCCAAC TCTTCCCGGACCCGGGTCTTCCGCGGGCCTCAGCCGAGACCCCCGACCCCCCTCAAC CCCGCGCCCAGCGACCCCAGGGGCTGTGCGGGTCGGGTCCGGTAG | 6026 |
| | 2 | MCKDCAWRTVSGEGKCPRHLRIQECFQTKSPRAFPPGY SEDFCCIRAVGRNYTDGPHGPRDLPDPG* | 6027 | ATGTGCAAGGATTGTGCTTGGGAGGGAAGTTGCCAAGACA CCTGAGGATCCAAGAATGTTTCAAACAAAGAGCCCTAGGGCATTCCTCCAGGGTA TTCTGAAGACTTCATCTGCTGCATTAGAGCGCGTTGGGAAGAACTACAGACGGGC CTCATGCGCCCAAACAAAGAGCCCTAG | 6028 |
| | 3 | MFPNKEP* | 6029 | ATGTTTCCAAACAAAGAGCCCTAG | 6030 |
| | 4 | MARGTCLILADLMLWCSWGAASCFWEPSVLGWVLDV SYD* | 6031 | ATGGCCCGAGGCACCTGTCTGATCTTTTAATGCTCGTGGCAGCTGG GGAGCTGCCTCTTGCTTCTGGAACCCTGCAGTTTGGGTTGGGTATTAGATGTTAGT TATGATTGA | 6032 |
| | 1 | MGCRQPGQRPGELRSLQTQAGAGPSPPQGKVGPCADA AGFRVWSHLGPTGCVFRARAQCVGSRHGVYPSGQGLGR GQAPRGVTFLPPT* | 6033 | ATGGGCTGTCGCCAGCCTGGCCAGGGAGCTCCGGTCACTGCAGACACA GGCTGAACCCGGACCGGTCCTTCAGGGAAAGTGGGCCCCTGCCAGATCGG CTGGGTTCGGGGTGGCGCTCCAGGATCATCTTGGACCCACGGGCTGCGCTTCCGGGCACGGG CACAGTGTGTGGCCTCCAGGAGGGTCACTTCTTGCCGCTACCTGA | 6034 |
| | 2 | MRLGFGCGAILDPRAASSGHGHSVWAPGMGCPQGRAW AEGRLREGSRSCRLFDSRPSRKFSPEAATAVLRHFVRRR EAVASEVGA* | 6035 | ATGCGGCTGGGTTTCGGGTGTGGAGCCATCTTGGACCCACGGGCTGCTTCTTCCGGG CACGGACACAGTGTGTGGGCTCCAGGCATGGAGTGCCCCAAGGCAGGGCTGGGC AGAGGGCAGGCTCGAGAGGCACCTCGAGAGTTCTGCGCTACCTGAGCACTTTGTGCGGAGAC CTAGAAGTTCTCTGCCTCAGAAGTTGTGTGCGTAG | 6036 |
| | 3 | MTASPLGSGVCGGKGLVSAPSGQRPAEPMGGEVGAWG RGWSGTGAQPGEAGAGSQAPRYDWGGGNVSREVFY LNVKRLSTVAAAGNKVRPTEAQP* | 6037 | ATGACCGGTCTCCTGGCTGGGTGCTGGGGAAGGCTGGTTTCAGCA CCCTCTGGTCAGAAGCCGGACCGGGCGGTCGGGGAAGGCCCCCAGG TGGCTGCTGGTACTGACCAGTTGGGGGCTCAGAAGGTGAGCGGTTCCAGG CCCGCGCTATGACTGGGGTGGGGAACGTCTCTGTGAGGTTTTTACTTAAATG TGAAACGGCTCAGTAGGCTGGCGCAGCGGGAACAAGGTCCGACCCCACCGAGGCC CAGCCTTGA | 6038 |
| | 4 | MTGVGATSLVRFT* | 6039 | ATGACTGGGGTGGGGCAACGTCTCGTGAGGTTTTACTTAA | 6040 |
| | 1 | MVNPILCT* | 6041 | ATGGTTAATCAATTCTGTGCACCTGA | 6042 |
| hsa-mir-429 | 2 | MTERMNGHMND* | 6043 | ATGACAAGAAATGAATGGACATGAACGACTGA | 6044 |

Figure 1 (Continued)

| | | | | |
|---|---|---|---|---|
| hsa-mir-431 | 3 | MEMPGTARKELPMGLSPISLWAPEVHKREKRQEEKCQGVKIDRAKERQK* | 6045 | ATGGAAATGCCTGGCACAGCCAGGAGGAGCTGCCCATGGGATTGTCATTCATCTCACTCTGGGCACCTGAGGTCCATAAGCGTGAAAGAGGCAGGAAGAAGTGTCAGGGAGTCAAAGATAGAGCTAAGGAAAGGCAAAAATGA |
| | 4 | MKLNESERENKEKPIKKRTNTWVYL* | 6046 | ATGAAACTAAATGAAAGRGAAAATAAAGAAAATAAAGAGAAA |
| | | | 6047 | CGAATACGTGGGTATCTGTAA |
| | 1 | MVNPILCT* | 6048 | ATGGTTAATCAATTCTGTGCACCTGA |
| | | | 6049 | |
| | 2 | MTERMNGHMND* | 6050 | ATGACAGAAGAATGAATGGACAATGAACGACTGA |
| | | | 6051 | |
| hsa-mir-432 | 3 | MEMPGTARKELPMGLSPISLWAPEVHKREKRQEEKCQGVKIDRAKERQK* | 6052 | ATGGAAATGCCTGGCACAGCCAGGAGGAGCTGCCATGGGATTGTCATTCATCTCACTCTGGGCACCTGAGGTCCATAAGCGTGAAAGAGGCAGGAAGAAGTGTCAGGGAGTCAAAGATAGAGCTAAGGAAAGGCAAAAATGA |
| | | | 6053 | |
| | 4 | MKLNESERENKEKPIKKRTNTWVYL* | 6054 | ATGAAACTAAATGAAAGCGAAAATGAAAAGAAAACCAATAAAAGAGAAACGAATACGTGGTGTATCTGTAA |
| | | | 6055 | |
| | 1 | MVNPILCT* | 6056 | ATGGTTAATCAATTCTGTGCACCTGA |
| | | | 6057 | |
| | 2 | MTERMNGHMND* | 6058 | ATGACAGAAAGAATGAATGGACACATGAACGACTGA |
| | | | 6059 | |
| hsa-mir-433 | 3 | MEMPGTARKELPMGLSPISLWAPEVHKREKRQEEKCQGVKIDRAKERQK* | 6060 | ATGGAAATGCCTGGCACAGCCAGGAGGAGCTGCCATGGATTGTCATTCATCTCACTCTGGGCACCTGAGGTCCATAAGCGTGAAAGAGGCAGGAAGAAGTGTCAGGGAGTCAAAGATAGAGCTAAGGAAAGGCAAAAATGA |
| | | | 6061 | |
| | 4 | MKLNESERENKEKPIKKRTNTWVYL* | 6062 | ATGAAACTAAATGAAAGCGAAAATAAAGAAAACCAATAAAAGAGAAACGAATACGTGGGTATCTGTAA |
| | | | 6063 | |
| hsa-mir-443 | 1 | MLSADWLLLAPPLIPLLAQERGADSPARGRRSGACCGRFLPQMHRSSRYCLWSG* | 6064 | ATGCTGAGTGCTGATTGGCTGCTCTCGCCCTCATCCGCTTTTGGCCAAGAGCGTGGTGCAGATTCACCTGCCGTAGGCGCTCTGGTGCTTGGCGGAAGGACGCTTCCTTCCTCAGATGCACGTCACGGGTCGATACTGCCTTTGGAGGGCTAG |
| | | | 6065 | |
| | 2 | MNSSSVVCTSLSSESSRSSWRSCDGLRPFRVV* | 6066 | ATGAACTCTTCTTCTGTGCTGTACATCGTTGTCGTCGGAGTCGTCGATCGTCGTCGTGGCGCTCGTGTGATGGCCTTGTGCCCGTTTAGAGTAG |
| | | | 6067 | |
| | 3 | MAFVRLE* | 6068 | ATGGCCTTCGTGAGGCTGTTTAGAGTAG |
| | | | 6069 | |
| | 4 | MLEVVSY* | 6070 | ATGCTCGAGGTCGTCAGTTACTAA |
| | | | 6071 | |
| hsa-mir-449a | 1 | MVPWGTPCSGGGRSGGPGGRW* | 6072 | ATGGTACCCTGGGGAACACCTTGCAGCGGGCGGTGGGAGGAGGTGGGGGACCTGGAGG |
| | | | 6073 | |
| | 2 | MVLGDGTPGV* | 6074 | ATGGTCCTGGGGACGGGACTCCAGGGGTTGA |
| | | | 6075 | |
| | 3 | MEWKLERTAPRRVRTEEEMLWVSNTLFCILPNSLMRGRRPRS* | 6076 | ATGGAGTGGAAACTGGAGCGCACCGCGCCTCGGAGGTCCGCACGGAAGGAGATGCTGTGGGTGAGTAACACCCTTTTCTGCATTCTCCCTAACCTCTAATGCGGGGCCGAAGGCCCGTTCATAA |
| | | | 6077 | |
| hsa-mir-449b | 4 | MIFLNSFSLNMLSYFSKESIMRVLSKDLKQKRSQDSANVSPGLVLVLCFNSDLEQTNSW* | 6078 | ATGATTTTCCTAAATAGTTTCTCCCTCAATATGTTATCTGTTTCAAGGAAAGTATCATGCGTGTGCTCTCAAAGACTTGAAGCAGAGAAGATTCGCAACTGAGTCCAGGGTCTGTTCTCGTTTTAATTCTGATCTTGAACAAACGAATTCTTGGTAA |
| | | | 6079 | |
| | 1 | MVPWGTPCSGGGRSGGPGGRW* | 6080 | ATGGTACCCTGGGGAACACCTTGCAGCGGGCGGTGGGAGGAGGTGGGGGACCTGGAGG |
| | | | 6081 | |
| | 2 | MVLGDGTPGV* | 6082 | ATGGTCCTGCGCGACGGGACTCCAGGGGTTGA |
| | | | 6083 | |
| | 3 | MEWKLERTAPRRVRTEEEMLWVSNTLFCILPNSLMRGRRPRS* | 6084 | ATGGAGTGGAAACTGGAGCGCACCGCGAGCGCACCGCCTCGGAGGGTCCGCACCCTTTTCTGCATTCTCCTAACTCTCTAATGCGGGGCCGAAGGCCCG |
| | | | 6085 | |
| | | | 6086 | |

Figure 1 (Continued)

| | | | | | |
|---|---|---|---|---|---|
| | 4 | MIFLNSFPSLNMLSVFSKESIMRVLSKDLKQKRSQDSANVSPGLVLVLCFNSDLEQTNSW* | 6087 | ATGATTTCCTAAATAGTTCTCCTCAATATGTTATCTGTGTTTCAAAGGAAAGTATCATGCTGTGTCTGCTCTCCAAAGACTTGAAGCAGAAGAGAAGTCAAGATTCCGCCAACGTGAGTCCAGGGCTTGTTCTGTTCTCTGTTTAATTCTGATCTTGAACAAACGAATTCTTGGTAA | 6088 |
| hsa-mir-450a-1 | 1 | MIQMSNCLYLTLFVYLQK* | 6089 | ATGATCCAGATGTCCAATTGCCTCTACTTAACCTTATTGGTCTGAGAAGTAA | 6090 |
| | 2 | MVKL* | 6091 | ATGGTGAAGTTATAA | 6092 |
| | 3 | MVQNVRRCYTPSWGR* | 6093 | ATGGTTCAAAACGTGAGGCGTGTATACCCCTCGTGGGAAGGTAG | 6094 |
| | 4 | MMLHFGTPFPCSGRM* | 6095 | ATGATGCTTCATTTTGGCACCCCTTTCCGTGCAGGTAGAAATGTAA | 6096 |
| | 1 | MIQMSNCLYLTLFVYLQK* | 6097 | ATGATCCAGATGTCCAATTGCCTCTACTTAACCTTATTGTCTCAGAAGTAA | 6098 |
| hsa-mir-450a-2 | 2 | MYKL* | 6099 | ATGGTGAAGTTATAA | 6100 |
| | 3 | MVQNVRRCYTPSWGR* | 6101 | ATGGTTCAAAACGTGAGGCGTGCTATACCCCTCGTGGGAAGGTAG | 6102 |
| | 4 | MMLHFGTPFPCSGRM* | 6103 | ATGATGCTTCATTTTGGCACCCCTTTCCGTGCTCAGGTAGAAATGTAA | 6104 |
| hsa-mir-450b | 1 | MIQMSNCLYLTLFVYLQK* | 6105 | ATGATCCAGATGTCCAATTGCCTCTACTTAACCTTATTGTCTCAGAAGTAA | 6106 |
| | 2 | MVKL* | 6107 | ATGGTGAAGTTATAA | 6108 |
| | 3 | MVQNVRRCYTPSWGR* | 6109 | ATGGTTCAAAACGTGAGGCGTCTATACCCCTCGTGGGAAGGTAG | 6110 |
| | 4 | MMLHFGTPFPCSGRM* | 6111 | ATGATGCTTCATTTTGGCACCCCTTCCGTGCTCAGGTAGAATGTAA | 6112 |
| hsa-mir-451 | 1 | MLVGAGMLAVSASCCCYPWEPGNVALGQGPA* | 6113 | ATGCTGGTAGGCGCGGGTAATCTGCAGTTCAGCTTCTGCGTTGTTGCTACCCTTGGGAACCTGGCAATGTGCCCTGTGAGCAAGGCCCAGCTGA | 6114 |
| | 2 | MLPLAKAQLELWQPAFQAKE* | 6115 | AAGTTGCCCTTGCCAAGGCTCAGCTGAGCTGTGGCAGCCTGTCCCAAGCCAAAGAATAA | 6116 |
| hsa-mir-452 | 3 | MPVIPALWAPKAGRSPEVRSSRPARPTWRNPISTNNLKISQTWWWLPVIPATWEAEAGESLESGRRKLH* | 6117 | ATGCCTGTGATCCCAGCACTTTGGGCACCTAAGGCACAGGCAGATCCAGAGGTTCGAGCAAGTTCAGGTCAGCCCGGCTCAACATGGCGAAACCCATCTCTACTAACAATTTAAAGATTAGCCAGACGTGGTGGTTGCCTGTAATCGCAGCACTTGGGAGCGCGGAAGTTGCATTGAAGGAGAATCACTTGAATCTGGGAGGCGGAAGTTGCATTGA | 6118 |
| | 4 | MAKPHLY* | 6119 | ATGGCGAAACCCCATCTCTACTAA | 6120 |
| | 1 | MLSKVLPVLLGILLIHLQSR* | 6121 | ATGTTGTCCAAAGTTCTTCCAGTCCTCCTAGGCATCTTATTGATCCTCCAGTCGGGTTGA | 6122 |
| | 2 | MRAGLGPPHCRMGSRGP* | 6123 | ATGCGCGCGCTCGGCCTCGGACCGCCGCACTGTAGGATGGGCTCCGGGGTCCTTGA | 6124 |
| hsa-mir-453 | 3 | MCECCLVCSLLTFFLRVPIEFQALRQATLTLLASHAAAPVGASLRHELWFSLRVPAPAMPPLHR* | 6125 | ATGTGTGAGTGTTGCCTGGTCTGCTCGTTGTTACATTTTTTAAGAGTGCTACTGAGTTCCAGGCACTCTCGACAAGGCAGCCAACTCTGACATTACTGCTCCATGCCGCTGCTCCTGTTGGTGCCAGTCAAGGCACGAGCTCTGGTTAGTCTAAGGGTTCCGCAC | 6126 |
| | 4 | MPLLLLVPYSGTSFGLV* | 6127 | ATGCCGCTCTCCTCCTGTTGTGCCAGTCAAGCGCACGAGCTTTGGTTAGTCTAA | 6128 |
| | 1 | MDQGVEGGCGPGVGRQSACSL* | 6129 | ATGGACCAGGGCGGTGAGGGTAGAGGAGGGCTGGGGTCGGGCGTCCAGTCAG | 6130 |
| hsa-mir-454 | 2 | MKDGKEGYRDRGRVGLRIARAAWHTVLG* | 6131 | ATGAAGGACGGAAAGGAGGGCTACAGAGATAGGGGAAGAGTGGGCTGAGGATAGCCAAGGGGCTTGGCACACAGTTTTAGGGTAA | 6132 |
| | 3 | MTEPVTPGSSFKACLMGDSVYPVTKLGPESQGRAHQVAALP** | 6133 | ATGACTGAGCCGGTCACCCCAGGTTCTTCCTTCAAAGCGTGTCTAATGGGAGACAGCGTTGTCCAGTAACCAAATTGGGACCAGAGTCCCAGGGAAGGCTCATCAGGTGGCCGCTCTGCCTTGA | 6134 |
| | 4 | MILPLLRPAPLVPFSL* | 6135 | ATGATTCTCTTCCTCCTGAGATCAGCCCCTCTAGTTCCTTCACTTGA | 6136 |
| hsa-mir-454 | 1 | MGGSRWNGGANECEMLSDSCPMEALRASTACGLSAAAVCGMSTIQHGGGR* | 6137 | ATGGGCGGGAGCCGGTGGAACGGGGAACGAGGAGCAATGAGCTAGTACGCTGCGGTCAACATGGAGGCGGAGTGCGATAA | 6138 |
| | 2 | MSARC* | 6139 | ATGAGTGCGAGATGTGA | 6140 |

Figure 1 (Continued)

| | | | | |
|---|---|---|---|---|
| | 3 | MEAEVIDKLELMVSAK* | 6141 | ATGGAGGCGGAGGTCGATAAGCTGGAACTGATGGTGAGTGCAAAGTGA | 6142 |
| | 4 | MASEVGHNLESPETPGGgGWTRVEFPPAPKGAAITVW CLNRLG* | 6143 | ATGGCCTCGGAGGTGGGGCACAACTTGGAGTCGCCGAAAACTCCGGCGGCGGAGG CTGGACCAGAGTCGAGTTCCCTCCTGCACCAAAGGGAGCCGCCACCGTCTGGTG TCTAAACCGCCTCGGGTAA | 6144 |
| hsa-mir-455 | 1 | MGNHCYPLDNNYCLVGNHCYLLENKYCLMGKHCYLL DNKY* | 6145 | ATGGGTAACCACTGTTACCCACTGTGAAATAATATTATTGCCTTGTGGTAACCACTGT TACCTGCTGGAAATAATATATTGCCTCATGGGTAAACACTGTTACCTGCTGGATAAT AAGTATTGA | 6146 |
| | 2 | MGNTCYPVDNKYGLMGNHC* | 6147 | ATGGGTAACACCTGTTACCCTGTGGATAATAAGTATGGCCTCATGGGTAACCACTGT TAA | 6148 |
| | 3 | MASWVTVNRWHSTGSWVTTVTQWHSIPSWVTTVTIW WHSTASSVTTVTVTRWHNIASWVATVTQWHSIASWVTTHT WWHSVASWLTTVIQWHSVAS* | 6149 | ATGGCCTCATGGGTAACCACTGTTACCGTGGATAATAAGTACTGGCTCATGGGTA ACCACTGTTACCCAGTGGATAATAAGTATTCCTTCATGGGATGGACAGTGTACCTGG TGGATAATAAGTACTGGCTCATCAGTAACCACCTGTTACCTGGTGGATAATAAGTATT GCCTCATGGGTAGCCACTGTTACCCAGTGGATAATAAGTGTTGCCTCGTAACACTGT TGCCTCATGGGTAACAGTGTTACCACTGTTACCCAGTGAATAAGTATTGTGCTCTGGGT ACTATTACCTGGTGGATAATAAGTGTTGCCTCTGGTAACCACTGTTACCCAGTGGAT AATAAGTGTCCAGTGGAACAGTGTTGCCTCGTTAATAATAAGTGTTGCCTCAGTGG ATAATAAGTGTTGCCTGTGA | 6150 |
| | 4 | MGNHCYPVDNKYSFMGNHCYLVDNKYCLISNHCYSV DNKYCLMGSHCYLVDNKYCLVGNHYYLVDNKCCLLV NHCYPVDNKCCLVSNHCYLLDNNCCLMGNHCYPMHH KCCLVGNHCYQVDNKYFLWVTTVTRCHSVAFCVTTVT QWTHSIASWITTVTKWKHIASWVTTVTLWHGIASWVTT ATRWVISITSWVNTVTQWHSVASWVTSYTRWHNVA* | 6151 | ATGGGTAACCACTGTTACCCAGTGGATAATAAGTATTCCTTCATGGGTAACCACTGT TACCTGGTGGATAATAAGTACTGCCTCATCAGTAACCACTGTTACCTGGTGGATAAT AAATATTGCCTCATGGGTAGCCACTGTTACCCAGTGGATAATAAGTATTGCCTCTGT GGTAACCACTATTACCTGGTGGATAATAAGTGTTGCCTCGTTAACCACTGTTAT TGTGCCTCATGGGAACCACTGTTACCAATGCATCATAAGTGTTGCCTCTGGATAAATAAT AACCACTGTTACCAAGTGGATAATAAGTATTTCTGTGGGTAACCACTGTTACCCGG TGTATAATAAGTGTTGCCTTCTACCAGTGGACAATAAGTATTGCCTCATGGGTAACC GCCTCATGGATAACCACTGTTACCAGTATTGCCTGTGGGTAACCACTGTTACCCATGGGTAACC ACTGTTACCCTGTGGATAATAAGTGTTACCCGTGGTAACCACTGTGATAATAAGTGTTGCC TCGTGGGTAACCAGTGTTACCCGTGTTACCCAGTGAATAAATGTTGCTTAG | 6152 |
| | 1 | MCDSCLAGPGLRGAG* | 6153 | ATGTGTGATTCGTGCCTTGCGGGCCAGGAGACGGGGAAGCGCTGCGGGTAA | 6154 |
| | 2 | MLTRCQRDRERKTGVGGARMERGVGRSHGRRHIRDI SPTPPLALSATFPNRSPGRGGEGLLV* | 6155 | ATGTTGACCAGGTGCCAGCGAGATCGCGAGCGGGAGAAGACGGGGGTGGCGGGGGCCA GGATGGAGAGGGGGCCAGTTGGCACGGCCATGCGGCAGGAGTCGGACATC TCCCCACACGCCCCCTCTGCTCTGTCCGCAACATTCCAAACAGAGTCCGGAGA GGGGAGAGGGGCTGCTGGTCTGA | 6156 |
| hsa-mir-483 | 3 | MADATFATSPPHPLWLCPQHFQTGVPGEGERGCWSEA KKGRAPDFERGRGPCPVGGSVEVSHQQGGKETPPFTALC RDEPGVQDGSPWHFATGWSRAPGWGCRREETGWEEG BGGSKGAGEWSAGRGVGGRVEPGLGGVGSHKAEALT SLQTGH* | 6157 | ATGGCAGACGCCACATTCGCGACATTCTCCCACACGCCCCTCTGGCTCTGTCCGCAA CATTTCCAAACAGAGCCTGGACCCGGAAGGGCAGAGGCCGGGCTGCTGGTCTGAGGCTAA GAAGGGCAGAGCTTCGATACAAGGAGGTGGGAAGGGAGACCCCCCCGTTCACTGCCTGT TGGAAGTTTCATACAAGGAGGTGGGAAGGGAGACCCCCGTTCACTGCCTGT GCAGAGATGAGCGGGGTGCAGGATGGGAGCCATGGCACTTCGCTACGGATGG TCCAGGGCTCCGGGTTGGGGCGTCAGGAAGCAGAAGAGACTGGGAGAGGGAG AGGGCGGGAGCAAGGCGGGGAAGGCGGGAGGGAGTGGTCAGCAGGGAGGGGGGGTAG GTGGGAGCCGGACCCGGGGCTGGGAGGAGTCGCTCACACATAAAAGCTGAGGCACTGACCA GCCTGCAAACTGGACATTAG | 6158 |
| | 4 | MSRGCRMGAHGTSLRDGPGLPVGGAGEKRLAGRRERA GAKARGSGQQGEGWGVGWSPGWEESAHT* | 6159 | ATGAGCCGGGGTGCAGAATGGCAGAATGGGAGCCCATGCCACTTGCTACGGATGGTCAGG GCTCCCGGTTGGGGTGCAGCGCGGGAGAGAAGAGACTGCTGGGAGGAGAGGCG GGAGCAAAGGCGCGCGGGAGGGAGTTGCTCAGCAGGGAGGCGTGGGGGTGGGTGA GCCTGGGCTGGGAGGAGTCGGCTCACACATA | 6160 |

Figure 1 (Continued)

| | | | | |
|---|---|---|---|---|
| hsa-mir-483 | 1 | MAERGRGRGPGGREIPPAAPSPWLGLGGGGLAGCGHLC VVFDLVKITVLSYIVQTLQEMVSPDPQHVVAPETELAS MQVQRTEDGVTIIQJFWVGRKGELLRRTPVSSAMQVGF ELCFPP* | 6161 | ATGGCGGAGCGAGGGGGCGAGGGGGCGAGGGGGCCAGGGGGCGCGAGATTCCGCCGGCGG CCCTTCCCCTTGGCTAGGCTTAGGCGGCGGAGGGCTGGCGGGGTGGAGATTTGT GGTGGTTTTGACTGGTAAAATCACAGTGCTTCTTACATCGTTCAAACTCTCA GAGATGGTTCCCAGATCCAACGCACTGAGGACGGGGTAACCATTATCCAGATATTTGGGT GCTATGCAAGTCAAGTCAACGCACTGAGGACGGGGTAACCATTATCCAGATATTTGGGT GGGCCGCAAAGGCGAGCTACTTAGACAGTCCGGTGAGCTCGGCCATGCAGGTAG GATTTGAGCTGTGTTTCCCGCCCTGA | 6162 |
| | 2 | MGPLNSLERAFSMALALCGSLPPTQPRPRAPSPCDRRP PPGAPGPPARTPRPALGSGCGCGPGAGRGLRGRPLARA RGQRGPRGPWAAGWRDYKSRAWAPAVRLLSGGAA* | 6163 | ATGGGGCCCCTGAATTCTCTAGAACGGGCATTCAGCATGGCCTTGGCCTCTTGCGCC TCCCTGCCCCAACCCAGTCTGCGCCCGCGCCACCGCAGCCTCCCCGCCCTCTTGCTCG GGTGCGGGGGCCGGGCCGGGAGGCCCGGAGGGCTCGCGGGGCGCCCATTGGCGC GGGCGCGAGGCGAGCCAGCGAGGCCCGGGCGGCTCGGCCCTGCCTCGCGGACTAT AAGAGCCGGGCTGGGGCCGTGCGGGCCAGTTGCGTGCCTCTCCGGCGGAGCTGCGTGA | 6164 |
| | 3 | MCDSCLAGPGLRGAG* | 6165 | ATGTGTGATTCGTGCTTGCGGGCCCTGCGGGGCTGGGTAA | 6166 |
| | 4 | MLTRCQRDRERKTGVGGARMERGRVGRSHGRRHIRDI SPTTPLALSATFPNRSPGRGGEGLLV* | 6167 | ATGTTGACGCGGTGCAGCGAGACGCGAGAGAAGACGCGGAGTCATGGCAGGAGCC GGATGGAGAGGGGCGAGTTGGCAGGCGTCGCAACATTCCAAACAGGAGTCCGGGAGA TCCCCACACCCCTCGCTCTGTGCCCGCAACATTCCAAACAGGAGTCCGGGAGA GGGGGAGAGGGCGGCTGGTCTGA | 6168 |
| hsa-mir-483 | 1 | MCQQSGLGCMGRGALLLKFVISAISFCFSPGAEESPPSL CGRRWIPAFSPRALNRCQLSPLPSLPHSLSPSRFESPVLR * | 6169 | ATGGGACAGGGCTCAGGTCTGGGGTGTATGGGAGGGCTTTGCTTTAAAAGA CTTGTGGGAGGAGTTGATTCGCTGAATGGCCGAAGTTCTGAATCGCTGCCA GCTCAGCCCTGCCCTGCCCAGCCTGAGCCTGAGCCTGAATCGCTGCCA AGTCCTGAGGTGA | 6170 |
| | 2 | MGGRKWVEREKGKISLGKNLKTQGKLGSAGGCETPGF SPPQAAGHGVLHQWPDLSVGLYLSKWVTVSGLLAVQN * | 6171 | ATGGGGGCAGAAAGGTCAGAAAGGGTAGAGAGGAAAAGGGAAAATATCATTGGGAAGA ACCTAAAAACCCAAGGAAAGCTGGCTTCTGCTGGCGTGTGAGACCCCGGGTTC TCCCCGCCCCAGCCTGCTGCCATGGGAGTTGCACTCAGGCCTCACTGACCTTCTGTC GGTCTGTATTATCAAAGTGGGTGACAGTCCTGGCGTTGTTCAGAATTGA | 6172 |
| | 3 | MGSCTNGLTFLSVCIYQSG* | 6173 | ATGGGCTCTGCACCAATGCCTGTACCTGCCACGACAGGGCCTGCAGGAGGGATCCAGC | 6174 |
| | 4 | MDWSPCTCPTTGPAGRDPAGDSSG* | 6175 | ATGGATTGAGTCCCTGTACCTGCCACGACAGGGCCTGCAGGAGGGATCCAGC AGTGACTCTTCAGGCTGA | 6176 |
| hsa-mir-484 | 1 | MRRA* | 6177 | ATGAGGAGAGCATAG | 6178 |
| | 2 | MGVIHETLQGRCLDYMR* | 6179 | ATGGGTGTGATAATAATAGAAACCACCTTACAAGGCCGTTGTTTGGATTACATGAGG TAA | 6180 |
| | 3 | MLFP* | 6181 | ATGTTGTTTCCTTAG | 6182 |
| | 4 | MTAETMFSYPLFQLLSLVQCLAYFNK* | 6183 | ATGACAGCAGAGACTATGTTTTCTTATCCAACTCTGTCCTTAGTACAAT GCCTGGCATATTTTAATAAATAA | 6184 |
| hsa-mir-485 | 1 | MDQGVEGGGCGPGVGRQSACSL* | 6185 | ATGGACCAGGGGGTAGAGGAGGAGGGCTACAGAGATAGGGAGGAAAGTGGGACCTGGGGGTCGGGCGCCAGTCAG CTTGCAGCCTATGA | 6186 |
| | 2 | MKDGKEGYRDRGRVGLRIARAAWHTVLG* | 6187 | ATGAAGGACGGAAAGGAAGGGCTACTCAGGGTCTTCTTCAAAGCGTGTAATGGGAGAGCAGC CCAGAGCGGGCTTGGCACACAGTTTAGGGTAA | 6188 |
| | 3 | MTEPVTPGSSFKACLMGDSVVPVTKLGPESQGRAHQV AALP* | 6189 | ATGACTGAGCCGGTCACTCCAGGGTCTTCTTCAAAGGCTTGTTTAATGGGAGACAGC GTTGTCCCAGTAACCAAATTGGGACCAGAGTCCCAGGGAAGGGCTCATCAGGTGGC CGGCTCTGCCTTGA | 6190 |

Figure 1 (Continued)

| | | | | |
|---|---|---|---|---|
| | 4 | MILFPLDPAPLVPFSL* | 6191 | ATGATTCTCTTCCCTCTGGATCCAGCCCCTCTAGTTCCTTTCACTTTGA | 6192 |
| hsa-mir-486_os | 1 | MPYSVGFREVSTGRLLGWTGRCQEGATQAAPVGSTRAAALHITPPASPPRGLPALA* | 6193 | ATGCCCTATTCTGTGGGCTTCCGCGAAGTGAGTACTGGGCGGCTGCTCCGGGTGACGGGGAGATGTCAGGAGGGCACCCAGGCCGCCAGTAGGCACGCAGCACGCGAGCAAGAGCAGCTTTGCACACCCAGCCTCGCCTCCCGTGAGCTCCCTGCCTTAGCAT AG | 6194 |
| | 2 | MSGGGHPGRASRQHASKSSPAHPTRLASPWAPCLSHAAHRPCS* | 6195 | ATGTCAGGAGGGGGCCACCCAGGCCGCGCCAGTAGGCACGCGAGCAAGAGCAGCTTTGCACACCCACCGCGCTCGCGCTCCCGTGGGCTCCCTGCCTTAGCATAGCGGCACATGCGACCTTGTGATCTGA | 6196 |
| | 3 | MSCQQ* | 6197 | ATGTCCTGTCTCAGCAATAG | 6198 |
| | 4 | MVFGL* | 6199 | ATGGTTTTTGGATTATAG | 6200 |
| | 1 | MDQGVEGGCGCGPGVGRQSACSL* | 6201 | ATGGACCAGGGGGTAGAGGGAGGTGGGTGTGGACTGGGGTCGGGCGCCAGTCAGCTTGCAGCCTATGA | 6202 |
| hsa-mir-487a | 2 | MKDGKEGYRDRGRVGLRLARAAWHTVLG* | 6203 | ATGAAGGACGGAAAGGAGGGCTACAGAGATAGGGGAAGAGTGGGGCTGAGGATAGCCAGAGCTGGGCTTGGCACACAGTTTAGGGTAA | 6204 |
| | 3 | MTEPVTPGSSFKACLMGDSVVPVTKLGPESQGRAHQVAALP* | 6205 | ATGACTGAGCCGGTCACTCCAGGTTCTTCTCAAAGCGTGTCTAATGGAGACAGCGTTGTCCCAGTAACCAAATTGGGACCAGAGTCCCAGGGAAGGGCTCATCAGGTGGCCGCTCTGCCTTGA | 6206 |
| | 4 | MILFPLDPAPLVPFSL* | 6207 | ATGATTCTCTTCCCTCTGGATCCAGCCCCTCTAGTTCCTTTCACTTTGA | 6208 |
| | 1 | MDQGVEGGCGCGPGVGRQSACSL* | 6209 | ATGGACCAGGGGGTAGAGGGAGGTGGGTGTGGACTGGGGTCGGGCGCCAGTCAGCTTGCAGCCTATGA | 6210 |
| hsa-mir-487b | 2 | MKDGKEGYRDRGRVGLRLARAAWHTVLG* | 6211 | ATGAAGGACGGAAAGGAGGGCTACAGAGATAGGGGAGAGTGGGGCTGAGGATAGCCAGAGCTGGGCTTGGCACACAGTTTAGGGTAA | 6212 |
| | 3 | MTEPVTPGSSFKACLMGDSVVPVTKLGPESQGRAHQVAALP* | 6213 | ATGACTGAGCCGGTCACTCCAGGTTCTTCTCAAAGCGTGTCTAATGGAGACAGCGTTGTCCCAGTAACCAAATTGGGACCAGAGTCCCAGGGAAGGGCTCATCAGGTGGCCGCTCTGCCTTGA | 6214 |
| | 4 | MILFPLDPAPLVPFSL* | 6215 | ATGATTCTCTTCCCTCTGGATCCAGCCCCTCTAGTTCCTTTCACTTTGA | 6216 |
| | 1 | MGAEA* | 6217 | ATGGGGCGCTGAAGCTTGA | 6218 |
| | 2 | MSGT* | 6219 | ATGAGCGGGACTTAA | 6220 |
| hsa-mir-489 | 3 | MPNSAGAIGTLLFDYRNVV* | 6221 | ATGTTTAACAGTGCAGGTGCTATAGGCACCTTGCTTTTTGATTATAGAAATGTGGTTTGA | 6222 |
| | 4 | MWFDCGACGSHVGSARS* | 6223 | ATGTGGTTTGATTGCGGTGCTTGTGGTTCTCATGTAGGGTCAGTCTAGGTCTTAG | 6224 |
| | 1 | MFSPEIVRPLQLIEHTRTNTDTLSCCTKGARAQRPRERARAHTHTHTHQTHTHSHTPGCGLARAWKSQJSPGNRRGTRIGVASQN* | 6225 | ATGTTCTCCCCAGAAATTGTCGCCTGTATGAGTAATGAACACACAGGGAGCGCGCGGGCGCAAAGACCTAGGGAGCGCGGGGCACACAGCTCACACAAGAGGACACAAGCACTAGGGAGCGCTCCAGGCGTGGGTTGCCAGCACAGACACACACAGACCTAGGGAGCCCTGAAATCGCAGATTTCACCAGGAAATCGCCGAGGTACCCGAATAGGTGTTGCCTCCAAAACTAA | 6226 |
| | 2 | MNPAQLAEASRSPFVFGLQALRESQV* | 6227 | ATGAATCAGCCCAGCTGACTCGCGAGCATCCAGGTCTCTATTTGGTCTCCAGGCTCTTCGTGAAAGCCAGGTTTGA | 6228 |

Figure 1 (Continued)

| | | | | |
|---|---|---|---|---|
| hsa-mir-490 | 3 | MAGLKGRGRGTARGEVPLRFRRSLSPAECGESHLGAA LSRRRSLFQPPRPSTVADPPPATHSRCSHGQDKESFVPPA PRVPSCWGLTASSVRVGWRPGSLGLRAVPRLRFRSSPW ALERFPIAVSRSRWPRRRSM* | 6229 | ATGGCRGTCTGAAACGAAGRGGCAAACGAGGCACAGGCGAGGCGAGGTACCC TACGGATTCCGACGGTCACTGGCTCCTGCTCCTATTCCAGCGTCCAGCCAGCAGCCTGGGAGCT GGGCTGTCCGGCGCTCCGCACCACTCCAGATGCAGCCATGGACAAGGAGGAGCTTCGTCC CCCCTCCCGCGACCCCTGGGTCCTCCGTTCCTTCCGGGTCTGACCGCGCGTCTTCTGTCGGTGTG GATGGAGGCCCGGCGCTCGCTCGGCGTCCGGCTCCGAGCTGTCCCCCGGCTCCGCTTCCGGAGCA GCCCTTGGGCGCTGGAGAGGGTTTCCAGGTCGGCTCCAGGTCATGGCCCAAGGAGG AGAAGCAATTAG | 6230 |
| | 4 | MWRKQPGSCAVPASLPIPAFHSLYCC* | 6231 | ATGTGGCGAAAGCAGCCTGGGAGCTGCGTCCCGGCGTCCCTCCCTATTCCAGCC CCCATTCCCTCTACTGTTGCTGA | 6232 |
| hsa-mir-491 | 1 | MAGAPPAASLPPCRLISDCCASMQ* | 6233 | ATGGCGGGGCCCCCTCCCGCAGCCTGCCTGCCGCTCTGCCGCTTGCAGGTTGATCTCAGACTGC TGTGCTAGCAATCAGTGA | 6234 |
| | 2 | MPRPASARARCMHPLTCAHCLALPSEMNSVSQMEMQK SPSSPSLTLGAVDRSCSYSAIFAPPCN* | 6235 | ATGCCTCGCCCTGTTCGGCTCGCAGGTGCATGCACCACTGACCTGCGCCAC TGTCTGCACTCCAGTGGAGATGAATAGTGAGATGCAGATCAACCTGTATCCAGACCTGCGGCCCAC CCGTCTTCTCATCGCTGACCTGTCGGAGCTGTAGACCGGAGCTGTCCCTATTGGCC ATCTTTGCTCCTCCCCTGCAACTAA | 6236 |
| | 3 | MLKFQPLVPQNVTVFGNRAFKEVIK* | 6237 | ATGCTGAAGTTCAACCCTAGTACCCTAGAATGTACGAATGTGACTGTATTGAAATAGGCC TTTAAAGAGGTGATTAAGTGA | 6238 |
| | 4 | MAKPHFY* | 6239 | ATGGCAAAACCCATTCTACTAA | 6240 |
| hsa-mir-491 | 1 | MFRPASARARCMHPLTCAHCLALPSEMNSVSQMEMQK SPSSPSLTLGAVDRSCSYSAIFAPPCN* | 6241 | ATGCCTCGCCCTGCTTCGGCTCGCAGGTGCATGCACCACTGACCTGCCGCCAC TGTCTGCACTCCTAGGTGAGATGAACTCGGTATCTCAGATGGAAATGCAGAATCA CGGTCTTCTCATCGCTGACCTGTCGGAGCTGTAGACCGGAGCTGTCCTATTGGCC ATCTTTGCTCCTCCCTGCAACTAA | 6242 |
| | 2 | MLKFQPLVPQNVTVFGNRAFKEVIK* | 6243 | ATGCTGAAGTTCAACCCTAGTACCCTAGAATGTGACTGTATTGGAAATAGGGCC TTTAAAGAGGTGATTTACTGA | 6244 |
| | 3 | MAKPHFY* | 6245 | ATGGCAAACCCATTCTACTAA | 6246 |
| | 4 | MAPLPSSLGNRVRLCSPPPAPHKKI* | 6247 | ATGGCACCACTGCCCTCCAGCCTAGGGAACAGAGTGAGACTCTGCTCCCCCCCC GCCCACACAAAAAATTTAA | 6248 |
| hsa-mir-491 | 1 | MQPPGSLLQSPPPGYVRGGGAGHVRQPALG* | 6249 | ATGCAGCCCCATTGGCTCCTCCTGCAGTCCCGCCCCCCGGGCGTTCGAGCGGCGGCGG CCACGTCAAGGCAGCCGGCGCTGGCTGA | 6250 |
| | 2 | MEGG* | 6251 | ATGGAGGGCGGCTGA | 6252 |
| | 3 | MWRQGRVAARGSREGAFCPRPVLLGLSASGGLGLLRL RSSEIPGQGWLW* | 6253 | ATGTGGCGCCAGGGCCGGTCGCGGCCGCAGGGCAGCCGGGAGGGGCAGCCGGGGCTTTTTGCCC TGTGCCGTCTGCTGGGGCTCTCAGCTTCTGGACTAGGCCTTCGAGGTTACG GAGCTCCGAGATACCTGGCAGGGCTGGCTGTGGTGA | 6254 |
| | 4 | MSTYNAKYG* | 6255 | ATGTCCACTTATAATGCAAAGGCTTATGGGTGA | 6256 |
| hsa-mir-492 | 1 | MEKWDIVEDQGDRVFEVLHVAWCTVSTQYILTHVTAF FLSPMFLPPYRGHHKYTMVPPRQHPSQYDGSSWPMRK SYRLMPSFEGMKSPHSDSQYSDSWFSSSSLVTLLPSTEN MKTQLRNFHRAESCKLF* | 6257 | ATGGAAAAGTGGGATATTGTGGAAGACCAAGGAGACATGATCATGATTGAAGTGCTTCA TGTTGCCTGGTGCACAGTAGTCACACATACCTCCTTACAGAGGAATAATCACAAATATACT CTCCTTCCTTTCAGGCAGCACCCCTCCAAGTGCACGGAAGCAGTTGGCTATGCAC ATGGTTCCTTTTCAGGCAGCACCCCTCCAAGTGCACGGAAGCAGTTGGCTATGCAC AAATCATATATCGGATGTTCTTCATGTCCTCATTCGTCCTATTCGATTCAC AGTACAGTGATTCATGTCAATTAAGAACCACAGGGTTCACCTCCTCCCCTCACTGA AAACATGAAAACACAATTAAGAACCACAGGETCAAAACCAACCAGGGTTCACAAAGTCCAGAGACTCTTCTAA | 6258 |
| | 2 | MYLKCFMLPGVQ* | 6259 | ATGTATTTGAAGTGCTTCATGTTGCCTGGTGTACAGTAA | 6260 |
| | 3 | MVLFLFSCHPPPLH* | 6261 | ATGGTTCTCTTCTTCTGTCATCCTCCTCCCACTGA | 6262 |
| | 4 | MPAEGLKQNTP* | 6263 | ATGCCGGCAGGGTCAGGAAGCAAATACACCCTGA | 6264 |

Figure 1 (Continued)

| | | | | |
|---|---|---|---|---|
| | 1 | MVNPILCT* | 6265 | ATGGTTAATCCAATTCTGTGCACTTGA | 6266 |
| | 2 | MTERMNGHMND* | 6267 | ATGACAGAAAGAATGAATGGACACATGAACGACTGA | 6268 |
| hsa-mir-493 | 3 | MEMPGTARKELPMGLSPISLWAPEVHKREKRQEEKCQGVKDRAKERQK* | 6269 | ATGGAAATGCCTGGCACAGCCAGGGAGCTGCCATGGATTGTCATTCATCTCACTCTGGGCACCTGAGGTCCATAAGCCTGAAAAGAGGCAGGAAGAGAAGTGTCAGGGAGTCAAAGATAGAGCTAAGGAAAGGCAAAAATGA | 6270 |
| | 4 | MKLNESERENKEKPKKRTNTWVYL* | 6271 | ATGAAACTAAATGAAAGCGAAAGTGAAAATAAGAAAAAACCAATAAAAAAGAGAACGAATACGTGGGTGTATCTGTAA | 6272 |
| | 1 | MDQGJVEGGGCGPGVGRQSACSL* | 6273 | ATGGACCAGGGGGTAGAGGGAGGTGGTGTGGACCTGGGGTCCGCGCCAGTCAGCTTGCAGCCTATGA | 6274 |
| hsa-mir-494 | 2 | MKIDGKEGYRDRGRVGLRIARAAWHTVLG* | 6275 | ATGAAGGACGGAAAGGAGGGCTACAGAGATAGGGGAAGAGTGGGGTGAGGATAGCCAGAGCGGCTTGGCACACAGTTTAGGGTAA | 6276 |
| | 3 | MTEPVTPGSSFKACLMGDSVVPVTKLGPESQGRAHQVAALP* | 6277 | ATGACTGAGCCGGTCACTCCAGGGTCTTCCTTCAAAGCGTGTCTAATGGGAGACAGCGTTGTCCCAGTAACCAAATTGGGACCAGAGTCCCAGGGAAGGGCTCATCAGGTGGCCGCTCTGCCTTGA | 6278 |
| | 4 | MILFPLDPAPLVPFSL* | 6279 | ATGATTCTTCCCCTGGATCCAGCCCCTCTAGTTCCCTTTCACTTGA | 6280 |
| | 1 | MDQGVEGGGCGPGVGRQSACSL* | 6281 | ATGACCAGGGGGGTAGAGGGAGGTGGTGTGGACCTGGGTCGGGCGCCAGTCAGCTTGCAGCCTATGA | 6282 |
| hsa-mir-495 | 2 | MKIDGKEGYRDRGRVGLRIARAAWHTVLG* | 6283 | ATGAAGGACGGAAAGGAGGGCTACAGAGATAGGGAAGAGTGGGGCTGAGGATAGCCAGAGCGGCTTGGCACACAGTTTAGGGTAA | 6284 |
| | 3 | MTEPVTPGSSPKACLMGDSVVPVTKLGPESQGRAHQVAALP* | 6285 | ATGACTGAGCCGGTCACTCCAGGGTCTTCCTCAAAGCGTGTCTAATGGGAGACAGCGTTGTCCCAGTAACCAAATTGGACCAGAGTCCCAGGGAAGGGCTCATCAGGTGGCCGCTCTGCCTTGA | 6286 |
| | 4 | MILFPLDPAPLVPFSL* | 6287 | ATGATTCTCTCCCTCTGGATCCAGCCTCTAGTTCCCTTTCACTTGA | 6288 |
| | 1 | MDQGVEGGGCGPGVGRQSACSL* | 6289 | ATGGACCAGGGGGTAGAGGGGAGGTGGTGTGGACCTGCGGTCGGGCGCCAGTCAGCTTGCAGCCTATGA | 6290 |
| hsa-mir-496 | 2 | MKIDGKEGYRDRGRVGLRIARAAWHTVLG* | 6291 | ATGAAGGACGGAAAGGAGGGCTACAGAGATAGGGAAGAGTGGGGCTGAGGATAGCCAGAGCGGCTTGGCACACAGTTTAGGGTAA | 6292 |
| | 3 | MTEPVTPGSSFKACLMGDSVVPVTKLGPESQGRAHQVAALP* | 6293 | ATGACTGAGCCGGTCACTCCAGGGTCTTCCTTCAAAGCGTGTCTAATGGGAGACAGCGTTGTCCCAGTAACCAAATTGGGACCAGAGTCCCAGGGAAGGGCTCATCAGGTGGCCGCTCTGCCTTGA | 6294 |
| | 4 | MILFPLDPAPLVPFSL* | 6295 | ATGATTCTTCTCCCTCTGGATCCAGCCCCTCTAGTTCCCTTTCACTTGA | 6296 |
| | 1 | MGWDGFWGGVPNSJDWEWRNPS* | 6297 | ATGGGCTGGGACGGGTTTTGGGGGGTGTCCCAATTCTGACTGGGAGTGGAGGAACCCCTCCTGA | 6298 |
| | 2 | MRLGRLLSPAPQM* | 6299 | ATGCGACTGGGCGGCTCCTTTCTCCTGCACCCCAAATGTGA | 6300 |
| hsa-mir-497 | 3 | MHPKFCSFQNRGPGSQGRVAEVSGEGSVLCFQERRGGWGGGLEVRAGVGLALSVLELGG* | 6301 | ATGCACCCTAAATTTGCTCTTTTCAAAATAGGGACCAGGATCTCAGGGGAGAGTAGCTGAGGTAAGTGGGGAGGGAAGTGTCCTGTTTCAGGAGACGTGGCGGTTGGGGGAGGTTTGGAGGTGCGTGCTGGGGTTGGCTTGTCAGTCTTGAATTGGGGGATGA | 6302 |
| | 4 | MIGEAFSYTPKLQPPRRKPKAETREPPMIPSR* | 6303 | ATGATTGGAGAGGCTTTCTCTTATACCCTAAACTGCAGCCCCCAGACGGAAACCAAAGGCTGAGACCAGAGAGCCCCCAACATCCCAGCCGTTAG | 6304 |
| | 1 | MSIR* | 6305 | ATGTCAATCAGATGA | 6306 |

Figure 1 (Continued)

| | | | | |
|---|---|---|---|---|
| hsa-mir-498 | 2 | MINYVKRPATREGTPPRTHQRHHKENSFECKDCGKAF SRGYQLSQHQKIHTGEKPYECKECKKAFRWGNQLTQH QKIHTGEKPYECKDCGKAFRWGSSLVIHKRIHTGEKPY ECKDCGKAFRRGDELTQHQRFHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGHQLTQHQKTHSGAKSYECKEC GKACNHLNHLREHQRIHNS* | 6307 | ATGATCATCAATTATGTCAAATATGTCTACTAGAGAAGGACCCCTAGAACA CATCAGAGACATCATCATAAGGAGAATTCCTTGAATGTAAGGACTGTGGGAAGGCTTT AGTCGTGGCTATCAACTTAGTCACATCAGAAAATCCATACTGGTGAGAAACCTTAT GAATGTAAAGAATGTAAGAAGGCCTTCCGTTGGGCAATCAGCTTACTCAACATCAA AAATTCATACTGGGAGAAGCCCTACGAATGTAAAGACTCATACTGGTGAAAACCCTATGA ATGTAAAGACTGTGGAAAGGCCTGTTATTCATAAGAGAATTCATACTGGTGAAAACCTATGA GATTCCACACTGGGGAGAAAGACTTACGAATGTACAAGACTGTGGGAAGACCTTTAGC CGTGTGTATAAACTTATTCAGCACACAGAGAATTCATAGTGGGAGAAGCTTACGA GTGTAAAGACTGTGGGAAGGCTTTATTGTGGTTCAAGCCTCATTCAGCATAAAG AATTCACACAGGTGAGAAACCCTATGAATGTCAAGAATGTGGAAGGCCTTTACTCG AGTCAATTACCTTACTCAGAAGGCCTTCGTGCAGCCTGTGAAGCCTCACGAATG TAAGGAGTGTGGGAAGGCTTTCATTTATGGATCGAGCCTCGTGAAACATGAGAGAAT TCATACCGGGTGAAACCTATGGTGTACAGAATGTGGGAAGAGCTTTAGTCACG GCCATCAGTTACAACAACATCGAAAAACCACAGTCGGGCGAAATTCTACGAATGT AAGGAGTCGGGAAGGCATGTAACCACCTAAACCATCTCGAGAACATCAGAGGAT CCACAACAGTTGA |
| | 3 | MSKDLLLEKAPLLEHIRDIRRIPLNVRFTYGRPLVVAINL VNIRKSILVRNLMNVKNVRRPSVGAISLLNIKKFILGRSP CTCGTTATTCTAAGAGGATTCATACTGGTGAAAGACTTGTGGGAAGGCTTTGATGGGCTCAAGC ERG... MSKDLLLEKAPLLEHIRDIRRIPLNVRFTYGRPLVVAINL VNIRKSILVRNLMNVKNVRRPSVGAISLLNIKKFILGRSP GVVMSSLSTRDSTLGRKTNAKTVGRPLAVCINLFSTRE FIVGRSLTSVKTVGRLLFVQASFSIKEFTQVRNPMNVK NVGRPLLESFLLSIRRSTPVRSLTNVRSYGRPFAGVRAS LSTRGYIRARSRTSAQNVGRPSIVAITSLSTRESTQAKPRI NVRSVGRLSFMDRAS* | 6309 | ATGTCAAAAGACCTGCTACTAGAGAAGGCACCTCCTAGAACACATCAGAGACATC ATAAGGAGTAGCCTTGAATGTAAGGACTGTGGAAAGCTTTAGTGTGGCTATC AACTTAGTCACATCAGAAAATCCATACTGGTGAGAAACCTTATGAATGTAAAGAAT GTAAGAATGTAAGAAGGCCTTCCGTTGGGCAATCAGCTTACTCAACATCATATACTG GGGAGAAGCCCTATAAGACTGTAAAGACTGTGGGAAGGCTTTTGATGGGCTCAAGC CTCGTTATTCTAAGAGGATTCATACTGGTGATGAGTCAAAGACCCTTAGCCGTGTATAAAC GGAAAGGCCTTTGGTGATGAGTCAAAGACCCTTAGCCGTGTATAAAC GVVMSSLSTRDSTLGRKTNAKTVGRPLAVCINLFSTRE GGAAAAGACTACGAATGCAAAGAGACTTACAGTGGGAGAAGCCTTAGCCGTGTATAAAC TTATTGTGCAACAAGAAAGACTTGTAGCTCAAGAGCTACCTCACAATAAAGAATTCACACAGGT GGGAAGGCCTTTATTGTGAATGTCAAGCCTCATTCAGCATAAAGAATTCACACAGGT GAGAAACCCTATGAATGTCAAGAATGTGGGAAGGCCTTTACTCGAGTCAATTACCT ACTCAGCATCAGTTACAAGCAGCAATGGAAGCGTCCACCGGTGAGAAGCCTCGTTAAGCACGA GAAGGCCGTACAAGTGCACAGAATGGGAAGGCCTTCAATTGTGGCTATCACCTC ACTCAGGCGTACAAGTGCACAGAATGGGAAGGCCTTCAATTGTGGCTATCACCTC GAAGGGCTTTCATTATGATCGAGCCTCGTGA | 6310 |
| | 4 | MGLKPRYS* | 6311 | ATGGCCTCAAGCCTCGTTATTCATAA | 6312 |
| hsa-mir-499 | 1 | MPPCLANFCLFVCLL* | 6313 | ATGCCACCATGCCTGCTGCCAGGCTGGTCTTGA | 6314 |
| | 2 | MCCPGWS* | 6315 | ATGTGTTGCCCAGGCTGGTCTTGA | 6316 |
| | 3 | MCPPGPPKVLELQT* | 6317 | ATGTGTCCGCCTGGCCTCCAAAGTGCTGGAATTACAGACATGA | 6318 |
| | 4 | MRYCA* | 6319 | ATGAGGTACTGTGCCTGA | 6320 |
| hsa-mir-500 | 1 | MSRAPASLPLLPGWAV* | 6321 | ATGAGCCGCGCGCCTCGCTCCCTTCTCCCCGGCTGGGCTGTGTGA | 6322 |
| | 2 | MKLCRLRGALTQLGVLDARADRARCPPAADTGSAAPD LGJDR* | 6323 | ATGAAGCTCTGCCGCCTACGTGGGGCTCTAACTCAACTTGGTCTCGACGCCAGA GCCGACCGAGGCGCGCTGCCACCGGCGGACACGGGCTCCGGACCT CGGCGACAGGTAA | 6324 |
| | 3 | MGLPRARRWQPGA* | 6325 | ATGGGGCTTCCCCGCGCCGGCGTTGGCAGCCGGCGCTTAG | 6326 |

Figure 1 (Continued)

| | | | | | |
|---|---|---|---|---|---|
| | 4 | MVPGLPERSFLAERRQARPAFESECLAACVPFPGLG* | 6327 | ATGGTCCCTGGGTTGCCCGAGCGAAGTTTCCTTGCGGAGCGGCGCCAAGCCCGCCCGCTTTTGAATCGGAGTGTTTAGCGCTGCGTCCTCTCCCGGCTGGGCTGTGTGA | 6328 |
| hsa-mir-503 | 1 | MSRAPASLPLPGWAV* | 6329 | ATGAGCCGCGCAGCGCTCCGTTCCTTGCCTGGGCTGGGCTGTGTGA | 6330 |
| | 2 | MKLLCRLRGALTQLGVLDARADRARCPPAADTGSAAPDLGDR* | 6331 | ATGAAGCTCTGCCGGCTACGTGGGCGCTCACTCAACTTGGTGTCTGACGCCAGAGCCGACCGAGCGCGTCGCCACCGGGCGGACACGGGCTCCGCCTCCGGACCTCGGCGACAGGTAA | 6332 |
| | 3 | MGLPRARRWQPGA* | 6333 | ATGGGCTTCCCGCGCGCCCGGCGTTGCAGCCCGGCGCTAA | 6334 |
| | 4 | MVPGLPERSFLAERRQARPAFESECLAACVPFPGLG* | 6335 | ATGGTCCCTGGGTTGCCCGAGCGAAGTTTCCTTGCGGAGCGGCGCCAAGCCCGCCCGCTTTTGAATCGGAGTGTTTAGCGCCTGCGTCCCCTTCCTGCGGACTGGGTAG | 6336 |
| hsa-mir-504 | 1 | MSRAPASLPLPGWAV* | 6337 | ATGAGCCGCGCAGCGCTCCGTTCCTTGCCTGGGCTGTGGGCTGTGA | 6338 |
| | 2 | MKLLCRLRGALTQLGVLDARADRARCPPAADTGSAAPDLGDR* | 6339 | ATGAAGCTCTGCCGGCTACGTGGGCGCTCACTCAACTTGGTGTCTGACGCCAGAGCCGACCGAGCGCGTCGCCACCGGGCGGACACGGGCTCCGCCTCCGGACCTCGGCGACAGGTAA | 6340 |
| | 3 | MGLPRARRWQPGA* | 6341 | ATGGGCTTCCCGCGCGCCCGGCGTTGCAGCCCGGCGCTAA | 6342 |
| | 4 | MVPGLPERSFLAERRQARPAFESECLAACVPFPGLG* | 6343 | ATGGTCCCTGGGTTGCCCGAGCGAAGTTTCCTTGCGGAGCGGCGCCAAGCCCGCCCGCTTTTGAATCGGAGTGTTTAGCGCCTGCGTCCCCTTCCTGCGGACTGGGTAG | 6344 |
| hsa-mir-505 | 1 | MIQMSNCLYLTLFVYLQK* | 6345 | ATGATCCAGATGTCCAATTGCCTCTACTTAACCTTATTCGTCTACCTTCAGAAGTAA | 6346 |
| | 2 | MVKL* | 6347 | ATGGTGAAGTTATAA | 6348 |
| | 3 | MVQNVRRCYTPSWGR* | 6349 | ATGGTTCAAAACGTGAGGCGCTGCTATACCCCGTCGTGGGAAGGTAG | 6350 |
| | 4 | MMLHFGTPFPCSGRM* | 6351 | ATGATGTTCATTTGGCACCCGTTCCCGTGTAGTGAGATGTAA | 6352 |
| hsa-mir-504 | 1 | MVCH* | 6353 | ATGGTCTGTCACTAA | 6354 |
| | 2 | MPINDLSILRVWA* | 6355 | ATGCCCATTAATGATCTCTCTATACTGAGAGTATGGGCTTGA | 6356 |
| | 3 | MISLY* | 6357 | ATGATCTCTATACTGA | 6358 |
| | 4 | MGLMFLAITLENTLDMP* | 6359 | ATGGGCTTGATGTTTCTGCCATTACTTGAGAATACTTTAGATATGCCTAA | 6360 |
| hsa-mir-505 | 1 | MGFSLIAE* | 6361 | ATGGGCTTCTCGTTGATCGCAGAATGA | 6362 |
| | 2 | MKFKLRNMFLKSFRF* | 6363 | ATGAAGTTCAAATTGCGTAACATTCTTCCTATTTTCTAG | 6364 |
| | 3 | MQCRSPLFL* | 6365 | ATGCAATGTCGCTCTCCCTATTTCTCTAGCACTTTGA | 6366 |
| | 4 | MSLSPISLAL* | 6367 | ATGTCTCTGTCTCCCATTTCTCTAGCACTTTGA | 6368 |
| | 1 | MSPQ* | 6369 | ATGTCTCCTCAGTAG | 6370 |
| hsa-mir-511 | 2 | MRLPLLLVFASVIPGAVLLLGKSALRQGISDLGGRNHTFLFWVTVNGFLSTSL* | 6371 | ATGAGGCTACCCCTGCTCCTGGTTTTGCCTCTGTCATTCCGGTGTGTCTCCTACTGGGTAAGTCTGCTCTGGGTACTGTGAACGGGTTCCCTGCACCACGGGCAG | 6372 |
| | 3 | MGSFQHLCEEETGFPCTTQSTAKPAAFTWRPGMGGLELECRGGCVSGLGCCPAGNPTDLQCPPDFSHRSLFLPCFLRAEISCSVVYSFWFSIHTISVSPPTNTF* | 6373 | ATGGGTTCCTTCAACATCTGTGAGGAGAAACGGGTTCCCTGCACCACGGGCAGTCCACGGCTAAGCTCGTGCCTGCTGCAGGCAATGGAGCCTGGAGTTGGAGGAGGCGGATGCGTTCAGGTGCTGCCTGCCGGGAACCCTACAGACCTCAGTTGCTCTGTGACTTCTCATGCTCGTCTTCCTGTTTCTTCGTGCAGAATTCCTGTCGTCTGTGTTTACTTCTTCAATTCACACTATTTCTGTCTCACCGGCCAACAACACCTTCTGA | 6374 |
| | 4 | MRLRSRLLPCREPYRPSVSS* | 6375 | ATGCGTCTAGGTCGCCTGCTTCCGTGCGAGCCCTACAGACCTCAGTGTCCTCCTGA | 6376 |
| | 1 | MSPQ* | 6377 | ATGTCTCCTCAGTAG | 6378 |
| | 2 | MRLPLLLVFASVIPGAVLLLGKSALRQGISDLGGRNHTFLFWVTVNGFLSTSL* | 6379 | ATGAGGCTACCCCTGCTCCTGGTTTTGCCTCTGTCATTCCGGTGTGTCTCCTACTGGGTAAGTCTGCTCTGAGCAGGGATCTCGACCTCGAACTCGTGCCGGAACCACACCTTCCCTTCTGA | 6380 |

Figure 1 (Continued)

| | | | | |
|---|---|---|---|---|
| hsa-mir-511-2 | 3 | MGSFQHLCEEETGFPCTTQSTAKPAAFTWRPCMGGLEL EEGGGCVSGLGCCPAGNPTDLQCPFDFSHRSLFLPCFLR AEISCSVVYSFWFSIHTISVSPFTNTF* | 6381 | ATGGGTTCTTCAACATCTTTGTGAGGAGAAACGGGTCCCCTGCACCACGCAG TCCACGGCTAAGCTGTCTGCCTTCAGTGGCTGCGGCCAGGCATGGGAGGCCTGGAGTTG GAGGAGGGAGGGAGGATGCGTCTCCTGACTTCCATCGCGCTCGGTTGCTGCCCTGCCCGGAACCCTAC AGACCTTCAGTTGCTCTCTGTCCTGTCCTGTGTCCTGTTTCTC GTGCAGAAATTCCTGCTCTGTGGTTTACTCTTTCTGGTTTCAATTCAGACTATTTC TGTCTCACCGGCCAACAAACACCTCTGA | 6382 |
| | 4 | MRLRSRLLPCREPYRPSVSS* | 6383 | ATGCGTCTCAGGTCTCGGTTGCTGCCCTGCCGGGAACCCTACAGACCTTCAGTGTCC TCCTGA | 6384 |
| | 1 | MSIR* | 6385 | ATGTCAATCAGATGA | 6386 |
| | 2 | MIINYVKRPATREGTPPRTHQRHHKENSFECKDCGKAF SRGYQLSIHQKIHTGEKPYECKECKKAFRWGNQLTQH QKIHTGEKPYECKDCCKAFRWGSSLVHKRIHTGEKPY ECKDCGKAFRRGDELTQHQREHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAPNCGY HLTQHERIHTGETPYKCKECGKAFIYGSSLVKHERIHTG VKPYGCTECGKSFSHGHQLTQHQKIHSGAKSYECKEC GKACNHLNHLREHQRIHNS* | 6387 | ATGATCATCAATATGTCAAAGACCTGCTACTAGAGAGGCACCCTCCTAGAACA CATCAGAGACATCAACTTAGTCAACATCAGAAAATCCATACTGGTGAGAAGTGTAAGGACTGTGGGAAGGCCTTT AGTCGTGGCTATCAACTTAGTCAACATCAGAAAATCCATACTGGTGAGAAACCTTAT GAATGTAAAGAATGTAAGAAGGCCTTCCGTTGGGGCAATCAGTTACTCAACATCAA AAAATTCATACTGGCGAGAAGCCCTACGAATGTAAAGACTGTGGGAAGGCTTTCG ATGGGCTCAAGCCTGCCGTTATTCTAAAGAGGATTCATACTGGTGAAAACCCCTAGA ATGTAAAGACTGTGGAAAGGCCTTTCGGCGTGGGTGTACATGCAAAGACTCACCAGCACCAGA GATTCCACACTGGGAGAAAGACTACGAATGCAAAGACTGTGGGAAGACCTTTAGC CGTGTGTATAAACTTATTCAGCACAAGAGAATTCATAGTGGGGAGAAGCCTTACGA GTGTAAAGACTGTGGGAAGGCCTTTATTTGTGGTTCAAGCCTCATTCAGCATAAAG AATTCACACAGGTGAGAAACCCTATGAATGTCAAGAATGTGGAAAGGCCTTTACTCG AGTCAATTACCTTACTCAGCACCAAATCCACACCGGTTCGAGAAGCCTCACCAGTG TAAGGAGTGTGGGAAGGCCTACAACATCAGAAACGCACAGTGGGGCGAAATCTACGAAGTGT TACATACCGGGCGAGAAGCCGTACAAGTGCACGAGAATGTGGGAAGGCCTTCACTG GCTATCACCTCACTCAGCACGAGAGAATCCATTATGGATGCAGAATGTGGCAAGCATGGCAGT GCCATCAGCTTCACACAACATCAGAAACGCACAGTGGGGCGAAATCTACGAAGTGT AAGGAGTGCGGGAAGGCATGTAACCATCTCCGAGAACATCCTAAGGAGCATCAGAGGAT CCACAACAGTTGA | 6388 |
| hsa-mir-512-1 | 3 | MSKDLLLEKAPLLEHIRDIRRRPLNVRTVGRPLYVAINL VNIRKSILVRNLMNVKNVRRPSVGAISLLNKKFILGRSP TNVKTVGRLFDGAQASLFIRGFHLVKNPMNVKTVERPF GVVMSSLSTRDSTLGRKITTNAKTVGRPLAVCINLFSTRE FIYGRSLTSVKTVGRLLFVVQASFSIKEFTQVRNPMNVK NVGRPLLESITLLSRRSTPVRSLTNVRSVGRPFAGVRAS LSTRGYIRARSRTSAQNVGRPSIVAITSLSTRESTQAKPRI NVRSVGRLSFFMDRAS* | 6389 | ATGTCAAAAGACCTGCTACTGGAGAAGGCACCCCTCCTAGAACACATCAGAGACATC ATAAGGAGAATTCGTTTGAATGTAAGGACTGTGGGAAGGCCTTTAGTCGTGGCTATC AACTTAGTCAACATCAGAAAATCCATACTGGTGAGAAGACCTATGAATGTAAAGAAT GTAAGAAGGCCTTCCGTTGGTGGGCAATCAGTTACTCAACATCCAAAAAATTCATACTG CTCGTTATTCATAAGAGGATTCATACTGGTGAGCTCACTCAGCACCAGAATTCATAAGACTGT GGAAAGGCCTTTCGCGTGGTGTACATGCAAAGACTCACCAGCACCAGAATTCCACACTGT GGAGAAAGACTACGAATGCAAAGACTGTGGGAAGAAGCCTTACGAGTGTAAAGACTGT TTATTCAGCACAAGAGAATTCATAGTGGGGAGAAGCCTTACGAGTGTAAAGACTGT GGGAAGGCCTTTATTTGTGGTTCAAGCCTCATTCAGGAAGGCCTCATAAAGAAATTCACACAGGT GAGAAACCCTATGAATGTCAAGAATGTGGAAGGCCTTTACTCGAGTCAATTACCTT ACTCAGCACCAAAGAATCCACACAGGCTGAGAATCTGACGAGTAAGGCCTTTCACCTC ACTCAGCACGAGAGAATCCATTATGAATCCACACAGGCTGAAACCCTGTCAATTGGGCTATCACCTC AAGCCGTTCACAAGAAGAATCCATTATGGGCTATCACCTCACAAGAAACCCGTATAAATGTAAGGAGTGTGG GAAGGCTTTCATTTATGGATCGAGCCTCGTGA | 6390 |
| | 4 | MGLKPRYS* | 6391 | ATGGGGCTCAAGCCTCGTTATTCATAA | 6392 |
| | 1 | MSIR* | 6393 | ATGTCAATCAGATGA | 6394 |

Figure 1 (Continued)

| | | | |
|---|---|---|---|
| hsa-tmr-512-2 | 2 | MHINYVKRPATREGTPPRTHQRHHKENSPECKDCGKAF SRGYQLSQEHQKIHTGEKPYECKECKCKAFRWGNQLTQH QKIHTGEKPYECKDCGKAFRWGSSLVIHKRIHTGEKPY ECKDCGKAFRKGDELTQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | ATGATCATCAATTATGTCAAAAGACTGTACTAGAGAAGGCACCCCTCCTAGAACA CATCAGAGACATCATAAGGAGAATTCCTTTGAATGTAAGGACTGTGGAAGGCCTT AGTCGTGGTATCAACTTAGTCAACATCAGAAATCCATACTGGTGAGAAACCTTAT GAATGTAAAGAATGTAAGAAGCCTTCCCGTTCGCAATGTGGCAATCAGCTTACTCAACATCAA AAAATTCATACTGGGGAGAAGCCTCGTTATTCATAAGAGAATTCATACTGGTGAAAAACCTATGA ATGGGGCTCAAGCTGTGGAAGCCTTTCCGCGTGGTATGCAATGTGGCGAGACCTCAGCACCAGA ATGTAAAGACTGTGGGAGACTGTGGGAGAAATGCAAAGACTGTGGGAAGACCTTAGC GATTCCACACTGGGGAGAAGACTACGAATGCAAAGACTGTGGGAGAAGACCTTTAGC CGTGTGTATAAACTTATTCAGCACACAAGAGAATTCATAGTGGGGAGAAGCCTTACGA CGTGTAAAGACTGTGGGAAGGCTTTTATTTGTGGTTCAAGCCTCATTCAGCATAAAG AATTCACACAGGTGAGAAACCCTATGAATGTCAAAGATGTGGGAAGGCCTTTACTCG AGTCAATTACCTTACTCAGCATCAGAGATCCACACCGGTGAGAAGCCTCACGAATG TAAGGAGTGTGGGAGCAAGGCCTTTCGCTGGGATTCGAGCTTTAAGCACGAGAGGA TACATACGGGCGAGAAGCCTACAAGTGCACAGAATGCACAGGCTTAAGCACGAGAGGA GGCTATCACCTCACTCAGCACGAGAATCCACACAGGCGAAACCCGTATAAATGT TCATACCGGGGTGAAACCCTATGGGTGCACAGAATGTGGGGAAGACTTTAGTCACG GCCATCAGCTTACACACACACACAGAAACGCACAGTGGGGCGAAATCCTACGAATGT AAGGAGTGCGGGAAGCCATGTAACCTAAACCATCTCCGAGAACATCAGAGGAT CCACAACAGTTGA | 6395 |
| | 3 | MSKDLLEKAPLLEHRIRRIPLNVRTVGRPLVVAINL VMRKSILVRNLMNVKNVRRPSVGAISLLNRKPILGRSP TNVKTVGRLFDGAQASLFIRGFILVKNPMNVKTVERPF GVVMSSLSTRDSTLGRKTTNAKTVGRPLAVCINLFSTRE PIVGRSLTSVKTVGRLLFVVQASPSIKEFTQVRNPMNYK NVGRPLLESTLLSIRRSFPVRSLTNVRSVGRPFAGVRAS LSTRGYIRARSKTSAQNVGRPSIVAIITSLSTRESTQAKFRI NVRSVGRLSFMDRAS* | ATGTCAAAAGACCTGCTACTAGAGAAGGCACCCCTCCTAGAACACATCAGAGACATC ATAAGGAGAATTCCTTTGAATGTAAGGACTGTGGGAAGGCCTTTAGTCGTGGCTATC AACTTAGTCAACATCAGAAATCCATACTGGTGAGAAATCCATACTGTAAAGAAT GTAAGAAGCCTTCCGTTGGAATGTAAAGACTTACTCAGCTTACTCAACATCAAAAATTCATACTG GGGAGAAGCCCTACGAATGTAAAGACTGTGGAAAGGCTTTCGATGGGGCTCAAGC CTCGTTATTCATAAGAGGATTCATACTGGTGAAAAACCTATGAATGTAAAGACTGT GGAAAGGCCTTTCGGCCTGTGATGAGCTACTGTGGGAAGACCTTAGCGTGTATAAAC CGGGAGAAAGACTACGAATGCAAAGACTGTGGGAAGACCTTAGCGTGTATAAAC CGGGAGAAAGACTACGAATGCAAAGACTGTGGGAAGAATCCACACTGG TTATTCAGCACACAGGTTTTATTTGGTTCAAGCCTCATTCAGCATAAAAGAATTCCACACGGT GGGAAGGCCTTTATTGGATTGAAGAATGTCAAGACCTCAATCAGCATAAAAGAATTCACACAGGT GAGAAACCCTATGAAGTTCAAGAATGTGGGAAGAGCCTCGTTAAGCACGAGGATACACAGGT ACTCAGCATCAGAGATCCACACCGGTGAGAAGCCTCACGAATGTAAGGAGTGTG GAAGGCCTTTGCTGGGTTCGACCGTCGACAGAATACGGGAGAGATACACGGGGCG GAAGCCGTAAGTGCACAGAATCCACACAGGGGGAAAGGCCTTCAATTGTGGCTATCACCTC ACTCAGCACGAGAGATCCCACACAGGGGGAAAGCCCGTATATAAATTCAAGGAGTGTGG GAAGGCTTTCATTTATGGATCGAGCCCTGTGA | 6397 |
| | 4 | MGLKPRYS* | ATRGGCTCAAGCCTCGTTATTCATAA | 6399 |
| | 1 | MSIR* | ATGTCAATCAGATGA | 6401 |

| | |
|---|---|
| | 6396 |
| | 6398 |
| | 6400 |
| | 6402 |

Figure 1 (Continued)

| | | | | |
|---|---|---|---|---|
| hsa-tmr-515-1 | 2 | MHINYVKRPATREGTPPRTHQRHHKENSPECKDCGKAF SRGYQLSQEHQKIHTGEKPYEECKECKAFRWGNQLTQH QKIHTGEKPYECKDCGKAFRWGSSLVIHKRIHTGEKPY ECKDCGKAFRRGDELTQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | ATGATCATCAATTATGTCAAAAGACTGCTACTAGAGAAGGCACCCCTCCTAGAACA CATCAGAGACATTCATAAGGAGAATTCCTTTGAATGTAAGGACTGTGGGAAGCCTTT AGTCGTGGCTATCAACTTAGTCAACATCAGAAAATCCATACTGGTGAAAACCTTAT GAATGTAAAGAATGTAAAGAAGGCCTTCCGTTGGGCAATCAGCTTACTCAACATCAA AAAATTCATACTGGGGAGAAGCCTTCTATTCATAAGAGATGTAAAGAACCCTATGA ATGGGGCTCAAGCTGTGAAAGCTCGTTATTCATAAGAGATTCATACTGGTGAAAAACCCTATGA ATGTAAAGACTGTGGGAAGCTGTTCGGCGTGGTGAGCTCACTCAGCACCAGA GATTCCACACTGGGGAGAAGATTACGAATGCAAAGACTGTGGGAAGACCTTTAGC CGTGTGTATAAACTTATTCAGCACACAAGAGAATTCATAGTGGGGAGAAGCCTTACGA GTGTAAAGACTGTGGGAAGGCTTTTATTTGTGGTTCAAGCCTCATTCAGCATAAAG AATTCACACAGGTGAAAACCCTATGAATGTCAAAGAATGTGGGAAGGCCTTTACTCG AGTCAATTACCTTACTCAGCATCAGAAGATCCACACCGGTGAGAAGCCTCACGAATG TAAGGAGTGTGGGAAGGCTTTCGCTGGGGTTCAGCCTCGTTAAGCACGAGAGGA TACATACGGGCGAGAAGCCTACAAGTGCACAGAATGCACACAGGCGAAACCCGTATAAATGT GGCTATCACCTCACTCAGCACGAGAATCCACACAGGCGAAACCCGTATAAATGT TCATATACGGGGTGAAACCCTATGGGTGCAGCAGAATGTGGGAAGACTTAGTCACG GCCATCAAGCTTACACAACACAGAAACCCAGTGGGCGAAATCTCACGAATGT AAGGAGTGCGGGAAGCATGTAACCTAAACCATCCGAGAACATCAGAGGAT CCACAACAGTTGA | 6403 | 6404 |
| | 3 | MSKDLLEKAPLLEHRDIRRIPLNVRTVGRPLVVAINL VMRKSILVRNLMNVKNVRRPSVGAISLUNIKKPILGRSP TNVKTVGRLFEDGAQASLFIRGFILVKNPMNVKTVERPF GVVMSSLSTRDSTLGRKTTNAKTVGRPLAVCINLFSTRE PTVGRSLTSVKTVGRLLFVVQASPSIKEFTQVRNPMNYK NVGRPLLESITLLSIBRRSFPVRSLTNVRSVGRPFAGVRAS LSTRGYIBARSKTSAQNVGRPSIVAITSLSTRESTQAKFRI NVRSVGRLSFMDRAS* | ATGTCAAAAGACCTGCTACTAGAGAAGGCACCCCTCCTAGAACACATCAGAGACATC ATAAGGAGAATTCCTTTGAATGTAAGGACTGTGGGAAGCCTTTAGTCGTGGCTATC AACTTAGTCAACATCAGAAAATCCATACTGGTGAAAATGTAAAGAAATCATACTGG GTAAGAAGGCCTTCACTACGAATGTAAAGACTGTTCAACATCAAAAATTCATACTG GGGAGAAGCCTACTAAGACTGTAAAGACTGTGGGAAGGCTTTCGATGGGCTCAAGC CTCGTTATTCATAAGAGATTCATACTGGTGAAAAACCCTATGAATGTAAAGACTGT GAAAAGGCCTTTATTCGGCGTGATGAGCTCACTCAGCACCAGAGATTCCACACTGG GGAGAAAGACTACGAATGCAAAGACTGTGGGAAGACCTTAGCCGTGTGTATAAAC TTATTCAGCACGACTACGAATGCAAAGAATTCATAGTGGGGAGAAGCCTTACGAGTCAGTGTAAAGACTGT GGGAAGGCCTTTTATTTGTGGTTCAAGCCTCGTTAAGCACGAGAGGATACATACG GGCGAGAAGCCTGCTACACAGGTCGACAGAATGTGCGGAAGCCTTCAATTGTGGCTATCGTC ACTCAGCACGAGATCAAGCCTCAGAACGAGCACTACGAATGTAAGGAGTGTGG GAAGGCTTTCATTTATGGATCGAGCCGTGA | 6405 | 6406 |
| | 4 | MGLKPRYS* | ATEGGCTCAAGCTCGTTATTCATAA | 6407 | 6408 |
| | 1 | MSIR* | ATGTCAATCAGATGA | 6409 | 6410 |

Figure 1 (Continued)

| | | | | |
|---|---|---|---|---|
| hsa-mir-515-2 | 2 | MHNYVKRPATREGTPPRTHQRHHKENSPECKDCGKAF SRGYQLSQHQKIHTGEKPYECKECKAFRWGNQLTQH QKIHTGEKPYECKDCGKAFRWGSSLVIHKRIHTGEKPY ECKDCGKAFRRGDELTQHQRFHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGHQLTQHQKTHSGAKSYECKEC GKACNHLNEHLREHQRIHNS* | ATGATCATCAATTAT... (sequence) | 6411 | 6412 |
| | 3 | MSKDLLLEKAPLLEHIRDIRRIPLNVRTVGRPLVVAINL VNIRKSILVRNLMNVKNVRRPSVGAISLLNIKKPILGRSP TNVKTVGRLLFDGAQASLFIRGFILVKNPMNVKTVERPF GVVMSSLSTRDSTLGRKTTNAKTVGRPLAVCINLFSTRE FIVGRSLTSVFKTVGRLLFVVQASPSIKEFTQVRNPMNYK NVGRPLLESITLLSIRRSTPVRSLTNVRSVGRPFAGVRAS LSTRGYIRARSRTSAQNVGRPSIVAITSLSTRESTQAKFRI NVRSVGRLSFMDRAS* | ATGTCAAAAGACCTG... (sequence) | 6413 | 6414 |
| | 4 | MGLKPRYS* | ATGGGGCTCAAGCCTCGTTATTCATAA | 6415 | 6416 |
| | 1 | MSIR* | ATGTCAATCAGATGA | 6417 | 6418 |

Figure 1 (Continued)

| | | | |
|---|---|---|---|
| hsa-mir-516a-1+C+A3210:A3213 | 2 | MHINYVKRPATREGTPPRTHQRHHKENSPECKDCGKAF SRGYQLSQEHQKIHTGEKPYECKECKCKAFRWGNQLTQH QKIHTGEKPYECKDCGKAFRWGSSLVIHKRIHTGEKPY ECKDCGKAFRKGDEITQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | ATGATCATCAATTATGTCAAAAGACTGTACTAGAGAAGGCACCCCTCCTAGAACA CATCAGAGACATCATAAGGAGAATTCCTTTGAATGTAAGGACTGTGGGAAGCCTTT AGTCGTGGCTATCAACTTAGTCAACATCAGAAAATCCATACTGGTGAGAAACCTTAT GAATGTAAAGAGTGTAAGGAAGCCTTCCGTTGGGCAATCAGCTTACTCAACATCAA AAAATTCATACTGGGGAGAAGCCTGTATTCATAAAGACTGTAAAGACTTTTCG ATGGGGCTCAAGCTCGTTATTCATAAGAGGATTCATACTGGTGAAAAACCTATGA ATGTAAAGACTGTGGGAAGCCTTTCCGCGTGGTAGCTCACTCAGCACCAGA GATTCACACTGGGGAGAAGACTACGAATGCAAAGACTGTGGGAAGACCTTTAGC CGTGTGTATAAACTTATTCAGCACACAAGAGAATTCATAGTGGGGAGAAGCCTTACGA CGTGTAAAGACTGTGGGAAGGCTTTCTATTTGGTTCAAGCCTCATTCAGCATAAAG AATTCACACAGGTGAGAAATGCAAAACCCTATGAATGTAAGAATGTGGGAAGCCTTTACTCG AGTCAATTACCTTACTCAGCATCAGAGAAGATCCACACCGGTGAGAAGCCTCACGAATG TAAGGAGTGTGGGAAGGCTTTCGCTGGGGTTCGAGCTCGTTAAGCACGAGAGGA TACATACGGGCGAGAAGCCTACAAGTGCACAGAATGGGAAGCCTTCAATTGT GGCTATCACCTCACTCAGCACGAGAGAATCCACACAGGCGAAACCCGTATAAATGT TCATACCGGGGTGAAACCTATGGGTGTACAGAATGTGGGAAGAGCTTTAGTCACG GCCATCAAGCTTACACAACAACCTCACAAGTGGGGGCAATCTCTACGAATGT AAGGAGTGCGGGAAGCCATGTAACCTAAACCATTCCGAGAACATCAGAGGAAT CCACAACAGTTGA | 6420 |
| | 3 | MSKDLLEKAPLLEHRDIRRIPLNVRTVGRPLVVAINL VMRKSILVRNLMNVKNVRRPSVGAISLLNIKKFILGRSP TNVKTVGRLFDCAQASLFIRGFILVKNPMNVKTVERPF GVVMSSLSTRDSTLGRKTNAKTVGRPLAVCINLFSTRE PTVGRSLTSVKTVGRLLFVVQASPSIKEFTQVRNPMNYK NVGRPFLLESTTLLSIRRSFPVRSLTNVRSVGRPFAGVRAS LSTRGYIRARSKTSAQNVGRPSIVAIITSLSTRESTQAKFRI NVRSVGRLSFMDRAS* | ATGTCAAAAGACCTGCTACTAGAGAAGGCACCCCTCCTAGAACACATCAGAGACATC ATAAGGAGAATTCCTTTGAATGTAAGGACTGTGGGAAGCCTTTAGTCGTGCTATC AACTTAGTCAACATCAGAAAATCCATACTGGTGAGAAACCTTATGAATGTAAAGAAT GTAAGGAAGCCTTCCGTTGGGCAATCAGCTTACTCAACATCAAAAATTCATACTG GGGAGAAGCCCTACGAATGTAAAGACTGTGGGAAGACTTTTCGATGGGGCTCAAGC CTCGTTATTCATAAGAGGATTCATACTGGTGAAAAACCTATGAATGTAAAGACTGT GGAAAGGCCTTTCGGCGTGGTGAGCTCACTCAGCACCAGAGACTTCACACTGG GGAGAAAGACTACGAATGCAAAGACTGTGGGAAGACCTTAGCCGTGTGTATAAAC TTATTCAGCACACAAGAATTCATAGTGGGAGAAGACCTTTCAGCCTCGTGTATAAAC GGGAAGGCTTTCTATTTGGTTCAAGCCTCGTTAAGCACGAGAGGATACATACGGGT GAGAAACCCTATGAATGTCAAGAATGTGGGAAGCCTTTACTCGAGTCAATTACTTT ACTCAGCATCAGAGAATCCACACCGGTGAGAAGCCTCACGAATGTAAGGAGTGTGG GAAGGCCTTTCGCTGGGGTTCGAGCCTCGTTAAGCACGAGGATACATACGGGCG AGAAGCCGTACAAGTGCACAGAATGTGGGAAGCCTTCAATTGTGGCTATCACCTC ACTCAGCACGAGAGAATCCACACAGGCGAAACCCGTATAAATGTAAGGAGTGTGG GAAGGCTTTCATTTATGGATCGAGCCCTCGTGA | 6422 |
| | 4 | MGLKPRYS* | ATGGGGCTCAAGCCTCGTTATTCATAA | 6424 |
| | 1 | MSIR* | ATGTCAATCAGATGA | 6426 |

| | | | |
|---|---|---|---|
| hsa-mir-516a-2 | 2 | MHINYVKRPATREGTPPRTHQRHHKENSPECKDCGKAF SRGYQLSQEHQKIHTGEKPYECKECKCKAFRWGNLTQH QKIHTGEKPYECKDCGKAFRWGSSLVIHKRIHTGEKPY ECKDCGKAFRRGDELTQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | ATGATCATCAATTATGTCAAAAGACCTGCTACTAGAGAAGGCACCCTCCTAGAACA CATCAGAGACATCATAAGGAGAATTCCTTTGAATGTAAGGACTGTGGAAGGCCTTT AGTCGTGGCTATCAACTTAGTCAACATCAGAAATTCATACTGGTGAGAAACCTTAT GAATGTAAAGAATGTAAGAAGGCCTTCCGTTGGGCAATCAGTCATCAACATCAA AAATTCATACTGGTGAAGAAGCCTTGTATTCATAAGACTGTAAAGACTGTGAAGAAGGCTTATGA ATGTAAAGACTGTGGGAAGGCCTTTCGCTGGTCAAGTCTCACTCAGCACCAGA GATTCCACACTGGGAGGAGAAAGACTACGAATGCAAAGACTGTGGGAAGACCTTAGC CGTGTGTATAAACTTATTCAGCACACAAGAGAATTCATAGTGGGGAGAAGCTTACGA GTGTAAAGACTGTGGGAAGGCTTTTATTGGTTCAAGCCTCATTCAGCATAAAG AATTCACACAGGTGACACAAACCCTATGAATGTCAAAGAATGTGGAAGGCCTTTACTCG AGTCAATTACCTTACTCAGCATCAGAGATCCACACCGGTGAGCCTCGTTAAGCACGAGGA TACATACGGGCGAGAAGGCCTACAAGTGCACAGAATGCGGAAGCCTCAATTGT GGCTATCACCTCACTCAGCACGAGAATCCACACAGGTGAAACCCGTATAGAGAAT TCATACCGGGGTGAACCCTATGGGGTACAGAATGTGGGAAGACTTTAGTCACG GCCATCAAGCTTACACAACACTCAGAAACGCACAGTGGGGCAAATCCACGAATGT AAGGAGTGCGGAAGCATGTAACCACCTAAACCATCTCGAGAACATCAGAGGAT CCACAACAGTTGA |
| | 3 | MSKIDLLEKAPLLEHRDIRRIPLNVRTVGRPLVVAINL VNIRKSILVRNLMNVKNVRRPSVGAISLLNIKKPILGRSP TNVKTVGRLFDGAQASLFIRGFILVKNPMNVKTVERPF GVVMSSLSTRDSTLGRKTTNAKTVGRPLAVCINLFSTRE PIVGRSLTSVTKVGRLLFVVQASPSIKEFTQVRNPMNYK NVGRPLLLESTTLLSIRRSFTPVRSLTNVRSVGRPFAGVRAS LSTRGYIBARSRKTSAQNVGRPSIVAITSLSTRESTQAKFRI NVRSVGRLSFMDRAS* | ATGTCAAAAGACCTGCTACTAGAGAAGGCACCCTCCTAGAACACATCAGAGACATC ATAAGGAGAATTCCTTTGAATGTAAGGACTGTGGGAAGGCCTATCAGTCGTGCTATC AACTTAGTCAACATCAGAAATCCATACTGGTGAGAAGGCCTATCAAGAATGTAAAGAAT GTAAGAAGGCCTTCCGTTACGAATGTAAAGACTGTGGGAAGGCTTTCGATGGGGCTCAAGC CTCGTTATTCATAAGAGGATTCATAGTGTGGGTGAAAAAACCCTATGAATGTAAAGACTGT GGAAAGGCCTTTCGGCGTGATGAGCTCACTCAGCACCAGAGACCTTCACACTGG GGAGAAAGACTACGAATGCAAAGACTGTGGAAGACCTTAGCCGTGTGTATAAAC TTATTCAGCACACTACAGTGGGAGAAGCTTATTCAGCAGTAAAGAATTCACACAGGT GGGAAGGCCTTTGCAGCCTCGTTAAGCACGAGGATACAGATACGGGCG GAGAAGGCCTTCGTGCGTACAGAATGTCGGAAGCCTCAATTGTGGCTATCACCTC ACTCAGCACGAGAATCCACACAGGTGGGAAACCCGTATAAATGTAAGGAGTGTGG GAAGGCTTTCATTTATGGATCGAGCCCTGTGA |
| | 4 | MGLKPRYS* | ATGGGCTCAAGCCTCGTTATTCATAA |
| | 1 | MSIR* | ATGTCAATCAGATGA |

Figure 1 (Continued)

| | | | | |
|---|---|---|---|---|
| hsa-mir-516b-1 | 2 | MHNYVKRPATREGTPPRTHQRRHKENSPECKDCGKAF SRGYQLSQEHQKIHTGEKPYECKECKCKAFRWGNQLTQH QKIHTGEKPYECKDCGKAFRWGSSLVIHKRIHTGEKPY ECKDCGKAFRKGDELTQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | 6435 | ATGATCATCAATTATGTCAAAAGACCTGCTACTAGAGAAGGCACCCTCCTAGAACA CATCAGAGACATCATAAGGAGAATTCCTTTGAATGTAAGGACTGTGGCTGCTATC AGTCGTGGCTATCAACTTAGTCAACATCAGAAATCCATACTGGTGAGAAACCTTAT GAATGTAAAGAATGTAAGGAGCCTTCCGTTGGGCAATGTAAAGACTGTAACATCAA AAAATTCATACTGGGGAGAAGGCCTCTATTCATAAGAGACTTCATACTGGTGAAAACCTATGA ATGGGGCTCAAGCTGTGGAAGACTCTGTGAAAGCCTTTCGCGTGGTAGAGCTCACTCAGCACCAGA ATGTAAAGACTGTGGGAGGAAGGCCTTTCGCGTGGTAGAGCTCACTCAGCACCAGA GATTCCACACTGGGGAGAAGACTACGAATGCAAAGACTGTGGGAAGACCTTTAGC CGTGTGTATAAACTTATTCAGCACACAGAAGAATTCATAGTGGGGAGAAGCTTACGA CGTGTAAAGACTGTGGGAAGGCTTTTATTGGTTCAAGCCTCATTCAGCATAAAG AATTCACACAGGTGAGAAGACCCTATGAATGTCAAGAATGTGGGAAGGCTTTACTCG AGTCAATTACCTTACTCAGCATCAGAGAATCCACACCGGTGAGAAGCCTCACGAATG TAAGGAGTGTGGGAGCGGACCTCTGTTAAGCACGAGAGGA TACATACGGGCGAGAAGGCCTACAAGTGCACAGAATGGGGAAGCCTTCAATTGT GGCTATCACCTCACTCAGCACGAGAAGAATCCACACAGGCGAAACCCGTATAAATGT TCATATCCGGGGTGAAACCCTATGGGTGTACAGAAATGTGGGAAGACTTAGTCACG GCCATCAAGCTTACACAACACAGAAAACGCAGTGGGGCAAAATCCTACGAATGT AAGGAGTGCGGGAAGCATGTAACCTAAACCATCTCCGAGAACATCAGAGGAT CCACAACAGTTGA | 6436 |
| | 3 | MSKDILLEKAPLLEHRDIRRIPLNVRTVGRPLVVAINL VNIRKSILVRNLMNVKNVRRPSVGAISLLNIKKPILGRSP TNVKTVGRLLFDGAQASLFIRGFILVKNPMNVKTVERPF GVVMSSLSTRDSTLGRKTNAKTVGRPLAVCINLFSTRE PIVGRSLTSVKTVGRLLFVVQASPSIKEFTQVRNPMNYK NVGRPLLESITLLSIRRSFPVRSLTNVRSVGRPFAGVRAS LSTRGYIBARSKTSAQNVGRPSIVAIITSLSTRESTQAKFRI NVRSVGRLSFMDRAS* | 6437 | ATGTCAAAAGACCTGCTACTAGAGAAGGCACCCTCCTAGAACACATCAGAGACATC ATAAGGAGAATTCCTTTGAATGTAAGGACTGTGGGAAGCCTATCAGTCGTGCTATC AACTTAGTCAACATCAGAAATCCATACTGGTGAGAAATGTAAAGAAT GTAAGAAGGCCTTCCGTACGAATCAGCTTACTCAACATCAAAAATTCATACTG GGGAGAAGCCCTACGAATGTAAAGACTGTGGGAAGGCTTTCGATGGGGCTCAAGC CTCGTTATTCGATAAGAGGATTCATACTGGTGAAAAACCTATGAATGTAAAGACTGT GAAAAGGCCTTTCGGCGTGATGTGAGCTCACTCAGCACCAGAGATTCCACACTGG GGAGAAAGACTACGAATGCAAAGACTGTGGGAAGACCTTAGCCGTGTGTATAAAC TTATTCAGCACACAGAATTCATAGTGGGAAGCTTACGAGTGTAAAGACTGT GGGAAGGCTTTTATTGGTTCAAGCCTCATTCAGCATAAAAGAATTCACACAGGT GAGAAACCCTATGAATGTCAAGAATGTGGGAAGCCTTTACTCGAGTCAATTGTGCC ACTCAGCACGAGAGGAATCCACACAGGCGAAACCCTTCAATTGTGGCTATCACCTC ACTCAGCACAAGCGTACAGAAATGTGGGAAGCCTTCAATTGTGGCTATCACCTC GAAGGCTTTCATTTATGGATCGAGCCTCGTGA | 6438 |
| | 4 | MGLKPRYS* | 6439 | ATGGGGCTCAAGCCTCGTTATTCATAA | 6440 |
| | 1 | MSIR* | 6441 | ATGTCAATCAGATGA | 6442 |

Figure 1 (Continued)

| | | | |
|---|---|---|---|
| hsa-mir-516b-2 | 2 | MHINYVKRPATREGTPPRTHQRHHKENSPECKDCGKAF SRGYQLSQHQKIHTGEKPYECKECKCKAFRWGNQLTQH QKIHTGEKPYECKDCGKAFRWGSSLVIHKRIHTGEKPY ECKDCGKAFRRGDEITQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | ATGATCATCAATTATGTCAAAAGACTGTACTAGAGAAGGCACCCCTCCTAGAACA CATCAGAGACATCATAAGGAGAATTCCTTTGAATGTAAGGACTGTGGCTGCTATC AGTCGTGGCTATCAACTTAGTCAACATCAGAAAATTCATACTGGTGAGAAACCTTAT GAATGTAAAGAATGTAAGAAGGCCTTCCGTTGGGCAATCAGCTTACTCAACATCAA AAAATTCATACTGGGGAGAAGCCTTCTATTCATAAGAGATTCATACTGGTGAAAAACCTATGA ATGGGGCTCAAGCTGTGGAAGCTCGTTATTCATAAGAGATTCATACTGGTGAAAAACCTATGA ATGTAAAGACTGTGGAAGACTGTGGGAGACCTTTCCGCGTGGTGAGCTCACTCAGCACCAGA GATTCCACACTGGGGAGAAGATCTACGAATGCAAAGACTGTGGGAAGACCTTTAGC CGTGTGTATAAACTTATTCAGCACACAAGAGAATTCATAGTGGGGAGAAGCCTTACGA GTGTAAAGACTGTGGGAAGGCTTTTATTGTGGTTCAAGCCTCATTCAGCATAAAG AATTCACACAGGTGAGAAACCCTATGAATGTCAAAGATGTGGGAAGGCCTTTACTCG AGTCAATTACCTTACTCAGCATCAGAGAATCCACAACCGGTGAGAAGCCTCACGAATG TAAGGAGTGTGGGCAGCTCACTCTCAGCACGAGAAGTCTGAGCCTCGTTAAGCACGAGAGA TACATACGGGCGAGAAGCCTACAAGTGCACAGAATGCACCAAGCGAAACCCGTATGGT GGCTATCACCTCACTCAGCACGAGAATCCACACAGGCGAAACCCGTATGAGAGAAT TCATACCGGGGTGAACCCTATGGGTGACAGAATGTGGGAAGACTTTAGTCACG GCCATCAAGCTTACACAACACAGAAACCAAGGGGCGAAACCCTAAACCATCTCGAGAATGT AAGGAGTGCGGGAAGCCATGTAACCTAAACCATCTCCGAGAACATCAGAGGAT CCACAACAGTTGA | 6444 |
| | 3 | MSKIDLLEKAPLLEHRDIRRRIPLNVRTVGRPLVVAINL VNIRKSILVRNLMNVKNVRRPSVGAISLUNIKKPILGRSP TNVKTVGRLFDGAQASLFIRGFILVKNPMNVKTVERPF GVVMSSLSTRDSTLGRKTTNAKTVGRPLAVCINLFSTRE PIVGRSLTSVTSVGRLLFVVQASPSIKEFTQVRNPMNYK NVGRPFLLESTLLSIRRSFPVRSLTVNVRSVGRPFAGVRAS LSTRGYIBARSRKTSAQNVGRPSIVAITSLSTRESTQAKPRI NVRSVGRLSFMDRAS* | ATGTCAAAAGACCTGCTACTAGAGAAGGCACCCCTCCTAGAACACATCAGAGACATC ATAAGGAGAATTCCTTTGAATGTAAGGACTGTGGGAAGGCCTTAGTCGTGCTATC AACTTAGTCAACATCAGAAAATCATACTGGTGAGAAACCCTTATGAATGTAAGAAT GTAAGAAGGCCTTCACTAAGGAAGTGGGCAATCAGCTTACTCAACATCAAAAATTCATACTG GGGAGAAGCCCCTACGAATGTAAAGACTGTGGGAAGGCTTTCGATGGGGCTCAAGC CTCGTTATTCATAAGAGATTCATACTGGTGAAAAACCCTATGAATGTAAAGACTGT GGAAAGGCCTTTCGGCGTGGTGAGCTCACTCAGCACCAGAGATCCACACTGG GGAGAAAGACTACGAATGCAAAGACTGTGGGAAGACCTTAGCCGTGTGTATAAAC TTATTCAGCACACAAGAGAATTCATAGTGGGGAGAAGCCTTACGAGTGTAAAGGT GGGAAGGCTTTTTATTGTGTTCAAGCCTCATTCAGCATAAAAGAATTCACACAGGT GAGAAACCCTATGAATGTCAAAGATGTGGGAAGACCTTTACTGGCATAATTACCTT ACTCAGCATCAGAGAATCCACACCGGTGAGAAGCCTCACGAATGTAAGGAGTGTGG GAAGGCCTTTGCTGGGGTCGACGAAGAGGATACATACGGGGCG GAGAAGCCGTACAAGTGCACACAGGAATGTGGGAAGGCCTTCAATTGTGGCTATCACCTC ACTCAGCACGAGAATCCACACAGGCGAAACCCGTATAAGGAGTGTGGAAGGCCTTTAAG GAAGGCTTCATTTATGGATCGAGCCCTCGTGA | 6446 |
| | 4 | MGLKPRYS* | ATGGGGCTCAAGCCTCGTTATTCATAA | 6448 |
| | 1 | MSIR* | ATGTCAATCAGATGA | 6450 |

Figure 1 (Continued)

| | | | |
|---|---|---|---|
| hsa-mir-517a-1 | 2 | MHINYVKRPATREGTPPRTHQRHHKENSPECKDCGKAF SRGYQLSQEHQKIHTGEKPYEECKECKKAFRWGNQLTQH QKIHTGEKPYECKDCGKAFRWGSSLVIHKRIHTGEKPY ECKDCGKAFRRKGDELTQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | ATGATCATCAATTATGTCAAAAGACTGCTACTAGAGAAGGCACCCTCCTAGAACA CATCAGAGACATCATAAGGAGAATTCCTTTGAATGTAAGGACTGTGGGAAGCCTTT AGTCGTGGCTATCAACTTAGTCAACATCAGAAATTCCATACTGGTGAGAAACCTTAT GAATGTAAAGAGCTGTGGAAGGCCTTCCGTTGGGCAATCAGCTTACTCAACATCAA AAAATTCATACTGGGGAGAAGCCTACGAATGTAAAGACTGTAAAGACCTTTTCG ATGGGGCTCAAGCTCGTTATTCATAAGAGAATTCATACTGGTGAAAAACCCTATGA ATGTAAAGACTGTGGAAAGGCCTTTCGCGTTGGTAGAGCTCACTCAGCACCAGA GATTCCACACTGGGGAGAAGACTACGAATGCAAAGACTGTGGGAAGACCTTTAGC CGTGTGTATAAACTTATTCAGCACACAAGAGAATTCATAGTGGGGAGAAGCCTTACGA GTCTAAAGACTGTGGAAGGCTTTATTTGTGGTTCAAGCCTCATTCAGCATAAAG AATTCACACAGGTGAGAACCCTATGAATGTCAAAGATGTCACAGAAGCCTTTACTCG AGTCAATTACCTTACTCAGCATCAGAGAATCCACACCGGTGAGAAGCCTCACGAATG TAAGGAGTGTGGGCGGAGAAGCCTACAAGTGCACAGAATGCACACCCCTTCAATTGT TACATACGGGCGAGAAGCCTACAACAGGTGAAACCCGTATAAGAGAGAT GGCTATCACCTCACTCAGCACGAGAAATCCACACAGGGAAACCCTCGTTAAGTCACG AAGGAGTGTGGGAAGCCTTTCATTTATGGATCGAGCCTGTACAGAATGTGGGAAGAAT GCCATCAAGCTTACAACACACAAGACACAGTGGGCGGGAGAAATCTCCGAGAATGT AAGGAGTGCGGAAGCCATGTAACCACCTAAACCATCCTCGAGAACATCAGAGGAT CCACAACAGTTGA | 6451 / 6452 |
| | 3 | MSKIDLLEKAPLLEHRDIRRFPLNVRTVGRPLVVAINL VMIRKSLVRNLMNVKNVRRPSVGAISLLNIKKFILGRSP TNVKTVGRLFEDGAQASLFIRGFILVKNPMNVKTVERPF GVVMSSLSTRDSTLGRKTVNAKTYGRPLAVCINLFSTRE PTVGRSLTSVKTVGRLLFVVQASPSIKEFTQVRNPMNVK NVGRPLLESITLLSIRRSFPVRSLTNVRSVGRPFAGVRAS LSTRGYIRARSRKTSAQNVGRPSIVAITSLSTRESTQAKFRI NVRSVGRLSFMDRAS* | ATGTCAAAAGACCTGCTACTAGAGAAGGCACCCTCCTAGAACACATCAGAGACATC ATAAGGAGAATTCCTTTGAATGTAAGGACTGTGGGAAGCCTTAGTCGTGGCTATC AACTTAGTCAACATCAGAAAATCCATACTGGTGAGAAACCTTATGAATGTAAAGAAT GTAAGAAGGCCTTCAACATCAGCTTACTCAACATCAAAAATTCATACTG GGGAGAAGCCCTACGAATGTAAAGACTGTGGGAAGGCTTTCGATGGGGCTCAAGC CTCGTTATTCATAAGAGAATTCATACTGGTGAAAAACCCTATGAATGTAAAGACTGT GGAAAGGCCTTTCGGCCTGATGAGCTCACTCAGCACCAGAGATTCCACACTGG GGAGAAAGACTACGAATGCAAAGACTGTGGGAAGACCTTAGCCGTGTGTATAAAC TTATTCAGCACACTACTGGTCTGCGGGAAGAATTCAGCATGTAAAGAAGGCTTACGAGTGT AAGAAGATTCAAGCATCAGGTGAAAGCCTTACTGAATGTAAGATCAAAACTTACACCTG ACTCAGCACGAGATCCACACACTCAGAAGCTACGAGAGGATCACACACGGGGCG GAAGGCCCTTCACTGACGTACGGTAAGATGCCACAGAAGTGGGAAGGCCTTCAAGAGGT ACTCAGCAGGACTACAAGGTGCACAGAATCCACACAGGCGGAAACCCGTATCACCTC GAAGGCTTTCATTTATGGATCGAGCCGTGA | 6453 / 6454 |
| | 4 | MGLKPRYS* | ATGGGCTCAAGCCTCGTTATTCATAA | 6455 / 6456 |
| | 1 | MSIR* | ATGTCAATCAGATGA | 6457 / 6458 |

Figure 1 (Continued)

| | | | |
|---|---|---|---|
| hsa-mir-517a-2 | 2 | MHNYVKRPATREGTPPRTHQRHHKENSPECKDCGKAF SRGYQLSQEHQKIHTGEKPYECKECKCKAFRWGNQLTQH QKIHTGEKPYECKDCGKAFRWGSSLVIHKRIHTGEKPY ECKDCGKAFRRGDELTQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | ATGATCATCAATTATGTCAAAAGACTGTACTAGAGAAGGCACCCTCCTAGAACA CATCAGAGACATCATAAGGAGAATTCCTTTGAATGTAAGGACTGTGGAAGGCCTTT AGTCGTGGCTATCAACTTAGTCAACATCAGAAAATCCATACTGGTGAGAAACCTTAT GAATGTAAAGAATGTAAGAAGGCCTTCCGTTGGCAATCAGCTTACTCAACATCAA AAAATTCATACTGGGGAGAAGCCTACGAATGTAAAGACTGTGGGGAAGGCTTTCG ATGGGGCTCAAGCTGTGATTCATAAAGAGAATTCATACTGGTGAAAAACCTATGA ATGTAAAGACTGTGGAAGGCCTTTCCGCGTGGTAAGCTCACTCAGCACCAGA GATTCCACACTGGGGAGAAGATACGAATGCAAAGACTGTGGGAAGACCTTAGC CGTGTGTATAAACTTATTCAGCACACAAGAGAATTCATAGTGGGGAGAAGCCTTACGA GTCTAAAGACTGTGGAAGGCTTTTATTGGTTCAAGCCTCATTCAGCATAAAG AATTCACACAGGTGAGAAGACCCTATGAATGTCAAAGATGTGGAAGGCCTTACTCG AGTCAATTACCTTACTCAGCATCAGAGAATCCACACCGGTGAGAAGCCTCACGAATG TAAGGAGTGTGGGAAAGGCCTTTCGCTGGGGTTCAGCCTCGTTAAGCACGAGAGGA TACATACGGGCGAGAAGCCTACAAGTGCACAGAATGCAAAGACCCTATGAATGT GCTATCACCTCACTCAGCACGAGAAATCCACACAGGGGAAACCCGTATGAGAGAAT TCATACCGGGGTGAAACCCTATGGGTGCACAGAATGTGGGAAGACCTTAGTCACG GCCATCAAGCTTACACAACATCAGAAAACGCACAGTGGGGCGAAAATCCTACGAATGT AAGGAGTGCGGGAAGGCATGTAACCTAAACCATCTCCGAGAACATCAGAGGAT CCACAACAGTTGA | 6459 6460 |
| | 3 | MSKDILLEKAPLLEHRDIRRRIPLNVRTVGRPLVVAINL VMRKSILVRNLMNVKNVRRPSVGAISLLNIKKPILGRSP TNVKTVGRLFDGAQASLFIRGFILVKNPMNVKTVERPF GVVMSSLSTRDSTLGRKTNAKTVGRPLAVCINLFSTRE PLVGRSLTSVKTVGRLLFVVQASPSIKEFTQVRNPMNYK NVGRPLLESTTLLSIRRSFPVRSLTNVRSVGRPFAGVRAS LSTRGYIBARSRKTSAQNVGRPSIVAITSLSTRESTQAKFRI NVRSVGRLSFMDRAS* | ATGTCAAAAGACCTGCTACTAGAGAAGGCACCCTCCTAGAACACATCAGAGACATC ATAAGGAGAATTCCTTTGAATGTAAGGACTGTGGGAAGGCCTTTAGTCGTGCTATC AACTTAGTCAACATCAGAAAATCCATACTGGTGAGAAACCTTATGAATGTAAAGAAT GTAAGAAGGCCTTCACTCAGCTTACTCAACATCAAAAAATTCATACTG GGGAGAAGCCCTACGAATGTAAAGACTGTGGGAAGGCTTTTCGATGGGGCTCAAGC CTCGTTATTCATAAAGAGGATTCATACTGGTGAAAAACCTATGAATGTAAAGACTGT GGAAAGGCCTTTCGGCGTGGTAAGCTCAACTCAGCACCAGAGATTCCACACTGG GGAGAAAGACTACGAATGCAAAGACTGTGGGAAGAACCTTAGCCGTGTAAGGACTGT TTATTCAGCACTACGAATGTAAGTGGGGAAGATTCATACTGGTGAAAGCCTGTATAAAC GGGAAGGCCTTTATTGGTTCAAGCCTCGTTAAGCACGAGAAGGATACACAGGT GAGAAACCCTATGAATGTCAAGATGTGGAAGGCCTTACTCGAGTCAATTACCTT ACTCAGCAGATCAGAGAATCCACACCGGTGAGAAGCCTCACGAATGTAAGGAGTGTG GAAGGCCTTTCGCTGGGGTTCAGCCTCGTTAAGCACGAGAGGATACATACGGGCG GAGAAGCCGTACAAGTGCACAGAATGTGGGAAGGCCTTCAATTGTGGCTATCACCTC ACTCAGCACGAGAAGATCCACACAGGGGAAACCCGTATGAATGTAAGGAGTGTGG GAAGGCTTTCATTTATGGATCGAGCCGTGA | 6461 6462 |
| | 4 | MGLKPRYS* | ATEGGCTCAAGCTCGTTATTCATAA | 6463 6464 |
| | 1 | MSIR* | ATGTCAATCAGATGA | 6465 6466 |

Figure 1 (Continued)

| | | | | |
|---|---|---|---|---|
| hsa-mir-517c | 2 | MHINYVKRPATREGTPPRTHQRHHKENSPECKDCGKAF SRGYQLSQHQKIHTGEKPYECKECKKAFRWGNQLTQH QKIHTGEKPYECKDCGKAFRWGSSLVIHKRIHTGEKPY ECKDCGKAFRKGDELTQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | ATGATCATCAATTATGTCAAAAGACTGCTACTAGAGAACA CATCAGAGACATCATAAGGAGAATTCCTTTGAATGTAAGGACCCCTCCTAGAACA AGTCGTGGCTATCAACTTAGTCAACATCAGAAATTCCATACTGGTGAGAAACCTTAT GAATGTAAAGAATGTAAGAAGGCCTTCCGTTGGGCAATCAGCTTACTCAACATCAA AAAATTCATACTGGGGAGAAGCCTCATAAAGACTGTAAAGACTTTTCG ATGGGCTCAAGCTCGTTATTCATAAGAGAATTCATACTGGTGAAAAACCCTATGA ATGTAAAGACTGTGGAAGAATGCAAAGACCCCTGATGAGCTCACTCAGCACCAGA GATTCCACACTGGGGAGAAGACTACGAATGCAAAGACTGTGGGAAGACCTTAGC CGTGTGTATAAAACTTATTCAGCACACAAGAGAATTCATAGTGGGAGAAGCCTTACGA GTGTAAAGACTGTGGAAGGCTTTTATTGGTTCAAGCCTCATTCAGCATAAAG AATTCACACAGGTGAGAATGCAAAACCCTATGAATGTCAAAGATGTGGAAGGCCTTTACTCG AGTCAATTACCTTACTCAGCATCAGAGAATGTCACACCGGGTGAGCCTCGTTAAGCACGAGGA TACATACGGGCGAGAAGGCCTACAACAGCAGCCTTCGAGCCCTCTGTTAAGCACGAGGA GGCTATCACCTCACTCAGCACGAGAATCCACACAGGAGAACCCGTATAATGT TCATACCGGGGTGAAACCTATGGGTGTACAGAAATGTGGGAAGACTTTAGTCACG GCCATCAAGCTTACACAACAACCGCACAGTGGGCGAAATCCGAAGAATGT AAGGAGTGCGGGAAGCATGTAACCATCTAAACCATCCGAGAACATCAGAGGAT CCACAACAGTTGA | 6467 6468 |
| | 3 | MSKIDLLEKAPLLEHRIDRRIPLNVRTVGRPLVVAINL VNIRKSILVRNLMNVKNVRRPSVGAISLLNIKKPILGRSP TNVKTVGRLIEDGAQASLFIRGFILVKNPMNVKTVERPF GVVMSSLSTRDSTLGRKTNAKTVGRPLAVCINLFSTRE PIVGRSLTSVKTVGRLLFVVQASPSIKEFTQVRNPMNYK NVGRPLLLESITLLSIRRSFTPVRSLTNVRSVGRPFAGVRAS LSTRGYIBARSRKTSAQNVGRPSIVAITSLSTRESTQAKFRI NVRSVGRLSFMDRAS* | ATGTCAAAAGACCTGCTACTAGAGAAGGCACCCCTCCTAGAACATCAGAGACATC ATAAGGAGAATTCCTTTGAATGTAAGGACTGTGGGAAGGCCTTAGTCGTGCTATC AACTTAGTCAACATCAGAAATTCCATACTGGTGAGAAGAATGTAAAGAAT GTAAGAAGGCCTTCCGTTACTCAGCTTACTCAACATCAAAAATTCATAACTG GGGAGAAGAAGCCCTACGAATGTAAGACTGTGGGAAGGCCTTCGATGGGGCTCAAGC CTCGTTATTCATAAGAGATTCATACTGGTGAAAAACCCTATGAATGTAAAGACTGT GGAAAAGGCCTTTATTCGGCCGTGATGAGCTCACTCAGCACCAGAGATTCCACACTGG GGAGAAAGACTACGAATGCAAAGACTGTGGGAAGAACCTTAGCCGTGTATAAAAC TTATTCAGCACACTACGAATGTCAAGTGGGAGAAGCCTTACGAGTGTAAAGACTGT GGAAGGCTTTATTGTGTTCAAGCCTCATTCAGCATAAAGAATTCACACAGGT GAGAAACCCTATGAATGTCAAGAATGTGGGAAGGCCTTACTGAGTCAATTACCTT ACTCAGCAGCACGAGAATCCACACCGGTGAGAAGCCTCAAGCACGAGGATGTGG GAAGGCCTTTCGCTGGGGTTCGAGCCTCGTTAAGCACGAGAAGGATACATACGGGCG ACTCAGCAAGCGTACAAGTCACACAGGGCGAAACCCTCAATTGTGGCTATCACCTC GAAGGCTTTCATTATGGATCGAGCCTCGTGA | 6469 6470 |
| | 4 | MGLKPRYS* | ATEGGGCTCAAGCTCGTTATTCATAA | 6471 6472 |
| | 1 | MSIR* | ATGTCAATCAGATGA | 6473 6474 |

Figure 1 (Continued)

| | | | |
|---|---|---|---|
| hsa-mir-518a-1 | 2 | MHINYVKRPATREGTPPRTHQRRHKENSPECKDCGKAF SRGYQLSQEHQKIHTGEKPYECKECKAFRWGNQLTQH QKIHTGEKPYECKDCGKAFRWGSSLVIHKRIHTGEKPY ECKDCGKAFRRGDELTQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | ATGATCATCAATTATGTCAAAAGACTGTACTAGAGAAGGCACCCTCCTAGAACA CATCAGAGACATCATAAGGAGAATTCCTTTGAATGTAAGGACTGTGGAAGGCCTTT AGTCGTGGCTATCAACTTAGTCAACATCAGAAAATCCATACTGGTGAGAAACCTTAT GAATGTAAAGAATGTAAGGACGCCTTCCGTTGGGCAATCAGCTTACTCAACATCAA AAAATTCATACTGGGGAGAAGCCTTACGAAGATGTAAAGACTGTGGGAAGGCTTTCG ATGGGGCTCAAGCTCGTTATTCATAAGAGGATTCATACTGGTGAAAAACCTATGA ATGTAAAGACTGTGGGAAGGCCTTTCGCGTGGTCAATCAGCTCACTCAGCACCAGA GATTCCACACTGGGGAGAAGATTACGACACAAGAGAATGCAAAGACTGTGGGAAGACCTTTAGC CGTGTGTATAAACTTATTCAGCACGACAAGAGAATTCATAGTGGGGAGAAGCCTTACGA GTGTAAAGACTGTGGGAAGGCTTTTATTGGTTCAAGCCTCATTCAGCACATAAAG AATTCACACAGGTGAGAAACCCTATGAATGTCAAGAATGTGGGAAGGCCTTTACTCG AGTCAATTACCTTACTCAGCATCAGAGATCCACACCGGTGAGAAGCCTCACGAATG TAAGGAGTGTGGGCGAGAAGCCTTTCGCTGGGGTTCGAGCCTCGTTAAGCACGAGGA TACATACGGGCGAGAAGCCTACAAGTGCACAGAATGGGGAAGCCTTAAGCACGAGGA GGCTATCACCTCACTCAGCACGAGAAGATCCACACAGGTGAAACCCGTATAAATGT TCATACCGGGGTGAAACCCTATGGTGTACAGAATGTGGGAAGACTTTAGTCACG GCCATCAAGCTTACACAACACAGAAACGACAAGTGGGGCGAAATCCTACGAATGT AAGGAGTGCGGGAAGCCATGTAACCACCTAAACCATCTCCGAGAACATCAGAGGAT CCACAACAGTTGA | 6475 6476 |
| | 3 | MSKDILLEKAPLLEHRDIRRIPLNVRTVGRPLVVAINL VMRKSILVRNLMNVKNVRRPSVGAISLLNIKKPILGRSP TNVKTVGRLFDGAQASLFIRGFILVKNPMNVKTVERPF GVVMSSLSTRDSTLGRKTNAKTVGRPLAVCINLFSTRE PIVGRSLTSVKTVGRLLFVVQASPSIKEFTQVRNPMNYK NVGRPLLESITLLSIRRSFPVRSLTNVRSVGRPFAGVRAS LSTRGYIBARSRKTSAQNVGRPSIVAIITSLSTRESTQAKFRI NVRSVGRLSFMDRAS* | ATGTCAAAAGACCTGCTACTAGAGAAGGCACCCTCCTAGAACAGATCAGAGACATC ATAAGGAGAATTCCTTTGAATGTAAGGACTGTGGGAAGGCCTTTAGTCGTGCTATC AACTTAGTCAACATCAGAAAATCCATACTGGTGAGAAACCTTATGAATGTAAAGAAT GTAAGAAGGCCTTCATCAGCTTACTCAACATCAAAAATTCATACTG GGGAGAAGAAGCCCTACGAATGTAAAGACTGTGGGAAGGCTTTCGATGGGGCTCAAGC CTCGTTATTCATAAGAGGATTCATACTGGTGAAAAACCTATGAATGTAAAGACTGT GGAAAAGGCCTTTCGGCGTGATGTGAGCTCACTCAGCACCAGAGATTCCACACTGG GGAGAAAGACTACGAATGCAAAGACTGTGGGAAGAACCTTAGCCGTGTGTATAAAC TTATTCAGCACGACAAGAGAATTCAATAGTGGGAGAAGCCTTCAGCATAAAAGGTT GGGAAGGCCTTTTATTGGTTCAAGCCTCGTTAAGCACGAGGAAGATCCACACGGT GAGAAACCTATGAATGTCAAGAATGTGGGAAGGCCTCGTTAAGCACGAGGATACATACGGGCG ACTCAGCATCAGAGATCCACCGGTGAGAAGCCTCACGAATGTAAGGAGTGTGG GAAGGCCTTTCGCTGGGGTTCGAGCCTCGTTAAGCACGAGGATACATACGGGCG GAGAAGCCGTACAAGTGCACAGAATGTGGGAAGCCTTCAATTGTGGCTATCACTC ACTCAGCACGAGAAGATCCACACAGGGCGAAACCCGTATAAATGTAAGGAGTGTGG GAAGGCTTTCATTTATGGATCGAGCCGTGA | 6477 6478 |
| | 4 | MGLKPRYS* | ATGGGGCTCAAGCCTCGTTATTCATAA | 6479 6480 |
| 1 | | MSIR* | ATGTCAATCAGATGA | 6481 6482 |

Figure 1 (Continued)

| | | | |
|---|---|---|---|
| hsa-mir-518a-2 | 2 | MHINYVKRPATREGTPPRTHQRHHKENSPECKDCGKAF SRGYQLSQHQKIHTGEKPYECKECKCKAFRWGNQLTQH QKIHTGEKPYECKDCGKAFRWGSSLVIHKRIHTGEKPY ECKDCGKAFRRGDELTQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | ATGATCATCAATTATGTCAAAAGACTGTACTAGAGAAGGCACCCCTCCTAGAACA CATCAGAGACATCATAAGGAGAATTCCTTTGAATGTAAGGACTGTGGGAAGGCCTTT AGTCGTGGCTATCAACTTAGTCAACATAGTCAGAAAATCCATACTGGTGAGAAACCTTAT GAATGTAAAGAATGTAAGAAGCCTTCCGTTGGCAATCAGCTTACTCAACATCAA AAAATTCATACTGGGGAGAAGCCTCGTTATTCATAAGAGACTTCATACTGGTGAAAAACCTATGA ATGTAAAGACTGTGGGAAGGCCTTTCGCGTGGTAGAGCTCACTCAGCACCAGA GATTCCACACTGGGAGAAGACTACGAATGCAAAGACTGTGGGAAGACCTTAGC CGTGTGTATAAACTTATTCAGCACACAAGAGAATTCATAGTGGGGAGAAGCCTTACGA GTGTAAAGACTGTGGGAAGGCTTTTATTGGTTCAAGCCTCATTCAGCACATAAAG AATTCACACAGGTGAGAAGCCTATGAATGTCAAAGAATGTGGGAAGGCCTTACTCG AGTCAATTACCTTACTCAGCATCAGAGATCCACACCGGTGAGAAGCCTCACGAATG TAAGGAGTGTGGGAAGGCTTTCGCTGGGGTTCAGCCTCGTTAAGCACGAGAGGA TACATACGGGCGAGAAGCCTACAAGTGCACAGAATGTCACAGGCCTACAAGAGTGT GGCTATCACCTCACTCAGCACGAGAAATCCACACAGGCGAAACCCGTATAAATGT AAGGAGTGTGGGAAGCCTTTCATTTATGGATCGAGCCTCGTGAAACATGAGAAT TCATACCGGGGTGAAACCTCTAGGGTGTACAGAATGTGGGAAGAGCTTTAGTCACG GCCATCAAGCTTACACAACACACAGAAAACGCACAGTGGGGCGAAATCCTACGAATGT AAGGAGTGCGGGAAGCCATGTAACCTAAACCATTCCGAGAACATCAGAGGAT CCACAACAGTTGA | 6483 |
| | 3 | MSKIDLLEKAPLLEHRDIRRRIPLNVRTVGRPLVVAINL VNIRKSILVRNLMNVKNVRRPSVGAISLLNIKKPILGRSP TNVKTVGRLFDGAQASLFIRGFILVKNPMNVKTVERPF GVVMSSLSTRDSTLGRKTNAKTVGRPLAVCINLFSTRE PIVGRSLTSVKTVGRLLFVVQASPSIKEFTQVRNPMNYK NVGRPLLESITLLSIRRSFPVRSLTNVRSVGRPFAGVRAS LSTRGYIBARSRKTSAQNVGRPSIVAIITSLSTRESTQAKFRI NVRSVGRLSFMDRAS* | ATGTCAAAAGACCTGCTACTAGAGAAGGCACCCCTCCTAGAACACATCAGAGACATC ATAAGGAGAATTCCTTTGAATGTAAGGACTGTGGGAAGGCCTTTAGTCGTGCTATC AACTTAGTCAACATCAGAAAATCCATACTGGTGAGAAACCTATGAATGTAAAGAAT GTAAGAAGGCCTTCAGTTACTCATCAGCTTACTCAACATCAAAAAATTCATACTG GGGAGAAGCCCTACGAATGTAAAGACTGTGGGAAGGCTTTTCGATGGGGCTCAAGC CTCGTTATTCATAAGAGGATTCATACTGGTGAAAAACCTATGAATGTAAAGACTGT GGAAAAGGCCTTTCGGCCTGTGATGAGCTCACTCAGCACCAGAGATTTCCACACTGG GGAGAAAGACTACGAATGCAAAGACTGTGGGAAGACCTTAGCCGTGTGTATAAAC TTATTCAGCACAGCTTTATTGGTTCAAGCCTCATTCAGCATAAAAGAATTCACACGGT GGGAAGGCCTTTTCGAGCCTGTTCAAGCCTCGTTAAGCACGAGAGGATACATACGGGCG AGAAACCCTATGAATGTCAACAGGCGGAAACCCTCAATTGTGGCTATCACTC ACTCAGCACGAGAAATCCACACAGGCGAAACCCGTATAAATGTAAGGAGTGTGG GAAGGCTTTCATTTATGGATCGAGCCTCGTGA | 6485 |
| | 4 | MGLKPRYS* | ATGGGCTCAAGCCTCGTTATTCATAA | 6487 |
| | 1 | MSIR* | ATGTCAATCAGATGA | 6489 |

| | |
|---|---|
| | 6484 |
| | 6486 |
| | 6488 |
| | 6490 |

Figure 1 (Continued)

| | | | |
|---|---|---|---|
| hsa-mir-518b | 2 | MHINYVKRPATREGTPPRTHQRHHKENSPECKDCGKAF SRGYQLSQHQKIHTGEKPYECKECKCKAFRWGNQLTQH QKIHTGEKPYECKDCGKAFRWGSSLVIHKRIHTGEKPY ECKDCGKAFRKGDELTQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | ATGATCATCAATTATGTCAAAAGACCTGCTACTAGAGAAGGCACCCCTCCTAGAACA CATCAGAGACATTAGTAAGGAGAATTCCTTTGAATGTAAGGACTGTGGAAGGCCTTT AGTCGTGGCTATCAACTTAGTCAACATCAGAAAATCCATACTGGTGAGAAACCTTAT GAATGTAAAGAATGTAAGAAGCCTTCCGTTGGGCAATCAGCTTACTCAACATCAA AAAATTCATACTGGGGAGAAGCCTCGTTATTCATAAGAGATGTAAAGACTGTGGG ATGGGGCTCAAGCTCGTTATTCATAAGAGATTCATACTGGTGAAAAACCTATGA ATGTAAAGACTGTGGAAGGCCTTTCGCGTGGTCAATCAGCTCACTCAGCACCAGA GATTCCACACTGGGGAGAAGACTACGAATGCAAAGACTGTGGGAAGACCTTTAGC CGTGTGTATAAACTTATTCAGCACACAGAGAATTCATAGTAGTGGGGAGAAGCCTTACGA GTGTAAAGACTGTGGGAAGGCTTTTATTTGTGTTCAAGCCTCATTCAGCATAAAG AATTCACACAGGTGAGAACCCTATGAATGTCAAGGATGTGGGAAGGCCTTTACTCG AGTCAATTACCTTACTCAGCATCAGAGATGTCACACCGGTGAGAAGCCTCACGAATG TAAGGAGTGTGGGCGAGAAGCCTACAAGTGCACAGAATGCACAGAGGAATGCACGAGAGGA TACATACGGGCGAGAAGCCTACAAGTGCACAGAATGCACAAGGCGAAACCCGTATAAATGT GGCTATCACCTCACTCAGCACGAGAATCCACACAGGCGAAACCCGTATAAATGT TCATATCCGGGGGTGAAACCTATGGGTGCACAGAATGTGAGGCTTAGTCACG GCCATCAAGCTTACACAACATCCAAGAAACGCACAGTGGGGGCGAAATCTACGAATGT AAGGAGTGCGGGAAGCCATGTAACCTAAACCATCCGAGAACATCAGAGGAT CCAACAGTTGA | 6492 |
| | 3 | MSKIDLLEKAPLLEHRIRRIPLNVRTVGRPLVVAINL VMRKSILVRNLMNVKNVRRPSVGAISLLNIKKPILGRSP TNVKTVGRLFDGAQASLFIRGFILVKNPMNVKTVERPF GVVMSSLSTRDSTLGRKTNAKTVGRPLAVCINLFSTRE PTVGRSLTSVKTVGRLLFVVQASPSIKEFTQVRNPMNYK NVGRPLLLESTTLLSIRRSFPVRSLTNVRSVGRPFAGVRAS LSTRGYIRARSKTSAQNVGRPSIVAITSLSTRESTQAKFRI NVRSVGRLSFMDRAS* | ATGTCAAAAGACCTGCTACTAGAGAAGGCACCCCTCCTAGAACACATCAGAGACATC ATAAGGAGAATTCCTTTGAATGTAAGGACTGTGGGAAGGCCTTTAGTCGTGCTATC AACTTAGTCAACATCAGAAAATCCATACTGGTGAGAAACCTTATGAATGTAAAGAAT GTAAGAAGCCTTCCGTTACTCAAGGCTTACTCAACATCAAAAAATTCATACTG GGGAGAAGCCCTACGAATGTAAAGACTGTGGGAAGGCTTTCGATGGGGCTCAAGC CTCGTTATTCATAAGAGATTCATACTGGTGAAAAACCTATGAATGTAAAGACTGT GAAAGGCCTTTCGCCGTGTGATGAGCTCACTCAGCACCAGATTCCACACTGG GGGAAAAGACTACGAATGCAAAGACTGTGGGAAGACCTTAGCCGTGTGTATAAAC TTATTCAGCACACAGAGAATTCATAGTGGGAAGAACCTTACGAATGTAAAGACCTTTATAAAC GGGAAGGCTTTTATTTGTGGTTCAAGCCTCGTTAAGCCCTACGAGATACGGGCG GAGAAGCCCTATGAATGTCAAGAATGTGGGAAGACGCTCATTGCATCACACGTG ACTCAGCAGCGTACAAGTGCACAGGCGAAGCCTCACAGGCCTTCAATTAGCATGT GAAGGCCGTACAAGTGCACACAGGGCGAAACCCGTATAAATGGTGCATCCTC ACTCAGCAGCAGAGAATTCATAGTGGGAAGCCTGCTTACTCGAGTGAATGTAAGGAGTGTGG GAAGGCTTTCATTATGGATCAGATGA | 6494 |
| | 4 | MGLKPRYS* | ATGGGGCTCAAGCCTCGTTATTCATAA | 6495 | 6496 |
| | 1 | MSIR* | ATGTCAATCAGATGA | 6497 | 6498 |

Figure 1 (Continued)

| | | | |
|---|---|---|---|
| hsa-mir-518c | 2 | MHINYVKRPATREGTPPRTHQRHHKENSPECKDCGKAF SRGYQLSQHQKIHTGEKPYECKECKCKAFRWGNQLTQH QKIHTGEKPYECKDCGKAFRWGSSLVIHKRIHTGEKPY ECKDCGKAFRKGDELTQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | ATGATCATCAATTATGTCAAAAGACTGCTACTAGAGAAGGCACCCCTCCTAGAACA CATCAGAGACATCATAAGGAGAATTCCTTTGAATGTAAGGACTGTGGCTATC AGTCGTGGCTATCAACTTAGTCAACATCAGAAAATTCCATACTGGTGAGAAACCTTAT GAATGTAAAGAATGTAAGAAGCCTTCCGTTCGGCAATCAGCTTACTCAACATCAA AAAATTCATACTGGGGAGAAGCCTCGTTATTCATAAGAGATGTAAAGACTTTTCG ATGGGGCTCAAGCTGTGGAGCTCGTTATTCATAAAGAGATTCATACTGGTGAAAAACCTATGA ATGTAAAGACTGTGGAAGGATTCGGCGTGGTAGAGCTCACTCAGCACCAGA GATTCCACACTGGGGAGAAGATACGAATGCAAAGACTGTGGGAAGACCTTTAGC CGTGTGTATAAACTTATTCAGCACAGAAGAATTCATAGTGGGAGAAGCCTTACGA GTGTAAAGACTGTGGGAAGGCTTTTATTTGTGGTTCAAGCCTCATTCAGCATAAAG AATTCACACAGGTGAGAAACCCTATGAATGTCAAAGATGTGGAAGGCTTTACTCG AGTCAATTACCTTACTCAGCATCAGAAGATCCACACCGGTGAGAAGCCTCACGAATG TAAGGAGTGTGGGCGCGAGAAGCCTTCGAGCCTCGTTAAGCACGAGAGGA TACATACGGGCGAGAAGCCGTACAAGTGCACAGAATGTGGGAAGCCTTCAATTGT GGCTATCACCTTACTCAGCACGAGAGAATCCACACAGGTGAAACCCGTATGAGAGAAT TCATATCCGGGGTGAAACCCTATGGGTGCACAGAATGTGGGAAGACTTTAGTCACG GCCATCAAGCTTACACAACACAGTGAGAAACCGACAGTGGGCGAACATCTACGAATGT AAGGAGTGCGGGAAGCCATGTAACCACCTAAACCATTCCGAGAACATCAGAGGAT CCACAACAGTTGA | 6500 |
| | 3 | MSKDILLEKAPLLEHRDIRRIPLNVRTVGRPLVVAINL VNIRKSILVRNLMNVKNVRRPSVGAISLLNIKKPILGRSP TNVKTVGRLFIRGFILVKNPMNVKTVERPF GVVMSSLSTRDSTLGRKTNAKTVGRPLAVCINLFSTRE PIVGRSLTSVKTVGRLLFVVQASPSIKEFTQVRNPMNYK NVGRPLLESITLLSIRRSFTPVRSLTNVRSVGRPFAGVRAS LSTRGYIRARSKTSAQNVGRPSIVAITSLSTRESTQAKFRI NVRSVGRLSFMDRAS* | ATGTCAAAAGACCTGCTACTAGAGAAGGCACCCTCCTAGAACACATCAGAGACATC ATAAGGAGAATTCCTTTGAATGTAAGGACTGTGGGAAGCCTATCAGTCGTGCTATC AACTTAGTCAACATCAGAAAATCCATACTGGTGAGAAACCTTATGAATGTAAAGAAT GTAAGAAGGCCTTCCGTACGAATGTAAAGACTGTGGGAATGAAAAACCTATGAATGTAAAGACTGT GGGAGAAGAAGCCCTACGAATGTAAAGACTGTGGGAAGGCTTTCGATGGGGCTCAAGC CTCGTTATTCATAAGAGATTCATACTGGTGAAAAACCCTATGAATGTAAAGACTGT GGAAAGGCCTTTCGGCGTGATGAAGCTCACTCAGCACCAGAGATTCCACACTGG GGAGAAAGACTACGAATGCAAAGACTGTGGGAAGACCTTAGCGTGTGTATAAAC TTATTCAGCACAGAAGAATTCATAGTGGGAGAAGCCTTACGAGTGTAAAGACT GGGAAGGCTTTTATTTGTGGTTCAAGCCTCATTCAGCATAAAGAATTCACACAGGT GAGAAACCCTATGAATGTCAAGAATGTCAAGAAGGCCTTTACTCGAGTCAATTACCT TACTCAGCACGAGAAGATCCACACCGGTGAGAAGCCTCACGAATGTAAGGAGTGTGG GAAGGCCTTTCGCTGGGGTTCGAGCCTCGTTAAGCACGAGAGGATACATACGGGCG AGAAGCCGTACAAGTGCACAGAATGTGGGAAGCCTTCAATTGTGGCTATCACCTC ACTCAGCACGAGAAGATCCACACAGGTGGGAAACCCGTATATAAATGTAAGGAGTGTGG GAAGGCTTTCATTTATGGATCGAGCCCGTGA | 6502 |
| | 4 | MGLKPRYS* | ATGGGCTCAAGCCTCGTTATTCATAA | 6503 | 6504 |
| 1 | MSIR* | ATGTCAATCAGATGA | 6505 | 6506 |

Figure 1 (Continued)

| | | | | |
|---|---|---|---|---|
| hsa-mir-518d | 2 | MHINYVKRPATREGTPPRTHQRHHKENSPECKDCGKAF SRGYQLSQEHQKIHTGEKPYECKECKAFRWGNQLTQH QKIHTGEKPYECKDCGKAFRWGSSLVIHKRIHTGEKPY ECKDCGKAFRKGDELTQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | 6507 | ATGATCATCAATTATGTCAAAAGACTGCTACTAGAGAAGGCACCCCTCCTAGAACA CATCAGAGACATCATAAGGAGAATTCCTTTGAATGTAAGGACTGTGGAAGGCCTTT AGTCGTGGCTATCAACTTAGTCAACATCAGAAATGTCCATACTGGTGAGAAACCTTAT GAATGTAAAGAATGTAAGGCCTTCCGTTGGCAATCAGCTTACTGAACATCAA AAAATTCATACTGGGGAGAAGCCTACGAATGTAAAGACTGTGGGAAGGCTTTCG ATGGGGCTCAAGCTCGTTATTCATAAGAGAATTCATACTGGTGAAAAACCTATGA ATGTAAAGACTGTGGGAAGGCCTTTCGGCGTGGTAGCTCACTCAGCACCAGA GATTCCACACTGGGAGAAGATACGAATGCAAAGACTGTGGGAAGACCTTTAGC CGTGTGTATAAACTTATTCAGCACAGAGAATTCATAGTGGGGAGAAGCCTTACGA GTGTAAAGACTGTGGGAAGGCTTTTATTTGTGTTCAAGCCTCATTCAGCATAAAG AATTCACACAGGTGGACAAACCCTATGAATGTCAAAGATGTGGGAAGGCCTTACTCG AGTCAATTACCTTACTCAGCATCAGAGAATCCACACCGGTGAGAAGCCTCACGAATG TAAGGAGTGTGGGAAGGCCTTTCGCTGGGGTTCGAGCCTCGTTAAGCACGAGAGA TACATACGGGCGAGAAGCCTACAAGTGCACAGAATGCAAGAAATCCTCAATTGT GGCTATCACCTCACTCAGCACGAGAATCCACACAGGAGAAACCCGTATAAATGT TCATACCGGGGTGAACCCTATGGGTGTACAGAATGTGGGAAGACTTTAGTCACG GCCATCAAGCTTACACAACACTCAGAAACGCACAGTGGGGCGAAATCTACGAATGT AAGGAGTGCGGGAAGCCATGTAACCACCTAAACCATCTCGAGAACATCAGAGGAT CCACAACAGTTGA |
| | 3 | MSKIDLLEKAPLLEHRIRRIPLNVRTVGRPLVVAINL VMRKSILVRNLMNVKNVRRPSVGAISLLNIKKPILGRSP TNVKTVGRLLFDGAQASLFIRGFILVKNPMNVKTVERPF GVVMSSLSTRDSTLGRKTNAKTVGRPLAVCINLFSTRE PTVGRSLTSVKTVGRLLFVVQASPSIKEFTQVRNPMNYK NVGRPLLESITLLSIBRRSFPVRSLTNVRSVGRPFAGVRAS LSTRGYIRARSKTSAQNVGRPSIVAITSLSTRESTQAKFRI NVRSVGRLSFMDRAS* | 6509 | ATGTCAAAAGACCTGCTACTAGAGGACACCCTCCTAGAACACATCAGAGACATC ATAAGGAGAATTCCTTTGAATGTAAGGACTGTGGGAAGGCCTTTAGTCGTGCTATC AACTTAGTCAACATCAGAAATCTGAATGTGAGAAAATCCATACTGGTGAGAAATGTAAAGAAT GTAAGAAGGCCTTCACTGAAGCCCTACGAATGTAAAGACTGTTCGATGGGGCTCAAGC CTCGTTATTCATAAGAGAATTCATAGACTGTGGTGAAAAACCTATGAATGTAAAGACTGT GGAAAGGCCTTTCGGCCTGTGATGAGCTCACTCAGCACCAGAGATTCCACACTGG GGAGAAAGACTACGAATGCAAAGACTGTGGGAAGACCTTAGCCGTGTATAAAC TTATTCAGCACAGAGAATTCATAGTGGGAGAAGCCTTACGAGTGTAAAGACTGT GGGAAGGCCTTTATTTGTGGTTCAAGAATGTCAAGAATGTGGGAAGCCTCGAGTCAAGGT GAGAACCCTATGAATGTCACAAGATGCACAGGGGAAGCCTTTACTCGCATAAAAGGTT ACTCAGCATCAGAGAATCCACACCGGTGAGAAGCCTCACGAATGTAAGGAGTGTG GAAGGCCTTTCGCTGGGGTTCGAGCCTCGTTAAGCACGAGGATACATACGGGCG GAGAAGCCGTACAAGTGCACAGAATCCACACAGGCGGAAACCCGTATATCACCTC ACTCAGCACGAGAATCCACACAGGCGGAAACCCGTATAAATGTTCGATCAATGTTCAC GAAGGCTTTCATTTATGGATCGAGCCCGTGA |
| | 4 | MGLKPRYS* | 6511 | ATGGGGCTCAAGCCTCGTTATTCATAA |
| | 1 | MSIR* | 6513 | ATGTCAATCAGATGA |

Figure 1 (Continued)

| | | | |
|---|---|---|---|
| hsa-mir-518e | 2 | MHINYVKRPATREGTPPRTHQRHHKENSPECKDCGKAF SRGYQLSQHQKIHTGEKPYECKECKCKAFRWGNQLTQH QKIHTGEKPYECKDCGKAFRWGSSLVIHKRIHTGEKPY ECKDCGKAFRRGDELTQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRHQLTQHQKTHSGAKSYECKEC GKACNHLNHLREHQRIHNS* | 6515 | ATGATCATCAATTATGTCAAAAGACCTGCTACTAGAGAAGGCACCCCTCCTAGAACA CATCAGAGACATCATAAGGAGAATTCCTTTGAATGTAAGGACTGTGGGAAGGCCTTT AGTCGTGGCTATCAACTTAGTCAACATCAGAAATTCCATACTGGTGAGAAACCTTAT GAATGTAAAGAATGTAAGAAGGCCTTCCGTTGGGCAATCAGCTTACTCAACATCAA AAAATTCATACTGGGGAGAAGCCTACTAAAGACTGTAAAGACTGTGGGAAGGCTTTTCG ATGGGCTCAAGCTCGTTATTCATAAGAGAATTCATACTGGTGAAAAACCTATGA ATGTAAAGACTGTGGGAAGGCCTTTCGCGTGGTAAGCTCACTCAGCACCAGA GATTCCACACTGGGGAGAAGACTACGAATGCAAAGACTGTGGGAAGACCTTTAGC CGTGTGTATAAACTTATTCAGCACACAAGAGAATTCATAGTGGGGAGAAGCCTTACGA GTGTAAAGACTGTGGGAAGGCTTTTATTTGTGGTTCAAGCCTCATTCAGCATAAAG AATTCACACAGGTGAGAAATGCAAACCCTATGAATGTCAAAGAATGTGGGAAGGCCTTTACTCG AGTCAATTACCTTACTCAGCATCAGAGAATGCACAGAAATGGGGAAGCCTCACGAATG TAAGGAGTGTGGGAGCCTACAAGGCCTTTCGAGCTGTTCAGCGTTTAAGCACGAGAGA TACATACGGGCGAGAAGCCTACAAGTGCACAGAATGGCAGGGAAGCCTTCAATTGT GGCTATCACCTCACTCAGCACGAGAATCCACACAGGTGAGAACCCGTATAAATGT AAGGAGTGTGGGAAGCTTTCATTTATGGATCGAGCCTCGTGAACATGAGAGAT TCATACCGGGGTGACAACCCTATGGGTGTACAGAAATGTGGGAAGAGCTTTAGTCACG GCCATCAAGCTTACACAACATCAGAAAACCGACAGTGGGGCGAAATCTACGAATGT AAGGAGTGCGGGAAGCCATGTAACCACCTAAACCAITCCGAGAACATCAGAGGAAT CCACAACAGTTGA |
| | 3 | MSKIDLLEKAPLLEHRDIRRRIPLNVRTVGRPLVVAINL VMRKSILVRNLMNVKNVRRPSVGAISLLNIKKFILGRSP TNVKTVGRLFDGAQASLFIRGFILVKNPMNVKTVERPF GVVMSSLSTRDSTLGRKTNAKTVGRPLAVCINLFSTRE PIVGRSLTSVTSVKTVGRLLFVVQASPSIKEFTQVRNPMNYK NVGRPLLESITLLSIRRSFPVRSLTNVRSVGRPFAGVRAS LSTRGYIRARSRKTSAQNVGRPSIVAIITSLSTRESTQAKFRI NVRSVGRLSFMDRAS* | 6517 | ATGTCAAAAGACCTGCTACTAGAGGACACCCCTCCTAGAACACATCAGAGACATC ATAAGGAGAATTCCTTTGAATGTAAGGACTGTGGGAAGGCCTTTAGTCGTGGCTATC AACTTAGTCAACATCAGAAATTCATACTGGTGAGAAGCCTTATGAATGTAAAGAAT GTAAGAAGGCCTTCACTCAGAATCAGCTTACTCAACATCAAAAAATTCATACTG GGGAGAAGCCCTACTAAAGACTGTAAAGATGTGGGAAGGCTTTTCGATGGGCTCAAGC CTCGTTATTCATAAGAGAATTCATACTGGTGAAAAAACCTATGAATGTAAAGACTGT GGGAAAGGCCTTTCGCCGTTACGAATGCAAAGACTGTGGGAAGACCTTTAGCCGTGTGTATAAAC TTATTCAGCACACTACGAATGCAAAGACTGTGGGAAGACCTTACGAGTGTAAAGACTGT GGGAAGGCTTTATTTGTGGTTCAAGCATCAGCATAAAGAATTCACACAGGT GAGAAACCCTATGAATGTCAAGAATGTGGGAAGCCTCTGATCGTTAAGGAGTGTGG GAAGGCCTTCACGGTACGAGAATCACACAGGTGAGAAGCCTCGTTAAGCACGAGGATACATGGCG ACTCAGCAGCGTACAAGTGCACAGAATGTGGGAAGGCCTTCAATTGTGGCTATCCTC ACTCAGCACGAGAATCCACACAGGTGGGAAACCCGTATAAATGTAAGGAGTGTGG GAAGGCTTTCATTTATGGATCGAGCCTCGTGA | 6518 |
| | 4 | MGLKPRYS* | 6519 | ATGGGCTCAAGCCTCGTTATTCATAA | 6520 |
| | 1 | MSIR* | 6521 | ATGTCAATCAGATGA | 6522 |

Figure 1 (Continued)

| | | | |
|---|---|---|---|
| hsa-mir-518f | 2 | MHNYVKRPATREGTPPRTHQRHHKENSPECKDCGKAF SRGYQLSQHQKIHTGEKPYECKECKCKAFRWGNQLTQH QKIHTGEKPYECKDCGKAFRWGSSLVIHKRIHTGEKPY ECKDCGKAFRKGDELTQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | ATGATCATCAATTATGTCAAAAGACTGCTACTAGAGAAGGCACCCCTCCTAGAACA CATCAGAGACATCATAAGGAGAATTCCTTTGAATGTAAGGACTGTGGCTGTATC AGTCGTGGCTATCAACTTAGTCAACATCAGAAATCCATACTGGTGAGAAACCTTAT GAATGTAAAGAATGTAAGAAGGCCTTCCGTTGGGCAATCAGCTTACTCAACATCAA AAAATTCATACTGGGGAGAAGCCTTCTATTCATAAGAGAATTCATACTGGTGAAAAACCTATGA ATGTGGGCTCAAGCTCGTTATTCATAAGAGAATTCATACTGGTGAAAAACCTATGA ATGTAAAGACTGTGGAAAGGCCTTTCCGCGTGGTCAGTGAGCTCACTCAGCACCAGA GATTCCACACTGGGGAGAAGACTACGAATGCAAAGACTGTGGGAAGACCTTTAGC CGTGTGTATAAACTTATTCAGCACACAAGAGAATTCATAGTGGGGAGAAGCCTTACGA GTGTAAAGACTGTGGGAAGGCTTTTATTTGTGTTCAAGCCTCATTCAGCATAAAG AATTCACACAGGTGAGAAATGCAAAACCCTATGAATGTCAAAGAGTGTGGAAGGCCTTTACTCG AGTCAATTACCTTACTCAGCATCAGAGAATGTCACACCGGTGAGAAGCCTCACGAATG TAAGGAGTGTGGGAGAAGGCCTTTCGCTGGGGTTCGAGCCTTCAAGCACGAGAGGA TACATACGGGCGAGAAGCCGTACAAGTGCACAGAATGTGGGAAGGCTTCAATTGT GGCTATCACCTCACTCAGCACGAGAAGCCACACAGGCGAAACCCGTATAAATGT TCATATCCGGGGGTGAAACCTATAGGGTGTACAGAAGTGTGGGAAGGCTTTAGTCACG GCCATCAAGCTTACACAACATCCAGAAACGCACAGTGGGGCGAAATCTACGAATGT AAGGAGTGCGGGAAGCCATGTAACCTAAACCATCTCCGAGAACATCAGAGGAT CCACAACAGTTGA | 6524 |
| | 3 | MSKDILLEKAPLLEHRDIRRIPLNVRTVGRPLVVAINL VMRKSILVRNLMNVKNVRRPSVGAISLLNIKKFILGRSP TNVKTVGRLFEDGAQASLFIRGFILVKNPMNVKTVERPF GVVMSSLSTRDSTLGRKTTNAKTVGRPLAVCINLFSTRE PTVGRSLTSVTSKTVGRLLFVVQASPSIKEFTQVRNPMNYK NVGRPFLLESITLLSIRRSFPVRSLTNVRSVGRPFAGVRAS LSTRGYIRARSRKTSAQNVGRPSIVAIITSLSTRESTQAKFRJ NVRSVGRLSFMDRAS* | ATGTCAAAAGACCTGCTACTAGAGAAGGCACCCTCCTAGAACACATCAGAGACATC ATAAGGAGAATTCCTTTGAATGTAAGGACTGTGGGAAGCCATTTAGTCGTGCTATC AACTTAGTCAACATCAGAAATCCATACTGGTGAGAAGCCTTATGAATGTAAAGAAT GTAAGAAGGCCTTCCGTTACTCAGCTTACTCAACATCAAAAATTCATACTG GGGAGAAGCCCTACGAATGTAAAGACTGTGGGAAGGCTTTCGATGGGGCTCAAGC CTCGTTATTCATAAGAGGATTCATACTGGTGAAAAACCTATGAATGTAAAGACTGT GGAAAAGGCCTTTACGCCTTTCGGCGTGATGAGCTCACTCAGCACCAGAGATTCCACACTGG GGAGAAGACTACGAATGCAAAGACTGTGGGAAGACCTTTAGCCGTGTGTATAAAC TTATTCAGCACACAAGAGAATTCATAGTGGGGAGAAGCCTTACGAGTGTAAAGCT GGGAAGGCCTTTATTTGTGGTTCAAGCCTCGTTAAGCCTCGTTAAGCCTCTTGAAGGAGGCTTGATATT ACTCAGCATCAGAGAATCCACACCGGTGAGAAGCCTCAGCATAAAGAATTCACACGGT GAAGGCCTTTCGCTGGGGTTCGAGCCTGTTAAGCACGAGAGGATACATACGGGCG ACAAGCCGTACAAGTGCACAGAATGTGGGAAGGCCTTCAATTGTGGCTATCACCTC ACTCAGCACGAGAAGCCACACAGGCGAAACCCGTATAAATGTAAGGAGTGTGG GAAGGCTTTCATTTATGGATCGAGCCGTCGTGA | 6526 |
| | 4 | MGLKPRYS* | ATGGGCTCAAGCCTCGTTATTCATAA | 6527 |
| | 1 | MSIR* | ATGTCAATCAGATGA | 6529 |
| | | | 6528 |
| | | | 6530 |

Figure 1 (Continued)

| | | | |
|---|---|---|---|
| hsa-mir-519a-1 | 2 | MHNYVKRPATREGTPPRTHQRHHKENSPECKDCGKAF SRGYQLSQEHQKIHTGEKPYECKECKKAFRWGNQLTQH QKIHTGEKPYECKDCGKAFRWGSSLVIHKRIHTGEKPY ECKDCGKAFRKGDELTQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | ATGATCATCAATTATGTCAAAAGACTGTACTAGAGAAGGCACCCTCCTAGAACA CATCAGAGACATCATAAGGAGAATTCCTTTGAATGTAAGGACTGTGGCTGTATC AGTCGTGGCTATCAACTTAGTCAACATCAGAAAATCCATACTGGTGAGAAACCTTAT GAATGTAAAGAATGTAAGAAGGCCTTCCGTTGGGCAATCAGCTTACTCAACATCAA AAATTCATACTGGGGAGAAGCCTGTATTCATAAGAGAATTCATACTGGTGAAAACCTATGA ATGTAAAGACTGTGGGAGACTGTGTGGCCGTGGCAATCAGCTCACTCAGCACCAGA GATTCCACACTGGGGAGAAGATACGAATGCAAAGACTGTGGGAAGACCTTTAGC CGTGTGTATAAACTTATTCAGCACACAAGAGAATTCATAGTGGGGAGAAGCCTTACGA GTGTAAAGACTGTGGGAAGGCTTTCATTTGTGGTTCAAGCCTCATTCAGCATAAAG AATTCACACAGGTGAGAAACCCTATGAATGTCAAAGAATGTGGGAAGGCCTTTACTCG AGTCAATTACCTTACTCAGCATCAGAGAATCCACACGGTGAGAAGCCTCACGAATG TAAGGAGTGTGGGAGCTGTGGGAGAAGCCGTACAAGTGCACAGAATGCGGGAAGGCCTCGTTAAGCACGAGAGGA TACATACGGGCGAGAAGCCGTACAAGTGCACAGAATGGGGAAGGCCTCGTTAAGCACGAGAGGA GGCTATCACCTCACTCAGCACGAGAAGCCACACAGGTGAAACCGTATGAGAGAAT TCATACCGGGGTGAAACCTATGGGTGTACAGAATGTGGGAAGGCTTAGTCACG GCCATCAGCTTACACAACACACAGAAAACCAGTGGGGCGAAATCCTACGAATGT AAGGAGTGCGGGAAGCATGTAACCACCTAAACCATTCCGAGAACATCAGAGGAT CCACAACAGTTGA | 6532 |
| | | | 6531 |
| | 3 | MSKDILLEKAPLLEHRDIRRIPLNVRTVGRPLVVAINL VMRKSILVRNLMNVKNVRRPSVGAISLLNIKKPILGRSP TNVKTVGRLFDGAQASLFIRGFILVKNPMNVKTVERPF GVVMSSLSTRDSTLGRKTNAKTVGRPLAVCINLFSTRE PIVGRSLTSVKTVGRLLFVVQASPSIKEFTQVRNPMNYK NVGRPLLESITLLSIRRSFPVRSLTNVRSVGRPFAGVRAS LSTRGYIRARSRKTSAQNVGRPSIVAITSLSTRESTQAKFRI NVRSVGRLSFMDRAS* | ATGTCAAAAGACCTGCTACTAGAGAAGGCACCCTCCTAGAACACATCAGAGACATC ATAAGGAGAATTCCTTTGAATGTAAGGACTGTGGGAAGGCCTTAGTCGTGGCTATC AACTTAGTCAACATCAGAAAATCCATACTGGTGAGAATGTAAGAACTTATAAAGAAT GTAAGAAGGCCTTCCGTTACTCAGCTTACTCAACATCAAAAATTCATACTG GGGAGAAGCCGCCTACGAATGTAAAGACTGTGGGAAGGCTTTCGATGGGGCTCAAGC CTCGTTATTCATAAGAGGATTCATACTGGTGAAAAACCTATGAATGTAAAGACTGT GGAAAGGCCTTTCGGCCTGTGATGAGCTACTCAGCACCAGAGACCTTCACACTGG GGAGAAAGACTACGAATGCAAAGACTGTGGGAAGACCTTAGCCGTGTGTATAAAC TTATTCAGCACACAAGAGAATTCATAGTGGGGAGAAGCCTTACGAGTGTAAAGACT GGGAAGGCCTTTATTTTGTGGTTCAAGCCTCATTCAGCATAAAGAATTCACACAGGT GAGAAACCCTATGAATGTCAAGAATGTGGGAAGGCCTTTACTCGAGTCAATTACCT ACTCAGCATCAGAGAATCCACACGGTGAGAAGCCTCACGAATGTAAGGAGTGTG GAAGGCCTTTCGCTGGGGTTCGAGCCTCGTTAAGCACGAGAGGATACATACGGGCG ACTCAGCGAGGTACAAGCTCACACAGGGCGAAACCGTCAATTGTGGCTATCACCTC GAAGGCTTTCATTTATGGATCGAGCCCTCGTGA | 6534 |
| | | | 6533 |
| | 4 | MGLKPRYS* | ATgGGCTCAAGCCTCGTTATTCATAA | 6535 |
| | | | 6536 |
| | 1 | MSIR* | ATGTCAATCAGATGA | 6537 |
| | | | 6538 |

Figure 1 (Continued)

| | | | |
|---|---|---|---|
| hsa-mir-519a-2 | 2 | MHINYVKRPATREGTPPRTHQRHHKENSPECKDCGKAF SRGYQLSQEHQKIHTGEKPYECKECKCKAFRWGNQLTQH QKIHTGEKPYECKDCGKAFRWGSSLVIHKRIHTGEKPY ECKDCGKAFRKGDELTQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | ATGATCATCAATTATGTCAAAAGACCTGCTACTAGAGAAGGCACCCCTCCTAGAACA CATCAGAGACATCATAAGGAGAATTCCTTTGAATGTAAGGACTGTGGGAAGCCTTT AGTCGTGGCTATCAACTTAGTCAACATCAGAAAATCCATACTGGTGAGAAACCTTAT GAATGTAAAGAATGTAAGAAGCCTTCCGTTGGGCAATCAGCTTACTCAACATCAA AAAATTCATACTGGGGAGAAGCCTCGTTATTCATAAGAGATGTAAAGACTGTGGGA ATGGGCTCAAGCACTGTGGAGCTCGTTATTCATAAGAGATTCATACTGGTGAAAAACCCTATGA ATGTAAAGACTGTGGGAGAAGCCTTTCGCGTGGTAGCTCACTCAGCACCAGA GATTCCACACTGTGGGAGGAAAGATACGAATGCAAAGACTGTGGGAAGACCTTAGC CGTGTGTATAAACTTATTCAGCACACAAGAGAATTCATAGTGGGGAGAAGCCTTACGA GTCTAAAGACTGTGGGAAGGCTTTTATTTGTGGTTCAAGCCTCATTCAGCATAAAG AATTCACACAGGTGAGAAGACCCTATGAATGTCAAAGATGTGGGAAGCCTTTACTCG AGTCAATTACCTTACTCAGCATCAGAGATGTCACACCGGTGAGAAGCCTCACGAATG TAAGGAGTGTGGGAGCGGAGAAGCCTTCGCTGGGGTTCGAGCCTCGTTAAGCACGAGGA TACATACGGGCGAGAAGCCTACAAGTGCACAGAATGCAAAATCCACACAGGCGAAAACCCGTATAAATGT GGCTATCACCTCACTCAGCACGAGAGAATCCACACAGGCGAAAACCCGTATGAGAGAAT TCATATACCGGGGTGAACCTATGGGTGTACAGAATGTGGGAAGACTTAAGTCACG GCCATCAAGCTTACACAACACGAGAAACGCACAGTGGGGCGAAATCCTACGAATGT AAGGAGTGCGGGAAGCATGTAACCACCTAAACCATCTCCGAGAACATCAGAGGAT CCACAACAGTTGA | 6539 6540 |
| | 3 | MSKDLLLEKAPLLEHRDIRRIPLNVRTVGRPLVVAINL VNRKSILVRNLMNVKNVRRPSVGAISLLNIKKPILGRSP TNVKTVGRLFEDGAQASLFIRGFILVKNPMNVKTVERPF GVVMSSLSTRDSTLGRKTNAKTVGRPLAVCINLFSTRE PIVGRSLTSVKTVGRLLFVVQASPSIKEFTQVRNPMNYK NVGRPLLESITLLSIRRSFPVRSLTNVRSVGRPFAGVRAS LSTRGYIBARSRKTSAQNVGRPSIVAIITSLSTRESTQAKFRI NVRSVGRLSFMDRAS* | ATGTCAAAAGACCTGCTACTAGAGGACCATCGAGAAGGCACCGCTGGGAAGCCTCTAGAACACATCAGAGACATCAGAGACATC ATAAGGAGAATTCCTTTGAATGTAAGGACTGTGGGAAGCCTTTAGTCGTGCTATC AACTTAGTCAACATCAGAAAATCCATACTGGTGAGAAACCCTTATGAATGTAAAGAAT GTAAGAAGCCTTCCGTTGGGCAATCAGCTTACTCAACATCAAAAAATTCATACTG GGGAGAAGCCTCGTTATTCATAAGAGACTGTAAAGGCTTTCGATGGGGCTCAAGC CTCGTTATTCATAAGAGACTGTAAAGACTGGAAAAACCCTATGAATGTAAAGACTGT GGAAAAGGCCTTTATTCGGCGTGATGAGCTCACTCAGCACCAGAGAGATTCCACACTGG GGAGAAAGACTACGAATGCAAAGACTGTGGGAAGAACCTTAGCCGTGTGTATAAAC TTATTCAGCACACAAGAGAATTCATAGTGGGAGAAGCCTTCAGCTGATAAAGAAGG GGGAAGGCCTTTCTGGGTTCAAGCCTCGTTAAGCACGAGGAGAGATACATACGGGGCG GAGAAGCCTATGAATGTCAAGGCCTTACGAGATGGGGAAGCCTTTACTCGAGTCAATTACCT ACTCAGCACGAGAGAATCCACACAGGCGAAGCCTTAAGCACGAGGAGATACATACGGGGCG GAAGGCCTTTCGCTGGGGTCAAGCACCGGGTTGAGCCTCGTTAAGCACGAGGATATACGGGCG GAAGGCCGTACAAGTGCACAGAATGTGGGAAGCCTTCAATTGTGGCTATCACCTC ACTCAGCACGAGAGAATCCACACAGGCGAAACCCCGTATAAATGTAAGGAGTGTGG GAAGGCTTTCATTTATGGATCGAGCCCGTGA | 6541 6542 |
| | 4 | MGLKPRYS* | ATEKGGCTCAAGCCTCGTTATTCATAA | 6543 6544 |
| | 1 | MSIR* | ATGTCAATCAGATGA | 6545 6546 |

Figure 1 (Continued)

| | | | |
|---|---|---|---|
| hsa-mir-519b | 2 | MHINYVKRPATREGTPPRTHQRHHKENSPECKDCGKAF SRGYQLSQHQKIHTGEKPYECKECKAFRWGNQLTQH QKIHTGEKPYECKDCGKAFRWGSSLVIHKRIHTGEKPY ECKDCGKAFRKGDELTQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | ATGATCATCAATTATGTCAAAAGACTGCTACTAGAGAAGGCACCCCTCCTAGAACA CATCAGAGACATCATAAGGAGAATTCCTTTGAATGTAAGGACTGTGGAAGGCCTTT AGTCGTGGCTATCAACTTAGTCAACATCAGAAAATCCATACTGGTGAGAAACCTAT GAATGTAAAGAATGTAAAGAAGGCCTTCCGTTGGGCAATCAGCTTACTCAACATCAA AAAATTCATACTGGGGAGAAGCCTTCGTTATTCATAAGAGATCTATACTGGTGAAAAACCTATGA ATGGGGCTCAAGCTGTGGAAGCTCGTTATTCATAAGAGATTCATACTGGTGAAAAACCTATGA ATGTAAAGACTGTGGAAGGACTTTCCGCCGTGGTGATGAGCTCACTCAGCACCAGA GATTCCACACTGGGGAGAAGACTACGAATGCAAAGACTGTGGGAAGACCTTAGC CGTGTGTATAAACTTATTCAGCACACAAGAGAATTCATAGTGGGGAGAAGCCTTACGA GTGTAAAGACTGTGGGAAGGCTTTTATTTGTGGTTCAAGCCTCATTCAGCATAAAG AATTCACACAGGTGAGAAATGCAAACCCTATGAATGTCAAAGAATGTGGGAAGGCCTTTACTCG AGTCAATTACCTTACTCAGCATCAGAGATCTACACGGTGAGAAGCCTCACGAATG TAAGGAGTGTGGGCGGAGAAGCCTACAAGTGCACAGAATGCGGGGAAGCCTTCAATTGT TACATACGGGCGAGAAGCCTACAAGTGCACAGAATGCACACCCCGCGTATAAATGT GGCTATCACCTTACTCAGCACGAGAATCCACACAGGCGAAACCCGTATAAATGT TCATACCGGGGTGAAACCCTATGGGTACAGAATGTGGGAAGGCTTTAGTCACG GCCATCAAGCTTACACAACACAGAAAACCACAGTGGGGCGAAATCTACGAATGT AAGGAGTGCGGGAAGCCATGTAACCATCCACCTAAACCATCCGAGAACATCAGAGGAAT CCAACAGTTGA | 6548 |
| | 3 | MSKDLLEKAPLLEHRIDRRFLPNLVRTVGRPLVVAINL VNRKSLVRNLMNVKNVRRPSVGAISLLNIKKFILGRSP TNVKTVGRLFEDGAQASLFIRGFILVKNPMNVKTVERPF GVVMSSLSTRDSTLGRKTTNAKTVGRPLAVCINLFSTRE PIVGRSLTSVTVGRLLFVVQASPSIKEFTQVRNPMNYK NVGRPLLESITLLSIRRSFPVRSLTNVRSVGRPFAGVRAS LSTRGYIRARSKTSAQNVGRPSIVAITSLSTRESTQAKFRI NVRSVGRLSFMDRAS* | ATGTCAAAAGACCTGCTACTAGAGAAGGCACCCCTCCTAGAACACATCAGAGACATC ATAAGGAGAATTCCTTTGAATGTAAGGACTGTGGGAAGGCCTTTAGTCGTGGCTATC AACTTAGTCAACATCAGAAAATCCATACTGGTGAGAAGCCTTATGAATGTAAAGAAT GTAAGAAGGCCTTCACTCAGCTTACTCAACATCAAAAAATTCATACTG GGGAGAAGCCTTATTCATAAGAGACTGTGGAAGGCTTTCGATGGGGCTCAAGC CTCGTTATTCATAAGAGATTCATACTGGTGAAAAACCCTATGAATGTAAAGACTGT GTAAAGAAGACTACGAATGCAAAGACGTGGAAGACGCTTACGAGGATTCCACACTGG GGAAAAGACTACGAATGCAAAGACGTGGGAAGACCTTTAGCCGTGTGTATAAAC TTATTCAGCACAGATACGAATGCAAAGACGTGGGAAGACCTTACGAGTGTATAAAC GGGAAGGCCTTTACTCGAGTCAATCAGCCTTCAGCATAAAGAATTCACACAGGT GAGAAACCCTATGAATGTCAAGATTCAAGCATAAAGAATTCACACAGGTGTGTGG ACTCAGCAGCAGAGATCCACACCGGTGAGAAGCCTCAGAATGTAAGGAGTGTGG GAAGGCCCTTCGCTGGGGTTCGAGCCTCGTTAAGCACGAGGATACATACGGGCG GAAGCCGTACAAGTGCACAGAATGTGGGAAGCCTTCAATTGTGGCTATCACCTC ACTCAGCAGCAGAGAATCCACACAGGCGAAACCCGTATAAATGTAAGGAGTGTGG GAAGCCCTTCATTTATGGATCGAGCCTCGTGA | 6550 |
| | 4 | MGLKPRYS* | ATGGGCTCAAGCCTCGTTATTCATAA | 6551 |
| | 1 | MSIR* | ATGTCAATCAGATGA | 6553 |

| | | | | |
|---|---|---|---|---|
| hsa-mir-519c | 2 | MHINYVKRPATREGTPPRTHQRHHKENSPECKDCGKAF SRGYQLSQEHQKIHTGEKPYECKECKCKAFRWGNQLTQH QKIHTGEKPYECKDCGKAFRWGSSLVIHKRIHTGEKPY ECKDCGKAFRRGDELTQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | 6555 | ATGATCATCAATTATGTCAAAAGACTGCTACTAGAGAAGGCACCCCTCCTAGAACA CATCAGAGACATCATAAGGAGAATTCCTTTGAATGTAAGGACTGTGGAAGGCCTTT AGTCGTGGCTATCAACTTAGTCAACATCAGAAAATCCATACTGGTGAGAAACCTTAT GAATGTAAAGAATGTAAGAAGGCCTTCCGTTGGGCAATCAGCTTACTCAACATCAA AAAATTCATACTGGGGAGAAGCCTACTAGAAGACTGTAAAGACTTTTCG ATGGGCTCAAGCTGTGGAAGCTCGTTATTCATAAGAGATTCATACTGGTGAAAAACCTATGA ATGTAAAGACTGTGGAAGCTTTCGGCGTGGTAACGAATCAGCTCACTCAGCACCAGA GATTCCACACTGGGGAGAAGACTACGAATGCAAAGACTGTGGGAAGACCTTTAGC CGTGTGTATAAACTTATTCAGCACACAAGAGAATTCATAGTGGGGAGAAGCCTTACGA GTGTAAAGACTGTGGGAAGGCTTTTATTTGGTTCAAGCCTCATTCAGCATAAAG AATTCACACAGGTGAGAAACCCTATGAATGTCAAAGATGTGGGAAGGCCTTTACTCG AGTCAATTACCTTACTCAGCACTACAGAGATCCACACCGGTGAGAAGCCTCACGAATG TAAGGAGTGTGGGAGCCGAGAAGCCTACAAGTGCACAGAATGCAGGGAAGCCTTCAATTGT TACATACGGGCGAGAAGCCCTACAAGTGCACAGAATGCACACGGTGAAACCCTCAATTGT GGCTATCACCTACTCAGCACGAGAATCCACACAGGCGAAACCCGTATAAATGT TCATACCGGGGTGAAACCCTATGGGTGTACAGAATGTGGGAAGAGCTTAGTCACG GCCATCAAGCTTACACAAACAACCACAGTGGGGCGAAATCCGAGAATGT AAGGAGTGCGGGAAGCCATGTAACCACCTAAACCATCCGAGAACATCAGAGGAT CCACAACAGTTGA | 6556 |
| | 3 | MSKDLLEKAPLLEHRDIRRRIPLNVRTVGRPLVVAINL VNRKSILVRNLMNVKNVRRPSVGAISLLNIKKPILGRSP TNVKTVGRLFDGAQASLFIRGFILVKNPMNVKTVERPF GVVMSSLSTRDSTLGRKTTNAKTVGRPLAVCINLFSTRE PTVGRSLTSVKTVGRLLFVVQASPSIKEFTQVRNPMNYK NVGRPLLESITLLSIRRSFPVRSLTNVRSVGRPFAGVRAS LSTRGYIBARSKTSAQNVGRPSIVAITSLSTRESTQAKFRI NVRSVGRLSFMDRAS* | 6557 | ATGTCAAAAGACCTGCTACTAGAGAAGGCACCCCTCCTAGAACACATCAGAGACATC ATAAGGAGAATTCCTTTGAATGTAAGGACTGTGGGAAGCCTTAGTCGTGGCTATC AACTTAGTCAACATCAGAAAATCCATACTGGTGAGAAACCTTATGAATGTAAAGAAT GTAAGAAGGCCTTCAATCAGCTTACTCAACATCAAAAAATTCATACTG GGGAGAAGCCTACTAGAAGACTGTGGGAAGGCTTTCGATGGGGCTCAAGC CTCGTTATTCATAAGAGATTCATACTGGTGAAAAACCTATGAATGTAAAGACTGT GGAAAGGCCTTTCGGCGTGATGAGCTCACTCAGCACCAGAGATTCCACACTGG GGAGAAAGACTACGAATGCAAAGACTGTGGGAAGACCTTAGCCGTGTGTATAAAC TTATTCAGCACACAAGAGAATTCATAGTGGGAGAAGCCTACGAGTGTAAAGACTGT GGGAAGGCTTTTATTTGGTTCAAGCCTCATTCAGCATAAAGAATTCACACACGGT GAGAAACCCTATGAATGTCAAGAATGTGGGAAGCCTTTACTCGAGTCAATTACCTTAC TCAGCACGAGAATCCACACCGGTGAGAAGCCTCACGAATGTAAGGAGTGTGGG ACTCAGCAGCGTGGAGCCTGAGCCTGTTAAGCACGAGGATACATACGGGCG GAAGCGTACAAGTGCACAGAATGTGGGAAGCCTTCAATTGTGGCTATCACCTC GAAGGCTTTCATTTATGGATCGAGCCCGTGA | 6558 |
| | 4 | MGLKPRYS* | 6559 | ATGGGGCTCAAGCCTCGTTATTCATAA | 6560 |
| | 1 | MSIR* | 6561 | ATGTCAATCAGATGA | 6562 |

Figure 1 (Continued)

| | | | |
|---|---|---|---|
| hsa-mir-519d | 2 | MHINYVKRPATREGTPPRTHQRHHKENSPECKDCGKAF SRGYQLSQEHQKIHTGEKPYECKECKAFRWGNQLTQH QKIHTGEKPYECKDCGKAFRWGSSLVIHKRIHTGEKPY ECKDCGKAFRKGDELTQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | ATGATCATCAATTATGTCAAAAGACTGCTACTAGAGAAGACCCCTCCTAGAACA CATCAGAGACATCATAAGGAGAATTCCTTTGAATGTAAGGACTGTGGAAGGCCTTT AGTCGTGGCTATCAACTTAGTCAACATCAGAAATTCCATACTGGTGAGAAACCTTAT GAATGTAAAGAATGTAAGGAAGCCTTCCGTTGGGCAATCAGCTTACTCAACATCAA AAAATTCATACTGGGGAGAAGCCTGTATTCATAAAGAGATCATACTGGTGAAAAACCTATGA ATGGGGCTCAAGCACTGTGTGAAAGACTTCGGCGTGGTAGAGCTCACTCAGCACCAGA ATGTAAAGACTGTGGGAGAAGCCTTTCGGCCGTGGTCAACTCAGCACCAGCAGA GATTCCACACTGGGGAGAAAGATACGAATGCAAAGACTGTGGGAAGACCTTTAGC CGTGTGTATAAACTTATTCAGCACACAAGAGAATTCATAGTGGGGAGAAGCCTTACGA GTGTAAAGACTGTGGGAAGGCTTTTATTTGTGGTTCAAGCCTCATTCAGCATAAAG AATTCACACAGGTGAGAAGCCCTATGAATGTCAAAGATGTGGGAAGGCTTTACTCG AGTCAATTACCTTACTCAGCATCAGAGATGTCACACCGGTGAGAAGCCTCACGAATG TAAGGAGTGTGGGGGACCTCACTCAGCACCGAGAAGCCGTACACAAGCGGAAATGCACACAGGAGAATGCACACAGGAGAAAATGCCACAAGCGGAAAATGCCACAAGCGGAAAATGCCACAAGCGGAAAATGCCACAAGCGGAAAATGCCACAAGCGGAAAATGCCACAAGCGGAAAATGCCACAAGCGGAAAATGCCACAAGCGGAAAATGCCACAAGCGGAAAATGCCACAAGCGGAAAATGCCACAAGCGGAAAATGCCACAAGCGGAAAATGCCACAAGCGGAAAATGCCACAAGCGGAAAATGCCACAAGCGGAAAATGCCACAAGCGGAAAATGCCACAAGCGGAAAATGCCACAAGCGGAAAATGCCACAAGCGGAAAATGCCACAAGCGGAAAATGCCACAAGCGGAAAATGCCACAAGCGGAAAATGCCACAAGCGGAAAATGCCACAAGCGGAAAATGCCACAAGCGGAAAATGCCACAAGCGGAAAATGCCACAAGCGGAAAATGCCACAAGCGG CCACAACAGTTGA | 6564 |
| | | MSKDLLEKAPLLEHRDRRRIPLNVRTVGRPLVVAINL VNRKSILVRNLMNVKNVRRPSVGAISLLNIKKPILGRSP TNVKTVGRLFEDGAQASLFIRGFILVKNPMNVKTVERPF GVVMSSLSTRDSTLGRKTNAKTVGRPLAVCINLFSTRE PIVGRSLTSVKTVGRLLFVVQASPSIKEFTQVRNPMNYK NVGRPLLESTTLLSIRRSFPVRSLTNVRSVGRPFAGVRAS LSTRGYIBARSKTSAQNVGRPSIVAITSLSTRESTQAKFRI NVRSVGRLSFMDRAS* | ATGTCAAAAGACCTGCTACTAGAGGATAAGGCACCCCTCCTAGAACATCAGAGACATC ATAAGGAGAATTCCTTTGAATGTAAGGACTGTGGGAAGGCCTTTAGTCGTGGCTATC AACTTAGTCAACATCAGAAATTCATACTGGTGAGAAACCTTATGAATGTAAAGAAT GTAAGAAGGCCTTCCGTACGAATGTAAAGACTGTGGGAAGGCTTTTCGATGGGGCTCAAGC CTCGTTATTCATAAGAGGATTCATACTGGTGAAAAACCTATGAATGTAAAGACTGT GGAAAGGCCTTTCGGCCGTGGTGGATGAGCTCACTCAGCACCAGCACGATTCCACACTGG GGAGAAAGACTACGAATGCAAAGACTGTGGGAAGACCTTAGCCGTGTGTATAAAC TTATTCAGCACACAAGAGAATTCATAGTGGGAGAAGCCTTACGAGTGTAAAGACT GGGAAGGCTTTTATTGTGGTTCAAGCCTCATTCAGCATAAAGAATTCACACAGGT GAGAAGCCGTACAAGTGCACAGAATGTGGGAAGGCCTTCAATTGTGGCTATCACGTT ACTCAGCACGAGAGAATCCACACAGGCGAAAAACCCGTATAAATGTAAGGAGTGTGG GAAGGCTTTCATTTATGGATCGAGCCGTGA | 6566 |
| | 4 | MGLKPRYS* | ATEKGGCTCAAGCCTCGTTATTCATAA | 6568 |
| | 1 | MSIR* | ATGTCAATCAGATGA | 6570 |

Figure 1 (Continued)

| | | | |
|---|---|---|---|
| hsa-mir-519e | 2 | MHINYVKRPATREGTPPRTHQRHHKENSPECKDCGKAF SRGYQLSQHQKIHTGEKPYECKECKCKAFRWGNQLTQH QKIHTGEKPYECKDCGKAFRWGSSLVIHKRIHTGEKPY ECKDCGKAFRKGDELTQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | ATGATCATCAATTATGTCAAAAGACTGCTACTAGAGAAGGCACCCCTCCTAGAACA CATCAGAGACATCATAAGGAGAATTCCTTTGAATGTAAGGACTGTGGCTGTATC AGTCGTGGCTATCAACTTAGTCAACATCAGAAATCCATACTGGTGAGAAACCTTAT GAATGTAAAGAATGTAAGGAAGCCTTCCGTTGGGCAATCAGCTTACTCAACATCAA AAAATTCATACTGGGGAGAAGCCTCGTTATTCATAAGGAATTCATACTGGTGAAAAACCTATGA ATGGGGCTCAAGCACTGTGGAAGACTGTGGAGCTCACTCAGCACCAGA ATGTAAAGACTGTGGAGAAGGCCTTTCGCGTCGTCCGTTGATGAGCTCACTCAGCACCAGA GATTCCACACTGGGGAGAAGACTACGAATGCAAAGACTGTGGAAGACCTTTAGC CGTGTGTATAAACTTATTCAGCACACAAGAGAATTCATAGTGGGGAGAAGCCTTACGA CGTGTAAAGACTGTGGAGAAGGCTTTTATTTGGTTCAAGCCTCATTCAGCATAAAG AATTCACACAGGTGAGAAACCCTATGAATGTCAAAGAATGTGGAAGGCTTTACTCG AGTCAATTACCTTACTCAGCATCAGAGATGTCACACCGGTGAGAAGCCTCACGAATG TAAGGAGTGTGGGCGACGAAGCCTACACGAGAGAATCCACACAGGTGAGAGGA TACATACGGGCGAGAAGCCGACAAGTGCACAGAATGGCACAGCCTTCAATTGT GGCTATCACCTCACTCAGCACGAGAATCCACACAGGCGAAACCCGTATGAGAGAAT TCATATACGGGGTGAAACCCTATGGGTGCAGAATGTGAGCCTCGTGAAACATGAGCTTAGTCACG GCCATCAAGCTTACACAACACCTAGAGAACCCAGAGTGGGGCGAAAGTTGGGGGCAATGT AAGGAGTGCGGGAAGCATGTAACCTAAACCATCCGAGAACATCAGAGGAT CCACAACAGTTGA | 6572 |
| | | | 6571 |
| | 3 | MSKIDLLEKAPLLEHRIDRRIPLNVRTVGRPLVVAINL VNIRKSLVRNLMNVKNVRRPSVGAISLLNIKKPILGRSP TNVKTVGRLFEDGAQASLFIRGFILVKNPMNVKTVERPF GVVMSSLSTRDSTLGRKTNAKTVGRPLAVCINLFSTRE PIVGRSLTSVKTVGRLLFVVQASPSIKEFTQVRNPMNYK NVGRPFLLESTLLSIRRSFPVRSLTNVRSVGRPFAGVRAS LSTRGYIBARSKTSAQNVGRPSIVAIITSLSTRESTQAKFRI NVRSVGRLSFMDRAS* | ATGTCAAAAGACCTGCTACTAGAGAAGGCACCCCTCCTAGAACACATCAGAGACATC ATAAGGAGAATTCCTTTGAATGTAAGGACTGTGGGAAGCCTGGCTATCAGTCGTGCTATC AACTTAGTCAACATCAGAAATCCATACTGGTGAGAAACCTTATGAATGTAAAGAAT GTAAGAAGGCCTTCCGTAGCAATCAGCTTACTCAACATCAAAAAATTCATACTG GGAGAGAAGCCTACGAATGTAAAGAACTGTAAGGAAGGCTTTCGATGGGCTCAAGC CTCGTTATTCATAAGGAGAATTCATACTGGTGAAAAACCTATGAATGTAAAGACTGT GAAAAGGCCTTTCGGCCTGGTGATGAGCTCACTCAGCACCAGAGATTCCACACTGG GAGAAAGACTACGAATGCAAAGACTGTGGAAGACCTTAGCGCTGTGTATAAAC TTATTCAGCACACAAGAATTCATAGTGGGGAGAAGACCTTACGAATGTAAAAGAT GGGAAGGCTTTTATTTGGTTCAAGCCTCGGTTCAAGAATGTGGGAAGGCTTACTCG GAGAAACCCATGAATGTAAGTCAAGAATCCACACAGGTGGGAGAAGCCGTTAAGC ACTCAGCATCAGAGAATCCACACAGGTGAGAAGCCTCACGAATGTAAGGAGTGTGG GAAGGCCTTTCGCTGGGTTCGAGCCTCGGTTAAGCACGAGGATACATACGGGCG AGAAGCCGTACAAGTGCACAGAATGGCGGAACCCGGGAAGCCACGTTAGGTCGCGC CTCAGCACGACGAGAATCCACACAGGCGGAATAAGAGCCTCAATTGTGGCTATCACCTC AAGGCTTCATTATGGATCGAGCCGCGTGA | 6574 |
| | | | 6573 |
| | 4 | MGLKPRYS* | ATGGGGCTCAAGCCTCGTTATTCATAA | 6575 |
| | 1 | MSIR* | ATGTCAATCAGATGA | 6577 |
| | | | 6576 |
| | | | 6578 |

Figure 1 (Continued)

| | | | | |
|---|---|---|---|---|
| hsa-mir-520a | 2 | MHINYVKRPATREGTPPRTHQRHHKENSPECKDCGKAF SRGYQLSQHQKIHTGEKPYECKECKCKAFRWGNQLTQH QKIHTGEKPYECKDCGKAFRWGSSLVIHKRIHTGEKPY ECKDCGKAFRKGDELTQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYECKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | ATGATCATCAATTATGTCAAAAGACTGCTACTAGAGAAGGCACCCCTCCTAGAACA CATCAGAGACATCATAAGGAGAATTCCTTTGAATGTAAGGACTGTGGCTGCTTT AGTCGTGGCTATCAACTTAGTCAACATCAGAAATCCATACTGGTGAGAAACCTAT GAATGTAAAGAATGTAAGAAGCCTTCCGTTGGCAATGACTCAGCTTACTCAACATCAA AAAATTCATACTGGGGAGAAGCCTCGTTATTCATAAGAGATCTATACTGGTGAAAAACCTATGA ATGGGGCTCAAGCACTGTGGAGAGCTGTGGGAGAATGACTATACTGGTGATGAGCTCACTCAGCACCAGA GATTCCACACTGGGGAGAAAGACTACGAATGCAAAGACTGTGGGAAGACCTTTAGC CGTGTGTATAAACTTATTCAGCACACAAGAGAATTCATAGTGGGGAGAAGCCTTACGA CGTGTAAAGACTGTGGGAAGGCTTTTATTTGTGGTTCAAGCCTCATTCAGCATAAAG AATTCACACAGGTGAAGAAACCCTATGAATGTCAAGATGTGGGAAGGCCTTTACTCG AGTCAATTACCTTACTCAGCATCAGAGATCCACACCGGTGAGAAGCCTCACGAATG TAAGGAGTGTGGGAGAAGCCTACAAGTGCACAGAATGCGAAGCCTCGTTAAGCACGAGAGGA TACATACGGGCGAGAAGCCGTATCAGAGAATGTGGGAAGCCTTCAATTGT GGCTATCACCTCACTCAGCACGAGAATCCACACAGGGGAAACCCGTATAAATGT TCATATCCGGGGTGAAACCTATGGGTGTACAGAATGTGGGAAGACTTTAGTCACG GCCATCAAGCTTACACAACACATCAGAAACGACAGTGGGCGAAATCTACGAATGT AAGGAGTGCGGGAAGCCATGTAACCATCCTAAACCATCTCCGAGAACATCAGAGGAT CCACAACAGTTGA | 6579 |
| | 3 | MSKDILLEKAPLLEHRIDRRRIPLNVRTVGRPLVVAINL VNRKSILVRNLMNVKNVRRPSVGAISLLNIKKPILGRSP TNVKTVGRLFEDGAQASLFIRGFILVKNPMNVKTVERPF GVVMSSLSTRDSTLGRKTTNAKTVGRPLAVCINLFSTRE PIVGRSLTSVKTVGRLLFVVQASPSIKEFTQVRNPMNYK NVGRPLLLESITLLSIRRSFPVRSLTNVRSVGRPFAGVRAS LSTRGYIRARSRKTSAQNVGRPSIVAIITSLSTRESTQAKFRI NVRSVGRLSFMDRAS* | ATGTCAAAAGACCTGCTACTAGAGAAGGCACCCCTCCTAGAACACATCAGAGACATC ATAAGGAGAATTCCTTTGAATGTAAGGACTGTGGGAAGCCATCTAGTCGTGCTATC AACTTAGTCAACATCAGAAATCCATACTGGTGAGAAGCCTATCAAAAATTCATACTG GTAAGAAGGCCTTCCGTTGAATCAGCTTACTCAACATCAAAAAATTCATACTG GGGAGAAGCCCTACGAATGTAAAGACTGTGGGAAGCCTTTCGATGGGGCTCAAGC CTCGTTATTCATAGAGGATTCATACTGGTGAAAAACCTATGAATGTAAAGACTGT GGAAAAGCCCTTTCGGCCGTGATGAGCTCACTCAGCACCAGAGATTCCACACTGG GGAGAAAGACTACGAATGCAAAGACTGTGGGAAGACCTTAGCCGTGTGTATAAAC TTATTCAGCACTACAGTAGTGGGGAGAAGCCTACGAGTGCACACAGGT GGGAAGGCCTTTATTGAATGTCAAGAAATGTGGGAAGACTAAAGAATTCACACAGGT GAGAACCCTATGAATGTAAAGAATGTGGGAAGCCTTACCTGAGTGAATTACCTT ACTCAGCATCAGAGATCCACACGGTGAGAAGCCTCACGAATGTAAGGAGTGTGG GAAGGCCTTTGCTGGGGTTCGAGCCTCGTTAAGCACGAGGATACATACGGGCG GAGAAGCGTACAAGTGCACAGAATGTGGGAAGCCTTCAATTGTGGCTATCACCTC ACTCAGCACAGGAATCCACACAGGGGAAACCCGTATAAATGTAAGGAGTGTGG GAAGGCTTTCATTTATGGATCGAGCCCTCGTGA | 6581 |
| | 4 | MGLKPRYS* | ATGGGGCTCAAGCCTCGTTATTCATAA | 6583 |
| | 1 | MSIR* | ATGTCAATCAGATGA | 6585 |

| | |
|---|---|
| | 6580 |
| | 6582 |
| | 6584 |
| | 6586 |

Figure 1 (Continued)

| | | | |
|---|---|---|---|
| hsa-mir-520e-1 | 2 | MHINYVKRPATREGTPPRTHQRHHKENSPECKDCGKAF SRGYQLSQHQKIHTGEKPYECKECKCKAFRWGNQLTQH QKIHTGEKPYECKDCGKAFRWGSSLVIHKRIHTGEKPY ECKDCGKAFRRGDELTQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | ATGATCATCAATTATGTCAAAAGACTGCTACTAGAGAAGGCACCCCTCCTAGAACA CATCAGAGACATCATAAGGAGAATTCCTTTGAATGTAAGGACTGTGGAAGGCCTTT AGTCGTGCTATCAACTTAGTCAACATCAGAAATCCATACTGGTGAGAAACCTTAT GAATGTAAAGAACTGTAAGAAGGCCTTCCGTTGGGCAATCAGCTTACTCAACATCAA AAAATTCATACTGGGGAGAAGCCTACGAATGTAAAGACTGTGAAAAACCTATGA ATGTGAAAGACTGTGGGAGGACTCGTATTCATAAGAGAATTCATACTGGTGAAAAACCTATGA ATGTAAAGACTGTGGGAGAAGGCCTTCGCGTGGTAAGAGCTCACTCAGCACCAGA GATTCCACACTGGGGAGAAGATACGAATGCAAAGACTGTGGGAAGACCTTAGC CGTGTGTATAAACTTATTCAGCACACAAGAGAATTCATAGTGGGGAGAAGCCTTACGA GTGTAAAGACTGTGGGAAGGCTTTCATTTGGTTCAAGCCTCATTCAGCATAAAG AATTCACACAGGTGAGAAATGCAAAACCCTATGAATGTCAAAGATGTGGGAAGGCCTTACTCG AGTCAATTACCTTACTCAGCATCAGAGAATGTCACACCGGTGAGAAGCCTCACGAATG TAAGGAGTGTGGGAGGACTCTTTGAGCGTTCAAGCACAGAGATGTCAAGCACGAGGA TACATACGGGCGAGAAGCCTACAAGAGAATGCACAGAGTGGGAAGCCTGTCGCAAACCCGTATAAATGT GCTATCACCTCACTCAGCACGAGAGAATCCACACAGGCGAAACCCGTATGAGAGAAT TCATACCGGGTGAAACCTATGGGTGCACAGAATGTGAGGGAAGAGCTTAGTCACG GCCATCAAGCTTACACAACACTCAGAAAACGCAAGTGGGGCGAAATCCACGAATGT AAGGAGTGCGGGAAGCGCATGTAACCACCTAAACCATCTCGAGAACATCAGAGGAT CCACAACAGTTGA | 6588 |
| | 3 | MSKDLLEKAPLLEHRDIRRIPLNVRTVGRPLVVAINL VMRKSILVRNLMNVKNVRRPSVGAISLLNIKKPILGRSP TNVKTVGRLFDGAQASLFIRGFILVKNPMNVKTVERPF GVVMSSLSTRDSTLGRKTNAKTVGRPLAVCINLFSTRE PIVGRSLTSVKTVGRLLFVVQASPSIKEFTQVRNPMNYK NVGRPLLESITLLSIRRSFPVRSLTNVRSVGRPFAGVRAS LSTRGYIRARSKTSAQNVGRPSIVAITSLSTRESTQAKFRI NVRSVGRLSFMDRAS* | ATGTCAAAAGACCTGCTACTAGAGAAGGCACCCCTCCTAGAACACATCAGAGACATC ATAAGGAGAATTCCTTTGAATGTAAGGACTGTGGGAAGGCCTTTAGTCGTGCTATC AACTTAGTCAACATCAGAAATCCATACTGGTGAGAAACCTTATGAATGTAAAGAAT GTAAGAAGGCCTTCAACATCAGCTTACTCAACATCAAAAATTCATACTG GGGAGAAGCCCTACGAATGTAAAGACTGTTTCGATGGGGCTCAAGC CTGTTATTCATAAGAGGATTCATACTGGTGAAAAAACCTATGAATGTAAAGACTGT GAAAAGGCCTTTCGGCCTGTGATGAGCTCACTCAGCACCAGAGATTCCACACTGG GGAGAAAGACTACGAATGCAAAGACTGTGGGAAGACCTTAGCCGTGTGTATAAAC TTATTCAGCACAGACCTTTATTTGGTTCAAGCCTCATTCAGCATAAAGAATTCACACAGGT GGGAAGGCCTTTACTAATGCAAGGTACAAGGATATACACGGGCG GAGAAACCCTATGAATGTCAAGATGTGGGAAGCCTTCACTGAGGAAATACATAGGGAAGAGTAAGAGTGTGGCG ACTCAGCACGAGAGAATCCAGCACAGGCGGAAACCCTCAATTACTCGAGTGAATGTAAGGAGTGTGG GAAGGCCTTTCATTTATGGATCGAGCCGCGTGA | 6590 |
| | 4 | MGLKPRYS* | ATGGGCTCAAGCCTCGTTATTCATAA | 6591 |
| | 1 | MSIR* | ATGTCAATCAGATGA | 6593 |

| | |
|---|---|
| | 6592 |
| | 6594 |

Figure 1 (Continued)

| | | | |
|---|---|---|---|
| hsa-mir-520e-2 | 2 | MHINYVKRPATREGTPPRTHQRHHKENSFECKDCGKAF SRGYQLSQHQKIHTGEKPYECKECKKAFRWGNQLTQH QKIHTGEKPYECKDCGKAFRWGSSLVIHKRIHTGEKPY ECKDCGKAFRRGDEITQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGHQLTQHQKTHSGAKSYECKEC GKACNHLNHLREHQRIHNS* | ATGATCATCAATTATTGTCAAAGACCTGCTACTAGAGAAGGCACCCTCCTAGAACA CATCAGAGACATCATAAGGAGAATTCCTTTGAATGTAAGGACTGTGGAAGGCTTT AGTCGTGGCTATCAACTTAGTCAACATCAGAAATGCATACTGTGAGAAACCTTAT GAATGTAAAGAGAATGTAAGAAGGCCTTCCGTTGGGCAATGCAAAAGCTCGGTTACTCAACATCAA AAAATTCATACTGGGGAGAAGCCTCGTTATTCATAAAGAAGCTTAAAGACTGTGGGAAGGCTTTCG ATGGGGCTCAAGCTCGTTATTCATAAGAGAATTCATACTGGTGAAAAACCTATGA ATGTAAAGACTGTGGGAGAAGCTCGCTGATGAGCTCACTCAGCACCAGA GATTCACACTGGGAGGAAGATACGAATGCAAAGACTGTGGGAAGACCTTAGC CGTGTGTATAAACTTATTCAGCACAAGAGAATTCATAGTGGGGAGAAGCCTTACGA CGTGTAAAGACTGTGGGAAGGCTTTTATTGTGTTCAAGCCTCATTCAGCATAAAG AATTCACACAGGTGAGAAACCCTATGAATGTAAGATGTGGGAAGGCCTTTACTCG AGTCAATTACCTTACTCAGCCATCAGAGATCCACACCGGTGAGAAGCCTCACGAATG TAAGGAGTGTGGGAAGGCTCTTTCGCTGGGGTTCAGCCTCGTTAAGCACGAGGA TACATACGGGCGAGAAGCCGTACAAGTGCACAGAATGCAAGCCTTTACTCG GGCTATCACCTCACTCAGCACGAGCAATCCACACAGGCGAAACCCGTATAAATGT TCATACCGGGGTGAAACCCTATGGGTGTACAGAATCGAGCCTCGTGAAACATGAGAGAAT GCCATCAGCTTCACACAAACCTAGAAAACGACAGTGGGCGAAATCCTCGAATGT AAGGAGTGCGGGAAGCCATGTAACCACCTAAACCATCCCGAGAACATCAGAGGAT CCACAACAGTTGA | 6596 |
| | 3 | MSKDLLLEKAPLLEHRDIRRIPLNVRTVGRPLVVAINL VNIRKSILVRNLMNVKNVRRPSVGAISLLNIKKFILGRSP TNVKTVGRLFDGAQASLFIRGFILVKNPMNVKTVERPF GVVMSSLSTRDSTLGRKTTNAKTVGRPLAVCINLFSTRE FIVGR8LTSVKTVGRLLFVVQASFSIKEFTQVRNPMNYK NVGRPLLESTTLLSIBRRSFPVRSLTNVRSVGRPFAGVRAS LSTRGYIBARSKTSAQNVGRPSIVAITSLSTRESTQAKFRI NVRSVGRLSFMDRAS* | ATGTCAAAAGACCTGCTACTAGAGAAGGCACCCTCCTAGAACACATCAGAGACATC ATAAGGAGAATTCCTTTGAATGTAAGGACTGTGGGAAGGCCTTAGTCGTGGCTATC AACTTAGTCAACATCAGAAATGCATACTGTGAGAAACCTATGGTGTGCTATCA GTAAGAAGGCCTTCCGTTGGGCAATCTACTCAACATCAAAAATTCATACTG GGGAGAAGCCCTACGAATGTAAAGACTGTGGGAAGCTTTTCGATGGGGCTCAAGC CTCGTTATTCATAAGAGAATTCATACTGGTGAAAAACCTATGAATGTAAAGACTGT GGGAAGGCCTTTCGGCCTTGTGATGAGCTCACTCAGCACCAGAGATTCCACACTGG GGAAGAAGACTACGAATGCAAAGACTGTGGGAAGACCTTTAGCCGTGTGTATAAAC TTATTCAGCACAAGAGAATTCATAGTGGGGAGAAGCCTTACGAGTGTAAAGACTGT GGGAAGGCTTTTATTGTGGTTCAAGCCTCATTCAGCATAAAGGAATTCACACGGT GAGAAACCCTATGAATGTAAGATGTGGGAAGGCCTCGTTAAGCACGAGGATACATACGGGCG AGAAGCCGTACAAGTGCACAGAATGTGGGAAGGCCTTCACTCGAGTCAATTACCTT ACTCAGCACAGAGATCAGAGATCCACACCGGTGAGAAGCCTCACGAATGTAAGGAGTGTGGG GAAGGCCTTTCGCTGGGGTTCGAGCCTCGTTAAGCACGAGGATACATACGGGCG GAAGCCGTACAAGGTGCACAGAATGTGCACAGGCGAAACCCTCAATTGTGGCTATCACCTC ACTCAGCACGAGAATCAGAGGCGAAACCCGTATAAATGTAAGGAGTGTGG GAAGGCTTTCATTTATGGATCGAGCCCTGTGA | 6598 |
| | 4 | MGLKPRYS* | ATGGGGCTCAAGCCTCGTTATTCATAA | 6599 |
| | 1 | MSIR* | ATGTCAATCAGATGA | 6601 |

| | | | |
|---|---|---|---|
| hsa-mir-520d | 2 | MHINYVKRPATREGTPPRTHQRHHKENSPECKDCGKAF SRGYQLSQEHQKIHTGEKPYECKECKCKAFRWGNQLTQH QKIHTGEKPYECKDCGKAFRWGSSLVIHKRIHTGEKPY ECKDCGKAFRKGDELTQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | ATGATCATCAATTATGTCAAAAGACTGCTACTAGAGAAGGCACCCCTCCTAGAACA CATCAGAGACATCATAAGGAGAATTCCTTTGAATGTAAGGACTGTGGAAGGCCTTT AGTCGTGGCTATCAACTTAGTCAACATCAGAAATCCATACTGGTGAGAAACCTTAT GAATGTAAAGAATGTAAGAAGGCCTTCCGTTGGGCAATCAGCTTACTCAACATCAA AAAATTCATACTGGGGAGAAGCCTTCATAAAGACTGTAAAGACTTCATACTGAGCT ATGGGGCTCAAGCTGTGGAAGCTCGTTATTCATAAGAGGATTCATACTGGTGAAAAACCTATGA ATGTAAAGACTGTGGAAGGCCTTTCGCGTGGTGATGAGCTCACTCAGCACCAGA GATTCCACACTGGGGAGAAGACTACGAATGCAAAGACTGTGGGAAGACCTTTAGC CGTGTGTATAAACTTATTCAGCACACAAGAGAATTCATAGTGGGGAGAAGCCTTACGA CGTGTAAAGACTGTGGGAAGGCTTTATTGGTTCAAGCTCATTCAGCATAAAG AATTCACACAGGTGAGAAACCCTATGAAATGTCAAGAATGTGGGAAGGCTTTACTCG AGTCAATTACCTTACTCAGCATATCAGAGATCCACACCGGTGAGAAGCCTCACGATG TAAGGAGTGTGGGAAGGCTTTCGAGCTGGTTCAGCATGCACAGAATGCCACAAGTG TACATACGGGCGAGAAGCCGTACAAGTGCACAGAATGCACACAGGCTTAAGCACGAGAGA GGCTATCACCTCACTCAGCACGAGAAGAATCCACACAGGGAAACCCGTATAAATGT TCATATACCGGGGTGAAACCCTATGGGTGACAGAATGTGAGCCTCGTGAAACATGAGCTTAGTCACG GCCATCAAGCTTACACAAACACAGAAAACGCACAGTGGGGCAAATCCTACGAATGT AAGGAGTGCGGGAAGCATGTAACCTAAACCATTCCGAGAACATCAGAGGAT CCACAACAGTTGA | 6604 |
| | 3 | MSKDLLEKAPLLEHRDIRRIPLNVRTVGRPLVVAINL VMRKSILVRNLMNVKNVRRPSVGAISLLNIKKFILGRSP TNVKTVGRLFDGAQASLFIRGFILVKNPMNVKTVERPF GVVMSSLSTRDSTLGRKTNAKTVGRPLAVCINLFSTRE PIVGRSLTSVKTVGRLLFVVQASPSIKEFTQVRNPMNYK NVGRPLLESITLLSIRRSFPVRSLTNVRSVGRPFAGVRAS LSTRGYIRARSKTSAQNVGRPSIVAIITSLSTRESTQAKFRI NVRSVGRLSFMDRAS* | ATGTCAAAAGACCTGCTACTAGAGAAGGCACCCCTCCTAGAACACATCAGAGACATC ATAAGGAGAATTCCTTTGAATGTAAGGACTGTGGGAAGCCTTAGTCGTGGCTATC AACTTAGTCAACATCAGAAATCCATACTGGTGAGAAACCTTATGAATGTAAAGAAT GTAAGAAGGCCTTCCGTTACTCAGCTTACTCAACATCAAAAATTCATACTG GGGAGAAGCCTTCATAAAGACTGTAAAGACTTCATACTGAGCTGTTTCGATGGGGCTCAAGC CTGTATTCGATGAGGATTCATACTGGTGATGAGCTCAGCACCAGAGATTCCACACTGG GGAAAGGCCTTTCGGCCTGGTGAATGCAAAGACTACGAGCTGTGTATAAAC TTATTCAGCACACAAGAGACTTTAGCCGTGTAAAGACTGTGGAAGATTCCACACTGG GGAAAAGACTACGAATGCAAGAACCTTATCAGTGGGGAGAAGACCTTACGAGTGTAAAAGACTGT TTATTCGACGATTCAGACTTTTGGGTTCAAGCTCATTCAGCATAAAGAATTCACACAGGT GGGAAGGCCTTTACTCGAGCCTCGTTAAGCACGAGAGGATACATACGGGCG AGAAACCCTATGAATGTCAAGAATGCGGAAATTCGAGTGAATGTAAGGAGTGTGG ACTCAGCATCAGAGATCCACACCGGTGAGAAGCCTCACGAATGTAAGGAGTGTGG GAAGGCCTTTCGCTGGGTTCGAGCTCGTTAAGCACGAGGATACATACGGGCG AGAGCCGTACAAGTGCACACAGGCGGAAACCCGTATCAATTGTGGCTATCACCTC ACTCAGCACGAGAAGAATCCACACAGGCGAAACCCGTATAAATGTAAGGAGTGTGG GAAGGCTTTCATTTATGGATCGAGCCGTGA | 6606 |
| | 4 | MGLKPRYS* | ATGGGCTCAAGCCTCGTTATTCATAA | 6607 |
| | 1 | MSIR* | ATGTCAATCAGATGA | 6609 |

Figure 1 (Continued)

| | | | |
|---|---|---|---|
| hsa-mir-520e | 2 | MHINYVKRPATREGTPPRTHQRHHKENSPECKDCGKAF SRGYQLSQHQKIHTGEKPYECKECKCKAFRWGNQLTQH QKIHTGEKPYECKDCGKAFRWGSSLVIHKRIHTGEKPY ECKDCGKAFRRGDEITQHQRPHTGEKDYECKDCGKTF SRVYKLIQHKRIHSGEKPYECKDCCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | ATGATCATCAATTATGTCAAAAGACCTGCTACTAGAGAAGGCACCCCTCCTAGAACA CATCAGAGACATCATAAGGAGAATTCCTTTGAATGTAAGGACTGTGGCTATC AGTCGTGGCTATCAACTTAGTCAACATCAGAAAATCCATACTGGTGAAAACCTTAT GAATGTAAAGAATGTAAGAAGGCCTTCCGTTGGGCAATCAGATCAGCTTACTCAACATCAA AAAATTCATACTGGGGAGAAGCCTCGTTATTCATAAGAGACTGTAAAGACTTCATGTGAAAAACCTATGA ATGTGAAGACTGTGGAGGACGCCTTTCGCCGTGGTAGATCAGCTCACTCAGCACCAGA GATTCCACACTGTGGGAGAAGATACGAATGCAAAGACTGTGGGAAGACCTTAGC CGTGTGTATAAACTTATTCAGCACACAAGAGAATTCATAGTGGGGAGAAGCCTTACGA GTGTAAAGACTGTGGGAAGGCTTTTATTGGTTCAAGCCTCATTCAGCATAAAG AATTCACACAGGTGAGAAACCCTATGAATGTCAAAGATGTGGAAGGCTTTACTCG AGTCAATTACCTTACTCAGCATCAGAGATGTCACACCGGTGAGAAGCCTCACGAATG TAAGGAGTGTGGGCGAGAAGCCTACAAGTGCACAGAATGCGGGAAGGCCTTCAATTGT TACATACGGGCGAGAAGCCGTACAAAGTGCACAGAGAAATCCACACAGGTGAAACCCGTATAAATGT GGCTATCACCTCACTCAGCACGAGAATCCACACAGGCGAAACCCTCCAATTGT TCATATCCGGGGTGAAACCTATGGGTACAGAATGTGAGCCTCGTGAAACATGAGAAT GCCATCAAGCTTACACAACAGCCTACAGAAAACGCACAGTGGGGCGAAATCTACGAATGT AAGGAGTGCGGGAAGCCATGTAACCTAAACCATCCGAGAACATCAGAGGAT CCACAACAGTTGA | 6612 |
| | 3 | MSKIDLLEKAPLLEHRDIRRIPLNVRTVGRPLVVAINL VNIRKSILVRNLMNVKNVRRPSVGAISLLNIKKPILGRSP TNVKTVGRLFEDGAQASLFIRGFILVKNPMNVKTVERPF GVVMSSLSTRDSTLGRKTTNAKTVGRPLAVCINLFSTRE PIVGRSLTSVKTVGRLLFVVQASPSIKEFTQVRNPMNYK NVGRPFLLESTLLSIRRSFPVRSLTNVRSVGRPFAGVRAS LSTRGYIBRARSRKTSAQNVGRPSIVAITSLSTRESTQAKFRI NVRSVGRLSFMDRAS* | ATGTCAAAAGACCTGCTACTAGAGAAGGCACCCCTCCTAGAACACATCAGAGACATC ATAAGGAGAATTCCTTTGAATGTAAGGACTGTGGGAAGCCATTAGTCGTGCTATC AACTTAGTCAACATCAGAAAATCCATACTGGTGAGAAATCATACTTATGAATGTAAAGAAT GTAAGAAGGCCTTCCGTTACTCAGCTTACTCAACATCAAAAAATTCATACTG GGGAGAAGCCCTACGAATGTAAAGACTGTGGGAAGGCTTTCGATGGGGCTCAAGC CTCGTTATTCATAAGAGACTGATTCATACTGGTGAAAACCCTATGAATGTAAAGACTGT AAGAAGGCCCTTCATCAGCCTTCGCCGTGATGAGCTCACTCAGCACCAGAGATTCCACACTGG GGAAAAGACTACGAATGCAAAGACTGTGGGAAGAACCTTACGAGTGTAAAGACTGTGTATAAAC TTATTCAGCACACAGAATTCATAGTGGGGAGAAGCCTTACGAGTGTAAAGACTGT GGGAAGGCTTTTATTGGTTCAAGCCTCATTCAGCATAAAAGAATTCACACAGGT GAGAAACCCTATGAATGTCACAGAATGTGGGAAGGCCTTAAGCACGAGGAGATACACGGGCG GAAGCCGTACAAGTGCACAGAATCCACACAGGCGAAACCCTCCAATTGTGGCTATCACCTC ACTCAGCACGAGAATCCACAGCAATGCGGGAAGCCCTCAGTGAAATGAAGGAGTGTGG GAAGGCTTTCATTTATGGATCGAGCCGTCGTGA | 6614 |
| | 4 | MGLKPRYS* | ATEGGCTCAAGCTCGTTATTCATAA | 6615 |
| | 1 | MSIR* | ATGTCAATCAGATGA | 6617 |
| | | | 6616 |
| | | | 6618 |

Figure 1 (Continued)

| | | | | |
|---|---|---|---|---|
| hsa-mir-526f | 2 | MHINYVKRPATREGTPPRTHQRHHKENSPECKDCGKAF SRGYQLSQEHQKIHTGEKPYECKECKCKAFRWGNQLTQH QKIHTGEKPYECKDCGKAFRWGSSLVIHKRIHTGEKPY ECKDCGKAFRKGDELTQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | ATGATCATCAATTATGTCAAAAGACCTGCTACTAGAGAAGGCACCCCTCCTAGAACA CATCAGAGACATCATAAGGAGAATTCCTTTGAATGTAAGGACTGTGGAAGGCCTTT AGTCGTGGCTATCAACTTAGTCAACATCAGAAATCCATACTGGTGAGAAACCTTAT GAATGTAAAGAATGTAAGAAGCCTTCCGTTCGGCAATGCAGTCACTCAACATCAA AAAATTCATACTGGGGAGAAGCCTCGTTATTCATAAGAGATGTAAAGACTTATACTGGTGAAAAACCTATGA ATGTAAAGACTGTGGAAGGCCTTTCCGCGTGGTAAGCTCACTCAGCACCAGA GATTCCACACTGGGGAGAAGACTACGAATGCAAAGACTGTGGAAGACCTTTAGC CGTGTGTATAAACTTATTCAGCACGACAAGAGAATTCATAGTGGGGAGAAGCCTTACGA CGTGTAAAGACTGTGGAAGGCTTTTATTTGTGGTTCAAGCCTCATTCAGCATAAAG AATTCACACAGGTGAGAATGCAAAACCCTATGAATGTCAAGAATGTGGGAAGGCCTTTACTCG AGTCAATTACCTTACTCAGCATCAGAGAGATCCACACCGGTGAGAAGCCTCACGAATG TAAGGAGTGTGGGAGGGCCTCTTCGCTGGGGTTCAGCCTTGTTAAGCACGAGAGGA TACATACGGGGCGAGAAGCCGTACAAGTGCACAGAGAGATCCACAGAATGCGAAACCCGTATCACGAAAT GGCTATCACCTCACTCAGCACGAGAATGCAAAAGCGAAACCGTATGAGAGAT TCATACCGGGGTGAAACCTCTAGGTGTACAGAAAATGTGGGAAGACTTTAGTCACG GCCATCAAGCTTACACACACATCAGAAACGCACAGTGGGGGAGAAATCTACGAATGT AAGGAGTGCGGGAAGCCATGTAACCTAAAACCATTCCGAGAACATCAGAGGAT CCACAACAGTTGA | 6620 | 6619 |
| | 3 | MSKDILLEKAPLLEHRDIRRIPLNVRTVGRPLVVAINL VNIRKSILVRNLMNVKNVRRPSVGAISLLNIKKPILGRSP TNVKTVGRLFDGAQASLFIRGFILVKNPMNVKTVERPF GVVMSSLSTRDSTLGRKTNAKTVGRPLAVCINLFSTRE PIVGRSLTSVSVKTVGRLLFVVQASPSIKEFTQVRNPMNYK NVGRPLLESITLLSIRRSFPVRSLTNVRSVGRPFAGVRAS LSTRGYIRARSKTSAQNVGRPSIVAITSLSTRESTQAKFRI NVRSVGRLSFMDRAS* | ATGTCAAAAGACCTGCTACTAGAGAAGGCACCCCTCCTAGAACACATCAGAGACATC ATAAGGAGAATTCCTTTGAATGTAAGGACTGTGGGAAGGCCTTCAGTCGTGCTATC AACTTAGTCAACATCAGAAATCCATACTGGTGAGAAACCCTATGAATGTAAAGAAT GTAAGAAGCCTTCCGTCGAATGCAATCAGCTTACTCAACATCAAAAATTCATACTG GGGAGAAGCCTCGTTATTCATAAGAGACTGTGGGAAGGCTTTCGATGGGGCTCAAGC CTCGTTATTCGAATGAGGATTCATACTGGTGAAAAACCCTATGAATGTAAAGACTGT GGAAAGGCCTTTCGGCGTGATGAGCTACTCAGCACTGGGAAGACTTCACACTGG GGAGAAAGACTACGAATGCAAAGACTGTGGAAGACCTTAGCCGTGTGTATAAAC TTATTCAGCACGACAAGAGAATTCATAGTGGGAGAAGCCTTACGAGTGTAAAGACT GGGAAGGCTTTTATTTGTGGTTCAAGCCTCATTCAGCATAAAGAATTCACACAGGT GAGAATGCAAACCTATGAATGTCAAGAATGTGGGAAGGCCTTACGCTAAAAGAATTCACACAGGT ACTCAGCACGAGAGATCCACACCGGTGAGAAGCCTCACGAATGTAAGGAGTGTGG GAAGGCCTTTGCTGGGTTCGAGCCTCGTTAAGCACGAGAGGATACATACGGGCG GAGAAGCCGTACAAGTGCACAGAATGGGGAAGGCCTTCAATTGTGGCTATCACCTC ACTCAGCACGAGAGAATCCACACAGGCGGAAACCCGTATAAAATGTAAGGAGTGTGG GAAGGCTTTCATTTATGGATCGAGCCGTGA | 6622 | 6621 |
| | 4 | MGLKPRYS* | ATtGGGCTCAAGCCTCGTTATTCATAA | 6624 | 6623 |
| | 1 | MSIR* | ATGTCAATCAGATGA | 6626 | 6625 |

Figure 1 (Continued)

| | | | |
|---|---|---|---|
| hsa-mir-520g | 2 | MHINYVKRPATREGTPPRTHQRHHKENSPECKDCGKAF SRGYQLSQHQKIHTGEKPYECKECKAFRWGNQLTQH QKIHTGEKPYECKDCGKAFRWGSSLVIHKRIHTGEKPY ECKDCGKAFRKGDELTQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | 6627 | ATGATCATCAATTATGTCAAAAGACTGCTACTAGAGAAGGCACCCCTCCTAGAACA CATCAGAGACATCATAAGGAGAATTCCTTTGAATGTAAGGACTGTGGAAGGCCTTT AGTCGTGGCTATCAACTTAGTCAACATCAGAAAATCCATACTGGTGAGAAACCTAT GAATGTAAAGAGTGTAAGGAAGGCCTTCCGTTGGGCAATGCAGTCACTCAACATCAA AAAATTCATACTGGGGAGAAGCCTACGAATGTAAAGACTGTAAAGACTGTGGGAAGGCTTTCG ATGGGGCTCAAGCTCGTTATTCATAAGAGAATTCATACTGGTGAAAAACCTATGA ATGTAAAGACTGTGGGAAGGCCTTTCGCGTGGTAGCTCACTCAGCACCAGA GATTCCACACTGGGGAGAAGACTACGAATGCAAAGACTGTGGGAAGACCTTAGC CGTGTGTATAAACTTATTCAGCACACAGAAGAATTCATAGTGGGGAGAAGCCTTACGA CGTGTAAAGACTGTGGAGAAGGCTTTTATTGTGGTTCAAGCCTCATTCAGCATAAAG AATTCACACAGGTGAGAAGACCCTATGAATGTCAAAGATGTGGGAAGGCCTTACTCG AGTCAATTACCTTACTCAGCATCAGAGATCCACACCGGTGAGCCTCGTTAAGCACGAAGGA TAAGGAGTGTGGGCGAGAAGCCTACAAGTGCACAGAATGTGGGAAGGCTTCAATTGT TACATACGGGCGAGAAGCCCTATGAATGTGAGCCTGTGAAACCTGTATAAATGT GGCTATCACCTTCAGCACGAGAATCCACACAGGCGAAACCCTATGAGAGAAT TCATACCGGGGGTGAAACCCTATGGGTGTACAGAATGTGGGAAGAGCTTTAGTCACG GCCATCAAGCTTACACAACACAGTGGGGGAGAAATCCCGAGATCTCACGAATGT AAGGAGTGCGGGAAGGCATGTAACCACCTAAAACCATTCCGAGAACATCAGAGGAT CCACAACAGTTGA | 6628 |
| | 3 | MSKDLLEKAPLLEHRDIRRIPLNVRTVGRPLVVAINL VMRKSILVRNLMNVKNVRRPSVGAISLLNIKKPILGRSP TNVKTVGRLLFDGAQASLFIRGFILVKNPMNVKTVERPF GVVMSSLSTRDSTLGRKTTNAKTVGRPLAVCINLFSTRE PTVGRSLTSVKTVGRLLFVVQASPSIKEFTQVRNPMNYK NVGRPFLLESTTLLSIRRSFPVRSLTNVRSVGRPFAGVRAS LSTRGYIBARSRKTSAQNVGRPSIVAITSLSTRESTQAKPRI NVRSVGRLSFMDRAS* | 6629 | ATGTCAAAAGACCTGCTACTAGAGAAGGCACCCCTCCTAGAACACATCAGAGACATC ATAAGGAGAATTCCTTTGAATGTAAGGACTGTGGGAAGGCCTTTAGTCGTGCTATC AACTTAGTCAACATCAGAAAATCCATACTGGTGAGAAACCTATGAATGTAAAGAAT GTAAGAAGGCCTTCAAGAGCCCCTACGAATGTAAAGACTGTTACTCAACATCAAAAATTCATACTG GGGAGAAGAAGCCCCTACGAATGTAAAGACTGTGGGAAGCTTTTCGATGGGGCTCAAGC CTCGTTATTCATAAGAGATTCATACTGGTGAAAACCCTATGAATGTAAAGACTGT GGAAAGGCCTTTCGGCCTGTGATGAGCTCACTCAGCACCAGAGACTTCACACTGG GGAGAAAGACTACGAATGCAAAGACTGTGGGAAGACCTTAGCCGTGTGTATAAAC TTATTCAGCACACAGAATTCATAGTGGGGAGAAGCCTTACGAGTGTAAAGACTGT GGGAAGGCTTTTATTGTGGTTCAAGCCTCATTCAGCATAAAGAATTCACACAGGT GAGAAACCCTATGAATGTCAAGAATGTGGGAAGGCCTTCACTCGAGTCAATTACCTT ACTCAGCACGAGAATCCACACAGGCGAAACCCTATGAATGTAAGGAGTGTGGG GAAGGCCTTCATTTATGGATGCGAGCCCGTGA | 6630 |
| | 4 | MGLKPRYS* | 6631 | ATGGGCTCAAGCCTCGTTATTCATAA | 6632 |
| | 1 | MSIR* | 6633 | ATGTCAATCAGATGA | 6634 |

Figure 1 (Continued)

| | | | |
|---|---|---|---|
| 2 | MHINYVKRPATREGTPPRTHQRHHKENSPECKDCGKAF SRGYQLSQEHQKIHTGEKPYECKECKCKAFRWGNQLTQH QKIHTGEKPYECKDCGKAFRWGSSLVIHKRIHTGEKPY ECKDCGKAFRKGDELTQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | ATGATCATCAATTATGTCAAAAGACTGCTACTAGAGAAGGACCCCTCCTAGAACA CATCAGAGACATCATAAGGAGAATTCCTTTGAATGTAAGGACTGTGGAAGGCCTTT AGTCGTGGCTATCAACTTAGTCAACATCAGAAAATCCATACTGGTGAGAAACCTTAT GAATGTAAAGAATGTAAGAAGGCCTTCCGTTGGCAATCAGCTTACTCACCATCAA AAAATTCATACTGGGGAGAAGCCTACGAATGTAAAGACTGTGGGAAGGCTTTTCG ATGGGGCTCAAGCTCGTTATTCATAAGAGAATTCATACTGGTGAAAAACCTATGA ATGTAAAGACTGTGGGAAGGCCTTTCGCTGGCGTTGGAGCTCACTCAGCACCAGA GATTCACACTGGGGAGAAGACTTACGAATGCAAAGACTGTGGGAAGACCTTTAGC CGTGTGTATAAACTTATTCAGCACACAAGAGAATTCATAGTGGGGAGAAGCCTTACGA GTGTAAAGACTGTGGGAAGGCTTTTATTTGTGTTCAAGCCTCATTCAGCATAAAG AATTCACACAGGTGAGAAAACCCTATGAATGTCAAAAGATGTGGGAAGGCCTTTACTCG AGTCAATTACCTTACTCAGCATCAGAGAATCCACACCGGTGAGAAGCCTCACGAATG TAAGGAGTGTGGGAAGGCTTTCGAGCCTCGTTAAGCACGAGAGGA TACATACGGGCGAGAAGCCTACAAGTGCACAGAATGCACACAGCCTTCAATTGT GGCTATCACCTCACTCAGCACGAGAATCCACACAGGCGAAACCCGTATAAATGT TCATACCGGGGTGAAACCTCTATGGGTGCACAGAATGTGGAAGACTTTAGTCACG GCCATCAAGCTTACACAACACACAGAAACCACAGTGGGGCGAAATCCTACGAATGT AAGGAGTGCGGGAAGCCATGTAACCTAAACCATCCGAGAACATCAGAGGAT CCACAACAGTTGA | 6636 |
| hsa-mir-520h | 6635 | | |
| 3 | MSKDLLEKAPLLEHRDIRRIPLNVRTVGRPLVVAINL VNIRKSLVRNLMNVKNVRRPSVGAISLLNIKKPILGRSP TNVKTVGRLFLFDGAQASLFIRGFILVKNPMNVKTVERPF GVVMSSLSTRDSTLGRKTNAKTYGRPLAVCINLFSTRE PIVGRSLTSVKTVGRLLFVVQASPSIKEFTQVRNPMNYK NVGRPFLLESITLLSIRRSFPVRSLTNVRSVGRPFAGVRAS LSTRGYIRARSKTSAQNVGRPSIVAITSLSTRESTQAKFRI NVRSVGRLSFMDRAS* | ATGTCAAAAGACCTGCTACTAGAGAAGGCACCCCTCCTAGAACACATCAGAGACATC ATAAGGAGAATTCCTTTGAATGTAAGGACTGTGGGAAGGCCTTTAGTCGTGGCTATC AACTTAGTCAACATCAGAAAATCCATACTGGTGAGAAACCTTATGAATGTAAAGAAT GTAAGAAGGCCTTCAACATCCATCAGCTTACTCACCATCAAAAAATTCATACTG GGGAGAAGCCCCTACGAATGTAAAGACTGTGGAAGGCTTTTCGATGGGGCTCAAGC CTCGTTATTCATAAGAGAATTCATACTGGTGAAAAACCTATGAATGTAAAGACTGT GGAAAGGCCTTTCGGCGTGATGAGCTCACTCAGCACCAGAGATTCACACTGG GGAGAAAGACTACGAATGCAAAGACTGTGGGAAGACCTTAGCCGTGCAGTGTAAAC TTATTCAGCACACAAGAATTCATAGTGGGGAGAAGCCTTACGAGTGTAAAGACTGT GGGAAGGCTTTATTTGTGTTCAAGCCTCGTTAAGCACGAGAGGATACATACGGGCG GAGAAGCCGTACAAGTGCACAGAATGTGGGAAGCCTCAATTCACACGGT GAGAAACCCTATGAATGTCAAGAATGTGGGAAGGCCTTACTCGAGTCAATTACCTTA ACTCAGCAGCCAGAGATCCACACCGGTGAGAAGCCTCACGAATGTAAGGAGTGTGG GAAGGCCTTCCTGGGGTGCAGCCTCGTTAAGCACGAGAGGATACACAGGCG GAGAAGCCGTACAAGTCCACAGAATGTGGGAAGCCTTCAATTGTGGCTATCACCTC ACTCAGCAGCCAAGTCCACACAGGCGAAACCCGTATAAATGTAAGGAGTGTGG GAAGGCTTTCATTTATGGATCGAGCCGTGA | 6638 |
| 4 | MGLKPRYS* | ATEGGGCTCAAGCTCGTTATTCATAA | 6640 |
| hsa-mir-521-J | 1 | MSIR* | ATGTCAATCAGATGA | 6642 |

Figure 1 (Continued)

| | | | | |
|---|---|---|---|---|
| hsa-mir-521-1 | 2 | MHNYVKRPATREGTPPRTHQRHHKENSPECKDCGKAF SRGYQLSQEHQKIHTGEKPYECKECKCKAFRWGNQLTQH QKIHTGEKPYECKDCGKAFRWGSSLVIHKRIHTGEKPY ECKDCGKAFRKGDELTQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | 6643 | ATGATCATCAATTATGTCAAAAGACTGCTACTAGAGAAGGCACCCCTCCTAGAACA CATCAGAGACATCATAAGGAGAATTCCTTTGAATGTAAGGACTGTGGAAGGCCTTT AGTCGTGGCTATCAACTTAGTCAACATCAGAAAATCCATACTGGTGAGAAACCTTAT GAATGTAAAGAATGTAAGAAGGCCTTCCGTTGGGCAATCAGCTTACTCAACATCAA AAAATTCATACTGGGGAGAAGCCTTCTATTCATAAGAGACTTCATACTGGTGAAAAACCTATGA ATGTAAAGACTGTGGAAGCTCGTGTGAAGGCCTTTCGCGTGGTGAGCTCACTCAGCACCAGA GATTCCACACTGGGGAGAAGACTACGAATGCAAAGACTGTGGGAAGACCTTTAGC CGTGTGTATAAACTTATTCAGCACACAAGAGAATTCATAGTGGGGAGAAGCCTTACGA CGTGTAAAGATGTGGGAAGGCTTTTATTGTGGTTCAAGCCTCATTCAGCATAAAG AATTCACACAGGTGAAGAAACCCTATGAATGTCAAAGATGTGGGAAGGCCTTACTCG AGTCAATTACCTTACTCAGCATCAGAGATGTCACACCGGTGAGAAGCCTCACGAATG TAAGGAGTGTGGGAAGGCCTTTCGCTGGGGTTCAGCCTCGTTAAGCACGAGAGA TACATACGGGCGAGAAGCCTACAAGTGCACAGAATGCACACGGTAAGCCTCAATTGT GGCTATCACCTCACTCAGCACGAGAAATCCACACAGGGAAACCCTATAAATGT TCATATCCGGGGTGAAACCTCTATGGGTGTACAGAATGTGGGAAGACTTTAGTCACG GCCATCAAGCTTACACAACACATGAATGCAAAAGGAGAATCCGATATGGGGGCGAAATCCTACGAATGT AAGGAGTGCGGGAAGCCATGTAACCTAACCATTCCGAGAACATCAGAGGAT CCAACAGTTGA |
| | 3 | MSKDLLLEKAPLLEHRDIRRIPLNVRTVGRPLVVAINL VMRKSILVRNLMNVKNVRRPSVGAISLUNIKKPILGRSP TNVKTVGRLFDGAQASLFIRGFILVKNPMNVKTVERPF GVVMSSLSTRDSTLGRKTTNAKTVGRPLAVCINLFSTRE PIVGRSLTSVTSVKTVGRLLFVVQASPSIKEFTQVRNPMNYK NVGRPLLESITLLSIRRSFPVRSLTNVRSVGRPFAGVRAS LSTRGYIBARSRKTSAQNVGRPSIVAITSLSTRESTQAKFRI NVRSVGRLSFMDRAS* | 6645 | ATGTCAAAAGACCTGCTACTAGAGGACACCCTCCTAGAACACATCAGAGACATC ATAAGGAGAATTCCTTTGAATGTAAGGACTGTGGGAAGGCCTTTAGTCGTGCTATC AACTTAGTCAACATCAGAAATCCATACTGGTGAGAAATGTAAGAAT GTAAGAAGGCCTTCCGTTACTCAGCTTACTCAACATCAAAAATTCATACTG GGGAGAAGCCCTACGAATGTAAAGACTGTGGGAAGGCTTTCGATGGGGCTCAAGC CTCGTTATTCATAGAGGATTCATACTGGTGAAAAACCCTATGAATGTAAAGACTGT GGAAAGGCCTTTCGGCCTGTGATGAGCTCACTCAGCACCAGAGATTCCACACTGG GGAGAAAGACTACGAATGCAAAGACTGTGGAAGACCTTAGCCGTGTGTATATAAAC TTATTCAGCACACAAGAGAATTCATAGTGGGAGAAGCCTTTACGACGTGTAAAGAT GGGAAGGCCTTTTATTGAATTCAAGAATGTCAAGAAAGGCTGTTAAGCACGAGGATACACAGGT GAGAAGCCGTACGAAGAATCCACACAGGGGAAACCTGTTAAGCACGAGGATACACAGGGCG ACTCAGCACGAGAGATCAGAAGCCTCAGCATCAGCATAAAGGCCTTACTCGAGTCAATTACCTT ACTCAGCAGCAAGATGCACAGAATGTGGGAAGGCCTTCAATTGTGGCTATCACCTC GAAGGCTTTCATTTATGGATCGAGCCCGTGA |
| | 4 | MGLKPRYS* | 6647 | ATGGGCTCAAGCCTCGTTATTCATAA |
| | 1 | MSIR* | 6649 | ATGTCAATCAGATGA |

Figure 1 (Continued)

| | | | |
|---|---|---|---|
| hsa-tmr-521-2 | 2 | MHINYVKRPATREGTPPRTHQRHHKENSPECKDCGKAF SRGYQLSQEHQKIHTGEKPYECKECKCKAFRWGNQLTQH QKIHTGEKPYECKDCGKAFRWGSSLVIHKRIHTGEKPY ECKDCGKAFRKGDEITQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | ATGATCATCAATTATGTCAAAAGACCTGCTACTAGAGAAGGCACCCCTCCTAGAACA CATCAGAGACATCATAAGGAGAATTCCTTTGAATGTAAGGACTGTGGAAGGCCTTT AGTCGTGGCTATCAACTTAGTCAACATCAGAAATCCATACTGGTGAGAAACCTTAT GAATGTAAAGAATGTAAGAAGGCCTTCCGTTGGGCAATCAGCTTACTCAACATCAA AAAATTCATACTGGGGAGAAGCCTTCTATTCATAAAGAACTGTAAAGACTTTTCG ATGGGGCTCAAGCTGTGGAAGCTCGTTATTCATAAGAGACTCATACTGGTGAAAACCCTATGA ATGTAAAGACTGTGGAAGGACCCTTTCCGCGTGGTGATGAGCTCACTCAGCACCAGA GATTCCACACTGGGGAGAAGACTACGAATGCAAAGACTGTGGGAAGACCTTTAGC CGTGTGTATAAACTTATTCAGCACACAAGAGAATTCATAGTGGGAGAAGCCTTACGA CGTGTAAAGACTGTGGGAAGGCTTTTATTGGTTCAAGCCTCATTCAGCATAAAG AATTCACACAGGTGAGAAACCCTATGAATGTCAAAGATGTGGGAAGGCTTTACTCG AGTCAATTACCTTACTCAGCATCAGAGATCCACACCGGTGAGCTCTGTTAAGCACGAGGA TACATACGGGCGAGAAGCCTACAAGTGCACAGAATGCACCCGGTGAGAAGCCTTCAAGATGT GGCTATCACCTCACTCAGCACGAGAATCCACACAGGCTGAAAACCCGTATAAATGT TCATATACCGGGGTGAAACCTATGGGTGTACAGAATGTGGGAAGACTTTAGTCACG GCCATCAAGCTTACACAACACTCAGAAACGCACAGTGGGGCAAAATCCTACGAATGT AAGGAGTGCGGGAAGCCATGTAACCTAAACCATCTCCGAGAACATCAGAGGAT CCACAACAGTTGA | 6651 |
| | 3 | MSKIDLLEKAPLLEHRDIRRRIPLNVRTVGRPLVVAINL VMRKSILVRNLMNVKNVRRPSVGAISLLNIKKPILGRSP TNVKTVGRLFDGAQASLFIRGFILVKNPMNVKTVERPF GVVMSSLSTRDSTLGRKTTNAKTVGRPLAVCINLFSTRE PIVGRSLTSVKTVGRLLFVVQASPSIKEFTQVRNPMNVK NVGRPFLLESTTLLSIRRSFPVRSLTNVRSVGRPFAGVRAS LSTRGYIBARSEKTSAQNVGRPSIVAITSLSTRESTQAKFRI NVRSVGRLSFMDRAS* | ATGTCAAAAGACCTGCTACTAGAGAAGGCACCCCTCCTAGAACACATCAGAGACATC ATAAGGAGAATTCCTTTGAATGTAAGGACTGTGGGAAGGCCTTTAGTCGTGCTATC AACTTAGTCAACATCAGAAATCCATACTGGTGAGAAACCTTATGAATGTAAAGAAT GTAAGAAGGCCTTCCGTTACTCAGCTTACTCAACATCAAAAAATTCATACTG GGGAGAAGCCCTACGAATGTAAAGACTGTGGGAAGGCTTTCGATGGGCTCAAGC CTCGTTATTCGATAAGAGACTCATACTGGTGAAAAACCCTATGAATGTAAAGACTGT GGAAAAGGCCTTTCGGCCTGGTGATGAGCTCACTCAGCACCAGAGATTCCACACTGG GGAGAAAGACTACGAATGCAAAGACTGTGGGAAGACCTTAGCCGTGTGTATAAAC TTATTCAGCACACTGGGAAGGCTTTTATTGGTTCAAGCCTCAATCAGCATAAAGAATTCACACAGGT GGGAAGGCCTTTCGAGCCTCGTTAAGCACCAGAATGTGGGAAGGCCTTTACTCG AGAAAACCCTATGAATGTCAAGAATGTGGGAAGGCCTTTACTCGAGTCAATTACCTT ACTCAGCAGCAGAGATCCACAGCGGTGAGAAGCCTCACGAATGTAAGGAGTGTGG GAAGGCCTTTGCTGGGGTTGAGCCTCGTTAAGCACGAGGATACATACGGGCG GAGAAGCCGTACAAGTGCACAGAATGTGGGAAGGCCTTCAATTGTGGCTATCACCTC ACTCAGCAGCGTAAGAGAATCCACACAGGGCGAAACCCGTATAAATGTAAGGAGTGTGG GAAGGCTTTCATTTATGGATCGAGCCGCTGTGA | 6653 |
| | 4 | MGLKPRYS* | ATGGGGCTCAAGCCTCGTTATTCATAA | 6655 |
| | 1 | MSIR* | ATGTCAATCAGATGA | 6657 |
| | | | 6656 |
| | | | 6658 |

| | |
|---|---|
| | 6652 |
| | 6654 |

Figure 1 (Continued)

| | | | | |
|---|---|---|---|---|
| hsa-mir-522 | 2 | MHINYVKRPATREGTPPRTHQRHHKENSPECKDCGKAF SRGYQLSQEHQKIHTGEKPYECKECKCKAFRWGNQLTQH QKIHTGEKPYECKDCGKAFRWGSSLVHKRIHTGEKPY ECKDCGKAFRKGDEITQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | ATGATCATCAATTATGTCAAAAGACTGCTACTAGAGAAGGCACCCCTCCTAGAACA CATCAGAGACATCATAAGGAGAATTCCTTTGAATGTAAGGACTGTGGCTATC AGTCGTGGCTATCAACTTAGTCAACATCAGAAATCCATACTGGTGAAAACCTTAT GAATGTAAAGAATGTAAGAAGGCCTTCCGTTGGCGAATGTAAACATCAACATCAA AAAATTCATACTGGGGAGAAGCCTTACTAAAGACTGTAAAGACTGTGGGAAGGCTTTCG ATGGGGCTCAAGCTGTGGAATCCGTTATTCATAAGAGATTCATACTGGTGAAAAACCTATGA ATGTAAAGACTGTGGGAAGGCCTTTCGCGCCGTGGTAGAGCTCACTCAGCACCAGA GATTCCACACTGGGGAGAAGACTACGAATGCAAAGACTGTGGGAAGACCTTTAGC CGTGTGTATAAACTTATTCAGCACACAGAGAATTCATAGTGGGAGAAGCCTTACGA GTGTAAAGACTGTGGGAAGGCTTTATTGGTTCAAGCCTCATTCAGCATAAAG AATTCACACAGGTGAAGAAACCCTATGAATGTCAAAGATGTGGGAAGGCTTTACTCG AGTCAATTACCTTACTCAGCATCAGAGATCCACACCGGTGAGCCTCGTTAAGCACGAGGA TACATACGGGCGAGAAGCCTACAAGTGCACAGAATGGGAAGCCTTCAATTGT GGCTATCACCTCACTCAGCACGAGAATCCACACAGGCGAAACCCGTATAAATGT AAGGAGTGTGGGAAGCTTTCATTTATGGATCGAGCCTGTGAAACATGAGAAT TCATACCGGGGTGAACCTATGGGTGCTACAGAATGTGGGAAGAGCTTAGTCACG GCCATCAAGCTTACACAACACTCAGAAACGCACAGTGGGGCGAAATCTACGAATGT AAGGAGTGCGGGAAGCATGTAACCACCTAAACCATCTCCGAGAACATCAGAGGAT CCACAACAGTTGA | 6659 | 6660 |
| | 3 | MSKIDLLEKAPLLEHRIDRRIPLNVRTVGRPLVVAINL VMRKSILVRNLMNVKNVRRPSVGAISLLNIKKPILGRSP TNVKTVGRLLFDGAQASLFIRGFILVKNPMNVKTVERPF GVVMSSLSTRDSTLGRKTTNAKTVGRPLAVCINLFSTRE PLVGRSLTSVKTVGRLLFVVQASPSIKEFTQVRNPMNYK NVGRPLLESLTLLSIBRRSFPVRSLTNVRSVGRPFAGVRAS LSTRGYIBARSRKTSAQNVGRPSIVAITSLSTRESTQAKFRI NVRSVGRLSFMDRAS* | ATGTCAAAAGACCTGCTACTAGAGAAGGCACCCCTCCTAGAACACATCAGAGACATC ATAAGGAGAATTCCTTTGAATGTAAGGACTGTGGGAAGGCCTTAGTCGTGCTATC AACTTAGTCAACATCAGAAATCCATACTGGTGAAGTTCATAACTGTAAAGAAT GTAAGAAGGCCTTACTAAGACTTACTCAACATCAAAAATTCATACTG GGGAGAAGCCCTACGAATGTAAAGACTGTGGGAAGGCTTTCGATGGGGCTCAAGC CTCGTTATTCATAAGAGATTCATACTGGTGAAAAAACCTATGAATGTAAAGACTGT CTGTTATTCAGCACTACGAATGCAAAGACTGTGGGAAGACCTTAGCCGTGTGTATAAAC TTATTCAGCACACAGAGAATCATAGTGGGAGAAGCCTTACGAGTGTAAAGACT GGGAAGGCTTTATTGGTTCAAGCCTCATTCAGCATAAAAGAATTCACACAGGT GAGAAACCCTATGAATGTCAAAGATGTGGGAAGGCCTTTACTCGAGTCAATTACCTT ACTCAGCATCAGAGATCCACACCGGTGAGCCTCGTTAAGCACGAGGATACATACGGGCG AGAAGCCGTACAAGTGCACAGAATGTGGGAAGGCCTTCAATTGTGGCTATCACCTC ACTCAGCACGAGAATCCACACAGGCGAAACCCGTATAAATGTAAGGAGTGTGG GAAGGCTTTCATTTATGGATCGAGCCTCGTGA | 6661 | 6662 |
| | 4 | MGLKPRYS* | ATEGGCTCAAGCTCGTTATTCATAA | 6663 | 6664 |
| | 1 | MSIR* | ATGTCAATCAGATGA | 6665 | 6666 |

Figure 1 (Continued)

| | | | | |
|---|---|---|---|---|
| hsa-mir-523 | 2 | MHINYVKRPATREGTPPRTHQRHHKENSPECKDCGKAF SRGYQLSQEHQKIHTGEKPYECKECKAFRWGNQLTQH QKIHTGEKPYECKDCGKAFRWGSSLVIHKRIHTGEKPY ECKDCGKAFRKGDELTQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | ATGATCATCAATTATGTCAAAAGACTGCTACTAGAGAAGGCACCCCTCCTAGAACA CATCAGAGACATCATAAGGAGAATTCCTTTGAATGTAAGGACTGTGGAAGGCCTTT AGTCGTGGCTATCAACTTAGTCAACATCAGAAATCCATACTGGTGAGAAACCTTAT GAATGTAAAGAATGTAAGGCCTTCCGTTGGGCAATCAGCTTACTCAACATCAA AAAATTCATACTGGGGAGAAGCCTCTATTCATAAGAGACTCATACTGGTGAAAAACCTATGA ATGTGAAAGACTGTGGAAGCCTTTCGCTGTGATGAGCTCACTCAGCACCAGA GATTCCACACTGGGGAGAAGACTACGAATGCAAAGACTGTGGGAAGACCTTAGC CGTGTGTATAAACTTATTCAGCACACAGAGAATTCATAGTGGGGAGAAGCCTTACGA GTGTAAAGACTGTGGGAAGGCTTTTATTGGTTCAGCCTCATTCAGCATAAAG AATTCACACAGGTGAGAAACCCTATGAATGTCAAAGATGTGGAAGGCTTTACTCG AGTCAATTACCTTACTCAGCATCAGAGATGTCACACCGGTGAGAAGCCTCACGAATG TAAGGAGTGTGGGCGAGAAGCCTACAAGTGCACAGAATGCACAGGAGAATCCACAGA GCCTATCACCTCACTCAGCACGAGAATCCACACAGGCGAAACCCGTATAAATGT TCATATACGGGGTGAAACCCTATGGGTGTACAGAATGTGGGAAGACTTTAGTCACG GCCATCAAGCTTACACAACATCAGAAACGCACAGTGGGGCGAAATCTACGAATGT AAGGAGTGCGGGAAGCATGTAACCATCCGAGAACATCAGGAGAAT CCACAACAGTTGA | 6667 | 6668 |
| | 3 | MSKIDLLEKAPLLEHRDIRRIPLNVRTVGRPLVVAINL VMRKSILVRNLMNVKNVRRPSVGAISLLNIKKPILGRSP TNVKTVGRLFEDGAQASLFIRGFILVKNPMNVKTVERPF GVVMSSLSTRDSTLGRKTTNAKTVGRPLAVCINLFSTRE PIVGRSLTSVKTVGRLLFVVQASPSIKEFTQVRNPMNYK NVGRPLLESTLLSIRRSFPVRSLTNVRSVGRPFAGVRAS LSTRGYIRARSKTSAQNVGRPSIVAITSLSTRESTQAKFRI NVRSVGRLSFMDRAS* | ATGTCAAAAGACCTGCTACTAGAGAAGGCACCCCTCCTAGAACACATCAGAGACATC ATAAGGAGAATTCCTTTGAATGTAAGGACTGTGGGAAGGCCTTAGTCGTGGCTATC AACTTAGTCAACATCAGAAATCCATACTGGTGAGAAGCCTCATACTCATAAAAATTCATACTG GTAAGAAGGCCTTCCGTACGAATGTAAAGACTGTGGGAAGGCTTTTCGATGGGCTCAAGC CTCGTTATTCGATCATACTGGTGAAAAAACCCTATGAATGTAAAGACTGT GGAAAGGCCTTTCGGCCTGTGATGAGCTCACTCAGCACCAGAGATTCCACACTGG GGAGAAAGACTACGAATGCAAAGACTGTGGAAGACCTTAGCCGTGTAGTGTAAACC TTATTCAGCACACAGAGAATTCATAGTGGGAGAAGCCTTACGAGTGTAAAAGACT GGGAAGGCCTTTTGTGGTTCAAGCCTCGTTAAGCACGAGAGGATACATACGGGCG GAGAAACCCTATGAATGTCAAGAATGTGGGAAGGCCTTCAATTGTGGCTATCACTC ACTCAGCAGGCGTACAAGTCACACAGGGCGAAACCTTACTCGAGTCAATTACCTTACC TTACTCAGCAGGAGATGCAGCAAGTCACACACGGTGAGAAGCCTCACGAATGTAAGGAGTGTG GAAGGCTTTCATTTATGGATCGAGCCGTGA | 6669 | 6670 |
| | 4 | MGLKPRYS* | ATGGGGCTCAAGCCTCGTTATTCATAA | 6671 | 6672 |
| | 1 | MSIR* | ATGTCAATCAGATGA | 6673 | 6674 |

Figure 1 (Continued)

| | | | |
|---|---|---|---|
| hsa-mir-524 | 2 | MHINYVKRPATREGTPPRTHQRHHKENSPECKDCGKAF SRGYQLSQHQKIHTGEKPYECKECKCKAFRWGNQLTQH QKIHTGEKPYECKDCGKAFRWGSSLVIHKRIHTGEKPY ECKDCGKAFRKGDELTQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | ATGATCATCAATTATGTCAAAAGACCTGCTACTAGAGAAGGCACCCCTCCTAGAACA CATCAGAGACATCATAAGGAGAATTCCTTTGAATGTAAGGACTGTGGAAGGCCTTT AGTCGTGGCTATCAACTTAGTCAACATCAGAAATCCATACTGGTGAGAAACCTTAT GAATGTAAAGACTGTGGGAGAAGCCTTCCGTTGGGCAATCAGCTTACTCAACATCAA AAATTCATACTGGGGAGAAGCCTCGTTATTCATAAGAGATTCATACTGGTGAAAAACCCTATGA ATGTGAAGACTGTGGGAGAAGCCTTTCGCGCTGGTGATGAGCTCACTCAGCACCAGA GATTCCACACTGGGGAGAAGACTTACGAATGCAAAGACTGTGGGAAGACCTTTAGC CGTGTGTATAAACTTATTCAGCACACAAGAGAATTCATAGTGGGGAGAAGCCTTACGA GTGTAAAGACTGTGGGAAGGCTTTTATTTGTGGTTCAAGCCTCATTCAGCATAAAG AATTCACACAGGTGAGAAGCCCTATGAATGTCAAAGATGTGGGAAGGCCTTTACTCG AGTCAATTACCTTACTCAGCATCAGAGAATCCACACCGGTGAGAAGCCTCACGAATG TAAGGAGTGTGGGGAGCCTTTCGCTGGGGTTCGAGCCTCGTTAAGCACGAGAGGA TACATACGGGCGAGAAGCCGTACAAGTGCACAGAATGTGGGAAGGCCTTCAATTGT GGCTATCACCTCACTCAGCACGAGAAGATCCACACAGGCGAAACCCGTATAGAGAT TCATACCGGGGTGAAACCCTATGGGTGCACAGAATGTGGGAAGGCTTTAGTCACG GCCATCAGCTTACACACAGCTTACAGAAAACGACAGTGGGGCGAAATCCTACGAATGT AAGGAGTGCGGGAAGCCATGTAACCACCTAAACCATCCGAGAACATCAGAGGAT CCACAACAGTTGA |
| | 3 | MSKIDLLEKAPLLEHRDHRRIPLNVRTVGRPLVVAINL VMRKSILVRNLMNVKNVRRPSVGAISLLNIKKPILGRSP TNVKTVGRLFDGAQASLFIRGFILVKNPMNVKTYERPF GVVMSSLSTRDSTLGRKTTNAKTVGRPLAVCINLFSTRE PIVGRSLTSVKTVGRLLFVVQASPSIKEFTQVRNPMNYK NVGRPLLESITLLSIRRSFPVRSLTNVRSVGRPFAGVRAS LSTRGYIBARSRKTSAQNVGRPSIVAITSLSTRESTQAKFRI NVRSVGRLSFMDRAS* | ATGTCAAAAGACCTGCTACTAGAGAAGGCACCCCTCCTAGAACACATCAGAGACATC ATAAGGAGAATTCCTTTGAATGTAAGGACTGTGGGAAGGCCTTAGTCGTGGCTATC AACTTAGTCAACATCAGAAATCCATACTGGTGAGAAGCCTTATGAATGTAAAGAAT GTAAGAAGGCCTTCCGTACGAATGTAAAGACTGTGGGAAGGCTTTCGATGGGGCTCAAGC CTCGTTATTCATAAGAGATTCATACTGGTGAAAAACCCTATGAATGTAAAGACTGT GGAAAGGCCTTTCGGCGTGATGAGCTCACTCAGCACCAGAGATTCCACACTGG GGAGAAAGACTACGAATGCAAAGACTGTGGGAAGACCTTTAGCCGTGTATAAAC TTATTCAGCACACACAAGAGAATTCATAGTGGGAAGACCTTCAGCATAAAGAATTCACACACAGGT GGGAAGCCTTTTGGTTCAAGCCTCGTTAAGCACGAGAGGATACATACGGGCG GAGAAGCCGTACAAGTGGGAAATGCACAGGCGAAACCCGTATAGAGATTCATACCGG GGTGAAACCCTATGGGTGCACAGAATGTGGGAAGGCCTTCAATTGTGGCTATCACCTC ACTCAGCACGAGAAGATCCACACAGGCGAAACCCGTATAGAGATTCATACTGGGGTGAAAC TGAAGGCTTTCATTTATGGATCGAGCCGTGA |
| | 4 | MGLKPRYS* | ATGGGGCTCAAGCCTCGTTATTCATAA |
| | 1 | MSIR* | ATGTCAATCAGATGA |

| | | | | |
|---|---|---|---|---|
| hsa-mir-525 | 2 | MHINYVKRPATREGTPPRTHQRRHIKENSPECKDCGKAF SRGYQLSQHQKIHTGEKPYECKECKCKAFRWGNQLTQH QKIHTGEKPYECKDCGKAFRWGSSLVIHKRIHTGEKPY ECKDCGKAFRRGDEITQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | 6683 | ATGATCATCAATTATGTCAAAAGACCTGCTACTAGAGAAGGCACCCCTCCTAGAACA CATCAGAGACATCATAAGGAGAATTCCTTTGAATGTAAGGACTGTGGGAAGCCTTT AGTCGTGGCTATCAACTTAGTCAACATCAGAAAATCCATACTGGTGAGAACCTTAT GAATGTAAAGAATGTAAGAAGGCCTTCCGTTGGGCAATCAGCTTACTCAACATCAA AAAATTCATACTGGGGAGAAGCCTACGAATGTAAAGACTGTAAAAACCTATCG ATGGGGCTCAAGCTCGTTATTCATAAGAGAATTCATACTGGTGAAAAACCCTATGA ATGTAAAGACTGTGGGAAGCCTTTCCGCGTGGTGAGCTCACTCAGCACCAGA GATTCCACACTGGGGAGAAGACTACGAATGCAAAGACTGTGGGAAGACCCTTAGC CGTGTGTATAAACTTATTCAGCACACAGAAGAGAATTCATAGTGGGGAGAAGCCTTACGA GTGTAAAGACTGTGGGAAGGCTTTTATTTGTGGTTCAAGCCTCATTCAGCATAAAG AATTCACACAGGTGAGAAACCCTATGAATGTCAAGAATGTGGGAAGGCCTTTACTCG AGTCAATTACCTTACTCAGCATCAGAGAATCCACACCGGTGAGAAGCCTCACGAATG TAAGGAGTGTGGGAAGGCTCTTTCGAGCCTTCAGTTAAGCACGAGAGGA TACATACGGGCGAGAAGCCGTACAAGTGCACAGAATGGGAAGCCTTCAATTGT GGCTATCACCTCACTCAGCACGAGAATCCACACAGGCGAAACCCGTATAAATGT AAGGAGTGTGGGAAGGCTTTCATTTATGGATCGAGCCTGTACAGAATGTGGGAAGCTTAGTCACG GCCATCAAGCTTACACAACACAGAAAACGCACAGTGGGGCGAAATCCTAGTCAATGT AAGGAGTGCGGGAAGGCATGTAACCATCCGAGAACATCAGAGGAT CCACAACAGTTGA |
| | 3 | MSKIDLLLEKAPLLEHRDIRRRIPLNVRTVGRPLVVAINL VMRKSILVRNLMNVKNVRRPSVGAISLLNIKKFILGRSP TNVKTVGRLLFDGAQASLFIRGFILVKNPMNVKTVERPF GVVMSSLSTRDSTLGRKTNAKTVGRPLAVCINLFSTRE PIVGRSLTSVTKVTGRLLFVVQASPSIKEFTQVRNPMNYK NVGRPLLLESITLLSIRRSFPVRSLTNVRSVGRPFAGVRAS LSTRGYIRARSRKTSAQNVGRPSIVAIITSLSTRESTQAKFRI NVRSVGRLSFMDRAS* | 6685 | ATGTCAAAAGACCTGCTACTAGAGAAGGCACCCCTCCTAGAACACATCAGAGACATC ATAAGGAGAATTCCTTTGAATGTAAGGACTGTGGGAAGCCTGGTTGAGTCGTGCTATC AACTTAGTCAACATCAGAAAATCCATACTGGTGAGAACTTATGAATGTAAAGAAT GTAAGAAGGCCTTCACTAACATCAGCTTACTCAACATCAAAAATTCATACTG GGGAGAAGCCCTACGAATGTAAAGACTGTGGGAAGCTTTTCGATGGGGCTCAAGC CTCGTTATTCATAAGAGAATTCATACTGGTGAGCTCACTGAGCTCACTCAGCACACTGT GAAAAGGCCTTTCGGCGTGATGCCTTTTCGAGGAGAGCCTTCACCAGGA GGGAAAAGACTACGAATGCAAAGACTGTGGGAAGACCTTAGCCGTGCGTGTATAAAC TTATTCAGCACAGACTTTTTGTGGTTCAAGCCTCATTCAGCATAAAAGAATTCACAC AGGTGAGAGGCCTTTTCGGCCTCGGTTCAAGAATGTGGGAAGGCCTCCACCAGGT GAGAAACCTTATGAATGTCAAGAATGCGGGAAGGCCTTTACTCGAGTCAATTACCTTACTT ACTCAGCAGCGTAGAAGATCCACACGTGAGAAGCCTCACGAATGTAAGGAGTGTGG GAAGGCCTTTGGCCTCTGGCGTTCGAGCCTCGTTAAGCACGAGAAGATACATACGGGCG GAGAAGCCGTACAAGATGCGCGGAATTGGGAAGCCTTCAATTGTGGCTATCACCTC ACTCAGCACGAGAATCCACACAGGCGGAAACCGTATAAATGTAAGGAGTGTGG GAAGGCTTTCATTATATGGATCGAGCCGTGA |
| | 4 | MGLKPRYS* | 6687 | ATGGGCTCAAGCCTCGTTATTCATAA |
| | 1 | MSIR* | 6689 | ATGTCAATCAGATGA |

Figure 1 (Continued)

| | | | | |
|---|---|---|---|---|
| hsa-mir-526a-1 | 2 | MHINYVKRPATREGTPPRTHQRHHKENSPECKDCGKAF SRGYQLSQEHQKIHTGEKPYECKECKAFRWGNQLTQH QKIHTGEKPYECKDCGKAFRWGSSLVIHKRIHTGEKPY ECKDCGKAFRRGDELTQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | ATGATCATCAATTATGTCAAAAGACCTGCTACTAGAGAAGGCACCCCTCCTAGAACA CATCAGAGACATCATAAGGAGAATTCCTTTGAATGTAAGGACTGTGGAAGGCCTTT AGTCGTGGCTATCAACTTAGTCAACATCAGAAATCCATACTGGTGAAAACCTTAT GAATGTAAAGAATGTAAGGAGCCTTCCGTTGGGCAATCAGCTTACTCAACATCAA AAAATTCATACTGGGGAGAAGCCTACGAATGTAAAGACTGTAAAGACTTTTCG ATGGGGCTCAAGCTCGTTATTCATAAGAGAATTCATACTGGTGAAAACCTATGA ATGTAAAGACTGTGGAAGGCCTTTCCGCGTGGTAGCTCACTCAGCACCAGA GATTCCACACTGGGGAGAAGACTACGAATGCAAAGACTGTGGGAAGACCTTAGC CGTGTGTATAAACTTATTCAGCACACAAGAGAATTCATAGTGGGGAGAAGCCTTACGA GTGTAAAGACTGTGGGAGGCTTTTATTTGGTTCAAGCCTCATTCAGCATAAAG AATTCACACAGGTGAGAAAACCCTATGAATGTCAAAGATGTGGAAGGCCTTTACTCG AGTCAATTACCTTACTCAGCATCAGAGAATCCACACGGTGAGAAGCCTCACGAATG TAAGGAGTGTGGGAAGGCTCTTTCGCTGGGGTTCAGCCTCGTTAAGCACGAGAGA TACATACGGGCGAGAAGCCTACAAGTGCACAGAATGCACACAGGTGGGAAGCCTTTACTGT GGCTATCACCTTCACTCAGCACGAGAATCCACACAGGTCGAAACCCGTATAAATGT CATATACCGGGGTGAAACCTATAGGGTGTACAGAATGTGGGAAGAGCTTTAGTCACG GCCATCAAGCTTACACAACACTAGCAGAAAACGCACAGTGGGGCGAAATCCACGAATGT AAGGAGTGCGGGAAGCCATGTAACCACCTAAACCATCCGAGAACATCAGAGGAT CCACAACAGTTGA | 6691 | 6692 |
| | 3 | MSKDLLEKAPLLEHRDIRRIPLNVRTVGRPLVVAINL VNIRKSILVRNLMNVKNVRRPSVGAISLLNIKKPILGRSP TNVKTVGRLLFDGAQASLFIRGFILVKNPMNVKTVERPF GVVMSSLSTRDSTLGRKTTNAKTVGRPLAVCINLFSTRE PIVGRSLTSVKTVGRLLFVVQASPSIKEFTQVRNPMNYK NVGRPLLESITLLSIRRSFPVRSLTNVRSVGRPFAGVRAS LSTRGYIBARSRKTSAQNVGRPSIVAIITSLSTRESTQAKFRI NVRSVGRLSFMDRAS* | ATGTCAAAAGACCTGCTACTAGAGAACCACCCTCCTAGAACACATCAGAGACATC ATAAGGAGAATTCCTTTGAATGTAAGGACTGTGGGAAGCCCTTAGTCGTGCTATC AACTTAGTCAACATCAGAAATCCATACTGGTGAGAAACCTTATGAATGTAAAGAAT GTAAGAAGGCCTTCAATCAGCTTACTCAACATCAAAAATTCATACTG GGGAGAAGCCTACGAATGTAAAGACTGTGGGAAGGCTTTCGATGGGGCTCAAGC CTCGTTATTCATAAGAGGATTCATACTGGTGAAAAACCTATGAATGTAAAGACTGT GGAAAGGCCTTCAGCCTTTCGGCGTGGTAGCTCACTCAGCACCAGAGATTCCACACTGG GGAGAAAGACTACGAATGCAAAGACTGTGGGAAGAGACCTTAGCCGTGTGTATAAAC TTATTCAGCACACAAGAGAATTCATAGTGGGAGAAGCCTTACGAGTGTAAAGAC GGGAAGGCTTTTATTTGGTTCAAGCCTCGTTAAGCATGGGGAGAAGCCTTCACACGGT GAGAAACCCTATGAATGTCAAGAATGTGGGAAGAGCCTTTACTCGAGTCAATTACCTT ACTCAGCAGGATCAGAGAATCCACGGTGAGAAGCCTCACGAATGTAAGGAGTGTGG GAAGGCCTTTCGCTGGGTTCGAGCCTCGTTAAGCACGAGGAGGATACATACGGGCG GAGAAGCCGTACAAGTGCACAGAATCCACACAGGCGGAAACCGCTTCAATTGTGGCTATCACCTC ACTCAGCACGACAAGCCACCTAAACCACACAGGGCGAAACCCGTATAAATGTAAGGAGTGTGG GAAGGCTTTCATTTATGGATCGAGCCGTGA | 6693 | 6694 |
| | 4 | MGLKPRYS* | ATEkGGCTCAAGCTCGTTATTCATAA | 6695 | 6696 |
| | 1 | MSIR* | ATGTCAATCAGATGA | 6697 | 6698 |

Figure 1 (Continued)

| | | | |
|---|---|---|---|
| hsa-mir-526a-2 | 2 | MHINYVKRPATREGTPPRTHQRHHKENSPECKDCGKAF SRGYQLSQHQKIHTGEKPYECKECKAFRWGNQLTQH QKIHTGEKPYECKDCGKAFRWGSSLVIHKRIHTGEKPY ECKDCGKAFRKGDEI TQHQRPHTGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | ATGATCATCAATTATGTCAAAAGACCTGCTACTAGAGAAGGCACCCCTCCTAGAACA CATCAGAGACATCATAAGGAGAATTCCTTTGAATGTAAGGACTGTGGCTGTGCTATC AGTCGTGGCTATCAACTTAGTCAACATCAGAAAGCCTCATACTGGTGAGAAACCTTAT GAATGTAAAGAATGTAAGGCCTTCCGTTGGGCAATCAGCTTACTCAACATCAA AAAATTCATACTGGGGAGAAGCCTACTAGAAGACTGTAAAGACTTCATACTG ATGGGCTCAAGCACTGTGGAAGCTCGTTATTCATAAGAGAATTCATACTGGTGAAAAACCTATGA ATGTAAAGACTGTGGAAGACATGCCTTTCGCCGTGGTAAGTGCCACTCAGCACCAGA GATTCCACACTGGGGAGAAGACTACGAATGCAAAGACTGTGGGAAGACCTTTAGC CGTGTGTATAAACTTATTCAGCACACAGAGAATTCATAGTGGGGAGAAGCCTTACGA GTGTAAAGACTGTGGGAAGGCTTTTATTTGTGTTCAAGCCTCATTCAGCATAAAG AATTCACACAGGTGAGAAACCCTATGAATGTCAAGAATGTGGGAAGGCTTTTACTCG AGTCAATTACCTTACTCAGCATCAGAGAATCCACACCGGTGAGAAGCCTCACGAATG TAAGGAGTGTGGGCGAGAAGCCTACAAGTGCACAGAATGCACAGAATGGTGGGGAAGCCTCGTTAAGCACGAGAGGA TACATACGGGCGAGAAGCCTACAAGTGCACAGAATGCACAGAGCGAAACCCGTATAAATGT GGCTATCACCTCACTCAGCACGAGAATCCACACAGGAGAAACCCTCTAACATGAGAGAT CATATCAGCTTACACAACACAGAATGTGGGGAGAAGTGTTAGTCACG GCCATCAAGCTTACACAACACAGAATGTGGGGAAGAATCCTAAGAATGT AAGGAGTGCGGGAAGCCATGTAACCACCTAAACCATCCGAGAACATCAGAGGAT CCACAACAGTTGA | 6699 6700 |
| | 3 | MSKDILLEKAPLLEHRDIRRIPLNVRTVGRPLVVAINL VNIRKSILVRNLMNVKNVRRPSVGAISLLNIKKPILGRSP TNVKTVGRLFIRGFILVKNPMNVKTVERPF GVVMSSLSTRDSTLGRKTNAKTVGRPLAVCINLFSTRE PIVGRSLTSVKTVGRLLFVVQASPSIKEFTQVRNPMNYK NVGRPLLESITLLSIRRSFPVRSLTNVRSVGRPFAGVRAS LSTRGYIRARSKTSAQNVGRPSIVAIITSLSTRESTQAKFRI NVRSVGRLSFMDRAS* | ATGTCAAAAGACCTGCTACTAGAGGCACCCCTCCTAGAACACATCAGAGACATC ATAAGGAGAATTCCTTTGAATGTAAGGACTGTGGCGAAGCCTTTAGTCGTGCTATC AACTTAGTCAACATCAGAAAATCCATACTGGTGAGAAACCTTATGAATGTAAAGAAT GTAAGAAGGCCTTCCGTTACTCAGCTTACTCAACATCAAAAATTCATACTG GGGAGAAGCCCTACTAGAAGACTGTGGGAAGGCTTTCGATGGGGCTCAAGC CTCGTTATTCATAAGAGAATTCATACTGGTGAAAAACCCTATGAATGTAAAGACTGT GGAAAAGCCTTTCATCAGCCTTTGATGAGCTACACTAGTGGGGAGAAGACTTACGA GGAGAAAGACTACGAATGCAAAGACTGTGGGAAGACCTTTAGCCGTGTGTATAAAC TTATTCAGCACACAGAGAATTGTGGTTTCAAGCCTCATTCAGCATAAAGAAGGCCTTT GGGAAGGCCTTTACTCGAGTCAATTACCTTACTCAGCATCAGAGAATCCACACCGGT GAGAAGCCTCAGGATCAGAGAGGTCGACGAATCCACCCGGTGAGCCTCGTTAAGCA CGAGGAGGCTTTTCGCTGGGTTCGACGAATGTGGGGAGAAGCCTACGAGGAGGATACATACGGGCG AGAAGCCGTACAAGTGCACAGAATGTGGGAAGGCCTTCAATTGTGGCTATCACCTC ACTCAGCACGAGAATCCACACAGGGCGAAACCCGTATAAATGTAAGGAGTGTGG GAAGGCTTTCATTTATGGATCGAGCCCTCGTGA | 6701 6702 |
| | 4 | MGLKPRYS* | ATGGGCTCAAGCCTCGTTATTCATAA | 6703 6704 |
| | 1 | MSIR* | ATGTCAATCAGATGA | 6705 6706 |

Figure 1 (Continued)

| | | | | |
|---|---|---|---|---|
| hsa-mir-526b | 2 | MHINYVKRPATREGTPPRTHQRHHKENSPECKDCGKAF SRGYQLSQHQKIHTGEKPYECKECKCKAFRWGNQLTQH QKIHTGEKPYECKDCGKAFRWGSSLVIHKRIHTGEKPY ECKDCGKAFRRGDELTQHQRPHTCGEKDYECKDCGKTF SRVYKLIQHKRIHSGEKPYECKDCGKAFICGSSLIQHKRI HTGEKPYECQECGKAFTRVNYLTQHQKIHTGEKPHECK ECGKAFRWGSSLVKHERIHTGEKPYKCTECGKAFNCGY HLTQHERIHTGETPYKCKECGKAFIYGSSLVKHERIHTG VKPYGCTECGKSFSHGRQLTQHQKTHSGAKSYECKEC GKACNHLNHLREHQRIHNS* | 6707 | ATGATCATCAATTATGTCAAAAGACTGCTACTAGAGAAGGCACCCCTCCTAGAACA CATCAGAGACATCATAAGGAGAATTCCTTTGAATGTAAGGACTGTGGAAGGCCTTT AGTCGTGGCTATCAACTTAGTCAACATCAGAAATCCATACTGGTGAGAAACCTTAT GAATGTAAAGAATGTAAGAAGCCTTCCGTTGGCAATCAGCTTACTCAACATCAA AAAATTCATACTGGGGAGAAGCCTCGTTATTCATAAGAGAATTCATACTGGTGAGAAAACCTATGA ATGGGGCTCAAGCTGTGGAAGACTGTGGGAAGGCCTTTCCGTGATGAGCTCACTCAGCACCAGA ATGTAAAGACTGTGGGGAGAAGACTTACGAATGCAAAGACTGTGGGAAGACCTTTAGC GATTCCACACTGGGAGAAGATACGCACACAAGAGAATTCAGCACCATAGTGGGGAGAAGCTTACGA CGTGTGTATAAACTTATTCAGCACCAAGAGAATTCATAGTGGGGAGAAGAAGCTTACGA GTGTAAAGACTGTGGGAAGGCTTTTATTTGGTTCAAGCCTCATTCAGCATAAAG AATTCACACAGGTGAGAAGAACCCTATGAATGTCAAAGAATGTGGAAGGCTTTACTCG AGTCAATTACCTTACTCAGCATCAGAGAATCCACACCGGTGAGCCTCGTTAAGCACGAGGA TAAGGAGTGTGGGACGGCGAGAAGCCTACAAGTGCACAGATGGGAAGCCTCAATTGT TACATACGGGCGAGAAGCCTACAAGTGCACAGATGGGAAGCCTTCAATTGT GGCTATCACCTCACTCAGCACGAGAATCCACACAGGCGAAACCCGTATAATGT TCATATCCGGGGTGAAACCTATGGGTGACAGAATGTGGGAAGAGCTTAGTCACG GCCATCAAGCTTACACACAACCACTCAGAAACCACAAGGTGGGGGGAAATCTACGAATGT AAGGAGTGCGGGAAGCATGTAACCACCTAAACCATCTCCGAGAACATCAGAGGAT CCACAACAGTTGA |
| | 3 | MSKDILLEKAPLLEHRDIRRRIPLNVRTVGRPLVVAINL VMRKSILVRNLMNVKNVRRPSVGAISLLNIKKPILGRSP TNVKTVGRLFDGCAQASLFIRGFILVKNPMNVKTVERPF GVVMSSLSTRDSTLGRKTTNAKTVGRPLAVCINLFSTRE PIVGRSLTSVKTVGRLLFVVQASPSIKEFTQVRNPMNYK NVGRPLLLESITLLSIRRSFPVRSLTNVRSVGRPFAGVRAS LSTRGYIBARSRKTSAQNVGRPSIVAITSLSTRESTQAKFRI NVRSVGRLSFMDRAS* | 6709 | ATGTCAAAAGACCTGCTACTAGAGGCACCCCTCCTAGAACAACATCAGAGACATC ATAAGGAGAATTCCTTTGAATGTAAGGACTGTGGGAAGGCCTTTAGTCGTGGCTATC AACTTAGTCAACATCAGAAATCCATACTGGTGAGAAACCTTATGAATGTAAGAAT GTAAGAAGGCCTTCCGTGAATGAGCTTACTCAGCTTACTCAACATCAAAATTCATACTG GGGAGAAGCCCTACGAATGTAAAGACTGTGGGAAGGCTTTCGATGGGGCTCAAGC CTCGTTATTCATAAGAGGATTCATACTGGTGAAAAAACCCTATGAATGTAAAGACTGT GAAAAGGCCTTTCGGCGTGATGAGCTCACTCAGCACCAGAGATTCCACACTGG GGAGAAAGACTACGAATGCAAAGACTGTGGGAAGACCTTACGAGTGTAAACCCTATAAAC TTATTCAGCACTGGTTCAAGCCTTTATTTGGTTCAAGCCTCAGTGTAAAGACTGT GGGAAGGCCTTTGAATGTCAAGAATGTCAAGAATGTGGGAAGGCCTTTACTCGAGTCAATTACCTT ACTCAGCATCAGAGAATCCACACCGGTGAGAAGCCTCAGAATGTAAGGAGTGTGG GAAGGCCTTTGCGGGTTCGACGAGAATGTGCGACAGGATATACACGGGCG GAAGCGCCGTACAAGTGCACACAGGCGGAAAGCCTTCAATTGTGGCTATCACCTC ACTCAGCAGCACGAGAGAATCCACACAGGCGGAAACCCGTATAAATGTAAGGAGTGTGG GAAGGCTTTCATTTATGGATCGAGCCGTGA |
| | 4 | MGLKPRYS* | 6711 | ATgggGCTCAAGCTCGTTATTCATAA |
| | 1 | MSIR* | 6713 | ATGTCAATCAGATGA |

Figure 1 (Continued)

| | | | | |
|---|---|---|---|---|
| hsa-mir-527 | 2 | MIINYYKRPATREGTPPRTHQRHRKENSPECKDCGKAF<br>SRGYQLSQHQKIHTGEKPYECKECKKAFRWGNQLTQH<br>QKIHTGEKPYECKDCGKAFRWGSSLVIHKRIHTGEKPY<br>ECKDCGKAFRRGIDELTQHQRFHTGEKDYECKDCGKTF<br>SRVYKLIQHHCRIHSGEKPYECKDCGKAFICGSSLIQHERI<br>HTGEKPYECQECGKAFTRVNYLTQHQKIHTGEKPHECK<br>ECGKAFRWGSSLVKHERIHTGEKPYKCTECGKAFNCGY<br>HLTQHERIHTGETPYKCKECGKAPIYGSSLVKHERIHTG<br>VKPYGCTECGKSFSHGHQLTQHQKTHSGAKSYECKFC<br>GKACNHLNHLREHQRIHNS* | 6715 | ATGATCATCAATTATGTCAAAAGACCTGCTACTAGAGAAGGCACCCCTCCTAGAACA<br>CATCAGAGACATCATAAGGAGAATTCCTTTGAATGTAAGGACTGTGGGAAGGCCTTT<br>AGTCGTGGCTATCAACTTAGTCAACATCAGAAATCCATACTGTGAGAAACCTTAT<br>GAATGTAAAGAATGTAAGAAGGCCTTCCGTTGGGGCAATCAGCTTACTCAACATCAA<br>AAAATTCATACTGTGGGAGAAGCCCTACGAATGTAAAGACTCATACTGTGGAAGCTTTCG<br>ATGGGGCTCAAGCACTGTGGAGCTCGTTATTCATAAGAACTTCATACTGTGAAAACCCTATGA<br>GATTCCACACTGTGGGAGAAGACTACGAATGTAAAGACTCATACTGTGGAAGACCTTTAGC<br>CGTGTGTATAAACTTATTCAGCACAAGAGAATTCATAGTGGGAGAAGCTTACGA<br>GTGTAAAGACTGTGGAAGGCTTTTATTTGTGTTCAAGCTCATTCAGCATAAAG<br>AATTCACACAGGTGAGAAACCCTATGAATGTCAAGAATGTGGGAAGGCCTTTACTCG<br>AGTCAATTACCTTACTCAGCATCAGAAGATCCACACCGGTGAGAAGCCTCACGAATG<br>TAAGAGTGTGGAAGAGCCGTACAAGTGCACAGAATGTGGAAGACCTTTAAGCAGAGGA<br>TACATACTGTGGGGAGAAGCCTCGTTAAGCAGTGCACAGGTGCAGAATGTCAGAATGTCACG<br>GGCTATCACCTCACTCAGCACGAGAATCCACAGGCGAAACCCTGTTAAGCACATGT<br>AAGGAGTGTGGAAGGCTTCATTATGGATCGAGCCTGTGAAACATGAGAGAAT<br>TCATACCGGGGTGAACCTAGCAATGCAGAAAACGCACAGTGTGGGAGAGCTTAGTCACG<br>GCCATCAGCTTACACACAACATCAGAAATCGACACCATCTCCGAGAACATCAGAGGAT<br>AAGGAGTCGGGAAGGCATGTAACCACCTAAACCATCTCCGAGAACATCAGAGGAT<br>CCACAACAGTTGA | 6716 |
| | 3 | MSKDLLEKAPLLEHIRDIHRRIPLAVRTVGRPLVVAINL<br>VAHRKSILVRNLMNVKNVRRPSVGAISLLNIKKFILGRSP<br>TNVKTVGRLFDGAQASLFIRGFILVKNPMNVKTVERPF<br>GVVMSSLSTRDSTLGRKTNAKTVGRPLAVCINLFSTRE<br>RIVGRSLTSVKJTYGRLLFVVQASFSIKEFTQVRNPMNVK<br>NVGRPLLESITLLSIRRSTPVRSLTNYRSVGRPFAGVRAS<br>LSTRGYIRARSRTSAQNVGRPSIVAITSLSTRESTQAKPRJ<br>NVRSVGRLSFMDRAS* | 6717 | ATGTCAAAGACTGCTACTAGAGAAGCACCCCTCCTAGAACACATCAGAGACATC<br>ATAAGGAGAATTCCTTTGAATGTAAGGACTGTGGAAGCCTTTAGTCGTGGCTATC<br>AACTTAGTCAACATCATGAAAATCCATACTGTGAGAAACCTTATGAATGTAAGAAT<br>GTAAGAAGGCCTTCCGTTGGGGCAATCAGCTTACTCAACATCAAAAATTCATACTG<br>GGGAGAAGCCCTACGAAGACTGTAAAGACTGTGGAAGCTTTTGATGGGGCTCAAGC<br>CTCGTTATTCATAAGAGGATTCATACTGGTGATGAGCTCACTCAGAGACTTTAGAATGT<br>GAAAGGCCTTTATTTGCAAGGCCTGTGATGAGCTCACTCAGCACCAGAGAGATTCCACACTGG<br>GAGAAAGCGCTACGAATTCATAGTGGGAGAAGCCTTACGAGTGTAAAGACTGT<br>TATTCAGCACGACGACAAGAGATGCATAGTGGGAGAAGCCTTACGAGTGTAAAGACTGT<br>GGGAGGCCTTTCGCCTGGGTTCGAGCCTGTTAAGCAGTGCACGAGGATACATACGGCG<br>GAAGGCCTTTCGCCTGGGTTCGAGCCTGTTAAGCACGAGGATACATACGGCG<br>GAGAAACCGTACAAGTGCACAGAATGTGGAAAGCGAAACCCGTATAAATGTAAGGAGTGTGG<br>ACTCAGCAGCTTTCATTATGATCGAGCTCGTGA | 6718 |
| | 4 | MGLKPRYS* | 6719 | ATGGGGCTCAAGCCTCGTTATTCATAA | 6720 |
| hsa-mir-532 | 1 | MSRAPASLPLPGWAY* | 6721 | ATGAGCCGGCCGCGAGCCTCGCTGCCCTTGCCTCGCCGCCGCTGGGCTGTGTGA | 6722 |
| | 2 | MKJLCRLRGALTQLGVLDARADRARCPPAADTGSAAPD<br>LGDR* | 6723 | ATGAAGCTCTGCCGAGCGCGGCCTACGGTGCTGGATGCTAGGAGCTGATGCTGCCCAGA<br>GCCGACCGAGCGCGCTGCCCACCGGGACACGGGCTCGGACGTCGGACCT<br>CGGCCGGACAGGTAA | 6724 |
| | 3 | MGLPRARRWQPGA* | 6725 | ATGGGGCTCCCTCGGGGTTGCGGGGAAGTTCTTGCGGAGGCGCCAAGCCGCGCGCGCTTAG | 6726 |
| | 4 | MVPGLPERSFLAERRQARPAFESECLAACYPFPGLG* | 6727 | ATGGTCCCTGGGTTGCCGAGGCAAGTTCTTGCGGAGGCGCCAAGCCGCGCCC<br>GCTTTTGAATCGCAGTCGTTTAGCGCCTCCCTTTCCGCGTCCTGTGGACCTGGAGCAGCCAGTGGGGTAG | 6728 |
| | 1 | MDQGVEGGGCGPGVGRQSACSL* | 6729 | ATGGACCAGGGGTGAGAGGGTAGAGGGAGGTGGGTTGGAGGTCGGGCGCCAGTCAG<br>CTTGCAGCCCTATGA | 6730 |

Figure 1 (Continued)

| | | | | | |
|---|---|---|---|---|---|
| hsa-mir-539 | 2 | MKIDGKEGYRDRGRVGLRIARAAWHTVLG* | 6731 | ATGAAGGACGGAAAGGAGGGCTACAGAGATAGGGGAAGAGTGGGGCTGAGGATAGCCAGAGCGGCTTGGCACACAGTTTAGGGTAA | 6732 |
| | 3 | MTEPVTPGSSFKACLMGDSVVPVTKLGPESQGRAHQVAALP* | 6733 | ATGACTGAGCCGGTCACTCCAGGGTCTTCCTTCAAAGCGTGTCTAATGGGAGACAGCGTTGTCCCAGTAACCAAATTGGGACCCAGAGTCCCAGGGAAGGGCTCATCAGGTGGCCGCTCTGCCTTGA | 6734 |
| | 4 | MILFPLIDPAPLVPFSL* | 6735 | ATGATTCTCTTCCCTCTGGATCAGCCGCCCTCTAGTTCCCTTTCACTTTGA | 6736 |
| | 1 | MDQGVEGGGCGPGVGRQSACSL* | 6737 | ATGACCAGGGGTAGAGGGGAGTGGGTGGACCTGGGGTCGGGGCCAGTCAGCTTGCAGCCTATGA | 6738 |
| | 2 | MKIDGKEGYRDRGRVGLRIARAAWHTVLG* | 6739 | ATGAAGGACGGAAAGGAGGGCTACAGAGATAGGGGAAGAGTGGGGCTGAGGATAGCCAGAGCGGCTTGGCACACAGTTTAGGGTAA | 6740 |
| hsa-mir-541 | 3 | MTEPVTPGSSFKACLMGDSVVPVTKLGPESQGRAHQVAALP* | 6741 | ATGACTGAGCCGGTCACTCCAGGGTCTTCCTTCAAAGCGTGTCTAATGGGAGACAGCGTTGTCCCAGTAACCAAATTGGGACCCAGAGTCCCAGGGAAGGGCTCATCAGGTGGCCGCTCTGCCTTGA | 6742 |
| | 4 | MILFPLIDPAPLVPFSL* | 6743 | ATGATTCTCTTCCCTCTGGATCAGCCGCCCTCTAGTTCCCTTTCACTTTGA | 6744 |
| | 1 | MIQMSNCLYLTLFVYLQK* | 6745 | ATGATCAGATGTCCAATGTCCCTCTACTTAACCTTATTGTCTACCTTCAGAAGTAA | 6746 |
| hsa-mir-542 | 2 | MVKL* | 6747 | ATGGTGAAGTTATAA | 6748 |
| | 3 | MVQNVRCYTPSWGR* | 6749 | ATGGTTCAAAACGTGAGGCGCTGCTATACCCCCTCGTGGGAAGTAG | 6750 |
| | 4 | MMLHFGTPEPCSGRM* | 6751 | ATGATGCTCATTTGGCACCCTTTCCCGTGCTCAGGTAGAATGTAA | 6752 |
| | 1 | MDQGVEGGGCGPGVGRQSACSL* | 6753 | ATGACCAGGGGTAGAGGGGAGTGGGTGGACCTGGGGTCGGGGCCAGTCAGCTTGCAGCCTATGA | 6754 |
| hsa-mir-543 | 2 | MKIDGKEGYRDRGRVGLRIARAAWHTVLG* | 6755 | ATGAAGGACGGAAAGGAGGGCTACAGAGATAGGGGAAGAGTGGGGCTGAGGATAGCCAGAGCGGCTTGGCACACAGTTTAGGGTAA | 6756 |
| | 3 | MTEPVTPGSSFKACLMGDSVVPVTKLGPESQGRAHQVAALP* | 6757 | ATGACTGAGCCGGTCACTCCAGGGTCTTCCTTCAAAGCGTGTCTAATGGGAGACAGCGTTGTCCCAGTAACCAAATTGGGACCCAGAGTCCCAGGGAAGGGCTCATCAGGTGGCCGCTCTGCCTTGA | 6758 |
| | 4 | MILFPLIDPAPLVPFSL* | 6759 | ATGATTCTCTTCCCTCTGGATCAGCCGCCCTCTAGTTCCCTTTCACTTTGA | 6760 |
| | 1 | MDQGVEGGGCGPGVGRQSACSL* | 6761 | ATGACCAGGGGTAGAGGGGAGTGGGTGGACCTGGGGTCGGGGCCAGTCAGCTTGCAGCCTATGA | 6762 |
| hsa-mir-544 | 2 | MKIDGKEGYRDRGRVGLRIARAAWHTVLG* | 6763 | ATGAAGGACGGAAAGGAGGGCTACAGAGATAGGGGAAGAGTGGGGCTGAGGATAGCCAGAGCGGCTTGGCACACAGTTTAGGGTAA | 6764 |
| | 3 | MTEPVTPGSSFKACLMGDSVVPVTKLGPESQGRAHQVAALP* | 6765 | ATGACTGAGCCGGTCACTCCAGGGTCTTCCTTCAAAGCGTGTCTAATGGGAGACAGCGTTGTCCCAGTAACCAAATTGGGACCCAGAGTCCCAGGGAAGGGCTCATCAGGTGGCCGCTCTGCCTTGA | 6766 |
| | 4 | MILFPLIDPAPLVPFSL* | 6767 | ATGATTCTCTTCCCTCTGGATCAGCCGCCCTCTAGTTCCCTTTCACTTTGA | 6768 |
| | 1 | MCGNJFFLPLRWGLTLLPRLATS* | 6769 | ATGTGTGGAAATATTTTTTTCTTTTTGAGATGGGTCTCACTCTGTTGCCCAGGCTGGCAACATCATAG | 6770 |
| hsa-mir-545 | 2 | MGSHSVAQAGNIIAGTIIAHCSLDFLGSSDSSTSAF* | 6771 | ATGGGTCTCACTCTGTTGCCCAGGCTGGCAACATCATAGCTGCACAATCATAGCTCACTGTGATTCTTCCACCTAGCCTTCTGA | 6772 |
| | 3 | MSPELVSNS* | 6773 | ATGTCACCCGAGCTGTCTGAACTCCTGA | 6774 |
| | 4 | MGEGLTKEVWAEGGMMVEASVTEGRGKVEEAEWDSVLGKK* | 6775 | ATGGGAGAGGGATTGACCAAAGAAGTATGGGCTGAGGAGGGGATGATGGTGGAGGCCAGTGTGACCGAGGGAGGGAAGGTGGAAGAAGCAGAGTGGGATAGCGTCCTGGGAAAGAAGTGA | 6776 |

Figure 1 (Continued)

| | | | | |
|---|---|---|---|---|
| hsa-mir-548a-1 | 1 | MLTRELGGQIPGIQKLNSTSVPSLYAIECVGPAWWKHRI PRLSTSTFCRENAFFPQLVSRQMHSDLRGKCVLLVINK* | 6777 | ATGTTAACCAGAGAGCTGGGAGGGCAAATCCTGTATCCAGAAGCTGAATAGCAC TTCTGTTCCCTCACTGTATCCTATTGAGTGTGTTGGCCCAGCATGGTGAAACACCG CATTCCCAGGCTGAGCACCTCAGCACCTCATGCTTTGAGTGTGTTCTGCAGAGAAATGC TGTGTCACGCCAGATGCACTCGATCTCAGAGGGAAATGTGTCTACTGGTAATTAA TAAATAA | 6778 |
| | 2 | MLLSVLAQHGGNTAFFG* | 6779 | ATGCTATTGAGTGTGTTGGCCCAGCATGGTGAAACACCGCATTCCCAGGCTGA | 6780 |
| | 3 | MVETPHSQAEHLMLLQRKCFSASACVTPDAL* | 6781 | ATGGTGGAAACACCGCATTCCCAGGCTGAGCACCTCATGCTTCTGCAGAGAAATGC TTTTCGCGCTCAGCTTGTGTCACGCCAGATGCACTCTGA | 6782 |
| | 4 | MLFRLSLCHARCTLISEGNVCYW* | 6783 | ATGCTTTTCCGCTCAGCTTGTGTCACGCCAGATGCACTCTGATCTCAGAGGGAAAT GTGTGCTACTGGTAA | 6784 |
| hsa-mir-548a-2 | 1 | MYLKCVCFFYL* | 6785 | ATGTATCTTAAATGTCTGCTTTTCTATTACCGTAA | 6786 |
| | 2 | MCLLFLLPVHLJVMTQYL* | 6787 | ATGTCTCTGCTTTTCTATTACCGTAATATCTTGTAGTAATGACACAATATTTATGA | 6788 |
| | 3 | MKCSQYAREEERGREKRRBKVMSER* | 6789 | ATGAAGTGTCTCAATATGTCTAGGGAAGAAGAAGAGGGAGAAGAGAAAGAAGAA GAAAGGTGATGTCTGAGAGGTGA | 6790 |
| | 4 | MLGKKKEGERKEEER* | 6791 | ATGCTAGGGAAGAAGAAGAAATATTTTGAGTGCTGTGTTGCTTTTTTTACCAGATGA | 6792 |
| hsa-mir-548a-3 | 1 | MENIFGVLVAFFTR* | 6793 | ATGGAAAACATTTTTGAGTGCTGTGTTTTTTTACCAGATGA | 6794 |
| | 2 | MYSPESMF* | 6795 | ATGTATTCCCAGAAAGTATGTTTTAA | 6796 |
| | 3 | MHQSALCKMHQSALCKTHQSAGPQK* | 6797 | ATGCACCAATCAGCGCTCTGTAAAATGCACTCTGTAAACGCACCAA TCAGCAGGATTCCAAAGTAG | 6798 |
| | 4 | MEHGRGPQGNKSWPPPASTWGSLPCCGSCPFALRNKPC YRSLFESVPSLRAVNSHREGLQLHS* | 6799 | ATGGAACATGGAGGGGACCACAGACGAATAAAAGCTGGCCACCACCAGCCAGCCAC CTGGGGTTCTCTTCCATGCTGTGGAAGCTGTCCTTTGCTCTTCGCAATAAAACCTGC TACCGCTCACTCTTTGAGTCGCTGCCATCTTTAAGAGCTGTTAACAGTCACCGGGAA GGTCTCGACTTCATTCTTGA | 6800 |
| hsa-mir-548b | 1 | MATPGMSWQQHYYGGSAAKFAPSPATAQLAGHSMDY SQEMHLKMSKKIAQLTKVRGAATGQVATPCSPRRTHL SPREAVRPAPAARGTLLLRRSNSKRRHLQKPANFGGTLA T* | 6801 | ATGGCGACCCCGGGCATGAGCTGGCAGCAGCACTATTACGGCGGCTCCGCGGCCAA ATTCGCGCCCTCGCCCGCAACGGCACAGCTGGCTGGCACAGCTGGCACATGGACTACAGCC AGGAGATGCACCTGAAAATGAGCAAGAAAATGCCCAGCCTCACCAAGGTAAGGGGG GCAGCGACGGACGGACCAGTTGGCGACCCGTCGCGGCGCGCCAGACTCACCTGTCTCC CGGGAGGAGCAGTGCGCCTCGCGCGCCAGCGAGGGGAACTTCCGCGTCTCCCGGAA GCAACAGCCGGAGACACCTCCAAAACCTGCAAACTTGGTGGAACGCTGGCAACA TGA | 6802 |
| | 2 | MNLS* | 6803 | ATGAATTTAAGCTAG | 6804 |
| | 3 | MHLPGLREASHYSTI* | 6805 | ATGCATCTGCCAGGGCTCCAGGAGCATCACACTAGTACCATTGA | 6806 |
| | 4 | MTRIN* | 6807 | ATGACTCGGAATTAA | 6808 |
| hsa-mir-548b | 1 | MITWATPSVLCKCVMTNQPGRPRDLPLEIGNFHLCL* | 6809 | ATGATTACCTGGCAACCTTTCTGTCTATGTAAATGTAATGACTAATCAACCA GGACGGCCAAGGAGTTTGTTTCTAGAGATAGCATTTCATTTGTGCCTGTGA | 6810 |
| | 2 | MCND* | 6811 | ATGTGTAATGACTAA | 6812 |
| | 3 | MMIDQNKRRNHFTHA* | 6813 | ATGATGATGACCAAAACAAAAGAAGAAATCATTTCACTCATGCTTAG | 6814 |
| | 4 | MCMR* | 6815 | ATGTGCATGCGTTGA | 6816 |
| | 1 | MSSGIYSSLEEDAEDFFTARTSFRRAPQGKPRSGQQVS GARRALQPAPQSSGEPASPRPLPRVSAGRSGDARREGG AGREVASAFSGPGNVPGACACRRGKAEEGRGG* | 6817 | ATGAGCAGCGGCTACAGCAGCCTGGAGGAGGACGCCGAGGACTTCTTTACCGC CAGGACCTCCTTCCGCCGGGCCCCTCAAGGAGAGCCCCAGGGCAAGCCCCGTCCGGCCAACAAG TGAGTGGCGCCGCGGCGGCGCTGCAGCCCGCCCAGAGTTCCGGGAACCCGCC AGCCCGCCGCCGCCGTCCACGTCCTCTCCGGACGTCCCTTTCGGAGATGCTCCGGGC GAAGGAGGAGCCGGCGAGCCCGAGAGTGCTCCTGCCTTTGCCTGCCGGCGAAGCCTTTGCCTGCCGGCGAAGCCGAGGCGCTGGAAGGCGCGGCGCTGA | 6818 |

Figure 1 (Continued)

| | | | | | |
|---|---|---|---|---|---|
| hsa-mir-548c | 2 | MLAGKEERAEKWLLPFRVPGTCLELVRVGEGRRRKGG EAEGRLLPSAPDGLCSSASGCRLRGAAPEPAGVPGPLPQ VSPSRPKWVDGRVRAPVLPVSQLTHLWPPEWLGSTCNS * | 6819 | ATGCTCGCCGGAAGGAGGAGCGGCCGAGAAGTGGCTTCTGCCTTTCGGGTCCC GGGAACGTGCTGGAGCTGGGGCCGGCTGTGTGCGTTGCAGCTGTAGCGAGGAAGGCGAGGAAGGGCGGG GAGGCTGAGGGCCGGCTTCTGCCTTCCGCCAGATGCCCTCAGATGCCTCTGCAGCTGCCGCTCG GCTGCCGCCTGCTGGGGAGCAGCCCGGACGCAGCCAGCAGGCGTCCCGCGGCACTCCC CAAGGTTTCCCCTTCGCGTCCGTGGGGTCCAGCAGGCGTCGGGTTCGGCGCTCTGTCCT CCTTGTTAGTCAGCTTACTCATCTGTGGCCCCCAGTCTGGGCTGGGTTGGGTCAACGTGTAA TAGCTAG | 6820 |
| | 3 | MASAAPPRAAACGEQPRSQQASPGHSPRFPLRVPAGST VGFARLSFLLVSLLICGPQSGLGQRVIARGGRVT* | 6821 | ATGGCCTCTGCAGCTCCGCTCCGCTCCGCTGCGGGGAGCAGCCCCGGAGCCA GCAGGCGTCCCAGGCCAACTCCGCTTTCCCCTTCGGTCCCGTCCGGGTCGAC GGTCGGGTTCGCGCGCCTGCTCCTTGTGAGTCTGTCAGTAGCTGTAGCGTGGGCCCCA GAGTGGCTTGGGTCAACGTGTAATAGCGGTGGCGGGTGACCTGA | 6822 |
| | 4 | MFCKQAPMLNTSQRQLTFSPVSSFGGSMPWEARVGKR WEGNLCQFRQL* | 6823 | ATGTTTGCAAACAAGCTCCTATGCTCAAATACTAGCAGCGACAGCAGCTAACCTTCG CCGGTTTCTTCCTTTTGAAGGCAGCATGCGTGGGAAGCACGAGTTGGGAAAGA TGGAAGGGAACTTGTGCCAGTTTCGCCAGCTGTAG | 6824 |
| hsa-mir-548d-1 | 1 | MALCCESPRGGSSNQGLSFCAVEKPGETLK* | 6825 | ATGGCGCTTTGCTGTGAATCTCCGGGGAGGCTCCCAACCAGGGCTGAGCTTC TGCGCTGTGGAGAAGCCAGGTGAGACACTGAAATAA | 6826 |
| | 2 | MTASRTLSERDSTPRLTLL* | 6827 | ATGACCGCATCGAGGATGCTTTCCGAAAGGGATAGCACCCAAATCTCACTCTATTG TAA | 6828 |
| | 3 | MVSFLC* | 6829 | ATGGTATCTTTTGTCTACTAA | 6830 |
| | 4 | MVKLRLY* | 6831 | ATGGTGAAACTCCGTCTACTAA | 6832 |
| | 1 | MGFQKLTYEKSCCVPNCDNNQVASHGPHRNRAESKTP STARKARTTATLJFRTKDPLRTRTSFPLHSSVLCAERTIRY SQESRALPHP* | 6833 | ATGGGCTTTCAGAAATTAACCTATGAGAAGAGCTGCTGTGTCCCAACTGTGATAAC AATCAAGTTGCTTCCCACGCCACACAGACACCGGCAGAAACGCAGAAACAACACCCTC GAACCAGAACTTCATTTCTCTTCCTGCATCATGGCCGTCTGCTGAAGGACCATCC GCTATTCCAAGAAAGCAGGGCCCTCCCTCATCATG | 6834 |
| hsa-mir-548d-2 | 2 | MRRAAVSPTVITIKLLPTAHTETAQKAKHPPPRGRLEPR QRPSEPKTLCEPELRELFIHLCCVLKGPSAJPKKAGPSLIH SVNVECSH* | 6835 | ATGAGAGAGCTGCTGTGTCCCAACTGTGATAACAATCAAGTTGCTTCCCACGGCC CACACAGAATGACGGAACGTTTCAGAACCAAAACACCCTCTGCAACCAGAAGCTAGAACC ACGGCAACGCTTTCAGAAGAACCCTCTGCAACCAGAACCATCGCTATTCCAAGAAAGCAGGGCCC CATTCCATCTGTGCTGTGTCTGAAAGGACGTTGAGTGTTCACACTAG | 6836 |
| | 3 | MPSS* | 6837 | ATGCCATCATCTTAG | 6838 |
| | 4 | MVKNPVGWMQWLMPHPTLWEAEVGGLLEPKSLRPA* | 6839 | ATGGTCAAGAATCCGTGGGGTGGATGCAGTGGCTCATGCCTATAATCCCAACACTT TGGGAGGCTGAGGTAGGAGATGCTTGAGCCCAAGAGTTTGAGACCAGCCTGA | 6840 |
| hsa-mir-549_08 | 1 | MKLPSTRPRLAQVGRGPCARAGPGRALAAALGDADLSP RSPGAQSPRARSSQVRALEARTRWSGRGPRRASPRASK EPGSPVPRSRPGAPSEAKRQWRTGEKVCACHRLAASRG PRLSLRJSF* | 6841 | ATGAAACTTCCTCCCACGCGCCTGCCACGCGGGGTCCTGTGCC CGGGGCCGGACCGGGGCGCGGGGACGCAGACCGCAGAGCCCTGGAGCC GTGGGCGAGTCCGGGTGCGCAGAGTCCGCCCCGACAGCGGAGCCCTGGAGG CAGGGACTCGGTGAGCGCGTGGAGCGCCGGCGGAGGAGCAAGTCCCGGGCTCC AGGAGCCAGTGAGGAGGACAGGAGAAAAGTTCTGCCACAGAATCGCGCAGTC GGGGTCCCAGGCTAAGTCTCAGGATCTCTTTTAA | 6842 |
| | 2 | MLGSLKGTLV* | 6843 | ATGTTGGGTGTTACTAAAGGCACCTTAGTTGA | 6844 |
| | 3 | MPVTTVYRLTPPSLSPLIRKMGSVMLPH* | 6845 | ATGCCAGTTACAACTGTTACAGGATCTTAACCCTCCAGTTCCTCATCA GGAAAATGGGTTCTGTGATGCTTCCTCACTAG | 6846 |
| | 4 | MVRLK* | 6847 | ATGGTGAGGCTTAAATGA | 6848 |

Figure 1 (Continued)

| | | | | |
|---|---|---|---|---|
| hsa-mir-550-1 | 1 | MAAVAAAREEAVPRSGAPSAAAESGSGPSWRTRTETS GSRTAT* | 6849 | ATGGCGGCGGTAGCAGCGGCCGCCGCCCGAGAGGAGGCGGTGCCGAGATCGGGGCGC CGAGCGCGGCCAGCAGAGAGCGGTAGCGGCCCGTGTGGCGCACCAGAACCGAAACC AGCGGCAGCCGCACGGCCACTTGA | 6850 |
| | 2 | MGAKQSGPAAANGRTRAYSGSDLPSSSSGGANGTAGG GGGARAAAAGRFPAQVPSASHGPSASGGAAAAAAPAA PAAPRSRSLGGAVGSVASGARAAQSPFSHPNSSSGPYGS QDSVHSSPEDGGGGRDRPVGGSPGGPRLYGSLPAHLSP HMFGGTIDPSPRTRARSSRGCTWAVAAGYFYPSPFLLLP GRRGLPGPARVGLHPGRNPALNTGGAATA* | 6851 | ATGGGCGCGAAACAGAGCGGACCGGCCGCCGCTAACGCGCCACGCGCGCGTACTC GGGCTGGATCTACCTCGGGGCGCGCAGTAGCAGGCGGGGGAACGGCCACCGCGGCGG GCGGGGGCGCTCGGGCGCCGCCGCGCAGGAGGTTCCGGCTCAGGTGCCAAGCGCG CACCAGCCCAGCGCCTCCAGCCGCCTCCCTCGGCGCGCTCCGCGGGGAGCCGCCCC GGCGCGGCCCGCAGCGCCTCCCCTTCAGCATCCGAACAGCAGCAGCGCCGTACGGCT CGCAGGACTCGGTGCACAGCAGCCTGAGGACGGGGCGGGACCGCCTGGTGATCGGCTCTTACCAGCTCACCT GTGGGCGGGAGCCCTGGGCCGTGGCCGCGCCTGGTACGGACCCTCTCGCACCGCGTCGGTCTC TCCGCGCACATTTTGGAGGTACGGACCCCTTCGACCAGCCCGCGGCGCGCTCGGTCTC CTCGGGGCGCTGCAGTGGGCCGTGGCCTGCCTCCGACCAGCCGCGCTCGGTCTCTTT CTGCCGGGGCGGCGGCGGGCGCTTAACACCGGTGGTGCGCTACCGCATAG | 6852 |
| | 3 | MGPRAAAGALGPPRGGSRLRCPARTSPAPPAAPRRFK RPRQPRPRAAAPSAGPWGAWRRGPARRSPPSASRTAA AARTARRTRCTAALRTAAAAGTGRWAGAPAGRAW* | 6853 | ATGGGACCCGCCGCGGCGGGCGCTCGGGCGGCGCCGCCGCGGGGAGGTTCCC GGCTCAGTTGCCCAGCGCGCACCAGCGCCCCAGCCGCGGCCGCCGCCGCCCCG GGGCGGCCCGCAGCCCGGCGGCTCCTCGCCGCAGCCGCAGCCCTCGGGGGGCCGTG GGGAGCTGGCGTCGAGCCCGTACGGCTGCAGGACTCGGTGCACAGCAGCCCTGAACAG CAGCAGGCGGCCGGGACCGGCCGCCTGGGGAGCCCTGAGGACGGCG GCGCGGCGGCCGGGAGCCCGGTGGGGAGCCCTGAGGACGGCGGCTGGTGA | 6854 |
| | 4 | MTGANVVLQQTDETALVVVFSTRKSGGDQLLNVVLS GDSSGEQFLKAKSQSVSNEH* | 6855 | ATGACTGGAGCAAATGTTGTTTTACAACAGACGGACGAAACAGCCCTTGTGGTTGTG GTTTTTAGTAGGAAGTCAGGAGGAGACCAGTTGCTAAATGTAGTTCTATCTGGG GACTCGAGTGGGGAACAGTTTTTAAAGGCCAAAAGTCAAAAGTGTCTCAAATGAACA CTGA | 6856 |
| hsa-mir-550-2 | 1 | MREGRPWPWGRRRELLCLHRSPCAALMCCAR* | 6857 | ATGAGGGAAGGCGGCCGGCCGTGGCCGTGGCGGGGAGCTGCTTGCCTCCACCTG ATCTCCCTGTGCGGCCTCAATGTGCTGCTGCTGA | 6858 |
| | 2 | MEKARRGGDGVPRGPVLHVVVGPHHKKGCQVRKGPA PAPSRSGVRPFRGPPALLLCAQLASCSPPHSACDPSPLNL TPFAAPPTRPT* | 6859 | ATGGAGAAGGCCAGGAGAGGCGGGATGGGTGCCCCGCGGGGGCTGCCCCGTACTGCACAT CGTGGTGGTCGGATTTCACCACAGAAAGGCTGCCAGGTGAGGAAAGGCCCGCTGC CCGCCCACAGCTCGGCCGCTTCGGCGTTCCGCCCTTCGCCCTGCGGGGCCCCGGCCCCTGCTCTGT GTGCTCAGCTCGGCGTCTTTTGCAGTCCTCTCCACAGCCGCTGCGACCCTTCGCCTCTCA ACCTGACTCTTTTACAGCAAACCACCACAGAAAGATAA | 6860 |
| | 3 | MASPGGPYCTSWWSDFTTRRAAR* | 6861 | ATGGCCGTCCCCGGCGGCCCGTACTGCAGCTGGTGGTCGGATTTCACCACAAGAA AGGGCTGCCAGGTGA | 6862 |
| | 4 | MKPSPHNLFLLPLKNG* | 6863 | ATGAAGCCCAGCCCACACAACCTCTTCCTTCTGCCCTTGAAAAATGGTTGA | 6864 |
| hsa-mir-550-2 | 1 | MAAAASTGRWAGAPAGRAW* | 6865 | ATGGCGGCGGCGGCGAGCACCGGCCGCTGGGCGGGAGCCCCGGGGCGGGCGCG CCTGGGTGA | 6866 |
| | 2 | MFGGTDPSPRARARFSRGCTWAVAAGYFYRSPFLLPPG RRGLLPGPARQGLLPGPARAGLHPGKKPGT* | 6867 | ATGTTTGGAGGTACGGACCCCTCTCCACGCGCCGTCGTCCCGCGCTGCACGTGCCGGGGCCCGGCTGC ACGTGGCCGTGGCCGCCGGGCTACTTTTACCGTTCGCCCTTCCTCCCCGGCGGGGC GCCGGGTCTCCATCCTGGGAAGAAAACCGGCACGTAA | 6868 |
| | 3 | MLFYSKPTK* | 6869 | ATGTTGTTTTACAGCAAACCACCAAATAG | 6870 |
| | 4 | MNSELPSLDRLLJ* | 6871 | ATGAACTCTGAGTTACCATTCTTGACCGACTTTAATATAA | 6872 |
| | 1 | MCQPQVTAMTRVRQA* | 6873 | ATGTGCCAGCCCCAGGTAACAGCCATGACCCGGGTAAGACAAGCTTAA | 6874 |

Figure 1 (Continued)

| | | | | | |
|---|---|---|---|---|---|
| | 2 | MGEFASVKAAAATSFFQTRRDGWSCWSCSSRLATRHPR SISLGSAEAPSPQQQPTMGLPVGGVKPSVFNSGMGSCL ADVEHVVPKSPRCTATRAGP* | | ATGGGAGAGTTGCTCTGTGAAAGCAGCAGCAGCCACTTCCTTCAGACTGA CGTGATGCTGGAGCTGCTCCGGAGTGCTGAGGTCTCAAGTCCACAGCAGCCGCTGCTTGCAACCCGACATCCACG CAGCATTAGTCTCCGGTGGAGAGGTCAAGCCCAGTGTGTTCAACTCTGGGATCATGGGTTCCT GCCTCCGGTGACGTAGAACACGTTGTTCCCAAGTCACCCCGGTGACAGCAGCCACCAGAG CCGGCCCTTGA | 6876 |
| hsa-mir-551a | 3 | MAGAAGAAAALQPDIHAALVSGVLRLQVHSSSPPWA SRWEGSSPVCSTLGSWVPVLLT* | | ATGGCTGAGCTGCTGGAGCTGCAGCAGCCGCTTGCAACCCGACATCCACGCAGC ATTAGTCTCCGGAGTGCTGAGGTCTGAGGTCTCAAGTCCACAGCAGCCACCATGGGCTC CGGTGGGAGGGTCAAGCCCAGTGTGTTCAACTCTGGGATCATGGGTTCCTGTCTT GCTGACGTAG | 6878 |
| | 4 | MVTGVAAGTHQGLPSRPWEAPGSWHLLGACECRKALG TQAPLHRPLHPTAPQGPTLTRRTLPEGWGLWARLRSGP GQRPAPPSGAGRGLRCGRRLEPKCKIKVTGEADLAKGRE GKVAGVGGPQQPQGAGQGAGRAVPALAPHRGLGRWG SVQGTPPPPVLSQRGRGRAQSHLPTAAAPGSRSPDPARLT CVPASLGSAGPGQGARAGAGPRGEGLEPAAGRCLV RKVAGLEWWAGPCGEGLGPVAGRRLVQKGPGAGREG AGRERGGAMRGRARAAAGRRLVQKGLGAGRVGPGDA SSQBRGSRPPSPGARRCRGAGQGLQRAALSAPRRLAL GASRVPDLLHPCWSPSDATSLPAPRGPGCSADETAGGS GRVWA* | | ATGGTCACAGGTGTGGCGGCAGGAACCCATCAGGGACTCCCCTCCAGGCCCTGGGA GGCTTCACCGGATCCTGGCACCTCTGGGGCTTGTGAGTGCAGGAAGCCCTAGGTA CACAGGGCCCCTCCATAGACCTCTTCACCCACAGGCCTCAGGGCCCCACACTTA CCCGGAGAACCTTGCTCGAGGGCTGGGCTCTGGGCCAGGTCAGGTTGCCGTCAGGGCCT CCTGAGCCTAAAGTCCACCTCCAGCGGAGCAGGTCGTGGGCTGAGGTGGCAGACG AAGGGAAAGTGGCTGGTGTCGGGGCGACCGGAGAAGGCGATCTTCTAAGGCCCGGG AGCCGGTGCGGGGCAGTTCGTCCCTGGCCGCAGCACGCGGGTTAGTCCGGTTGGGGGGT CAGTCCAGGGCACGGCCCCACGCCCCCACCCCCAGTTCTCAGCGAAGCCGCAGCCCGGGACAGA TCGCACCTGTCTCCCCGCTCCTCGGCTCCGCAGGGCCGAGCTGGGCAGGGGCGA GGGCCGGAAGGTGCGGAGGGCCCACGCGGGGCTAGAGTGTGCTGGTCAGAAGGGCTGAGGGCCTGA GGTCCGGAAGGTAGGCCCCACCGTGGAGCGCCTACGGGGCCAGGGGGCCAGGGAAGGTGCTG GGAGCGGCCCTGGTCCAGAAGGGCGCGGAGCCATGCGGGGCTGAGGCCGCAGGAGAGG GGGCCCGGCAGGCTCTGCAGAGGCCTCCCCAGCCCTGCCCCAGAGCTCGCGCC TTGGGGCCCAGGGGCCCAGAGCCCTGCCCGGCTCAGCCGGAGCCCTGACGCA GCAGCCTCCAGGAGCTCCAGCCGGACCCTGCAGCCGCTGCAGGAGCGAGAGTGCGCCGGGGAGGC TCTGGGCGCCGTCTGGCCTGA | 6880 |
| | 1 | MCLLLAGSTFVCLPLR* | | ATGTGCCTCTTCTGGCTGGCTGGAAGCACGTTTGTTTGCTTACCGCTCAGGTGA | 6881 |
| | 2 | MRKASLUS* | | ATGAGAAAAGCAAGTCTATCACATCTTGA | 6883 |
| hsa-mir-551b | 3 | MGANYMFPHTQSLCLWLNLERTTPVVVWKLPSISS* | | ATGGGGGCGAATTACATGTTTCCACACACAGTCTCTTGTCTCTGCTAAATCTA GAAAGAACAACTCCAGTGTGTTTGAAAATTACCTAGCATCAGCAGCTAA | 6886 |
| | 4 | MHQYIPPLTPTSTSVHCV* | | ATGATTCAGTACATCCACACTAACTCCCACATCGAACTCAGTTCACTGTGTTGA | 6888 |
| | 1 | MGSKGSLGQVIGDHPLPE* | | ATGGGCAGCAAGGGCAGCCTTGGACAGGTGATAGGTGACCATCCCCTTCCAGAGTGA | 6890 |
| | 2 | MRARGLVCAPSLRSLGRELPPSGRDPE* | | ATGAGAGCCAGAGGCCTGGTATGTGCACCCTCATTGCGAGGCCTGGTCGGGAACT CCCTCTTCCGGTCGGACCCCGGAGTGA | 6892 |
| hsa-mir-552 | 3 | MCTLIAEPGSGTPSFGSGPGVKNRLCCELLRTAPPGGAR TRRALVENVGH* | | ATGTGCACCCTCATTGCCGAGCCTGGTCGGGATCTCCTCTTCGGGTCGGACCCC GGAGTGAAGAACCGGCTGCGCTTTGGTGAGCTGTTGAGAACGGCCACCAGGGGCGC TCGAACGCCGCGCTTTGATTGGGGATTTGA | 6894 |
| | 4 | MWGFDLVGTGAPGASCHGHRGGF* | | ATGTGGGGATTTGACCTTGTCGGAACAGGAGCACCTGGGCTTCAGGTCACCGGGAT CCGGTGGCGGATTCTGA | 6896 |

Figure 1 (Continued)

| | | | | | |
|---|---|---|---|---|---|
| hsa-mir-553 | 1 | MRTDCGTGRTRGFVSADSSVPRGAASSAFSSGSCAPGM NQGF* | 6897 | ATGCGCACTGACTGCGGAACTGGGCGAACCCGGGGGTTCGTTCTGCTGACTCCAGT GTCCCGAGAGGCGCCGCTTCTTCCGCTTCTGTCAGGCTCCTCAGGTCCTCAGGCATG AACCAAGGTTTCTGA | 6898 |
| | 2 | MAGPRVEVDGSIMEGVSTERSGRGCSLTKEGSSHHRCA YPSSPCTPTFAGRPDPESLYGLELSPRPPLAGAEDPSRPE HARPEVNLAGGGVGP* | 6899 | ATGGCTGGGGCCGCGAGGGTCGAGGTCGATGGCAGCATCATGGAAGGGGTGAGTACAG AGCGAAGCGGCCGCGGCTGCAGCCTACCCAACCTTTGCAGGGCGCGCACCACCGGTGT GCTTACTTCTCTTCCTCCGTACCCCAACCTTTGCAGGGCGCGCAGATCCTGAGAGT CTCTACGGCCCTTGAGCTGTCCTGTCCTAGGGCCTCCTGCCGGTGCAGAAGATCCGAGC CGGCCGGGAGCACGCCAGGGCTGAGGTAAATCTGGCTGAGGGGGAGTTGGGCCGTG A | 6900 |
| | 3 | MAASWKG* | 6901 | ATGGCAGCATCATGGAAGGGTGA | 6902 |
| | 4 | MGDPGRGTLPGRWPGL* | 6903 | ATGGGCGATCCAGGCGGGCACTCTGCCTGGCGCTGGTGTAA | 6904 |
| hsa-mir-554 | 1 | MGLYKGAVPRAPAQLEPDSGVDKWRVCCDPEGR* | 6905 | ATGGGCCTATACAAGGGGGCGGTTCCGGCGCCCAGTTGGAGCCAGACAG CGGGGTGGACAAGTGGCGTGTGTGCTGCGACCCGGAGGGAAGATGA | 6906 |
| | 2 | MNGTRNWCTLVDVHPEDQAAVRKSALAVFSVLYSRFL SPPLPCPAPCWLTSPGARLARSALRGASLFFCLRRAV GVAG* | 6907 | ATGAACGGGACGGCAAACTGGTACCCTGGTGACGTGCACCCAGAGGACCAGCC GGGGTAAGAAAAGCGTCGCTGCTTCTCCGTTGTATTCCGGTTTCTAAG TCCGCCCCTTCCGTGCCCGCCCGCCGTGTGCTGACATCACCTGGTCGCGCTCGC GCGGTCAGCCCTGCGCGCCAGCTTCTCTCTTTATTCTTTGACGTTGTGTCCTCGCGAGGAG GGAGTCGCGGGTGA | 6908 |
| | 3 | MSSSDWVPERLWTLCPAEEA* | 6909 | ATGAGCTCAAGCGACTGGGTCCTGAGCGCCTTGAGGAGGCTTAG GCTAG | 6910 |
| | 4 | MVLWMHSMKKNGRVNYRAWTGGRGASRGR* | 6911 | ATGGTGCTTTGGATGATCAGTAACAAGAAAAATGGTAGAGTAAATTACAGGGCTTG GACTCGAGGGGCGGCGAGGCAAGTAGGGGACGGTAG | 6912 |
| hsa-mir-555 | 1 | MGEGRAGRGILSLPGSPSRRGEGVSLTGRLPEGAGK* | 6913 | ATGGGGGAGGGAGGGAGAGCGAGGGTGCTCCTGACAGGCAGACTCCGGAGGGCTCGGGAAGTA | 6914 |
| | 2 | MIGASPIYQFYCV* | 6915 | ATGATCGGAGCTCCCCATAGTCCAGTTGTGTGTGTTAA | 6916 |
| | 3 | MWERQDDLSVVSLINVTG* | 6917 | ATGTGGGAACGACAGGATGATCTCAGTGTTGAAGTTAATAAATGTCACTGGTTAA | 6918 |
| | 4 | MISVL* | 6919 | ATGATCTCAGTGTTGTAA | 6920 |
| hsa-mir-556 | 1 | MPSKTKYNLVIDGHDLRIPLHNEDAFQHGICFEAKVRG LRGGCYLWWRLGGHV* | 6921 | ATGCCAAGCAAAACCAAGTACAACCTGGTCGACGATCCGGATCCC CTTGCACAACGGCAGCGTCCCTGTTGGAGGCCAAGGTGAGGG GGCTCCGGAGGGCTACCTGTGGTGCGGGTGCCATGTTGA | 6922 |
| | 2 | MGITCGSPCTTIRTPSSTASALRPR* | 6923 | ATGGGGACGACGACCTGCGATCCGGACGACCTCGAGACGCCTCAGCACGGCATCT GCTTGAGGCAAGGTGA | 6924 |
| | 3 | MFERMGCTAYLDPELAG* | 6925 | ATGTTTGAGCGGATGGGATGCACAGCGTCCTGGACCCAGAGCTGCGGGCTAG | 6926 |
| | 4 | MHSRPGPRAGGLGRFGGLSLREGNSPF* | 6927 | ATGCACAGCCGTCCTGGACCGAGCTGGCGGGCTAGCCGATTTGGGGGCCTTTCT CTTAGGGAGGTAACTCTCCCTTCTGA | 6928 |
| hsa-mir-557 | 1 | MLIFPYDSSPFFSVL* | 6929 | ATGCTTATATTCCCTTATGACTCTTCCCCTTTTCTGTCCTATAG | 6930 |
| | 2 | MTLPLFLFLSYRISLFSSLLIVSFAVQKRFSLTRYHLSIFFC SCNCPWGLSQKFFAKADVEKSTS* | 6931 | ATGACTCTTCCCTTTTCCTTTTCGTCCTATAGGATTAGCTTATTTCTAGTCTGTT GATAGTTCTTCTGCGTGCAGAAGCGCTTAGTTAACTAGTACCATTTGTCAATT TTCTTTTTGTTCTTGCAATTGCCCTTGGGACTTAGCCCAAAAATTCTTTGCCAAGGCTG ATGTTGAGAAGAGCACTTCCTAG | 6932 |
| | 3 | MLRRALPRFSSRFIV* | 6933 | ATGTTGAGAAGAGCACTTCCTAGGTTTTCTTCTAGAATTTTATAGTTTGA | 6934 |
| | 4 | MSYI* | 6935 | ATGTCTTACATTTAA | 6936 |

Figure 1 (Continued)

| | | | | |
|---|---|---|---|---|
| hsa-mir-558 | 1 | MGRAGVVKGTLGRSLGSFQSKREASDCLFSHQSRDRD PEVRFRPRPNSCTVRTENGQKAAGTAAKGLRAYRTGK KGGGPHLAEMHGGQPLPPRGAGRTREPPLPRLTGRN WDAADAELARPAARGTIREPSRACSTRRPARAPGPASL PASPPLPSASLRVWFLRPGDRRSACVRAPDFTSG* | 6937 | ATGGGAGGGCAGGCGTGGTAAAAGGTACAGGTTTGGGAAGGTCGCTCGGTTCCTT CCAATCCAAACGAGAGGCTTCTGCGCACGAGCTTATTCTCAACCAGAGCGTGACCGAGA CCCAGAGGTCGCTTCGCCGCCGAACCGCTGGAACCGCGCTACGGGAACG GTCAAGGCGCAGCTGGGGTCCCCACCTAGCGAAATGCACGAGAGCGCAACCTCTCCCTGCC AAGGGCCGGGGTCCCCACCTAGCGGAAATGCACGAGAGCCAACCTCTCCCTGCC CCCGCGAGGAGGCGGGGCGGACTGCAGCTGGCGGAACTGGCCAGAGACCCCGGCGCTCCCAGGTCACAGGAAGAA ACTTGGGAGCGGAGCCGACCGGAACTGGCCAGACCCCGCGCTGCACCGCGCGAG PASPCCTGCTTCGCCACCGGCGTGGAATGTCCAGCCGCCTCCCGAGTTGCCCTCCGGGT GCGATCGACGTTCCCGCGTCGGGCGCCCTGACTTCACTTCCGGCTAA | 6938 |
| | 2 | MLHPPASSPRPGPRLPPCFSPSPVYSLPPSLAPPAGRSTERV RAGA* | 6939 | ATGCTCCACCCGCCGCTCTCCCGTCAGCTCCTCCCTGCAGCTTCCTCCGTTC TCCCCTCTCCCGTCAGCTCCGTTCCCTCCGGCCCCGCCCGCTCCTCCTGTTC TTCCCGTGCGTGCGGGCGCCTGA | 6940 |
| | 3 | MVTGGGAAPPGTVTEPLPSVIVLSAGRKMAAAAAAAAS GPGCSSAAGAGAAGVSEWLVLRDGCMHCDADGLHSLS YHPALNAILAVTSRGTIKVIDGTSGATLQASALSGESSA RRAGAKPGKEAVQPRGSASRLGEARWREGRAGGSGPA VKGGPEADGGGP* | 6941 | ATGGTACTGGTCGTGGTGCTGCAGGCCGGAACGTCTCACTGAGCGCTTCCCAGT GTGATTGTGCTGAGCGCAGCCGGAAGATGGCGGCTGCGCGGCGGCTCAGAGTGGCTGG CCCCGGCTGCTCCTCCTGCACGCGCGGAGGCGCCCGCCCCGGCTCCAGAGTGCTCGG TGCTGCGGGACGGCTGCATGCACTGCGACGCCGACGGGCTGCACAGCCTGTCTAC CACCCTGCCTCAACGCCATCCTGCCGTCAGCCTGCGCTGAGCACATCAAAGTCATC GACGGCACCTCGGGGCCACACTGCAGGCCTCCGCTCAGCCAGTGGTGAGTCTTCGC AGCGCCGGCGGCGAAGCGTGGGAAGAAGCCGTCAGCCCGGGCTTGGCCT CGCGACTCGGGGAAGCCCGGAAGCCAGGGGGCGAGATGGCGAGGGGACCCTAG | 6942 |
| | 4 | MARCGQGWGPGPSREGRPGS* | 6943 | ATGGCGAGAGGGCAGGGCTGGGGTCCGGTTCGAAGGGAGGCCGGAA GCTGA | 6944 |
| hsa-mir-559 | 1 | MSHRPGVGVSRLPSPSPGAAVGARPSPQVWARAPRSA PPQVLRLHCKGVRDLWWPPRRFEDSVLRLFPNRRSAALK P* | 6945 | ATGAGTCACCGCCCGGAGTTGGGCGAGTAGGCTCCCCCCTCCCAGCCCGG CGCTGCAGTTGCGGCCGAAGGCCCTCTCCACAGGTGTGGGCCCGCGGCTCCGC CCCGCCCCCAGCTGCTTCGTTCGTCCATGGCGGTTAGGAGATCTTTGGTGGCCCGAG GAGGTTGAAGATTCTGTGTGAGACTTCCTTTAACCGAGGAGCGCTGCTCTGAA GCCTTGA | 6946 |
| | 2 | MAALGIFGGLRGGLKLC* | 6947 | ATGGCGGCGTTAGGGATCTTTGGTGGCCTCGAGGAGGTTTGAAGATTCTGTGCTGA | 6948 |
| | 3 | MGPGGKGAGTG* | 6949 | ATGGGCCGCTGGGGAAGGGTGGGAACTGTATAG | 6950 |
| | 4 | MSVSL* | 6951 | ATGAGTGTTTCTTTATAA | 6952 |
| hsa-mir-561 | 1 | MGFSLIPPSTHLRFRVHARDSPVGPQJTTJRD* | 6953 | ATGGGTTTCTCTCTCATTCCACCTCCACCTCCGGTTCGCGTGCACGCGCGA GATAGTCCAGTGGAGCCCACAGATAAACGACCATCAGAGATTAA | 6954 |
| | 2 | MSKETARSAQAGVG* | 6955 | ATGTCAAGGAGATCGCAAGAGTCGCAAGCCGGAGTCGGCTAG | 6956 |
| | 3 | MLRESSSTKGG* | 6957 | ATGCTCAGGGAGTCGTTCAGCACTAAAGGAGGCTAA | 6958 |
| | 4 | MAALEK* | 6959 | ATGGCAGCGCTTGAGAAATGA | 6960 |
| hsa-mir-562 | 1 | MSPAPHSPLLTDPASQAALIAPGPL* | 6961 | ATGTCCCAGCTCCCACTCTTGCCTCTGACCGACCCGCCTCCCAGGCCGCTT ATAGCGCCGGGCCCTTGTAG | 6962 |
| | 2 | MFRTGRDGEPRES* | 6963 | ATGTTCAGGACTGGCAGGGATGGGGAGCCTCGGGAATCTTGA | 6964 |
| | 3 | MGSLGNLEGQPLNYNMSLTFALSTVIHFISFIDHREFFEFL INF* | 6965 | ATGGGGAGCCTCGGGAATCTTGAAGGGCAGCCGCTTAATTATAACATGTCCTTGACG TTTGCGCTTTTCCACAGTGATACACTTTATCTCCTTTATTGATCATGAGAGTTTTTT TTTTAATAAACTTTTAG | 6966 |
| | 4 | MGHJTHAG* | 6967 | ATGGGCGATACCCATGCAGGTTAG | 6968 |

Figure 1 (Continued)

| | | | | |
|---|---|---|---|---|
| hsa-mir-563 | 1 | MGEFDLHVERA* | 6969 | ATGGGCGAGCCGACTTGCACGTGAGAAAGCGTGA | 6970 |
| | 2 | MCPWVWGGWGAKEWDERWSRNGGRCCPPRGLQAET G* | 6971 | ATGTGCCCCTGGGTTTGGGAGGATGGGGAGCCAAGGAGTGGGATGGAGAGGTGTC ACGGAATGGGGGCGCTGCTGTCTCCCGGGAGCCTGAGACCGGAGACCGGGGTGA | 6972 |
| | 3 | MRKGRGMGGAAVLPGGCRPRPGEGRG* | 6973 | ATGAGAGGTGGTCAGGAATGGGGGGCGCTGTCTGTCCTCCCGGGGGCTGCAGGCC GAGACCGGGTGAGGGCGCGGCGGTGA | 6974 |
| | 4 | MLALWTEGRRLRSRTGCGRPIVFLPVVPIRS* | 6975 | ATGCTGGCACTCGGAACGGAAGGGCGTCGTTCTGCAGCCGACAGGTTGTGGACG CCCAATCGTTTTCTGCCCGTAGTCCAATCCGAAGCTAA | 6976 |
| hsa-mir-564 | 1 | MAERPGPPGGAVSATAYPDTPAEFPPHLQAGAMRRRF WGVPNCLCAGAFGALAAASAKLAPGSEVEPGALLVLLL RAGGRGAAGRRGAAGPAGLLGWGGGGRRAPPHPRRS VPPGPRAAGGAAVSWGGRECFASNHAKPSSSVGGKRR RGLRPLPLPGT* | 6977 | ATGGCCGAGAGGCCGGGAGCTCCGGGCGGCGCCGTGTCCGCGACCGCGTACCCTGA CACCCCCGCGGAATTCCCTCCGCAACCTCAGGCCGGTGCAATGCGCCGCCGCTTTG GGGCGTATTCAACTGCTGCTGCGGCGGCGTTCTCGCGGCCCTGCCGCCGCTCCGC CAAGCTGGCCTTCGGCAGCGAGGTCGAGCCGGGCGCTGTTGGTGCTGCTCCTGC GGGCCGGGCGTGGGGCGCGCTGGGCGCCGTGGGGCGAGGACGGCGCCCCCACGGGG GCTCTTGGGGTGGGCGGGGCGGGCAGGGCGGCCAGGGCGCCCACCCTGCCGGTCTG CCCGGCGGGAGCTCCTAATGACGCCAAACCCTGTCAGGTAGGTGGTCAGAGAG TGTTTCGCCTCTAATCACGCCAAACCCTGTCAGGTAGGTGGTCAGAGAG GGACTGAGGCGCTCTTCCCTTACCAGGGACCTAA | 6978 |
| | 2 | MTSLPHYQENWEFGH* | 6979 | ATGACCAGTCTGCCCACTACCAAGAGAAATTGGAGTTTGGATACTGTAG | 6980 |
| | 3 | MLQVSPLGVVHGVSGRK* | 6981 | ATGCTTCAGGTAGTATCCATTGGGGTGGTCATGGGGTAAGTTCATGGGTCGAAAGTAA | 6982 |
| | 4 | MNNFVWAVKFVVRN* | 6983 | ATGAATAACTTTGTATGGGCGGTGAAGTTTGTTGTCAGGAACTAG | 6984 |
| hsa-mir-566 | 1 | MARAGARALGC* | 6985 | ATGGCCCGAGCTGGGCGGGGGCTCTAG | 6986 |
| | 2 | MAPGGR* | 6987 | ATGGCCCCTGGGGGCGCTAG | 6988 |
| | 3 | MDVWMMWPAGSPMCKATESCKYLGGCSRTPPPSRFW SGSSDPPSASALSPINARGSALPRRCACPTSVSLLEDWPA RREAVYWQSPRGGSPTSAEWEDLQS* | 6989 | ATGGATGTGTGGATGATGTGGCCTGCGGGTCACCCATGTGCAAAGCAACTTTTCC TGCAAGGTTCTGGGTGCGGTCTCTGCCTCAGCTCTTCCATACACCCCCACCTTCACGCTTCGAACGGGG AGTTCCGATCCCTCCTTCGCCTTGCCCTGCCATTAACGCCAGCGCAGCGCTC TTCCCGTAGATGCGCTTGCCTATCCTACTGCAGTGTCTCTACTTGAGGACTGCCAGCC GAAGGAAGCGGTATACTGGCAGTCCCACGTGGGGGGTCTCCACATCAGCAGAG TGGGAGGAGCCTGCCTACTCAGTCTCTACTCGA | 6990 |
| | 4 | MRLPYLSVST* | 6991 | ATGCGCTTGCCTACCTCAGTGTCTCTACTGA | 6992 |
| hsa-mir-567 | 1 | MDLAQPSQPYDELELSVLERQPEENTPLNGADKVFPSL DEEVPPAEVRSPWRWP* | 6993 | ATGGACCTGGCCCAACCTCACAGCAGTAGACGAGCTGGAGCTCGGTGCTCGA GCGGCAGCCAGAAGAGAACACGCCTCTCAATGTGCCGACAAGGTCTTCCCTTCTTT GGACGAGGAGGTCCCCCGGCCGAGGTAAGGTCCCTGGCGCTGGCCTAA | 6994 |
| | 2 | MVPTRSSLLWTRRSPRPR* | 6995 | ATGGTGCCGACAAGGTCTCTCCCCTTCTTTGGACGAGGAGGTCCCCGGCCGAGGTAA | 6996 |
| | 3 | MEPSHRDTFRPEQSPPQPLGSSNPSDPRGALGILVVRCG RCCLQRGIPEMEVVP* | 6997 | ATGGAGCCAGTCACGCGACACCCTTCGGCCGACACTTCGGCCGACAGTCCTCCCCCAGCCCTG GGGTCCTCCAACCCTCTGACCCCGAGGCGCTTAGGAATCCTAGTGTGAGGTGT GGCCGCGTCTGTCTTCAGAGAGGTATTCCGGAGATCGAAGTAGTTTTTAA | 6998 |
| | 4 | MRMTN* | 6999 | ATGAGAATGACAAATTGA | 7000 |
| hsa-mir-568 | 1 | MLQKALPSLYVCNMCKRV* | 7001 | ATGTTGCAGAAAGCATTGCCATCACTGTATGTGTGCAATATGTGCAAAAGAGTGTGA | 7002 |
| | 2 | MCAICAKECEIJYTSNAADLVNFHAPNMLNTYHHNMF* | 7003 | ATGTGTGCAATATGTGCAAAAGAGTGTGAAATATATATCATCAAATGCCGCGATCTG GTTAATTTCCATGCATTTAACATGCTTAATACCATCATCAATATGTTTAA | 7004 |
| | 3 | MPPIWLISMHLTCLIPTISSICFNAYFPHTIWSS* | 7005 | ATGCCGCCGATCTGGTTAATTTCCATGCATTTAACATGCTTAATACCATCATCAT CAATATGTTTAATGCATATTTCTTTCCACAATACAATATGGTCTAGTTAG | 7006 |

Figure 1 (Continued)

| | | | | |
|---|---|---|---|---|
| | 4 | MHRSFHQYGLVRKEPTSSTALLTAMFQPKTSCWGQHNES* | 7007 | ATGCATATATTCTTCCACATACAATATGGTCAGTTAGGAAAGAGCCAACATCTCCACAGCCTTACTCACTGCTATGTTCAGCTAAAACTTCTGGCCAGCACAATGAGAGTTAA | 7008 |
| hsa-mir-569 | 1 | MCLIITANASAIHAQAKKHVPFKYTHAAPAPLADRGAQPTRTAARGLEIRAGWAPGPGGPTRGGSGSGAVGLGWAGEAGPGASGATPA* | 7009 | ATGTGTCTCATTATAACAGCCAATCAGCCGCCATCCACGCACAAGCAAAGAAGCATCCCACCACCGCCGTCTCCAGCAGCCCTTAGCGATCGGGCTCGGGCTCGCTCAGGCTGGACCGACCGCGGAGGATCCGGAGGCTGGGGCTGGGGGTGGGCGGGGGAGTCTGGGCCTGGGGCCCTCTGGCGCGACACCCGCATGA | 7010 |
| | 2 | MQPPSTHKQRSMSHLNTPTQPQRP* | 7011 | ATGCAGCCGCCATCACGCACAAGCAAAGAAGCATGTCCATTTAAATACACCACGCAGCCCCAGCGCCCTTAG | 7012 |
| | 3 | MRTRYK* | 7013 | ATGAGGACGCGAGTGAAATAG | 7014 |
| | 4 | MASDSPARSLDEIDLSALRVSRTFSGFFPVYWVRVNGLGAWTGGWGWGRGTAAGHECVGEGTWIPVLIRGC* | 7015 | ATGGCGAGCGACTCCCCGCTCGATGAAATAGATCTCTCGGCTCTGAGGGTGAGCAGGACGTTTCGTGTTTCTTCAGTCGTTTGGGTTAGGGTGAATGGCTGGTTGCGTGACTGGGCGCTTGGGCGCAGGGGAGCAGCAGCGGGAGAATGCGTCGGGGAGGGAACCTGGATTCCGTTTGATTCGGGGTTGCTGA | 7016 |
| hsa-mir-570 | 1 | MTQWSTGHLTGPPAVRPVRHPLSIPLCC* | 7017 | ATGACACAGTGGAGCACTGGCATCTCACAGGTCCTCCTGCTTGTCAGGCCCGTTGCATCCCCTCTCCATTCCCCTTCTGCTAG | 7018 |
| | 2 | MNDSALYSCLGPTSPFLIRSWHSL* | 7019 | ATGAATGACTCTGCTTAGTCAGCTGCCTGGCCTTTACCAGCCCCTTCCTCATCAGATCCTGGCATTCTCTGTAG | 7020 |
| | 3 | MILL* | 7021 | ATGACTCTGCTTAG | 7022 |
| | 4 | MSWFTKLLSVIWPLATCSTSPLQGPGP* | 7023 | ATGTCATGGTTTACAAAGCTGTCAGTGATCTGGCCTTGGCCACCTGTCTACTCTCCTCTGCAGGTCCCGGACCCTAG | 7024 |
| hsa-mir-571 | 1 | MWRGSLRLATTRPRVRGFISLRSQLWEALVIRPQLSLRRSVTCGYWMHGS* | 7025 | ATGTGGCGCGGGTCTTTGCGTCTGGCTACTACCAGACCGCGGTTAGGGGCTTCATCTCTGCGGTCCAGTTGTGGGAGGCCTTGGTGATTCGGCCACAAGCTCAGCCTCCGTCGCTCTGTGACCTGCGGGATTGGATGATTGGTAGCTAA | 7026 |
| | 2 | MVSVRGRASQG* | 7027 | ATGGTGAGTGTGCGGGGACGAGCGTCCCAAGGCTGA | 7028 |
| | 3 | MAAGPSLRTESPLPLPLSPGASVPSGEGPGLLSVPAQRLWPSLQPSLCCSSAPAAPHLPQAVG* | 7029 | ATGGCCGCGGGACCGAGTCTGCGAACGGAGTCCCCGCTCCCGCTTCCGCTCAGCCTGGGGCCTCAGTACCCTCCGGTGAGGGACCTGGGCCTCTCGGTCCCGTCGGCACAGCGGCTCTGGCCCAGCCTCTGCTGCCGCTCCAGCCCGCCACCTTCCCCAGGCTGTCGGGTGA | 7030 |
| | 4 | MPAWEELWEKLWSGDPVPALPCSE* | 7031 | ATGCCGGCGTGGGAAGAAGCTGTGGAAGCTGTGGTCTGGGAGATCCGGTCCCTGCTTTACCCTGTTCGAATGA | 7032 |
| hsa-mir-572 | 1 | MAWEREBJAL* | 7033 | ATGGCTTGGGAAAGGAGGAGAAATAGCCCTTTAA | 7034 |
| | 2 | MQSLNDIQLEDVINTSYGRETRLGKFPACRENH* | 7035 | ATGCAAATCTTTGAATGACATACAATTGGAAGATGTCATAAATACCAGTTACGGCAGAGAGACCAGGCTGGGTAAATTCCCAGCATGCAGAGAAATCACTGA | 7036 |
| | 3 | MTYNWKMS* | 7037 | ATGACATACAATTGGAAGATGTCATAA | 7038 |
| | 4 | MQRKSLSSLLLSPFGTH* | 7039 | ATGCAGAGAAAATCACTGAGCAGCTACTCCTACTCAGCCCTTTGAACTCACTAA | 7040 |
| hsa-mir-573 | 1 | MVSVLGKKRAK* | 7041 | ATGGTGTCGGTCGTGGCGAAGAAAAGGCAAAATAG | 7042 |
| | 2 | MTSLNIFSLQFPHCN* | 7043 | ATGACAACATTTCTCAACATTTTCTACTTCAGTTTCCTCACTGA | 7044 |
| | 3 | MNRIS* | 7045 | ATGAATAGGATTTCCTAA | 7046 |
| | 4 | MESEGLQYLPNSRSEEGKATGRGRRPKKGRTNEAAGGTGVPAFGRRARAPRSHAHSHARTLRKRARAQAPSSPPPE* | 7047 | ATGGAAAGTGAAGGTTCCTCAGGTTCTTCCTAACAGCCGCTCCGAGGAGGGAAAGCTTACAGGAAGAGAGGAGGAGGAGACCCAAGAAAGGTCGGACAATAGGCAGCGGCGGACAGGAGTTCCCGCCGTTTGGGCGTCGTGCGCGCGAATGCCTCCGCTCACACGCACACTCGCACCGCCAGCCCCAGGCCCTGTCGGCCGCCGCCATTTTAG | 7048 |

| | | | | |
|---|---|---|---|---|
| | 3 | MLYKCNCNPDPYRPQELSLPLRLLKLLEFACSV* | 7069 | ATGCTATATAAGTGTAACTGTAACCTGACCCAGTTGGCCTCAAGAACTGTCATTG CCGCTGCGGCTGCTGCTCAAGCTTTTGGAGTTGCTTGTAGTGTTGA | 7070 |
| | 4 | MKKRARVGPALRQGLHTGSSQMQHESRFHIKVVGF* | 7071 | ATGAAAAAACGTGCCAGAGTTGGCCCTGCTTGAGGCAGGCCTTCATACAGGCAG CAGCCAAATGCAGCACGAAAGCCGTTTCATATTAAGGTCGTGGGCTTTTAG | 7072 |
| hsa-mir-577 | 1 | MPQPGELEALAVRGE* | 7073 | ATGCCCCAGCCCGGGGAGCTGGAGGCGCTCGCAGTTCAGAGGCGAGTGA | 7074 |
| | 2 | MAAVQGRGGN* | 7075 | ATGGCTGCTGTCCAGGGGCGCGGGGGGTGGGAATTAG | 7076 |
| | 3 | MASVRGFSRVCALKAEGGTYNGEAIRPRTLYLTPEGMGT AEPRGQSQLPGQGWRWGTRRSFGTSSTPLYSVFPLRRN KSGMCWGWGMSWGCTSSLRLFGARRFVPARLSTMDS VQRWWQGFTGPRADLGMVRGALALEKPVRAPGIREEVS ACGRGEKDALLAKRRAPSMDWRSKGEGAWYVCFGFEG GKPHRRVQVDAVRRGKRIT* | 7077 | ATGGCATCCGTTCGAGGGTTCTCTCGCGTTGTGCGCTCAAGGCAGAGGGAGGGTAT AACGGGGAGGCGATTCGGCCGAGGACTCTGTACTTGACCCTGAAGGGATGGGCAC CGGGAGGAGTTCGGGACCTTCAACTCCGTTACTCGCCCTTCCCCTAAGGAGG AGGAGAGCTTCGGGGACCAGCAGCTCCAACGCCCGTCTTCCCCTAAGGAGG AACAAGAGCGGGATGTGTTGGGGTGCGGGAATGTCTTGGGCGTACAAGCTCGCT GAGACTTTTCGGAGGCCGCGTTTCGGGTGCCCGCGACTCTGACAATGGACAG TGTACAGTGGTGGCAGGGTTTCACGGGGCCGATTTGGGAATGGTACGGG GTGCCCTTGCATTAGAGAGAGAAGTCAGTGCCGGTGCTGGCAAAAGAAGGGCGCTTCAT GGACTGCGGGCGAGGGAGCCGCGTGGATGGCAAAGAAGGGCGCTTCAT AACCGCATCGGAGAGTGCAAGTAGATGCAGTGCGTCGGGCAAAGGACAATCTGA | 7078 |
| | 4 | MEVGDQEELRDLFNSPLLRLPPKEEQERDVLGVGNVLG LYKLAETFRGPFPRARATLDNGQCTVVAGFHGSPRRF GNGTGCPCIREACAGPRD* | 7079 | ATGGAGGTGGGGGACCAAGAGGAGCTTCGGGACCTTTTCAACTCCCCTTTACTCGT CTTCCCCCTAAGGAGGAAGAACAAGAGCGGGATGTGTTGGGGGTGGGGAATGTCTTGGG CTGTACAAGCTCGCTGAGACTTTTCGGGCCATTTCCGCGTTCCGCCGCGAC TCTGACAATGGACAGTGTACAGTGGTGGCAGGGTTTCACGGTCATCCGGGATT TGGGAATGGTACGGGGTGCCCTTGCATTAGAGAAGCCTGTGCGGGCCCGGGATT AG | 7080 |
| | 1 | MAGRGGSALLALCGALAACGWLLGAEAQEPGAPAAG MRRRRRLQQEDGISFEYHRYPELREALVSVWLQCTAIS RIYTVGRSFEGRELLVIELSDNPGVHEPGKGAAP* | 7081 | ATGGCCGGGCGGGGCGAGCGGCAGGCGCTCGGCCTCGTGCGGGCACTGGCTGCCTG CGGGGTGGCTCCTGGGCGGCCGCTGCAGAGCCGCAAGAGGACGGCCATCCTTCGAGTACCACCGCTAC CCCGAGCTGCGCGAGGCGCTCGTGTCCGTGTGGCTGCAGTGCACCGCATCAGCAG GATTTACACGGTGGGGCGCAGTCTGGGAGCGCCTGGTCATCGAGCTGT CCGACAACCCTGGCGTCCATGAGCCTGGTAAGGCGCTGCCCCTGA | 7082 |
| | 2 | MSLVRALPPDSPGHPEGGGRGWDWRWGKEGGMGP GVPLGKRYLRWKVGSGGRIDNGNGEEPDLERQWPNFCFP VPSPQHQSHLPRP* | 7083 | ATGAGCCTGGTAAGGCGTGGGACTGGTGGCGGTGGGGAGGCAGGGGCATCCGGAGGGGG CGGCAGGAGCTGGGACTGGTGGCGGTGGGGAAGGAGGGGAGGGGATGGGGCCAGGG GTGCCCCTTGGTCAAAAGGTATCTAAGGTGGGAAGGTGGAAGGTGGAAGGGGATGG AAATGGGAAGAAAACCGACTTAGAGCGCCAGTGGCCCAATTTCTGCTTTCCGTCCC ATCCCCCAGCACCAATCCATCTCCCCAGACCTTAG | 7084 |
| hsa-mir-578 | 3 | MEMGKNPT* | 7085 | ATGGAAAATGGGGAAGAAACCCGACTTAG | 7086 |
| | 4 | MGGIAIQKKQHLTHATPAVALTILCIEKPKGMIASPPQGG LVFLADKSRKIRCRRQ* | 7087 | ATGGGGGGGATAGCAATACAGAAAAAACAATCTGACGCACGCAACCCAGCGGT CGCTCTCACTTTGCTGTGTGAAAAAACCAAAGGAATGATTGCCAGTCCCCGAAGG GGGGTTGGTCTTCTTCGTGCTGCTTGACAAGAGTAGAAAGATAAGGTCAGAAGGCAGTGA | 7088 |
| | 1 | MPSTGAPAQCCGRRRRSVLR* | 7089 | ATGCCGAGCACAGGCGCGCCTGGCACGGCGGTCGGCAGTGCGGAGGCGGTCTGTTCTCCG CTGA | 7090 |

Figure 1 (Continued)

| | | | | |
|---|---|---|---|---|
| hsa-mir-579 | 2 | MIPCPYVSFTYGFSNVAREASARPPWPRLAGSRGGW GRLRGGGGRHPGVRVSEGVRGGRGRRRGHLGPARRA ALTAPLSFSPCPPSASRLLCVSCPAMGPDSSCPPQCPAG WGKMPKWRPATTLDSPTAGRRRRRLRPWKGNGILPSLC SPLALIPSVRHLSMRRPRARPQPSQSPGPLQAWPGPARRP LPPRPAPPRLARPGPARGGERPPVGGR* | 7091 | ATGATTCCCATATGCCCTGAGTTCTTCACCTATGGTAGTCTAATGTGCCGCGG AGGCCTCTGCCCGGCCCCCTGGCCCCGGAGGGCAGCCGCCGGGGGGTTGG GGCAGGCTCCGGGAGGAGGGGCGGACGCCACCGGGGGTGCGAGTGAGGG GAGTGCGAGGGGGGAGGCGGGACGGCGGCGGCGGCCTGGGCCCCGCAGGGC GCTCTCACGGCGCCGCCTCTCTCCTGCCCTCTGCCCGCCGCGTCCGACTCCTC TGTGTCTCTTGTCCCGCCATGGAGACCGACTCTTGTCCCGCCGACTATTCACCACAGCC GGCTGGGGAAGATGCCAAATGCGACCGGCAACTACTTTGATTCACCAGCC GGGGCGGCGGCGGCGGCTGCGGCCAATATAGGTAACGCATCCTGCCTTCTC TCTGTTCGCCCCTTGCTCTCCCTCGGTCCTGACGGATCCTGATGCGACGCCCGGGGC CGGTCCCCAGCCATCGCAGAGCCCGACCCCTGCAGGCCTGCCAGGCCGCAGCCG CGGGCCTCTGCCGCCCCCAGTGGGGGAGGTAG | 7092 |
| | 3 | MPCSFHL.W* | 7093 | ATGCCCTGTAGTTCTTCACCTATGGTGA | 7094 |
| | 4 | MVSLMWPARPLPGPLPGPGQRGAAGYGAGSGEEAAAA TRACE* | 7095 | ATGGTGAGTCTAATGTGGCCGCAGCCCTCTGCCGGCCCCCTGGCCCCGGG CAGCGGCACCGGCGGGGGGTTGGGGCAGGCTCCGGGAGGAGGCGGCGGCCGCGCCA CCCGGGCGTGCGAGTGA | 7096 |
| hsa-mir-580 | 1 | MSAAGL* | 7097 | ATGTCAGCGCTGGACTGTAG | 7098 |
| | 2 | MPLQP* | 7099 | ATGCCCTTGCAGCCTTGA | 7100 |
| | 3 | MGINERTVFGNELYPCTQGASSKAIWLLAVAQLATCVC VAA* | 7101 | ATGGGAATAAATGAAAGGACTGTATTTGCAACGAGCTTTACCGTGCACGCAGGG GGCCTCCAGCAAAGCCATTTGGTTGCTGCTCAGCTGGCTACGTGTGTTG CGTCGCGCCTAA | 7102 |
| | 4 | MKGLYFATSFTRARRGPPAKPPGCLLSLSWLRVFASPPK SELLSAYLC* | 7103 | ATGAAAGGACTGTATTTTGCAACGAGCTTTACCGTGCACGCAGGAGGGCCTCCAGCA AAGCCATTTGGTTGCTGCTCAGCTGGCTACGTGTTTGCGTCGCGCCT AAAAGCGAGCTGCTTTCAGCTATCTCTGCTGA | 7104 |
| | 1 | MSTLLSRCPPAWPIAAPLV* | 7105 | ATGAGCACGCTTCTTCCTTCCCTCGCCCGCCAATCGCCGCGCCCCTGTGT AA | 7106 |
| hsa-mir-581 | 2 | MSDLRITEAFLYMDYLVGAGQGWHVASRISACPMAPC LEEQPFCFLSLG* | 7107 | ATGTCTGATCTCCGAATAACTGAGACGTTTCTGTACATGGATATCTGGTAGGTGCA GGGCAGGGGTGCATGCGCCTCCGATCTCGGCGTCCGATGGCCCCTGCCTT GAGGAGCAGCTTTTTGCCTTTCTTCTTGGGATAG | 7108 |
| | 3 | MSPLGSRRARWPPALRSSLFAFFLWDRMPLGPFLPQPAG KPFPGLGGAASRAGGWWS* | 7109 | ATGTCGCCTCTCGTTCTTCTTTGGGATAGGATGCCTCTGGGGTTCTTCTCCCGCAGCCGGCTG GTAAGCCTTTCCCGGACTCGGAGGGGCAGCCTCCAGGGGGTGGTGGAGC TGA | 7110 |
| | 4 | MGRPRJRRVPCPRSASWLPSALSAEDFLSGGAGVFLSPW SRTPGAIKEP* | 7111 | ATGGGGCGGCCGCGGCGGCGGCGGCACTTTCTTCCGGGGAGCAGGAGTTTCTTCCCCTGG AGCAGAACTCCAGGTGCTATTAAAAGAGCCATAA | 7112 |
| | 1 | MAQGTSPDTLTVPEVEDNPHCPNPWLNEDLVKSLRENLL QHEKSKTARKSVSPKLSPVISPRNSPRLLRRMLLSSNPK QRRFTVAHTW* | 7113 | ATGGCTCAGCAGCAGCAAGCCCGGACACTTAACAGTACCTGAAGTGGATAATCGCAT TGTTCCAAACCCGGTCGTCAAACGAAAGCCTTGTGAAATCCTTGCGAGAAACCTGTTG CAGCATGAGAAGTCCAAGACAGCTCGAAGACCTTCTGGTTCTCCAAGCTCTCTCAGTG ATCTCCGAGAAATTCCCCAGCCTTCTCGCAGAATGCTTCTCAGCAACATC CCCAAACAGGCGTTTCACGGTGCACATACATGGTAA | 7114 |
| hsa-mir-582 | 2 | MRSPRQRGNRFLPSSLQ* | 7115 | ATGAGAAGTCCAAGACAGGAGGAAATGGTTTCTCCAAGCTCTCTCCAGTGA | 7116 |
| | 3 | MVRFAQTSQKWWPFFRESCSRAFNFGGREGGPSSFLT GDLWPSDLP* | 7117 | ATGGTAAGGTTTGCGCAGACCTCGCAGAAATGTGGCCGTTTCCCTTCAGGAGTCC TGCTCTCGCGCCTTTAATTTGGGGGTAGGGAGGAGGAGGACCATCATTCCTCACC GGGGATTTATGCCAAGTGATCTCCCTTAA | 7118 |
| | 4 | MVAVSLQGVLLSRL* | 7119 | ATGGTGCCGTTCCCTTCAGGAGTCCTGCTCTCGCGCCTTTAA | 7120 |

Figure 1 (Continued)

| | | | | | |
|---|---|---|---|---|---|
| hsa-mir-582 | 1 | MPLS* | 7121 | ATGTTCTGTCCTAA | 7122 |
| | 2 | MPWEGVIVSRKY* | 7123 | ATGCCCTGGAGGAGTGATTGTAAGTAGAAAATACTGA | 7124 |
| | 3 | MIRF* | 7125 | ATGATTCGTTTTTAA | 7126 |
| | 4 | MCRFKTMNLKASKNWQGYSSFVP* | 7127 | ATGTGTATCAAGTTCAAGACGATGAATCTTAAAGTTCTTAAGAACTGGCAGGGTTAT TCCAGCTTGTGCCATGA | 7128 |
| hsa-mir-583 | 1 | MSDVTSGRLG* | 7129 | ATGTCTGACGTCACGTCTGGTCGTCTTGGCTAG | 7130 |
| | 2 | MAVTK* | 7131 | ATGGCCGTGACCAAATAA | 7132 |
| | 3 | MPFVWWAWYNRELSFVFPTCPVVILWDHNWWG* | 7133 | ATGCCTTTCGTATGTGGGCATGTATAATAGAATTGAGTTCGAGGTCTTTCCT ACGCCATGCCTGTTGTGATTCTCTGGGATCACAACTGGTGGGGATGA | 7134 |
| | 4 | MVGMV* | 7135 | ATGGTGGCATGGTATAA | 7136 |
| hsa-mir-584 | 1 | MVHTWVAASASPGSGV* | 7137 | ATGGTACACACATGGTGGCTGCTTCTGCATCCCAGGGAGGCGAGTCGA | 7138 |
| | 2 | MGGFCFPRERSLTRGPGEFPRGPLACGLAKVDGPVEA QGPAGLEKLFSQRWGDDCAFWLPLLPPWVSVCHAGSV KREQSLEASFS* | 7139 | ATGGGTGGCTGCTTCCCAGGGAGCGAGTCTGACCGGGCTGAGCTGATGGAGTC TGTTTCCCAGGGGCCTTGCCGTGGTTGGCCAAAGTGGATGGTCAGTAGAGG CTCAGGACACTGCTGGGTTGGAGAACTTTCTCCAAAGATGGAGATGATTGTG CTTCTGGCTGCCTCCTCCTCCTGGTAAGTGTTGTCATGGCTGGCTCTGTAAA AGGGAGCAAAGCTGAAGCATCTATTTTTCCTGA | 7140 |
| | 3 | MIVLSKCLSFLPG* | 7141 | ATGATTGTCTTTCTGGCTGCTCCTCTTCCTGGGTAA | 7142 |
| | 4 | MLAL* | 7143 | ATGCTGCTCTGTAA | 7144 |
| hsa-mir-585 | 1 | MRSGAAPAPPMELLLPPPPGAPRSARAPCA* | 7145 | ATGCCCAGCGGGGCAGCCCCCGCTCCGCCGATGGAGCTGCTGTTGCTGCCGCCT GCCGCCCGAGCCCGGGTGCAGCAGGGCCCCGCTGCCGCCTGCGCTGCTGA | 7146 |
| | 2 | MAPGWAGVGAAVRARLALALASVLSGPPAVACPTK CTCSAASVDCHGLGLRAVPRGIPRNAERL* | 7147 | ATGGCCCCCGGGTGGCGAGCGGTCCTGAGCTGCGGTCCTGAGCTGCCCGCTGGC CTTGGCCTGCTGGCGAGCGTCCTGAGTGGGCCTCCAGCCGTCGCCTGCCCAAGTG TACCTGCTCCGCTCCACGGGCTGCCAACGCTGGAGCGCTGTGA | 7148 |
| | 3 | MQSLFSSLPGYDPSLSELGVCRLGQIWKERSRMPQRWA KSSASPGVRVPDAGPADSFQQVAEERRGEARALQPOGL RVRVRGLRSLKRGAGEGESYRMMGRQGAEAGERARD C* | 7149 | ATGCAGTCGCTATTCTCATCCTCACCTGGATACGATCCGAGCTCCGAGCTGGGG TCTGTAGGCTGTGGTCAGATCTGGAAAGAGAGGTCTCAGACGCCAGGGATGGCA AAGAGCAGTGCCTCTCAGGGGTGAGGGTTCAGACGCCCGCTGACAGCTT CCAAGGAGTAGCTGAGGAGGCGAGGGAGGCAAGAGCACTGCAGCCTCAAGGT CTTAGGGTGAGGGTCAGGGGTCAGGGGCCGTCAGGCCGTGTAAAAGGGGCGCGGGCGAAGGAGA AAGCTATAGGGATGAGGGGCCCGAGGCGCGGAGAGGCCCGAGAC TGTTGA | 7150 |
| | 4 | MGKEQCLSRGEGSRRRAR* | 7151 | ATGGGCAAAGAGCAGTGCCTCTCCAGGGTGAGGTTCAGACGCAGGGCCCGCTGA | 7152 |
| hsa-mir-586 | 1 | MARREKS* | 7153 | ATGGCACGCAGAGAGAAGAGTTAG | 7154 |
| | 2 | MAHL* | 7155 | ATGGCGCATCTTATAG | 7156 |
| | 3 | MRKYTLNA* | 7157 | ATGAGAAATACACGTAAACGCTTAG | 7158 |
| | 4 | MTVTLFSQRIRTLGLTRESEVMKTVICNI* | 7159 | ATGACTGTGACCTTATTTCTCAGAGAATCAGGACACTTGGTCTCACACGTGAGAGT GAAGTTATGAAGACAGTGATATGTAATATTTGA | 7160 |
| hsa-mir-587 | 1 | MMRNTCGA* | 7161 | ATGATGAGAAACACTTGTGGGCGTGA | 7162 |
| | 2 | MRKRGRWASPWMRRGHHDARLTSAIE* | 7163 | ATGAGGAAGAGAGGAAGGTGGCGAGGCCCTGGATGAGAAGGGCCACCACGATG CCAGGCTCACCTCTGCCATTGAATAG | 7164 |
| | 3 | MPGSPLNSCSVTPHSLQSNLLIIYSSPSQTTNLGRKQG* | 7165 | ATGCCAGGCTCACCTCTGAATAGCTGCTCGGTGACTCCTCACAGTCTGCAA AGCAACCTCCTTATAATCTATAGCTCACCAAGTCAGACTACCAATTAGGACGTAAA CAAGGCTGA | 7166 |

Figure 1 (Continued)

| | | | | |
|---|---|---|---|---|
| | 4 | MTATLKDSSGQLEDHSLWLLPQLYLPLGIVTI* | 7167 | ATGACAGCCACACTTAAGGACAGCAGCGGGCAGCTGGAGGATCATTCCCTCTGGCT GCTCCCCAGCTGTATTTACCTCTGGCATAGTGACTATCTAA | 7168 |
| hsa-mir-588 | 1 | MKRPKIRSNEIT* | 7169 | ATGAAAAGACCTAAGATAAGATCAAATGAAATTCTTAACGTAG | 7170 |
| | 2 | MKLRRSVkFLTVSI* | 7171 | ATGAAAATTACGTAGAAGGTGTAAAATTCTTAACTGTAGTATCGA | 7172 |
| | 3 | MHSLLGRHGISAVGHLRHHKLLFVGBRDSIE* | 7173 | ATGCATTCCTGCTAGGAAGGCATGCATTAGTGCTGCGGAATCCTGATAAAACAT CACAAACTTCTGTTCGTTGGTATTAGGGACAGTATAGAGTGA | 7174 |
| | 4 | MALVLSES* | 7175 | ATGGCCATTAGHGTCGTGCGGAATCCTGA | 7176 |
| | 1 | MAAA* | 7177 | ATGGCGGCGGCCTAG | 7178 |
| | 2 | MASSGEVLSATVSALLLPRRPRSPWVLPSRPGFPCILSIP TPTPRRPSHPDPGLAPAPVLPASCPQDSYPVSEGTSCLPL RSCIPDRQSCPRLSVP* | 7179 | ATGGCCAGCTCCGGAGAGGTACTGTCCGGACTGTCTCCGCTCTGCTTCTGCCTCGG CGGGACTCCGGTTCCTCCGGGTTCCTACGACCGGGTCCGCCTCCGCATCCTTCTA TCCCGAACCCCTACCCGCCGCTGTGTCCCAAGACTCTACCTCTCGCCTTGCCCTGCTCC CGTCCTTCCCGCATCCTCTGTCCCAAGACTCTACCTGTCGATCGCCAGAGGCACAAGCTG TCTCCCCCTTGCCTCGTGCATGCCAGAGTTGTCCCGTCTCAGAGTTGTCCCGTCCCCC TGA | 7180 |
| hsa-mir-589 | 3 | MLSFSPSPLLPGACLLNDVGGG* | 7181 | ATGCTCAGTTTCAGCCCGTCCTGAGCCTGCTTGCTGAATGACGTG GGGGTGGGTGA | 7182 |
| | 4 | MTWGVGDGGKAISPEGLTTYPGILSQHSPNLGPMEKPA ASL* | 7183 | ATGACGTGGGGGGTGGGTGATGAGAAAAGCCATTCACTGAGGGACTTACGAC GTACCCGGAATTCTTCCAACACTCCCAAATCTGGGTCGATGGAGAAGCCGGC CGGTCCCTGTAA | 7184 |
| | 1 | MADFDTYDDRAYSSPGGGRG* | 7185 | ATGGCGGAGACTTCGACACTTACGACGATCGGGCTTACACGCAGTTCGGCGGGGGCCAG AGGGTGA | 7186 |
| | 2 | MARSFGRRRLGSRGLACGADPFHCLPPTTTCWFLPCL GRGGADARRRAPASSSPIPPTVGPVRG* | 7187 | ATGGCGCGGCTCGGAGACGGCGGGGCGGGGCTCCCGGGGTCTTCCTGCGG GGCGGATCCCTTCCACTGCCTCCGCCAACGACACCGTGTTGGTTTTGCCCTGCCTT GGCCTCGCGGCGCCCGATGCCGGAGACGGAGGCGCCGCCCATCCCCCC TACGGTAGGACCAGTGCGGGGCTGA | 7188 |
| hsa-mir-590 | 3 | MPGDERPLPAPSPLR* | 7189 | ATGCCGGGAGACGAGCGCCCGCTTCCAGCCTCCCCATCCCGCTACGGTAG | 7190 |
| | 4 | MVRLLAGGGRPRR* | 7191 | ATGGTACTCCTTGCGGGCGGAGGCGAACCAAGGAGATAA | 7192 |
| | 1 | MGGQHPHDPRRREGVGRQARNARCLAVSPPPPPPGL EVSRPGPKRQPASQWVPQSPATGANHGGRQGNRGPEA GGSAPAGSAWGCERLGRSRVWVGATGGAKWGAGQPF HLAAGGRGPLLPGSTGGRCRDRGPTSQRKLCGPDTPT WPGREVGA* | 7193 | ATGGGCGGGCAGCACCCGCACGATCCACATGACCCTCGCCGCGGAGGGTGGGAGGCAGG CCAGGAACGAGCCGCCAACGGACGCCAGCCAGTCAGTGGGTCCCGCA CTAGAAAGTGAGCCGCCAACGGACGCCAGCCAGTCAGTGGGTCCCGCA GTCGCCGCAACGGGCGAATCATGGCGGCGCCACAAGGTAACCGCGGGCCGAGG CCGGGGGAGCCAGCCTGCCTGCCGGATCAGCTGGGGTGCGAGAGCTCGGCGCTCA CGTGTCTGGTTGGTGCCACAGGGAGGCGAAATGGGGTGCGGCAGCCGTTCCA CCTTGCGCTGCTGCGAGGAGGGCCACTCTCCCGGCCACGCAGGCGGGTCGGT GCAGAGACCGAGGCCCGACCTGCAGCGGGAAACTTTGTGGGCGGCCGCCCACT TGGCCGGGAGGGGAAGTTGGTGCCTGA | 7194 |
| | 2 | MTRAGGRAWGGRPGTHAAWPYRRPHRRRRRD* | 7195 | ATGACCCGCGCCGCGGCGGGGAGGCGTGGGGAGGCAGGCCAGGAAACGCACGCTGCCT GGCCGTATCGCGCCGCCGCCGCCGCGGGACTAG | 7196 |

Figure 1 (Continued)

| | | | | |
|---|---|---|---|---|
| hsa-mir-591 | 3 | MAAAKVTAGPRPGGARLPDQRGGARGSGAHVSGLVPQ AEQNGYVPGSKSTLRLLEGGHSSRAAQAVGAETEARPR SGNFVGRTLPLGERGGKLVPDGAEPGPTRRSGRDWGLV HPGPASAGGPLYLPSALLLLTPLVVDSGFFQGPEPGLKP DPITFQGHLRPPAGGEVILTSYLETA* | 7197 | ATGGCGGCCGCCAAGGTTAACGTCGGGCGCCTGAGCCGGGGAGCGCGCCTGCCGG ATCAGCCTGGAGGGTGCAGAGGCTCGGAGGCTCACGTCTGGGTTGGTGCCACAG GCGGAGCAAATGGAGGTGCCGGGCAGCCGTTCGACCTTGCGGCTGCTGAGGGAGG GGGCCACTCCTCCGGGCAGCACAAGGCCGGTCGGTCAGAGAACCGGGCCGACCTC CAGGCGGAAACTTTGTGGGCGGAACTCCACTTGCCGGGGAGGGAAGTTGGTG CCTGACGGGCTGAGCCAGGGCCAGGGCGAGGAGCGGCGGCGACTGGGGCTGG HGCACCCTGGCCGGCAAGGCGTGGGGTCCGGCTTCCAGGGCAGAGCCGGGCTGA TCCTGACCCGGCTGGTTGTTGACTCCGGCTTCTTCCAGGGCCAGAGCCGGGCTGA AGCCTGATCTATTACGTTCAAGGGCTCCGCCTCCGGGGTGGGGAAGTTACTT TGACTTCCGTTTTGGAAACTGCCTAG | 7198 |
| hsa-mir-592 | 4 | MGCRAAVPPCGCWREGATTPPGQHRRSVQRPRPDLAAE TLWAGHSHLAGEGSWCLTLGLSQGRRGGAGATGAWCT LGRQALGVLSTFPARSCS* | 7199 | ATGGGGTGCCGGGCAGCACAGGCCGGTCGGGGCTGCAGAGACCGAGGCCCACTCC TCCCGGGCAGCACAGCGGTCGGTCGCTGCAGAGACCGAGGCCGACCTGCAGCGGAAA CTTTGTGGGGCCGGACACTCCCACTTGGCCGGGGAGGGAAGTTGGTGCCTGACGGGG CTGAGCCAGGGCCGACTGAGGAGGAGGACGGGACTGGGCTGTGCACCCTGGG CCGGCAAGGCCGTGGGGTCCTCTACCTTCCAGGCGGGCTCCTGCTCCTGA | 7200 |
| hsa-mir-592 | 1 | MPTEPPFHGP* | 7201 | ATGCCCACAGAGCCTTTCCCACATGGGCCTGA | 7202 |
| hsa-mir-592 | 2 | MGHDGSLQKVQPQVVPFLLWQE* | 7203 | ATGGGCCCTGATGTAGCCTCCAGAAGGTGCAGCCTCAGGTGGTGCCCTTTCTTCTG TGGCAAGAATAA | 7204 |
| hsa-mir-592 | 3 | MVASRRCSLRWCPFFCGKNKLWVLDCNTTCGENGMR GKAISLLPLFLPLDRQVLLDPHNDAKNSQPGVCPFHTOG WGHYFGGSLPCPRKGRERGALWGAEEGKGDSQTGGH ALCN* | 7205 | AAACTTTGGTCTTGCAGAAGTGCAGCTCAGTGGTGCCTTTCTTCTGTGGCAAGAAT AGCGGATCAGCCTCTTGCCCTTGTCTTCTCCTGGAGAAAATGTATGCGAGGAA CACAATGATGCAAAGAACTCACAGCCAGGAGTAATGCCCATTCCATACGGGTGGATG GGGACATTATTTGGGAGCTGAAAGAACGCCGGGGATCAAGGGAGAGAGAGGGGTG TTGTGGGAGCTGAAAGAAGGGAATCACAGATCACAGATGGAGGCCATGCTTTA TGCAATTGA | 7206 |
| hsa-mir-592 | 4 | MVCEGKRSASCPCFFLLTAKFYWILTMMQRTHSQEVA HESIRVDGDHILGGLFPVHAKGERGVPCGELKKEKGIHRL EAMLYAIDQENKDPDLLSNJFLGVRRJLDTCSRDTYALEQ SLTFVQALIEKDASIDVKCANGDPPIFTKPDKISGVIGAAA SSVSIMVANILRLFKVGKGIVFLTIVKEQ* | 7207 | ATGGTAGGCGAAGGAAAAGGGATCAGCTCTTTGCCCTTGTTCTTCCTTGACCGCC AAGTTCTACTGGGTGGATGGGACATTATTTGGGAGCTGAAAGAACTCACAGCCAGGAGTAFGCCAT TCCATACGGGTGGATGGGGACATTATTGGGAGCTGAAAGAAGGGATTCACAGAC TGGAGGCCATGCTTTATGCAATTGACCAGATTAACAAGGACCCTGATCTCCTTCCA ACATCACTCTGGCCCTGCTCCGCAACATTCTCGACACGTGCTCTAGGGACACCTATGCTTTGG GAGCAGTGCTTAACAATGCCAAGCCATTTCTAACGATGGTGAAGATCTTCGATGCATAGAGGT GCTGCTAATGACGATCCACCATTTCTACCCAAGCCGACAAGATTTCTGGCGATGCATAGAGT GTTCGCAGCAAGGCATTGCTTCTGTGACCATTGAAAGACAATGA TAGGTAAAGGCATTGTTTGAAAGACAATGA | 7208 |
| hsa-mir-592 | 1 | MEVKGLN* | 7209 | ATGGAGGTGAAAGGGTTAAACTGA | 7210 |
| | 2 | MKLALKC* | 7211 | ATGAAACTGGCATTGAAATGTTAA | 7212 |
| hsa-mir-593 | 3 | MLTVSAKKGLSSEEVAVEISWTVASDAPFTEWHDYGE* | 7213 | ATGTTAACAGTGTCTGCTAAAAAGGGCTTTCTCTGAGGAAGTGGCTGTTGAGATT TCCTGGACTGTTGCATCTGATGCACCTTTCACAGAATGGCATGACTATGGCGAGTAA | 7214 |
| | 4 | MHLSQNGMTMASKCPRRSTI* | 7215 | ATGCACCTTTCACAGAATGGCATGACTATGGCATGGATGAGTAAGAAGTGTCCCAGGAGATCCACC ATTTAA | 7216 |
| | 1 | MGPPLPLLLLLLLPPRVLPAAPSSVPRGRQLPGRLGE WGAPGEGRLNELVGGVVRGAPP* | 7217 | ATGGGGCCGCCGCTCCCGCTGCTGCTGCTGCTGCTGCCGCCACGCGTC CTGCCTGCCGCCCCTTCGTCCGTCCCGGGGAGACCTCCAGCTCCCGCGCCGTCTGGT GAGTGGGGGGGCCGCGGGAGGGAGCGCCTCAATGAATTAGTTGGGGGCGTGTGAG AGGGGCGCCTCCGTGA | 7218 |

Figure 1 (Continued)

| | | | | |
|---|---|---|---|---|
| hsa-mir-595 | 2 | MQGRRLNK* | 7219 | ATGCAGGGAAGGCGCCTCAATAAATGA | 7220 |
| | 3 | MSGGVGGGAPLRGSGGGTPQ* | 7221 | ATGAGTGGGGGCGTTGGGGGAGGGGCGCCTCTGAGAGGTTCTGGGGGAGGGACGCCTCAATGA | 7222 |
| | 4 | MNERGAWGEGRLNECGAWGKGRLNE* | 7223 | ATGAATGAGAGGGGCGTGGGGGAGGGGCCCTCAATGAATGCGGGGCGTGGGGGAAGGGGCGCCTCAATGAATGA | 7224 |
| hsa-mir-596 | 1 | MHRPAAHALAAEPRAACAACIGPTGRRPRGKPSVTIRA* | 7225 | ATGCACCGTCCTGCGCCACGGAGCCCCACGGAGCGCCAGCGCAGCGGAGATCCCACGGAGAAGCGTCTGTAACCATCCGAGCCTAG | 7226 |
| | 2 | MAAAALRRPTRRPIPGCCLGHCPCVPLFYFRTLIKTQTDE* | 7227 | ATGGCAGCTGCTGCCCTTCGGAGGCCGACTCGACGCCATCCGTGGTCTGTCTAGTCACTGTCCTTGTGTTTTGTTTTACTTTAGAACTCTTAAAGACACAAACCGATGAGTAG | 7228 |
| | 3 | MSRDKLTLGNGLGVYVCKAGSAVCVRNPLSSGSVLGCFL GQRPQPSYLQSILLSWRASAMAPRLYCSL* | 7229 | ATGAGTAGAGACAAACTCACACTAGGAAATGGACTGGGTGTGTTTGCAAGCGGGGAGCGCCGTCTGTGTCCGAACCCTCTGAGCTCAGGAGCGTCTCGGGTCTTTCTGGGGCAGCGGCCACAGCCGTCCACGCGGCTCATCTGCAGAGCATCTGCTTCCTGGAGGGCATCTGCGATGGCCCCAGGCTGTACTGTTCCCTGTAA | 7230 |
| | 4 | MDWVWFAKRGARSVSGTL* | 7231 | ATGGACTGGGTGTTGGTTTGCAAAGCGGCGAGCGGTCGTGTCGTGTCCGAACCCTGA | 7232 |
| hsa-mir-597 | 1 | MLIGFTVGSEGGRWGPLPQ* | 7233 | ATGCTGATTGGTTCCGACAGTCGGAAGTCGAAGGTGAGGGCCGTGTGGGGGCCGTTGCCGCAGTGA | 7234 |
| | 2 | MAASRRSQHHHHHQQQLQPAPGASAPPPPPPLSPG LAPGTTPASPTASGLAPFASPRHGLALPEGDGSRDPPDR PRSPDPVDGTSCCSTSTHCTVAAAPVVPAVSTSSAAGV APNPAGSGSNNSPSSSSSPTSSSSSSPS&PQSSLAESPEAA GVSSTAPLGPGAAGPGTGVPAVSGALRELLEACRNGDV SRVKRLVDAANYVNAKDMAGRKSSPLHFAAGQRLLNCL LRVMGLLGAGSG* | 7235 | ATGGCAGCAGTCGCGTCGCGTCAGCATCATCACCACCATCATCAACACAGCTCCAGCCCCCCAGGGGCTTCAGCGCCGCAGCCTCTCCCCGACTCTGCCGGAGGACAGCCCTGGCCTGCCCCCGGGGACCACCCCGAGCGCTGCGGAGGACAGCCCTGTGCCGGAGCAGTCGGAGCAGCCGGATCCGCCGACAGGGCCGCGATCCGTCGCCGCGCCCAACCCAGCCGGCAGTGGCCCCGCTCTCCTCCCGTCTCCCGGGTTCCCGGGGTCTCAACAATTCACCGTCGTCTACTTCATCGTCGCTGGGTCGCTCCCGACTCTTCCTCCGACGTTACGTGCGCCGCCAACCAGCCGGGGACAATCCCTCCGATCCGAGTAGCAGCAGCACAGCAGCCGGAGGCCCCGAGGCCCGCGGGAACGGCCTGCCCCGGAGCGGGACAGGGGAACTGCTGGAGCGCCTGCCAGGGAACGCGGGGGACAGGCCTGCAATGGACATGGCGCCGCAGCGGGAAGGAGGCCTGTGGTGGACAAACAAGATGCATGGCCAAATGAGCGAGTTCCTCTGGTAACGCTGCTGGGTCCGGACTTGGGTGTCCAGGGTCCCAGGGGAGCAAACGATAATGTTTGAATTGTTATTAAGGGTTATGGGTTTGGGTCAGGGTCCGGTTAG | 7236 |
| | 3 | MAVGIRPTGPDPRTRLTVPAVAVPPAQSVPSPPLPWSQR FLLHLPLGSLPTQPAVATHRRPLLPHLPLPHPPLD RAWRRAPRRPELAAQHHWGLGQQDLGQGSQQ* | 7237 | ATGGCAGTCGGGATCCGGCCGACAGGCCCGATCCGACAGGCCCGGTTGACGGTACCAGCTGTTGCAGTACCACCAGACAATCGTACCGTCGCCGCCCAACCAGCCGCAGTGGCAGTGCGGGTTTCTACTTCACCTCGCCCCTGGGTCCCTGCCCACTCAGCCCGCCGTCGCCCAACCCAGCCGCCAGTGGCAGTGAACAATTCACCGTCGTCTACTTCATCGTCCCTCCATCTCCCCTGGATCGAGCTTGCGGAGAGCCCTGAGGCCCCGGAGCTTAGCAGCACAGCAGCCGGAGGTGA | 7238 |
| | 4 | MGTCPG* | 7239 | ATGGGGACGTGTCCGGGTAA | 7240 |

Figure 1 (Continued)

| | | | | |
|---|---|---|---|---|
| hsa-mir-598 | 1 | MAAKSDGGGVGVGFAQLHNLDEAVGSGGEEDGEPGG GGCGGGDGSEPGESSSMHBCHCCNTSSCYWGCRSACL RSLLGRKPRRSAAADGGDQPLQPPAAPGAGRQPPTPSA ARPEPPPQVERPWLDCLWIVLALLVPFGDVGTDLWLA LDYYRKGIDYVYPGLTLFVLVPSLLVQSLSFRWFVQDY TGGGLGAVEGLTSRGPPMMGAGYVHGAARGGPGVRV SPTPGAQRLCRLSVWIWQSVIHLLQMGQVWR* | 7241 | ATGGCGGCGAAATCCGATGGCGGTGGCGTGGGGTGGCCTTCGCTCAGCTGCACAA CCTGGACGAGCCGGTGGGCAGCGGCGGCGAGGAGGACGGCGAGCCCGGGGAGGC GGCTGGCGGCGACGGCAGCGAGCCCGGCGAGAGCAGCAGCAGCTCGATGCACAT CTBCCACTGCTGCAACACCTCGTGCTACTGGGGCTGCCGCTCCGCCTGCCTGCG CTCCCTCCTGGGCAGGAAGCCTCGCCGGCGGAAGCCCCGCAACCCGACGCCTGCCGGCG CGCTCAGCCTGGGCGGCCCCGCGCCCCGGCCCCCCGGCGCCAACCCGACGCCTGGCCG CGGGGCCGAGCGCTGGGCTGCTGGTGTTCTTCGGGACGTGGGGACCTGTGGCTGGCC ATCGTGCTGGGGCTGCTGCCAAGGGGACTACGTCGTACCGGGCTGACCCTCTTCGTG CTCGACTACTACCGCAAGGGGACTACGTCTACCCTGGGCTGACCCTCTTCGTG CTGGTGCTCGTCGCTGGGTGCAGCCTGAGCTTCCGCTGGTTCGTGCAGGACTAC TGGGGCCGGACTAGCGGCAAGGGCTGAGGGCTCACCAGCGGGGCTCCC CCACGCGGGGGCCGCTGCCACGCGCGCAGCGCCTGTGCCCTCCGTGTGATCTGGCAGTCGGTCA TCCACCTGCTGCAGATGGGGCAGGTGTGGAGGTAA | 7242 |
| | 2 | MAVAWGWASLSCTTWTRRWAAAARRTGSPGEAAAAA AATAASPARAARCTSATAATPPRATGAAAPACAPSWA GSRAAAPPPTGGTSRCSLPRPPAPAANPRRPRPRGRSRR RRRWSGRGSTACCGSCWRCWCSSGTWAPTCGWPSTTTA RGTTSTSG* | 7243 | ATGGCGGTGGCGTGGGGGTGGCTTCGCTCAGCTGCACAACCTGAGCAGCCTGTG GGCAGCGGCGGGCAGCGAGCCCGGCAGGAGGAGCAGCTGCATCTGCACTGCTGCAAC ACCTCCTGCTGGGGCGGCCGGGAGCCGGGCTGTGCACATCGCACTGCTGCAAC AAGCCGCCGCCAGCGCCGCCAACCCGACGCCGCTGCAGCCTGCCGC GCCCCGGCCGCCGCAACCCGACCCCTGGCCTGCAGCGCCGCCGGCCGC CGGTGTTCTTCGGGACGCGTGGGCACCGTGGGGCACCGACCTGTGGCTGGCCATCGTGCTGGGGCTG CTGGTGTTCTTCGGGACGTGGGCACCGTGGGCACCGACCTGTGGCTGGCCATCGTGCTGGGGCTG AAGGGGGACTACGTCTACTTCGGGCTGA | 7244 |
| | 3 | MTPNHCFPRRKKDFFFWFAGLDVSFS* | 7245 | ATGACTCCAAACCACTGCTTCCCAGAAGGAAAAAAAGACTTTTTTTTTGGTTTG CTGGATTAGACGTCTTGTCCTTTTCTTAG | 7246 |
| | 4 | MGASVWC* | 7247 | ATGGGCGCTCGAGCGTTTGTGTTAA | 7248 |
| | 1 | MSESAA* | 7249 | ATGTCAGAATCTGCAGCTTAG | 7250 |
| | 2 | MESTGRGRKRCRGFEQNESPPLCREKGFSGSPPPC* | 7251 | ATGGAGAGTACAGGGAGGGAGGAAAGAGTGCAGAGGATTTGAACAGAATGAGA GTCTTCTCTTGCAGGAGAAAGGCTTCAGTGGGTCTCCCCTGCCTAG | 7252 |
| hsa-mir-600 | 3 | MRVLLCAGRKASVGLPLPARDPPCQPWAGRWQARSQV SRRGQERSQASGEKCLLSNLPRAIGFPLSQTGSPGGESE AGLACMHRESVPTWGV* | 7253 | ATGAGAGTCCTCCTCTGTGCCAGCAGGAAGGCCTCAGTGGGTCTCCCCTGCT AGGGATCCTCCTTGCCAGCCTGGGCTGCCAGGCCGTGTCCCAGGTCCTCC CGCCGAGGGCAGGAGAGGAGGCCAGGGTCCAGGGAGAAGTGCTTACTGAGTAATTT ACCAAGAGCGATAGGCTTCCCACTGAGGCTCACAGAGAGTGGATCCCAGGAGGGAGTCAG AGGCAGGCCTGGCATGCCATGCACAGAGAGGTGCCCACTGGGAGTGTGA | 7254 |
| | 4 | MHAQRECAHLGSVKGLAVGPERMSRVKWQVGHTVCS HFLKGPGWCVLQ* | 7255 | ATGCATGCACAGAGAGTGTGCCCACTTGGGAGTGTGAAGGGCCTGCTGTGGG ACCCGGAGAGATGAGCAGAGTCAAGTGGCAGTGGGACACACAGTCTGCAGTCACT TCTTAAAAGGCCCTGGGTGGTGTCCTTCAATGA | 7256 |
| | 1 | MAFAGLERVH* | 7257 | ATGGCGTTCGCCGGGCTGGAGCGTGAGCTGAGTACATTAA | 7258 |

Figure 1 (Continued)

| | | | | |
|---|---|---|---|---|
| hsa-mir-601 | 2 | MRRPGDHGLQDQVSAAGPGGAGPGAGRRGRARAAGR GPRGGL VAEFRGAPRVTPARGEGDGCYGDPGRRGGGV RAGWQGAGGQVSPPHLGVGTAEHTGRPPPRVYGEPLK MVLQLWGRGVGKPRKHLPMFGHVWGAPESWQVRRGC SLAA* | 7259 | ATGAGGAGGCCTGGGGACCATGAGCTCCAGGATCAAGTGAGTGCGGCGGCCGGG CGGAGCCGGGCCGGGGCACTGTTGCCGAGACCAGAGGGCGCCCCGTGACGCCGCACG CCGGCGCGGGGGACGGTTGCTATGGCGATCCAGGAGGCGCCCAGAGGAGGGCGCGGGTTCGC GGGGGGGTGGCAGGGCGCCGGAGGGTCAGGTGTCCCTCCAGGAGGCGCCTCCTCAGCTGGGGTCGAAC AGCTGAGATTACAGGCGGCGCCGGTTACGAGGAGCCCCTGAAAATGG TCCTTCAACTGTGGGGCGTCGGGGAAGGGAGTGGGAAAGCCCCTGAAAGCCACTCCCATGTT GGGCATGTTTCGGGCTGCGCCCCTGAAAGTTGGCAGGTCCGAGAGGTTGCAGCCTGGC CGCTTGA | 7260 |
| | 3 | MGSRIK* | 7261 | ATGGGCTCCAGGATCAAGTGA | 7262 |
| | 4 | MAIQGEAGAGCAARGGRAPGVRCPLLTWGSEQLRLQGG PLPGFTESP* | 7263 | ATGGCGATCCAGGGAGAGGCGGGAGGGCGGGGTGCGCGCGGGTGCAGGGCGCCGG GGGTCAGGTGTCCCTCACCTGGGGGTCCGAACAGCTGAGATTACAGGGCGGCC CCCTTCCCCGGGTTTACGGAGAGCCCCTGA | 7264 |
| hsa-mir-602 | 1 | MARGRGGATLRARAMAAADAEVSSGAGGGRRGGGGQ RRERRGGEEPGGAAAGGRRAGGAPGPPAAAAAAAAS GRGRAEAAGRPARAPAGRALCAARAGRRLLGERAGAQV REATAYLCPRPPRTPCRRRRRPQAGSAGRASARVPGRCG GQKEK* | 7265 | ATGGCGCGCGGAGGGGCGATCTCGCGCGCCGCGGCCATGGCCGCCGCCGCCG ATGCCGAGGTGAGCAGCGGCGCGCGGAGGGCGGCGGGGGGGCGTAGGCGGCCAGCGG CCGAGGGGCGGCCCGGGTCCCCCGCCGAAGAACCGGGTGGCGCGGTCAGCGGTCGCGCG GGAGGCGACCGCGTACCTGTGCCCGCGCGTACCTGTGGGGAGCGAGGGCAGGCGCAGGTTGAG CCCGCAAGCCGGATCTCCGGGAGGCCCTCGCCAGGTGGCCGGGGAGGGTCGG AGGACAAAAGGAAAGTAG | 7266 |
| | 2 | MAPSLTKSWPVPACFSHDNAAPALLAVRSRKARSVGSL RTQVYFQTSSFKGLSM* | 7267 | ATGGCACCATCTTTAACGAAAAGTTGGCCAGTCCGCGTGTTTCTCCCCAGACAAT GCTCTCCAGCCCTGCTGCAGAAGCAGAAAGCACGCTCGGTGGGAAGCTT GCGGACTTCAAGTTTATTTCCAAACCAGCAGCTTTAAAGGCTCTCGATGTAA | 7268 |
| | 3 | MLLQPCWLSEAGKHARWEACGLKHSKPAALKGSRCK KFTFFC* | 7269 | ATGCTCTTCCAGCCCTGCTGCTGTCAGAAGCAGAAAGCACGCTCGGTTGGGAAGC TTGCGGACTCAAGTTTATTTCCAAACCAGCAGCTTTAAAGGCTCTCGATGTAAAA GTTCACATCTCTTTTGTTAA | 7270 |
| | 4 | MVSAPPVLHLKDSLFPCLGKEAA* | 7271 | ATGGTCTCGGCCTTCCCGTGCTCATTCTCAAGGATAGTTGTTCCTTGCTAGGAA AGGAAGCAGCGTAG | 7272 |
| hsa-mir-603 | 1 | MRARWLQVSAEQLPYGERGEARGRQPRPEVSAAEVCV GCPAAPPARVGGTSPLLG* | 7273 | ATGAGAGGCGAGGTGGCTCCAGCAGGTCCGGGGAGCAGCTGCCAGTGGAGGAGGAG AGAGGCGAGGGGCGGCAGCGTCGGCCGAGTAAGTGCAGCAGAAGTTTGCGTCG GTTGCCCGCCCCCAGCGGAGGGGAGGCACATCTCCCTCCTTGGATAA | 7274 |
| | 2 | MGCQKEKTPNWEEGLERNRTPGISEREGCGESEGGGSH TYPGDLGVPPWSGEPGAYIGATRMLPRFSLGAAKRALL FLMAGRCQGGEREPAPRRAGGWGHWGVWSWGFGVG GLGLLRRSRLSGGGRGRGRRRM* | 7275 | ATGGGGTGCCAAAAGGAAAAGAACCCCAACTGGAGGAGGGACTGGAGAGGAACC GGACCCGGGATCTCAGAAAGGGAAGATGTGGGAGACAGGGGAAGTGGCAGCCAGGGCTTA TCACACCTATCCTATGCCTAGGATGTTGGGGACACTGTTGCCTGTTTCACCTGGAGAGGGCATT GCTTTTTCTGATGGCTGGAAGACAGGCAAGGAGAGAGAAACCGGCCCGAGACGAGAGGGAGG TTTGGGTCTTCTGAGAGCTCCGGAGGCCGGGCAGAGGTCGAGTGGAGG GGCGAATGTGA | 7276 |
| | 3 | MWGE* | 7277 | ATGTGGGGAGAGTGA | 7278 |
| | 4 | MLGAFGSWSLILVIGRFRGEIRQRPGAG* | 7279 | ATGTTTGGCGCCTTTGGCAGCTGGTCATTAATTGTCATCGGGAGGTTTCGCGGA GGGCGACAGCGCCCGGAAGCAGGGTGA | 7280 |
| | 1 | MEENESQKCEPCLPYSADRRQMQGK* | 7281 | ATGGAAGAAAATGAAAGCCAGAAATGTGAGCCGTGCCTTCCTTACTCAGCAGACAG AAGACAGATGCAGGGTAAGTAA | 7282 |

Figure 1 (Continued)

| | | | | |
|---|---|---|---|---|
| hsa-mir-603 | 2 | MKARNVSRAFLTQQTEDRCRVSNRPIQRWSYRDACPLP LAAFYKLQLWDPAKEKKKGNFLGWYIFQTE* | 7283 | ATGAAAGCCAGAAATGTGAGCCGTGCCTTCCTTACTCAGCAGAAGACAGATG CAGGGTAAGTAACGAACCATTCAAAGATGAGTTACAGGACCGTGCCCCTTGC CGCTTGCTGCTTTTATAAACTGCAGCTCTGGGACCCGCAAAGGAAAAAAAAA AAGGCAATTTCTTGGGATGTACATTTCAAACTGAGTAG | 7284 |
| | 3 | MELQGRVPLAACCPL* | 7285 | ATGGAGTTACAGGACCGTGCCCCTTGCGCTTGCTGCTTTTATAA | 7286 |
| | 4 | MVHFPN* | 7287 | ATGGTTACATTTCAAACTGA | 7288 |
| | 1 | MAGRRVARGVARQ* | 7289 | ATGGCGGGGAGGCGGGTGGCCCGGGAGTGCGCCAGTGA | 7290 |
| | 2 | MRGAPGHPSCPRPCARAGSPKGVV* | 7291 | ATGCGCGTGGTGCGCCAGGCACCCAGCTGCCCACGTTTCTGTGCGCGTGCGGGCTCC CGAAGGGAGTGGTTTAG | 7292 |
| hsa-mir-604 | 3 | MRDLYKSDSLLQ* | 7293 | ATGAGAGATCTTGTGAAGTCTGACAGTTTATTGCAATGA | 7294 |
| | 4 | MRSSSQGERPAGEIKGAPVRHPQPHPEVVITCACANPST GTRFVIEMSEAASLLRQMFLSI* | 7295 | ATGAGAAGTTCCTCACAAGGGAGAGCCAGCTGGGGAAATTAAAGGAGTCCTGT CCGCCATCCACAAATGCCAATCCGAGGTTGTGATAACTTGTGCCTGCAAACCTAG CACAGGCACGTTTGTCATAGAAATGTCAGAGGCAGCATCTCTACTGCGCCAGAT GTTTCTCAGCATCTGA | 7296 |
| | 1 | MSFLEEDFAKILMLKEERIKELEKRLSEKEEEIQELKRKL HKCQSVLPVPSTHGPRTTRAQGISAEPQTYRSFHDLRQ AFRKFTKSER* | 7297 | ATGAGCGAGCTAGAGGAAGACTTTGCCAAGATTCTCATGCTCAAGGAGGAGGAT CAAAGAGCTGGAGAAGCGGCTCTGTCAGAGAAGGAAGAAATTCAGGAGCTGAAG AGGAAACTCCACAAATGCCAGTCAGTCCTGCCCGTGCCCAGCACACATGGACCCCC CGGACCACCGGGCGCAGGGCATTCTCGGCCATCTGTGCGGGGCTACTTCACCAAGTCC GACCTCTCAGACGGCATTCCGGAAGTTCACCAAGTCCGAAAGGTAG | 7298 |
| | 2 | MPVGAPSALIDPHRPPDHPGAGHLGRAADVQVLPRPPTG IIPEVHQVRKVGAEAVGPGARPGPRRRGWGLWPRRRGR VGPGRPLLAAARGVGVAPRPGNGKCLFLFLPITCCACLR RAGKGELHGETRPCGVGVGRRTAESLLARANLCPPHM AAVARLSFVRPAGSVHAGTQPCPSRGLESSPAATPRTQA TGHAQWGCPSLLGRGDWRLDRVGLNLGTELAQNPSSA GGCGDRERRDRGLSLGQGSSLERGGEEGRGLFTGSLSR QL* | 7299 | ATGCCAGTCGGTGCTCCAGTGCTCCAGTCGCCCCTCGCGCCCCGGACCACCCGGGC GCAGGCATTCTCGGCCATCTGTGCGGGGCTACACGGTCCTCGACAGG CATTCCGGAAGTTCACCAAGTCCGAGAAGGTCCGAGACGTAGGCGCGCGGAGCCGGG CTGTCCGGCCGCAGGGCGCCGCCTCGCGCGAGGCCCGCGGGCGGGGCGGGGCGG GCCCGGGCGGAATGGAAGTTCATTTTTATTTCTGCCACATCCTGTCCCTCGTCTC GCCCGGGCTGCAGGGCAGCTAGCGGCGGGAGACCGCGCCCCTGTGCGTGCGGGGT GGGGAGGAGGAGGACCGCGGAAAGTTTACTCGCGGGCCGGGTCTGCCCTCCACACA TGGCTGCAGTGCAGCCCATCCAGCTGCCGCGGGCCGTGCACAGGTC ACCAACCTGGAACATGCTGGGCAGGTTGGGCTCAACTTAGGGACTGAACTTGCCCAGAACCCGAGCT GAGGCTGGACAGGGTTGGCTCAACTTAGGGACTGAACTTGCCCAGAACCGAGCT GGATCAGCTCGGCGATGGGCGTGGGGCGTGGGGGCGAGGAGGGCGAGACTGGGGACT TTCAAGGCAGCAGTGTGA | 7300 |
| hsa-mir-605 | 3 | MGSVYFYFCPSRAVLVSAGLGKASCTGRRAPVAWGWG GGPRKVYSRGLTCALHTWLQSRGCPSCAPLGASTQGPN PAHPGAWRASQRRPGLRPLDMLSGAVRAS* | 7301 | ATGGGAAGTGTTTATTTTATTTCTGCCATCAGCGTGCTGTGCCTGTCGCCGGGC TGGGAAAGGCAGCTGCACGGGAGGACGGCCCCTTGGCGTGGCGGGTGGGAGG AGGACCGCGGAAAGTTTACTCGCGCGAAATTGTGCCCTCACACATGGCTGCA GTCGCGCGGCTGTCTTCGTCGCAGGCTAACCTCAGGCAGGACCAGGCCTAG TGCCCATCATGCTGAGCGGGGCTGTCCGAGCTCGAGCCTCTAG | 7302 |
| | 4 | MRGQQEAGQGLVSRAGIQPGAWRGGEKFHRVTFKA AVMSARHCKETPPSGRFFALIVPLPEVQHLRLL* | 7303 | ATGCGGGGACAGGGGAGGCGGAGGCGGAGGATCCAGGGCTTGTCTCTAGGGCAGGATCCAGCC TGGAGCGTGGGGGCGAGGGGGGAGGAGTTATTCACAGGGTCACTTTCAAGGCAG TGTGATGTCAGCAAGACATTGCAAGAAACCCACCTTCTGACGTTTCTTTGCTC TGATTGTGCCTCTTCCAGAAGTTCAACACCTAAGGCTGCTCTAG | 7304 |

Figure 1 (Continued)

| | | | | |
|---|---|---|---|---|
| hsa-mir-605 | 1 | MGTLRDLQYALQEKIEELRQRDALIIDELELEDQKDELJQKLQNELDKYRSVIRPATQQAQKQSASTLQGEPRTKRQAISAEPTAFDKQDLSHVTLPFYPKSPQ* | 7305 | ATGGGCACCTTGCGGGATTTACAGTACGCGCCTCCAGGAGAAGATCGAGGAGCTGAGGCAGCGGGATGCTCTCATGCGACGAGCTGGAGCTGGAAGTTGGATCGAGAAGGACGAACTGATCAGAAGCTGCAGAACGAGCTGGACAAGTACCGCTCGGTGATCCGACCAGCCACCCAGCAGGCGCAGAAACAGAGCGCTGAGCCGGAGCCACCTTGCAGGGCGAGCGCGCACCAACGGGCAGGCGATCTCCGCGAGAAGCAGGCGATCGCGGCCAAGGATCCAAGGATCTCAGCTCAGCCATGTGACCCTGCCCCTTCTACCCTAAGAGCCCACAGTAA | 7306 |
| | 2 | MLSSTSWSWSWIRRTN* | 7307 | ATGCTCTCATCGACGAGCTGGAGTCGAGTTGGATCAGAAGGACGAACTGA | 7308 |
| | 3 | MWRPGDGELRVSVLSVGPRPSRLPCLSSSSEMFHFNGHPLRGCARFSEPDSLHRRCLRVFVRCQGHFKYTYIPV* | 7309 | ATGTGGCGCCCTGGCGATGGGGAGCTGCGGGTCTCTGTATTGTCTGTCGGCCCCGCCCTCCCGCTTGCACTGATCCTCAGAAATGTTCATTTTAACGGCACTCTGTCGGGGCTGTGCACGTTCTCAGAGCCAGATCACTGCACATACGTTGCTTCGTGTCTTTGTCAGATGTCAAGGTATTATTTTAAATATACATTCGTATAA | 7310 |
| | 4 | MGSCGSLYCLSAPAPPACHVCPHPQKCFILTGTSCGAVHVSQSQTHCTYVAFVSLSDVKVLFLNHHSYKPPSVRRV* | 7311 | ATGGGGAGCTGCGGGTCTCTGTATTGTCTGTCGGCCCCGCCCCTCCGCTTGCCATGTCTGTCCTCATCCTGCAGCCCATGGGCACTTCTTGCGGGCTGTGCACGTTCTCAGAACTCACTGCACATACGTTGCTTCGTGTCTTTGTCAGATGTCAAGGTATTATTTTAAATATACATTCGTATAAGCCACCTAGTGTACGTAGAGTTTGA | 7312 |
| hsa-mir-606 | 1 | MAAGLVVRGTQVSPGQPRLRPGRSPRGEGQRGTEAPQGLDTPVPASGGCVCRG* | 7313 | ATGGCCGGAGTCGTGGTGCGTGGGACTCAAGTAAGTCCCGGCCAGCCCGCCTCCGCCCGGGCGCAGTCCCGTGGGACGGACGGGGCACAGAGGCTCCCAGGGCCTAGACACCCCTGTCCGCCCTCAGGGGCTGCGTCTGCACAGGGGTGA | 7314 |
| | 2 | MCGKNTRKVSSRSPHFLLPLAPH* | 7315 | ATGTGCGGGAAGAACACCCGCAAGGTCTCCGTTCCCCACTTCCTCTCGCCCTTA GCGCCCTCACTGA | 7316 |
| | 3 | MFQPHNLNFKNFWSKNPF* | 7317 | ATGTTCCAATTCATAATCTGAATTTAAAAACTTTGGTCAAAGAATCATTTGA | 7318 |
| | 4 | MEEGVYEGKSV* | 7319 | ATGGAGGAAGGGTTTATGAGGCAAAAGTGTCTAG | 7320 |
| hsa-mir-607 | 1 | MQRELE* | 7321 | ATGCAAAGAGAATTAGAATAA | 7322 |
| | 2 | MELRKSTGQDYHNLKFQRLKSPAEKTNH* | 7323 | ATGGAACTCAGAAAGTCTACAGGACAGGACTACATTATAAATTTAAAAATCTTTCAAAGACTAAAAAGCCCTGCTGAAAAAACCAATCACTAA | 7324 |
| | 3 | MLLKTCYMLSSMIVRNTK* | 7325 | ATGCTTCTCAAAACTGCTATATGCTCTCTTATGATAGTCGAAATACCAAGTAA | 7326 |
| | 4 | MHNNTLKE* | 7327 | ATGCATAATAATACTTTGAAAGAATAA | 7328 |
| hsa-mir-608 | 1 | MAPDPSAKVSKARSAGGALA* | 7329 | ATGGCCCCGGATCCGAGCGCAAAGGTGAGCAAGGCGAGGAGTGCGGCGGCGCCT GGCGTGA | 7330 |
| | 2 | MTALEGRGPGLGLRGVQTGHHGVGDQRGEGAAWRTVFPRIWVTSPGVRRDRRRACPRAAAVETEVRPDEGRGPRTVQDVGRGSRGRGSLKPGETAILLGRGKYRLH* | 7331 | ATGACGGCTCTAGAGGGCCGAGGGCCGGGCCTCGGGCTGAGAGGGGTGCAAACCGGCCACCACGGAGTCGGGGACCAGCGCGGCGAGGGGGCCGCTGGCGGACAGTGTTCCCCAGGATCGGGTCACGTCCGGGCGGATCGAAGCACTGCGGAGTTGTTCTCGAGCTGCAGCAGTAGAGACTAGAGTTAGACCTGCGACGAAGGGAGGACGACCGCGGACTGTCCAGGATGTTGGAGGGGAGGGGTCTCTCAAGCCAGGAGAGACCGCCTACACTAG | 7332 |
| | 3 | MLEGGGPGGGALSSQERPPSY* | 7333 | ATGTTGGAGGGAGGGGGTCCCGGGGAGGGGCTCTCTCAAGCCAGGAGAGACCGCC ATCCTACTAG | 7334 |
| | 4 | MKVESLLLH* | 7335 | ATGAAGGTCGAGAGCCTGCTGCTGATCCTCCATTGA | 7336 |

Figure 1 (Continued)

| | | | | |
|---|---|---|---|---|
| hsa-mir-609 | 1 | MGAGLTVSGRVYTAAASRPAAPRRRKGNRPALGCCVR CLLPPEENTAHGARPGARRRPH.RRRRVLVREVRCSRPR DRSGSRGTSCPKSPPPSSPSGSLGRLSPQLRPLPLCPQCL PSASLPV* | 7337 | ATGGGCGCGGGGCTTACGGTCTCCGGATACGGTGTACACAGCAGCGGCGTCGCG GCCCGCAGCCCCGGCGCCCGGCCTGCTGCCCGAGGAAAACACTGCCGCCGACCGTGCGTGCTGC CGAAGGCCCCACTCCGCGCCGGCCGGCCTCCTGTCCGTGAGTGCGGTGTTCACGG CCCCGACGATCTGGGTCTCGGGAACCTCCTGCCCAAGTCCTGCCCTCCCTCC TCTCCCTCCGGTTCCTTAGGGGCGCTTCCGCCCAGCTTGACCTCTTCCCCTGCC CCCAGTGCCTCCTCCCAGCCTCGTGTGA | 7338 |
| | 2 | MAQGRERDEGPHSAGGASLSVRCGVHGPATDLGLAEP PAPSPLLPPLPVP* | 7339 | ATGGCGCAAGGCGGGAGCGGGAGCGTGTCAGGTGCCAGCCCACTCCGCGGCGCGGCGGCGGTCTT GTCCGTGAGGTGCGGTGTTCAGGCCCGACCGATTCGGTTCGCGGAACCTCC TGCCCAAGTCCTCCCTCCTCCCCCTCCGGTTCCTTAG | 7340 |
| | 3 | MSRGFSPNQCPSLAFSTIFKHTPNI* | 7341 | ATGTCTCGAGGTTTCTCACCAAACCAGTGCTTCACTTGCCTTTCCACCATCTCA AGCATACCTTTAATATTTAA | 7342 |
| | 4 | MFFLCASLSFTSTSFLLFSTFICFKSKIWPHTLHLCK* | 7343 | ATGTTCTTTTGTGTGCTAGCCTTTCATTCACGTCGACTTCATTCCTTTATTTCTAC GTTTATCTGTATTTTAAATCTAAAATGGCACATACTCTTCATCTGTGTAAATAA | 7344 |
| hsa-mir-611 | 1 | MPLAPEALPFPVVLGACSCRRVLPVAERRISLRGAKW* | 7345 | ATGCCACTTGCCGAGGCACTTCCTTTCGGTTGTGTCTAGGCGCCTGCCTCG CGACGTGTTCTTCGCCGGACGGGCGGAGCGGGATTAGCCTTCGCGCGGCAAATGGTG A | 7346 |
| | 2 | MVRALRGVPDGDARTPRGLTHTALISSDAGDPEG* | 7347 | ATGGTTGAGAGCGTTGAGGGAGTTCCAGACGGAGATGCGAGGACCCCTCCGGGTCTT GACCCACACCGGCGCTTATCTCCAGACGCCGGAGATCCAGAGGGCTAG | 7348 |
| | 3 | MRGPLGV* | 7349 | ATGCGAGGACCCCTCGGGTCTGA | 7350 |
| | 4 | MNSLGFSARDF* | 7351 | ATGAACTCCTTAGGTTTCTCAGCTCGCGGATTTCTAA | 7352 |
| hsa-mir-611 | 1 | MTTASTSQVRQNYHQDSEAAINRQINLELYASYVYLSM VSAGGPKRWRGPGAVPGARAGAGRGCGHPRALPPPCA LLENGGCSRFPRTSLAQKVGAAGSSRLYPEMAPS* | 7353 | ATGACGACCGCGTCACCTGCAGTCGCGCAGAACTACCACCAGGACTCAGAGGC CGCCATCAACCGCCAGATCAACTGGAGCTCTACGCCTCTACGTTTACCGTCCAT GGTGAGCGCGGGCCGGGCCTAAGCGGGTGTGCCACGGCGGAGGGGCGGTTCCGGGGCG CGCGCTGGGGCGGCCGGCGGGCCCGGGGTTGTGCCACCGGGGTTCGAGGGCTCTCCGCCG CCTTCTGGAAATGGAGGGCTGTCTCGAGTTTCGCAGGACTTCTGTGGCGCAGAAAGT CGGGACAGCTGGTTCTTCGGGTGTACCGTGAGAATGCTCCCTCCTAG | 7354 |
| | 2 | MEAARGFRGLLWRRKSGQLVLLGCTLRMLPRPGPPLH TLLF* | 7355 | ATGGAGGCTGCTCGCGGTTTCCGAGGTTCCTGGCGCAGAAAGTCGGGCAGCT GGTTCTTCTGCTGTACCGTGAGAATGCTCCCTCCTAGCCAGGCCCGCTCTGCA CACCCTTCTTTTGCTTAG | 7356 |
| | 3 | MPAFFA* | 7357 | ATGCCAGCGTTTTTGCTTAG | 7358 |
| | 4 | MYLTVRGVEFGLLIEPPVLG* | 7359 | ATGTATCTTACTGTAAGAGAGTGTGGAGTTTGGCCTACTAATTGAACCCCAGTCCTT GGATAA | 7360 |
| hsa-mir-611 | 1 | MGVFLR* | 7361 | ATGGGCGTCTTCCTGCGGTAG | 7362 |
| | 2 | MEPTRPAQSCPGNRRFGSRTPGLAMRTRKGAMSKCFA SLPAGSRAGLAPGNCTVLALGSGRR* | 7363 | ATGGAGCCGACCCGGCCAGCGCTCAAGTGCCTGCCGGGAACCGCAGGTTGGTTCGG CACCGCCGGACTGGCCAACCGCCCAAAAATCGGGCAGTCCAGTGTTTCGC TTCGTCGCCGGCAGGGAGCCGCGCGGCTCGCTCCTGGGATCAACTGCACAGTCCT GGCTTGGGGAGCGGGAGGCGGTGA | 7364 |
| hsa-mir-612 | 3 | MFRPAAGREPRRARSWDQLHSPGFGEREAVSLPAPRPL PHQCVWGEVGMGSPGVRKRMGEEKEEVLGTGELSQFS TNPIVNAFN* | 7365 | ATGTTTCGTTCGGCTGCCGGACGAGAGGAGCCGCGCCGGCTGCTCCTGGGATCAACTG CACAGTCCTCACCAGTGTCTGGGTGCTCGGGGTGAGTGGGAGTGGGAGGAAGTGTTAGGAAGTGGTAGCTTTCACAAAAG GATGGGAGGGAGGAGAAGAGAGAAGGAAGTTAGGAAGTGGTAGCACTTTCACAAACTTCCA CAAACCCTATTGTAAATGCCTTCAATTAA | 7366 |

Figure 1 (Continued)

| | | | | | |
|---|---|---|---|---|---|
| | 4 | MPSINWDFFLYWLIDLRQGLARAPRLQCSGTTHAHCGLDLPGSNDPPTSASVVARTTGACHQARAHF* | 7367 | ATGCCTTCAATTAACTGGAGTCTTTTCTTACTGGTTGATTTGATTTAAGACAAGTCTTGCTTCGGGCACCCAGGCTGCAGTGCAGGCTGCACAATCATAGCTCACTGCGGCTCGAACCTCCCAGGCTCAAACGATCCTCCCACCTCAGCCTCTGTAGTAGCTAGGACTACAGGTGCCTGCCACCAAGCCGGCTCATTTTAA | 7368 |
| hsa-mir-613 | 1 | MGGASVPKISPKCG* | 7369 | ATGGGCGGAGCTTCGTTCCAAAATTTCCCTAAGTGCGGTGA | 7370 |
| | 2 | MFRAPCHRLRARGTRKARAGAWRGCTPPCLGKVELGSAGGWRWPGKEHLFATKKKKKKKEEIEEKCVISTATQNPS* | 7371 | ATGTTCCGCGCGCCGTGTCACCGGCTCGGGGCCCAGGGTACTCGAAGGCGCGGGCAGGAGCCTGGCGAGGATGCCACTCGCCCTGCTTGGAAAGGTAGAACTGGGAGTGCGGGAGGGTGGAGGTGGCCGGATGGCAATTACAGGAAAATAGAGGAGAAATGGTATTTCAACGCCACTCAGAAAAAAAAAAAAAAGAGGAGAAATAGAGGAGAAATGGTATTTCAACGCCACTCAGAACCCATCATAA | 7372 |
| | 3 | MHLFLPWKGRTGCGRYEVARKRTPLRNQKKKKKKRGNRGKMCYFNRHSEPHQPVGVIFIELNFKKVFFDPQSVFAGGIC* | 7373 | ATGCACCTTCCCTGCCTTGGAAAGGTAGAACTGGGAGTGCGGGAGGGTGGAGGTGGCCCGGAAAAGAACACCTTCGCAACCAAAAAAAAAAAAAGAGGGAAATAGAGGAAAAATGTGTTATTTCAACGCCACTCAGAACCCATCATAATTCAGCCAGTCGGTGTCATTTTATTGAATTAAATTTAAAAAAGTTTCTTTGATTTCCAGAGCGTTTTTGCGGGAGGAATATGTTAA | 7374 |
| | 4 | MLKQTQDTK* | 7375 | ATGTTAAAACAAACTCAAGATACGAAATGA | 7376 |
| | 1 | MGDSFSFL* | 7377 | ATGGGTGATTCCTTTCTTTCTTGTAA | 7378 |
| | 2 | MICKFIDLPVVSI* | 7379 | ATGATATGCAAATTTATAGACCTTCCAGTTGTTCATCTGA | 7380 |
| | 3 | MQJYRPSSCFHLSPLFRLFISASPCSPIRHLSSQLFFPIPLS* | 7381 | ATGCAATTTATAGACCTTCCAGTTGTTCATCTGAGTCCCTTTCAGGCTTTTATCTCTGCTTCCCCTTGCCTCCCAATCAGGATCCCTCCCTCAGCTCTCTTCTTTCCCATTCCACTCTAA | 7382 |
| hsa-mir-614 | 4 | MQSQDESRGSKINTAAAFSLCFYRKVCVAAFEESCFRLCKMMLSLVKVLVWSQETWLFFFFLRSLALLPRLECSGMISACCDLHLPGSSNSPASASRVAGITGSQYHTQLIPVFLVETGFHHDDQAGLELLTSGDPSTSAFQIAGITGVNHCPQSKRLGFYSCLL* | 7383 | ATGCAATCACAGGATGAGTCAAGGAGCAAATAAATACTGCAGCTGCTTCTCTCTTTGTTTACAGAAGATGCTCTTTTGAGACGAAGAAGTGCTTGGAATGGTCTCTTTTGAGACGGAGTCTTGCTCTGTTGCCAGGGCTGGAGTGCAGTGCATGATCTCGGCTTGCTCGACCTCCAGCTGCTCCAGGTTCAAGCAACCACCCAGCTAATTTCTCAGCTCCTGAGTAGCTGGGATTACAGGGTTCACCATGACAGCCAGGCTGTCTTGAACTCCTGATTAGTTAGAGACAGGTTCACCATGACAGCCAGGCTGTCTTGAACTCCTGACCTCAGGTGATCCATCTACCAGGGCATTACAGGGTCTGAACTCCTGACCTCAGGTGATCCATCTACCAGGGCATTACAGGTGTGAACCATTGCCCCAGTTAGAGGCTTGGCTTCTATTCTTGTCTCTGTAA | 7384 |
| | 1 | MGGHRQKLRASLSSFPTLWPPKGRRNAGAGVELGSCRCLRPSSLPGSSSCPLLATLLNFVWLLDDYNYFYF* | 7385 | ATGGGAGGGGAGAGACAGAAGTTGAGGGCATCTCTTCCTCCGACCCTCTGGCCCCAAGGGCAGGAGGAATGCAGGAGGAGAGTTGAGCTTGGGAGCTGCAGATGCTCCGCGGCCCCTCTCCGGCTTTGAGCTCTCCTGCCGCCTCTTGCAACTCTCCTAAATTTGTTGGCTTTGGCCTTTTGA | 7386 |
| hsa-mir-615 | 2 | MQEQELSLGAADASAPPLSQALPPAPFLQLSLLPGFWMHHFHFEFI* | 7387 | ATGCAGGAGCAGGAGTTGAGCTTGGGAGCTGCAGATGCCTCAGGCACTCCTGCCCTTAATTTGTTTGGCTTTTGGATGATTTATAATTTTTATTTTTGAATTTATATAA | 7388 |
| | 3 | MPPPLLSPRLFLLPPSCNSP* | 7389 | ATGCCTCCGCGCCCTCTCTCCTCGGCTCTCCTCCTGCCCTCTTGCAACTCTC | 7390 |
| | 4 | MCVCVELRQARQRHRMREDEKESGRERGRGEGERESDSSAR* | 7391 | ATGTGTGTCTGTGAGCTGAGACAGGCTCGGCAGCGGCACCAGAATGAGGGAAGACGAGAAAGAGTGGGAGACAGGAGGAGAGCAGAGGGGAGAGGAGTGACAGCAGGCGCTCGGTAA | 7392 |
| | 1 | MRLGATGEEDGAEWLQIPCEGYPGACPAHPPGPFHSSW* | 7393 | ATGAGACTTGGGGCTACGGGGAAGGATGGGCGAATGGCTGCAGATACCCTGCGAAGGCTACTCAGGCGCCTGCCACCCCCAGGTCGCCTCGCCCATTCCTCTTGGTAG | 7394 |

Figure 1 (Continued)

| | | | | | |
|---|---|---|---|---|---|
| hsa-mir-615 | 2 | MGPNGGCRYPAKATQAPALPTPQVRPIPLGSSEIALL* | 7395 | ATGGGGCCGAATGGCTGCAGATACCCTGCGAAGGCTACCCAGGCGCCTGCCCTGCC CACCCCCAGTGCAGTCCGCCCATTCCTGGAAGGCTACCCAGGCGCTGCCTGCCACCCCAGG | 7396 |
| | 3 | MAADTLRRLPRRLPCPPPRSAPFLLVAQKLLSCEPYGPR SLESLAQRPFPQRAHNGPFPLPCSRNICGFNLASPCPQL TSIFCLKPLA* | 7397 | ATGGCTGCAGACACCCTGCGCCTGCCTCGCCGCCTGCCCTGCCCGCCACGCCGCCCAGG TCCGCCCCCATTCCTCTTGGTAGCTCAGAAATTGCTCTCTTGTGAACCTTATGGATTCA GGTCCCTGGAAAGCCTAGCCCAGAGACCTTTCCCAAAGGGCACATAACGGGCCTT GTCCTCTGCCATGCCACGTAATATTTGTGGAGGCTTCAATCTTGCTTCTCCATGTCC TCAATTAACATCTATTTTCTGTCTAAAACCCTGCCATAG | 7398 |
| | 4 | MDSGPWKA* | 7399 | ATGGATTCAGGTCCTGGAAAGCCTAG | 7400 |
| hsa-mir-615 | 1 | MSSYVANSFYKQSPNIPAYNMQTCGMYGSASEVQASR YCYGGLDLSITFPPPAFSNSLHGVDMAANPRAHPDRPA CSAAAAPGHAPGRDEAAPLNPGMYSQKAARPALEEFRA KSSGEIKEEQAQTGPAGLSQPPAPPQIYPWMTKLHMS HGKL* | 7401 | ATGAGCTCCTACGTAGCCAATTCATTCTATAAGCAGAGCCCAAATATCCTGCCTAT AACATGCAAACTGTGGGAACTATGGATCGGCTCAGAGGTGCAGGCATCCAGGTA CTGCTACGGCGGATTGGACATGGCTGCCAACCACATCACTTTCCCACCGCCTCCAACTC TCTCCACGGGGTAGACATGGCTGCCAACCGCTCACCCGACGCGGCTCCTCTGA CAGCGCGCCGGCCCTCCGGGACACGTCCCGGGCAGAGACGAAGCGGCTCCTCTGA ACCCGGGATGTACAGTCAAAGAAGGCGGCTCGCCGCCAGACCGCTGAGGAGCAGCTAA AGCAGTGGGGAGATCAAAGAGGAGCAGGCCAGACAGGCAGCCCGCCAGACTAA GCCAGCCACCGCCCGCCCACAGATTTACCCGTGGATGACCAAACTGCACATGAGCC ACGGTAAACTTTAG | 7402 |
| | 2 | MDRPQRCRHPGTATADWT* | 7403 | ATGGATCGGCCTCAGAGGTGCAGGCATCCAGGTACTGCTACGGCGGATTGGACTTAA | 7404 |
| | 3 | MRGK* | 7405 | ATGCGGGGCAAATAA | 7406 |
| | 4 | MARKTVH* | 7407 | ATGGCTCGTAAAACTGTCCACTAA | 7408 |
| | 1 | MPACHFLIGRFWGPAPESRRARPW* | 7409 | ATGCCGGCTGCCACTTTCTGATTGGTAGGTTTGGGGTCCGCCCTGAGAGGAGG GCAAGGCCATGGTAA | 7410 |
| | 2 | MVKDYSQALPRSET* | 7411 | ATGGTAAAAGATTACAGCCAGGCGCTCCGAGTCAGAGACTTAA | 7412 |
| hsa-mir-616 | 3 | MLKMSGWQRQSQNQSWNLRREASTDSHLPETLLPSPQS WGIVRSLGRASLLHSEVRDRPREEWGESLILGWCLQTPI ASDDGVSPPLPGAGTIRALLCAAGQRDLGCPWEIHSFP* | 7413 | ATGTTAAAAGATGAGCAGGCGGTGGCAGCGACGAGCCAAAATCAGAGCTGGAACCTGAG GAGAGAGGCGAGTACTGATCTCCATCGATTCCCATCAGTCCCATCTCTCCTCAAAGTTG GGGCGTCCGCTCTTTAGGATGCGGCCTCACTCCTCCCACAGTGAAGTTAGGGACCGTCC GAGAGAGAATGGGAGAGTCCCTTATTCTGGGGTGGTGCTTACAAACCCTATTG CTTCGGACGACGGCGTCTCTCCACCCTGCCTGGTTGCCCTTGGGAAATTCATTCTTTCCGTAG GTGCTGCTGGGCAAAGGAACCTCGGTTGCCCTTGGGAAATTCATTCTTTCCGTAG | 7414 |
| | 4 | MGRVPYSGYVLTNPYCFGRRRLSTPARSRNTGPALCCW AKGPRLPLGNSFFPVANFRPHR* | 7415 | ATGGGGAGAGTCCCTTATTCTGGGGTGTGTTACAAACCCTATTGCTTCGGACGA CGGCGTCTCTCCACCCTGCCTGGAGCCGGAACACGGGCCTCTGCTCTGTGCTGTGG GCAAAGGACCTCGGTTGCCCTTGGGAAATTCATTCTTTCCGTAGCCAACTTCAGG CCTCATCGTTAG | 7416 |
| | 1 | MQSLSDTCSAPHRN* | 7417 | ATGCAGTCGCTTCGGATACCTGCTCAGCTCCGCACGCAACTGA | 7418 |

Figure 1 (Continued)

| | | | | |
|---|---|---|---|---|
| hsa-mir-617 | 2 | MLKPSVTSAPTADMATLTVVQPLTLDRGKGAARSPGH RVPSPLLPSPPANSQRDMGRAQAGGEGERGRARKAFAP RTEHFLPLSLPATFPLPTVLAPPRGRLLLALGSPLPLPA PRRVVSGPLALLEPLRGDGYRRQGLGVGEGQRASSPGQ SPEETGEGAACQLAWRRGPGGRKFVQAPEGEGRSNCW SPGGHSGGGLGAPLGCRAHSGAAAGRELPSAERARQS AGSRAPAAEIGSPRLLRDPKRRGSRLLPPPAAPGR* | 7419 | ATGCTGAAGCCGAGCGTCACTTCGGCTCCACGGCAGACATGGCGACATTGACAGT GGTCCAGCCGCTCACCCTGGACAGAGGTAAGGGAGCGGCTCGTGCCAGGCCAGT GCGTCCCCTTCCTCCTCCCTGCCAATTCCCAAGCGGACATGGGAC GCGCTCAGGCAGGAGGAGAACGAGCGAGCCAGGAGACGAGCCAGGAAGGCGTTCGCGCC GAGAACAGAACACTTCTTCCCCTTCTCCCGAGGGAGCACTTCTCCGAGTCCTGCCGCTGCCA CTGTACTTCCGCTCGCCGTCCTGTCCCGGCTCTCTGGCTCTTGTTGAGCCGCTGCCA GGGGACGGCTATAGGCGCCAGAGGAGACCGGAGGGAGGAGCCGCTGTCAGTTGCTTGG CGCAGGGGCCCGGGAGGAAGAAGTTGTCCAGGCGCCGGGAGGGCGAGGGTCGGT CCAACTGCTGGAGTCCGGTGGCCACAGTGGCCTGCGAGCAGCAGGAGCTGCCTCTGCGAAAG GGCAAGCAGCAGCCCGGGAGCCGCGGAGCCCAGCAGCCCAGATGCTCTCCGGGCC TTCGAGATCGAAAGCGGCACGGGTGCGCTGCCGCCGAGCTCCCGGT CGATAG | 7420 |
| | 3 | MESSAAIGASLVHPCGVIPVPECVGFLPGSSVQ* | 7421 | ATGGAGTCCTCCGCTGCGATCGGGGCCTCACTGGTGCACCCTGTGGGGTTATACCT GTCCCTGAGTGTGTGGGTTTCCTTCCGGCTCCAGCGTCCAGTGA | 7422 |
| | 4 | MKALESYGSAEEDTL* | 7423 | ATGAAGGCGCTCGAGTCCTACGGCTCTGCAGAAGAGGACACCCTCTAG | 7424 |
| | 1 | MQSLSDTCSAPHRN* | 7425 | ATGCAGTCGCTCTCGGATACCTGCTCAGCTCCGCACCGCAACTGA | 7426 |
| hsa-mir-618 | 2 | MLKPSVTSAPTADMATLTVVQPLTLDRGKGAARSPGH RVPSPLLPSPPANSQRDMGRAQAGGEGERGRARKAFAP RTEHFLPLSLPATFPLPTVLAPPRGRLLLALGSPLPLPA PRRVVSGPLALLEPLRGDGYRRQGLGVGEGQRASSPGQ SPEETGEGAACQLAWRRGPGGRKFVQAPEGEGRSNCW SPGGHSGGGLGAPLGCRAHSGAAAGRELPSAERARQS AGSRAPAAEIGSPRLLRDPKRRGSRLLPPPAAPGR* | 7427 | ATGCTGAAGCCGAGCGTCACTTCGGCTCCACGGCAGACATGGCGACATTGACAGT GGTCCAGCCGCTCACCCTGGACAGAGGTAAGGGAGCGGCTCGTGCCAGGCCACC GCGTCCCCTTCCTCCTCCCTTCCCCAGCGGAACATGGGAC GCGCTCAGGCAGGAGGAGAACGAGCGAGCCAGGAGACGAGCCAGGAAGGCGTTCGCGCC ACTGTACTTCCGCTCGCCCCCGCCAGGGTCGTCTCCGGTCCTGGCTTTGTTGAGCCGCTGCGC CTCCCAGCCTGCCAGCCGGGTCGTCTCCGGTCCTGGCTTTGTTGAGCCGCTGCGC GGGGACGGCTATAGGCGCCAGAGGAGACCTGGGGTTGAGAGGGCAGAGAGCAAGCT CGCAGGGGCCCGGGAGGCGCAGGGGGAGGAGCCCGCTGTCAGCTTGCTTGG CCAACTGCTGGAGTCCGGTGGCCACTCGGGGGTGCGGGTCGGGCGAGCAGCAGGAGGTCGGT TGCGGGGCGCACAGTGGCGGGAGAAGTTGTCCAGGCGCGGTGAGGGCGAGGGTCGGT GGAAGGCAGAGCGGGGAGCCGGGAGCCGAGCCCCGAGCAGGGACGCAGATCGGCTCCCGGAAAG TTGAGATCGAAAGCGGGCACGGGTGCCGAGGGTGCGCCGGCAGGGGCGGCTGCCGCCGAGCTCCCGGT CGATAG | 7428 |
| | 3 | MESSAAIGASLVHPCGVIPVPECVGFLPGSSVQ* | 7429 | ATGGAGTCCTCCGCTGCGATCGGGGCCTCACTGGTGCACCCTGTGGGGTTATACCT GTCCCTGAGTGTGTGGGTTTCCTTCCGGCTCCAGCGTCCAGTGA | 7430 |
| | 4 | MKALESYGSAEEDTL* | 7431 | ATGAAGGCGCTCGAGTCCTACGGCTCTGCAGAAGAGGACACCCTCTAG | 7432 |
| | 1 | MALVTLQRSPTPSAASSSASNSEVSPGLAAPGLGRRTPR RGRRSSWGRACGAGGRLRGLLGAPP* | 7433 | ATGGCCCTTGTGACCCTGCAGCGCTCGCCACGCCAGGCGCGCTCCTCTCGGCC AGCAACAGCGAGGTGAGCCCGGAGCCCGGCTGCGCCGCCGGCGACGCC GCGCCGAGGCGCCGCGGAGCTGCGGAGCTGGGCCCCGCGTACCGCGGC GGCTCCTCGGGGACCCCGCGTAG | 7434 |
| hsa-mir-619 | 2 | MQCDPSGSVCRILCVRCDPHQQVTFILG* | 7435 | ATGCAGTGCGACCCCTCTGGGAGTGTCTGCAGGATACTGTGTGTGCGCTGTGACCCA CATCAGGGGGTTACCCCATCTTGGGGTGA | 7436 |
| | 3 | MCNWDP* | 7437 | ATGTGCAACTGGGACCCTTGA | 7438 |
| | 4 | MPGCAM* | 7439 | ATGCCTGGCTGTGCGATGTGA | 7440 |
| | 1 | MPRSGGRARGS* | 7441 | ATGCCCCGCTCTGGCGGCCGGGCTCGCGGAGGATCATGA | 7442 |

Figure 1 (Continued)

| | | | | |
|---|---|---|---|---|
| hsa-mir-620 | 2 | MTAAANWVANGASLEDCHSNLFSLVSSRAAGRGLCRG RGGVPDLRRRPTFSSRRDFAPPSRLPAVRLSPILPLLDR LSLALDPKQCLFGSLKHCERGARRGICMWKSRSCGFWV ALRTPTLCCNRTPLLLPFPPFFSPRKCGRLCLVLPRLRSA TSSPVVGSAACPPACLLNFFKFHNDTCNFALK* | 7443 | ATGACTGCGGCAGCGAACTGGGTGGCGAACGGGGCAGCCTGGAGGATTGTCACTC CAACCTCTTTTCGCTGGTGAGTAGCCGCGGCGCAGGGGAGGGGCTGTCCGGGAA GGGGGTCCCCTGCGACTTCTCCCCGCCATCTCTGGAATCCCAGTGTTTATTTGGCTCTTTAAAAATCATT TGTGAGCGCGGCTCGGCGTGGAATTTGCATGTGGAAGTCTCGGAGCTGCGGATT CTGGGTCGCCACTGTTTCCCCGTAAATGTGGAAGGCTTTGCTCGTCCTGCCGCC TTCCCCCTTTTTTCCCCGTAAATGTTTGGATCAGCTGCCGCCCCGCCTGCTCCT TTGAATTTTTAAATTCCATAATGACACCTGCAATTTCGCCCTAAATAG | 7444 |
| | 3 | MWKALPCAAAPPIGNLFPRCWISCLPARLPEFF* | 7445 | ATGTGGAAGGCTTTGCCTTGTCTGCCGCGCCTCCGATCGGCAACCTCTTCCCCGT TGTTGGATCAGTCGCCTGCCCCGCCCCTGCCTTTCGAATTTTTTAA | 7446 |
| | 4 | MTPAISP* | 7447 | ATGACACCTGCAATTTCGCCCTAA | 7448 |
| hsa-mir-621 | 1 | MPARREGRRAGRCRRGC* | 7449 | ATGCCTGCGCGAAGGGAGGGCGGCGTTGCGACGTGGGTGTTAA | 7450 |
| | 2 | MEPLVNGDLLAAQEWAAGQGR* | 7451 | ATGGAGCCGCTTGTGAATGGAGACTTGCTGGCCGCCAGGAGTGGGCGGCTGGCA GGGGCGGTGA | 7452 |
| | 3 | METCWLPRSGRLGRGGERLGSGQESWKSSP* | 7453 | ATGGAGACTTGCTGGCTGCCCAGGAGTGGGCGGCTGGGCAGGGGCGGTGAACGTTT AGGGTCCGGCAAGAAGTTGGAAGTCTGTCCTGA | 7454 |
| | 4 | MASWPAAPLARSWDLPAAVRVPWVWKMQPHLLTLPSK KKLFSPRVEKSGWSALLFLSCTLV* | 7455 | ATGGCATGGCCTGGCCTGGCCGCTTAGCGAAGCTGGGATCTTCCGCAGCAGTT CGTGTTCCTGGTGCAAAATGCAGCTCATCTACTGACTCTCCTCCAAAAAAAG TTATTTTCCCAAGGGTCGAGAAAGTGGTGGTCGGCACTGTTGTTCCTCAGTTGC ACCCTGGTGTAA | 7456 |
| hsa-mir-623 | 1 | MRRVRRSSAASGLAAPDSSLRQECACAVAGARTSASPP PAPSGAPSPAGPCSPAPAPVCGSVSTGLRHPGCPLHATLG TSLRRLGQRGPSGLPEVVGPTLQTRVRTLLVPGLGGQR KPPFRPGGANGDKAPPPAPTPGIPRCSAQESLGAAAS GQVPWCSRGPAPGPLRSVCRAEGRGRPPPYHAPFF* | 7457 | ATGCGCCGGGTGCGCCGTTCGTCAGCGGCAGGGAGTGGCCTCGCCGCCGATTCGTC GCTCCGCAAGTGCACTCCTGGGGCCTCCGAGCCGGCCGGGACCCATGTTCACCAGCACCGGCTCC CCCGGCGCTCTGTGAGTAGCACCGGCGCCTCGCAACCTGGCTGCCGCCCTACACGCACCCT AGGCACCTCTTTGAAGGAGGTGAGAGGCAGCAGGGACCCTGCAGGTTGCCGGAGGTGG TGGGGCGAACCCTCCAGACCCCATTCGGAACCCTGCTAGTTCCCGGTCTTGGGGTC AGCGGAAACCCGCCCCACCTGGTATCCTGCCCAGGGGCGAATGGGGACAAAGCCCCGCCG GCCGCAAGTGGGACCCCAGGCAGTGCCCGGTATCCGCAGGGCCGGCCCAGCGTCTTGGGGC AGCGTGTGCCGCGCGGCGTGAAGGGGCCGTCCCCCATTCCTTTTTAG | 7458 |
| | 2 | MFTSTGSSGLCEYRPPPSWLPPTRHPRHLFEEAGAAGTL GFAGGGGADPPDPRPNPASSRSWGSAETAPISAWRGEW GQSPAARPDPTWYPQVLCPGVSWGRCKWAGALVFSW AGPRPFAERVPR* | 7459 | ATGTTCACCAGCACCGGCTCCAGTGGGCTCTGTGAGTACCGACCCCCATCCTGG CTCCCCCCTACACCGCCACCCCTCGACATCTTGAGGAGGCTGGGGCAGCGGGGAC CTCTGGGTTGCCGGAGGTGGTGGGGCCGACGACCCCCAGACCCCGGGAACCCTGC TAGTTCCGGTTCTGGGTGTCAGTGGAGCAAGGGAACCGCCGATTGCTGGAGGGTG AATGGGGAAGCCCCGCCGCCCGCCCGCCGACCCCTCGACCCCACCGGTATCCCCAGGTGCTCT GCCCAGGAGTCTTGGGGCCCCTTTGCCGGGCAAGGTGGTGCCGCGCTGA | 7460 |
| | 3 | MGTKPRRPPRPHLVSPGALPRSLLGPLQVGRCPGVLVG RPQALCGACAALKEGAVPLTMPHSPRLGGPN* | 7461 | ATGGGGACAAAGCCCCGCCGTCTTGGGCCGCACCCCGACCCCACTGGTATCCCAGGTGCTCTG CGGCCCAGGAGCTCTTGCCAGCCCTTGCAGCGTGTGCCGCCAGTGGGACCCGGGAATCCCT TACCATGCCCCATTCTTTAGGCTTGGGGGACCGAACTAA | 7462 |

Figure 1 (Continued)

| | | | | | |
|---|---|---|---|---|---|
| | 4 | | MCFFFSLQEEFLDKHTLMRVLSSGGKLGSRGEGAQLCC WMLLFSWRVSGGQVGGGVFLQPVKRLFSLSVWN* | 7463 | ATGTGTTCTCTTCAGTCTCCAAGAAGAGTTTTAGACAAACACACTGATGAGA GTGCTTTCAAGTGGAGTGGAAGTAGGAAGTCGTGGCGAGGGAGGCCAGCTGTCTG CTGGATGTTGCTGTTTCCTGGCGTGTAGCGGTGGTCAGCAGGTAGGGCGGAGT ATTTTACAGCCAGTTAAACGGCTTTCACTGAGTGTGTGAATTGA | 7464 |
| hsa-mir-623 | 1 | | MITFIQSRTTSR* | 7465 | ATGACCTTCACGCAGTCAGAACGACTTCCAGGTAA | 7466 |
| | 2 | | MKQWQYFLLLGTFVFSFTFYSEKCNL* | 7467 | ATGAAGCAATGGCAGTATTCCTTTATTAGGCACATTGTTTCAGTTTCACTTTT ACTCAGAGAAGTGTAATTATAA | 7468 |
| | 3 | | MAVPFFIRHICFQFHFLLREV* | 7469 | ATGGCAGTATTCCTTTATTAGGCACATTGTTTCAGTTCACTTTTACTCAGAG AAGTGTAA | 7470 |
| | 4 | | MFNLFLMPSRHT* | 7471 | ATGTTTAATCTTTTTTAATGCCAGTAGGCATACTAG | 7472 |
| hsa-mir-623 | 1 | | MVASPFAKWFAVKTRVLLSRLHLKSRFANPQRMSIAP CWAPGLW* | 7473 | ATGGTAGCGTCACCATTTGCTAAATGTTTGCTGTGAAGACTACTAGTACTGT TCCAGGTACATTTGAAAAGCTTCTTTGCCAATCCTCAGCGAATGTCAATTGCTCCCT GCTGGGGCTCCAGGTCTGTGGTAG | 7474 |
| | 2 | | MAVCCEDY* | 7475 | ATGGTTTGCTGTGAAGACTACTAG | 7476 |
| | 3 | | MIPSFLSVLPVTFLLLSRLLM* | 7477 | ATGATTTTCAGTTTTCTATCTGTACTGTCACTTTTCTTTACTCTCACGGCTTTT GATGTAA | 7478 |
| | 4 | | MCKLAF* | 7479 | ATGTGTCGCTTGGCCTTTGA | 7480 |
| | 1 | | MSGL* | 7481 | ATGTCAGGCCTCTGA | 7482 |
| | 2 | | MSLK* | 7483 | ATGTCATTAAAGHAA | 7484 |
| hsa-mir-623 | 3 | | MSVRLYTVEASLAGAVGLHPKLLCWSFPMYSVDVFAPS VLIAIPNQSLEHQLWP* | 7485 | AGTCTGTCAGAGTAGTACACAGTAGAAGCATCCTTGCAGGGCTGTTGGGTTGCAT CCTAAGCTGTGCTGGACTTCCGATGTACTCTGTAGATGTCTTTGCACCTTCTGTCC TCATTGCCATCCCAATCAGTCCTGAACCACGTGGCCCTGA | 7486 |
| | 4 | | MSLHLLSSLPSPISPWNTSCGPDSFSPCMECTGKACGLW DSSRLEQDRGRRDGAEGSR* | 7487 | ATGTCTTTGCACCTTCTGTCTGCATTGGCGATCCATCCCAATCAGTCCTGAACCAGCT GTGGGCTCGGTTGGAGATGGAGCAGTCAGCAGCTGAATGCCAGGCAAGCGTGTGCCTTT GGGACTCCAGCCGACTAGAGCAAGACAGAGGAAGAGACGAGGCAGAGGGCAG CCGATAG | 7488 |
| | 1 | | MEEGL* | 7489 | ATGGAGGAGGATTGTAA | 7490 |
| | 2 | | MAAAGGSSLL* | 7491 | ATGGCGGCAGCCGGCAGTTCCCTGCTGTGA | 7492 |
| hsa-mir-624 | 3 | | MDELAGGGRGGPGMAAPPRQQQGPGGNLGLSPGGNG AAGGGRPPASEGAGPAAGPELSRPQQYTIPGILHYIQHE WARFEMERAHWEVERAELQVPRWGRCAAGAAAAGFPA GGWGWGLHSAGAGALGGRAEPTCAAQVYMVLSTAFP GVPLPLSRISLLPNLHWLRGAGLLGAAHLAFSMASAGAP PEAAFPGLRGLGPSTSLWESPVWGLSTLSLLLFVPLEMK SPKRGTRIGILPPFSGGPPFPIWRIWPPSDLVRACPLTAT LLSWAARVHSDLGLTCEVLFPIVNFKYFLT* | 7493 | ATGGACGACGAGCTGGCCGGAGGCGGTGGTGGGGAGGGATGGCGGCCCCTCCCG GCAGCAGCAGGGACTGGGGGGAACCTGGGCCTTCGCCGGGGGAACCGGACG GCGGGGCGGCCGGCGGTCCTCGGAGGGAGCGGGTCCGGCAGGCCCGA GCTGTCCGGTGAGATGGAGCCACTGGGAGGTGCCACTACTACCAGCAGCA GGTACCTCGTTGGGGTCGGTGCGGGAGCTGGGTTCCCGGCCGGG ACCTACCTGTGCTGCAGTTGTGATGTCCCCAACCTTCACTGCTACGGTGGCGGC CTCCCCTCTTTGCCGCCATAAGCTTGCCTTTAGTATGGCGTCTCCGGAGTCCC GCGGCCTTCCCGGCCTCCCACCCATTGGCCGAGCACCTTCCTGTTGTTCGAGAAGAG GGTTTGGGCCTCTCAACACTGAGTTTGCTCTTGTTTGTTCGGACCACCCCTT TCCGAATTGGCGATCTTCCTGGCTCTACGGGTGCACAGTACTTGGACTGACCTGAA GTTTTATTTCCCATGCGTCAACTTTAAGTACTTTCTCACCTGA | 7494 |

Figure 1 (Continued)

| | | | | | |
|---|---|---|---|---|---|
| | 4 | MLPYSLGFSVVHPYLVTHQRFQH* | 7495 | ATGCTGCCTTACTCACTTGGATTCTCTGTAGTTATTCCTTACTTAGTGACTCATCAAC GCTTTCAGCACTGA | 7496 |
| hsa-mir-625 | 1 | MHQILGKTFLGQVPFFFFSWKEVGKISALIPRILEVKME HQTKMEFLGKCKALYLGJSKYYTV* | 7497 | ATGCACCAAATCCTGGGCAAAACATTCCTAGGACAGGTTTTTTTTTTTTCA GTTGGAAGGAGGTAGGGACAACAAGTGCTTTAATTCCTAGGATTTGGAAGTAAAA ATGGAACACCAGACAACTAGTATTACAAGTGTAA | 7498 |
| | 2 | MHNQLEVVLFFKFYF* | 7499 | ARGATTATTAACCACTAGAAGTAGTTCTTTTTAAATTTATTTTAA | 7500 |
| | 3 | MRVLLCCPG* | 7501 | ATGAGGGTCTTGCTATGTTGCCCAGCTGA | 7502 |
| | 4 | MLPRLKWLLTGTMWHCSLELLGLSDPSCFPYLKKKKLR LLVKIFLKCCV* | 7503 | ATGTTGCCTAGGCTGAAGTGGCTACTGACAGGCACGATGTGGCACTGCAGCCTGA ACTCTTGGGCTTAAGTGATCCTTCCTGCTTCTTATTCTATCTTAAAAAAAAAGTTACGC TTGCTTGTTAAAATATTTTTAAAATGCTGTGTTAA | 7504 |
| hsa-mir-625 | 1 | MLLLRSPPAQRGRGRGESLAHARVAVGGSGRRMRALS QKPGTPRGALPHSRAHAGARGRGFFPACARCQSRSGACAR YLRPTRAAGSLLSRPPPHPTPAAWPQTRPFVSPRNGAG TAQGRAPWTQLALGLALSATARLAPPRALPQSVAPKAP LSGGGGSCFRFFLSVRSGVASSTQPPFPLPHRGAAAAEG CGFGSCDGERRRPPLLPPGVRGRFGSRAPRASGSWAGL RAGSEEAPRLSLLVHPGLLLQLLPVNQRLSEKWGGSPR DALADALAQPRGRGQRVRGARLSSRDAELRRCCPRRR ASLPLRAGAKA* | 7505 | ATGCTGCTGCTACGCTCTCCACCGGCAGCGAGAAGGGCGGGGAGAATCCT GGCACATGCCAGGTTCGCGTAGGTGGCAGCGGCTGGCAGCATGCGGCCTCTCCC AGAAGCCAGGAACGCCCGAGCGGCCGCCCATTCGCGGCGCACGCGGCCT GGCCGAGGCTTCCCCCGGCTGCTCGTTGTCAGAGCCGTCCCTCCCCCATCGC TATCTCCGGCGACCCGAGCAGCCGGTTCCCCCCCCGTCTCTCCCAGCCCCCATCGC ACCCGCGACCCCGCGACCCGACCCGCCAGCGCCCGTCCCCGCAGCCTGCTCGCGGAGGCC GGCACTGCTCAGGGTGCGGCGCTCGCGGCGCCCGCGCCCAGCTGCTCGGCCGCGTCA GCGACTGCCGGCTGCGGCGGCGGCGTTCGCGTTTCGCTCCCACTCCCTCGTCGGTCGGGA CCGTTAAGCAGCCACGGCCCGGGCCGCTCTGTCGGGCAGCAGCCGGGCCCTCTGGC GAGGCTGGCTTTGGCAGCTGCCAGCGCGCGGGGAGCCGGCGAGACCCCTCTGCTCCC GCCTGGGGTAAGGGGCGTTTTGGAGGGCCATCTGCAGCGCCCCCCGAGCCCAGGGGCTCGGTCTTGGG CTGGGCTGCTGCAACTGCTGCCGGTTAACCAGGCGGCTCTGGAAAAGTGGGAGGG AGCCCCGGACCCCTGCCCCCTCTCCAGCGAGGCAACGTGCCCCGCCCCCTCCCCCTC GCGCTCGCGCATCCTTGCCTAGGCAGGCAGGCCAAAGCCTAG | 7506 |
| | 2 | MPGSP* | 7507 | ATGCCAAGGTTCGCGTAG | 7508 |
| | 3 | MGPALLRVARPGPSSLSVSRCQRLPGSRRLALCLSQWR RRLR* | 7509 | ATGGGGCCGGCACTGCTCAGGGTCGCGCGCCCTGGACCCAGCTCGCTCTCGTTCG CGCTGTCAGCGGACTGCCCGGCTCGGCCTCCGCCCGGTGCCTGGCCGCCAGTCAGTGAGCGCC CGAAGGCTCCGTTAA | 7510 |
| | 4 | MPWRSPGGAGRG* | 7511 | ATGCCTTGGCGCAGCTCCGGCCGCGGGGCGCGGGCAGAGGGTGA | 7512 |
| | 1 | MLCSTPRGARRIPACIGERPRAMVPGSWRGVRS* | 7513 | ATGCTCTGCAGCACACTCCGGGCACGGAGGGCGCCAGGGCGTATCCGGCGTGCATCGGGGAGGCG CCCAAGGGCCATGTTCCCGGCTCGGAGAGGCGTGCGAAGTTAA | 7514 |
| | 2 | MGLNP* | 7515 | ATGGGTTTAAATCATAA | 7516 |
| hsa-mir-626 | 3 | MTSRVVQQREDSGTRERSGAWVCGGRPRQVCAGATLA TRYARPHAPGGVFLARSVKSLGRVFVRWGEGERGRGGGG ALRRHVDATANLRPRRTHSFPRRPGVRRVH* | 7517 | ATGACTAGCCGGGTGGTCCAGCAGCGCGAGGATTCCGGAACGCCGCGAGCGGGAGCG CGGTGGTCGGCGGTGCCGGCCCCGGCCGCCTGGTGCCAGGTATGCAGGCCTTGCTTGCCA CGCTAGCGGCCGCGCGTCGCTACCGCCGTCGGTCGGTGTCGCGAGTGGGCGCGGTGGCGGGC GCTGAGGCGGTCACGTGACGCCACAGCAATCTCAGGCCGGACGTGTTCACTGA | 7518 |
| | 4 | MRRRLACHALRPSPRAWWRVLGAKC* | 7519 | ATGCGGCAGGGCGCCTTGCTTGCCACGCTACGCCCGTCCCACCGGAGCGCGAGCGG GTTCTTGGCGCGAAGTGTAA | 7520 |

Figure 1 (Continued)

| | | | | |
|---|---|---|---|---|
| hsa-mir-626 | 1 | MSPRARPRPHFRVAQLPNWEHRRQRERPRGGRGEKRP WLGPALACVGCRSAWTGPRDDFSPGAGL* | 7521 | ATGTCACCTCGCGCGTCCCGGCCTCACTTCCGCGTCGTCAGCTACTAACTGG GAACATGACGCCAGAGAGCGGCCACGAGGCGGAGAAGGCTGAGAAGCGCCAT GGCTCGGCCCTGCCTCCGTGTGGGGTGCCGCTCCGCGTACGGTCCGGTG ACGACTTCTCGCCGGCGCCGGCTCTAG | 7522 |
| | 2 | MARFCPRVCGVPLRVVRSA* | 7523 | ATGGCTCGGCCTGCCTCGCGTGTGGGAAGCAGGTGTTATTTCTTATTCCTCTGTG TGA | 7524 |
| | 3 | MREGKTGGKSRCVFLYSSVGQPFT* | 7525 | ATGAGGGAGGGAAAACAGGTGGAATGTCAAGTAGCTCTGCCCTCAGTGCAAGGT GGGCAGCCTTTACCTAG | 7526 |
| | 4 | MGFFVSVKWSSRSLPSVQGFWDINITPPPPQSSSSQS* | 7527 | ATGGGGTTCCCGTTCTGTTAAATGTCAACATAGCTCTGCCCTCAGTGCAAGGT ATCTGGGACATTAACATCACCCCCCCCAAAGCTCCAGTAGCCAAAGT TGA | 7528 |
| hsa-mir-627 | 1 | MATQQQNNSFRVHREEGAGLRLRKRRA* | 7529 | ATGGCAACTCAGCAACAAAACAATTCATTAGAGTGCACCGGAGGAAGGGCGGGG ACTTCGCGTCCGAAGAGGCGGGCTAA | 7530 |
| | 2 | MAVLLKGL* | 7531 | ATGGCTGTGTTGTTGAAGGGCTGTAG | 7532 |
| | 3 | MHDAFEPVPHLEKLPLQHDCLAAWGPPRGRGAEAESAQ ERSGSFLRPGKWTGVHPCGLRLDATRREGLRMREGREM TTGYRHRCLWGYLGDPSDFVJ* | 7533 | ATGCACGACGCTTTCGAGCCAGTGCCGATCCTAGAAAAAGCTGCTCTGCAAATCGAC TGTCTGCTGCCTGGCGTGAGCCAGGGCCGTCGAGGCGGACAGGCGTCATCCGTGTG GGAGCGGTCGGTTGGATGCTACACGAGAGGGGGCTTAGGATGAGAGAAGGCAGAGATG GCCTTCGGTTGGATGCTACACGAGAGGGGGCTTAGGATGAGAGAAGGCAGAGATG ACCACCGGCTATAGACATCGATGTCTGTGGGGCTACTTGGGTGATCCCAGTGATCCA GTCATTTAG | 7534 |
| | 4 | MLHERGLG* | 7535 | ATGCTACACGAGAGGGCTTAGGATGA | 7536 |
| hsa-mir-628 | 1 | MHCGAQPVTACRLQTPASRLFL* | 7537 | ATGCACTIGCGGCGCCAGCGCCGTCACCGCCGTCAGAGCGCCTCGGACGCAG GTTGTTTTATA | 7538 |
| | 2 | MKIHMVRCYVRHPAGFNASLSFDDI* | 7539 | ATGAAAATCATATGGTAAGATGTTATGTGCGTCACCCTGCCGGGTTAATGCAAGC CTGTCTTTTGATGACATTTGA | 7540 |
| | 3 | MLCASPCRV* | 7541 | ATGTTATGTGCGTCACCCTGCCGGGTTAA | 7542 |
| | 4 | MCVTLPGLMPACLLMTFEPP* | 7543 | ATGTGCGTCACCCTGCCGGGTTAATGCAGCCTGCTTTTGATGACATTTGAGCCC CCGTGA | 7544 |
| hsa-mir-629 | 1 | MPGRLJCTY* | 7545 | ATGCCAGGGCGTTTGATTTGCACTCTGA | 7546 |
| | 2 | MLGAAPARPPTGATR* | 7547 | ATGCTTGGGCGTGCCTGCCGGCGCGCCCCCTACAGGCGTGACCCGCTGA | 7548 |
| | 3 | MSAQSQALLTRSTQPPREGGRPLPAEP* | 7549 | ATGTCCGCTGCAGTGCCAGGCATTGACGGCGCTCGACGCAGCGAAGGCGGCCG GCGCTCGCCCGAGCCCTAG | 7550 |
| | 4 | MYPQRRHPVSNCNSVYLSIYHGRVNEAVYLAPPFCLLL PLWCVCLCVCSHTKGDAAGGRR* | 7551 | ATGTATCCGCAGGGCAGACATCCGGTAATTGCAACTCGGTTATTTAAGCATC TATCATGCCAGGGTAAACAGAGCAGTTATCTGGCACCTCCATTTGCTTGTTGCTA CCTTTATGTGTGTGTGTGTGTTGTGCTCTCACACAAAGGGGATGCGGCGGG GGGCGCGTTGA | 7552 |
| hsa-mir-630 | 1 | MEYIFPYLHSSY* | 7553 | ATGGAGTACATCTTCCCGTACTTGCACTCATCCTATTAG | 7554 |
| | 2 | MTKISLVKHNLSQSPSQKS* | 7555 | ATGACCAAAATTAGTCTAGTAAAGCACAACTATCACAAATCTCCTCACAAAATCC TAG | 7556 |
| | 3 | MTNFIQRMENLQSSREGVQTRDREMNQGFDFHLLSFA SRGALSQVM* | 7557 | ATGACAAATTTATTCAAAGAATGGAAAATCTTCAAGTAGCATAAGAGAAGGAGT ACAGACTAGAACAGAGAATGAGAATCAGGGCCTTGATTTCCACCTCTTATCATTGC AAGCCGAGAGCCTTGACCAAGTTATGTAA | 7558 |
| | 4 | MAFLAGFCFVLRQGLALSPGWSAVVRSWLTATSASRV QAILVPQSPRVAVFTGKCH* | 7559 | ATGGCATTTCTAGCAGGTTTTTGTTTGTTTGAGACAGGGTCTCGCTCTGTCTCCAG GCTGGAGTGCAGTGGTGCGATCTTGGCTCACTGCAACCTCTGCCTCCCGGGTTCAAG CGATTCTTGTGCCTCAGCCCTCCCCGAGTAGGTGATTACAGGAGCAAGTGCCACT AG | 7560 |

Figure 1 (Continued)

| | | | | | |
|---|---|---|---|---|---|
| hsa-mir-631 | 1 | MFYYSGVLFYKQHQRGPLENCI* | 7561 | ATGTTCTATATTCTGTGTGTTTATTCTATAAGCAACATCAGAGAGGCCCACTAGAG AACTGTATTTAA | 7562 |
| | 2 | MSRPGVVAHACNPSTLGGRGRWTR* | 7563 | ATGTCTCGCCCTGGGGTGGTGGTCACGCCTGTAATCCCAGCACTTTGGGAGGCCG AGGCAGGTGGATCACCTGTCTATTAA | 7564 |
| | 3 | MVKPCLY* | 7565 | ATGGTGAAACCCTGTCTATTAA | 7566 |
| | 4 | MSPGEFTDWLEFYFWDLSVLTSFSPHLSSF* | 7567 | ATGTCTCCTGGGGAATTTACTGACTGGCTAGAGTTTTATTCTGGGATCTTCTGTGC TCACTTCTTTTCCTTCCATCTTCCTCATTTTGA | 7568 |
| hsa-mir-632 | 1 | MQHPWVP* | 7569 | ATGCAGATTCCCTGGGTGCCGTGA | 7570 |
| | 2 | MLLPVLAGKHGSPLF* | 7571 | ATGTTGCCTCCCGTGCTGGCTGGAAAGCACGGTTCTCCTGCCTTAA | 7572 |
| | 3 | MFVSKYFCTVYILYIFVTYYLSTDSIKYPFSFSKPLVIQE VT* | 7573 | ATGTTTGTTTCTAAGTACTTCTGTATTGTACATTCTGTATATTTTGTGTAACATA TTATTTGAGCACAGATTCCATTAAATATTTTTTCTTTTTCAAGCCATTGGTTATTC AGGAAGTGACCTGA | 7574 |
| | 4 | MGGRG* | 7575 | ATGGGTGGAGAGGTGA | 7576 |
| hsa-mir-633 | 1 | MGRKKKQLKPWCWYPLSV* | 7577 | ATGGGTCGCAAGAAGAAGAAGCAGCTGAAGCCGTGGTGTGGTATCCTTTGTCGGT TTGA | 7578 |
| | 2 | MGFRGRQAFAVVGRVTL* | 7579 | ATGGGTTCCGAGGTCGACAGGTCTTTGCAGTTGTGGGTGTGACTCTGA | 7580 |
| | 3 | MEGWGQLRSLSPITFSVFTYFMCVLCLFPRHGGHLVKNQVS QPWFRTFFFFFSGREEN* | 7581 | ATGGAGGGTTGGGGACAGCTTCACAGTCTGCACCCACTTTTCTGTTTTATTACT TATGTGTGTTTCGAATTGGCGGTTAGTAAAGAACCAAGTTAG TCAACCCTGGTTTCGAACCTTTTTTTTTTCTTTCGGCGGGAGGAGAAAC TAG | 7582 |
| | 4 | MLFLEALIFFTLKLILFTVLYVKAACYSTAPM* | 7583 | ATGCTTTTTCTGGAAGCGTTAATATTCTTTACATTAAAATTGATTTATTTACTGTT TGTACGTAAAGGCGGCTTGTTTACAGTACGTGCGTTTATGTAA | 7584 |
| hsa-mir-634 | 1 | MCPRNTSQPHNSGRKPSEPRPDFTSPARMASVPLSGQDAL* | 7585 | ATGTGCCCCAGGAACACTTCCCAGCCTCATCCCAGCCAGATGGCATCAGAACCA CGACCCGACTTTACATCTCCAGCCAGAATGCATCGTTCCTCTATCCAGGATGCA CTTTGA | 7586 |
| | 2 | MHFEKWELPLPSVGPFELLFLRSDLHTPESGLHVLGDHK VH* | 7587 | ATGCACTTTGAGAAGTGGGAGTTGCCACTTCCTTCAGTTGGTTTTCTTTGTTGT TGCATCGACTTGCATACCCAGAGTCTGGCATTTTAATTGTCCTCGGTGACAT TATTAAAGTTCATTAA | 7588 |
| | 3 | MGRKVDLSPFQLPEWTTPNPCHPL* | 7589 | ATGGGAAGAAAGTTGATTTATCCCGTTCAGCCTCCTGAGTGGACAACTCCAAAC CCTTGCCACCCGCTATAA | 7590 |
| | 4 | MYEHFS* | 7591 | ATGTATATTGAGATATTTAGTTGA | 7592 |
| | 1 | MADVFPGNDSTASQDVAMRFARKGALRQKNVHEVKD HKFIARFFKQPFFCSRCTDFW* | 7593 | ATGGCTGACGTTTTCCCGGGCAACTGCACTGCCAGTCAGGACGTGGCCAACCGC TTCGCCCGCAAAGGGCGCTTGAGGCAGAAGAACGTGCACGAGGTGAAGGACCACAA ATTCATGCGCGCGTTCTTCAAGCAGCCACTTCTGCAGCCACTGCACCGACTTCATC TGGTAG | 7594 |
| | 2 | MAQGQRDSFKHDPVGQARWLTPVIPALWEAEAGGSPK VSSSRPAWQTW* | 7595 | ATGGCACAAGGGCAGAGGGACTCATTAAAATAGACCCTGCGCCAGGCGCGTG GCTCACGCCGCTGTAATCCAGCACTTGGAGGCGGAGGCGGGATCACCTAAGG TCAGTAGTTGAGACCAGCCTGGCAAACATGGTGA | 7596 |
| | 3 | MVKPRLLKIQN* | 7597 | ATGGTGAAACCCGTCTACTAAAATACAAAATTAG | 7598 |
| | 4 | MKQTILSTRD* | 7599 | ATGAAACAGACCCTGTCAACTCAGATTAG | 7600 |
| | 1 | MEAEAADAPPGGVESALSCFSFNQDCT* | 7601 | ATGGAGGCCGAGGCCGCGGACGCGCCTCCCGGGCGGGGTTGAGTCGGCAAGCTG CTTCTCTTTCAACCAGGACTGCACGTAA | 7602 |
| | 2 | MGGAGRWESQ* | 7603 | ATGGGGGAGCAGGGCGGTGGGAAAGCCAGTGA | 7604 |
| | 3 | MRKERKLQVDPGLCSWGPGR* | 7605 | ATGAGAAAGGAGAAGAAGTTGACCAGGAAGTGCGGGTTGAGTCGGCCCAAGG AAGATGA | 7606 |

Figure 1 (Continued)

| | | | | |
|---|---|---|---|---|
| hsa-mir-635 | 4 | MRVQEKLSHLSLSISTWHLGRASDKEAAYPCGQASPCPI PDAGHRACPLWMEETFGFLWLFSHRPPSQAGSPSRSPRL FSRAQTAFSPGNRSSTLLFLSGFLMPYFDVHIWALRGSW AEVCFRHLQDSVTYRQTPVSRPIFMEASPGDHMESSFW NVHPEHQAGMTDSQFPTSCCTSFCALAAGD* | 7607 | ATGAGAGTACAGGAAGAAAAACTTTGTCTTGAGCATTCTCCATTTGTCTTGAGCATTCTCAACGTGGCATCTG GGCAGGGCCTCGGACGCAGGGCATGTCGCCCACCCAGCCAGGCAGGATCTCCTCTGGAGTCC CATCCCGACGCTGTTTTCACATGCCGCCCACCCAGCCAGGCAGGATCTCCTCTGGAGTCC TCTTTGGCCTGTTTTCCGGCGCAGAGCTCTTCTCCAGGAAACAGGAGTCCACCCT AAGACTCTTTTCCGGCGCAGAGCTCTTCTCCAGGAAACAGGAGTCCACCCT GTTGTTTTTGAGTGGATTTTTAATGTTTTACTTCGATGTTCACATTTGGGCTTTGAGA GGGAGCTGGGCTGGAAGTGTGTTTCAGGCATCTCAGGAGTTCAGAAGCAACGCCTGTCTTCTTTCCCTATTTCATGGAAGCAGCCTGGGGACCATATGGAATCA ACGCCTGTTCTTTCCCTATTTCATGGAAGCAGCCTGGGGACCATATGGAATCA TCTTTTGGAATGTGCACCCTACCAGTTCTGTGCCTTGGCTGCTGGTGACTGA ACTTCCTCTGTCTGTACCAGTTCTGTGCCTTGGCTGCTGGTGACTGA | 7608 |
| | 1 | MSYGRPPDVEGMTSLKVDNLTYRTSPDTLRRVFEKYG RVGDVYIPRDRYTKESRGFAFVRFHDKRDAEDAMDAM DGAVLDGRELRVQMARYGRPPDSHHSRKGPPFRRYGG GGYGRRSRR* | 7609 | ATGAGCTACGGCCGCCCCCCTCCGATGTGGAGGTATGACCTCCTCCAAGGTGAC AACCTGACCTACCGCACTCCGCCCGACACGCTGAGGCGCGTCTTCGAGAAGTACGG GCGGGTCGGGCAGTGTACATCCCGGGACGCTACACCAAGGAGTCCCGCGGCT TCGCCTTCGTTCGCTTCACGACAAGCGCGACGCTGAGGACGCTATGGATGCCATGG ACGGGGCCGTGCTGGACGGCCGCGAGCTGCGGGTGCAAATGGCAAGATGGCCGC CCCCCGGACTCACACCACAGCGCGGGACCGCCACCCGCAGGTACGGGGGCGG TGGCTACGGACGCCGGAGCCGCAGGTAA | 7610 |
| | 2 | MWRV* | 7611 | ATGTGGAGGGTATGA | 7612 |
| hsa-mir-636 | 3 | MPWTGPCWTAASCCCKWRATAAPRTHTTAAGDRHPA GTGAVATDAGAAGKRG* | 7613 | ATGCCATGGACGGGCCGTGCTGGACGGCCGCGAGCTGCGGTGCAAATGGCGC TACGGCCCCCCGCCCGGACTCACACCACGCCGGAGCCGCCACCCGCAGGTA CGGGGGCCGTGCTGCTACGGACGCCGGAGCCGCAGGTAAACGGGGCTGA | 7614 |
| | 4 | MASGGEIMAAWAGARGRGRPRCLETPLCLLVPPAALG GVAAADPGVGVVPGLAADLATAARSLGPALVLDLGRP BSPDPHEGPSPSPRRSPDLVRGPGPGLGPGVLPQCPRGN PNPGRDRRVPPSLLKRKERCPLKKMVMSGNPRHITLHK WDLG* | 7615 | ATGGCGTCTGGGGGCGAGATAATGGCAGCCTGGGCGGAGCGCGGGGCGGGGCC GCCCCCGGCGTCGCCGCGGCCGATCCCGGAGTCGGTTCCAGCTCGCCAGCGAT CTCGCCTACAGCGCTCTCGGTCCCGCCACTCGTTCTCGAATCTCGGTCGACCT CCAAGTCCAGATCCAGATCCGCACGAAGTCCAAGTCGACACTCGGTTCGGTCTCCAGATCTC GTTCGGGTCCAGTCCGGTTCGGTTCGCAGAGTCCTCTCCCCCAAGTCTCCAGAAGAGGA AATCCAAATCCAGGTCGCGATCGAAAAATGGTAATGTCTGGAATCCAGAACACATAACCCTAAT TCATAAATGGGATTTGGGGTAG | 7616 |
| | 1 | MLERSLRDGQGLGLGGGRFCKGSHWGLPRGLCGDCGRE GAEDGGGDSDGALFGGPFWGVGETAVGGL* | 7617 | ATGCTGGAGCGGAGCCTTAGGGATGGGCAAGCCTTGGCGGCGAGGGGGAGGTTCTG CAAAGGGAGCCACTGGGGGTCTGCCTAGGGGTCTGTGCGGAGATTGCGGCGAGAAG GGGGCAGGAGACGGTGAGGAGACGCGGTTGGGGACTTTGA GGGGGAAGGAAGAACGCGGTTGGGGACTTTGG GGGTAGGGGAGGAACGCGGTTGGGGACTTTGA | 7618 |
| hsa-mir-637 | 2 | MGKALGAGGGSAKGATGVCLGACAEHAGEKGQRTVEE TQMGPFLAARFGG* | 7619 | ATGGGCAAGGCTTGGGGCGCGGGAGGTTCTGCAAAGGGAGCCACTGGGGTCTG CCTAGGGCTGTGGGAGATTGCGGGAGAAGGGACGAGGAGACGAGGAG ACTCAGGATGGGCCCTTTTTGCGGCGCCGTTTTGGGGTAG | 7620 |
| | 3 | MERGGRG* | 7621 | ATGGAGCGTGGGAGGAAGAGGTTAA | 7622 |
| | 4 | MVGGGRGCSIDEGLRPAEGKDQEGLR* | 7623 | ATGGTTGGGGGTGGGCGGGGGTGTCATCGATGAGGGGTCTTAAGAGACCTGCCGA GGGCAAGGACCAGGAGGCGTTAAGGTAG | 7624 |
| | 1 | MRRRP* | 7625 | ATGAGGCGGCGACCGTGA | 7626 |
| hsa-mir-638 | 2 | MGNRGMEELIPLVNKLQDAFSSIGQSCHLDLPQAVVG GQSAGKSSVLENFVGR* | 7627 | ATGGGCAACCGCGGATGGAAGAGCTGATCCGCTGGTCAACAAACTGCAGGACGC CTTCAGCTCCATCGGCCAGAGCTGCCACCTGGACCTGCCCAGATCGCTGTAGTGGG CGGCCAGAGCGCCGGCAAGAGCTCGGTTGCTGGGAGAACTTCGTGGGCCGGTGA | 7628 |
| | 3 | MARKAPPA* | 7629 | ATGGCGCGCGTGCGCCGGCCGGCGTAA | 7630 |

Figure 1 (Continued)

| | | | | | |
|---|---|---|---|---|---|
| | 4 | MTTPECLAQRLWKGVVGG* | 7631 | ATGACTACCCCTGAGTGTCTGGCACAACGGCTCTGGAAAGGGGTGGTAGGAGGGTAG | 7632 |
| | 1 | MAEQQTLSRASLTGGNSLEAMGEELFCLSGESKEEPQV STSHCQQQRRPPTNSISA* | 7633 | ATGGCTGAACAGCAGACTCTCTCTGAGCTCTCTCTGGAGCTTCCCTTACAGGGGAAACAGCTTGGAA GCCATGGGGAGGGAGGAACTTTTTGTCTGTCAGGGAGGAAGCAAGGAAGAACCCCAAGT TCTACCTCTCACTGCCAACAGCAGAGAGACGCCCCCCACCCAACAGTATTCCGCGTA G | 7634 |
| | 2 | MRLGYHLQVPPRPCHSWTDPSSWQHHQEMAKDTWSR VGFR* | 7635 | ATGCGGTTAGGTGTTCACCTCCAGGTGCCACCTCAGGCCTGCCACTCCTGGACTGAC CCATCCTCCTGGCAACATCACCAAGAGATGGCTAAGACACATGTCCAGGGTCGG CTTTTCGGTAA | 7636 |
| hsa-mir-639 | 3 | MVQRLLSVSVYSQRFKANGA* | 7637 | ATGGTCCAGGGTCGGCTTTCGGTAAGTGTTTACTCTCAACGTTTTAGGGCTAATGGT GCGTAG | 7638 |
| | 4 | MVRRKRRRKKTKINREFLNPHTLAFTATTLAQKVSSRSS PEASLNHQRAQEQKALLSLPSEAAPLSGPGRPLPPACPA GARSSLPGNYPNPAPKPTNGVGSCIHNPSPRS* | 7639 | ATGGTGCGTAGGAAGAGAAGAAGAAAAACAAAATAAATAGGAGTTTTTAAA TCCTCACACATTAGCACTTGCCACCATTCACTGCACAAAAAGTCAGCTCCAGATC AAGCCAGAAGCCAGCTGAATCATCAACGGCACAGGAACAAAAAGCCCTGCTCT CCTTACCCTCCGAGGCGCCCGGCTCTCCGGACCTGGGCGGCCGCTGCCTCTGCGT GCCCTGCCGGGGCAGGTCATCACTTCCGGAATTATCCAACCCAGCCCCAAGC CACGAACGGGTCGGCTCCGCATTCACAACCCTCACAACCCTGCCCGCAGCTGA | 7640 |
| | 1 | MKHYEYRSEKQCPCGHC* | 7641 | ATGAAGCATTACGAGTATCGGAGCGAAAACAGGGCGTGTGGCCACTCTGA | 7642 |
| | 2 | MRMCAGSIYKSATQAVLGVLFLGGLCRGWDACRFLAA PPAG* | 7643 | ATGCGCATGTGCGCAGGAAGTATTTATAAATCTGCAACCCAGGCTGTTTTGGGGTA CTTTTTCTTGGGGTCTCTGCAGGGCGTGGGACGCTTGCAGGTTCCTTGCAGCTCCC CCAGCGGGCTGA | 7644 |
| | 3 | MGATKVRDPCSQSEGVLHKSCATPPSPA* | 7645 | ATGGGAGCCACGAAGGTGCGGGACCCTTGCTCCCAATCCGAGGGAGTCTTGCACAA AATCTTGCCACGCCACCCCGCCGTCACCAGCTAG | 7646 |
| | 4 | MCLSP* | 7647 | ATGTGCTTATGCCCTAG | 7648 |
| | 1 | MLARLVSNF* | 7649 | ATGTTGGCCAGGCTGGTCTGGAACTTCTGA | 7650 |
| hsa-mir-639 | 2 | MSAFTFLRGSPTSLKCPSDWIVSFLRYTPTLPVSFFSISSG PPNALWLQFSEGSPVSPEVFPLT* | 7651 | ATGAGTGCCTTCACTTTCCTGAGGGGTCCCCACTCTTTGAAATGCCATCTGACT GGATCGTTAGTTTTCTGAGGTATACCCTACTTTACCAGTATCCTCTTTTCTATTC TTCTGCGCCCCAAATGCTCTATGGATCCTGCAGTTTCTGAGGGTCCCCAGTTTCT CCAGAGGTTTTCCCCTTAACTTGA | 7652 |
| | 3 | MLYGSCSFLRGPQFLQRFSP* | 7653 | ATGCTCTATGGATCCTGCAGTTTCTGAGAGGGTCCCAGTTTCTCAGAGGTTTTCCC CTTAA | 7654 |
| | 4 | MBPAVF* | 7655 | ATGGATCCTGCAGTTTCTGA | 7656 |
| hsa-mir-640 | 1 | MSRAVTPAPGSMCAAEFGRIIWPAARAGGRTGAASAAGP GGPTGGTSARGPASPAPPPGPAPAGDPCPAAPVTCALP* | 7657 | ATGTCCCGGGCCGTGACGCCGGCGCCCGGGTCCATGTGTGCCGAGGGGCGCAT TATCTGGCCGGCCGCCCAGGCGGAGCCGGCTCGGCCAGGCTCGCCGGCGGGC CGGGGCGGGCCCGGCGGCGGGAACGAGCGCCGCGCGCCGGCCCCGCCCCTCC GGGCCGCCCGGCTGGTAGCCCGGAGCAGCCGCCGGGACCAGCAGCCCCAAGCTGCGCGTGC CCTAG | 7658 |
| | 2 | MSVEK* | 7659 | ATGAGCGTGGAAAAGTGA | 7660 |
| | 3 | MGRAQAESLTDTWIVRTLGPRNEW* | 7661 | ATGGGCCAGGGCCCAGGCTGAGGCTGAGAGCCTGACGGACACTTGGATTGTGCGCACACTGGGG ACCCAGAAATGAATGGTGA | 7662 |
| | 4 | MNGDPSLRK* | 7663 | ATGAATGGTGATCCCTCCCTTAGGAAGTGA | 7664 |
| | 1 | MCGGRAPPERLGGCR* | 7665 | ATGGGCGGGCGGGCTAGAGCCCCGGAGCCCTGGCGCCTGCCGGTGA | 7666 |

Figure 1 (Continued)

| | | | | |
|---|---|---|---|---|
| hsa-mir-641 | 2 | MVASGPPAVPRWAVPPVPGGGTAALEPLLQELSGGGR AGAVGPASGGRGGGGGPYH* | 7667 | ATGGTCGCGTCCGGCCCCCGCGGTGCCGGGAATGGGCTGTACCACCGTGCCGG CGGGGGACCGGACCGCGGGGCCCCTCGAGCCCGCCCTCTCAGGAGGTGGCCGAG CGGGGCGGTGGGACCAGCCTCGGGGGCCGGGGCGGGGCCGGGGCCATACCA CTGA | 7668 |
| | 3 | MGCTTRARRGDRGPRAPPSGAEWGWPSGGGGTSLGGP GRWRRAIPLRRWGERCKPAGRGAQAAACAGRGLELSG AAGRSSLACAG* | 7669 | ATGGGCTGTACCACCCGTGCCCGCGCCGGGGAGACCGCGCCCTCCAGCCCCCTCTTCA GGAGCTGAGTGGGGGGCCCATACCTGAGGGCGGTTGGACCAGCCTCGGGGGGCCGG GGACGGGGACGCCAGGCGCACGGCGCCGAGCGCCGCCGGGGCGCAAGTTGCG GGACGGGGAGCGCAGAGTGAGCCTGGGCGTGCGCGGCTAA | 7670 |
| | 4 | MLPQLWLGYTTALGEPCLERRGTQIRGL* | 7671 | ATGCTTCCCAACTGTGGCTGGGTTATATCACCACGCGTTGGGAGGAGCCCTGCTTA GAACGTAGGGGACCCAAATCAGAGACTGTGA | 7672 |
| hsa-mir-642 | 1 | MSLSACFHLWLAAR* | 7673 | ATGTCTCTGTCTGCGTTTCATCTCTGTTAGCTGCTAGATAA | 7674 |
| | 2 | MHLGKGCSTYSGLYLPPAGKVL* | 7675 | ATGCTTGGGAAAGGGTTGTTGTCACTTACTCTGGGCTTTATCTACCCCAGCGGGGAAA GTTTGTAA | 7676 |
| | 3 | MCARKPFGLGEWELGWAFQVLHQAVGTQMCVSSTPL GGTENLQVFQPHEKGSRLLTVSTPSSPRRSPGSQESVGPD PGDTDTSAQRSSRATARSANTPPFHLCCPNNSQGRPGN HLRGPAHHRSSTHSACLSLPPDHHAWELRERVRCLGVP RVYGSPAVCPCV* | 7677 | ATGTGTGCTAGAAACCTTTGGGCTTGGAGAGTGGAGCTCGGATGGGGGCGTTTCA TACTGAAAACCTTCAAGTTTCAGCATGAGTGGGCGTTCAAGTACCCACTAGGGG TTTACCCCCCTCCTCTCAAGGCGGTCCCCATAGAAAAGGGCTTAGCGTGACCGT TCTCGGTGACACTGACACTTCCGCCAGCGTAGCTCAGGGCAACCGCCGGCTAGC AAACACCCCCCCCTTCCACCTTTGCTGCCCAACAACAGTCAGGGAGGCGGGGAA TCACTTAAGGACCCCGCCACCACCTCGCGTGCCTCCCT CGCGTATACGGCTCCCAGCCCTGTCCCCTGTGTGA | 7678 |
| | 4 | MGVSSSPPGCGNSDGRFKYPTRGY* | 7679 | ATGGGGGTTTCAAGTTCTCCACCAGGCTGTGGAACTCAGATGGGCGTTTCAAGTAC CCCACTAGGGGTACTGA | 7680 |
| hsa-mir-643 | 1 | MAWRYGATAAREFSV* | 7681 | ATGGCGTGTAGATATGGCGCAACTGCGGCGCGTGAGTTTTCTGTTTAG | 7682 |
| | 2 | MAQLRRVSFPLFRLSVRLAVPSRPCTRDVGGGTDLEPA PLSPPRVNSCVPSEC* | 7683 | ATGGCGCAACTGCGACGCTTCGTGTACCGGGATGTGGGGCGGTACAGACCTTGAAATCCCC GCACGGCTCTCTCCACCCCGAGTAATTCATGCGTCCGTCAGAGTGTTAA | 7684 |
| | 3 | MWGAVQTLKSPHRSLHPE* | 7685 | ATGTGGGGCGGTACAGACCTTGAAATCCCCAGCTCTCCACCCGAGTAA | 7686 |
| | 4 | MRPVRVLKSP* | 7687 | ATGCGTCCGTCAGAGTGTTAAAATCCCCTAG | 7688 |
| hsa-mir-644 | 1 | MRMFGENKGKGVGKAVRDPFKAAAAPSSRAGVCRGRG ELGLLARAGRWGWAVWTFGGISVWHRLPEAFASRAPS CERAGPFRAWVPSGPSPLSPAWGHSPAVRPTRGARRRG RRGRRGPVRGGGRVPRHPAGLLETFPSPQSLEGPSTAAA SPSLSHSPPPSIVPPAWWSRLRRPPRPPSWRRRLLQT WSCHCPSSGECPEL* | 7689 | ATGAGAATGTTCGGCGAGAACAAGGGTAGAGGAGTGGACGCGGTTCGGAGACCC CAGAGCCGCGGCTACTGGCCGCGGGTGCTCTCCAGGAGCCGGTGTCTGTGGGAGG TCGGCTACTGGCCGCCGCAGGCTTCGGAGGTTCGGAGGTTCGGAGACGTCGAACGG ATCAGTGCTCGGCAGCAGGCTTCGGCTCGCTCGGCGGTGTCCGCGCTCAAGTTGTGAA AGGGCTGCGCACTCTCAGCGGTGCCGCCGGGGTTCGCGTCACGCCGCTCAGGC CTGGGGGCCACTCTCAGCGGTGCCGCCGGGGTTCGCGTCACGCCGCTCAGGC CTTCTCGAGACTTCTCCCACTGCCTCTCTTCCCAGCGCCCAGAAGGGCCACAGCCGGCTGCC TCCCCTTCTCTCTCCCCACTGCCTCTCTTCCCATTGTCCCCCCGGCGTGGTGGTCC CCGGAGCTGTCACTGCCTGCCGCCACTGCTGTGCCGCCGACTTTGCAGA CGTGGAGCTGTCACTGCCTGCCGCCCTCTCCGGAGAGTGCCTTTCTTAG | 7690 |
| | 2 | MTFKWRTQVFQDSSRPQKRESQNLCARSRRWA* | 7691 | ATGACTTTTAAGTGGAGAACTCAAGTTTCCAAGACAGTTCCCGTTCCGCAGAAAA AGAGAATCGCAGAATTGTCGCCCGAAGTAGACGCTGGCCTAA | 7692 |

Figure 1 (Continued)

| | | | | | |
|---|---|---|---|---|---|
| | 3 | MGNCHFALKISKTLEPATHLGGFSCIFS* | 7693 | ATGGGGAATTGTGGGATTTTGCCTTGAAAATTAGTAAGACCCTGGAGCCAGCCACCCACTTAGGTGGGTTCTCCTGCATCTTTTCCTGA | 7694 |
| | 4 | MVYQLR* | 7695 | ATGGTTTATCAGTTGAGGTGA | 7696 |
| hsa-mir-645 | 1 | MVLHTSG* | 7697 | ATGGTTCTCCATACTTCAGGGTAG | 7698 |
| | 2 | MWIPMIPESLGPWRAAAGD* | 7699 | ATGTGGATTCCTATGATACCTTTCTCCCTGGGACCATGGAGGGCAGCAGCTGGTGATTGA | 7700 |
| | 3 | MEGSSW* | 7701 | ATGAGGGCAGCAGCTGGTGA | 7702 |
| | 4 | MSANYMCP* | 7703 | ATGTCTGCCAACTACATGTGTCCTTAG | 7704 |
| | 1 | MLPGSPAV* | 7705 | ATGCTCCCAGGCTCTCCCGCAGTTTAA | 7706 |
| | 2 | MGVLHDYS* | 7707 | ATGGGAGTCTTACATGATTATTCATGA | 7708 |
| hsa-mir-646 | 3 | MIHEGLGRGVAVKHVLGCLLVAHVLWLCMLVHTSHVSLAS* | 7709 | ATGATTATTCATGAAGGCTGGAAGGGTGTGCCGTGAAGCATGTTCTGGGCTGTCCCTGGTTGGCACATGTCTGTGGTTGTGCATGCTAGTACACACATCGCATGTCTCGTTAGCATCGTAA | 7710 |
| | 4 | MKGWEGVLP* | 7711 | ATGAAGGCTGGAAGGGTGTTGCCGTGA | 7712 |
| | 1 | MRAARPGPQRGLRAPWLRPRPARTLILRPRRIHLRPETHQAGRLRKARPRARTGRRGPRLHSTGEREGAADPAELGGWSVPAASPSPPLPEARRRRPVLPRAGWNPAGLKRPGGRTWPKPAGSSGLGEGVRVRTPSVDLGLCPRWVGPSASSARRAVCLLDCASWSMLSARGVALPDPRGQGLGFGGAAAHGAFGLPRTRVAPSSLCGGFARA* | 7713 | ATGCGCGCCGCCGCCGGCCAGGCCGCAAAGAGGCCTCGAGGCCATGCTGCGCCCCGGCCGCCGCGGACGCTGATCTTGGCCAGTCCGCACTCCAGGCGCCCACTCGGCAAGGCGATCACACACCAAGGCCGGACAGCTGAGAAAAGCGAGACTCGAGGCCGGTAGGCGTGGGCCTCGCCTCCACTCGCGAGCGGCGAGCTCCCACTCCCGAGATCGGCAGCTGGGCGGTGGTCGTCCGCGCGAGCCGCCCTGCCACCCGGAGCAGGCGGCCGAGTCAGGCGGCCGGCGCCCCGTTCTCCCACGCGGTCCCGGTGGAAACCCCGCGCCGGCTTGAAGCGGCGCCGGAGGAACCTGGCCAAGGAGGGTGAAGGAGGAGTGCCGGGTGCGCACCTGGGAGCCGGTGCCGCTCGCCAGCCGGTGCCAGGCAGGTCCCGGCTTCCATGGGCGCCGCCGAGTGTGGCCCTGTCGCGCACCGCGCCGCCCGGAGTCCAGGCGCGCACAGGGCGCACCGCCCCGGAAGGCCAGGGGCCGAGGGCTTGGCTGTCTATGTTGTCGGCCGGGTGTGCCACGCACAGGTCCTTCGGATTGCCTGCGGCTCCACGCCGGTGGCCAGGCTTAGGATTGGAGGTGCTGCGGGGCACGCCCACGGCCACCGGACCGCGGCTGCTCCAGCCTCTGCGGGGGCTTTGCAAGAGACATGA | 7714 |
| | 2 | MAAPPARADADPSPTSPPTARDTPGRQAEKSETACEDR* | 7715 | ATGGCTGCGCCCCGCCGCGGCGGACGCTGATCTTCGCCACGTCGCCACCTACGGCCCGAGACACCAGCCGGCAGCCGGCAGCCGGCAGCCGGCAGCCGGCAGCCGGCAGCAGCGGCAGCCGGCAGCCGGCAGCTGAGAAAGCGAGAGCGCTGTCGAAGAGACCGGTAG | 7716 |
| hsa-mir-647 | 3 | MKWGSCGGAAGGTRPHPGSSPRVAPLGAGPCAAPLGPWPSCGGGHAVPGAARGRSGRCPSLPGLKCPLLGSPRGPQEGVVPTQAPLAWVQAVTPVRNAVSQDSLRDGLRWMPQGEGCPGTGSLLSR5C* | 7717 | ATGAAGTGGAGTTGTGGGGTGCAGCGGGAGGAGAACCTGCCGCCCCGCCCGTCGTCACCCGGAGTGGGCCTGTGGCCACGCAGTGCCGGGTGCCCAAGAGGTGCTCTTGGGCCTGTGGCCCCTCCTTGGAGTCTGAAGTCTGCCTGGCTCCCAGGGATGCCTGGGGTTTCCCAGAAGGGGTTGCCCACTCAGGCGAGCAGGACTCCCTGCGCTGTCTCCAAGAGATGGCTGCGCTGGATGCCGCAGGGGGAAGGTGTCCGGGCACAGGTCCGGCACAGGTGCTCTCTCCAAGGAGTGACTAG | 7718 |
| | 4 | MGCAGCRRGKGVPAQGRSSPGAAEQKELSPGPASLQVHTLPVGSD* | 7719 | ATGGGCTGCAGCTGTGAATGCCGCTGAGCAGGAAGACGTGTCCCGGCCTGCGTCCTTCAAGGTCCACACCCTCCAGTGGGCAGTGACTAG | 7720 |
| | 1 | MRQK* | 7721 | ATGAGGCAGAGTAA | 7722 |
| hsa-mir-648 | 2 | MRGQVRRLVLSSGAAGACKRGEAARFRREAEGGGLARLWVRGRGVLFGAGFVSVFTGVRRLRAEAPPGPASAAWPSGPPRPAAPAWS* | 7723 | ATGCGTGGCCAGGTGCGCCGGCTGGTCCTGGGCAGGCGCCGGGAAGCGCGGGAGGCTGCCTGCCCGCCGGGGGCAAGAGGCGAGGGCTTAGCCGGCTCTGGGTGCGCGGGGCCGGGGGAAGGTCTCTGTCTTTACCGGAGTCCGCAGGGTCCCGGGTCCCCGGTCGCCCGCTGGCCCGAGCTAG | 7724 |

Figure 1 (Continued)

| | | | | | |
|---|---|---|---|---|---|
| | 3 | MPLPWLPSEGTALLEVSGAHGKFPAKKPS* | 7725 | ATGCCCCTTCCCTGGCTGCCTTCCGAGGGACCCTGCTGCTTTGGAGGTCTCCGGGGCA CATGGGAAATTCCAGCTAAGAAGAACCATCTTGA | 7726 |
| | 4 | MGNSQLRNHLEEPYTEPGLPGLAESQPQRDPPPGMRH W* | 7727 | ATGGGAAATTCCAGCTAGCAGAAAGCCAGCGCAGGAGACCCTCGCCTGGCATGCGGCACT GGTGA | 7728 |
| hsa-mir-648 | 1 | MIRLCVLLDYF* | 7729 | ATGACAAGGTTATGTGTTTGCTGGATGTCTCTAA | 7730 |
| | 2 | MCFAGCLLRHYLDCLWWGSVSFVTSLCFSDLRFPLNA ALSPLVGKTPSIRVSHARHPPVRMPRTTHSPEPAREQGC LPATSTPPSLCFYPAGKGRAYTPGTPEVGQVSGQPAGFW RSRVRSG* | 7731 | ATGTGTTTTGCTGGAGTCTTCTAAGAATCATTATTTAGATTGCTTATGGTGGGAA GCGTTTCCTTTGTGGACATCTTGTTCTCGGATCTATTTCGTTTCCTCTAAACGC AGCCCTCTCCCCGAGTGGGAAAGACACCTATCCGTGTCTGATCATCGCACG ACACCACCAGTCGGATGCATGTACCACACACTCCCAGATCTGCCAGAGAGC AGGGCTGTCTCCCAGCCACTCCCACCCATTTCATTGTGCTTCTATCCGGAGGCA AAGGAAGAGCGTACCAGGCACCCGAGTTAGGCCAGGTCAGGACAGCCAGCA GGCCCTTGCTGGGTCCGCTCTGGCTAG | 7732 |
| | 3 | MSSKNHLFRLLMVGKREFLCDJFVFLGSISFPSKRSPLSPS GKDTQYFCLDHRTPPTSADATYHTLPRACQRAGLSPSH VHPHFIVLLSRRQRKSVPREHPRGRPGVRTASRPLAKPGPL WLAQRGEPMSSLGAAAALRGHERRFPCGRGALHPPAAR GGGPGPVAHTLALPGCRARCAGAAPGRVQQKDGQVHS LLEAERGGAA* | 7733 | ATGTCTTCTAAGAATCATTATTTAGATTGCTTATGGTGGGAAGGCGTTTCCTTTGTG ACATCTTTGTGTTTCTGGATCTATTCGTTTCCTCTAAACGCAGCCCTCTCCCC TAGTGGGAAAGACACCTATCCAGTATGCCCCAGAGCCTGCAGAGAGCAGGCTGTCTCCCA GGATGCCAGTCACCCACACACCAGTCGCCAGCTCTCCAGAGAGCAGGCTCTCCCA GCCACGTCCACCCCATTTCATTGTCCTTCTATCCGCAGGCAAGGAAGACGTAC CCAGGGCTAGGCCAGGTGTCAGGACGCCAGCCATGAGCAGCCAGCCCTGCGAAG CCGGGTGCTCGTGGCCTAGTCAGCGCGTGAAACCGAGTCTCAGGAGCAGC CGCGCGCGGCGCTGCCCGGCGACTTCCCTGCCGCAGGTGCGGCCCTGCACCCGC TGCAGGGCGCGCTGCACCCGCCGGCGTGCAACAAAGGACGGCCA AGTTCATTCCCTCCTGGAAGCAGAGGCCGGGGCCGCATGA | 7734 |
| | 4 | MTSGGCMCLRIKWL* | 7735 | ATGACTTCTGGAGGCTGCATCGTCTTAGAATGCTTATGA | 7736 |
| hsa-mir-649 | 1 | MSKDQLFPSPGMASVTSTSHDGCDIH* | 7737 | ATGTCAAAGATCAATTATTTCCTCTCTGGCATGCCTCTGTGACATCCACTAGTC ATGATGGCTGTGACATCCACTAG | 7738 |
| | 2 | MMAVTSTSASARPMTQPQPLPVPSNIFHYCPCHACMRL WPPRRPLDAPLASSLLGAHHTAAKLNPHTRHHESLQP LFLPSGGPPPMVATHPS* | 7739 | ATGATGGCTGTGACATCCACTAGTGCTTCAGCCAGACCCATGACTCAGCCTCAACCC CTTCCTGTCCCTCAACATTTTCACTACTGCCCATGCCATGCCTGCATGCTGAGACTAT GGCTCCTAGAAGGCCTTAGATGCCTCTCGCCTACTGCTACTCGTTGGTGCAC ACCACAGCAGCAGCCAAGTGAACTTTCACACGCAAGCATCATGAGAGCCTGCAGCCCC TGTTTCTACCCTCAGGAGGCCCAATGATAGTGGCCACCCATCCTCCTAA | 7740 |
| | 3 | MPCLHEIMAS* | 7741 | ATGCCATGCCTGCATGAGACTATGCTCTAG | 7742 |
| | 4 | MPLSPPPYCLVHTTQPS* | 7743 | ATGCCCCTCTGCCTCCTCATGGTCCACACCACACAGCAGCCAAGTGA | 7744 |
| hsa-mir-650 | 1 | MAWTALLLSLLAHPTGAAPSVPATYPAPRLWVQPGLTV ISAGPCLWCAGCS* | 7745 | ATGGCCTGGACCGCTCTCCTTCTCTCTTGCTCACTTACAGGTGCTGCCCCA GTGTCCAGCCACCTACCCTGCCTTGGGTCTGGGTCAGCGGCCTGACAGTGA TCTCAGCAGGGCCCTGCCTGTGGTGCAGAATGCTCATGA | 7746 |
| | 2 | MLMILLQGEGLLEVKSPHTVLLCSWSPEDTSIPETQARQ VGRHCWVEPLSFKSRLFSPLFLQVLWPPMS* | 7747 | ATGCTCATGATCCTGCTGCAGGGGGAGGGCTGCTGGAGGTGAAATCCCCACAC TGTTCTCTGTGTCCATGGTCCCCTGAGACACTCTATTCTGAAACTCAGGCAG GCAGGTGGGAAGGCATTGTTGGGTTGAGCCCTCTCAGTTTCAAGTTCTATTCTC TCCCCTTTTCTTGCAGGTTCGTGTGGCCTCTATGAGCTGA | 7748 |
| | 3 | MCTGTSRSQARPLCWSSIGHATGPGLSDSLAPTRGTR PP* | 7749 | ATGTGCACTGGTACCAGCAGAAGCCAGGCCAGGCCCTGTGCTGGTCATCTATAGG GATAGCAACCGGCCCTGCTGGAATCCTGGGACATCCCTGAGGCGATTCCTGGCTCCAACTCGGGAAC ACGGCCACCCTGA | 7750 |

Figure 1 (Continued)

| | | | | | |
|---|---|---|---|---|---|
| | 4 | MRLTITVRCGTAALHTVTQADEEVRHKPERHLCHPLSLI QGGL* | 7751 | ATGAGGCTGACTATTACTGTCAGGTGTGGCGACAAGCAGCACTGCACAGTAACACA GGCAGATGAAGAAGTGAGACAACCCTTTGCCCATCTATGTCACCCTCTTTCTCT AATTCAAGGAGGACTATGA | 7752 |
| hsa-mir-651 | 1 | MKQKHRDRIKFQMNRTFVLGKCIRRFQIQEPTPLPNFYC EHPCFYERQYNYSVTQ* | 7753 | ATGAAACAGAAAATTATTAGAGACCGTATCAAATTCAAATGAACAATACAATTGTT CTTGGTAAGTGTATCAGAAGATTTCAAATACAGTTCCCTACCCCTCCAATTCT ATTGTGAGCACCCATGCTTTTATGAACGCCAATACAATTACTCAGTAACGCAATAA | 7754 |
| | 2 | MNANTITQ* | 7755 | ATGAACGCCAATACAATTACTCAGTAA | 7756 |
| | 3 | MQYISLPSISTQTEVMPGEGNLRLYEMSATPLYTWNTS KYKJTCPPMPQCAQFAQVNEIVPPQGCPP* | 7757 | ATGCAATACATTCTTGCCAAGTATCTCAACAACAACTGAGGTCATGCCTGGTGAA GGCAGATGTCTATGAAATGTCAGCCACGCCACTTATACTGTGAACACATCT AAATACAAAATTACATGTTTTCTATGCCTCAGTGGCACAATTTGCCCAAGTGAAT GAAATTGTGCCTCACAAGGCTGTCCATTCTGA | 7758 |
| | 4 | MKCQPRHFLGTHLNTKLHVFLCLSAFNLJK* | 7759 | ATGAAATGTCAGCCACGCCACTTTATACTTGGAACACATCTAAATACAAATTACAT GTTTTCCTATGCCTCAGTGCGCACAATTTGCCCAAGTGA | 7760 |
| | 1 | MVHHPGNPLGLCSISLLLPVLWSRGTTASCPGIATRVSW TGSMGAWTPVLQAMGAPTVLPSSLGSSGCWKVWWS* | 7761 | ATGGTCCACCACCGGGCAACCCTCTGGGCTTGTGTTCCATCTCACTCTTGCTTCTG TACTGTGGTCAAGGGAACCACTGCATCATGTCCCGTATAGCTACCAGAGTCCT GGACTGGCTCATGGGGGCTGGACCCCAGTTTGCAGGCAATGGGGCCCCGACT GTGCTGCCTTCCTCTCTTGGCAGCAGCGGCTGCTGGAAAGTGTGGTGGTCCTGA | 7762 |
| hsa-mir-652 | 2 | MSRYSYQSLLDWLYGGVDPSFAGNGGPDCAAFLSWQQ RLLESVVVLTLALLEHVALRHLRQTKEDGRGSPGSQP EQVTQRPEEGCKESLSKNLLLVALCLIFGVEVGFKFATKT VIYLLNPCHLVTMMHVSLLTPSWAS* | 7763 | ATGTCCCGGTATAGCTACCAGAGTCTCCTGGACTGGCTCTATGGGGGCTGGAGCCCC AGTTTTGCAGGCAATGTGGGCAGGCAGACGCTTAGTGTTGGGTAGCCTGGCAGCCTG CTGCTGGAACATCTGAGGCAGCAGAAGAAGGACGGGTAGGGGTAGCCTGGCAGCAGGCGAGCTG CGGCACACATCCTGAGGCAGCAGAAGAGGACGGGCAAGGAGGAGCCTGGCAGCCAGCCAGCCAGCCAGCCTG GCAGCAGGTGACCCAGCCCGTGACCTGCTCAACCCTGTCACCTGGTCACCATGACAGTGAGT CTCTTAGTAGCCTGCCATCTACCTGCTCAACCCTGTCACCTGGTCACCATGACAGTGAGT AAGACCCGTACATCTACCTGCTCAACCCTGTCACCTGGTCACCATGACAGTGAGT CTGTTGACTTTTTCCTGGGCATCCTAA | 7764 |
| | 3 | MCSGHSIVYSTSSRRAGGPLKMIPQRVAAFVPISGLAFF HLCTVRQPHSGGEEPCA* | 7765 | ATGTGCTCAGGACGCACTCCATAGTCTACAGCAGCCTCATCCCGGCGGCAGGGACC TTTAAAAATGATTTTCCAACGAGTGCTGCTTGTGCCGATTCAGTTTGGCTTC TTTCACCTTTGCACAGTGGCTGCAGCCCCACAGTGAGGTGAGGAAACCCTTGCCTGA | 7766 |
| | 4 | MTQLPCLLW* | 7767 | ATGACCCAGCTGCCTTGTGGTAG | 7768 |
| hsa-mir-653 | 1 | MGAEA* | 7769 | ATGGGCGCTGAAGCTTGA | 7770 |
| | 2 | MSG† | 7771 | ATGAGCGGGACTTAA | 7772 |
| | 3 | MFNSAGAIGTLLFDYRNVV* | 7773 | ATGTTTAACAGTGCAGGTGCTATAGGCACCTTGCTTTTTGATTATAGAAATGTGGTTTGA | 7774 |
| | 4 | MWFDCGACGSHVGSARS* | 7775 | ATGTGGTTTGATTGCGGTGCGTCGCATGTTGGTTCTGCCAGGTCTAG | 7776 |
| hsa-mir-654 | 1 | MDQGVEGGGCGPGVGRQSACSL* | 7777 | ATGGACCAGGGGGTAGAGGGAGGGCTACAGAGATAGGCGAAAGAGTGGGGCTGAGGATAG CTTGCAGCTATGA | 7778 |
| | 2 | MKDGKEGYRDRGRVGLRIARAAWHTVLG* | 7779 | ATGAAGGACGGGAAAGGGAATACAGAGGGCTGTCTTCAAGGTCTTCTTCAAGCGTGTCTAATGGGAGACAGC CCAGAGCGGGCTTGGCACACAGTTTTAGGGTAA | 7780 |
| | 3 | MTEPYTPGSSFKACLMGDSVVPVTKLGPESQGRAHQV AALP* | 7781 | ATGACTGAGCCGGTCACTCCAGTAACCAAATTGGGACCAGAGTCCCAGGGAAGTCCCAGGGAAGGGCTCATCAGGTGGC CGCTCTGCCTTGA | 7782 |
| | 4 | MILFPLDPAPLVPFSL* | 7783 | ATGATTCTCTTCCCTCTGGATCCAGCCCCTCTAGTTCCCTTTGA | 7784 |

Figure 1 (Continued)

| | | | | | |
|---|---|---|---|---|---|
| hsa-mir-655 | 1 | MDQGVEGGGCGPGVGRQSACSL* | 7785 | ATGGACCAGGGGGGTAGAGGGAGGTGGGTGGACCTGGGGTCGCGCCAGTCAGCTTGCAGCCTATGA | 7786 |
| | 2 | MKDGKEGYRDRGRVGLRIARAAWHTVLG* | 7787 | ATGAAGGACGGGAAAGGAGGGCTACAGAGATAGGGGAAGAGTAGGGCTGAGGATAGCCAGAGCGGCTTGGCACACAGTTTAGGGTAA | 7788 |
| | 3 | MTEPVTPGSSPKACLMGDSVVPVTKLGPESQGRAHQVAALP* | 7789 | ATGACTGAGCCGGTCACTCAGGGTCTTCCTTCAAAGCGTGTCTAATGGAGACAGCGTTGTCCCAGTAACCAAATTGGGACCAGAGTCCCAGGGAAGGGCTCATCAGGTGGCCGCTCTGCCTTGA | 7790 |
| | 4 | MILFPLDPAPLVPFSL* | 7791 | ATGATTCTTCCCTCTGGATCCAGCCCCTAGTTCCTTTTCACTTTGA | 7792 |
| hsa-mir-656 | 1 | MDQGVEGGGCGPGVGRQSACSL* | 7793 | ATGGACCAGGGGGGTAGAGGGAGGTGGGTGTGGACCTGGGGTCGCGCCAGTCAGCTTGCAGCCTATGA | 7794 |
| | 2 | MKDGKEGYRDRGRVGLRIARAAWHTVLG* | 7795 | ATGAAGGACGGAAAGGAGGGCTACAGAGATAGGGGAAGAGTGGGGCTGAGGATAGCCAGAGCGGCTTGGCACACAGTTTAGGGTAA | 7796 |
| | 3 | MTEPVTPGSSPKACLMGDSVVPVTKLGPESQGRAHQVAALP* | 7797 | ATGACTGAGCCGGTCACTCAGGGTCTTCCTTCAAAGCGTGTCTAATGGAGACAGCGTTGTCCCAGTAACCAAATTGGGACCAGAGTCCCAGGGAAGGGCTCATCAGGTGGCCGCTCTGCCTTGA | 7798 |
| | 4 | MILFPLDPAPLVPFSL* | 7799 | ATGATTCTTCCCTCTGGATCCAGCCCCTAGTTCCTTTTCACTTTGA | 7800 |
| hsa-mir-657 | 1 | MGDPGRNIGEGMAPQRPGQPAALSTWYSPRQVETQPGSSFMAVAARYRSRPVCKASHPHSTSTGATQRAWGGGAAASRLETCK* | 7801 | ATGGGGGATCCTGCCCTAAGCACCTGGTACAGTCCAGCGCCCAGCCAACCTGCTGCCCTAAGCACCTGGTACAGTCCAGCGCCCAGCCAGTTCTTCCTTCATGGCTGTCGCAGCACGGTACAGGAGCAGGCTGTGCAAAGCCAGCCACCCCACTCACCAGCACCAGGTGCCACCCAAAGGGCATGGGTGCGGGGGGCGCTGCCAGCCGCCTCGCCTCGAAAACCTGCAAGTGA | 7802 |
| | 2 | MGWGGGCQPPRNLQVRRGPLSTKTRPGCAPGFPHLSP* | 7803 | ATGGGGTGGGGGGGGCCGCTGCCAGCGCCTGCAAGCTGCAAGTGAGGCGAGGCCCTGAGCACCAAGAACCCGCCCTGGGTGTGCCCACCGTGTCCCCTG | 7804 |
| | 3 | MPPLRVPPPSPLLCPPLRAPLCLPLRVPLSVLPPCHPGRGGPPPPPRRSARAPARVFGLHQRSPAAPGPGGAPRLSPPPPPVRALRLRRGARGAGAGALRTCGGRWVMRRLGPGPRAS* | 7805 | ATGCCTCCTCGTCCCCCTCCGTCTCCCTGCTCCTCCTGCTCCTCGTGTCTCCTGTCTCCCTGCTCTGGAGGGCCCCCCCCGCCGCCGAGCCCGCGCGCTCCCGCGCGTCCGCAAGGCCGACTGCACCAGCCGGGCCGCGAGCAGTTCCGGACTGCACCAGCCGGGCCGCGAGCAGCGCCTCGTCTGTCGCGCGGGCGCGCCCGGGCGCGGGGCGCGGCTCCGGCGCCCACCAGAGGGCGCCAGCGGCCTCCGCGCCGCTCA | 7806 |
| | 4 | MPPRPRRAPPSPAPLRARSRPRFRTAPAEPRGARAGRSASSVAAAPTGAGSAAAGGAGRGGRRAPHLRRPLGDAAARAGAAGVLSAAPSRDARRPLARPCRRPSSTPASPSARTSTPVSPWRPGLRAAASLRCGRDAPGPHGSRFAWKLTLSPPRAQQQKQPDPLAAPDLGGAGPGPQHKPASACGLASPAWS* | 7807 | ATGCCACCCCGGCCACGGCGCGGAGGGCCCCCCTCCCCGCCCGCCGCTCCCGCCCCCGGTTTCGGACTGCACCAGCAGCTGGACTGCGGCTGCAAGGCCGGGGCGGAGGCGGCTCGTCGTGCGCTGGCGCCGGGGATGCGGGCGGCTCGGAGCCCCGCCGCCTCCGAGGCTCGCCGCAGCCTCCGCGCCTTCTTCAACCCAGCTTCGCCTTCAGCTCCGCACTTCGACCCGACCCGGTGAGTCCCTGGGTCCTCCTGGGCCCCACGGCTGCCCGGGTTGCATGGAAATTAACCCTTTCCCGCGCCCGATGCCCGCAGCAGCACCGGAGCCGGACCGCGACCTGACCGACAGCCGCCCAGATCTCGGAGGGCCCTGGCGCCTGGATGCGCCAGCACAAACCGGCCTGCTGCGGCCTGCCGCGTCCCCGCGTGGTCGTGA | 7808 |

Figure 1 (Continued)

| | | | | |
|---|---|---|---|---|
| hsa-mir-658 | 1 | MAAAAGDADDEPRSGHSSSEGECAVAPEPLTDAEGLFS FADPGSALGGGGAGLSGRASGGAQSPLRYLHVLWQQD AEPRDELRCKIPAGRLRRAARPHRRLGPTGKEVHGERR ERRGPGRGJSPGEGRGLRGPVAALWSPPTLSRGPPTSA LRATLTLESPFSNDGDDGFFRKSSCSEPVTPVFSHWVISE WKLPMTRNAYW* | 7809 | ATGGCAGCGCCGCGGGACGCGGACGACGAGCCGCGCTCAGCGCACTCGAGCTC GGAGGGCGAGTCTGCGGCGGCGCGGAGCGCGCCGAGCGCGTGACGGCTGAGGGCTCTCT CCTTCGCCTGACTTCGGGTCGCGGTGCCCAGTCGCCGCCGCTGCTCACTGCTCGGCCGG GGGTCCGGGGCGCGCGAGCTGCGCTGCAAGATACCGCTTGGCCGGCTGAGGCGCG TGCCGGAGCCGCCGCCGACGAGCTGCGCTGCAAGATACCGCTTGGCCGGCTGAGGCGCG CTGCCAGGGCCACCGGCGCTCGCTGCGGCCCACCGGCAAGGAGGTCACGGTGAGGCGG CAGGACCAGTGCGCCCGCGGTGGCGCAGCCGGGCAGCCGGACCCTCAGCCGGGTCCCCGACGT CTGCGCTGAGGGCCACACTGACCTCTGAGTCCTTCAGTAACATGGTGATGATG GTTTTTTAGAAAGTCTTCCTGCTCGAGCCAGTCACCCCAGTCTTCTCTCACTGGGT AATTTCTCAATGGAAACTTCCCATGACTCGGAACGCTTATTGGTGA |
| | 2 | MRSRATSCAARYPLAG* | 7811 | ATGCGGAGCCGCGCACGAGCTGCGTCAAGATACCGCTGGCCGGCTGA | 7810 |
| | | | | | 7812 |
| | 3 | MVMMVFLESLPALSQSPQSSLLTG* | 7813 | ATGGTGATGATGGTTTTTTAGAAAGTCTTCCTGCTCGAGCCAGTCACCCCAGTCTT CTCTCACTGGGTAA | 7814 |
| | 4 | METSHDSERLLVNNKMRYWGTLLLSWRGEARACSQV VPACLNARTWTPLPQLDLKANDRPFQP* | 7815 | ATGGAAACTTCCCATGACTCGGAACGCTTATTGGTGAATAATAAAATGAGGTACTGG GGAACACTTCTTATTATCATGGAGAGGGAGGCGAGACCTGCAGCCAAGTCGTACC AGCTTGTTTAAATGCACGGACTTGGACTCCTTTACCACCAGTTAGAACCTTAGGGCAAA TGATAGACCCTTTCAACCTTAG | 7816 |
| hsa-mir-659 | 1 | MARPPQKLNSGLRKIPF* | 7817 | ATGGCAAGACACCCCAGAAACTAAACTCAGGTCTGCGTAAAATTCCTTTGA | 7818 |
| | 2 | MNNCHLLNI* | 7819 | ATGAATAACTGTCACCTTTTAAATATATGA | 7820 |
| | 3 | MTYPSYY* | 7821 | ATGACTGTCCAAGTTACTACTAA | 7822 |
| | 4 | MDNTDY* | 7823 | ATGGATAACACTGACTACTAA | 7824 |
| hsa-mir-660 | 1 | MSRAPASLPLLPGWAV* | 7825 | ATGAAGCTGCGCGCTACGTCGCCTCCCCTCCCGCTGGGCTGTGTGA | 7826 |
| | 2 | MKLCRLRGALTQLGVLDARADRARCFPAADTGSAAPD LGDR* | 7827 | ATGAAGCTGCGCGAGCCGGCTACGTCGGGGCTGCTCACTCAACTTGGTGTCCTGGACGCCAGA GCCGACCGAGCGCGTGCTGCCACCGGCGGCGACAGCGTGCTCCGCCGCTCCGGACCT CGGCGACAGGTAA | 7828 |
| | 3 | MGLPRARRWQPGA* | 7829 | ATGGGGCTTCCCCGGGCTCGGAGGCGTTGGCAGCCCGGCTTAG | 7830 |
| | 4 | MVPGLPERSFLAERRQARPAPESECLAACVPFPGLG* | 7831 | ATGGTCCCTGGGTTGCCCGAGAGCTTCCTTGCGAGCGGCGCCAAGCCCGCCCC GCTTTGAATCGGAGTTGTTTAGCGCGCGCCTTTCCCGGACTGGGTAG | 7832 |
| hsa-mir-661 | 1 | MDPSRAIQNEISSLKGAVLGPGPSRGARTTQ* | 7833 | ATGGACCCCTCGGAGCAATCCAGAACGAGATCAGCTCCCTCAAAGGTGCGGTCCTG GGGCCGGCCGAGCCGGCGGACCACAGTGA | 7834 |
| | 2 | MPQCGVCGAGRVGGEHSAPGSSLRLPFPPAGPWLVGG RGLPPSPAPSLLEEATALSCPEPAWGRRGWLGGGPAGV SPGTPAGLCRREPRSTCF* | 7835 | ATGCCGCAGTGCGGGGTGTGTGGAGCTGGCAGGGTGGGCCAGGAACATTCTGCTCC GGCTCCTCCCTGCCGGTTCCCTCGCTTCCTGCCAGGCCCTGCAGGCCCTGCTGGTGGGAGGAG GGGACTTCCTGCCGGCTTGGGGAGGCGGTTGGGTGCCAGCCGTACCGCCCTTCCTG CCCGAGCCGGCTTGGGGAGGCGGTTGGGTGCCAGCAGGAAGCTACCGCCCTTCCTG GTCCTGGCACCCTGCAGGCCTGTGTAGAGAGAACTAGGTCCACGTGCTTTTAA | 7836 |
| | 3 | MRSACRECRRSVWGGALRDWPRG* | 7837 | ATGCGGTCGGCCTGCCGGGAGTGCCGGAGTGCAGGGAGTTCAGTGTGGGGGTGCGTGAGGTA CTGGCCAAGAGGGTAG | 7838 |
| | 4 | MPQRAGPARGLWEPWLCLRSFPATIPLCTQACACACV CARVCVCVCVFGACTVAPWRRPHKPAPTSCLLAAC RLLASASHLGPPLSHSPPPYL* | 7839 | ATGCCGCAGCGCGCCGGCCCTGCCCGGGAGTGCTGGGAACCGTGGCTATGCCTTCG GAGTTTCCCGCGCCACCATCCCGTATACCAGCGTGCCGTGCAGGTGGTGTGTG TGCGCGCGTGTGTGTGTGTGCCCCATAAACCCGCCACAACCGCCCTCTGCCCGGCTCG ATGGCGAGCCAGCGCTCCACCGTCCCCCTTGTTGGGGCGTCCTGCTGGCT GCTGGCCAGCAGCCACCTCGGGATCCCCCCCCTCCTCCCCACCGCCC TATTATAA | 7840 |

Figure 1 (Continued)

| | | | | | |
|---|---|---|---|---|---|
| hsa-mir-661 | 1 | MSGEDAEVRAVSEDVSNGSSGSPSPGDTLPWNLGKTQR SRRSGGGAGSNGSVLDPAERAVIRIAGNCAGPCLCTSLA REVD* | 7841 | ATGTCGGGTGAGGACGCTGAGGTCCGGGCAGTTCTGAAGATGTCTCAATGGAAG CAGTGGCTCGCCCAGCCTGCGGGACACACTGCCCTGGAACCTTGGGAAACGCAGC GGAGCCGGCGCATGGGGGTGGCGCTGGAGCAACGGAGTGTCTGGACCCAGCT GAGCGGGCGGCGTCATTGCATGCAGGTAACTGCGCAGGGCCTTGCCTGTGCACCTCC TTGGCACGCGAGGTTGACTGA | 7842 |
| | 2 | MSPMEAVARPALGTHCPGTLGKRSEiAGAAGVALGATG VSWTQLSGRSFASQVTAQGLACAPPWHARLTEFPLRAR RWSGDWVGEA* | 7843 | ATGTCTCCAATGGAAGCAGTGGCTCGCCCAGCCTGGCACACACTGCCCTGGAACC TTGGGAAAACGCAGTGGGAGCCGGCAGCGGCACCGGGAGGGTGGCGCTGGAGCAACGGAGG TGTCCTTGGACCCAGCTGAGCGGGCGGTCATTGCATGCAGGTAACTGCAGGGC CTTGCCTGTGCACCTCCTTGGCACGCGAGGTTGACTGAGTTCCCGCTGCAGGGCTAG CGCTGGAGCGGGGACTGGGTGGGGAGGCTAG | 7844 |
| | 3 | MRPGVGLLAAASILDFNTVQCPDATRIHFWVPHQALGL GCHRNGGQVGMYRSSY* | 7845 | ATGAGGCCTGGGGTTGGACTTCTTGCCGCGGCGTCCATCCTTGATTTAACACGGTC CAGTGCCCAGATGCAACAAGGATAATTTTTGGGTTCCACCAGGCCCTGGTCTT GGCTGCCACAATGCGGTCCAGGTGGAATGTACAGGAGCAGTGTATAG | 7846 |
| | 4 | MQQG* | 7847 | ATGCAACAAGGATAA | 7848 |
| hsa-mir-662 | 1 | MLIPGGQSRTVRCCQLWRGQASSIKSLFFFNTESHSVA QAGVQWCDRSSLHATSASQVQPPG* | 7849 | ATGCTGATTCCTGGTGGCCAGAGCCGCACGGTGAGATGCTGTAGCTGTGGAGAGG GCAGGCCAGCTCCATCAAGAGCTCTTTTTTTCTTTAACACAGAGTCTCACTCTGTT GCCCAGGCTGGAGTGCAGTGGTTGCCATCGAGCTCACTGCAACCTCCGCCTCC CAGGTTCAGCTCCTGGGTAG | 7850 |
| | 2 | MLSAVERAGQLHQESFFF* | 7851 | ATGCTGTCAGCTGTGGAGAGAGGGCAGGCCAGCTCCATCAAGAGCTCTTCTGGTGATAGAATGGGATTACAGGCGTGAA | 7852 |
| | 3 | MQPPPPRFSLLGRWDYRREPPCLAKGHVFF* | 7853 | ATGCAACCTCCGCCTCCAGGTTCAGCTCCTGGCCAGGTGTATCGTGTTTTTTTGA | 7854 |
| | 4 | MGLQA* | 7855 | ATGGGATTACAGGCGTGA | 7856 |
| hsa-mir-665 | 1 | MVNPILCT* | 7857 | ATGGTTAATCCAATTCTGTGCACCTGA | 7858 |
| | 2 | MTERMNGHMND* | 7859 | ATGACAGAAAGAATGAATGGACACATGAACGACTGA | 7860 |
| | 3 | MEMPGTARKELPMGLSFISLWAPEVHKREKRQEEKCQ GVKDRAKERQK* | 7861 | ATGGAAATGCCTGGCACAGCTCGGAAGGAGCTGCCCATGGGATTGTCATTCATTCA CTCTGGGCACCTGAGGTCCATAAGCGTGAAAAGAGGCAGGAAGAAGTGTCAGGG AGTCAAAGATAGAGCTAAGGAAAGGCAAAATGA | 7862 |
| | 4 | MKLNESERENKEKPIKKRITNTWVYL* | 7863 | ATGAAACTAAATGAAAGCGAAAGGAAAATAAAGAAAAACCAATAAAAAGAGAA CGAATACGTGGGTGTATCTGTAA | 7864 |
| | 1 | MRSP* | 7865 | ATGCGGTCACCATAG | 7866 |
| hsa-mir-671 | 2 | MLSLARPPLPFPTGLRTRSVPQSPSRDLRFPRLAERPELVSR APFSAAR* | 7867 | ATGCTGTCTCTGGCGCGGCCTCCGCTCCCGCTCCCGACTGGCCTGAGAACGAGGTCTGTG CCCGAGCTCCCAGCCGGCGACCTCCGACCCGCTCGCAGAACGACCCGGAGCTGGTC TCCCGAGCCGCCCTTCTCAGCAGCCGGTGA | 7868 |
| | 3 | MPCKMAPSAMALLRGCQC* | 7869 | ATGCCCTGCAAGATGGCTCCATGGCGCTCCTGAGAGGCTGTCAGTGCTGA | 7870 |
| | 4 | MCAMRVAPDRS* | 7871 | ATGTGTGCCATGCGAGTGGCTCCGGACCGCTCCTGA | 7872 |
| hsa-mir-708 | 1 | MRPQLLALCNFRGARLSSPGARPRY* | 7873 | ATGCGACCTCAGCTCCTGGCCCTGTGCAACCGCGGGGCCCGCCTCTCCTCATCG GGCGCCGGCCGGTATTGA | 7874 |
| | 2 | MDAWRAPGCECDCMTTLTPSFGKCALG* | 7875 | ATGGACGCTTGGAGGGCTCCGGTTGCGAGTGTGACTGTATGACTACTCTCACCCCC AGCTTCGGGAAATGTGCTCTGGGTTGA | 7876 |
| | 3 | MCSGLKCDHRAPQSF* | 7877 | ATGTGCTCTGGGTTGAAATGTGATCACCGAGCTCCTCAGTCATTTTAA | 7878 |
| | 4 | MRSLHWRSRLEGSGAACVCVCVCGHTHATEEYTTN YLGEGRGVHLVSPSWRGGRAS* | 7879 | ATGCGGTCGTTACATTGGAGGAGCAGACTGGAAGGTAGTGGGCGGCGTGTGTGTG TGTGTGTGGTTGAAGGCGGGGGGTTCACCCATGCAGAGGAATACAACCAACT ACTTCGGTGAAGGCGGGGGGTTCACCTAGTGAGTCCTTCTTGGCGGGGGTCGG GCGAGTTAG | 7880 |

Figure 1 (Continued)

| | | | | |
|---|---|---|---|---|
| hsa-mir-7-1 | 1 | MSWSYVALGTRDLVEERRPVRGEGRAAALFV* | 7881 | ATGAGCTGGAGCTATGTGGCACTGGGAACTAGGGACCTCGTGGAGGAAAGGAGGCCGGTGCGGGGAGAAGGTCGCCGCGCTCTTGTGTGA | 7882 |
| | 2 | MWHWELGTSWRKGGRCGEKVAPPLSLCEPRLTLGLPARGRSWSGGDGTVRAASMALSRAVGGGCGG* | 7883 | ATGTGGCACTGGGAACTAGGGACCTCGTGTGAGCCCCGCCTCACCTTGGGTCGCGGTGAGGTCGCCGCCCGCCTGAGCTCGAGCTGGAGCGCTGGAGCGGCTGGAGCGCGGGGTCGGGCAGTGGGGGAGGATGCGGGGGATGA | 7884 |
| | 3 | MERSGLPRWLCLGQWGEDAGDETSGPRGGWGRGSALGSA* | 7885 | ATGGAACGGTCAGGGCTGCCTCGATGGCTTGTCTCGGGCAGTGGGGGGAGGATGCGGGGGATGAGAGACCTCGGGACCGCGGTGGGGACCGCGTGGTGGGTGGGGGAGGCGGTCGGCGCTCGGCTCCGCCTAG | 7886 |
| | 4 | MRGMRPRDRVVGGGGRRSAPPSST* | 7887 | ATGCGGGGATGAGACCTCGGGACCGCGTGGTGGGTGGGGGAGGCGGTCGGCGCTCGGCTCCGCCTAGTAGCACGTAG | 7888 |
| | 1 | MLAFSLSPANTIDVGRLSKSiVKEL* | 7889 | ATGTTGCTTTCTCTCTCCAGCAACATACCGATGTAGGCAGACTGAGCAAGTCAATCGTAAAGGAACTTTAG | 7890 |
| | 2 | MSGVQPCAPTVGRGPSYLPCCLTVTQSWILTKHTPRlSAGVMQDSLWLTPLVPRFPLLLAAVLVCKAELISFSPWRRV* | 7891 | ATGTCAGGAGTGCAACCATGTGCTCCACTGTGGGCAGAGCGCCTCAGTACTACCGGTGTTGTCTGACAGTTACACAGTTGGATACTTCACAAAAACACTCCTCGTATCAGTGCTGGGTCATGCAGGATGCACTGACTATGGTTGACACCTGTTGACCTCTGCTCTTGCCGCTGTCCTGTCCTAGTCGTGAAAGCAGAGCTAATAAGCCCAGCCCTGGAGAAGGGTGTAA | 7892 |
| hsa-mir-7-2 | 3 | MCSHCGQRALSTTVLSDSYTVLDTHKTHSSYQCWGHAGLTMVDTSCAQTSALGRCPSL* | 7893 | ATGTGCTCCACTGTGGCAGAGGGCCCTCAGTACTACCGTGTTGTCTGACAGTTACACTGGATACTCACAAAACACTCCTCGTATCAGTGCTGGGTCATGCAGGACTCACTATGGTTGACACCTGTTGCCCAGACTCTGCTCTGCCAGCTCTGCTCTTGGACCCTGGAGAAGGGTGTAA | 7894 |
| | 4 | MQSTWHTMGVHPVPTPSSLLPFDIDKLC* | 7895 | ATGCAAAGTACCTGGCACACAATGGGTGTTCACCCAGTGCCAACGCCCTCCTCTCCTCCCCTTTGACGACAAGCTGTGCTAA | 7896 |
| | 1 | MPGMRLVCRLAHGHPPRKGQRRRSLTVWKAETSRADCLGGKFWGHGTG* | 7897 | ATGCCGGGAATGAGAGCTGGTTGCAGGTGGCGCATGGACATTTTCCAGAAAGGACAGAGACGGCGAAGTTGACGGTCTGAAAGCAGAGACCAGCAGGGCTGACTGCTTGGGAGGTAAGTTCTGGGGACATGGTACAGGGTGA | 7898 |
| | 2 | MDIFPERDRDGEV* | 7899 | ATGGACATTTTCCAGAAAGGAGACAGAGACGGCGAAGTTTGA | 7900 |
| hsa-mir-7-3 | 3 | MVQGEEQVSVLVATPLCLPPATPLPF* | 7901 | ATGGTACAGGGTGAGGAGCAAGTATCAGTGTCAGTTGCGACCCCTCTGTGTCTCCCCGCCGCCACCCCAGCCATTGCCATTCTGA | 7902 |
| | 4 | MLFISAPNIRTAPLGRSEKRTAICFSTGAQDSSQRAPPRLQNPGQLLQVTGEPFDPFAGGRERVV* | 7903 | ATGCTATTTATTTCAGCACCAAATATCCGACAGCACCCTGTTTTCAGCAGCGCTCCTCGGACAGGCGCTCTCGGAGAGTCCGAGAAGAGAACCGATCTGTTTCAGCACCGGTCTCAGGACAGTCTCCAGCAGCCCTTTGACCCTGATTCGTCCAGAACCCTGGACAGCTCCTCCAGTAAGGAGAGCCCTTTGACCCTGATTTTGCAGGGGGAGGACGAGAGGGTGGTCTGA | 7904 |
| | 1 | MAAPSPSGGGSGGGSGGSGTPGPVGSPAPGHPAVSSMQGKERGRAEIPAP* | 7905 | ATGGCGGCTCCAGCCCTGAGCCTGGAGGCGGCGCGCCGGGCAGCGGCAGCGGCAGCGGCGCACCCCGGCCCCGTAGGGGTCCCGGCCCCGGCGCCACCCGGCCGTCAGCAGCATGCAGGGGTAAGGAAGCGGCCGCGAGATCCCAGCCCCTAG | 7906 |
| hsa-mir-744 | 2 | MGVGGLPRPVPPVR* | 7907 | ATGGGGGTGGGGGGCCTGCCAGGCCTGTTGCCTAAGTAG | 7908 |
| | 3 | MERYRK* | 7909 | ATGGAGAGATACAGGAAATAG | 7910 |
| | 4 | MTPFTGNAY* | 7911 | ATGACTTTTCCCACTGGGAATGCTTATTAG | 7912 |
| hsa-mir-758 | 1 | MDQGIVEGGGCGPGVGRQSACSL* | 7913 | ATGGACCAGGGGATAGAGGGTGGTGTTGACCTGGGGTCGGGCGCCAGTCAGCTTGCAGCCTATGA | 7914 |
| | 2 | MKIDGKEGYRDRGRVGLRIARAAWHTVLG* | 7915 | ATGAAGGACGGAAAGGAGGGCTACAGAGATAGGGGAAGAGTTGGGCTGAGGATAGCCAGAGCGGCTTGGCACACAGTTTTAGGGTAA | 7916 |

Figure 1 (Continued)

| | | | | | |
|---|---|---|---|---|---|
| | 3 | MTEPVTPGSSFKACLMGDSVVPVTKLGPESQGRAHQV AALP* | 7917 | ATGACTGAGCCGGTCACTCCAGGGTCTTCCTTCAAAGCGTGTCTAATGGGAGACAGC GTTGTCCCAGTAACCAAATTGGGACCAGAGTCCCAGGGAAGGGCTCATCAGGTGGC CGCTCTGCCTGA | 7918 |
| hsa-mir-760 | 4 | MILFPLDPAPLVPFSL* | 7919 | ATGATTCTTCCTCCTGGATCCAGCCCCTCAGTTCCTTTCACTTTGA | 7920 |
| | 1 | MTKDVKNADMGIK* | 7921 | ATGACAAAGATGTTAAAATGCTGATATGGGCATAA | 7922 |
| | 2 | MLKMLIWA* | 7923 | ATGTTAAAAATGCTGATATGGGCATAA | 7924 |
| | 3 | MACGENCKAGL* | 7925 | ATGGCTTGTGGAGAATGCAAGCTGACTATAG | 7926 |
| | 4 | MDYYFSLYLF* | 7927 | ATGGATGTTACTTTCCTGTATCTTTTGA | 7928 |
| | 1 | MVAPHLCT* | 7929 | ATGGTTAATCAATTCTTGCACTGA | 7930 |
| | 2 | MTERMNGHMND* | 7931 | ATGACAAGAAGAATGAATGAACATGAACGACTGA | 7932 |
| hsa-mir-770 | 3 | MEMPGTARKELPMGLSFISLWAPEVHKREKRQEEKCQ GVKDRAKERQK* | 7933 | ATGGAAATGCCTGGCACAGCCAGGAAGGAGCTGCCATGGATGTTCATTCATTCTCA CCTGGGCACCTGAAGTCCATAAGCGTGAAAAGGACCAGGAAGAGAAGTGTCAGGG AGTCAAAGATAGAGCTAAGGAAAGGCAAAAATGA | 7934 |
| | 4 | MKLNESERENKEKPKKRTNTWVYL* | 7935 | ATGAAACTAAATGAAAGCGAAAGGGAAATAAAGAAAGAAAAACCAATAAAAAGAGAA CGAATACGTGGGTATCTGTAA | 7936 |
| | 1 | MTSMC* | 7937 | ATGACATCAATGTGCTAG | 7938 |
| hsa-mir-802 | 2 | MHTSWL* | 7939 | ATGCATACATCATGGCTTTGA | 7940 |
| | 3 | MALKKIGLRTRQSKTKQTDKNSNQT* | 7941 | ATGGCTTTGAAAAAAATAGTCTGAGAACGAGGCAAAGTAAAACTAAGCAAACAGA TAAGAATAGCAACCTGA | 7942 |
| | 4 | MTTILSFYIAYLETYD* | 7943 | ATGACAACAATTCTAAGTTTTACATTGCTACCTGAAACCTATGATTGA | 7944 |
| | 1 | MGAGEGVGASISRASIDELPDSLQPRQRRQEPQGRANRL GWGCLGRCRGSWKGGSAPGSLELPPFLGDQGAASLRG RGSKWVAAFSS* | 7945 | ATGGGAGCCAGGGAGGGTGTAGGGGCCAGTATTTCTCGGGCTAGTGACGAACTGCC TGATTCTTTGCAGCCTCAGACAGAGGAGGGCAGGAGCCCAGGGCGGCGCTAATGCC TGGGCTGGGATGCCTGGCACAGCAGGGATGCAGAGGAAGTGGAAAGTGGCAGTGCACCT GGTGCTCTGGAGCTCGCCGCGCGTTCCTAGGAGACCAAGGAGCAGCAAGCTGCGGCG GAGGGGAGCAAGTGGGTTGCTGCTTTTAGCAGCTGA | 7946 |
| hsa-mir-874 | 2 | MPGQMQRKLERWQCTWVAGAAAVPRRPRSSKPAGEG EQVGCCF* | 7947 | ATGCCTGGGCAGATGCAGAGGAAGTGGAAAGTTGCACCTGGGTCGCTGG AGCTGCGCCGCCGTTCCTAGGAGACCAAGGAGCAGCAAGCTGCGGCGGAGGGGAGC AAGTGGGTTGCTGCTTTTAG | 7948 |
| | 3 | MLNHCC* | 7949 | ATGCTGAATCACTGTTGCTGA | 7950 |
| | 4 | MEGERYVCISVCCVVCVCKCMCACGAATSFCVCIG* | 7951 | ATGGAGGGTGAAAGGTATGTATGTATCAGTGTGCTGTCGTGTGTGTGTATGTAAG TGTATGTGTCGCTGTTGCGTGACCACCAGCTTGTGTCACCAGCTTCAGCGGCCATAA | 7952 |
| | 1 | MIKTYNH* | 7953 | ATGATAAAAACATATAATCATTAG | 7954 |
| hsa-mir-875 | 2 | MVFL* | 7955 | ATGGTGTTTCTCTAA | 7956 |
| | 3 | MMPLRSVFDCVY* | 7957 | ATGATGTTTTTGCACAGTTGTTTTGACTGTGTTTATTAA | 7958 |
| | 4 | MQJHNKCKLLRF* | 7959 | ATGCAGATTCACATAACAAGTGCAAATTGTTGAGGTTTAA | 7960 |
| | 1 | MMGHRLPVRGVGLFLSPLPAPAAAVGTGAQPILKPCGE GPVTPVLASSQGP* | 7961 | ATGATGGGGTCACAGACTCCCGTCGAGGTGTCGTTCCTTCGCTCGCTCCCG GCTCCGCTGCGCTGCCGGCTGTTGGAACTGGAGCGCAGCCATCTGAAGCCCTGCGGGA GGGCCGTGGACGGTGACGCAGTGCTGCCACGTTCAGCGGCCATAA | 7962 |
| hsa-mir-877 | 2 | MFSPPRHPIWTDPPGCAWGESLLQGAVGTAPRASWRDSP PPTLHPSPFLPDVGGVGDPLRDRPRGLTRSHDPLPRSPE VQRAHPSFQMCGSPSPAPSSRSRTDLSSAPVCPATASSS ASR* | 7963 | ATGTTCAGTCCTCACAGACTCCCCAGAACACCCTATTTGGGACCCTGCCGGATGTGCGTGGCGGGAG TCAACTCTCGATCCTCATCCTCCCACCCTCCAGATGGAGCGGCCCGTAGCTGGAGGATTCCCT CCCCAACTCTGCATCTCCCTCGCGCTTGACGCGGTCAGATGTGCGGAAGGCCGAGCCGCCGCA GAGGTGCAGCGGGCACCACCCTCCTTCAGATGTGCGGAAGCCGAGCCCGCCGCCCTC CTCCTCCCGCTCCCCAGTCCCCCACTGACCTCTTCCGCTTGTCTGCTGCAACTGCTTCT TCTTCTCTGCTTCACGCTGA | 7964 |

Figure 1 (Continued)

| | | | | | |
|---|---|---|---|---|---|
| | 3 | MCVGGVTPSGSSGDGAPC* | 7965 | ATGTGCGTCGGGGTGAGTCACTCCTTCAGGGAGCAGTGGGGACGGCGGGCCCGTGCTAG | 7966 |
| | 4 | MASSSAWPGPVTWPALRRAPAASTDCPPGQPPPQPGT LEEAGLAGDVSGRARQNYRRGGDRRTGEI* | 7967 | ATGGCTTCTTCCGCATGGGCCCGGACCAGTCACCTGGCCGCCCGCGGCCCTCCGCGAGCT CCGGGCCGCCTCAACTGACCTGCCCCGGGGCAGCGCCGCCGCGGCCAGGGGCCGGAC CCTAGAGGAGGCGGGCGTAGCAGGTGACGTCAGGTGCGCTCAGGGCCCGACAGAATTACC GCCGGCGGCGATGGAAGGCGGACGGGGAGATATAG | 7968 |
| hsa-mir-877 | 1 | MSIISQ* | 7969 | ATGTCAATTATATCTCAGTAA | 7970 |
| | 2 | MNRSSTAP* | 7971 | ATGAACCGAAGCTCCACTGCACCCGTGA | 7972 |
| | 3 | MLGSSSLFTVHFGIL* | 7973 | ATGTTGGGCTCCAGTTCCCTGTTTACAATTGTACACTTGGATTTTGTGA | 7974 |
| | 4 | MTQSVSRPMTLS* | 7975 | ATGACCCAGTCAGTCTCGCGCCCATGACCCTCTCTAA | 7976 |
| hsa-mir-885 | 1 | MWPPVPGLCHSLCACPTGATPDHVDASSREQHGPH* | 7977 | ATGTGGCCTCCAGTGCCTGGCCTTTGTCACTCACTCGTGCTTGTCCCACAGGAGCC ACCACCCTGACCATGTAGATGCCAGTTCAGGGAGCAGCATGGGCCCACTGA | 7978 |
| | 2 | MPVGSSMGPTEWRLLGLQP* | 7979 | ATGCCAGTTCCAGGGAGCAGCATGGGCCCACTGAATGGAGACTCCTGGGTCTACA GCCCTGA | 7980 |
| | 3 | METPGSTALSPSGPWTSSHTGGHLLELTTVTSPPRPPPP PGTRSRPPGATADQ* | 7981 | ATGGAGACTCCTGGGTCTACAGCCCTGAGCCCCTGGCCCTGGACCCTCGTCCAC ACCGGAGGACACCTTGGAGCTCACCACCGTCACCAGCCGCCTCGGCCACCC CACCCCCCGGGACCGGAGTCGCGGCCGCTGGTGCCACAGTCGACCAGTGA | 7982 |
| | 4 | MGDMTNSDFYSKNQRNESSHGGHFGCTMEELRSLMEL RGTEAVVKIKETYGDTEAICRRLKTSPVEGKCSRLEPRA AA* | 7983 | ATGGGTGACATGACCAACAGCGACTTTTACTCCAAGAACCAAAGAAATGAGTCGAG CCATGGGGGCGAGTTCGGGTGCACAATGGAGGAGCTCCGCTCCCTCATGGAGCTGC GGGCACTGAGGCTGTGGTCAAGATCAAGGAGACTTATGGGGACACCGAAGCCATC TGCCGCCGCCTCAAAACCTCACCTGTGGAAGGTAAGTGTCAAGACTTGAACCCAGG GCTGCAGCCTAG | 7984 |
| | 1 | MGTRRRRGEPLGGPGARAVRGAAPAGPQRGL* | 7985 | ATGGGGACCCGGCGGCGGCGGCGGCGGGAGCCTCTGGGCGGCCCGGGCGGCGCGG CTGTGCGCGGCGCTCCGGGAGACGCGGGCATGA | 7986 |
| | 2 | MECPGRKRA* | 7987 | ATGGAGTGTCCGGGAGACGCGGCCATGA | 7988 |
| hsa-mir-887 | 3 | MTATGWARTMANSTAVRVSGPPVLRLPDRVPPPLSLAL PTGKGGSRPRP* | 7989 | ATGACGGCTACAGGATGGGCGCGAACAATGGCAAACAGTACGGCAGTGAGGGTGAG TGGGCGCGCGGTCCTCAGACTCGGATCGTCCCGGTCCTCCGCCCTTTCCCTCGCCCTC CCGACTGGGAAGGGAGGTTCTGCGCCGCGGCCGTGA | 7990 |
| | 4 | MGANNGKQYGEGEWAARPQTTPGSRPSSPFPRPPDWE GRFSPAAVTHPIWHPVWVTTFSFGSE* | 7991 | ATGGGCGCGAACAATGGCAAACAGTACGGCGAGGGTGAGTGGGCGCGACCCGTCC TCAGACTCCGGATCGCGTCCTCCTCCTTCCCTCCGCCTCCGACTGGGAAGG GAGGTTCTCGCGCCGGCCGTGACGACCCCATTTGGCACCCGTCTGGGTCACCAC CTTCTTCTTTGCAGTGAGTGA | 7992 |
| | 1 | MDQGVEGGGCGPGVGRQSACSL* | 7993 | ATGGACCAGGGGGTAGAGGAGGAGGTGGGGTGGACCTGGGGTCGGGGCCAGTCAG CTTTGCACCTATGA | 7994 |
| hsa-mir-889 | 2 | MKDGKEGYRDRGRVGLRLARAAWHTYLG* | 7995 | ATGAAGGACGGAAAGGAGGGCTACAGAGATAGGGGAAGAGTGGGGCTGAGGATAG CCAGAGCGGCTGGCACACAGTTTTAGGGTAA | 7996 |
| | 3 | MTEPVTPGSSFKACLMGDSVVPVTKLGPESQGRAHQV AALP* | 7997 | ATGACTGAGCCGGTCACTCCAGGGTCTCCTTCAAAGCGTGTCTAATGGAGACAGC GTTGTCCCAGTAACAAATTGGGACCCAGAGTCCCAGGGAAGGGCTCATCAGGTGGC CGCTCTGCCTGA | 7998 |
| | 4 | MILFPLDPAPLVPFSL* | 7999 | ATGATTCTCTTCCCTCTGGATCCAGCCCCTCTAGTTCCTTTCACTTGA | 8000 |
| | 1 | MGTILPDLFPGGVSAVSPSP* | 8001 | ATGGGTACTCTCCCCGGATCTCTTCCCGGGTGGGTCTGCTGTTCCTTCCTCTCTTGA | 8002 |

Figure 1 (Continued)

| | | Protein | SEQ ID | Nucleotide | SEQ ID |
|---|---|---|---|---|---|
| hsa-mir-9-1 | 2 | MRPRSSREGQWRPGEAGEASAWVAAVFPGGTKSPRYPSTWDQKNSCSWPEWESGKWGTRMPLGLDRGQLPDFDATGHRVLSTPFSVSVVSVSPCLRFLLLFCLGLHFSLHPPFQLESCPFFPTPADGRPGSCGGAGGGGREAAWKRRQQPGGGVGCYLWLSSCMSGVESS* | 8003 | ATGCGCCCTCGACTTCCAGAGAAGGGCAGTGAGACCCGGCGAGGCTGGGAGGCCTTGCCTGGGCTGCCTGCTGAGCGGAACTCCTGCTCCTGGGTCTCCGGGTGGCACGAAAAGCCCGCGAGGCCCTTCCACCTGGACCAGGAACTTTTGGGTCTGGATCGGGGTCAACTCCCCGACTTCGACGCCACGGGCACCAGAAACTTTTGGGTCTGGATCGGGGTCAACTCCCCGACTTCGACGCCACGGGTCATCGCGTCCTTCCACGCGTCCTTCTGTTTGTTTGTTTGCGGTTCTGTGTCTCTATCTCCGTGTCTGAGGTTTTGTTGTTTGTCCGACTTCATTTCTCTTCCAACCCTCCCCTCAACTCCACTCGTCCTTCCCTTCCCTGACCTCCTCCCGCCGGGCAGCTGGCGGAAGCTGCGAGGTGTGGCGGCGGCCGGGCGCCGGAGGCGCGTGGAAGAGCGCGCGAGCAGCCAGGAGGCGGGGTGGTTTGGTGTATCTTGGTTATCTGAGTGTGAGTGGTGTGGAGTCTTCATAA | 8004 |
| | 3 | MGEREMGHQKLFGSGSGSTPRLRRHGSSRPFHAFFGLCRVCJSVSEVFVVVLSRTSFLSSPSPSTPLVSLPSYSR* | 8005 | ATGGGAGAGCGGGAAATGGGGCACCAGAAACTTTTTGGGTCTGGATCGGGGTCAACTCCCCGACTTCGACGCCACGGGTCCATCGCGCTCCGTCTGAGGTTTTGTTGTTTGTCCGACTTCATTTCGTGTCTGTATCCCGTGTCTGAGGTTTTGTTGTTTGTCCTCCTCCCGCCGCCATCTCTTCACCTCCACTCGTGTCCTTCCCTGTCCCTACTCCGCTGATAA | 8006 |
| | 4 | MGPFLAVWVTAWEADLREKSVEI* | 8007 | ATGGGCCTTTTCTGCAGTCTGGGTCACGTCGGTGATCTAAGGGAGAAATCAGTTGAAATCTAG | 8008 |
| | 1 | MDRQMLRHRSCILHSTRG* | 8009 | ATGGATAGACAGATGCTACGTCATCGAGCTGCATCTCCACTCCACAAGAGGCTAG | 8010 |
| | 2 | MEAGAKSSQKEKADKRFRGVPKMDEACV* | 8011 | ATGGAGGCTGGTGCAAATCATCACAGAAGAAAAGGCTGATAAAAGATTTAGGGGGGTCCCCAAATGGATGAGGCATGTGTAG | 8012 |
| hsa-mir-9-1 | 3 | MRHVCRGGVGSKALTSSLLGTYR* | 8013 | ATGAGGCATGTGTAGAGAGCCCAAGGCAGTGGCAGCAAGGCTCTCACTTGCCACCGGCTCCAGCGCTCGAGCCTCTGGGCACCTATCGCTGA | 8014 |
| | 4 | MCVEYELAARLSPPASWAPIAEPKAVALPTRPRVSPGSPPSPSPCRLETAH* | 8015 | ATGTGTGTAGAGGTGGAGTTGGCAGCAACAAAGGCTCTCACTTGCCAGCGCTCTCTGGGCACCTATCGCTGAGCCCAAGGCAGTGGCAGTGGCTCTGCCACCGCCCAGAGTGTCTCTGGTTCCCCTCCTTCCCCCAGCGCCATGCAGGCTGGAGACAGCTCACTAA | 8016 |
| | 1 | MKIDV* | 8017 | ATGAAAATTGATGTTTAA | 8018 |
| | 2 | MFKTIDKGSGFFSLQQSCVQH* | 8019 | ATGTTTAAAACAATAGACAAAGGCTCAGGATTTTCATTACAGCAGAGTTGTGTACAGCATTAG | 8020 |
| | 3 | MKSACLEHSVRTYRTKYAALSPWYIDTKHD* | 8021 | ATGAAAGTCCGCTTGCTTAGAGCATTCAGTTCAGATTCGAACTTACAGAACAAAATATGCTGCCTATCGCCATGTACATAGATACAAAACATGACTGA | 8022 |
| | 4 | MLPYRHGT* | 8023 | ATGCTGCCTATCGCCATGTACATAG | 8024 |
| | 1 | MLLGHHLPGPRSR* | 8025 | ATGCTTCTGGGCCACCATTTGCCAGGCCTCGAGGTAA | 8026 |
| hsa-mir-9-2 | 2 | MGTLTWAQIMIKMERGWDAGEGVLQPEGPGPRG* | 8027 | ATGGGCACCCTTACCTGGGCTATTCAAATAATGATCAAATGAACCGGGATGGGATGGGAGGGGTGAGGGAGTGGTCCAGGCCGGAGGGCCCGGGGCCCCAGAGGATGA | 8028 |
| | 3 | MGCG* | 8029 | ATGGGATGCGGGTGA | 8030 |
| hsa-mir-9-2 | 4 | MRVRECSSRRARGPEDDVRLEAWTPGSCPWAPCASSQGSERLRGAPAIRFPFLSRAFDSSLLYTPACK* | 8031 | ATGCGGGTGAGGGAGTGCTCCAGCCGGAGGGCCCGGGGCCCCGAGGATGTGCGCCTGGAAGCTTGGACCCCTGGGTCCTGCCCATGGGCCCCTTGCCAGCTATCCGATTTCCCTTCCTAAGTCGCGCGTTCGACAGCAGCCTCCTTTACACACCGCGTGCAAATGA | 8032 |

Figure 1 (Continued)

| | | | | |
|---|---|---|---|---|
| | 1 | MVAATPPCESARPSEDGGKPVVCGPGLAGGAERPGAD WPGAAWRRRGRGESRPLAAPACGSRIWLPPRSFPAGRR RGAGPGREGGBGRBRARGGRRARDPRRPCLGRPEGGWAD GEHRNGPSGRGRARPVPSPGPGARAGRGVSG* | 8033 | ATGGTGGCGGCTACTCCTCCTGGTGAGTCTGCCGCCCTCTGCCGCCCTCCGGCACGAGGGAA ACCTGTTGTGCGGACCGTGGCGGACGGGCTGGGCGGGGCGGGAGGGCGGCGGGCGGACT GGCCCGGAGCAGGTGGCAGCGTGTGCAGCCGCATCTGGCTGCCCCTCGCCCTGCGCGGTTGGCC GCCCGGCGGTGTGGCAGCCGCATGGCTGCCCCTCGCGGGGCGGGCGAGGAGGCGGGCG GAGGAGGCCAGGGCGGATGGGAGGTGGCGAGAGGGAGCGGCCGTGCGGGTGCGTGGCGGC CGGGGCCCCGGGACCCCAGACCCTGCCTGGCCGCAGACCCCGAAGGGCGGGGTGGGCGGA CGGCGAACACAATGGCCTGCGCGGGAGGACGTGGAGAGCCCTGTGCCTTCTCCGG GCGCCCGGGGGGTGCGCGGGGTGGGTCTCGGGTAG | 8034 |
| hsa-mir-92a-1 | 2 | MAPRGEDVRGPCLLRGPGRARGIVGSLGRKVSPEGES* | 8035 | ATGGCCCCTCGGGAGGAGACGTGCGAGGCCCTGTGCTTCTCCGGGCCCGGGGCG CGCGCGGACGTGGGTCTCTGCGTAGGAAAGTTCTCCCGAGGGCGAGAGTTAA | 8036 |
| | 3 | MGQAAGREGARPRGTCAPAGGVAWAGARGSPNFVRA RVGGGAPRSARPGRHPRSAWALLARVGSLGAGPATSPP GRCTTTGTTAGCCCGGTGGGGCAGCCTCGGGGCGGCCTGAGCTCGCAACTTCCCGCTGTG WPSEEAAVGLSRGVEPPAPGRLLGVWRGRASPARRERR PRRHVPAGRAARG* | 8037 | ATGGGGCAGGCCGCTGGCCGGGAGGGGCGCCCGCGAGTAGTTACTGCGCTCAG GTGGGCGGGAGGCCGCGAGATCGGGCGCGCCTGGGCGCGACAACTTGTAGCGCGCAGG GGCTTGTTAGCCCGGTGGGCAGCCTCGGGGCGGCCTGAGCTCGCAACTTCCCGCTGTG CCCTCGGAGGAGGCCGCAGTCGATCTCAACCGCGCGTGAGCCGCGCGCTGCCGGCG GCGCTTCGTGCTGGAGTGCGCCGCGGAGGCCAGCCGGCTCGGCGGGAGCGGCGT CCCCGGCGCTCATGTCCCTGCGGGCGCGGCTGCACGGGGGTGA | 8038 |
| | 4 | MFLRGGLHGGEGGHGGGGIDEAPPIVPGLGLGPRATGTA AAEPPPLWAGLGGAGGHKGGAARPRRTRASAPPVA ARLPGNGLGGLPRPAGPDSDPHPPGGYAENRRAALPL VRHVLPARAP* | 8039 | ATGTTCCTGCGGGGCGGCTGCACGGGGGGGTGCACGGGGGGACATGCGGCGACTG CGGCGGCGGCGATTGTTCCCGGCTTGGGCTCGGGGGGGCCCTCGGGGGGACACCG GCGGCGCGGAAGCCCCCGCCCTCTGGGCGTGGCGTGGGGACTCTGGCACACAAA GGAGGGGCGGCTGGCAGGGAAAACGGGTTGGGCCGCGCCCGCGGCTG CGGCGCGGCTGCCGCCGCCGCCCCTGGGCGCTGGGCTACGGGGAGAATGCCAGGGCGCGGCTG ACTCTGACCGCATGTCCTCCGCCGCCCCTGGCCGCTGGGCCGGGCTGCATGA TTGTGCGACATGTGCTGCGGTCCATGA | 8040 |
| | 1 | MGGGE* | 8041 | ATGGGGGGTGGCGAATAG | 8042 |
| | 2 | MSCLMNC* | 8043 | ATGTCTTGTTTAATGAACTGTAA | 8044 |
| hsa-mir-92a-2 | 3 | MSLLGSYFVLFPLIG* | 8045 | ATGTCACTCTTGGAGAGTTACTTCTACTTGTTCCTTTAATAGGATGA | 8046 |
| | 4 | MRSSFPTRFCLSNQDT* | 8047 | ATGATTTCATCTTTTCAACCTTTCTTCTGTCTCTTCAACCAAGACACATAG | 8048 |
| | 1 | MVVVKWVGRGQNRFRQALAA* | 8049 | ATGGTGGTTGTTGAAATGGGTGGGAGGGGCAGAACAGATTCAGGCAGGCGCTGG CTGCTTGA | 8050 |
| hsa-mir-92b | 2 | MGGBGAEQIQAGAGCLRGGAGTGAYRFHPVPPLPARPP* | 8051 | ATGGGTGGTGGAGGGGGCAGAACAGATTCAGGCAGGCGCTGCTCTTGAGAGGTG GAGGGGGACACAGGCGGCCTACGGTGCCCCCCACTCCCGCCCCGCGCCC CCTAG | 8052 |
| | 3 | MGNKAS* | 8053 | ATGGGGAACAAAGCCAGTAG | 8054 |
| | 4 | MSGLGASFGLPPFTTSRNSPTLLTAPCPVPHAVLP* | 8055 | ATGAGTGGACTAGGTGCTAGTTTTGGGCTCCCCCCACCACTTCCCGGAATAGC CCCACCCCTTCTAACCGCTCCCTGTCCCGTTCCACACGCAGTTCTACCCTGA | 8056 |
| | 1 | MSGSPLEDRMKNWEIMAVLESRQEDGESRACPALRPR NKRTRVRWPFKSDSPPAPARTAGNPAPALPRPEIPFRRP HRLPVTHSRPAR* | 8057 | ATGAGCGGGTCCCCTTGGAGGACAAGAAGACGGACAAGAATGGGATGCCGTTCT GGAGAGTAGAACAAGAAGACGGGAGAGCTGGCCGTCTCCTTAAGAGCGATTCTGCCGGAA ACAAAAGAACCGGGGAGTGTGCCCTGGCCTTAAAGAGCGATTCTGCCGCCAG CTCGGACCGCCACCGGGAAACCCGGCCTGCACTAACCCGCGAGATTCCCTTCGAC GCCCGCACCGCCGTCACTCATTCTAGGCCCACGGTGA | 8058 |
| hsa-mir-93 | 2 | MALKDYALEKGTGLRAREGVLRGPPGEHLLV* | 8059 | ATGGCACTGAAGGACTACGCGCTAGAGAAGGGTACGGGTTCTACGAGCCGGGAGGG CGTCCTGCGCGGGGAGCCTCCCGGGAAGCACCTGTTGGTGTGA | 8060 |
| | 3 | MLKKS* | 8061 | ATGTTGAAGAAAAGCTAG | 8062 |
| | 4 | MANGWTGSRPQRRNPEL* | 8063 | ATGGCCAATGGCTGGACTGGCTCCGCGCCTGGGCGGAGGAATCCGAGCTGTGA | 8064 |

Figure 1 (Continued)

| | | | | | |
|---|---|---|---|---|---|
| hsa-mir-9-3 | 1 | MSATEFS* | 8665 | ATGAGTGCCACAGAGCCGTCATAA | 8666 |
| | 2 | MILTTSACERPPHRPPRPGPQEPEEPRGAQRRPSGLQLD GAAAPRPGT* | 8667 | ATGATTCTCACAACTTCTGCGTGCGAGCGCCCGCCTCATGACGCCCGGCCGGC CCGCAAGAGCCAGAGGAGCCGAGAGGAGCCCAGCGCCCAGCGGACTCCAGCT CGACGGAGCGGCCGCGCCCCGGACCAGGTACCTGA | 8668 |
| | 3 | MQMRWERDSGR* | 8669 | ATGCAAATGCGATGGGAGAGAGACAGCGGTCGGTAG | 8670 |
| | 4 | MGERQRSVGGGWRE* | 8671 | ATGGAGAGACAGCGGTCGGTAGGGGTGGTGGAGGGAGTGA | 8672 |
| | 1 | MSAGGCWGPRDQRVPALARGAARAGWHSEAAPATPG KTQRLHPTFAPGCFSPEGPERSPLPCARSA* | 8673 | ATGAGTGCAGTGGGGTGCTGGGACCAGAGGGACCAACGGGTCCCGCGCTGGCTCG CGGCCGCCAAGGCTGGAGCATTCGAAGGAGCTGCAACGCTCGGGGAAAA TCACCCAGCGCCTCCACCCAACTTTGCTCCAGGATTTTGCAGCCCGCAGGGGCCAG AGCGCAGCCCTTCTGCCTGCCGCCCGAGCGCGTAG | 8674 |
| hsa-mir-95 | 2 | MSGRRPFFASHGGPGCSRLQKAVRVRAGAWGPGEGPG PQQT* | 8675 | ATGTCTGAAGGCGCCCTTCTTTGCTTCTACGGGGTCCGGTTGTTCAGCTG CAGAAAGCGGTCAGGTGTCCGCGGGGGCCTGGGTCCGGGCGAAGGGCCGGGC CCCAGCAGACCTAG | 8676 |
| | 3 | MIGGALQLGAPPLRRSGSAAWVGGVRPTLGAQDSPQQIW GPGARMCQTRFRPDLCASPAPRPCASHPCLSRRTHPPGS DSLCAGLEKSHSAGAQPRLVLLGRKLRPRTGALGGEPWR RPEDARJ* | 8677 | ATGATAGGGCGGGGTCTTTGCAGCTGGGCGCCCCTTGCGCCGCTCTGGCAGCGC CTGGGTTGGGCGGCGTCAGCGCCACCTTCGGCGCCCAGGACTCTCCGCAGCAGATCT GGCCCGGAGCCCGCATGGTCAGACCCGGCTGTCAGACCCGGCTCTCCGCGCTCC CAGGGCCCCTCGCGCCCTGCGGTCACCACCCGGCACCACCCTCCGG GATCTGACAGCCTCTGTGCGCGGTGGGAAAACTCCACAGCGCTGGAGCCAGCCG CGCCTTGTGCTGTGGGAAACTAGAACTGGAGCCCTTGGGGGTGAGCC CTGAGGGCGGCCTGAGGATGCCCGGATCTGA | 8678 |
| | 4 | MPGSESLLGPAPG* | 8679 | ATGCCTGGATCTGAGAGCCTCCTTGGGGCCCGCACCGGGCTGA | 8680 |
| hsa-mir-96 | 1 | MCIFFHPRGASHSAHFANGKLRLREVE* | 8681 | ATGTGCATTTTCTTCATCCCAGAGGGTGCGAGTCATTCTGCCATTTGCAAATGGG AAACTGAGGCTTAGAGAGGTGAAGTGA | 8682 |
| | 2 | MPWGQG* | 8683 | ATGCCATGGGGCCAGGGTTAG | 8684 |
| | 3 | MGPGLAGEPHRSERGQWQNHGRISGSA* | 8685 | ATGGGGCCAGGGTTAGCAGGAGAACCTCACCATTCGAGAGGGGCCAATGGCAGAA CCACCGCCGCATCAGTGGGTCTGCGTGA | 8686 |
| | 4 | MAEPRFHQWVCVRGLYPGHLSP* | 8687 | ATGGCTGAACCACGGCGCATCAGTGGGTCTGCGTGAGGGCCTTGTATCCCGGGCA CCTTTCCCCCTAG | 8688 |
| hsa-mir-98 | 1 | MKVDRTKLKKTPTEAVSIQKFTLLIFSSLKMKKIFVNSSS MLFKSHHPYIQKAVKQQLV* | 8689 | ATGAAAGTGAGACAGGACTAAACTGAAGAAGACACCTACTGAGGCTGTAAGTATCCA AAAGTTTACTTTGCTTCAAATCTCCAGTCAAAATATTGTGAACAGTT TCATCCATGCTCTTCAAATCCATCACCATATACAAAAGGCAGTAAAAACAACAA CTTGTCTAG | 8690 |
| | 2 | MDSQETSGK* | 8691 | ATGGATAGCCAAGAGACCAGTGGAAAGTGA | 8692 |
| | 3 | MQKGCVV* | 8693 | ATGCAGAAAGGATGTGTGGTATAA | 8694 |
| | 4 | MCGHMERADMGSDF* | 8695 | ATGTGTGGTATAATGGAAAGAGCAGATATGGTCAGATTTTAA | 8696 |
| hsa-mir-99a | 1 | MHLLCPCCRKEPADWPLSAAHSTGWL* | 8697 | ATGCACCTATTGTGTCCGTGCTGCAGAAGGAGCCTGCCGATTGGCCACTGTCTGCA GCACATAGCACTGGCTGTATAA | 8698 |
| | 2 | MTAFFLQCGWRESGEGGGVSSTVKAAQIFFLSLSLPLHR LLFLHALSHFA* | 8699 | ATGACTGCATTCTTTTTGCAAGGGGGTGGAGGGAGGGAGCGGAAGGAGGGGTGT CAGTCAACTGCTAAAAGCTGCACAGATTTTTTTCTCTCCGCCTCTCCAT AGATTGTTTCTTGCATGCCCTGTCATTCGCATAG | 8700 |
| | 3 | MPCLISHS* | 8701 | ATGCCCTGTCTCATTTCGCATAGTAA | 8702 |
| | 4 | MLRIPCLNLKNNDSAVIRNLVRV* | 8703 | ATGCTAATTAAGATCCTTGTCTTAACCTGAAAATAATGACTCGGCTGTAATTAGA AATCTGGTGAGAGTTAA | 8704 |
| | 1 | MVCERISVCLGRKLFLDLQKSQKTSR* | 8705 | ATGGTTTGTGAAAGAATATCTGTGCTTAGGGAGGAAACTTTTGATCTGCAGAAA AGCCAGAAGACATCTAGGTAA | 8706 |

Figure 1 (Continued)

| | | | | | |
|---|---|---|---|---|---|
| hsa-mir-99a | 2 | MFIFVEVQNVLITVCLFFVCLFKS* | 8107 | ATGTTCACTTTTGTAGAAGTTCAAAATGTACTGACGATTGTTTGCTTATTTTTGTTTGTTTGTTTAAATCTTAA | 8108 |
| | 3 | MLLWKEY* | 8109 | ATGTTGCTTTGGAAGGAATATTAA | 8110 |
| | 4 | MRPLCT* | 8111 | ATGAGGCCCTTTGCACATGA | 8112 |
| hsa-mir-99a | 1 | MLLLDSSCLFFLLLWLF* | 8113 | ATGCTCCTCCTAGACAGCAGTTGTTCTGATATTCTCCTTTGTGTGTTTTAG | 8114 |
| | 2 | MDMKSEESDHRRKPFQVKIKNKEQIRFTVFKEKQHSFDCVLL* | 8115 | ATGGATATGAAAAGTGAAGAAAGTGATCATAGGAGAAAACCATTCAGGTAAAAT AAAAACAAAGAGCAAATAAGATTTACTGTTTTAAAGAAAAACAACATTCTTTTGA CTGTGTTTTGTTATAA | 8116 |
| | 3 | MSVTVEILLMVFI* | 8117 | ATGAGTGTAACTGTTGAAATTTTTATTGATGGTTTCATTTGA | 8118 |
| | 4 | MCAMTYLCEKFLVVNWAVCYPLMICLCIHTLKIGAIRFTRKLYRKRKKLYFLICCTI* | 8119 | ATGTGTGCTATGACCTACCTTTGTGAAAATTTCTTGGTCAATTGGGCAGTTTGT GTCCCATTGAATATATGTCTGTGTATCCATACGCTTAAGATAGGTGCAATACGTTT ACTAGAAAGCTTTATAGGAAAAGAAAAATTATATTTCTTATTTGTTGTACCATA TAA | 8120 |
| hsa-mir-99b | 1 | MGDTDNAPQAEKEDGDREREAKGRTDVQRQGGQTER DYTERQQKQPRMTGAERRRERGRERERREGGREG ERERESTHRARRRRREEGGRPARDRTGRRCGGELGKA GEERDWPRRAGERERRPRRLPASFVPSLLCYRLLWPG LPLPLPPPRGWMEFFLDLGQLRGRGEARPDWAGRW GGAGACGPLGRGLVRRPRSRRGPGSPGPQSRGGGD GRRESGRREGGWRGRREEGERRPCGEGGERMESARRR WGPACCGPGAAEKTPSLRRGSRGSRESAEREGGGH.GPAL LGP* | 8121 | ATGGGAGACACAGATAATGCCCCACAGCCAGAGACAGAAGAGGATGGAGATAGGGAGA GGGCGAAAGGAAGGAGCAGCAAAAGAAGACAGCAACCAAGAGTGGAGGAGCACAGGAAAAGAGA CACAGAGGAGGCAGCAAACAAGACAACAAGAGAATGACAGGAGCAGAGAGGAGGAGGGAA GAGAGGAGGAGGCGAGAGAGCACGCACAGAGCGAGGAGGAGGAGGCGAGGAGAGAGAG GGAGAGGAGGCCAGCGAGGGACAGGACTGGCCGAGAGGAGCCGAGAGGGAGCTAGGG AAAGCCGGGAGGAGCGCTCCCGGCCTCCCGGCCTCTTTGTCCTTCCCCTCTCCCGGGCTCAGCTTCTG GCCCCCGCGCCTCCCCCTCCCCGCTCCCCCGGCCTCTGGCGCAGGCTCGCAGCCTTCTG CTGGACCTGGGCCAGCTCCCGACCAGGGCGGAAGCCAGGTCGACGACGGGAGGCTGAGCC GGCGCTCGCGGAGCCCCCCCCGGCGGGAGAAGCAGAGTCGCTGCCGGGCCGAGGAGGA GGCAGCGCGGCGGGGTCCAGGGAGTCGGGCCGCCGTGCCGCCGCCGGCGAGAGCGCTCG GGAACCGGCGGAGAGCCCCGCGGAGCCGTGAGTCTGCGGAAAGGAGGGTGGGGCTGGG GCCCGCACTCTGGGTCCCTGA | 8122 |
| | 2 | MPHRQRKRMEJGRGRKEGQMCRDRREDRRKETQRGSK SNQE* | 8123 | ATGCCCCACAGGCAGAGGAAGAGAATGGAGATAGGGAGAGGGCGAAAGGAAGGAC AGATGTGCAGAGACAGAGGAGGGAGGATGGGAGAGAGACGAAAGAGACACAGAGAGGGCAGCAA AAGCAACCAAGAATGA | 8124 |
| | 3 | MAGTAGGRGEAAVRRRGEDGERSAAVGPGLRARGG GEDPFPATREPREP* | 8125 | ATGGCCGTGGACGGCGGAGGAGGCGTGAGGAGGAGGCCGCGTGCGCGAAGGCGGGGAG AGGATGGAGAGCGCTCCGGGGTGGACCGCGGGGGACCGGAGCCGGGCCGGGGCGG AGAAGACCCCTTCCTCCTGACGCCGGAGGCCGCGGAGCCGTGA | 8126 |
| | 4 | MGAGAGRIVAGRD* | 8127 | ATGGGGCTGGCGTGGTGTAGGAATCGGCGTGCTGGAAGAGACTAG | 8128 |
| hsa-let-7a-1 | 2 | MKFGR* | 8129 | ATGAAGAGGAAGTAG | 8130 |
| | 3 | MPLLPAAKCSLPS* | 8131 | ATGCCCCTGCTCGCGGCCAAGTGCAGCCTCCCTGA | 8132 |
| | 4 | MSLASNALRSFNFLQ* | 8133 | ATGTCTCAGTAATGCCTCTTCAACTTTTACAGTAG | 8134 |
| hsa-let-7a-2 | 1 | MPFGLSTPYSRFCVRGNGMYSSTYRPLKN* | 8135 | ATGCCCTTCAACTTACGGTTTTACACTAGATTCGTGTCAGAGGTAATGTATGT ATTCTTAAACTTACCGGTTTTAAAAATTGA | 8136 |
| | | MATAVQISATALLLQVHDPYRGTSVNMPVTRLGYKJW EEQRRSFPLYFSFSVLPSSLSISTTPPPIQRPCNSN* | 8137 | ATGGCTACAGCTGTGCAGATTTCTGCCACAGCCTTGCTGCTTCAAGTGCACGATCCT GTGCGTGGCACAAGTGTAAATATGCCTGTTACACGCCTGGGTTATAAAATCTGGAG GAACAACGGCGCTCCTTCCCTCTCTACTTTTCTTTTTCGTCTGCTCCCTCCCCTTTC TATTCCTCTACCACCCCCCAACAACAAAGACCCTGTAATTCTAATTAG | 8138 |

Figure 1 (Continued)

| | | | | | |
|---|---|---|---|---|---|
| hsa-let-7c | 2 | MNIKLLGKNPDF* | 8139 | ATGAATATAAAGCTATTAGGAAAAATCTGACTTTTAG | 8140 |
| | 3 | MLDFMWLGLLQQKRP* | 8141 | ATGTTGGATTTTATGTGGCTGGGTTGCTGCAGGGAGACGACCATAA | 8142 |
| | 4 | MLPHWSRC* | 8143 | ATGCTGCCTCATTGGAGCCGATGTGA | 8144 |
| | 1 | MLPQLMYHQLSLA* | 8145 | ATGCTGCCTCAGCTAATGTACCACCATTTCACTGCTTAA | 8146 |
| | 2 | MFQDPFKNHLMVIESSH* | 8147 | ATGTTTCAAGATCCGTTTAAAAACATTATTTAAATGTTATTTTAGCAGCCATTAA | 8148 |
| | 3 | MLFLAAPLYTLNYLRLHAKSKSLFSFRYFIVQNLVASLTAIYLSLSKLLL* | 8149 | ATGTTATTTTTAGCAGCCATTAAGTCTCTACACTCTTAATTATCTTATTAAGCTCCATGCCAAATCCAAATCTCTTTCAGCTTCGTCACTTCATTGTCACTACTTGCAAACCTAGTCGCTTCTTTAACAGCCATCGTCCTTCACTTTCAAAACCTAGTGTGA | 8150 |
| | 4 | MPNPNLFSAFATSLCKT* | 8151 | ATGCAAATCAAATCTCTTTTCAGCTTTGCTACTTCATTGTCAAAACCTAG | 8152 |
| hsa-let-7d | 1 | MKEGR* | 8153 | ATGAAGGAGGAAGGTAG | 8154 |
| | 2 | MPLLPAAKCSLPS* | 8155 | ATGCCCCTGCTCCCGGCCAAGTGCAGCCTCCCTTCTGA | 8156 |
| | 3 | MSLASNALRSFNFLQ* | 8157 | ATGTCCTTGGCCAGTAATGCCTTCCGTCTTTCAACTTTTTACAGTAG | 8158 |
| | 4 | MPFGLSTFYSRFCVRGNGMYSSTYRFLKN* | 8159 | ATGCCCTTCGGTCTCTTCAACTTTTACAGTAGAGGTCGTGTCAGAGGTAATGGTATGT ATTCTTCAACTTACCGGTTTTTAAAAAATTGA | 8160 |
| | 1 | MAGTAGGRGEAAVRRRGEDGERSAAVGPGLRARGGGEDPFPATREPREP* | 8161 | ATGGCGGGACGGCGGAGGGAAGGGAGAAGCCGCCGTCGGCGAAGCGGGGAGAGGATGGAGAGCGCTCGGGAGAGCCGCCGGCGCGGGGAGCCGTGA | 8162 |
| | 2 | MESARRRWGPACGPGAAEKTPSLRRGSRGSRESAEREGGGLGPALLGP* | 8163 | ATGGAGAGCGCTGGCGCGGCGCCTCCTGCACGCGGAGCCCGGCGAAGCCGCCGTGATCCTGGAAGGGAGGGAGGAGACCGCTGGCGCTCCTGGTCCCTGA | 8164 |
| | 3 | MGAGAGRIVAGRD* | 8165 | ATGGGCGCTGGCGCTGGTAGGATTGTGGCTGGAAGAGACTAG | 8166 |
| | 4 | MGLRGFEGSRVSRASGRGPRRRGRLSGLPDRPGSAAGAGDVWRRRGPASMLPRGPGIPGPRPLLPQIWEYTIQSPTHSRIRAPSPLFSRIQESEPPVCSLRPGNPHSSP* | 8167 | ATGGGGCTGCGGGGCTTTGAGGGTCAAGGTGAGCCGTGCCAGTGGGAGCGGGCCGAGGAGGAGGGGAGGTTGTCGGGCTGCCAGACAGGCAGGCAGGCCAGGGGCGGGGGCAGGAGAGATTCTGGAGGCGCATCGGCAGCGATCGGCTGCAGATGCTACCGCGACCCCGGCACCCATTCCAGGAATCCGAGCCTCCCAGCGGCGAGTACTACCACCAGTCGCCGCCAGTAGTTCGCAGGATCGTCAGAGTCCGAGCCGTAGCCGAGGAGTCTGAGTCCCCCAGTCTTTTCTCTCAGACACAGGAATCCACACTCCAGCCCTAA | 8168 |
| hsa-let-7e | 1 | MKEGR* | 8169 | ATGAAGGAGGAAGGTAG | 8170 |
| | 2 | MPLLPAAKCSLPS* | 8171 | ATGCCCCTGCTCCCGGCCAAGTGCAGCCTCCCTTCTGA | 8172 |
| | 3 | MSLASNALRSFNFLQ* | 8173 | ATGTCCTTGGCCAGTAATGCCTTGCGGTCTTTCAACTTTTTACAGTAG | 8174 |
| | 4 | MPFGLSTFYSRPCVRGNGMYSSTYRFLKN* | 8175 | ATGCCCTTCGGTCTCTTCAACTTTTACAGATTCGTGTCAGAGGTAATGGTATGTATTCTTCAACTTACCGGTTTTTAAAAAATTGA | 8176 |
| hsa-let-7f-1 | 1 | MFTTLGIASPTLLLYCRGELQRSVGFIGALVRIFTVL* | 8177 | ATGTTCACTACCCTGGGAATCGCCAGCCCAACCCTCCTCTTATACTGCAGAGGTGAGTTACAGAGATCTGTTGGATTCATCGGAGCTCTTGTAAGAATTTCACTGTCTTTAG | 8178 |
| | 2 | MFLSYTQIRYLPHFFVDYMCSLLGSAAFWGHPNYVNSSAHVFSNY* | 8179 | ATGTTCTTGTCATACACACAAATAAGGTATTTGTTCCATTTCTTTGTGGATTACATGTGTAGCCTTTTGGGGAGTGCAGCCTTTTGGGGGAATACACAAATTATGTCAATAGTTCTGCACATGTATTTAGCAATTATTAA | 8180 |
| | 3 | MSIVLRMYLAHKCLMPST* | 8181 | ATGTCAATAGTTCTGCGCATGTATTTAGCACATAAGTGTCATGCCAAGCACTTAA | 8182 |
| | 4 | MVGVQTTERV* | 8183 | ATGGTTGGTGTACAGACGACAGAGAGGGTGTAG | 8184 |
| hsa-let-7f-2 | 1 | MKLTDSVLRSFRVAKVFRENSDKINCFDFSPNGETVISSSDDDSFVLYDCQEGK* | 8185 | ATGAAGCTTGACCGACAGCGTGTTGCGGAGCTTCCGGTTGCTAAGGTGTTCCGGAAAACTCGGACAAGATTAACTGCTTCAGCCGCCAACGGCGAGACGGTCATCTCGAGTAGCGACGACGACTCCATCGTGCTCTATGACTGCCAGGAGGGCAAGTGA | 8186 |

Figure 1 (Continued)

| | | | | |
|---|---|---|---|---|
| hsa-let-7g | 2 | MTARRASECGGGPGPESQCLPPVAQHRSLGLPSVPTSAPSLFCTRSCQGRLHPAAVQEFFYFHLKKKR* | 8187 | ATGACTGCCAGGAGGGCAAGTGAGTGCGGTGGAGGCCCTGGCCCGAGTCTCAGTGCCTCCCTCCGGTGGCCCAGCACAGGTCCTGGCCTCGGCCTCGCCTCCGACTTCAGCCCCAGCCTATTTGCACGGGTTCCTGCCAGGGTCCCGTCCCACCCCAGCCGTCCAGGAGACCTTTTATTTTTTCTTGAGCGCTATGCATCACTTGCCAAACCCACCTGACCTTGGGAGACCTTTTATTTTTTCTTTAAAAAAAAGATAA | 8188 |
| | 3 | MSSVSFERYASLAKPHLDLDL* | 8189 | ATGTCTTCGGTCTCCTTTGAGCGCTATGCATCACTTGCCAAACCCACCTGACCTTGACCTTTAA | 8190 |
| | 4 | MHHLPNPTLTLTFKRPVPFWAHQVAFSAPQAVKGAGLLRPRRTAGAAFLPPSAASALSCALSTVTSIPPWHSAHPLPLSFPRPFCRQTAWVALLSCQDLFVVPL* | 8191 | ATGCATCACTTACTTGCCAAACCCACCACCTTGACCTTGACTTTTAAACGCCGGTCCGCCACCCTTGGGCCCACCAGCTAGGGTTTCAGCCTCCTCAGCGTGTCAAAGGTGTGGTCTGCTCGGACGCACGAGGACTGCAGGAGCTCTCCACTGTGACCTGCAGTCCGCCCATCGCTCTCTGTGTGCCGGCGTGACCTTTCTCGCCCTGGCACTCCGCCCATCCCTGCCCCTCAGCTTCCGGTCACGCTCAGCCTGTAGCTGGGGTTGCACTTCTTAGCTGTCAGGATTTATTTGTTGTCCCCTTTGA | 8192 |
| | 5 | MPWLLFGGAGGSLCGMPAGDYRRERAGGGFDSAARVGARVPDSAAAQPPPGTRSREGRERRSSGRGGSS* | 8193 | CGATTATCGCCGCGAGAGCGGCCGCGGCGGCCGGTCGACAGCCGGCGCGGGTGGGGGCCGGTACCGGACTCCGCGCCGCAGCCGCCAGCCCAGCTCGGGAGGACTCGGAGCAGGGAGGGGCGCGAGCGGCAGCGGCGGCAGCTCGGGACGTGGGCAGCTCCTAG | 8194 |
| hsa-let-7i | 2 | MALAEVVYCAVGRVVTLPAVEITAQATALLVLVMLSAAEDNGWESPLFSGALPGDSPRSLGARPARPPRKPLVSHFPRRN* | 8195 | ATGGCCCTGGCTGAAGGTAGTAGTTTGTCGTTGTCGGTTGTGACATTGCCGCTGTGGAGATAACTGCCAAGCTACTGCCTTGCTAGTGCGTGGTGATGCTCAGCGCCGCGAGGACAATGGCTGGGAATCCCTTGTTTTCGGGCGCTGCCTGCGGACAGGCCGAAGCCTCGGCGCCGGCGCCATCACGGAAACCGTTAGTTTCACATTTTCCTAGAAGGAATTGA | 8196 |
| | 3 | MAGNPLCFPGRCLGFAREASAPGRRGHHGNR* | 8197 | ATGGCTGGGAATCCCTTGTTTTCGGGCGCTGCCTGCGGACAGGCCGAAGCCTCGGCGCCGCGGCGCCATCACGGAAACCGTAG | 8198 |
| | 4 | MHFKGWERAKPLDSFS* | 8199 | ATGCATTTTAAAGGTTGGGAAAGAGCTAAGCCATTGGATTCCTTTCTTGA | 8200 |
| hsa-mir-101-1 | 1 | MATAVQISATALLLQYHDPVRGTSVNMPVTRLGYKJWBEQRRSFPLYFSFSVLPSSLSISTTPPTQRPCNSN* | 8201 | ATGGCTACAGCTGTGCAGATTTCGCAGCCCTGCTCGTTCAAGTCACGATCCTGTCGTTGGCACAAGTGAAATATGCCTGTTACACGCCTGGGTTATAAAATCTGGAGGAACAACGGCGCTCCTTCCCTCTATTTTCCTCTCATTCTGTTTCTGTTCTTTACCCTCTCCCTTTCTATCCTCTACCACCCCCAACACAACAAGACCCTGTAATTCTAATTAG | 8202 |
| | 2 | MNIKLLGKNPDF* | 8203 | ATGAATATAAAGCTATTAGGAAAAATCTGACTTTAG | 8204 |
| | 3 | MLDFMWLGLLQGRRP* | 8205 | ATGTTGGATTTTATGTGGCTGGGCTTGCTGCAGGGAGACGACCATAA | 8206 |
| | 4 | MLPHWSRC* | 8207 | ATGCTCCTCATTGGAGCCGATGCTGA | 8208 |
| hsa-mir-101-2 | 1 | MGISAVLRGPRWGVSGNAGSPGRLARPHEGSGAEGRGVCVNVAHSLFPRPRPRPGCWRGSLAVRRRL* | 8209 | ATGGGCATTTCCGCGGTTTTGCGCGGCCTGCGCTGGGGTGTCAGTGGCAACGGCGGGGAGCCCCGGCTGGCTCGCCACCCGAGGGAGGGCTCCGGCGCGGAGGGGGCGGGTGTGTGTAAATGTTGCGCACTCGCTTTCCGCCGCTCCTCGGGGCGAGGGGCCGTCAGGGGTGCTGGCGTGGGTCCCTTGCCGCCGGCGACTGTAA | 8210 |
| | 2 | MLRTRFSPAPARVQGAGVGPLPSGGDCK* | 8211 | ATGTTGCGCACTCGCTTTCCGCCGCTCCTCGGGGCGAGGGCTCCGGCGCCGGCGACTGTAAATAG | 8212 |
| | 3 | MLFT* | 8213 | ATGTTGTTTACATGA | 8214 |
| | 4 | MKDPACKGY* | 8215 | ATGAAGGATCCGGCKGGGGAGAGTCTAA | 8216 |
| hsa-mir-103-1 | 1 | MKIKDAKKPCKTGAGARQVGRAPLGPV* | 8217 | ATGAAGATCAAAGATGCAAGAAACCCTGTAAGACCGGGCTGGGGCCCGCCAGGT | 8218 |
| | 2 | MPRNPVRRGLGPARLGGHPWAPSESPLAGRSASKPVAPRRRFVRYGGGGTJ* | 8219 | ATGCCAAGAAACCCTGTAAGACGGGCTGGGGCCGGGCCTGGGCTGGGCCCCAGGTTGGGGCCCGGTCGAAGCCCGTCGCTCCAAGCCCGTCGCTCCGAGGCCACCCCTTGGCTCCGGTGCGGCGGCGCTTCGTCCGGTATGGGGGGAGGGACCATTTGA | 8220 |
| | 3 | MGAEGPFEPFRVRGRPRPRPHHAW* | 8221 | ATGGGGGCGGAAGGACCATTTGAGCCACGAGTTCGAGGCTTCCGTCCTCCCCATCCCCCTATTCATGCATGCGTGA | 8222 |

Figure 1 (Continued)

| | | | | | |
|---|---|---|---|---|---|
| | 4 | MHGECLPPPSLSSHFLFEHWEVPEGISDSDFCQTRLVSSP SSP* | 8223 | ATGCATGGTGAATGCCTGCCGCGCCCCTAGCCTTTCCTCCCACTTTCTTCTTCGAGATCT GGGAGGTGCCAGAGGGAATTTCTGATTTCTGATTTTGTCAAACCAGACTAGTCTCCT CTCCCAGCTCCCCTGA | 8224 |
| hsa-mir-106a | 1 | MVEREGSGFILHPFPPSLPPACLPGLSSSDPACSLVSDL* | 8225 | ATGGTGGAAAGGGAGGGGTCCGGCTTCATTTGCACCCTTCCTCCTTCCTGCCC CCGGCTTGCCTTCCAGGCTTCCTTCCTGACCCAGGCGTGCTCACTGGTCTCTGATT TGTAA | 8226 |
| | 2 | MLNSLIVRLKLRHHFILQSAVGLWP* | 8227 | ATGCTTAATTCATTTGATTGTGCTCTTAAACTAAGACATCATTTTATTCTACAGA GCGCTGTCGGGCTTTGGCTTGA | 8228 |
| | 3 | MRGESKIIAPYLPHCACIRWLLPLTPAKKP* | 8229 | ATGAGAGGAGAAAGCAAGATAATTGCACGTATCTCCGCACATTTGCGCGTGTATT CGGTGGCTACGCGTTAACGATACCTGCCAAGAAACCCTGA | 8230 |
| | 4 | MCRE* | 8231 | ATGTGCAGAGAGTAA | 8232 |
| hsa-mir-106b | 1 | MANGWTGSRPGRRNPEL* | 8233 | ATGGCCAATGCTGGACTGGCTCCCGCCCTGGGCGAGGAATCCGAGCTGTGA | 8234 |
| | 2 | MAGLAPALGGGIPSCEAAGIRAHVLLCLLRAEAMAGAG VGCGCGVRWRRSR* | 8235 | AATGGCTGGACTGGCTCCCGCCCTGGGCGGACGGAATCCGAGCTGTGAAGCGGCTGG AATCCGGGCCATGTGTCTTCTTTGTTTACTAAGAGCGGAAGCGATGCGGGAGCGG GGGTGGGTGCGTGCGGGTGCGTGCGGAGGTCCCGGTGA | 8236 |
| | 3 | MCPFYY* | 8237 | ATGTGCTTCTTTGTTTACTAA | 8238 |
| | 4 | MLDGPVHCHGSLFILRWLETDL* | 8239 | ATGTTGGATGGCCCGTGCACTGCCACGGGCTCTTTATTCTTCGCTGGTTAGAAACA GACTTGTGA | 8240 |
| | 1 | MHRSLQYPLASPPRKQFPVCEAALWTASPLVDPG* | 8241 | ATGCACTCTCTGCAGTATCCTCTAGCTTCTCCTCCCGGAAACAGTTCCAGTCTCCG AGGCCGCCCTCTGGACTGCCTCCCCTAGTGGATCCGGGCTGA | 8242 |
| hsa-mir-10a | 2 | MHLGRKGTSQAPDHPALPKDPCQLERWGVRTERHT* | 8243 | ATGCATCTAGGGAGGAAAGGTACTCGTCAGGCCCCAGACCATTTGCCTTACCAAAA GATGACCCAGCCAGTGGAAAGGTGGAGTCAGGAGTCAGGACGACGGAAAGGCACACCTAG | 8244 |
| | 3 | MTQASWKGGESGRKGTPRGEVEGKCQPVWGVAS* | 8245 | ATGACCCAGGCCAGTGGAAAGGTGGGAGGGAAAGTGCCAGCTGTGTGTGGGGCGTGCGCTCTGA | 8246 |
| | 4 | MIEDTLFRGSCRLVLRCMHLSNSPSFLFSESQGIPRREKG NPSQGVEVGVWEAIFGRKGNRKRTGCPHRRCSGPEAEAV TSRSCQ* | 8247 | ATGATAGAGATACCTATTTCGGAGGGATCCTGTCCTTAGGTGCATGCAT CTCTCTAATTCGTTTTCTTTCTGTTTTCTGAATCCAAGGGATCCAAGGAGGGAGA AGGAAAATCCTTCCCAGGAGAGGAGAGGTGGGGTCTGGGAGGCGATATTTGGGCGAAG GGCTGTAACATCCGGAGCTGCGCCAGTAG | 8248 |
| | 1 | MPPRSLGRRPPWAAQSGCSPTFPGEVGGRCLSPFPQSLR S* | 8249 | ATGCCACCAAGAGCCTGGGCGCCGACCCCTTGGCAGTCAGTCGGCTGCTCC CCTACATTTCCCGGGAAGTGGGGGGTCGTGTCTAAGCCCCTTCCCCAATCACTT CGTTCCTAG | 8250 |
| hsa-mir-10b | 2 | MESPSILP* | 8251 | ATGGAGAGCCCCTCAATCTACCCTAG | 8252 |
| | 3 | MCLYFESRL* | 8253 | ATGTGTCTTGGTGTTTGAATCTAGGCTTTAG | 8254 |
| | 4 | MLVNF* | 8255 | ATGCTGGTTAATTTCTAG | 8256 |
| hsa-mir-125a | 1 | MAGTAGGRGEAAVRRRRGEDGERSAAVGPGLRARGG GEDPFPATREPREP* | 8257 | ATGGCGGGGACGGCGGGGAGGAAGGAGAGGCGCCGTGCGGCGAAGGCGGGGAG AGATGGAGAGCGCTCGCGGCGTGGGGCCGGCCCGGGGCCCCGGCCCGGGGCCGG AGAAGACCCCTTCCCTGCGACGGCAGAGCCGGAGCCGTGA | 8258 |
| | 2 | MESARRRWGPACGPGAAEKTPSLRRGSRGSRESAEREG GGLGPALLGP* | 8259 | ATGGAGAGCGCTCGCGGCGCCGTGGGCCCGGCCTGCGGGCCGGGGGCCGGGGA AGACCCCTTCCCTGCGACGCGGAGCCGGAGCCGTGAGCGGAGCGTGAAGGCGGG GGGCTGGGGCCGGCCCGCACTCTCGGTCCTGA | 8260 |
| | 3 | MGAGAGRIVAGRD* | 8261 | ATGGGGGCTGGGGCTGGTAGGATCGTGGCTGAAGAGACTAG | 8262 |

Figure 1 (Continued)

| | | | | | |
|---|---|---|---|---|---|
| | 4 | MGLRGFFEGSRVSRASGRGPRRRGRLSGLPDRPGSAAGA GDVWRRRGPASMLPRGPGIPGPRPLLPQJWEYTTQSPIJH SRIRAPSPLFSRIQESEPPVCSLRPGNPHSSP* | 8263 | ATGGGGCTGCCGGGGCTTTGAGGGGTCAAGGGTGAGCCGTGCCAGTGGGAGGGGAGGCC GAGGAGGAGGGGAGGGAGGTTGTCTGGAGGAGCAGGCCAGGGTCAGGGACCGG GCAGGAGATGTCTGAGGAGGAGGAGGAGCCCAGCAGCCATCCAGGCCCCTGGAGGACCCG GATTCCAGTTCCCAGACGTCCAGACCCCTCCTCCCTCAGATCTGGAGTACACCACCAGTCCA CACCCATTCCAGTCTGTCTCTCAGAATCCAGCCCGGGAATCCACACTCCAGCCCTAA GCCCCCAGTCTGTTCTTCTCAGAATCCACCAGGGAATCCACACTCCAGCCCTAA | 8264 |
| hsa-mir-125b-2 | 1 | MYSLRRMGLRDGGGHMLMSFLWRGEIFHSDNWLNAM VKNCKAIFSFREKHGLRSKGCFHFSLFVSAAFLFFWFLFF NYLF* | 8265 | ATGTATTCCCTAAGGAGGATGGGTCTCCGTGATGGGGTGGTATAATTATTGTTAATG TCATTTTTATGGAGGGGTGAGATTTTCATTCTGATAATTGGTTGAATGCTATGTCA AAAATTGTAAAGCATATTCAGTTTTAGGGAAAAGCATGGACTTAAGGACTAAGGGCT GTTTTATTTTTCGCTTTTCGCTTTTATTTTTCGCTTTTGTTTTGTTTTGTTTTTTA ACTATTTATTTTAA | 8266 |
| | 2 | MGVV* | 8267 | ATGGGGGTGGTATAA | 8268 |
| | 3 | MLWSKIVKPYSVLGKSMDLDLRAVLFFRFL* | 8269 | ATGCTATGGTCAAAAATTGTAAAGCCATATCAGTTTAGGGAAAAGCATGGACTTA GATCTAAGGGCTGTTTTATTTTTCGCTTTGTGA | 8270 |
| | 4 | MGNQMINRKRSYIMMHYIMEQNI* | 8271 | ATGGGAAATCAAATGATAAACAGAAGGATCTTATATATGATGCATTACATCATG GAGCAGAATATTTAA | 8272 |
| hsa-mir-128-2 | 1 | MPYTYS* | 8273 | ATGCCTGTGACCTACAGCTGA | 8274 |
| | 2 | MHFDLYLSM* | 8275 | ATGCATTTTGACCTTATCTTTCTATGTAG | 8276 |
| | 3 | MHQLFKVIGLRK* | 8277 | ATGCATCAGTTGTTCAAAGTTATAGGGCTCAGAAAGTGA | 8278 |
| | 4 | MKLIQLPMKTTGEYPIFQAAGTIETIRKHSLPCDIQLRGLP RKEKPWGRERSAPRRLSILSCCCPK*NAFPPFLSILKHFLG LHCCSRQELLYEYKGGR* | 8279 | ATGAAACTGATCAACTACAGACCACATGAAAAACAACAGGGGAATATCCATTTCCAGGCT GCTGGTACAGAGCGTGGGTGGGGAACGTTTCCAAAGGCGGTGTTGCAAACACAACGCGATT TTGCACGAGGGTGGGTGGGGAACGTTGGGAAGGGTATGGATGATTTTTTTTTTCCTCAT AATACTCTCTTGCTGCTGCCCAAAATGCATTCTTCCTTCCTTATCAATTCTCAAG CATTTTCTCTGGGGCTAATCTGTCCAGGCAGGAGCTCCTCTATGAATATAAAGGA GGAAGGTAA | 8280 |
| | 1 | MSLFSPAPS* | 8281 | ATGAGTCTATTTCCCAGCCCCTCGTAG | 8282 |
| | 2 | MQLSKYTFPKAVCCKRNAILQSVGGKRGKGMDDFFFP HLGISIVDSNRF* | 8283 | ATGCAGCTTTCAAAATATACATTTCCAAAGGCGGTGTGTTGCAAACACAACGCGATT TTGCACGAGGGTGGGTGGGGAACGTGGAAGGGTATGGATGATTTTTTTTTTCCTCAT CTGGGAAATCTCCATCGTGGATAGCAATCGTCTAG | 8284 |
| | 3 | MIFFFLIWESPSWIAIASRALLGSSSGEGAMPPHPLLSSA CRESDQWRHAALRIQPLQRLLLGETARSLQQAETDGS* | 8285 | ATGATTTTTTTTCGGAAAGCTCTCTACATCTGGGAATCCATCGTGGATAGCAATCGCTTCTAGAG CTCCTCTGGGAAAGCTCTCTACATCTGGGGAGCTATGCCCCCACCCCTACTTTCCT CAGCATGTAGGGAATCTGATCAATGCAGACTGAGACGCTCAGCTCTAAGAATACAACCACTCC AACGCCTTCTGCTCCGGGGAGACTGCGAGAGCTTGCAACAGGACAGAGACAGATGGG AGTTAA | 8286 |
| | 4 | METCSSKNTTTPTPSARGDCEELATGRDRWELTGGREN HRNTWVFF* | 8287 | ATGGAGACATGCAGCTGCAACAGCTGCAACAGCAGATACAACCACTCAACGCCTTCTGCTCCGGGAGAC TGCGAGGAGCTTGCAACAGGACAGATGGGAGTTAACGGAGCGGAGGGAGAGA ATATAAGAAATATTTGGGTATTTTTCTGA | 8288 |
| | 1 | MAGILFRLTLRVLTGPWAEGMSA* | 8289 | ATGGCCGGGATCCTCTTCCGTCTAACCCTCCGCGTCCTGACCGGGCCCTGGGCGAA GGGATGTCTGCGTGA | 8290 |
| hsa-mir-130b | 2 | MLEKNPECP* | 8291 | ATGTTAGAAAAGAATCCAGAGTGTATCTAG | 8292 |
| | 3 | MESSARRGASSRGGAALFLLEPRAESGRRVVGLYPPRS GR* | 8293 | ATGGAGTCGTCAGCTAGAAGGGGCGCGTCGTCCCGGGGTGGGGCCGCCCTTTTCTC CTGGAGCCCCGGGCCGAGTCAGGCGCCAGGGTCGTCGGGGCTGTACCCACCCCGGTC CGGGCGCTAG | 8294 |
| | 4 | MDWTGALPRPPHG* | 8295 | ATGGACTGGACGGCGGGCTCTGCCCCACCCACCATGCATGGTTGA | 8296 |

Figure 1 (Continued)

| | | | | | |
|---|---|---|---|---|---|
| hsa-mir-138-2 | 1 | MPSFFTHELGGLIKEQEVPILHWGQDADPAPVLRELTV* | 8297 | ATGCCTTCCTTTTTCACTCACGAGCTGGCGGGCTCATCAAAGAGCAGGAAGTGCCC ATTTTACACTGGGGCCAGGATGCAGGACCCAGCTCCTGTCCTCCGCGAACTTACAGTC TAA | 8298 |
| | 2 | MQTQLLSSANLQSN* | 8299 | ATGCAGACTCAGCTCCTGTCTCCGGAACTACAGTCTAATTAG | 8300 |
| | 3 | MHHLNPRTGSFKAKNYRLFRSVQHLLTKKNLRVIFLSL NFYPCLRLARTLNTREAVICSSANAFLL* | 8301 | ATGCATCATTTAAATCCTAGAACAGGCAGCTTTAAGCAAAGAACTACAGACTTTTC CGCAGTGTCCAGCATTTGCTGACCTAGCAGAACCCTTAATACTAAATTTCTCTCTTG AATTTTATACCCTGCCTGCCTCGACTAGCAGAACCCTTAATACTAAATTTGCAGTTATAT GCAGCTCTGCCAACGCCTTCCTGCTTTAG | 8302 |
| | 4 | MQLCQRLPALDWISTILFLY* | 8303 | ATGCAGCTCTGCCAACGCCTTCCTGCCTTTAGACTGGATCTCTACTATCTTTTTCTCT ACTAG | 8304 |
| hsa-mir-141 | 1 | MGARDLQLFRRDPGPEAA* | 8305 | ATGGGAGCCAGGGATCTGCAGCTTTCCGCAGGGATCCTGGGCCTGAAGCTGCCTGA | 8306 |
| | 2 | MMEAPVPVSATSIASGPQPLAGCSPLPTSHAPRKPLVLS* | 8307 | ATGATGGAGGCCCCTGTCCCTGTCAGCAACATCATCGCTCAGGTCCCAGGCC TTAGCTGGCTGCAGCCCCCCCCACTTCCCACGCACCCGGAAGCCCCTGTCTTG AGCTGA | 8308 |
| | 3 | MGPSPSSHPVRFVTWWIQNPQSTLSLGLARPLSRDLTW PVARVPCSNW* | 8309 | ATGGGCCCCAGCCCTCCTCCCACCCAGTGCGATTGTCACCTGGTGGATCCAGAAC CCACAGTGACCTTGAGCTTGGGTTGGCTCGCCCCTCTCAAGAGACCTCACCTGG CCTGTGGCCAGGGTCCCTGTAGCAACTGTGA | 8310 |
| | 4 | MAFGWVLSAVTFREP* | 8311 | ATGGCTCCGGTGGGTTCTCGGCAGTAACCTTCAGGGAGCCCTGA | 8312 |
| hsa-mir-142 | 1 | MSLGNQLEAGRHQSLLLLRD* | 8313 | ATGTCCCTGGGGAATCAGTCGGAGGCAGGCATCAGTCTCTTCTGCTTTGCTT AGGGACTAA | 8314 |
| | 2 | MISLQRDRL* | 8315 | ATGATATCTTTGCAAAGGATCGTTTATAG | 8316 |
| | 3 | MAISRFKMGHLYYCI* | 8317 | ATGCAATTTCCAGTTCAAATGCCACTCTTATTATTGCATTGA | 8318 |
| | 4 | MRKLSFHYSRPQSVAW* | 8319 | ATGAGAAACTGAGTTTCCATTACATCTCTCGCCCAGAGTCAGTCGCCTGGTGA | 8320 |
| hsa-mir-146a | 1 | MQIGLSCLPLPQQIRVSPERCSFSKTLDRSSFPGWHQQG RLEW* | 8321 | ATGCAAATAGGCCTCTTAGCTGCCTTCCTCCACCCAGCAAATAAGAGTCTCCAGAA AGATGCTCTTTTCTCCAAGACGCTCTTGACCGCTCTTCCTGGATGGCACCAGCAG GCCGATTGGAGTGGTAA | 8322 |
| | 2 | MLFLQDA* | 8323 | ATGCTTCTTTCTCCAAGACGCTTGA | 8324 |
| | 3 | MAPAGPLGVVNPGPEGMPKGGQDGQETVAQRGGGEQR LNWK* | 8325 | ATGGCACCAGCAGGGCCGATTGGAGTGGTAAACCCTGGCGCCGGAAGGCATGCAAA GGGTGGACAGGATGGACAGGAGACAGTAGCACGAGGAGGRGGAGAACAGCGG CTGAATTGGAAATGA | 8326 |
| | 4 | MDRKQ* | 8327 | ATGGACAGGAAGACAGTAG | 8328 |
| | 1 | MGCP* | 8329 | ATGGGGTGCCCCTGA | 8330 |
| | 2 | MKVCFRELFLLHSTIPGTSNLYSGFWGDFWGARTPGLG SYLGDPYLGDSL* | 8331 | ATGAAAGTGTGTTTCAGGGAACTCTTTCTCCTCCACTCCACTATCCCAGGTACTTCAA ATCTTTATTCAGGGTTTTGGGGAGAATTTCTGGGAGCTACTAGGACTCTGGGCT CCTATCTTGGGATCCATATCTTGGGGACTTCCTTAG | 8332 |
| hsa-mir-146b | 3 | MPFSVCVFWLFPQPLTPPAPHQAPPGTHLGRKRQMDPC HGPEPPPLLTYSNSCWNLWNSCPPP* | 8333 | ATGCCCTTCTCAGTGTGCGTGTTCTGGCTCTTCCCCAGCCCCTCACCCCTCCAGCC CACATCAGCCCCACCAGGAACACATCTGGCAGGAAGGCACAGATGGATCCTGC CATGGCCCTGAACCTCCCCCCTCTAACCTACTCCAATTCCGAATTTATGGA ACTCCTGTCGTTCCTTAG | 8334 |
| | 4 | MALSPLPS* | 8335 | ATGGCCCTGAGCCCTCCCCCCTCTAA | 8336 |
| | 1 | MERWRGVWGKMGKHFPDLLHARNSCSGAVCGRGSA RMGDRVVAYAAGKRGCREGEKSSLGDCVQGCARTGS AGSTA* | 8337 | ATGGAACGGTGGCGAGGGTGTGGGGGAAGATGGGAAAGCACTTCCAGACCTGTT GCACGCGCGCAACAGCTGTTCAGGTGCGTATGTGGGGGAGGGGTCGTGCTAGGA TGGGGGACAGAGTGGTTGGTCGTTATGCTGCAGGGAAAAGGGGTGCCGGAGGGGA GAAGAGCAGTCTTGGGGACTCTTGGGCGAACGGGGTGCGAACGGGGTCCGCGGGAA GCACTGCCTAA | 8338 |

Figure 1 (Continued)

| | | | | |
|---|---|---|---|---|
| hsa-mir-148a | 2 | MWGEGVC* | 8339 | ATGTGGGAGAGGGGTCTGCTAG | 8340 |
| | 3 | MLQGKGGAGRGRRAVLGTVCKYVRERGPREALPNGAGRIPKSGWYERRGWDDFDPSSRGWARAAGRPGHEYWEWLGKGVSGEAPQSGSFLGRPILGAFPGPVFVPHRLTLSAPNIRPRAAPPPPAFQMCGR* | 8341 | ATGCTGCAGGGAAAAGGGGAGGGTGCCGGAGGGGAGAAGAGCAGTCTTGGGGACTGTGTGCAAGGTTGTCGCGAACGGGATCCGCGGAGGAGAAGCACTGCCTAATCGGGGCAGGGAGAATCCAAAGAGTGGGTGGGTGAGTGGCCGGCTGAACGGGATGGGACGACTTCGACCGAGTTCCCGGGTGCTGGCCGCCACGGCTGAAGACCGGGAATAGAGTACTGGGAATGGCTGGGGAAGGGGTCTCAGGGAGGAGCCCCGCAAAGCGGGTCTTTCTTGGGTCTGCTCATCTTAGGGGCTTTTCCCGGGCCTGTATTTGTTCCCACCGTTTAACTCTTTCAGCTCCGAATATTCGTCCTGCAGCGCCCCAGCTTTCCAGATGGGAAGGTAA | 8342 |
| | 4 | MGQGESQRVYGGWNGGDGTTSTRVPGAGRGRLEDRE* | 8343 | ATGGGGCAGGGAGAATCCAAAGAGTGGTGGTGGAACGGAGGGGATGGGACGACTTCGACCGAGTTCCCGGGCTGGGCGCTGGGAAGACCGGGAATAG | 8344 |
| hsa-mir-148b | 1 | MGNRRSDC* | 8345 | ATGGGGAACAGAAGAAGCGATTGTTAA | 8346 |
| | 2 | MHSVASPSLMLAQVTSASSQKVCTTIE* | 8347 | ATGATCTCTGTGGCTAGCCCTTCCCTCATGTTGCTCAGGTCACTTCAGCATCCTACAGAAAGCTGCACAACCATAGAGTAG | 8348 |
| | 3 | MLIT* | 8349 | ATGTTAACTACATAA | 8350 |
| | 4 | MRSQFVKANLSST* | 8351 | ATGAGAAGTCAGTTTGTAAAGGCAAACTTGAGCTCAACGTGA | 8352 |
| hsa-mir-149 | 1 | MELRARGWWLLCAAAALVACARGEPASKSRSCGEVRQIYGAKGFSLSDVPQAEESGE* | 8353 | ATGGAGCTCCGGGCCTGGTGGCTGCTATGTGCGGCGGCAGCGCTGGTCGCCTGCGCCGCGGACCCGGCCAGCAGAGCCGGAAGTCGCCAGATCTACGGAGCCAAGGGCTTCAGCCTGAGCGACGTGCCCCAGGCCGAGGAGATCTCCGGTGAGTGA | 8354 |
| | 2 | MCGRSAGRLRPRGPGQEPELRRGPPDLRSQGLQPERRAPGDLG* | 8355 | ATGTGTGGCCGCAGCGTGGTTCGCCAGGCGACCCTGCCAGGAAGACCGGAGCTGCGGCGAGATCGCGGAGAGCTACCGGAGCCAAGGGCTTCAGCCTGAGCGACGTGCCCCAGGCGGAGATCTCGGGTGA | 8356 |
| | 3 | MAPCAAAPLQPHGPRLQAPRRTPSPGSPPPRSVVLRPSPPFARRLLPCGADLAGLRARGAPPGPRLELGVFCPPLGPARLQAGSPSPGAGCRGAVOLGVAGLSGRR* | 8357 | ATGGCTCCTGCGGCCGCTCCGCTCCAGCCTCATGGCCCTCGGCTCCAGGCCCCGCGCCGCACTCCGTCTCCCGGCTCGTCCTCCGCCCCGGTCGGTTCTCCGCCGGTTGGGCACTGGCTGCGGCGCTCTCTCCGGCTGCCAGCGTGCGGCCGCCACCGGGAGCCGCCCGAGAGCTCGCTGCCTCTGCCGGTCCGCGAGTCCAAGCCCCGCCGCTCCGGCCCAGGTGTGCGGGCGCTGCTGTG | 8358 |
| | 4 | MGTQRRNAHGPGDSEQEGSVHLGEGGLWPCLAAGGGVVGGGSRALDPCPSRRNRTHROPLALGGSPDAPSLRFL* | 8359 | ATGGGGACTCAAGGCAGAAATGCCATGGTCCTGGGGATTCTGAGCAAGAAGGATCCGTGCATCTGGTGAAGGGGTGGAGGGCAGTGCAGTCTCTGGAGGACCCCTGCCCTCCAGGAGGAACAGAACCCAGAACAGCCCCTTGCCTGGTGGATCTCCAGCCCCAGCTGAGGTTCTTGTAA | 8360 |
| hsa-mir-152 | 1 | MQRPEAGHVRTRGRGPRRQAGGRRRLLEPGSPRGCGYGAGRGRGDPGRRELGRDRAGLGGAANSELARPAAGNFVSPLTGPRTREEKFVPAPTGEEACPESVGAGLKFWVRLEWGWRVSCDSAGRVRSGLSVPDSAPITGG* | 8361 | ATGCAGCGGCCGGAGGCTGGCCATGTCCGCACGCGGGCCGGGGGGCCCGGCGGAGGCGGCGGCTGCTGGAGCCCGGGAGCCCGCGGGGCTGCGGGTACGGTTAGGGGAGGGGAGCAGCCAATCAGAACTCGAGACCCGGAGGAGGGGACGGGGCCGCGGCTGGGAACTTTGTGTCACCCTGACTGGCCTCGCCCCAGGACCCGGGGAGGAAAAGTTCGTCCCAGCGACCGGAGAGGCCTGTCCGGTGAGTTGGGCTGAAGTTTCGGTCGTTTGGAGTGGGGTGGGGTGAGTTGCAGTTCGCGGGAGTCCGGGAGGGGTAAGGAGGGGCCTGTCCGTCCCAGACTCCGGTCCATCACCGGGGTGA | 8362 |
| | 2 | MGMLLESTRARAWGRADSAGPARPGISWKKEARPAVPPGPGSVIHSDSGSGAVSA* | 8363 | ATGGGCATGCTTCTGGAGTCTACCCGGGCACGCGGTGGGGCCGCTGATAGCGCAGGTCAGCGCCCCGCCACCGGGAATCACTGGAAGAAGGAGGCTCGGCCCGCTGTCCCCCGCGCCCAGGTTCTTGTGATACACTCCGACTCGGGCTCTGGAGCAGTGCATGA | 8364 |

Figure 1 (Continued)

| | | | | | |
|---|---|---|---|---|---|
| | 3 | MTELGPGPRTFCTQRAQRPLGACSGTSAAWEWSGHLGWP MWHRAGQNQLWTLRTGVAGA* | 8365 | ATGACAGAACTTGGCCCGGAAGGACTTCTGCACCCAACGGGCACAGGCCCACT CGGGGCCTGCAGTGGAACATTCCTGGGAGTGGAGTGGGCACCTGGGTTGGCCCA TGTGGCACCAGGGCTGGGCAGAACCAGCTGTTGGACCTTGAGGACTGGGGTTGCTGGG GCCTGA | 8366 |
| | 4 | MYPRASRSHRHRVSTSSQGPNGTLLSGVSGRNLPSTPSR LFSS* | 8367 | ATGTATCCTAGGGGCCAGCAGATCCATAGACACAGGGTGTCCACTCAGTCAGGG GCCAAACGGAACTTCCTCCGGTGTCAGTTGCAGGAACCTTCCCTCTACACATC AAGGCTGTTTTCATCCTAG | 8368 |
| hsa-mir-153-1 | 1 | MGGKGAGVRPPLGLEPRVGPGASASDFWPPAPDPTLPP LKAGLRLRLCPSPSLHHPRGPAPRRPHLLCSLPLTLPGLA PSPPPASSRGPSAFCLPSLSRTPASFLLPVPSCPAVSRPCT ALPCCPLRLSLPPARLPSFIPLRPSFIPLRLFASFFCVFHSF SFPLSSSSLSPSLSHSYSASPFPSLSISPSPRFSSFLSALSPV PLRLPLSASFSLLCPSLPLPPAACLSSLCPSLSLLPSFSL SLTAASFVFVFCS* | 8369 | ATGGGGGCGGGAGCGGGCCCCGCCCGGCCCTGCCCTCGCCCTCGGAGCCCGGGTCGG GCCTGGACTCTGCCTCTGCCGCCTCGCGCCGCGCCCAGACCCCACGCTCCCACC CCTAAAAGCAGGGCTGGAGGCTCTGGAGCCTGTGCGCTGTCTGCTCCACCACCGG TGGGCCAGCTCCGCGCCGCCCACCTGCTTCCTCCAGAGGGCCCTCTTCTGTCTCCCC ACTGGCTCCTTCTCCAGGACCCCTGCCTCGCCCCTCCTCCTCCACCCGTCCGTCT CCAGGCCCTGCACTGCGCTGCCTCTCCTCCTCCATCCCTCCCTCTCCGCCTGCCGG TCTCCCCTCGTCACTGCACTGCCTCTCGCCTCCATTCTCTCCCATCTC TTTCTGTCTCTTTCATTCTTCTTTCCTCGCCTCACTCCTCCTCTCCCCATCTC TCTCTCACTCTGTCTCTGCCTGCCTCCTCCGCCCTGTTTTCTCCACTCCTCCTGTCTGC CAGTTTCTCTGCCTTCTCCTCGCCTCCTCCTCGGGACCCACCCGAGCTGGGAGCAAGGGTAC AGGGAAAGGCAAAGACTGTCGAAAGGAGTGTGGAGGATCTCGGAATTCTGGGG GCTCAGTGGAGCAGGTGGGACTAGACAGGGGCTACCTGAGGGACTTACCCTTTC CAACACTGA | 8370 |
| | 2 | MDRQDMWPGDHPELGARGTGKRQRLSKGVWEDLWL GGSVEQVGTRQGLPEGLTLFQH* | 8371 | ATGGACACAGAGACAGTGGCCGGGACTGCCACCCGAGCTGGGAGCAAGGGTAC AGGGAAAGGCAAAGACTGTCGAAAGGAGTGTGGAGGATCTCGGAATTCTGGGG GCTCAGTGGAGCAGGTGGGACTAGACAGGGGCTACCTGAGGGACTTACCCTTTC | 8372 |
| | 3 | MSLGTGQRSRAGGGDMGVSEPQDSSF* | 8373 | ATGTCTCTAGGTACTGGACAGAGAGGAGCAGAGAGCTGGGGTGGGGGACATGGGTATAGT TCTGAACCTTCAAGGACAGCAGTTTCTAA | 8374 |
| | 4 | MDLF* | 8375 | ATGGATCTGTTTAA | 8376 |
| hsa-mir-155 | 1 | MDSRGQRQGFGGVFET* | 8377 | ATGGATTCCCGCGGCAGAGGCAGGGAAGGAGGGGTCGTTCGAAACCTAA | 8378 |
| | 2 | MVGDVPV* | 8379 | ATGGTTGGGGACGTACTGTATAA | 8380 |
| | 3 | MALDLPCWSGQRSV* | 8381 | ATGGCCCTTGGACCAGCTTCCTGTTGGAGTGGCCAGGAAGTGTGTAA | 8382 |
| | 4 | MSSFNRSEDGANAQSASVFIRSCCARVFCRAVAFLYSQ NPLDVCPPRFTRESRIF* | 8383 | ATGTCTTCATTTAACAGAAGTGAAGATGGAGCAAACGCTCAATCAGGCGTCTGTATTT ATTCGCTCTGTTGTGCCAGGGTGCGTTTTGCCAGGGTTGCCTTCTTTACTCAC AAAACCCCCTTGATGTCTGTCCTCCACGTTTACGAGGGAGAGCCGGATCTTTGA | 8384 |
| hsa-mir-15b | 1 | MAFFPKSRCL* | 8385 | ATGGCTTCCTTCCGAAGTCCGCTGCCTAA | 8386 |
| | 2 | MPRKGTQPSTARRREEGPPPPSPDGASSDAEPEPPSGRT ESPATAAGE* | 8387 | ATGCCCCGTAAAGCACCCAGCCTCCACTGCCGGCCAGAGAGGAAGGGCCGGCC GCCACCCCCTGACCGCGCAGCGACGCCGGAGCCTGAGCCGCCGTCCGGCC GCACGGAGGAGCCAGCAAACGGGTTCAGTTGTGA | 8388 |
| | 3 | MGASKRVQL* | 8389 | ATGGGCGAGCAAACGGGTTCAGTTGTGA | 8390 |
| | 4 | MVQVTNKNSISLLYSR* | 8391 | ATGGTACAGGTCACAAACAAAATTCAATATCTTTATTGTATTCCGCTAA | 8392 |
| hsa-mir-16-2 | 1 | MAFFPKSRCL* | 8393 | ATGGCTTCCTTCCGAAGTCCGCTGCCTAA | 8394 |
| | 2 | MPRKGTQPSTARRREEGPPPPSPDGASSDAEPEPPSGRT ESPATAAGE* | 8395 | ATGCCCCGTAAAGCACCCAGCCTCCACTGCCGGCCAGAGAGGAAGGGCCGGCC GCCACCCCCTGACCGCGCAGCGACGCCGGAGCCTGAGCCGCCGTCCGGCC GCACGGAGGAGCCAGCAAACGGGTTCAGTTGTGA | 8396 |
| | 3 | MGASKRVQL* | 8397 | ATGGGCGAGCAAACGGGTTCAGTTGTGA | 8398 |

Figure 1 (Continued)

| | | | | |
|---|---|---|---|---|
| | 4 | MVQYTNKNSISLLYSR* | 8399 | ATGGTACAGGTCACAAACAAAAATTCAATATCTTTATTGTATTCCGCTAA | 8400 |
| | 1 | MYLIAKDESTLFSYVFFNCKLLGP* | 8401 | ATGTATCTGATAGCTAAGGATTTTCAACTTTATTCTCTACGTATTTTCAACTGTAAATTATTGGGCTTTTAA | 8402 |
| hsa-mir-17 | 2 | MDGlNCC* | 8403 | ATGGATGGAATTAATTGCTGTTAA | 8404 |
| | 3 | MELIAVRRLENSKYRFGRW* | 8405 | ATGGAATTAATTGCTGTTAAGGAGGTTGGAAAAATAGCAAATATAGATTTGACGGTGGTAA | 8406 |
| | 4 | MFYLFFPYFSLFQSYTWT* | 8407 | ATGTTTTATCTTTTTTCCTTATTTTCCTATTCCAGTCATACACGTGACCTAA | 8408 |
| | 1 | METPKITRYTQTYSTPINTQSKVMLTHTYSPHNNTATCVDTSPTRARTSRDSAH* | 8409 | ATGGAGACCCCAAAATTACACGTATACAGAGACATACAGCACCCGATTAATACGCAGTCGAAAGTGATGCTGACACACAGTCACCAATAACACTGCCACGTGTGTAGACACGTCGGACACTCCAGGGATAGTGCCATTGA | 8410 |
| | 2 | MEPPTKAATT* | 8411 | ATGGAGCCACCAACGAAGGCAGCTACAACATAG | 8412 |
| | 3 | MSLRVAMTNADP* | 8413 | ATGTCACTCAGGTAGCAATGACAAACGAGATCCTAA | 8414 |
| hsa-mir-181c | 4 | MCPPNQVHTCTLTVTHSHPHTHTHTHRRYKACRNTSDSRSHHFFHFYLFILRWSLSWLPRLECRGTTSRIQAHLPQPPE* | 8415 | ATGTGTCCTCCAACCAAGTTCACACTGCACCACTCACAGTCACCACAGTCACCCCCACCACACACAAGTCACACATACAAGACGGTACAAGGCCTGCAGAAACACATCTGACAGCAGGTCTCTCTGCCTCCCAGGTTGAATCTTTTATTTTTATTTACTTATTTATTTTGAGATGGAGTCTCTCTTGCCTGCCCAGGTTGAATGCCGTGGCACGATCTCCCGGATTCAAGCAATTCTCTTCGCCTCAGCCTCTGAGTAG | 8416 |
| | 1 | METPKITRYTQTYSTPINTQSKVMLTHTYSPHNNTATCVDTSPTRARTSRDSAH* | 8417 | ATGGAGACCCCCAAAATTACACGCTATACACAGAGACATACAGCACCCGATTAATACGCAGTCGAAAGTGATGCTGACACACAGTCACCCCAATAACACTGCCACGTGTGTAGACACGTCACCCACAAGGCTCGGACATCCAGGGATAGTGCCATGA | 8418 |
| | 2 | MEPPTKAATT* | 8419 | ATGGAGCCACCAACGAAGGCAGCTACAACATAG | 8420 |
| | 3 | MSLRVAMTNADP* | 8421 | ATGTCACTCAGGTAGCAATGACAAACGAGATCCTAA | 8422 |
| hsa-mir-181d | 4 | MCPPNQVHTCTLTVTHSHPHTHTHTHRRYKACRNTSDSRSHHFFHFYLFILRWSLSWLPRLECRGTTSRIQAHLPQPPE* | 8423 | ATGTGTCCTCCAACCAAGTTCACACTGCACCACTCACAGTCACCACAGTCACCCCCACCACACACAAGTCACACATACAAGACCTGCAGAAACACATCTGACAGCAGGTCACACATACAAGACGGTACAAGGCCTGCAGAAACACATCTGACAGCAGGTCTCTCTGCCTCCCAGGTTGAATCTTTTATTTTTATTTACTTATTTATTTTGAGATGGAGTCTCTCTTGCCTGCCCAGGTTGAATGCCGTGGCACGATCTCCCGGATTCCCGAGTAGGCAATTCTCTTCGCCTCAGCCTCTGAGTAG | 8424 |
| | 1 | MPRALLEGVFDNPRWHGMRGTLAGGTRLAAGRLRSAGLGAAWSLQGVWAARPWPASGTALAPGHSAPYPRPAAGRQQGDS* | 8425 | ATGCCCCGCGCGTTACTGGAAGGTGTTTTGATAATCCGCTGGCACGGATGCGAGGGACTCTGGCAGGTGGGACCCAGAGTCCGTCGCGGGAGGCTGAGATCGGCAGGGTTGGGAGCTGCGTGGTGCCTCGCAGGGTGTTGGGGCTTGTGGCTTGCCAGCATCAGAGCACAGCTGCGTGGCGCCCGGTCACTCTGGGCACAGTGCCTCCACCCGCGGCCTCGTCGGGCGCAGCAGGGTGACAGCTAA | 8426 |
| | 2 | MRPSWGGHLGS* | 8427 | ATGCGGCCTTCCTGGGGAGGTTTGGGTAGTTAG | 8428 |
| hsa-mir-185 | 3 | MSHALPWPGLFALSCGSRPADHCFAATLGTVPSSMRQM* | 8429 | ATGTCACATGCCCTGCCTGGCCAGGCTGTTTGCACTCTGGCACAGTGCCCTTCCATGAGGCAGATGTGA | 8430 |
| | 4 | MPCPGQACLHCRVALDLLTTVLLPLWAQCPLP* | 8431 | ATGCCCTGCCCTGGCCAGGCCTGTTTGCACTGTGTGTGTGGGCTCTAGACCTACTGTTTTGCTGCCACTCTGGGCACAGTGCCCTCCATGA | 8432 |
| | 1 | MSTKNFRVSDGIDWICPDKK* | 8433 | ATGTCGACCAAGAATTCCGAGTCAGTGACGGGACTGGATTGCCCTGACAAAAAGTGA | 8434 |

Figure 1 (Continued)

| | | | | |
|---|---|---|---|---|
| hsa-mir-186 | 2 | MIFCALRRVEAANRQFPGGKKAPNLLTREVPPGAFVLD MSSAFPRHYLRKVASLFRVRDGLPFCPHPPPPRPGFSD RKPLQSGQLGVGSPPRDFSLQNFTLVHGKYCFLALVLLP LIVHLVLYFYSNFSSILPSPFPEALPSSVWEILTFSLWISP QELGFSPP* | 8435 | ATGATTTTCTGTGCCTTAAGACGGGTGAGGCGGCGAACCGCCAGTTCCTGCGGGG AAGAAGGCTCCAATCTCCTCGACATTACCTCCGCAAGGTAGCCTCTCTTTGTTCTAGAT ATGTCTTCAGCGTTTCCTTTTGCCCCCACCCCCGCTTGCCCCGCCCAGGTTTAGCG GAGATGGCCTACCTTCTCCAGTCAAGACCAAGCTTGTGTTGGATCTCCGCACGTGACTTTT CTCTGCAGAAACCTTCACTCTTGTTCACGGAAATATGCTTTCTCGCACTCGTCCTTT GCCTCTTATAGTTCACCTTGTTTTGTATTTTACTCAAACTTTCCTCCATACTATTT CCCCTTTTCCGGAAGCTCTACCCTCTTCCGTTTCGGAAATTCTGACATTTCTTTGTG GATCATTTCTCCACAAGAATTGGGCTTTTGCCCTCTAG | 8436 |
| | 3 | MAYLFAPTPLPRPGQVLAIGNLSSQASLVLDLPHVTFLC RTLLLFTENIAFSHSSFCLL* | 8437 | ATGGCCTACCTTTTGCCCACCCACCTGCCTCCGCTCGGCCAGGTTTAGGATAG GAAACCTCTCCAGTCAGCCAGCCAGCTTGGTCTTGGATCTCCCCAGTGACTTTCTCT GCAGAACTTTACTCTTGTTCACGGAAATATTGCTTTCTCGCACTCGTCCTTTTGCCT CTATAG | 8438 |
| | 4 | MPAAEKHVC* | 8439 | ATGCCTGCAGCAGAGAAGCACGTGTGTAG | 8440 |
| hsa-mir-18a | 1 | MYLIAKDFSTLFSYVFFNCKLLGF* | 8441 | ATGTATCTGAAATAGCTAAGGATTTTCAACTTTATTCTTACGTATTTTCAACTGTA AATTATTGGGCTTTTAA | 8442 |
| | 2 | MDGNCC* | 8443 | ATGGATGGAATTAATTGCTGTGTAG | 8444 |
| | 3 | MELJAVRRLENSKYRFGRW* | 8445 | ATGGAATTAATTGCTGTGTTAGGAGGTTGGAAAATAGCAAATATAGATTGGACGGTG GTAG | 8446 |
| | 4 | MFYLFPPYFSLLFQSYTWT* | 8447 | ATGTTTTATCTTTTTTTCCTATTTTCCTATTCCAGTCATACACGTGGACTTAA | 8448 |
| hsa-mir-18b | 1 | MYEREGSGFILHPFPSLPFACLPGLSSSDPACSLVSDL* | 8449 | ATGGTGGAAAGGAGGGGTCCGGCTTCATTTTGCACCCTTCCTCCCTTCCCTTGCCC CCGCTTGCCTGCCTGCCAGGGCTTCCTGCGACCCAGCGTGCTCACTGGTCTCTGATT TGTAA | 8450 |
| | 2 | MLNSILIVRLKLRHHFILQSAVGLWP* | 8451 | ATGCTTAATTCCATTTGATTGTCGTCTTAAACTAAGACATCATTTATTCTACAGA GCGCTTCGGCGTTGGCTTAA | 8452 |
| | 3 | MRGESKHAPYLPHCACIRWLLPLTHPAKKP* | 8453 | ATGAGAGGAGAAAGCAAAGATAATTGCACCGTATCTTCCGCACATTTGCGCGTGTATT CGGTTGGCTGCTACCGTTAACGATAACCTGCCAAGAAACCCTGA | 8454 |
| | 4 | MCRE* | 8455 | ATGTGCAGAGAGTAA | 8456 |
| hsa-mir-191 | 1 | MGGF* | 8457 | ATGGGGGGGTTCTGA | 8458 |
| | 2 | MWPQGE* | 8459 | ATGTGGCCCCAGGGCGAGTGA | 8460 |
| | 3 | MGCP* | 8461 | ATGGGGTGCCCTGA | 8462 |
| | 4 | MGVDVGEPRLVAISGTLGRIGEGGWTQDLWVGLQW* | 8463 | ATGGGTGTAGACGTGGAGGCGGAGAGCGAGGCTGGTGCCATCTCTGGAACCCTGGGGAG GATTGGCGAGGGAGGGTGGACCCAGGACCTCTGGGTAGGGCTGCAATGGTAG | 8464 |
| hsa-mir-193a | 1 | MGAEGWVPAGEMRVSDQLAYKVPVLGPRDQRLLPGPR PRPASSRAGVRSGQAASQVHAGEGVVRCARPGCVR* | 8465 | ATGGGAGCTGAGGCTGGGGTCCAGTTCTGGGAGAGCCAGTCGTCTCCCGGTCCTGCCC CAGGGCCGTCTCCAGGCCTAGAGGGGACCCAGGACCAGCGTCTTCTCCCCAGGTCTCAGGTCA CCGTGGAAGGAAGAGTGGTGAGGTGCTCTGCCCCCGGCTGCTGGTGCGGTGA | 8466 |
| | 2 | MGQALPLTEACPAVLSRAATLSLGVGRTGPDF* | 8467 | ATGGGTCAAGCCCTGCCACTTACCGAGGCCTGCCCTGCTGTGCTTCCAGGGCA ACCTTGAGCTTTGGGATGGGGAGAACGGGCCGGTCTTTGTTCCCTAG | 8468 |
| | 3 | MDLCGCVPNGRSFVP* | 8469 | ATGGATCTTTGTGGATGTGTCCAATGGCCGGTCTTTGTTCCCTGACCGATGCAACATAA | 8470 |
| | 4 | MCSQWPVFCSLLIDAT* | 8471 | ATGTGTTCCCAATTGCCGGTCTTTGTTCCCTGACCGATGCAACATAA | 8472 |
| | 1 | MDVSSEDISGAPQRSAWWGLEAKRNQKRHSPHPQJKM PFSFFF* | 8473 | ATGGATGTGTCCTCAGAGGACATAAGCGGCGCATTCAAGCGGTCAGGGAAACCAGAAAACGCCACTCCCCACCCCCAAATGC CTTTTCTTTTTTTCTAA | 8474 |
| | 2 | MCPQRT* | 8475 | ATGTGTCCTCAGAGGACATAA | 8476 |

Figure 1 (Continued)

| | | | | | |
|---|---|---|---|---|---|
| hsa-mir-193b | 3 | MPAGLGRTWSGGRGRPAPRAALRSGSRSESVSRAGFPG WGRGRGRSTASSHSKPRH* | 8477 | ATGCCAGCGGGGCTCGGGCGCACGTGGAGGCGGCGGCGGCGGCCTGCTCGCG CCCGGCATTGAGATCGGGGTCACGCAGCGAGTCAGTTTCCGAGCGGGCTTTCCGG GGTGGGGCGGGGACGCCGGAACGCTCCACCGCTCAATTTCCAAGCCCAGGCAC TAG | 8478 |
| | 4 | MGGERRKSFSAESAQPTGLHPASTVRCRHKAAPPPPTP QRPMAGPGRGLGRPGVGRAGEAAAAAQAAAGRLLPGQ AERARAWKPSAPARVGVGVGVGVGAGAGVGGRLP RNARQI* | 8479 | ATGGGCGGGGAGCGTCCAAGGAGCGAAATCCTTTCTGCAGAGACGGCGGGGCT GCACCCGGCCTCCACGGTCCGCTGCCACAAAGCGCGCGCCGCCCGCCCCAAC CCCCAGCGCCCTATGGCCGGCGGGGCTGGGCGGGGCTGTTGGCC GCGGTGGGAGGGCGGCGAGAGCCTGAAGCTAGAGGCGGGGCTCCTCCCCGGC CAGGGCAGAGAGGCGCGTGCGGGTGCGGGTGCGGGTGGCGGCGGGGCTGG GGTGGGGTGCGGGTGCGGGTGCGGGTGCGGGGTGCAGGAGAGGGCGCTTCC TAGAAACGCTCGCCAAATATAG | 8480 |
| hsa-mir-195 | 1 | MRIRLGALPLASGWSH* | 8481 | ATGAGAATTAGACTAGGGCTCTCCCTTTGCATCAGGATGGAGTATTATTGA | 8482 |
| | 2 | MEYYLISCGVSVSYYGVLI* | 8483 | ATGGAGTATTATTTGATCAGTTGTGGGGTGTCAGTTATGTGGTGTTGATTTGA | 8484 |
| | 3 | MVSFRYGADLEVTLVLGVLTPTIWRLCSPVSSWTISRTK VLMLIWGCSLFWGAI* | 8485 | ATGGTAAGTTTCAGGTATGGGGCTGACTTGGAAGTTACATTAGTTCTGGGGGTTCTG ACACCCACAATTTGGAGATTGTGTCCACCTGTCATCTTGGACTATCAGCAGAACC AAAGTACTCATGCTGATTTGGGGTGCAGTCTATTTGGCGGTGCCATCTAA | 8486 |
| | 4 | MGLTWKLH* | 8487 | ATGGGGCTGACTTGAAGTTACATTAG | 8488 |
| hsa-mir-196a-2 | 1 | MGVGVWLVCVSSPHSPTHSHTAFCSPCKVKIESIRL* | 8489 | ATGGGGGTGGGAGTTGTGGCTGTGTGTCCAAGCCCTCACTCACCCACGCACTCA CACACAGCATTCTGTTCTCCATGCAAGTTAAGATCGAATCATCCGCTGTAG | 8490 |
| | 2 | MSLPPSRSKNLLEVSYLYCFLLFSHPS* | 8491 | ATGTCTTTACCTCCCAGTCGCTCTAAGAATCTGCTTGAAGTCTCGTATTTGTACTGCT TTCTGCTTTTCTCCCACCCCTCTAG | 8492 |
| | 3 | MPPPPNIVLSLSGSCVF* | 8493 | ATGCCCCCCCCCAATATGTCTGTCCGTGTCGGAGTTGTGTTATTTAA | 8494 |
| | 4 | MLYLLHVASLMEKKFPNKFFES* | 8495 | ATGTTGTATCTTTTGCATGAGTCATCTCTAATGGAGAAAAAAACCTAATAAATTT CCAGAATCATAA | 8496 |
| hsa-mir-19b-1 | 1 | MYLIAKDFSTLFSYVFFNCKLLGF* | 8497 | ATGTATCTGATAGCTAAGGATTTTCAACTTTATTCTTACGTATTTTCAACTGTA AATTATTGGGCTTTAA | 8498 |
| | 2 | MDGINCC* | 8499 | ATGGATGGAATTAATTGCTGTTAA | 8500 |
| | 3 | MELJAVRRLENSKYRPGRW* | 8501 | ATGGAATTAATTGCTGTTAGGAGGTTGGAAAATAGCAAATATAGAATTGGACGGTG GTAA | 8502 |
| | 4 | MFYLFFPYFSLFQSYTWT* | 8503 | ATGTTTTATCTTTTTCCTATTTGTGGAATTAATCCAGTCATACACGTGGACCTAA | 8504 |
| hsa-mir-19b-2 | 1 | MYLIAKDFSTLFSYVFFNCKLLGF* | 8505 | ATGTATCTGATAGCTAAGGATTTTCAACTTTATTCTCTACGTATTTTCAACTGTA AATTATTGGGCTTTAA | 8506 |
| | 2 | MDGINCC* | 8507 | ATGGATGGAATTAATTGCTGTAA | 8508 |
| | 3 | MELJAVRRLENSKYRFGRW* | 8509 | ATGGAATTAATTGCTGTTAGGAGGTTGGAAAATAGCAAATATAGATTGGACGGTG GTAA | 8510 |
| | 4 | MFYLFFPYFSLFQSYTWT* | 8511 | ATGTTTTATCTTTTTCCTATTTGTCACCCTCATTTGCACCCCTTCCTCCTTGCCC CCGGTTGCCTTCCTCCAGCGGCTTCCCTCCCGACCCAGCGTGCTCACTGGTCTCTGATT TGTAA | 8512 |
| | 1 | MVEREGSGFILHPFPPSLPPACLPGLSSSDPACSLVSDL* | 8513 | ATGGTGGAAAGGGAGGGGGTCCGGCTTCCATTTCCAGTCACCCCTCCCTTGCCC CCGGTTGCCTTCCTCCAGCGGCTTCCCTCCCGACCCAGCGTGCTCACTGGTCTCTGATT TGTAA | 8514 |
| hsa-mir-19b-2 | 2 | MLNSILIVRLKLRHHFHLQSAVGLWP* | 8515 | ATGCTTAATTCCATTTGATTGTGCGTCTTAAACTAAGACATCATTTATTCTACAGA GCGCTGTCGGGCTTTGGCCTTGA | 8516 |
| | 3 | MRGESKHAPYLFHCACIRWLLPLTIPAKKP* | 8517 | ATGAGAGGAGAAAGCAAGATAATTGCACCGTATCTTCCGCACATTGCGCCGTGATT CGGTTGGCTGCTACCGTTAACGATACGTGCCAAGAAACCCTGA | 8518 |
| | 4 | MCRF* | 8519 | ATGTGCAGAGAGTAA | 8520 |

Figure 1 (Continued)

| | | | | |
|---|---|---|---|---|
| hsa-mir-200c | 1 | MGARDLQLPRRDPGIPEAA* | 8521 | ATGGGAGCAGGGATCGCAGTTTTCCGCAGGGATCCTGGCCTGAAGCTGCCTGA | 8522 |
| | 2 | MMEAPVPVSATSIASGPQPLAGCSPLPTSHAPRKPLVLS* | 8523 | ATGATGGAGGCCGTGCCAGCCCCATCGATCCATCGCCTCAGGTCCAGGCCCTTAGCTGGCTGCCAGCCCCCACGCACCCCGAAGCCCCCTGTCTTGAGCTGA | 8524 |
| | 3 | MGFSPSSHPVRFVTWWIQMPQSTLSLGLARPLSRDLTWPVARVPCSNW* | 8525 | ATGGGGCCAGCCTCTCCAGCCCTCTCCACCAGTGTGCGATTTGTCACCTGGATCCAGATGCCACAGTCGACTCAGGTGGGGTTGCTGCCCCCTCAAGAGACCTCACCTGGCCTGTGGCCAGGGTCCCGTAGCAACTGGTGA | 8526 |
| | 4 | MAPGWVLSAVTPREP* | 8527 | ATGGCTCCCGGGTGGGTTCTCTCGGCAGTAACCTTCAGGGAGCCCTGA | 8528 |
| hsa-mir-20a | 1 | MYLIAKDFSTLFSYVFFNCKLLGF* | 8529 | ATGTATCTGATAGCTAAGGATTTTTCAACTTTATTCTCTTATGTATTTTTCAACTGTAAATTATTGGGCTTTTAA | 8530 |
| | 2 | MDGIMCC* | 8531 | ATGGATGAATTAATTGCTGTTAG | 8532 |
| | 3 | MELIAVRRLENSKYRFGRW* | 8533 | ATGGAATTAATTGCTGTTAGGAGGTTGGAAATAGCAAATATAGATTTGGACGGTGGTAG | 8534 |
| | 4 | MFYLFFPYFSLPQSYTWT* | 8535 | ATGTTTTATCTTTTTTTCCTTATTTCCTATTCGAGTCAATACACGTGGACCTAA | 8536 |
| hsa-mir-20b | 1 | MVEREGSGFILHPFPPSLPFACLPGLSSSDPACSLVSDL* | 8537 | ATGGTGGAAAGGGAGGGTCGGCTTCCTCCCCAGGGCTTCCTCCTCGACCCAGCGTGCTCACTGGTCTCGATTTGTAA | 8538 |
| | 2 | MLNSILIVRLKLRHHFILQSAVGLWP* | 8539 | ATGCTTAATTCCATTTGATTGTCGTCTTAAACTAAGACATCATTTTATTCTACAGAGCGCTGTCGGCTTTGGCCTGA | 8540 |
| | 3 | MRGESKHAPYLPHCACJRWLLPLTHPAKKP* | 8541 | ATGAGAGGAGAAAGCAAGATAATTGCACCGTATCTTCCGCACATTTGCCGTGTATTCGGTGCTGCTACCGTTAACGATACCTGCCAAGAAACCCTGA | 8542 |
| | 4 | MCRE* | 8543 | ATGTGCAGAGAGTAA | 8544 |
| hsa-mir-21 | 1 | MCLFLWATVPCFQCCPRHRSISAFAIASGVPGGSTAEAASPQKRMGHTTGKTLIRFLLPSGKFRAEITPTALTHFRQISEVGLPVFLDRS* | 8545 | ATGTGTCTTTTTCTTGGCTACGTGCCTTGCTTCCAGTGCTGTCCCGGCATAGGTCATTCTGCAGAAGCCATTTCAGGAGTACCTGGAGGCTCAACGGCAGAAGCTTCACCACAAAAGCGAAATGGTCACACACCACACCACAGGTCACGTAAGACTTTAATCCGGTTTCTCTCCCTCTGGGAAGTTTCGGCCTGAAATTACATTCACAGCTCTACTCACTTTTAGGCAAATAAGTGAAGTTGGCCAGGTGTTCTTGACAGAGTTAA | 8546 |
| | 2 | MGTPQYRL* | 8547 | ATGGGCACCACCAGGTAAGACTTTAA | 8548 |
| | 3 | MLYWEICLCLRLESVTSVHLLLKTRVEPMESNGSVT* | 8549 | ATGCTCTACTGGGAAATTGTCTTGTCTTAGACTAGAAAGTGTAACTTCTGTACATCTTCTCCTAAAAACAAGGTAGAGCCAATGGAAAGTAATGGTCTGTACATAG | 8550 |
| | 4 | MVLLFHRMSCCLDLK* | 8551 | ATGGTTCTGTTACATAGAATGAGTTGTTGCCTTGATCTTAAATGA | 8552 |
| | 1 | MCGIRGGGJD* | 8553 | ATGGGAATTAGGGATTAGGGAGGGGGCCAGGATTAG | 8554 |
| hsa-mir-219-1 | 2 | MNQPMKGAGESRREGAGKRRRRKGRGVCANRLWRPHKDWPRTEGEDREVGGNWGGGRGHPLLPCPRDRPPPGSRSPSPGASARAGTRCPSGSLTAPHPLALYPSHSLHRSMGIALPLPLLFPPHPLRLL* | 8555 | ATGAACCAGCCATGAAAGGCGATGGAGAAGGGACTGGAGAAGGAGAAAGGAGAGGAGTGGAAGAGTGGCAGAAGGCGCTGAAGGAGGAACTGGCGCCCACATAAGGACTGGCCACGGACTGAAGGAGCAGGAGGAGCAGGGAACTGGGGTGGGGGCGAGGGGCACCACTGTCCCAGGGACAGGCCACAGCGGCAGCCAAGTGCGGAGCCCACCCCTGTCCAGGGAGCCGGGGACAAGCCCATCAATGCCATCCTCTAACCTGCCCCCACCCTCCTCCCCATCCCCTTGTTACTTAG | 8556 |
| | 3 | MPIRVSNCPPHPRPVSLSFPTLNGDRSAPSSSLSSPSPSFTLESSKRLLPTSHSRHSAPVPYHTRTPPSQWELHLVYVPVSAWCLHSPFPPVRLPPFPAPCRGS* | 8557 | ATGCCCATCAGGGTCTCTAACTGCCCACCCCTCACCGCCCTCGTATCCTCTCATTCCTACACTCAATGGGGATCCTGGTCTGCTCCAGCCCAGTCTCTCCTGCCACTCCATGAGTCCTCACACGCGCACACATTCTGCCCTGTACCCACCCACATGGGAGTCCATCTTGTGTATGTCCCTGTTTCCCGGTGGTGTCCCAGGTCCATTCCAGGATCGGTCAATGGGGATGCTAACTGCCCCTCCTCCCCATCCCCTTGTTACTTAG | 8558 |

Figure 1 (Continued)

| | | | | | |
|---|---|---|---|---|---|
| | 4 | MGAPSCVCPCFRVVSPFPLSSRAPPSLPRPGPRLLIVQTQ FSSLWLRPRVESGRPEPPPPNLERESCSEGLGRAKAEGG GSPQGGKGNPGHHGT* | 8559 | ATGGGAGCTCCATTCTGTGTATGTCCCTGTTTCGCGTGGTGTCTCATTCCCTTT CCTCCCGTGCGCCTCCCTTCCCGCCTCGAGTCTATGCTCCGCCGCGAGCTCCTGATTGTCAAA CGCAATTCTGAGTCTATGCTCCGCCGCGAGAGTTGAGTCTGGACCTCCGAGCGC CGCCCCAAACCTCGAGCGCGGAGAGCGGTCGGAGGTCGGAGAGCCAAAGCA GAGGGTGGAGGGAGTCCCAGGGTGGTAAGGGAATCCGGGACATCGGGACCTA G | 8560 |
| hsa-mir-22 | 1 | MEGESGVYRAATPSPSGRRRGGGGRGASGRGAWTGRVS VSGATRKESGTGVVAEGLAEWRGAGGEPRGRRAGGGS PGGPRSEDTGAGHLAWGGKSGPPERAARRCFASAGVHW VRASSAPWQGRGRWAGRPLLSFSPGDVM* | 8561 | ATGGAGGGTGAAAGTGGTCCGGCGGGCGGCCACCCAGCCTTCCGGGAGGAGAAG GGGCGGCGGGGCAGGGGCGCTACGAGGAAAGAGTCTGGACGGGAGTCGTGGCGGAAGGGCTGG GTGTCAGGAGCTACGAGGAAAGAGTCTGGACGGGAGTCGTGGCGGAAGGGCTGG GTGAGTGGCGGCGGCGCGGGGGGAGAGCGGAGAGCGGGAGCGGGAGGGCGGGGCCGGGTC ACCCGGCGGCCGCCCCCCGGCTCTGAGGATACAGGGGCCCATCTAGCCTGGGAGGGT CTGAGCACCCCGAGCGGGCGGCGAGGAGGTCTTTGCCTGCCGCGTTCACTGG GTCAGGGCCAGTTCAGCGCCTGCAGGAGGAAGGGGTGCTGGGCGGCGCCGGCCCCT CCTCTCGTTCTTCCAGGGATGTTATGTAA | 8562 |
| | 2 | MLCKGGHERSRGRRCRGLMQPKG* | 8563 | ATGTTATGTAAGGGGGAGGGGAGGAGAGAGTAGGGGCGCGCGTGCCGGGCCTTA TGCAACCCAAAGGTTAG | 8564 |
| | 3 | MASGEAVTPTSLRPWFQPPTPLACHPGCQHGLGAVRVP EG* | 8565 | ATGGCCTCCGGCGAGGCTGTCACCCCACCCCGAGCTGCCCCAGCCTGGTTCCAGCCTCCA ACTCCTTTGCCTGTCATCCTGGCTTGCAGATTGGGCTAGGAGCTGTCAGAGTGCCA GAGGGTTGA | 8566 |
| | 4 | MEQLVRGSYPWAHPALQPRAPAWHRLSAAAESSGHNR AISDRGRSDGVGLVTQGKEDTQSSCLPRGFRNLNRTPY PPFLTL* | 8567 | ATGGAGCAGCTGGTCAGAGGGTCAGTGCCCTGGCCATCACCCCGCCCTGCAGCCAAG GGCACCTGCTTGGCACAGAGGAAGTTCTGGACGCAGCTGCTGAGTCCTCTGGTTGAACAGAGC TATCTCAGACAGGAGAAGTTCGGACGGAGTTGAGTGACTGGTCAGGGAAGGAAG ATACACAAAGTTCAGCCTCCCAAGAGGGGTTCGGAATTTGAACCGACCGTATC CCCCAATCTTCTTACCCCTCTGA | 8568 |
| | 1 | MWKIS* | 8569 | ATGTGGAAAATTTCATGA | 8570 |
| | 2 | MSLDICKHL* | 8571 | ATGAGTTTGGATATATGCAAACACCTGTGA | 8572 |
| hsa-mir-221 | 3 | MQTPVIPSF* | 8573 | ATGCAAACACCTGTATTGTGATACCATCACCATAA | 8574 |
| | 4 | MDYFNSQSFIVSLWFCVCVCVYKMHLT* | 8575 | ATGGATGTATTCAACATCTCAAAGTTTCATTGTATCCCTTTGGTTTGTGTCTGTG TTTGTTGTATAATGTTAAGAATCACTTAACATGA | 8576 |
| | 1 | MWKIS* | 8577 | ATGTGGAAAATTTCATGA | 8578 |
| | 2 | MSLDICKHL* | 8579 | ATGAGTTTGGATATATGCAAACACCTGTGA | 8580 |
| hsa-mir-222 | 3 | MQTPVIPSP* | 8581 | ATGCAAACACCTGTGATACCATCACCATAA | 8582 |
| | 4 | MDYFNISQSFIVSLWFCVCVCVYKNHLT* | 8583 | ATGGATGTATTCAACATCTCAAAGTTTCATTGTATCCCTTTGGTTTGTGTCTGTG TTTGTTGTATAATGTTAAGAATCACTTAACATGA | 8584 |
| | 1 | MANGWTGSRPGRRNPEL* | 8585 | ATGGCCAATGGCTGGACTGGCTCCCGCCCTGGGCGGAGGAATCCGAGCTGTGA | 8586 |
| hsa-mir-25 | 2 | MAGLAPALGGGIPSCEAAGIRARVLLCLLRAEAMAGAG VGCGGGVRWRRSR* | 8587 | ATGGCTGGACTGGCTCCCGCCCTGGGCGGAGGAATCCGAGCTGTGAAGCGGCTGG AATCCGGGCCCATGCGTCTTGTTTACTAAGAGCGGAAGCGATGGCGGGAGCGG GGGTGAGGTGCGGTGGCGGGTGCGGTGCGGAGGTCCCGGTGA | 8588 |
| | 3 | MCPFVY* | 8589 | ATGTGCTTCTTTGTTTACTAA | 8590 |
| | 4 | MLDGPVHCHGLFILRWLETDL* | 8591 | ATGTTGGATGGCCCTGCACTGCCACGGGCTCTTTATTCTTCGCTGGTTAGAAACA GACTTGTGTGA | 8592 |

Figure 1 (Continued)

| | | | | |
|---|---|---|---|---|
| hsa-mir-26b | 1 | MDSSAVITQJSKEEARGPLRGKGTGAAGRGPKPGRRGR REGAGIFPRGAAAAPGGRLSCARSSQPEREQGESLNSE EAQRRKGAGPGAFGALLFARGEETEAGHERELFGGFLAGH AWCMGAPPPLAPMGLGDGGAEEGAYGPPAETTPHPPPP PPRAAVR* | 8593 | ATGGACAGCTGGCCGTCATTACTCAGATCAGCAAGGAGGAGGCTCGGGCCGCT GTGGGGCAAAGGTACCGGGGATCTTCCCAGGGAGCCGCGAAGCCGGGGCGCCGTGG AGGAGAGAAGGRGCCGGATCTCCCAGGGAGCGAGTCCGCGGGGAGCCCGGCGG CCGCCTTAGCTGTGCCCGAAGCTCCAGCCGACCCCAGCCAGAGGGAGCAGGGAGAGAGTTGA ACTCAAGAGGAGGTCAGAGACGCGGGGCTGGGCGCTGGCGCCTTTGGGGCGCTCCTG TTCGCTCCAGGGCAGGGAAACTGAGGCAGGAATAGAGAGGGAACTTCTCGGGGTTT CCTGGAGGCATTGCTGGTTGCATGGCGGTCATGGGCGCCCCCCACCATTGGGCCAATGGGCT GGGAGATGGGAGCTGAGGGGTTGCCGCTATGGTCAGCCGCTGACCTCGCCC ACCCCCCACCCCACCCCCGtrCCTGCGGTCCGGTAG | 8594 |
| | 2 | MGELRRAPMGHPLRLRPTPHPHPPGLRSGRVLGGGAEV TAGWGGLEGSPANTQLRSPQTSRHAWRRRPPRRHRED GRHFQESLGARGESRAPSGHAPPRKASPPRGCVPQRG WAGVGGSVFSFSPCGPQDLDAAPRSAHPRLLGLAAPELR ARWKG* | 8595 | ATGGGGGAGCTGAGGAGGGCGCCTATGGCCACCGCTGAGACTCGCCCCACCCC CCACCCCCACCCCCCGGGCTGGGGGCTGTAGGCTTGGGAGGGGCGCGGAGG TGACAGCAGGCTGGGAGGCTTGGAGGGATCTCCCCGCAACACAACCAGCTACGTTCC CACAAACTTCGGCTCACGGTGAAGGGCGACCCCCTCGGAGGCACAGAGGA CCGGCCGACCTTCAAGAATCTGTCTGCGCCGCGGAGACTTGCCCGCGTCCTAGTG GCACGCAGCACCCCGCAAAGCTCCCCCGACGAGGCTGCGTCCCCAGCGT GCTGGGCCGGGGGGGGCCCAGTCTGCCCACCCCAGTCTGGGTGGACTCCAGGAT CTGAACCGTGCCCCCAGTCTGCCCAGTCTCTGGGTGCTGGCTGCCCGGAACTG AGGGCAAGGTGGAAAGGCTAG | 8596 |
| | 3 | MATGHWPQAAGLHPCLWAQPQ* | 8597 | ATGGCCACTGGACACTGGCCCAGGCTGCCGGGACTGCACCCTGCCTCTGGGCCA GCCGCAGTGA | 8598 |
| | 4 | MEGGQGWTALGPRPWLS* | 8599 | ATGGAGGGACGGGACAGTGGACTGCCTCCAGGCGTGAGTGTCCTGA | 8600 |
| hsa-mir-301a | 1 | MEAEVDKLEMVSAK* | 8601 | ATGGAGGCGGAAGTCGATAAGCTGGAACTGATGTCAGTGAAGTGA | 8602 |
| | 2 | MASEVGHNLESPETPGGGGWTRVEFPPPAPKGAAITVW CLNRLG* | 8603 | ATGGCCTCGGAGGTGGGCACAATTTGGAAGTCGCCGAAACTTGGAGTCGCCGAGG CTGGACCAGAGTCGAGTTGCCTCCTGCACCAAAGGGAGCCGCCACCGTCTGGTG TCTAAACCGCTCGGGTAA | 8604 |
| | 3 | MAGDAEGAGPLEFLVPCHLYTPYETAPGADRILCLYQ KRCEWNGP* | 8605 | ATGGCCGGAGATGCTGAGGTGCGAGGCCTTTGGAATTCCTTGTTCCTGCCTCAC CTTTACACCCCTACGAAACCCGCCGGGTGCAGACCGCATTCTGTGTTGTACCAA AAAGATGTGAATGGAACGGTCCTAA | 8606 |
| | 4 | MLRVRGLWNSLFLALTFTPLTKLRRVQTAFCVCTKKDV NGTVPKRPKKGEYVHTPRKGNGGWGGE* | 8607 | TTACGAAACTGGGCTGCCGGGTTGCAGACGGCATTCTGTTGTTGTACCAAAAAGATGTGA ATGGAACGGTCCTAAGCTGCCAAGAAGGAGGAGGTGGTTCACACTCCAAGAAAG GGGAACGGAGGGTGGGGTGGGGAATAA | 8608 |
| hsa-mir-30a | 1 | MGFQSDVCSCLLPRTSRGYFRSNYLVY* | 8609 | ATGGGCTTTCAGTCGGATGTTTGCAGTGCCTACTGCCTCGGACTTCAAGGGCTAC TTTAGGAGCAATTATCTGTTTACTAA | 8610 |
| | 2 | MFAAAYCLGLQGATLGAILFTKIEYLAISLHPYKAELK WYKLNEHFKTMSVHF* | 8611 | ATGTTTGCAGCTGCCTACTGCCTCGGACTTCAAGGGGCTACTTTAGGAGCAATTATC TTGTTTACTAAAACTGGAGCAACCTTGCTATCTTTGATACATTTTTACAAAGCTGAAT TAAAATGGTATAAAATTAAATCACTTTAAAACCATGCTGTACATTTTTAG | 8612 |
| | 3 | MBIRICNIKKKVPVREMRKCVTVPLFFLKA* | 8613 | ATGCATAGAATTTGCAATATCAAATAGAAAGATATTCGTAAGAGAAATGAGGAAATG TGTTACAGTATTTTATTTTTTTTAAAAGCGTAG | 8614 |
| | 4 | MCYSIFFFKSVVGQYFPEKSMK* | 8615 | ATGTGTTACAGTATTTTATTTTTTAAAGGTAGTAGGGCAATATTTCCAGAAAA AATCTATGAAGTGA | 8616 |
| hsa-mir-30b | 1 | MCVQHFSPSS* | 8617 | ATGTGTGTGCAACATTTTCCGTCTCTTAG | 8618 |
| | 2 | MGMHVFLY* | 8619 | ATGGHATGCATGTCTTTTATATTAA | 8620 |
| | 3 | MSFYINIFFKYFQIVAFRFIASSLKYSCPESSCTVSJFCVSP QJ* | 8621 | ATGTCTTTTTATATTAATATTTTCCTAAGTATTTCAGATTTGTTTGTATCTATTTTTTGT TGCTTCCTCCTTAAAATATAGCTGCCCTGAAAGCAGCTGTATTGTATCTATTTTTGT GTTTCCCCACAGATCTGA | 8622 |

Figure 1 (Continued)

| | | | | | |
|---|---|---|---|---|---|
| hsa-mir-30d | 4 | MTLSVD* | 8623 | ATGACACTCAGTGTGGACTAA | 8624 |
| | 1 | MCVQHFSPSS* | 8625 | ATGTGTGTGCAACATTTTCTCCGTCCTCTTAG | 8626 |
| | 2 | MGMHVFLY* | 8627 | ATGGGTATGCATGTCTTTTTATATTAA | 8628 |
| | 3 | MSFYINIFPKYFQIVAFRFIASSLKYSCPESSCIVSIFCVSPQI* | 8629 | ATGTCTTTTATATTAATATTTTCCAAGTATTTTCAGATTGTTGCTTTCAGATTTAT TGCTTCCTCCTTAAAATATAGCTGCCCTGAAAGGCAGCTGTATTGTATCTATTTTTGT GTTTCCCACAGATCTGA | 8630 |
| | 4 | MTLSVD* | 8631 | ATGACACTCAGTGTGGACTAA | 8632 |
| | 1 | MLRRSGVLASGRWRGGAKIRVPGFVGHHAAM* | 8633 | ATGCTGCGGAGCTGCGAGGGTTGGCTCCGGCGGTGGCTGGAGGCGCCAAGAT CAGGGTCCCGGGTTTTGTCGGCCACCACGCGCAATGTGA | 8634 |
| | 2 | MGRGARRGAESETWT* | 8635 | ATGGGGCGAGGGCCGCAGGCGCGGCGAGAGTGAGACCTGACTTAA | 8636 |
| hsa-mir-320 | 3 | MVTLEWSLFPGSDLAHFRGPLPCAPGGVLG* | 8637 | ATGGTGACCTTGGAGTGGTCATTACCTCCGGGCAGGACCTCGCCCACTTTCGGGGA CCCCTTCCCTGTGCTCCTGTGAGTCCTGGGGTGA | 8638 |
| | 4 | MLSPIPQTV* | 8639 | ATGTTATCCCCATCCCAGACCGTATAA | 8640 |
| | 1 | MGDKGTR* | 8641 | ATGGKCGACAAGGGACCGGTGA | 8642 |
| | 2 | MWAAARPGPDTQLADTQHWPAAAETHGGRLTHNTRTG TLTRGTGMLAHTLATASTRSSHAVARRHTRLGQHILAD SLVGMHSSQSNTHQF* | 8643 | ATGTGGGCCGCAGCTCCTGCCCGGACACACAGTCTGCTGACACCAGCATTGGCC GGCAGCCGACCGAGAGACCCACGGGGCAGGTTGACACACAATACACGGGCACAC TAACCCGTGCACAGGCATGCTGGCGCACACATGCACAGTCGCACACGCTCAT CACACGCAGTGGCACGCCGTCACATCCAACACCACCAACCAATTCTAG TTGTTGGCATGCACAGTCACAATCCAACACCACCAACCAATTCTAG | 8644 |
| hsa-mir-326 | 3 | MSRQHSGAQGHTNTDPHRHMQIDALKDWHPTGTSC* | 8645 | ATGTCTCACCAACAGAGTGGAGCCAAGGCACACTAACTGACCCCACAGACA CAATCAGACTGATGCTCCTCAAAGACTGGACACCCCACAGGCAGCTGCTAG | 8646 |
| | 4 | MPSKTGTPQARAASPRPADTHASGFTWPEVETHTSHRV ERPPFPAWGKQIAFHPNRSHPSTLFPFPLTS* | 8647 | ATGCCCTCAAAGACTGGCACCCCACAGGCCAAGGCACGAGCTGTAGCCACAGGG CACACACGTTCAGGCCCCGCACCCGCCGACACATCACAATCGCCGTGA TAGAGCGCCCCCCATTCCATGCGCCAGCTGGGGAAAACAGATGCCATTTCATCCAAATA GATCCCATCCATCTACTCTGTCCCTTCCCTGACCTCTGA | 8648 |
| | 1 | MSSFGAG* | 8649 | ATGAGTAGCTTTGGAGCTGGGTGA | 8650 |
| | 2 | MVSPLF* | 8651 | ATGTGTTTCCCCTTTCTGA | 8652 |
| | 3 | MGKGSVEACLLG* | 8653 | ATGGGGAAGGGTCGGTGAAGCTTGCTTGTTGGGGTGA | 8654 |
| hsa-mir-330 | 4 | MGLVSVPDLWGCPGRGWLRENVPEGPPCAHDDPRRAG TRLQPGHTLGAAFLPAQAGVGVSFCWNLLGAPIPPGGN RKAVKAAQACNLSTLGRSFEAKSLRPAWATHKTSTARS RAMWPEWDWCI* | 8655 | ATGGGGCTGGTGTCAGTGCCTGACCTCTGGGGGTGTCCTGGCAGAGGATGGCTCCG TGAAAATGTTCTGAGGGCCGCCTTGTCCATGATGACCCAGACGGCAGCTGGCAC CCACCTACAGCCTGGACACACGCTCGGAGCTGCCTTCTTGCCGACCCAAGCTGGAGT GGGTGTATCCTTTGCTGAAGCAGTCAGGCCTGAATCTCAGGCACTTTGGAGGATCGTTTG AAAGGCGGTCAAGCAGTCAGGCCTGGCAACACACACAAAAACAAGCACAGCAGCGTTCA AGGGCTATGTGGCCAGAGTGGGATTGGTGCATTGA | 8656 |
| | 1 | MPGWILQLRGFSGKQRPLLSRDPGS* | 8657 | ATGCCCGGATGGATCCTGCAGCTCCGCAGCTGTTTCTCGGGAAGCAGGGCCCTGCTC TCAAGAGACCCTGGCTCTGA | 8658 |
| hsa-mir-338 | 2 | MDPAAPWLFWEAAAPALKRPWLLMVAPRLPAGARDSG QFPRKGQAGSPSRGRVRKLGGAEATLGP* | 8659 | ATGGATCCTGCAGCTCCGTGGCTCTTCTGGGAAGCGGCCGCCCCTGCTCTTCAAGAGA CCCTGGCTCTGATTGTGGCCCAAGGTTGCCAGCTGGAGCTGGGACTCAGGACA GTTTCCCAGAAAAGGCCAAGCGGGCAGCCCTCCAGGGGTCGGTGAGGAAGCTGG GGGGTGCGGAGGCCACACTGGGTCCTGA | 8660 |
| | 3 | MAFP* | 8661 | ATGGCCTTCCCCTGA | 8662 |
| | 4 | MSGRGTGGEVSCPGGRRGAGGRRVRPGSRGRWRRSSRG* | 8663 | ATGAGTGGACGGGGCACAGGAGGAGAAGTGTCTGTCCTGGGGGCCGGTGGGGC GGGTGGGAGAAGAGTAAGGCCTGGAAGCCTGGAAGCCGGGAGCCGGGAGAGCCGT GGGTGA | 8664 |

Figure 1 (Continued)

| | | | | |
|---|---|---|---|---|
| hsa-mir-339 | 1 | MGGALPQPRPAATGGRSRCRPWRPDAAAAGPAPPCRPR AGRAALLGAPLRAGPRAGPGRSRALLPLTLLGAQGRAA GGRVGVQALQALRALERPRNRPGSPALWGRTGPPAAM QQPPGETRALRTLGGLESSAAA* | 8665 | ATGGGAGGGGCCCTGCCTGCCCAGCCCCGCCCCGGCGACAGCCTGCGCCTCCCGTGG GAGGCCGTGGCGTCCAGACGCTGCTGGGGCGTCTGCGGCGTCCCGCTGGAGACCCGGG CCGGCCGAGCGTCCCGGCCGCTTCTCGGGCGTCGCTGCGCCGGTCCCGAGCAGGCCT GGACGGTCCGCCGCCCTCACTTACTCTCTGGGGCGCCAGGGCCGGCAGGGCCGCG GGTGGCAGGGTGGGGGGTCCAGGCGTTCCAGCCTGCAGGCACTGCAGGCCCTCGAGCTCGAGCGCCCCG CAACGGGCCAGGTCCCGGTCGCTGCGTCCCTCGCGTGGGGCGGACCCGGGTGGGCTGGAGTCGTCG GCCGCCGCGTGA | 8666 |
| | 2 | MMKTIGIASLGSLPEDGGAGRQLLQEALPLLRRGSAGF GLESAEVLGVCLLSSEEAVARAGGGPVLVLRCVLGASS AARTAGRGRGPGVRTDTRTGLPSLLLGLTAAETAGMV TVASESFAYE* | 8667 | ATGATGAAAACAATTGGGATAGCTTCACTGGGAGCCTTCCTGAGGACGGCGAGC AGGGACCGGCAGCTGCTTCAAGAGGCTCTGCCGCTCCCGCTCCTGCGGCTCAGCCGGTT TGGGTTGGAGAGCGCAGAGGTCTTGGGAGTACAGAGGTCTTTATCTCTGAGGAGCGG TGGCCCGGGCAGGTGGCCGCCCTGTCGTCCTTGCGCTGTGTCCTCGGAGCGTCCT CAGTGCTGCGGCACAGCCGGGGCGTCGGACCAGGCGTCGCACGGACACGGA ACCCGGCTGCTGCCTAGCCTGCTGCTGGGCCTCACTGCTCAGAGACGCTGGAATGGT GACCGTTGCTTCAGAGTCCTTTGCTTATGAGTAA | 8668 |
| | 3 | MSNSPN* | 8669 | ATGAGTAACTACCGAATGA | 8670 |
| | 4 | MNSLLCSLRSCGKVRKPNPYLVPRCECFKLCVTTNKIDM MIHFTDI* | 8671 | ATGAATTCGTTGTTGTTCACTGAGGAGTTGTGGCAAAGTGAGAAAACCTAACCGTAC TTAGTTCCCAGATGTGAGTGTTTTAAACTATGTGTAACAACTAACAAAATTGACATG ATGATACACTTCACGGACATTTAA | 8672 |
| hsa-mir-33b | 1 | MPPSPAGSPGVGHAGYAT* | 8673 | ATGCCTCCGTCTCCTGCAGGTTCTCCGAGGTTGGGGGCATGCGGGCTACGCAACT TGA | 8674 |
| | 2 | MRATQLEQERAPSRGRRCDSYQLAGEVEGYLQPN* | 8675 | ATGCGGGCTACGCAACTGAGCAGGAAAGAGCCCTTCCGAGGGAGAAGGTGTGA CAGTTACCAGCTCGCTGGGGAAGTGGAGGGCTACCTCCAACCAAATTAG | 8676 |
| | 3 | MGNPAVESPL* | 8677 | ATGGGAAACCCTGCAGTTGAAAGTCCATTATGA | 8678 |
| | 4 | MTCDLGPQTRRVST* | 8679 | ATGACTTGTGACCTGGGGGTCCACAAACCAGGAGAGTTCTACTTGA | 8680 |
| hsa-mir-345 | 1 | MGCGDE* | 8681 | ATGGGCTGCGGGATGAATGA | 8682 |
| | 2 | MNESRV* | 8683 | ATGAATGAGAGCCGAGTCTGA | 8684 |
| | 3 | MRAESDSAPQESLTFAVARDCPGPCGASHSVTSHQPFPS ASGGPDCQVGAWEQGRARRFLFAVGVRSALGRAQLFS LGPAGRQGHHTVCHVSRFRVTWFFYPNSSGYLPPGGAGR KVLCIWY* | 8685 | ATGAGAGCCGAGTCTGACTCGGCCCCCAGGAGTCCTGACTTCGCAGTGGCAAG GGACTGCCCCTGTCCTGTCCTGGAGCCATTGGTGAGCTGTCAGGTTGGAGCAGGGACGGGCCA CAGCGCCTCTGAGGTCCAGACTGCCAGGTTGGAGCGTGGGAGCAGGAGGACGGGCCA GGCGCTTTCTGCGCTTAGGAGTCAGATCAGCCTTAGGCCGGGCCAGTTCCTT CTTTAGGGCGGCAGGCAGGCAAGCCACACCGGTGTGCACGTTTGCAGGTTTAGGG TCCATGGTTCTTTTTATCCAATTCAGTGGGTACCTCCTGGAGGTGCAGGTC GAAAGGTTCTGTGTATTTGGTACTAG | 8686 |
| | 4 | MVLLSKFQWVPTSWRCRSKGSVYLVLGHTGRCCQ* | 8687 | ATGGTTCTTTTATCCAAATTCCAGTGGGTACCTACCTCCTGCAGGTGCAGGTCGAAA GGTTCTGTGTATTTGGTACTAGGACACACAGGTAGTGTGTCAGTAG | 8688 |
| hsa-mir-363 | 1 | MVEREGSGFILHPPPSLPPACLPGLSSSDPACSLVSDL* | 8689 | ATGGTGGAAAGGGAGGGGCTCGGCTTCATTCCGCCTCCCTCCTCCTGCCC CCCGGCTTGCCTTCCTCTCGACCCAGCGTGCTCACTGGTCTCTGATT TGTAA | 8690 |
| | 2 | MLNSHLIVRLKLRHHPHLQSAVGLWP* | 8691 | ATGCTTAATTCCATTTGATTGTGCGTCTTAAACTAAGACATCATTTTATTCTACAGA GCGCTGTCGGGCTTTGGCCTTGA | 8692 |
| | 3 | MRGESKHAPYLPHCACIRWLLPLTIPAKKP* | 8693 | ATGAGAGGAGAAAGCAAGATAATTGCACGTATCTTCCGCACATTTGCGGTGTATT CGGTGGCGCTGCTACCGTTAACGATACCTGCCAAGAAACCCTGA | 8694 |
| | 4 | MCRE* | 8695 | ATGTGCAGAGTAA | 8696 |

Figure 1 (Continued)

| | | | | | |
|---|---|---|---|---|---|
| hsa-mir-365-1 | 1 | MDYSSEDISGAFQRSAWWGLEAKRNQKRH8P)HPQ|KM PFSFFF* | 8697 | ATGGATGTGTCCTCAGAGGACATAAGCGGCATTCCAACGCTCGCTTGGTGGGG ATTGGAAGCAAAGCAAAGAAAACCAGAAACGCCACTCCCCCACCCCCCAAATCAAAATGC CTTTTCTTTTTTCTAA | 8698 |
| | 2 | MCPQRT* | 8699 | ATGTGTCCTCAGAGGACATAA | 8700 |
| | 3 | MPAGLGRTWSGGRGRPAPRAALRSGSRSESVSRAGFPG WGRGRGRSTASSISKPRH* | 8701 | ATGCCAGCAGGGGCTCGGGCGCACTGAGCGGGGCGCGGCCGGCCTGCTCGCG CGCGGCATTGAGATCGGGGGTCACCGCAGGCGAGTCAGTTTCCCGAGCGGGCTTTCCGG GGTGGGGCGGGGACGCGGACGCTCCACCGCCTCGTCAATTCCAAGCCCAGGCAC TAG | 8702 |
| | 4 | MGGERRKSFSAESAQPTGLHPASTVRCRHKAAPPPPTP QRPMAGPGRGLGRPGVGRAGEAAAAQAAGRLLPGQ AERARAWKPSAPARVGVGVGVGVGAGAGVGGRLP RNARQI* | 8703 | ATGGGCGGGGAGCGTAGAAAATCCTTTCTGCAGAGAGCGCCAGCCGACGGGCT GCACCCGGCCTCCACGGTCCGTGCGCCACAAAGCCGCGCTCCGCCCCCCCCAAC CCCCAGCGCCCTATGGCCGCCCGGGCGTGGGGGCTGGGGCGTGGGGGTTGGCC CAGCTGGGAGGCGCAGCGCCAGCGGCCAGGGAAGCCTGAAGCCTCGGCAGCCAGGC CAGGCAGAGAGGGCGAGAGCCTGGAGCCTGGAAGCCTGGAGCGCGGCGCGGGCCGGC GGGTGGGGTGGGGTGGGGTGGGGTGGGGTGGGGTGGGGCGCGCCCCCCGGGCTGGGGCGTGG TAGAAACGCTCGCAAATATAG | 8704 |
| hsa-mir-365-2 | 1 | MGAEGWVFAGEMRVSDQLAYKVPVLGPRDQRLLPGPR PRPASSRAGVRSGQAASQVHAGEGVVRCARPGCVR* | 8705 | ATGGGAGCTGAGGGCTGGGTCTTTGCGGGCGAGATGAGGGTGTCGGATCAACTGGC CTACAAAGTCCCAGTTCTCGGCCCCCGGGACCAGGCTCTTCTCCGGTCCTCGCCC CAGGCCGGCTTCCTCCGCGGAGTGCGTGAGTGCCTCCGGCAGCTGCCTCTCAGGTCCA CGCTGGAAGGAGTGGTGAGTGCGCTCGCCCGGTGCGTGCGGTGA | 8706 |
| | 2 | MGQALPLTEACPAVLSRAATLSLGVGRTGPDF* | 8707 | ATGGGCCAAGCTCCCTGCCACTTACCGAGGCCTGCTGCCCCTGCCCTGTGCTTTCCAGGGCGGCA ACCTTGAGCTTGGGGATGGTTCCAAATGCCGGTCTTTGTTCCCTGA | 8708 |
| | 3 | MDLCGCVPNGRSFVP* | 8709 | ATGGATCTTTGTGAGTGGTTCCAAATGCCGGTCTTTGTTCCCTGA | 8710 |
| | 4 | MCSQWPVPCSLTDAT* | 8711 | ATGTGTCCAATGCCGGTCTTTGTCCCTGACGATGCAACATAA | 8712 |
| hsa-mir-371 | 1 | MMTCALVFFTEPLFIKCSIKS* | 8713 | ATGATGACATGCGCTTGGTCTTTTCACTGAACCTCTTTTATAAAGTGTTCAATAA AAAGCTGA | 8714 |
| | 2 | MRFGLFH* | 8715 | ATGCGCTTGGTCTTTTCACTGA | 8716 |
| | 3 | MYSLHLA* | 8717 | ATGTATTCTTTGCATCGGCATAG | 8718 |
| | 4 | MQEDHLSPGVPVQPGLTGRTPSLERKKCKKAFFVYYFF ETGSPSIPQTGVPWYHHSLLQP* | 8719 | ATGCAGGAGGATCATTGAGTCCAGGAGTTCCAGTCCAGCCTGGGTTAACAGGTAG AACCCCTTCTCTGAAAAGAAAAATGTAAAAAGCATTCTTTGTGTATTATTTTTT GAAACAGGGTCTCCCCTCTATACCCCAGACTGGAGTGCCTTGGTATCACAGCTTA CTACAGCCTGA | 8720 |
| hsa-mir-372 | 1 | MMTCALVFFTEPLFIKCSIKS* | 8721 | ATGATGACATGCGCTTGGTCTTTTCACTGAACCTCTTTTATAAAGTGTTCAATAA AAAGCTGA | 8722 |
| | 2 | MRFGLFH* | 8723 | ATGCGCTTGGTCTTTTCACTGA | 8724 |
| | 3 | MYSLHLA* | 8725 | ATGTATTCTTTGCATCGGCATAG | 8726 |
| | 4 | MQEDHLSPGVPVQPGLTGRTPSLERKKCKKAFFVYYFF ETGSPSIPQTGVPWYHHSLLQP* | 8727 | ATGCAGGAGGATCATTGAGTCCAGGAGTTCCAGCCTGGGTTAACAGGTAG AACCCCTCTCTGAAAAGAAAAATGTAAAAAGCATTCTTTGTGTATTATTTTTT GAAACAGGGTCTCCCCTCTATACCCCAGACTGGAGTGCCTTGGTATCACAGCTTA CTACAGCCTGA | 8728 |
| hsa-mir-373 | 1 | MMTCALVFFTEPLFIKCSIKS* | 8729 | ATGATGACATGCGCTTGGTCTTTTCACTGAACCTCTTTTATAAAGTGTTCAATAA AAAGCTGA | 8730 |
| | 2 | MRFGLFH* | 8731 | ATGCGCTTGGTCTTTTCACTGA | 8732 |
| | 3 | MYSLHLA* | 8733 | ATGTATTCTTTGCATCGGCATAG | 8734 |

Figure 1 (Continued)

| | | | | |
|---|---|---|---|---|
| | 4 | MQEDHLSPGQVPVQPGLTGRTPSLERKKCCKKAFFVYYFF ETGSPSHPQTGVPWYHHSLLQP* | 8735 | ATGCAGGAGGATCATTTGAGTCCAGGAGTCCAGTTCAGCTGGGTTAACAGGTAG AACCCCTTCTCTGGAAAGAAGAAAAAATGTAAAAAGGCATTCTTTGTGTATTATTTTT GAAACAGGGTCTCCCTCTATACCCAGACTGGAGTGCCTTGTATCATCACAGCTTA CTACAGCCTTGA |
| hsa-mir-374a | 1 | MARGEVSCLCLAILG* | 8737 | ATGGCGAGGGAGGTAAGGTCGTCTTTGCTTGGCCATCTTGGCTAG |
| | 2 | MLWPDPLEINPES* | 8739 | ATGCTGTGGCAGATCCACTAGAATTAACCAGAATCTTAG |
| | 3 | MRRR* | 8741 | ATGAGGAGGCGATGA |
| | 4 | MMTLQKVAAAGGA* | 8743 | ATGATGACTCTGCAAAAGGTTGCGGCAGCTGGGCGGTGCGTAG |
| hsa-mir-374b | 1 | MARGEVSCLCLAILG* | 8745 | ATGGCGAGGGAGGTGTCTTGTCTTGCGATCTTGGCTAG |
| | 2 | MLWPDPLEINPES* | 8747 | ATGCTGTGGCCAGATCCACTAGAAATTAACCAGAATCTTAG |
| | 3 | MRRR* | 8749 | ATGAGGAGGCGATGA |
| | 4 | MMTLQKVAAAGGA* | 8751 | ATGATGACTCTGCAAAAGTTGCGGCAGCTGGCGGTGCGTAG |
| | 1 | MAGNDCGALLDEELSSFFLNYLADTQVRPAGAAGPGP GVLSCGGJRSCSRGGREAAVGALG* | 8753 | ATGGCGGGAACGACTGCTGGCGCGCTGCTGGACGAAGAGCTCTCCTCTTCTCTC AACTATCTGCTGAGCTGCACGCAGGTACCGCCGTGGGCTGCGGCCGGCCCAGG GGTGCTGAGCTGCGGGGTACGCAGCTGCAGCCGCGGGAGGCAGCGGTG GGAGCCCTGGGGTAA |
| hsa-mir-378 | 1 | MRSVTGAGSRRSPGACRSAGGATAAGEGLALAAWSLP PRGQNWGVPRFLWEVEARHGVGYPQAGAGCWRRAVS ARHLLPYFHVDLWPRHGCMPGSPESPSPPGCSPQSAVA GPPRLSTRARSAEFPASCRLKA* | 8755 | ATGCGCTCCGTTACCGGGCAGGAGCCGGAGGTCTCCGGCGCGTGCCGAGCGC TGGGGCGCTACGCCGGCTGGGAGGGTATCGCTGCCTTCGCGTTGGAGTCTGCCAC CGCGCGCAAAACTGGGGGTACCACAAAAACTGGGGGTAGCTTTCGCGGACTGCGGCCGCGGGAGTGCGACTTGCTGCCGCTACTTCACGTGGACTTGTGTCCGCACGGGTGCATGCCGGGTCTCCGAGTCTCCTAGTCCAGGTGTAGTCCAGCAGCGCGAGTGCGGGTGTTGCTGCCC CCGCGGGGCTTTCTACCCGCAGCCGAGTTCCTGCCAGTTGCGGCTAAA GGCATAA |
| | 2 | MRAETASSWFRYRAEPPGGKSQAGWGRKDCLGAPGSP CGARPRCALHDAGGREGEAESQALAEPGSPTGDTRVTG EGALVCRGAGERGSWWLGDWERGAAGTSSHQKCQHE ACAAPTPSHFPTQCLLQA* | 8757 | ATGCGGGCGGAGACAGCGTCTTCGCTGTTCTCGTTCAGGTGCGGTGGCCCCTGGGGG GAAAAGCCAGGCTGGATGGCGGCGAAGGACTGTCTGGGAGCCGCTGGGTCCCCT GCGGCCGCCGCAGGGGGCCGCCGCAGCGGGCCCACGATGCAGGGGAAGGGAGGC GGAGTCCAGGCACTGGCCGAGCCGGAGGCCGGAGCTGAAGAAGCCGGTGAGC GAGAGGTGCTCTGGTGTGTGGTGCGGTGCTGGACAAGCAGCCACCCAAAATGCCTTGTGCAGCAGGCGTGCCGGCCGGCCCACCCATTCCCACCACCAATGCCTGTGCAAGCATA A |
| | 3 | MGAEGLSGGAWVPLRCAAPVRAPRCRGKGRRGGVPGT G* | 8759 | ATGGGGGCGGAAGGACTGTCTGGGGCTGGGTGTCCCCCTGCGGTGCCGGGCCC GGTGCGCGCTCCACGATGCAGGGGAGAAGGGAAGGCGAGTGCCAGGCACT GGCTGA |
| hsa-mir-423 | 1 | MAIPGRQ* | 8761 | ATGGCGATTCCGGGCAGGCAGTGA |
| | 2 | MRNYGDCIFGRGVLNALEVKGLCRQ* | 8763 | ATGAGAAACTACGGCGACTGTATCTTTGGCCGGAGGAGTTTAAATGCGCTGGAAGTG AAGGGACTGTGTGTCAAGGGTAG |
| | 3 | MRWK* | 8765 | ATGCGCTGGAAGTGA |
| | 4 | MEARSLREKLVRK* | 8767 | ATGGAAGCCCGAAGTTTGAGGGAGAAACTTGTGAGGAAATAA |
| | 1 | MGANLTFKVPNK* | 8769 | ATGGGGGCAAATCTGACATTTAAAGTGTTTAACAATGA |
| hsa-mir-424 | 2 | MSAAGKFSGNGLGKKKQQLTWRGGERKLSKGQ* | 8771 | ATGAGTGCGCGCCGGAAATTCTCAGGAAACGGACTGGGAAAAAAAACAACT AACATGAGGGGCGGGAGGAGAAAACTGAGTAA |
| | 3 | MEGRGEKTE* | 8773 | ATGGAGCGGGGCGGGAGAAGACAAACTGAGTAA |
| | 4 | MNFSSYLQEVSYVLERNV* | 8775 | ATGAACTTTTCCTCTTATTGCAAGAGTTAGTTATGTCTTGAAAAGAAATGTGTGA |

Figure 1 (Continued)

| | | | | | |
|---|---|---|---|---|---|
| hsa-mir-425 | 1 | MGGF* | 8777 | ATGGGCGGTTCTGA | 8778 |
| | 2 | MWPQGE* | 8779 | ATGTGGCCCAGGGCGAGTGA | 8780 |
| | 3 | MGCP* | 8781 | ATGGGGTGCCCCTGA | 8782 |
| | 4 | MGVDVGEPRLVAISGTLGRGEGGWTQDLWVGLQW* | 8783 | ATGGGTGTAGACGTGGGAGAGCCGAGGCTGGTGGCCATCTCTGGAACCCTGGGGAG GATTGGCGAGGGAGAGGTGGACCCAGGACCTCTGGGTAGGGCTGCAATGGTAG | 8784 |
| hsa-mir-449b | 1 | MYLGDGTPGY* | 8785 | ATGGTCCTGGGGACAGGGACTCCAGGGGTTTGA | 8786 |
| | 2 | MEWKLERTAPRRVRTEEEMLWVSNTLFCILPNSLMRGR RPR3* | 8787 | ATGGAGTGGAAACTGGAGCGCACCGCGCCTCGGAGGGTCCGCACGGAAGAGGAGAT GCTGTGGGTGAGTAACACCCTTTCTGCATTCTGCCCTAACTCTCTAATGCGCGGCCG AAGGCCCCGTTCATAA | 8788 |
| | 3 | MIFLNSFSLNMLSVFSKESIMRVLSKDLKQKRSQDSANV SPGLVLVLCFNSDLEQTNSW* | 8789 | ATGATTTTCTAAATAGTTTCTCCCTCAATATGTTATCTGTGTTTCAAAGGAAAGTA TCATGCGTGTCCTCTCCAAGACTTGAAGGACGAAGAAGTCAAGATTCCGCCAAC GTGAGTCCAGGGCTTGTGTCTTGTTCTGTGTTTAATTCTGATCTTGAACAAACGAATT CTTGGTAA | 8790 |
| | 4 | MRILVSYYILKKISL* | 8791 | ATGAGAATTTTAGTATCTTATTACATACTAAAAAATTTCTTATGA | 8792 |
| hsa-mir-450a-1 | 1 | MGANLTFKVFNK* | 8793 | ATGGGGGCAAATCTGACATTTAAGTGTTTAACAAATGA | 8794 |
| | 2 | MSAAGKFSGNGLGKKKQQLTWRGGERKLSKGQ* | 8795 | ATGAGTGCGGCCCTGGGAACGGGCTGGGAAATTCTCAGGAAAACGACTGGGAAAAAACAACT AACATGGAGGGGCGGGAGGGAGAAAACTGAGTAAGGGCAGTGA | 8796 |
| | 3 | MEGRGEKTE* | 8797 | ATGGAGCGCGGGGAGAAAACTGAGTAA | 8798 |
| | 4 | MNFSSYLQEVSYVLERNV* | 8799 | ATGAACTTTTCCTCTTATTGCAAGAAGTTAGTTATGTCTTGAAAGAAATGTGTGA | 8800 |
| hsa-mir-450a-2 | 1 | MGANLTFKVFNK* | 8801 | ATGGGGGCAAATCTGACATTTAAGTGTTTAACAAATGA | 8802 |
| | 2 | MSAAGKFSGNGLGKKKQQLTWRGGERKLSKGQ* | 8803 | ATGAGTGCGGCCTGGGAATTCTCAAGGAAAACGGACTGGGAAAAAAACAACACT AACATGGAGGGGCGGGAGGGAGAAAACTGAGTAAGGGCAGTGA | 8804 |
| | 3 | MEGRGEKTE* | 8805 | ATGGAGGGGCGGGAGAAAACTGAGTAA | 8806 |
| | 4 | MNFSSYLQEVSYVLERNV* | 8807 | ATGAACTTTCCTCTTATTGCAAGAAGTTAGTATGTCTTGGAAAGAAATGTGTGA | 8808 |
| hsa-mir-484 | 1 | MLGTPGGAGPRGPAASSGSVPSR* | 8809 | ATGCTCGGAACCCCGGGGGAGCTGGCTTTTTTTTCTCTCGAGCCTCGTCAGGCTC AGTCCCCCGATAA | 8810 |
| | 2 | MKMPVPSAPPFSSLGSRHVMLLYF* | 8811 | ATGAAAATGCCTGTCCCTCAGCATCTAAATCTAGTGCAACCTAG | 8812 |
| | 3 | MAHRPQHPKSSAT* | 8813 | TGGTTCCCACTTTATTTTTAA | 8814 |
| | 4 | MNTAPPVTGWASRKEILRLVSNTLCFRWPDMLCGLL* | 8815 | ATGAATACTGCGTTTCAGTTGGGCGAGCAGAAAGGAAATCTTACGGTT AGTTTTCAAACACTTGTGTTTTAGGTGGCCAGATATGCTGTGTGGTTTGCTTTAA | 8816 |
| hsa-mir-497 | 1 | MRIRLGALPLASGWSH* | 8817 | ATGAGAATTAGATTATTGGCTCTCCCTTGCATCAGGATGGAGTATTATTGA | 8818 |
| | 2 | MEYYLISCGVSVYYGVLL* | 8819 | ATGGAGTATTATTACGTGTGTTGTGTCATGGGTATCAGTTTATTATGGGTGATTGA | 8820 |
| | 3 | MVSFRYGADLEVTLVLGVLTPTIWRLCSPVSSWTISRTK VLMLJWGCSLFWGAF* | 8821 | ATGGTAAGTTTCAGGTATGGACTGACTTGGAAAGTTACATTAGTTCTGGGGTTCTG ACACCCAATTGGAGATTGGTGTCTCACCTGTCATCTGGACTATCAGCAGAACC AAAGTACTCATGCTGATTGGGGGCTGCAGTCTATTTGGGGGTGCCATCTAA | 8822 |
| | 4 | MGLTWKLH* | 8823 | ATGGGGCTGACTGGAAGTTACATTAG | 8824 |
| hsa-mir-503 | 1 | MGANLTFKVFNK* | 8825 | ATGGGGGCAAATCTGACATTTAAGTGTTTAACAAATGA | 8826 |
| | 2 | MSAAGKFSGNGLGKKKQQLTWRGGERKLSKGQ* | 8827 | ATGAGTGCGGCCTGGGAATTCTCACGAAACTGACTGGGAAAAAAAACAACAACT AACATGGAGGGGCGGGAGAGAAAACTGAGTAAGGGCAGTGA | 8828 |
| | 3 | MEGRGEKTE* | 8829 | ATGGAGGGGCGGGAGAAAACTGAGTAA | 8830 |
| | 4 | MNFSSYLQEVSYVLERNV* | 8831 | ATGAACTTTTCCTCTTATTGCAAGAAGTTAGTTATGTCTTGAAAGAAATGTGTGA | 8832 |
| | 1 | MFRRSLNRFVSTLAAAPRVPVCLLASPFAGSLTTF* | 8833 | ATGTTCCGCCGAAGCTTGAATCGTTTGTGAAGTACACTGCTGCGGTCCGCGGTG CCGGTTGCTTGCTCGCCAGCCCTGCCGGGTCCCTCACACAATTTTCTGA | 8834 |

Figure 1 (Continued)

| | | | | | |
|---|---|---|---|---|---|
| hsa-mir-505 | 2 | MAFYSQGGGFLLPPLPRAHGGKPRPVTVAQKKSWGLRE PETRARLSLA* | 8835 | ATGGCGTTTTATTCTCAGGGAGGTGCTTCTTTTGTTCCTCCGCACGAGCACATG GAGGTAAAACCTAGACCTGTCACGGTGGCCCAAAAGAAGAGCTGGGGGCTGAGGGAG CCGGAGACTAGGCAAGACTCAGCCTTGCCTAG | 8836 |
| | 3 | MEVNLDLSRWPKRRAGG* | 8837 | ATGGAGGTAAACCTAGACCTCACGGTGGCCCAAAGAAGAGCTGGGGCTGA | 8838 |
| | 4 | MCSREEAAPPLPVLPISGLKPRGGLSTPDLEPMGEGGL* | 8839 | ATGTGCAGCCGCGAGGAGGCTGCGCCGCCACTGCCGGATCTCTGGCTG AAGCCTCGCGGAGACTGAGCACTCCAGAACCTTGAACCCATGGAGAAGGCCGACT GTGA | 8840 |
| hsa-mir-542 | 1 | MGANLTFKVFNK* | 8841 | ATGGCGGGCAAATCTGACATTTAAGTGTTAACAATGA | 8842 |
| | 2 | MSAAGKFSGMGLGKKKQQLTWRGGERKLSKGQ* | 8843 | ATGAGTGCGCCGGGAAATTCTCAGGAAACGGACTGGGAAAAAAAAACAACT AACATGGAGGGGCGGGGAGAGAGAAAACTGAGTAAGGGGCAGTGA | 8844 |
| | 3 | MEGRGEKTE* | 8845 | ATGGAGGGCGGGGAGAGAAAACTGAGTAA | 8846 |
| | 4 | MNFSSYLQEVSYVLERNV* | 8847 | ATGAACTTTTCTCTTATTGCAAGAAGTTAGTTATGTCTTGAAAGAAATGTGTGA | 8848 |
| hsa-mir-545 | 1 | MARGEVSCLCLAILG* | 8849 | ATGGCCAGGGAGGTAAGCTGTCTTGCTTGCCATCTGGCTAG | 8850 |
| | 2 | MLWPDPLEINPES* | 8851 | ATGCTGTGGCCAGATCCACTAGAAATTAACCAGAATCTTAG | 8852 |
| | 3 | MRRR* | 8853 | ATGAGGAGGCGATGA | 8854 |
| | 4 | MMTLQKVAAAGGA* | 8855 | ATGATGACTCTGCAAAGGTTGCGGCAGCTGGCGGTGCGTAG | 8856 |
| hsa-mir-548b | 1 | MSLDWACLSSWGRATSWGPAHTRTHVERVCKSTPVLL TEEGDYSIVFLGHLFFFTSGLTLAARGSPPGLGCWIPATRG KHWRHDPGSTSRGARTGRGAAGLAAAAARGWAGL GCGEMTSRSPRAPW* | 8857 | ATGTCTCTGGATTGGGCTTGCCTCTCTTCTTGGGAAGAGCCACTTCTTGGGCGCCT GCACACAGAGGACTGCATGTGGAAGAGGTCTGAAATGCACACCGTTCTGCTAAC CGAAGGTGATTACAGCAGCTTCTTGGGGATACTTTTTTTTACGTCAGGCCTC ACGCTCGCTCACGGGGATCTGGGCTGTGATCTCCGCCACACG AGCGGAAGCACTGGCGGCACGATCCGGATCTGACCTGGCGGCGAGGCGCCCACTGGCC GGGGGCTGCGGGACTGGCGGCGTCGTCCCGCGCCGCCCTGGTAA | 8858 |
| | 2 | MWKGSVNRHPFC* | 8859 | ATGTGGAAAGGTCTGTAAATGACACCGTTCTGCTAA | 8860 |
| | 3 | MSPPHAAARPVSSSLRSLAESSVRAASGTRGAALSSTFP PGAGRGIASKSWPGPRPPPMPGHLPRAVVPAASGRRDR PVPSRGDPGIVAGGTAPAAESGGRRVSGREAAAATLASR ASLLHGPASTRGDRCPGWGLLGRWRPPA* | 8861 | ATGTCTCCTCCTCGGCTATCCCGCGCTGCCAGGCCGTCTCGCCGAGCCTCG CCGAGTCCTCGCTCCGCCAGTCCGCGCTGCGAGGCCGGCGACCCGGAGCGGTGCCGCTCGCTCGACG CCTCCGCCAACCGCGCGGCATCTGCCCGCCGGTTGTCCGCGGCTTCGGCCGGCG GAGCCGCGTCGCTCCCTCCAGGGTGACCCGGAGCCGCGGGGGTCGGGTCAGGAACGCGCCTG GCGTCGAGTCTGCGGCGGCGTCGGGTGCCGGTCGGAAGCGCGCGCGGACTCTT GCTCCCGCGGCCGTCGTTGTTGGGAAGATGGCGACCACCCGGCATGA | 8862 |
| | 4 | MATPGMSWQQHYYGGSAAKFAPSPATAQLAGHSMDY SQEMHLKMSKKIAQLTKVRGAATGVATPCGPRRTHL SPREAVRPAPAARGTLLLRRSNSRRHLQNPANFGGTLA T* | 8863 | ATGGCGACCCCGGCATGAGCTGGCAGCAGCACTATTACGGCGGCTCGCGCCAA ATTCGGCCTCGCCGACCTGAAATGCACCTGCTGGGCACGAGCTGACTACAGCC AGGAGATGCACCTGAAAATGAGCAAGAAAATCGCCCAGCTCACCAAGGTAAGGGGG GCAGCGACGGGCAGTCGGCGACCCGTGCGGCCGCCGGGAACTCACCTGTCTC CGGGAGGCAGCGCCCGTGCGCCGCAAACCCGTCCAGGGAACTCTACTCTCCGCCGAA GCAACAGCCGGAGACACCTCCAAAACCTTGGTGAACGCTGGCAACA TGA | 8864 |
| hsa-mir-548c | 1 | MVKRQ* | 8865 | ATGGTGAAAAGACAGTAG | 8866 |
| | 2 | MINACKGASILLYDKSWLT* | 8867 | ATGATAAATGCAAAGGCTTCTTCTATATGACAAGTTGGCTAACTTAG | 8868 |
| | 3 | MHAKELLFYMTSLG* | 8869 | ATGCATGCAAAGGAGCTTCTCTTCTATATGA | 8870 |
| | 4 | MQRSFSSI* | 8871 | ATGCAAAGGAGCTTCTCTATATGA | 8872 |
| | 1 | MPSS* | 8873 | ATGCCATCATCTTAG | 8874 |
| | 2 | MVKNPVGWMQWLMPHPTLWEAEVGGLLEPKSLRPA* | 8875 | ATGGTGAAGAATCCCGTGGGCTGGATGCAGTGGCTCATGCCTATAATCCCAACACTT TGGGAGGCTGAAGGTAGGAGGACTGCTTGAGCCCAAGAGTTTGAGACCAGCCTGA | 8876 |

| | | | | |
|---|---|---|---|---|
| | 3 | MCPWVWGGWGAKEWDERWSRNGGRCCPPRGLQAET G* | 8909 | ATGTGCCCTGGGTTTGGGGAGGGTGGGGAGCCAAGGAGTGGGATGGAGAGGTGGTC ACGGAATGGGGCGGCTGCTGTCCTCCCCGGGGCTGCAGGCCGAGACCGGGTGA | 8910 |
| hsa-mir-564 | 4 | MRGGHGMGGAAVLPGGCRPRPGEGRG* | 8911 | ATGAGAGGTGTCACGGAATGGGGCGGGGCGCTGCTGTCCTCCCCGGGGCTGCAGGCC GAGACCGGGTGAGCGCGCGGGGGTGA | 8912 |
| | 1 | MDSVGRRGAR* | 8913 | ATGGACTCGGTGGGCCGGCGCGGCCGTTAG | 8914 |
| | 2 | METAKPREVYLLPQRPQYPAWPQASGPDVLPRAQIYY RLGRRPPQPRVSATWPAPSEAPESDSQGACRSVASQER RVT* | 8915 | ATGGAGACGGCTAAGCCGCGAGAAGTTACCTTCTACCACAGCGTCCACAGTACCG GCTTCGCCTCAGGCTCCGGGTCCGACGTCCTGCCACGTCCAGAGCACAAACCTACTACAGG TTAGGCCGGAGGCGCCACAGCCAGGGTCTGCCACCTGGCCGCCCCCCTCCGAG GCGCCGGAGAGCGATTCCAAGGGGCGTGGCGTCACAGGAGGGTCG CGTCACGTGA | 8916 |
| | 3 | MAERPGPPGGAVSATAYPDTPAEFPPHLQAGAMRRF WGVPNCLCAGAPGALAAASAKLAFGSEVEPCGALLVLLL RAGGRGAAGRRRGAAGPAGLLGWGGGRRAPPHPRRS VPPGRPRAAGGAAVSWGGRECFASNHAKPSSSVGGKRR RGLRPLPLPGT* | 8917 | ATGGCCGAGAGGCCGGGCTCCGGGAGGCTCCGCACCTCAGGCGGTGCGATGCGGCGCCTTG CACCCCGCGGGCGAATTCCTCCCACACTCAGGGCGGCTCCGATGCGGCGCCGCCTTG GGGCGTATTCACTCAGGCTGCGGCCCTTGCCCGCCCCTCCGCCCGCCCGC CAAGCTGCCTTGGCAGCGAGTCGAGCCCTGCCCCTCCCGCGCC GGGCGCGGCGGCGGCGCGGCGCCGCGAGGGACGCGCGCGGGGCCCGCGGG GCTCTTGCGGGCTGGGCCGGGCCCCGCGGGCCCGGGCGCACCCCTGCGCGCTCG TGTTCGCTCTAATCACGCAAACCTGCGCAGTGAGTGGTAGGTTAAGAGACGTCGG GGACTGAGGCCTCTGCCCACTACCAGGAGACCCTAA | 8918 |
| | 4 | MTSLPHYQENWFPGIL* | 8919 | ATGACCAGTCTGCCGCACTACCAGGAGAATTGGAGTTTGGGATACGTAG | 8920 |
| | 1 | MPPTRRVGVRRRAP* | 8921 | ATGCCGCCGACCGCGGCGGTTGGAGTTGCGACGAGCGCCGTGA | 8922 |
| hsa-mir-565 | 2 | MDRWYPEARSNCIRVISYHGEGFSKSGPVAQWITRLTT DQKILGSTPGWLAMSVLPHLIHVLLGLVKMYIHNVKV LQDLGKYYG* | 8923 | ATGGATCGTTGGTACCCCGAAGCCGTTCAAACTGTAAGGTTGATCAGCTATTAC GGAGAAGGCTTTAGCAAGTCTACTAGTTCGACTCCTGGTGATAACCGTCTGACTAC GGATCAGAAGATTCTAGGTTGCAGCACTTCGGGTCTTGACTCCTGGCTCGATGTCGTTTGCCACA CTTGACCCATGTGGCTTAGGTTCGGGTCTTGTAAAGATGTATATTCACAATGTGAAAGTATT ACAAGACCTTGGAAAGGTGTATGGTTAG | 8924 |
| | 3 | MDNASDYGGSEDSRFDSWLARDVCFATLDPCTTGSCKD VYSQCESTRRPWKGVWLECES* | 8925 | ATGGATAACGCGTCTGACTACGGATCAGAAGATTCTAGGTTCGACTCCTGGCT CGGATGTCTGTTTGCCACACTTGACCCATGTACTACTGGGTCTTGTAAAGATGTA TATTCACAATGTGAAAGTGAGACTAGAAGACCTTGGAAAGGTGTATGGTTAGAATGTGAA AGTTAA | 8926 |
| | 4 | MYYWVL* | 8927 | ATGTACTACTGGGTCTTGTAA | 8928 |
| | 1 | MAPGGR* | 8929 | ATGGCCCCGGGGGCCGCTAG | 8930 |
| hsa-mir-566 | 2 | MDVWMMWPAGSPMCKATFSCKVLGGCSHTPPPSRFW SGSSDPPSASALSPINARGSALPRRCACPTSVSLLEDWPA RREAVYWQSPRGGSPTSAEWEDLQS* | 8931 | ATGGATGTGTGGATGATGTGGCCTGCGGGTCACCATGTGCAAAGCAACTTTTTCC TGCAAGGTTCTGGGATGCCCTTGCCTGCCTACGTTCATACACCGCACCACTTCTCGAGCGG AGTTCCCGTAGAGATGGGCCTTGCCTGCCTACTTCAGCTCTCTCGCCATTAACGCCAGGCAGCGCTC TTCCCCGTAGATGCCGCCTACTTGGCAGGTCTCTACTTGAGGACTGGCCAGCC GAAGGAAGCGTATACTTGGCAGTGGGGGTCTCCCACATCAGCAGAG TGGGAGGACCCTCCAGTCCTGA | 8932 |
| | 3 | MRLPYLSVST* | 8933 | ATGCGCTTGCCCTACCTCAGTGTCTCTACTTGA | 8934 |
| | 4 | MGQEGIKVGLGMRQCWRELACAGAGAGGPTG* | 8935 | ATGGGACAGGAGGGTATCAAAGTTGGCTAGGAATGAGGCAGTGCTGGCGGAGTT GGCTGGAGCTGGGGGTGGGGGCCCCACTGGATAA | 8936 |
| | 1 | MTTKFCTSFPEAPDRLAWSIYYWTYS* | 8937 | ATGACTACTATCAAATTCTGTACTTCATTTCCAGAGGCTCCTGACAGACTTGCTTGGTCA ATATACTACTGGACATATTCATGA | 8938 |

Figure 1 (Continued)

| | | | | | |
|---|---|---|---|---|---|
| hsa-mir-570 | 2 | MRLSHTGHSNPVCPTLFLSMPVPLPLPHMSVTVHLLSLS PSPFGS* | 8939 | ATGAGACTGTCTCACACAGGCATCTGAACCCAGTGTCCACAATTCTCTCCTA TCCATGCCTCTTCCTCCTCCACTGCCTCATATGTCGGGTGACTGTCCACCTTCTCTCTC TCTCCCCCTCTCCGTTTGCTCATAG | 8940 |
| | 3 | MAITLLQINIFNHWNDGNNLIGFILSSI* | 8941 | ATGGCCATTACCCTATTACAGATCAACATCTTCAATCACTGGAATGATGGCAATAAT CTAAATTGGGTTCATTTTATCCTCTATCTAA | 8942 |
| | 4 | MMAII* | 8943 | ATGATGGCAATAATCTAA | 8944 |
| | 1 | MIGS* | 8945 | ATGATTGGTAGCTAA | 8946 |
| | 2 | MVSVRGRASQG* | 8947 | ATGGTGAGTGTGCGTGGCAGGGCGTCCAAGGCTGA | 8948 |
| hsa-mir-571 | 3 | MAAGPSLRTESPLPPLSPGASVPSGEGPGLLSVPAQRLW PSLQPSLCSSAPAAPHLPQAVG* | 8949 | ATGGCGGCAGGACCGAGTCTGCAACGGAGTCCCGCTCCGCCCCTCAGTCCTGG GGCTCAGTACCCTCCGGTGGAGGGACCTGGGCTCCTGTCGGTCCCCGCACAGGCGCT CTGGCCCCAGCCTGCAGCCTCCTTGTGCAGCTCTGGCACCCGCAGCCCCGCACCTTCC CCAGGCTGTGGGGTGA | 8950 |
| | 4 | MPAWEELWEKLWSGDPVPALPCSE* | 8951 | ATGCCGGCCTGGGAGGAGCTGTGGGAGAAGCTGTGGTCTGGGGATCCGGTCCCTGC TTTACCCTGTTCGGAATGA | 8952 |
| hsa-mir-574 | 1 | MHPTPRPHSGSAPSACVNLRGACLDLPKYPVLAPSKSG KVPPMARGQVRGGLQGPPARARREQVPVRQRPRPRVR LPSALAQGAQALTSPLPSPYSSPNSRPTPCLLFQSSQHSK QAPPPLAAPGMGPTPYRRSPGPLRPVG* | 8953 | ATGCACACACCACACGCCACACTCAGGGTCGCCCCTCGCCTGCGTAACCTC CGGTGGAGCCTGCCTGGATCTCCAAAGTATCCAGTCCTGGCACCAAGCAAGTCTGGA AAAGTGCCCCAATGCTCGGGCGACAAGTGCAGGGCCCTCCAGGGTGGCGCC CCGGGCCACGAGGAGCAGGTCCTGTAAGACACAGAGAGCCTCGCAGGGTGCGCC TGCCCTCGCCCTTGGCACAGGAGCTCAGGCCCAGCCCAGCTCAGCCTCTGACCTCCGCCTT ACTCTCCCCCACAGCCTGCCCTCGACCCAGCCCACTCGCAGCTCCAGTCCAGCCAACACT CTAAGCAGGCACCGCCTCCACTCGCAGCCCCCGGGATGGGTCCCACTCCCTACCGCA GATCCCAGCCCCTCCACCCAGTGCGGCTAG | 8954 |
| | 2 | MGGCIESHTYALLIPSFPILMRKDTGRWLLKSVCSELPVTS AML* | 8955 | ATGGGCTGTGAGAGCATTACCTATGCCTCATCATGCCTACTGATCCATCATTCCCATCTAAAC ATCTTTGAAGGACACAGGCAGGTGGCTTCTAAATCAGTGTGCTCTGAACTCCCTGTG ACCTCAGCGCCGCTAG | 8956 |
| | 3 | MRQALSSEPLFALSAA* | 8957 | ATGAGACAGGCTCTATCCTCAGAGCCTCTGTTTTGCCTCTCTGCAGCTAG | 8958 |
| | 4 | MDLRHK* | 8959 | ATGGATTTGAGGCACAAGTGA | 8960 |
| | 1 | MSAAGL* | 8961 | ATGTCAGCGCTGGACTGTAG | 8962 |
| | 2 | MPLQP* | 8963 | ATGCCCTTGCAGCCTTGA | 8964 |
| hsa-mir-580 | 3 | MGINERTVFCNELVPCTQGASSKAIWLLAVAQLATCVC VAA* | 8965 | ATGGGAATAAATGAAAGGACTGTATTTTGCAACGAGCTTACCCGTGCACGCAGG GGCCTCCAGCAAAGCCATTTGGTTGCTTGCTGCAGCTTACCGTGCACGCAGGGGCCTCCAGCA CGTCGCGCCTAA | 8966 |
| | 4 | MKGLYFATSFTRARRGPPAKPFGCLLSLSWLRVFASPPK SELLSAYLC* | 8967 | ATGAAAGGACTGTATTTTGCCAACGAGCTTACCCGTGCACGCAGGGGCCTCCAGCA AAGCCATTTGGTTTGCTGTCTGCCTCAGCTGGCTACGTGTTGCGTGCGCT AAAAGCGAGCTGCTTTCAGCCTTCAGCTGCTGA | 8968 |
| | 1 | MASSGEVLSATVSALLPRRPRSPWVLPSRPGFPCILSIP TPTPRPSHPDPGLAPAPVLPASCPQDSYPVSEGTSCLPL RSCIPDRQSCPRLSVP* | 8969 | ATGGCCAGCTCGGGAGAAGTCCTGTCTCCGGCGACTGTCTCCGCTCTCTTGCCTCGG CGGCCCGACCCGGAGCCCGCGCCCCCGCGTCCCCATCCGACCCGGGTTCCCTTGCCATCCTTCTA TCCCACCCCTCCCCACCCCGTCCCAAGACTCCTACCCTGTCGGAAGGCACAAGCTG TCCTCCTGCCCCCTCGCGTCGCATTCGCTGATCGCCAGAGTTGTCCGTCTCTCGGTCCCG TGA | 8970 |
| hsa-mir-589 | 2 | MLSPSPSPLLPGACLLNDVGGG* | 8971 | ATGCTCAGTTCAGCCCCAGCCCTCCGTGGACCCCTGA | 8972 |
| | 3 | MTWGVGDGGKAISPEGLTTYPGILSQHSPNLGPMERKPA ASL* | 8973 | ATGACGTGGGGTGTGGGTGATGGAGGAAAAGCCATTTCACTGAGGACTTACGAC GTACCCTGGAATTCTTTCCCAACACTCCCAAATCTGGGTCCGATGGAGAAGCCCGGC CGGGTCCCTGTAA | 8974 |

Figure 1 (Continued)

| | | | | |
|---|---|---|---|---|
| hsa-mir-590 | 4 | MEEKPFHLRDLRRTLEFFPNTPQIWVRWRSPPRPCNVV QSIVSAERGAAGTLDSD* | 8975 | ATGGAGGAAAAGCCATTTCACCTGAGGGACTTACGACGTACCCTGGAATTCTTTCCC AACACTCCCAAATCTGGGTCCGATGGAGAAGCCGCGCCGCCCTGTAATGTGGTG CAAAGTATGTCTGCAGACTCTAGAGTCTGACTCTGA | 8976 |
| | 1 | MADFDTYDDRAYSSFGGGRG* | 8977 | ATGGCGGACTTCGACACTTACGACGATCGGGCCTACAGCAGCTTCGGCGGCGGCAG AGGGTGA | 8978 |
| | 2 | MARSETGRRRLGSRGLACGADPFHCLPPTTTCWFLPCL GRGGADARRRAPASSPFPPTVGPVRG* | 8979 | ATGGCGCGCTCGGAGACGGGGCGCCGGCTCGGCAAGCGTGTTGGTTTTTGCCCTGCCTT GGCCGCGGGACGCCCGGATRCTCGGAGACGAGCGTCCGCTTCCAGCCCATCCCCC TACGGTAGGACCAGTGCGGGRCTGA | 8980 |
| | 3 | MPGDIERPLPAPSPLR* | 8981 | ATGCCCGGAGACGAGCGCCCGCTTCCAGCCCATCCCCCTACGGTAG | 8982 |
| | 4 | MVRLLAGGGRPRR* | 8983 | ATGGTACGACTCCTTGCCGGCGGCGGRAGACCAAGGAGATAA | 8984 |
| hsa-mir-594 | 1 | MWTFVL* | 8985 | ATGTGGACTTTTGTTCTCTAA | 8986 |
| | 2 | MTYQRGK* | 8987 | ATGACGTACCAAAGAGGAAAATAG | 8988 |
| | 3 | MLCERVVCRSPSGLMDKALAS* | 8989 | ATGTTGTGTGAGCGCGTCGTTTGCAGAAGCCCAGTGCCTAATGGATAAGGCATTG GCCTCCTAA | 8990 |
| | 4 | MPTLLFFFLNGKCVCVFTSWWAAIPENLHTPMSFV* | 8991 | ATGCCAACTTTACTTTTTTTTCGAGAATGGAAGTGTGTGTTTTACTAGCT GGTGGGCTGCAATTTCGAGAATCTGCACACCATGTCCTTTGTCGA | 8992 |
| | 1 | MRASDPASPHGERGACGWPHFQQAAAWLVTSCPFHPVVS EHEJFHRSELCGYNFFSTRFHSVTQAGMQEYDHSSLQP* | 8993 | ATGAGAGCCAGCGACCCTGCACCCCATCGGTGACCCGTTCGACCCAGTGGTATC CATTTTCCAGCCAGGCTGCCTGCCAGAAGTGAATTGTGTGGATATAATTTTTAGCACAAG AGAACATGAGATATTCCACAGAAGCTGAATGCAGGAGTATGATCATAGCTCGCTGCAGCC GTTCACTCTGTCACACAGGCTGGAATGCAGGAGTATGATCATAGCTCGCTGCAGCC TTAA | 8994 |
| | 2 | MRYSTEVNCVDIIFLAQGFTLSHRLECRSMIIARCSLNS WAQAQGFSRPSLLSCWDYRLTPPHQANPFF* | 8995 | ATGAGATATTCCACAGAAGTGAATTGTGTGGATATAATTTTTAGCACAAGGTTTC ACTCTGTCACACAGGCTGGAATGCAGGAGTATGATCATAGCTCGCTGCAGCCTTAAC TCCTGGGCTCAAGTCAAGGGTTCCTCCCGCAGCCTCTGAGTTGCTGGGACTAC AGGCTTACACCACCACACGCCAGGCTAATTTTATTTTTATTTTTTAG | 8996 |
| | 3 | MYLFFVYFYFYF* | 8997 | ATGTATTTGTTTTTGTTTATTTTTTAG | 8998 |
| | 4 | MSACHHAWLLNRFAKASSNMYVISAPPHGSGLPCHSS MK* | 8999 | ATGAGCGCGGTGCCACCATGCCTGGCTATTAAATAGATTTGCTAAAAACAGCAACAAC ATGTATGTCATCTCGCCCCGGATCTGGCTTCCATGTCACCACGCAGTATG AAATGA | 9000 |
| hsa-mir-604 | 1 | MNFSVETAPPQSLFKKQK* | 9001 | ATGAACTTCTCCGTCGAAAACTGCCTCTCCCAGAGCCTGTTTAAGAAGCAGAAATAA | 9002 |
| | 2 | MPVDALTSKIFKGEVDTRY* | 9003 | ATGCCGGTGGATGCACTGACCTCAAAGTGAAGTGGATACACGTTAT TAA | 9004 |
| | 3 | MSKPLGHESP* | 9005 | ATGAGCAAGCCTCTTGGAATAATTGAATCACCTTAA | 9006 |
| | 4 | MGNERRKGKEMGWKEKSRRDRPIPVGLVP* | 9007 | ATGGGAAACGAAGGAGAAAGGGAAAGAAATGGGTTGGAAAGAAAAAGCAGAA GAGATCGCCCTATACCAGTAGGCTAGTACCCTAG | 9008 |
| hsa-mir-607 | 1 | MAQGRERDEGPHSAGGASLSVRCGVHGPATDLGLAEP PAPSPLLPPLPPVP* | 9009 | ATGGCGCAAGGTGCGGGAGTGCCGGGTTCAGGGCGCCAGCCGATCGGGTCTCGGGAACCTCC TGCCCAAGTGCCCTCCTCCCTCTCCTCCCCTGGTTCCTAG | 9010 |
| | 2 | MSRGPSPNQCPSLAFSTFKHTFNI* | 9011 | ATGTCTCGAGGTTCTCACCAAACCAGTGTCCTTTCCACCATCTTCA AGCATACCTTTAAATATTTAA | 9012 |
| | 3 | MFFLCASLSFTSTSFLLFSTFPICIFKSKIWPHTLHLCK* | 9013 | ATGTTTCTTTTGTGTGCTAGCCTTTCATTCACGTCGACTTCATTCCTTTATTTCTAC GTTTATCTGTATTTAAATCTAAAATGGCCACATACTCTTCATCGTGTAAATAA | 9014 |
| hsa-mir-609 | 4 | MATYSSSV* | 9015 | ATGGCCACATACTCTTCATCGTGTAA | 9016 |

Figure 1 (Continued)

| | | | | |
|---|---|---|---|---|
| hsa-mir-611 | 1 | MVRALRGVPDGDAKTPRGLTHTALISSDAGDPEG* | 9017 | ATGGTTGAGAGCGGTTGAGGGAGGAGTTCCAGACGGAGATGCGAGGACCCCTCGGGGTCTGACCCACACGGCGCTTATCTCCTCGGGGTCTGA | 9018 |
| | 2 | MRGPLGV* | 9019 | ATGCGAGGACCCCTCGGGGTCTGA | 9020 |
| | 3 | MNSLGPSARDF* | 9021 | ATGAACTCCTTAGGTTCTCAGCTCGCGATTCTAA | 9022 |
| | 4 | MPWANYYW* | 9023 | ATGCCCTGGGCAAATGTTATTGGTGA | 9024 |
| hsa-mir-612 | 1 | MRVKKGRGLVRDTVWVGVGVGNAG* | 9025 | ATGAGGGTGAAGAAGGGGAGAGGGTTGGTTAGAGATACAGTGTGGTGGTGGGGTGGTAGGAAATGCAGGTTGA | 9026 |
| | 2 | MQVEGNSLGLWGI* | 9027 | ATGCAGGTTGAAGGAAATTCTCGGGCTTTGGGAATTTGA | 9028 |
| | 3 | MPSHRQGKCLYQLPPGGQDSLFQRVVLFGVWVLSSELVT* | 9029 | ATGCCATTCACAGGCAGGGAAATGTCTTTACCAGCTTCCTCTGTTGCCAAGACAGCCTGTTTCAGAGGGTTGTTTTGGGGTGTGGGTGTATCAAGTGAATTAGTCACTTGA | 9030 |
| | 4 | MSLPASSWWPRQPVSEGCFVWGVGVIK* | 9031 | ATGTCTTTACCAGCTTCCTCTGTGGCCAAGACAGCCTGTTTCAGAGGGTTGTTTGTTTGGGGTGTGGGTGTATCAAGTGA | 9032 |
| hsa-mir-613 | 1 | MMSELYNTMKKIKTSN* | 9033 | ATGATGTCGGAACTATACAACACCATGAAAAAATTAAGACAAGCAACTGA | 9034 |
| | 2 | MLYT* | 9035 | ATGTTATATACATAA | 9036 |
| | 3 | MPVIPALLEAKAGGSLEPRSSRPAWAT* | 9037 | ATGCCTGTCATCCCAGCACTTTTGGAAGCCAAGGCAGGGATCACTTGAGCCTAGG | 9038 |
| | 4 | MTKPPLYK* | 9039 | ATGACGAAACCCCTCTTTACAAAATGA | 9040 |
| hsa-mir-615 | 1 | MSSYVANSFYKQSPNIPAYNMQTECGNYGSASEVQASRYCYGGLDLSITPPPAPSNSLHGVDMAANPRAHPDRPACSAAAAPGHAPGRDEAAPLNPGMYSQKAARPALEERAKSSGEIKEEQAQTGQPAGLSQPPAPPQJYPWMTIKLHMSHGKL* | 9041 | ATGAGCTCCTACGTAGCAATTCATTCTATAAGCAGAGCCCAATATCCTGCTATAACATGCAAACTTGTGGAACTATGGACATGGCTGCAGCATCCAAGTACTGCTACGGCGGATTGGAACTATGGACTTCCCACCCCGGCTCTCACCCGACCGCCCCGCCTGTCTCCAACGGCGGGTAGACATGGCCTAACATCACTTCCCACCCCGGCTCTCACCGCCCGCCTTCCAACTCCAGCGCCGCGGCCGCTCCGGACACGCTCCGGCACGGGACACGGGCTCTCGAACGCCGGATGTACAGTCAGGAGGAGGCGGCTCCGCCGGCTGGAGGACGGAGCTAAGAGCAGTGGGAGGAGTCAAAGAGGAGCAGGGCAACAGGGCAGCCTCCCCGACTGAGCCAGCCACCGGCCCGGCCACCAGATTTACCGTGGATGACCAACTGCACATGAGCCACGGTAAACTTTAG | 9042 |
| | 2 | MDRPQRCRHPGTATADWT* | 9043 | ATGGATCGGCCTCAGAGGTGCAGCATCCAGGTACTGCTACGGCCGATTGGACTTAA | 9044 |
| | 3 | MRGK* | 9045 | ATGCGCGGGCAAATAA | 9046 |
| | 4 | MARKTVH* | 9047 | ATGGCTCGTAAAACTGTCCACTAA | 9048 |
| hsa-mir-616 | 1 | MLKMSGWQRQSQNQSWNLRREASTDSHLPFTLPSPQSWGVRSLGSASLLHSEYRDRPREEWGESLJLGWCLQTPIASDDGVSPPLPGAGTRALLCAAGQRDLGCPWEJHSFP* | 9049 | ATGTTAAAGATGAGCGGGTGGCAGCGACAGAGCCAAAATCAGAGCTGGAACCTGAGGAGAGAGGCGAGTACTGACTCTTTAGGATCGGCCTCTTCCTCAAAGTTGGGGCGTCCGCTCTTTAGGATCGGCCTCTTCCTCACAGTGAAGTTAGGGACCGTCCGAGAGGAGAATGCGGAGGAGTCCCTTATTCTGGGGTTGGTGCTTACAAACCCTATTGCTTCGGACGACGGCGTCTCTCACCCGGTCCGGAGCGGGAACACGGGCCCTGCTCTGTGCTGCTGGGCAAAGGGACCTCGGTTGCCCTTGGGAATTCATTCTTTCCGGTAG | 9050 |
| | 2 | MGRVPYSGVVLTNPYCFGRRRLSTPARSRNTGPALCCWAKGPRLPLGNSFFPVANPRPHR* | 9051 | ATGGGGGAGGTCCTCCACCGTCCCTATTCTGGGGTGGTGCTTACAAACCCTATTGCTTCGGACGACGACGGCGTCTCCACCGGCTCCGGAGCCGGAACACGGGCCCTGCTGTTGTGCTGCTGGGCAAAGGGACCTCGGTTGCCCTTGGGAATTCATTCTTTCCGGTTGCCAACCGCCCCATCGTTAG | 9052 |
| | 3 | MATLVAGATGPCSG* | 9053 | ATGGCCACTTGGTAGCTGGGGCTACTGGACCTGCAGCAGGCGATAG | 9054 |
| | 4 | MDREWCVFLLP* | 9055 | ATGGACAGGGAGGGTGTTTTCCTTTGCCGTAG | 9056 |

Figure 1 (Continued)

| | | Protein | SEQ ID | Nucleotide | SEQ ID |
|---|---|---|---|---|---|
| hsa-mir-619 | 1 | MALVTLQRSPTPSAASSSASNSEVSPGLAAPGLGRRTPRRGRRSWGRACGAGGRLRGLLGAPP* | 9057 | ATGGCCCTGGTGACCCTGCAGCGCTCGCCACGCGCCAGCCCTCCTCCTCGGCCAGCAACAGCGAGGTGAGCCCCGGACTCGCCGCCCCCGGCCTGGGTCGCCGGAGGACGCCGGCCCGAGCCTGAGCCTGAGGGCCGAGCTGGGGCCGCCGCCGTGCGGGGACAGGGGCCGCTGCGGGCTCCTCGGGGCTCCCCGGCCGTAG | 9058 |
| | 2 | MQCDPSGSVCRILCVRCDPHQGVTPILG* | 9059 | ATGCAGTGCGACCCCTCTGGGAGTGTCTGCAGGATACTGTGTGCGCTGTGACCCACATCAGGGGGTTACCCCCATCTGGGGTGA | 9060 |
| | 3 | MCNWDP* | 9061 | ATGTGCAACTGGGACCTTGA | 9062 |
| | 4 | MPGCAM* | 9063 | ATGCCTGGCTGTGCGATGTGA | 9064 |
| hsa-mir-623 | 1 | MAATSSRLLVPPTQGGLRHVTLPFLAPPPTAVLDGRRSGERGRRPFCVCFLWDVVVAVGLGK* | 9065 | ATGGCTGCCACTCTTCTGCGCTCTTAGTCCACCACTCAGGGCGGGAGGTCTGCGTCATGTGACCCCTGCCCCTTCGGCTCCTGCCCCTCCTATCGCAGTGCTTGACGGAGGCGGAGCGGGAACGAGGCGTCGGCCCATTTTGTGTCTGCTTGTCTGGGACGTGGTGGTAGCCGTTGGGTTGGGAAGTGA | 9066 |
| | 2 | MGRKKKKQLKPWCWYPLSV* | 9067 | ATGGGTCGCAAGAAGAAGAAGCAGCTGAAGCCGTGGTGCTGGTATCCTTTGTCGGTTGA | 9068 |
| | 3 | MGFRGRQAFAVVGRVTL* | 9069 | ATGGGGTTCCGAGGTCGACAGGCTTTCGCAGTTGTGGGTCGTGTGACTCTGTGA | 9070 |
| | 4 | MEGWGQLHSLSPTFSVPIYFMCVLCLFFRIGGLVKNQVSQPWFRTFFFFFSGREEN* | 9071 | ATGGAGGGTTGGGGACAAGCTTCACAGTCTGTCACCACTTTTCGTTTTATTTACTTTATGTGTGTTTTATTTTACGAATTGGCGGTTTAGTAAGAACCAAGTTAGTCAACCCTGGTTTGAACCTTTTTTTTTTTTTTTCTTTTCGGGGCGGGAGGAGAACTAG | 9072 |
| | 1 | MEEGL* | 9073 | ATGGAGGAGGGATTGTAA | 9074 |
| | 2 | MAAAGSSLL* | 9075 | ATGGCGGCAGCGGCAGCTCCTCCTGCTCTGA | 9076 |
| hsa-mir-624 | 3 | MDELAGGGGGPGMAAPPRQQQGPGGGNLGLSPGGNGAAGGGGPPASEGAGPAAGPELSRPQQYTIPGLHYIQHEWARFEMERAHWEVERAELQVPRWGRCAGAAAAGFPAGGWGWGLHSAGAGALGGRAEPTCAAQVVMVLSTAFPGVPLPLSRISLLPNLHWLRGAGLLGAAHLAFSMASAGAPPEAAFPGLRGLGPSTSLWESPVWGLSTLSLLLFVPLEMKSPKRGTRIGILPPFSGPPPFFIWRIWPPFSDLVRACPLTATLLSWAARVHSDLGLTCEVLFPVNFKYFLT* | 9077 | ATGGACGAGCTTGCCGGAGGCGGTGGTGCGGGCCGGCCCCTCCCGGCAGCAGCAGGGCGCCCGGGAACCTGGCGTTCGCCGGGGGAACGGAGCGGCGGCGGCGGCGGCGGCTCCTCCGGAGGAGCGGGCTCACTGCACTCCAGCACGAGCTGTCCCGGCCAGCAGTACAGCTATCCGGGAGATACTGCACTAATCCAGCAGGAGTGGGCTCGGTTCGAGAGAGCGCATTGGGAAGTGGAGCGCGAGCTGCAGGTGCCACGGTGGGCGCTGCGGAGCGCCACTGAGGTAAGCGCGAGGTTCCGGCGGGAGGTACCTCGTTGGGGTCGGTGGGACTTCAGCATCAGCGGAGCCCACTCAGTCGCAGCGGCCTTGGAGGCCGAGCGGAGGACCTACCCTGTGCTTCCCGCATAAGCTTGCTCCCAACTTGCACTGGCTACGCGGTGCGGGCCTCCTCCGGAGCTCCCGGGGCAGCCATTTGGCTTTAGTATGGCGTCTGCTTTGTTCCTCTTGAGATGAAGAGCCCGAAGAGAGGGACTAGGATCGGAGATCCGTTGGGGCCTCCAACCTACAGTTGCTTCTCCTTGAGATGAAGAGCCCGAAGAGAGGGACTAGGATAGGCACTCCCCCCTTTCCGATTTGGCGTATCGGGAAGGCTCTTGCCCATTGGGCAGCTTCTGGGGAGCCCGAGACCACTCCCTTTCCCGACTGTCTGGGAGACCACTCCTTGCCTGACAGCCACCGCTCTTCCCATCGTCAACTTAAGTACTTCTCACCTGA | 9078 |
| | 4 | MLPYSLGFSVVIPYLVTHQRFQH* | 9079 | ATGCTGCCTTACTCACTGGGATTCTCTGTAGTTATTCCTTACTTAGTGACTCATCAAC | 9080 |
| | 1 | MAVLLKGL* | 9081 | ATGGCTGTGTTGTTGAAGGGCCTGTAG | 9082 |

Figure 1 (Continued)

| | | | | |
|---|---|---|---|---|
| hsa-mir-627 | 2 | MHDAFEPVPILEKLPLQJDCLAAWGEPRGRGAEAESAQ ERSGSFLRPGKWTGYHPCGLRLDATREGLRMREGREM TTGYRHRCLWGYLGDPSDPVI* | 9083 | ATGCACGACGCTTTCGAGCCAGTICGCGATCCTAGAAAAGCTGCCTCTGCAAATCGAC TGTCTCGGCTGCCTCGGCGTGAGCCGAGGGCCGCGGGGCTGAGGCGGAGTCAGCACA GGAGCGGTCCGGATCTTTCTGAGGCCGGGAAGTGGACAGGCGTCCATCCGTGTG GGCTTCGGTTGGATGCTACGAGAGGGGCTTAGGATGAGGAAGGCAGAGATGG ACCACCGGCTATAGACATCGATTCTGTGGGCTACTTGGTGATCCCAGTGATCCA GTCATTTAG | 9084 |
| | 3 | MLHERGLG* | 9085 | ATGCTACAACGAGAGGGGCTTAGGATGA | 9086 |
| | 4 | MSVGLLG* | 9087 | ATGTCTGTGGGGCTACTTGGGTGA | 9088 |
| hsa-mir-629 | 1 | MYPQGRHPVSNCRSVYLSIYHGRVNEAVYLAFPPCLLL PLWCVCLCVCSHTKGDAAGGRR* | 9089 | ATGTATCCGCAGGGCAGACATCCGTGAGTAATTGCAACTCGGTTTATTAAGCATC TATCATGGCAGGGTAAACGAGGCAGTTTATCTGCACCTCCATTTGCTTGTTGCTA CCTTATCGTGTGTTGTGTGTGTCTGCTCTCACACAAAGGGGGATGCGGCCGGG GGCGCCGTTGA | 9090 |
| | 2 | MVCVFVCVLSHKGGCGRGAPLREEVNSARVARGAACV PGGAVHAVPGPALKSPNSPGLSPAPALLGRGRPLVKGM GAPLPTCGRDGAPPLRPVGELRNLLGRFWAEGGLFWLGA VGEGRGPL* | 9091 | ATGGTGTGTGTGTTGTGTCTGTCTCACACAAAGGGGATGCGGCCGGGGGGC GCCGTTGAGAGAGGTTAATTCCGGCGAGTGGCGCGGGGGGCTGCTTGTGTC CAGGGGGAGCTGTTCACGGGGTCCCCCGGCCCCTCTGAAGTTCCCAACTCACCG GCTTGTTCCCCCCGCCCGCGACGGGGAGATGGGGCCCCCTTGGTGAAAGGCATG GGAGCCCGCGTGCCAGGGAGACTTGCTGGGAAGGTTCTGGGGTGGCCTCTTTGGTTGGGCGC CGTTGGGAGGGCGCGGGCCGGGGCCCGCTGA | 9092 |
| | 3 | MRPGGAVERGG* | 9093 | ATGCGCCCGGGGGCGCCCTCGCCGTTGAGAGGAGGTTAA | 9094 |
| | 4 | MGRPPSAPSES* | 9095 | ATGGGGCGCCCTCCAGCCCCCTCGCCGTCGAGAGCTGA | 9096 |
| | 1 | MAAAPALKHWRTTLERVEKFVSPLYFIDCNLRGRCGP WSPAAGRPQPCASSFPSGEKPKLQPPGPRIDKVPAAGRA GAGEEGVGNGLCRGAARQPSWRRIQCKCCGPTGQLAPR RKRGGLQHVPTGPSHAGFLGPAALWLCSPAS* | 9097 | ATGGCGGCTGCCGCGGGACGGCGCCARGCAGCCCTCTTGGGCRAGGATCCAGGAAAG GTTCGTGTCGCCGGCTCTACTTACCGACTGAACCTCGCCACCACTGCGCCACCACCCTCCTG CTCCCCCAGCACGCAGCCGCCACCGGAGCCACAAGTCTCCCGCCGGCCAGGGGAGAA ACCTAAGCTGCAAGCGCACCGCCGGGCTCGCCCGGCGGCCCGGCGCGGGCCCGGGAA GGGCCGGGGAGGAGGGGTAGGAGAAGTGCGCACCGGCGGCCCCAGGCAGGAAGG CTCTTTGCCGCRGGAGATCCAGGGAAAGTGCCAGCTGCCCCAGGCCCACCCACCCTCGTT GAAACGGGGCGCCTGCCCTGTGCCTCTGCCTCCAGCCCAGGGCCTCCAGG GGGCCAGCTGCCCTGTGCCTCTGTCTCTCCAGCTCCTGA | 9098 |
| | 2 | MDCAAERPGSPLCGGGSRESAAPPASWPPGGNGAASSM CPFARPTQAFWGQLPCGCALQLPDAGETSLFGGSPAGL PPRACGRRQLRTHVGNAQRVGGATGLGEVPTQLPATPSL SALCRRQLRGHEQHPLLGAAPSAGNSSLVPGSSGDGFHS HVAASGHPLGRAP* | 9099 | ATGGACTGTGCCGCGGAGCGGCCCARGCAGCCCTCTTGGGCRAGGATCCAGGAAAG TGCGGGGCGCAGCTGCCCTGTGCCTCAGGAGCGGCCTCCAGTCCAGCGGACTTC TCAGCTTCCTGACGCCGGAGGACTTCCTGCCTACCAGGAGCAGTCCAGGGACTTC TCAGCTTCCTGACGCCGGAGGACTTCCTGCCTACCAGGAGCAGTCCAGGGACTTC GGCCCCGCGCCAGGTCGRGACAGCTCGARCCGAACTGACCCGTAATGCCCAGCGGTG GTCTGCCCTGCCCTGAGACAACTAGGGATCGAGCAGCACCCCCTGCTGGGAGC AGCACCCTTGCTCGGCGGCCCTCTGGACATCGGACATCCGTCTTAGGAAGGCACCCTAG TTCCCACGTGGCGCCCTCTGGACATCGTCTGACTATCCTGGACATCCCTTAG | 9100 |
| | 3 | MVFIPTWPPLDIP* | 9101 | ATGGTTTTCATTCCACGTGGCCGCCCTCTGGACATCCCTTAG | 9102 |
| | 4 | MLGEFQAPADTLSKEGYQDRTSTSRPTTALLQMVDLL VPGGADHPRGMGGPGSSPLLGK* | 9103 | ATGCTTGGAGAGTTCAAGCCCCTCAAGGCCTTATCCAAGGAAGGATATCAGGAT AGGACTTCTACCTCTAGGCCTATGACCACTGCTCTTGCAGATGGTGGACCTGCTG GTTCCCGGTGGAGCTGAACCATGGCCATGGTGGGCCAGGAAGTTCAACCTTT GCTGGGAAAGTGA | 9104 |
| | 1 | MCSLYQPFQFLPGLSWKPDHRGDCAL* | 9105 | ATGTGCTCTCTCTATCAACCATTCCAATTCTTACCTGGCCTATCCTGGAAGCCTGACT TCAGGGGAGATTGTGCTTTATGA | 9106 |

Figure 1 (Continued)

| | | | | |
|---|---|---|---|---|
| hsa-mir-635 | 2 | MMETPW* | 9107 | ATGATGGAAACTCCTGGTAA | 9108 |
| | 3 | MEGDR* | 9109 | ATGGAAGGAGATAGATAA | 9110 |
| | 4 | MKTTCQQGASCLPECVTLSHATA* | 9111 | ATGAAAACCACTTGCCAGCAGGGGCCAGTTGTCTCCTGAATGTCACCCTGTCCCATGCCACAGCCTGA | 9112 |
| hsa-mir-636 | 1 | MSYGRPPPDVEGMTSLKVDNLTYRTSPDTLRRVFEKYGRVGDVVYIPRDRYTKESRGFAFVRFHDKRDAEDAMDAMDGAVLDGRELRVQMARYQRPPDSHHSRRGPPPRRYGGGGYGRRSRR* | 9113 | ATGAGCTACGGCCGCCCCCCTCCGATTGGAGGGTATGAACCTCCTCAAGGTGGACAACCTGACTACGGCCGACGTGTACATCCCGCGACACGTGAGGGCGGTCTTCGAGAAGTACGGCGCGGTCGGGGACGTGGTGTACATCCCGCGAGACCGCTACACCAAGGAGTCCCGGGCTTTCGCCTTCGTTCGCTTCACGACAAGCGCGACGCTGAGGACGCTATGGATGCCATGGACGGGGCCGTGCTTGACGGCCGCGAGCTGCGGGTGCAAATGGCGCGTTACCGGCCGCCCCCGGACTCACACAGCCGCCGAGGGCCCCACCCCAGTTACGGGCCGGGGTGGCTACGGACGCGAGCCGCAGGTAA | 9114 |
| | 2 | MWRV* | 9115 | ATGTGGAGGGTATGA | 9116 |
| | 3 | MPWTGPCWTAASCGCKWRATAAPRTHTTAAGDRRHPAGTGAVATDAGAAGKRG* | 9117 | ATGCCATGGACGGGGCCTGCTGGACGGCCGCCGGGGCCCGAGCTGCGGGTGCAAATGGCGCGCTACGGCCGCCCCCGGACTCACACAGCCGCCGAGGGCCCCACCCACGCCGGAGCCGCAGTAAAGGGGCTGA | 9118 |
| | 4 | MASGGERIMAAAWAGARGRPRCLELTPLCLLVPPAALGGVAAADPGVGVVPGLAADLATAARSLGPALVLDLGRPPSPDPHEGPSPSPRRSPDLVRGPGPGLGPGVLPQCPRGNPNPGRDRRKVPPSLLKRKERCPLKKMVMSGNPRHITLHKWDLG* | 9119 | ATGGCGTCTGGCGGCGAGATAATGGCCGCCGCCTGGGCGGAGCGCGGGCGCCCGCGCTGCGAGCTGACCCCTCTGTGCCTGCTGGTGCCCCCAGCCGCTCTGGGCGGCGTCGCAGCCGCTCGGAGTCCGGCACTCGCGTCTGATCTCGGTCGACCTCGCTACAGCGCCCGCAGTCGCTCCGAAGTCCGGAGTCGGAGCCCACTCAAGTCCAAGCTCCGGTCCAGTTCTCAGATCTCGCAAGTCAGATCGCACGCCGGTTCAGATTCGCGTCGAAGGAGTCCCCAGTGTCCAAGGGAATCCAAATCCAGGGAATTCTAAGAAGAAATGTAATGTCTCCCCAAGTGTCTCCAAGTGCCCAAGTGGTGTCTCTTAAGAAAATGGTAATGTCTGGGAATCCGAGACACATAACCCTAATCATAAATGGGATTTGGGGTAG | 9120 |
| hsa-mir-637 | 1 | MSTFRQEDVEDHYEMGEELGR* | 9121 | ATGTCCACGTTCAGGCAGGAGGATGTGGAGGACCATTATGAGATGGGGAGGAGCTGGGCAGGTGA | 9122 |
| | 2 | MRWGRSWAGELSARTAGHLQG* | 9123 | ATGAGATGGGGGAGGAGCTGGGCAGGTGAGCTGTCTGCCCGCACGGCTGGGCTCCAGGGATAG | 9124 |
| | 3 | MLRRNESVSCGGGTNLGRGVRQPRL* | 9125 | ATGCTGAGAAGGAATGAGTCAGTATCATGCGTGGGGAACGAATTTGGCCGTGGAGTCAGACAGCCCCGGCTGTGA | 9126 |
| | 4 | MSQYHAVGERIWAVESDSPGCEFLLGNPLCVSCGEKSN* | 9127 | ATGAGTCAGTATCATGCGGTGGGGGAACGAATTTGGCCGTGGAGTCAGACAGCCCCGGCTGTGATTCCGATGAATCCTCGTGTGTTCCTGTGGGGAAACCCCTGAGGGAAAAAGTAATTGA | 9128 |
| hsa-mir-639 | 1 | MVKPLLFSPSYRRSAPFDWSRKLIGQSPGASPSLGSDRPQGAGANVGASCPDWPTGRARPGGAGRTQSRV* | 9129 | ATGGTCAAGCCCCTTCTTCTTTAGCCCTCTACGGCGTTCCGCCCCCTTGATTGGTCTCGCAAGTTGATTGGTCAATCCCCTGGTGCATCCCTGGTGCTAGTCCTACCTCGTCTTGGTTGGGACCGGCCCAAGGAGCAGGGGCGAACGTGGGCGAAGTGGGCTCAGTGCCCTGATTGGCCGACGGGGCGCGGCGGCGCTGGAGGGCGGCGGACAGAGCCGCGTTAG | 9130 |
| | 2 | MKHYEVRSEKQGPCGHC* | 9131 | ATGAAGCATTACGAGGTAAGAGAAGGCGAGAAACAGGGCCGTGTGGCCACTGCTGA | 9132 |
| | 3 | MRMCAGSIYKSATQAVLGVLFLGGLCRGWDACRFLAAPPAG* | 9133 | ATGCGCATGTGCGCAGGAAGTATTTATAAATCTGCAACCCAGGCTGTTTTGGGGTACTTTTTCTTGGGGGTCTCTGCAGGGGCTGGGACGCTTCCTTGCAGGTTCCC | 9134 |
| | 4 | MGATKVRDPCSQSEGVLHKSCATPFSPA* | 9135 | ATGGGAGCCACGAAGGTGCGGGACCCTTGCTCCCAATCCGAGGGAGTCTTGCACAAATCTTGCGCCACGCCGTCACCAGCGTGA | 9136 |
| | 1 | MGGGRAPPESLGGCR* | 9137 | ATGGGGCGGGGAGGGTAGAGCCCCGCCGAGAGGGTGGCGGCCTGCCGGTGA | 9138 |

Figure 1 (Continued)

| | | | | |
|---|---|---|---|---|
| hsa-mir-641 | 2 | MVASGPPAVPRWAVPPVPGGGTAALEPLLQELSGGGR AGAVGPASGGRGHGHGPYH* | 9139 | ATGGTCGCGTCCGGACCCCCGCGCGGTCGTGTACCACCGTGCCGG CGGGGGGACCGGCAGCCCCTCCTGAAGCCCTCCTTCAGGAGCTGAGTGGGGTGGCCGAG CGGGGCGTGGGAACCAGCCTCGGGGACCGTGCCGCCGGGCCATACCA CTGA | 9140 |
| | 3 | MGCTTRARRGDRGPRAPPSGAEWGWPSGGGGTSLGGP GRWRRAIPLRRWGERCKFAGRGAQAAACAGRGLDLSG AAGRSSLACAG* | 9141 | ATGGGCTGTACCACCGTGCCGCCGGCGGGGGACCGGGGACCCCTCCTCA GGAGCTGAGTGGGGGTCGCCAGCGGGAACCACTCTCGGGGGCCGG GGCGGTGGCGGCGGGCCCATACCACTGAGGGGTGCGGGGAGCGCTCGAAGTTGCG GGACGGGGAGCGCAGCGCGAGCGTGCCAGCGCGGCAGCCTGGCGTTGCGGCGGCTAA GGCCGGCAGATCGAGCCTGGCCTGCGCGGCTAA | 9142 |
| | 4 | MLPQLWLGYITALGEPCLERRGTQIRGL* | 9143 | ATGCTTCCCAACTGTGGCTGGGTTATATCACCAGGCGTTGGGGGAGCCTGCTTA GAACGTAGGGGAACCCAAATCAGAGGACTGTGA | 9144 |
| | 1 | MSLSACFHLWLAAR* | 9145 | ATGTCTCTGTCTGCTGCGTGTTCTATCTCTGGTTAGCTGCTAGATAA | 9146 |
| | 2 | MLGKGCSTYSGLYLPPAGKVL* | 9147 | ATGCTGGGAAAGGGTTGTTCCACTTACTCTGGCTTTATCTACCCCAGCGGGGAAA GTTTTGTAA | 9148 |
| hsa-mir-642 | 3 | MCARKPGLGEWELGWAFQVLHQAVGTQMGVSSTPL GGTENLQVFQPHEKGSRLTVSTPSSPRRSPCSQESVGPD FGDIDTSAQRSSRATARSANTPPHLCCPNNSQGRPGN HLRGPAHHRSSTHSACLSLPDHAWELRERVRCLGVP RVYGSPAVCPCV* | 9149 | ATGTGTGCTAGAAAACCCTTTGGCTTGGAGAGTGGAGCTCGGATGGGCGTTTCA AGTTCTCCACCAGGTCTGTGACAACTTCAAGTTTTCAGTTCCCATAGAAAGGGCTTCAAGTACCCACTAGGAGG TACTACCCCTCCTCCTCCCAAGTGTGTCGTCTCCTAGGAGTCTGTAGGTCCAGA CTTCGGTGACACTGACATTCGCCCCAGCGTAGTCTAGGCAACCGCCGCTCAGC AACACCCCCCCCCTTCCACCCGAGGGCCCACCGAGTTCCACACAGTCCAGGAGGCCGGGAA TCACTTAAGGGCCCCCAGATCATCACGCTGGAGTTGCGGAGGCGGTGCGTCGGAGTCC CGCGTGTATAGCGTCCCAGCCGTTCGCCCTGTGTGA | 9150 |
| | 4 | MGVSSSPPGCGNSDGRFKYPTRGY* | 9151 | ATGGGCGTTTCAAGGTTCTCCACCAGGCTGTGGGAACTCAGATGGGCGTTTCAAGTAC CCCACTAGGGGTACTGA | 9152 |
| | 1 | MAWRYGATAAREFSPV* | 9153 | ATGGCGTGGAGATATGGCGCAACTGCGGCGCGTGAGTTTTCCTTTGTTAG | 9154 |
| hsa-mir-643 | 2 | MAQLRRVSFPLFRLSVRLAVPSRFCTRDVGGGTDLFIPA PLSPPRVNSCVPSEC* | 9155 | ATGGCCAACTGCGGCGCGGTCAGTTTCCTTTGTTAGATTAAGTTGCGTTAGCG GTGCCCTCACGCTTCGTACCCGGATGTGGGGCGTCAGTACAGACCTTGAAATCCCC GCACGCTCTCTCCACCCGAGTAAATTCATGCGTCCGTCAGAGTGTTAA | 9156 |
| | 3 | MWGAVQTLKSPHRSLHPE* | 9157 | ATGTGGGGGGCGGTCCGTCAGAGTGTTAAAATCCGCCTAAATCGCCTAG | 9158 |
| | 4 | MRPVRVLKSP* | 9159 | ATGCGTCCGTCAGGCTGACCCGGTAG | 9160 |
| | 1 | MVRLTR* | 9161 | ATGGTCAGGCTGACCCGGTAG | 9162 |
| | 2 | MSRNICVTEAET* | 9163 | ATGAGCAGAAACATTTGTGTAACTGAGGCAGAAACTTAG | 9164 |
| hsa-mir-645 | 3 | MSLNSSQFLS* | 9165 | ATGTCACTAATTCGAGTCAGTTTTGTCTTAG | 9166 |
| | 4 | MKPNFHKFSCPKEKFNELHLN* | 9167 | ATGAAACCAAATTTCATAAATTTCTTGTTTAAAGAAAAATTTAATGAGCTACATT TAAACTGA | 9168 |
| | 1 | MAAPPARADADPSPTSPPTARDTPGRQAEKSETACEDR* | 9169 | ATGGCTGCGCCCCGGCCCGCGCGACGCTGATCCTTCGCCACGTCGCCACCTACG GCCCGAGACACACCAGGCCGGCACGTTGAGGCAGAAACTTAG GGTAG | 9170 |
| | 2 | MLSARGVALPDPRGQGLGFGGAAAHGAFGLPRTRVAP SSLCGGFARA* | 9171 | ATGTTGTCGGCTCGGGTGGCCCTGCCCGACCCGCGCAGGGCTTAGGATTT GGAGGTGCTGCGGCGCACGGCACGTGCCTTCGGATTGCCTGCACGCGGCGTGGAGGACC AGCCTCTGCGGGGGCTTTGCAAGAGCATGA | 9172 |

Figure 1 (Continued)

| | | | | |
|---|---|---|---|---|
| hsa-mir-647 | 3 | MKWGSCGBAAGGTRPHPGSSPRVAPLGAGPCAAPLGP WPSGGRGHAVPGAARGRSGRCPSLPGLKCPLGSPRGPQ EGVVFPTQAPLAWVQAVTPVRNAVSQDSLRDGLRWMP QGEGCPGTGSLLSRSC* | 9173 | ATGAAGTGGGGAAGTTGTGCGGTGCAGCGGGAGGAACCCGCCCCACCCGGTTC GTCACCCCGAGTGGCCCCTCTGGGACCGGAGCCCTGCGCGCGCCCTTGGGGCCGT GGCCGGTCAGGGGCGCGTGACCCACGCAGTGCCGGGACTGCCAAGGGGCGCTGGG CGCTGCGCCCTCCCTTGTCCGGTCTGAAGTGTCCCTTGGGGAGCCCGCGGGTCCCAG AAGGGGTTGTTCCCACTCAGGCGCCTCTTGCCTGGGTTCAGGCTGTGAACTCCTGT AGAAACGCTGTGAGCAGGACTCCCTGAGAGATGGGCTGCGCTGGATGCCGCAGGG GGAAGGGTGTCCGGCACAGGGTCGCTCCTCTCCAGGAGCGTGCTGA | 9174 |
| | 4 | MGCCAGGCRRGKGYPAQCGRSSPGAAFQKELSPGPASLQV HTLPVGSD* | 9175 | ATGGGCTGCGTTGGATGCCGCAGGGGAAGGGTCCCGGCAGGGTCGCTCCTC TCCAGGAGCGTGCTGAAGCAGAAAGAGCTTTCCCGGCCCTGCGTCCTTCAGGTCCA CACCCTTCCAGTGGGCAGTGACTAG | 9176 |
| hsa-mir-657 | 1 | MPGWILQLRGFSGKQRPLLSRDPGS* | 9177 | ATGCCCGGATGGATCCTGCAGCTCCGTGGCTTTCTGGGAAGCAGGAGCCCCTGCTC TCAAGAGACCCTGCTCCTGA | 9178 |
| | 2 | MBPAAPWLFWEAAAPALKRPWLLMVAPRLPAGARDSG QFPRKGQAGSPSRGRVRKLGGAETLGP* | 9179 | ATGGATCCTGCAGCTCCGTGGCTTTCTGGGAAGCAGGAGCCCCTGCTCTCAAGAGA CCCTGCTCCTGATGGTGGCCCCAAGGTTGCCAGCTGGTGCTAGGGACTCAGGACA GTTCCCAGAAAAGCGACCAAGCGGCAAGCCCTCCCAGGGGCCGGGTGAGGAAGCTGG GGGGTGCGGAGGCACACTGGGGTCCCTGA | 9180 |
| | 3 | MAFP* | 9181 | ATGGCCTTCCCGTGA | 9182 |
| | 4 | MSGRGTGGEVSCPGGRRGAGGRRVRPGSRGRWRSSRG* | 9183 | ATGAGTGGACGGGCACAGGAGGCACAGGAGAAGTGTCCTGTCCTGGGGCCGGCGTGGGGC GGTGGGAGAAGAGTAAGGCCTGAAGCCCTGGAAGCCGGTGAGGGGAGCAGCCGT GGGTGA | 9184 |
| hsa-mir-658 | 1 | MSGPRLRPEAGSSAPLGPACKPEAPPRPLAI* | 9185 | ATGAGCGGCCGCGCGCTGCTCGCGAGGAGTGTCCTGAGGCCGAAGTTCAGCCCCACTCGGGCCTGC CGGGAAACCGGAAGCCCGTTCTCTACTAA | 9186 |
| | 2 | MEKPRLY* | 9187 | ATGGAGAAACCCGTTCGGGTA | 9188 |
| | 3 | MPVIPATREAEAGESLEPGIRRRLR* | 9189 | ATGCCTGTAATTCCAGCTACTCGGGAGGCAGGAGAGTCGCTTGAACCCGG GAGGCGAGGTTGCGGTGA | 9190 |
| | 4 | MLHKRWPASRVKEDSDTGA* | 9191 | ATGCTACACAAAAGATGGCGGCTTCTCGCGTGAAGGAAGATTCGGATACGGGGGC CTGA | 9192 |
| hsa-mir-659 | 1 | MSGPRLRPEAGSSAPLGPAGKPEAFPRPLAI* | 9193 | ATGAGCGGCCGCGCGCTGCGTCCTGAGGCCGGAAGTTCAGCCCCACTCGGGCCTGC CGGGAAACCGGAAGCCCTTTCCGAGGCCTTCTGCTACTAA | 9194 |
| | 2 | MEKPRLY* | 9195 | ATGGAGAAACCCGTTGCGGTGA | 9196 |
| | 3 | MPVIPATREAEAGESLEPGRRRRLR* | 9197 | ATGCCTGTAATTCCAGCTACTCGGGAGGCTGAGGCAGGAGAGTCGCTTGAACCCGG GAGGCGGAGGTTGCGGTGA | 9198 |
| | 4 | MLHKRWPASRVKEDSDTGA* | 9199 | ATGCTACACAAAAGATGGCGGCTTCTCGCGTGAAGGAAGATTCGGATACGGGGGC CTGA | 9200 |
| hsa-mir-661 | 1 | MVAGMLMPRDQLRAIYEVLFREGYMVAKKDRRPRSLH PHVPGVTNLQVMRAMASLRARGLVREIFAWCHFYWY LTNEGIAHLRQYLHLPPEYPASLQRVRRPYAMVMPAR RTPHVQAVQGPLGSPPKRGPLFTEEQRVYRRKELEEVS PETPVVPATTQRITLARPGFPPAPATGQLHFDFKS* | 9201 | ATGGTGGCCGGCATGCTCATGCCACGGGACCAGCTGCGGGCCATCTATGAGGTGCT TCTCCGCGAGGGCTACATGGTGGCCAAGAAGTACCGCCGCCCGCAGCTTGCACC CCATGTGCCGGGCGTCACCAACCTGCAGGTCATGCGTGCCATGCGCTCACTCACCA CAGGGGCGCTGGTCCGCGAGACCTTTGCCTGGTGCCACTTTTACTGGTACCTCACCA ATGAAGGCATGCGCCGCCGCCATCGCCAGTACCTGCACCTGCCCCCAGAGATCCGCCCG CCTCTCGCAGCGCGTGCGCCGCCCATACGCCATGGTCATGCCGGCCCGGACCCCG CCACGTGCAGGCTGTGCAGGGACCACTGGGCTCCCCCACCAAGCGTGGGGCCGCTG CCGCAGTGCAGCTCCTTACCGAGGAAGCTTCGAAGAGGTGTCACCTGA GACCCCTTGGTGCCTGCTACCACCAACGACCCTACCATTCAGCGTCAGGCGCCTGA CTGCCCCAGCGCAACAGTCAGCTGCACCCTGACCGACGCTCATGA | 9202 |
| | 2 | MRCSSARA* | 9203 | ATGAGGTGCTCTTCCGCGAGGCGTGA | 9204 |

Figure 1 (Continued)

| | | | | | |
|---|---|---|---|---|---|
| | 3 | MCPASPTCRSCVPWRPCGHGAWSARPLPGATFTGTSPMKASPTSASTCTCRQRSCPPLCSACAAPSPW* | 9205 | ATGTGCCCGGCGTCACCAACCTGAGTCATGCGTGCCATGGCGTCCTGCGGCACGGGGCCTGGTCCGCGAGACCTTGCCTGGTGCCACTTTACTGACCTCACCAATGAAGGCATGCGCCCACCTCCGCACTACTGCACTGCCGCCAGAGATCGTGCCCGCCTCTCCAGGCGGTGCGCCGCCCGTGCCATGGTGA | 9206 |
| | 4 | MMGGK* | 9207 | ATGATGGGTGGCAAGTAG | 9208 |
| hsa-mir-7-1 | 1 | MSWSYVALGTRDLVEERRPVRGEGRAAALFV* | 9209 | ATGAGCTGGAGCTATGTGGCACTGGAACTAGGGACCTGTGAGGAAAGGAGGCCGGTGCGGGGAGAAGGAGGACCTGTGCGGGGAGA | 9210 |
| | 2 | MWHWELGTSWRKGGRCGEKVAPPLSLCEPRLTLGLPARGRSWSGGDGTVRAASMALSRAVGGGCGG* | 9211 | ATGTGGCACTGGGAACTCGGAGACCTCGTTGTGAGCCCCGCCTCACTTGGGTCTCCCGGCCGGGGTCGGAGCTGGAACGGCGGGGATGAACGGTCAGGGCTGCCCTGGATGGCTTTGTCTCGGGCAGTGGGGAGGATGCGGGGGATGA | 9212 |
| | 3 | MERSGLPRWLCLGQWGEDACIDETSGPRGGWGRGSALGSA* | 9213 | ATGGAACGGTCAGGGCTGCCTCGATGGCTTGTCTCGGCAGTGGGGAGGATGCCGGGGATGAGAACCTCGGGAGCCGCGTGGTGGTGGGGAGGTGGGGGTCCGGCGCTCGGCTCCGGCTAG | 9214 |
| | 4 | MRGMRPRDRVVGGCGKGRRSAPPSST* | 9215 | ATGCGCGGGATGAGACCTCGGGACCGCTGGGTGGTGGGTGGCGGGGTGCGGCGCTCGGCTCCGCTAGTAGCACGTAG | 9216 |
| | 1 | MDVTSQLNLEREAGMGHENTERQPAEPESAGGGGSSRAQAGVPRDQCRPRGRTSRRLLSAPRGSQTRQPSGRTRRLLP* | 9217 | ATGGACGTGACCTCGCAGTAAACCTGAACGTGAAGCGGGATGGGGAAAACACGGAGCGGCAGGCCGGGTGCCAAGGGACCAGTGCCGCGCCACGTCGCCAGCCGCCGCCTTCTTTCTGCACCGGCGGCTCCAGACTGCGAGCTCGCCAGCTTCCGGCCGCACGCAGACTCTTGCCCTGA | 9218 |
| hsa-mir-9-2 | 1 | MRLGFENGRIMSARFNVMGVLCCVCVCMYYCVLGGACASEHRGRRSEQREISLSMATSGTHLRSHLGQQS* | 9219 | ATGCGCCTCGGTTCATTAACGGCAGGATCAATGAGCGGCGGTTTAATGTGATGGGAGTGCTGTGTGTGTGTCGGCGTCTAGTATGTGTGTTGGGAGGTGCTTGCGCTAGTGACGCACCGAGGCAGGCGCTCTGAGCAAGAGAATCAGTCAGGCCATCTAG | 9220 |
| | 2 | MYVCWEVLALVYSTEAGALSRERSVFPWPRLGLLGCGAI* | 9221 | ATGTATGTGTGTTGGGAGGTGCTGGCACCGAGGCGCTCTGAGCAGAGAGAATCAGTCTTCCATGGCCTAGTGAGCACCGAGGCAGGCGCTCTGAGGTCTGGAGACTCATCTGGAGCCATCTAG | 9222 |
| | 3 | MCVGRCLR* | 9223 | ATGTGTGTTGGGAGGTGCTTGCGCTAG | 9224 |
| | 4 | MYLIAKDFSTLFSYVFFNCKLLGF* | 9225 | ATGTATCTGAATAGCTAAGGATTTTCAACTTTATTCTCTTACGTATTTTCAACTGTA | 9226 |
| hsa-mir-92a-1 | 1 | MDGINCC* | 9227 | ATGGATGGAATTAATTGCTAG | 9228 |
| | 2 | MELIAVRRLEFNSKYRFGRW* | 9229 | ATGGAATTAATTGCTGTTAGGAGGTTGGAAAATAGCAAATAGATTGGACGGTGGTAG | 9230 |
| | 3 | MFYLFFPYTSLFQSYTWT* | 9231 | ATGTTTTTATCTTTTTTTCCCTATTCCAGTCATACACGTTGGACCTAA | 9232 |
| | 4 | MVEREGSGFHLHPFPPSLPPACLPGLSSSDPACSLVSDL* | 9233 | ATGGTGGAAAGGGAGGGGTCGGGCTTCATTTGCACCCCTTCCTCATTTGCACCCCAGCGTGCTCACTGGTCTCTGATTTGTAA | 9234 |
| hsa-mir-92a-2 | 1 | MLNSILIVRLKLRHHFILQSAVGLWP* | 9235 | ATGCTTAATTCCATTTTGATTGCGTCTTAACTAAGACATCATTTATTCTACAGAGCGCTGTCGGCGGCTTGGCCTGA | 9236 |
| | 2 | MRGESKHAPYLPHCACIRWLLPLTIPAKKP* | 9237 | ATGAGAGGAGAAAGCAAGATAATTGCACCGTATCTCCGCACATTGCGCGTGTATTCGGTTGGCTGCTACCGTTAACGATACCTGCCAAGAAACCTGA | 9238 |
| | 3 | MCRE* | 9239 | ATGTGCAGAGAGTAA | 9240 |
| | 4 | MELSGWGPEVCGRGTEVCGRGRWNVGGGVGHVLCGPLCT* | 9241 | ATGGAGCTAAGCGGGTGGGGTCCTGAGTATGTGGAAGGGCACCGAGGTATGTGGGAGAGGACGTTGGAACGTGGGGGGGGAGTTGGACACGTTCTGTGTGGCCGTTATGTACTTAA | 9242 |

Figure 1 (Continued)

| | | | | | |
|---|---|---|---|---|---|
| hsa-mir-92b | 2 | MWKGHRGMWERTLERGRGSWTRSVWAVMYLRGRSG VARWLTPVIPTLWKAEASCSGQGEKTSLAKMVKPRL Y* | 9243 | ATGTGGAAGGGGCACCGAGGTATGTGGGAGAGAGGACGTTGGAACGTTGGCGCGGCGA GTTGGACACGTTCTGTGTGGGCCGTTATGTACTTAAGAGGCAGAATCCGGCGTTGGCAC GGTGGCTCACGCGCCGTAATCCAACACTTGGAAGGCCGAGTGAGTTGGATAACAA GGTCAGGGGGTTCAAGACCAGCCTGGCCAAGATGGTGAAACCTCGTCTCTACTAA | 9244 |
| | 3 | MGFTDTELSFGEQSGCGDR* | 9245 | ATGGGATTTACGGACACAGAACTATCCTTTGGGGAGCAGAGTGTATTGGGGACAG GTAG | 9246 |
| | 4 | MRDSQEVCAAAVHEGRKLSQAAAARGTWVPQSQAAL* | 9247 | ATGCGTGACAGCCAAGAGGTTGTGTGCGCAGCAGTGCACGGAGGGAGGAAGCTATC CCAGGCCGCGGCAGCAGCGTTGGAACTTGGGTCCGCAGTTGCAGGCTGCGCTCTAG | 9248 |
| hsa-mir-93 | 1 | MANGWTGSSRPGRRNPEL* | 9249 | ATGGCCAATGGCTGGACTGGCTCCCGCCCTGGGCGGAGGAATCCGAGCGGAATCCGAGCTGTGA | 9250 |
| | 2 | MAGLAPALGCGHPSCEAAGHRAHVLLCLLRAEAMAGAG VGCGGGVRWRRSR* | 9251 | ATGGCTGGACTGGCTCCCGCCCTGGGCGGAGGAATCCCGAGCTGTGAAGCGGCTGG AATCCGGGCCCATGTGCTTCTTTGTTTACTAAGAGCGGATGGCGGGAGCGG GGGTGGGGTGCGTGCGCGGTGCGTGCGGAGGTCCGGTA | 9252 |
| | 3 | MCEFVY* | 9253 | ATGTGCTTCTTTGTTTACTAA | 9254 |
| | 4 | MLDGPVHCHGLFILRWLETDL* | 9255 | ATGTTGGATGCCCTGTGCACTGCCACGGCCTCTTTATTCTTCGCTGGTTAGAAACA GACTTGTGA | 9256 |
| hsa-mir-98 | 1 | MFTTLGIASPTLLLYCRGELQRSVGFIGALVRIFTVL* | 9257 | ATGTTCACTACCCTGGGAATCGCAGCCACCCTCCTCTTATACTGCAGAGGTGAAG TTACAGAGATCGTTGGATTCATGCAGCTCGTGTAAGAATTTTCACTGTGCTTAG | 9258 |
| | 2 | MFLSYTQIRYLFHFFVDYMCSLLGSAAFWGIPNYVNSS AHVFSNY* | 9259 | ATGTTCTGTCATACACACAAATAAGGTATTTGTTCCATTTCTTGTGGATTACATGT GTAGCCTTTTGGGGAGTGCAGCCTTTTGGGGAATACCAACTATGTCAATAGTTCTG CCCATGTATTTAGCAATTATTAA | 9260 |
| | 3 | MSIVLRMYLAIHCLMPST* | 9261 | ATGTCAATAGTTCTGCGCATGTATTTAGCAATTATTAAGTCTCATGCCAAGCACTTAA | 9262 |
| | 4 | MVGVQTTERV* | 9263 | ATGGTTGGTGTACAGAGACTAGAGAGGGTAG | 9264 |
| | 1 | MLPQLMVHQLSLA* | 9265 | ATGCTCCCTCAGCTAATGGTACCAACTTCACTGGCTTAA | 9266 |
| | 2 | MFQDPFFKNHLNVIFSSH* | 9267 | ATGTTTCAAGATCCGTTTAAAACATTATTTAAATGTTATTTTAGCAGCCATTAA | 9268 |
| hsa-mir-99a | 3 | MLFLAAINLYTLNYLIKLHAKSKSLFSFRYFIVQNLVASL TIAIVLSLSKLLL* | 9269 | ATGTTATTTTTAGCAGCCATTAATCTCTACACTCTTAATATCTTATTAAAGCTCCATG CCAAATCAAATCTCTTCAGCTTCGTACTTCATTGTGCAAAACCTAGTCGCTTC TTTAACAGCCATCGTCCTTCACTTGAAACTGTTACTGTGA | 9270 |
| | 4 | MPNPNLFSAFATSLCKT* | 9271 | ATGCCAAATCAAATCTCTTCAGCTTTCGCTACTTCATTGTGCAAAACCTAG | 9272 |
| | 1 | MAGTAGGRGEAAVRRRRGEDGERSAAVGPGLRARGG GEDPFPATREPREP* | 9273 | ATGGCGGGAACGGCGGGGGAGGCAGCGGTGCGTCGCGGACGCGGCGAGGCGGGGAGG AGGATGGAGAGCGGTCGGCGGCTGTGGGAGCCGGGCCTGAGGGCGCCGGCGGGAGGGG AGAAGACCCCTTCCGCTGCAGACGCGGAGCCGGAGCCCTGA | 9274 |
| | 2 | MESARRRWGPACGPGAAEKTPSLRRGSRGSRESAEREG GGLGPALLGP* | 9275 | ATGGAGAGCCGTCGACGCCGTGGGGGACCCGGGGAGCCGGGGGCCGGGGCCGGGGCCGG GGTGGGGGCTGGGGCGCCGCACTCCTGGGTCCCTGA | 9276 |
| hsa-mir-99b | 3 | MGAGAGRIVAGRD* | 9277 | ATGGGGGCTGGGGCTGGTAGGATCGTGGCTGGAAGAGACTAG | 9278 |
| | 4 | MGLRGFEGSRVSRASGRGPRRRGRLSGLPDRPGSAAGA GDVWRRRGPASMLPRGPGIPGPPRPLLPQIWEYTTQSPTH SRIRAPSPLFSRIQESEPPVCSLRPGNPHSSP* | 9279 | ATGGGGCTGCGGGGCTTTGAGGGTTCAAGGGTTGAGCCGTGCCAGTGGAGGGCC GAGGAGGAGGGGAGGTTGTCGAGGAGGAGGGCCTCCAGACACCGCAGGTGCAGCCGCGGGG GCAGGAGATGTCTGAGGAGGAGAGCCCAGCATCCATGCTCCCTGGGGACCCGG GATTCCAAGGCTGCAAGCCCCTCCTCCAGAATCGTGGGAGTACACCAGTCGCC CACCCATTCCAGAATCGCAGGAGCCCCTTTTTCCAGGATCCAACCACTGGAGCTGA GCCCCGCAGTGTCTCTCAGACGGAATCACACACTGCAGGAGAGTCTAA | 9280 |

Figure 1 (Continued)

| | | | | |
|---|---|---|---|---|
| hsa-mir-553 | 1 | MNQGF* | 9281 | ATGAACCAAGGTTTCTGA | 9282 |
| | 2 | MAGPRVEVDGSIMEGVSTERSGRGCSLTKEGSSHHRCAYFSSPCTPTFAGRPDPESLYGLIELSPRPPLAGAEDPSRPEHARPEVNLAGGGVGP* | 9283 | ATGGCGGGGCCGGCGGTGGAGGTCGAGCATCATGGAAGGGGTGAGTACAGAGCGAAGCGGCCGGGGCTCAGCTAACCTAAGGAGGGAGCTCTCACCACGGTGTGCTTACTTCTCTTCCTGTACCCAACCTTTGCAGGGCGGCCAGATCCTGAGAGTCTCTACGGCCTTGAGCTGTCTCCCTAGGCCTCCCTTTCGGGTTGCAGAAGATCGAGCCGGCCGGAGCACGGCCAGGCCTGAGGTAAATCTGGCTGGAGGTGGAGTTGGGCGTGA | 9284 |
| | 3 | MAASWKG* | 9285 | ATGGCAGCATCATGGAAGGGGTGA | 9286 |
| | 4 | MGDPGRGTLPGRWPGL* | 9287 | ATGGGCGATCCAGGGCGGGGCACTCTGCCTGGGCGTTGGCCTGGGTTGTAA | 9288 |
| hsa-let-7a-1 | 1 | MSLASNALRSFNFLQ* | 9289 | ATGTCCTTGGCCAGTAATGCCCTTCGGTCTTTCAACTTTTTACAGTAG | 9290 |
| | 2 | MPFGLSTPYSRFCVRGNGMYSSTYRFLKN* | 9291 | ATGCCCTTCGGTCTTTCAACTTTTTACAGTATCTGTGTCAGAGGTAATGGTATGTAGTTCTTCAACTTACCGGTTTTTAAAAAATTGA | 9292 |
| | 3 | MVCHLQLTGF* | 9293 | ATGTATGTATGTCTTCAACTTACCGGTTTTAA | 9294 |
| | 4 | MLKF* | 9295 | ATGTTAAAATTTTGA | 9296 |
| hsa-let-7d | 1 | MSLASNALRSFNFLQ* | 9297 | ATGTCCTTGGCCAGTAATGCCCTTCGGTCTTTCAACTTTTTACAGTAG | 9298 |
| | 2 | MPFGLSIFYSRFCVRGNGMYSSTYRFLKN* | 9299 | ATGCCCTTCGGTCTTTCAACTTTTTACAGTAGATTCTGTGTCAGAGGTAATGGTATGTATTCTTCAACTTACCGGTTTTTAAAAAATTGA | 9300 |
| | 3 | MVCHLQLTGF* | 9301 | ATGGTATGTATGTCTTCAACTTACCGGTTTTTAA | 9302 |
| | 4 | MLKF* | 9303 | ATGTTAAAATTTGA | 9304 |
| hsa-let-7e | 1 | MAGTAGGRGEAAVRRRRGEIDGERSAAVGPGLRARGGGEDPFPATREPREP* | 9305 | ATGGCTGGGACGGCGGGAGAAGGAGCCGCCGTCGTCGCGAAGCGCGGGAGAGGATGGAGAGCGCTCGGGGCGTGGGAAGCCGGTTGGGGGCCCCGGCTGCCCCGGAGCCTGCGGCCGGCCGAGAAGAAGACCCCTTCCCTGCAACGCGGACGGGTGGGCCTGCCGGCCCTGGGGCGGCCGGCGAGAAGAAAGGGAGGGTGTGGCGCTGGTAGGATCGGCTGAAGAGACTAG | 9306 |
| | 2 | MESARRRWGPACGPGAAEKTPSLRRGSRGSRESAEREGGGLGPALLGP* | 9307 | ATGGAGAGCGCTCGGGGCGTGGGAAGCCGGTTGGGGGCCCCGGCTGCCCCGGAGCCTGCGGCCGGCCGAGAAGAAGACCCCTTCCCTGCAACGCGGACGGGTGGGCCTGCCGGCCCTGGGGCGGCCGGCGAGAAGAAAGGGAGGGTGTGGCGCTGGTAGGATCGGCTGAAGAGACTAG | 9308 |
| | 3 | MGAGAGRIVAGRD* | 9309 | ATGGGCGCTGGCGCTGGTAGGATCGGCTGAAGAGACTAG | 9310 |
| hsa-let-7f-1 | 1 | MGLRGFEGSRVSRASGRPGPRRRGRLSGLPDRPGSAAGAGDVWRRRGPASMLPRGPGIPGPRPLLPQJWEYTIQSPTHSRIRAPSLFSRIQESEPPVCSLRPGNFHSSP* | 9311 | ATGGGGCTGCGGGGCTTTGAGGGTCAAGGTGAGCCGTGCCAGTGGGAGGGGGCCGAGGAGGAGGAGGGAGTGTCTGAGGAGGAGAGCCTCCCGAGCATCCAGGAGAGCCCGGGGGACCCGGGCAGGAGATGTCTGAGGAGACCCCTCCAGCCACCATGGGAGTACACACCAGCACCCCAGTCCCCGATTCCAGGTCCAGAATCCGAGCCCGTCCAGCCCCTTTTCCAGGATCCAGGAGTCTGACACCCCATTCCAGCACCCCAGATCTGTTCTCCAGACCAGGAATCCACACTCCAGCCCTGA | 9312 |
| | 2 | MSLASNALRSFNFLQ* | 9313 | ATGTCCTTGGCCAGTAATGCCCTTCGGTCTTTCAACTTTTTACAGTAG | 9314 |
| | 3 | MPFGLSIFYSRFCVRGNGMYSSTYRFLKN* | 9315 | ATGCCCTTCGGTCTTTCAACTTTTTACAGTAGATTCTGTGTCAGAGGTAATGGTATGTATGTTCTTCAACTTACCGGTTTTTAA | 9316 |
| | 4 | MVCHLQLTGF* | 9317 | ATGGTATGTATGTCTTCAACTTACCGGTTTTTAA | 9318 |
| | 5 | MLKF* | 9319 | ATGTTAAAATTTTGA | 9320 |
| | 1 | MKLTDSVLRSFRVAKVFRENSDKINCFDFSPNGETVISSSDDDSIVLYDCQEGK* | 9321 | ATGAAGCTGACCGACAGTGTTCTGCGGAGCTTCCGCGTTGCGCTAAGGTGTTCCGCGAAACTCGGACAAGATTAACTGCTTCGATTTCAGCCCCAAGGCGAGACGCGTCATCTCGAGTAGCGACGACGACTCCATCGTGCTCTATGACTGCCAGGAGGGCAAGTGA | 9322 |
| | 2 | MTARRASECGGGPGPESQCLPPVAQHRSLGLPSVPTSAPSLECTRSCQGRLRPAAVQEITFYFFLLKKKR* | 9323 | ATGACTGCCAGGAGGGCAAGTGAGTGCGGCGAGCCCTGGCCCTGGCCGGCCCTGTCCTCCCGAGTTCAGCCCCAGCCTATTTTGCACGCGTCTATTTGCACGCGCCGCTGCACCCACCGTCGGAGCCGCTTCAGGCGGAGAGGGCAAGTGA | 9324 |

Figure 1 (Continued)

| | | | | | |
|---|---|---|---|---|---|
| hsa-let-7g | 3 | MSSVSFERYASLAKPHLDLDL* | 9325 | ATGTCTTCGGTCTCCTTTGAGCGCTATGCATCACTTGCCAAACCCCACCTTGACCTTG ACCTTTAA | 9326 |
| | 4 | MHHLPNPTLTLTFKRPVRPPWAHQVAFSAPQAVKGAGL LRPRRRTAGAAPLPPSAAASALSCALSTVTSIPPWHSAHPL PLSFRPFCRQTAWVALLSCQDLFVVPL* | 9327 | ATGCATCACTTGCCAAACCCACCTTGACCTTTCAGCCTTTAAAGCGCGGTCGCCA CCCTGGAGCCCACCAGGTAGGCTTTCTGACCTTTCAGCTGTCAAGGTGCTGGTCTG CTCGGCCTTGACGCAGGACTCACAGGGCTGCTTTCTGCCTCTCGGCAGCGTCA GCTCTCTTGTGTCCTCTCCACTGTAACTCGATTCGCATTGCCGCCACTCGCCCATC CCCTGCCCCTCACGCTTCCGCGGCCCTTTCTGCCGCCAGAACCGCGGGTTGCACTTCT TAGCTGTCAGGATTATTTGTTGTGCCCTTTGA | 9328 |
| | 1 | MAARGAAWRGGHVVRSSARASLSDL* | 9329 | ATGGCGGCGCGGGGGGCGGCTGGCGGGGCGGGTCACGTGGTGAGGAGTAGCGCGC GAGCCCTCTAAGTGATCTCTAA | 9330 |
| | 2 | MPWLLFGGAGGSLCGMPAGDYRRRERAGGGFDSAAAR VGARVPDSAAAQPPPGTRSREGRERRSSSGRGGSS* | 9331 | ATGCCCTTGGCTCTGTTTGGCGGAGCCGGAGCCGGGATGCCCGGTGG CGATTATCGCGCGCCGAGAGCGGGACTCCAGCGGGGTTCGACACGGCGGCCGGGTGG GGGCCCGGGTACCGGCGGCGGCAGCCCAGCCCCACCGGGACTCGGAGCAGG GAGGGGCGGAGCGGCAGCTCGGCAGCGTGGCGCAGCTCCTAG | 9332 |
| | 3 | MALAEVVCAVGRVVTLPAVEITAQATALLVLVMLSA AEDNGWESPLFSGALPGDSPRSLGARPARPPRKPLVSHF PRRN* | 9333 | ATGGCCCTGGCTGAGGTAGTTGTGTGTGCGGGTTGTGTCTTGTGACATTGCCGCT GTGAGATAACTGCGCAAGCTACTACCTTCTGCGGTTTAGTCGTCGGTCGGGGCGCCG GAGGACAATGGCTGGGAATCCCCTTTGTTTCCGGGCGCTGCTCGGGGACAGCCG GCGAAGCCTCCGCCGCCGGCCCGGCCACCACGGAAACCGTTAGTTTCACATTT TCCTAGAAGGAATTGA | 9334 |
| | 4 | MAGNPLCFPGRCLGTAREASAPGRRGHHGNR* | 9335 | ATGGCTGGGAATCCCCTTTGTTTCCGGGACGTGCTCGGGACAGCCGGGAAGCC TCGGCCCGGCGGTCACGTTGTGCGGAGCTTGCTGGTCATTAG | 9336 |
| | 1 | MAIVTLWRALLRH* | 9337 | ATGGCGATCGTCACGTTGTGGCGAGCTTGCTGGTCATTAG | 9338 |
| | 2 | MQIAGRTKEGEPGTPGGAGGCCGGGRARGRRGAARGRA PAGGGLRGACGRARLGAQSVDVRVRARAPPWSSAGCCA PGPVSRRVGAGLGTREAVGRTERLRRGWPRRTRTRSRG ARPARHPHWGLGAGQAAPGAEGAPLPSA* | 9339 | ATGCAAATAGCGGGAAGAACAAAGGAAGGGGAGCCCGGGACCCCGGGGGCGAG GTGGGTGTGGGAGGCGGCGGTCGGGGCGCGCGCAAGGCTCGGGGCGCAG AGTGTGGACGTCGAGTCGGCCCCGTCGCCCCCGTGCGCCGGCGCGCGAGGCCGCC TCCCGAGCCGTCCGTCTCGCGGGACGCCCGCGAGCCCACGCCGGGAAGCCGTGG GCCACAGAGCGGTCGGCGCGAGCGCACTAGGCGTCTAGGCATCCGACTGCCAGCGCGT GGGGCCGGCCCGGCGGCGCCGCCCACTGCCCAGCCCTAG | 9340 |
| | 3 | MGISAVLRGPRWGVSGNAGSPGRLARPPEGSGAEGRG VCVNVAHSLFPRPRPRPGCWRGSLAVRRRL* | 9341 | ATGGGCATTTCCGCGGTTTTGCGCGGCCCTCGGTGGGTCAGTGGGCAACGCGGG GAGCCCCGGCCCTGGCTCGGCCCCGGAGGGAAGCGGCGGGAGGGGCGGGT GTGTGTAAATTGCGCACTCGTTTGCCGCTCGCAGGGAGGGAGGGTGCCAGGGTGC TGCCGTGGGTCCCTTGCCGCGGCGCAGGGACTGTAA | 9342 |
| | 4 | MLRTRFSPAPARVQGAGVGPLPSGGDCK* | 9343 | ATGTTCGCACTCGCTTTCGCGGCGCTCGCGGTTCCAGGGTGCTGCGTGGGT CCCTTGCCGCGGCGCAGGGACTGTAATAG | 9344 |
| hsa-mir-103-1 | 1 | MKIKDAKKPCKTGAGARQVGRAPLGPV* | 9345 | ATGAAGATCAAAGATGCAAGAAACCTGTAAGACGGGCTGGGCCCGCCAGGT TGGGAGGGCACCCTTGGGCCGTCTGA | 9346 |
| | 2 | MPRMPVRRGLGPARLLGGHPWAPSESPLAGRSASKPVAP RRRPVRYGGGGTT* | 9347 | ATGCCAAGAAACCTGTAAGACCGGGCTGGGCCCGCCAGGTTGGGAGGCACCC TTGGGCCCGTCTGAAAGCCCCTTGGCGTGGGGCCGGCCTTCCAAGCGCGTCGCTCC TCCGCCGGACGTTCGTCCGTATGGGGCGGGAGGGACCATTTGA | 9348 |
| | 3 | MGAEGPFEPRVRGFRPFPHPHHAW* | 9349 | ATGGGGCGGGAGGGACCATTTGAGCACGAGTTCGAGCCTCCGTCTCCCCATCCC CCTATTCATGCATGGTGA | 9350 |
| | 4 | MHRGECLPPPSLSSHFLFEIWEVPEGISDSDFCQTRLVSSP SSP* | 9351 | ATGCATGGTGAATGCCTGCCGCCCTAGCCTTTCTCCCCACTTCTCTTCGAGATCT GGGAGGTGCCAGAGGGAATTTCGATTCGATTTGTCAAACCAGACTAGTTCTCCT CTCCCAGCTCCCCCTGA | 9352 |

Figure 1 (Continued)

| | | | | | |
|---|---|---|---|---|---|
| hsa-mir-106a | 1 | MGQGGSECALARMPVAPAPATASAWAAVPGAPLIK DSSLGEERRENADCGPPVGNWGSVGFSLWRGGGSVS* | 9353 | ATGGGACAAGGTGGTAGTGAGTGCGCCATCCTGGCCCGATCCGGTGGCACCCGC ACCGGCTCCGGCCACGGCTTCTGCGGCCCTCTGGCCGGCGGCCTTAATTAA GGACTCCAGTTGGCGGAAGAGAAGGGAAAATGCGACTGCTGGTCCGCCCGTGG GTAACTGGGGCTCGGTGGGGTTTCCGTTTGGCGGGTGGGGTTTGCGTTTGGC | 9354 |
| | 2 | MPTAVRPWVTGARWGFFRFGGVGVPFPNSCAGRVGkG GLFSLGY* | 9355 | ATGCCGACTGCTGCGTCCGCCGTCGTCCGCCGTGCAACTGGGGCTCGGTGGGGTTT CCGTTTGGCGGGTGGGGTTCGTTCGTTCCTAATTCCTGTCGCCGTGCAACTCTTTGCT TTTTCCTTGGGCTATTAA | 9356 |
| | 3 | MCARGLDPFSGRFESLLFPEWLRGRLRSHPAPERSSCAL GHWVYVWRGHPERAARAGSPRSPPARGGPELGPARGF PSGWLGKKGALRWGSCDPVELTGWVGGDGAGGT* | 9357 | ATGTGCGCTGCGCTGGCGGCCTTGATCCATTAGTGGACGCTTTTCTCACTTCTCTCCCT TCTGCCTCCGCGGAGACTGCGTATACGTGTGGAGGGGACACCCGGAGGGCGGCCCTGCGGG CTGGGACACTGGGTATACGTGTGGAGGGGACACCCGGAGGGCGCCCTGCGGG CTCCCCGGCGCTCTCCACCTGGCACTGGAGCCTTCGTTGGGCAGCTGTGATCCG GTAGAGTTGACTGGGTCTGGGTGGCAGCGACGAGCGGAGTGGGACGTTGA | 9358 |
| | 4 | MRGCTWREKRDSPFSWLLSHQPGNGGGRRGLGAFLV L* | 9359 | ATGAGGGGGTGCACGTGAGGGAAAAAGGGACTCCCCTCCCTCTGGCTCTATCC CACCAAACCGGGAATGGAGGGAGGGCTGTGGGCTTGGCGCGTTTTTGGTGCT TTGA | 9360 |
| hsa-mir-106b | 1 | MANGWTGSRPGRRNPEL* | 9361 | ATGGCCAATGCTGGACTGGCTCCGCCCTGGCGGAGGAATCCGAGCTGTGTGA | 9362 |
| | 2 | MAGLAPALGGGIPSCEAAGIRAHVLLCLLRAEAMAGAG VGCGGGVRWRRSR* | 9363 | ATGGCTGGACTGGCTCCGCCCTGGCGGAGGAATCCGAGCGTGAAGCGGCTGG AATCCGGGCCCATGTGCTTCTTGTTTACTAAGAGCGGAAGCGATGGCGGGAGCGG GTGGGGGTGCAGTGCGGGGTGCGGTGCGGAGGTCCGGTGA | 9364 |
| | 3 | MCFFVY* | 9365 | ATGTGCTTCTTTGTTTACTAA | 9366 |
| | 4 | MLJGPVHCHGLFILRWLETDL* | 9367 | ATGTTGGATGGCCCTGTGCACTGCCACGGGCTCTTTATTCTTCGCTGGTTAGAAACA GACTTGTGA | 9368 |
| | 1 | MHSLQYPLASPPRKQFPVCEAALWTASPLVDPG* | 9369 | ATGCACTCTCTGCAGTATCCTCTAGCTTCTCCTCCCCGGAAACAGTTCCAGTCTCCG AGGCCGCCCTTGGCACTTGCCTCCCGGACTTGGATCGGACTGA | 9370 |
| | 2 | MHLGRKGITSQAPDHFALPKDDPGQLERWGVRTERHT* | 9371 | ATGCATCTAGGGAGGAAGAAAGGTACCTCGCAGCCCGCAGACCATTTGCCTTACCAAAA GATGACCCAGGCCAGTGGAAAGGTGGGAGTCAGGAGCGGAGGACGAGGCACACTAG | 9372 |
| | 3 | MTQASWKGKGESGRKGTPRGEVEGKCQPVWGYAS* | 9373 | ATGACCCAGGCCAGTGGAAAGGTGGAGTCAGCTGGGAGGACCTCTGA | 9374 |
| hsa-mir-10a | 4 | MIEDTLFRGSCRLVLRCMHLSNSTSFLFSESQGIPRREKG NPSQGEVGVWEAIFGRKGNRRKRTGCPHRRCSGPEAEAV TSRSCQ* | 9375 | ATGATAGAGGATACCCTATTTCGGGGCTGTCCTAGGTGCTGTCTTAGTGAGGAGCAT CTCTCTAATTCGTTTCTTTTCTTTGTTTCTGAATCCCAAGGGATCCAAGGAGGAGGA AGGAAAATCCTTCCCAGGGAGAGGTCACGGGTGTTCGTGGAGGCGCAATATTGGGCGGAAG GGAAACCGAAAGTGCACGGGTTGTCCGCACCGCGCTCTGGACCAGAGGCAGA GGCTGTAACATCCGGAGCTGCAGTGA | 9376 |
| | 1 | MDSLEKHL* | 9377 | ATGGACAGCCTTGAAAAGCACATCTTTAG | 9378 |
| | 2 | MGLALAHLEQDLGPGTPWRLRAWVNPICSAAQEN* | 9379 | ATGGGCCTTGCCCTTGCTCTCACTTAGAACAGGACTCTGGGTCTCGGACTCCTGGAGA CTCAGAGTCTGGTTAAATCCCATTTGCTCTGCAGCTCAAGAGAACTAG | 9380 |
| hsa-mir-10b | 3 | MRMSTPHHPTTLLSPLRSFQAFCGLHWALLAPGSRASD TLLK* | 9381 | ATGCGCATGTCTACTCCACACCACCACACCAACCACTCTTCTACCAGCACTTCGCTCATTTC AGGCCTTTTTGTGGGCTCCACTGGGCACTCCTCGCACCAGGTTCAAGAGCCAGCGACCA CCTTACTTAAATAA | 9382 |
| | 4 | MQSFVPLSPPPSLG* | 9383 | ATGCAGTCTTTGTCGTCCTCCCACCCACGGCTTCTCTAGGTAA | 9384 |
| | 1 | MAGTAGGRGEAAVRRRRGEIDGERSAAVGPGLRARGG GEDPFPATREPREP* | 9385 | ATGGCTGGGACGGCGGCGGAGAGCGGGAGGAGGGAAGGGAGCCGCCGTGGCGGCGAAGGCGGGAG AGGATGGAGAGCCCTTCCCTGCGACGCGCGAGCCGGGAGCCGTGA | 9386 |

Figure 1 (Continued)

| | | | | | |
|---|---|---|---|---|---|
| hsa-mir-125a | 2 | MESARRRRWGPACGPGAAEKTPSLRRCGSRGSRESAEREG GGLGPALLGP* | 9387 | ATGGAGAGCGCTCGCGCGGTGGGCCCGGCCTGCCGGCCTGCCGGCGCGGCGGAGA AGACCCCTTCCCTGCGACCGGRAGCCGCGGAGCCGTGAGTCTGCGGAAAGGGAG GGTGGRGGGCTGRGGCCGCACTCCTGAGTCCCTGA | 9388 |
| | 3 | MGAGAGRIVAGRD* | 9389 | ATGGGGGCTGCGCGCTGGTAGGATCGTCGCTGAAGAGACTAG | 9390 |
| | 4 | MGLRGFECGSRVSRASCGRGPRRRGRLSGLPERPCGSAAGA GDVWRRRGPASMLPRGPGIPGPRPLLPQIWEYTTQSPTH SRIRAFPSLFSRIQESEPPVCSLRFGNPHSSP* | 9391 | ATGGGGCTGCGCGGGCTTTGAGGGGTCAAGGGTGAGCCGTGCCAGTGGGAGGGGCC GAGGAGGAGGGGAGGTTGTCTGRGCAGGTTGTCCAGACAGGTCAGRGTCAGCGGCGGGG GCAGGAGATGTCTGAGGAGGAGGAGCCAGCATCCATGCTCCCTGGGGACCCGG GATTCAAGGTCCAGACCCCTCCTCCCTGCAGATCGGGAGTACACCACCAGTCCC CACCCATTCCAGAATCCGAGCCCGCCAGCCCCCTTTTCCAGGATCCAAGAGTCTGA GCCCCAGTCTGTTCTCTCAGACCAGGGAATCCACACTCCACTCCAGCCCCTAA | 9392 |
| hsa-mir-125b-2 | 1 | MYSLRRMGLRDGGHMLMSFLWRGEHSDNWLNAM VKNCKAFSFREKHGLRSKGCFHFSLFVSAAFLFWFLEF NYLF* | 9393 | ATGTATTCCCTAAGGAGGATGGGTCTCCGTGATGGGGHTGTATAATTATGTTAAG TCATTTTATGGAGGGTGAGATTTTCATTCGTATAATTGGTTGAATCGTATGGTCA AAATTGTAAAGCCATATTCAGTTTAGGGAAAAGCATGACTTAGATCTAAGGCT GTTTATTATTTCGCTTTTTGTGAGTGCTGCTTTTTGTTTTTTGTTTTTGTTTTTA ACTATTTATTTAA | 9394 |
| | 2 | MGVV* | 9395 | ATGGGCGTGGTATAA | 9396 |
| | 3 | MLWSKIYKPYSVLGKSMDLDLRAVLFFREL* | 9397 | ATGCTATGGTCAAAAATTGTAAAGCCATATTCAGTTTTAGGGAAAAGCATGGACTTA GATCTAAGGCTGTTTTATTTTCGCTTTGTGA | 9398 |
| | 4 | MGMQMINRKRSYIMMHYIMEQNI* | 9399 | ATGGGGAAATCAAATTGATAAACAAGAAGAGATCTTATATAATGATGCATTACATCATG GAGCAGCAGAATATTTAA | 9400 |
| hsa-mir-136b | 1 | MEPAGEGPPRGAGSSGRGPGGRRWPGSSSV* | 9401 | ATGGAGCCAGCGGAGGGCCGAGGGCCGCCACGAGGCGGCGAGGTCGTCGTCTGGACGGGGAC CCGGGGCAGACGATGGCCGGGATCTCTTCCGTTCA | 9402 |
| | 2 | MAGRLFRLTLRVLTGPWAEGMSA* | 9403 | ATGGCCGGGATCTCTCTCCGTCTAACCCTCGTCGTCCTGACCGGCCCTGGGCGGAA GGGATGTCTGCGTGA | 9404 |
| | 3 | MLEKNPECT* | 9405 | ATGTTAGAAAAGAATCCAGAGTTGTATCTAG | 9406 |
| | 4 | MESSARRGASSRGAALFLLEPRAESGRRVVGLYPPRS GR* | 9407 | ATGGAGTCGTCAGCTAGAAGGGGCGGTCGTCCCGGGGTGGGCGCCGCCCTTTTCTC CTGAGCCGCGGGCCGAGTCAGGCGCCACGGTCGTCGGCCTGTACCCACCCGGCTC CGGGCGCTAG | 9408 |
| hsa-mir-132 | 1 | MFWIHLTHSLSHVSP* | 9409 | ATGTTCTGGATCCATCTTACCCACTCCCTCTCCCACGTGTCCCCATAG | 9410 |
| | 2 | MSPHSHLTLEAVRSQRGKRRPPELPVSREGPRHLARGT CCGLRWKLRSVEGRWRGSS* | 9411 | ATGTCTCCGCAGTCCCATAGCACTCTCACTTTAGAAGCAGTGAGGTCCAAGAGGAAAACGG AGGCCTCCGGAAGTCTGCCGGTCTCTAGAAGGCCGGACATCTCGCCGAGG CACGTGCTGCGTGGCCTGAGGTGAAGTTACGGCAGGTGGAGGTGAGGAGGCT CCTCATAA | 9412 |
| | 3 | MNRSSSTEQEGICE* | 9413 | ATGAATAGGAGTTCTTCTACCGAGCAGGAAGCATTTGTAATAA | 9414 |
| | 4 | MQGLSDPISHFSLFDRVRSPTHDFQRAPPPHVSCAVESV HC* | 9415 | ATGCAGGGGCTCTCTGACCCCATCTCTCATTTCTCTTTTGATAGAGTCAGAT CCCCCACCCACGTCCGACTTCCAAAGAGCCCCCTTCCACTTCTTGTCACAGGTGGAGT CGTGCATTGCTAA | 9416 |
| | 1 | MHLIFLPPSQYLAKGSHCGHYNHDNFPLTAPLKNKILAQ ED* | 9417 | ATGCATCTAATCTTCTTCCTCTCCCATTCTCCCAGTTCTTGCTAAAGGATCACACTGTGAA TCTACAACCATGACAACTTCCACTTACTGCTCCCTTGAAAAACAAAATATTAGCAC AAGAAGATTAG | 9418 |
| hsa-mir-135a-2 | 2 | MITFHLLLP* | 9419 | ATGACAACTTTCCACTTACTGCTCCCTTGA | 9420 |
| | 3 | MLSLRSPQ* | 9421 | ATGTTGTCTTTGAGAAGCCCTGGTTGA | 9422 |
| | 4 | MGELSNIKAAKIREFLLC* | 9423 | ATGGGCATTCTCTGAATATTAAAGCGGCAAAAATACGTTGAATTCTTTTATGTTAA | 9424 |
| | 1 | MGARDLQLFRRDPGPEAA* | 9425 | ATGGGAGCCAGGGATCTGCAGCTTTTCCGCAGGGATCCTGGGCCTGAAGCTGCCTGA | 9426 |

Figure 1 (Continued)

| | | | | |
|---|---|---|---|---|
| hsa-mir-141 | 2 | MMEAPVPVSATSHASGPQPLAGCSPLPTSHAPRKPLVLS* | 9427 | ATGATGGAGGCCCCTGTCCCTGTCGTCAGCAACATCCATGCCTCAGGTCCCCAGCCC TTAGCTGGCTGCAGCCCCACTTCCCACGCACCCCGGAAGCCCCTCGTCTTG AGCTGA | 9428 |
| | 3 | MGPSPSSHPVRFVTWWIQNPQSTLSLGLARPLSRDLTW PVARVPCSNW* | 9429 | ATGGGCCCCAGCCCTTCCTCCACCAGTGCGATTTGTCACTTGGTGGATCAGAAC CCACAGTCGACTTGGGTTGGCTGCCCCCTCTCAAGAGACCTCACCTGG CCTGTGGCCAGGGTCCCCTGTCCCCTGTAGCAACTGGTGA | 9430 |
| | 4 | MAPGWVLSAVTPREP* | 9431 | ATGGCCTCCCGGTGCAGGGTTCTCTGGCAGTAACCTTCAGGAGCCCTGA | 9432 |
| hsa-mir-148a | 1 | MERWRGVWGKMGKHPPDLLHARNSCSGAVCGGRGSA RMGDRVVAYAAGKRGCREGEKSSLGDCVQGCARTGS AGSTA* | 9433 | ATGGAACGGTGGCGAGGGGTTTGGGGAAGATGGGAAAGCACTTTCCAGACCTGTT GCACCGCGCAACAGAGTGGTCGCTTATGCTGCAGGGAAGATGGGGGAGGGGTCTCTAGGA TGGGGACAGAGCAGTCTTGGGGACTGGTGTCGCTTATGCTGCAGGGAAAAGGGGGTGCCGGGAGGGGGA GAAGAGCAGTCTTGGGGACTGTGTCGCAAGGTTGTGCGCGAACGRGGTCCGCGGGAA GCACTGCCTAA | 9434 |
| | 2 | MWGEGVC* | 9435 | ATGTGGGGGAGGGGTCTGCTAA | 9436 |
| | 3 | MLQGKGGAGRGRRAVLGTVCKVVPERGPREALPNGA GRIPKSGWVERRGWDFDPSSRGWARAAGRPGIEYWE WLGKGVSGEAPQSGSFLGRPHLGAFPGPVFVPHRLILSA PNIRPRAAPPPPAFQMCR* | 9437 | ATGCTGCAGGGAAAAGGGGGTGCCGGAGGGCGGAGAAGAGCAGTCTTGGGGACTG TGTGCAAGGTTGTGCGCGAACGGGGTCCGCGGGAAGCACTGCCTAATGGGGCAGGG AGAATCCAAAGAGTGGGTGGCTGAAACGGAGGGATGGGACGACTTCGACCCGA GTTCCCGGGGCTGGGCCGGGCGGTCGAGGGAGCCCCGCAAAGCGGGTCTTTCTTGGTCGTC CTGGGAAGGGGGTCTCAGGGAGGCCCTGTATTTGTTCCAACGTTTAACTCTTTCAGCT CATCTTAGGGGCTTTCCGGGCAGCCCTGTATTGTCCAACGTTTAACTCTTTCAGCT CCGAATATTCGTCCTGTGCAGCCCCCCAGCTTTCCAGATGGGAAGGTAA | 9438 |
| | 4 | MGQGESQRVGGWNGGDGTTSTRVPGAGRGRLEDRE* | 9439 | ATGGGGCAGGGAGAATCCCAAAGAGTGGGTGGGTGGAACCGAGGGGATGGGACGA CTTCGACCCGAGTTCCGGGGCTGCGGCCGGCGGTCGTGGAAGACCGGGAATAG | 9440 |
| hsa-mir-148b | 1 | MEALILVGAGGAAEMLWCPQGPGVRVQPEWETGKESS G* | 9441 | ATGGAGGCGCTGATTTTGGTAGGAGCTGGAGGCGCAGCAGATGCTGTGTCC ACAGGGCCGGAGTCAGGGTTCAGCCGAGTGGGAGACGGGGAAAGAGAGTTCC GGGTAA | 9442 |
| | 2 | MDSLGYTDL* | 9443 | ATGGACTCCTTAGGATACACAGACCTGTAG | 9444 |
| | 3 | MFCRYRLLLMVSQY* | 9445 | ATGTTTTGTCGTTACAGACTCCTCGATGGTTCCAAGTTTGA | 9446 |
| | 4 | MDCGIFFLDSLFCSPFLYPFRP* | 9447 | ATGGATTGTGGAATATTTTTCTAGACTCCTTATTCGTTCTCCTTTCTCTACCCATT TAGACCTTAG | 9448 |
| hsa-mir-149 | 1 | MVAGGLRADGRGVGRGGKHDGVSLGAVDAVDEELRC RGRSTSQVGPRLPLAQTSGAQADRDWPGAQAS* | 9449 | ATGGTGGCGGGGGGGCTTCGGGGCAGAGGAGGGGGTGTGCGCAGGGAGGGAAGC ACGATGGGGTGAGTCTGGGGCGCTGAGCCGTTGACGAGGAGCTGAGATGCCGT GGCCGGTCCACCTCGCAGTTGGGCAAGGCTGCCTCTGGCTCAGAGCGTCAGGAGC CAGGAGCGGACAGGGACTGGCCAGGGGCGCAGGCTTCTTAG | 9450 |
| | 2 | MPLTRS* | 9451 | ATGCCCTTGACGAGGACTGA | 9452 |
| | 3 | MPWPVHLAGGAKAASGSDVRSPGGQGLARGAGFLEDG AKVPKKRSSAAWAVGGPQETPWVVCFVHHPRRLLDVP EDATATGAGWGPRADGPGAGAGFEKRVRAWGKPSQPS ASQEGPVAGCRAE* | 9453 | ATGCCGTGGCCGGTCCACCTCGCAGGTGGGGCCAAGGCTGCCTCTGGCTCAGACGTC AGGAGCCGGGAGTCCGACCAGGGACTGGCCAGGGCGCAGCTTCTTAGAGGATGGGG CAAAAGTGAGGAAAAGATCCTCGCAGCCTCTGCAGCCTGGCAGTGGGTGGTCCCCAGGAAACC CCCTGGGTCGTTTGTCAGTGCAGTCACCCTGCGGTCCGAGGAGCCTGCTGACGTGCCGAG GATGCACAGCCACGGAGCTGTTGCGGTCGAGAGCAGAGATGGGCCAGGGCTGG GGCAGGCTTGGAGAAGCGGGTTCGCGGTTGGGGAAAGCCTTCCAGCCATCGCCA GCCAGGAAGGCCCCGTTGCCGGGTGCAGAGCTGAGTAG | 9454 |
| | 4 | MGQK* | 9455 | ATGGGGCAAAAGTGA | 9456 |

Figure 1 (Continued)

| | | | | |
|---|---|---|---|---|
| hsa-mir-152 | 1 | MQRPEAGHVRTRGRGPRRQAGGRRRLLEPGSPRGCGY GAGGRGDPGRRELGRDRAGLGGAANSELARPAAGNFV SPLTGPRTREEKFVPAPTGEEACPESVGAGLKPWVRLE WGWRVSCDSAGRVRSGLSVPDSAPITGG* | ATGCAGCAGGCCGAGGCTGGCCACGTCCGCACGTCGGGGAGGGGCGCGGGCACGGCCGGGGGAGCCCGCCGGGGATCCCGGGAGCCGGAGCTGGCAGGGACAGAGGAGGGAGGGGGAGCAGCCAACTCAGAACTCGCGCCGCGGCCCGGCCTGGAACTTTGTGTCACCCCTGACTGGCCCCCAGGACCCGGGAGGAAAAGTTCGTCCAGCGCCGACCGGAGAGGCCTGTCCTGAGTCCGCGCGCCGGATTCCGCGGGAGGGCTGAAGTTCTGGTCCGTTGGATGGGGGTGGCGGGTGAGTTGCAGGGGTAAGGAGTGGCCGTCCGTCCCAGACTCCGGCTCCCATCACCGGTGGGTGA | 9458 |
| | 2 | MGMLLESTRARAWGRADSAGPARPGISWKKEARPAVP PGRGSVIHSDSGSGAVSA* | ATGGGCATGCTCTTGGAGTCTACCGGAGCACAGGCTCAGGGCAGGGCCGATAGCGCAGGTCAGCCGGCCAGGGATCAGCTGGAAGAAGAGGCTCGAAGGGGCTGTCCCCCCGGCCCAGTTCTGTGATACACTCCGACTCGGCTCTGAGCAGTCAGTGCATGA | 9460 |
| | 3 | MTELGPGRTFCTQRAQPLGACSGTSAWEWSGHLGWP MWHRAGQNQLWTLRTGVAGA* | ATGACAGAACTTGGGCCTGGAAGGACTTTCTGCACCAACGGCACACGGCCACTCCGGGCTCAGTGGAAACATCTGCCTGGAGTGGAGTGGGCACTCGGGTTTAGCCCATGTGCACAGGGCTGGGACAGCCAGCTGTGACCTTGAGGACTGAGGACGTGGGGTTGCTGGGGCCTGA | 9462 |
| | 4 | MYPRASKSRHRHVSTSSXQPNGTLLSGVSCRNLPSTPSR LPSS* | ATGTATCCTACGGCCAGCAGGATCCCAGCAGACACAGGTGTCCACCTCGAGTCAGGGCCAAACGGAACTCTCCTCCGGTCAGTTGCAGGAACCTTCCCTCTACCATCAAGGCTGTTTTCATCCTAG | 9464 |
| hsa-mir-153-1 | 1 | MGGGGAGVRPPLGLEPRVGPGASASDFWPPAPDPTLPP LKAGLRLRLCPSPSLHHPRGPAPRRPLLCSLPLTLPGLA PSPPPASSRGPSAFCLPSLSRTPASFLLPVPSCPAVSRPCT ALPCCPLRLSLPPARLPSFIPLRPSFIPLRLFASFFCVFHSF SFPLSSSSLSPSLSHSVSASPPFSLSTSPSPRPFSSFLSALSPV FLRLLPLSASFSLLLCPSLPLPPAACLSSLSSLLPSFSL SLTAASVFFVICS* | ATGGGCGGGGAGGGAGCCGGGTCCGGCCTGAGCCCCGGGTCGGCCTGAGCCTCGGCTGCACCCCTCTGAGCGCCGACTTCTGGCCGCCAGACCCAACGGCCTGCCGCCCTCTGCCCGAGCCTGACCCTCCACCGCGCTAAAAAGCAGGCCTGAGGCTGAGCCTGCCTTCCGCCCTTCTGCTCCTCCGGGCTGCTCCCTCTCCAGGGCCCTCTGCTTCCTCTGTCTCCCGACTGCACTCCCAGGACCCTGGTGCTCCTCAGTTCCGTCCGCCTCAGTGTCCAGGCGGCCCTGTCCTCAGGCCTGCACTGCGTCCTCGGGTCCTCCCTCCTTCATCCTTTCGTGCCAGTCTCCCCATCTCTCCTCACTCGCTTCTCGTCTCCACCCTTCTCCACCCTCTGCCAGTTCCTGCTCCCCTGTCTCTCGCGCGCGCGCCAGGTCTCATTTCTGTGATCTGCAGTAG | 9466 |
| | 2 | MDRQDMWPGDHPELGARGTGKRQRLSKGVWEDLWIL GGSVEQVGTRQGLPEGLTLFQH* | ATGGACAGACAGGACATGTGGCCGGGAGACATGGAGGGACCTGGGGGCAGAAGAGGCAAAGACTGTCGAAAGGAGTGTGGAGGAATCTCGGATTCTGGGGGCTCAGTGGAGCAGGTGGGGACTAGACAAGGGCTACCTGAGGGACTTACCCTTTCCAACACTGA | 9468 |
| | 3 | MSLGTGQRSRAGGGDMGIVSEPQDSSF* | ATGTCTCTAGGTACTGGACAGAGGAGCAGAGGGGATGGGGATCATGGGATATGGTATAGTTTCTGAACCTCAGGACAGGACAGTTCTAA | 9470 |
| | 4 | MDLF* | ATGGATCTCGTTTAA | 9472 |
| hsa-mir-15b | 1 | MAPFPKSRCL* | ATGGCTCCCTTCCCGAAGTCCCGATGCCTCTAA | 9474 |
| | 2 | MPRKGTQPSTARRREEGPPPSPDGASSDAEPEPPSGRT ESPATAAGE* | ATGCCCCGTAAAGCACTCCACGCCCCTCCACTGCCGCGGCGCAGAGAGGAAGGGCCCCGCGCCGCCTGACCGGCGCCAGCAGCGGGACCCGCCGAGCCTGAGCCTCGAGCGCCGTCCGGGCCGCACGGAGAGCCCAGCCACCGCCGCAGGTGAGTGA | 9476 |
| | 3 | MGASKRVQL* | ATGGGGCGGAGCAAACGGGTTCAGTGTGA | 9478 |
| | 4 | MVQVTNKNSISLLYSR* | ATGGTACACGGTCACAAACAAAATTCAATATCTTTATTGTATCCCGCTAA | 9480 |

Figure 1 (Continued)

| | | | | | |
|---|---|---|---|---|---|
| hsa-mir-16-2 | 1 | MAPFPKSRCL* | 9481 | ATGGCTCCTTCCCGAAGTCCGCTGCCTAA | 9482 |
| | 2 | MPRKGTQPSTARRREEGPPPPSPDGASSDAEPEPPSSGRT ESPATAAGE* | 9483 | ATGCCCCGTAAAGGCACCCAGCCCTCACTGCCGGCGCAGAGGAAGGCCGGC GCCGCCGTCCCTGACGGCGCCAGCACGCACGCGGAGCCTGAGCCGCCGTCCGGCC GCACGGAGAGCCAGCCACCGCGCCAGGTGAGTGA | 9484 |
| | 3 | MGASKRVQL* | 9485 | ATGGGGGCGAGCAAACGGGTTCAGTTGTGA | 9486 |
| | 4 | MVQVTNKNSISLLYSR* | 9487 | ATGGTACAGGTCACAAACAAAATTCAATATCTTTATTGTATTCCCGCTAA | 9488 |
| hsa-mir-17 | 1 | MYLIAKDFSTLFSYVFFNCKLLGF* | 9489 | ATGTATCTGATAGCTAAGGATTTTTCAACTTTATTCTCTTACGTATTTTCAACTGTA AATTATTGGGCTTTTAA | 9490 |
| | 2 | MDGHCC* | 9491 | ATGGATGGAATTAATTGCRGTTAG | 9492 |
| | 3 | MELIAVRRLENSKYRFGRW* | 9493 | ATGGAATTAATTGCYGTTAGGAGGTTGGAAATAGCAAATATAGATTTGGACGGTG GTAG | 9494 |
| | 4 | MFYLFFPYFSLFQSYTWT* | 9495 | ATGTTTTATCTTTTTTTCCTTATTTCCCTATTCCAGTCATACACGTGGACCTAA | 9496 |
| hsa-mir-181c | 1 | METPKITRYTQTYSTPINTQSKVMLTHTYSPHNNTATC VDTSPTRARTSRDSAH* | 9497 | ATGGAGACCCCAAAATTACACGTCTATACACAGATCACACACAGAGTCCGATTAATACG CAGTCGAAGTGATGTGACACACACATACACACAGACAATCCCCACACAACTGCCACGTGT GTAGACAGTCACCCACAGGGCTCGGACATCCAGGGATAGTGCCATTGA | 9498 |
| | 2 | MEPPTKAATT* | 9499 | ATGGAGCCACCAACGAAGGCAGCTACAACATAG | 9500 |
| | 3 | MSLRVAMTNADP* | 9501 | ATGTCACTCAGGTAGCAATGACAAACGCAGATCCCTAG | 9502 |
| | 4 | MCPPNQVHTCTLTVTHSHPHTHTHTHTHRRYKACRN TSDSRSHHFPFIYLFILRWSLSWLPRLECRGTISRIQAILL PQPPE* | 9503 | ATGTGTCTCCCAACCAAGTTCACACTGACACTGACAGTCACCCACAGTCACCCC CACCACACACACAGCAGGTCACACATCTTTTATTTTATTACTATTATTTTGAGA ATCTGACAGCAGGTCACACATCTTTTATTTTATTACTATTATTTTGAGAA TGGAGTCTCTCTTGCCTCAGGTTGGACATGCCGTGGCACGATCCCGGATTCAA GCAATTCTCTCTGCCTCAGCCTCCTGAGTAG | 9504 |
| | 1 | METPKITRYTQTYSTPINTQSKVMLTHTYSPHNNTATC VDTSPTRARTSRDSAH* | 9505 | ATGGAGACCCCCAAATTACACGCTATACACAGATCACACACAGAGCACCCCGATTAATACG CAGTCGAAAGTGATGTGACACACACATACACACAGACAATCCCCACACATTGCCACGTGT GTAGACAGTCACCCACAAGGGCTCGGACATCGAGGATAGTGCCATTGA | 9506 |
| hsa-mir-181d | 2 | MEPPTKAATT* | 9507 | ATGGAGCCACCAACGAAGGCAGCTACAACATAG | 9508 |
| | 3 | MSLRVAMTNADP* | 9509 | ATGTCACTCAGGTAGCAATGACAAACGCAGATCCCTAA | 9510 |
| | 4 | MCPPNQVHTCTLTVTHSHPHTHTHTHTHRRYKACRN TSDSRSHHFPFIYLFILRWSLSWLPRLECRGTISRIQAILL PQPPE* | 9511 | ATGTGTCTCCCAACCAAGTTCACACTGACACTGACAGTCACCCACAGTCACCCC CACCACACACACAGCAGGTCACACATCTTTTATTTTATTACTATTATTTTGAGAA ATCTGACAGCAGGTCACACATCTTTTATTTTATTACTATTATTTTGAGAA TGGAGTCTCTCTTGCCTCAGGTTGGACATGCCGTGGCACGATCCCGGATTCAA GCAATTCTCTCTGCCTCAGCCTCCTGAGTAG | 9512 |
| hsa-mir-182 | 1 | MRLFPNRGRPCLASLVWTPRGAERRLCAQPGAGAGECL GPGAGGRAGRSQSGAQ* | 9513 | ATGCGGCTCTTTCCAAACCGGGGCCCGTTTTGCTGGCTTCTCTGGTGTGGACTCCG CGGGAGCTGAGGCGGCTGTGCGCCCAGCCTGGAGCGGGCAGGTGAGTGTCT GGGGCCGGAGCGGGGGCGGGCGGGGCCCGGAGGGCCAGAGCCGGGGCTCAGTAG | 9514 |
| | 2 | MTRQCLLALPRLQAEAPTGRLGPGSASGVCPAFSAVPG RGRGRERLRSECGRCLRGAYPKGVWLGSGCVSPPWWA QAEAPGWEGAAESAGAPELAPPASCQGCAAGSRLLPWP GAAPPSLWGKAALRPPVCLLHFAATHPGNPGARE* | 9515 | ATGACGCGGCAGTGCCTACTCGCTCTTCCGCGCCTTCAGGCGGCAGGCGCCCACGGG GCGCCTGGGCGGGGGCTGGAGAGTTTGGCTGGGAGTCGGCGTTCGCGCCCTGGTCGGCT GCCTACCCGCGGAGGAGCTCCGCTCGCCAGGCGTCTGCCCAGTGCGCTGCGGCT CAGGGCGAAGGCCAGCTGGGAGGGGGCTGCAGCAGCTGCCAGTCCGCCGGAGC TGGCCCCTCCAGGTCTTGTCAGGGCTCGCAGGCGCTCGCTGGTTCGAGGCTGCTTCCGTGCC CCGGGAAGGCCGCCCTCCGGGCGCGTCGGGGGAAAGCGCTCTCAGAACGCGCTGTGCC TCCACTTCCGGCCACTCATCCCGGAACCCGGAACCCGGGAAGCCCGGGGCACGCGAATGA | 9516 |

Figure 1 (Continued)

| | | | | | |
|---|---|---|---|---|---|
| hsa-mir-183 | 3 | MRHRSPPSTAPFLLIALVAPRFPALPQDRRLDGLPLAPH RSAHPRTMGSEGVTRGQGSPDSTVSSRLSHSFALPTRAP GHRVQ* | 9517 | ATGAGACACCGTTCCCGCCCTTCCCGCCCCATTCCTGTTAATAGCGGCTAGTGGCA CCCAGGTTCCCAGCCTTCCCAGCCGCCATCCCAAGGACTATGGGCAGTGGCTCCT CACGGGTCAGCGCCATCCACGGTTCCTCCAGCCTGTCCAGGTGAGGGTGTCACCCGGCGGTCACCCGG GTGCCGGTCAGCGCCATCCACGGTTCCTCCAGGCAGTGAGGGTGTCACCCGGCGTCAGGG GCTCCCGGACACCGTGTACAGTAA | 9518 |
| | 4 | MGTESADL* | 9519 | ATGGGCACCGAGTCGGCGGATCTCTGA | 9520 |
| | 1 | MRLFPNRGRFCLASLVWTPRGAERRLLCAQPGAGAGECL GPGAGGRAGRSQSGAQ* | 9521 | ATGCGGCTCTTTCCAAACGGGGGCGTTTTGCCTGGCTCTCTGGTGTGGACTCCG CGGGGAGCTGAGAGGCGTGTGCCAGCCTGGCGCAGGCGCAGGTGAGTGTCT GGGGCCGGGAGCGGGGCGTGGCCGCGGAGCCGGAGCCAGCGGGGCTCAGTAG | 9522 |
| | 2 | MTRQCLLALPRLQAEAPTGRLGPGSASGVCPAPSAVPG RGRGRERLRSECGRCLRGAYPRGVWLGSGCVSPPWWA QAEAPGWEGAAESAGAPELAPPASCQGCAAGSRLLPWP GAAPPSLWGKAALRPPVCLHFAATHPGNPGARE* | 9523 | ATGACGCGGCAGTGCCTCCTGGCTCTGCCTCGGCTCCAGGCAGCGAGGCCGCCACGG GCGGGAGCTGGGCCGGAGCGCGTCCTGCCGAGTGCGCCAGCGCCGATGCTGTTCCGG GCTACCCGCGAGGAGTTTGGCTGGGCTGTGGGCTGCGTTTCGCGCGCCTGTGGGCT CAGGGCGGAAGCGCCAGGTCCAGGCTGGAGAGGCGTGCGGAGAGCGGCCGGAGC TGGCCCTGCAGTCTGTCAGGCTGGGCCAGTCGCGGCTGTTCGAAGCTGCTTCCGTGCC GCCCCTGCAGCGCCCCGCCCAGTCTCTGGGGAAAGCGGCCCTCTCAGACCTCCCGGTGCC TCCACTTGCGCGGCCACTCATCCGGGAACCCCGGCGCACGGCGAATGA | 9524 |
| | 3 | MRHRSPPSTAPFLLIALVAPRFPALPQERRLDGLPLAPH RSAHPRTMGSEGVTRGQGSPDSTVSSRLSHSFALPTRAP GHRVQ* | 9525 | ATGAGACACCGTTCCCGCCCTTCCCGCCCCATTCCTGTTAATAGCGGCTAGTGGCA CCCAGGTTCCCAGCCTTCCCAGCCGCCATCCCAAGGACATCGGGCAGTGGCTCCT CACGGGTCAGCGCCATCCACGGTTCCTCCAGCCTGTCCAGGTGAGGGTGTCACCCGG GTGCCGGATTCCTCCAGCCTGTCCAGGTGAGGGTGTCACCCGGCGGTCACCCGG GCTCCCGGACACCGTGTACAGTAA | 9526 |
| | 4 | MGTESADL* | 9527 | ATGGGCACCGAGTCGGCGGATCTCTGA | 9528 |
| hsa-mir-185 | 1 | MPRALLEGVFDNPRWHGMRGTLAGGTRLAAGRLRSAG LGAAWSLQGVWAARPWPASGTALAPGHSAPYPRPAAG QQGDS* | 9529 | ATGCCCCGGCGGTTACTGGAAGGTTGTTGATAATCCCCGTCGACTGGCACGGGATCGGA GGGACTCTGGCAGGTGGAAGCGAGATCTCGGCGTGAGATCGGCAGCATCAG GGGAGCTGCGTGGTCCTGCAGGGTCGGCCGCGCGTTGGCCAGCATCAG GGACAGCTCTGCGCCGGTCACTCGCCCGCGCCTGCTGCGGCCCCCAGCAGCAGTCAG AGGGTGACAGCTAA | 9530 |
| | 2 | MRPSWGGLGS* | 9531 | ATGCGGCCTTCCTGGGGAGGTTTGGGTAGTTAG | 9532 |
| | 3 | MSHALPWPGLFALSCGSRPADHCFAAILGTYPSSMRQ M* | 9533 | ATGTCACATGCCCTGCCTGGCCTGCCTGGCCTGGCCTGTGCACTGCCTGTGCACTGGCCACATGCC CGTGACCACTGTTTGCTGCCACTCGGGACACAGTGCCCTCTCCATGA | 9534 |
| | 4 | MPCPGQACLHCRYALDLLTTVLLPLWAQCPLP* | 9535 | ATGCCCTGCCCTGGCCAGGCCTGTCAGCCTGTGTGTTGCACTGTCGTGTGCTAGACCTGCTGACC ACTGTTTTGCTGCCACTCGGACACAGTGCCCTCTCCATGA | 9536 |
| | 1 | MSTKNFRVSDGDWICPDKK* | 9537 | ATGTCGACCAAGAATTTCCGAGTCAGTGACGGGACTGGATTGCCCTGACAAAA GTGA | 9538 |
| hsa-mir-186 | 2 | MIFCALRRVEAAMRQFPGGKKAPNLLTREVFPGAFVLD MSSAFPRHYLRKVASLFRVRDGLPFCPHPPPPRPGFSD RKPLQSGQLGVGSPPRDFSLQNFTLVHGKYCFLALVLLP LIVHLVLYFYSNFSSILFSPFFEALPSSVWEILTFSLWIISP QELGFSPP* | 9539 | ATGATTTTCTGTGCCTTAAGACGGGTTGAGGCGGCGAACCGCCAGTTCCCTGGCGGG AAGAAGGCTCCAATCTCCTCACGAGAGAGGTCTTTCCGGGAGCCTTTGTTCTAGAT AGTGTTCAGCGTTTCTGGCCCTACGATTACCTCGCAAGGTAGCCTCTCTTTAGAGTGC GAGATGCGTACCTTTTGACCCGCAGCTTGGTGTTGGAGATCCCCCAGGTTTAGCG ATAGGAAACCTCTCCAGTCAGCCAGCTTGGTGTTGGAGATCCCCCAGGTGACTTTT CTCTGCAGAACTTTACTCTTGTTCACGGAAAATATTGCTTTCTGCACTCGTCTTTT GCCTCTATAGTTACCTTGTTTGTATTTACTCAACCTTTCTCCACTATTTT CCCTTTTCCGGAAGCTCACCCTCTTGGTTGGGAAATTCTGACATTTCTTTGTG GATCATTTCCCACAAGAATTGGCGTTTCTGCCTCTTAG | 9540 |

Figure 1 (Continued)

| | | | | |
|---|---|---|---|---|
| | 3 | MAYLFAPTHLPRPGQVLAIGNLSSQASLVLDLPHVTFLCRTLLLPTENIAFSHSSFCLL* | 9541 | ATGGCCTACCTTTTGCCCCACCCCTCCCCGCCCCGGCCAGGTTTAGCGATAGGAAACCTCTCCAGTCAGGCAGTTGGGTGTTGGATCTCCCACGTGACTTTCTGCAGAACTTACTCTGTTCACGGAAAATATTGCTTCTCGCACTCGTCCTTTGCCTCTTATAG | 9542 |
| | 4 | MPAAEKHVC* | 9543 | ATGCCTGCAGCAGGAAGCACGTGTGTTAG | 9544 |
| hsa-mir-18a | 1 | MYLIAKDFSTLFSYVFFNCKLLGP* | 9545 | ATGTATCTGATACTAAGGATTTTCAACTTATTCTCTTACGTATTTTCAACTGTAAATTATTGGGCTTTAA | 9546 |
| | 2 | MDGNCC* | 9547 | ATGGATGGAATTAATTGCTGTTAG | 9548 |
| | 3 | MELJAVRRLENSKYRFGRW* | 9549 | ATGGAATTAATTGCTGTGTTACGGAGGTTGGAAATAGCAAATATAGAATTGGAACGGTTGGTAG | 9550 |
| | 4 | MFYLFPYFSLFQSYTWT* | 9551 | ATGTTTTATCTTTTTTTCCTATTTCCAGTCATACACGTGACCTAA | 9552 |
| | 1 | MGQGGSECAILARMPVAPAPAPATASAWAAVPGAPLIKDSSLGEFRRENAIDCGPPVGNWGGSVGFSLWRGGGSVS* | 9553 | ATGGGACAAGGTGGTAGTGAGTGCGCCATCCTGGCCCGGATGCCGGTGGCACCGCACCGGCTCCGGCCACGCCGTCCTGCCTGCTGGCCGTGTCCAGGCGCGCCTTTAATTAAGGACTCCAGTTGGGGAAGAGAGAAGGGAAAATGCCGACTGCGGTCCGCCGGGGGTAACTGGGGCTCGGTCGGTGGGGTTTCGGTTTGGCGGGTAACTGTTCCGTTTCCTAA | 9554 |
| hsa-mir-18b | 2 | MPTAVRPWVTGARWGFRFCGGVGYPEPNSCAGRVGGGGLFSLGY* | 9555 | ATGCCGACTGCGCGTCCGCGGTCCGCCCCGTGGTAACTGGGGCTCGGTGGGTTTCGCTTGGCGGGTGGGGTTTCGGTGGGAGGGGCTTTTCTTGGGGCTATTAA | 9556 |
| | 3 | MCARGLDPFSGRFFSLLPPFWLRGRLRSHPAPERSSCALGHWVYVWRGHPERAARAGSPRSPPARGGPELGPARGFPSGWLGKKGALRWGSCDPVELTGWVGGIDGAGGT* | 9557 | ATGTGCGCTCGCGGGGACCTGCCGGAGACTGATCCATTTAGTGAGCGCTTTTCTCACTTCTCTCCCTCTGGACACTGGGTATACGTGGAGGCCACCCCGGAACAAAGGGCCCCGTGCGAGATCCCCGCGCTCTCCAACTTGCGAAGGGACCAGGTTCCCGAGCTCCTCGTTGGGCAGCGTGATCGGTAGAGGTTGACTGGGTTGGGAGGGGAAGCCGGGGGACTTGA | 9558 |
| | 4 | MRGCTWREKRDSPPSWLLSHQPGNGGGGRRGLGAFLVL* | 9559 | ATGAGGGGGTGCACGTGGAGGTGGAGCGGAAAAAGGGACTCCCTCCTCTTGGCTTCTATCCCACCAACCGGGAATGGAGGGGAGGGAGGCGTGGGCTTGGCGCGTTTTGGTGCTTTGA | 9560 |
| | 1 | MGGF* | 9561 | ATGGGCGGGTTCTGA | 9562 |
| | 2 | MWPQGE* | 9563 | ATGTGGCCCCAGGGCGAGTGA | 9564 |
| hsa-mir-191 | 3 | MGCP* | 9565 | ATGGGTGCCCTGA | 9566 |
| | 4 | MGVDVGEPRLVAISGTLGRIGEGGWTQDLWVGLQW* | 9567 | ATGGGTGTAGACGTGGGAGAGCCGAGGCTGGTGGCATCTGGAACCTGGAACCTGGGGAGCGAGATCAACTGGCGATTGGGCGAGGAGGGTGGACCCAGATGCCTCTGGGGCTGCAATGGTAG | 9568 |
| | 1 | MGAEGWVFAGEMRVSDQLAYKVPVLGPRDQRLLPGPRPRPASSRAGVRSGQAASQVHAGEGVVRCARPGCVR* | 9569 | ATGGGAGCTGAGGGCTGGGTCTTTGCGGGCGAGATGAGAGTCTCGGATCAACTGGCCTACAAAGTCCCAGTTCTGGCCCCGGGACCAGCGTCTTCTCCCGGGCCTCGCCCCAGGCCGGTCCTCTCCTCCGGGCTGCTCCGGCCAGGTGCATGCTGGAGAAGGAGGTGTAAGGTGCGCTGCCGCCGCCTGCGTGCGGTGA | 9570 |
| hsa-mir-193a | 2 | MGQALPLTEACPAVLSRAATLSLGVGRTGPDF* | 9571 | ATGGGCCAAGCCTTGCCACTTACCGAGGCCTGCCCTGTGCTGTTCGCGGGCTCTTTGTTCCCTGA | 9572 |
| | 3 | MDLCGCVPNGRSFVP* | 9573 | ATGGATCTTTGTGATGTTCCAATGGCCGGTCTTCCCTGACCGATCAACATAA | 9574 |
| | 4 | MCSQWPVFCSLTDAT* | 9575 | ATGTGTTCCAATGGCCGGTCTTCCCTGACCGATCAACATAG | 9576 |
| | 1 | MRRKGAWGSGLSRT* | 9577 | ATGAGGAGGAAAGGTGCGTGGGGGAGTGGCTTTCCAGAACCTAG | 9578 |
| hsa-mir-193b | 2 | MEHSPNLGAQQJ* | 9579 | ATGGAAATCATTCCCCAACTTGGGCGCGCAGCAAATTTGA | 9580 |
| | 3 | MRDD* | 9581 | ATGAGAGACGATTAA | 9582 |

Figure 1 (Continued)

| | | | | |
|---|---|---|---|---|
| | 4 | MGWGELYEAPRTPDLSAAKGRLGHPSCCPGSF* | 9583 | ATGGGGTGGGGGAACTGTACGAGGCAACCTCGGACACCCGATTTATCCGCTGCTAA GGGACGTTTGGGGCGTCACCCCTCGTGTTCCGGGAAGCTTTAG | 9584 |
| hsa-mir-195 | 1 | MSKPPHRPEFPSSRFLSCSFMHSNKDTLRSEGEGPGPDIQ PRGPWSAIPGQLYTLPSPNPGSFCLAAGFSSSTPSFNELC LACPQCLPKQNMRV* | 9585 | ATGTCAAAGCCACACCTCAGTTCCATCGTCCTGAATTCCAGTTCCGGTTTCTCAGCTGTCTT TCATGCATTCAAATAAAGACACACTCCGGTCTGAAGGGGAGGGCCCCGGCCTGAT ATCCAGCCCGTGACAATGTCGGCCATTCCTGCCTGCCAACTGTACACTCCCAGC CCAAATCGGGAGAGCTTCTGCCTGCCGCCAATGTCTCCGCAGCTGATTCAGCTCTACACCCTTCTCCA AATGAGCTTTGCCTGCCACCCTGCCCCGAAACAAATATGAGGGTGTGA | 9586 |
| | 2 | MVGHSWPTVHSPQPKSGELLPCSWIQL* | 9587 | ATGGTCGGCCATTCCTGGCCAACTGTACACTCTCCCAGCCAAATCGGGGAGCTT CTGCCTTGCAGCTGGATTCAGCTCTAG | 9588 |
| | 3 | MSFALPARNVSRNKI* | 9589 | ATGAGCTTTGCCTTGCCTGCCGCAATGTCCGTAAACAAATATGA | 9590 |
| | 4 | MSPETKYEGVIHAHLSDQGLQIRVVKPPPALSPSSLFSLL VYPTQF* | 9591 | ATGTCTCCGGAAACAAATATGAGGGTGATACATCTGATCAGGGACTTCAGATCAGGGA CTTCAAATTAGGGTCGGATCCCCGTCCTGCCATCTCTCAGATCAGGGA TTCTCGTTTACCCCACCCAATTTTAA | 9592 |
| hsa-mir-196a-2 | 1 | MGVGVWLVCVSSPHSPHTSHTAPCSPCKVKIESIRL* | 9593 | ATGGGGTGGGAGTTGGCTGGCTGTGTGTTCAAGCCCTCACTCACCACGACTCA CACACAGCATTCGTCTCCATGCAAAGTTAAGATCGAATCCATCCGCTGTAG | 9594 |
| | 2 | MSLPPSRSKNLLEVSYLYCFLLFSHPS* | 9595 | ATGTCTTACCTCCCAGTCGCTCTAAGAATCTGCTTGAAGTCTGCTGTATTGTACTGCT TCTGCTTTCTCCCACCCCTCCTAG | 9596 |
| | 3 | MPPPPM[IVLSLSGSCVI* | 9597 | ATGCCCCCCCCAAATGTCGTCCTGTCCCTGTGGAGTTGTGTTATTTAA | 9598 |
| | 4 | MLYLLHVASLMEKKPNKFPES* | 9599 | ATGTTGTATCTTTTGCATGTAGCTTCCTTAATGGAGAAAAACCTAATAAATTT CCAGAATCATAA | 9600 |
| hsa-mir-196a | 1 | MYLIAKDFSTLFSYVFFNCKLLGP* | 9601 | ATGTATCTGATAGCTAAGGATTTTCAACTTTATTCTTACGTATTTTCAACTGTA AATTATTGGGCTTTAG | 9602 |
| | 2 | MDGNCC* | 9603 | ATGGATGGAATTAATTGCTGTTAG | 9604 |
| | 3 | MELIAVRRLENSKYRFGRW* | 9605 | ATGGAATTAATTGCTGTTAGGAGAGTTGGAAATAGCAAATATAGATTGGACGGTG GTAG | 9606 |
| | 4 | MFYLFFPYFSLFQSYTWT* | 9607 | ATGTTTTATCTTTTTCCTTATTTCTCAGTACACGTGGACTAA | 9608 |
| hsa-mir-196b-1 | 1 | MYLIAKDFSTLFSYVFFNCKLLGP* | 9609 | ATGTATCTGATAGCTAAGGATTTTCAACTTTATTCTTACGTATTTTCAACTGTA AATTATTGGGCTTTAG | 9610 |
| | 2 | MDGNCC* | 9611 | ATGGATGGAATTAATTGCTGTTAG | 9612 |
| | 3 | MELIAVRRLENSKYRFGRW* | 9613 | ATGGAATTAATTGCTGTTAGGAGAGTTGGAAATAGCAAATATAGATTGGACGGTG GTAG | 9614 |
| | 4 | MFYLFFPYFSLFQSYTWT* | 9615 | ATGTTTTATCTTTTTCCTTATTCCAGTCATACACGTGGACCTAA | 9616 |
| | 1 | MGQGGSECAILARMPVAPAPATASAWAAVPGAPLIK DSSLGEFRRENADCGPPVGNWGSVGFSLWRGGGSVS* | 9617 | ATGGGACAAGGTGGTAGTGAGTGCGCCATCCTGGCCCGGATGCCGGTGGCCACCGC ACCGGCTCCAGCTGGGAAGAAGGAAGGAAATGCCGACTGCGGTCCGCCCGTGG GTAACTGGGGCTCGGTGGGGTTTCGTTGCCGGGGTTCGTTCCTAA | 9618 |
| | 2 | MPTAVRPWVTGARWGFRFGVGVPFPNSCAGRVGGG GLFSLGY* | 9619 | ATGCCGACTGCGGTCCGCCCGTGGGGCTGTACCTGGGCTGTGGTGGCTCGGGTGGCGG GGGGTGGGGGTTCCGTTCCGTAATTCCGTGTCGTAATTCCTGTCGCCCTTTGCTTTGC TTTTCCTTGGGCTATTAA | 9620 |

Figure 1 (Continued)

| | | | | |
|---|---|---|---|---|
| hsa-mir-19b-2 | 3 | MCARGLDPFSGRHFSLLFPWLRGRLRSHPAPERSSCAL GHWYVWRGHPERAARAGSPRSPARGGPELGPARGF PSGWLGKKGALRWGSCDPVELTGWVGGDGAGGT* | 9621 | ATGTGCGCTCGCGGCCTTGATCCATTTAGTGACGCTTTTCTCACTTCTCTCCCT TCTCGCTCCGCGCGGAGACTGCGCTCGCACCGGCCCGGAGCGCTCGAGCTGCGCG CTGGGACACTGGGTATACGTGTGGAGGGGACACCCGGAGCGAGGGCGGCCGGTGCGGG ATCCCCGAGCTCTCCAACTGGCTGGGCAAGAGGAGCCCGGGCCGGGCCTGGTCCCGCGCGCGGTT TCCCGAGCGGGTGCTGGGCAAGAGGAGCCTTCGTTGGGGCAGTGTGATCCG GTAGAGTTGACTGGTTGGTGGTGGGAGAGCGGGACTTGA |
| | 4 | MRGCTWREKRDSPPSWLLSHQPGNGGGRRGLGAFLV L* | 9623 | ATGAGGGGTGCACGHGAGtGGAAGGGAAAAAAGGACTCCCCTCCTTGGCTTCTATCC CACCAACCCGGGAATGGAGGCGGAGGGAGGCGTGGCTTGGCGCGTTTTGGtGCT TTGA |
| | 1 | MGCRQPGQRPGELRSLQTQAGAGPSPPQGKVGPCADA AGFRVWSHLGPTGCVFRARAQCVGSRHGVPSGQGLGR GQAPRGVTFLPPT* | 9625 | ATGGGCTGTCGCCAGCCTGGCCAGCGTCCAGGGGAGCTCAGGTCACTGCAGACACA GGCTGGAGCGGGTCCTTCCCCCCCAGGGAAAGTGGCCCCTGCGCAGATGCGG CTGGGTTTCGGGTGTGGAGCTCATCTTGGACCACAGGGCTGTCTTCGGGCACGGG CACAGTGTGTGGGCTCCAGGCATGGGGGGTGCCTCAGGGCAGGGCCTGGGCAGAGGG CAGGCTCCGAGAGGGGTCACGTTCTTGCCGCTACCTGA |
| hsa-mir-200a | 2 | MRLGFGCGAILDPRAASSGHGHSVWAPGMGCPQGRAW AEGRLREGSRSCRLPDSRPSRKFSPEAATAVLRHFVRRR EAVASEVGA* | 9627 | ATGCGGCTGGGTTTCGGGTGTGAGCCATTCTGGACCCAGGCTGCGTCTTCCGGG CACGGGCACAGTGTGTGGGCTCCAGGCATGGGGTGCCCTCAGGGCAAGGGCCTGGGC AGAGGCAGGCTCCGAGAGGTCAGGGTCACGTTCTTGCCGCTACCTGACAGCAGGCTT CTAGAAAGTTCTCTCGCCCTCGAAGCAGCTCTGAGGCACTTTGTGCGGAGAC GGGAAGCTGTCGCCTCAGAGGGTGGGTGCGTAG |
| | 3 | MTASPLGSGVCGGKGLVSAPSGQRPAEPMCGGEVGAWG RGWSGTGAQPGEAGAGSQAPRYDWGGGNVSREVFY LNVKRLSTVAAAGNKVRPTEAQP* | 9629 | ATGACCGCGTCTCCTTGGCTCTGAGCCCGGAGTCGCGGTGGGAAGGGCTTGGTTTCAGCA CCCTTCTCAGAGGGTACAGTGGGCCGGCCATGGGCGGTGAGAAGCTGGAGCCGGTTCCAAGG TGGCTGGTCTGGTACAGTGGGGTGGGGCAACGTCTCTGAGGTTTTTACTTAAATG CCCCGCTATGACTGGGGGTGGGGCAACGCCGGGAACAAGGTCCGACCCACCGAGGCC CAGCCTTGA |
| | 4 | ATGACTGGGGTGGGGTGCAACGTCTCTCGTGAGGTTTTACTTAA | 9631 | |
| | 1 | MGCRQPGQRPGELRSLQTQAGAGPSPPQGKVGPCADA AGFRVWSHLGPTGCVFRARAQCVGSRHGVPSGQGLGR GQAPRGVTFLPPT* | 9633 | ATGGGCTGTCGCCAGCCTGGCCAGCGTCCAGGGGAGCTCAGGTCACTGCAGACACA GGCTGGAGCGGGTCCTTCCCCCCCAGGGAAAGTGGCCCCTGCGCAATGCGG CTGGGTTTCGGGTGTGGAGCTCATCTTGACCACAGGGCTGTCTTCCGGGCACAATGCGG CACAGTGTGTGGGCTCCAGGCATGGGGGTGCCTCAGGGCAGGGCCTGGGCAGAGGG CAGGCTCCGAGAGGGGTCACGTTCTTGCCGCCCTACCTGA |
| hsa-mir-200b | 2 | MRLGFGCGAILDPRAASSGHGHSVWAPGMGCPQGRAW AEGRLREGSRSCRLPDSRPSRKFSPEAATAVLRHFVRRR EAVASEVGA* | 9635 | ATGCGGCTGGGTTTCGGGTGTGGCTCAGTTCTTGGACCACAGGCTGCGTCTTCCGGG CACGGGCACAGTGTGTCCGAGAGGCAGGTCATGGGGTGCCGCTACCTGACAGCAGGCTT AGAGGGCAGGCTCGAGAGGTTCTCCXAGAAGCAGCAGCGCCGTCGTGAGCACAGGGAGAC CTAGAAAGTTCTCTCCAGCAGCTCTGAGGCACTTTGTGCGGAGAC GGAAGCTGTCGCCTCAGAGGTGGTGCGTAG |
| | 3 | MTASPLGSGVCGGKGLVSAPSGQRPAEPMCGGEVGAWG RGWSGTGAQPGEAGAGSQAPRYDWGGGNVSREVFY LNVKRLSTVAAAGNKVRPTEAQP* | 9637 | ATGACTGCGTCTCCTTGAGTCTCGGGTGGAAGGGCTTGGTTTCAGCA CCCTTCTGGTCAGAGGTTACAGTGGGCCGGCCATGGGCGTGAGAAGCTGGAGGTCG TGGCTGGTCTGGTACAGTGGGGCTCAGCCGGAGAAGCTGGAGCCGGTTCCAGG CCCGCGCTATGACTGGGGTGGGGCAACGTCTCTGAGGTTTTTACTTAAATG TGAAACGGCTCAGTACGGTGGGCCAGCCGGGAACAAGGTCCGACCCACCGAGGCC CAGCCTTGA |
| | 4 | MTGVGATSLVRFFT* | 9639 | ATGACTGGGGTGGGGTGCAACGTCTCTCGTGAGGTTTTACTTAA |
| | 1 | MGARDLQLFRRDPGPEAA* | 9641 | ATGGGAGCCAGGGATCTGCAGCTTTTCCGCAGGGATCCTGGCCTGAAGCTGCCTGA |

Figure 1 (Continued)

| | | | | | |
|---|---|---|---|---|---|
| hsa-mir-200c | 2 | MMEAPVPVSATSLASGPQPLAGCSPLPTSHAPRKPLVLS* | 9643 | ATGATGGAGGCCCGTCCTGTCGCTGTCAGCAACATCCATCGCCTCAGGTCCCAGCCC TTAGCTGGCTGCAGCCCCCTCCCCACTTCCCACGCACCCGGAAGCCCCTCGTCTTG AGCTGA | 9644 |
| | 3 | MGPSPSSHPVRFVTWWIQNPQSTLSLGLARPLSRDLTW PVARVPCSNW* | 9645 | ATGGGCCCCAGCCTCCTCCCACCAGTGCGATTTGTCACTGGTGGATCCAGAAC CCACAGTGACCTTGAGCTTGGGGTTGGCTCGCCCCTCTCAAGAGACCTCACCTGG CCTGTGGCCAGGGTCCCGTGAGCAACTGGTGA | 9646 |
| | 4 | MAPGWVLSAVTFREP* | 9647 | ATGGCTCCCGGGTGGGTTCTCGGACAGTAACTTCAGGGAGCCCTGA | 9648 |
| | 1 | MGQRRCRRRIWSR* | 9649 | ATGGGTCAAAGGCGGTGCAGGAGGAGGATCGGTCCAGATAA | 9650 |
| | 2 | MNQSSPHYPDLCLPTSPVFTLAKSLYIQTKESVTPSQH* | 9651 | ATGAACCAGTCTTCTCCCCTCACTTACCCAGATCTGCCTGCCAACAGCCCGTGT TCACCCTGGCAAAGAGTCTTTACATTCAGACCAAGGAGAGTGACTCTTCTCAGC ACTAG | 9652 |
| hsa-mir-205 | 3 | MPERLDAWGGATYEKLPCFGSEQAPGRKYFKQQGAS APTHPACMLVLRTAFYGACTEPWACLNTTRKRPEQQQ HAKG* | 9653 | ATGCCCAAGAGCTAGATGCGTGGGGAGGAGCCACATACGAGAAACTGCCTCCTG CTTCGGGTCAGAACAAGCCCAGCCTGAGACCTTCAAACAACAAGGTGCATCTG CCCCAACCATCCAGCTGCATGTTGGTCTGAGAACAGCCTTTATGGGCTTGCA CTGAGCCATGGCATGTCTGAACACAAGGAAGAGGCCAGAGCAGCAACAGCAC GCAAAGGGTGA | 9654 |
| | 4 | MRGEEPHTRNCLPASGQMKPQEESISNMKVHLPQPIQPA CWC* | 9655 | ATGCGTGGGGAGGAGCCACATACGAGAAACTGCCTCCGTCTTCGGGTCAGAACAA GCCCCAGGAAGAGAAATATTCAAACAACAAGGTGCATCTGCCCCAACCCATCCAGCCC TGCATGTTGGTGCTGA | 9656 |
| | 1 | MYLIAKDFSTLFSYVFFNCKLLGF* | 9657 | ATGTATCTGATAGCTAAGGATTTTTCAACTTTATTCTCTTACGTATTTTTCAACTGTA AATTATTGGGCTTTTAA | 9658 |
| | 2 | MDGINCC* | 9659 | ATGGATGGAATTAATTGCTGTTAG | 9660 |
| hsa-mir-20a | 3 | MELIAVRRLENSKYRFGRW* | 9661 | ATGGAATTAATTGCTGTTAGGAGAGTTGGAAAATAGCAAATATAGATTTGGACGGTG GTAG | 9662 |
| | 4 | MPYLFFPYFSLFQSYTWT* | 9663 | ATGTTTTATCTTTTTTCCTTATTCTGTCCTATTCCAGTCATACACGTGACCTAA | 9664 |
| | 1 | MGQGGSECAILARMPVAPAPATASAWAAVPGAPLIK DSSLGEERRENADCGPPVGNWGSVGFSLWRGGGGSVS* | 9665 | ATGGGACAAGGTGGTAGTGAGTGCGCCATCCTGGCCCGATGCCGGTGCCACCCGC ACCGGCTCCGGCCACGGCTCTCGCAGGCCCGTCCCAGGCGCGCCTTTAATTAA GGACTCCAGCTTGGGGAAGGAAGAAATGCGACTGGCCGTTCGCCGTTGG GTAACTGGGGCTCGGTGGGTTTCGCTTTGGCGGGTGGGGTTCCGTTTCCTAA | 9666 |
| | 2 | MPTAVRPWVTGARWGFRFGGVGVPFPNSCAGRVGGG GLFSLGY* | 9667 | ATGCCGACTGCCGTCCGCGTCCGGTTCTGAACTGGGCTCGTGGGGTTTTCGTTTGGC GGGTGGGGTTCCGTTTCCTAATTCCGTGTGCCAGGGGTGGGCGGGGCGGGCT TTTTTCCTTGGGCTATTAA | 9668 |
| hsa-mir-20b | 3 | MCARGLDFFSGRFFSLLFPFWLRGRLRSHPAPERSSCAL GHWVYVWRGHPERAARAGSPRSPPARGGPELGPARGF PSGWLGKKGALRWGSCDPVELTGWVGGDGAGGT* | 9669 | ATGTGCGCTCGCGGCTTGGACTTCTTCAGTGGACGCTTTTTCACTCTTCCCT CTGGGACACTGGTATACGTGTGGAGGGGACACCCGGACGCGGCCCGTGCGGG ATCCCCGCGCTCTCCACTCGCGGGCGGACGCCGAGCTGGTCCCGCGCGGTT TCCCGAGCGGTGACTGGTTGGGTGGGGACGCGGACGGAGGGGAGGGCGGGACTGA | 9670 |
| | 4 | MRGCTWREEKRDSPPSWLLSHQPGNGGGGRRGLGAFLV L* | 9671 | ATGAGGGGGTGCACGTGGAGGGAATGGAGGGGGAGGGGAGGGACTCCCTCTTGGCTTCTATCC CACCAACCCGGGAATGGAGGGGAGGGGAGGGGCGTGGGCTTGGCGGTTTTTGGTGCT TTGA | 9672 |

Figure 1 (Continued)

| | | | | |
|---|---|---|---|---|
| hsa-mir-210 | 1 | MDGVCLSGQQGRRVGVSEIRGLCCPPLGGAEAGPDTL LEGTFFSSLCVQGTSVRSSCCQAEGGRPGQAQVWSYLQPT GPSSGGPPLGTSYGKRVTDLVLLCVSAASVGPLRETAG GSSSSLSAEPAFSSLLLKSGPGRVRAYRPCLRSPGLQELR AAPARWRGRGRFSGRLAWTRTGLWKLPALTGLPVTTA K* | 9673 | ATGGACGGGGTGTGCCTGTCTGGCCAGCAGGGACGGCGGTGGGGTAAGCGAAAT CATTCGGGGGCTTGCTGCCTCCGCTGGTGTCCCCTTCTTTCTTTGTGTCCAGGTACCAGGGGCTGGGTGGGCTGGGGTA AGGACCATCCCGAGGGCCACTCTGGGACTTCCTACGGGACAAGAGAGTGACAG ATTTGGTGCTTCTGTGTTTCTGCCGCTTCAGTGGGCGCTGCGGGAGACAGCCG GTGATCCTCCAGCAGCCTGTCGCAGCTACAGGCCTCTGTCTGCCTTCAAGTCTACTGTTAAAT CAGGAGGCTGCTCACCTGCTGCTGGAAGAGGGCAGAGGACAGATTTAGTGACGCCTG GCATGGACTCGGACTGGCCTTTGGAAGCTCCCGCTGACGGGGTTGCCTGTCACC ACTGCGAAGTGA | 9674 |
| | 2 | MDSDWPLEAPCPDGVACHHCEVRLGRTCT* | 9675 | ATGGACTCGGACTGGCCTTTGGAAGCTCCCGCTGACGGGTTGCCTGTCACCAC TGCGAAGTGAGGCTTGGCAGGAACTGCACCTGA | 9676 |
| | 3 | MSRNSGRGGSQRRPSIQPGSALCPYLHQVGSLPCIAWGL AGLGPALLWWMFSGSPAPPHYNTVFNIVFKVQFKIQ K* | 9677 | ATGAGTAGGAACTCTGGCGAGGAACTACACCAGGTGGATCCTGCCTGCATTGGGG CTGCCCTCTGGCGCCCTTGGGCCGCCTCGCCGCTGACTTACACCAGGTGGGAACTGATGTTTCAGGGAGCCAGCC ATTGGCTGGGCTTGGGACCCCGCGCTGGTGGAACTGATGTTTCAGGGAGCCAGCC CTTCCTCATGTCAACACAGTTCACAATATAGTTTCAAAGTACAGTTAAAACTCAA AAGTAA | 9678 |
| | 4 | MSTQFTI* | 9679 | ATGTCAACACAGTTCACAATATAG | 9680 |
| hsa-mir-212 | 1 | MPWHLTHSLSHVSP* | 9681 | ATGTTCTGGATCCATCTTACCCACTCCCTCCCATGTCTCCCATAG | 9682 |
| | 2 | MSPHSHLTLEAVRSQRGKRRPPELPVSREGGPRHLARGT CCGLRWKLRSVEGRWRGSS* | 9683 | ATGTCTCCCATAGCATCCTCACTTTAGAAGCAGTGAGGTCCAAAGAGGAAAACGG AGGCTCCAGGACAGAGCATCCCGGTCTAGGAAGGCGACCGACATCTCGCCGAGG GACGTGCTGGGCCTGAGGTGGAAGTTACGAGGTGTTGAGGGAGGTGGAGAGCT CCTCATAA | 9684 |
| | 3 | MNRSSTEQEGICE* | 9685 | ATGAATAGGAGTTCTTCTACCGAGCAGGAAGGCATTGTGAATAA | 9686 |
| | 4 | MQGLSDPISFHFSLFEDRVRSPTPDFQRAPPPHYSCAVESV HC* | 9687 | ATGCAGGGCCTCTCTGACCCCATCTCTTTCATCTTTTCTCTTTTTGATAGAGTCAGAT CCCCCACCCCAGACTTCCAAAGAGCCCTCCCGCCCATGTATCTGTGCAGTGGAGT CTGTGCATTGCTAA | 9688 |
| | 1 | MCGRGGGQD* | 9689 | ATGTGCGGGGGATTAGGGGAGGGGCAGGATTAG | 9690 |
| | 2 | MNQPMKGAGESRREGACKRRRKGRGVCANRLWRPHK DWPRTEGEDREVGGNWGGRGHPLLPCPRDRPPPGSR SPSPGASARAGTRCPSGSLTAPHPLALYPSHSLHSMGIA LPLLFPPHPLRLL* | 9691 | ATGAACCAGCCGATGAAAGGGGCTGGAGAGAGCAGGAGGGAGGCTGGAAGAG GGAGGAGGAAGGGGACTGGAAGGGAGAGGGAGGCTGCGGCCCACATAAGGAC TGGCCACGGACTGGACTGAACTTGCCTTGTCCAGGGAACTGGGGTGGGGGCCACCACTGGCCTTGTCCAGGGACAAGCCACCCCATCCGGCAGCCGCAG CCAAGTCCGGGAGCCTCAGCTGCCGGGGGACAAGCCACCTCATCCTGGCAGCCGCAG TGCCCCACCCCTCTCTTCCTCCATCCCTCGTTTACTCTAG | 9692 |
| hsa-mir-219-1 | 3 | MPIRVSNCPPPRPVSLSFPTLNGDRSAPSSSLSSPSPSFT LESSKRLLPTSHSRHSAPVYPTHTRTPPSQWELHLVYVP VSAWCLHSPFPPVRLPFPAPGRGS* | 9693 | ATGCCCATCAGGGTCTCTAACTGCCCTCCACCCCGCCCGCCCCTGTATCCTCTCATTCC CTACACTCAATGGGGATCGCTCGAAGAGCTCTGCCACCCCCTCTCCGCTCCTTTCC GTTTACTCTAGAGTCCTCCACCCACCCCTGCCCCACTCCAAATGCCCAAGGGAGCTCCATCTGTG TATGTCCCCTGTTTCCGCGTAGTCCCCAAGCACCCCTTTCCCCGTTCTCCAATTCTGCC CCTTCCCCGCCCGGGCGGGCCGGCTCCTGA | 9694 |

Figure 1 (Continued)

| | | | | |
|---|---|---|---|---|
| | 4 | MGAPSCYCPCFRVVSPPPLSSRAPPSLPRPGPRLLJVQTQ FSSLWLRPRVESGRPEFPPPNLERESGSEGLRAKAEGG GSPQGGKGNPGHIGT* | 9695 | ATGGGAGCTCCATCTGTATGTCCCTGTTCCGCTGTGTCTCCATTCCCCTTT CCTCCCGTGCGCCTCCTCCGGACCCCGGACCCGGGTCGCGGCTCCTGATTGTCAAA CGCAATTCTGAGTCTATGGCGCCGAGAGCGGGTTGAGTCTGGACGTTCCGAGCGC CGCCCCCAAACCTGAGCGGACAGCGGGTCGGAGAGCGGGTCTAGGGAGAGCCAAGCA GAGGGTGGAGGGAGTCCCAGGGTTGGTAAGGGGAATCCGGGCACATCGGGACCTA G | 9696 |
| | 1 | MEGESGVRAATPSPSGRRRGGGGRGASGRGAWTGRVS VSGATRKESGTGVVAEGLAEWRGAGGEPRGRAGGGS PGGPRSEDTGAGHLAWGGSGPPERAARRCFASAGVHW VRASSAPWQGRGRWAGRPLLSFSPGIDVM* | 9697 | ATGGAGGGTGAAAGTGGGGTCGGGGCGGCCACACCCAGCCCTTCCGGAGGAGAAG GGGCGCGGGGCGCGGCAAGGGCACGCGGCAGCGGGATCTGGGACGGAGAAGGGCTGG GTGTTCAGGAGCTACGAGGAAAAGAGTCTGGGACGGAGAGGGCGGGAGGGCTGG CGAGTGGCGCGGCCGCGGGGGAGACGCGAGGGGCGAGGGCGGGCCATCTAGCTCGGGAGGGT ACCYGGCGGCCCCCGTCTGAGGATACAAGGGCCGGCCATCTAGCTCGGGAGGGT CTGGACCCCGAGCGGGCGGCGGCCCCTGAGGAGGTGCTTTGCCTCTGCGGCGTTCACTGG GTCAGGGCCAGTTCAGCGCTGCAGCGGAAGGGGTCGCTGGGCGGCGCGGCCCT CCTCTCGTTCTCCAGGGATGTTATGTAA | 9698 |
| hsa-mir-22 | 2 | MLCKGGGERSRGRRCRGLMQPKG* | 9699 | ATGTTATGTTAAGGGGGGAGGGGAGAGGAGTAGGGGCGGCGGTGCCGGGGCCTTA TGCAACCCAAAGGTTAG | 9700 |
| | 3 | MASGEAVTPTSLRPWFQPPTPLACHPGCQIGLGAVRVP EG* | 9701 | ATGGCCTCGGCGGAGGCTGTCACCCCACCTCCTCGGCCCTGGTTCCAGCCTCCA ACTCCCTTTGCCTGTCATCCTGRCCGGCTGCAGATTGGGCTAGGAGGCTGTCAGAGTGCCA GAGGGTTGA | 9702 |
| | 4 | MEQLVRGSVPWAHPALQPRAPAWHRLSAAAESSGLMR AISDRGRSDGVGLVTQGKEDTQSSCLPRGFRNLNRTPY PPIFLTIL* | 9703 | ATGGAGCAGCTGGTCAGGGAGTCAGTGCCTTGGGCCCACCCCGCTGCAGCCAAG GCCACTGCCTTGGCACAGAGGGCGCTCTCAGCCGCCGAGTGCCAGCGCTCTGGTTGAACAGAGC TATTCAGACAGAGAAGGTCGGACGGGGAGTTGGACTCGGTACCAGGGGAAGGAAG ATACACAAAGTTCATGCCTCCAAGAGAGGGTTCGGAATTTGAACCGCACCCGTATC CCCAATCTTCTTACCCTCTGA | 9704 |
| | 1 | MANGWTGSRPGRRNPEL* | 9705 | ATGGCCAATGGCTGGACTGGCTCCCGCCTGGGCGGAGGAATCCGAGCTGTGA | 9706 |
| | 2 | MAGLAPALGGGIPSCEAAGIRAHVLLCLLRAEAMAGAG VGCGGGVRWRRSR* | 9707 | ATGGCTGGACTGGCTCCTGCCCATGTGCTCTTGTTTACTAAGAGCGGAAGCGATGCGGGAGCGG GGGTGGGGTGCGGTGCGGGGAGCGGCGGGAGGTCCGGTGA | 9708 |
| hsa-mir-25 | 3 | MCFFVY* | 9709 | ATGTGCTTCTTTGTTTACTAA | 9710 |
| | 4 | MLDGPVHCJHGLFILRWLEITDL* | 9711 | ATGTTGGATGGCCCTGTGCACTGCACGGGCTCTTTATTCTTGCGTGGTTAGAAACA GACTTGTGA | 9712 |
| | 1 | MDSSAVITQISKEEARGPLRGKGTGAAGRGPKPGRRGR REGAGHFFRGAAAAAPGGRLSCARSSQPEKEQGESLNSE EAQRRGAGPGAFCALLFARGEETEAGIEREEFGGFLAGI AWCMGAPPLAPMGLGDGGAEEGAYGPPAETPFHPPPP PPRAAVR* | 9713 | ATGGACAGCTCGGCCGTCATTACTCAGATCAGCAAGGAGGAGGCTCGGGGCCGCT GCGGGCAAAGGTACCGGGCTCGGGAGCTGGAGGCGCCGCCGCCGCCGCCCGGCGG CCGGGCCTTAGCTGTGCCGAAGCTCCCAGCCGAGGCCGAGAGGAGCAGGGAGAGTTGA ACTCAGAGGAGCTCAGAGACGGAGGCCTGGCGCCTTTGGGCGCCTCCTG TTCGCTCGAGGTGAGGAAACTGAGGAATAGAGGGAACCATTGGCGCCAATGGGCT CCTGGCAGGGCATTGCGTGGTGCATGGGGCCTATGGCGCACCCGTGACGCAATGGGCT GGGAGATGGGGAGCTGAGGAGCTGAGACTCCCCCCGGGTGCGGTCCGGTAG | 9714 |

Figure 1 (Continued)

| | | | | | |
|---|---|---|---|---|---|
| hsa-mir-26b | 2 | MGELRRAPMGHPLRLRPTPHPHPPGLRSGRVLGGGAEV TAGWGGLEGSPANTQLRSPQTSRHAWRRPPRRHRED GRHFQESLGARGESRAPSGHAPPLKASPPRRGCVPQRG WAGVGGSVFSFSPCGPQDLDAAPRSAHPRLGLAAPELR ARWKG* | 9715 | ATGGGGGAGCTGAGGAGGGCGCCTATGGGCACCCGCTGAGACTCCGCCCCACCCC CCACCAGCAGGCTGGGGAGGCCCCGGCTGCGGTCCGGTAGGGTCTTGGGAGGGGGGCCGAGG TGACAGCAGGAGGCTGGGGAGGCTGGAGGGATCTCCCGCCAACACAGCTACGTTCC CCACAAACTTCGCGTCACGGTGGAGGCGCCGACCCCTCGGAGGCACAGAGAGGA CGGCCGGCACTTCCAAGAGTCCACTTGGCGCCGCGGGAGAGTCGTGCGCCTAGTG GGCACGCACCACCCGCAAAGCTCCGCAAGCTGCCCGACGAAGGCTGCTCCCCAGCGT GGCTGGGCCGGGGTGGGGGGTCGTCTTCTTCCCCGTGGACCTCAGGAT CTGGACGCTGCCCCAGGTCTGCCCACCCTCGCCTCGCCCGTGCCCCGGAACTG AGGGCAAGGTGAAAGGCTAG | 9716 |
| | 3 | MATGHWPQAAGLHPCLWAQPQ* | 9717 | ATGGCCACTGGACACTGGCCCCAGGCCGCGGGACTGCACCCTGCCTCTGGGCCCA GCCGCAGTGA | 9718 |
| | 4 | MEGGQGWTALGPRPWLS* | 9719 | ATGGAGGGAGGCAGGGTGACTGCCTGGCTACGCCCGCTGA | 9720 |
| | 1 | MEAEVDKLELMVSAK* | 9721 | ATGGAGGCCGAGGTCGATAAGCTGGAACTGATGGTGAGTGCAAGTGA | 9722 |
| hsa-mir-30a | 2 | MASEVGHNLESPETPGGGGWTRVEFPPPAPKGAAATYW CLNRLG* | 9723 | ATGGCTTCGGAGGTGGGGCACAATTTGGAGTCGCCGAACTCCGGCGCGGAGG CTGGACCAGAGTCGAGTTCCCTCCTCCTGCACCAAAGGGAGCCGCCACCGTCTGGTG TCTAAACCGCCTCGGGTAA | 9724 |
| | 3 | MAGDAEGAGPLEFLYPCPHLYTPYETAPGADRILCLYQ KRCFWNGP* | 9725 | ATGGCAGGAGATGCGAGGTGCGGGCCTTTGGAATTCCTTGCCTGTTCCTTGCCCTAC CTTTACACCCTTACGAAACTGCGCGGTGCAGACCGCATTCTGTGTTTGTACCAA AAAGATGTGAATGGAACGGTCCCTAA | 9726 |
| | 4 | MLRVRGLWNSLFLALTFTPLTKLRRVQTAFCVCTKKDV NGTVPKRPKGEVVHTPRKGNGGWGGE* | 9727 | ATGCTGAGGGTGCGGGGCCTTTGGAATTCCTTGTTCCTGCCCTCACCTTTACACCC TTACGAAACTGCGCCGGTGCAGACCGCATTCTGTGTTGTACCAAAAAGATGTGA ATGGAACGGTCCCTAAGCGTCCCAAGGGTGAAGTGGTTCACACTCCAAGAAAG GGGAACGGAGGGTGGGGTGGGGAATAA | 9728 |
| | 1 | MGFQSDVCSCLLPRTSRGYFRSNYLVY* | 9729 | ATGGGCTTTCAGTCGGATGTTTGCAGCTGCCTACTGCCTCGACTTCAAGGGCTAC TTTAGGAGCAATTATCTGTTTACTAA | 9730 |
| hsa-mir-30c-1 | 2 | MFAAAYCLGLQGATLGAHLPTKTEYLAISLIHFYKAELK WYKLNHFKTMSVHF* | 9731 | ATGTTTGCAGCTGCCTGCCTCAAGCTGCACATTTCAAGGGCTACTTTAGGAGCAATTATC TTGTTTACTAAACTGCAATTGTCTGTATCTCTTTGATACATTTTACAAAGCTGAAT TAAAATGGTATAAGAATTTGCAATATCAAAAGAAAGTATTCGTAAGAAAATGAGGAAATG TGTTTACAGTATATTTTATTTTTTAATTTTTTTTAAAAGCGTAG | 9732 |
| | 3 | MHRICNIKKKVFVREMRKCVTVPLFFLKA* | 9733 | ATGCATAGAATTTGCAATATCAAAAGAAAGTATTCGTAAGAAAATGAGGAAATG TGTTTACAGTATATTTTATTTTTTAATTTTTTTTAAAAGCGTAG | 9734 |
| | 4 | MCYSIFIFFKSVVGQYFPEKSMK* | 9735 | ATGTGTTTACAGTATATTTTATTTTTTAAAAGCGTAGTAGGGCAATATTCCAGAAA AATCTATGAAGTGA | 9736 |
| | 1 | MEKLDVLVYILS* | 9737 | ATGGAAAAATTAGATGTCTTGGTGTACATTTTATCCTAA | 9738 |
| hsa-mir-30d | 2 | MSWCTFYPNRFSSFYNHKIGSGKTVDVFPKYLFLTYI* | 9739 | ATGTCTTGGTGTACATTTTATCCTAATAGATTCTCTTCTTTCTATAATCATAAATAG GTTCTGGAAGACTGTTTGATGTTTTCCAAATACCTTTTTTGACATATATTTGA | 9740 |
| | 3 | MFFQNTFF* | 9741 | ATGTTTTTCCAAATACCTTTTTGA | 9742 |
| | 4 | MLVNYIKSEHYAPSIM* | 9743 | ATGCTTGTTAATTACATCAAATCTGAACATTATGCTCCATCAATGTGA | 9744 |
| | 1 | MEKLDVLVYILS* | 9745 | ATGGAAAAATTAGATGTCTTGGTGTACATTTTATCCTAA | 9746 |
| hsa-mir-30e | 2 | MSWCTFYPNRFSSFYNHKIGSGKTVDVFPKYLFLTYI* | 9747 | ATGTCTTGGTGTACATTTTATCCTAATAGATTCTCTTCTTTCTATAATCATAAATAG GTTCTGGGAAGACTGTTTGATGTTTTCCAAATACCTTTTTTGACATATATTTGA | 9748 |
| | 3 | MFFQNTFF* | 9749 | ATGTTTTTCCAAATACCTTTTTGA | 9750 |
| | 4 | MLVNYIKSEHYAPSIM* | 9751 | ATGCTTGTTAATTACATCAAATCTGAATAATATGCTCCTCCATAATGTGA | 9752 |
| hsa-mir-320 | 1 | MLRRSGVLASGRWRGGAKIRVPGFVGHHAAM* | 9753 | ATGCTGCGGCGCTCGGGGTCTGCGCTCCGGGCGGTGGCGTGGAGGCGTGGAGGCGCAAGAT CAGGGTCCGGGTTTTGTCGGCCACCACCGCGCAATGTGA | 9754 |
| | 2 | MGRGARRGAESFWT* | 9755 | ATGGGGCGAGGGCGCCGCCGCGGCGGCAGAGTGAGACCTGGACTTAA | 9756 |

Figure 1 (Continued)

| | | | | | |
|---|---|---|---|---|---|
| | 3 | MVTLEWSLPPGSDLAHFRGPLPCAPGGVLG* | 9757 | ATGGTGACCTTGGAGTGGTCATTACCTCCGGCAGCGACCTGGCCCACTTTCGGGGA CCCTTCCTGTTCCTGTGGAGTCCTGGGTGA | 9758 |
| | 4 | MLSPIPQTV* | 9759 | ATGTTATCCCCATCCCAGACCGTATAA | 9760 |
| | 1 | MSSFGAG* | 9761 | ATGAGTTAGTTTGAGCTGGGTGA | 9762 |
| | 2 | MVSPLF* | 9763 | ATGGTTTCTCCCTTTCTGA | 9764 |
| | 3 | MGKGSVEACLLG* | 9765 | ATGGGGAAGGGCTGGGTGGAAGCTTGCTTGTTGGGGTGA | 9766 |
| hsa-mir-330 | 4 | MGLVSVPDLWGCPGRGWLRENVPEGPGCAHDDPRRAG THLQPGHTLLGAAFLPAQAGVGVSFCWNLLGAPIPPGGN RKAVKAAQACNLSTLLGGSFEAKSLRPAWATHKTSTARS RAMWPEWDWCI* | 9767 | ATGGGGCTGGTGTCAGTGCCTGACCTCTGGGGGTGTCCTGGCAGAGGATGGCTCCG TGAAAATGTTCCTGAGGGGCGCTCCTGGCGCCATGATGATCCAGACGAGCTGGCAC CACCTACAGCTTGGAACACGCTTGGAAGCTGCCTCTGGCGCTCAAGCTGGAGT GGGTGTATCCTTTTGCTGGAATCTCCTTGGTCTCCCCATCCCCCAGGAGGAAATAG AAAGGCGGTCAAGGCAGCTCAGGCTGTAATCTCAGCACACTTTGGAGGATCGTTTG AGGCCAAGAGTTTGAGACCTGCTGGGCAACACACAAAACAAGCACGACGTTCA AGGGCTATGTGGCCAGAGTGGGATTGGTGCATTGA | 9768 |
| | 1 | MGGALPQPRPAATGGRSRGRPWRPDAAAGPAPPCRPR AGRAALLGAPLRAGPRAGPGRSRALLPLTLLGAQGRAA GGRVGVQALQALRALERPRNRPCSPALWGRTGPPAAM QQPPGETRALRTLGGLESSAAA* | 9769 | ATGGGAGGGGCCCTGCCCCAGCCCGCCCGGCCGCCGACCAGGTGGGCGCTCCCGTGG GAGGCCGTGGGCCTGGCCGTCCAGACGCTGCGCAGGGCCCCCGTCCGCCTGCAGACCCCGGG GGACGGTCCGCGCGCTTCCTGGGGCTCCGCTGCGCGCTGTGGCGCCAGGGCCCT CGGGTGGTCCAGCCAGCCCTGCAGGGCCTGCAGGGCCACTGCTCGGAGCGCGAAA CAACCGGCCAGGGGCTCCCCAGCCCGCAGGAAAACCCCAGGCCCTGAGCGGCCCG AGCAGCCCCGGGGAGACACGAGCTCTGAGGACCCTGGGTGGGCTGGAGTCGTCG GCCGCGCGTGA | 9770 |
| hsa-mir-339 | 2 | MMKTIGHASLGSLPEDGGAGRQLLQEALPLLRRGSAGF GLESAEVLLGVGLLSSEEAVARAGGGPVLVLRCVLGASS AAARTAGGRGPGVRTDTRTGLPSLLLGLTAAETAGMV TVASESPAYE* | 9771 | ATGATGAAAACAATTGGGATAGTTCACTCGGGAGCCTTCTGAGGACGGCGAGC TGGGTCGGCAGTCCTTGAAGGAGGCGGAGCGTCTGCTTGGTCGGGCTCAGCGGGTT CCGGTCTGGAGGCGAGAGGAGGCTGGAGCCCGTTTATCTTCTGAGGAGGG TGGCCCGGGCAGTGGGGCCCCGTGGGGTCAGTGCCGGGAGCACCGCTGCCAGAGTCTCT CAGCTGCTGCTGCAGCACCACCTGGGCAACAGTCCGCCAGCCACCACTGCCATCAACGCA ACCGGTGCTAGCTGTCCTCAGAGTCCTTTGCTTTATGAGTAA | 9772 |
| | 3 | MSNSPN* | 9773 | ATGAGTAACTCACCGAATTGA | 9774 |
| | 4 | MNSLCSLRSCGKVRKPNPYLVPRCECFKLCVTTNKIDM MHHFTDI* | 9775 | ATGAATTCGTTCGTTGTTTCACTGAGGAGTTGTGCAAAGTGAGAAAACCTAACCGTAC TAGTTGTCCAGATGTGAGTGTTTAAACTATGTGTAACAACTAACAAATTGACATG ATGATACACTTCACGGACATTTAA | 9776 |
| hsa-mir-33b | 1 | MDCTEGIPGGLPTSPLYNASVSCRFSWGGRACGLRNL SRKEPLPEGEGVTVTSSLGKWRATSWQISVPCNSRGKGL LRDPKAASRPKRVWRERVVFSTFSAPALGQDQEEAGRR ARCPSATASALFSTPAYCGHLRLFRKTVGALDCQNCQF FPQASVSPIYRRGSHGLG* | 9777 | ATGGATTGCACTTTCGAAGGTATTTTGGAGGCGTCCTCGCACCACCCCCCTTATACAAT GCCTAGTGCACTTCTCTGCAGGTTCCTGGGTGGCGGACATGGCGGCTACGCAACTTG AGCAGGAAAAGAGCCCCTTCCGAGGGAGAAGGTGTGACAGTTACCAGCTCGCTGGG GAAGTGGAGGGCTACCTGCAACAAATTAGTGTCCCTGCAACTCAAGGGGAAGG GTTTGCTTAGAGACCCAACATCCGACCATCCGCCTTTGGACAGGACCAGGAACAGG GTGGCCTTCTCTACATTTGTCCGTGCACCGGCCTATCGCAGCACCCCTGCCTAT TGTGGGCATCTAGACTTTTCAGGAAGACAGTGGGCCTTCAGAATGTCAAAATTGT CAGTTTTTCTTTCAGGCCTCAGTTTCCCCATCTATGGAAGAGGGCTCACGGACTG GGGTAA | 9778 |
| | 2 | MPPSPAGSPGVGGHAGYAT* | 9779 | ATGCCTCCGTCTCCTGCAGGTTCCTCGGGTGGCGGGCATGGGGGCTACGCAACT TGA | 9780 |
| | 3 | MRATQLEQERAPSRGRRCDSYQLAGEVEGYLQPN* | 9781 | ATGCGGGCTACGCAACTTGAGCAGGAAAGAGCCCCTTCCGAGGGAGAAGGTGTGA CAGTTACCAGCTCGCTGGCGAAGTTGGAGGGCTACCTGCAACCAAATTAG | 9782 |

Figure 1 (Continued)

| | | | | | |
|---|---|---|---|---|---|
| hsa-mir-340 | 4 | MGNPAVESPL* | 9783 | ATGGGAAACCCTGCAGTTGAAAGTCCATTATGA | 9784 |
| | 1 | MAMT* | 9785 | ATGGCTATGACGTGA | 9786 |
| | 2 | MDFGHGWQ* | 9787 | ATGGACTTCGGGATTGGATGGCAGTGA | 9788 |
| | 3 | MAVTHQC* | 9789 | ATGGCAGTGACACATCAGTGTTAA | 9790 |
| | 4 | MEINFVCRKIPHRG* | 9791 | ATGTTTATAAATTTGTTTGTTAGGAAAATACCACATATTCGTGGTGA | 9792 |
| | 1 | MGCGDE* | 9793 | ATGGGCTGCGGGGATGAATGA | 9794 |
| | 2 | MNESRV* | 9795 | ATGAATGAGAGCCGAGTCTGA | 9796 |
| hsa-mir-345 | 3 | MRAESDSAPQESLTFAVARDCPGPCGASHSVTSHQFFPSASGGPDCQVGAWEQGRARRFLFAVGVRSALLGRAQLPSLGPAGRQGHTVCHYSRPRVTWFFYPNSSGYLPPGGAGRKVLCIWY* | 9797 | ATGAGAGCCGAGTCTGACTCGGCCCCCCAGGAGTTCCTGACATTGCAGTTGCCAGTGGCAAGCAGCCCCCTCGCAGCAGTCCGCTCAGGAGTCTGGGTCCATTCGGTGACTTCCACCAGCCTTCCCGGGCGCCTTGCAGATCTCCAGAGTTCTTCGCTGTAGGAGTCAGATCACCCTTAGGCGTGGCCCAGTTCCTTCTTTAGGCCTGCAGGCAGGCCACAGTTGCCACGTGTGCCACGTTTCCAGGTTAGGGTCACATGGTTCTTTATCCAAATCCAGTGGGTACCTACCTCTGGAGTGCAGTCAGGTCGAAAAGTTCGTGTATTGGTACTAG | 9798 |
| | 4 | MVLLSKFQWVPTSWRCRSKGSVYLVLGHTGRCCQ* | 9799 | ATGGTTCTTTTATCCAAATCCAGTGGGTACCTACCTCTGGAGTGCAGGTCGAAGGTTCTGTGTATTGGTACTACGGACACACAGGTAGGTTGTTGTCAGTAG | 9800 |
| | 1 | MGQGGSECAILARMPVAPAPATASAWAAVPGAPLIKDSSLGEERRENADCGPPVGNWGSVGFSLWRGGGSVS* | 9801 | ATGGGACAAGGTGGTAGTGAGTTGCGCATCCTGGCCCGGATGCCGGTTGGCACCGCTACCGGCTCCAGCTGCCTCTGCCTGGGCGTGTCCAGCTGCGACTGCGATCCGCCCGTGGGTAACTCCAGCTTGGGGAGGACAAGAAGGGAAAATGCGACTGCGATCCGCCCGTGGGTAACTGGGGCTGGTGGCGTTTCGCTTGGCGGTGCGGGGTTCCGTTTCTAA | 9802 |
| | 2 | MPTAVRPWVTGARWGFRFGGGVGVPFPNSCAGRVGGGGLFSLGY* | 9803 | ATGCCGACTGCGGTCCGCCGGCGTGGGCTGGGCGTCGGGGTGTTTCGCTTGGCGGGGTGTTCCTAATTCCTGTGCGGGCCGGGCGGCTGGCTTTTTCCTTGGGCTATTAA | 9804 |
| | 3 | MCARGLDPFSGRPFSLLFPFWLRGRLRSHPAPERSSCALGHWYYVWRGHPERAARAGSPRSPPARGGPELGPARGFPPSGWLGKKGALRWGSCDPVELTGWVGGDGAGGT* | 9805 | ATGTGCGCTCGCGGCCTTGATCCATTTAGTGGACGCCTTTTTCCACTTCTCTCCCTTCTGGCTCTGGGAGACTTACGGTCGCATCGCCGGCCCTGAAGGCTCCAGCTGCGCGCTGGGACACTGGTATTATCGTGGAGGGACACCCGGAGATCCCGGCTCGCCAGGGGACCTGGTGCCGCCGCGGTGCTGGAACTGGGGGCTGTCGAGGAGAGAGCAGCGTCGAGCCGGGACTTGA | 9806 |
| | 4 | MRGCTWREKRDSPPSWLLSHQPGNGGGGRRGLGAFLVL* | 9807 | ATGAGGGGCTGGACGTGGGAGCGGGAAAAAGGGATGGCCTCCTCTCCTTGGCTTCTATCCGGGGAGGGGGTGGAATGGAGGGGAGGGAGGCGTGGAGCTTGGCGCGTTTTTGGGTGCTTTGA | 9808 |
| | 1 | MRRKGAWGSGLSRT* | 9809 | ATGAGGAGAAAAGGTGCGTGGGAGCGGGAGTGCGCTTTCAGAACCTAG | 9810 |
| | 2 | MEHSPNLGAQQI* | 9811 | ATGGAATCATTTCCCAACTGGGGCGCAGCAAATTTGA | 9812 |
| | 3 | MRDD* | 9813 | ATGAGAGACGATTAA | 9814 |
| hsa-mir-365-1 | 4 | MGWGELYEAPRTPDLSAAKGRLGHPSCCPGSP* | 9815 | ATGGGGTGGGGGGAACTGTACGAGGCACTCGGACACCCGGGACCTGCTAAGGGACGTTGGGCACCCCTCGTGTTGTCCGGGAAGCTTTAG | 9816 |
| | 1 | MGAEGWVFAGEMRVSDQLAYKVPVLGPRDQRLLPGPRFPRPASSRAGVRSGQAASQVHAGEGVVRCARPGCVR* | 9817 | ATGGGAGCTGAAGGCTGGGTCTTTGCGGGCGAGATGAGGGTGTCGGATCAACTGGCCTACAAAGTCCAGTTCTCGGCCCGCGGACCAGCAGCTCTTCCGGGACCAAGCAGCTCTTCCGGGCGGCGCCTGGACAGCTGCCTCTCAGGTCCACCCCTGGAGAAGGAGTTGTGAGGTGCGCCCGGCCGGGGTGA | 9818 |
| hsa-mir-365-2 | 2 | MGQALPLTEACPAVLSRAATLSLGVGRTGPDF* | 9819 | ATGGGCCAAGCCCTGCCACTTACGGAGGCCTGCCCTGCTGTTCTGAGCCGGGCCTGAGGAGCTAG | 9820 |
| | 3 | MDLCGCVPNGRSFVP* | 9821 | ATGGATCTTTGTGGATGTGTTCCCAATGGCCGGTCTTTTGTTCCTTGA | 9822 |
| | 4 | MCSQWPVFCSLTDAT* | 9823 | ATGTGTTCCCAATGCCCCGTCTTTTGTTCCCTGACCGATGCAACATAA | 9824 |

Figure 1 (Continued)

| | | | | | |
|---|---|---|---|---|---|
| hsa-mir-371 | 1 | MMTCALVFFTEPLFIKCSIKS* | 9825 | ATGATGACATGCGCTTGGTCTTTTTCACTGAACCTCTTTTTATAAAGTGTTCAATAAAAAGCTGA | 9826 |
| | 2 | MRFGLFH* | 9827 | ATGCGCTTTGGTCTTTTTCACTGA | 9828 |
| | 3 | MYSLHLA* | 9829 | ATGTATTCTTTGCATCTGGCATAG | 9830 |
| | 4 | MQEDHLSPGVPVQPGLTGRTPSLERKKCKKAFFVYYFFETGSPSIPQTGVPWYHHSLLQP* | 9831 | ATGCAGGAGGATCATTTGAGTCCAGGAGTTCCAGTCCAGCCTGGTAACCCCTTCTCTGGAAAGAAAAATGTAAAAGGCATTCTTTGTGTATTATTTTTTGAAACAGGGTCTCCCTCTATACCCCAGACTGGAGTGCCTTGGTATCATCACAGCTTACTACAGCCTGA | 9832 |
| hsa-mir-372 | 1 | MMTCALVFFTEPLFIKCSIKS* | 9833 | ATGATGACATGCGCTTGGTCTTTTTCACTGAACCTCTTTTTATAAAGTGTTCAATAAAAAGCTGA | 9834 |
| | 2 | MRFGLFH* | 9835 | ATGCGCTTTGGTCTTTTTCACTGA | 9836 |
| | 3 | MYSLHLA* | 9837 | ATGTATTCTTTGCATCTGGCATAG | 9838 |
| | 4 | MQEDHLSPGVPVQPGLTGRTPSLERKKCKKAFFVYYFFETGSPSIPQTGVPWYHHSLLQP* | 9839 | ATGCAGGAGGATCATTTGAGTCCAGGAGTTCCAGTCCAGCCTGGTAACAGGTAGAACCCCTTCTCTGGAAAGAAAAATGTAAAAGGCATTCTTTGTGTATTATTTTTTGAAACAGGGTCTCCCTCTATACCCCAGACTGGAGTGCCTTGGTATCATCACAGCTTACTACAGCCTGA | 9840 |
| hsa-mir-373 | 1 | MMTCALVFFTEPLFIKCSIKS* | 9841 | ATGATGACATGCGCTTGGTCTTTTTCACTGAACCTCTTTTTATAAAGTGTTCAATAAAAAGCTGA | 9842 |
| | 2 | MRFGLFH* | 9843 | ATGCGCTTTGGTCTTTTTCACTGA | 9844 |
| | 3 | MYSLHLA* | 9845 | ATGTATTCTTTGCATCTGGCATAG | 9846 |
| | 4 | MQEDHLSPGVPVQPGLTGRTPSLERKKCKKAFFVYYFFETGSPSIPQTGVPWYHHSLLQP* | 9847 | ATGCAGGAGGATCATTTGAGTCCAGGAGTTCCAGCTGTCCAGCCTGGTAACAGGTAGAACCCCTTCTCTGGAAAGAAAAATGCATTCTTTGTGTATTATTTTTTGAAACAGGGTCTCCCTCTATACCCCAGACTGGAGTGCCTTGGTATCATCACAGCTTACTACAGCCTGA | 9848 |
| hsa-mir-374a | 1 | MLWPDPLEINPES* | 9849 | ATGCTGTGGCCAGATCCACTAGAAATTAACCCAGAAATCTTAG | 9850 |
| | 2 | MRRR* | 9851 | ATGAGGAGGCGATGA | 9852 |
| | 3 | MMTLQKVAAAGGA* | 9853 | ATGATGACTCTGCAAAAGGTTGCGGCAGCTGGCGGTGCGTAG | 9854 |
| | 4 | MRKKGALGDRPHLGSTHSEGSLAFRSWVAVLGSEYSHPRVAKHCGCSVRIQC* | 9855 | ATGCGTAAAAAGGGAGCACTTGGAGACAGGCCACATTGGGCAGTACGCATTCGGAGGCTCTCTGGCTTCCGATCTTGGGTCTGTACTTGGCTCTGAATACAGTCACCCCATCAGAGTAGCAAAACACTGTGTTGTAGTGTGAGAATCAATGTAA | 9856 |
| hsa-mir-374b | 1 | MLWPDPLEINPES* | 9857 | ATGCTTGTGGCCAGATCCACTAGAAATTAACCCAGAATCTTAG | 9858 |
| | 2 | MRRR* | 9859 | ATGAGGAGGCGATGA | 9860 |
| | 3 | MMTLQKVAAAGGA* | 9861 | ATGATGACTCTGCAAAAGGTTGCGGCAGCTGGCGGTGCGTAG | 9862 |
| | 4 | MRKKGALGDRPHLGSTHSEGSLAFRSWVAVLGSEYSHPRVAKHCGCSVRIQC* | 9863 | ATGCGTAAAAAGGGAGCACTTGGAGACAGGCCACATTGGGCAGTACGCATTCGGAGGCTCTCTGGCTTCCGATCTTGGGTCTGTACTTGGCTCTGAATACAGTCACCCCATCAGAGTAGCAAAACACTGTGTTGTAGTGTGAGAATCAATGTAA | 9864 |
| | 1 | MAGNDCGALLDEELSSFFLNYLADTQVRPAGAAGPGPGVLSCGGRSCSRGGREAAVGALG* | 9865 | ATGGCGGGAACGACTGCGGCGGCTGCTGGACAGCAGAAGGCTGCTCCTCCTCCTCCTCAACTATCTGCTGACAGCAGCAGCTTCTTCCTGAACTACCTGGCCGACACGCAGGTCCGCCCTGCGGGCGCTGCGGGGCCTGGACCTGGGGGCCAGGGGTGCTGAGCTGCGGGGGCCGCAGCTGCAGCTGCAGCTGCAGCGGGGAGGGCAGCGGTGGGAGCCCTGGGGTAA | 9866 |

Figure 1 (Continued)

| | | | | |
|---|---|---|---|---|
| hsa-mir-378 | 2 | MRSVTGAGSRRSPGCACRSAGGATAAGEGLALAAWSLP PRGQMWGVPRFLWEVEARHGVGYPQAGAGCWRRAVS ARHLLPYFHVDLWPRHGCMPGSPESPPGCSPQSAVA GPPRLSTRARSAEPPASCRLK A* | 9867 | ATGCGCTCCGTTACCGGGCAGGGAGCCGGAGGAGCCGGAGGTCTCCGCGCCGTGCCGAGCGC TGGGGGCGCTACGGCCGCCGCTGGGAGGGTCTAGCCTTGGCCGCTTGGGAGGTGGAGGCGCGCAC CCGCGCGGGCAAAACTGGGCGGTACCCTCAGCTGGCGCTGCGCTGGGTGCTGAGGCCCGTCAGCGCCG GGTGTGGGTACCCTCAGCTGGCGCTGGGCGACTTTCACGTGACTGTGCCCCGGCACGGGTGCATGCCGG GCACTTGCTGCCGTACCTCCGCGCCCAGGCCTGTAGTCCCAGAGTGCTGTTGCTGGCC GTCCCGGAGTCCCCTTTCTACCGGCCAGCGCGGAGTTCCTGCCAGTTGCCGGCTAA GGCATAA |
| | 3 | MRAETASSWFRYRAEPPGKSQAGWGRKDCLGAPGSP CGARPRCALHDAGGREGEAESQALAEPGSPTGDTRVTG EGALVCRGAGERGSWWLGDWERGAAGTSSHQKCCQHE ACAAPTPSPEPTQCLLQA* | 9869 | ATGCGGGCGGAGACAGCGTCTTCCTGGTTCGATTCCGAGAGCCGGGCCAGCCGCCTGGGGG GAAAAGCCAGCTGGATGGGGCGCGAAGGACTCTGCAGTCCACGATGCAGGGGAAGGAAGGCGAGGC GCGGTGCGCGGCCGGTCACTGGCTCGAGCCGGAGCCCACTGGCGACACCGCGTGACAG GGAGTCCCAAGCACTGGCTCGAGCCGGAGCCCACTGGCGACACCGCGTGACAG GAGAGGGTGCTCTGGTGTGGCCGGGCGCGAGCAGGAAGGAAGCTGGTGGCTTGG AGACTGGGAGAGGGGTCTGCTGGGACAAGCAGCCACCAAAATGTCAGCACGAGG GTGCGCGGCGGCCCCACCCCTTCCCATTTCCCAGCAGCCAATGCCTGTTGCAAGCATA A |
| | 4 | MGAEGLSGGAWVPLRCAAPVRAPRCRGKGRRGGVPGT G* | 9871 | ATGGGGGCTGAAGGACTGTCTTGGGGCGCCTGGGTCCCCTGCGTGCCGGGCCCC GGTCGCGCGTCACGATGCAGGGGAAGGCGAGGCGGAGTCCCAGGCACT |
| | 1 | MAIPGRQ* | 9873 | ATGGCGATTCCGGCAGGCAGTGA |
| hsa-mir-423 | 2 | MRNYGDCIFCRGVLNALEVKGLCRQG* | 9875 | ATGAGAAACTACGGCGACTGTATCTTCGGCGAGGAGTTTAAATGCGCTGGAAGTG AAGGGACTGTGTCGTCAAGGGTAG |
| | 3 | MRWK* | 9877 | ATGCGCTGGAAGTGA |
| | 4 | MEARSLREKLYFK* | 9879 | ATGGAAGCGCAAATCTAACATTTAAGTTGAGGAGAAAACTTGTGAGGAAATAA |
| | 1 | MGANLTFKVFNK* | 9881 | ATGGGGGCAAATCTGACATTTAAGGTTAACAAATGA |
| hsa-mir-424 | 2 | MSAAGKPSGNGLGKKKQQLTWRGGERKLSKGQ* | 9883 | ATGAGTGCGCGGCCGGAAATTCTCAGGAAAACGGACTGGGAAAAAACAACAACT AACATGGAGGGCGGGGGAGAGAAAACTGAGTAA |
| | 3 | MEGRGEKTE* | 9885 | ATGGAGGGCGGGGGAGAGAAAACTGAGTAA |
| | 4 | MNFSSYLQEVSYVLERNV* | 9887 | ATGAACTTTCCTCTTATTTGCAAGAAGTTAGTATGTCTTGAAAGAAATGTCTGA |
| hsa-mir-425 | 1 | MGGF* | 9889 | ATGGGCGGGTTCTGA |
| | 2 | MWPQGE* | 9891 | ATGTGGCCCCAGGGCGAGTGA |
| | 3 | MGCP* | 9893 | ATGGGGTGCCCCTGA |
| | 4 | MGVDVGEPRLVAISGTLGRGEGGWTQDLWVGLQW* | 9895 | ATGGGTGTAGACGTGGGAGAGCCGAGGCTGGTTGCCATCTCTGGAACCCTGGGGAG GATTGGCGAGGAGGGTGGACCTGGACCTCTGGGTAGGCTGCAATGGTAG |
| hsa-mir-429 | 1 | MGCRQPGQRPGELRSLQTQAGAGPSPPQGKVGPCADA AGFRVWSHLGPTGCVFRARAQCVGSRHGVPSEGQGLGR GQAPRGYTFLPPT* | 9897 | ATGGGCTGTCGCCAGCCGGGTCCTTCCCCCCACCAGGGAGCTCCGTTCACTGCAGACACA GGCTGAAGCGGGTCCTTCCCCCCACCAGGGAGCTCCGTTCACTGCAGACACA CTGGGTTCGGCGTTGGGGCTCAGGCATGGGGTGCCCTCAGGGAGGGCTGGCAGAGGG CAGGCTCCAGAGAGGGTCACGTTCTTCGCGCCTACCTGA |
| | 2 | MRLGFGCGAILDPRAASSGHGHSVWAPGMGCPQGRAW AEGRLREGSRSCRLPDSRPSRKFSPEAATAVLRHFVRRR EAVASEVGA* | 9899 | ATGCGGCTGGGTTCGGCGTGGGCGCCATCTTGACCCACGGGCTGCTCTCCGG CACGGGCACAGTGTGGGCTCCAGCATGGGGTGCCCTCAGGGAGGGCTGGCAGAGGG AGAGGGCAGGCTCCGAGAGGGTCACGTTCTTCGCCGCTACCTGACAGCAGGCCTT CTAGAAAGTTCTCTCCGCCTCAGAGAGTCGGAGAC GGGAAGCTGTCGCCTCAGAGTCGGTCGTGA |

Figure 1 (Continued)

| | | | | | |
|---|---|---|---|---|---|
| | 3 | MTASPLQSSGVCGGKGLVSAPSGQRPAEPMGGEVGAWG RGWSGTGGAQPGEAGAGSQAPRYDWGGGNVSREVFY LNVKRLSTVAAGNKVRPTEAQP* | 9901 | ATGACCGCGTCTCCTTGGGCTCTGGAGTCTGCGGTGGGAAGGGCTTGTTTCAGCA CCCTCTGGTCAGAGGCCGGCCGGCCATGGGCGGTGAGGTTGGTGCCTGGGGTCG TGGCTGGTCGGTACAGGTGGGGCTCAGCCCGAGAAGCTGGAGCCGGTTCCAGG CCCCGGCTATGACTGGTGGTGGGGGCAACGTCTCTGTGAGGTTTTTACTTAAATG TGAAACGGCTCAGTACGGTGGCCGCAGCCGGGAACAAGGTCCGACCACCGAGCCG CAGCCTTGA | 9902 |
| hsa-mir-449a | 4 | MTGVGATSLVRFFT* | 9903 | ATGACTGGGGTGGGGGCAACGTCTCTCGTGAGGTTTTTACTTAA | 9904 |
| | 1 | MVLGDGTPGV* | 9905 | ATGGTTCTGGAGGACGGGACTCCAGGGTTTGA | 9906 |
| | 2 | MEWKLERTAPRRVRTEEEMLWVSNTLFCILPNSLMRGR RPRS* | 9907 | ATGGAGTGGAAACTGGAGCGCACCGCGCCGCGCTGGAGGTCCGCACGGAAGAGGAGAT GCTGTGGGTGAGTAACACCCTTTTCTGCATTCTCCCTAACTCTCTAATGCGGGGCCG AAGGCCCCGTTCATAA | 9908 |
| | 3 | MIFLNSFSLNMLSVPSKESIMRVLSKDLKQKRSQDSANV SPGLVLVLCFNSDLEQTNSW* | 9909 | ATGATTTTCCTAAATAGTTTCTCCCTCAATAGTTATCTGTTTCAAGGAAAGTA TCATGCGTGTCCTCAAAGACTTGAAGCAGAAGAAGTCAAGATTCGACCCAAC GTGAGTCAGGGCTGTCTTGTTCTGTTTTAATTCGATCTGAACAAACGAATT CTTGGTAA | 9910 |
| | 4 | MRILVSYYILKKISL* | 9911 | ATGAGAATTTAGTATCTTATTACATACTAAAAAAATTTCTTATGA | 9912 |
| | 1 | MVLGDGTPGV* | 9913 | ATGGTTCTGGAGGACGGGACTCCAGGGTTTGA | 9914 |
| | 2 | MEWKLERTAPRRVRTEEEMLWVSNTLFCILPNSLMRGR RPRS* | 9915 | ATGGAGTGGAAACTGGAGCGCACCGCGCCGCGCTGGAGGTCCGCACGGAAGAGGAGAT GCTGTGGGTGAGTAACACCCTTTTCTGCATTCTCCCTAACTCTCTAATGCGGGGCCG AAGGCCCCGTTCATAA | 9916 |
| hsa-mir-449b | 3 | MIFLNSFSLNMLSVFSKESIMRVLSKDLKQKRSQDSANV SPGLVLVLCFNSDLEQTNSW* | 9917 | ATGATTTTCCTAAATAGTTTCTCCCTCAATATGTTATCTGTGTTTCAAAGGAAAGTA TCATGCGTGTCCTCAAAGACTTGAAGCAGAAGAAGTCAAGATTCCGCCAAC GTGAGTCAGGGCTGTCTTGTTCTGTTTTAATTCGATCTGAACAAACGAATT CTTGGTAA | 9918 |
| | 4 | MRILVSYYILKKISL* | 9919 | ATGAGAATTTAGTATCTTATTACATACTAAAAAAATTTCTTATGA | 9920 |
| | 1 | MGANLTFKVFNK* | 9921 | ATGGGGGCAAATCTGACATTTAAAGTGTTTAACAAATGA | 9922 |
| | 2 | MSSAAGKFSGNGLGKKKQQLTWRGGERKLSKGQ* | 9923 | ATGAGTGGCGCCGGGAAGTTCTCAGGAAACGGACTGGGAAAAAAAAACAACT AACATGGAGGGGCGGGAGAGAGAAACTGAGTAAGGGGCAGTGA | 9924 |
| hsa-mir-450a-1 | 3 | MEGRGEKTE* | 9925 | ATGGAGGGGCGGGAGAAAACTGAGTAA | 9926 |
| | 4 | MNFSSYLQEVSYVLERNV* | 9927 | ATGAACTTTTCCTCTTATTGCAAGAAGTTAGTATGTGTTGAAAGAAATGTGA | 9928 |
| | 1 | MGANLTFKVFNK* | 9929 | ATGGGGCAAATCGACATTTAAAGTGTTTAACAAATGA | 9930 |
| hsa-mir-450a-2 | 2 | MSAAGKFSGNGLGKKKQQLTWRGGERKLSKGQ* | 9931 | ATGAGTGCGGCCGGGAAATTCTCAGGAAACGGACTGGGAAAAAAACAACT AACATGGAGGGGCGGGAGAGAAAACTGAGTAA | 9932 |
| | 3 | MEGRGEKTE* | 9933 | ATGGAGGGGCGGGAGAAAACTGAGTAA | 9934 |
| | 4 | MNFSSYLQEVSYVLERNV* | 9935 | ATGAACTTTTCCTCTTATTGCAAGAAGTTAGTATGTGTTGAAAGAAATGTGA | 9936 |
| | 1 | MLGTPGGACPRGPAASSGSVPSR* | 9937 | ATGCTGGGAACCCCTGCTGCCCTCGGCTTTTTTTCCTCTCGCCCTGCAGCCTCGTCAGGCTC AGTCCTCCGATAA | 9938 |
| hsa-mir-484 | 2 | MKNPYPSAFFFSSLGSRHVMYLLYF* | 9939 | ATGAAAAACCCCTGCTCCCTTGTTTCCCCAGCAATCCTAAATCTAGTGCAACCTAG | 9940 |
| | 3 | MAHPQHPKSSAT* | 9941 | ATGGCACATATTCCCAGCAATCCTAAATCTAGTGCAACCTAG | 9942 |
| | 4 | MNTAPPVTGWASRKEJLRLVSSNTLCFRWPDMILCGLL* | 9943 | ATGAATACTGCGTTCCAGTTCCAGTGGACAGGTTGGGCGAGCAGAAGGAAATCTTACGGTT AGTTTCAAACACTTTGTGTTTTAGGTGGCCAGATATGCTGTGTGGTTTGCTTTAA | 9944 |

Figure 1 (Continued)

| | | | | |
|---|---|---|---|---|
| hsa-mir-497 | 1 | MSKPPHRPEHPSSRFLSCSPMHSNKDTLRSEGEGPGPDIQ PRGPWSAIPGQLYTLPSPNPGSPCLAAGPESSTPSPNELC LACPQCYLPKQNMRV* | 9945 | ATGTCAAAGCCACCTCAATGTCCTGAATTTCCCAGTTCCCGGTTTCCTGAGCTGTTCTT TCATGCATTCAAATAAGAGACACACTTCCAGTCTCGGAGGGAGGGCCTGGGCCTGAT ATCCAGCCCGGTGAACCATGTCGGGCATTCCTGGCCAACTGTACACTCTCCCCAGCC CCAAATCCGGGGGAGCTTCTGCCTGCCCGGCCAATGTCCCCAGCTGATTCAGCTGCCTTCTCA AATGAGCTTTGCCTTGCCTTGCCTGCCCGCCAATGTCTCCGAAACAAATATGAGGGTGTGA |
| | 2 | MVGHSWPTVHSPQPKSGELLPCSWIQL* | 9947 | ATGGTCGGCCATTCCTGGCCAACTGTACACTCTCCCCAGCCCAAATCCGGGGAGCTT CTGCCTTGCCAGCTGGATTCAGCTCTAG | 9948 |
| | 3 | MSFALPARNVSRNKI* | 9949 | ATGAGCTTTGCCTTGCCTTGCCGCAATGTCCCGCAAACAAAATATGA | 9950 |
| | 4 | MSPETKYEGVIHAHLSDQGLQIRVVKPPPALSPSSLFSLL VYPTQF* | 9951 | ATGTCTCCCGAAACAAAATAGAGGGTGATCCATGCCAGATCTCAGATCAGGGA CTTCAAATTAGGGTGGTTAAGCCCCCTCCTGCCCTCTCCTCAGTCTCCTTGTTTTCCC TTCTCGTTTACCCCACCCAATTTTAA |
| hsa-mir-503 | 1 | MGANLTFKVFNK* | 9953 | ATGGGAGCAAATCTGACATTTAAAGTGTTTAACAAATGA | 9954 |
| | 2 | MSAAGKFSGNGLGKKKKQQLTWRGGERKLSKGQ* | 9955 | ATGAGTGCGGCCGGAAATTCTCAGGAAACGGACTGGGAAAAAAAAACAACT AACATGGAGGGCGGGAGGCGGGAGAGAAACTGAGTAAGGGGCAGTGA | 9956 |
| | 3 | MEGRGEKTE* | 9957 | ATGAGCGGCGGCGGGAGAGAAACTGAGTAA | 9958 |
| | 4 | MNFSSYLQEVSYVLERNV* | 9959 | ATGAACTTTCCTCTTATTTGCAAGAAGTTAGTTATGCTTTGCAAGAAATGTGTGA | 9960 |
| hsa-mir-505 | 1 | MFRRSLNRFVSTLAAAPRYPVCLLASPFAGSLTIH* | 9961 | ATGTTCCGCCGGAGCTTGAATCGTTTTGTAAGTACACTGCTGGCTCCGCGGTG CCGGTTTGCTCGCCAGCCCTTCGCCGGCCTCACAACAATTTCTGA | 9962 |
| | 2 | MAFYSQGGCFLLPLPRAHGGKPRPVTVAQKKSWGLRE PEIRARLSLA* | 9963 | ATGGCGTTTATTCTCAGGAGGTTGCTTTCTTTGTTTCCTCTGCCAGCAGCACATG GAGGTAAACCTAGAGCCGTCACGGTGGCCCAAAAGAAGAGCTGAGGAGG CCGGAGACTAGGGCAAGACTCAGCCTTGCCTAG | 9964 |
| | 3 | MEVNLDLSRWPKRRAGG* | 9965 | ATGGAGGTAAACCTAGACCTGCACGGTGGCCCAAAGAAGAGCTGAGGGCTGA | 9966 |
| | 4 | MCSREEAAPPLPVLPISGLKPRGGLSTPDLEPMGEGGL* | 9967 | ATGTGCAGCCGCCGGAGGAGCTGCGCCGCACTGCCCGTGCTGCCGATCTCTGGTCTG AAGCCTCGCGGAGGACTGAGCACTCCAGACTTGAACCCATGGGAGAAGGCGGACT GTGA | 9968 |
| hsa-mir-542 | 1 | MGANLTFKVFNK* | 9969 | ATGGGAGCAAATCTGACATTTAAAGTGTTTAACAATGA | 9970 |
| | 2 | MSAAGKFSGNGLGKKKKQQLTWRGGERKLSKGQ* | 9971 | ATGAGTGCGGCCGGAAATTCTCAGGAAACGGACTGGGAAAAAAAAAACAACT AACATGGAGGGCGGGAGGCGGGAGAGAAACTGAGTAAGGGGCAGTGA | 9972 |
| | 3 | MEGRGEKTE* | 9973 | ATGGAGGGCGGCGGGAGAGAAACTGAGTAA | 9974 |
| | 4 | MNFSSYLQEVSYVLERNV* | 9975 | ATGAACTTTCCTCTTATTTGCAAGAAGTTAGTTATGCTTTGCAAGAAATGTGTGA | 9976 |
| | 1 | MLWPDPLEINPES* | 9977 | ATGCTGTGGCCAGATCCACTAGAAATTAACCAGAATCTTAG | 9978 |
| | 2 | MRRR* | 9979 | ATGAGGAGGCGATGA | 9980 |
| | 3 | MMTLQKVAAAGGA* | 9981 | ATGATGACTCTGCAAAGGTTGCGCAGCTGCCGGTCGTAG | 9982 |
| hsa-mir-545 | 4 | MRKKGALGDRPHLGSTHSEGSLAFRSWVAVLGSEYSHP BRVAKHCGCSVRIQC* | 9983 | ATGCGTAAAAAGGGAGCACTTGGAGACAGGCCACATTTGGGCAGTACGCATTCGGA GGGCTCTTGGCTTCCGATCTTGGGTCTGTACTTGGCTCTGAATACAGTCACCC CATCAGAGTAGCAAAACACTGTGGTTGTAGTGTGAAGAATCCAATGTAA | 9984 |
| | 1 | MSLDWACLSSWGRATSWGPAHTRTHVERVCKSTPVLL TEGDYSTVFLGLFFTSGLTLAARGSPPGLGCWIPATRG KHWRHDPGSTSRGARTGRGAAGLAAAAAARGWAGL GCGEMTSPSPRAPW* | 9985 | ATGTCTCTGGATTGGGCTTGCCTCTCTTCCTGGGGAAGAGCYCACTCTTGGGCCT GCACAAGGTGATTACAGCAGCCGTGGTGTAATTTACGTCAGGCCTC ACGCTCGCTGCACTGGGATCGCGCAGGAGCTGCTGGATCCCGGGCACTG GGGAAGCACTGCGGCACGATCCCGATCGACCTCGGCCCGGCCACTGGCC GCGGGCTGTGGGACTGGGGCCGGGCCGGCGCGGGGTGGGGCCCGGCT TGGCCTGCGGGAATGACGTCCCCGGTTCGCTAA |
| | 2 | MWKGSVNRHPFC* | 9987 | ATGTGGAAAGGGTCTGTAAATGACACGCCCTGCTAA | 9988 |

Figure 1 (Continued)

| | | | | |
|---|---|---|---|---|
| hsa-mir-548b | 3 | MSPPIPAAARPVSSSLRSLAESSVRAASGTRGAALSSTPP PGAGRGASKSWPGPRPPPPNPGHLPRAVVPAASGRRBR PVPSRGIDPGVAGGTAPAAESGGRRVSGREAAAATLASR ASLLHGPASTRGDRCPGWGLLGRWRPRA* | 9989 | ATGTCCCCGCCTATCCCCGCGCAGCCGCCCGTCTCTCCTCCGCAGCTCG CCGAGTCCTCGGTGCCGGCGTGCGAGCGGGACCCGGAGCTGCGTCCTGACG CCTCCCGCCAGGCGGCCATCTCCGAGGAGCTCGCCGTTGTCCCGCCTGGTC GCGGCCCAACCCCGGCATCTCCCGCCGTTGTCCCGCCTGGCTTCGGGCCGGC GGACCCGCCTCCTCCAGGGGTGACCCCGGGTGCCGCGGTTGGGACGGCGCCTG CGGCCGAGTCTGGGCGCGCCGTCCACGGCCGTGCGGTCGCCTCCACCGACCCGGACTCTT GCCTCCCGGGTCGTTGGGAAGATGGCGACCCGGACATGA GGCTGGGGTCTGTTGGGAAGATGGCGACCCGGACATGA | 9990 |
| | 4 | MATPGMSWQQHYYGGSAAKEAPSPATAQLAGHSMDY SQEMHLKMSKKIAQLTKVRGAATGQVATPCGPRRTHL SPREAVRPAPAARGTLLRRSNSRRHLQNPANFGGTLA I* | 9991 | ATGGCGACCCGGCATGAGCTGGCAGCAGCACTATTACGGCGGCTCGGCGGCCAA ATTCGCGCCCTCGCCGCCACCGCACAGCTGGCTGGGCACAGTGACTACAGCC AGGAGATGCACCTGAAAATGAGCAAGAAAATGCCCAGCTCACCAAGGTAAGGGGG CGGGACGACGGGCAGGTGGCGACCCCGTGCCGGGCCGGGACTCACCTGTCTC CGGGAGGCAGTGCGCGCTCCAGCGAGGGGAACTCTACTCCTCCGCGAA GCAACAGCCGGAGACCTGAACACCCTGCAAACTTTGGTGGAACGCTGCAACA TGA | 9992 |
| hsa-mir-548c | 1 | MVKRQ* | 9993 | ATGGTGAAAGACAGTAG | 9994 |
| | 2 | MINACKGASLLYDKSWLI* | 9995 | ATGATAAATGCATGCAAAGGAGCTTCTCTATGACAAGTCTTGGCTAACTTAG | 9996 |
| | 3 | MHAKELLFYMISLG* | 9997 | ATGCATGCAAAGGAGCTTCTCTATGACAAGTCTTGGCTAA | 9998 |
| | 4 | MQRSFSSI* | 9999 | ATGCAAAGGAGCTTCTCTATGA | 10000 |
| | 1 | MPGGTDPSPRTRARSSRGCTWAVAAGYFYPSPFLLLPG RRGLPPGPARVGLHPGRNPALNTGGAATA* | 10001 | ATGTTTGGAGGTACGGACCCTCGCGCACCCGCGCTCTCGGTCTCGCGGCTGC ACGTTGGGCCGTGCCGCCGCCGGCTATTTTACCCTTCCGGCCGCCGTCTCCGGCCGGGCC GCCGGGGCTGCCTCCCGGGACCCAGCCCCGCTGCGGTCTCCATCCTGGAAGAAACCCG GCGCTTAACACCGGCGGTGCCGCTACCGGCATAG | 10002 |
| hsa-mir-550-1 | 2 | MTGANVVLQQTDETALVLVVVFSTRKSGGDQLLNVVLS GDSSGEQFLKAKSQSVSNEH* | 10003 | ATGACTGGAGCAAATGTGTTTTTACAACAACCGACGAAACAGCCCTTGTGGTTGTG GTTTTTAGTACCAGGAAGTCAGGAAGTCAGGAGAACCAGTTGCTAAATGTAGTTCTATCTGGG GACTCGAGTGGGGAACAGTTTTAAAGGCCAAAAGTCAAAATGAACA CTGA | 10004 |
| | 3 | MLFYNKPTKQPLWLWFLVPGSQEETSC* | 10005 | ATGTTGTTTTACAACAAACCGACGAAACAGCCCTTGTGGTTGTTGGTTTTTAGTACCA GGAAGTCAGGAGGAGACCAGTTGCTAA | 10006 |
| | 4 | MNTELPCLDRLLV* | 10007 | ATGAACACTGAGTTACCATGTTTGACCGACTTTTAGTATAA | 10008 |
| hsa-mir-550-2 | 1 | MAAVTAAAGEEAVGRPGAPSATAESGGPSWRTETSGS RTAT* | 10009 | ATGGCGGCCGTAACAGCGGCGGCGCCGAGGAAGAGGCCGGTGGGAGGCCCGGGCGC CAAGCGCCGACGGCAGAAAGCGGCAGCGGCCGTCATGGCACCGAAACCAGCGGC AGTCGCACGGCCACCTGA | 10010 |
| | 2 | MAHRNQRQSHGHLSRPFLLEPARGACSRDTFLSASPRLP RPRQAASLAHRPEKSAPGADCPSGRRAAALDVRGPLWA GRGASALPSSSRVRSYPLCSRGTARGPVRSKADRSARQS GLAAANGARARTRLGSTFQ* | 10011 | ATGGCCGCACGAACCAGCGGCACGGCACGTGCCAGCGGACACCTTCCTCTCGCCTCTG GAGCCAGCCGTCAGGCGCCAGCTTGCCCACCGCCCGAGAAGAGCGGCCGCCCT CGGACTGCCCTCGGGGCCCTGGCCCTGGACGGTGGGTCCGGTTCGCTCTACCCTC TTGGCTCTCGGGGGCACAGCGGCCAGGCGGCGGACCAGGGGACGAGGCGCC AGGCAGAGCGGCCTGCCCGCCCGTAACGCGCACGGCGCGCTACTCCGGCTCCGGATC TACCCTTCCAGTAG | 10012 |

Figure 1 (Continued)

| | | | | | |
|---|---|---|---|---|---|
| | 3 | MGPGPGLGAGGPPRCGSRLRCPALTSPAPRAAPRWPR QPRAAVSWGAWRRGPARRSPPSASRTAAAVRRTRRTR CTAALRMAAAASTGRWAGAPAGRAW* | 10013 | ATGGGACCGGGACCAGGCTGGGGCGGGGGCCCGCCCGCCGCGGGGAGGTTCCC GGCTCAGGTGCCCAGCGCTCACCAGCCCAGCTGTTTCCTGGGGGCGCCTCGGGGCGCGCCTGCCCT CGGCAGCCCCGGCCCAGCTGTTTCCGAACAGCAGCAGCGGTCCGCAGGACTCGGAGGACTCG CAGTCCTCCTTCAGCATCCGAACAGCAGCAGCGGTCCGCAGGACTCGGAGGACTCG GTGCACAGCAGCCCTGAGGATGGCGGCGGCCAGCAGCCGCGCTGCTCCGGCGCTGC GAGCCCCGGCCGGGCCGCTGGTGA | 10014 |
| | 4 | MFGGTDPSPRARARFSRGCTWAVAAGYFYRSPFLLPPG RRGLLPGPARQGLLPGPARAGLHPGKKPGT* | 10015 | ATGTTTGGAGGTACGGACCCTCGCCCGGCTATTTTACCGTTCCTGTTCTCCGCCTGC ACGTGGGGCCGTGCCGGCCTCCCGCGCCCCAGCCCCAGGCGCTGCTTCCCGGGCCGCCGGGGC GCCGGGGGCCTGTTCCCGCCGCCCCAGCCGCGGCTGCTTCCCGGGCCGCCGGGGC GCCGGTCTCCATCCTGGGAAGAAACCGGCACGTAA | 10016 |
| hsa-mir-553 | 1 | MNQGF* | 10017 | ATGAACCAAGGTTTCTGA | 10018 |
| | 2 | MAGPRVEVDGSIMEGVSTERSORGCSLTKEGSSHHRCA YFSSPCTPTFAGRPDPESLYGLIELSPRPPLAGAEDFSRPE HARPEVNLAGHGVGP* | 10019 | ATGGCGGGGCCGGTGGAGGTCGATGGCAGCATCATGGAAGGGTGAGTACAG AGCGAAGCGGCCGGGCTGCAGCTCAACTAAGGAGGGGAGCTCTCACCACCGGTGT CTTACTTCTCTCCCGTACCCCAACCTTTGCAGGGCGGCCAGATCCGAGAGT CTCTACGCCGCCTTGAGCTGTCTCCTAGGCTCCCTTGCGGTGCAGAAGATCCGAGC CGGCCGAGCACGCCAGCCTGAGGTAAATCTGCTGAGGGGAGTGGGCCGTG A | 10020 |
| | 3 | MAASWKG* | 10021 | ATGGCAGCATCATGAAGGGTGA | 10022 |
| | 4 | MGDPGRGTLPGRWPGL* | 10023 | ATGGGGATCCAGGCGGGCACTCTGCCGCGTGGCTGGGTTGTAA | 10024 |
| hsa-mir-554 | 1 | MNGTRNWCTLVDVHPEDQAAVRKSALAVFSVLYSRFL SPPLPCPAPCWLTSPGARLARSALRGASLFFFCLRRAV GVAG* | 10025 | ATGAACGGGACGCGGAACTGGTGTACCCTAGTTGAACGTGACCTAGAGGACCAGGC GCGGTAAGAAAAGCGCTCTCGCCGTGTTTGTATTCCGGTTTCTAAG TCGCCCCTTCCGTGCCCGCCGGCCCGTGTTGCCATCACCTGGTGCCGGCTCGC GCGGTCAGCCTGCCGGCGCTTCTCTTTATTCTTTGCCTGCGACGGCAGTG GGAGTCGCGGGGTGA | 10026 |
| | 2 | MSSSDWVPERLWTLCPAEEA* | 10027 | ATGAGCTCAAGTGACTGGGTCCCTGAGCGCCTTTGGACGTTGTGTCCTGCCGAGGAG GCTTAG | 10028 |
| | 3 | MVLWMISNKKNGRVNYRAWTGKRGASRGR* | 10029 | ATGGTGCTTTGCATGATCAGTAACAAGAAAAATGGTAGAGTAAATTACAGGGCTTG GACTGGAAGGGGCGGGGAAGTAGGGGACGGTAG | 10030 |
| | 4 | MQNPGREGEGSDPSEGFWTGRGLRRKGAFSSAGWSTP LSSFSGSQSQFSPP* | 10031 | ATGCAAGAACCGGGTTGCGGAGGCCGAGAAGGAGGGAGCGTTCTCCAGTGCAGGCGAAGGCTTCTGA CGGGAGAGGGTTGCGGAGGCCGAGAAGGAGGGAGCGTTCTCCAGTGCAGGCTGGTCTACCCCT CTCTCCTCTTTCTCTGGCTCCCCAGTTCCCAGTTCTCCCACCCTAG | 10032 |
| hsa-mir-559 | 1 | MAPPQVLAFGLLLAAATATFAAAQEGEARIGAELWSW AGLGLGSGPRFSAPETGHGRGPRGRAFQRGDRTVRPCSG SGPPRGRKRRGPSRGAASLRSFARLGREMALGGGGGQA GNGVATSRFFAATEPVPRALAHPRPFGVDLGFQNSPSR WRSLYDRDQRARPCPC3GPRMWA8GGDRRPQGGLQGR YAPARGRRPGPHRACCGFPFSKDHMSNARLJVGENAEHT VKSKNI* | 10033 | ATGGCCCCCCCGCAGGTCCTGCGTTCGCGTTCGGGCTTCGTTGCCGGCGACGGCGACT TTGCCGCCAGTCAGGTCGGGAGGTGAGGCGTCGATTGAGCAGAGTTGTGAACTGGGC TGGGGGGGCCCAGCTCAGGAACGTCCAGGTGAGACGGGCAGGGGCGGGCAGAGGGCATAATAGGAA GGGACCAAGAGGCCGCCGCCTTCCAGCTGGAAACGGCAGGGCGGCCGTCCGGGAGCAGCTC GGCTCAGGCGCCCTTGCCGCCGTCGCGTGGTAGGAAACGGGAGGCCCGTCCGGGAGCAGCTC ACTTCGCAGCTTTGCCGCCGTCGCGTGGTAGGAAATGGCCTTGGGGAGCGGGGGAC AGGCAGGGAACGGAGTGCCCACCCACGTGGCACGCCACGGGAACGTCAGGGAGCCAGTGGGGACTTGGGGTTCAAAACAGC CCCAGCGCCTGCGAGTCTTACCAGCAGGGACCAGGGACGCGCCCGTTGGGGACTTGGGGTTCAAAACAGC AGCGGGCCGCCGATGGCTGGGCTCCAGGGGGGACAGGGACGGCCCCCCCGGAGGAGCGGGCGCCCCCCGCCCCCGAGAGCCTCCA GGGCGCCCGGCTGATCACTTGCGGCCGGACCAGAGGCTCCTCAAGGCTCTTCAAGGCCGGTGGCCGGTGGGGCCCCGATCATAGAGTAAAAAACATGTA AATAATAACCGTAAAGAGTAAAAACATATAA | 10034 |
| | 2 | MHLRAAGGPDHTGRVGVFPFLRII* | 10035 | ATGCACCTTGCGCGCGGCAGGCGGCCCGGACCACACAGGCGTGTGGGTGTTTTCCC TTTTCTCAAGGATCATATGA | 10036 |

Figure 1 (Continued)

| | | | | | |
|---|---|---|---|---|---|
| | 3 | MPGLL* | 10037 | ATGCCAGGCTTATTGTAG | 10038 |
| | 4 | MARSRLTATFASRVQVILLPQPPE* | 10039 | ATGGCGCGATCTCGGCTCACTGCAACTTTCGCCTCCTGCCCGGGTCAAGTGATTCTCCTG CCTCAGCCTCCTGAGTAG | 10040 |
| hsa-mir-561 | 1 | MWAWGWGGAKLRGRAADTLKLRGRAQRKGRRPHG YPSAARVK* | 10041 | ATGTGGGCATGGGGGTGGGGAGGGCGCGAAGCTCAGAGCTGGGTAGGAGGCCAAAGGAAGGGGCGCGTCCACATGGTTACCCTT CTGCTGCGCGGGTCAAGTAG | 10042 |
| | 2 | MGVGRREAPRPGRGYFKAQSWEGPKEGAASTWLPFCC AGQVASSGGRKARRG* | 10043 | ATGGGGGTGGGGAGGCGCGAACTCCGAGGCCGGATACTTTAAAGCTCA GAGCTGGGAGGGGCCCAAAGGAAGGGCGCGTCCACATGGTTACCCTCTGCTGCG CGGGTCAAGTAGCTTCTCTGGAGGCGCAAGGACGCGGGGGTGA | 10044 |
| | 3 | MVTLLLRGSSSFFWRAQGAAGVMSPWVLAPTAKFAWP GPPSRGLTRHTDQNPEQAVLSILRLLRLPR* | 10045 | ATGGTTACCCTTCTGCTCGCGGGGTCAAGTAGCTTCTCTGGAGGCGCAAGGACGCG GCCACCCTTCTGCGCCTCACTCGCCACACGGATCAGAATCCGAGCAGGCAGTTCTC TCTATTCTGAGGCTCCTGCGCTCGCCGGCTGA | 10046 |
| | 4 | MCLRC* | 10047 | ATGTGTTTACGATGTGA | 10048 |
| hsa-mir-563 | 1 | MRRRKPQGWARGRGSGGAGESAGVRACGGRPGVPAPR RCRLRRGRRSSPGRRWRGEVGNGPGLARGGGARTPPSA RARLRSWVRDRKGWKGWAPGGCGEWRWASRTCTWR KRENVPLGLGRVGSQQVG* | 10049 | ATGCGGAGGAAGCCGCAAGGTTGGCGCGGCAGGCCGCCGCTCTGCGGGGCGGGGG AGTCGGCAGGGTGCCGGCCGTGTAGGCGCCCGGGGCGGAGTTCCGGGAGTGGCGCG TGCCGCCTCAGGCCCGGCGACTCGCACGTTGAGGTGAGGGACGGCGACCCTCAGCCAGG GAACGGCCCGGGACTCGCACGTTGAGGTGAGGGACGGCGGGAGTCCGGGGCACCTG GCAAGACTAAGGAGGCTGGGGTGGCGGACGTGGTGGCGGGAAGCGTGGGCACCTG GCGGCTGCGACGAGTGCGGATGCGCAGGCCGGACTTGCACGTGGAGAAAGCGTGA GAATGTGCCCTGGGTTGGGGAGCGTGGAGAAAGCGTGA | 10050 |
| | 2 | MGEPDLHVEKA* | 10051 | ATGTGCCCTGGGTTTGGGAGGACCCAAGGAGTGGGATGGAGAGGTGGTC | 10052 |
| | 3 | MCPWVWGGWGAKEWDERWSRNGGRCCPPRGLQAET G* | 10053 | ATGTGCCCTGGGTTTGGGAGGACCCAAGGAGTGGGATGGAGAGGTGGTC ACGGAATGGGGGGGCTGCTGTCTCCCCGGGGCGTCAGGCCGAGACCGGGTGA | 10054 |
| | 4 | MRGBHGMGGAAVLPGGCRPRPGEGRG* | 10055 | ATGAGAGGTGGTCACGGAATGGGGGGCTGCGAGAATGGGCGCAGCCGGTTGA GAGACCCGGTGAGGGTCGGCCACGCGCAGGCCGTTGA | 10056 |
| hsa-mir-564 | 1 | MDSVGRRGAR* | 10057 | ATGGACTCGGTGGGCCGGCACGGAGCCGTTAG | 10058 |
| | 2 | METAKPREVYLLPQRPQYPAWPQASGPDVLPRAQTYY RLGRRPPQPPRVSATWPAPSEAPESDSQGACRSVASQER RVT* | 10059 | ATGGAGACAGGCTAAGGCCTCAGGCCGAGAAGTTTACTTCTACCCAGAGCACAAACTTACTACAGG TTAAGCCGGAGCCGGAGGCCGCCACAGCCAGGGTCTCTGCCACCTGGCCGCCCTCGAG GCCGCGGAGGAGCCGATTCCCAAGGGCCTGCCGCGCTCACAGGAGCCGTCG CGTCACGTGA | 10060 |
| | 2 | MAERPGPPGGAVSATAYPDTPAEFPPHLQAGAMRRRF WGVFNCLCAGAFGALAAASAKLAFGSEVEPGALLVLLI RAGGRGAAGRRRGAAGPAGLLGWGGGGRRAPPHPRRS VPPGPRAAGGAAVSWGGRECFASNHARPSSSVGGKRR RGLRPLPLPGT* | 10061 | ATGGCCGAGAGGCCGGGAGCCCGGGAGCTCCTCGGCACTCCGGCACGCCGTACCCTGA CACCCCCGCGGAATTCCCTCCGCAGCGCAGGGCACCCGGAGGCCGGGATGGGCGGGCGCGGCGGCTTTG GCCCTCTAACTTCAACTCTGTGCGCCAGCGGAGGTCGAGCCGGGCCGCGTTGGTTGGCTGCTGC CAAGCTGGCCTTCGGCAGCGAAGGTCGAACGCCTGGGGCGGAGGGGCCGCGGCACCCTGGC GCCTCTTGGGGTCGGGGGTCAGGGGCGCAGGGCGCGGCCGCGTCAGCGGGGTGGCAGAGAG TGTTTCGCTCTAATCACGCAAACCCTCGTCAGTGAGGTAGTAAGAGAGAGCGTCGG GGACTGAGGCCCTCTTCCCTTACCCAGGGAACCTAA | 10062 |
| | 4 | MFSLPHYQENWEFGIL.* | 10063 | ATGACCAGTCTGCCCCACTGCCCAGGAAAATTGGGAGTTGGATACGTGTAG | 10064 |
| | 1 | MPFTRRVGVRRRAP* | 10065 | ATGCCGCCTACGCACGGCGGTTGGAGTGCGACGAAGAGCGCCGTGA | 10066 |

Figure 1 (Continued)

| | | | | | |
|---|---|---|---|---|---|
| hsa-mir-565 | 2 | MDRWYPEARSNCIRVISYHGEGPSKSGPVAQWITRLTI DQKILGSTPGWLAMSVLPHLTHVLLGLVKMYIHNVKV LQDLGKVYG* | 10067 | ATGGATCGTTGTACCGGAAGCCCGTTCAAACTGTATAAGGGTGATCAGCTATCAC GGAGAAGGCTTTAGCAAGTCGGGGCCAGTGGCCAATGGATAACCGCGTCTGACTAC GGATCAGAAGATTCTAGGTTCGACTCCTGGCTGGCTCGCGATGTCTGTTTGCCACA CTTGACCCATGTACTACTGGGTCTTGTAAAGATGTATATTCACAATGAAAGTATT ACAAGACCTTGGAAAGGTGTATGGTTAG | 10068 |
| | 3 | MDNASDYGSEDSRFDSWLARDVCFATLDPCTTGSCKD VYSQCESJTRPWKGVWLECES* | 10069 | ATGGATAACGCGTCTGACTACGGATCAGAAGATTCTAGGTTCGACTCCTGGCTGCT CCGGATGTCTGTTTGCCACACTTGACCCATGTACTACTGGGTCTTGTAAAGATGTA TATTCACAATGTGAAAGTATTACAAGACCTTGGAAAGGTGTATGGTTAGAATGTGAA AGTTAA | 10070 |
| | 4 | MYYWVL* | 10071 | ATGTACTACTGGGTCTTGTAA | 10072 |
| | 1 | MAPGGR* | 10073 | ATGGCCCCGGGGGGCGCTAG | 10074 |
| hsa-mir-566 | 2 | MDVWMMWPAGSPMCKATFSCKVLGGCSHTPPPSRFW SGSSDPPSASALSPINARGSALPRRCACPTSVSLLEDWPA RREAVYWQSPRGGSPTSAEWEDLQS* | 10075 | ATGGATGTTGTGGAATGATGTGGCTCCGGGGTCACCCATGTGCAAAGCAACTTTTCC TGCAAGGTTCGGGTGGGTTCTCATACACCCCACCTTCACGCTTCTGGAGCGGG AGTTCGATCCCCCTTCTGCCTGCCTACACCTCCAGTCTCTTCCATTAACGCCGAAGGCAGCGCTC TTCCCGTAGATGCGGTTGCCTACCTCAGTCTCTACTTGAGGACTGGGCAGCC GAAGGGAAGCGGTATACTGGCAGTCCCACGTGGGGGTCTCCACATCAGCAGAG TGGGAGGACCTCCAGTCCTGA | 10076 |
| | 3 | MRLPYLSVST* | 10077 | ATGCGCCTTGCCTACCTCAGTGTCTCTACTTGA | 10078 |
| | 4 | MGQEGIKVGLGMRQCWRELAGAGAGGPTG* | 10079 | ATGGGACAGGAGGGTATCAAAGTTGGCTAGGAATGAGGCAGTGCTGGCGGGAGTT GGCTGGAGCTGGGGCTGGGGCTGCCCCACTGGATAA | 10080 |
| hsa-mir-570 | 1 | MTIKFCTSFPEAPDRLAWSIYYWTYS* | 10081 | ATGACTATCAAATTCTGTACCTCATTTCCAGAGGCTCCTGACAGACTTGCTTGGTCA ATATACTACTGGACATATTCATGA | 10082 |
| | 2 | MRLSHTGISNPVCPTLFLSMPVPLPLPHMSVTVHLLSLS PSPFGS* | 10083 | ATGAGACTGTCTCACACAGCATCTGAACCCAGTGTGTCCACAATTCTCTTCCTA TCCATGCCTGTTCCTCTCCACTGCCTCATATGTCGGTGACTGTCCACCTTCTCTC TCTCCCCCTCCGTTTGGCTCATAG | 10084 |
| | 3 | MAHTLLQIMIFNHWNDGNNLIGFHLSSI* | 10085 | ATGGCCATTACCTATTACAGATCAACACTTCAATCACTGGAAATGATGGCAATAAT CTAAATTGGGTTCAITTTATCCTCTATCTAA | 10086 |
| | 4 | MMAH* | 10087 | ATGATGGCAATAATCTAA | 10088 |
| | 1 | MGS* | 10089 | ATGATTGGTAGCTAA | 10090 |
| | 2 | MVSVYRGRASQG* | 10091 | ATGGTGAGTGTCGGGCGCAGGGCGTCCAAGGCTGA | 10092 |
| hsa-mir-571 | 3 | MAAGPSLRTESPLPLSPGASVPSGFGPGLLSVPAQRLW PSLQPSLCSSAPAAPHLPQAVG* | 10093 | ATGGCGGCGGGAACTGAGTCTGCGAACGGAGTCCCGGCTGCCGCCTGCAGCCTGG GGCCTCAGTACCCCCAGTGGAGGGACCTGGCCTCTGCAGCCTCCCGCACCAGGGCT CTGGCCCAGCCTGCAGCTGCAGGAGCTGTGCAGCTGCGGCCCGCAGCCCCGCACCTTCC CCAGGCTGTGGGGTGA | 10094 |
| | 4 | MPAWEELWEKLWSGDPVALPCSE* | 10095 | ATGCCGGCGTGGGAGGAGCTGTGGGAGAAGCTGTGGTCTGGGGATCCGGTCCCCTGC TTTACCCTGTTCGGAATGA | 10096 |
| hsa-mir-574 | 1 | MHTPTRPHSGSAPSACVNLRGACLDLPKYPVLAPSKSG KVPPMARGQVRGGLQGPPARARREQVPVRQRPRPVR LPSALAQGAQALTSPLPSPYSSPNSRPTPCLLPQSSQHSK QAPPPLAAPGMGPTPYRRSPGPLHPVG* | 10097 | ATGCACACACCACGCCACACTCAGGTCTGCCCCCTGGCCTCGGTGAACCTC CGGGAACGCCCCACCCTGGATCTCCAAGTATCCAGTACTCAGCCTGGCACCAAGCTGTGA AAAGTGCCCCCAATGCTCTCGGGCCAGTTGGGGGCCCCCTGTAAGACAGAGGTCGCCCAGCGC CCGGCACGAAGGCGAGCAGGTCCCCTGTAAGACAGAGGCCTCGTCCGCCAGGGTGCGCC TGCCCTCGCCTTGGCACAGCCACCTCAGGCTTGAGCCCTGCCTGCCTGGCCTCAGCCCC ACTCCTCCCCAACAGCCGACCCACGCCCACCTCCAGCCCGGATGGGTCTGCTTCCAGCCAACACT CTAAGCAGGCACCGCCCCCTCCACCACCAGCGGCTAG | 10098 |

Figure 1 (Continued)

| | | | | | |
|---|---|---|---|---|---|
| | 2 | MGCESITYALLIPSFPILMLKDTGRWLLKSVCSELPVTS AML* | 10099 | ATGGGCTGTGAGAGCATTACCTATGCCCTACTGATCCCATCATTCCATCTAAAC ATCTTGAAGGACACAAGGCAGGTGGCTTCTTAAATCAGTGTGCTCTGAACTCCCTGTG ACCTCAGCCAACCTGTGA | 10100 |
| | 3 | MRQALSSEPLFALSAA* | 10101 | ATGAGACAGICTCTATCCTCAGAGCCTCTTTTGCCCTCTCGAGCTAG | 10102 |
| | 3 | MDLRHK* | 10103 | ATGGATTTGAGGCACAAGTGA | 10104 |
| | 4 | MSAAGL* | 10105 | ATGTCAGCCCTGGACTGTAG | 10106 |
| | 1 | MPLQP* | 10107 | ATGCCCTTGCAGCCTTGA | 10108 |
| hsa-mir-586 | 2 | MGINERTVFCNELYPCTQGASSKAIWLLAVAQLATCVC VAA* | 10109 | ATGGGAATAAATAGAAGGACTGTATTTTGCAACGACTGTATTTTGCCCTGTGCACGCAGGG GGCCTCCAGCAAAGCCATTTGGTTGCTTGCTGCTTGCAGCTGGCTACGTGTGTTTG CGTGCGCGCTAA | 10110 |
| | 3 | MKGLYFATSFTRABRGPPAKPFGCLLSLSWLRVFASPPK SELLSAYLC* | 10111 | ATGAAAGGACTGTATTTTGCAACGAGCTTTACCGTGCACGCAGGGCTCCAGCA AAGCCATTTGGTTGCTTGCTGCTTCAGCTGGCTACGTGTGTTGCGTCGCGCCT AAAAGCGAGCTGCTTTCAGCTGTCTCTGCTGA | 10112 |
| | 1 | MFQL* | 10113 | ATGTTCCAGCTTGA | 10114 |
| | 2 | MNFARVWQIQPQ* | 10115 | ATGAACTTTGCCAGGGTCTGGCAGGACTCAACCCAGTAG | 10116 |
| hsa-mir-587 | 3 | MGTVCYVRIPLRWSSVPASQQPAPRGMSSAPPCHLQNEL VYYPFFSVKSLLLPKPKVISSSSSDLASLGPRTAGRNADSQ APPQITS* | 10117 | ATGGGCACAGTTGCTACGTACGGAGATCCCTCCGTGGTCCAGTGTGCCTGCCTC CAGCAGCCGCACAGTTGCTACGTACGGAGATCCCTCCGTGGTCCAGTGTGCCTGCCTC CTGTTATGTTCCCTCTTTCGTGAAGTCTTGCTACCTAAACCAAGGTCATTT CTTTCTCCCCTGATCCTCGCAGCCTGGGTCCAAGAACAGCTGTAGAAATGCAGATT CTCAGGCTCCACCCCAGACATCCTAA | 10118 |
| | 4 | MYSSKPCLCSLLFCCEVFAT* | 10119 | ATGTATTCTTCAAAACTGTTGTTTATGTTCCCTTTTCTGTGAAGTCTTGCTACCTAA | 10120 |
| | 1 | MASSGEVLSATVSALLPRRPRSPWVLPSRPGPPCILSIP TPTPRPRSHPDPGLAPAPVLPASCPQDSYPVSEGTSCLPL RSCIPDRQSCPRLSVP* | 10121 | ATGGCCAGTCCAGGGAGTCCCGGAGAGGTACTGTCCGCGACTGTCTCCGCTTCGTCTGCTGCTCGG CGGCCGTCCGGTCTCCGCTACCCGCCGCTCCATCCGACCCGGGTTCCCTGGCATCCTTTCTA TCCCGACCCCGTACCCCGTCCTGCCATCCTGACCCTGGCCTTGCCCCCTGCTC CGCTCCTTCCCGCATCTCTGTCATTCTGATCGCAGCCTCTACCTGTGTCCCGTCTCTCCGTCCC TCTCCCCCTTGCTCCAGAGTTGTCCCGTCTCTCCGTCCCTGA | 10122 |
| hsa-mir-589 | 2 | MLSFSPSPLLPGACLLNDVGGG* | 10123 | ATGCTCAGTTTCAGCCCCGACCTCTGCCTGAATGACGTG GGGGTGGGTGA | 10124 |
| | 3 | MTWGVGDGGKAISPEGLTTYPGILSQHSPNLGPMEKPA ASL* | 10125 | ATGACGTGGGGTGGGTGGGTGGATGGTGATGGAATGGAGCATTTCACCTGAGGGACTTACGAC GTACCTCGAATTCTTTCCAACACTCGAAATCTGGGTCGCAGATGGAGAAGCCGGC CGCGTCCTGTGA | 10126 |
| | 4 | MEEKPFHLRDLRRTLEFFPNTPQJWVRWRSPPRPCNVV QSIVSAERGAAGTLDSD* | 10127 | ATGGAGGAAAAGCCATTTCACTTGGGGACTTACGAGCGAACCCTGGAATTCTTTCC AACACTCCCAAATCTGGGTCCGATGGAGAAGCCGCCGTCCGTATGTAATGTGGTG CAAAGTATTGTCTCTGCAGAAGGGGTGCAGCGGGACTCTAGACTCTGACTGA | 10128 |
| | 1 | MADFDTYDDRAYSSFGGGRG* | 10129 | ATGGCGGACTTCGACACCTACGACGATCGGGCCTACAGCAGCTTCGGCGCGGCAG AGGGTGA | 10130 |
| hsa-mir-590 | 2 | MARSEVGRRRLGSRGLACGADPFHCLPFTTCWFLPCL GRGGADARRAPASSPIPPTVGPVRG* | 10131 | ATGGCGAGCGTCGGACGACGGCTGGGATCCCGCGGCCTGGCTCCCGGCGCTCCGG GCGGATCCCTTCCACTGCCTCCCGCCAACGACAACGTGTTGTTTTGCCTGCCTT GGCCGCGGCGGGGCCGATGCCGGACCAGCCGCCGCCCGCTTCCAGCCCATCCCCC TACGGTAGGACCAGTGCGTGGGCTGA | 10132 |
| | 3 | MPGDERPLPAPSPLR* | 10133 | ATGCCCGGAGACGAGCGGCCGCTTCCAGCCCCATCCCCTACCGTAG | 10134 |
| | 4 | MVRLLAGGGRPRR* | 10135 | ATGTACGGACTCCTTGCGGCGGCGGGGGAGACCAAGGAGATAA | 10136 |
| | 1 | MWTFVL* | 10137 | ATGTGGACTTTTGTCTCTAA | 10138 |

Figure 1 (Continued)

| | | | | | |
|---|---|---|---|---|---|
| hsa-mir-594 | 2 | MTYQRGK* | 10139 | ATGACGTACCAAAGAGGAAAATAG | 10140 |
| | 3 | MLCERVVCRSPSGLMDKALAS* | 10141 | ATGTTGTGTGAGCGCGTCGTTTGCAGAAGCCCAGTGGCTAATGGCCTAATAAGGCATTG GCCTCCTAA | 10142 |
| | 4 | MPTLLFFFLNGKCVCVFTSWWAAIFENLHTMSFV* | 10143 | ATGCCAACTTCTACTTTTTTTTAAATGGAAGTGTGTGTGTTTTACTAGCT GGTGGGCTGCAATTTCGAGAATCTGCACACCATGTCCTTGTCTGA | 10144 |
| hsa-mir-607 | 1 | MNFSVEIAPPQSLFKQK* | 10145 | ATGAACTTCTCCGTCGAAACTGCTCCTCCCAGAGCCTGTTTAAGAAGCAGAAATAA | 10146 |
| | 2 | MPVDALTSKIFPKGEVDTRY* | 10147 | ATGCCGGTGGATGCACTGACCTCTAAGATTTTCAAGGTGAAGTGGATACACGTTATT AA | 10148 |
| | 3 | MSKPLGHESP* | 10149 | ATGAGCAAGCCTCTTGGAATAATGAATCACCTTAA | 10150 |
| | 4 | MGNERRKGKEMGWKEKSRRDRPIPVGLVP* | 10151 | ATGGGAAACGAAAGGAGAAAGGAGAAAATGGGTGGAAAAGAAAAAGCAGAA GAGATCGCCCTATACCAGTAGGCCTAGTACCCTAG | 10152 |
| hsa-mir-609 | 1 | MAQCRERDEGPHSAGGASLSVRCCGVHGPATDLGLAEP PAPSPLLPPLPPVP* | 10153 | ATGGCGCAAGGCGGGAGCGCGGAGCGCGGAAGGCCCCACTCCGCCGGCGGCGTCCTT GTCCGTGAGGTCGCGGTGTTCACGGCCGCCGACCGATCGGGTCTCGCGGAACCTCC TGCCCCAAGTCCCCTCTCCCCTCCCCTCCGGTTCCTTAG | 10154 |
| | 2 | MSRGFSPNQCPSLAFSTFKHTFNI* | 10155 | ATGTCTCGAGGTTTCTCACCAAACCAGTGTCCTTCACTGCCTTTCCACCATCTTCA AGCATATCCTTTAATATTTAA | 10156 |
| | 3 | MFFLCASLSFTSTSFLLFSTFICFKSKIWPHTLHLCK* | 10157 | ATGTTCTTTTTGTGTGCTAGCCTTTCATTCAGTGACTTCATTCCTTTATTTCTAC GTTTATCTGATTTTAAATCAAATATGCCACATACTCTTCATCTGTGTAAATAA | 10158 |
| | 4 | MATYSSSV* | 10159 | ATGGCCACATACTCTTCATCTGTGTAA | 10160 |
| hsa-mir-611 | 1 | MVRALRGVPDGDARTPRGLTHETALISSDAGDPEG* | 10161 | ATGGTGAGAGCGTTGAGGGGAGTTCCTCAGACGGAGATGCGAGGACCCTCGGGGTCT GACCCACACCGGCTTATCTCCGGGGTCTGA | 10162 |
| | 2 | MRGPLGV* | 10163 | ATGCGAGGGACCCTCGGGGTCTGA | 10164 |
| | 3 | MNSLGFSARDF* | 10165 | ATGAACTCTTAGTTTCTAGCTCGGATTCTAA | 10166 |
| | 4 | MPWANVYW* | 10167 | ATGCCCTGGGCAAATGTTTATTGGTGA | 10168 |
| hsa-mir-612 | 1 | MRVEKGRGLVRDTVWVGVVGNAG* | 10169 | ATGAGGGTGAAGAAGGGAGAGGGTTGGTTAGAGATACAGTGGGTGGTGGGGG TGGTAGGAAATGCAGGTTGA | 10170 |
| | 2 | MQVEGNSLIGLWGI* | 10171 | ATGCAGGTTGAAGGGAATTCTCTGGGCTTTGGGGAATTTAG | 10172 |
| | 3 | MPSHRQGKCLYQLPPCGQDSLFQRVVLFGVWVLSSEL VT* | 10173 | ATGCCATCTCACAGGCAAGGCAAGTGTTTTACCAGCTTCCTCCTGGTGCCAAGAC AGCCTGTTTCAGAGGGTGTTTGTTGGGGTGTGGTGTTATCAAGTGAATTAGTC ACTTGA | 10174 |
| | 4 | MSLPASSWWPRQPVSEGCFVWGVGVIK* | 10175 | ATGTCTTTACCAGCTTCCTCCTGGTGCCAAGACAGCCTGTTTCAGAGGGTGTTTT GTTTGGGGTGTGGTGTTATCAAGTGA | 10176 |
| hsa-mir-615 | 1 | MSSSYVANSFYKQSPNIPAYNMQTCGNYGSASEVQASR YCYGGLDLSTFPPPAPSNSLHGVDMAANPRAHPDRPA CSAAAAPGHAPGRDEAAPLMPGMYSQKAARPALEERA KSSGEJKEEQAQTGQPAGLSQPPAPPQTYPWMTKLJHMS HGKL* | 10177 | ATGAGTCCTTCCACTTAGCCAATTCATTCATTCTATAAGCAGAGCCCAATATCCTACTAT AACATGCTACGGCGGATTGACCATGGAACTATGGCCTCAGAGGTGCAGGCATCCAGGTA CTGCTACGGCGGATTAGAACATGGCTGCCAACCCCCCGGCTCACCCGCCGCCCCGCTG TCTCCACGCGGGTAGACATGGCTGCCAACCCCCCGGCTCACCCGCCGCCCCGCTG CAGCGCCGCGGATGACGAAGGCCGCGCCAGGAGGAGGCAGGCAGCGCAGGAGCAGCGACAGGAGGAGGACTAAG ACCCGGGATGACGGGAGATCAAAGAGGAGGCAGCGCAGAGCAGGAGCAGCGCCGGACTGA AGCAGTGGGGAGATCAAAGAGGAGGCAGCGCAGAGCAGCGCGCCGGACTGA GCCAGCGACGGCGCCACAGATTTACCCGTGGATGACCAAACTGCACATGAGCC ACGGTAAACTTTAG | 10178 |
| | 2 | MDRPQRCRHPGTATADWT* | 10179 | ATGGATCGGCCTCAGAGGTGCAGGCATCCAGGTACTGCTACGGCGGATTGGACTTAA | 10180 |
| | 3 | MRGK* | 10181 | ATGCGGGGCAAATAA | 10182 |

Figure 1 (Continued)

| | | | | |
|---|---|---|---|---|
| | 4 | MARKTVH* | 10183 | ATGGCTCGTAAAACTGTCCACTAA |
| hsa-mir-616 | | | 10184 | |
| | 1 | MLKMSGWQRQSQNQSWNLRREASTDSHLPFTLPSPQS WGVRSLGSASLLHSEVRDRPREEWGIESLILGWCLQTPH ASDDGVSPPLPGAGTRALLCAAGQRDLGCPWEIHSFP* | 10185 | ATGTTAAAGATGAGCGGTGGCAGTGACAGGCAGAGCCAAAATCAGAGCTGAACCTGAG GAGAGAGGCGAGTACTGATTCCCATCCAGCCTCACTCCTTTACCCTCCGTTCCTCAAAGTTG GGGCGTCCGCTCTTTAGGATGGGATCGCCCTCACTCCTCACAGTGAAGTTAGGACGCGTC GAGAGAGGAATGGGGAGAGTCCCTTATTCTGGGGTGGTGCTTACAAACCCTATTG CTTCGGACGACCGGCGTTCTCCACCCTGCCCGGAGCCGGAACACGGGCCTGCTCT GTGTGCTGGCAAGGACCTCGTTGCCCTTGGGAAATTCATTCTTTCCCGCTAG | 10186 |
| | 2 | MGRVPYSGVVLTNPYCFGRRRLSTPARSRNTGPALLCCW AKGPRLPLGNSFFPVANFRPHR* | 10187 | ATGGGGAGAGTCCCTTATTCTGGGGTGTGCTTACAAACCCTATTGTTCGGACGA CCGGCGTTCTCCACCCTGCCCGGAGCCGGAACACGGGCCTGCTCTGTCTGCTGG GCAAAGGGACCTGCTTGCCCTTGGGAAATTCATTCTTCCCGCTAGCCAACTTCAGG CCTCATCGTTAG | 10188 |
| | 3 | MAILVAGATGPCSG* | 10189 | ATGGCTCACCTTGGTAGCTGGGCTACTGGACCCTGCAGCGGATAG | 10190 |
| | 4 | MDREWCVFLLP* | 10191 | ATGGACAGGGAGTGGTGTTTCCTTTTGCCGTAG | 10192 |
| hsa-mir-618 | 1 | MLKPSVTSAPTADMATLTVVQPLTLDRGKGAARSPGH RVPSPLLPSPPANSQRDMGRAQAGGEGERGRARKAFAP RTEHFLPLSLPATFPLPLPTVLAPPRGRLLLALGSPLPLPA PRRVVSGPLALLEPLRGDGYRRQLGVGEGQRASSPGQ SPEFTGEGAACQLAWRRGPGGRKFVQAPEGEGRSNCW SPGGHSGGGLGAPLGCRAHSGGAAAGRELPSAERAROS AGSRAPAAEIGSPRLRDRKRRGSRLLPPPAAPCR* | 10193 | ATGCTGAAGCCTGAGCGTCACTTCGGCTCCACGGCAGACATGGCGACATTGACAGT GGTCCAGCCGCTCACCCTGGACAGAGGTAAGGGAGCGGCTCGCTCGGCCAGGCCACC GCGTCCCCTCCTCCCCCGCCTCCCCGCCTGCCAATTCCAACGAGCAGGAAGCTTCGCGCC GAGAACAGAACACTTTCTTTCCCGCTCCCGGCCCCTCCCGGCACGTTCGCGCC ACTGTACTGCGCCCCGCCGCGGGGCTCTGGCCGCCCGCGCCACCTCGCTCGCGGT CTGCCGGAGTATCTAGGGCCGCAGGGGCTCCAGGGGGTTGGAGAGGGCAGAGAGCAAGCT CGCCCGGCCAGAGCCAGCCAGGGGGCGAGGAGACCGGCGAGGAGCCGCTCAGTTGCTGG CGCAGGGGCCCGGAGAGGAAGGAAGTTGTCAGCGCGCCGGAGGGCGAGGGTCGGT CCAACTGCTCGGAGTCCGGCGCTGCACTCGGGGCGGGCGCGGCCTGGGCGCACCCTGGGC TGCCGGGCGACAGTCCGGGGCTCAGCAGCCAGGAGCTGGCGAGATCGGCTCCGGCCGC TTCGAGATCGAAAGCGGCGAGGGTTCCTTCCTGGCTGTGCAGAGGAGGACACCCTCAGTGA CGATAG | 10194 |
| | 2 | MESSAAIGASLVHPCGVIPVPECVGPLPGSSVQ* | 10195 | ATGGAGTCCTCCGCTCGCTGCGATCGGGGCCTCACTGGTGCACCCTGTGGGGTTATACCT GTCCCTGAGTGTGTGGGTTTCCTTCCTGGCTCCAGCGTCCAGTGA | 10196 |
| | 3 | MKALESYGSAEIDTL* | 10197 | ATGAAGGCGCTCGAGTCCTACGGCTCTGCAGAGGAGGACACCCTCTAG | 10198 |
| | 4 | MVYSEENDLVRCTSKNFLSRGLN* | 10199 | ATGGTGTACTCAGAAGAAAATGATTAGTCGATGTACCTCTAAAAATTTCTTTCT AGAGGATTAAACTGA | 10200 |
| hsa-mir-619 | 1 | MALVTLQRSPTPSAASSSASNSEVSPGLAAPGLGRRTPR RGRRSWGRACGAGGRLRGLLGAPP* | 10201 | ATGGCCCCTGGTTGACCCTGCAGCGTTCGCCACGCGCACGGCGCCTCTTCGGCC AGCAACAGCGAGGTGAGCCCGGCTGCCCGGAGCCTGGGGCGCCGCCGCCGGACGCC GGGCTCCTCGGAGCCGCGCGTAG | 10202 |
| | 2 | MQCDPSGSVCRILCVRCDPHQGVTPHLG* | 10203 | ATGCAGTGCGACCCTTCTGGGAGTGTCTGCAGGATACTGTGTGTGCGTGTGACCCA CATCAGGGGGTTACCCCATCTGGGGGTGA | 10204 |
| | 3 | MCNWDP* | 10205 | ATGTGCAACTGGACCCTTGA | 10206 |
| | 4 | MPGCAM* | 10207 | ATGCCTGGCTGTGCGATGTGA | 10208 |
| hsa-mir-619 | 1 | MPVLLLMTLESSMRQSWPCVSLWRVTSMGSSARSLMTL MSLSCSRETEIEALKEELLFMKKN* | 10209 | ATGCCCGTCTTACTGCTGATGACCTTAGAGTCAAGTATGAGACAGAGCTGGCATGC GTCAGTCTGTGGAGAGTGACATCCATGGCCTCTGCAAGGTCATTGATGACACTAATG TCACTCAGCTGTAGCAGGAGAGATCAGGAGACAAGAATGAGGCTCTCAAAGAGAAGAACTAG | 10210 |

Figure 1 (Continued)

| | | | | | |
|---|---|---|---|---|---|
| hsa-mir-622 | 2 | MRQSVESDHGLCKVIDEYTNVTQL* | 10211 | ATGCGTCAGTCTGTGAGAGTGACATCCATGGGCTCTGCAAGGTCATTGATGACACTAATGTCACTCAGCTGTAG | 10212 |
| | 3 | MEIEAPKSQDLTKIMADIRPNTMSWLGRTERSWTSTGLSRLRRAPQWSSHSLLRLELLR* | 10213 | ATGGAGATAGAAGCCCCAAATCGCAGGACTTCACCAAGATCATGGCAGACATTCGGCCCAATACGATGAGCTGGCTGGGAAGAACCGAGAGAAGTCTGGACAAGTACTGGTCTCAGCAGATTGAGAGGAAGGCACCAGTGGTCATCACACAGTCTGCTGAGGTTGGAGCTGCTGAGATGA | 10214 |
| | 4 | MTLTELRHTV* | 10215 | ATGACACTCACGGAGCTGAGACATACAGTCTAG | 10216 |
| | 1 | MEEGL* | 10217 | ATGGAGGAGGATTGTAA | 10218 |
| | 2 | MAAAGSSLL* | 10219 | ATGGCGGCAGCCGGCAGCTCCTCCCTGCTCTGA | 10220 |
| hsa-mir-624 | 3 | MDELAGGGGGGPGMAAPPRQQQGPGGNLGLSPGGNGAAGGGPPASEGAGPAAGPELSRPQQYTIPGILHYIQHEWARFEMERAHWEVERAELQVPRWGRCAGAAAAAGFPAGGWGWGLHSAGAGALGGRAEPTCAAQVVMVLSTAFPGVPLPLSRISLLPNLHWLRGAGLLGAARLAFSMASAGAPPEAAPPGLRGLGPSTSLWESPVWGLSTLSLLLFVPLEMKSPKRGTRIGILPPFSGPPPFPIWRIWPPPSDLVRACPLTATLLSWAARVHSDLGLTCEVLFPIVNFKYFLT* | 10221 | ATGGACGAGCTTGCCGGAGGCGGTGGTGGCGGCCCGGGAATGGCGGCCCCTCCCCGGCAGCAGCAGGGACCTGGGGGAAACCTGGGCTTTGCCCTGGGGAATGGGGCGGCTGGGCCACTACAGCACACTGAGCCCCTGGTTGCCAGCAGATGAGGCTGGCCATCTCCGGAGGATACTGGCACTACCACCAGCACGAGTGTCCGGATGGTGAACTGCTGGGCGGCCGAACTGCAGGTACCTCGGTTGCTGTGGGGTCGGCGGTGCGGGAACTGCAGCCGGAGCCGGAGTCGCTGCTGGGTTGGGAGGCCAAGCGGAACCTACCTGTGCTGCTCAGCCATATAAGCTTGCTCCCAACCTTGTGATGGTCCTCTCAAGGCTTTCCTGGAGTCCCCTCCCTTCTCGGAGCAGCCATTTGGCTTTAGTATGGCGTCCTCTGGGAGTCCCTGGGGCCCTCCAACACTGAGTTTGCTCTGTTGTCTCTGAGATAAGAGCGCGAAGAGAGGACTTAGGATAGGCATCTTCCGCCACCCCCCTTCCGAATTTGGCGTATCTGGCCCCCTCCAGAGTTGGTACGGCGTTGCCCCTTGACAGCCACGCTTCTTTCCCATCGTCAACTTAAGTACTTTCTCACCTGAGTTTTATTCCC* | 10222 |
| | 4 | MLPYSLGFSVVIPYLVTHQRFQH* | 10223 | ATGCTGCCTTACTCACTTGGATTCTCTGTAGTTATTCCTTAGTGACTCATCAACGCTTTCAGCACTGA | 10224 |
| | 1 | MAVLLKGL* | 10225 | ATGGCTGTGTTGTTGAAGGGCCTGTAG | 10226 |
| hsa-mir-627 | 2 | MHDAFEPVPILEKLPLQIDCLAAWGEPRGRGAEAESAQERSGSFLRPGKWTGVHPCGLRLDATREGLRMREGREMFTGYRHRCLWGYLGDPSDPVI* | 10227 | ATGCACGACGCTTTCGAGCCAGTGCCGATCTGGAAAAGCTGCCTCTGCAAATGACTGTCTGCTGGCTGGGGTGAGCCAGGTGACCGAGCGAGTCAGCACAGGAGGGTTCGGGATCTTTCTCACGAGAGCGGAAGGCGTCCATCCGTGTGGGCTTCGGTTGGATGCTACAAGGAGAGAAGGCAGAGATGAGAGGAGAGAAGGCAGAAGTGGATCCAGTGATCCAGTCATTTAG | 10228 |
| | 3 | MLHERGLG* | 10229 | ATGCTACACGAGAGGGCTTAGGATGA | 10230 |
| | 4 | MSYGLLG* | 10231 | ATGTCTGTGGGCTACTTGGGTGA | 10232 |
| | 1 | MYPQRHPVSNCNSVVYLSIYHGRVNEAVYLAPPFCLLLPLWCVCLCVCSHTKGDAAGGRR* | 10233 | ATGTATCCGCAGGGCAGGACATCCGGTGAGTAATTGCACTCGGTTTATTTAAGCATCTATCATGGCAGGGTAAACGAGGCAGTTTATCTGGCACTCCATTTGCTTGTGCTACCTTTTATGTGTGTTGTGCTCTCACACAAAGGGGATGCGGCGGGGGGCGCCGTTGA | 10234 |

Figure 1 (Continued)

| | | | | |
|---|---|---|---|---|
| hsa-mir-629 | 2 | MVCVFVCVLSHKGGCGRGAPLREEVNSARVARGAACV PGGAVHAVPGPALKSPNSPGLSPAPALLGRGRPLVKGM GAPLPTGRDGAPPLRPVGELRNLLGRFWAEGGLFWLGA VGEGPGPL* | 10235 | ATGGTGTGTGTTTGTGTGTGTCTCACACAAAGGGGATGCGCGCCGGGGGC GCCGTTGGAGAGAGGAGGTTAATTCCGGCGGCAGTGGCGCGGGGGCTGCTGTGTTC CAGGGGGAGCTGTTCACGGCGGTCCCGGTCCCCCCGCCTCTGAAGTTCTCCAACTCACCCG GCTTGTCTCCGCCCGCCGCCTTACTGGGGAGGAGGAGGCCCTTGTGAAAGGCATG GGAGCCCCGCCTGCCGACGGGGAGGAGAGATGGGGCCCCCTCCGCCCGTCGGAGA GCTGAGAAACTTGCTGGGAGCTTCTGGGCTGAGGGCTTCTGGGGGCCCTCTTTTGGGTGGGGC CGTTGGGGAGGGGCCGGGGCCGCTCTGA | 10236 |
| | 3 | MRPCGAVERGG* | 10237 | ATGCGCCGGGGGCGCTGTTGAGAGGAGGTTAA | 10238 |
| | 4 | MGRPPSAPSES* | 10239 | ATGGGGCGGCCGCCCTCCGCTCGTGAGAGCTGA | 10240 |
| hsa-mir-631 | 1 | MAAAPALKHWRTTLERVEKFVSPLYFTDCNLRGRCGP WSPAACBRPQPCASSFPSGEKPKLQPPGPRDKVPAAGRA ACCTAAGCTGCAGCACCTGGGACCACCCGGGACGCCGGAGGACTGCCGGACGCCG GAGEEGVGNGLCRGAARQPSWRRIQGKCGPTGQLAPK RKRGGLQHVPTGPSHAGFLGPAALWLCSPAS* | 10241 | ATGGCCGGCTGCGCCGCTCCGGCCTCTACTTTACCGACTGTAACCTCCGCGGACGTGGAGCGGGTGGGCCCTG GTCCCCGGCAGCTGCAGCACCTGGGACCACCCGGGACGAGAAGTGCCCGCCGCGGCAGGGCAG AACCTAAGCTGCAGCACCTGGGACCACCCGGGACGAGAAGTGCCCGCCGCGGCAGGGCAG GGGCCGGGAGGAGGGGGTAGGAATGGACTGTTGGCCGCGGAGGCCAGCCAGGGCCCCAGCC CTCTTGGCGGAGGATCCAGGAAACGTTGGCCGCCACGGCCAGCTGGCCCCCAGGGC GGAAACGGGCGGCCTCCAGCATGTGCCCCACCGGCCGTCCACGCAGGCTTTTG GGGCCCAGCTGCCCTGTGGCTGCGTGCTCTCCAGCTCCTGA | 10242 |
| | 2 | MDCAAERPGSPLGGGSRESAAPPASWPGGNGAASSM CPPARPTQAFWGQLPCGCALQLPDAGETSLPGGSPAGL PPRAGRRQLRTHVGNAQRVGGATGLGEVPTQLPATPSL SALCRRQLRGHEQHPLLGAAPSAGNSSLVPGSSGDGFHS HVAASGHPLGRAP* | 10243 | ATGGACTGTGCCGCGGAGCGGCCAGGCAGCCCTCTTGGCCGAGGATCCAGGGAGAAAG TGGCGCCCCACCGGCGCCTGGGCTCCCCAACGGGGCGGCTCCAGCATGT GCCCAGCCCCGCCTGACGCTGAGCTTCCCTACCAGGAGGCAGTCCAGCGGGACTTC TCCAGCTTCCTGACGCTGGAGAGACTTTCCTACCAGGAGGCAGTCCAGCGGGACTTC CGCCCCGCCTCGGCTCGGCGACAGTCTCGGACGCCACGTAGGTAAGCCCAGCGGGTG GGGCGGGCCACAGCCTAGGGAGCCAACCAGCCCCAGCTCCAGCACACCTTCGTT GTCTGCCCTCTGCCTGCTGGGAACAACAGCTCTCTGGCTTCCTGGGATTGTTTTCA AGCACCCTCTGCCTGCCCACCGTGGCGGCGCTCCGACATCCCTAG | 10244 |
| | 3 | MVFIPTWPLDIP* | 10245 | ATGGTTTTCATTCCACGTGGCCGCTCTGACATCCCTAG | 10246 |
| | 4 | MLGEFQAPADTLSKEGYQDRTSTSRPITTALLQMVDLL VPGGADHPRGMGPGSSPLLGK* | 10247 | ATGCTTGGAGAGTTTCAAGCCCTGCCGACACTTATCCAAGGAAGGATATCAGGAT AGGACTTCTACCTCAGCCTGACCTGCAGACACAGCTCTCTTGCAGATGGTGGACCTGCTG GTTCCGGGTGGAGCTGACCATCCCAGAGGCATGGGTGGCCAGGAAGTTCACCTTT GCTGGGAAAGTGA | 10248 |
| hsa-mir-632 | 1 | MGRKKKQLKPWCWYPLSV* | 10249 | ATGGGTGCAAGAAGAAGAAGCAGCTGAAGCCGTGGTGCTGGTATCCTTGTCGGT TTGA | 10250 |
| | 2 | MGFPRGFAVVGRVIL* | 10251 | ATGGGGTTCCGAGGTTGGACAGTCTTTGCAGTGTGGTCGTGACTCTGTGA | 10252 |
| | 3 | MEGWGQLHSLSPTFSVFIYFMCVLCLFFRIGGLVKNQVS QPWFRTFPFFFFSGREEN* | 10253 | ATGGAGGGTTGGGGACAGCTTCACAGTCTGTCACCCACTTTTGTTTATTTACT TATGTGTTTGTTGTTATTTTTGCGAATTGGCGGTTTAGTAAGAACCAAGTTAG TCAACCCTGGTTTCGAACCTTTTTTTTTTTCTTTCGGGAGGAGAAGTTAG TAG | 10254 |
| | 4 | MLFLEALIFFTLKLILFFTVLYVKAACYSTAFM* | 10255 | ATGCTTTTTCTGGAAGCCGTTAATATTCTTACATTAAAATTGATTTATTTACTGTTT TGTACGTAAAGGCGGGCTTGTTGTTACAGTACTGCGTTTATGTAA | 10256 |

Figure 1 (Continued)

| | | | | | |
|---|---|---|---|---|---|
| hsa-mir-636 | 1 | MSYGRPPPDVEGMTSLKVDNLTYRTSPDTLRRVFEKYGRVGDVYIPRDRYTKESRGPAFVRFHDKRDAEDAMIDAMDGAVLDGRELRVQMARYGRPPDSHHSRRGPPPRRYGGGGYGRRSRR* | | ATGAGCTACGGCGCCCCCCCTCCGGATGTGGAGGGTATGACCTCCCTCAAGGTGGACAACCTGACCTACGGCGACGTGTACGACATCCCGCGGGACCGCTACACCAAGGAGTCCCGCGGCTGCGCCTTCGTTCGCTTCACGACAAGCGCGACTGGAGGACGCTATGGATGCCATGGACGGGGCCGGTGCTGGACGGCGCGGAGCTGCGGGTGCAAATGGCGCGCTACGGCCGCCCGGACTCACACCAGCACCACACCGCAGCACAGGACGCTCCGGGTGCAAATGCGGGCCCCGGACTCACACCAGCACCACACCGCAGCCCCCGGACTGCGGACTCGGACGCCGGAGCCGGCAGGTAA | 10258 |
| | 2 | MWRV* | | ATGTGGAGGGTATGA | 10260 |
| | 3 | MPWTGPCWTAASCGCKWRATAAPRTHTTAAGDRHPAGTGAVATDAGAAGKRG* | | ATGCCATGGACGGGCCTGTCTGGACGGCCGTGAGCTGCGGTGCAAATGCGCGCTACGGCCGCCCGGACTCACACCAGCACCACACCGCAGCCCCCGGACTGCGGACTCGGACGCCGGAGCCGGCAGGTAAACGGGCTGA | 10262 |
| | 4 | MASGGEIMAAAWAGARGRGRPRCLELTPLCLLVPPAALGGVAAADPGVGVVPGLAADLATAARSLGPALVLDLGRPPSPDPHEGPSPSPRRSPDLVRGPGPGLGPGVLPQCPRGNPNPGRDRRVFPSLLKRKERCPLKKMVMSGNPRHITLHKWDLG* | | ATGGCGTCTGGGGCGGAGATAATGCGGCTGGGCGGAGCGCGCGGGGCGCGGCCCCGCTGTGTCTGCTGGTTCCCGGCTCCCGCGGCCGCTGGCGGCGTGCGGCAGCCGTCAGCGCGGGAGCTGACTACCCCTGCCTGGAGCTCACCCCGCTGTGCCTGCTGGTCCCGGCCGCCCTGGGCGGAGCCGGCTCCGGGAGCTCCCCGGGTGCCCCCGAGCCCCGAGCCGCGGCCCCAGCCGCCCCGCCCGCCCCCCAGTGCCCCCGGGGAAATCCCAGCACAAGTCTCCTTGGAATCCGAGACACATAACCCTAATTCATAAATGGATTTGGGGTAG | 10264 |
| | 1 | MSTPRQEDVEDHYEMGEELGR* | | ATGTCCACGTTCAGGCAGGAGGACGTTGAGGACCATTATGAGATGGGGGAGGAGCTGGGCAGGTGA | 10266 |
| | 2 | MRWGRSWAGELSARTAGLQG* | | ATGAGATGGGGGCGGAGGAGCTGGGCAGGTGAGCCCAGGCGCGCACGGCTGGGCTGGGCGTGGGGGGATAG | 10268 |
| hsa-mir-637 | 3 | MLRRNESVSCGGGTNLGRGVRQPRL* | | ATGCTGAGAAGGAATGAGTCAGTATCATGCGGTGGGGAACGAATTTGGGCGTGCGGCTCAGGCCGCGGCGGTGGGCGTGGGGGGCTGTGAGTCAGACAGCCCCGGCTGTGA | 10270 |
| | 4 | MSQYHAVGERWAVESDSPGCEFLLGNPLCYSCGEKSN* | | ATGAGTCAGTATCATGCGGTGGGGAACGAATTTGGGCGTGAGTCAGACAGCCCCGGCTGTGAATTCCTGCTTGGGAATCCTCGTGTGTTCTGTGGGAGAAAGTAATTGA | 10272 |
| | 1 | MVKPLLFSPSYRRSAPFDWSRKLIGQSPGASPSLGSDRPQGAGANVGASCPDWPTGRARPGAGRTQSRV* | | ATGGTCAAGCTCCTGCCCCTTCGGCGTTCGCGCCCCCTTGGTTCGATTGGTCTCGCAAGGAGCTCCGGCGTCAGTCCTAGTCCTGGACCGGCCCCAAGGAGCACCAGTGGGAGCGTGAACGGTCTACGACAGGGCCGGGGCGCGGCGGGCCCGGAGACGCGGGACCAGAGCCGCGTTTAG | 10274 |
| | 2 | MKHYEVRSEKQEPCCHC* | | ATGAAGCATTACGAGTGAGAAGCTAGAAAGCGAGAAAGCAAAATCTGCAACCCAGGCTGTTTTGGGGTGCTGCTGA | 10276 |
| hsa-mir-639 | 3 | MRMCAGSIYKSATQAVLGVLPLGGLCRGWDACRFLAAPPAG* | | ATGCGCATGTGCGCCAGGAAGTATTTATAAATCTGCAACCCAGGCTGTTCCTTGCAGCTCCCCAGCGGGCTGA | 10278 |
| | 4 | MGATKVRDPCSQSEGVLHKSCATPSPA* | | ATGGGAGCCACGAAGGTGCGGGACCCTTGCTCCCAATCGGGGAGTGCTGCACAAATCTTGCGCCACGCCGCGTCACCAGCGTAG | 10280 |
| | 1 | MGGGRAPPERLGGGR* | | ATGGGTGCGGCCCCGGAGCGCCTGGGTGGCGGCCGGTGA | 10282 |
| | 2 | MVASGPPAVPRWAVPPVPGGGTAALEPLLQELSGGGRAGAVGPASGGRGGGGGPYH* | | ATGGTCGCGTCGGGACCGCCGGCCGTCCCGCGATGGGCTGTACCACCCGTGCCGGCGGGGGACCGCGCCTTCGAGGAGCTAGTGGGGGGGCCGAGGCCGGCATACCACTGA | 10284 |

Figure 1 (Continued)

| | | | | |
|---|---|---|---|---|
| hsa-mir-641 | 3 | MGCTTRARRGDRGPRAPPSGAEWGWPSGGGGTSLGGP GRWRRAPLRRWGERCKFAGRGAQAAACAGRGLDLSG AAGRSSLACAG* | 10285 | ATGGGCTGTACCACCGTGCCGCTGCCGGGGGGACCGCGGCCCTGAGCCCTCTCA GGAGCTGAGTGCGGCGGCGGGGCCGGAGCGGTGGCGAGCGGTGGCGGCGGACGGG GGCGGTGGCGCGGGGAGCGCAGGCGCAGCGTGCGCAGCGTGGCGGGCGGGGCGAAGTTGCG GGACAGGGGAGCGCAGGCGCAGCCTGAGCCTGGCGTGCGCGGGCTGA | 10286 |
| | 4 | MLPQLWLGYTTFALGEPCLERRGTQRGL* | 10287 | ATGTTCCCAACTGTTGCTGGTTTATATCACCACGCGTTGGCGGAGCCTGCTTA GAACGTAGGGAACCAAATCAGAGGACTGTGA | 10288 |
| | 1 | MSLSACFHLWLAAR* | 10289 | ATGTCTCTGTCTGCGTGTTTCCATCTCTGTTAGCTGCTAGATAA | 10290 |
| | 2 | MLCKGCSTYSGLYLPPAGKVL* | 10291 | ATGCTGGAAAAGGTTGTTCCACTTACTCTGGGCTTTATCTACCCCAGCGGGGAAA GTTTTGTAA | 10292 |
| hsa-mir-642 | 3 | MCARKPFGLGEWELGWAPQVLHQAVGTQMGVSSTPL GGTENLQVFQFPIEKGSRLTVSTPSSPRRSPGSQESVGPD FGDTDTSAQRSSRATARSANTPPFHLCCPNNSQGRPGN HLRGPAHHRSSTHSACLSLPPDHHAWELRERVRCLGVP RVYGSPAVCPCV* | 10293 | ATGTGTGCTAGAAAACCCTTTGGCTTGAGAGTGGAGCTCGGATGGCGTTTCA AGTTCTCACCAGCTGTGGAACTCAGATGGGCGTTTCAAGTACCCACTAGGGGG TACTGAAAACCTTCAAGTTTTCAGTTCCCATAGAAAAGGGGCTCTAGGCTGACGGT TTCTACCCCCTCCTCTCAAGGCGGTCCCCAGCGTAGCTCTAGGCAACCGCCCGCTCAGC CTTCGGTGACACTGACACTTGTCCCAACAACAGTCAGGGAGCGCGGAAA AACACCCCGCCTTTGCCAACACAGTCAGGGAGCGCGGGGAA TCACTTAAGAGGCCCCGCCAGGAGTTGCACCACTCCGCGTGCTCCCT CCCCAGATCATCACACGCTCCCCCAGAGTTGCGGAGGCGGGCTGCCGCTCGGAGTCC CGGTGTATACGGGGTACTGA | 10294 |
| | 4 | MGYSSSPPGCGNSDGRFKYPTRGY* | 10295 | ATGGGCGTTTCAGTTCTCCACCAGCTGTGGGAACTCAGATGGCGTTTCAAGTAC CCACTAGGGGGTACTGA | 10296 |
| | 1 | MAWRYGATAAREFSFV* | 10297 | ATGGCGTGGAGATATGGCGCAACTGCGGCGGTGAGTTTCCTTTGTTTAG | 10298 |
| | 2 | MAQLRRVSFPLFRLSVRLAVPSRFCTRDVGGGTDLEIPA PLSPPAVNSCVPSEC* | 10299 | ATGGCGCAACTGCGCGTCTGTACCCGGGAGTTTCCTTTGTTTAGATTAAGTGTTCGCTTAGCG GTGCCCTCACGCTCTGCACCCGGGATGTCGCGGCGGTACAGACCTTGAAATCCCC GCACCGCTCTCTCCACCCGAGTAAATTCATCGTCCCGTCAGAGTGTTAA | 10300 |
| | 3 | MWGAVQTLKSPHRSLHPE* | 10301 | ATGTGGGGGGCGGTACAGACCTTGAAATCCCACCGCTCTCCACCCGAGTAA | 10302 |
| | 4 | MRPYRVLKSP* | 10303 | ATGCGTCCCGTCAGAGTGTTAAAATCGCCTAG | 10304 |
| hsa-mir-643 | 1 | MAAFPARADADPSPTTARDTPGRQAEKSETACEDR* | 10305 | ATGGCGGCCCGCCCGCCGCGGCCGACGTGATCGTTCGCCACGTCGCCACTACG GCCGAGACACACACCAGGCCGGCAGGCTGGCAGAAAAGCGAGACCGTGCGAGGACC GGTAG | 10306 |
| | 2 | MLSARGYALPDRGQGLGFGGAAAHGAFGLPKTRVAP SSLCGGFARA* | 10307 | ATGTTGTCGCTCGGGGTGCGCTCGGGGTGCCCTGGAGCGCGGCCAGGCTTAGGATTT GGAGGTGCGCGGCGCACGGTCGCTGAAGGGGCGCTCTGGG AGCCCTCTGCGGGGGCTTTGCAAGAGCATGA | 10308 |
| | 3 | MKWGSCGGAAGGTRPHPGSSPRVAPLGAGPCAAPLGP WPSGGGGHAVPGAARGRSGRCPSLPGLKCPLGSPRGPQ EGVVPTQAPLAWVQAVTPVRNAVSQDSLRDGLRWMP QGEGCPGTGSLLSRSC* | 10309 | ATGAAGTGGGGAAGTTGTGGGGGGTGCAGCGGGGAAGAACCGGCCCCCACCGGTTC GTCACCCGAGTGGCTCGGGAGGGTGGCCGGCCGGACGGTGTCCGCGGCCCTTGGGGCCGT GCCGTCAGGGCGTGGCCAGTGCCAGTGCAAGAGGGCGCTGTGGG GCTGCCCTCCCCTGCCACTCAGCGCCTTGCTGGGTTCAGCTGTGACTCCTGTC AGAAACGTGAAGCGTGGACAGACTCCCTGAGCAGGACGGTGAGATGGCTGATGCCGCAGGG GGAAGGGTCGCGCTCAGGGCACAGGTCTCCTCCTCCAGAGCTGCTGA | 10310 |
| | 4 | MGCAGCRRGKGVPAQGRSSPGAAEQKELSPGPASLQV HTLPVGSD* | 10311 | ATGGGCTGCGCTGGATGCCCAGGGGAAGGTGTCCGGCACAGGGTCGCTCTC TCCAGGAGCTGCTGAGCAGAAAGAGCTTTCCCCTGGGCCAGCGTTCCCTTCAGGTCCA CACCCTCCCAGTGGGCAGTGACTAG | 10312 |
| hsa-mir-647 | 1 | MRMNWVLS* | 10313 | ATGAGGATGAACTGGGTTTTAAGCTGA | 10314 |

Figure 1 (Continued)

| | | | | | |
|---|---|---|---|---|---|
| hsa-mir-648 | 2 | MPFIPYLIARCTSQVRNPAPDCSSLIVSFSCAPGLEVLNL PYSVFNSLS* | 10315 | ATGCCGTTCATTCCATATTTGATTGCCAGATGTACTTCTCAGGTCAGAAATCCAGCC CCAGATTGTTCAAGTCTTATAGTGAGTTTTCTGTCTCCAGGTTAGAAGTTTAA ATCTCTTTATAGTGTATTCAACAGCTTGAGTTAA | 10316 |
| | 3 | MYFSGQKSSPRLFKSYSEFFLCSRFRSIEKSLL* | 10317 | ATGTACTTCTCAGGTCAGAAATCCAGCCCAGATTGTTCAAGTCTTATAGTGAGTTT TCTTGTCTCCAGGTTAGAAGTTTAAATCTCTTTATAG | 10318 |
| | 4 | MVCVFLL* | 10319 | ATGGTTTGTGTGTTCCTGTAA | 10320 |
| hsa-mir-658 | 1 | MEKPRLY* | 10321 | ATGGAGAAACCCGTCTCTACTAA | 10322 |
| | 2 | MPVIPATREAEAGESLEPGRRRLR* | 10323 | ATGCCTGTAATTCAGTCTACTCGGGAGGCTGAGGCAGGAGAGTCGCTTGAACCCGG GAGGCGGAGGTTGCGGTGA | 10324 |
| | 3 | MLHKRWPASRVKEDSDTGA* | 10325 | ATGCTACACAAAGATGGCCGGCTTCTCGCGTGAAGGAAGATTCGGATACGGGGGC CTGA | 10326 |
| | 4 | MAGFSREGRFGYCRGLMDLVVGGLPAASKLFKRSDFTRL NLLGIKIEIWPGAMAHACNPYTLGGRGGWMI* | 10327 | ATGGCCGGCTTCTCGCGTGAAGGAAGATTCGGATACGGGGCCTGATGGATTTAGT TGTAGGCGGTTTGCCTGCAGCGAGTAAAATTATTCAAACGTTCGGACTTCACAAGACT AAACTTACTGGGGATAAAAATTGAGATTTGGCCGGGCGCGATGGCTCACGCCTGTA ATCCTACACTTTGGGAGGCCGAGGCGGGTGGATGGATCTGA | 10328 |
| hsa-mir-659 | 1 | MEKPRLY* | 10329 | ATGGAGAAACCCGTCTCTACTAA | 10330 |
| | 2 | MPVIPATREAEAGESLEPGRRRLR* | 10331 | ATGCCTGTAATTCAGTCTACTCGGGAGGCTGAGGCAGGAGAGTCGCTTGAACCCGG GAGGCGGAGGTTGCGGTGA | 10332 |
| | 3 | MLHKRWPASRVKEDSDTGA* | 10333 | ATGCTACACAAAGATGGCCGGCTTCTCGCGTGAAGGAAGATTCGGATACGGGGGC CTGA | 10334 |
| | 4 | MAGFSREGRFGYCRGLMDLVVGGLPAASKLFKRSDFTRL NLLGIKIEIWPGAMAHACNPYTLGGRGGWMI* | 10335 | ATGGCCGGCTTCTCGCGTGAAGGAAGATTCGGATACGGGGCCTGATGGATTTAGT TGTAGGCGGTTTGCCTGCAGCGAGTAAAATTATTCAAACGTTCGGACTTCACAAGACT AAACTTACTGGGGATAAAAATTGAGATTTGGCCGGGCGCGATGGCTCACGCCTGTA ATCCTACACTTTGGGAGGCCGAGGCGGGTGGATCTGA | 10336 |
| | 1 | MRLGFINGRIMSARFNVAMGVLCCVCVCMYVCVLGGAC ASEHRGRRSEQREISLSMATSGTHLRSHLGQGS* | 10337 | ATGCGCCTCCGGCTTCATTAACGGCAGGATCATGAGCGCGCGTTTAATGTGATGGA GTGCTGTGTTGTGTGTGTGTGTGTATGTGTGCTGAGGTGCTTGCT AGTGAGCACCAGGCAGGCGCTGAGCAGGAGAGATCAGTCTTTCCATGGCCAC GTCTGGGACTCATCTGCCGAGCGTATCTAGCCCAGCGCTCTAG | 10338 |
| | 2 | MYVCWEVLALVSTEAGALSRERSVFPWPRLGLICGAI* | 10339 | ATGTATGTGTGTTGGGAGGTTGCGCTAGTGAGGCGCAGGCAGGCGCTGAG CAGAGAGATCAGTCTTTCCATGGCCACGTCTGGGACTCATCTGCGGAGCCATCTA G | 10340 |
| | 3 | MCVGRCLR* | 10341 | ATGTGTGTTGGGAGGTGCTTGCGCTAG | 10342 |
| hsa-mir-9-2 | 4 | MVLGLFWAGGQHYEQARKGRRWLWWRLLRSALGRQV CRFIVPRSPSFVFLTCSWPLGPTPARGVCACARGSGAR GGWGLSRQGHAWLSVLRLHLAGKLGAAGGAERQRLSL PPCSPRAAFTYGPLV* | 10343 | ATGGTTCTCGGCTTTGGGCCGGTGGGCAGCATTACGAGGCAGATCTAGAGCAGCAAGAAAGGG GCGCGCAGGCTGTGTCACCTCGCAGCCCCAGCTTGTTTCTGACATGTTCGTGCCATTG TTTCATCGTTCACCTCGCGAGGGAGTGGTGCCAGCCATGGCGTGTCGGCGCGGCGGCGG CGGGGCCACGCTCGCCGCCAAGGAGCACATGCGCCAGCATGCTGTCTCTCCGCGCACTT GGCGGGAAAGCTAGGGGCGCCGGGCTGCGGGGCTGAGCGCCAGCGCGTCATTACCGC CTCCCTGCTCCCGCGGGCTGCATTACATACGGGCCACTCGTCTGA | 10344 |
| | 1 | MYLIAKDFSTLFSYVFFNCKLLGP* | 10345 | ATGTATCTGATAGCTAAGGATTTTCAACTTTATCTTACGTATTTTCAACTGTA AATTATTGGGCTTTAA | 10346 |
| | 2 | MDGFNCC* | 10347 | ATGGATGGAATTAATTGCTGTAG | 10348 |
| hsa-mir-92a-1 | 3 | MELIAVRRLENSKYRFGRW* | 10349 | ATGAATTAATTGCTGTTAGGAGGTTGGAAAATAGCAAATATAGATTTGGACGGTG GTAG | 10350 |
| | 4 | MPYLFFPYFSLFQSYTWT* | 10351 | ATGTTTTATCTTTTTTCCTTATTTCCTATTCAGTCATACACGTGGACCTAA | 10352 |

Figure 1 (Continued)

| | | | | |
|---|---|---|---|---|
| hsa-mir-92a-2 | 1 | MCQGGSECAILARMPVAPAPATASAWAAVPGAPLIK DSSLGEERRENADCGPPVGNWGSVGFSLWRGGGSVS* | 10353 | ATGGGACAAGGTGTAGTGAGTGCGCCCATCCTGACCCGGATGCCGCCTGGTGCCACCCGC ACCGGCTCCGGCACGGCCTCGCTGCCTGGCCGTGTCCAGGCGCGCCTTTAATTAA GGACTCCAGCTTGGGGGAAGGAGAGAAGGAAATGCCGACTCCGGGGTCCCGCCGTGG GTAACTGGGGCTCGGTGGGGTTTCGCTTGGCGCGTGGGGTTCCGTTCCTAA | 10354 |
| | 2 | MPTAVRPWVTGARWGFRFGGVQVPPFNSCAGRVGGG GLFSLGY* | 10355 | ATGCCGACTGCGGTCCGCCCGTGGGTAACTGGGGCTCGGTGGGGTTTTGCGCTTGGC GGGGTTGGGGGTTCCGTTCCTAATTCCTGTGCGGGCCGGTGGGCCGGGGCGGGCT TTTTCCTTGGGCTATTAA | 10356 |
| | 3 | MCARGLDPFSGRFFSLLFPFWLRGRLRSHPAPERSSCAL GHWVYVWRGHPERAARAGSPRSPPARGGFELGPARGF PSGWLGKKGALRWGSCIDPVELTGWVGGDGAGGT* | 10357 | ATGTGCGCTCGCGGCCTTGATCATTTAGTGAGCTTTTTCTCACTTCTTCCCCT TCTGCCTCCGCGGGAGACTGCCTCCGACCCCGACCCCGTCGAGCTGCGCG CTTGGGACACTGGGTATACGTGTGGAGGGGACACCTCCGAGAGGGTCGCCCCTGCGGG AATCCCCGGCTCTCCACCTGCGGTCTGGTCCGGAGCTGGGCAGTGATCCGG TCCCGAGCGGTGCAAGAGAGAGCCCTTCGTTGGGACAGTGTGATCCG GTAGAGTTGACTGGTTGGTGGGAGGGAGGGAGGGGACGGAGCGGGGACTTGA | 10358 |
| | 4 | MRGCTWREKRDSPSPSWLLSHQPGNGGGRRGLGAFLV L* | 10359 | ATGTGGGGTGCACGTGGAGGGAAAAAAGGGACTCCCCTCCCTTGGCTTCTATCC CACCAACCCGGGAATGGAGGGAGGAGGAGGAGGGACGTGGGCTTGGCCGTGTTTTGTGCT TTGA | 10360 |
| | 1 | MELSGWGPEVCGRGTEVCGRGRWNVGGGVGHVLCGP LCT* | 10361 | ATGGAGCTAAGCGGGTGGGGTCCTGAGGTATGTGGAAGGGCACCGAGGTATGTGG GAGAGGACGTTGGAACGTGCGCGAGGAGTTGGACACGTTCTGTGTGAGCGTTAT GTACTTAA | 10362 |
| hsa-mir-92b | 2 | MWKGHRGMWERTLERGRGSWTRSVWAVMYLRGRSG VARWLTPVIPTLWKAEASGSQGQGFKTSLAKMVKPRL Y* | 10363 | ATGTGGAAGGGCACGAGGTATGTGGAGAGGACGTTGGAACGTGGCGGGGGA GTTGGACACGTTCTGTGTGGGCGTTATGTACCTTAAGAGGCAGATCCGCGTGCAC GGTGCTCACGCCGTAATCCAACACTTGGAAGGCGAGGCGAGTGGATCACAA GGTCAGGGGTTCAAGACCAGCCTGGCCAAGATGGTGAAACCTCGTCTACTAA | 10364 |
| | 3 | MGFTDIELSFGEQSRGDR* | 10365 | ATGGGATTTACGGACCAGACACAGAACTATCCTTTGGGAGGCAGAGTGGTATTGGGACAG GTAG | 10366 |
| | 4 | MRDSQEYCAAAVHEGRKLSQAAAARGTWVPQSQAAL* | 10367 | ATGCGCGACAGCCAAGAGGTGTGTGCGCAGCAGTGCACGAGGGGAGGAAGCTATC CCAGGCCGGCAGCACGTGGGAACTTGGGTCCCGCAGTCGCAGGCTGCGCTCTAG | 10368 |
| | 1 | MANGWTGSRPGRRNPEL* | 10369 | ATGGCCAATGCTGACTGGTCTCCCGACCTGGCGAGGCGAGGAATCCGAGCTGTGA | 10370 |
| hsa-mir-93 | 2 | MAGLAPALGGGIPSCEAAGIRAHVLLCLLRAEAMAGAG VGCGGGVRWRRSR* | 10371 | ATGGCTGGACTGGCCCCAGTGCTGTCTTTGTTTACTAAGAGCGAAGCATGCCGGAGCGG GGGTGGGTGCGCGTGGCGGGGTGCGGTGCGGAGGTCCCGGTGA | 10372 |
| | 3 | MCFFVY* | 10373 | ATGTGCTTCTTCGTTTACTAA | 10374 |
| | 4 | MLDGPVHCHGLFILRWLEIDL* | 10375 | ATGTTGGATGGCCCTGTGCACTGCCACGGGCTCTTTATTCTTCGGCTGGTTAGAAACA GACTTGTGA | 10376 |
| | 1 | MRLFPNRGRFCLASLVWTPRGAERRLCAQPGAGAGECL GPAGGRAGRSQSGAQ* | 10377 | ATGCGGCTCTTTCCAAACCGGGCTGCCGTTTTGCTGCTTCTGTGCTTGGACTCCG CGCGGAGCTGAGGCGGCTGTGCGCCAGCCTGAGCCGCAGGTGAGTGTCT GGGCCCGGAGCGCGGGAGCCAGAGCGGGGCTCAGTAG | 10378 |

Figure 1 (Continued)

| | | | | |
|---|---|---|---|---|
| hsa-mir-96 | 2 | MTRQCLLALPRLQAEAPTGRLGPGSASGVCPAPSAVPGRGRGRERLRSECGRCLRGAYPRGVWLGSGCVSPPWWAQAEAPGWEGAAESSAGAPELAPPASCQGCAAAGSRLLPWPGAAPPSLWGKAALRPPVCLHFAATHPGNPCGARE* | 10379 | ATGACGCGGCAGTGCCTACTGCTCTTCCGCGCCTTCAGGCAGGAGGCGCCACGGGGCGCCTGGGTCCCGGGTCCGGCAGTGCCCGGGTCCCAGGTCCTGCCCAGTCGCAGCCCAGCCGGTCCAGCCGGTTCCGAGGTGCGGGGGCGGGGCGGGGCAGAGCTGCCTGCGGCTCCAGCCGGTCCGAGGAGCTGCGGGGTCTGGGGAGGGCGGGCGGCGGCGGGGCTGCGCGCCGCCCGATGGGCTGCGGGAGGAGAGCGCCAGGCTGGTAGCAGGTCTCGAGCCTCCGTGCCCCGAGCCGCCCCCAGTCTGCCCAGTCGGGTGGGGGGAAAGCGGCTCTCAGACTCTCCGTGTCCCCTGCCCACCACTCATCCCGGGAACCCCGGCACGCGGAATGA | 10380 |
| | 3 | MRHRSPFSTAPFLLIALVAPREPALFQDRRLDGLPLAPHRSAHPRTMGSEGVTRGQGSPDSTVSSRLSHSFALPLTRAPGHRVQ* | 10381 | ATGAGACACCGTTCCCGCCTCAACTGCCCATTCCTGTTAATAGCGCTAGTGGCACCCAGGTTCCCAGCCTTCCTGCCCGCGCCCTTCCCAAGATCGGGCGCTGGACGCTTGCCTGCTGGCGCTCACCGGTCAGCCATCCCAGGACTATGGGCAGTGAGGGTGTCACCGGGGTCAGGGGTCGCCGGATTCACGGTGTCCTCACGGCTGAGCCATTCGTTGCTCTTCCAACCCGGCCTCCCGACACCGTGTACAGTAA | 10382 |
| | 4 | MGTESADL* | 10383 | ATGGGCACCGAGTCGGCGGATCTGA | 10384 |
| hsa-mir-99b | 1 | MAGTAGGRGEAAVRRRRGEDGERSAAVGPGLRARGGGEDPFPATREPREP* | 10385 | ATGGCGGGACGGGGAGGAAGGGCCGCCTGCGGCGAAGGCGGGAGAGGATGGAAGGCGGGCGGGAGGCCCGCCTCGCGGCCCGCCCCCGCCCAGCCCCCTCGCGACCGGGAGCCGTGA | 10386 |
| | 2 | MESARRRWGPACGPGAAEKTPSLRRGSRGSRESAEREGGGLGPALLGP* | 10387 | ATGGAGAGCGCTCGGCGGCGACGCGGAGCCCGGCCCTGCGGGGCGGCGGCAGAGAAGACCCCTTCCCTGCGGAGACGCGGGAGCCGGAGCCGTGAGTCTGCGGAAGGGAGGGTGGGGGGCTGGGCCTGGGCTGGTAGGATCGTGGCTGAAGAGACTAG | 10388 |
| | 3 | MGAGAGRIVAGRD* | 10389 | ATGGGGGCTGCGGGGCTTTGAGGGGTCAAGGGTGAGCCGTAGAGACTAG | 10390 |
| | 4 | MGLRGFEGSRVSRASGRGPRERRGRLSGLPDRPGSAAGAGDVWRRRGPASMLPRGPGIPGPRPLLPQJWEYTTQSPTHSRIRAPSPLFSRIQESEPPVCSLRPGNPHSSP* | 10391 | ATGGGGCTGCGGGGCTTTGAGGGGTCAAGGGTGAGCCGTAGCCAGTGGAGGGAGCCGAGGAGGGCGGAGGGTCTGGAGGAGGAGGAGCCCAGAGGTCAGCAGGCCAGGGTCAGCCGTGGGACCCGGGATTCAGTTGCCAGACCGTTCAGATCTGGAGTACCACCACCAGTCCCCACCCCATTCCAAGAATCCGAGCCCCGAGCCCTTTTTCAGGATCCAGGAGTCGTGAGCCCCCAGTCGTGTCTCTCAGGAATCCACACTCCAGCCGTGA | 10392 |
| | 1 | MPLLPAAKCSLPS* | 10393 | ATGCCCCTGCTCCCGGCGGCCAAGTGCAGCCTGCCCCTGA | 10394 |
| | 2 | MSLASNALRSFNFLQ* | 10395 | ATGTCCTTGGCCAGTAATGCCCTTCGGTCTTTCAACTTTTACAGTAG | 10396 |
| | 3 | MPPGLSTPYSRFCVRGNGMYSSTYRFLKN* | 10397 | ATGCCCCTTCGGTCTTCGTCTTCAACTTTTACAGTAGATTCTGTGTCAGAGGTAATGGTATGT | 10398 |
| | 4 | MVCHLQLTGP* | 10399 | ATGGTATGHGATTCTTCAACTTACCGGTTTTAA | 10400 |
| hsa-let-7a-1 | 1 | MSEPVSDGYSCADFCHSLAASSARSCAWHKCKYACYTPGL* | 10401 | ATGAGCGAGCCTGTTTCTGATGCTTACAGCTGTGCAGACTTCTGCCACAGCCTTGCTGCTTCAAGTGCACGATCTGTGCGGCACAAGTGTAAATATGCCTGTTACACGCCTGGGTTATATAA | 10402 |
| | 2 | MATAYVQISATALLLQVHDPVRGTSVNMPVTRLLGYKIWEBQRRRSFPLYFSFSVLPSSLSISTTPPPTQRPCNSN* | 10403 | ATGGCTACAGCTGTCAGTGCACAGATTCTGCCACAGCTTGCCTGCTTCAAGTCACGATCCTGTGCGGGCACAAGTGTAAATGCCTGTTATACGCCTGGGTTATAGCCGTCTATTTTTCTTTTCGTAATCTTACCTCTCCCTTTCTACTCTACCACCCGTAATGTACACCAACTTCACTGGCTTAA | 10404 |
| | 3 | MNIKLLGKNPF* | 10405 | ATGAATATAAAGCTATTAGGAAAAAATCCTGACTTTTAG | 10406 |
| | 4 | MLDFMWLGLLQGRRP* | 10407 | ATGTTGGATTTTATGTGGCTGGGACTTCTGCAGGGGAGACCATAA | 10408 |
| hsa-let-7a-2 | 1 | MLPQLMVHQLSLA* | 10409 | ATGCTGCCTCAGCTAATGGTACCACCAACTTCACTGGCTTAA | 10410 |
| | 2 | MFQDPFKNILNVIFSSH* | 10411 | ATGTTTCAAGATCCGTTTAAAAACATTATTTAAATGTATTTTTAGCAGCCATTAA | 10412 |

Figure 1 (Continued)

| | | | | | |
|---|---|---|---|---|---|
| hsa-let-7c | 3 | MLFLAAIMLYTLNYLIKLHAK3KSLFSFRYFIVQNLVASL FAIVLSLSKLLL* | 10413 | ATGTTATTTTAGCAGCCATTAATCTCTACACTCTTAATTATCTTATTAAGCTCCATG CCAAATCCAAATCTCTTTTCAGCTTTCGCTACTTCATTGTGCAAACCTAGTGCTTC TTTAACAGCCATGTCTCTTTCACTTTCAAAACTGTACTGTGA | 10414 |
| | 4 | MPNPNLFSAFATSLCKT* | 10415 | ATGCCAAATCCAAATCTCTTTCAGCTTTCGCTACTTCATTGTGCAAAACCTAG | 10416 |
| hsa-let-7d | 1 | MPLLPAAKCSLPS* | 10417 | ATGCCCCTGCTCCCCGCGGCCAAGTGCAGCCTCCCTTCCTGA | 10418 |
| | 2 | MSLASNALRSFNFLQ* | 10419 | ATGTCTTGGCCAGTAATGCCCTTCGGTCTTTCAACTTTTACAGTAG | 10420 |
| | 3 | MPFGLSTFYSRFCVRGNGMYSSTYRFLKN* | 10421 | ATGCCCTTCGGTCTTTCAACTTTTACAGTAGATTCTGTCAGAGAGTAATGGTATGT ATTCTTCAACTTACGGTTTTAAAAAATGA | 10422 |
| | 4 | MVCHLQLTGF* | 10423 | ATGGTATGTATTCTTCAACTTACCGGTTTTTAA | 10424 |
| | 1 | MAGTAGGRGEAAVRRRRGEDGERSAAVGPGLRARGG GEDPFPATREPREP* | 10425 | ATGGCGGGGACGGCGGGAGGAGGAGAGGCCGCCGTGCGGCGAAGGCGGGAG AGGATGGAGAGCGCTCCGCGCGGGTGGGGCCGGCCCGCGCGGGGCGGGG AGAAGACCCCTTCCTGA | 10426 |
| hsa-let-7e | 2 | MESARRRWGPACGPGAAEKTPSLRRGSRGSRESAEREG GGLGPALLGP* | 10427 | ATGGAGAGCGCTCCGCGGCGGTGGGGCCCGGCTGCGGGCCCCGGGCGGCGAAGA AGACCCCTTCCTGACGGCGGAGAGGCCCAGCATCCATGCTCCCTGGGGACCCGG GGTGGGGGCGCTGGAGCCGCACTCCTGGGTCC.CTGA | 10428 |
| | 3 | MGAGAGRIVAGRD* | 10429 | ATGGGAGGGCTGGAGCGTGGTAGGATCGTGGCTGGAAGAGACTAG | 10430 |
| | 4 | MGLRGFEGCSRVSRASGRGPRRRGRLSGLPDRPGSAAGA GDYWRRRGPASMLPRGPGIPGPRPLLPQIWEYTTQSPTR SRIRAPSLFSRIQESEPPVCSLRPGNPHSSP* | 10431 | ATGGGGCTGCGCGGCTTTGAGCGGTCAAGGGTGAGCGTGCCAGTGGGAGGGGCC GAGGAGGAGGGGAGGTTGTCTGGGCGTGCCAGACAGGCAGGGTCAGCGGTCGGG GCAGGAGAGTCTGGAGGAGGAGCCCAGCATCCATGCTCCCTGGGGACCCGG GATTCCAGGTGCAAGTGTCCCAGAATCCTCCTCAGCCCCTTTTTCCAGGATCCAGGAGTCTGA CACCCAGTCTGTTCTCTCAGACCAGGGAATCCACACTCCAGCCCCTGA | 10432 |
| | 1 | MPLLPAAKCSLPS* | 10433 | ATGCCCCTGCTCCCCGCGGCCAAGTGCAGCCTCCCTTCCTGA | 10434 |
| | 2 | MSLASNALRSFNFLQ* | 10435 | ATGTCCTTGGCCAGTAATGCCCTTCAACTTTTACAGTAG | 10436 |
| hsa-let-7f-1 | 3 | MPFGLSTFYSRFCVRGNGMYSSTYRFLKN* | 10437 | ATGCCCTTCGGTCTTTCAACTTTTACAGTAGATTCTGTCAGAGGTAATGGTATGT ATTCTTCAACTTACAGTGA | 10438 |
| | 4 | MVCHLQLTGF* | 10439 | ATGGTATGTATTCTTCAACTTACCGGTTTTAA | 10440 |
| | 1 | MKLTDSVLRSFRVAKVFREMSDKINCFDFSPNGETVISS SDDDSIVLYDCQEGK* | 10441 | ATGAAGCTGACCGACAGCGTGTTGCGGAGCTTCCGCGTAGCTAAGGTGTTCCGGA AAACTGGACAAGATTAACTGCTTCGATTTCAGCCCAACGGCGAGACGGTCATCTC AGTAGGCGACGACGACTCCATCGTGCTATGACTGCCAGGAGGGCAAGTGA | 10442 |
| hsa-let-7g | 2 | MTARRASECGGGPGPESQCLPPVAQHRSLGLPSVPTSAP SLFCTRSCQGGRLHPAAVQETFYFLLKKKR* | 10443 | ATGACTGCCAGGAGGGCAAGTGAGGGCCCTGGGCCTGAGAGCCAGTGCCTTCCTG CCTTCCTCCGGTTGCACAGCCAGCACAGCCTCGGCCTGCCTGGGGGTCCAGC CCCCAGCTATTTGCACGGGTTCTGCAGGGCGCCTCCACCCGCCAGCCGTCCA GGAGACCTTTTATTTTTTATTTCTTAAAAAAAAGATAA | 10444 |
| | 3 | MSSVSFERYASLAKPHLDLDL* | 10445 | ATGTCTTCGGTCTCTTTGAGCGCTATGCATCACTGCCAAAGCCCACCTTGACCTTG ACCTTTTAA | 10446 |
| | 4 | MHHLPNPFLTLTFKRPVRPPWAHQVAPSAPQAVKGAGL LRPRRTAGAAFLPPSAASALSCALSTVTSIPPWHSAHPL PLSFPRPFCRQTAWVALLSCQDLFVVPL* | 10447 | ATGCATCACTTGCCAAACCCCACCTTGACCTTGACCTTTAAACGCCCGGTCCGCA CCTGGGCCCACCACCAGGTAGCGTTTCAGCCTCCAGCGTGTCAAGGTGCTGTCTG CTCCTGGGCCCTGACGCAGGACTGCAGGGGCTGTTCTGCCTCTCGGCAGCGTCA CCTCCTCCTCCTGTCTCTCCACTGTGACCTGGATTCGGCACTCGCCCATC CCCTGCCCCTCCAGCTCGCCTTCTGCCGTCAGACCGCGGGTTGCACTTGA TAGCTGTCAGGATTATTGTTGTGCCCTTTGA | 10448 |

Figure 1 (Continued)

| | | | | |
|---|---|---|---|---|
| hsa-let-7i | 1 | MFWLLFGGAGGSLCGMPAGDYRRRERAGGFDSAAR VGARVPDSAAAQPPPGTRSREGRERSSGRGGSS* | 10449 | ATGCCTTGGCTGCTGTTTGGCGGAGCGGAGGGAGCCTCTGGGATGCCGCCGG CGATTATCGGTCGCTGAGAGCGGTCCGTGGCTGCGGGTTCGACAGCGCGGGGTGG GGGCCCGGTACCGGACTCCGCGCCGCAGCCCAGCCCCACCGGGGACTCGGAGCAGG GAGGGGCGCGAGCGGCGCGACGTGGCGCAGCTCTAG | 10450 |
| | 2 | MALAEVVCAVGRVVTLPAVEITAQATATALLVLVMLSA AEDMGWESPLFSGALPGDSPRSLGARPARPPRKPLVSHF PRRN* | 10451 | ATGGCCCTGGCTGAGGTAGTAGTTGTGTGTGTGGGTAGTTGGGTCGGGATGCCGCT GAGAGATAACTGCGCAAGCTACTGCCTTTGTTTCTAGTGCTGTTGGTGATCTCAGCGCGCG GAGGACAAATGGCTGGGAATCCCCTTGTTTCGAGGCCCTGCCTGCGGGACAGCCC GCGAAGCCTGGCGCCGCCGGCCGGGGCGCGCACCGGCCACCACGGAAACGTTTCACATTT TCCTAGAAGGAATTGA | 10452 |
| | 3 | MAGNPLCFPGRCLGTAREASAPGRRGHHGNR* | 10453 | ATGGCTGGGAATCCCCTTGTTTCCGGGCGGTGCCTGGGGACAGCCCGCGAAGCC TCGGCGCCCGCCGGCGCGACCACCGGAAACGTTAG | 10454 |
| | 4 | MHFKGWERAKPLDSFS* | 10455 | ATGCATTTTAAAGGTTGGGAAAGAGCTAAGCCATTGGATTCCTTTCTTGA | 10456 |
| hsa-mir-100 | 1 | MSEPVSDGYSCADFCHSLAASSARSCAWHKCKYACYT PGL* | 10457 | ATGAGCGAGCCTGTTTCTGATGGCTACAGCTGTGCAGATTTCTGCCACAGCCTTGCT GCTTCAAGTGCACGATCCTGTGCGTGGCACAAGTGTAAATATGCCTGTTACACGCCT GGGTTATAA | 10458 |
| | 2 | MATAVQISATALLLQVHDPVRGTSVNMPVTRLGYKIW EEQRRSFPLYFSFSV1PSSLSHSTTPPPTQRPCNSN* | 10459 | ATGGCTACAGCTGTGCAGATTTCTGCCACAGCCTTGCTGCTTCAAGTGCACGATCCT GTGCGTGGCACAAGTGTAAATATGCCTGTTACACGCCTGGGTTATAAAATCTGGGAG AACAACGGCGCTCCTTTCCTCTATTTTCTTTCTGTCTTACCCTCCTCCCTTC TATCTCTACCACCCCTCCCAACAAAGACCCTGTAATTCTAATTAG | 10460 |
| | 3 | MNKLLGKNPDF* | 10461 | ATGAATATAAAGCTATTAGGAAAATCTGACTTTAG | 10462 |
| | 4 | MLDPMWLGLLQCRRP* | 10463 | ATGTTTGGATTTATGGCTGGGGCTTGCTGCAGGAGAGACGACCATAA | 10464 |
| hsa-mir-103-1 | 1 | MGISAVLRGPRWGVSGNAGSPGRLARPPEGSGAEGRG VCVNVAHSLFPRPRPRPGCWRGSLAVRRRL* | 10465 | ATGGGCATTTCCGCGGTTTTGCGCGGCCCCTCGCTGGGGTCAGTGGCAACGCGGG GAGCCCCGGGCCGCTCCGCCGCCCCGGAGGAGCGGCGGGGAGCGGCGGGGT GTGTGTGTAAATGTTGCGCACTCGTCTTCCCCGCCGCCGCCGCCCGTCCAGGGTGC TGGCCGTGGATCCCTTGCCGCCGGCGACTGTAA | 10466 |
| | 2 | MLRTRFSPAPARVQGAGVGPLPSGGDCK* | 10467 | ATGTTGCGCACTCGTCTTTCCCGGCGGCCGCTGTCCCAGGGTGCTGGCGTGGGT CCCTTGCCGTCCGGCGGCGACTGTAAATAG | 10468 |
| | 3 | MLFT* | 10469 | ATGTTGTTTACATGA | 10470 |
| | 4 | MKDPAGGY* | 10471 | ATGAAGGATCCGGCGGGAGGAGAGTCTAA | 10472 |
| hsa-mir-103-2 | 1 | MKIKDAKKPCKTGAGARQVGRAPLGFV* | 10473 | ATGAAGATCAAAGATGCAAAGAAGCCCTGTAAGACGGGGGCTGGGCGCCCCAGGT TGGGAGGGCACCCTTGGCGCCCGTCTGA | 10474 |
| | 2 | MPRNPVRRGLGPARLGGHPWAPSESPLAGRSASKPVAP RRRFVRYGGGGTJ* | 10475 | ATGCCAAGAAACCTGTAAGACGGGGGCTGGGCGCCCCAGGTTGGGAGGGCACCC TTGGCGCCCGTCTGAAAGCCCCTTGGCTGGGGCGGTGGCTTCCAAGCCCGTCGTCCC TCGCCGGCGCTTCGTCGGTATGGGGCGGAGGGACCATTTGA | 10476 |
| | 3 | MGAEGPFEPRVRGPRPPHPRHAW* | 10477 | ATGGGGGCTGGAGGGACCATTTGACCGCCGTTCCGGCTTCCGTCCTCCCCATCCC CCTATTCATGATGCAGTGTAA | 10478 |
| | 4 | MHGECLPPPSLSSHFLFEIWEVPEGISDSDFCQTRLVSSP SSP* | 10479 | ATGCATGGTGAATGCCTGCCGCCCCCTAGCCTTTCCTCCCACTTTCTCTTCGAGATCT GGGAGGTGCCAGAGGGAATTTCTGATTCTGATTTGTCAAACCAGACTAGTCTCCT CTCCCAGCTCCCCTGA | 10480 |
| hsa-mir-106a | 1 | MVEREGSGFILHPFPPSLPPACLPGLSSSDPACSLVSDL* | 10481 | ATGGTGGAAAGGGAAGGGTCCGGCTTCATTTGCCACCCTTCCTCCCTTCCCTGCCC CCGGCTTGCCTTCCAGGGCTTGTCGGTCTTAAACTAAGACATCATTTATTCTACAGA TGTAA | 10482 |
| | 2 | MLNSILVRLKLRHHFILQSAVGLWP* | 10483 | ATGCTTAATTCATTTGATTGTCGTTCTTAAACTAAGACATCATTTATTCTACAGA GCGGTGCTGCGGGCTTTGGCCTTGA | 10484 |
| | 3 | MRGESKHAPYLPHCACIRWLLPLTPAKKP* | 10485 | ATGAGAGGAGAAAGCAAGATAATTGCACGTATCTTCCGCACATTTCCGCGTGTATT CGGTGGCTGCTACCGTTAACGATACCGCAAGAAACCTGA | 10486 |

Figure 1 (Continued)

| | | | | | |
|---|---|---|---|---|---|
| | 4 | MCRIE* | 10487 | ATGTGCAGAGAGTAA | 10488 |
| hsa-mir-106b | 1 | MANGWTGSRPGRRNPEL* | 10489 | ATGGCCAATGCTGGACTGGCTCCGCCCTGGCGGAGGAATCCGAGTCGTGA | 10490 |
| | 2 | MAGLAPALGGGHPSCEAAGRAHVLLCLLRAEAMAGAGVGCGGGVRWRRSR* | 10491 | ATGGCTGGACTGGCTCCGCCCTGGCGGAGGAATCCGAGTGTGAAGCGGCTGGAATCCGGACGGCCCATGTGCTTCTTGTTACTAAGAGCGAAGCGATGGCGGGAGCGGGGGTGGGGTGCGGTGCGGTGGGGTGCGGTGGCGGAGGTCCGGTGA | 10492 |
| | 3 | MCFFVY* | 10493 | ATGTGCTTCTTTGTTTACTAA | 10494 |
| | 4 | MLDGPVHCHGLFHLRWLETDL* | 10495 | ATGTTGGATGCCCTGTGCACTGCCACGGGCTCTTTATTCTTCGCTGGTTAGAAACAGACTTGTGA | 10496 |
| hsa-mir-10a | 1 | MHSLQYPLASPPRKQFPVCEAALWTASPLVDPG* | 10497 | ATGCACTCTCTGCAGTATCCTCTAGCTTCTCCTCCCCGGAAACAGTTCCAGTCTGCGAGGCCGCCCTCTGGACTGCTCCCTAGTGGATCCGGGCTGA | 10498 |
| | 2 | MHLGRKGTSQAPDHFALPKDDPGQLERWGVRTERHT* | 10499 | ATGCATCTCTAGGAGGAGAAAGGTACCTCGCAGGCCCAGACCATTTGCCTTACCAAAAGATGACCCAGCCAGTTGAAAAGGTGGGAGTCAGGACGGAAAGGCACCTAG | 10500 |
| | 3 | MTQASWKGGESGRKGTPRGEVEGKCQPVWGVAS* | 10501 | ATGACCCAGGCCAGTTGGAAAAGGTGGGGAGTCAGGACGGAAAGCACCTGGAGAAGTGGAGGGAAAAGTGCCAGCTGTGTGGGGTGTCGCCTCTGA | 10502 |
| | 4 | MIEDTLFRGSCRLVLRCMHLSNSFSFLPSESQGHPREKGNPSQGEVGVWEAIFGRKGNRKRTGCPHRRCSGPEAEAVTSR3CQ* | 10503 | ATGATAGAGGATACCCTATTTCGGGGTCTTGTCGCTGCAGGCTTGTCTTAAGTGCATGCATCTCTCAATTCGTTTCTTTTCGATAATCCAAGGAGTCCAAGGAGGAGAAAAGGAAATCCTTCCCAGGGAGAGGTGGGGTCTGGGAGCGCGATATTTGGGCGAAGGGAAACCGAAAGCACGGTTGTCGCACCGCTGCTCTGACCAGAGGCAGAGGCTGTAACATCCGGAGCTGCAGTAG | 10504 |
| hsa-mir-10b | 1 | MPPRSLGRRPPWAAQSGCSPTFPGEVGGRCLSPFPQSLRS* | 10505 | ATGCCACCAAGAAGCCTGGCGCCGACCCCCTTGGCAGTCAGTCGGCTGCTCCCGTACATTTCCCGGGGAAGTGGGGGTCGTCTAAGCCCTGTCTTCCCCCAATCACTTCGTTCCTAG | 10506 |
| | 2 | MESPSILP* | 10507 | ATGGAGAGCCCCTCAATCTACCCTAG | 10508 |
| | 3 | MCLVFESRL* | 10509 | ATGTGCTTGGTGTTTGAATCTAGGCTTTAG | 10510 |
| | 4 | MLVNF* | 10511 | ATGCTGGTTAATTTTAG | 10512 |
| hsa-mir-125a | 1 | MAGTAGGRGEAAVRRRRGEDGERSAAVGPGLRARGGGEDPPPATREPREP* | 10513 | ATGGCGGGGACGGCGGGAGGAAGGGAAGGCGCGCGTGCGGCGAAGGCGGGGAGAGGATGGAGAGCCCTCCTGACCGGGAGGCGCGGAGCCGCCCGCCTCGCGCGCCCGGGCCGCGGAGAAGACCCCTTCCTGCGACCGCGGAAGGCCGAGCGCGGGAGCCGTGA | 10514 |
| | 2 | MESARRRWGPACGPGAAEKTPSLRRGSRGSRESAEREGGGLGPALLGP* | 10515 | ATGGAGAGCGGCTCGCGGCGGTCGCGCTGCGACGCGGAGAGCGCCGAGCGTGAGTCTGCGGAAGGGAGGTGGGGCTGGGCCCACTCCTGGTCCTGA | 10516 |
| | 3 | MGAGAGRIVAGRD* | 10517 | ATGGGGCTGGGGCTGGTAGGATCGTGGCTGGAAGAGACTAG | 10518 |
| | 4 | MGLRGFECGSRVSRASGRGPRRRGRLSGLPDRPGSAAGAGDVWRRRGPASMLPRGPGPGPRPLLPQIWEYTTQSPTHSRIRAPSPLFSRIQESEPPVCSLRPGNPHSSP* | 10519 | ATGGGGCTGCGGGGGCTTTGAGCGGTGCAAGGGTGAGCCGTGCCAGTGGAGGGGGCCGAGGAGGAGGGGAGGGTTGTCTCGGGCTGCCAGACAGCCAGGTCACGCGGCGGGCGGAGAGATGTCTGGAGAGGAGAGGCAGCATCCATGCTCCCTGGGGACCCGGGAATTCCAGGTCCCACCCCCCTCCCAGATCTGGAGTACACCACCCAGTCCCCCACCCAATCCAGAAATCCGAGCCCCCAGCCCCTTTTCCAGGATCCAGGAGTCTGAGCCCCCAGTCTGTTCTCTCAGACCAGGAATCCACACTCCAGCCCTAA | 10520 |
| hsa-mir-125b-2 | 1 | MYSLRRMGLRDGGGHMLMSPLWRGEIFHSDNWLNAMVKNCKAIFSPREKHGLRSKGCFHFSLFVSAAFLFPWFLFFNYLF* | 10521 | ATGTATTCCTTATGGAGGATGGGTCTCCGTGATGGGGTGTATAATTATGTTAATGTCATTTTATGGAGGGGTGAGATTTTCATTCGATCTGATAATTGTTGAATGCTATGGTCAAAATTGTAAAGCCATATTCAGTTTAGGGAAAAGCATGGACTTAGAATCTAAGGGCTGTTTATTTTTCGCTTTTTGAGTGCGCTTTTTGGTTTTGTTTTTAACTATTTATTTTAA | 10522 |
| | 2 | MGVV* | 10523 | ATGGGGGTCGGTATAA | 10524 |

Figure 1 (Continued)

| | | | | |
|---|---|---|---|---|
| | 3 | MLWSKIVKPYSVLGKSMIDLDLRAVLFFRFL* | 10525 | ATGCTATGTGTCAAAAATTGTAAAGCCATATTCAGTTTAGGGAAAAGCATGGACTTAGATCTAAGGGCTGTTTTATTTTCGTTTTGTGA | 10526 |
| | 4 | MGNQMINRKRSYIMMHYIMEQNI* | 10527 | ATGGGAAATCAAATGATAAACAGAAAGAGATCTTATATAATGATGCATTACATCATGGAGCAGAAATATTTAA | 10528 |
| | 1 | MPVIYS* | 10529 | ATGCCTGTGACCTACAGCTGA | 10530 |
| | 2 | MHFDLYLSM* | 10531 | ATGCATTTGACCTTTATCTTCTATCAG | 10532 |
| | 3 | MHQLFKVIGLRK* | 10533 | ATGCATCAGTTGTTCAAAGTTATAGGCTCAGAAAGTGA | 10534 |
| hsa-mir-128-2 | 4 | MKLRQLPMKTTGEYPIFQAAGTETRKHSLPCDIQLRGLPRKEKPWGRERSAPRRLSILSCCCPKNAFFPELSILKHFLGLICCSRQEELLYEYKGGR* | 10535 | ATGAAACTGATCCAACTGCCCATGAAACAACAGGGGAATATCCATTTCCAGGCTGCTGGTACAGAGACCATAGAAAGCATTCCTCCCATGTGATATCCAGCTCAGGGGATTGCCTAGGAAGGAAAAGCTTGGGGAAGAGCTTGCACCTAGGAGACTTTCAATACTCTTGTCTGCTGCCCAAAATGCATTCTTCCTTTCTTATCATCTCAAGCATTTTCTGGGCTAATCTGCTCCAGGCAGGAGCTCTCTATGAATATAAAGGAGGAAGGTAA | 10536 |
| | 1 | MSLFSPAPS* | 10537 | ATGAGTCTATTTCTCCAGCCGCCCTGTAG | 10538 |
| | 2 | MQLSKYTFPKAVCCKHNAILQSVGGKRGKGMDDFFPPHLGISIVDSNRF* | 10539 | ATGCAGCTTTCAAAATATACATTTCCAAAGGCGGTGTGTTGCAAACACAACGCGATTTTGCAGAGCGTGGTGGAAAACGTGGAAGGTATGGATGATGTTTTTTTCCTCATCTGGGAATCTCATCTGGAATGCAATCGCTTCTAG | 10540 |
| hsa-mir-129-2 | 3 | MFPPLJWESPSWIAIASRALLGSSSGEGAAMPPHPLLSSACRESDQWRHAALRIQPLQRLLLGETARSLQQAETDGS* | 10541 | ATGATTTTTTTTCCTCATCTGGAATCTCCATGTGGATAGCAATCGCTTCTAGAGCTCTCCTGGGAAGCTCTCTGGGAAGGGCTATGCCCCCCCACCCCTACTTTCCTCAGCATGTAGGGAATCTGATCAATGGAGACATGCAGCTCAATGGACATGCAGCTCTAAGAATACAACCACTCCAAACGCCTTCTGCTCGGGGAGACTGCAACAGGCAGGAGCTGCAACAGACAGAGACATGGGAGTTAA | 10542 |
| | 4 | METCSSKNTTTPTPSARGDCEELATGRDRWELTGGRENBRNIWVFF* | 10543 | ATGGAGACATGCAGCTCTAAGAATACAACCACTCCAAGCGCCTTCTGCTCGGGGAGACTGCGAGGAGCTCGCAACAGGCAGGAGCAGATGGGAGTTAACGCAGGGAGGGAGGAATATAAGAAAAAGAATCCAGAGTGTATCTAG | 10544 |
| | 1 | MLEKNPECI* | 10545 | ATGTTAGAAAAGAATCCAGAGTGTATCTAG | 10546 |
| | 2 | MESSARRGASSRGGAALFLLEPRAESCRRVVGLYPPRSGR* | 10547 | ATGGAGTCGTCAGCTAGAAGGGGCGCGTCGTCCGGGTGGGCGCGCCCTTTTCTCCTGGAGCCGCGGGGCCGAGTCAGGGCGCAGGGTCGTCCGGCTGTACCCACCCCGCTCCGGGGCTAG | 10548 |
| | 3 | MDWTGALPIRPPIHG* | 10549 | ATGGACTGGACGGGAGCGCTCTGCCCACCGACCATCCATGGTTGA | 10550 |
| hsa-mir-130b | 4 | MVELPALRVLGVVGSPLLAAGALTRLHYCALRSSAMILSKHLGPALGISLPTLTSHSPGRAPWACRPSPPPYPIRSLLHGNLRF* | 10551 | ATGGTTGAGCTTCCCGCCCTGCGTGTATTGGGGTGGTTCCCCTGCTGGCCGCAGGTGCTCTGACGAGTTGCACTACTGTGCTCTGAAGAAGTGCAATGCAATTGTCAAAGCATTCTGGACCAGCCTTGGGGATCTCCGCCTTCACGCTCCACTCCCCAGGCAGGCCCCTTGGGTTGCAGGCGCCCGACCCCTACCCACTTGCCCCCTTCTCCATGGAAACTTGAGATTCTAG | 10552 |
| | 1 | MALCRAWVWGSGGP* | 10553 | ATGGCTTTATGCAGGGCCTGGGTCTGGGGTCCTGGGGGCCCATGA | 10554 |
| hsa-mir-135b | 2 | MQGLGLGFWGPMREEGCKENQRGLGLGQMAQSSGGRPQDAWLFGPEGWACLECVEGRAVLCCVLCCAVLCCAVVGECRIPVQ* | 10555 | ATGCAGGGCCTGGGTCTGGGTTCTGGGGCCCATGAGAGAAGGAAAGGAGAACCAGAGAGGGTTGGGGCTGGGCAGATGGCCCAAAGTTCAGGTCGAGGGCCGCAGGATGCCTGGTTGTTGGCCCTGAAGGTTGGGCATGTCTGAGTGTGTGGAGGGCGGTGCTGTGTGCTGTGTGCTGTTTCCTACCAGGGTTGCAGGGTACCAGTTGCTTCTTCTTACCAGGGGTTGCAGGGTACCAGTTGTTGGGGAATGCAGATTCCTGCCAGTAG | 10556 |
| | 3 | MPGCLALKVGHVWSVWRGVLCCAVCCVLCCAVLLLGNAGFLSSENRLLLPGLCREPASVALGLRVQLGWERQLLPGRGRA* | 10557 | ATGCCTGGCTGTTTGCCCTGAAGGTTGGGCATGTCTGAGTGTGTGCTGTGTGTGCTGTGTGCTGTTTCCTACCAGGGTTGCAGGGTACCAGTTGCTTCTTCAGTGAAAAACAGGTTGCTTCTCAGGGGTTCTTGCAGGGTTGGCAGGGTAGCAGCAAGTGTTGCCCTGGGGCTGAGGGAGCAGCTACTCCCTGGCAGAGGCAGGGCCTGA | 10558 |

Figure 1 (Continued)

| | | | | | |
|---|---|---|---|---|---|
| | 4 | MSGVCGGDACCAVLCAVCCAVLCCCWGMQDSCPVKTG CFYQGCAGSQQVLPWG* | 10559 | ATGTCTGGAGTGTGTGGAGGGGCTGCTGTCTGTGTCTGTGTGTCTGTGCTGTGCT GTGCTGTGCTGTGTTGTGGGAATGCAGGATTCCTGTCCAGTGAAACAGGTTGCTTC TACCAGGGTTGTGCAGGAGCCAGCAGCAAGTGTTGCCGTGGGGCTGA | 10560 |
| hsa-mir-138-1 | 1 | MTLCC* | 10561 | ATGACTCTTTGTTGTTAA | 10562 |
| | 2 | MISKSWVH* | 10563 | ATGATTTCTAAGAGCTGGGTCCACTAG | 10564 |
| | 3 | MCNVLISLILFLSLIGRIWFSLILLPGKGALTGNC* | 10565 | ATGTGCAATGTACTTATTTCTCTTATCCGTGTTCTTAAGCTTGATTGGAGATTTGGT TTTCGCTTATTCTCTTACTGCCTGGAATAGGAGCTTTAACTGGAAATTGCTAA | 10566 |
| | 4 | MYLPLLSCS* | 10567 | ATGTACTTATTTCTCTTATCCGTCTTAA | 10568 |
| hsa-mir-138-2 | 1 | MPSFFTHELGGLIKEQEVPILHWGQDADPAPVLRELTV* | 10569 | ATGCCCTTCCTTTTCACTCACGAGCTGGGCGGCTCATCAAAGAGCAGGAAGTGCCC ATTTTACACTGGGCCAGGATGCAGACCCAGTCGCTGTCCTCCGCGAACTTACAGTC TAA | 10570 |
| | 2 | MQTQLLSSANLQSN* | 10571 | ATGCAGACCCAGCTCTGTCTCCGGAACTTACAGTCTAATTAG | 10572 |
| | 3 | MHHLNPRTGSFKAKNYRLFRSVQHLLTKKNLRVIFLSL NFYPCLHLARTLNTKFAVICSSANAFLL* | 10573 | ATGCATCATTAAATCCTAGAACAGGCAGTTAAAGCAAGAACTACAGACTTTTC CGCATGTCCAGCATTTGCTGACCAAAAAAGCCTTTAAAGCAAGAACTACAGACTTTTC AATTTTTACCCTTGCCTGCCACCTAGCCAGAACCCTTAATACTAAATTTGCAGTTATAT GCAGCTCTGCCAACGCCTTCTGCTTAG | 10574 |
| | 4 | MQLCQRLPALDWISTILFLY* | 10575 | ATGCAGCTCTGCCAACGCCTTCTGCTTAGACTGATCTTACTATCTTTTCTCT ACTAG | 10576 |
| | 1 | MPGLLPASATLAHLHPRTASSFSLCLFQNSLGPSVRRVL PWPRCKNQNKKQRLLRGADAT* | 10577 | ATGCCAGGGCTGCTCCCTGCCTCGCACCTTCACCCGCTACCGCC TCTCCCCGTCGCTCGCTCTGCCTTTTCAAAACTCACTGGGCCCTCCGTGCGCAGGGTTC TTTTTTGGTTTTTCTGTAAAATCAAAACAGAGACTTTTGAGAGGAGCAG ATGCCACCTAA | 10578 |
| hsa-mir-140 | 2 | MPPKVPLJHSLQSAQMWKPVIGIFPY* | 10579 | ATGCCACCTAAAGTCCCACTGCATTCCCTGCCTCTGGCTGGGTAAGTACTGAGTTCTTCCTGG AATTGGCATTTTATTTTTAATTTA | 10580 |
| | 3 | MIPWAPSLLAGVSTEFSSWPLAFRQPRCSVLSSRVSSFP VPVLFSISPLSSTLSGHAPPEEQLQVMEFLGSWESNQAPP NHCSHPPSLKECDPKKRCP* | 10581 | ATGATCCCCTGGGCCCTCCTCCTCGCTGGCTGGGGTAAGTACTGAGTTCTTCCTGG CCCTTGGCCTTCCGTCCAGCCAGGTGCTCTTCATCTCCCCGCTGTCTTCCTCC TGTTTCCTGCCTGTCCCTCGTGTTTTCCATCTCCCCGCTGCACACTCTGCATGC CCACCAGAGCAATTACAGGTGATGAGCTGGGCAGCTGGGAAAGTAACAAGCTC CACGGAACCACTGTAGCATCCACCACCACCATGCTAAAGGAGTGTGACCCTAAGAAAA GATGTCCCTGA | 10582 |
| | 4 | MPHQSNYR* | 10583 | ATGCCCCACCAGAGCAATTACAGGTGA | 10584 |
| hsa-mir-141 | 1 | MGARDLQLFRRDPGPEAA* | 10585 | ATGGGAGCCAGGGATCTGCAGCTTTTCCGCAGGGATCCTGGGCCTGAAGCTGCCTGA | 10586 |
| | 2 | MMEAPVPVSATSASGPQPLAGCSPLPTSHAPRKPLVLS* | 10587 | ATGATGGAGGCCCCTGTCCCTGTGCCAGCGACAATATCCATGCCTCAGTCCCCAGCCC TTAGCTGGCTGCAGCCCCCCACTCCACGCACCCGGAAGCCCCTCGTCTTG AGCTGA | 10588 |
| | 3 | MGPSPSSHPVRFVTWWIQNPQSTLSLGLARPLSRDLTW PVARVPCSNW* | 10589 | ATGGGCCCCAGCCCTCCTCCCACCACCAGCCGATTGTCACCTGGATCAGAAAC CCACAGTCGACCTTGAGCTTGGGGTTGGCTGCCCCTCAAGAGACCTCACCTGG CCTGTGGCCAGGGTCCCCGTAGCAACTGTGA | 10590 |
| | 4 | MAPGWVLSAVTFREP* | 10591 | ATGGCTCCTGGGTTGGTTCTCGGCAGTAACCTTCAGGAGCCTGA | 10592 |
| hsa-mir-146a | 1 | MQIGLSCLPLPQQIRVSPERCSFSKTLDRSSFPGWHQQG RLEW* | 10593 | ATGCAAATAGGCCTTAGTGCTTCCTCTACCCCAGCAAATAAGAGTCTCTCCAGAA AGATGCTCTTTCTCCAAGACGCTTGACCGCTTCCTTCCTTCCTTGATGGCACCAGCAG GGCCGATTGGAGTGGTAA | 10594 |
| | 2 | MLFLQDA* | 10595 | ATGCTCTTTCTCCAAGACGCTGA | 10596 |

Figure 1 (Continued)

| | | | | | |
|---|---|---|---|---|---|
| | 3 | MAPAGPIGVVNPGPEGMPKGGQDGQQETVAQRGGGEQR LNWK* | 10597 | ATGGCACCAGCAGGGCCGATTGGAGTGGTAAACCCTGGCCGGAAGGCCATGCCAAA GGGTGGACAGGATGGACAGGACAGTAGCACAACGAGGAGGGGGAGAACAGCGG CTGAATTGGAAATGA | 10598 |
| hsa-mir-146b | 4 | MDRRQ* | 10599 | ATGGACAGGAGACAGTGA | 10600 |
| | 1 | MGCP* | 10601 | ATGGGGTGCCCTGA | 10602 |
| | 2 | MKVCPRELFLLHSTIPGTSNLYSGPWGIDWGARTPGLG SYLGDPYLGDSL* | 10603 | ATGAAAGTGTGCCTTCAGGGAACTCTTTCTCCACTCCACTATCCAGGTACTTCAA ATCTTTATTCAGGGTTTTGGGGAGATTTCTGGGGAGTCCCTGGGGCTGGGCT CCTATCTTGGGGATCCATATCTGGGGACTCCCTTAG | 10604 |
| | 3 | MPFSVCVFWLPPQPLTPPAPHQAPPGTHLGRKRQMDPC HGPEPPPLLTYSNSCWNLWNSCPFP* | 10605 | ATGCCCTTCAGTGTGCGTGTTCTGGCTCTTTCCCAGCCTCACCCTCCAGCC CACATCAGGCCCTGAGCCCCCCACCAGGAACACATCTGGCAGGAAGCGACAGATCCTGC CATGGCCCTGAGCCCTGCAGCCCCTTAACCTACTCCAATTCTGTTGGAATTTATGGA ACTCCTGTCCATTCCTTAG | 10606 |
| | 4 | MALSPLPS* | 10607 | ATGGCCCTGAGCCCTGCCCCTCCCTCTTAA | 10608 |
| | 1 | MERWRGVWGRMGKHFPDLLHARNSCSGAVCGGRGSA RMGDRVVAYAAGKRGCREGEKSSLGDCVQGCARTGS AGSTA* | 10609 | ATGGAACGGTGGCGAGGGGTTTGGCGAGAAGATGGGAAAGCACTTTCCAGACCTGT GCACGCGCGCAACAGCTGTTCAGTTGCGGTATGTCAGGGAAAGGGGTCTGCTAGGA TGGGGGACAGAGTGGTCGCTTATGCTGCAGGGGAAAAGGGGTGCCGGGAGGGGA GAAGACTGCTTGGGGACTGTGTGCAAGGTTGTGCGAACGGGGTCCCGCGGGAA GCACTGCCTAA | 10610 |
| | 2 | MWGEGVC* | 10611 | ATGTGGGGGAGGGGTCTGCTAG | 10612 |
| hsa-mir-148a | 3 | MLQGKGGACRGRRAVLGTVCKVVRERGPREALPNGA GRIPKSGWYERRGWDFDFSSRGWARAAGRPGIEYWE WLGKGVSGEAPQSGSFLGRPHLGAPPGPVFVPHRLTLSA PNIRIPRAAPPPPAFQMCR* | 10613 | ATGCTGCAGGGGAAAAGGTGGGTGCCGGAGGGGAGAAGAGCAGTCTTGGGACTG TGTGCAAGGTTGTGCGCGAACCGAGGGTCCGCCGGAAGCACTGCCTAATGGGGCAGGG AGAATCCCAAAGATCCAAAGAGTGGGTGGAACGGAAGGGATGGGACGACTTGCGACCGA GTTCCCGGGGCTGGGCGCCGGGCGCTGGAAGACCGGGAATAGAGTACTGGGAATGG CTGGGGAAGGGGCGTTTCCTCCTCGTCAGTGGAGGCCCCCTGTATTTGTTCCCCACCGTTTAACTCTTCAGCT CATCTTAGGGGGCTTTCGTCCTCGGGCCTGCAGCGCCCCCAGCTTTGTCCCCAGCTTTCAGAGATGGGAAGGTAA CCGAATATTCGTCCTCGGGCCTGCAGCGCCCCCAGCTTCAGATGGGAAGGTAA | 10614 |
| | 4 | MGQGESSQRVGGWNGGDGTTSTRVPGAGRGRLEDRE* | 10615 | ATGGGGCAGGGAGAATCCAAAGAGTGGGTGGGTGGAAGAGGGATGGGACGA CTTCGACCCAGTTCCCGGGCTGGGCGCTGGGCGCTGGAAGACCGGAATAG | 10616 |
| | 1 | MEALILVGAGGAAEMLWCPQGPGVRVQPEWETGKESS G* | 10617 | ATGGAGGCGCTGATTTTGGTAGGAGCTGGAGGTCAGCCGAGATGCTGTGGTGTCC ACAGGGGGCCGGAGTCAGGGTTCAGCCCAGGGAGACCGGGAAAGAGAGTTCC GGGTAA | 10618 |
| hsa-mir-148b | 2 | MDSLGYTDL* | 10619 | ATGGACTCCTTAGGATACACAGACCTGTAG | 10620 |
| | 3 | MFCRYRLLLMVSQV* | 10621 | ATGTTTTGTCGTTACAGATATTTTTCTAGACTCCTTATTCTGTTTCCTCCAAGTTGA | 10622 |
| | 4 | MDCGHFFLDSLECSPFLYPFRP* | 10623 | ATGGATTGTGGAATATTTTTTCTTGACTCCCTTATTCTGTTCCTTTTCCTCTACCCATT TAGACCTTAG | 10624 |
| | 1 | MELRARGWWLLCAAAALVACARGDPASKSRSCGEVR QIYGAKGFSLSDVPQAEISGE* | 10625 | ATGGAGCTCCGGGCCCGAGGCTGGTGGCTGCTATGTGCGGCCGCGCTGGTCGC CTGCGCCCGCGGGGACCCGGCAGCCAAAGAGCCGGAGCTGCCGCGAGGTCCGCAGA TCTACGGGGAGCCAGGGGCGGTTCAGCGCCCAGATCTCAGCGACGTCCCCCAGGCCGAGATCTCGGGT GAGTGA | 10626 |
| | 2 | MCGRSAGRLRPRGPGQQEPELRRGPPDLRSQGLQPERR APGGDLG* | 10627 | ATGTGCGGCCGCAGCGCTGGTCGCCTGCGCCCGCGGGGACCCGGCAAGAGCC GGAGCTGCGCGAGGTCCGCCAGATCTACGGGGACCCAAGGGCTCAGCCTGGGAGCGGT GTGCCCCAGGGGATCTCGGGTGA | 10628 |

Figure 1 (Continued)

| | | | | |
|---|---|---|---|---|
| hsa-mir-149 | 3 | MAPCAAAPLQPHGPRLQAPRRTPSPGSPPPRSVVLRPSP PPARRLLPCGADLAGLRARGAPPGPRLELGVFCPPLGPA RLQAGSPSPGAGCRGAVGLGVAGLSGRR* | 10629 | ATGGCTCCCTGCGCTGCGGCTGCTGCGGCTCCTCTGCAACCCACGGCCGCCTGCCTCCAAGCCCG CGCCGGCACTCCCTGCCCAGGGTCCTCTCCCTGCCGAGCTGATCTGCCGGGCTGCGGCTC CGCCGCCGCACGCGCGGCCTCCCGGGCCACCGGCTGAGCTGAGCGTCTTCTACCCCGCTCGGCC GGGGCTCCGCCTGCAGGCCGGAGTCCAGCCCGGGGCGGCTGTCGGGGCGCTGTG GGGCTCGGCGTGCCGTGGCCGGGCTTCGGGGCGCGCTGA |
| | | | 10630 | |
| | 4 | MGTQRRNAHGPGIDSEQEGSVHLGEGGLWPCLAAGGG VVGGGSRALDPCPSRRMRTHRQPLALGGSPDAPSLRPL* | 10631 | ATGGGGACTCAGCGCAGAAATGCCCATGGTCCTGGGGATTCTGAGCAAGAAGGATC CGTGCATCTGGGGTGAGGGGGGTCTGGCATGCCTTGCCGCGGGGGCGGCGAGTGG TGGGAGGAGGCAGTCGGGCTCTGGACCCTCGCCCTCAAGGAGGAACAGAACCCAC AGACAGCCCTTGCCTTGGTGGATCTCCCGATGCCCCAGCCTGAGGTTCTTGTAA |
| | | | 10632 | |
| hsa-mir-15b | 1 | MAPFFKSRCL* | 10633 | ATGGCTCCTCCTTCCCGAAGTCCGCTGCCTCTAA |
| | | | 10634 | |
| | 2 | MPRKGTQPSTARRREEGPPPPSPDGASSDAEPEPPSGRT ESPATAAGE* | 10635 | ATGCCCCGTAAAGGCACCCAGCCTCACTGCCCGGCAGAGAGGAGGGGCCGCC GCCGCCGTCCCTGACGGCGCCAGCGACGCGGAGCCTGAGCCGCCGTCCGGCC GCACGGAGAGCCCAGCCACCGCCGCAGGTGAGTGA |
| | | | 10636 | |
| | 3 | MGASKRVQL* | 10637 | ATGGGGGCGAGCAAACGGGTTCAGTGTGA |
| | | | 10638 | |
| | 4 | MVQVTNKNSISLLYSR* | 10639 | ATGGTACAGGTCACAAACAAAATTCAATATCTTTATTGTATTCCGCTAA |
| | | | 10640 | |
| hsa-mir-16-2 | 1 | MAPFFKSRCL* | 10641 | ATGGCTCCTTCTTCCCGAAGTCCGCTGCCTCTAA |
| | | | 10642 | |
| | 2 | MPRKGTQPSTARRREEGPPPPSPDGASSDAEPEPPSGRT ESPATAAGE* | 10643 | ATGCCCCGTAAAGGCACCCAGCCTCACTGCCCGGCGCAGAGGAGGAAGGGCCGCC GCCGCCGTCCCTGACGGCGACGCGGAGCCTGAGCCGCCGTCCGGCC GCACGGAGAGCCCAGCCACCGCCGCAGGTGAGTGA |
| | | | 10644 | |
| | 3 | MGASKRVQL* | 10645 | ATGGGGGCGAGCAAACGGGTTCAGTGTGA |
| | | | 10646 | |
| | 4 | MVQVTNKNSISLLYSR* | 10647 | ATGGTACAGGTCACAACAAACAAAATTCAATATCTTTATTGTATTCCGCTAA |
| | | | 10648 | |
| hsa-mir-17 | 1 | MYLIAKDFSTLFSYVFFNCKLLGF* | 10649 | ATGTATCTGATAGCTAAGGATTTTTCAACTTTATTCTCTTACGTATTTTTCAACTGTA AATTATTGGGCTTTTAA |
| | | | 10650 | |
| | 2 | MDGINCC* | 10651 | ATGGATGGAATTAATTGCTGTTAG |
| | | | 10652 | |
| | 3 | MELIAVRRLENSKYRFGRW* | 10653 | ATGGAATTAATCGCTGTGTAGGAGGTTGAAAATAGCAAATATAGATTTGGACGGTG GTAA |
| | | | 10654 | |
| | 4 | MPYLFFPYFSLFQSYTWT* | 10655 | ATGTTTTTATCTTTCCTATTCCAGTCATACACGTGGACCTAA |
| | | | 10656 | |
| hsa-mir-185 | 1 | MPRALLEGVFDNPRWRGMRGTLAGGTRLAAGRLRSAG LGAAWSLQGVWAARPWPASGTALAPGHSAPYPRPAAG QQGDS* | 10657 | ATGCCCCGGCTTACTGGAAGTGTTTTTGATAATCCCGTGGCACGGGATGCGA GGGACTCTGGCAGGTGGGACCAGAGCTGCGGGGAGGCTGAGATCGGCAGGGTT GGGAGCTGCGTGGTCCCTGCCAGGGTGTGGGCTGCTGCGGCCTGGCCAGCATCAG CAGCAGTCTGGCCGCCGGTCACTCTGCCCCCTCACCCGCGGCCTCTGCGGCCCAGC AGGGTGACAGCTAA |
| | | | 10658 | |
| | 2 | MRPSWGGLGS* | 10659 | ATGCGCCCTTCCTGGGGAGGTTTGGGTAGTTAG |
| | | | 10660 | |
| | 3 | MSHALPWPGLFALSCGSRPADHCFAATLGTVPSSMRQ M* | 10661 | ATGTCACATGCCCTGCCCTGGCCAGGCTGTTGCACTGTGTGTCCTAGACCT GCTGACCACTGTTTTGCTGCCACTCTGGCACAGTGCCCTTCCATGAGGCAGATG TGA |
| | | | 10662 | |
| | 4 | MPCPGQACLHCRVALDLLTVLLPLWAQCPLP* | 10663 | ATGCCCTGCCCTGGCCAGCCTGTTTGCACTGTGTGTGGCTCTAGACCTGCTGACC ACTGTTTTGCTGCCACTCTGGGCACAGTGCCCTCTTCCATGA |
| | | | 10664 | |
| | 1 | MSTKNFRVSDGDWICPDKK* | 10665 | ATGTCGACCAAGAATTTCCGAGTCAGTGACGGGGACTGGATTTGCCCTGACAAAAA GTGA |
| | | | 10666 | |

Figure 1 (Continued)

| | | | | |
|---|---|---|---|---|
| hsa-mir-186 | 2 | MHFCALRRVEAANRQFPGGKKAPNLLTREVFPGAFVLD MSSAFPRHYLRKVASLFRVRDGLPFCPHPPPPRPGFSD RKPLQSGQLGVGSPPRDFSLQNFTLVHGKYCFLALVLLP LIVHLVLYFYSNFSSLLFSPFPEALPSSVWEILTFSLWESP QELGFSPP* | 10667 | ATGATTTTCTGTGCCTTAAGACGGGTTGAGGCGGCGAACCGCAGTTCCTGGCGGG AAGAAGGCTCCCAATCTCCTACGAGAGAGGTCTTCCGGAGCCTCTCTTGTTCTAGAT ATGTCTTCAGCGTTTCCTGACATTACCTCCGCAAGTAGCCTCCTCTTTTAGAGTGC GAGATGGCCTACCTTTGCCCCACCCCCTCCCCGGCCAGGGTAGCCGCCAGGTTTAGCG ATAGGAAACCTCTCCAGTCAGCCAGCTTGGTGTTGGATCCCCCACGTGACTTTT CTCTGCAGAACTTTACTCTTGTTCACGGAAAATATTGCTTTCTCGCACTGTCCTTT GCCTCTATAGTCGCAGTTCACCTGTTTGTATTTTCCTATTCAGTCATACACGTGACTAA GATCATTTCTCCACAAGAATTGGGCTTTCGCTCCTAG | 10668 |
| | 3 | MAYLFAPTPLPRPGQVLAIGNLSSQASLVLDLPHVTFLC RTLLLFTENIAFSHSSFCLL* | 10669 | ATGGCCTACCTTTTGCCCCACCCCCTCCCCGGCCAGGTTTAGCGATAG GAAACCTCTCCAGTCAGCCAGCTTGGTGTTGGATCCCCCACGTGACTTTTCTCT GCAGAACTTTACTCTTGTTCACGGAAAATATTGCTTCTCGCACTGTCCTTTTGCCT CTTATAG | 10670 |
| | 4 | MPAAEKHVC* | 10671 | ATGCCTGCAGCAGAAGAAGCACGTGTTAG | 10672 |
| hsa-mir-18a | 1 | MYLIAKDFSTLFSYVFFNCKLLGF* | 10673 | ATGTATCTGATAGCTAAGGATTTTCAACTTTATTCTTACGTATTTTCAACTGTA AATTATTGGGCTTTTAA | 10674 |
| | 2 | MDGINCC* | 10675 | ATGGATGGAATTAATTGCTGTAG | 10676 |
| | 3 | MELIAVRRLENSKYRFGRW* | 10677 | ATGGAATTAATTGCTGTAGGAGGTTGGAAAATAGCAAATATAGATTGGACGGTG GTAG | 10678 |
| | 4 | MFYLFPPYFSLFQSYTWT* | 10679 | ATGTTTTATCTTTTTTTTCCTATTTTCCTATTCAGTCATACACGTGACTAA | 10680 |
| hsa-mir-18b | 1 | MVEREGSGFILHPFPPSLPPACLPGLSSSDPACSLVSDL* | 10681 | ATGGTGGAAAGGAGGGGTCCGGCTTCATTTTGCACCCTTCCACCCTCCTTGCC CCGGCTTGCCTTCCAGGGCTTTCCTTCCTCCGACCCAGCGTGCTCACTGGTCTCTGATT TGTAA | 10682 |
| | 2 | MLNSILJVRLKLRHHFILQSAVGLWP* | 10683 | ATGCTTAATTCATTTGATTGTGCGTCTTAAACTAAGACATCATTTTATTCTACAGA GCGCTGTCGGGCTTGGCCTGA | 10684 |
| | 3 | MRGESKHAFYLPHICACIRWLLPLTIPAKKP* | 10685 | ATGAGAGGAGAAAGCAAAGATAATTGCACCGTATCTTCCGCACATTTGCGCGTGTATT CGGTGGCTGCTACCGTTAACGATACCTGCCAAGAAACCCTGA | 10686 |
| | 4 | MCRE* | 10687 | ATGTGCAGAGAGTAA | 10688 |
| | 1 | MGGF* | 10689 | ATGGGCCGGTTCTGA | 10690 |
| | 2 | MWPQGF* | 10691 | ATGTGGCCTCCAGGGCGAGTGA | 10692 |
| | 3 | MGCP* | 10693 | ATGGGGTTGCCCTGA | 10694 |
| hsa-mir-191 | 4 | MGVDVGEPRLVAISGTLGRIGEGGWTQDLWVGLQW* | 10695 | ATGGGTGTAGACGTGGGAGACGCCGAGGCTGGTGGCCATCTCTGGAACCCTGGGGAG GATTGGCGAGGGAGGGTGGACCTCCAGGAGCCTCTGGGTAGGGCTGCAATGGTAG | 10696 |
| | 1 | MGAEGWVFAGEMRVSDQLAYKVPVLGPRIDQRLLPGPR PRPASSRAGVRSGQAASQVHAGEGYVRCARPGCVR* | 10697 | ATGGGAGCTGAAGGCTGGGTCTTTGCGGCGAGATGAGGGTGTCGATCAACTGC CTACAAAGTCCCAGTTCTCGGCCCCCGGACCAGCGTCTTCCTCTCGGGCTCCTCGCC CGGCCGGCTTGCTCGCCGGCTGGCGTGGCTGCCGGCTGCCTCTCAGGTCCA CGCTGGAGAAGGAGGTGTGAGGTGCGCTGCGGCTGCGGTGA | 10698 |
| hsa-mir-193a | 2 | MGQALPLTEACPAVLSRAATLSLGVGRTGPDF* | 10699 | ATGGGCCAAGCCTTGGCGCATTGGCGGAGAACGGGGCCTGACTTCTAG | 10700 |
| | 3 | MDLCGCVPNGRSFVP* | 10701 | ATGGATCTTTGTGCATGTCCGTCTTTTTGTCCAATGCGGTCTTTCTCCTGA | 10702 |
| | 4 | MCSQWPVFCSLTDAT* | 10703 | ATGTGTTCCCAATGCCGGTCTTTTTGTCCCTGACGATGCAACATAA | 10704 |
| | 1 | MEIISPNLGAQQI* | 10705 | ATGGAAATCATTTCCCCAACTTGGGCGCGAGCAAATTTGA | 10706 |
| | 2 | MRDD* | 10707 | ATGAGAGACGATTAA | 10708 |
| hsa-mir-193b | 3 | MGWGELYEAPRTPDLSAAKGRLGHPSCCPGSF* | 10709 | ATGGGGGTGGGGGGAACTGTACGAGGCACCTCGGACACCGATTTATCCGCTGCTAA GGGACGTTTGGGGCACGTTTGTCGGGAAGCTTTTAG | 10710 |

Figure 1 (Continued)

| | | | | |
|---|---|---|---|---|
| | 4 | MVWQMSPPPTATPWHFGEMNRRPEGTPSNDSFSSDPGSPNSCLKGGLPRCCQP* | 10711 | ATGGTGTGGCAAATGTCCCCTCCTCCACAGGACCCCTGGCATTTGGTGAGATGAACCGCGCCCTGAGGGAACACCCAGTAACGATTCCTCAGTGATCCCGGTTCTCCAAACTCTTGCCTCTCCAAAGGCGGCCGGTTGCTGTTGCAGCCGTGA | 10712 |
| hsa-mir-195 | 1 | MRIRLGALPLASGWSH* | 10713 | ATGAGAATTAGACTAGGGCTCTCCTTGGCATCAGGATGGAGTATTATTGA | 10714 |
| | 2 | MEYYLISCGVSVYYGVI* | 10715 | ATGGAGTATATTGATCAGTTGTGGGTCTCGTTTATTATGGGTGTGATTTGA | 10716 |
| | 3 | MVSFRYGADLEVTLVLGVLTPTIWRLCSPVSSWTISRTKVLMLIWGCSLFWGAI* | 10717 | ATGGTAAGTTTCAGGTATGGGGCTGACTTGGAAGTTACATTAGTTCTGGGGTTCTGACACCCACAATTTGGAGATTGTGTCACCTGTGTCATCTTGGACTATCAGCAGAACCAAAGTACTCATGCTGATTTGGGGTGCAGTCTATTTGGGGCATCTAA | 10718 |
| | 4 | MGLTWKLH* | 10719 | ATGGGGCTGACTTGGAAGTTACATTAG | 10720 |
| hsa-mir-196a-2 | 1 | MGVGVWLVCVSSPHSPTHSHTAFCSPCKVKIESIRL* | 10721 | ATGGGGGTGGAGTGGGTGTGGTCGTGGTGTCAAGCCTCACTCACCACCGCACTCACACACGCATTCTGTTCTCATGCAAAGTTAAGATCGAATCCATCCGCTGTAG | 10722 |
| | 2 | MSLPPSRSKNLLEVSYLYCFLLFSHPS* | 10723 | ATGTCTTTACCTCCCAGTCGTCTCAAGAATCGCTGAAGTCTGTATTTGTACTGCTTTCTGCTTTTCTCCACCCCTCTAG | 10724 |
| | 3 | MPPPNIVLSLSGSCVI* | 10725 | ATGCCCCCCCCCAAATATTGTCTGTCCTGTGTCGGGAGTTGTGTTATTTAA | 10726 |
| | 4 | MLYLLHVASLMEKKPNKFPES* | 10727 | ATGTGTATCTTTTGCATGTGAGCTTCCTTAATGAGAAAAAAACCTAATAAATTCCAGAATCATAA | 10728 |
| | 1 | MSSSAHPEAPPQPSAGHAHARKPLPAAPLRRSPELKPRPQRRQRPSSTQPCSQLSTASPAPRQAPPSLSSAPRSRWEPPR* | 10729 | ATGAGCAGCTCCGCAGCCCATCCGAAGCCCCAGCCCTGCCGCCAAGCTCCGCCACCCTCAAGCGGTCGCCGGAGCTTAAGCCCGCCCCAGCGGGGCCAAGCCCAACCTTGCAGCCAGCTTCCACGGCAAGCCCCTCCCAAGCTCTCTAAGCTCGCCCCTCGCTCCAGGTGGGAGCCACCGCACCCCGGTGA | 10730 |
| hsa-mir-199b | 2 | MHASPSLPH* | 10731 | ATGCACGCAAGCCCCTCCTGCCGCACCCTAA | 10732 |
| | 3 | MGVLTVVVLMSPMMLSASFSAWYMRSISSRRCACSSADSSISVFWSPHEYRLASSSEKMNSLVCE* | 10733 | ATGGGTGGTACATGCGCAGCATCTGTCGCCGCTGTCGCCGCTCGCCGCCGCTCAGTGTTCTCGTCCCACACGAGTTGGCCAGCAGGTTGGCCAGCAGTCCGAGAAGATGAACTCCTTGGTCTGTGAGTAG | 10734 |
| | 4 | MPVPPWPPHRALLGL* | 10735 | ATGCCTGTGCCGCCCTGGCCGCCACCGGCCCTGCTGGGACTGTGA | 10736 |
| | 1 | MYLIAKDFSTLFSYVFFNCKLLGF* | 10737 | ATGTATCTGATAGCTAAGGATTTTCAACTTTATTCTACGTATTTTCAACTGTAAATTATTGGGCTTTAA | 10738 |
| hsa-mir-19a | 2 | MIDGNCC* | 10739 | ATGGATGGAATTAATTGCTGTTAG | 10740 |
| | 3 | MELIAVRRLENSKYRFGRW* | 10741 | ATGGAATTAATAGCTGTTAGGAGAGTTGGAAAATAGCAAATAGATTGGACGGTGGTAG | 10742 |
| | 4 | MFYLFPYFSLFQSYTWT* | 10743 | ATGTTTTATCTTTTTTTCCTATTTCCAGTCATACACGTGACCTAA | 10744 |
| | 1 | MYLIAKDFSTLFSYVFFNCKLLGF* | 10745 | ATGTATCTGATAGCTAAGGATTTTCAACTTTATTCTACGTATTTTCAACTGTAAATTATTGGGCTTTAA | 10746 |
| hsa-mir-19b-1 | 2 | MIDGNCC* | 10747 | ATGGATGGAATTAATTGCTGTTAG | 10748 |
| | 3 | MELIAVRRLENSKYRFGRW* | 10749 | ATGGAATTAATAGCTGTTAGGAGGTTGGAAAATAGCAAATAGATTGGACGGTGGTAG | 10750 |
| | 4 | MFYLFPYFSLFQSYTWT* | 10751 | ATGTTTTATCTTTTTTTCCTATTTCCAGTCATACACGTGACCTAA | 10752 |
| | 1 | MVEREGSGFILBPFPPSLPPACLPGLSSSDPACSLVSDL* | 10753 | ATGGTGGAAAGGGAGGGGTCCGGCTTCATTTTGCACCCTTCCTCCTTCCTGCCCCGGCTTGCCTTCCTCCGGAGGGCTCACGTGCTCACGTCTCTGATTTGTTAA | 10754 |
| hsa-mir-19b-2 | 2 | MLNSLIVRLKLRHHFILQSAVGLWP* | 10755 | ATGCTTAATTCCATTTGATTGTGCGTCTTAAACTAAGACATCATTTTATTCTACAGAGCGCTGTCGGGCTTTGA | 10756 |

Figure 1 (Continued)

| | | | | |
|---|---|---|---|---|
| | 3 | MRGESKHAPYLPHCACIRWLLPLTIPAKKP* | 10757 | ATGAGAGGAGAAAGCAAGATAATTGCACCGTATCTTCCGCACATTTGCGCGTGTATT CGGTIGGCTGCTACCGTTAACGATACCTGCCAAGAAACCCTGA | 10758 |
| | 4 | MCRE* | 10759 | ATGTGCAGAGAGTAA | 10760 |
| hsa-mir-200a | 1 | MTMSYPAGGPGRNLWQPPVPGBSDTKCSHCAGPGVE WPHTDQLTPAGRATGPPPWRREASGATRCAPGPLTSL VGGGCRPGPPET* | 10761 | ATGACAATGTCCTACCCAGCAGGAGGACCAGGCCGGAACCTTTGGCAGCCACCAGT TCCTGGAGATTCCGACACCAAGTGCAGCCACTGTGCGGACCGGTGTGGAGTGGC CCACACCGACCAGCTCACGCCAGCTGGCAGAGCCACTGGGCCCCTCCGTGGAGG AGGAGAGAGGCCTCGGGGCCACGGCTGTGCCCAGGGCCACTCACTTCCTTGGT AGGTGGGGGATGCCGGCCTCCGAGACTTGA | 10762 |
| | 2 | MPAWASRDLSPAPALAPRETCASERPRPPLPEPCTRAVR GPCCTPERASALSHSVSNPPPSSGPQNWPSTELRGTRGP WGLGRDWPARGPPAAIPRFIQDESRAVGTT* | 10763 | ATGCCGGCCTGGGCTTCCGAGACTTGAGCCCTCCGCCCTTGCCCTGCACCCGAGAG ACCTGTGCCAGTGAGCGTCCGCACCCAGAGCCCTCGAGCCTGCACCGGGCGTG CGGGGGCCCTGCTGCACCCAGAGCGGGCATCAGCCCTCACGGACTCAGAGGCACCCGA CCTCCCCCAGCTCAGGGCCTCAGAACTGGCCATCCAGGACTGGCCAGCTCAGAGGCACCCGA GGGCCCTGGGGCCTGGTAGGGACTGGCCAGCTGGGGTCTCCAGCAGCCATACC CAGGTTCATCCAGGATGAAAGCAGGGCAGTGGGAACCACGTGA | 10764 |
| | 3 | MKAGQWEPRDWFKSR* | 10765 | ATGAAAGCAGGGCAGTGGGAACCACGTGATTGGTTTAAAAGCAGGTGA | 10766 |
| | 4 | MVAHACNPGTFGGQGRRITRGQEFETSLANTAKPLSLL KIQKLAGHGSAHL* | 10767 | CTGAGGTGGCTCATGCCTGTAATCCTGCACTTTTGGAGGCCAAGGCAGGCGGATCACC TGAGGTCAGGAGTTGAGACTAGCCTGGCCAACACGGCAAAACCCCTGTCTACTA AAAATACAAAAATTAGTGGGCATGGTAGTGCACACCTGTAG | 10768 |
| hsa-mir-200b | 1 | MTMSYPAGGPGRNLWQPPVPGBSDTKCSHCAGPGVE WPHTDQLTPAGRATGPPPWRREASGATRCAPGPLTSL VGGGCRPGPPET* | 10769 | ATGACAATGTCCTACCCAGCAGGAGGACCAGGCCGGAACCTTTGGCAGCCACCAGT TCCTGGAGATTCCGACACCAAGTGCAGCCACTGTGCGGACCGGTGTGGAGTGGC CCACACCGACCAGCTCACGCCAGCTGGCAGAGCCACTGGGCCCCTCCGTGGAGG AGGAGAGAGGCCTCGGGGCCACGGCTGTGCCCAGGGCCACTCACTTCCTTGGT AGGTGGGGGATGCCGGCCTCCGAGACTTGA | 10770 |
| | 2 | MPAWASRDLSPAPALAPRETCASERPRPPLPEPCTRAVR GPCCTPERASALSHSVSNPPPSSGPQNWPSTELRGTRGP WGLGRDWPARGPPAAIPRFIQDESRAVGTT* | 10771 | ATGCCGGCCTGGGCTTCCGAGACTTGAGCCCTCCGCCCTTGCCCTGCACCCGAGAG ACCTGTGCCAGTGAGCGTCCGCACCCAGAGCCCTCGAGCCTGCACCGGGCGTG CGGGGGCCCTGCTGCACCCAGAGCGGGCATCAGCCCTCACGGACTCAGAGGCACCCGA CCTCCCCCAGCTCAGGGCCTCAGAACTGGCCATCCAGGACTGGCCAGCTCAGAGGCACCCGA GGGCCCTGGGGCCTGGTAGGGACTGGCCAGCTGGGGTCTCCAGCAGCCATACC CAGGTTCATCCAGGATGAAAGCAGGGCAGTGGGAACCACGTGA | 10772 |
| | 3 | MKAGQWEPRDWFKSR* | 10773 | ATGAAAGCAGGGCAGTGGGAACCACGTGATTGGTTTAAAAGCAGGTGA | 10774 |
| | 4 | MVAHACNPGTFGGQGRRITRGQEFETSLANTAKPLSLL KIQKLAGHGSAHL* | 10775 | ATGGTGGCTCATGCCTGTAATCCTGCACTTTTGGAGGCCAAGGCAGGCGGATCACC TGAGGTCAGGAGTTGAGACTAGCCTGGCCAACACGGCAAAACCCCTGTCTACTA AAAATACAAAAATTAGTGGGCATGGTAGTGCACACCTGTAG | 10776 |
| hsa-mir-200c | 1 | MLPPGLAHSSVASDPAHSGAAGQRDP* | 10777 | ATGCTGCCCCCAGGACTAGCCCATTCCTCGTGGCCTCAGACCCGCCCACAGCGGA GCTGCAGGCCAGAGAGATCCCTGA | 10778 |
| | 2 | MLVIGL* | 10779 | ATGCTTGTGATCGGTTTGTGA | 10780 |
| | 3 | MPYTPGAL* | 10781 | ATGCCTGTACGCCCGGGGCTCTGTAA | 10782 |
| | 4 | MHAQPLGFGTCAVSAFPGVGASTS* | 10783 | ATGCACGCCCAGCCTCTGGGCTTTGGGACCTGTGTCTCAGCCTTTCCAGGAGTG GGCGCCAGCACTTCCTGA | 10784 |
| hsa-mir-20a | 1 | MYLIAKDFSTLFSYVFFNCKLLGF* | 10785 | ATGTATCTGATAGCTAAGGATTTTCAACTTTATTCTTACGTATTTTCAACTGTA AATTATTGGGCTTTAA | 10786 |
| | 2 | MDGFNCC* | 10787 | ATGGATGGAATTAATTGCTGTAG | 10788 |
| | 3 | MELIAVRRLENSKYRFGRW* | 10789 | ATGGAATTAATTGCTGTTAGGAGGTTGGAAAAATAGCAAATATAGATTTGGACGGTG GTAG | 10790 |
| | 4 | MFYLPFPYFSLFQSYTWT* | 10791 | ATGTTTTATCTTTTTTTCCTTATTTCCTTATTCCAGTCATACGTACACGTGGACCTAA | 10792 |

Figure 1 (Continued)

| | | | | | |
|---|---|---|---|---|---|
| hsa-mir-20b | 1 | MVEREGSGFILHPFPPSLPPACLPGLSSSDPACSLVSDL* | 10793 | ATGGTGGAAAGGGAGGGGTCCGGCTTCATTTGCACCCCTTCCTCCTTCCTTGCCC CCCGGCTTGCCTTCCAGGGCTTCCTCCTCCGACCCAGCGTGCTCACTGTCTCTGATT TGTAA | 10794 |
| | 2 | MLNSILIVRLKLRHHPFLQSAVGLWP* | 10795 | ATGCTTAATTCCATTTTGATTGTGCGTCTTAAACTAAGACATCATTTTATTCTACAGA GCGCTGTCGGGCTTTGGCCTTGA | 10796 |
| | 3 | MRGESKRAPYLPHCACIRWLLPLTIPAKKP* | 10797 | ATGAGAGGAGAAAGCAAGATAAATTGCACCGTATCTTCCGCACATTTGCGCGTGTATT CGGTGGCTGCTACCGTTAACGATACCTGCCAAGAAACCCTGA | 10798 |
| | 4 | MCRE* | 10799 | ATGTGCAGAGAGTAA | 10800 |
| hsa-mir-21 | 1 | MLVGEILVFKGLLDGVNFLFHFFF* | 10801 | ATGTTGGTGGAGAGATTTGGTTTTTAAGGGGTTGTTAGATGGAGTAAATTTCTT TTTTTTTTTTTTTTAA | 10802 |
| | 2 | MCLFLWATVPCFQCCPRHRSISAEAISGVPGGSTAEASP QKRNGHITGKTLIRPLLPSGKFRAEITFTALTHHPRQISEV GLPVFLLDRS* | 10803 | ATGTGCCTCTTCTTTCTGTGGGCTACTGTACCCGTGCTTCCAGTGCTGTCCCGCGCATAGGT CCATCTCTGCAGAAGCATTTCAGGAGTACCTGAGGCTCAACGGCCAGAAGCTTCAC CACAAAAGCGAAATGGCACACCACCACAGGTACACCACCAGGTAAGACTTTAATCCGGTTTCTTCTCCCCT CTGGGAAGTTCCGGCTGAAATTACAATTCACAGCTCTCACTCACATTTTTAGGCAAA TAAGTGAAGTTGGTTTGCCAGTGTTCCTTGACAGAAGTTGA | 10804 |
| | 3 | MGTPQVRL* | 10805 | ATGGCACCACCAGGTAAGACTTTAA | 10806 |
| | 4 | MLYWEICLCLRLESVTSVHLLLKTRVEPMESMQSVT* | 10807 | ATGCTCTACTGGGAAATTGTCTTGTCTTAGACTAGAAAGTGTAACTTCTGTACATC TTCTCCTAAAACAAGGTAGAGCCAATGGAAAGTAATGTTCTGTTACATAG | 10808 |
| | 1 | MDGVCLSGQQGRRVGVSEIIRGLCCPPLGGAEAGPDTL LEGTTFFSLCVQGTSVRSSCCQAEGGPGQAQVWSYLQPT GPSSGGPPLGTSYGKRVTDLVLLCVSAASVGPLRETAG GSSSSLSAEPAFSSLLLKSGPGRVAYRPCLRSPGHLQELR AAPARWRGRGRFSGRLAWTRTGLWKLPALTGLPVTTA K* | 10809 | ATGGACGGGGTGTGCCTGTCTGGCCAGCAGGGACGGCGGGTTGGGGGTAAGGAAAT CATTCGGGGCTTTGCTGCCCCCTGCTTGGTGGCGCTGAGGCTGGGCCCAGATACCCT CTTGGAGGGAACTTCTTTTTCTCTGTGTCAGGTACCAGTGTGCGAGTTCCTG TGCCAAGCTGAAGGTGGCCCTGGGCAGCCACCTCTGGGAACTCTCCGGGAGCTGGTTC AGGTGGTCATATCTTCAGCAAGC AGGACCATCTCCGAGGGACCTCTGGGACTTCTGCCGTTCAGTCCTCAGAGAGTGACAG ATTTGGTCTTCTCTGTGTTCTCGCCGTTCGAGCCTGCTGTGAGGCTTCAAGTCTACTGTAAAT GTGGATCTCCAGCAGCCTGTCTGCAGCCTACAGGCCCCTCAAGTCTACTGTAAAT CAGGACCGGGTCGTGTCACCTGGCTCTGCGAGCCTGGAGAGAGGACAGATTTAGTGAGCGCTG GCATGACTCGGACTGCCTTTGAAGCTCCCTGCCTTGAAGCTCCCTGGCGGGTTGCCTGTCACC ACTGCGAAGTGA | 10810 |
| | 2 | MDSDWPLEAPCPDGVACHHCEVRLGRTCT* | 10811 | ATGGACTCGGACTGGCCTTTGAAGCTCCCTGCCTTGAAGCTCCTGTGACGGGTTGCCTGTCACCAAC TGCGAAGTGAGGCTTGGCAGGACCTGCACCTGA | 10812 |
| | 3 | MSRNSGRGGSQRRPSIQPGSALCPYLHQVGSLPCIAWGL AGLGPALLWNWMFSGSPAFFHVNTVHNIVFKVQFKTQ K* | 10813 | ATGAGTAGGAACTCTGGCCGTACTTACACCAGGTCCAGCAGGGATCCCAGCGCCCTGTGTCCCCTCGATACAGCTGG CTCTGCTGGCCTGGCCGTACTTACACCAGGTCCAGCAGGGATCCCAGCGCCCTGTGTCCCGATACAGCTGG ATTGGCTGGGCTTGGCCCGCCACCTGCTTGTGGAACTGGATGTTTTCAGGGAGCCAGC CTTTCCTCATGTCAACACACAGTTCACAATATAGTTTCAAAGTACAGTTTAAAACTCAA AAGTAA | 10814 |
| | 4 | MSTQFTI* | 10815 | ATGTCAACACAGTTCACAATATAG | 10816 |
| hsa-mir-210 | 1 | MGGIRGGGQD* | 10817 | ATGGGGGGGATTAGGGAGGGGCAGGATTAG | 10818 |
| | 2 | MNQPMKGAGESRREGAGKIRRRKGRGVCANRLWRPHK DWPRTEGEDREVGGNWGGGRGHPLLPCPRDRPPPGSR GAGGGCACCCACTGCTTCAGGGACAGCAGCAAGATGCCATCACTCAGGGTCTCTAAC SPSPGASARAGTRCPSGSLTAPHPLALYPSHSLHSSMGIA LPLLFPPHPLRLL* | 10819 | ATGAACCAGCCGATGAAGGGGCTGGAGAAGGAGCAGGAGGGAGGAGGAGGCTGGAAAGA GGAGGAGGAAGGCGACTGAAGGGTCGGCGCCCACATAAGGAC TGGCCACGGACTGAAGGAGGGACACCAGGAAAGTAGGGGGGAACTGGGTGGCGGGC GAGGGCACCCACTGCTTCAGGGACAGCAAGATGCCATCACTCAGGGTCTCTAAC CCAAGTGCGGGAGCCTCAGCTGGGCGGGGGACAAGATCCATCATTCCTACACTCCTAC TGCCCCCACCCACTGCCCTCGCGCTGACCCGTCCCGATCCCTCCTCATTCCTACACTCCTAC CTGCCCTCTTCTCTTTCCTCCCCATCCCCTTGTTTACTCTAG | 10820 |

Figure 1 (Continued)

| | | | | | |
|---|---|---|---|---|---|
| hsa-mir-219-1 | 3 | MPIRVSNCPPPPRPVSLSFPTLNGDRSAPSSSLSSPSPSFT LESSKRLLPTSHSRHSAPVYPTHTRTPPSQWELHLVYVP VSAWCLHSPFPPVRLPPFPAPGRGS* | 10821 | ATGCCCATCAGGGTCTCTTAACTGCCCCCCACCCTCGCCCTGTATCCTCATTCC CTACACTCTCAGAGTCCTGAAGAGGCTTCTGCCACTCCCACTCCAGACATTCTGCC GTTTACTCTAGAGTCCTGAAGAGGGCTTCTGCCACTCCCACTCCAGACATTCTGCC CTGTTACCCCACCACACTGCACCGCACCCGCACCCCCCCTTCCCAATGGAGCTCCATCTGTG TATGTCCCGTTTCCGCGTGTGTCTCCAATTCCTCCCGTGCCGCTCCTA CCTTCCCGCCGCCCGGGCCGCGGCTCCTGA | 10822 |
| | 4 | MGAFSCVCPCFRVVSPFFLSSRAPPSLPRPGPRLLIVQTQ FSSLWLRPRVESGRPEHPPPPNLRESGSEGLGRAKAEGG GSPQGGKGNPGHGT* | 10823 | ATGGGAGCTCCATCTTGTGTATGTCCTGTTTCGCGTGTGTCTCCATTCCCCTTT CCTCCCGTGCCTCCCTCCCGCGCCCCGGCCGCCGCTCCTGATTGTCCAAA CGCAATTCTCGAGTCTATGGCTCCGCGGCCGAGAGTTGAGTCTGGACGTCCGAGCCGC CGCCCCAAACCTCGAGGCGAGTCGGGTCGGAGGGCTCAGGGAGAGCCAAAGCA GAGGGTGAGGGGAGTCCCCAGGGTGGTAAGGGGAATCCCGGGCACATCGGGACCTA G | 10824 |
| | 1 | MEGESGVRAATPSPSGRRRGGGGRGASGRGAWTGRVS VSGATRKESGTGVVAEGLAEWRGACGEPRGRRAGGGS PGGPRSEDTGAGHLAWGUSGPPERAARRCFASAGVHW VRASSAPWQGBRGRWAGRPLLSFSPGDVM* | 10825 | ATGGAGGGTGAAAGTGGGGTCCGGGCGGCACACCAGCCTTCCGGGAGGAGAAG GGGCGGCGGGCGTCGCGGAGGACAGGGCGCTGGACCTGGCGGAGTTAGT GTGTCAGGAGGTACGAGAAAGAGTCTGGACGGAGAGGGCCTGGACTGGCGAAAGGCTGG CGGAGTGCGGCGGGCGCGGGAGAGCCGAGGGGCCGAGGGCGCGGAGGCGGCTC AACCCGGCGGCCCCGGTCTGAGGATACAGGGCGCGGCCATCTAGCCTGGGAGGGT CTGGACCCCGAGCGGTGGCGGCAGGGAGGGGAGTGCTTTGCCTCTGCCGGTTCACTGG GTCAGGGCAGTTCAGCGCCCTGGCAGGAAGGGGTCGCAGGGAAGGGTCGCGGCCCGGCCCCT CCCTCTCGTTCTCTCCAGGGGATGTTATGTAA | 10826 |
| | 2 | MLCKGGGERSRGRRCRGLMQPKG* | 10827 | ATGTTATGTAAGGGGAGGGGAGAGCGTAGGGGGCGGCGGTGCCGGGGCTTA TGCAACCCAAAGGTTAG | 10828 |
| | 3 | MASGEAVTPTSLRPWFQPPTTPLACHPGCQIGHGAVRVP EG* | 10829 | ATGGCCTCCTTTGGCCTGTCATCCTGGCCTGTTCAGTTCCAGCCTGTTCAGCCTCA ACTCCTTTGGCCTGTCATCCGGCTGTCAGATTGGGCTAGGAGCTGTCAGAGTGCCA GAGGGTTGA | 10830 |
| | 4 | MEQLVRGSVFWAHPALOPRAPAWHRLSAAAESSGLNR AISDRGRSDGVGLVTQGKEDTQSSCLPRGFRNLNRTFY PPIFLTL* | 10831 | ATGGAGCAGCTGGTCAGAGGGTCAGTGCCCTGGGCCCACCCCGCCTGCAGCCAAG GGCACCTGCTGCTTGGACACAGGAAGCGTCGAGCAGCTGGAGTTGGACCTCTGGGTTGAACAGAGC TATCTTCAGACAGAGGAAGGTCGGACGGAGTTGGACTGGTCACCAGGGAAGGAAG ATACACAAAGTTCATGCTCCAAGAGGGTTTCGGAATTTGAACCGCACCCGTATC CCCAATCTTCTTACCCTCTGA | 10832 |
| | 1 | MWKIS* | 10833 | ATGTGGAAAATTCATGA | 10834 |
| | 2 | MSLDICKHL* | 10835 | ATGAGTTTGGATATATGCAAACACCTGTGA | 10836 |
| | 3 | MQTPVIPSH* | 10837 | ATGCAAACACCTGTGATACCATCACCATAA | 10838 |
| | 4 | MDVFNISQSFIVSLWPCVCVCVYVKNHLT* | 10839 | ATGGATGTATTCAACATCTCAAAGTTCATTGTATCCCTTGGTTTTGTGTCTGTG TTTGTGTATATGTTAAGAATCACTTAACATGA | 10840 |
| hsa-mir-221 | 1 | MWKIS* | 10841 | ATGTGGAAAATTCATGA | 10842 |
| | 2 | MSLDICKHL* | 10843 | ATGAGTTTGGATATATGCAAACACCTGTGA | 10844 |
| | 3 | MQTPVIPSP* | 10845 | ATGCAAACACCTGTGATACCATCACCATAA | 10846 |
| hsa-mir-222 | 4 | MDVFNISQSFIVSLWFCVCVCVYVKNHLT* | 10847 | ATGGATGTATTCAACATCTCAAAGTTCATTGTATCCCTTTGGTTTTGTGTCTGTG TTTGTGTATATGTTAAGAATCACTTAACATGA | 10848 |
| | 1 | MANGWTGSRPGRRNPEL* | 10849 | ATGGCCAATGGCTGGACTGGCTCCCGCCCTGGTCGGAGGAATCCGGAGCTGA | 10850 |
| | 2 | MAGLAPALGGGIPSCEAAGIRAHYLLCLLRAEAMAGAG VGCGGGVRWRRSR* | 10851 | ATGGCTGGACTGGCTCCCGCCCTGGGCGGAGGAATCCCGAGCTGTGAAGGCTGG AATCCGGGCACAGGCCCATGTGCTTCTTGTTTACTAAGAGCGGAAGCGGATGCGGGGAGCGG GGGTGGGGTGCGGTGCGGGTGCGGTGGCGGAGGTTCCGGTGA | 10852 |
| hsa-mir-25 | 3 | MCFFVY* | 10853 | ATGTGCTTCTTGTTTACTAA | 10854 |

Figure 1 (Continued)

| | | | | | |
|---|---|---|---|---|---|
| | 4 | MLDGPVHCHGLFILRWLETDL* | 10855 | ATGTTGGATGGCCTGTGCACTGCCACGGGCTCTTTATTCTCGGTTAGAAACAGACTTGTGA | 10856 |
| hsa-mir-301a | 1 | MEAEVDKLELMVSAK* | 10857 | ATGGAGGCGGAGGTCGATAAGCTGGAACTGATGGTGAGTGCAAAGTGA | 10858 |
| | 2 | MASEVGRNLESPETPGGGGWTRVEFPPPAPKGAAATVWCLNRLG* | 10859 | ATGGCCTCGGAGGTGGGGCACAATTTGGAGTCGCCGGAAACTCCGGGCGGTCGGAGGCTGACCCAGAGTGGAGTTCCTCCTCGCACCAAAGGGAGCCGCCACCGTCTGGTGTCTAAACCGCCTCGGGTAA | 10860 |
| | 3 | MAGIDAEGAGPLEFLVPCPHLYTPYETAPGADRILCLYQKRCEWNGP* | 10861 | ATGGCGGGAGAGATGCTGAGGGTGCGGGGCTTTGGAATTCCTTGTTCCTTGCCCTCACCTTTACACCCCTACGAAACTGCGCCGGTGCCAGGGTGCAGACCGCATTCTGTGTTTGTACCAAAAAGATGTTGAATGGAACGTCCTAA | 10862 |
| | 4 | MLRVRGLWNSLFLALTPTPLTKLRRVQTAPCVCTKKDVNGTVPKRPKKGEVVHTPRKGNGGWGGE* | 10863 | ATGCTGAGGGTGCGGGGCTTTGGAATTCCTGTTCCTGCCCTCACCTTTACACCCCTTACGAAACTGCGCCGGTGCCAGACCGCATTCTGTGTTGTACCAAAAAGATGTGAATGGAACGGTCCCTAAGCGTCCAAGAAGGGAGGAGGTGGTTCACTGCTCCAAGAAAGGGGAACGTGAGGGTGGGGTGGGGAATAA | 10864 |
| hsa-mir-30a | 1 | MGFQSDVCSCLLPRTSRGYFRSNYLVY* | 10865 | ATGGGCTTTCAGTCGGATGTTTGCAGCTGCCTACTGCCTCGGACTTCAAGGGGCTACTTAAGGAGCAATTATCTGTTTACTAA | 10866 |
| | 2 | MFAAAYCLGLQGATLGAIILFTKTEYLAISLIHFYKAELKWYKLNHFPKTMSVHF* | 10867 | ATGTTTGCAGCTGCCTACTGCCTCGGACTTCAAGGGGCTACTTTAGGAGCAATTATCTTGTTTTACTAAACTGAATACCTCTGATCTCTATCTTTTGTATACATTTTACACTTTAAACAAAGCTGAATTAAAATGGTATAAATTAAATCACTTTAAACCATGTCTGTACATTTTAG | 10868 |
| | 3 | MHRICNRKKKVFVREMRKCVTVFLFFLKA* | 10869 | ATGCATAGAAATTGCAATATCAAAAGAAATATTCGTAAGAAATGAGGAATGA | 10870 |
| | 4 | MCYSIFIFFKSVYGQYFPEKSMK* | 10871 | ATGTGTTACAGTATTATTTTTTAAAGGTAGTAGGGCAATATTTCCCAGAAAAATCTATGAAGTGA | 10872 |
| hsa-mir-30c-2 | 1 | MQSRNFSPYT* | 10873 | ATGCAATCTAGAAATTTCAGTTTCTCGTCCTATACTTAA | 10874 |
| | 2 | MCVQHFSPSS* | 10875 | ATGTGTGTGCAACATTTTCTCCGTCTCTTAG | 10876 |
| | 3 | MGMHVFLY* | 10877 | ATGGGATGCATGGTCTTTTATATTAA | 10878 |
| | 4 | MSFYINIFPKYFQIVAFRFIASSLKYSCPESSCIVSIFCVSPQI* | 10879 | ATGTCTTTTATATTAAATATTTTCCTAAGTATTTGCGTTTCAGATTGTTGCTTTCAGATTATTGCTTCCTCCTTAAAAATATAGCTGCCCTGAAAGCAGCTGTATTGATCTATTTTTGTGTTTCCCACAGATCTGA | 10880 |
| | 1 | MKGSPQKKMWSLNFHPLNVLLKGN* | 10881 | ATGAAAGGTAGTCCTCAGAAGAAAAAATGTGGTCTCTTAACTCATACCAATCTTAATGTTTTGCTTAAGGGGAATTAG | 10882 |
| hsa-mir-30e-2 | 2 | MFCLRGISEEJTVSGRLKTVILLNKYCSFNLSSHARNVEVIFFHTCTVRPGILKSFKYK* | 10883 | ATGTTTTGCTTAAGGGGAATTAGTAGTGAGGAAATAACAGTCTCAGGAAGGTTGAAACTGTTGATTTTACTCCAACAAATATTGCTCTTTAATCTCTCCAGCCATGCCAGAAACTATGAAGTTATTTTCTTACACACTGCTACACTGTAAGACCTGGTATTTTAAAAAGCTTTAAATATAAGTAG | 10884 |
| | 3 | MPEIMKLFSFTHAL* | 10885 | ATGCCAGAAACTATGAAGTTATTTTCTTTCACACATGCACTGAA | 10886 |
| | 4 | MHCKTWYFKKL* | 10887 | ATGCACTGTAAGACCTGGTATTTTAAAAAGCTTTAA | 10888 |
| hsa-mir-30d | 1 | MQSRNFSPYT* | 10889 | ATGCAATCTAGAAATTTCAGTTCCTATACTTAA | 10890 |
| | 2 | MCVQHFSPSS* | 10891 | ATGTGTGTGCAACATTTTCTCCGTCTCTTAG | 10892 |
| | 3 | MGMHVFLY* | 10893 | ATGGGTATGCATGTCTTTTTATATTAA | 10894 |
| | 4 | MSFYINIFPKYFQIVAFRFIASSLKYSCPESSCIVSIFCVSPQI* | 10895 | ATGTCTTTTATATTAATATTTTCCTAAGTATTTTCAGATTGTTGCTTTCAGATTATTGCTTCCTCCTTAAAAATATAGCTGCCCTGAAAGCAGCTGTATTGATCTATTTTTGTGTTTCCCACAGATCTGA | 10896 |
| hsa-mir-320 | 1 | MLRRSGVLASGRWRGGAKIRVPGFVGRHAAM* | 10897 | ATGCTGCGCGCGGTCGCGGGGGTCTTGGCCTCTGGACGCTGGCGTGGCGTGGAGGCGCCAAGATCAGGGTCCCGGGTTTTGTCGGCGCCACCACGCGCAATGTGA | 10898 |
| | 2 | MGRGARRGAESESEWT* | 10899 | ATGGGACGCGAGCGGCGCGGCGCGGCGGAGAGTGAGAGCGAATGTGA | 10900 |

Figure 1 (Continued)

| | | | | | |
|---|---|---|---|---|---|
| hsa-mir-326 | 3 | MVTLEWSLPPGSDLAHFRGPLPCAPGGVLG* | 10901 | ATGGTGACCTTGGAGTGGTCATTACCTCCGGGCAGGCAGCGACCTCGCCACTTTCGGGGA CCCTTCCCTGTCGTCTCTGGTGGAGTCCTGGGGTGA | 10902 |
| | 4 | MLSPIPQTV* | 10903 | ATGTTATCCCCATCCCCAGACCGTATAA | 10904 |
| | 1 | MGDKGTR* | 10905 | ATGGGCGACAAAGGGACCCGGTGA | 10906 |
| | 2 | MWAAAPGPDTQLADTQHWPAAAETHGGRLTHNTRTG FLTRGTGMLAHTLATASTRSSHAVARRHTRLGQHILAD SLVGMHRSSQSNTHQF* | 10907 | ATGTGGGCCGCAGCCCCGGGACCCGACACAGTCTGCTGACACCCAGATTGGCC GGCAGCCGAGAGCCACGCAGGCAGTTGACACAGCAGGTTCACACATACGACGGGCACAC TAACCCGTGGCACGCAGCATGTGGGCACACAGTCTGGCAACGCTAGCACACGCTCAT CACACGCAGTTGGACGCCGTCATACAGGGCCCGGTCAACATTCTTGCTGACAGCC TTGTTGCCATCAGCAGTCACACAGCTCAACATCCAACACACACCAATTCTAG | 10908 |
| | 3 | MSHQHSGAQGHTNTDPHRHNQTDALKDWHPTGTSC* | 10909 | ATGTCTCACCAACACAGCGGAGCGCAAGCCACACTGACCCCACAGACA CAATCAGAGTGATGCCTCAAAGACTGGCACCCACAGGCAGGACGAGTCGTAG | 10910 |
| | 4 | MPSKTGTPQARAASPRPADTHASGPTWPEVETHTSHRV ERPPPPAWGKQIAFHPNRSHPSTLFPFPLTS* | 10911 | ATGCCCTCAAAGACTGGCACCCCACAGGCACGAGCTGCTAGCCCAAGGCCGTGA CACACACGCTTCAGGCCCCACATGGCCAGAAGTGGAAACACACACATCACACAGGG TAGAGCGCCCCCGCCACCCGCCAGCTGGCCTTCCCTTCCCTGTGACCTCCTGA GATCCCATCCATCTACTCGTTCCCTTTCCCTGTGACCTCCTGA | 10912 |
| hsa-mir-330 | 1 | MSSFGAG* | 10913 | ATGAGTAGCTTTGGAGCTGGGTGA | 10914 |
| | 2 | MVSPLF* | 10915 | ATGGTTTCTCCCTTTTCTGA | 10916 |
| | 3 | MGKGSYEACLLG* | 10917 | ATGGGGAAGGGCTCGTTGAAGCTTGCTTGTTGGGGTGA | 10918 |
| | 4 | MGLVSVFDLWGCPGRGWLRENVPEGGPPCAHDDPRRAG THLQPGHTLGAAFLPAQAGVGVSFCWNLLGAPIPPGGN RKAVKAAQACNLSTLGGSSPEAKSLRPAWATHKTSTARS RAMWPEWDWCI* | 10919 | ATGGGACTGGTGTCAGTGCCTGGACCTCTGGGGTGTTCTGGCAGGATGGCTCCG TGAAAATGTTCCTGAGGGCGCCCCATGAGATCCCAGACGAGTCGGCAC CCACCTACAGCCTGGACACACGTCGGACTGCTCTTCCTGCGGTCAAGCTGGAGT GGGTGTATCCTTTGCTGGAAATCTCTTGGTGCTCCCATCCCCAGGAGGAAATAG AAAGGCGGTCAAGGCAGCTCAAGGCGTAATCTCAGCACTTGGAGGATCGTTTG AGGCCAAGAGTTTGAGACCTGCTGCTGGACCAACACACAAAACAAGCACAGCAGTTCA AGGGCTATGTGGGCCAGAGTGGGATTGGTGCATTGA | 10920 |
| | 1 | MPGWHLQLRGFSGKQRPLLSRDPGS* | 10921 | ATGCCCGGATGGATCCTGCAGCTCCGCAGCTTTTCTGGAAGCAGCGGCCCCTGCTC TCAAGAGACCCTGGCTCCTGA | 10922 |
| | 2 | MDPAAPWLFWEAAAPALKRPWLLMVAPRLPAGARDSG QFPRKGQAGSPSRGRVRKLGGAEATLGP* | 10923 | ATGGATCCTGCAGCCTCCTGGCTTTCTGGAAGCAGCAGCGGCCCCTGCTCTCAAGAGA CCCTGGCTCCTGATGGTGGCCAAGCGGCCTGGTTGCCAGTGGTTGCTAGGACTCAGGACA GTTTCCCAGAAAAGCCAAGCAGCCAGCCCTCCAGGGCCCGGGTGCTAGGGACTCAGGACA GGGGTGCGGAGGCCACACTGGGTCCTGA | 10924 |
| hsa-mir-338 | 3 | MAFP* | 10925 | ATGGCCTTCCCCTGA | 10926 |
| | 4 | MSGRGTLGGEVSCPGGRRGAGGRRVRPGSRGRWRRSSR G* | 10927 | ATGAGTGGACGGGGCACAGGAGGAGAAGTGTCCTGCCCTGGGGGCCCGCGTGGGC GGGTGGGAGAAGAGTAAGGCCCGGAGCCGGTGGAGGCGGAGCAGCCGT GGGTGA | 10928 |
| | 1 | MGGALPGPRPAATGGRSRGRPWRPDAAAAGPAPPCRPR AGRAALLGAPLRAGPRAGGPGRSRALLPLTLLGAQGRAA GGRVYGVQALQALRALERPRNRPGSPALWGRTGPPAAM QQPPGETRALRTLGGLESSAAA* | 10929 | ATGGGAGGGCCCTGCCCAGCCCGTCCCGAGGGACCAGGTGGCGCTCCGTGG GAGCCGAGAGCCGGCTGCTGGGAAACCCTCCGGCCTGCCGCCGTCCCGAGCAGCCCT CCGGCGAGCCGTTCGGCGGCCTGGGGAGCTGGCCTGCGCCGTCCTCGGGGGCCG GGTGCACGGTTGGGGTTCGGCGGCCACCGGCGACGGCGCCCGAGCGCCG CAACCGCAGCCCAGGCTCCCCGCTCGTGTGGGGGCGGCCGAACCGGACCCTGAAGCGCCAAGGACGCAG AGCAGCCCCCGGGAGGGAGACACCGAGCTGTCTGAGGAGACCTGGAGTCGTCG GCCGCCGCGCGCTGA | 10930 |

Figure 1 (Continued)

| | | | | | |
|---|---|---|---|---|---|
| hsa-mir-339 | | MMKTIGHASLGSLPEDGGAGRQLLQEALPLLRRGSAGP GLESAEVLGVGLLSSEEAVARAGGGPVLVLRCVLGASS AAARTACGRGPGVRIDTRTGLPSLLLGLTAAETAGMV TVASESFAYE* | 10931 | ATGATGAAAACAATTGGGATAGCTTCACTCGGAGCCTTCCTGAGGACGGCGAGC AGGCCGGCAGCTCCTTGAAGAGGCTCTGCTGGCTGCCGCTTGGGGTCAGCCGGTT TGGGTTGGAGAGCGCAGAGGTGCTTGGAGTGGTTGGTGGGTCTTTATCTCTGAGGAGGCGG TGGCCCCGGGCAGGTTGCGGCGCGCCCCGTGCTGGTCCGTGTCCGCGCTCCTCGAGCGTCCT CAGCTGCTGCGGCACAGCCCTGTCTGGGGGGCCGTTGAACCAGGCGTCCGCAGGACACGCGA ACCGGGCTGCGCTGCTGCTGCGGGCCTGCTGCGGGCCTGCAAGAGACGGCGGGAATGGT GACCGTTGCTTCAGAGTCCTTTGCTTATGAGTAA | 10932 |
| | 3 | MSNSPN* | 10933 | ATGAGTAACTCACCGAATTGA | 10934 |
| | 4 | MNSLCSLRSCGKVRKPNPYLVPRCECFKLCVTTNKIDM MIHFTDI* | 10935 | ATGAATTCGTTGTGTCACTGAGGAGTTGTGGCAAAGTGAGAAAACTAACCGTAC TTAGTTCCAGATGTGAGTGTTTAAACTATGTGTAACACTATGTAACAATTGACATG ATGATACACTTCACGGACATTTAA | 10936 |
| hsa-mir-33b | 1 | MPPSPAGSPGVGGHAGYAT* | 10937 | ATGCCTCCGTCTCCTGCAGGTTCTCCTGGAGGTGGGCAGGCATGCGGGCTACGCAACTTGA | 10938 |
| | 2 | MRATQLEQERAPSRGRRCDSYQLAGEVEGYLQPN* | 10939 | ATGCGGGCTACGCAACTTGAGCAGGAAAGAGGCCCCTCCGAGGGAGAAGGTGTGA CAGTTACCAGTCGTCGGGGAGAAGTGGAGGGCTACCTCCAACCAAATTAG | 10940 |
| | 3 | MGNPAVESPL* | 10941 | ATGGGAAACCCTGCAGTTGAAAGTCCATTATGA | 10942 |
| | 4 | MTCDLGGPQTRRVST* | 10943 | ATGACTTGTGACCTGGCGGGTCCACAACCAGGAGAGTTTCTACTTGA | 10944 |
| | 1 | MGCGDE* | 10945 | ATGGGCTGCGGGGATGAATGA | 10946 |
| | 2 | MNESRV* | 10947 | ATGAATGAGAGCCGAGTCTGA | 10948 |
| hsa-mir-345 | 3 | MRAESDSAPQESLTFAVARDCPGPCGASHSVTSHQPPPS ASGGPDCQVGAWEQGRARRLFAVGVRSALGRAQLPS LGPAGRQGHTVCHVSRFRVTWFFYPNSSGYLPPGGAGR KVLCIWY* | 10949 | ATGAGAGCCGAGTCTGACTCGGCCCCCCAGGAGTCCCTGACATTCGCAGTGCAAG GACTGCCCTGGTCCTGTGGAGCGTCCATTCGGTAGCCTGGAGCCTGGAGCAGGGACGGGCCA CAGCGCCTGGAGGTCAGATGTCAGATGCAGATGAGTCCCGGCCCGGCCCAGCTTCCTT GGGCCTTTAGGGCTGCAGGCAGGCAAGGCCACGTGTGCCAGTTCCAGTTAGG CTTAGGGCTGCAGGCAGGCAAGGCCACGTGTGCCAGTTCCAGTTTAGG TCACATGGTTCTGTCTTTATCCAAATTCCAGTGGGTACCTACCTCTGGAGGTCAGGTC GAAAGGTTCTGTATTTGGTACTAG | 10950 |
| | 4 | MVLLSKFQWVPTSWRCRSKGSVYLVLGHTGRCCQ* | 10951 | ATGGTTCTTTTATCCAAATTCCAGTGGGTACCTACCTCTGGAGGTGCAGGTCGAAA GGTTCTGTGTATTTGGTACTAGGACACACAGGTAGGTGTGCACTGTGTCAGTAG | 10952 |
| hsa-mir-363 | 1 | MVEREGSGFHLHPPPPSLPPACLPGLSSSDPACSLVSDL* | 10953 | ATGGTGGAGCGGGGGTCGGGCTTCCATTTGCACCCGCCTCCCTCCTCTGCCTC CCCGGCTTCCTCCAGGGCTTCCTGCCGACCCAGTGGTGCTCACTGGTCTCTGATT TGTAA | 10954 |
| | 2 | MLNSILIVRLKLRHHFILQSAVGLWP* | 10955 | ATGCTTAATTCATTTGATTGTGCGTCTTAAACTAAGACATCATTTATTCTACAGA GCGCTGTCGGGCTTTGGCTTGA | 10956 |
| | 3 | MRGESKHAPYLPHCACIRWLLPLTIPAKKP* | 10957 | ATGAGAGGAGAAAGCAAAGATAATTGCACCGTATCTTCCGCACATTTGCGCGTATT CGGTGCTGCTACCGTTAACGATACCTGCCAAGAAACCCTGA | 10958 |
| | 4 | MCRE* | 10959 | ATGTGCAAGAGAGTAA | 10960 |
| | 1 | MEIISPNLGAQQI* | 10961 | ATGGAAATCATTCCCCAACTTGGGGCGCAGCAAATTGA | 10962 |
| | 2 | MRDD* | 10963 | ATGAGAGACGATTAA | 10964 |
| hsa-mir-365-1 | 3 | MGWGELYEAPRTPELSAAKGRLGHPSCCPGSF* | 10965 | ATGGGGTGGGGGAACTGTACGAGGCACCTGGACACCCGATTTATCCGCTAA GGGACGTTTGGGGCACCCCTCGGTGTCGGGAAGCTTTAG | 10966 |
| | 4 | MVWQMSPPTATPWHFGEMNRRPEGTPSNDSFSDPGSP NSCLKGGLPRCCQP* | 10967 | ATGGTGTGGCAAATGTCCCCTCCCACAGCGACCCCTGGCATTTGGTGAGATG AACCGCCGCCCTGAGGGAACACCAGTAACGATTCTTCAGTGATCCGGTTCTCCA AACTCTTGCCTCAAAGCGGCCTGCCCGTCGTGTCAGCCGTGA | 10968 |

Figure 1 (Continued)

| | | | | | |
|---|---|---|---|---|---|
| hsa-mir-365-2 | 1 | MGARGWVFAGEMRVSDQLAYKVPVLGPRDQRLLPGPRPRPASSRAGVRSGQAASQVHAGEGVVRCARPGCVR* | 10969 | ATGGGAGCTGAGGCTGGGTCTTTGCGGCGAGGGCGAGATAGGGTGTCGGATCAACTGGCCTACAAAGTCCCAGTTCTCGGCCCCGGGACCAGGGTCTTCTCCGGTCCTCGCCCCAGGCCGGCTTCCTCCCCGGGCTGGCGTCCGGCCAGGGTGCCTCTCAGGTCCACGCTGGAGAAGGAGGTGTGAGGTGCGCTCGCCCGGCTGCGTGCGGTGA | 10970 |
| | 2 | MGQALPLTEACPAVLSRAATLSLGVGRTGPDF* | 10971 | ACCTTGAGCTTGGGGGTGGGGAGCTTACCTGCACTTACCGAGGCCTGCCTGCCTGCTGCTGTGCTTTCCAGGGCGGTAACCTTGACTTCTAG | 10972 |
| | 3 | MDLCGCVPNGRSFVP* | 10973 | ATGGATCTTTGTGGATGTGTTCCAATGGCCGTCTTTGTTCCTGA | 10974 |
| | 4 | MCSQWPVFCSLTDAT* | 10975 | ATGTGTTCCCAATGCGGTCTTTGTTCCCTGACCGATGCAACATAA | 10976 |
| hsa-mir-371 | 1 | MMTCALVFFTEPLFKCSIKS* | 10977 | ATGATGACATGCGCTTTGGTCTTTTCACTGAACCTCTTTTATAAAGTGTTCAATAA | 10978 |
| | 2 | MRFGLFH* | 10979 | ATGCGCTTTGGTCTTTTCACTGA | 10980 |
| | 3 | MYSLHLA* | 10981 | ATGTATTCTTTGCATCTGGCATAG | 10982 |
| | 4 | MQEDHLSPGVPVQPGLTGRTPSLERKKCKKAFFVYYFFETGSPSIPQTGVPWYHHSLLQP* | 10983 | ATGCAGGAGGATCATTTGAGTCCAGGAGTTCCAGTCCAGCCTGGGTTAACAGGTAGAACCCCTTCTCTGGAAAGAAAAATGTAAAAAGGCATTCTTGTGTATTATTTTTTGAAACAGGGTCTCCCTCTATACCCAGACTGGAGTGCCTTGGTATCATCACAGCTTACTACAGCCTTGA | 10984 |
| hsa-mir-372 | 1 | MLTPYPSPSRELPCFVLSHREMISEVSPTTQFIHATPGTPAQKALAEDLLRGWSPCPHPCFLQ* | 10985 | GGGAAGATCTCAGAGGGTCTCTCACAACACAGTTCATTCACGGACACCGGACACCTGCACAGAAGGCACTTGCTGAGGACTTGCTTGCTGCGTGGGTGGAGTCCGTGCCTCCACCATGTCCCTTCAGTGA | 10986 |
| | 2 | MSPSVTLRRMGA* | 10987 | ATGTCCCTTCAGTGACCTTGAGAAGAATGGTGCTAG | 10988 |
| | 3 | MLPDP* | 10989 | ATGCTGCCTGACCCTGA | 10990 |
| | 4 | MEGLSSQETLELAVQLACAAFSKAGENGLG* | 10991 | ATGGAGGGCCTCTCTCTCAGGAGACGTTGGAACTTGCTGTCCAGCTGGCTTGTGCTGCCTTCAAAGCAGGAAATGTTGGGGTGA | 10992 |
| hsa-mir-372 | 1 | MMTCALVFFTEPLFKCSIKS* | 10993 | ATGATGACATGCGCTTTGGTCTTTGCACTGAACCTCTTTTATAAAGTGTTCAATAAAAAGCTGA | 10994 |
| | 2 | MRFGLFH* | 10995 | ATGCGCTTTGGTCTTTTCACTGA | 10996 |
| | 3 | MYSLHLA* | 10997 | ATGTATTCTTTGCATCTGGCATAG | 10998 |
| | 4 | MQEDHLSPGVPVQPGLTGRTPSLERKKCKKAFFVYYFFETGSPSIPQTGVPWYHHSLLQP* | 10999 | ATGCAGGAGGATCATTTGAGTCCAGGAGTTCCAGCTGGGTTAACAGGTAGAACCCCTTCTCTGGAAAGAAAAATGTAAAAAGGCATTCTTTGTATTATTTTTGAAACAGGGTCTCCCTCTATACCCAGACTGGAGTGCCTTGGTATCATCACAGCTTACTACAGCCTTGA | 11000 |
| hsa-mir-373 | 1 | MMTCALVFFTEPLFKCSIKS* | 11001 | ATGATGACATGCGCTTTGGTCTTTTCACTGAACCTCTTTTATAAAGTGTTCAATAAAAAGCTGA | 11002 |
| | 2 | MRFGLFH* | 11003 | ATGCGCTTTGGTCTTTTCACTGA | 11004 |
| | 3 | MYSLHLA* | 11005 | ATGTATTCTTTGCATCTGGCATAG | 11006 |
| | 4 | MQEDHLSPGVPVQPGLTGRTPSLERKKCKKAFFVYYFFETGSPSIPQTGVPWYHHSLLQP* | 11007 | ATGCAGGAGGATCATTTGAGTCCAGGAGTTCCAGTCCAGCCTGGGTTAACAGGTAGAACCCCTTCTCTGGAAAGAAAAATGTAAAAAGGCATTCTTTGTATTATTTTTGAAACAGGGTCTCCCTCTATACCCAGACTGGAGTGCCTTGGTATCATCACAGCTTACTACAGCCTTGA | 11008 |
| hsa-mir-374a | 1 | MVGENGKEEAARMRISDGVPGRGGAQHSGN* | 11009 | ATGGTTGGGGAGAACGGTAAGGAGGAAGCGGCGGCATGCGTATTTCAGACGGAGTGCCGGGAGGGGAGGGGAGGGCTCAGCATTGGGTAATTAA | 11010 |
| | 2 | MARGEVSCLCLAILG* | 11011 | ATGCGAGGGGAGGTCAGCTGTCTTTGCTTGGCATCTGGGCTAG | 11012 |
| | 3 | MLWPDFLERNPES* | 11013 | ATGCTGTGGCCAGATCCACTAGAAATTAACCCAGAATCTTAG | 11014 |
| | 4 | MRRR* | 11015 | ATGAGGAGGCGATGA | 11016 |

Figure 1 (Continued)

| | | | | | |
|---|---|---|---|---|---|
| hsa-mir-374b | 1 | MVGENGKEEAARMRISDGVPGRGGAQHSGN* | 11017 | ATGGTTGGGGAGAACGGTAAGGAGGAAGCGGCGCGCATGCGTATTTCAGACGGAGTGCCGGGGAGGGGAGGGGCTCAGCATTCGGGTAATTAA | 11018 |
| | 2 | MARGEVSCLCLAILG* | 11019 | ATGGCGAGGGGGAGTAAGCCTGTCTTTGCTGCATCTTGGCTAG | 11020 |
| | 3 | MLWPDPLEINPES* | 11021 | ATGCTGTGGCCAGATCCACTAGAGAATTAACCAGAATCTTAG | 11022 |
| | 4 | MRRR* | 11023 | ATGAGGAGGCGATGA | 11024 |
| hsa-mir-378 | 1 | MAGNDCGALLDEELSSFPLNYLADTQVRPAGAAGPGPGVLSCGGRSCSRGGREAAVGALG* | 11025 | ATGGCGGGGAACGACTGCGGCGCGCTGCTGGACGAAGAGCTCTCCTTCTTCTCTCAACTATCTGCTGACACGCAAGTTCGGCCCGCCCGCTGGGCCGGGGCCCCAGGGGTGCTGAGCTGCCGGGGCGCGGGCCCAGCTGCAGCGGCGGGAGGCAGCGGTGGGAGCCCTGGGGTAA | 11026 |
| | 2 | MRSVTGAGSRRSPGACRSAGGATAAGEGLALAAAWSLPPRGQNWGVPRFLWEVEARHGVGYPQAGAGCWRRAVSARHLLPYFHVDLWPRHGCMPGSPESPSPPGCSPQSAVAGPPRLSTRARSAEFPASCRLKA* | 11027 | ATGCGCGCTCCGTTACCGGGGCAGGGAGCCGGAGGTCTCCCGGCGCGTGCCGGAGCGCTGGGGCGCTACGGCCGCTGGGAGGGGTACCGCGCTTCTTTGCGGAGGTGGAGCGCGCACCCCGCGGGCAAAACTGGGCGGTACCCTCAGGCTCGCGCTGGTGTGCGCTGCGTCAGCGCCGGTGTGGGTACCCTCAGGCTCGCGCTGCGTGGTGGCCCCCCGCCCGGGGCGGGGCGCACTTGCTGCCGTACTTTCACGTGGACTTGGCGTGCGCACCTGCATGCCGGGTCTCCGAGTCCGTACTGCCTCAGGTGTCCCAGATTGCTGTGTGTGCGCGCCCCGGCGGGTTTCTACCGCCGAGTTTCCTGCCAGTTGCCGGCTAAAGGGCATAA | 11028 |
| | 3 | MRAETASSWFRYRAEPPGGKSQAGWGRKDCLGAPGSPCGARPRCALHDAGGREGEAESQALAEPGSPTGDTRVTGEGALVCRGAGERGSWWLGDWERGAAGTSSHQKCQHEACAAPTSPFPTQCLLQA* | 11029 | ATGCGGGCGGAGACAGCGTCTTCCTGGTTCGCTATCGGCGGAGCCCTGGGGGAAAGCCAGCGTGCATGGGGCGGATGGCGGCGCCCTGGGTCCCCTGGGGTGCCGGCCCCCGGTGCCAGGCACTGGCTGGAATGGGCCCTGAGCCCGGAGCCCCACTGGCTGGACACGCGCGTGACAGGGAGTCCCAGGCACTGGCTGGGTGCTCTGGTGTGTCCCGGGCGCGGGAAGCAAGCAACCACCAAAATGCTCACGACGAGGCGTGCGGGCGCCGTCGCTGGGACAAGCAGCGCCATTTCCCACCAATGCCTGTTGCAAGCATAA | 11030 |
| | 4 | MGAEGLSGGAWVPLRCAAPVRAPRCRGKGRRGGVPGTG* | 11031 | ATGGGGGCGGAAGGACTGTCTGGCGGCGCCTGGGTCCCCGAGGCGCGGGGTGCGCGCTCCACGATGCAGGGGGAAGGGAAGGCGAGTCGAGTCCCAGGCACTGGCTGA | 11032 |
| hsa-mir-423 | 1 | MAIPGRQ* | 11033 | ATGGCGATTCCGGGCAGGCAGTGA | 11034 |
| | 2 | MRNYGDCIFGRGVLNALEVKGLCRQG* | 11035 | ATGAGAAACTACGGCGACTGTATCTTTGGCCGAGGAGTTTAAATGCGCTGGAAGTGAAGGGACTGTGTCGTCAAGGGTAG | 11036 |
| | 3 | MRWK* | 11037 | ATGCGCTGGAAGTGA | 11038 |
| | 4 | MFARSLREKLVRK* | 11039 | ATGGAAGCCGAAATCTGACATTTGAGCGAGAAACTTGTGAGGAAATAA | 11040 |
| hsa-mir-424 | 1 | MGANLTFKVFNK* | 11041 | ATGGGCGCAAATCTGACATTTAAAGTGTTTAACAAATGA | 11042 |
| | 2 | MSAAGKFSGNGLGKKKQQLTWRGGERKLSKGQ* | 11043 | ATGAGTGCGGCCGGGAAATTCTCAGGAAACGGACTGGGAAAAAAAAAACAACACTAACATGAGGGGTGGGGAGAGAAAAACTGAGTAA | 11044 |
| | 3 | MEGRGEKTE* | 11045 | ATGGAGGGGCGGGGAGAGAAAACTGAGTAA | 11046 |
| | 4 | MNFSSYLQEVSYVLERNV* | 11047 | ATGAACTTTTCCTCTTATTTGCAAGAAGTTAGTTATGTCTTGGAAAGAAATGTGTGA | 11048 |
| hsa-mir-425 | 1 | MGGF* | 11049 | ATCGGCGGGTTCTGA | 11050 |
| | 2 | MWPQGE* | 11051 | ATGTGGCCCCAGGGCGAGTGA | 11052 |
| | 3 | MGLP* | 11053 | ATGGGGTGCCCCTGA | 11054 |
| | 4 | MGVDVGEPRLVAISGTLGRIGEGGWTQDLWVGLQW* | 11055 | ATGGGGTGTAGACGTGGGAGAGGCCAGGCTGGTGGCCATCTGGGGGAGGGTGGGGTTCAGGGAGGTGACCCTCTGGGAGGATTGGGTAGGGCTGCAATGGTAG | 11056 |

Figure 1 (Continued)

| | | | | | |
|---|---|---|---|---|---|
| hsa-mir-429 | 1 | MTMSYPAGGPGRNLWQPPVPGDSDTKCSHCAGPGYE WPHTDQLTPAGRATGPPPWRREASGATRCAPGPLTSL VGGGCRPGPPET* | 11057 | ATGACAAATGTCTACCCAGCAGGAGGACCAGGCCGGAACCTTTGGCAGCCACCAGT TCCTGGAGATTCCGACACCAAGTGCAGCCACTGTGCGGCGCCGGTGTGGAGTGGC CCCACACCGACCAGCTCACGCCAGCTGGCAGAGCCACTGGCGCCCCTCCGTGGAGG AGGAGAGAGGCCTCCGGCGCCACGGCTGTGCCCAGGGCCACTCCTTGGT AGGTGGGGATGCCGGCCTGGGCTCCGAGACTTGA | 11058 |
| | 2 | MPAWASRDLSPAPALAPRETCASERPRPPLPEPCTRAVR GPCCTPERASALSHSVSNPPPSSGPQNWPSTELRGTRGP WGLGRDWPARGPPAAIPRFHQDESRAVGTT* | 11059 | ATGCCGGCCTGGCCTCCGGGACTTGAGCCTGCCCTGCCCTTGCCCCCAGAGAG ACCTGTGCCAGCGAGACTTGCGCTTCCCGTGAGCCTGCACCGGCGGTG CGGGGCCCTGCTGCACCCCAGAGCGGGCATCAGCCCTGCAGCCACTCCGTTAGCAAT CCTCCCCCAGCTCAGGGCCTCAGAACTGACCATCCACGGAGCTCAGAGGGCACCCGA GGGCCCTGGGACCTGGGTAGGGACTGGCCAGCTGGGGGTCCTCCAGCAGCCATACC CAGGTTCATCCAGGATGAAAGCAGGGCAGTGGAACCACGTGA | 11060 |
| | 3 | MKAGQWEPRIDWFKSR* | 11061 | ATGAAAGCAGGACAGTGGGAACCACGTGATTGGTTTAAAGCAGGTGA | 11062 |
| | 4 | MVAHACNPGTFGGQGRRITRGQEFETSLANTAKPLSLL KIQKLAGHGSAHL* | 11063 | ATGGTGGCTCATGCTGTAATCTGGCACTTTTGGAGGCAAGGCAGGCGGATCACC GAGGTTCAGGAGTTTGAGACTAGCCTGGCCAACACTGGCAAAACCCCGTGTCTCTACTA AAATACAAAATTAGCTGGGCATGGTAGTGCACCTGTAG | 11064 |
| hsa-mir-449a | 1 | MVLGDGIPGY* | 11065 | ATGGTCCTGGGGGACGGGGACTCCAGGGGTTTGA | 11066 |
| | 2 | MEWKLERTAPRRVRTEEEMLWVSNTLFCILPNSLMRGR RPRS* | 11067 | ATGGAGTGGAAATTGGAGCGCAACTGCCGCCGGAGGGTCCGCACGGAAGAGGAGAT GCTGTGGGTGAGTAACACCCTTTTCTCCCTAACTCTCCTAATGTTATCTGTTTTCATGA AGGCCCCGTTCATAA | 11068 |
| | 3 | MIFLNSFSLNMLSVFSKESIMRVLSKDLKQKRSQDSANV SPGLVLVLCFNSDLEQTNSW* | 11069 | ATGATTTTCCTAAATAGTTCTCCTCAATATGTTATCTGTTTCAAAGGAAAGTA TCATGCGTGTCCTCCAAAGACTTGAAGCAGAAGAAGTTCCGCCAAC GTGAGTCCAGGCTTGTTCTTGTTCTCTGTTTTAATTCTGATCTGAACAAACGAATT CTTGGTAA | 11070 |
| | 4 | MRILVSYYILKKISL* | 11071 | ATGAGAATTTTAGTATCTTATTACATACTAAAAAAATTTCTTTATGA | 11072 |
| hsa-mir-449b | 1 | MVLGDGIPGY* | 11073 | ATGGTCCTGGGGACGGGACTCCAGGGGTTTGA | 11074 |
| | 2 | MEWKLERTAPRRVRTEEEMLWVSNTLFCILPNSLMRGR RPRS* | 11075 | ATGGAGTGGAAACTGGAGCGCACCGCCTCCGGAGGGTCCGCACGGAAGAGGAGAT GCTGTGGGTGAGTAACACCCTTTTCTGCATTCTCCTAACTCTCCTAATGCCGGGGCCG AAGGCCCCGTTCATAA | 11076 |
| | 3 | MIFLNSFSLNMLSVFSKESIMRVLSKDLKQKRSQDSANV SPGLVLVLCFNSDLEQTNSW* | 11077 | ATGATTTTCCTAAATAGTTCTCCTCAATATGTTATCTGTTTCAAAGGAAAGTA TCATGCGTGTCCTCCAAAGACTTGAAGCAGAAGAAGTTCCGCCAAC GTGAGTCCAGGCTTGTTCTTGTTCTCTGTTTTAATTCTGATCTGAACAAACGAATT CTTGGTAA | 11078 |
| | 4 | MRILVSYYILKKISL* | 11079 | ATGAGAATTTTAGTATCTTATTACATACTAAAAAAATTTCTTTATGA | 11080 |
| hsa-mir-450a-1 | 1 | MGANLTFKVFNK* | 11081 | ATGGGGCAAATCTGACATTTAAAGTTTTAACAAATGA | 11082 |
| | 2 | MSAAGKFSGNGLGKKKQQLTWRGGERKLSKGQ* | 11083 | ATGAGTGCGCCGGAAGTCTCAGGAAACGGACTGGGAACTGAGTAAGGGGCAGTGA | 11084 |
| | 3 | MEGRGEKTE* | 11085 | ATGGAGCGGGCGGGAGAAAACTGAGTAA | 11086 |
| | 4 | MNFSSYLQEVSYVLERNV* | 11087 | ATGAACTTTTCCTCTTATTGCAAGAAGTTAGTATGTCTTGAAAGAAATGTGA | 11088 |
| hsa-mir-450a-2 | 1 | MGANLTFKVFNK* | 11089 | ATGGGGCAAATCTGACATTTAAAGTTTTAACAAATGA | 11090 |
| | 2 | MSAAGKFSGNGLGKKKQQLTWRGGERKLSKGQ* | 11091 | AACATGGAGTGCGGCGGGGAGAAAACTGAGTAAGGGGCAGTGA | 11092 |
| | 3 | MEGRGEKTE* | 11093 | ATGGAGCGGGCGGGAGAAAACTGAGTAA | 11094 |
| | 4 | MNFSSYLQEVSYVLERNV* | 11095 | ATGAACTTTTCCTCTTATTGCAAGAAGTTAGTATGTCTTGAAAGAAATGTGA | 11096 |
| hsa-mir-450b | 1 | MLGTPGAGPRGPAASSGSVPSR* | 11097 | ATGCTGGGAACCCTGGGGCGGGGCCCTGCCAGCCTGGTCAGGGCTC AGTCCCTCCGATAA | 11098 |

Figure 1 (Continued)

| | | | | |
|---|---|---|---|---|
| hsa-mir-484 | 2 | MKNPVPSAFFFSSLGSRHVMVLLYP* | 11099 | ATGAAAAACCCTGTCCCTTCGGCTTTTTTTTCCTCTCTCGGGTCTCGTCACGTGATGGTCCTACTTTATTTTAA | 11100 |
| | 3 | MAHPQHPKSSAT* | 11101 | ATGGCGCATATTCCCAGATTCCTAAATCTAGTGCAACCTAG | 11102 |
| | 4 | MNTAPPVTGWASRKEJLRLVSNTLCPRWPDMLCGLL* | 11103 | ATGAATACTGCGTTTCCAGTTGACAGTTGGGCGAGATATGCGAAGGAGAAATCTTACGGTTAGTTTCAAACACTTTGTGTTTTAGTTGCGGCCAGATATGCTGTGTGGTTGCTTAA | 11104 |
| hsa-mir-497 | 1 | MRIRLGALPLASGWSH* | 11105 | ATGAGAATTAGACTAGGCGCTCTCCCTTGTGGGTCTCTTTATTATGGGTGTTATTTGA | 11106 |
| | 2 | MEYYLISCGVSVYGVLI* | 11107 | ATGGAGTATTATTTGATCAGTTGTGGGTCTCTTGTTTATTATGGGTGTTGATTTGA | 11108 |
| | 3 | MVSFRYGADLFVTLVLGVLTPTIWRLCSPVSSWTHSRTKVLMLIWGCSLFWGAI* | 11109 | ATGGTAAGTTTCAGGTATGGGGCTGACTTGGAAGTTACATTAGTTCTGGGGGTTCTGACACCCACAATTTGGAGATTGTGCTCACCTGTGTCATCTTGGACTATCAGCAGAACCAAAGTACTCATGCTGATTGGGGGTGCAGTCTATTTGGGGTGCCATCTAA | 11110 |
| | 4 | MGLTWKLH* | 11111 | ATGGGGCTGACTTGGAAGTTACATTGA | 11112 |
| hsa-mir-503 | 1 | MGANLTFKVFNK* | 11113 | ATGGGGGCAAATCTGACATTTAAAGTGTTTAACAATGA | 11114 |
| | 2 | MSAAGKPSGNGLGKKKQQLTWRGGERKLSKGQ* | 11115 | ATGAGTGCGGCCGGAAAATTCTCAGGAAACGGACTGGGAAAAAAAACAACAACTAACATGGAGGCGGGGGACGAGAAAACTGAGTAAGGGCAGTGA | 11116 |
| | 3 | MEGRGEKTE* | 11117 | ATGGAGGGGCGGGAGAAAACTGAGTAA | 11118 |
| | 4 | MNFSSYLQEVSYVLERNV* | 11119 | ATGAACTTTTCCTCTTATTGCAAGAAGTTAGTTATGTCTTGGAAAGAAATGTGTGA | 11120 |
| hsa-mir-505 | 1 | MFRRSLNRFVSTLAAAPRVPVCLLASPFAGSLTTTF* | 11121 | ATGTTCCGCCGGAGCTTGAATCGTTTGTAAGTACACTGCTGCCTCCGCGTGCCGGTTTGCTTGCTCGCCAGGCCCTTCGCCAGGGCCCCTTCACAACAATTTTCTGA | 11122 |
| | 2 | MAFYSQGCFLLFPLPRAHGGKPRPVTVAQKKSWGLREPETRARLSLA* | 11123 | ATGGCGTTTTATTCTCAGGAGGTTGCTTTCTTGTTTCCTCTGCCACGAGCACATGGAGGTAAACCTAGACCTGTCACGGTGGCCAAAAAGAGAGCTGGGGGCTGAGGGAGCCGGAGACTAGGGCAAGACTCAGCCTTGCCTAG | 11124 |
| | 3 | MEVNLDLSRWPKRRAGG* | 11125 | ATGGAGGTAAACCTAGACCTGTCACGGTGGCCAAAGAAGAGCTGGGGCTGA | 11126 |
| | 4 | MCSREEAAPPLPVLPISGLKPRGGLSTPDLEPMGEGGL* | 11127 | ATGTGCAGCCGCGAGGAGACTGAGGCGCTGCCTCCCGTGCTGCCGATCTCTGGTCTGAAGCCTCGCGGAGGACTGAGCACCCAGACCTTGAACCTGAACCATGGAGAAGGCGGACTGTGA | 11128 |
| hsa-mir-542 | 1 | MGANLTFKVFNK* | 11129 | ATGGGGGCAAATCTGACATTTAAAGTGTTTAACAATGA | 11130 |
| | 2 | MSAAGKPSGNGLGKKKQQLTWRGGERKLSKGQ* | 11131 | ATGAGTGCGGCCGGAAAACCCTCAGGAAACGGACTGGGAAAAAAAACAACAACTAACATGGAGGGCGGGGACGAGAAAACTGAGTAAGGGCAGTGA | 11132 |
| | 3 | MEGRGEKTE* | 11133 | ATGGAGGGGCGGGAGAAAACTGAGTAA | 11134 |
| | 4 | MNFSSYLQEVSYVLERNV* | 11135 | ATGAACTTTTCCTCTTATTGCAAGAAGTTAGTTATGTCTTGGAAAGAAATGTGTGA | 11136 |
| hsa-mir-545 | 1 | MVGENGKEEAARMRISDGVPGRGGAQHSGN* | 11137 | ATGGTTGGGGAGAACGGTAAGGAGGAAGCGCTCAGACATTCGGGTAATTAA | 11138 |
| | 2 | MARGEVSCLCLAILG* | 11139 | ATGGCGCGAGGGGAGGTAAGTGTCTTGCTTGGCCATCTGGGCTAG | 11140 |
| | 3 | MLWFDPLEJNPES* | 11141 | ATGCTGTGGCCCAGATCCACTAGAAATTAACCCAGAATCTTAG | 11142 |
| | 4 | MRRR* | 11143 | ATGAGGAGGCGATGA | 11144 |
| | 1 | MSLDWACLSSWGRATSWGPAHTRJHVERVCKSTPVLLTEGDYSTVFLGILFFFTSGLTLAARGSPPGLGCWIPATRGKHWRHDPGSTSRGARTGRGAAGLAAAAARGWAGLGCGEMTSPSPRAPW* | 11145 | ATGTCTCTGGATTGGGCTTGCCTCTCTTCTTGGGGAAGAGCCACTTCTTGGGCCCTGCACACGACGAGCGCATGTGGAAGGTCGTAAATGACCACCGTTCCTAACCGAAGGTGATTACAGACACCGTCTCTTGGGGGATACTTTTTTTTACGTCAGGCCTCACGCTCCGCTGCACGGGATCGCCGCAGGGCTGGACTTGCCCACACGGGGGAAGCACTGGCGGCACGATCCGAGATCCGGAGGCGCCCGCCACTGCCGCGGGGCTGCGGACTGCGCCGGCGGCGGCGGGGCTGGGGGGCTTGGCTGCGGGGAAATGACGCCCGCGCGGTGCCCCTGGTAA | 11146 |
| | 2 | MWKGSVNRHPFC* | 11147 | ATGTGGAAAGGGTCTGTAAATCGACACCGTTCGTCTAA | 11148 |

Figure 1 (Continued)

| | | | | |
|---|---|---|---|---|
| hsa-mir-548b | 3 | MSPPIPAAARPVSSSLRSLAESSVRAASGTRGAALSSTPP PGAGRGASKSWPGPRPPPNPGHLPRAVVPAASGRRDR PVPSRGIDPGVAGGTAPAAESGGRRVSGREAAAATLASR ASLLHGPASTRGDRCPGWGLLGRWRPRA* | 11149 | ATGTCCCCGCCTATCCCCGCGCAGCCGCCGCCCGTCTCTCCTCCGCAGCTTCG CCGAGTCCTCGGTTGCGGGGCTGCGAGCGGGAACCCGGAGCTGCGCTGTCCTGACG CCTCCGCAGGCGCGGCCAACGCCTCCAAGAGCTGGCCTCGGCGCCGGCC GCGGCCAACCCGGCATCCGCCCCTTCCCCCGCGTTGTCCCCGCGCTTCGGCCGAGG GGACCGGCCCCTCTCCTTCCAGGGGTGACCCGGGGTGAGCCCGGGGTAGGGGG CGGCCGAGTCTGGGGCGCGCCTCGGGGCGTCGTCCACGGCCTCGCCGGACTCTT GCCTCCGGGCGTCGTTGGGAAGATGGCGACCCGGACATGA | 11150 |
| hsa-mir-548c | 4 | MATPGMSWQQHYYGGSAAKEAPSPATAQLAGHSMDY SQEMHLKMSKKIAQLTKVRGAATGQVATPCGPRRTHL SPREAVRPAPAARGTLLRRSNSRRHLQNPANFGGTLA T* | 11151 | ATGGCGACCCCGGCATGAGCTGGCAGCAGCACTATTACGGCGGCTCGGCGGCAA ATTCGGCGCCTGCGCGCCACGCACAGCTGCTGGCACAGCTGAAATCGCCCAGCTCACCAAGTAAGGGG AGGAGATGCACCTGAAAATGAGCAAGAAAATGCCCAGCTCACCAAGTAAGGGGG GCAGGCAGGGGCAGGTGCGACCCGTGCGGGCCGTGCGGGCGACTCACCTGTCTC CGGGAGGCAGTGCGCGTCAGCGAGGGAACTCTACTCCTCCGCGAA GCAACAGCCGGAGACACCTGCAAACCTTGGTGGAACGCTGGCAACA TGA | 11152 |
| | 1 | MVKRQ* | 11153 | ATGGTGAAAGACAGTAG | 11154 |
| | 2 | MINACKGASLLYDKSWLI* | 11155 | ATGATAAATGCATGCAAAGGAGCTTCTCTATGACAAGTCTTGGCTAACTTAG | 11156 |
| | 3 | MHAKELFYMFSLG* | 11157 | ATGCATGCAAAGGAGCTTCTCTATATGACAAGTCTTGGCTAA | 11158 |
| | 4 | MQRSFSSI* | 11159 | ATGCAAAGGAGCTTCTCTCTATATGA | 11160 |
| hsa-mir-550-1 | 1 | MPGGTDPSPRTRARSSRGCTWAVAAGYFYPSPFLLLPG RRGLPPGPARVGLHPGRNPALNTGGAATA* | 11161 | ATGTTTGGAGGTACGGACCCCTCGCGACACCCGTCGCGCTCGGTCTCCCGGCTGC ACGTGGGCCGTGCCGCGGCGCCGGCTATTTTTACCCTTCTCCTTCTCCTCCGGGCG GCCGGGGGCTGCCTCCCCGGACCCAGCCCGCGGGTGCTGCCCATCCTGGAAGAAACCCG GCGCTTAACACCGGCGGTGCCGCTACCGCATAG | 11162 |
| hsa-mir-550-2 | 2 | MTGANVVLQQTDETALVLVVVFSTRKSGGDQLLNVVLS GDSSGEQFLKAKSQSVSNEH* | 11163 | ATGACTGGAGCAAATGTTGTTTTACAACAACCGACGAAACAGCCCTTGTGGTTGTG GTTTTTAGTACCAGGAAGTCAGGAAGTCAAGGAGAGACCAGTTGCTAAATGTAGTTCTATCTGGG GACTCGAGTGGGGAACAGTTTTAAAGGCCAAAAGTCAAAGTGTCTCAAATGAACA CTGA | 11164 |
| | 3 | MLFYNKPTKQPLWLWFLVPGSQEETSC* | 11165 | ATGTTGTTTTTACAACAACCGACGAAACAGCCCTTGTGGTTGTTGGTTTTTAGTACCA GGAAGTCAGGAGGAGACCAGTTGCTAA | 11166 |
| | 4 | MNTELPCLDRLLV* | 11167 | ATGAACACTGAGTTACCATGTTTGGACCGACTTTTAGTATAA | 11168 |
| | 1 | MAAVTAAAGEEAVGRPGAPSATAESGSPSWRTETSGS RTAT* | 11169 | ATGGCGGCCGTAACAGCGGCGGCCGCCGCCGGAGAGGAGGCCGTGGGAGGCCCGGAGCGC CAAGCGCGACGGCAGAAGCGGCCAGCAGCGGCCCGTCATGGCACCGAAACCAGCGGC AGTCGCACGGCCACCTGA | 11170 |
| | 2 | MAHRNQRQSHGHLSRPFLLEPARGACSRDTFLSASPRLP RPRQAASLAHRPEKSAPGADCPSGRRAAALDVRGPLWA GRGASALPSSSRVRSYPLGSRGTARGPVRSKADRSARQS GLAAANGARARTRLGSTFQ* | 11171 | ATGGCCCACCGAAACCAGCGGCACAGTGCACGGCCACTGAGTCTGCCCTTCCTGCTG GAGCCAGCCGAGGGGTGCCTGCAGCCGGACACCTTCCTGTCCGCCTCGCCGCTGCCGG CGCCGACTGCCCGTCAGCGCCCAGCTTGCCCACCGCCCGGGAGAAGAGCGCCGCGG CGGCCGACTGCCCATCTGGGCGGCGTGCCCTGGCCTGCCTTCTAGCTCCGCCTCTACCCTC TTGGCTCTCCGGGCACAGCGGCTTGTTCGCCCTAACGCGCAAGGCGGACAGGAGCGCC AGGCAGAGGCGGCCTGGCCGCCGCTAACCGGCACGCGCGCGCGCTACTCGGCTCGGATC TACCTTCCAGTAG | 11172 |

Figure 1 (Continued)

| | | | | |
|---|---|---|---|---|
| | 3 | MGPGPGLGAGGPPPRGGSRLLRCPALTSPAPRAAPKWPR QPRAAVSWGAWRRGPARRSPPSASRTAAVRRTRRTR CTAALRMAAAAASTGRWAGAPAGRAW* | 11173 | ATGGGACCGGGACTCAGGGCTGAGGGCCTGAGGGCCGGGGGCCGGGGGCCGCCGCCGGCGGCGGAGGTTCCC GGCTCAGGTGCCTGCCCCGCGGAGCTGCCTCACCAGCGCCTCGGGCGGCCGCGGCCCCGCGGCG CGGCAGGCCCGCGGCCAAGCTGTTTCCTGGGCGGTCGCTGCCGGGGCCCCGCCGGCG CAGTCCTCCTTCAGCATCCGAACAGCAGCAGCAGGGTCCGCAGGAGGTCGCAGGACTCG GTGCACAGCAGCCCTGAGGATGCCGGCGGCGGCGGCGCAGCACCGGCCGGTGGGCGG GAGCCCCGGCGGGGCCGGGCCGGCTGGTGA | 11174 |
| | 4 | MFGGTDPSPRARARFSRGCTWAVAAGYFYRSPFLLPPG RRGLLPGPARQGLLPGPARAGLHPGKKPGT* | 11175 | ATGTTTGGAGGTACGGACCCCTCTCCACGCGCCGCCTCGGTTCTCCCGGCTGC ACGTGGGGCGTGCGCCGCGCTATTTTACGTTCCTTTCTCCTTCCGCCGGGGC GCCGGGGCTGCTTCCGGCGCCACCCGCCAGGGCGTGCTTCCCGGCCCAGCCGC GCCGGTCTCCATCCTGGGAAGAAACCCGGCACGTAA | 11176 |
| | 1 | MNQGF* | 11177 | ATGAACCAAGGTTTCTGA | 11178 |
| hsa-mir-553 | 2 | MAGPRVEVDGSIMEGVSTERSGRGCSLTKEGSSHHRCA YFSSPCTPFAGRPDPESLYGLELSPRPPLAGAEDPSRPE HARPEVNLAGGGVGP* | 11179 | ATGGCCGGGCCCCGGGTGGAGGTCGATGGCAGCATCATGGAAGGGGTGAGTACAG GCGAAGCGGCCGGGCTGCAGCCTAACTAAGGAGGGGAGCTCTCACCACCGGTGT GCTTACTTCCTCCTTCCGTACCCAACCTTTGCAGGGCGCAGATCCTGAGAGT CTCTACAGCGCCTGAGCTGTCTCCTAGCCTCCCCTGGGGTGCAGAAGATCCGAGC CGGCCCGGAGCACGTCCAGGCCTGAGGTAAATCTGCTGGAGGGGAGTTGGGCCGTG A | 11180 |
| | 3 | MAASWKG* | 11181 | ATGGCAGCATCATGAAGGGGTGA | 11182 |
| | 4 | MGDPGRGTLPGRWPGH* | 11183 | ATGGGCGATCCAGGCCGTGGCACTTCTGCCTGGCGGTGCCTGGGTTGTAA | 11184 |
| hsa-mir-554 | 1 | MNGTRNWCTLVDVHPEDQAAVRKSALAVFSVLYSRFL SPPLPCPAPCWLTSPGARLARSALRGASLFLFFCLRRAV GVAG* | 11185 | ATGAACGGACACGGAACTGGTGTACCCTGTGGACGTGCACCTGAGGACCAAGC CGGTAAGAACAAAAGCGCTCTCAGCTGTCTTCTCCGTTTTGTATTCCGGTTCTAAG TCCGCCCCCCCGTGCCGCGCCGGTTGCGCTGACATCACCTGGTCGCCGGCTCGC GCGGTCAGCCTGCGCGGCACGGAATCTTTTATTCTTTGCCTGCGACGGGCAGTG GGAGTCGCGGGGTGA | 11186 |
| | 2 | MSSSIDWVPERLWTLCPAEEA* | 11187 | ATGAGCTCAAGCGACTTGGGTCCCTTGAGCCGTTGTCCTGAGGAG GCTTAG | 11188 |
| | 3 | MVLWMISNKKNGRVNYRAWTGRGCIASRGR* | 11189 | ATGGTGCTTTGGATGATCAGTAACAAGAAAAATGTAGAGTAAATTACAGGGCTTG GACTGGAGGGCGGGGGCAAGTAGGGCAAGTGGAACGGTAG | 11190 |
| | 4 | MQMPGREGEGSDPSEGFWTGRGLRRKGAPSSAGWSTP LSSFSGSQSQF5PP* | 11191 | ATGCAGAACCCGTGCCATGGCCGAGAAGGGGAGGAAGGGAAGTGACCAAGCAAGCGAAGCCTTCTGGA CGGGAGAGGGTTCCATGGATCCTCAGTGCAGGCTGGTCTACCCCCT CTCTCCTCTTTCTGCCTCCCAGTGCTCCCAGTTCCTCTCCCACCCTAG | 11192 |
| | 1 | MWAWGWGGAKLRGRAADTLKLRAGRAQRKGRRPHG YPSAARVK* | 11193 | ATGTGGGCATGGGGTGGGAGGGCTGGAAGGCGAAGCTCCGAGGCCGGGCGCGGATACTTT AAACTCAGAGCTGGAGGGGCCCAAAGGAAGGGGGGCGTCCACATGGTTACCCTT CTGCTGCGCGGGTCAAGTAG | 11194 |
| hsa-mir-561 | 2 | MGVGRREAPRPGRGYFKAQSWEGFKEGAASTWLPFCC AGQVASSGGRKARRG* | 11195 | ATGGGGGTGGGAGGCGGAAGCTCGAGGCCCGCGATACTTTAAAGCTCA GAGCTGGAGGGGCCCAAAGGAAGGGGCGGTCACATGGTTACCTTCTGCTGCG AGGGTCAAGTAGCTTCTTCTGGAGGGCGCAAGGCGGGGGGTGA | 11196 |
| | 3 | MVTLLLRGSSSFPWRAQGAAGVAASPWVLAPTAKPAWP GPPSRGLTRHTDQNPEQAVLSLRLLRLPR* | 11197 | ATGGTTACCCTTCTGCTGCGCGGGAGTAGTTCTTCTGGAGGGCGCAAGGCGG GCGGGGGTGATGAGCCTTGGCCTCACTGCGGCTGCTAATTCGCTTGGCCGGGT CCACCTTCTGTGGCCTCACTCGCCACACGAATCCGGAGCAGGCAGTTCTC TCTATTCTGAGGCTTCTGCGGCTGCGCGCTGA | 11198 |
| | 4 | MCLRC* | 11199 | ATGTGTTTACGATGTTGA | 11200 |
| hsa-mir-563 | 1 | MGEPDLHVEKA* | 11201 | ATGGGCGACCGGACTTGCACGTGGAGAAGCGTGA | 11202 |
| | 2 | MCPWVWGGWGAKEWDERWSRNGHRCCPPRGLQAET G* | 11203 | ATGTGCCCCTGGGTTTGGGGAGGTGGGGAGCCAAGGAGTGGGATGGGATGAGAGGTGGTC ACGGAATGGGGGGCTGCAGGGGCTGCAGGCCGAGACCGGGTGA | 11204 |

Figure 1 (Continued)

| | | | | | |
|---|---|---|---|---|---|
| hsa-mir-568 | 3 | MRGGHGMGGAAVLPGGCRPRPGEGRG* | 11205 | ATGAGAGGTGGTCACGGAATGGGCGGGGCGGCTGCTGTCCTCCCGGGGCTGCAGGCCGAGACCCGGGTGAGGGCGCGGGGTGA | 11206 |
| | 4 | MLALWTEGRRLRSRTGCGRPIYFLPVVPIRS* | 11207 | ATGCTGGCACTCTGGACGGAAGGGCGTCGTCTTCCCAGCGAACCGGTTGTGGACGCCCAATCGTTTTCTGCCCGTAGTCCAATCCGAAGCTAA | 11208 |
| | 1 | MPPTRRVGVRRRAP* | 11209 | ATGCCGCTGACCGCGGTGGTTGGAGTGCGACGAAGAGGCGTGA | 11210 |
| | 2 | MDRWYPEARSNCIRVISYHGEGFSKSGPVAQWITRLTIDQKILGSTPGWLAMSVLPHLTHVLGLVKMYIHNVKVLQDLGKVYG* | 11211 | ATGGATCGTTGGTACCCGGAAGCCCGTTCAAACTGTATAAGGGTGATCAGTATCACGGATCAGAAGATTCTAGTTCGACTCTAGTTCACGGCGCAATGGATAACGCGTCTGACTACCTGACCAGTAGTGTCTGGCTGGCTGTCTTTGCCACACTTGACCCATGTACTACTGGGTCTTACTGGGCTCTCACAAGACCTTGAAAGGGTATGTTAG | 11212 |
| hsa-mir-571 | 3 | MDNASDYGSEDSRFDSWLARDVCFATILDPCTTGSCKDVYSQCESITRPWKGVWLECES* | 11213 | ATGGATAACGCGTCTGACTACGGATCAGAAGATTCTAGTTCGACTCCTGGCTCGCGATGTCTGTTTTGCCACACTTGGCTGAAAGTGTTGTACCACCATTGAAAGGTCTTGGATGGGTAAAAGCGGTCTTGGATGGGTCTGTGATCACAATGTGAAAGCTGTAAATAGTTAA | 11214 |
| | 4 | MYYWVL* | 11215 | ATGTACTACTGGGTCTTGTAA | 11216 |
| | 1 | MVSVRGRASQG* | 11217 | ATGGTGAGTGTGCGGGGCAGGGCGTCCAAGGCTGA | 11218 |
| hsa-mir-572 | 2 | MAAGPSLRTESPLPPLSPGASVPSGEPGLLSVPAQRLWPSLQPSLCSSAPAAPHLPQAVG* | 11219 | ATGGCGGCGGGACCGAGTCTCCGAACGGAGTCCCGCCTCCCGGCTCAGCCCTGGGGCCTCAGTACCCTCCGGTGAGGGACCTGGGCTCGTGGCTCGTGCAGCTCGGCACGACAGCGCTTGGCCCAGCTGACCCCTCTGTGCGCCCCTCTGTGCGCCAGCCGCCCGCACCCTCCCAGGCTGTGGGGTGA | 11220 |
| | 3 | MPAWEELWEKLWSGDPVPALPCSE* | 11221 | ATGCCGGCTGGGAGGAGCTGTGGGAGAAGCTGTGGTCGGGGATCCCGTCCCTGCTTTACCCTGTTCGGAATGA | 11222 |
| | 4 | MRSRPHQNRVHVSKWGLNGTAPAVARGLGAASGS* | 11223 | ATGAGATCGAGGCCCCATCAAAACAGAGTTCATGTGAGCAAATGGGACTCATTAATGGGACAGCGCCGGCGTGCCGGGCTGTCTGCATGCGGGCTGCCAGCGGGTCTTGA | 11224 |
| | 1 | MRWKVG* | 11225 | ATGCGGTGGAAGGTCGGCTGA | 11226 |
| | 2 | MDRARWPSSV* | 11227 | ATGGACCGAGCACGGTGGCCGAGCTCAGTTGA | 11228 |
| hsa-mir-573 | 3 | MGYPRGADTGRLRLLEEKRGVGFLS* | 11229 | ATGGGTTACCCCAGAGGGGCGGATACGGGAAGATTAAGGTTGTGGAGGAGAAACGTGGAGTAGGCTTTGTCTTGA | 11230 |
| | 4 | MNCA* | 11231 | ATGAACTGTGCTGA | 11232 |
| hsa-mir-574 | 1 | MHTPTRPHSGSAPSACVNLRGACLDLPKYPVLAPSKSGKVPPMARGQVRGGLQGPFARARREQVPVRQRPRPRVRLPSALAQGAQALTSPLPSPYSSPNSRPTPCLLFQSSQHSKQAPPLAAPGMGPTPYRRSPGPLHPVG* | 11233 | ATGCACACACCACACGCCACACTCAGGTTCTGCCCCTGGCCTGCGTGAACCTCGCGGGAGCTGCCCCAATGGCTGCGGATCTCCAAAGTACCCAAGTCTGGCACCAAGCAAGTCTGGAAAAGTGCCCCAATGGCTGCCGGGCAGTGGGCTGCAGGGTCCCCAGCCCGGGGCACGAAGGGAGCCAGGTCCCTGTAAGACAGAGCCTCGTCCAGGCTGCCCTGCCCTCGGCTTGGCAGGGAGCCAGGCTCAGGTCACCTGGCCTTCGCCTCCGTCCAGCCGGCCCGGCCCCACCTGCCTCCAGTCAGTCAGCCCGGGATGGGTCCACTCCAGTCCTACCGCACTAAGCAGGCACCGCCCCCTCCACTGCCTCCAGTCCTACCGCAGATCCCCAGGCCCCCCTCCACCAGTCGGCTAG | 11234 |
| | 2 | MGCESITYALLIPSFPILNILKDTGRWLLKSVCSELPVTSANL* | 11235 | ATGGGCTGTGAGAGCATTACCTATGCCCTACTGATCCCATCATTTCCATCTAAACATCTTGAAGGACACAGGCAGGTGCTTCTTAAATCAGTGTGCTCTGAACTCCCTGTGACCTCAGCCAACCTGTGA | 11236 |
| | 3 | MRQALSSEPLFALSAA* | 11237 | ATGAGACAGGCTCTATCCTCCGAGCCTCTTTTTGCCCTCTCTGCAGCCTAG | 11238 |
| | 4 | MDLRHK* | 11239 | ATGGATTTGAGGCACAAGTGA | 11240 |

Figure 1 (Continued)

| | | | | |
|---|---|---|---|---|
| hsa-mir-578 | 1 | MAGRGGSALLALCGALAACGWLLGAEAQEPGAPAAG MRRRRRLQQEDGISFEYHRYPELREALVSVWLQCTAIS RIYTVGRSFEGRELLVIELSDNPGVHEPGKGAAP* | 11241 | ATGGCCGGGCAGGGGGCAGGCGCTGCTGGCTCTGTGCGGGGACACTGCTGCCTG CGGGTGGCTCCTGGCGCTGCAAGCGCTGCAAGGAGGCCCCGGGCGCTCAGCAGCCATGA GGCGGCGCCGGCGGCTGCAGCAAGAGGACGGCATCTTCTTGAGTACCACCGCTAC CCCGAGCTGCGCGAGGGCGCTCTGGTGTCCGTGTGGCTGCAGTGCACCGCCATCAGCAG GATTTACACGGTGGGGCGCAGGTTCGAGGGCCGGGAGCTCCTGGTCATCGAGCTGT CCGACAACCCTGGCGTCCATGAGCCTGGTAAGGGCGCTGCCCCTGA | 11242 |
| | 2 | MSLVRALPPDSPGGPEGGGRGWDWWRWGKEGGMGP GVPLGKRYLRWKVGSGGRDGNGEEPDLERQWPNFCFP VPSPQHQSHLPRP* | 11243 | ATGAGCCTGGTAAGGGCGCTGCCGCCTGACAGCCCTGGGGGCATCCGGAGGGGG CGGCAGAGGGTGGACTGGTGGCGTTGGGGAAGGAGGGAGGGATGGCCCAGGG GTGCCTCTTGGTAAAAGGTATCTAAGGTGAAGGTGGAAGTGGAGGAGGGATGG AAATGGGAAGAACCCGACTTAGAGCGCCAGTGGCCCCAATTTCTGCTTCCCGTCCC ATCCCCCAGCACCAATCCCATCCCCAGAACCTTAG | 11244 |
| | 3 | MEMGKNFT* | 11245 | ATGGAAATGGGGAAGAACCGACTTAG | 11246 |
| | 4 | MGGIAIQKKQILTHATPAVALTLLCEKPKGMIASPPQGG LVFLADKSRKIRCRRQ* | 11247 | ATGGGGATAGCAATACAGAAAAAACAAATCCTGACGCACGCAACCCCAGCGGT CGCTCTCACTTTGCTGTGTGAACAAAACCCAAGGAATGATTGCGAGCTCCCCGCAAGG GGGGTTGGGTCTTCCTTGCTGACAGAGTAGAAAGATAAGGTCAGAAGGCAGTGA | 11248 |
| hsa-mir-580 | 1 | MSAAGL* | 11249 | ATGTCAGCCGCTGGACTGTAG | 11250 |
| | 2 | MPLQP* | 11251 | ATGCCCTTGCAGCCTGA | 11252 |
| | 3 | MGINERTVFCNELYPCTQGASSKJAIWLLAVAQLATCVC VAA* | 11253 | ATGGGAATAAATGAAAGGACGTGTATTTGCAACGAGCTTTACCCGTGCACGCAGGG GGCCTCCAGCAAAGCCATTTGGTTGCTGGCTGTCGGTCAGCTGGCTACGTGTGTTTG CGTTGCGCGCCTAA | 11254 |
| | 4 | MKGLYFATSFTRARRGPPAKPFGCLLSLSWLRVFASPPK SELLSAYLC* | 11255 | ATGAAAGGACTGTATTTTGCAACGAGCTTTACCCGTGCACGCAGGGGCCTCCAGCA AAGCCATTTGGTTGCTGCTGTCGCTCAGCTGGCTACGTGTGTTTGCGTCGCCGCCT AAAAGCGAGCTGCTTTCAGCTACTCTGTCTGA | 11256 |
| | 5 | MVHTWVAASASPG3GV* | 11257 | ATGGTACACATGGGTGGCTGCTTCTGCATCCCAGGGAGCGGAGTCTGA | 11258 |
| hsa-mir-584 | 2 | MGGGFCIPRERSLTRGPCEFPRGPLACGLAKVDGPVEA QGPAGLEKLFSQRWGDDCAFWLPLLPPWYSVCHAGSV KREQSLEASIFS* | 11259 | ATGGGGTGGCTGCTTCTGCATCCCAGGGAGCGGAGTCTGACCGTGGGCCCAGGTGA GTTTCCCAGGGGGCCCTTGGCTGGTTGGCTTGGCCAAAGTGGATGGTCCAGTAGAGG CTCACGGACCTGCTGCCTCTCCTTGGTGGAAAACTTTTGTCATGCTGGCTCTGTAAA AAGGGAGCAAAGCCTGGAAGCCTGGAAGCATCTATTTTTCCTGA | 11260 |
| | 3 | MIVLSGCLSFLPG* | 11261 | ATGATTGTCTTCTGGCGTCTGCTTCCCTGGGTAA | 11262 |
| | 4 | MLAL* | 11263 | ATGCTGCTCTGTAA | 11264 |
| | 1 | MASSGEVLSATVSALLLPRPRPRSPWVLPSRPGFPCILSIP TPTPRPSHPDPGLAPAPVLPASCPQDSYPVSEGTSCLPL RSCIPDRQSCPRLSVP* | 11265 | ATGGCCAGCTCCGGAGAGGTACTGTCCGCAGACGTGTCCGCTCTGCTTCTGCCTCGG CGGCCTCGGCCTCGGTCCCGGGTTCCTCCATCCGACCGGGTTCCTTGCATCTTCTA TCCCGACCCGGCCTACCCGCGCATCTGTCCCAAGACTCCTACCCGTCTCGGAAGGCACAAGCTG CGTCCTTCCCGCCATCCTCCGCATCTGTCCGGTGCATTCCTGATCGCCAGAGTTGTCCCGTCTCCGGTCCCC TGA | 11266 |
| | 2 | MLSFSPSPLLPGACLLNDVGGG* | 11267 | ATGCTCAGTTTCAGCCCCAGCCCCACTTCTCCCTGGAGCCTGCTTGCTGAATGACGTG GGGGTGGGTGA | 11268 |
| hsa-mir-589 | 3 | MTWGVGJDGGKAISPFGLTTYPGILSQHSPNLGPMEKPA ASL* | 11269 | ATGACGTGGGGAGGTGGGTGATGAGGAAAAGCCATTTCACCTGAGGACTTACGAC GTACCCGGAATTCTTTCCAACACTCCCAAATCTGGTCGATGGAGAAGCCGGC CGCGTCCCCTGTAA | 11270 |

Figure 1 (Continued)

| | | | | |
|---|---|---|---|---|
| | 4 | MEEKPFHLRDLRRTLEFFPNTPQJWVRWRSPPRPCNVV QSIVSAERGAAGTLDSD* | 11271 | ATGGAGGAAAAGCCATTTCACCTGAGGGACTTACGACGTACCCTGGAATTCTTTCCC AACACTCCCAAATCTGGGTTCCGATGGAGAAGCCCGCGCCCGTCCCTGTAATGTGGTG CAAAGTATTGTCTGTCAGAAGCGGGTGCAGCGGGGACTCTAGACTCGACTAG | 11272 |
| hsa-mir-590 | 1 | MADHDTYDDRAYSSFGGGRG* | 11273 | ATGGCGGACTTCGACACCTACGACGATCGGGCCTACAGCAGCTTCGGCGGCGGCTAG AGGGTGA | 11274 |
| | 2 | MARSETGRRRLGSRGLACGADPPHCLPPTTCWFLPCL GRGGADARRRAPASSPIPPTVGPVRG* | 11275 | ATGGCGCGCTCGGACACGGGGCGGCGGCGCGCTGGCTCCGGCGTCTTGCTTGCGG GCGGATCCCTTCCACTGCCTCCGCCAACGACACCGTTGTTTTGCCCTGCCTT GGCGGCGGAGCGAGCGGCCATGCCGGAGCGAGCGCCGCTTCCAGCCGACCCATCCCC TACGGTAGGAGGACCAGTGCGGGGCTGA | 11276 |
| | 3 | MPGDERPLPAPSPLR* | 11277 | ATGCCCGGAGACGAGCCGCTTCCAGCCCATCCCCTACGGTAG | 11278 |
| | 4 | MVRLLAGGGRPRR* | 11279 | ATGGTACGACTCTTGCGGGAGGGAGACCAAGGAGATAA | 11280 |
| | 1 | MWTFVL* | 11281 | ATGTGGACTTTTGTTCTCTAA | 11282 |
| | 2 | MTYQRGK* | 11283 | ATGACGTACCAAAGAGGAAAATAG | 11284 |
| hsa-mir-594 | 3 | MLCERVVCRSPSGLMDKALAS* | 11285 | ATGTTGTGTGAAGCGCGTCGTTGCCAGAAGCCCAGTGGCTAATGGATAAGGCATTG GCCTCCTAA | 11286 |
| | 4 | MPTLLFFLNGKCVCVFTSWWAAIFENLHTPMSFV* | 11287 | ATGCCAACTTACTTTTTTTTTTAAATGGAAGTGTGTGTTTTACTAGCT GGTGGGCTGCAATTTTGAGAATCTGCACACCATGTCCTTGTCTGA | 11288 |
| | 1 | MNFSVETAPPQSLFKKQK* | 11289 | ATGAACTTCTCCGTCGAAACTGCTCCCCAGAGCCTGTTAAGAAGCAGAAATAA | 11290 |
| hsa-mir-607 | 2 | MPVDALTSKIFKGEVDTRY* | 11291 | ATGCCGGTGGATGCACTGACTCTAAGATTTCAAAGGTGAAGTGGATACACGTTAT TAA | 11292 |
| | 3 | MSKPLGHESP* | 11293 | ATGAGCAAGCCTCTTGAATAATTGAATCACCTTAA | 11294 |
| | 4 | MGNERRKGKEMGWKEKSRJDRPIPVGLVP* | 11295 | ATGGGAAACGCCGAAAGGAGAAATGGGTGGAAAGAAAAGCAGAA GAGATGCGCCTATACCAGTAGGCCTAGTACCTAG | 11296 |
| | 1 | MAQGREREGPHSAGGASLSVRCGVHGPATDLGLAEP PAPSPLLPPLPVP* | 11297 | ATGGCGCAAGGCGGGAGCGCGACGGAAGGCCCACTCCCGGCGGCGGCGTCTT GTCCGTGAGGTGCGGTGTTCACGGCCCGACCGATCTGGGTCTCGCGGAACCTCC TGCCCCAAGTGCCCTCTCCTCCTCCACCAGTGTCCTTCACTGCCTTTCCACCATCTTCA | 11298 |
| hsa-mir-609 | 2 | MSRGFSPNQCPSLAFSTIFKHTFNI* | 11299 | ATGTCTCGAGGTTCTCTCCAAACCAGTGTCCTTCACTGCCTTTCCACCATCTTCA AGCATAACTTTAATATTTAA | 11300 |
| | 3 | MFFLCASLSFTSTSRLLFSTPICIFKSKIWPHTLHLCK* | 11301 | ATGTTCTTTTTGTGTGCTAGCTTTCATTCAGTGACTTCATTCCTTTATTTCTAC GTTTATCTGTATTTTAAATCTAAAATATGGCACATACTCTTCATCTGTGTAAATAA | 11302 |
| | 4 | MATYSSSV* | 11303 | ATGGCCACATACTCTTCATCTGTGA | 11304 |
| | 1 | MVRALRGVPDGDARTPRGLTHTALRSSDAGDPREG* | 11305 | ATGGTGAGACGTCTCAGGGGAGTTCCAGACGGAGATGCGAGGACCCCTCGGGTCT GACCACACCGCGCTTATCTCTCAGACCGCGAGATCAGAGGCTAG | 11306 |
| hsa-mir-611 | 2 | MRGPLGV* | 11307 | ATGCGAGGACCCCTCGGGGTCTGA | 11308 |
| | 3 | MNSLGFSARDF* | 11309 | ATGAACTCCTTAGGTTCTCAGCTCGCGATTCTAA | 11310 |
| | 4 | MPWANVYW* | 11311 | ATGCCCTGGGCAAATGTTTATTGGTGA | 11312 |
| | 1 | MRVKKGRGHVRDTYWVVGVVGNAG* | 11313 | ATGAGGGTGAAGAAGGGGAGGGGTTGGTTAGAGATACAGTGGTGGTGGGGG TGGTAGGAAATGCAGGTGA | 11314 |
| hsa-mir-612 | 2 | MQVEGNSLGLWGI* | 11315 | ATGCAGGTTGAAGGGAATTCTCTGGGCTTTGGGAATTTAG | 11316 |
| | 3 | MPSHRQGKCLYQLPPGGQDSLFQRVVLFGYWVLSSEL VT* | 11317 | ATGCCATCTCACAGGCAGGGAAATGTCTTTACCAGTTCCTCCTGGTGGCCAAGAC AGCCTGTTTCAGAGAGGTTGTTTTGTTTGGGGTGTTATCAAGTGAATTAGTC ACTTGA | 11318 |

Figure 1 (Continued)

| | | | | |
|---|---|---|---|---|
| | 4 | MSLPASSWWPRQPVSEEGCFVWGVGVIK* | 11319 | ATGTCTTTACCAGCTTCCTCCTGGTGGCCAAGACAGCCTGTTTCAGAGGGTTGTTTT GTTTGGGGTGTGGGTGTTATCAAGTGA | 11320 |
| hsa-mir-616 | 1 | MLKMSGWQRQSQNQSWNLRREASTDSHLPFTLPSPQS WGIVRSLGSASLLHSEVRDRPREEWGESLILGWCLQTPH ASDDGVSPPLPGAGTRALLCAAGQRDLGCPWEIHSFP* | 11321 | ATGTTAAAGATGAGCGGATGGTGGAGACAGAGCAAGACAGGCAAAATCAGAGCTGGAACCTGAG GGGGCGTCCGCTCTTTAGGATGGGCCATCCAATTCCTCCGTCTCCCGTCTCCCTCAAAGTTG GAGAGGAGGAATGGGGAGAGTCCCTTATTCTGGGGTGGTGCTTACAAACCCTATTG CTTCGGACGACGGCGTCTCCACCCGTCCTCCACCCGTGCCCTGCCCTGGAGCCGGAACACGGCGCCTGCTCT GTGCTGCTGGCAAGGGACCTGGTTGCCTGGGAAATTCATTCTTTCCGGTAG | 11322 |
| | 2 | MGRVPYSGVVLTNPYCFGRRRLSTPARSRNTGPALCCW AKGPRLPLGNSFFPVANPRPHR* | 11323 | ATGGGGAGAGTCCCTTATTCTGGGGTGGTTGTTACAAACCCTATTGCTTCGGACGA CGGCGTCTCCACCCGTCCTCCACCCGTGCCCGGAGCCGGAACACGGCGCCTGCTGCTGG GCAAAGGGACCTCGTTGCCCTTGGGAATTCATTCTTTCCGGTAGCCAACTTCAGG CCTCATCGTTAG | 11324 |
| | 3 | MATLVAGATGRPCSG* | 11325 | ATGGCCACTTGGTAGCTGGGGCTACTGACCCTGCAGCGGATAG | 11326 |
| | 4 | MBREWCVFLLP* | 11327 | ATGACAGGACAGTGGAGTGGTGTGTTTCCTTTGCCGTAG | 11328 |
| hsa-mir-618 | 1 | MLKPSVTSAPTADMATLTVVQPLTLDRGKGAARSPGH RVPSPLLPSPPANSQRDMGRAQAGGEGERGRARKAFAP RTEHFPLSLPATFPLPLPTVLAPPRGRLLLALGSPLPLPA PRRVVSGFPLALLEFPLRGDYTRRQGLGVGEGQRASSPGQ SPEETGBEGAACQLAWRRGPGGRKFVQAPEGEGRSNCW SPGGHSGGGLGAPLGCRAHSGGAAAGREEPSAEFARQS ACGSRAPAAEHGSPRLRDRKRRGSRLLPPPAAPGR* | 11329 | ATGCTGAAGCCGAGCGTCACTTCGGCTCCCACGGCAGACATGGCAGATTGACAGT GGTCCAGCGCTCACCGTGACAGAGGTAAGGGAGGCTCTGCCTCGCCAGGCCACC GCGCTCCAGGCGAGCCTCCTCCTCCCCGCCAATTCCAACGGGACATGGGAC GCGCTCCAGGACAGAGGAGAGAAAGGGAGCAGGGAACGAGGACCAGGGCGTTGCCGCC GAGAACAGAACACTTCTCCCTCCGCCGCTACGTTCCGCTCCGCTGCCTCCC ACTGTACTCACCCCCTCGCCGGGCTCTCGCCTCTGGCTCTGGGTGTGTCGCCA CTCCCAGCGCTCCAGGCCTATAGGCGCCAGGGCTCGGGGTTGGAGGGCAGAGGAACAAGCT GGGGGACGGCTATAGGCGCCAGGGCTCGGGGTTGGAGGGCAGAGAGGCAAGCT CGGGGAACCGAGAGCCCGGGGAGCGCCCAGAGCAGCCGGGAACGAGGCGCACCCTGGGT CGCGGGCGCACAGTGGCGGGCGAGCCCAGCAGCCCCAGAGAATCCCTTGG CCAACTGCTGCAAGGTCCGGCCACTCGGGGAGTGGCCGAGTGGCGCACCCTGGGT TGCCGGGGCCACAGTGGCGGGCGAGCCCAGCAGCCCCAGCAGCCCCCTGCCGAAAGG TTCGAGATCGAAAGCGCGAGGCGGGAGGGTCCGCAGCCGAGATCGGCGTCGCGGC CGATAG | 11330 |
| | 2 | MESSAAKGASLVHPCGVIPYPECVGFLPGSSVQ* | 11331 | ATGGAGTCCTCCGCTGCGATCGGGCCTCACTGGTGCACCCTGTGGGGTTATACCT GTCCCTGAGTGTGGAGGCCTTCCTTGCCTGGCTCCAGCGTCCAGTGA | 11332 |
| | 3 | MKALESYGSAEEDHL* | 11333 | ATGAAGGCTCGAGTTCTACGGCTCCAGAGGAGGACACCCTAG | 11334 |
| | 4 | MVYSEENDLVRCTSKNFLSRGLN* | 11335 | ATGGTGTACTCAGAAGAAATGATTTAGTCGATGTACCTCTAAAATTTCTTTCT AGAGGATTAAACTGA | 11336 |
| hsa-mir-619 | 1 | MALYTLQRSPTPSAASSSASNSEVSPGLAAPGLGRRTPR RGRRSWGRACGGAGGGRLRGLLGAPP* | 11337 | ATGGCCCTGGTGACCCTGCAGCGGTCGCCCACGCCCAGCGCGCCCTCCTCTCGGCC AGCAACGAGCAGTGAGCCCGGGTCGCCGGTCGGGGCCGCGGCCCGGACGCC GCGCCGAGGGGCGCCGGGAGTCGCCGCTCGGGGCAGGGGGGGGCTGCGC GGGCTCCTCCGGGGCCCGCCGTAG | 11338 |
| | 2 | MQCDPSGSVCRILCVRCDPHQGVTPILG* | 11339 | ATGCAGTGCGACCCCTCTGGGAGTGTCTGCAGGATACTGTGTGTGCGCTGTGACCCA CATCAGGGGGTTACCCCCATCTTGGGGTGA | 11340 |
| | 3 | MCNWDP* | 11341 | ATGTGCAACTGGGACCCTTGA | 11342 |
| | 4 | MPGCAM* | 11343 | ATGCCTGGCTGTGCGATGTGA | 11344 |
| | 1 | MEEGL* | 11345 | ATGGAGGAGGGGATTGTAA | 11346 |
| | 2 | MAAAGSSLL* | 11347 | ATGGCGGCAGCCGGCAGCTCGCTGCTCTGA | 11348 |

Figure 1 (Continued)

| | | | | |
|---|---|---|---|---|
| hsa-mir-624 | 3 | MDELAGGGGKGPGMAAPPRQQGPGGNLLGLSPGGNG AGGGGPPASEGAGPAAGPELSRPQQYTPGILHYIQHE WARFEMERAHWEVERAELQVPRWGRCAGAAAAGFPA GGWGWGLHSAGAGALGGRAEPTCAAQVVMVLSTAFP GVPLPLSRISLLPNLHWLRGAGLLGAAILAFSMASAGAP PEAAFPGLRGLGPSTSLWESPVWGLSTLSLLLFVPLEMK SPKRGTRIGHLPPFSGPPPFPIWRIWPPPSDLVRACPLTAT LLSWAARVHSDLGLTCEVLFPIVNFKYFLT* | 11349 | ATGGACGAGCTTGCCGGAGGCGGTGGTGGCGGCCCGGGATGGCGGCCCCTCCCCG GCAGCAGCAGGGACCTGGGGGAACCTGGGGGAACCGGGAACGGAGCG GGGGGCGGCGGGGGTCCTCCGGTACTACTATCCCGGGAT... | 11350 |
| | 4 | MLPYSLGFSVVIPYLVTHQRFQH* | 11351 | ATGTGCCTTACTCACTTGGATTCTCTGTAGTTATTCCTTACTTAGTGACTCATCAAC GCTTTCAGCACTGA | 11352 |
| hsa-mir-627 | 1 | MAVLLKGL* | 11353 | ATGGCTGTGTTGTTGAAGGKCCTGTAG | 11354 |
| | 2 | MHDAFEPVPILEKLPLQIDCLAAWGEPRCRGAEAESAQ ERSCGSFLRPGKWTGVHPCGLRLDATREGLRMREGREM TTGYRHRCLWGYLGDPSDPVI* | 11355 | ATGCACGACGCTTTCGAGCCAGTGCCGATCCTAGAAAAGCTGCCTCTGCAAATCGAC TGTTGCTGCTGCCTGGGGTGAGCCGAGCCGAGGGCCGAGGCGAGTCAGCACA... | 11356 |
| | 3 | MLHERGLG* | 11357 | ATGTCTACACGAGAGGGCGTTAGGATGA | 11358 |
| | 4 | MSVGLLG* | 11359 | ATGTCTGTGGGCTACTTGGGTGA | 11360 |
| hsa-mir-629 | 1 | MGAPLPTGRDGAPPLRPVGELRNLLGRFWAEGGLFWL GAVGEGPGPL* | 11361 | ATGGGAGCCCCGCTGCCGACGGGCGAGAGATGGGGCCCCCCCTCCGCGCCCCGTCGG AGAGCTGAGAACTTGCTGGGAAGTTCTGGCTGAGGGTGGCCTCTTTTGGTTGG GCGCCGTTGGGGAGGGGCGTGGGGCCGGCTCTGA | 11362 |
| | 2 | MGRPPSAPSES* | 11363 | ATGGGCCGCCCCGCGCCCCTCCCGCCGTCGAGAGCTGA | 11364 |
| | 3 | MPPPPLSCLRGLQAPHQPGQPGFKFTVAESCDRIKDEF QFLQAQYHR* | 11365 | ATGCCCCCCCCGCCCTCCCTGTCTTCGCGGGCTCCAGGCTCCCATCAACCGG GGCAGCCGGGGATTTAAATTCACGGTGGCTGAGTCTTGTGACAGGATCAAAGACGAA TTTCAGTTCCTGCAAGCTCAGTATCACAGGTAA | 11366 |
| | 4 | MGAPPGGCQESGKVALEALGSGPQRRLSRRHA* | 11367 | ATGGGGGCGCCCCCGGGGGGTGTCAGGAAGCACTGACGGCACGCTGAGCGGGTGGAGAA TGGGTCGGGCCTCAGAGGAGGCTGTCCAGGCGCCACGCTGA | 11368 |
| | 1 | MAAAPALKHWRTLERVEKFVSPLYFTDCNLRGRCGP WSPAAGRPQPCASSFPSGEKPKLQPPGPPIDKVPAAGRA GAGEEGVGNGLCRGAARQPSWRRIQGKCGPTGQLAPR RKRGGLQHVPTGPSHAGFLGPAALWLCSPAS* | 11369 | ATGGCGGCTGCGCCGGCGCTCTAGTTTACGACTGTAACCTCGCACCACGCTGAGCGGGTGGAGAA GTCCCCGCCAGCGCCGCAGCGACGCCGCCAACCTGCCGCTGCAAGTGCCGGGGGCTCGCTGCAGGGAAGAA ACCTAAGCTGCAGGGAGGACGCGAGCACCCGGGCGGCCTGGGGAATGACTGCTCCGCGGACGGCAGCC CTCTTGGCGGAGGATCCAGGAAGTGCCGGGAAAGTGCCGGATGCCACCGCGCGCCGCTGGCCTGAGGCC GGAAACGGGCGGCCTGCCAGCATGTGCCACCGCCGCTGGGCTGTGCTCTGTGCTCCAGCTTTTG GGGCCAGCTGCCTGTGGCTGTCGTCTGTGCTCTCCAGCTTCCTGA | 11370 |

Figure 1 (Continued)

| | | | | | |
|---|---|---|---|---|---|
| hsa-mir-631 | 2 | MDCAAERPGSPLGGGSRESAAPPASWPPGGNGAAASSMCPPARPTQAFWGQLPCGCALQLPDAGETSLPGGSPAGLPPRAGRRQLRTHAVGNAQRVGGATGLGEVPTQLPATPSLSALCRRQLRGHEQHPLLGAAPSAGNSSLVPGSSGDGFHSHVAASGHPLGRAP* | 11371 | ATGGACTGTGCCGCGGAGGCGGTCAGGAGCGGCTCAGGAGGATCCAGGGAAAGTGCGGCCCCACCGGCCCGTGCCACCGGCCAGTTGGCCCAGGGTGGCGAAACGGRGGCGCCTCCAGCATGTGCCCACCGGCCCGTCGACGCGGAGAGACTTCCCTACCAGGAGGACTTCAGGGACTTCTCCAAGCTTCCTGACGCGGAGAGACTTCCCTACCAGGAGGACAGTTCAGGGACTTCCCCCGCCAGGTCGCGACAGCTTCGGACCACAGTTCGGACCCAGTTAACGCCCAGGGGTGGGCGGGCCACAGGCCTAGGGAGGTCCAACCAGCTCCAGCTCCAGCCACACCTCGTTGCTGCCCCTCGCCGTAGACAACTACGTGGGATCGGACAGCAGCACCCTCTGCTGGACGCACCACCCTGCTGCCGCCGCCCCCTCGCCGTGCGCCCCTCTTCTAGGAAGGGCACCCTAG | 11372 |
| | 3 | MVFIPTWPPLDIP* | 11373 | ATGGTTTTCATTCCACGTGGCCGCCTCTGGACATCCCTAG | 11374 |
| | 4 | MLGEFQAPADTLSKEEGYQDRKTSTSRPITTALLQMVDLLVPGGADHPRGMGGPGSSPLLGK* | 11375 | ATGCTTGGAGAGTTTCAAGCCTCCGACACTTTATCCAAGGAAGGATATCAGGATAGGACTTCTACCTCTAGGCTATCACAACAGCTCTCTTGCAGATGGTGGACCTGCTGGTTCCGGTGAGCTGAGTCGACCATCCAGAGGCATGGGTGGGCCAGGAAGTTCACCTTTGCTGGGAAAGTGA | 11376 |
| hsa-mir-632 | 1 | MAATSSRLLVPPTQGGGLRHVTLPPLAPPPTAVLDGRRSGERGRRPFCVCHLWDVVVAVGLGK* | 11377 | ATGGCTGCCACCTCTCGCGCCTCTAGTCCCACCCACTCAGGCGGAGGTCTGCGTCATGTGACCCTCCCCTTTGGCCTCGCGCCTCTACCGCAGTGCTTGACGGAGGCGGAGCGGGAACGAGGCCGTCGGCCATTTGTGTCTGCTTCTGTGGGACGTGGTGGTAGCCGTTGGGTTTGGGAAAGTGA | 11378 |
| | 2 | MGRKKKKQLKPWCWYPLSV* | 11379 | ATGGGTCGCAAGAAGAAGAAGCAGCTGAAGCCGTGGTGCTGGTATCCTTTGTCGT TTGA | 11380 |
| | 3 | MGFRGRQAFAVYGRVTL* | 11381 | ATGGGGTTCCGAGGTCGCAAGCTTCACAGTCTGTCACCCACTTTCTGTTTATTACTTGA | 11382 |
| | 4 | MEGWGQLHSLSPTFSVFIYFMCVLCLFFRIGGLVKMQVSQPWFRTFFFFFSGREEN* | 11383 | ATGGAGGGTTGGGGACAGCTTCACAGTCTGTCACCCACTTTCTGTTTATTACTTTATGTGTTTGTTTGTTTATTTTCGAATTGCGGTTAGTAAGAACCAAGTAGTCAACCCTGGTTTCGAACCTTTTTTTTTTCGGGCGGGAGGAAACTAG | 11384 |
| hsa-mir-634 | 1 | MLSSGREVPFGGCILKLCHTGLRPHLQGLR* | 11385 | ATGCTTCTTCTGCGAGAAGTCCCTTTGGGGGGTGCATTTGAAGCTCTGCCACACTGCGCCTCAGACTTCATTTGCAAATTGGCCTGAGGTGA | 11386 |
| | 2 | MHTFRSPSSLLKTVMAGPGGSHL* | 11387 | ATGCATATTTCAGGTCTCCATCATCTCTATTAAAACGGTGATGCGTGGGCCCGGTGGCTCACACCTGTAA | 11388 |
| | 3 | MQKKISR VVWWRAPVVPATREEAEAGEWREPGRRSLQ* | 11389 | ATGCAAAAAAAATTAGCCGAGTGTGGTGGCGGGCGCCTGTAGTCCCAGCTACTCGGGAGGCTGAGGCAGGAGAATGGCGTGAACCCGGGAGGCGGAGCTTGCAGTGA | 11390 |
| | 4 | MTKSRLQKMQK* | 11391 | ATGACAAAATCCCGTCTACAAAGATGCAAAATGA | 11392 |
| hsa-mir-637 | 1 | MSTPRQEDVEDHYEMGEELCR* | 11393 | ATGTCCACGTCAGGCAGGAGGATGTGGAGCGTGGAGGACCATTATGAGATGGGGAGGAGCTGGGCAGGTGA | 11394 |
| | 2 | MRWGRSWAGELSARTAGLQG* | 11395 | ATGAGATGGGGGAGGAGCTGGGCAGCTGTCTGCCCGCAGGCTGGGCTCCAGGGATAG | 11396 |
| | 3 | MLRRNESVSCGGGTNLGRGVRQPRL* | 11397 | ATGCTGAGAAGGAATGAGTCAGTATCATGCGGTGGGGGAACGAATTTGGGCCGTGGAGTCAGACAGCCCGGCTGTGA | 11398 |
| | 4 | MSQYHAVGERIWAVESIDSPGCEFLLGNPLCVSCGEKSN* | 11399 | ATGAGTCAGTATCATGCGGTGGGAGAACGAATTTGGCCGTGGAGTCAGATAGACAGCCCGGGCTGTGAATTCCCTGCTGTTCCTGTGTTTCCTGTGTGGGAGAAAAGTAATTGA | 11400 |
| | | MVKPLLFSPSYRRSAPFDWSRKLLGQSPGASPSLGSDRPQGAGANVGASCPDWPTGRARPGGAGRTQSRV* | 11401 | ATGGTCAAGCCCCTTCTCTTTAGCCTCCTACAGGCGTTCCGCCCCCCTTCGATTGGTCTCGCAAGTTGATTGGTCAATCCCTGGTGTCAGTCCTAGTCCCTGTGCCCGTCCTAGTCTTGGTTCGGACCGGCCCAAGGAGCAGGGGCGAACGTGGGGCGAACGTGGGGCCGGGGCGGAGGGCCTGAGGGCGCTGGAGGGCCGGGGCGCGGGAGCCGCAGAGCCGGCGTTTAG | 11402 |

Figure 1 (Continued)

| | | | | | |
|---|---|---|---|---|---|
| hsa-mir-639 | 2 | MKHYEVRSEKQGPCGHC* | 11403 | ATGAAGCATTACGAGGTAAGAAGCGAGAAACACGGGCCGTGGCCACTGCTGA | 11404 |
| | 3 | MRMCAGSIYKSATQAVLGVLPLGGLCRGWDACRFLAAPPAG* | 11405 | ATGCGCATGTGCGCAGGAAGTATTTATAAATCTGCAACCCAGGTGTTTGGGGTACTTTTCTTGGGGTCTCTGCAGGGTCTGCAGCCCTGGGACGCTTGCAGGTTCCTTGCAGCTCCCCCAGCGGGCTGA | 11406 |
| | 4 | MGATKVRDPCSQSEGVLHKSCATPPSPA* | 11407 | ATGGGAGCCACGAAGGTGCGAGACCCTTCTCCCAATCCGAGGGAGTCTTGCACAAATCTTGCGCCACGGCCGTCACCAGCGTAG | 11408 |
| | 1 | MGGIRAPPERLGGCR* | 11409 | ATGGGCGGTCGTAGAGCCCCGGAGCGCCTGGGCGGCTGCCGCTGA | 11410 |
| | 2 | MVASGPPAVPRWAVPPVPGGGTAALLEPLLQELSGGGRAGAVGPASGGRGGGGGPYH* | 11411 | ATGGTTCGCGTCCCGGGCCCCGCCGCCCCGTGGCCGATGGGTCCTGGCCGATGGGGTCTTCAGGAGCTCCTTGGGGGGTGGCGCAACGCGGGGACCGCGCGGTGGGCGGCGGGGGCCATACCACGGGGGAGCCCTCGAGCCCCTCCTCACCGGGGAGCCCTCGAGCCCCTCCTCGGGGGGCCGGCGGGGGGCCATACCACTGA | 11412 |
| hsa-mir-641 | 3 | MGCTTRARRGDRGPRAPPSGAEWGWPSGGGTSLGGPGRWRRAIPLRRWGERCKPAGRGAQAAACAGRGLDLSGAAGRSSLACAG* | 11413 | ATGGGCTGTACCACCCGTGCCCGGCGGGGGGACCGCGCCCCTGAGCCCTCCTCAGGGGGGGGCCGGGCCGGGGTGGCGGCGGCGGGGACCAGCTCGGGGCCGGGGGAGCTGAGGAGCGGTGCAAGTTTGCGGACGGGGAGCGCAGGCGCCATACCACTGAGGCGTGCGGGGGCTGAGCCTGGACCTTTCGGGCGCGGCGGGGCAGATCAGAGCCTGGCGTGCGCGGGCTAA | 11414 |
| | 4 | MLPQLWLGYITTALGEPCLERRGTQIRGL* | 11415 | ATGCTTCCCAACTGTGGCTGGGTTATATCACCGCGTTGGGGGAGCCCTGCTTAGAACGTAGGGAACCCAAATCAGAGGACTGTGA | 11416 |
| | 1 | MSLSACFHLWLAAR* | 11417 | ATGTCTCTGTCTGCGTGTTTCCATCTCTGGTTAGCTGCTAGATAA | 11418 |
| | 2 | MLGKGCSTYSGLYLPAGKVL* | 11419 | ATGCTGGGAAAGGGTTGTTCCACTTACTCTGGGCTTTATCTACCCCAGCGGGGAAAGTTTTGTAA | 11420 |
| hsa-mir-642 | 3 | MCARKPEGLGEWELGWAFQVLHQAVGTQMGVSSTPLGGTENLQVFQFPIEKGSRLTVSTPSSPRRSPSGSQESVGPDFGDTDTSAQRSSRATARSANTPPFHLCCPNNSQGRPGNHLRGPAHHRSSTHSACLSLPPDHHAWELRERVRCLGVPRVYGSPAVCPCV* | 11421 | ATGTGTGCTAGAAAACCCTTGGGCTTGGAGATGGGAGCTCGATGGCGTTTCAAGTACCCACTAGGGCGGAGTTCTCAAGGGATGGCGTTCCAGGAGTCTGATGGGACTTTCAGGTCCCATAGAAAGGGTCTAGGCTCGACGGTCTTCGGTGACACTGACACTTCGCTCGACACTTCGCTGTAGTCAGACTTCGGTGACACTGACACTTCGCTGCCCCAGCGTCTCGGTCAACACCAGTCAGGGAGGCCGGGAACTTAAGGGGCCGCCGGAGTTGCCACCACCGGAGTTGCACCACTCGGCGTCCTCCCTCCGCCAGATCATCACGCTGGGAGTTGCGGAGGTCGCTCGCTGGAGTCCCGGGTGTATACGGGGGTACTGA | 11422 |
| | 4 | MGVSSSPPGCGNSDGRFKYPTRGY* | 11423 | ATGGGGTTTCAAGTCTCCACCAGGCTGTGGGAACTCAGATGGGCGTTTCAAGTACCCCACTAGGGGGTACTGA | 11424 |
| | 1 | MAWRYGATAAREFSFV* | 11425 | ATGGCGTGAGATATGGCGAACTGCGGCGTGAGTTTCCTTGTTTAG | 11426 |
| hsa-mir-643 | 2 | MAQLRRVSPPLFRLSVRLAVPSRFCTRDVGGGTDLEIPAPLSPPRVNSCVPSEC* | 11427 | ATGGCGCAACTGCGGCGGGTCTCTACCCCGGAGTTTCGTTGTTTAGATTAAGTGTCGCTTAGCGTGGCCCTCACGCTCTGTACCCCGGAGTGTGGGGCGGTACAGACCTTGAAATCCCCGCACCGCTCTCTCCACCCGAGTAACTTGAAATCATGCGTCCGTCAGAGTGTAA | 11428 |
| | 3 | MWGAVQTLKSPHRSLHPE* | 11429 | ATGTGGGGAGCGGTACAGACCTTGAAATCCCGCACCGCTCTCTCCACCCGAGTAA | 11430 |
| | 4 | MRPVRYLKSP* | 11431 | ATGCGTCCGTCAGAGTGTTAAATCGCCTAG | 11432 |
| | 1 | MRMNWVLS* | 11433 | ATGAGGATGAACTGGGTTTAAGTGA | 11434 |
| hsa-mir-648 | 2 | MPPIPYLIARCTSQVRNPAPDCSSLIVSFSCAPGLEVLNLPYSVPMSLS* | 11435 | ATGCCGTTCATTCCATATTTGATTGCCAGATGTACTTCTCAGTTGCAGAAATCCAGCCCCAGATTGTTCAAGTCTTATAGTGAGTTTCTTGTGCTCCAGGTTTAGAAGTTTTAAATCTCTTTTATAGTGTATTCAACAGCTTGAGTTAA | 11436 |
| | 3 | MYFSGQKSSPRLFKSYSEFFLCSREFSFKSLL* | 11437 | ATGTACTTCTCAGGTACGAAAATCCAGCCCCAGATTGTTCAAGTCTTATAGTGAGTTT | 11438 |
| | 4 | MVCVFLL* | 11439 | ATGGTTTGTGTTCCTCGTAA | 11440 |

Figure 1 (Continued)

| | | | | | |
|---|---|---|---|---|---|
| hsa-mir-657 | 1 | MPGWILQLRGFSGKQRPLLSRDPGS* | 11441 | ATGCCCGGATGGATCCTGCAGCTCCGGTGGCTTTTCTGGGAAGCAGCGGCCCCTGCTCTCAAGAGACCCTGGCTCCTGA | 11442 |
| | 2 | MDPAAPWLFWEAAAPALKRPWLLMVAPRLPAGARDSGQFPRKGQAGSPSRGRVRKLGGAEATLGP* | 11443 | ATGGATCCTGCAGCTCCGGTGCTGATGGTGGCCCAAGGTTGCCAGCTGCCAGGGACTCAGGACAGTTTCCCAGAAAAGGCCAAGCGGCCACGCCTCCAGGGCCGGGTGAGGAAGCTGGGGGGTGCGGAGGCCACACTGGGTCCCTGA | 11444 |
| | 3 | MAFP* | 11445 | ATGGCCTTCCCCTGA | 11446 |
| | 4 | MSGRGTCGGEVSCPGGRRGAGGRRVRPGSRGRWRSSRG* | 11447 | ATGAGTGGACGGGGCACAGGAGGAGAAGTCCTGTCCTGGGGCCGGGTGGGGCGGTGTGGGAGAAGAGTAAGGCCTGGAAGCCGGTGAGGCGGAGCAGCCGTGGGTGA | 11448 |
| hsa-mir-658 | 1 | MSGPRLRPEAGSSAPLGPAGKPEAFPRPLAI* | 11449 | ATGAGCGGCCCGCGCCTGCGCCTCCTGAGGCCGGAAGTTCAGCCCCACTCGGGCCTGCCGGGAAACCGGAAGCCTTTCGAGGCCCTCTGGCCATCTGA | 11450 |
| | 2 | MEKPRLY* | 11451 | ATGGAGAAACCCGTCTACTAA | 11452 |
| | 3 | MPVIPATREAEAGESLEPGRRRLR* | 11453 | ATGCCTGTAATTCCAGCTACTCGGGAGGCTGAGGCAGGAGAGTCGCTTGAACCGGGAGGCGGAGGTTGCGGTGA | 11454 |
| | 4 | MLHKRWPASRVKEDSDTGA* | 11455 | ATGCTACACAAAAGATGGCCGGCTTCTCGCGTGAAGGAAGATTCGGATACGGGGCCTGA | 11456 |
| hsa-mir-659 | 1 | MSGPRLRPEAGSSAPLGPAGKPEAFPRPLAI* | 11457 | ATGAGCGGCCCGCGCCTGCGCCTCCTGAGGCCGGAAGTTCAGCCCCACTCGGGCCTGCCGGGAAACCGGAAGCCTTTCGAGGCCCTCTGGCCATCTGA | 11458 |
| | 2 | MEKPRLY* | 11459 | ATGGAGAAACCCGTCTTACTAA | 11460 |
| | 3 | MPVIPATREAEAGESLEPGRRRLR* | 11461 | ATGCCTGTAATTCCAGCTACTCGGGAGGCTGAGGCAGGAGAGTCGCTTGAACCGGGAGGCGGAGGTTGCGGTGA | 11462 |
| | 4 | MLHKRWPASRVKEDSDTGA* | 11463 | ATGCTACACAAAAGATGGCCGGCTTCTCGCGTGAAGGAAGATTCGGATACGGGGCCTGA | 11464 |
| hsa-mir-661 | 1 | MVAGMLMPRDQLRAIYEVLFREGVMVAKKDRRPRSLHPHVPGVTNLQVMRAMASLRARGLVRETFAWCHFYWYLTNEGIAHLRQYLHLPPEIVPASHLQRYRRPVAMVMPARRTPHVQAVQGPLGSPPKRGPLPTEEQRVYRRKELEEVSPETPVVPATTQRTLARPGPEPAPATGQLHPDPKS* | 11465 | ATGGTGGCCGGCATGCTCATGCCCAGGGACCAGCTGCGGGCCATCTATGAGGTGCTCTTCCGCGAGGGCGTGATGGTGGCCAAGAAGGACCGCCGCCCCAGGTCGCTGCACCCCCATGTGCCCGGGGTCACCAACCTGCAGGTCATGCGCGCCATGGCCTCGCTGCGGGCACGGGGCCTGGTCCGCGAGACCTTTGCCTGGTGCCACTTTTACTGGTACCTCACCAATGAAGGCATCGCCCACCTGCGCCAGTACCTGCACCTGCCGCCAGAGATCGTGCCCGCCTCTCAGCGCGTGCGGCGCCCCGTCGCCATGGTGATGCCCGCACGGCCCACCCCACGTGCAGGTCAGGGCCCGCTGGGCTCCCCACCAAAGCGGGGCCCGCTGCCAACGGAGGAGCAGCGGGTCTACCGCCGCAAGGAGCTTGAGGAGGTTCACTGAGACCCCTGTGGTGCCTGCTACCACCCAGCGGACCCTGGCCAGGCCAGGCCCGGAGCCTGCCCCAGCCACCCGCACCGCAGGGCAACTGCACCCCGACCCCAAGTCATGA | 11466 |
| | 2 | MRCSSARA* | 11467 | ATGAGGTGCTCTTCCGCGAGGCGTGA | 11468 |
| | 3 | MCPASPTCRSCVPWRPCGHGAWSARPLPGATFTGTSPMKASPTSASTCTCRQRSCPPLCSACAAPSPW* | 11469 | ATGTGCCCGGCGTCACCAACCTGCAGGTCATGCGCGCCATGGCCTCGCTGCGGGCACGGGGCCTGGTCCGCGAGACCTTTGCCTGGTGCCACTTTTACTGGTACCTCACCAATGAAGGCATCGCCCACCTGCGCCAGTACCTGCACCTGCCGCCAGAGATCGTGCCCGCCATGA | 11470 |
| | 4 | MMGGK* | 11471 | ATGATGGGTGGCAAGTAG | 11472 |
| | 1 | MSWSYVALGTRDLVEERRPVRGEGRAAALFV* | 11473 | ATGAGCTGGAGCTATGTGGCACTGGGAACTAGGGACCTGGTGGAGGAAAGGAGGCCGGTGCGGGGAGAAGGTCGCGCCGCTCTCTTTGTGTGA | 11474 |

Figure 1 (Continued)

| | | Protein | | Nucleotide | |
|---|---|---|---|---|---|
| hsa-mir-7-1 | 2 | MWHWELGTSWRKGGRCGEKVAPPLSLCEPRLTLGLPA RGRSWSGGDGTVRAASMALSRAVGGGCGG* | 11475 | ATGTGGCACTGGGAACTAGGGACCTCTGGAGGAAGAGGCCGTGCGGGAGA AGGTCGCGCCGCCCGCTCTGTGAGCCCCGCTCACCTTGGGTCTCCGGCC GGGGTCGGAGCTGGAGCGGCGGGGATGGAAGCGGTCAGGGTGCTCGATGGCTTTG TCTCGGGCAGTGGGGGGAGGAGTGCGGGGATGA | 11476 |
| | 3 | MERSGLPRWLCLGQWGHEDAGDETSGPRGGWGRGSAL GSA* | 11477 | ATGGAACGGTCAGGGCTGCTGCTCGATGGCTTGTCTCGGCAGTGGARGGAGGATGC GGGGGGATGAGACCTCGGGAACCGCGTGATGGGGCGGAGGGGTCGGCGCTCGGC TCCGCCTAG | 11478 |
| | 4 | MRGGMRPRDRVVGGGGRRSAPPSST* | 11479 | ATGCGGGGGATGAGACCCCGGGACCGCGTGGTGGGTGGGGCGGAGGGGTCGGCT CGGCTCTCGCCTAGTAGCACGTAG | 11480 |
| | 1 | MGTLPDLFPGGVSAVSFSP* | 11481 | ATGGGTACTCTCCCGGATCTCTCCCGGTGGGGTCTCTGCTGTTCCTTCCTGA | 11482 |
| | 2 | MRPRSSREGQWRPGEAGEASAWVAAVPPCGTKSPRVP STWDQRNSCSWPEWESGKWGTRMFLGGLDRGQLPDFDA TGHRVLSTPFSVSVSVSPCLRFLLLFCLGLHFSLRPPFQ LRSCPFPPTPADGRPGSCGJAGGGGGRCEAAWKRRRQQ PGGGVGCYLWLSSCMSGVESS* | 11483 | ATGCGCCCCTCGATCTTCCAGAGAAGGCAGTGGAGACCCCGGCGAGCTGGGAGGC CTCTGCCTGGGTCGCTGCATTCTTCCGGGTGCACGAAAAGCCGGCGTCCTTC CACCTGGACCAGCGGAACTCGCCCTCTGCCCGAATGGAGAGCGGGGAAATGG GCACCAGAGAACTTTTGGTCTGGATCGGGGTCAACTCCCGACTCGAGCGCACGG TCATCGCGCCTTCCACGCCTTTTGCGTCTCTGGTCTGTATCTCCGTGTCT GAGGTTTTGTTTTGTTTGCCTGGACTTCATTTCTCTCTTCACCCCACCAAC TCCACPTCCTGCCCTCCCTCTCCACTCCGCTGACGCGACGGGAAGCTGCGAG GTGCTGGCGGCGGCGGCGGCGGACGGAAGAGGCGGCGACAGCAGCC AGGAGCGGGGGTTGGTTGTTATCTTTGGTTATCTAGCTGTATAAGTGTGGAGTC TTCATATA | 11484 |
| hsa-mir-9-1 | 2 | MGEREMGHQKLFGSGSGSTPRLRRHGSSRPFHAFFGLC RVCISVSEVPVVVLSRTSPLSSPSPSTPLVSLPSYSR* | 11485 | ATGGGAGAGCGGGGAAATGGGGCACCAGAAACTTTTTGGGTCTGGATCTGGGGTCAAC TCCCCGACTTCGACGCCACGGGTCATCGGGTCATCCACGCCTTTTGCGGCCTCTCGT CGTTCTCGTATCCGTGTCTGAGGTTTTTGTTGTTTTGTCTCGGACTTCATTTC TCTCTTCACCCTCCCCCCCAACTCCACTCGTGTCCCTCCACTCCGGCTGA | 11486 |
| | 3 | MGPFLAVWVTAWEADLREKSVEI* | 11487 | ATGGGGCCTTTTCTGGCAGTCTGGGTCACGTGGGAAGCTGATCTAAGGAGAGAAA TCAGTTGAAATCTAG | 11488 |
| | 4 | MYLIAKDFSTLFSYVFFNCKLLGF* | 11489 | ATGTATCTGATAGCTAAGGATTTCAACTTATTCTCTTACGTATTTTTCAACTGTA AATTATTGGGCTTTAA | 11490 |
| | 1 | MDGINCC* | 11491 | ATGGATGGAATTAATTGCTGTTAG | 11492 |
| hsa-mir-92a-1 | 2 | MELIAVRRLENSKYRFGRW* | 11493 | ATGGAATTAATTGCTGTTAGGAGGTTGGAAAATAGCAAATAGATTTGGACGGTG GTAG | 11494 |
| | 3 | MFYLFPFYFSLPQSYTWT* | 11495 | ATGTTTTATCTTTTTCCTTATTTTCCTATTCCAGTCATACACGTGACCTAA | 11496 |
| | 4 | MYERFCSGFILHPFPPSLPPACLPGLSSSDPACSLVSDL* | 11497 | ATGGTGGAAAGGAGGGGTCCAGGGCTTCCATTTGCACCCTCCTTCCTGCCC CCGGCTTCCTCCAGGGCTTTCCTCCTGGACCCAGCGTGCTCACTGGTCTCTGATTT TGTAA | 11498 |
| hsa-mir-92a-2 | 1 | MLNSLIVRLKLRHHFILQSAVGLWP* | 11499 | ATGCTTAATTCCATTTGATTGTGCGTCTTAAACTAAGACATCATTTATTCTACAGA GCGCTGTCGGGCTTTGGCCTTGA | 11500 |
| | 2 | MRGESKHAPYLPHICACIRWLLPLTIPAKKP* | 11501 | ATGAGAGGAGAAAGCAAGATAATTGCACCGTATCTCCGCACATTGCGCGTGTATT CGGTTGCTGCTACCGTTAACGATACCTGCCAAGAAACCCTGA | 11502 |
| | 3 | MCRE* | 11503 | ATGTGCAGAGAGTAA | 11504 |
| | 4 | MELSGWGPEVCGRGTEVCGRGRWNVGGVGHVLCGP LCT* | 11505 | ATGGAGCTAAGCGGGTGGGGTCCTGAGGTATGTGAAGGGCACCGAGTATGTGG GAGAGGACGTTGAACGTGGGCGGGGAGTTGGACACGTTCTGTGTGGGCCGTTAT GTACTTAA | 11506 |

Figure 1 (Continued)

| | | | | |
|---|---|---|---|---|
| hsa-mir-92b | 2 | MWKGHRGMWERTLERGRGSWTRSVWAVMYLRGRSGVARWLTFVIPTLWKAEASGSQGQGFKTSLAKMVKPRLY* | 11507 | ATGTGGAAGGGCACCGAGGTATGTGGGAGAGGACGTTGGAAGAGGACGTTGGAACGTTGGGCGGGGAGTTGGACACGTTCTGTGTGGCGTTATGATGCGTTATGTACTTAAGAGGCAGATCGGGCGTGGCACGGTGGCTCACGCCGTAATCCAACACTTGAAGGCGAGCCGAGTGGATCACAAGGTCAGGGGTTCAAGACCAGCCTGGCCAAGATGGTGAAACCTCGTCTCTACTAA | 11508 |
| | 3 | MGFTDTELSFGEQSGKGDR* | 11509 | ATGGGATTTACGGACACAGAACTATCCTTTGGGAGCAGAGTGGTATTGGGGACAGGTAG | 11510 |
| | 4 | MRDSQEVCAAAVHEGRKLSQAAAARGTWVPQSQAAL* | 11511 | ATGCGCGACAGCCAAGAGGTGTGTGCGCAGCAGTGCACGAGGGGAGGAAGCTATCCCAGGCCGCGGCAGCACGTTGGGAACTTGGGTCCGCAGTCGCAGGCTGCGCTCTAG | 11512 |
| hsa-mir-93 | 1 | MANGWTGSRPGRRNPEL* | 11513 | ATGGCCAATGCTGGACTGCCTCCCGCCCTGGCGTGAGGAATCCGAGCTGTGA | 11514 |
| | 2 | MAGLAPALGGGHPSCEAAGIRAHVLLCLLRAEAMAGAGVGCGGGVRWRRSR* | 11515 | ATGGCTGGACTGGCCCTCGCGCCCCTGGGCGGGGAGGAATCCGAGCTGTGAAGGCGGCTGGAATCCGGGCCATGTGCTCTTGTTTACTAAGAGCGGAAGCGATGGCGGGAGCGGGGTGGGTGCGGTGCGGTGGGTGCGGTGGTCCCGGTGA | 11516 |
| | 3 | MCFFYY* | 11517 | ATGTGCTTCTTTGTTTACTAA | 11518 |
| | 4 | MLDGPVHCHGLFLRWLETDL* | 11519 | ATGTTGGATGGCCCTGTGCACTGCCACGGGCTCTTTATTCTTCGCTGGTTAGAAACAGACTTGTGA | 11520 |
| hsa-mir-99a | 1 | MLPQLMYHQLSLA* | 11521 | ATGTTGCCTCAGTAGTGTACACCAACTTTATTTAAATGTTATTTTAGCAGCATTAA | 11522 |
| | 2 | MFQDPFKNIILNVIFSSH* | 11523 | ATGTTTCAAGATCGTTAAAACATTATTTAAATCTCTACACTCTTATATCTTATTAAGCTCCATGCCAAATCCAAATCTCTGTCCTTTCAGCTTTCAGCTTTCATTGTCAAAACCTAGTCGCTTCTTTAACAGCAGCCATGCAAATCCAAATCCAAATCTCTTACTTCAGCTTTCAGCTTTCATTGTCAAACCTAG | 11524 |
| | 3 | MLFLAAINLYTLNYLIKLHAKSKSLFSPRYPIVQNLVASLTAIVLSLSKLLL* | 11525 | ATGTTATTTTAGCAGCATTAATCTCTACACTCTTATATCTTATTAAGCTCCATGCCAAATCCAAATCTCTGTCCTTTCAGCTTACTTCATTGTGCAAAACCTAGTCGCTTCTTTAACAGCAGCCATGCAAATCCAAATCTCTTCAGCTTTCAGCTTTCATTGTCAAAACCTAG | 11526 |
| | 4 | MPNPNLPSAFATSLCKJ* | 11527 | ATGCCAAATCCAAATCTCTTCAGCTTTCAGCTTTCATTGTCAAACCTAG | 11528 |
| | 1 | MAGTAGGRGEAAVRRRGEDGERSAAVGPGLRARGGGEDPPPATREPREP* | 11529 | ATGGCGGGACGGCGGGAGGAAGGGAAGAGGGGAGAGGGCCGTGCGGAAGGCGGGAGGCCGTGCGGGAGGGGGGGGGGGAGGATGGAGAGCCGCTCGGACGGCGGGGACGCGCGGAGCGGGGAGCCGTCGGTGA | 11530 |
| | 2 | MESARRRWGPACGPGAAEKTPSLRRGSRGSRESAEREGGGLGPALLGP* | 11531 | ATGGAGAGCGCTCGGACGCGGTGGGCCCGGCCTGCGGGGGCGGGAGAAGACCCCTTCCTCGGACGCGGGAGCCGTGAGTCTGCGACTCTGGGTCCTGAGGTGGGGCTGGGGCTGGACGCCGCACTCTGGGTCCTGA | 11532 |
| | 3 | MGAGAGRIVAGRD* | 11533 | ATGGGGGCTGGGGCTGGTTAGGATCGTGGCTGGAAGAGACTAG | 11534 |
| hsa-mir-99b | 4 | MGLRGFEGSRVSRASGRGPRRRGRLSGLPDRPGSAAGAGDVWRRRGPASMLPRGPGIPGPRPLLPQIWEYTTQSPTHSRIRAPSPLFSRIQESEPPVCSLRPGNPHASSP* | 11535 | ATGGGGCTGCGGGGCTTGAAGGGTCAAGGGTGAGCGTGCCAGTGGAGGTGAGGGCCGAGGAGGAGGGGGGGCCGAGGAGGGGAGTTGTCTGGGCTGCCAGACAGGCCAGGTTCAGCGCGGGGGCGGAGAGAGATGTCTGGAGGAGGAGGGCCATCCATGCTGCCTCCGGGACCCCGGCGCCAGGTCCCAGACCCCTCCGAGCCGCCAGCAGATCTGGAGTACACCAGTCCCGATCCAGGTCCCAGAATCCGAGCCGCCAGCCGTTTCCAGGATCCAGGAGTCTGACACCCATTCCAGTCTGTTCTCTCAGACCAGGAATCCACTCCACTCCAGCCCTAA | 11536 |
| | 1 | MAAPPARADADPSFTSPPTARDTPGRQAEKSETACEDR* | 11537 | ATGGCTGCGCCCGCCCGGCCCGCGCCGGACGCTGATCCTTCGCCCACGTCGCCACCTACGCCCGAGACACACCAGGCGCGGCAGGCCGCAGCCGCGTGCGAGGACGGGTAG | 11538 |
| | 2 | MLSARGVALPDPRGQGLGFGGAAAHGAFGLPRTRVAPSSLCGGFARA* | 11539 | ATGTTGTCGGCTCGGGGTGTGGCCCTGCCCGACCCGCGGGGTCAGGGTCTGGGGTTTGGCGGCGCCGCGCACGGCGCGTTCGGATTGCCGCGGACCCGGGTCGCTCCGAGCAGCCTCTGCGGGGGCTTTGCAAGAGCATGA | 11540 |

Figure 1 (Continued)

| | | | | |
|---|---|---|---|---|
| hsa-mir-647 | 3 | MKWGSCGGAAGGTRPHPGSSPRVAPLGAGPCAAPLGP WPSGGGGHAVPGAARGRSGRCPSLPGLKCPLGSPRGPQ EGVVPTQAPLAWVQAVTPVRNAVSQDSLRDGLRWMP QGEGCPGTGSLLSRSC* | 11541 | ATGAAGTGGGAAGTTGTGGGGTGCAGCGGAGGAACCCGCCACCCGGTTC GTCACCCCGAGTGGGCCCTCTGGAGCCGGACCCAGTGCCCGGCCGT GCCGTCAGGGGCGGTGGCCACGCAGTGCCGGGCCTGAAGAGGGCCTCTGGG CCCTGCCCCTCCCTTCCGGGTCTGAAGTGTCCTTGAAGTCCTTGGGAGCCGCGGGGTCCCAG GAAGGGGTTGTTCCCACTCAGGCGCCCTCTTGCTGGTTCTGGGTTCAGGCTGTGACTCGTC AGAAACGCTGTGAGCCAGGACTCCGCTGAGATGGCTGCCGCTGAATGCGCAGAGG GGAAGGGGTCCCGGCACAGGGTCGCTCCTCTCCCAGGAGCTGCTGA | 11542 |
| | 4 | MGCAGCRRGKGVPAQGRSSPGAAEQKELSPGPASLQV HTLPVGSD* | 11543 | ATGGGCTGCGCTGATCGCCAGGGGAAGGGTGTCCGGCACAGGTCGCTCCTC TCCAGGAGCTGCTGAAGCAGAAAGAGTTTCCCTGGCCCTGCGTCCCTTCAGGTCA CACCCTCCCAGTGGGCAGTGACTAG | 11544 |
| hsa-let-7e | 1 | MSGGGEAQHPCSLGDPGFQVPDPSSLRSGSTPPSPPPIPE SEPPAPFFPGSRSLSPQSYLSDQGIHTPAPNSFKTPEFRTS APLPKERGPQOPSVPLEPKRSGGIFLPLKPAVLGIPRPLLL RNPGVPTSSLAPAGVQPSRG* | 11545 | ATGTCTGGAGGAGGAGAGGCCCAGCATCCATGTCTCCCTGCGGGACCCGGATTCCA GGTCCCAGAACCCTCCTCCCTCAGCCCTCCCAGATCTGGGAGTACACCACCAGTCCCCACCCAT TCCAGAATCGAGCCCCAGCCCTCCCAGCCCCCTTTTCCAGGATCCAGGAGTCTGAACCCCA GTCTGTTTCTCAGACCAGGAATCCACACTCAGCCCTCCAACTCTTCAAAACCC AGAGTTCGAACCAAGCGTTCAGGCTTCGGCATCTTCTCCTTGAAGCCTGCAGTTCT TCTAGAACCCAAGCGTTCAGGCTTCGGCTCCTCCGAACCCAGGAGTCCCACCCTCCTCTTTAGC GGGATCCCAGGCCCTCCAGCCTTCCAGGGGTTAA | 11546 |
| | 2 | MLPRGPGIPGPRPLLPQIWEYTTQSPTHSRIRAPSLFSRI QESEFPVCSLRPGNPHSSP* | 11547 | ATGCTCCCTCGGGGACCCGGGATTCCAGGTCCAGACCCCTCCCTCAGATCTGG GAGTACACCACCCAGTCCCACCCACATTCCAGAATCCGAGCCCAGCCCCTTTT TCCAGGATCCAAGGAGTCTGAGCCCCAGTCTGTTTCTCAGACCAGGGAATCCACAC TCCAGCCCCTAA | 11548 |
| | 3 | MVPDCLGLLSDFWGLPRVRREGEGDLGLGEVQSLPLPQ SGAMGPGSSRFHQRLVQ* | 11549 | ATGGTCCCAGACTGTTTGGGTCTGCTCTCTGACCCTTGGGGCTCCCAGGGTCGCG AGAGAGGGGAGGGGACTAGGCCAAGCCTAGGCAGTTCGCGTTCACCAACGCTTGTCCAGTGA AAGCGGCTATGGGCCAGGGAGTTCGCGTTCACCAACGCTTGTCCAGTGA | 11550 |
| | 4 | MLRSGESLRFSASPLPSPSSSGPRQPRGMLGTQAAWAPGQ VGVGGWGRCQPPPFPLPTLA* | 11551 | ATGCTTAGGTCCGGGGAATCTCGAGATTCTCGCCTCCCCTCCCTCACCCCTCCT CCTCAGCCCGTCAGCAGCCCGGGCATGCTGGGAACCCAGCCTGCGCCTGCGGC CAGGTTGGTGTGGGGATGGGGTGGGAGCAGCCTCCTGCCCCC ACCTTGGCCTGA | 11552 |
| hsa-let-7i | 1 | MALAEVYVCAVGRVVTLPAVEITAQATALLVLVMLSA AEDNGWESPLFSGALPGDSPRSLGARPARPPRKPLVSHF PRRN* | 11553 | ATGGCTCTGGCTGAGGTAGGTAGTAGTTGTGCGTGTTGTAGTGCCGGTGTGCCGCT GTGGAGATAACTGCGCAAGCTACTGCCTTGCTAGTGCTGGCTAGTGCAGCGCGCGG GAGGACAATGGCTGGGAATCCCCTCTGTTTCCGGGGCGCTGCCTGGGGACAGCC GCGAAGCTCGGCGCCCGGCTGGCGGCCACCACGGAAACCGTTAGTTTCACATTT TCCTAGAAGGAATTGA | 11554 |
| | 2 | MAGNPLCFPGRCLGTAREASAPGRRGHHGNR* | 11555 | ATGGCTGGGAATCCCCTTGTTTCCGGGGCGTGCCTGGGGACAGCCCGGAAGCC TGCCGCCGGCGCGGCGCCACCACGGAAACCGTAG | 11556 |
| | 3 | MHFKGWERAKPLDSFS* | 11557 | ATGCATTTTAAAGGTTGGAAAGAGTAAGCCATTGGATTCCTTTCTTGA | 11558 |
| | 4 | MPNLVCTCFTSFFSCRLEWCERSAELALEGQEK* | 11559 | ATGCCAAATTTAGTTGTTACCTGTTTTACTTCATTCTTTAGCTGTAGGTTGGAGTGGT GTGAGCGATCTGCAGAACTGGCATTAGAGGGGCAGAAGAAGTAG | 11560 |
| | 1 | MLWFTKRETDFF* | 11561 | ATGCTCTGGTTCACCAAGAGAGACTGATTTTTTAA | 11562 |
| | 2 | MLRHHHHHTFLIMVISSCQVERPPAPARLLRLPQRRQQA VRAWPWRPLPGCFLHLQHPPYSSACVLSRSFSFQ* | 11563 | ATGCTCATCATCATCATCATCATCACTGTCCTTATCATGGTTA TCATTTCCTCTGCCAGGTGGAGCGCCCAGCCGCGCGCCCGGCCGCTCGCCTTC CCAGCGAAGGCAGCAAGCAGTTCGGGCTTGGCCGTGCCGCCGGGCCGGATGC TTCCTGCACCTCCAGCATCCCCCCCTTATTCATCTGCCTGTGATTATCTCGATCCT TTTCATTTCAGTAG | 11564 |

Figure 1 (Continued)

| | | | | |
|---|---|---|---|---|
| hsa-mir-124-1 | 3 | MLPAPPASPPLFICLCIISILFISVDPLPLVGPAESLGTAAS LLKKENKKPKTLCGRRDKAPWVRREGITRRSAEPRTRV AAEGRPPGVRMAEGIRTVFYLSLWLAFTVST* | 11565 | ATGCTTCCTGCACCTCCAGCATCCCCCCCTTATTCATTCTGCCTGTATTATCTCGA TCCTTTTCATTCAGTTAGATCCACTGCCTTTGGTTGGGCCGCTGAATCGCTGGGGA CTGCGGCCAGTTCCTTAAAAAAGGAGAACAAAAAGCCAAAAACCTTGTGTGGCGC CGGGACAAAGCCACCTTGGGTTCGGCGAGAAGGGACGGCGAGGAGCGCTGAACCCAG AACACGCGTGGCCGCTGGCCGCGTTGCCCGGGCTGCGGAACGCTGAGGGTA TTCGGATTGTCTTTTATTGTCCCGTGCCTTGCCTTTCACAGTGTCTACGTAG | 11566 |
| | 4 | MRIGLERGQGTQGLEKRRSPLLPCGGLRE* | 11567 | ATGCGGGGGTTGGAAAGGAGACAGGGGACTCAAGGCTTAGAAAAGAGAAGGAGCC CTCTGCTGCCTGGAGGGCTAAGGGAGTAG | 11568 |
| | 1 | MSGGGEAQHPCSLGDPGFQVPDPSSLRSGSTPPSPPPIPE SEPPAPFFPGSRSLSPQSVLSDQIHTPAPNSPKTIPEFRTS APLPKERGPQPSVPLEPKRSGSGIFLPLKPAVLGIPRPLLL RNPGVPTSSLAPAGVQPSRG* | 11569 | ATGTCTGGAGGAGGAGAGGCCCAGCATCCATGCTCCCTCGGGGACCGGGATTCCA GGTCCCAGAATCCGAGCCCTGGGACCCAGAGCCCCCTCCCAGCCCCCA TCCAGAATCCGAGCCCCCAGCCCCCAGCCCTTTTCCAGATGCAGTCCAGGAGTCTGAGCCCCA GTCTGTTCTCTCAGACCAGGAATCCACACTCCAGCCCTACTCCTTCAAAACCC AGAGTTCAGAACCTGCAGTCCAGCGCCCTCCCAAGGAGCGCGCCCAACCTCTGTTCC TCTAGAACCAAGCGTTCAGGCTCCAGCATTCTCCCTTTGAAGCTGCAGTTCT GGGGATCCCCAGCCTCCTCTCTCCTCGGAACCCAGGAGTCCCCACCTCTCTTTAGC CCCAGCTGGAGTCCAGCCCTCCAGGGGTTAA | 11570 |
| hsa-mir-125a | 2 | MLPRCPGIPCGPRPLLPQIWEYTTQSPTHSRIRAPSPLPSRI QESEPPVCSLRPGNPHSSP* | 11571 | ATGCTCCTCTGGGACCGGGATTCCAGTTCCAGACCCTCCTCCTCCTCCAGATCTGG GAGTACACACCAGTCCCACCACCAGGACCTCAGATCCAGCCCCCAGCCCCTTTTT TCCAGGATCCAGGAGTCTGAGCCCCAGTTCTGTTCTCTCAGACCAGGAATCCACAC TCCAGCCCCCTAA | 11572 |
| | 3 | MVPDCLGLLSDPWGLPVRREGEGDLGLGEVQSLPLPQ SGAMCPGSSSRFHQRLVQ* | 11573 | ATGGTGCCAGACTGTTTGGGTCTGCTCCTGAACCTTGGGGTCCCAGGGTGCCGC AGAGAGGGGAGGGGAGGGGACCTAGGCTGGGGAAGTCCAGAGTCAGACCAACCGCTTGTCCAGTGA AAGCGGGGCTATGGGCCCAGGGAGTTCGCGTTCCACCAACGCCTTGTCCAGTGA | 11574 |
| | 4 | MLRSGESLRFSASPLPSPSSSGPRQPRGMLGTQAWAPGQ VGVGWGRGQPPPPFLPTLA* | 11575 | ATGCTTAGGTCCGGGAGAATCTGAGATTCTGAGCTTCCCTCCCTCCCTCACCTCCT CCTCAGGCCCAGCAGCCCCGGGCAGCCCGGCATGCTGGGAACCCAGGCCTGGGCTCCGGGC CAGTTGGTGTGTGGGGCGGGGTGGGGGCGGGGCAGCCCTCCCTTCCCCCTTCCCCC AACCTTGGCCTGA | 11576 |
| | 1 | MRVGKSVCVAGRERLPGVGEGGSEAAGRRSRGFGGPA WTATWAS* | 11577 | ATGAGGGTGGGTAAATCGGTGTGTGTCGCGGGTCGGGAAAGGCTGCCGGGGGTAGG GGAAGGTGGCTCAGACGCGGCGGCGGCCGACGGTCGAGGGCTTCGGAGGGCCTGCTTT GGACTGCAACCTGGGCTCGTGA | 11578 |
| | 2 | MGARDLQLFRRDPGPEAA* | 11579 | ATGGGAGACCAGGAGATCTGCAGCTTTCCGCAGGGATCCTGGGCCTGAAGCTGCCTGA | 11580 |
| hsa-mir-141 | 3 | MMEAPVPVSATSIASGPQPLAGCSPLPTSHAPRKPLVLS* | 11581 | ATGATGGAGGCCCCGTCCGTCCGTCAGCAACATCCATGCCTCAGTCCCAGCCC TTAGCTGGCTGCAGCCCCCACTTCCCACGCACCCCGGAAGCCCCTCGTCTTG AGCTGA | 11582 |
| | 4 | MGPSPSSHPVRFVTWWRQNPQSTLSLGLARPLSRDLTW PVARVPCSNW* | 11583 | ATGGGCCCCAGCCCTCCTCCACCAGTGCGATTTGTCACTGGTGGATCCAGAAC CCACAGTGACCTTGAGCTTGGGGTTGGCTCGCCCCCTCAAGAGACCTCACCTGG CCTGTGGGCCAGGGTCCCGTAGCAACCTGGTGTGA | 11584 |
| | 1 | MGWDGFWGGVPNSDWEWRNPS* | 11585 | ATGGGCTGGGACGGGTTTGGGGGGGTGTCCCAATTCTGACTGGGAGTGGAGGAA CCCCTCCTGA | 11586 |
| | 2 | MRLGRLLSPAPQM* | 11587 | ATGCGACTGGGGCGGCTCCTTTCTCCTGCACCCCAAATGTGA | 11588 |

Figure 1 (Continued)

| | | | | |
|---|---|---|---|---|
| hsa-mir-195 | 3 | MHPKFCSFQNRGPGSQGRVAEVSGEGSVLCFQERRGG WGGGLEVRAGVGLALSVLELGG* | 11589 | ATGCACCCTAAATTTGTCTCTTTCAAATAGGGACCAGGATCTCAGGGGAGAGTA GCTGAGGTAAGTGGGGAGGGAAGTGTCCTCTGTTTCAGGAGAGACGTGGCGGTG GGGGGAGGTTGGAGGTGCGTGCGTGGGGTGGGGGTTGGCTTTGTCAGTCTTGGAAT TGGGGGATGA | 11590 |
| | 4 | MIGEAFSYTPKLQPPRRKPKAETREPPNIPSR* | 11591 | ATGATTGGAGAGGCTTTCTTCTTATACCCTAAACTGCAGCCCCCAGACGGAAACCA AAGGCTGAGACCAGAGAGCCCCAACATCCCAGCCGTTAG | 11592 |
| | 1 | MQKPLLY* | 11593 | ATGCAGAAACCCTTCTCTACTAA | 11594 |
| hsa-mir-200a | 2 | MNPGGRACSEPRLCHCTPAWATETDSISKKKKLASVS PSASCPSIKFFLLRQRESRPLLTYFGAETQHSASNRALK AHLSSTLHLGTRNPQPEW* | 11595 | ATGAACCCGGGAGGCAGAGCTTGCAGTGAGCCGAGATTGTGCCACTGCACTCCAGC CTGGGCGACAGAGACAGATCCATGTCCTCCATCCATCAAAAAAAAAACTGCCTCAGTCT CTCCTTCAGCCTCATGTCCTCCATCCATCAAATTCTTCTTCTGAGGCAGCGAGAATCGAG GCCGCTGCTGACATACTTTGGTGCTGAAACTCAGATACATTCTGCCAGTAATAGAGC TCTGAAGGCTCACCTGAGCTCCACCTCGGCACACGCAACCCTCAGCCAGA GTGGTGA | 11596 |
| | 3 | MSFHQILSSEAARIEAAADILWC* | 11597 | ATGTCCTTCCATCAAATTCTTCTTCTGAGGCAGCGAGAATCGAGGCCGCTGCTGAC ATACTTTGGTGCTGA | 11598 |
| | 4 | MSHF* | 11599 | ATGTCCCACTTCTGA | 11600 |
| | 1 | MQKPLLY* | 11601 | ATGCAGAAACCCTTCTCTACTAA | 11602 |
| hsa-mir-200b | 2 | MNPGGRACSEPRLCHCTPAWATETDSISKKKKLASVS PSASCPSIKFFLLRQRESRPLLTYFGAETQHSASNRALK AHLSSTLHLGTRNPQPEW* | 11603 | ATGAACCCGGGAGGCAGAGCTTGCAGTGAGCCGAGATTGTGCCACTGCACTCCAGC CTGGGCGACAGAGACAGATCCATGTCCTCCATCCATCAAAAAAAAAACTGCCTCAGTCT CTCCTTCAGCCTCATGTCCTCCATCCATCAAATTCTTCTTCTGAGGCAGCGAGAATCGAG GCCGCTGCTGACATACTTTGGTGCTGAAACTCAGATACATTCTGCCAGTAATAGAGC TCTGAAGGCTCACCTGAGCTCCACCTCGGCACACGCAACCCTCAGCCAGA GTGGTGA | 11604 |
| | 3 | MSFHQILSSEAARIEAAADILWC* | 11605 | ATGTCCTTCCATCAAATTCTTCTTCTGAGGCAGCGAGAATCGAGGCCGCTGCTGAC ATACTTTGGTGCTGA | 11606 |
| | 4 | MSHF* | 11607 | ATGTCCCACTTCTGA | 11608 |
| | 1 | MRVGKSVCVAGRERLPGVGEGGSEAAGRRSRGFGGPA WTATWAS* | 11609 | ATGAGGGTGGGTAAATCCGTGTGTGTCGCGGGTCGGGAAAGGCTGCCGGCGGGTAGG GGAAGGTCGCTCAGAGGCGGGACCGGTGGCGGGCCGACGGTCGAGGGGCTTCCGAGGGCTGCTT GGACTGCAACCTGGGCCTCGTGA | 11610 |
| hsa-mir-200c | 2 | MGARDLQLFRRDPGPEAA* | 11611 | ATGGGAGCAGGGATCTGCAGCTTTCCGCAGGATCCTGGGCCTGAAGTGCCTGA | 11612 |
| | 3 | MMEAPVPVSATSIASGPQPLAGCSPLPTSHAPRKPLVLS* | 11613 | ATGATGGAGGCCCCTGTCCCTGTGTCAGCAACATCCATCGCCTCAGGTCCCCAGCCC TTAGCTGGCTGCAGCCCCACTTGAGCTTGGGTTGGCTGCCCCCTCGTCAAGAGACCTCACCTGTCTTG AGCTGA | 11614 |
| | 4 | MGPSPSSHPVRFVTWWIQNPQSTLSLGLARPLSRDLTW PVARVPCSNW* | 11615 | ATGGGCCCCAGCCCCTCCTCCCACCAGTGCGATTTGTCACCTGGTGGATCCAGAAC CCACAGTCGACCTTGAGCTTGGGTTGGCTCGCCCCTCTCAAGAGACCTCACCTGG CCTGTGGCCAGGGTGCCCCGTAGCAACTGGTGA | 11616 |

Figure 1 (Continued)

| | | | | | |
|---|---|---|---|---|---|
| hsa-mir-210 | 1 | MDGVCLSGGQQGRRVGVSEHRGLCCPLGGAEAGPDTL LEGTFFSLCVQGTSVRSSCCQAEGGPGQAQVWSYLQFT GPSSGGPPLCTSYGERVTDLVLLCVSAASVGPLRETAG GSSSSLSAEPAFSSLLLKSGPGRVRAYRPCLRSPGLQEFLR AAPARWRGRGRFSGRLAWTRTGLWKLPALTGLPVTTA K* | 11617 | ATGGACGGGGTGTGCCTGTCTGGCCAGCAGGGACGGCGGTGGGGTAAGCGAAAT CATTCTGGGGGCTTTGCTGCCCCTCCGTTGGTGTGTCCAGGGTACCAGTGCGGAGTTCCTG TTGCCAAGCTGAAGTTCTTTCCTTGTGTGTCCAGGCACAGTGTGTCATATCTCAGCGAC AGGACCATCCTCCGAGRGCCACCTCTGGGACTTCCTACGGAAGAGAGTGACAG ATTTGGTGCTTCTGTGTTTCGAGCCTCAGTGGGCGCTGCTTCCAAGTGACAGGCGG GTGGATCTCCAGCAGGCTGTCTGCTGCAGCCGCTACACAGGCCCTGTCTCCGTCCCAGGCTACTGTTAAAT CAGGACCCGGTCGTGTGGACCCTACACGGCCCTGTCTCCGTCCCAGGCCTGCAGG AGTTGAGGGCTGACCATCGCGTGCGCTGGAGAGGGAGAGGCAGATTTAGTTGGACGCTG GCATGGACTGGACTGGCCTTTGGAAGCCTTTGGAAGCCTCCTGCCCTGACGGGGTTGCTGTCACC ACTGCGAAGTGA | 11618 |
| | 2 | MDSDWPLEAPCPDGVACHHCEVRLGRTCT* | 11619 | ATGGACTCGGACTGGCCTTGGAAGCCTTTGAAGCCTCCTGCCCTGACGGGGTTGCCTGTCACAC TGCGAAGTGAGGCTTGGCAGGACCTGCACCTGA | 11620 |
| | 3 | MSRNSGRGGSQRRPSIQPGSALCPYLHQVGSLPCIAWGI AGLGPALLWNWMFSGSPAFPHVNTVHNIVFKVQFKTQ K* | 11621 | ATGAGTAGGAACTCTGGGCGAGGAGGGTCCCAGCCGCCCTCTGCTGACCAGGGTC CTCTGCCCTGCCCCGTACTTACACAGGGATCCTCCTGCCCTGCATTGCCTGGGG ATTGGCTGGGCTTGGCCCCGCCCGTGGACCTGATGTTTCAGGGAGCCAGC CTTTCCTCATGTCAACACAGTTCACATATAGTTTCAAAGTACAGTTTAAAACTCAA AAGTAA | 11622 |
| | 4 | MSTQFT1* | 11623 | ATGTCAACACAGTTCACATATAG | 11624 |
| hsa-mir-223 | 1 | MGMRSEGEENKDEEKRKCE* | 11625 | ATGGGAATGAGGAGTGAGGAGTGAGGGAGAAGAGAATAAAGATGAAGAAAGAAATGTG AGTAG | 11626 |
| | 2 | MKRKENVSRKWYKDKEMDLIGEGEK* | 11627 | ATGAAGAGAAAAGAAAATGTAGTAGAAAAATGGTACAAGGACAAGGAAATGGACTT AATAGGAGAGTGGAGAGAAGTGA | 11628 |
| | 3 | MVQGQGNGLNRRGREVNEKKRRGDR* | 11629 | ATGGTACAAGGACAAGGAAATGGACTTAATAGGAGAGTGGAGAGAAGTGAATGAGA AAAAAGGAGGAGGAGACAGATGA | 11630 |
| | 4 | MRKKGEETDEERRKNFK* | 11631 | ATGAGAAAAAAAGGAGGAGGATACAGATGAAGAAGAAAAATTTAAGTAA | 11632 |
| | 1 | MAPFGLPRAQ* | 11633 | ATGGCCCCATTGGCTGCCCAGGCTCAATGA | 11634 |
| | 2 | MRGELGHASCCSLLVPHGPSRYLCLSSPGAGTEGTARL QLPVWWLLHMRKELPCTDQRKHLGTWRGGVPKSHYLL CSLSLSPLQVPASGPARCPPHPCATAGWGSWGWDLLPV TNHIARDFQPTLSSATEDAARGRGGREAPKPVPGLRSRA * | 11635 | ATGAGGGGAGCTTGGCCATGCAAGTTGCTTGTAGCCTCCTTGTCCGCATGGGCC TCTAGGTATCTCCCGTCCAGTCGTCGCCTCCGACTCGAACGGACTCCTGTGATCAAAGG AGCATCTGGGGAACCTGGAGGGAGGTGTCCAGCCTGCCAGCCTCCAAATCTCATTACCTCTTTGCTCT CTGTCTCTTTCTCCCCCAGCAAGCGCGCTTGGCCCGTGCTCCAGCTCGGCTGGGATTCCTGGGATCGATTGCTTCCTGTGTCACAAATC ACATTGCCAAGGATTCCAACGACCCTGAGCTCTGCACCAAGGATGCTGCCGGG GACGGGTGGCAGAGAGCCCGAGCCTGCCTGGCCTGGCAGCCTGAGGAGCAGGGCTTAG | 11636 |
| | 3 | MQVAVASLSRMGPLGISASPVLGLERRAQLGSSSPCGG SCI* | 11637 | ATGCAAGTTGCTTGTAGCCTCCTTGTCCGCATGGGCCCCTCTAGGTATCTCTGCCTCTC CAGTCGTGGGCTGGAACGGACAGGGCACAGCCTAGGCTCCAGCTCCCGTGTGGTGGC TCCTGCAATATGA | 11638 |
| | 4 | MGFASCHKSRCQGFPTDPELCHRGCCPGTGWQRGPEA CAWPEEQGLAACEQGFHQVVFTVAKFRPPGPHLLWPC RLSPAAACLPAIHLPGLPGLCPCLLS* | 11639 | ATGGGATTTGCTTCCTGTCACAAATCACATTGCCAAGGATTTCAACCGACCTGAG CTCTGCCACGGAGGATGTCGCCGGGGACGCGGGTGGCAGAGGCCCGAGGCCTG TGCCTGGCCTGAGGAGCAGGGCTTAGCTGCTTGTGAGCAGGGCTTCCACCAAGTCG TGTTCACAGTTGCTAAGTTCGACCCCACCAGGCCCCATCCCTGGCTTCGCGCCT GTCCCCTGCTGCCTCCATCCGCTCCCATCCTGCCTGGCCTCCTGGGCTCTGC | 11640 |
| | 1 | MAPFGLPRAQ* | 11641 | ATGGCCCCCATTGGCTGCCCAGGCTCAATGA | 11642 |

Figure 1 (Continued)

| | | | | |
|---|---|---|---|---|
| hsa-mir-24-2 | 2 | MRGELGHASCCSLLVPHGPSRYLCLSSPGAGTEGTARL QLPVWWLLHMRKELPCDQRKHLGTWRGGVPKSHYLL CSLSLSPLQVPASGPARCPPHPCATAGWGSWGWDLLPV TNHIARDFQPTLSSATEDAARGRGREAPKPVPGLRSRA * | 11643 | ATGAGGGGGGAGCTTGGCCATGCAAGTTGCTGTGCCCTCCTTGTCCGCATGGCCC TCTAGGTATCTCTGCCTCTCCAGTCCTGGGCTGGAACGGAGGCAGCTAGGCTC CAGCTCCCGTGTGGCTCCTGCATATGAGAAAGAGCTTCCCTGTGATCAAAGG AAGCATCTGGAGGACCTGAAGGGAGGTGTCCCAAATCTCATTACCTCCTTTGCCT CTCTCCTTCTCCCCTCAGGTGCCAGCTCCAGCCTGGGGATGCCCAGCTGGGGGGGGTGGGATCTGAACCGACCTGAGCTCTGCCAACCGACCTCTGGGATTGCTTCCGTCACAAATC ACATTCAGGGATTCCAACGACCTGAGCTCTGCCAACGACCCCGAAGCCCTGCCTGAGGAGCAGGGCTTAG | 11644 |
| | 3 | MQVAVASLSRMGPLGISASPVLGLERRAQLGSSSPCGG SCI* | 11645 | ATGCAAGTTGCTGTAGCCTCTCTGTCCGCATGGCCCTCTAGGTATCTCTGCCTCTC CAGTCCTGGGCTGGAACGGAGGCACAGCTAGGCTCCAGCTCCCGTGTGGTGCC TCCTGCATATGA | 11646 |
| | 4 | MGFASCIRKSHCQGFPTDPELCHRGCCPGTGWQRGPEA CAWPEEGQLAACEQGPHQVVFTVAKFRPPGPHLLWPC RLSPAAACLPAILLPGLCLPCLLS* | 11647 | ATGGGATTTGCTTCCTGTCACAAATCACATTGCCAGGGATTTCCAACGACCCTGAG CTCTGCCACCGAGATGCTGCCCGGGACGGAGCGGTGTGGCAGAGAGGCCCGAAGCCTG TGCCTGGCCTGAGGACCTGAGGGCTTAGCTGCTTGTGAGCAGGGTCACACCAAGTG TGTTCACAGTGGCTAAGTTCCACCCCCAGCCCTGCTGCCATCCTGGGCATTCCTCGCCT GTCCCCTGCTGCCGCCTGTCTGCCTGCACTGGAAGCCCTCGCTGCCTCCTCCTGGGCCTCTGC CTCCCGTCCTACTGAGCTGA | 11648 |
| | 1 | MAPFGLPRAQ* | 11649 | ATGGCCCCATTTGGCCTGCCAGGGCTCAATGA | 11650 |
| | 2 | MRGELGHASCCSLLVPHGPSRYLCLSSPGAGTEGTARL QLPVWWLLHMRKELPCDQRKHLGTWRGGVPKSHYLL CSLSLSPLQVPASGPARCPPHPCATAGWGSWGWDLLPV TNHIARDFQPTLSSATEDAARGRGREAPKPVPGLRSRA * | 11651 | ATGAGGGGGGAGCTTGGCCATGCAAGTTGCTGTAGCCTCCTTGTCCGCATGGCCC TCTAGGTATCTCTGCCTCTCCAGTCCTGGGCTGGAACGGAGGCACAGCTAGGCTC CAGTCCTGTGGTGCCTCCTGCATATGAGACGCTGAGAAAAGAGCTTCCCTGTGATCAAAGG AAGCATCTGGAGGACCTGAAGGGAGGTGTCCCAAATCTCATTACCTCCTTTGCCT CTCTCCTTCTCCCCTCAGGTGCCAGCTCCAGCCTGGGGATGCCCAGCTGGGGTTCCTGGGGATTGCTTCCGTCACAAATC ACATTGCCAGGGATTCCAACGACCTGAGCTCTGCCACCGAGGATGCTGCCGGGG GACGGGGTGGCAGAGAGGCCCGAAGCCTGTGCCTGGCCTGAGGAGCAGGGCTTAG | 11652 |
| | 3 | MQVAVASLSRMGPLGISASPVLGLERRAQLGSSSPCGG SCI* | 11653 | ATGCAAGTTGCTGTAGCCTCTCTGTCCGCATGGCCCTCTAGGTATCTCTGCCTCTC CAGTCCTGGGCTGGAACGGAGGCACAGCTAGGCTCCAGCTCCCGTGTGGTGCC TCCTGCATATGA | 11654 |
| | 4 | MGFASCIRKSHCQGFPTDPELCHRGCCPGTGWQRGPEA CAWPEEGQLAACEQGPHQVVFTVAKFRPPGPHLLWPC RLSPAAACLPAILLPGLCLPCLLS* | 11655 | ATGGGATTTGCTTCCTGTCACAAATCACATTGCCAGGGATTTCCAACGACCCTGAG CTCTGCCACCGAGATGCTGCCCGGGACGGAGCGGTGTGGCAGAGAGGCCCGAAGCCTG TGCCTGGCCTGAGGACCTGAGGGCTTAGCTGCTTGTGAGCAGGGTCACACCAAGTG TGTTCACAGTGGCTAAGTTCCACCCCCAGCCCTGCCATCCTGGGCATTCCTCGCCT GTCCCCTGCTGCCGCCTGTCTGCCTGCACTGGAAGCCCTCGCTGCCTCCTCCTGGGCCTCTGC CTCCCGTCCTACTGAGCTGA | 11656 |
| | 1 | MVSCI* | 11657 | ATGGTGTCTTGCATCTAG | 11658 |
| hsa-mir-27a | 2 | MVSICILRQNPVVFSLLQYVTNEVKTVGMGNLNEWH SSALSPTHTCQHAPQPSRK* | 11659 | ATGGTTTCCATTTGTATACTCCATCAAAATTTGTGGTTGTTCAGCCTATTACAAT ATGTCACTAATGAGGTCAAGACTGTAGGTATGGTAACCTGAATGAGTGGCACAGC TCTGCCCTGTCCCCACCCATACTTGTCAACATGCTCCACAGCTTCAAGAAAATAG | 11660 |
| | 3 | MSLMRSRL* | 11661 | ATGTCACTAATGAGGTCAAGACTGTAG | 11662 |
| | 4 | MSGTALPCPPPLVNMLHSLQENRTYQRFRRLGENTAM CAGNGTWHWQLHP* | 11663 | ATGAGTGGCACATTGCCTTGCCCTCCTCCACTATCAGAGATTTAGAAGATTGGAGTGAGAATACGGCTAT GTGTGCTGGGAATGGCACTTGGCAATTGCAACTTCATCCATGA | 11664 |
| hsa-mir-29b-2 | 1 | MVSCI* | 11665 | ATGGTGTCTTGCATCTAG | 11666 |

Figure 1 (Continued)

| | | | | | |
|---|---|---|---|---|---|
| hsa-mir-29c | 2 | MVSICILHQNPVVVFSLLQYVTNEVKTVGMGNLNEWH SSALSPTHTCQHAPQPSRK* | 11667 | ATGGTTCCAITTGTATACTCCATCATCAAAAATTTGTGGTTGTGTTCAGCTATTACAAT AGTGCACTAATGAGGTCAAGACTGTAGGTATGGGTAACCTGAATGAGTTGGCACAGC TCTGCCCTGTCCCCACCATACTTGTCAACATGCTCCACAGCCTTCAAGAAAATAG | 11668 |
| | 3 | MSLMRSRL* | 11669 | ATGTCACTAATGAGGTCAAGACTGTAG | 11670 |
| | 4 | MSGTALPCPPPHLVMMLHSLQENRTYQRFRRLGENTAM CAGNGTWHWQLHP* | 11671 | ATGAGTGGCACAGCTCTGCCCTGTCCCCACCATACTTGTCAACATGCTCCACAGC CTTCAAGAAAATAGGACCTATCAGAGATTTAGAAGATTGGGTAGAATACGGCTAT GTGTGCTGGAATGGCACTTGGCATTGGCAACTTCATCATCATGA | 11672 |
| hsa-mir-34b | 1 | MVGRPPVKWGPRRAPTPRRRCGPSGSCSRGCPVLGL* | 11673 | ATGGTAGGGCGTCCCCCGGTGAAATGGGTTCGAGGCGGGCGCCCGACCCGCGTCG GCGCCGCGACCGTCGGGACTCGGGAGCGTGCCCGGTGTCGGTTCGGTTGTAG | 11674 |
| | 2 | MGSEAGPDPASALRTVRELQPRVPGARFVGSVIS* | 11675 | ATGGGGTCCGAGGCGGGCCCCGACCCGGCGTCTGCGCTGCGGACCGTCCGGGAGCT GCAGCCGCGGGTGCCCGGTGTCGGTTCGGTCATTAGCTGA | 11676 |
| | 3 | MPEKRGVGVGPAQPAPRAPAASARKPAVSPDTVKLLAL SRSHRR* | 11677 | CCGCTCAAGTTCAAGGACTAGCAGTTCGGTCTCTGCGCAGCCTGCCGCGAGCGCC CGCTCAAGTTCGAGGCGGCGGTTCTCCAGATACAGTTAAACTGTTAGCTCT CTCTAGGAGTCACAGAAGATGA | 11678 |
| | 4 | MKQSHARKAKSLEVKPLHPCNG* | 11679 | ATGAAACAGTCTCATGCCAGGAAAGCAAAATCCTGGAGGTGAAGCCCCTCCATCC ATGTAACGGTTAA | 11680 |
| hsa-mir-34c | 1 | MVGRPPVKWGPRRAPTPRRRCGPSGSCSRGCPVLGL* | 11681 | ATGGTAGGGCCGTCCCCCGGTGAAATGGGTCGAGGCGGGCGCCCGACCCCGCGTCG GGGCTGGGACCGTCGGGACTCGGGAGCGTGCCCGGTGTCCGGTGCCCCGGGAGCT GCAGCCGCGGGTGCCCGGTGTCGGTTCGGTCATTAGCTGA | 11682 |
| | 2 | MGSEAGPDPASALRTVRELQPRVPGARFVGSVIS* | 11683 | ATGGGGTCCGAGGCGGGCCCCGACCCGGCGTCTGCGCTGCGGACCGTCCGGGAGCT GCAGCCGCGGGTGCCCGGTTCGGTTCGGTCAGTGTCATTAGCTGA | 11684 |
| | 3 | MPEKRGVGVGPAQPAPRAPAASARKPAVSPDTVKLLAL SRSHRR* | 11685 | ATGCCTGAGAAGCGAGGCGTCGGCGTGGGCCCCGCTCAGCCTGCCAGCCTGCCGGAGCGCC CGCTCAAGTTCGAGGAGAAAGCCGGTCCGGTTCTCCAGATACAGTTAAACTGTTAGCTCT CTCTAGGAGTCACAGAAGATGA | 11686 |
| | 4 | MKQSHARKAKSLEVKPLHPCNG* | 11687 | ATGAAACAGTCTCATGCCAGGAAAGCAAAATCCTGGAGGTGAAGCCCCTCCATCC ATGTAACGGTTAA | 11688 |
| | 1 | MRRTEEERGFEKGEGYRD* | 11689 | ATGAGGAGGACAGAGGAAAGAAAGGGCGGAAAAGGTGAGGGGTGAGAGACTAG | 11690 |
| | 2 | MFGVGTVGRTHGADSSAS* | 11691 | ATGTTTGGAGTAGGGACAGCTCCATGGCGCTGACAGCTCCGCATCTTGA | 11692 |
| | 3 | MALTAPHLDKVISCLSDIIRALEFSYQRFIQE* | 11693 | ATGGCGCTGACAGCTCCCACTTGATAAGTCATTCCTGTTATCAGACATCATT AGGGCATTAGAGTTCTCATACCAAAGATTTATCCAAGAGTAG | 11694 |
| | 4 | MSFLKTPEKFQPCVPHCSAVLCPNELLRGSCHPVSSGFS CPQFHLERSPQDRMVRSYQSTAPVMLLIFCMAFSSW LRQNSPLSNKDNMLLTELFLQFTY* | 11695 | ATGAGCTTCTTAAAGACACCAGAAAGTTCAACCTTGTGTGCCACATTGTTCTGCT GTGCTTTGTCCAAATGAACTTTGGAGGCAGCTGCATCCAGTTCAAGTGGATTC CTTGGGCCACAATTTCACTTGGAAAGACCAAGTCCTCAAGATCGCATGGTACGCAGC ATCAGAGTACAGCTCTGCGTTTTCATTTTCAATGGTATGGCTTTTCAAGTT GGCTTAGGCAGAATTCCTCTGTGCAATAAAGACAACATGTTCTCACTGAACTTT TCTCCAATTCACATACTAG | 11696 |
| hsa-mir-424 | 1 | MQKPLLY* | 11697 | ATGCAAGAAACCGCTTCTGTACTAA | 11698 |
| hsa-mir-429 | 2 | MNFGGCACSEPRLLCHCTPAWATFTDSISKKKKKLASVS PSASCPSIKFFLLRQRESRPLLTYPGAFTQHSASNRALK AHLSSTLHLGTRNPQPEW* | 11699 | ATGAACCGGAGGCAGAGCTTGCAGTTGACGCAGATTGTGCACTCAGCT CTGGGCGACAGAGACCAGCTCCATCTCAAAAAAAAAACTTCCTCAGTCT CCTGTTCAGCCTGCGACATACTTGGTGCTGAAACTCAGATACATTCTGCCAGTAATAGAGC GCCGCTGCTGACATACTTGGTGCTGAAACTCAGATACATTCTGCCAGTAATAGAGC TCTGAAGGCTCACCTGAGCTCCACTCCACCTCGGCACCGCACCCCTCAGCCAGA GTGGTGA | 11700 |

Figure 1 (Continued)

| | | | | | |
|---|---|---|---|---|---|
| | 3 | MSFHQJLSSEAARIEAAADLWC* | 11701 | ATGTCCTTCCATCAAATTCTTCTTCTGAGGCAGCGAGAATCGAGGCCGCTGCTGAC ATACTTGGTGCTGA | 11702 |
| | 4 | MSHF* | 11703 | ATGTCCCACTTCTGA | 11704 |
| hsa-mir-497 | 1 | MGWDGFWGGVPNSDWEWRNPS* | 11705 | ATGGGCTGGACGGGTTTTGGGGGGGTGTCCCAATTCTGACTGGGAGTGGAGGAA CCCCTCCTGA | 11706 |
| | 2 | MRLGRLLSPAPQM* | 11707 | ATGAGACTGGGCCGTCCTTCTCTGACCCCAAATGTGA | 11708 |
| | 3 | MHPKFCSFQNRGPGSQGRVAEVSGEGSVLCFQERRGG WGGGLEVRAGVGLALSVLELGG* | 11709 | ATGCACCCTAAATTTGCTCTTTCAAAATAGGGACCAGGATCTCAGGGGAGAGTA GCTGAGGTAAGTGGGGAGGGAAGGTGTCCTCTGTTTCAGGAGAGACGTGGCCGTTG GGGGGAGGTTTGGAGTGCGTGCTGGGGTGGGGTTGGCTTGTCAGTCTTGGAAT TGGGGGATGA | 11710 |
| | 4 | MIGEAFSYTPKLQPPRRKPKAETREPPNIPSR* | 11711 | ATGATTGGAGAGGCTTTCTTATACCCTAAACTGCAGCCCCCAGACGAAACCA AAGGCTGAGACCAGAGAGGAAGAACATCCCAGCCGTTAG | 11712 |
| | 1 | MRRTEEERGEKGEGVRD* | 11713 | ATGAGGAGGACAGAGGAAGAAAAGGGGGAAAAAGTGAGGGGTGAGAGACTAG | 11714 |
| | 2 | MPGVGTVGRTHGADSSAS* | 11715 | ATGTTTGGACTGAGGACAGTTGGAGACAGACCATGGGACGCTGACAGCTCGCATCTTGA | 11716 |
| | 3 | MALTAPHLDKVISCLSDURALEPSYQRFIQE* | 11717 | ATGGCGCTGACAGCTCCGCATCTTGATAAAGTCATTTCCTGTTTATCAGACATCATT AGGGCATTAGAGTTCTCATACCAAAGATTTATCCAAGATAG | 11718 |
| hsa-mir-503 | 4 | MSFLKTPEKFQPCVPHCSAVLCFNELLRGSCHPVSSGFS CPQFHLERPSPQDRMVRSYQSTAPVMLLLIFCMAFSSSW LRQNSPLSNKDNMLLTELFLQFTY* | 11719 | ATGAGCTTCTTAAAGACACCAGAGAAGTTCAACCTTGTGTTCGCCACATTGTTCTGCT GTCTTTGTCCCACATTGCGAGGCCATCCAGTTCAAGTGGATTC TCTTGCCCACATTCCTCACTGAATTCTTGCGAAAGACCAAGCTCCAGTTCAAGTGGATCC ATCAGAGTACAGCTCCTGTGATGCCTTATTTGTATGGCTTTTCAAGTT CAGAGCAGAATTCCTCTGAGCAATAAAGACAACATGCTTCTCACTGAACTTT | 11720 |
| | 1 | MQLLFMRSASLNPSHMHKGGSYQKAGVILGAAHHTPV YEESYNNYILVITCKLLKFGNALTKHHISKKEDYLRKRV LPLILTLAFRNLAV* | 11721 | ATGCAGCTCATTCATTCTATGAGAAGTGCGTCATGAAGGCAGGGTCATCTAGGGGCTGCCACCCACCACCTGT GTATGAAGAAAGTTACAACAATTACATTCTAGTCATTACGTGCAAATTACTAAAGTT TGGGAATGCACTTACTAATCTAATCATATCTCAAAAGGAAGATTATCTCAGAAAACG AGTTCTGCCTTAATCCTGACTCGACAATTACATTCTAG | 11722 |
| hsa-mir-527 | 2 | MKKVTTTF* | 11723 | ATGAAGAAAGTTACAACATTTACATTCTAG | 11724 |
| | 3 | MHLLNISSPKRKIISENEFCL* | 11725 | ATGCACTTACTAAACATATCATCTCCAAAAAGAAGATTATCTCAGAAAACGAGTTC TGCCTTTAA | 11726 |
| | 4 | MLLFPLLPVLACCVKTQTHRPTISGELNFPKQFLYSFTSE CLFMPIPVFI* | 11727 | ATGCTCCTGTTTCCTCTTCCGCTGCTTGGCATGTGTGTAAAGACACAAACACAGA GACCCACCATTTCAGGAGAGCTCAACTTTCCAAACAATTCCTATATTCCTTTACCTC TGAGTGTCTGTTCATGCCATCGACGCCAGTGTTTATTTAG | 11728 |
| hsa-mir-92b | 1 | MTIKVSARQQDTEENSSTTCQVDSVHDSAEQEVWAPSL* | 11729 | ATGACCAAAGTCTCAGCCAGGCAGCAGGATACCGAGTTAACTCATCTACCACCTGC CAGTGGACTCTGTGCATGCATGGATGACCAAGAGAAGTTGGCCCATCTCTTTGA | 11730 |
| | 2 | MTLQNKKFGPHLFEL* | 11731 | ATGACTCTGCAGAACAAGAAGTTTGGCCCATCTCTTTGAGCTCTAA | 11732 |
| | 3 | MRELEKLAQGSHGRPEWKELPAA* | 11733 | ATGAGGGAACTGGAAAGCTTGCCCAGGGTTCCATGGGAGACCAGAGTGGAAGGA GCTACCAGCTGCCTGA | 11734 |
| | 4 | MGDQSGRSYQLPDNPAFSSPPRRTVPG* | 11735 | ATGGGAGACCAGGAGTGGAAGGAGCTACCAGCTGCCTGATAACCCAGCTTCTCTCT CCACCCAGGAGAACTGTTCCTGGGTGA | 11736 |

Figure 1 (Continued)

| | | | | | |
|---|---|---|---|---|---|
| hsa-mir-99b | 1 | MSGGGEAQHPCSLGDPGFQVPDPSSLRSGSTPPSPPIPE SEPPAPFPGSRSLSPQSVLSDQGIHTPAPNSFKTPEFRTS APLPKERGPQPSVPLEPKRSGSGIFLPLKPAVLGIPRPLL RNPGVPTSSLAPAGVQPSRG* | 11737 | ATGTCTGGAGGAGGAGAGGCCCAGCATCCATGCTCCCTCGGGGACCCGGATTCCA GGTCCCAGACCCCCTCCCTCAGATCTGGAGTAGCACCACCAGTCCCCACCCAT TCCAGAGATCGAGCCCCCGAGCCCCAGCCCCTTTTCCAGGATCTCAGGAGTCTGAGCCCCA GTCTGTTCTCTCAGACCCTCAGAACCTCCAGGGAATCCACACTCCAGCCCCTAACTCCTTCAAACCCC AGAGTTCAGAACCTCAGCCCTTCAGGAGCCCCCAACCCTCTGTTCC TCTAGAACCCAAGCGTTCAGGGTCTCCGGCATCTTCCCTTGAAGCCTGCAGTTCT GGGGATCCCCAAGGCCCCTCCCTCCCTCCGGAACCCAGGAGTCCCCACCTCCTCTTTAGC CCCAGCTGGAGTCCAGCCCTCCAGGGGTTAA | 11738 |
| | 2 | MLPRGPGIPGPRPLLPQIWEYTTQSPTHSRIRAPSPLFSRI QESEPPVCSLRPGNPHSSP* | 11739 | ATGCTCCCTCGGGGACCCGGGATTCCAGGTCCCAGACCCCTCCTCCCTCAGATCTGG GAGTACACCACCAGTCCCCACCCATTCCAGAATCGAGCCCGAGCCCCAGCCCCTTTTT TCCAGGATCCAGGAGTCTGAGCCCCCAGTCTGTTCTCTCAGACCCAGGGAATCCACAC TCCAGCCCCTAA | 11740 |
| | 3 | MVPDCLGLLSDPWGLPRVRREGEGDLGLGEVQSLPLPQ SGAMGPGSSRFHQRLVQ* | 11741 | ATGGTGCCAGACTGTTTGGGTCTGCTCTCTGACCCTTGGGGCTCCCAGGGTCCGC AGAGAGGGGAGGGGGACCTAGGCTGGGGAAGTCAGAGCCTACCCTTCCCCA AAGCGGGGCTATGGGGCCCAGGGAGTTCGCGTTTCCACCAACGCCTTGTCCAGTGA | 11742 |
| | 4 | MLRSGESLRFSASPLPSPSSSGPRQPRGMLGTQAWAPGQ VGVGGWGRGQPPPPFLPTLA* | 11743 | ATGCTTAGGTCGGGAATCTGAGATTCTCGGCTTCCCCTCCCCACCCTCCT CCTCAGCCCAGGCAGCCCCGGACAGCATGCTGGAACCCAGGATCTGGGGCTCGGGC CAGGTTGGTGTGGGGCGGGGGTGGGGGCCAGCCTCCTCCCCTTCCCCTTCCTCCCCC ACCCTTGGCCTGA | 11744 |
| hsa-miR 145-2 | | MVGLNPPLWQETGEYT | 11745 | ATGGTTGGTTTAAATCCACCCTCTGGCAGGAGACTGGGAATACACATGA | 11746 |
| hsa-miR 125a-1 | | MSLCLSPSLTPPGSTGPPHTMLPVSRSLRPFNL | 11747 | ATGTCTCTGTGCCTATCTCCATCTCTGACCCCCACCCCAGGGTCTACCGGGCCACCG CACACCATGTTGCCAGTTCTCAGGTCCCGAGACCCTTTAACCTGTGA | 11748 |
| hsa-miR 15a-16-1 | | MFKHRFFYMHSFPERKYPLYSLGANVCLKKIKPWSKV AAHNGLWILKRCRPYCAASKIQGSDLLKKIYFFLFIALMI AMSAVP | 11749 | ATGTTTAAACATAGATTTTTCCTTAGGCGCGAATGTGTTTACATGCATTCTTTTTCCTGAAAGAAAATATTTTT TATATTCTTTAGGCGCGAATGTGTTTGTGGATTTGTTTAAAAAATAAAACCTTGGAGTGAAGTAG CAGCACATAATGGTTTGTGGATTTGTTTGAAAAGGTGCAGGCATATTGTGCTGCCTCAA AAATACAAGGATCTGATCTTCTGAAGAAAATATATTCTTTTATTCATAGCTCTTAT GATAGCGAATGTCAGCAGTGCCTTAG | 11750 |

*iBSP*: DIF + BMP4 medium

*PTHR1*: DIF + BMP4 medium

*STMN2*: DIF + BMP4 medium

*OSTERIX*: DIF + BMP4 medium

STMN2: DIF + BMP4 medium

STMN2: DIF Δ BMP4 medium

*OSTERIX*: DIF Δ BMP4 medium

*STMN2*: DIF Δ BMP4 medium

*OSTERIX*: DIF Δ BMP4 medium

*STMN2*: PROLIF medium

THERAPEUTIC PEPTIDES

FIELD

The present invention relates to therapeutic peptides.

BACKGROUND

The microRNAs (miRs) are small non-coding RNAs, about 21 nucleotides in length after maturation, which control expression of target genes at the post-transcriptional level, by degrading the target mRNA or by inhibiting its translation, in eukaryotic organisms.

The miRs can in particular regulate the expression of specific genes involved in certain pathologies in humans and animals. It is now recognized that miRs play an important role in many pathologies, and these are therefore attractive targets for the development of new drugs. The regulation of expression of the miRs is very poorly understood, but it is known in particular that the latter involves, like most coding genes, an RNA polymerase II: this enzyme produces a primary transcript, called "pri-miR", which is then matured by a protein complex in particular containing the Dicer type enzymes. This maturation leads firstly to the formation of a precursor of miR called "pre-miR", having a stem-loop secondary structure containing the miR and its complementary sequence miR*. Then the precursor is matured, which leads to formation of a shorter double-stranded RNA containing the miRNA and the miR*. The miR is then manipulated by the RISC complex, which cleaves the mRNA of the target gene or inhibits its translation.

At present, there are mainly two types of therapeutic approaches for regulating the expression of miRs in vivo.

The first approach is to mimic the effect of miR using synthetic RNA duplexes designed to mimic the miR of interest. One strand is identical to the miR of interest, while the other strand can be modified to facilitate cellular uptake of the molecule. However, since one of the strands must function as a miR and be recognized as such by the cell, the allowed modifications are chemically limited. In addition, although this approach allows for the replacement of the amounts of miRs lost during a pathology, it is difficult to target the RNA molecules to specific tissues, and the tissues that do not normally express the miR of interest. can also capture the synthetic RNA duplex and lead to undesirable side effects.

The second approach is to use antisense oligonucleotides. Such antisense oligonucleotides have a sequence complementary to all or part of that of the target miR and will reduce the endogenous amount of miRs. However, because of the low in vivo stability of this type of molecule, their manipulation is made difficult and expensive.

It is therefore necessary to provide a means of regulating more simply, and specifically, the miRs involved in certain pathologies.

Recently, small open reading frames (ORFs) have also been found in long intergenic non-coding RNAs (lincRNAs) whose putative function, if any, is not known (Ingolia et al., *Cell*, 147(4):789-802, 2011; Guttman & Rinn, *Nature*, 482 (7385):339-46, 2012). However, no examples have yet been reported concerning the existence of ORFs encoding peptides within miRs. So far, the miRs, and by extension their primary transcript, have always been considered, by their particular mode of action, as noncoding regulatory RNAs producing no peptide.

However, the inventors have recently demonstrated the existence of micropeptides (or "miPEPs", microRNA encoded PEPtides) capable of modulating the accumulation of miRs in cells (Lauressergues et al., *Nature*, 520(7545): 90-3, 2015; International Application WO 2015/063431).

SUMMARY

One of the aspects of the invention is therefore to propose compositions containing micropeptides capable of modulating the accumulation of miRs involved in certain pathologies.

Another aspect of the invention relates to these micropeptides for their use as medicaments, and for the treatment of specific pathologies.

Another aspect of the invention relates to a method of identifying micropeptides for modulating the accumulation of miRs involved in pathologies.

Other aspects of the invention also relate to micropeptides as such and the nucleic acids encoding them.

BRIEF DESCRIPTION OF THE DRAWINGS

FIG. 1: List indicating the corresponding miPEPs and miORPs, as well as the associated miRs.

The mesenchymal stem cells were treated for 4 days with 100 μM of miPEP//125a-1, with 100 μM of control peptide (ScmiPEP//125a) or untreated (NT). The y-axis indicates the relative expression of the iBSP gene. Analyzes and statistics were performed with the Mann-Withney test (p-value: * $p<0.05$;  $p<0.01$ and * $p<0.001$).

Figure 2:
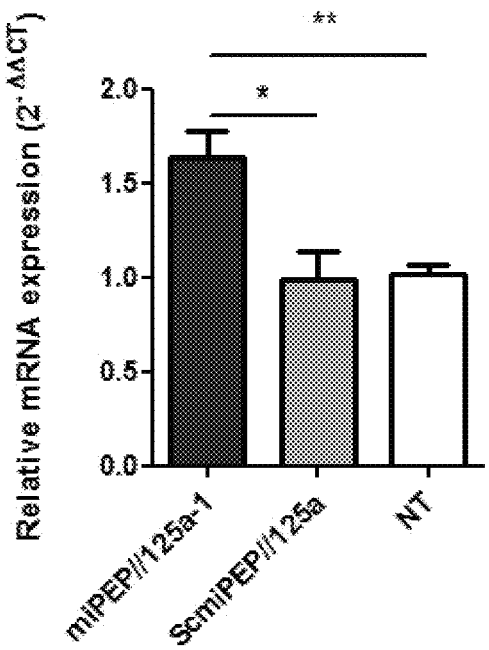
FIG. 2: Expression of the iBSP gene in mesenchymal stem cells cultured in DIF+BMP4 medium in presence of miPEP//125a-1.
Figure 3:
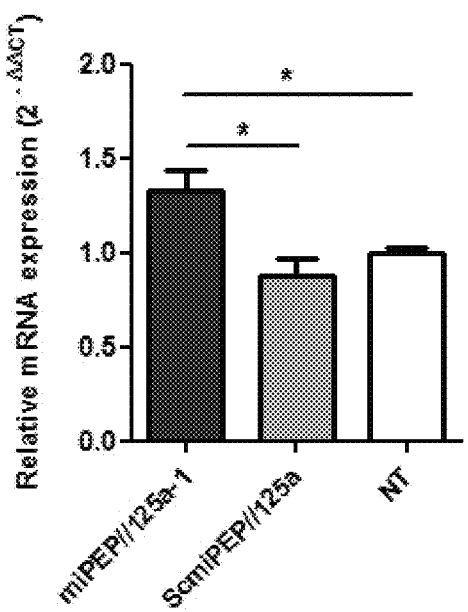

FIG. 3: Expression of the PTHR1 gene in mesenchymal stem cells cultured in DIF+BMP4 medium in presence of miPEP//125a-1.

The mesenchymal stem cells were treated for 4 days with 100 μM of miPEP//125a-1, with 100 μM of control peptide (ScmiPEP//125a) or untreated (NT). The y-axis indicates the relative expression of the PTHR1. Analyzes and statistics were performed with the Mann-Withney test (p-value: * $p<0.05$;  $p<0.01$ and * $p<0.001$).

Figure 4:
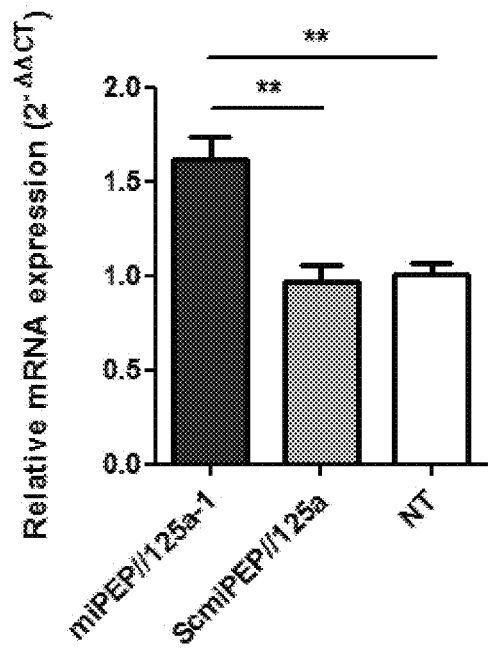

FIG. 4: Expression of the STMN2 gene in mesenchymal stem cells cultured in DIF+BMP4 medium in presence of miPEP//125a-1.

The mesenchymal stem cells were treated for 4 days with 100 μM of miPEP//125a-1, with 100 μM of control peptide (ScmiPEP//125a) or untreated (NT). The y-axis indicates the relative expression of the STMN2 gene. Analyzes and statistics were performed with the Mann-Withney test (p-value: * $p<0.05$;  $p<0.01$ and * $p<0.001$).

Figure 5:
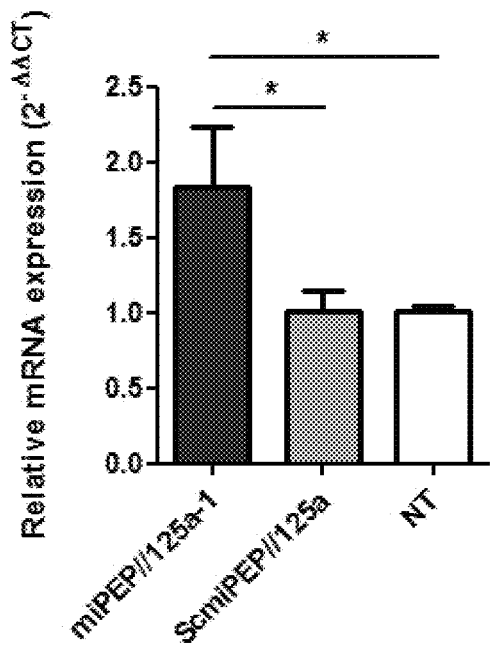

FIG. 5: Expression of the OSTERIX gene in mesenchymal stem cells cultured in DIF+BMP4 medium in presence of miPEP//125a-1.

The mesenchymal stem cells were treated for 4 days with 100 μM of miPEP//125a-1, with 100 μM of control peptide (ScmiPEP//125a) or untreated (NT). The y-axis indicates the relative expression of the OSTERIX gene. Analyzes and statistics were performed with the Mann-Withney test (p-value: * $p<0.05$;  $p<0.01$ and * $p<0.001$).

Figure 6:
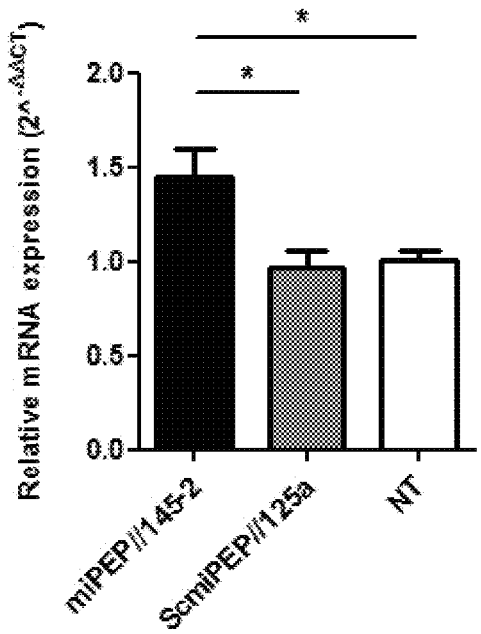

FIG. 6: Expression of the STMN2 gene in mesenchymal stem cells cultured in DIF+BMP4 medium in presence of miPEP//145-2.

The mesenchymal stem cells were treated for 4 days with 100 μM of miPEP//145-2, with 100 μM of control peptide (ScmiPEP//125a) or untreated (NT). The y-axis indicates the relative expression of the STMN2 gene. Analyzes and statistics were performed with the Mann-Withney test (p-value: * p<0.05;  p<0.01 and * p<0.001).

Figure 7:
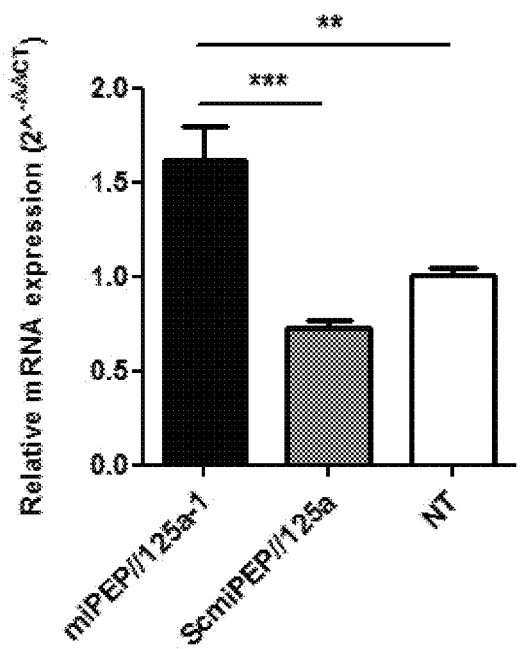

FIG. 7: Expression of the STMN2 gene in mesenchymal stem cells cultured in DIF 4 BMP4 medium in presence of miPEP//125a-1.

The mesenchymal stem cells were treated for 4 days with 100 μM of miPEP//125a-1, with 100 μM of control peptide (ScmiPEP//125a) or untreated (NT). The y-axis indicates the relative expression of the STMN2 gene. Analyzes and statistics were performed with the Mann-Withney test (p-value: * p<0.05;  p<0.01 and * p<0.001).

Figure 8:
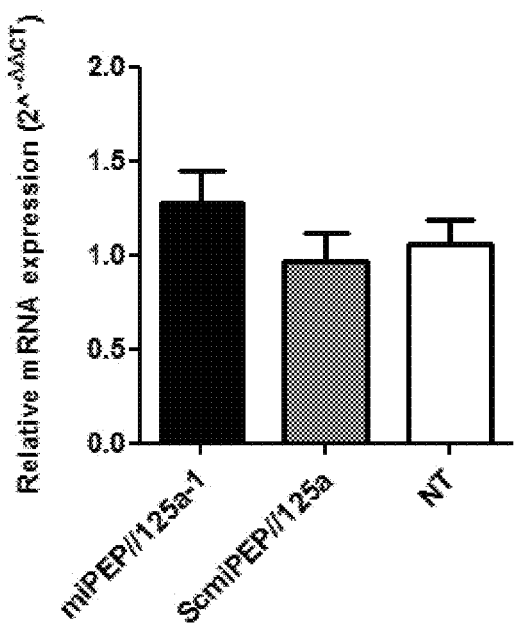

FIG. 8: Expression of the OSTERIX gene in mesenchymal stem cells cultured in DIF BMP4 medium in presence of miPEP//125a-1.

The mesenchymal stem cells were treated for 4 days with 100 μM of miPEP//125a-1, with 100 μM of control peptide (ScmiPEP//125a) or untreated (NT). The y-axis indicates the relative expression of the OSTERIX gene. Analyzes and statistics were performed with the Mann-Withney test (p-value: * p<0.05;  p<0.01 and * p<0.001).

Figure 9:
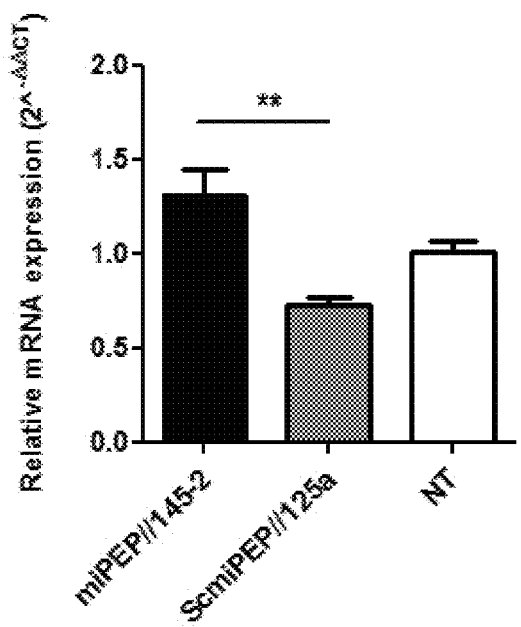

FIG. 9: Expression of the STMN2 gene in mesenchymal stem cells cultured in DIF 4 BMP4 medium in presence of miPEP//145-2.

The mesenchymal stem cells were treated for 4 days with 100 μM of miPEP//145-2, with 100 μM of control peptide (ScmiPEP//125a) or untreated (NT). The y-axis indicates the relative expression of the STMN2 gene. Analyzes and statistics were performed with the Mann-Withney test (p-value: * p<0.05;  p<0.01 and * p<0.001).

Figure 10:
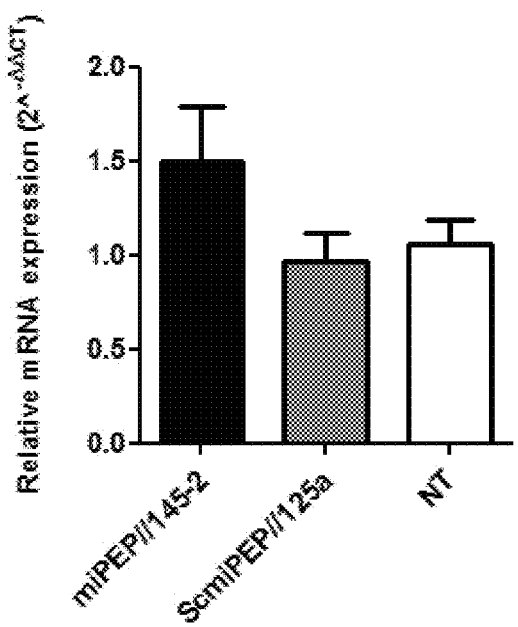

FIG. 10: Expression of the OSTERIX gene in mesenchymal stem cells cultured in DIF BMP4 medium in presence of miPEP//145-2.

The mesenchymal stem cells were treated for 4 days with 100 μM of miPEP//145-2, with 100 μM of control peptide (ScmiPEP//125a) or untreated (NT). The y-axis indicates the relative expression of the OSTERIX gene. Analyzes and statistics were performed with the Mann-Withney test (p-value: * p<0.05;  p<0.01 and * p<0.001).

Figure 11:
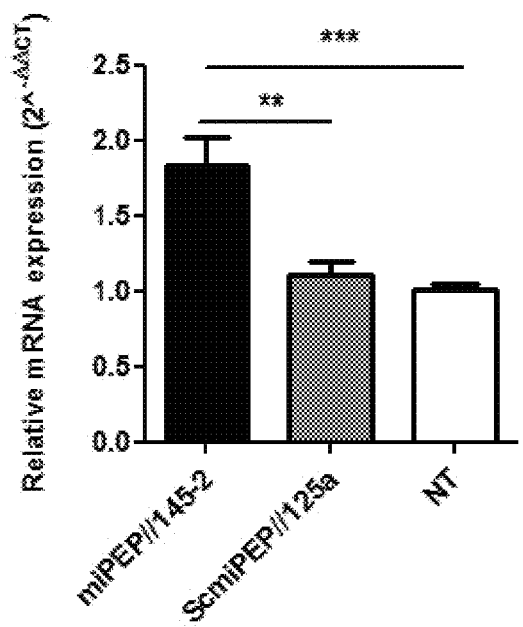

FIG. 11: Expression of the STMN2 gene in mesenchymal stem cells cultured in DIF BMP4 medium in presence of miPEP//145-2.

The mesenchymal stem cells were treated for 4 days with 100 μM of miPEP//145-2, with 100 μM of control peptide (ScmiPEP//125a) or untreated (NT). The y-axis indicates the relative expression of the STMN2 gene. Analyzes and statistics were performed with the Mann-Withney test (p-value: * p<0.05;  p<0.01 and * p<0.001).

Figure 12:
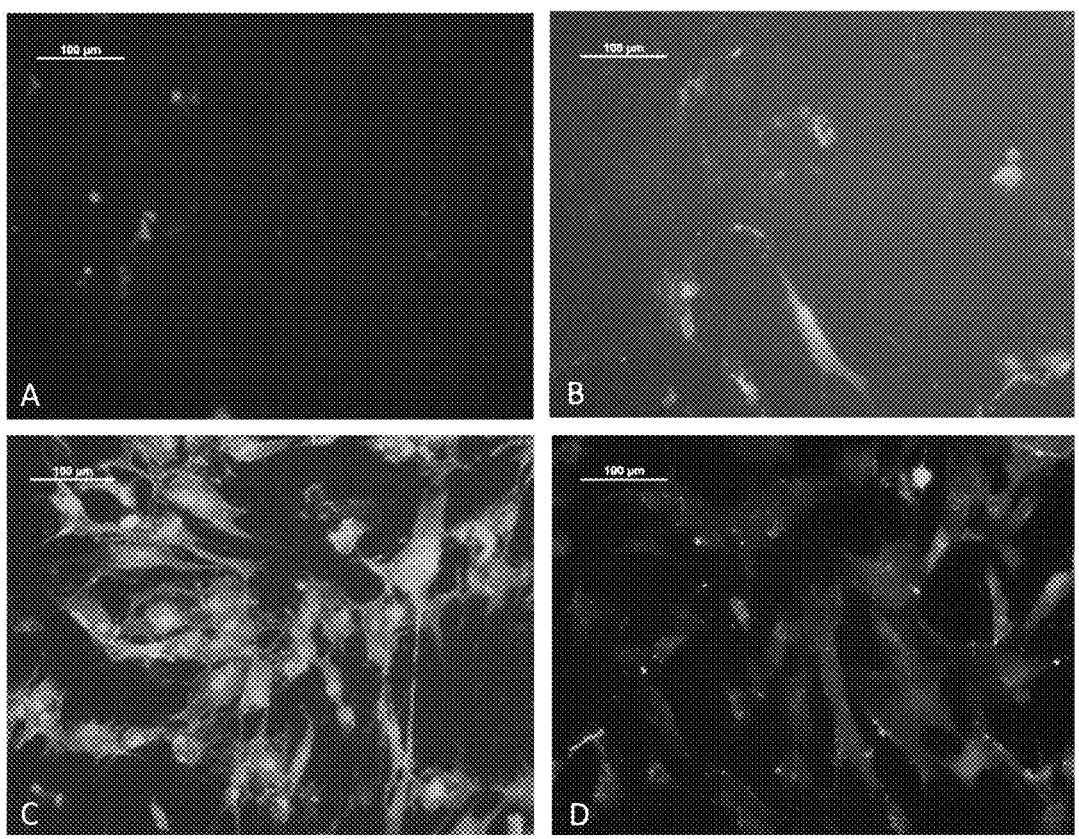

FIG. 12: Entry of miPEP//15a-16-FAM in mesenchymal stem cells.

The undifferentiated mesenchymal stem cells were treated for 6 hours with miPEP//15a-16-1-1-FAM at 5 μM (A), 10 μM (B), 50 μM (C) or 100 μM (D).

Figure 13:
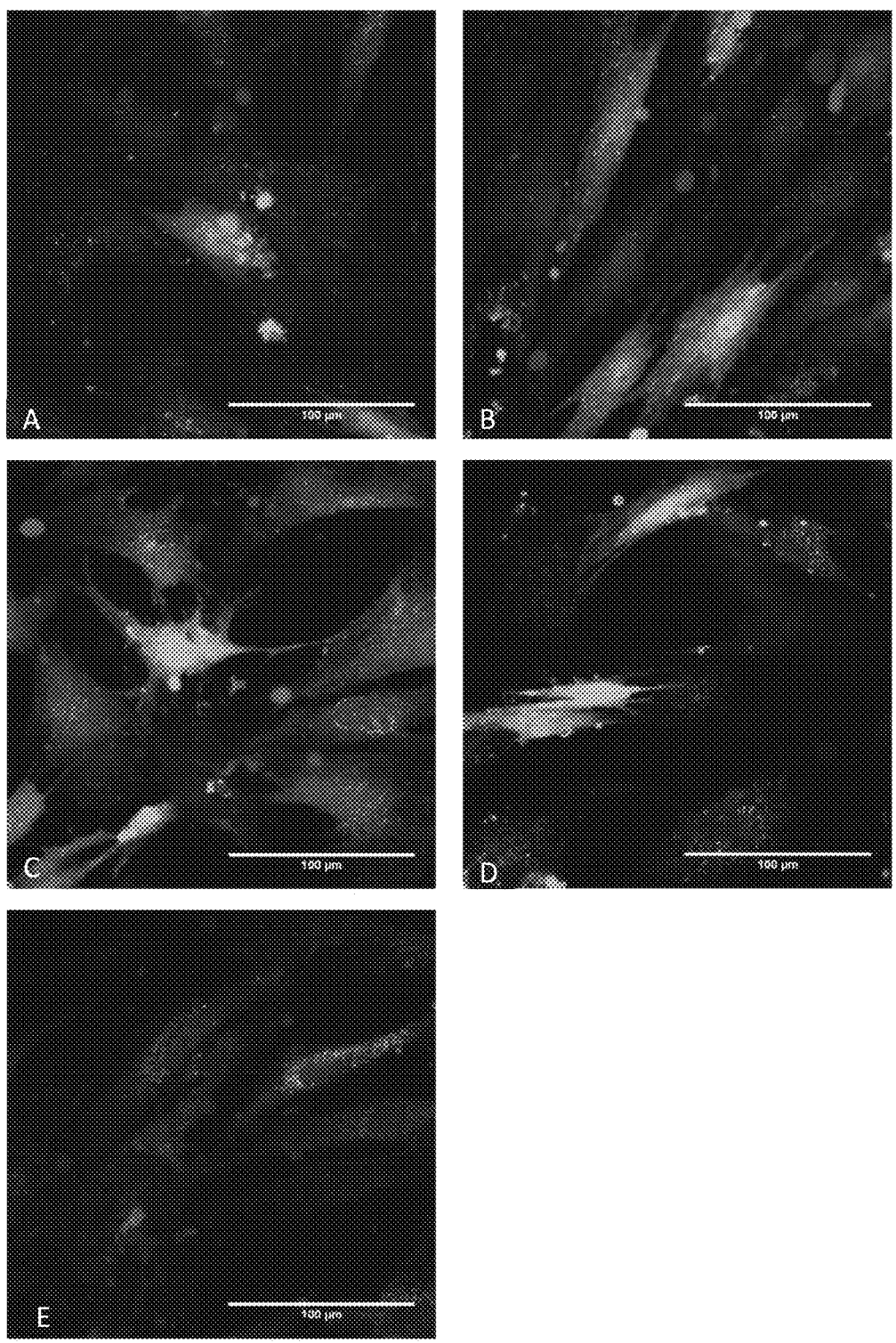

FIG. 13: Entry of miPEP//15a-16-FAM in mesenchymal stem cells.

The undifferentiated mesenchymal stem cells were treated with 100 μM of miPEP//15a-16-1-1-FAM for 2 hours (A), 4 hours (B), 6 hours (C), 8 hours (D) and 24 hours (E).

Figure 14:
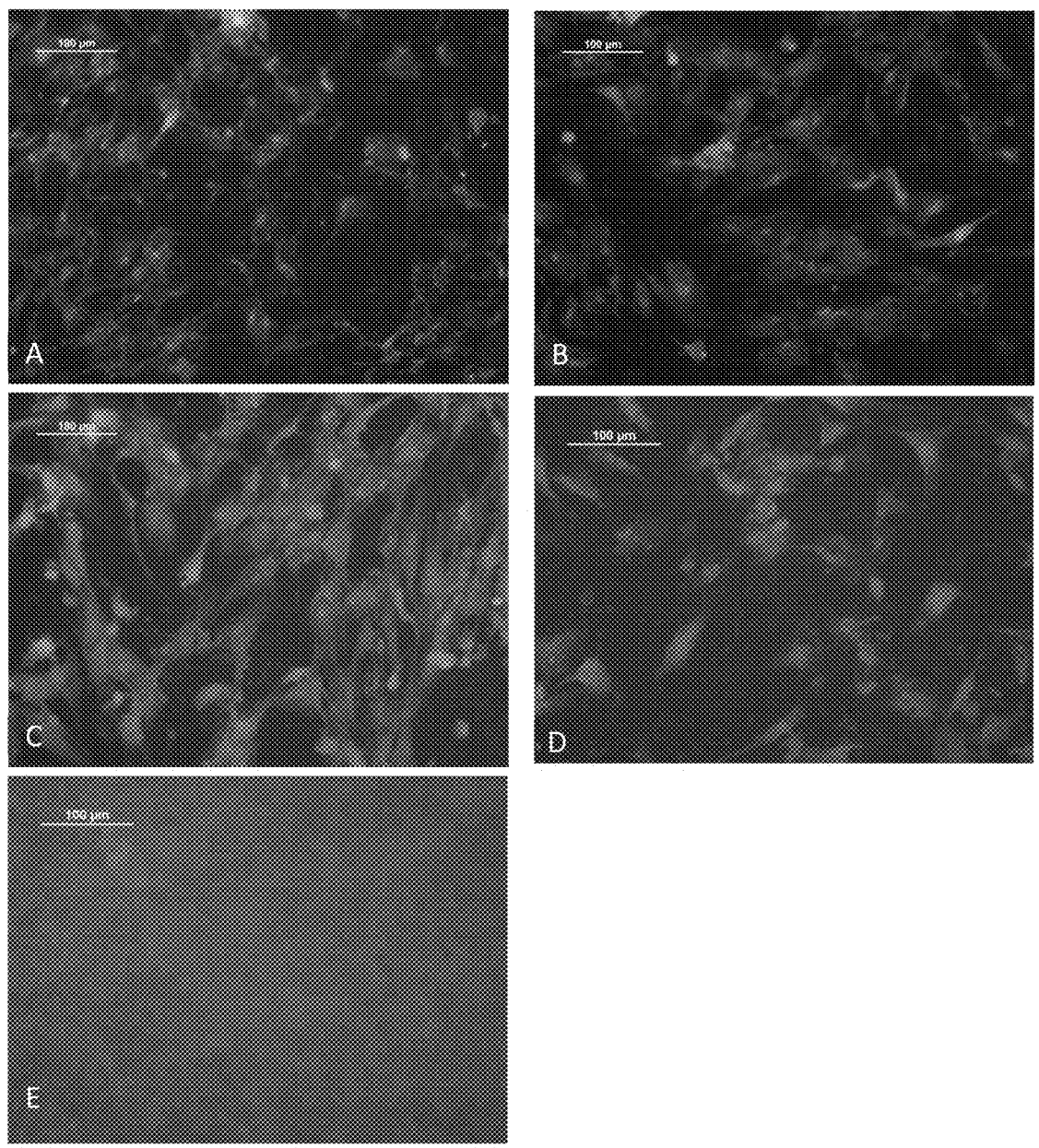

FIG. 14: Entry of miPEP//15a-16-FAM-TAT in mesenchymal stem cells.

The undifferentiated mesenchymal stem cells were treated for 6 hours with miPEP//15a-16-1-1-FAM-TAT at 5 μM (A), 10 μM (B), 20 μM (C), 50 μM (D) or 100 μM (E).

Figure 15:
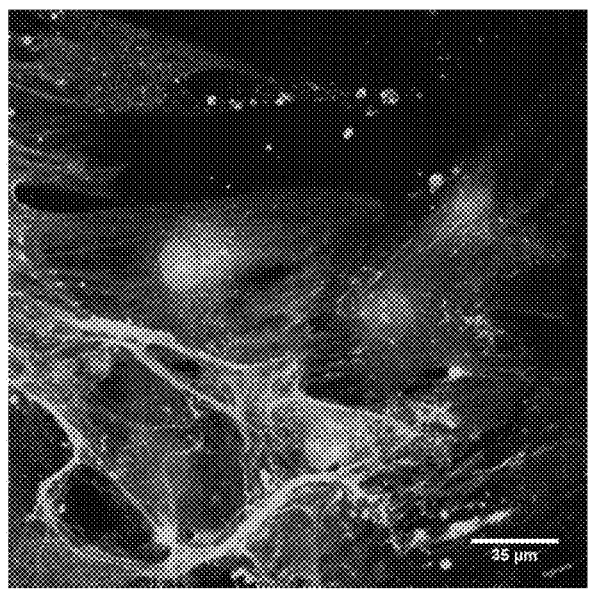

FIG. 15: Entry of miPEP//15a-16-FAM-TAT in mesenchymal stem cells.

The undifferentiated mesenchymal stem cells were treated for 2 hours with miPEP//15 a-16-1-1-FAM-TAT at 10 μM.

Figure 16:
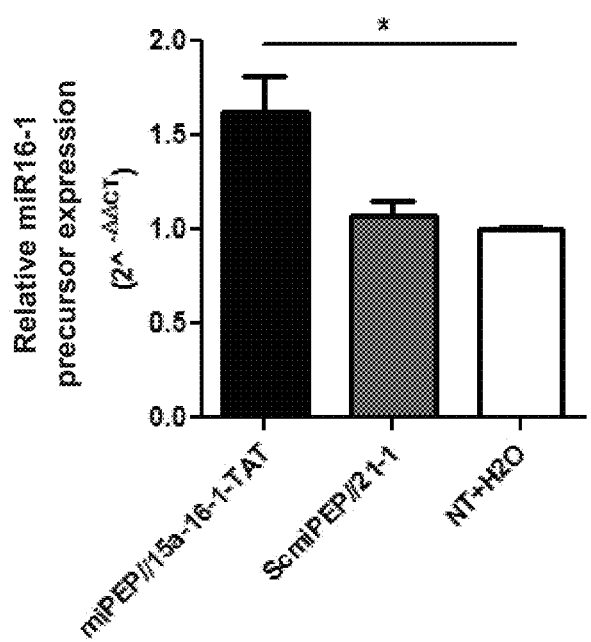

FIG. 16: Accumulation of the miR16-1 precursor in the presence of miPEP//15a-16-1-TAT.

The mesenchymal stem cells were treated with 10 μM of miPEP//15a-16-1-TAT, treated with 10 μM of control peptide (ScmiPEP//21-1) or untreated (NT) for 3 hours. The amount of miR16-1 precursor in cells has been measured by quantitative RT-PCR. The measurement of the amount of miR16-1 precursor was normalized with respect to the PPIA household gene. Analyzes and statistics were performed with the Mann-Withney test (p-value: * p<0.05;  p<0.01 and * p<0.001).

Figure 17:
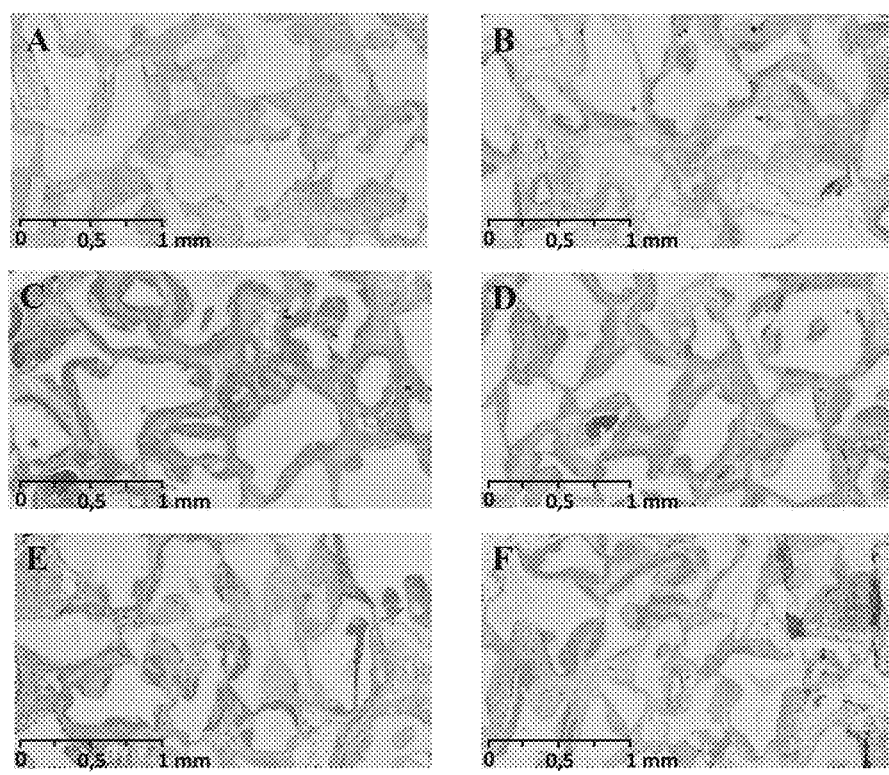
Figure 17:
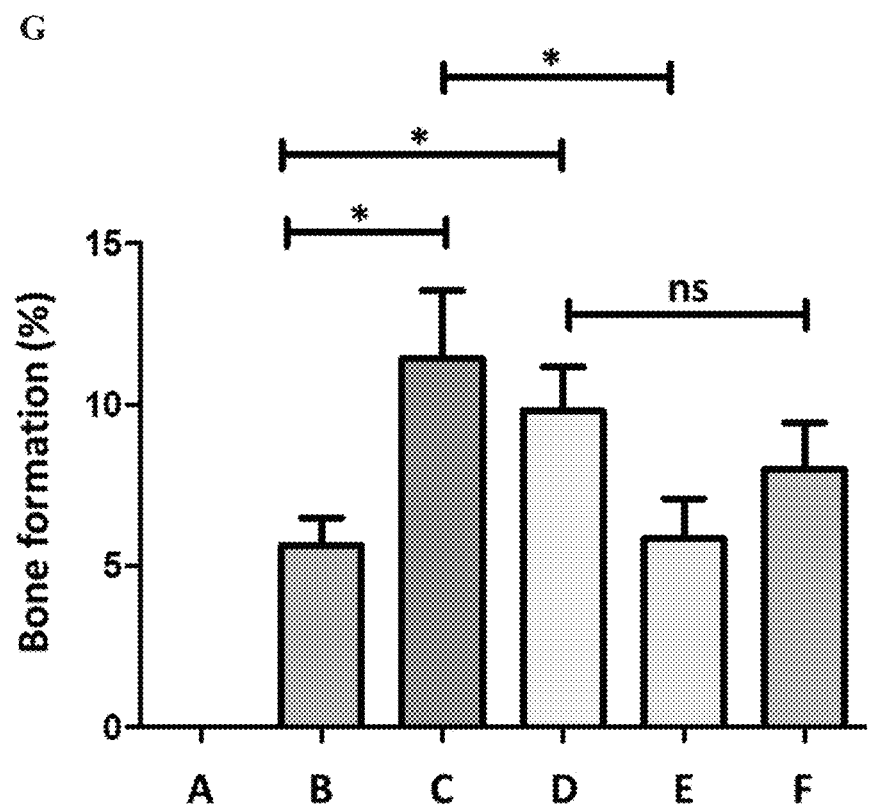

FIG. 17: Evaluation of the effects of miPEP125a-1 on bone formation in vivo.

Nude mice were grafted with
- A. the biomaterial alone,
- B. mesenchymal stem cells mixed with biomaterial (granules of βTCP [20/80]),
- C. & D. mesenchymal stem cells pretreated for 4 days with miPEP//125a-1 mixed with biomaterial (granules of βTCP [20/80]),
- E. & F. mesenchymal stem cells pre-treated 4 days with the control miPEP (scramble) mixed with biomaterial (granules of βTCP [20/80]).

For D. and F. conditions, mice also received regular injections (once a week) of either miPEP//125a-1 (D) or scramble miPEP (F) during the study. After 4 weeks, the mice are euthanized and the grafts were then isolated, fixed, included in methacrylate, cut and treated for histology. The cuts were scanned (NDPview) and bone formation (dark grey) is evaluated (A to F) and is also quantified (G) using the Fiji image analysis software and the total area of new bone is reported to the total area of the cut With regard to microscopic photographs A to F, the scale is indicated in the figure. For G, the y-axis indicates the percentage of bone formation and the statistical analyzes were performed with the paired t-test (p-value: * p<0.05;  p<0.01 and * p<0.001).

DETAILED DESCRIPTION

In one aspect, the invention relates to a pharmaceutical composition comprising:
- a miPEP from 3 to 500 amino acids encoded by a nucleotide sequence contained in the primary transcript of a miR, or a fragment of said miPEP, said miPEP being capable of modulating the accumulation of said miR in a eukaryotic cell, and
- a pharmaceutically acceptable excipient.

In the invention, the terms "microARN", "non coding microARN" and "miR" are equivalent and may be used interchangeably. They define small molecules of RNA of about 21 nucleotides, which are not translated and do not lead to a peptide or a protein.

However, in this mature form, the microRNAs perform a function of regulation of certain genes via post-transcriptional mechanisms, for example by means of the RISC complex.

The primary transcript of the microRNA or "pri-miR" corresponds to the RNA molecule obtained directly from transcription of the DNA molecule. Generally, this primary transcript undergoes one or more post-transcriptional modifications, involving for example a particular structure of the RNA or cleavage of certain portions of the RNA, and which lead to the precursor form of the microRNA or "pre-miR", then to the mature form of the microRNA or "miR".

The terms "micropeptides" and "miPEPs" (microRNA encoded PEPtides) are equivalent and may be used interchangeably. They define a peptide that is encoded by an open reading frame present on the primary transcript of a microRNA, and which is capable of modulating the accumulation of said microRNA. The micropeptides within the meaning of the present invention are not to be understood as necessarily being small peptides, as "micro" does not correspond to the size of the peptide.

According to the invention, a miPEP can also be considered as a transcription modulator, and in particular a transcription activator. Such a transcription modulator can operate at the transcription level to modulate the accumulation of pri-miR, pre-miR and miR.

Taking into account the degeneracy of the genetic code, one and the same micropeptide may be encoded by several nucleotide sequences. Nucleotide sequences of this kind, differing from one another by at least one nucleotide but encoding one and the same peptide, are called "degenerate sequences".

The terms "open reading frame" or "ORF" are equivalent and may be used interchangeably. They correspond to a nucleotide sequence in a DNA or RNA molecule that may potentially encode a peptide or a protein: said open reading frame begins with a start codon (the start codon generally encoding a methionine), followed by a series of codons (each codon encoding an amino acid), and ends with a stop codon (the stop codon not being translated).

In the invention, the ORFs may be called specifically "miORFs" when they are present on the primary transcripts of microRNA.

The miORFs may be contained in the 5' or 3' portion of said primary microAR transcript, preferably in the 5' portion.

The 5 or 3 portions of the primary microRNA transcript correspond to the terminal portions of the RNA molecule that are cleaved during microRNA processing.

The miORFs as defined in the particular invention may have a size from 12 to 1503 nucleotides and may encode peptides from 3 to 500 amino acids.

In particular, the miORFs encode miPEPs having a size of: 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499 or 500 amino acids.

The miPEPs may especially have a size from 100 to 500 amino acids, from 101 to 500 amino acids, from 200 to 500 amino acids, from 300 to 500 amino acids, or from 400 to 500 amino acids.

According to the invention, a "miPEP fragment" corresponds to an N-terminal part, a C-terminal part or an internal part of the sequence of a miPEP.

In others words, a "miPEP fragment" corresponds to a part of a miPEP containing the first N-terminal amino acid, to a part of the miPEP containing the last C-terminal amino acid or to a part containing neither the first N-terminal amino acid or the last C-terminal amino acid.

In particular, a miPEP fragment has a size from 2 to 20 amino acids, preferably from 5 to 10 amino acids.

In particular, a miPEP fragment has a size of 2, 3, 4, 5, 6, 7, 8, 9, 10, 11, 12, 13, 14, 15, 16, 17, 18, 19 or 20 amino acids.

Preferably, a miPEP fragment has a size of 10 amino acids and corresponds to the N-terminal portion of a miPEP.

In the present invention, a miPEP fragment may be referred to as "miPEP//".

In the invention, "accumulation" means the production of a molecule, such as a microRNA or a micropeptide, in the cell.

The accumulation of a microRNA or a micropeptide can be determined using assay methods known to those skilled in the art, such as for example by RT-qPCR or by the quantification of the fluorescence due to the fusion of a peptide or protein to a fluorescent marker.

Thus, "modulation" of the accumulation of a molecule in a cell corresponds to a modification of the quantity of this molecule present in the cell.

Moreover, the effect of a miPEP can be observed through the modulation of the accumulation of the miR, but also through the modulation of the accumulation of the corresponding pri-miR or pre-miR.

In one embodiment, the invention relates to a composition as defined above, wherein the modulation of the accumulation of said microRNA is a decrease or an increase in the accumulation of said microRNA, in particular an increase.

A "decrease in the accumulation" corresponds to a decrease in the quantity of said molecule in a cell relative to a control cell.

Conversely, an "increase in the accumulation" corresponds to an increase in the quantity of said molecule in a cell relative to a control cell.

According to the invention, a miPEP is capable of modulating the accumulation of pri-miR, pre-miR and miR. Therefore, if a primary transcript contains more than one miR, a same miPEP encoded by said primary transcript is capable of modulating the accumulation of at least one of the miRs present on the primary transcript.

In a particular embodiment, the invention relates to a pharmaceutical composition comprising:
- a miPEP from 3 to 500 amino acids encoded by a nucleotide sequence contained in the primary transcript of a miR, or a fragment of said miPEP, said miPEP being capable of modulating the accumulation of said miR in a eukaryotic cell, which miR regulates expression of at least one gene involved in a pathology,
- a pharmaceutically acceptable excipient.

According to the invention, said pharmaceutical composition comprises at least one miPEP but may also comprise a mixture of several miPEPs.

In a nonlimiting manner, said pharmaceutical composition may for example comprise 2, 3, 4, 5, 6, 7, 8, 9 or 10 miPEPs.

In a particular embodiment, the invention relates to a pharmaceutical composition as defined above, wherein said miPEP is selected from the group of miPEPs consisting of SEQ ID NO: 2q-1, q varying from 1 to 5 875.

In a particular embodiment, the invention relates to a pharmaceutical composition as defined above, wherein said miPEP is selected from the group of miPEPs consisting of:

miPEP 145-2
(MVGLNPPLWQETGEYT, SEQ ID NO: 11 745), miPEP 125a-1
(MSLCLSPSLTPTPGSTGPPHTMLPVSRSLRPFNL, SEQ ID NO:
11 747), ant miPEP 15a-16-1
(MFKHRFFYMHSFFPERKYFLYSLGANVCLKKIKPWSKV

AAHNGLWILKRCRPYCAASKIQGSDLLKKIYFFLFIALMIAMSAVP,

SEQ ID NO: 11 749).

In a particular embodiment, the invention relates to a pharmaceutical composition as defined above, wherein said miPEP fragment is a fragment of miPEP 145-2, preferably consisting of SEQ ID NO: 11 751 (MVGLNPPLWQ).

In a particular embodiment, the invention relates to a pharmaceutical composition as defined above, wherein said miPEP fragment is the miPEP//145-2 consisting of SEQ ID NO: 11 751 (MVGLNPPLWQ).

In a particular embodiment, the invention relates to a pharmaceutical composition as defined above, wherein said miPEP fragment is a fragment of miPEP 125a-1, preferably consisting of SEQ ID NO: 11 752 (MSLCLSPSLT).

In a particular embodiment, the invention relates to a pharmaceutical composition as defined above, wherein said miPEP fragment is the miPEP//125a-1 consisting of SEQ ID NO: 11 752 (MSLCLSPSLT).

In a particular embodiment, the invention relates to a pharmaceutical composition as defined above, wherein said miPEP fragment is a fragment of miPEP 15a-16-1, preferably consisting of SEQ ID NO: 11 753 (MFKHRFFYMH).

In a particular embodiment, the invention relates to a pharmaceutical composition as defined above, wherein said miPEP fragment is the miPEP//15a-16-1 consisting of SEQ ID NO: 11 753 (MFKHRFFYMH).

Figure 1:
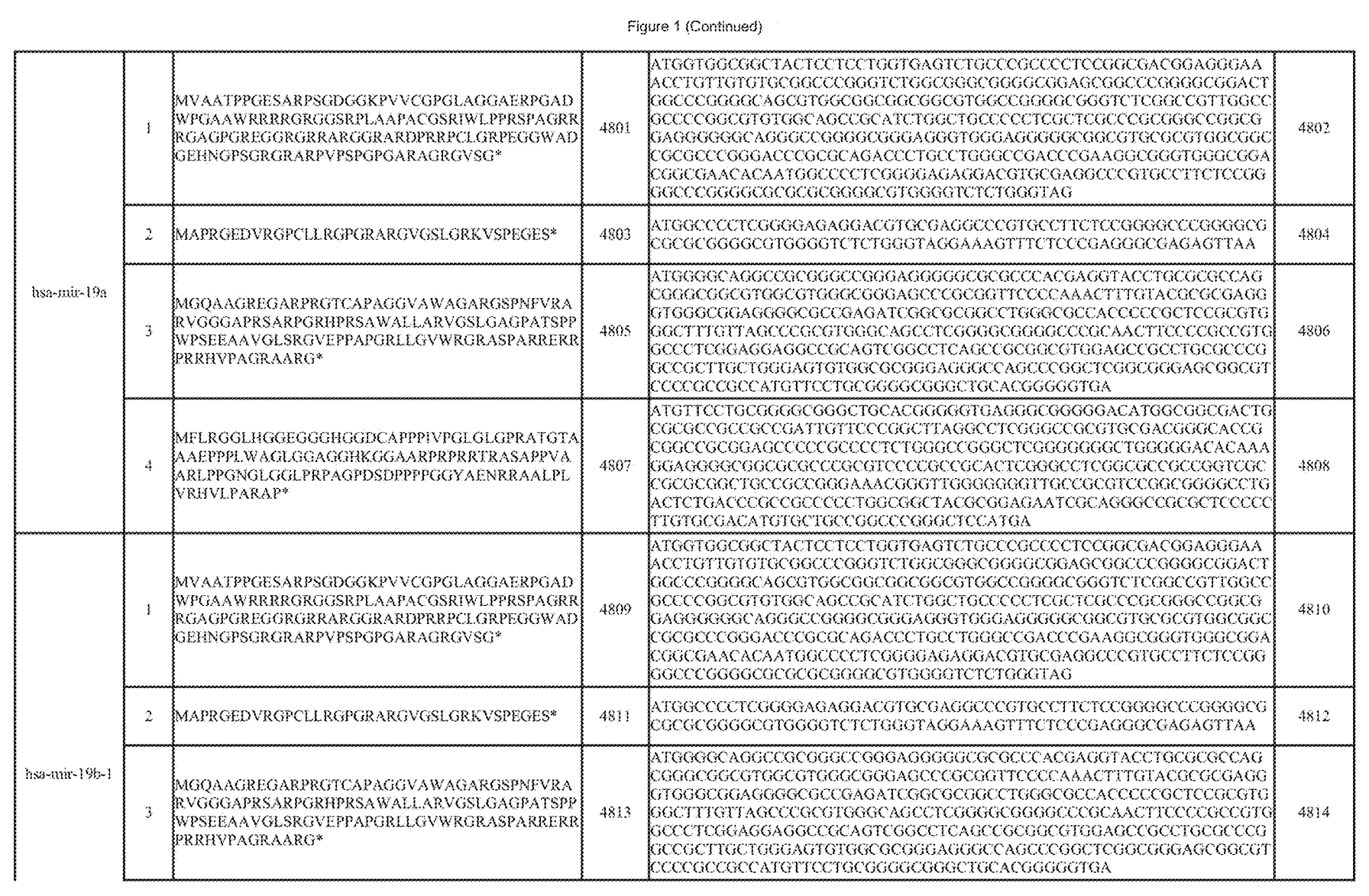
Figure 1:
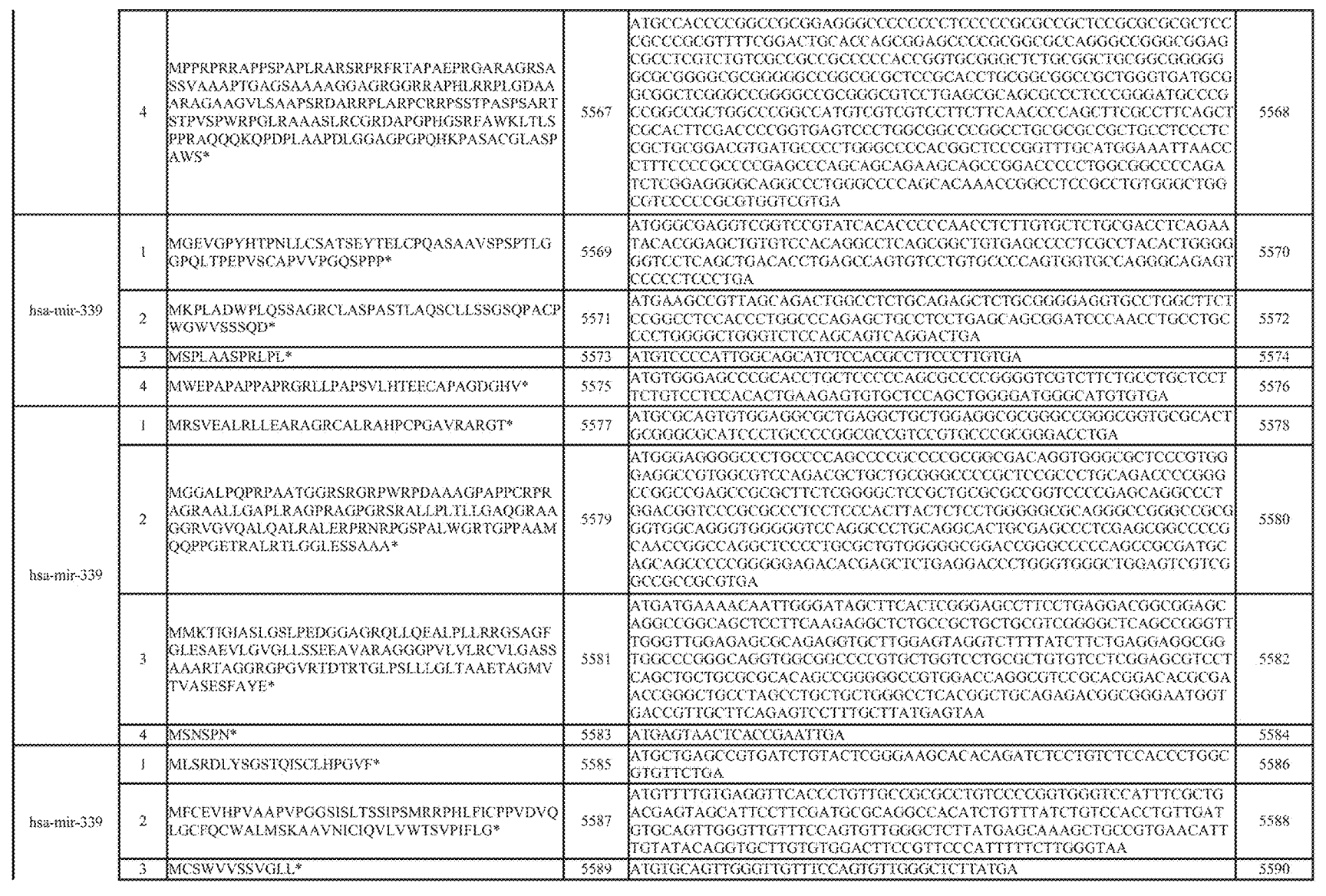
Figure 1:
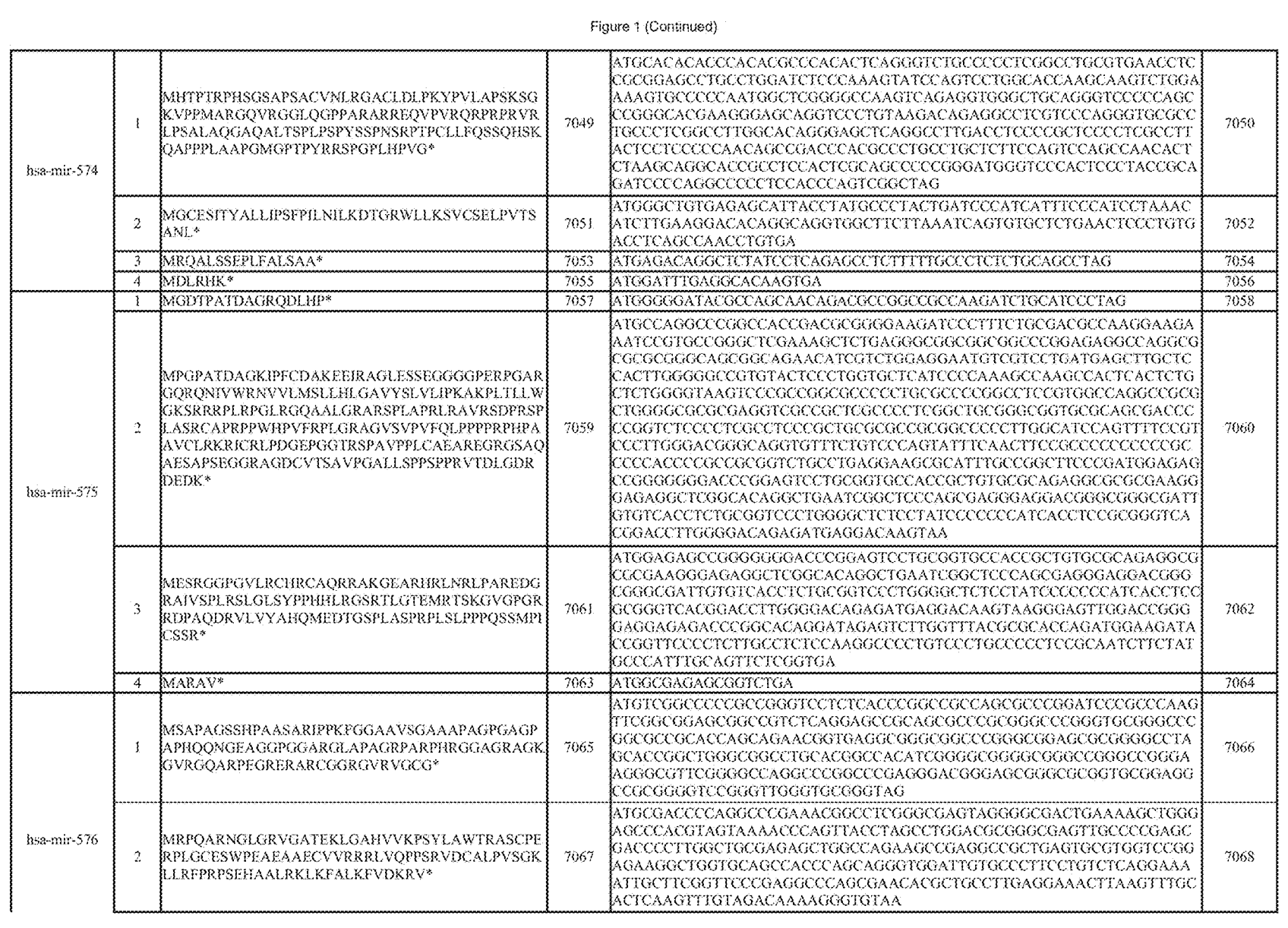
Figure 1:
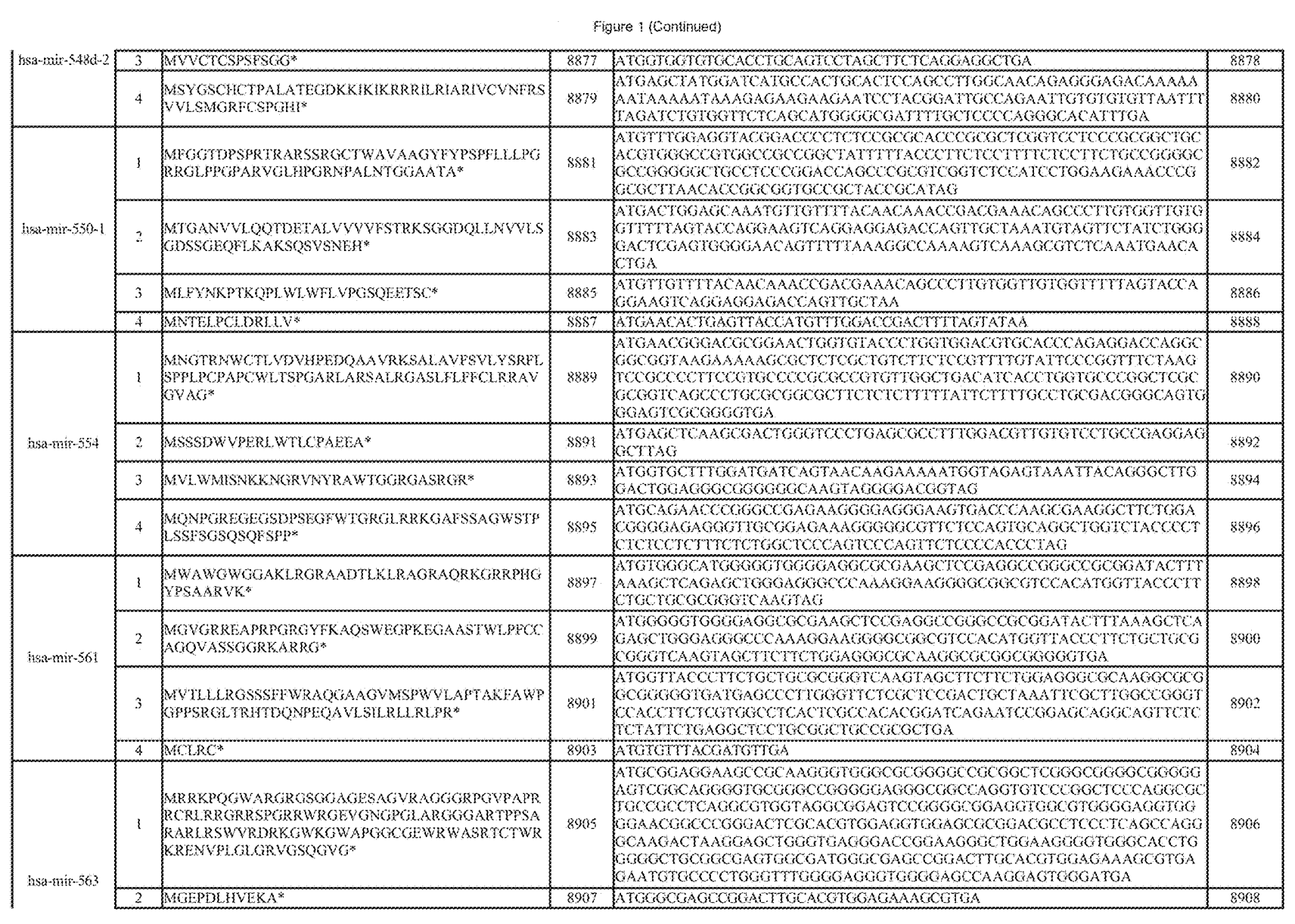

The list of all miPEPs, and corresponding miORPs, is presented in FIG. 1 and is incorporated in this application.

In a particular embodiment, the pharmaceutical compositions comprising the miPEPs are in the form of a unit dose comprising from $10^{-4}$ M to $10^{-10}$ M of miPEP.

In a particular embodiment, the compositions according to the invention can be administered in one or more times.

In a particular embodiment, the pharmaceutical compositions are suitable for oral, ocular, nasal, parenteral (intravenous, intraarterial, subcutaneous, intradermal, intramuscular), rectal, vaginal, topical or auricular administration.

In a particular embodiment, the miPEP can be vectorized or encapsulated.

In the invention, the miPEP, or the fragment of said miPEP, may be fused or linked to one or more molecules facilitating the entry of the miPEP, or miPEP fragment, into the cell.

In a particular embodiment, the invention relates to a pharmaceutical composition as defined above, wherein said miPEP, or said fragment of said miPEP, is fused to a peptide facilitating the entry into the cell of the miPEP, or miPEP fragment.

In a particular embodiment, the invention relates to a pharmaceutical composition as defined above, wherein said miPEP, or said fragment of said miPEP, is fused to the TAT peptide (YGRKKRRQRRR, SEQ ID NO: 11 754).

In a particular embodiment, the invention relates to a pharmaceutical composition as defined above, wherein said miPEP, or said fragment of said miPEP, is fused in N-ter or in C-ter to the TAT peptide (YGRKKRRQRRR, SEQ ID NO: 11 754).

In a particular embodiment, the invention relates to a pharmaceutical composition as defined above, wherein said miPEP fragment is selected from:

miPEP//145-2-TAT consisting of SEQ ID NO: 11 755
(MVGLNPPLWQ-YGRKKRRQRRR), miPEP//125a-1-TAT consisting of SEQ ID NO: 11 756
(MSLCLSPSLT-YGRKKRRQRRR),
and miPEP//15a-16-1-TAT consisting of SEQ ID NO: 11 757
(MFKHRFFYMH-YGRKKRRQRRR).

In a particular embodiment, the invention relates to a pharmaceutical composition as defined above, wherein said miPEP, or said fragment of said miPEP, is fused to penetratin, to a polyhistidine peptide (in particular a peptide of at least 6 histidine residues) or to a polyarginine peptide (in particular a peptide of 9 arginine residues).

In a particular embodiment, the invention relates to a pharmaceutical composition as defined above, wherein said miPEP, or said fragment of said miPEP, is linked to one or more palmitic acid molecules.

The amount of miPEP present in the composition or used for the treatment of a pathology may vary depending on whether or not the miPEP is modified with a molecule facilitating cell penetration.

In another aspect, the invention relates to a miPEP from 3 to 500 amino acids encoded by a nucleotide sequence contained in the primary transcript of a miR, or a fragment of said miPEP, said miPEP being capable of modulating the accumulation of said miR in a eukaryotic cell, for its use as a drug.

In a particular embodiment, the invention relates to a miPEP from 3 to 500 amino acids encoded by a nucleotide sequence contained in the primary transcript of a miR, or a fragment of said miPEP, said miPEP being capable of modulating the accumulation of said miR in a eukaryotic cell, which miR regulates expression of at least one gene involved in a pathology, for its use as a drug.

In the invention, a gene is involved in a pathology if the expression of said gene varies significantly between a patient suffering from said pathology and a healthy individual.

In a particular embodiment, the invention relates to a miPEP, or a fragment of said miPEP, for its use as defined above, said miPEP being identified, or as identified, by implementing of a process for identifying a miPEP modulating the accumulation of a miR involved in a pathology, comprising:
  a) a step of detecting an open reading frame from 12 to 1 503 nucleotides contained in the sequence of the primary transcript of said miR, then
  b) a step of comparison between:
    i. the accumulation of said miR in a specified eukaryotic cell expressing the primary transcript of said miR, in the presence of a peptide encoded by a nucleotide sequence that is identical or degenerate relative to that of said open reading frame, said peptide being present in the cell independently of transcription of the primary transcript of said miR, and
    ii. the accumulation of said miR in a eukaryotic cell of the same type as the aforesaid specified eukaryotic cell expressing the primary transcript of said miR, in the absence of said peptide,
in which a modulation of the accumulation of said miR in the presence of said peptide relative to the accumulation of said miR in the absence of said peptide indicates the existence of a miPEP, the latter being encoded by said open reading frame and being capable of modulating the accumulation of said miR involved in a pathology.

In the invention, a miR is involved in a pathology if said miR is capable of regulating the expression of a gene involved in said pathology and/or of reducing the symptoms of said pathology.

In a particular embodiment, the invention relates to a miPEP, or a fragment of said miPEP, for its use as defined above, said miPEP being encoded by a nucleotide sequence contained in the primary transcript of a miR selected from those presented in Tables 2, 3, 4, 5 and 6.

In a particular embodiment, the invention relates to a miPEP, or a fragment of said miPEP, for its use as defined above, said miPEP being encoded by a nucleotide sequence contained in the primary transcript of a miR selected from the group consisting of:
hsa-mir-103-1, hsa-mir-103-2, hsa-mir-107, hsa-mir-122, hsa-mir-155, hsa-mir-21, hsa-mir-33, hsa-mir-15a, hsa-miR-15b, hsa-mir-451, hsa-mir-92a-1, hsa-mir-92a-2, hsa-mir-92b, hsa-mir-208, hsa-mir-208b, hsa-mir-29a, hsa-mir-29b-1, hsa-mir-29b-2, hsa-mir-29c, hsa-mir-143, hsa-mir-145, hsa-mir-206, hsa-mir-378, hsa-mir-34a, hsa-mir-34b, hsa-mir-34c, hsa-let-7, hsa-mir-16-1, hsa-mir-16-2 and hsa-mir-125a.

In a particular embodiment, the invention relates to a miPEP, or a fragment of said miPEP, for its use as defined above, said miPEP being encoded by a nucleotide sequence contained in the primary transcript of a miR selected from the group consisting of: hsa-mir-125a, hsa-mir-15a-16-1 and hsa-mir145.

In a particular embodiment, the invention relates to a miPEP, or a fragment of said miPEP, for its use as defined above, said miPEP being selected from the group consisting of SEQ ID NO: 2q-1, q varying from 1 to 5 875.

In a particular embodiment, the invention relates to a miPEP, or a fragment of said miPEP, for its use as defined above, said miPEP being selected from the group consisting of: miPEP 145-2 (SEQ ID NO: 11745), miPEP 125a-1 (SEQ ID NO: 11747) and miPEP 15a-16-1 (SEQ ID NO: 11 749).

In a particular embodiment, the invention relates to a miPEP, or a fragment of said miPEP, for its use as defined above, said miPEP fragment being a fragment of miPEP 145-2, preferably consisting of SEQ ID NO: 11 751.

In a particular embodiment, the invention relates to a miPEP, or a fragment of said miPEP, for its use as defined above, said miPEP fragment being miPEP//145-2 consisting of SEQ ID NO: 11 751.

In a particular embodiment, the invention relates to a miPEP, or a fragment of said miPEP, for its use as defined above, said miPEP fragment being a fragment of miPEP 125a-1, preferably consisting of SEQ ID NO: 11 752.

In a particular embodiment, the invention relates to a miPEP, or a fragment of said miPEP, for its use as defined above, said miPEP fragment being miPEP//125a-1 consisting of SEQ ID NO: 11 752.

In a particular embodiment, the invention relates to a miPEP, or a fragment of said miPEP, for its use as defined above, said miPEP fragment being a fragment of miPEP 15a-16-1, preferably consisting of SEQ ID NO: 11 753.

In a particular embodiment, the invention relates to a miPEP, or a fragment of said miPEP, for its use as defined above, said miPEP fragment being miPEP//15a-16-1 consisting of SEQ ID NO: 11 753.

In a particular embodiment, the invention relates to a miPEP, or a fragment of said miPEP, for its use as defined above, wherein said miPEP, or said fragment of said miPEP, is fused to the TAT peptide.

In a particular embodiment, the invention relates to a miPEP fragment for its use as defined above, said miPEP fragment being selected from:

```
miPEP//145-2-TAT consisting of SEQ ID NO: 11 755
(MVGLNPPLWQ-YGRKKRRQRRR), miPEP//125a-1-TAT consisting of SEQ ID NO: 11 756
(MSLCLSPSLT-YGRKKRRQRRR),
and miPEP//15a-16-1-TAT consisting of SEQ ID NO: 11 757
(MFKHRFFYMH-YGRKKRRQRRR).
```

In a particular embodiment, the invention relates to a miPEP, or a fragment of said miPEP, for its use as defined above, wherein said miPEP, or said fragment of said miPEP, being fused to penetratin, to a polyhistidine peptide (in particular a peptide of at least 6 histidine residues) or to a polyarginine peptide (in particular a peptide of 9 arginine residues).

In a particular embodiment, the invention relates to a miPEP, or a fragment of said miPEP, for its use as defined above, wherein said miPEP, or said fragment of said miPEP, being linked to one or more palmitic acid molecules.

Another aspect of the invention relates to a miPEP from 3 to 500 amino acids encoded by a nucleotide sequence contained in the primary transcript of a miR, or a fragment of said miPEP, said miPEP being capable of modulating the accumulation of said miR in a eukaryotic cell, for its use in the treatment of a pathology selected from: cancer, bacterial infections, mycoses, cardiovascular diseases, hereditary congenital diseases, skin diseases, eye diseases, diseases of the digestive system, diseases of the endocrine system, diseases of the nervous system, diseases related to viruses, diseases related to nutrition and metabolism, lymphatic diseases and hemopathies, neonatal and hereditary diseases, respiratory diseases, urogenital diseases in humans, urogenital diseases in women, disorders of the immune system, musculoskeletal disorders, diseases or trauma of bone tissue or cartilage tissue.

Another aspect of the invention relates to a miPEP from 3 to 500 amino acids encoded by a nucleotide sequence contained in the primary transcript of a miR, or a fragment of said miPEP, said miPEP being capable of modulating the accumulation of said miR in a eukaryotic cell, for its use in the treatment of a disease or trauma of bone tissue or cartilage tissue.

In the invention, the term "bone tissue disease" refers to any disease reducing bone capital, such as osteoporosis.

In the invention, the term "bone tissue trauma" refers to a break in continuity or fracture of a bone.

In a particular embodiment, the invention relates to a miPEP from 3 to 500 amino acids encoded by a nucleotide sequence contained in the primary transcript of a miR, or a fragment of said miPEP, said miPEP being capable of modulating the accumulation of said miR in a eukaryotic cell, for its use as defined above, which miR regulates expression of at least one gene involved in a pathology.

In a particular embodiment, the invention relates to a miPEP, or a fragment of said miPEP, for its use as defined above, said miPEP being identified, or as identified, by implementing of a process for identifying a miPEP modulating the accumulation of a miR involved in a pathology, comprising:
  a) a step of detecting an open reading frame from 12 to 1 503 nucleotides contained in the sequence of the primary transcript of said miR, then
  b) a step of comparison between:
    i. the accumulation of said miR in a specified eukaryotic cell expressing the primary transcript of said miR, in the presence of a peptide encoded by a nucleotide sequence that is identical or degenerate relative to that of said open reading frame, said peptide being present in the cell independently of transcription of the primary transcript of said miR, and
    ii. the accumulation of said miR in a eukaryotic cell of the same type as the aforesaid specified eukaryotic cell expressing the primary transcript of said miR, in the absence of said peptide, in which a modulation of the accumulation of said miR in the presence of said peptide relative to the accumulation of said miR in the absence of said peptide indicates the existence of a miPEP, the latter being encoded by said open reading frame and being capable of modulating the accumulation of said miR involved in a pathology.

In a particular embodiment, the invention relates to a miPEP, or a fragment of said miPEP, for its use as defined above, said miPEP being selected from the group consisting of SEQ ID NO: 2q-1, q varying from 1 to 5 875.

In a particular embodiment, the invention relates to a miPEP, or a fragment of said miPEP, for its use as defined above, said miPEP being selected from the group consisting of: miPEP 145-2 (SEQ ID NO: 11745), miPEP 125a-1 (SEQ ID NO: 11747) and miPEP 15a-16-1 (SEQ ID NO: 11 749).

In a particular embodiment, the invention relates to a miPEP, or a fragment of said miPEP, for its use as defined above, said miPEP fragment being a fragment of miPEP 145-2, preferably consisting of SEQ ID NO: 11 751.

In a particular embodiment, the invention relates to a miPEP, or a fragment of said miPEP, for its use as defined above, said miPEP fragment being miPEP//145-2 consisting of SEQ ID NO: 11 751.

In a particular embodiment, the invention relates to a miPEP, or a fragment of said miPEP, for its use as defined above, said miPEP fragment being a fragment of miPEP 125a-1, preferably consisting of SEQ ID NO: 11 752.

In a particular embodiment, the invention relates to a miPEP, or a fragment of said miPEP, for its use as defined above, said miPEP fragment being miPEP//125a-1 consisting of SEQ ID NO: 11 752.

In a particular embodiment, the invention relates to a miPEP, or a fragment of said miPEP, for its use as defined above, said miPEP fragment being a fragment of miPEP 15a-16-1, preferably consisting of SEQ ID NO: 11 753.

In a particular embodiment, the invention relates to a miPEP, or a fragment of said miPEP, for its use as defined above, said miPEP fragment being miPEP//15a-16-1 consisting of SEQ ID NO: 11 753.

In a particular embodiment, the invention relates to a miPEP, or a fragment of said miPEP, for its use as defined above, wherein said miPEP, or said fragment of said miPEP, is fused to the TAT peptide.

In a particular embodiment, the invention relates to a miPEP fragment for its use as defined above, said miPEP fragment being selected from:

miPEP//145-2-TAT consisting of SEQ ID NO: 11 755 (MVGLNPPLWQ-YGRKKRRQRRR), miPEP//125a-1-TAT consisting of SEQ ID NO: 11 756 (MSLCLSPSLT-YGRKKRRQRRR), and miPEP//15a-16-1-TAT consisting of SEQ ID NO: 11 757 (MFKHRFFYMH-YGRKKRRQRRR).

In a particular embodiment, the invention relates to a miPEP, or a fragment of said miPEP, for its use as defined above, wherein said miPEP, or said fragment of said miPEP, being fused to penetratin, to a polyhistidine peptide (in particular a peptide of at least 6 histidine residues) or to a polyarginine peptide (in particular a peptide of 9 arginine residues).

In a particular embodiment, the invention relates to a miPEP, or a fragment of said miPEP, for its use as defined above, wherein said miPEP, or said fragment of said miPEP, being linked to one or more palmitic acid molecules.

Tables 2 to 6 present the different miRs and the pathologies in which they are involved.

In a particular embodiment, the invention relates to a miPEP, or a fragment of said miPEP, for its use as defined above, said pathology being a cancer, said miPEP being encoded by a nucleotide sequence contained in the primary transcript of a miR selected from the cancer-related miRs in Table 2, particularly among the cancer-related miRs in Table 5.

In a particular embodiment, the invention relates to a miPEP, or a fragment of said miPEP, for its use as defined above, said pathology being a bacterial infection or mycosis, said miPEP being encoded by a nucleotide sequence contained in the primary transcript of a miR selected from the bacterial infection- and mycosis-related miRs in Table 2, particularly among the bacterial infection- and mycosis-related miRs in Table 5.

In a particular embodiment, the invention relates to a miPEP, or a fragment of said miPEP, for its use as defined above, said pathology being a cardiovascular disease, said miPEP being encoded by a nucleotide sequence contained in the primary transcript of a miR selected from the cardiovascular disease-related miRs in Table 2, particularly among the cardiovascular disease-related miRs in Table 5.

In a particular embodiment, the invention relates to a miPEP, or a fragment of said miPEP, for its use as defined above, said pathology being a hereditary congenital disease, said miPEP being encoded by a nucleotide sequence contained in the primary transcript of a miR selected from the hereditary congenital disease-related miRs in Table 2, particularly among the hereditary congenital disease-related miRs in Table 5.

In a particular embodiment, the invention relates to a miPEP, or a fragment of said miPEP, for its use as defined above, said pathology being a skin disease, said miPEP being encoded by a nucleotide sequence contained in the primary transcript of a miR selected from the skin disease-related miRs in Table 2, particularly among the skin disease-related miRs in Table 5.

In a particular embodiment, the invention relates to a miPEP, or a fragment of said miPEP, for its use as defined above, said pathology being a eye disease, said miPEP being encoded by a nucleotide sequence contained in the primary transcript of a miR selected from the eye disease-related miRs in Table 2, particularly among the eye disease-related miRs in Table 5.

In a particular embodiment, the invention relates to a miPEP, or a fragment of said miPEP, for its use as defined above, said pathology being a disease of the digestive system, said miPEP being encoded by a nucleotide sequence contained in the primary transcript of a miR selected from disease of the digestive system-related miRs in Table 3, particularly among disease of the digestive system-related miRs in Table 5.

In a particular embodiment, the invention relates to a miPEP, or a fragment of said miPEP, for its use as defined above, said pathology being a disease of the endocrine system, said miPEP being encoded by a nucleotide sequence contained in the primary transcript of a miR selected from disease of the endocrine system-related miRs in Table 3, particularly among disease of the endocrine system-related miRs in Table 6.

In a particular embodiment, the invention relates to a miPEP, or a fragment of said miPEP, for its use as defined above, said pathology being a disease of the nervous system, said miPEP being encoded by a nucleotide sequence contained in the primary transcript of a miR selected from disease of the nervous system-related miRs in Table 3, particularly among disease of the nervous system-related miRs in Table 6.

In a particular embodiment, the invention relates to a miPEP, or a fragment of said miPEP, for its use as defined above, said pathology being a disease linked to a virus, said miPEP being encoded by a nucleotide sequence contained in the primary transcript of a miR selected from disease linked to a virus-related miRs in Table 3, particularly among disease linked to a virus-related miRs in Table 6.

In a particular embodiment, the invention relates to a miPEP, or a fragment of said miPEP, for its use as defined above, said pathology being a disease related to nutrition and metabolism, said miPEP being encoded by a nucleotide sequence contained in the primary transcript of a miR selected from disease related to nutrition and metabolism-related miRs in Table 3, particularly among disease related to nutrition and metabolism-related miRs in Table 6.

In a particular embodiment, the invention relates to a miPEP, or a fragment of said miPEP, for its use as defined above, said pathology being a lymphatic disease or hemopathy, said miPEP being encoded by a nucleotide sequence contained in the primary transcript of a miR selected from lymphatic disease or hemopathy-related miRs in Table 3, particularly among lymphatic disease or hemopathy-related miRs in Table 6.

In a particular embodiment, the invention relates to a miPEP, or a fragment of said miPEP, for its use as defined above, said pathology being a neonatal and hereditary disease, said miPEP being encoded by a nucleotide sequence contained in the primary transcript of a miR selected from neonatal and hereditary disease-related miRs in Table 3, particularly among neonatal and hereditary disease-related miRs in Table 6.

In a particular embodiment, the invention relates to a miPEP, or a fragment of said miPEP, for its use as defined above, said pathology being a respiratory disease, said miPEP being encoded by a nucleotide sequence contained in the primary transcript of a miR selected from respiratory disease-related miRs in Table 4, particularly among respiratory disease-related miRs in Table 6.

In a particular embodiment, the invention relates to a miPEP, or a fragment of said miPEP, for its use as defined above, said pathology being a urogenital disease in men, said miPEP being encoded by a nucleotide sequence contained in the primary transcript of a miR selected from urogenital disease in men-related miRs in Table 4, particularly among urogenital disease in men-related miRs in Table 6.

In a particular embodiment, the invention relates to a miPEP, or a fragment of said miPEP, for its use as defined above, said pathology being a urogenital disease in women, said miPEP being encoded by a nucleotide sequence contained in the primary transcript of a miR selected from urogenital disease in women-related miRs in Table 4, particularly among urogenital disease in women-related miRs in Table 6.

In a particular embodiment, the invention relates to a miPEP, or a fragment of said miPEP, for its use as defined above, said pathology being a disorder of the immune system, said miPEP being encoded by a nucleotide sequence contained in the primary transcript of a miR selected from disorder of the immune system-related miRs in Table 4, particularly among disorder of the immune system-related miRs in Table 6.

In a particular embodiment, the invention relates to a miPEP, or a fragment of said miPEP, for its use as defined above, said pathology being a musculoskeletal disorder, said miPEP being encoded by a nucleotide sequence contained in the primary transcript of a miR selected from musculoskeletal disorder-related miRs in Table 4, particularly among musculoskeletal disorder-related miRs in Table 6.

In a particular embodiment, the invention relates to a miPEP, or a fragment of said miPEP, for its use as defined above, said pathology being a metabolism disorder, said miR being selected from: hsa-miR-103-1, hsa-miR-103-2 and hsa-mir-107, said miPEP being preferably selected from SEQ ID NOs: 73, 75, 77, 79, 81, 83, 85, 87, 2 547, 2 549, 2 551, 2 553, 3 921, 3 923, 3 925 and 3 927.

In a particular embodiment, the invention relates to a miPEP, or a fragment of said miPEP, for its use as defined above, said pathology being a hepatitis C virus infection, said miR being the hsa-miR-122, said miPEP being preferably selected from SEQ ID NOs: 97, 99, 101, 103, 2561, 2563, 2 565 and 2 567.

In a particular embodiment, the invention relates to a miPEP, or a fragment of said miPEP, for its use as defined above, said pathology being an inflammatory disease, said miR being the hsa-miR-155, said miPEP being preferably selected from SEQ ID NOs: 4 433, 4 435, 4 437, 4 439, 4 441, 4 443, 4 445, 4 447, 8 377, 8 379, 8 381 and 8 383.

In a particular embodiment, the invention relates to a miPEP, or a fragment of said miPEP, for its use as defined above, said pathology being a fibrosis, said miR being the hsa-miR-21, said miPEP being preferably selected from SEQ ID NOs: 497, 499, 501, 503, 2 793, 2 795, 2 797, 2 799, 3 425, 3 427, 3 429, 3 431, 4 937, 4 939, 4 941, 4 943, 8 545, 8 547, 8 549, 8 551, 801, 10 803, 10 805 and 10 807.

In a particular embodiment, the invention relates to a miPEP, or a fragment of said miPEP, for its use as defined above, said pathology being atherosclerosis, said miR being the hsa-miR-33, said miPEP being preferably selected from SEQ ID NOs: 5 609, 5 611, 5 613, 5 615, 8 673, 8 675, 8 677 and 8 679.

In a particular embodiment, the invention relates to a miPEP, or a fragment of said miPEP, for its use as defined above, said pathology being a cardiovascular disease, said miR being selected from: hsa-miR-15a and has-miR-15b, said miPEP being preferably selected from SEQ ID NOs: 4 449, 4 451, 4 453, 4 455, 4 457, 4 459, 4 461, 4 463, 4 465, 4 467, 4 469 and 4 471.

In a particular embodiment, the invention relates to a miPEP, or a fragment of said miPEP, for its use as defined above, said pathology being a myeloproliferative disease, said miR being the hsa-miR-451, said miPEP being preferably selected from SEQ ID NOs: 1 017, 1 019, 1 021, 1 023, 3 609, 3 611, 3 613, 3 615, 6 113, 6 115, 6 117 and 6 119.

In a particular embodiment, the invention relates to a miPEP, or a fragment of said miPEP, for its use as defined above, said pathology being linked to neoangiogenesis, said miR being selected from: hsa-mir-92a-1, hsa-mir-92a-2 and hsa-mir-92b, said miPEP being preferably selected from SEQ ID NOs: 1 777, 1 779, 1 781, 1 783, 1 785, 1 787, 1 789, 1 791, 8 033, 8 035, 8 037, 8 039, 8 041, 8 043, 8 045, 8 047, 8 049, 8 051, 8 053, 8 055, 9 225, 9 227, 9 229, 9 231, 9 233, 9 235, 9 237, 9 239, 9 241, 9 243, 9 245, 9 247, 10 345, 10 347, 10 349, 351, 10 353, 10 355, 10 357, 10 359, 10 361, 10 363, 10 365, 10 367, 11 489, 11 491, 11 493, 11 495, 11 497, 11 499, 11 501, 11 503, 11 505, 11 507, 11 509 and 11 511.

In a particular embodiment, the invention relates to a miPEP, or a fragment of said miPEP, for its use as defined above, said pathology being a cardiac disorder, said miR being selected from: hsa-mir-208 and hsa-mir-208b, said miPEP being preferably selected from SEQ ID NOs: 4 889, 4 891, 4 893, 4 895, 4 897, 4 899, 4 901, 4 903, 4 905, 4 907, 4 909, 4911, 4913, 4915, 4 917 and 4919.

In a particular embodiment, the invention relates to a miPEP, or a fragment of said miPEP, for its use as defined above, said pathology being a pulmonary fibrosis, said miR being the hsa-mir-208, said miPEP being preferably selected from SEQ ID NOs: 4 889, 4 891, 4 893, 4 895, 4 897, 4 899, 4 901, 4 903, 4 905, 4 905, 4 907, 4 909, 4 911, 4 913, 4 915, 4 917 and 4 919.

In a particular embodiment, the invention relates to a miPEP, or a fragment of said miPEP, for its use as defined above, said pathology being a cancer, said miR being the hsa-let-7, said miPEP being preferably selected from SEQ ID NO: 2q-1, q varying from 1 to 28, from 1 225 to 1 260, from 1 561 to 1 576, from 1 865 to 1 916, from 4 065 to 4 100, from 4 645 to 4 668, from 5 197 to 5 228.

In a particular embodiment, the invention relates to a miPEP, or a fragment of said miPEP, for its use as defined above, said pathology being a cardiovascular disease, in particular the ischemia-reperfusion syndrome, said miR being the hsa-miR-7, said miPEP being preferably selected from SEQ ID NOs: 3 089, 3 091, 3 093, 3 095, 3 689, 3 691, 3 693, 3 695, 7 881, 7 883, 7 885, 7 887, 7 889, 7 891, 7 893, 7 895, 7 897, 7 899, 7 901, 7 903, 9 209, 9 211, 9 213, 9 215, 11 473, 11 475, 11 477 and 11 479.

In a particular embodiment, the invention relates to a miPEP, or a fragment of said miPEP, for its use as defined above, said pathology being a hepatitis C virus infection, said miR being the hsa-mir-181c, said miPEP being preferably selected from SEQ ID NOs: 321, 323, 325, 327, 2 657, 2 659, 2 661, 2 663, 4 537, 4 539, 4 541, 4 543, 8 409, 8 411, 8 413, 8 415, 9 497, 9499, 9 501 and 9503.

In a particular embodiment, the invention relates to a miPEP, or a fragment of said miPEP, for its use as defined above, said pathology being a pulmonary fibrosis, said miR being the hsa-miR-29, said miPEP being preferably selected from SEQ ID NOs: 633, 635, 637, 639, 641, 643, 645, 647, 649, 651, 653, 655, 657, 659, 661, 663, 2 905, 2 907, 2 909, 2 911, 2 913, 2 915, 2 917, 2 919, 3 529, 3 531, 3 533, 3 535, 3 537, 3 539, 3 541, 3 543, 5 281, 5 283, 285, 5 287, 5 289, 5 291, 5 293, 5 295, 5 297, 5 299, 5 301, 5 303, 5 305, 5 307, 5 309, 311, 11 657, 11 659, 11 661, 11 663, 11 665, 11 667, 11 669 and 11 671.

In a particular embodiment, the invention relates to a miPEP for its use in the treatment of a disease or trauma of bone tissue or cartilage tissue, said miPEP being selected from the group of miPEPs consisting of: miPEP 145-2 (SEQ ID NO: 11 745), miPEP 125a-1 (SEQ ID NO: 11 747) and miPEP 15a-16-1 (SEQ ID NO: 11 749).

In a particular embodiment, the invention relates to a miPEP fragment for its use in the treatment of a disease or trauma of bone tissue or cartilage tissue, said miPEP fragment being a fragment of the miPEP 145-2, preferably consisting of SEQ ID NO: 11 751.

In a particular embodiment, the invention relates to a miPEP fragment for its use in the treatment of a disease or trauma of bone tissue or cartilage tissue, said miPEP fragment being the miPEP//145-2 consisting of SEQ ID NO: 11 751.

In a particular embodiment, the invention relates to a miPEP fragment for its use in the treatment of a disease or trauma of bone tissue or cartilage tissue, said miPEP fragment being a fragment of the miPEP 125a-1, preferably consisting of SEQ ID NO: 11 752.

In a particular embodiment, the invention relates to a miPEP fragment for its use in the treatment of a disease or trauma of bone tissue or cartilage tissue, said miPEP fragment being the miPEP//125a-1 consisting of SEQ ID NO: 11 752.

In a particular embodiment, the invention relates to a miPEP fragment for its use in the treatment of a disease or trauma of bone tissue or cartilage tissue, said miPEP fragment being a fragment of the miPEP 15a-16-1, preferably consisting of SEQ ID NO: 11 753.

In a particular embodiment, the invention relates to a miPEP fragment for its use in the treatment of a disease or trauma of bone tissue or cartilage tissue, said miPEP fragment being the miPEP//15a-16-1 consisting of SEQ ID NO: 11 754.

In a particular embodiment, the invention relates to a miPEP fragment for its use in the treatment of a disease or trauma of bone tissue or cartilage tissue, said miPEP fragment being selected from:

```
miPEP//145-2-TAT consisting of SEQ ID NO: 11 755
(MVGLNPPLWQ-YGRKKRRQRRR), miPEP//125a-1-TAT consisting of SEQ ID NO: 11 756
(MSLCLSPSLT-YGRKKRRQRRR),
and
```

-continued miPEP//15a-16-1-TAT consisting of SEQ ID NO: 11 757
(MFKHRFFYMH-YGRKKRRQRRR).

Another aspect of the invention relates to process for identifying a miPEP, or a fragment of said miPEP, modulating the accumulation of a miR involved in a pathology, said miPEP being encoded by a nucleotide sequence contained in the primary transcript of a miR, comprising:
 a) a step of detecting an open reading frame from 12 to 1 503 nucleotides contained in the sequence of the primary transcript of said miR, then
 b) a step of comparison between:
  i. the accumulation of said miR in a specified eukaryotic cell expressing the primary transcript of said miR, in the presence of a peptide encoded by a nucleotide sequence that is identical or degenerate relative to that of said open reading frame, said peptide being present in the cell independently of transcription of the primary transcript of said miR, and
  ii. the accumulation of said miR in a eukaryotic cell of the same type as the aforesaid specified eukaryotic cell expressing the primary transcript of said miR, in the absence of said peptide,
in which a modulation of the accumulation of said miR in the presence of said peptide relative to the accumulation of said miR in the absence of said peptide indicates the existence of a miPEP, the latter being encoded by said open reading frame and being capable of modulating the accumulation of said miR involved in a pathology.

Another aspect of the invention also relates to a miPEP from 101 to 500 amino acids, or a fragment of said miPEP, encoded by a nucleotide sequence contained in the primary transcript of a microRNA, said miPEP being capable of modulating the accumulation of said miR in a eukaryotic cell.

In particular, a miPEP may have a size from 200 to 500 amino acids, from 300 to 500 amino acids or from 400 to 500 amino acids.

In particular, a miPEP may have a size of 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499 or 500 amino acids.

In a particular embodiment, the invention relates to a miPEP selected from the group consisting of SEQ ID NO: 2q-1, q varying from 1 to 5 875, or a fragment of said miPEP.

In a particular embodiment, the invention relates to a miPEP selected from the group consisting of: miPEP 145-2 (SEQ ID NO: 11 745), miPEP 125a-1 (SEQ ID NO: 11 747) and miPEP 15a-16-1 (SEQ ID NO: 11 749).

In a particular embodiment, the invention relates to a fragment of miPEP 145-2, preferably consisting of SEQ ID NO: 11 751.

In a particular embodiment, the invention relates to miPEP//145-2 consisting of SEQ ID NO: 11 751.

In a particular embodiment, the invention relates to a fragment of miPEP 125a-1, preferably consisting of SEQ ID NO: 11 752.

In a particular embodiment, the invention relates to miPEP//125a-1 consisting of SEQ ID NO: 11 752.

In a particular embodiment, the invention relates to a fragment of miPEP 15a-16-1, preferably consisting of SEQ ID NO: 11 753.

In a particular embodiment, the invention relates to miPEP//15a-16-1 consisting of SEQ ID NO: 11 753.

In a particular embodiment, the invention relates to a miPEP, or a fragment of said miPEP, vectorized or encapsulated.

In a particular embodiment, the invention relates to a miPEP, or a fragment of said miPEP, fused to a peptide facilitating the entry into the cell of the miPEP, or miPEP fragment.

In a particular embodiment, the invention relates to a miPEP, or a fragment of said miPEP, wherein said miPEP, or said fragment of said miPEP, fused to the TAT peptide (YGRKKRRQRRR, SEQ ID NO: 11 754).

In a particular embodiment, the invention relates to a miPEP fragment, said miPEP fragment being selected from:

miPEP//145-2-TAT consisting of SEQ ID NO: 11 755
(MVGLNPPLWQ-YGRKKRRQRRR), miPEP//125a-1-TAT consisting of SEQ ID NO: 11 756
(MSLCLSPSLT-YGRKKRRQRRR),
and miPEP//15a-16-1-TAT consisting of SEQ ID NO: 11 757
(MFKHRFFYMH-YGRKKRRQRRR).

In a particular embodiment, the invention relates to a miPEP, or a fragment of said miPEP, as defined above, fused to penetratin, to a polyhistidine peptide (in particular a peptide of at least 6 histidine residues) or to a polyarginine peptide (in particular a peptide of 9 arginine residues).

In a particular embodiment, the invention relates to a miPEP, or a fragment of said miPEP, as defined above, linked to one or more palmitic acid molecules.

In another aspect, the invention relates to a composition comprising a miPEP or a fragment of said miPEP.

In a particular embodiment, the invention relates to a composition as defined above, wherein said miPEP is selected from the group of miPEP consisting of SEQ ID NO: 2q-1, q varying from 1 to 5 875.

In a particular embodiment, the invention relates to a composition as defined above, wherein said miPEP is selected from the group of miPEP consisting of: miPEP 145-2 (SEQ ID NO: 11745), miPEP 125a-1 (SEQ ID NO: 11747) and miPEP 15a-16-1 (SEQ ID NO: 11 749).

In a particular embodiment, the invention relates to a composition as defined above, wherein said miPEP fragment is a fragment of miPEP 145-2, preferably consisting of SEQ ID NO: 11 751.

In a particular embodiment, the invention relates to a composition as defined above, wherein said miPEP fragment is the miPEP//145-2 consisting of SEQ ID NO: 11 751.

In a particular embodiment, the invention relates to a composition as defined above, wherein said miPEP fragment is a fragment of miPEP 125a-1, preferably consisting of SEQ ID NO: 11 752.

In a particular embodiment, the invention relates to a composition as defined above, wherein said miPEP fragment is the miPEP//125a-1 consisting of SEQ ID NO: 11 752.

In a particular embodiment, the invention relates to a composition as defined above, wherein said miPEP fragment is a fragment of miPEP 15a-16-1, preferably consisting of SEQ ID NO 11 753.

In a particular embodiment, the invention relates to a composition as defined above, wherein said miPEP fragment is the miPEP//15a-16-1 consisting of SEQ ID NO: 11 753.

In a particular embodiment, the invention relates to a composition as defined above, wherein said miPEP fragment being selected from:

```
miPEP//145-2-TAT consisting of SEQ ID NO: 11 755
(MVGLNPPLWQ-YGRKKRRQRRR), miPEP//125a-1-TAT consisting of SEQ ID NO: 11 756
(MSLCLSPSLT-YGRKKRRQRRR),
and miPEP//15a-16-1-TAT consisting of SEQ ID NO: 11 757
(MFKHRFFYMH-YGRKKRRQRRR).
```

In a particular embodiment, the invention relates to a composition as defined above, wherein said composition additionally contains growth factors and/or cell differentiation factors.

In a particular embodiment, the invention relates to a composition as defined above, wherein said composition additionally contains BMP4.

In a particular embodiment, the invention relates to a composition as defined above, wherein said composition additionally contains cell culture medium.

In another aspect, the invention relates to the in vitro or ex vivo use of a miPEP from 3 to 500 amino acids encoded by a nucleotide sequence contained in the primary transcript of a miR, or a fragment of said miPEP, said miPEP being capable of modulating the accumulation of said miR in a eukaryotic cell, to promote cell differentiation of cells.

In a particular embodiment, the invention relates to the in vitro or ex vivo use of a miPEP, or a fragment of said miPEP, to promote cell differentiation of mesenchymal stem cells (also called bone marrow stromal cells or mesenchymal stromal cells).

In a particular embodiment, the invention relates to the in vitro or ex vivo use of a miPEP, or a fragment of said miPEP, to promote cell differentiation of mesenchymal stem cells in osteoblasts.

In a particular embodiment, the invention relates to the use as defined above, wherein cells are cultured in the presence of said miPEP, or a fragment of said miPEP.

In a particular embodiment, the invention relates to the use as defined above, wherein cells are cultured in the presence of said miPEP, or a fragment of said miPEP, and in the presence of growth factors and/or cell differentiation factors.

In a particular embodiment, the invention relates to the use as defined above, wherein cells are cultured in the presence of said miPEP, or a fragment of said miPEP, and in the presence of BMP4 (Bone Morphogenetic Protein 4).

In a particular embodiment, the invention relates to the use as defined above, wherein said miPEP is selected from the group of miPEPs consisting of SEQ ID NO: 2q-1, q varying from 1 to 5 875.

In a particular embodiment, the invention relates to the use as defined above, wherein said miPEP selected from the group consisting of: miPEP 145-2 (SEQ ID NO: 11 745), miPEP 125a-1 (SEQ ID NO: 11 747) and miPEP 15a-16-1 (SEQ ID NO: 11 749).

In a particular embodiment, the invention relates to the use as defined above, wherein said fragment is a fragment of miPEP 145-2, preferably consisting of SEQ ID NO: 11 751.

In a particular embodiment, the invention relates to the use as defined above, wherein said fragment is the miPEP//145-2 consisting of SEQ ID NO: 11 751.

In a particular embodiment, the invention relates to the use as defined above, wherein said fragment is a fragment of miPEP 125a-1, preferably consisting of SEQ ID NO: 11 752.

In a particular embodiment, the invention relates to the use as defined above, wherein said fragment is the miPEP//125a-1 consisting of SEQ ID NO: 11 752.

In a particular embodiment, the invention relates to the use as defined above, wherein said fragment is a fragment of miPEP 15a-16-1, preferably consisting of SEQ ID NO: 11 753.

In a particular embodiment, the invention relates to the use as defined above, wherein said fragment is the miPEP//15a-16-1 consisting of SEQ ID NO: 11 753.

In a particular embodiment, the invention relates to the use as defined above, wherein said miPEP fragment is selected from:

```
miPEP//145-2-TAT consisting of SEQ ID NO: 11 755
(MVGLNPPLWQ-YGRKKRRQRRR), miPEP//125a-1-TAT consisting of SEQ ID NO: 11 756
(MSLCLSPSLT-YGRKKRRQRRR),
and miPEP//15a-16-1-TAT consisting of SEQ ID NO: 11 757
(MFKHRFFYMH-YGRKKRRQRRR).
```

In a particular embodiment, the invention relates to the in vitro or ex vivo use of a miPEP, or a fragment of said miPEP, to induce or promote bone formation.

In a particular embodiment, the invention relates to the in vitro or ex vivo use of a miPEP, or a fragment of said miPEP, to form a mineralized bone matrix.

In a particular embodiment, the invention relates to the in vitro or ex vivo use of a miPEP, or a fragment of said miPEP, to promote bone formation with the help of a bone biomaterial.

In a particular embodiment, the invention relates to the use as defined above, wherein mesenchymal stem cells are cultured in the presence of said miPEP, or a fragment of said miPEP.

In a particular embodiment, the invention relates to the use as defined above, wherein mesenchymal stem cells are cultured in the presence of said miPEP, or a fragment of said miPEP, and in the presence of growth factors and/or cell differentiation factors.

In a particular embodiment, the invention relates to the use as defined above, wherein mesenchymal stem cells are cultured in the presence of said miPEP, or a fragment of said miPEP, and in the presence of BMP4.

In a particular embodiment, the invention relates to the use as defined above, wherein said miPEP is selected from the group of miPEPs consisting of SEQ ID NO: 2q-1, q varying from 1 to 5 875.

In a particular embodiment, the invention relates to the use as defined above, wherein said miPEP selected from the group consisting of: miPEP 145-2 (SEQ ID NO: 11 745), miPEP 125a-1 (SEQ ID NO: 11 747) and miPEP 15a-16-1 (SEQ ID NO: 11 749).

In a particular embodiment, the invention relates to the use as defined above, wherein said fragment is a fragment of miPEP 145-2, preferably consisting of SEQ ID NO: 11 751.

In a particular embodiment, the invention relates to the use as defined above, wherein said fragment is the miPEP// 145-2 consisting of SEQ ID NO: 11 751.

In a particular embodiment, the invention relates to the use as defined above, wherein said fragment is a fragment of miPEP 125a-1, preferably consisting of SEQ ID NO: 11 752.

In a particular embodiment, the invention relates to the use as defined above, wherein said fragment is the miPEP// 125a-1 consisting of SEQ ID NO: 11 752.

In a particular embodiment, the invention relates to the use as defined above, wherein said fragment is a fragment of miPEP 15a-16-1, preferably consisting of SEQ ID NO: 11 753.

In a particular embodiment, the invention relates to the use as defined above, wherein said fragment is the miPEP// 15a-16-1 consisting of SEQ ID NO: 11 753.

In a particular embodiment, the invention relates to the use as defined above, wherein said miPEP fragment is selected from:

```
miPEP//145-2-TAT consisting of SEQ ID NO: 11 755
(MVGLNPPLWQ-YGRKKRRQRRR), miPEP//125a-1-TAT consisting of SEQ ID NO: 11 756
(MSLCLSPSLT-YGRKKRRQRRR),
and miPEP//15a-16-1-TAT consisting of SEQ ID NO: 11 757
(MFKHRFFYMH-YGRKKRRQRRR).
```

In another aspect, the invention relates to the in vivo use of a miPEP, or a fragment of said miPEP, to induce or promote bone formation.

In another aspect, the invention relates to the in vivo use of a miPEP, or a fragment of said miPEP, to form a mineralized bone matrix.

In another aspect, the invention relates to the in vivo use of a miPEP, or a fragment of said miPEP, to promote bone formation with the help of a bone biomaterial.

Another aspect of the invention relates to a nucleic acid encoding a miPEP as defined above, or a fragment of said miPEP.

In a particular embodiment, the invention relates to a nucleic acid as defined above, said nucleic acid being selected from the group consisting of SEQ ID NO: 2q, q varying from 1 to 5 875.

In another aspect, the invention relates to an antibody specifically recognizing a miPEP selected from the group consisting of SEQ ID NO: 2q-1, q varying from 1 to 5 875, or a fragment of said miPEP.

Such antibody can be obtained from a method known to those skilled in the art, such as for example by injecting said miPEP with a non-human animal to trigger an immunization reaction and the production of antibodies by said animal.

In another aspect, the invention relates to an antibody specifically recognizing a miPEP, or a fragment of said miPEP, for its use as a drug.

In a particular embodiment, the invention relates to an antibody specifically recognizing a miPEP selected from the group consisting of SEQ ID NO: 2q-1, q varying from 1 to 5 875, or a fragment of said miPEP, for its use as a drug.

In another aspect, the invention relates to an antibody specifically recognizing a miPEP, or a fragment of said miPEP, for immunostaining said miPEP or a fragment of said miPEP.

In a particular embodiment, the invention relates to the use of an antibody as defined above, wherein said specifically recognizing a miPEP selected from the group consisting of SEQ ID NO: 2q-1, q varying from 1 to 5 875, or a fragment of said miPEP.

According to a particular embodiment, the invention relates to a miPEP from 3 to 500 amino acids encoded by a nucleotide sequence contained in the primary transcript of a miR, or a fragment of said miPEP, said miPEP being capable of modulating the accumulation of said miR in a eukaryotic cell, for its use as a drug in the treatment of musculoskeletal disorders, or disease or trauma of bone tissue or cartilage tissue, said primary transcript of a miR being selected from the group consisting of:

let-7b, let-7g, miR-15a, miR16-1, miR106a, miR10a, miR10b, miR1246, miR125a-1, miR132, miR134, miR142, miR145, miR145-2, miR146a, miR150, miR155, miR181c, miR182, miR183, miR184, miR18b, miR192, miR195, miR200a, miR202, miR203, miR205, miR206, miR20b, miR21, miR210, miR27a, miR29a, miR29c, miR30b, miR345, miR377, miR409, miR495, miR520h, miR542, miR572, miR648, miR96 and miR99b;

preferably among the group consisting of: miR15a, miR16-1, miR125a-1 and miR145-2.

According to another particular embodiment, the invention relates to a miPEP as defined above having in particular a size from 3 to 50 amino acids, from 50 to 100 amino acids, from 100 to 500 amino acids, from 101 to 500 amino acids, from 200 to 500 amino acids, from 300 to 500 amino acids, from 400 to 500 amino acids, from 100 to 200 amino acids, from 200 to 300 amino acids or from 300 to 400 amino acids.

According to another particular embodiment, the invention relates to a miPEP, or a fragment of said miPEP, for its use as defined above, said miPEP being identified, or as identified, by implementing of a process for identifying a miPEP modulating the accumulation of a miR involved in a musculoskeletal disorder, or disease or trauma of bone tissue or cartilage tissue, comprising:

a) a step of detecting an open reading frame from 12 to 1 503 nucleotides contained in the sequence of the primary transcript of said miR, then b) a step of comparison between:
   i. the accumulation of said miR in a specified eukaryotic cell expressing the primary transcript of said miR, in the presence of a peptide encoded by a nucleotide sequence that is identical or degenerate relative to that of said open reading frame, said peptide being present in the cell independently of transcription of the primary transcript of said miR, and ii. the accumulation of said miR in a eukaryotic cell of the same type as the aforesaid specified eukaryotic cell expressing the primary transcript of said miR, in the absence of said peptide, in which a modulation of the accumulation of said miR in the presence of said peptide relative to the accumulation of said miR in the absence of said peptide indicates the existence of a miPEP, the latter being encoded by said open reading frame and being capable of modulating the accumulation of said miR involved in a musculoskeletal disorder, or disease or trauma of bone tissue or cartilage tissue.

According to another particular embodiment, the invention relates to a miPEP, or a fragment of said miPEP, for its use as defined above, said miPEP being selected from the group of miPEPs consisting of SEQ ID NO: 2q-1, q varying from 45 to 48, from 89 to 92, from 101 to 104, from 121 to 124, from 133 to 140, from 153 to 156, from 161 to 164, from 169 to 192, from 221 to 224, from 233 to 256, from 301 to 304, from 317 to 320, from 329 to 332, from 337 to 340, from 381 to 384, from 445 to 448, from 469 to 472, from 533 to 536, from 693 to 696, from 789 to 792, from 909 to 916, from 977 to 980, from 1 021 to 1 024, from 1 237 to 1 240, from 1 277 to 1 280, from 1 329 to 1 332, from 1 337 to 1 344, from 1 350 to 1 353, from 1 361 to 1 364, from 1 374 to 1 377, from 1 385 to 1 388, from 1 393 to 1 404, from 1 445 to 1 448, from 1 453 to 1 456, from 1 469 to 1 472, from 1 533 to 1 536, from 1 549 to 1 552, from 1 557 to 1 560, from 1 581 to 1 584, from 1 645 to 1 652, from 1 677 to 1 680, from 1 705 to 1 716, from 1 769 to 1 772, from 1 877 to 1 880, from 1 909 to 1 912, from 1 953 to 1 956, from 1 965 to 1972, from 2 061 to 2 064, from 2 073 to 2 076, from 2 117 to 2 120, from 2 129 to 2 140, from 2 185 to 2 188, from 2 217 to 2 244, from 2 269 to 2 288, from 2 317 to 2 320, from 2 337 to 2 340, from 2 361 to 2 364, from 2 413 to 2 416, from 2 425 to 2 432, from 2 437 to 2 444, from 2 465 to 2 476, from 2 609 to 2 612, from 2 641 to 2 644, from 2 653 to 2 656, from 2 689 to 2 692, from 2 825 to 2 828, from 2 949 to 2 952, from 2 977 to 2 980, from 3 141 to 3 144, from 3 317 to 3 320, from 3 373 to 3 376, from 3 517 to 3 520, from 3 861 to 3 868, from 4 041 to 4 044, from 4 061 to 4 064, from 4 093 to 4 096, from 4 113 to 4 116, from 4 121 to 4 128, from 4 157 to 4 164, from 4 189 to 4 192, from 4 205 to 4 208, from 4 225 to 4 228, from 4 242 to 4 245, from 4 269 to 4 276, from 4 309 to 4 312, from 4 341 to 4 344, from 4 421 to 4 424, from 4 637 to 4 640, from 4 661 to 4 664, from 4 677 to 4 680, from 4 685 to 4 692, from 4 705 to 4 708, from 4 749 to 4 752, from 4 757 to 4 764, from 4 777 to 4 780, from 4 793 to 4 796, from 4 813 to 4 816, from 4 825 to 4 828, from 4 833 to 4 840, from 4 898 to 4 901, from 4 985 to 4 988, from 5 157 to 5 160, from 5 189 to 5 196, from 5 221 to 5 224, from 5 241 to 5 244, from 5 249 to 5 300, from 5 341 to 5 344, from 5 357 to 5 360, from 5 381 to 5 384, from 5 397 to 5 408, from 5 437 to 5 440, from 5 473 to 5 476, from 5 563 to 5 570, from 5 717 to 5 720, from 5 765 to 5 768, from 5 793 to 5 800, from 5 809 to 5 812, from 5 826 to 5 829, from 5 833 to 5 836 and from 5 869 to 5 875;

preferably selected from the group consisting of: SEQ ID NO: 11 745, SEQ ID NO: 11 747 and SEQ ID NO: 11 749.

According to another particular embodiment, the invention relates to a miPEP, or a fragment of said miPEP, for its use as defined above for its use in the treatment of one or more musculoskeletal disorders, or diseases or traumas of bone tissue or cartilage tissue, selected from the group comprising:

arthritis, craniosynostosis, fibrous dysplasia, multiple hereditary exostoses, cleft palates, fibrodysplasia ossificans progressiva, non-ossifying fibroma, bone fracture, hyperostosis, infantile cortical hyperostosis, hyperostosis porotid, hyperparathyroidism, hypophosphatasia, Kienbock's disease, Kohler-Mouchet's disease, Paget's disease, Panner's disease, Scheuermann's disease, Osgood-Schlatter's disease or tibial osteochondrosis, melorheostosis, multiple myeloma, osteitis, osteitis condensas, osteitis fibrosa cystica or osteitis fibrosa or von Recklinghausen's disease, osteoarthritis, deforming osteochondritis of the hip, osteochondritis dissecans, osteochondroma, osteogenesis imperfecta or glass bone disease, osteolysis, osteomalacia, osteomyelitis, osteopenia, osteopetrosis, osteophyte, osteoporosis, osteosclerosis, pseudarthrosis, pseudarthritis pink (or non-consolidation or delayed consolidation), pycnodysostosis, Coffin-Lowry syndrome, Hajdu-Cheney syndrome, Klippel-Feil syndrome, giant cell tumor and bone tumor.

According to another particular embodiment, the invention relates to a miPEP, or a fragment of said miPEP, for its use as defined above, said miPEP being selected from the group of miPEPs consisting of: SEQ ID NO: 2q-1, q varying from 45 to 48, from 89 to 92, from 101 to 104, from 121 to 124, from 133 to 140, from 153 to 156, from 161 to 164, from 169 to 192, from 221 to 224, from 233 to 256, from 301 to 304, from 317 to 320, from 329 to 332, from 337 to 340, from 381 to 384, from 445 to 448, from 469 to 472, from 533 to 536, from 693 to 696, from 789 to 792, from 909 to 916, from 977 to 980, from 1 021 to 1 024, from 1 237 to 1 240, from 1 277 to 1 280, from 1 329 to 1 332, from 1 337 to 1 344, from 1 350 to 1 353, from 1 361 to 1 364, from 1 374 to 1 377, from 1 385 to 1 388, from 1 393 to 1 404, from 1 445 to 1 448, from 1 453 to 1 456, from 1 469 to 1 472, from 1 533 to 1 536, from 1 549 to 1 552, from 1 557 to 1 560, from 1 581 to 1 584, from 1 645 to 1 652, from 1 677 to 1 680, from 1 705 to 1 716, from 1 769 to 1 772, from 1 877 to 1 880, from 1 909 to 1 912, from 1 953 to 1 956, from 1 965 to 1 972, from 2 061 to 2 064, from 2 073 to 2 076, from 2 117 to 2 120, from 2 129 to 2 140, from 2 185 to 2 188, from 2 217 to 2 244, from 2 269 to 2 288, from 2 317 to 2 320, from 2 337 to 2 340, from 2 361 to 2 364, from 2 413 to 2 416, from 2 425 to 2 432, from 2 437 to 2 444, from 2 465 to 2 476, from 2 609 to 2 612, from 2 641 to 2 644, from 2 653 to 2 656, from 2 689 to 2 692, from 2 825 to 2 828, from 2 949 to 2 952, from 2 977 to 2 980, from 3 141 to 3 144, from 3 317 to 3 320, from 3 373 to 3 376, from 3 517 to 3 520, from 3 861 to 3 868, from 4 041 to 4 044, from 4 061 to 4 064, from 4 093 to 4 096, from 4 113 to 4 116, from 4 121 to 4 128, from 4 157 to 4 164, from 4 189 to 4 192, from 4 205 to 4 208, from 4 225 to 4 228, from 4 242 to 4 245, from 4 269 to 4 276, from 4 309 to 4 312, from 4 341 to 4 344, from 4 421 to 4 424, from 4 637 to 4 640, from 4 661 to 4 664, from 4 677 to 4 680, from 4 685 to 4 692, from 4 705 to 4 708, from 4 749 to 4 752, from 4 757 to 4 764, from 4 777 to 4 780, from 4 793 to 4 796, from 4 813 to 4 816, from 4 825 to 4 828, from 4 833 to 4 840, from 4 898 to 4 901, from 4 985 to 4 988, from 5 157 to 5 160, from 5 189 to 5 196, from 5 221 to 5 224, from 5 241 to 5 244, from 5 249 to 5 300, from 5 341 to 5 344, from 5 357 to 5 360, from 5 381 to 5 384, from 5 397 to 5 408, from 5 437 to 5 440, from 5 473 to 5 476, from 5 563 to 5 570, from 5 717 to 5 720, from 5 765 to 5 768, from 5 793 to 5 800, from 5 809 to 5 812, from 5 826 to 5 829, from 5 833 to 5 836 and from 5 869 to 5 875;

preferably selected from the group consisting of: SEQ ID NO: 11 745, SEQ ID NO: 11 747 and SEQ ID NO: 11 749.

According to another particular embodiment, the invention relates to a miPEP fragment for its use as defined above, said miPEP fragment being selected from:
 miPEP//145-2 consisting of SEQ ID NO: 11 751,
 miPEP//125a-1 consisting of SEQ ID NO: 11 752, and
 miPEP//15a-16-1 consisting of SEQ ID NO: 11 753.

According to another particular embodiment, the invention relates to a miPEP, or a fragment of said miPEP, for its use as defined above, said miPEP, or said fragment of said miPEP, being fused to or linked to one or more molecules facilitating the entry into the cell of the miPEP or miPEP fragment,
 said miPEP, or fragment of said miPEP, being preferably fused in N-ter or in C-ter to the TAT peptide (YGRKKRRQRRR, SEQ ID NO: 11 754).

According to another particular embodiment, the invention relates to a miPEP selected from the group of miPEPs consisting of: SEQ ID NO: 2q-1, q varying from 45 to 48, from 89 to 92, from 101 to 104, from 121 to 124, from 133 to 140, from 153 to 156, from 161 to 164, from 169 to 192, from 221 to 224, from 233 to 256, from 301 to 304, from 317 to 320, from 329 to 332, from 337 to 340, from 381 to 384, from 445 to 448, from 469 to 472, from 533 to 536, from 693 to 696, from 789 to 792, from 909 to 916, from 977 to 980, from 1 021 to 1 024, from 1 237 to 1 240, from 1 277 to 1 280, from 1 329 to 1 332, from 1 337 to 1 344, from 1 350 to 1 353, from 1 361 to 1 364, from 1 374 to 1 377, from 1 385 to 1 388, from 1 393 to 1 404, from 1 445 to 1 448, from 1 453 to 1 456, from 1 469 to 1 472, from 1 533 to 1 536, from 1 549 to 1 552, from 1 557 to 1 560, from 1 581 to 1 584, from 1 645 to 1 652, from 1 677 to 1 680, from 1 705 to 1 716, from 1 769 to 1 772, from 1 877 to 1 880, from 1 909 to 1 912, from 1 953 to 1 956, from 1 965 to 1 972, from 2 061 to 2 064, from 2 073 to 2 076, from 2 117 to 2 120, from 2 129 to 2 140, from 2 185 to 2 188, from 2 217 to 2 244, from 2 269 to 2 288, from 2 317 to 2 320, from 2 337 to 2 340, from 2 361 to 2 364, from 2 413 to 2 416, from 2 425 to 2 432, from 2 437 to 2 444, from 2 465 to 2 476, from 2 609 to 2 612, from 2 641 to 2 644, from 2 653 to 2 656, from 2 689 to 2 692, from 2 825 to 2 828, from 2 949 to 2 952, from 2 977 to 2 980, from 3 141 to 3 144, from 3 317 to 3 320, from 3 373 to 3 376, from 3 517 to 3 520, from 3 861 to 3 868, from 4 041 to 4 044, from 4 061 to 4 064, from 4 093 to 4 096, from 4 113 to 4 116, from 4 121 to 4 128, from 4 157 to 4 164, from 4 189 to 4 192, from 4 205 to 4 208, from 4 225 to 4 228, from 4 242 to 4 245, from 4 269 to 4 276, from 4 309 to 4 312, from 4 341 to 4 344, from 4 421 to 4 424, from 4 637 to 4 640, from 4 661 to 4 664, from 4 677 to 4 680, from 4 685 to 4 692, from 4 705 to 4 708, from 4 749 to 4 752, from 4 757 to 4 764, from 4 777 to 4 780, from 4 793 to 4 796, from 4 813 to 4 816, from 4 825 to 4 828, from 4 833 to 4 840, from 4 898 to 4 901, from 4 985 to 4 988, from 5 157 to 5 160, from 5 189 to 5 196, from 5 221 to 5 224, from 5 241 to 5 244, from 5 249 to 5 300, from 5 341 to 5 344, from 5 357 to 5 360, from 5 381 to 5 384, from 5 397 to 5 408, from 5 437 to 5 440, from 5 473 to 5 476, from 5 563 to 5 570, from 5 717 to 5 720, from 5 765 to 5 768, from 5 793 to 5 800, from 5 809 to 5 812, from 5 826 to 5 829, from 5 833 to 5 836 and from 5 869 to 5 875;
 preferably selected from the group consisting of: SEQ ID NO: 11 745, SEQ ID NO: 11 747 and SEQ ID NO: 11 749,
 said miPEP, or fragment of said miPEP, being preferably fused to the TAT peptide (YGRKKRRQRRR, SEQ ID NO: 11 754), fused to penetratin, fused to a polyhistidine peptide, fused to a polyarginine peptide, or linked to one or more palmitic acid molecules.

According to another particular embodiment, the invention relates to a nucleic acid encoding one of the miPEPs selected from the group of miPEPs consisting of SEQ ID NO: 2q, q varying from 45 to 48, from 89 to 92, from 101 to 104, from 121 to 124, from 133 to 140, from 153 to 156, from 161 to 164, from 169 to 192, from 221 to 224, from 233 to 256, from 301 to 304, from 317 to 320, from 329 to 332, from 337 to 340, from 381 to 384, from 445 to 448, from 469 to 472, from 533 to 536, from 693 to 696, from 789 to 792, from 909 to 916, from 977 to 980, from 1 021 to 1 024, from 1 237 to 1 240, from 1 277 to 1 280, from 1 329 to 1 332, from 1 337 to 1 344, from 1 350 to 1 353, from 1 361 to 1 364, from 1 374 to 1 377, from 1 385 to 1 388, from 1 393 to 1 404, from 1 445 to 1 448, from 1 453 to 1 456, from 1 469 to 1 472, from 1 533 to 1 536, from 1 549 to 1 552, from 1 557 to 1 560, from 1 581 to 1 584, from 1 645 to 1 652, from 1 677 to 1 680, from 1 705 to 1 716, from 1 769 to 1 772, from 1 877 to 1 880, from 1 909 to 1 912, from 1 953 to 1 956, from 1 965 to 1 972, from 2 061 to 2 064, from 2 073 to 2 076, from 2 117 to 2 120, from 2 129 to 2 140, from 2 185 to 2 188, from 2 217 to 2 244, from 2 269 to 2 288, from 2 317 to 2 320, from 2 337 to 2 340, from 2 361 to 2 364, from 2 413 to 2 416, from 2 425 to 2 432, from 2 437 to 2 444, from 2 465 to 2 476, from 2 609 to 2 612, from 2 641 to 2 644, from 2 653 to 2 656, from 2 689 to 2 692, from 2 825 to 2 828, from 2 949 to 2 952, from 2 977 to 2 980, from 3 141 to 3 144, from 3 317 to 3 320, from 3 373 to 3 376, from 3 517 to 3 520, from 3 861 to 3 868, from 4 041 to 4 044, from 4 061 to 4 064, from 4 093 to 4 096, from 4 113 to 4 116, from 4 121 to 4 128, from 4 157 to 4 164, from 4 189 to 4 192, from 4 205 to 4 208, from 4 225 to 4 228, from 4 242 to 4 245, from 4 269 to 4 276, from 4 309 to 4 312, from 4 341 to 4 344, from 4 421 to 4 424, from 4 637 to 4 640, from 4 661 to 4 664, from 4 677 to 4 680, from 4 685 to 4 692, from 4 705 to 4 708, from 4 749 to 4 752, from 4 757 to 4 764, from 4 777 to 4 780, from 4 793 to 4 796, from 4 813 to 4 816, from 4 825 to 4 828, from 4 833 to 4 840, from 4 898 to 4 901, from 4 985 to 4 988, from 5 157 to 5 160, from 5 189 to 5 196, from 5 221 to 5 224, from 5 241 to 5 244, from 5 249 to 5 300, from 5 341 to 5 344, from 5 357 to 5 360, from 5 381 to 5 384, from 5 397 to 5 408, from 5 437 to 5 440, from 5 473 to 5 476, from 5 563 to 5 570, from 5 717 to 5 720, from 5 765 to 5 768, from 5 793 to 5 800, from 5 809 to 5 812, from 5 826 to 5 829, from 5 833 to 5 836 and from 5 869 to 5 875;
 preferably selected from the group consisting of: SEQ ID NO: 11 746, SEQ ID NO: 11 748 and SEQ ID NO: 11 750.

Furthermore, the invention also relates to a process for identifying a miPEP modulating the accumulation of a miR involved in a musculoskeletal disorder, or disease or trauma of bone tissue or cartilage tissue, said miPEP being encoded by a nucleotide sequence contained in the primary transcript of a miR, comprising:
 a) a step of detecting an open reading frame from 12 to 1 503 nucleotides contained in the sequence of the primary transcript of said miR, then
 b) a step of comparison between:
  i. the accumulation of said miR in a specified eukaryotic cell expressing the primary transcript of said miR,
   in the presence of a peptide encoded by a nucleotide sequence that is identical or degenerate relative to that of said open reading frame, said peptide being present in the cell independently of transcription of the primary transcript of said miR, and
  ii. the accumulation of said miR in a eukaryotic cell of the same type as the aforesaid specified eukaryotic cell expressing the primary transcript of said miR, in the absence of said peptide, in which a modulation of the accumulation of said miR in the presence of said peptide relative to the accumulation of said miR in the absence of said peptide indicates the existence of a miPEP, the latter being encoded by said open reading frame and being capable of modulating the accumulation of said miR involved in a musculoskeletal disorder, or disease or trauma of bone tissue or cartilage tissue.

According to another aspect, the invention also relates to the in vitro, in vivo or ex vivo use of a miPEP or a fragment of said miPEP, said miPEP being selected from the group of miPEPs consisting of: SEQ ID NO: 2q-1, q varying from 45 to 48, from 89 to 92, from 101 to 104, from 121 to 124, from 133 to 140, from 153 to 156, from 161 to 164, from 169 to 192, from 221 to 224, from 233 to 256, from 301 to 304, from 317 to 320, from 329 to 332, from 337 to 340, from 381 to 384, from 445 to 448, from 469 to 472, from 533 to 536, from 693 to 696, from 789 to 792, from 909 to 916, from 977 to 980, from 1 021 to 1 024, from 1 237 to 1 240, from 1 277 to 1 280, from 1 329 to 1 332, from 1 337 to 1 344, from 1 350 to 1 353, from 1 361 to 1 364, from 1 374 to 1 377, from 1 385 to 1 388, from 1 393 to 1 404, from 1 445 to 1 448, from 1 453 to 1 456, from 1 469 to 1 472, from 1 533 to 1 536, from 1 549 to 1 552, from 1 557 to 1 560, from 1 581 to 1 584, from 1 645 to 1 652, from 1 677 to 1 680, from 1 705 to 1 716, from 1 769 to 1 772, from 1 877 to 1 880, from 1 909 to 1 912, from 1 953 to 1 956, from 1 965 to 1972, from 2 061 to 2 064, from 2 073 to 2 076, from 2 117 to 2 120, from 2 129 to 2 140, from 2 185 to 2 188, from 2 217 to 2 244, from 2 269 to 2 288, from 2 317 to 2 320, from 2 337 to 2 340, from 2 361 to 2 364, from 2 413 to 2 416, from 2 425 to 2 432, from 2 437 to 2 444, from 2 465 to 2 476, from 2 609 to 2 612, from 2 641 to 2 644, from 2 653 to 2 656, from 2 689 to 2 692, from 2 825 to 2 828, from 2 949 to 2 952, from 2 977 to 2 980, from 3 141 to 3 144, from 3 317 to 3 320, from 3 373 to 3 376, from 3 517 to 3 520, from 3 861 to 3 868, from 4 041 to 4 044, from 4 061 to 4 064, from 4 093 to 4 096, from 4 113 to 4 116, from 4 121 to 4 128, from 4 157 to 4 164, from 4 189 to 4 192, from 4 205 to 4 208, from 4 225 to 4 228, from 4 242 to 4 245, from 4 269 to 4 276, from 4 309 to 4 312, from 4 341 to 4 344, from 4 421 to 4 424, from 4 637 to 4 640, from 4 661 to 4 664, from 4 677 to 4 680, from 4 685 to 4 692, from 4 705 to 4 708, from 4 749 to 4 752, from 4 757 to 4 764, from 4 777 to 4 780, from 4 793 to 4 796, from 4 813 to 4 816, from 4 825 to 4 828, from 4 833 to 4 840, from 4 898 to 4 901, from 4 985 to 4 988, from 5 157 to 5 160, from 5 189 to 5 196, from 5 221 to 5 224, from 5 241 to 5 244, from 5 249 to 5 300, from 5 341 to 5 344, from 5 357 to 5 360, from 5 381 to 5 384, from 5 397 to 5 408, from 5 437 to 5 440, from 5 473 to 5 476, from 5 563 to 5 570, from 5 717 to 5 720, from 5 765 to 5 768, from 5 793 to 5 800, from 5 809 to 5 812, from 5 826 to 5 829, from 5 833 to 5 836 and from 5 869 to 5 875;

preferably selected from the group consisting of: SEQ ID NO: 11 745, SEQ ID NO: 11 747 and SEQ ID NO: 11 749, to promote osteogenesis of cells, particularly mesenchymal stem cells.

According to another particular aspect, the invention relates to the use of a miPEP or fragment of said miPEP as defined above, in combination with one or more additives, said additives being selected from the group consisting of: cytokines such as bone morphogenetic protein (BMP) and/or dexamethasone.

According to another particular aspect, the invention relates to a use of a miPEP or fragment of said miPEP as defined above, in combination with a biomaterial, said biomaterial being selected from the following table:

TABLE 1

List of possible biomaterials for implementing the invention.

| a) natural polymers | b) synthetic polymers | c) bioactive glasses |
|---|---|---|
| gelatin/chitooligosaccharide, collagen, chitosan, chitosan/collagen/beta-glycerophosphate (β-GP), silk fibroins, alginate/calcium phosphate cement (CPC)[= alginate/CPC] alginate, hyaluronic acid, RAD16-I BD ™ (PuraMatrix ™, registered trademark of 3-D Matrix, Ltd.), or chitosan/peptide "Arginine-Glycine-Aspartic acid" (RGD) [=chitosan/peptide RGD] | poly(lactide-co-glycolide) [PLGA], poly(ε-caprolactone) [PCL] or poly(hydroxymethylglycolide-co-ε-caprolactone) [pHMGCL], PLGA-poly(ethylene oxide) (PEO) [=PLGA-PEO], poly(L-lactide-co-ε-caprolactone)/poly(L-lactide-co-1,5-dioxepan-2-one)[poly(LLA-co-CL)/poly(LLA-co-DXO)], poly[(ethylglycinato)(p-methylphenoxy) phosphazene]/PLGA [= PPHOS/PLGA], PCL/poly(diisopropyl fumarate) (PDIPF) [= PCL/PDIPF], poly(ester amide)-g-TA [PEA-g-TA], PLGA-poly(ethylene glycol-aspartic acid (PEG-ASP) [=PLGA-(PEG-ASP)], poly(ethylene oxide terephthalate)/poly(butylene terephthalate) [PEOT/PBT], or poly (hydroxyethyl methacrylate) [poly-HEMA] | 45S5 Bioglass ® (registered trademark of the University of Florida), $CaMgSi_2O_6$, 45S5 bioactive glass ® (registered trademark of the University of Florida), 45S bioactive glass ®, bioactive glass ® (BG20), bioglass ®, or bioactive glass ® (13-93) |
| d) calcium phosphates | e) coral | f) metals |
| CPC, hydroxyapatite [HA] β-tricalcium phosphate [βTCP] HA/βTCP, calcium Aluminate/melatonine, or | Porites sp., Goniopora coral, hydroxyapatite coral, coralline in the shape of a condyle, Porites lutea, | NiTi/Ti, titanium (Ti) fiber sheets, titanium wire, Ti, $TiO_2$, |

TABLE 1-continued

List of possible biomaterials for implementing the invention.

| CPC/Bioglass ® | Porites acropora, or natural coral matrices | $Ti_6Ta_4Sn$ alloy, Magnesium W4 alloy (MgY4), or Iron-Manganese alloy |
|---|---|---|

| g) polymer/ceramic composites | h) metal/ceramic composites |
|---|---|
| Nano-apatite/PCL,<br>PLGA-PCL-Calcium Phosphate (CP)<br>[= PLGA-PCL-CP],<br>PEOT/PBT-CP,<br>Collagen-CPC,<br>PCL-TCP,<br>Chitosan-CPC,<br>Magnesium Phosphate-PCL,<br>PLGA-βTCP,<br>PCLF-PVA-HA (PVA: poly(alcool vinylic)),<br>Chitosan/poly(DL, lactide-co-glycolide),<br>PLGA-nHA, ou<br>poly-3-hydroxybutyrate-HA (P3HB-HA) | polyNaSS/Ti,<br>polylactic acid in crystalline form/PLGA/Ti<br>[=PLLA/PLGA/Ti],<br>polyNaSS/Ti,<br>NaSS/methacrylic acid,<br>$MA/Ti_6Al_4V$ alloy,<br>polyNaSS/Ti,<br>$SiO_2/CaO/Na_2O/MgO/B_2O_3$,<br>Niobium/fluorapatite,<br>Ti-HA,<br>$TiO_2$,<br>$ZrO_2$-CP/PCL,<br>K/Sr-calcium polyphosphate (CPP)<br>[=K/Sr-CPP],<br>$ZrO_2$/HA,<br>porous material containing cobalt and a mesoporous Bioglass ® [Co-MBG],<br>porous material containing copper and a mesoporous Bioglass ® [Cu-MBG],<br>β-TCP/Mg, or<br>Sr/CPP |

According to another particular aspect, the invention relates to the use of a miPEP or fragment of said miPEP as defined above, in combination with one or more additives, said additives being chosen from the group consisting of: cytokines as well as bone morphogenetic protein (BMP) and/or dexamethasone;

and in combination with a biomaterial, said biomaterial being selected from the group shown in Table 1 (cf. p 39-41).

According to another particular aspect, the invention relates to the use of a miPEP fragment of sequence SEQ ID NO: 11 752 to promote osteogenesis of mesenchymal stem cells in combination with a biomaterial, said biomaterial being the HA/β-TCP in a ratio of 20/80.

Another aspect of the invention is that it relates to osteo-induced cells with one or more miPEP or fragment of said miPEP as defined above, said cells being in particular mesenchymal stem cells.

Another aspect of the invention is that it relates to cells comprising a nucleic acid encoding one or more of the miPEPs as defined above, the expression of said nucleic acid being inducible or not, said cells being in particular mesenchymal stem cells.

According to another particular aspect, the invention relates to a composite biomaterial comprising osteo-induced cells as defined above or cells as defined above, in combination or not with one or more additives, said additives being chosen from the group consisting of: cytokines such as bone morphogenetic proteins (BMP) and/or dexamethasone, said biomaterial being selected from the group shown in Table 1 (cf. p. 39-41).

According to another particular aspect, the invention relates to a composite biomaterial comprising osteo-induced mesenchymal stem cells with a miPEP fragment of sequence SEQ ID NO: 11 752, said biomaterial being the HA/β-TCP in a ratio of 20/80.

TABLE 2

MiRs involved in cancer, bacterial or fungal infections, cardiovascular diseases, hereditary congenital diseases, skin diseases and eye diseases

| Cancer | Bacterial or fungal infections | Cardiovascular diseases | Hereditary congenital diseases | Skin diseases | Eye diseases |
|---|---|---|---|---|---|
| hsa-let-7a-2 | hsa-let-7a-2 | hsa-let-7a-2 | hsa-let-7a-2 | hsa-let-7b | hsa-let-7a-2 |
| hsa-let-7a-3 | hsa-let-7a-3 | hsa-let-7a-3 | hsa-let-7a-3 | hsa-let-7g | hsa-let-7a-3 |
| hsa-let-7b | hsa-let-7b | hsa-let-7b | hsa-let-7i | hsa-let-7i | hsa-let-7b |
| hsa-let-7d | hsa-let-7d | hsa-let-7d | hsa-let-7d | hsa-mir-106a | hsa-let-7d |
| hsa-let-7e | hsa-let-7e | hsa-let-7e | hsa-let-7e | hsa-mir-10a | hsa-let-7e |
| hsa-let-7g | hsa-let-7g | hsa-let-7g | hsa-let-7g | hsa-mir-10b | hsa-let-7g |
| hsa-let-7i | hsa-let-7i | hsa-let-7i | hsa-let-7i | hsa-mir-1246 | hsa-let-7i |
| hsa-mir-100 | hsa-mir-100 | hsa-mir-100 | hsa-mir-100 | hsa-mir-132 | hsa-mir-106a |
| hsa-mir-106a | hsa-mir-106a | hsa-mir-106a | hsa-mir-106a | hsa-mir-134 | hsa-mir-10a |
| hsa-mir-10a | hsa-mir-10a | hsa-mir-10a | hsa-mir-10a | hsa-mir-141 | hsa-mir-10b |
| hsa-mir-10b | hsa-mir-10b | hsa-mir-10b | hsa-mir-10b | hsa-mir-142 | hsa-mir-1246 |
| hsa-mir-122 | hsa-mir-122 | hsa-mir-122 | hsa-mir-122 | hsa-mir-145 | hsa-mir-125a |
| hsa-mir-1246 | hsa-mir-1246 | hsa-mir-1246 | hsa-mir-1246 | hsa-mir-146a | hsa-mir-134 |
| hsa-mir-125a | hsa-mir-129-1 | hsa-mir-125a | hsa-mir-125a | hsa-mir-148a | hsa-mir-141 |
| hsa-mir-130b | hsa-mir-130b | hsa-mir-129-1 | hsa-mir-130b | hsa-mir-150 | hsa-mir-143 |
| hsa-mir-132 | hsa-mir-133b | hsa-mir-130b | hsa-mir-132 | hsa-mir-155 | hsa-mir-144 |

TABLE 2-continued

MiRs involved in cancer, bacterial or fungal infections, cardiovascular diseases, hereditary congenital diseases, skin diseases and eye diseases

| Cancer | Bacterial or fungal infections | Cardiovascular diseases | Hereditary congenital diseases | Skin diseases | Eye diseases |
|---|---|---|---|---|---|
| hsa-mir-133b | hsa-mir-134 | hsa-mir-132 | hsa-mir-134 | hsa-mir-181c | hsa-mir-145 |
| hsa-mir-134 | hsa-mir-141 | hsa-mir-133b | hsa-mir-141 | hsa-mir-182 | hsa-mir-155 |
| hsa-mir-141 | hsa-mir-142 | hsa-mir-134 | hsa-mir-142 | hsa-mir-183 | hsa-mir-181c |
| hsa-mir-142 | hsa-mir-143 | hsa-mir-141 | hsa-mir-143 | hsa-mir-184 | hsa-mir-182 |
| hsa-mir-143 | hsa-mir-144 | hsa-mir-142 | hsa-mir-145 | hsa-mir-18b | hsa-mir-183 |
| hsa-mir-144 | hsa-mir-145 | hsa-mir-143 | hsa-mir-146a | hsa-mir-192 | hsa-mir-18b |
| hsa-mir-145 | hsa-mir-146a | hsa-mir-144 | hsa-mir-146b | hsa-mir-195 | hsa-mir-192 |
| hsa-mir-146a | hsa-mir-154 | hsa-mir-145 | hsa-mir-148a | hsa-mir-200a | hsa-mir-195 |
| hsa-mir-146b | hsa-mir-155 | hsa-mir-146a | hsa-mir-154 | hsa-mir-202 | hsa-mir-200b |
| hsa-mir-148a | hsa-mir-181a-1 | hsa-mir-146b | hsa-mir-155 | hsa-mir-203 | hsa-mir-202 |
| hsa-mir-150 | hsa-mir-181a-2 | hsa-mir-150 | hsa-mir-181a-2 | hsa-mir-205 | hsa-mir-203 |
| hsa-mir-154 | hsa-mir-181c | hsa-mir-154 | hsa-mir-181c | hsa-mir-206 | hsa-mir-205 |
| hsa-mir-155 | hsa-mir-182 | hsa-mir-155 | hsa-mir-181d | hsa-mir-20b | hsa-mir-20b |
| hsa-mir-181c | hsa-mir-183 | hsa-mir-181a-1 | hsa-mir-182 | hsa-mir-21 | hsa-mir-21 |
| hsa-mir-181d | hsa-mir-184 | hsa-mir-181a-2 | hsa-mir-183 | hsa-mir-210 | hsa-mir-210 |
| hsa-mir-182 | hsa-mir-187 | hsa-mir-181c | hsa-mir-18b | hsa-mir-221 | hsa-mir-212 |
| hsa-mir-183 | hsa-mir-18b | hsa-mir-181d | hsa-mir-192 | hsa-mir-222 | hsa-mir-221 |
| hsa-mir-184 | hsa-mir-192 | hsa-mir-182 | hsa-mir-193a | hsa-mir-27a | hsa-mir-222 |
| hsa-mir-187 | hsa-mir-193b | hsa-mir-183 | hsa-mir-193b | hsa-mir-29a | hsa-mir-23a |
| hsa-mir-18b | hsa-mir-195 | hsa-mir-184 | hsa-mir-195 | hsa-mir-29c | hsa-mir-27a |
| hsa-mir-192 | hsa-mir-196a-2 | hsa-mir-187 | hsa-mir-202 | hsa-mir-30a | hsa-mir-298 |
| hsa-mir-193b | hsa-mir-19b-2 | hsa-mir-18b | hsa-mir-203 | hsa-mir-30b | hsa-mir-30a |
| hsa-mir-195 | hsa-mir-200b | hsa-mir-192 | hsa-mir-206 | hsa-mir-345 | hsa-mir-30d |
| hsa-mir-200a | hsa-mir-200c | hsa-mir-193a | hsa-mir-20b | hsa-mir-34a | hsa-mir-331 |
| hsa-mir-200b | hsa-mir-202 | hsa-mir-193b | hsa-mir-21 | hsa-mir-377 | hsa-mir-345 |
| hsa-mir-200c | hsa-mir-203 | hsa-mir-195 | hsa-mir-210 | hsa-mir-409 | hsa-mir-377 |
| hsa-mir-202 | hsa-mir-205 | hsa-mir-19b-2 | hsa-mir-212 | hsa-mir-495 | hsa-mir-495 |
| hsa-mir-203 | hsa-mir-206 | hsa-mir-200a | hsa-mir-217 | hsa-mir-520h | hsa-mir-542 |
| hsa-mir-205 | hsa-mir-20b | hsa-mir-200c | hsa-mir-221 | hsa-mir-542 | hsa-mir-572 |
| hsa-mir-206 | hsa-mir-21 | hsa-mir-202 | hsa-mir-222 | hsa-mir-572 | hsa-mir-648 |
| hsa-mir-20b | hsa-mir-210 | hsa-mir-203 | hsa-mir-23a | hsa-mir-648 | hsa-mir-96 |
| hsa-mir-21 | hsa-mir-2114 | hsa-mir-205 | hsa-mir-27a | hsa-mir-92b | hsa-mir-99b |
| hsa-mir-210 | hsa-mir-212 | hsa-mir-206 | hsa-mir-29a | hsa-mir-96 | |
| hsa-mir-212 | hsa-mir-217 | hsa-mir-20b | hsa-mir-29c | hsa-mir-99b | |
| hsa-mir-216a | hsa-mir-219-2 | hsa-mir-21 | hsa-mir-30a | | |
| hsa-mir-217 | hsa-mir-221 | hsa-mir-210 | hsa-mir-30b | | |
| hsa-mir-221 | hsa-mir-222 | hsa-mir-212 | hsa-mir-30c-2 | | |
| hsa-mir-222 | hsa-mir-23a | hsa-mir-217 | hsa-mir-30d | | |
| hsa-mir-23a | hsa-mir-24-2 | hsa-mir-221 | hsa-mir-3178 | | |
| hsa-mir-27a | hsa-mir-27a | hsa-mir-222 | hsa-mir-331 | | |
| hsa-mir-297 | hsa-mir-296 | hsa-mir-23a | hsa-mir-345 | | |
| hsa-mir-298 | hsa-mir-29a | hsa-mir-24-2 | hsa-mir-34a | | |
| hsa-mir-29a | hsa-mir-29b-1 | hsa-mir-27a | hsa-mir-363 | | |
| hsa-mir-29b-1 | hsa-mir-29b-2 | hsa-mir-29a | hsa-mir-369 | | |
| hsa-mir-29c | hsa-mir-29c | hsa-mir-29b-1 | hsa-mir-371 | | |
| hsa-mir-301b | hsa-mir-30a | hsa-mir-29b-2 | hsa-mir-372 | | |
| hsa-mir-30a | hsa-mir-30b | hsa-mir-29c | hsa-mir-373 | | |
| hsa-mir-30b | hsa-mir-30d | hsa-mir-30a | hsa-mir-374a | | |
| hsa-mir-30d | hsa-mir-331 | hsa-mir-30b | hsa-mir-377 | | |
| hsa-mir-320 | hsa-mir-345 | hsa-mir-30c-2 | hsa-mir-379 | | |
| hsa-mir-331 | hsa-mir-34a | hsa-mir-30d | hsa-mir-409 | | |
| hsa-mir-345 | hsa-mir-648 | hsa-mir-3178 | hsa-mir-422a | | |
| hsa-mir-34a | hsa-mir-96 | hsa-mir-331 | hsa-mir-494 | | |
| hsa-mir-373 | hsa-mir-99b | hsa-mir-345 | hsa-mir-495 | | |
| hsa-mir-374a | | hsa-mir-34a | hsa-mir-497 | | |
| hsa-mir-377 | | hsa-mir-363 | hsa-mir-505 | | |
| hsa-mir-379 | | hsa-mir-369 | hsa-mir-518c | | |
| hsa-mir-382 | | hsa-mir-371 | hsa-mir-519e | | |
| hsa-mir-409 | | hsa-mir-372 | hsa-mir-520a | | |
| hsa-mir-422a | | hsa-mir-373 | hsa-mir-520g | | |
| hsa-mir-429 | | hsa-mir-374a | hsa-mir-522 | | |
| hsa-mir-485 | | hsa-mir-377 | hsa-mir-523 | | |
| hsa-mir-493 | | hsa-mir-379 | hsa-mir-542 | | |
| hsa-mir-494 | | hsa-mir-409 | hsa-mir-572 | | |
| hsa-mir-495 | | hsa-mir-422a | hsa-mir-648 | | |
| hsa-mir-496 | | hsa-mir-494 | hsa-mir-654 | | |
| hsa-mir-497 | | hsa-mir-495 | hsa-mir-665 | | |
| hsa-mir-506 | | hsa-mir-497 | hsa-mir-769 | | |
| hsa-mir-507 | | hsa-mir-505 | hsa-mir-92b | | |
| hsa-mir-508 | | hsa-mir-518c | hsa-mir-96 | | |
| hsa-mir-509-1 | | hsa-mir-519e | hsa-mir-99b | | |
| hsa-mir-510 | | hsa-mir-520a | | | |
| hsa-mir-520h | | hsa-mir-520g | | | |

TABLE 2-continued

MiRs involved in cancer, bacterial or fungal infections, cardiovascular diseases, hereditary congenital diseases, skin diseases and eye diseases

| Cancer | Bacterial or fungal infections | Cardiovascular diseases | Hereditary congenital diseases | Skin diseases | Eye diseases |
|---|---|---|---|---|---|
| hsa-mir-523 | | hsa-mir-520h | | | |
| hsa-mir-525 | | hsa-mir-522 | | | |
| hsa-mir-542 | | hsa-mir-523 | | | |
| hsa-mir-568 | | hsa-mir-542 | | | |
| hsa-mir-570 | | hsa-mir-572 | | | |
| hsa-mir-572 | | hsa-mir-648 | | | |
| hsa-mir-633 | | hsa-mir-654 | | | |
| hsa-mir-648 | | hsa-mir-665 | | | |
| hsa-mir-7-2 | | hsa-mir-769 | | | |
| hsa-mir-92b | | hsa-mir-92b | | | |
| hsa-mir-940 | | hsa-mir-96 | | | |
| hsa-mir-96 | | hsa-mir-99b | | | |
| hsa-mir-99b | | hsa-mir-15a | | | |
| | | hsa-mir-15b | | | |

TABLE 3

MiRs involved in diseases of the digestive system, diseases of the endocrine system, diseases of the nervous system, diseases related to viruses, diseases related to nutrition and metabolism and lymphatic diseases and hemopathies

| Diseases of the digestive system | Diseases of the endocrine system | Diseases of the nervous system | Diseases related to viruses | Diseases related to nutrition and metabolism | Lymphatic diseases and hemopathies |
|---|---|---|---|---|---|
| hsa-let-7a-2 | hsa-let-7a-2 | hsa-let-7b | hsa-let-7b | hsa-let-7b | hsa-let-7a-2 |
| hsa-let-7a-3 | hsa-let-7a-3 | hsa-let-7d | hsa-let-7d | hsa-let-7g | hsa-let-7a-3 |
| hsa-let-7b | hsa-let-7b | hsa-let-7g | hsa-let-7g | hsa-let-7i | hsa-let-7b |
| hsa-let-7d | hsa-let-7d | hsa-let-7i | hsa-mir-106a | hsa-mir-100 | hsa-let-7d |
| hsa-let-7e | hsa-let-7e | hsa-mir-100 | hsa-mir-10a | hsa-mir-106a | hsa-let-7e |
| hsa-let-7g | hsa-let-7g | hsa-mir-106a | hsa-mir-10b | hsa-mir-10a | hsa-let-7g |
| hsa-let-7i | hsa-let-7i | hsa-mir-10a | hsa-mir-122 | hsa-mir-10b | hsa-let-7i |
| hsa-mir-100 | hsa-mir-106a | hsa-mir-10b | hsa-mir-1246 | hsa-mir-122 | hsa-mir-106a |
| hsa-mir-106a | hsa-mir-10a | hsa-mir-122 | hsa-mir-132 | hsa-mir-1246 | hsa-mir-10a |
| hsa-mir-10a | hsa-mir-10b | hsa-mir-1246 | hsa-mir-134 | hsa-mir-125a | hsa-mir-125a |
| hsa-mir-10b | hsa-mir-1246 | hsa-mir-125a | hsa-mir-145 | hsa-mir-129-1 | hsa-mir-130b |
| hsa-mir-122 | hsa-mir-132 | hsa-mir-129-1 | hsa-mir-155 | hsa-mir-130b | hsa-mir-132 |
| hsa-mir-1246 | hsa-mir-134 | hsa-mir-130b | hsa-mir-181c | hsa-mir-132 | hsa-mir-141 |
| hsa-mir-125a | hsa-mir-142 | hsa-mir-132 | hsa-mir-182 | hsa-mir-133b | hsa-mir-142 |
| hsa-mir-130b | hsa-mir-145 | hsa-mir-133b | hsa-mir-183 | hsa-mir-134 | hsa-mir-143 |
| hsa-mir-132 | hsa-mir-150 | hsa-mir-134 | hsa-mir-18b | hsa-mir-141 | hsa-mir-144 |
| hsa-mir-134 | hsa-mir-155 | hsa-mir-141 | hsa-mir-192 | hsa-mir-142 | hsa-mir-145 |
| hsa-mir-141 | hsa-mir-181c | hsa-mir-142 | hsa-mir-195 | hsa-mir-143 | hsa-mir-146a |
| hsa-mir-143 | hsa-mir-182 | hsa-mir-143 | hsa-mir-202 | hsa-mir-144 | hsa-mir-150 |
| hsa-mir-145 | hsa-mir-183 | hsa-mir-144 | hsa-mir-206 | hsa-mir-145 | hsa-mir-155 |
| hsa-mir-146a | hsa-mir-184 | hsa-mir-145 | hsa-mir-20b | hsa-mir-146a | hsa-mir-181c |
| hsa-mir-148a | hsa-mir-18b | hsa-mir-146a | hsa-mir-21 | hsa-mir-146b | hsa-mir-182 |
| hsa-mir-150 | hsa-mir-192 | hsa-mir-146b | hsa-mir-210 | hsa-mir-154 | hsa-mir-183 |
| hsa-mir-154 | hsa-mir-195 | hsa-mir-154 | hsa-mir-212 | hsa-mir-155 | hsa-mir-187 |
| hsa-mir-155 | hsa-mir-200a | hsa-mir-155 | hsa-mir-217 | hsa-mir-181a-1 | hsa-mir-18b |
| hsa-mir-182 | hsa-mir-202 | hsa-mir-181a-1 | hsa-mir-296 | hsa-mir-181a-2 | hsa-mir-192 |
| hsa-mir-183 | hsa-mir-203 | hsa-mir-181a-2 | hsa-mir-30d | hsa-mir-181c | hsa-mir-193b |
| hsa-mir-18b | hsa-mir-205 | hsa-mir-181c | hsa-mir-345 | hsa-mir-181d | hsa-mir-195 |
| hsa-mir-192 | hsa-mir-20b | hsa-mir-181d | hsa-mir-34a | hsa-mir-182 | hsa-mir-200b |
| hsa-mir-195 | hsa-mir-21 | hsa-mir-182 | hsa-mir-648 | hsa-mir-183 | hsa-mir-202 |
| hsa-mir-200a | hsa-mir-210 | hsa-mir-183 | hsa-mir-96 | hsa-mir-184 | hsa-mir-203 |
| hsa-mir-200b | hsa-mir-212 | hsa-mir-184 | hsa-mir-99b | hsa-mir-187 | hsa-mir-205 |
| hsa-mir-200c | hsa-mir-29a | hsa-mir-187 | | hsa-mir-18b | hsa-mir-20b |
| hsa-mir-202 | hsa-mir-29c | hsa-mir-18b | | hsa-mir-192 | hsa-mir-21 |
| hsa-mir-203 | hsa-mir-30b | hsa-mir-192 | | hsa-mir-193a | hsa-mir-210 |
| hsa-mir-205 | hsa-mir-30d | hsa-mir-193a | | hsa-mir-193b | hsa-mir-216a |
| hsa-mir-206 | hsa-mir-331 | hsa-mir-193b | | hsa-mir-195 | hsa-mir-221 |
| hsa-mir-20b | hsa-mir-345 | hsa-mir-195 | | hsa-mir-19b-2 | hsa-mir-222 |
| hsa-mir-21 | hsa-mir-34a | hsa-mir-19b-2 | | hsa-mir-200c | hsa-mir-23a |
| hsa-mir-210 | hsa-mir-377 | hsa-mir-200c | | hsa-mir-202 | hsa-mir-27a |
| hsa-mir-212 | hsa-mir-409 | hsa-mir-202 | | hsa-mir-203 | hsa-mir-298 |
| hsa-mir-217 | hsa-mir-495 | hsa-mir-203 | | hsa-mir-205 | hsa-mir-301b |
| hsa-mir-221 | hsa-mir-520h | hsa-mir-205 | | hsa-mir-206 | hsa-mir-30a |
| hsa-mir-222 | hsa-mir-542 | hsa-mir-206 | | hsa-mir-20b | hsa-mir-331 |
| hsa-mir-23a | hsa-mir-572 | hsa-mir-20b | | hsa-mir-21 | hsa-mir-345 |

TABLE 3-continued

MiRs involved in diseases of the digestive system, diseases of the endocrine system, diseases of the nervous system, diseases related to viruses, diseases related to nutrition and metabolism and lymphatic diseases and hemopathies

| Diseases of the digestive system | Diseases of the endocrine system | Diseases of the nervous system | Diseases related to viruses | Diseases related to nutrition and metabolism | Lymphatic diseases and hemopathies |
|---|---|---|---|---|---|
| hsa-mir-27a | hsa-mir-648 | hsa-mir-21 | | hsa-mir-210 | hsa-mir-34a |
| hsa-mir-296 | hsa-mir-96 | hsa-mir-210 | | hsa-mir-212 | hsa-mir-373 |
| hsa-mir-29a | hsa-mir-99b | hsa-mir-212 | | hsa-mir-217 | hsa-mir-374a |
| hsa-mir-29c | | hsa-mir-217 | | hsa-mir-221 | hsa-mir-377 |
| hsa-mir-30a | | hsa-mir-221 | | hsa-mir-222 | hsa-mir-485 |
| hsa-mir-30b | | hsa-mir-222 | | hsa-mir-23a | hsa-mir-493 |
| hsa-mir-30d | | hsa-mir-23a | | hsa-mir-24-2 | hsa-mir-495 |
| hsa-mir-320 | | hsa-mir-24-2 | | hsa-mir-27a | hsa-mir-496 |
| hsa-mir-331 | | hsa-mir-27a | | hsa-mir-29a | hsa-mir-523 |
| hsa-mir-345 | | hsa-mir-29a | | hsa-mir-29b-1 | hsa-mir-525 |
| hsa-mir-34a | | hsa-mir-29b-1 | | hsa-mir-29b-2 | hsa-mir-542 |
| hsa-mir-377 | | hsa-mir-29b-2 | | hsa-mir-29c | hsa-mir-568 |
| hsa-mir-379 | | hsa-mir-29c | | hsa-mir-30a | hsa-mir-570 |
| hsa-mir-411 | | hsa-mir-30a | | hsa-mir-30b | hsa-mir-572 |
| hsa-mir-429 | | hsa-mir-30b | | hsa-mir-30c-2 | hsa-mir-633 |
| hsa-mir-494 | | hsa-mir-30c-2 | | hsa-mir-30d | hsa-mir-648 |
| hsa-mir-497 | | hsa-mir-30d | | hsa-mir-3178 | hsa-mir-92b |
| hsa-mir-648 | | hsa-mir-3178 | | hsa-mir-331 | hsa-mir-99b |
| hsa-mir-96 | | hsa-mir-331 | | hsa-mir-345 | hsa-mir-451 |
| hsa-mir-99b | | hsa-mir-345 | | hsa-mir-34a | |
| | | hsa-mir-34a | | hsa-mir-363 | |
| | | hsa-mir-363 | | hsa-mir-369 | |
| | | hsa-mir-369 | | hsa-mir-371 | |
| | | hsa-mir-371 | | hsa-mir-372 | |
| | | hsa-mir-372 | | hsa-mir-373 | |
| | | hsa-mir-373 | | hsa-mir-374a | |
| | | hsa-mir-374a | | hsa-mir-379 | |
| | | hsa-mir-379 | | hsa-mir-409 | |
| | | hsa-mir-409 | | hsa-mir-422a | |
| | | hsa-mir-422a | | hsa-mir-494 | |
| | | hsa-mir-494 | | hsa-mir-497 | |
| | | hsa-mir-495 | | hsa-mir-505 | |
| | | hsa-mir-497 | | hsa-mir-518c | |
| | | hsa-mir-505 | | hsa-mir-519e | |
| | | hsa-mir-518c | | hsa-mir-520a | |
| | | hsa-mir-519e | | hsa-mir-520g | |
| | | hsa-mir-520a | | hsa-mir-522 | |
| | | hsa-mir-520g | | hsa-mir-523 | |
| | | hsa-mir-522 | | hsa-mir-572 | |
| | | hsa-mir-523 | | hsa-mir-648 | |
| | | hsa-mir-572 | | hsa-mir-654 | |
| | | hsa-mir-648 | | hsa-mir-665 | |
| | | hsa-mir-654 | | hsa-mir-769 | |
| | | hsa-mir-665 | | hsa-mir-92b | |
| | | hsa-mir-769 | | hsa-mir-96 | |
| | | hsa-mir-92b | | hsa-mir-99b | |
| | | hsa-mir-96 | | hsa-mir-103-1 | |
| | | hsa-mir-99b | | hsa-mir-103-2 | |
| | | | | hsa-mir-107 | |

TABLE 4

MiRs involved in neonatal and hereditary diseases, respiratory diseases, urogenital diseases in men, urogenital diseases in women, disorders of the immune system and musculoskeletal disorders

| Neonatal and hereditary diseases | Respiratory diseases | Urogenital diseases in men | Urogenital diseases in women | Disorders of the immune system | Musculoskeletal disorders |
|---|---|---|---|---|---|
| hsa-let-7a-2 | hsa-let-7a-2 | hsa-let-7a-2 | hsa-let-7a-2 | hsa-let-7a-2 | hsa-let-7b |
| hsa-let-7a-3 | hsa-let-7a-3 | hsa-let-7a-3 | hsa-let-7a-3 | hsa-let-7a-3 | hsa-let-7g |
| hsa-let-7b | hsa-let-7b | hsa-let-7b | hsa-let-7b | hsa-let-7b | hsa-mir-106a |
| hsa-let-7d | hsa-let-7d | hsa-let-7d | hsa-let-7d | hsa-let-7d | hsa-mir-10a |
| hsa-let-7e | hsa-let-7e | hsa-let-7e | hsa-let-7e | hsa-let-7e | hsa-mir-10b |
| hsa-let-7g | hsa-let-7g | hsa-let-7g | hsa-let-7g | hsa-let-7g | hsa-mir-1246 |
| hsa-let-7i | hsa-let-7i | hsa-let-7i | hsa-let-7i | hsa-let-7i | hsa-mir-132 |
| hsa-mir-100 | hsa-mir-106a | hsa-mir-106a | hsa-mir-106a | hsa-mir-100 | hsa-mir-134 |
| hsa-mir-106a | hsa-mir-10a | hsa-mir-10b | hsa-mir-10b | hsa-mir-106a | hsa-mir-142 |
| hsa-mir-10a | hsa-mir-10b | hsa-mir-132 | hsa-mir-132 | hsa-mir-10a | hsa-mir-145 |

TABLE 4-continued

MiRs involved in neonatal and hereditary diseases, respiratory diseases, urogenital diseases in men, urogenital diseases in women, disorders of the immune system and musculoskeletal disorders

| Neonatal and hereditary diseases | Respiratory diseases | Urogenital diseases in men | Urogenital diseases in women | Disorders of the immune system | Musculoskeletal disorders |
|---|---|---|---|---|---|
| hsa-mir-10b | hsa-mir-1197 | hsa-mir-142 | hsa-mir-142 | hsa-mir-10b | hsa-mir-146a |
| hsa-mir-122 | hsa-mir-122 | hsa-mir-143 | hsa-mir-143 | hsa-mir-122 | hsa-mir-150 |
| hsa-mir-1246 | hsa-mir-1246 | hsa-mir-145 | hsa-mir-145 | hsa-mir-1246 | hsa-mir-155 |
| hsa-mir-125a | hsa-mir-125a | hsa-mir-150 | hsa-mir-150 | hsa-mir-125a | hsa-mir-181c |
| hsa-mir-130b | hsa-mir-130b | hsa-mir-181c | hsa-mir-181c | hsa-mir-130b | hsa-mir-182 |
| hsa-mir-132 | hsa-mir-132 | hsa-mir-182 | hsa-mir-182 | hsa-mir-132 | hsa-mir-183 |
| hsa-mir-134 | hsa-mir-134 | hsa-mir-183 | hsa-mir-183 | hsa-mir-134 | hsa-mir-184 |
| hsa-mir-141 | hsa-mir-135b | hsa-mir-184 | hsa-mir-184 | hsa-mir-141 | hsa-mir-18b |
| hsa-mir-142 | hsa-mir-141 | hsa-mir-192 | hsa-mir-192 | hsa-mir-142 | hsa-mir-192 |
| hsa-mir-143 | hsa-mir-142 | hsa-mir-195 | hsa-mir-195 | hsa-mir-143 | hsa-mir-195 |
| hsa-mir-145 | hsa-mir-143 | hsa-mir-200a | hsa-mir-200a | hsa-mir-144 | hsa-mir-200a |
| hsa-mir-146a | hsa-mir-144 | hsa-mir-202 | hsa-mir-202 | hsa-mir-145 | hsa-mir-202 |
| hsa-mir-146b | hsa-mir-145 | hsa-mir-203 | hsa-mir-203 | hsa-mir-146a | hsa-mir-203 |
| hsa-mir-148a | hsa-mir-146a | hsa-mir-205 | hsa-mir-205 | hsa-mir-146b | hsa-mir-205 |
| hsa-mir-154 | hsa-mir-146b | hsa-mir-21 | hsa-mir-21 | hsa-mir-148a | hsa-mir-206 |
| hsa-mir-155 | hsa-mir-148a | hsa-mir-210 | hsa-mir-210 | hsa-mir-150 | hsa-mir-20b |
| hsa-mir-181a-2 | hsa-mir-150 | hsa-mir-212 | hsa-mir-212 | hsa-mir-154 | hsa-mir-21 |
| hsa-mir-181c | hsa-mir-154 | hsa-mir-29a | hsa-mir-29a | hsa-mir-155 | hsa-mir-210 |
| hsa-mir-181d | hsa-mir-155 | hsa-mir-29c | hsa-mir-29c | hsa-mir-181a-2 | hsa-mir-27a |
| hsa-mir-182 | hsa-mir-181a-2 | hsa-mir-30b | hsa-mir-30b | hsa-mir-181c | hsa-mir-29a |
| hsa-mir-183 | hsa-mir-181c | hsa-mir-30d | hsa-mir-30d | hsa-mir-181d | hsa-mir-29c |
| hsa-mir-18b | hsa-mir-182 | hsa-mir-331 | hsa-mir-331 | hsa-mir-182 | hsa-mir-30b |
| hsa-mir-192 | hsa-mir-183 | hsa-mir-34a | hsa-mir-34a | hsa-mir-183 | hsa-mir-345 |
| hsa-mir-193a | hsa-mir-18b | hsa-mir-377 | hsa-mir-377 | hsa-mir-184 | hsa-mir-377 |
| hsa-mir-193b | hsa-mir-192 | hsa-mir-409 | hsa-mir-409 | hsa-mir-187 | hsa-mir-409 |
| hsa-mir-195 | hsa-mir-193a | hsa-mir-495 | hsa-mir-495 | hsa-mir-18b | hsa-mir-495 |
| hsa-mir-202 | hsa-mir-193b | hsa-mir-520h | hsa-mir-520h | hsa-mir-192 | hsa-mir-520h |
| hsa-mir-203 | hsa-mir-195 | hsa-mir-542 | hsa-mir-542 | hsa-mir-193a | hsa-mir-542 |
| hsa-mir-206 | hsa-mir-200a | hsa-mir-572 | hsa-mir-572 | hsa-mir-193b | hsa-mir-572 |
| hsa-mir-20b | hsa-mir-200b | hsa-mir-648 | hsa-mir-648 | hsa-mir-195 | hsa-mir-648 |
| hsa-mir-21 | hsa-mir-200c | hsa-mir-96 | hsa-mir-96 | hsa-mir-200a | hsa-mir-96 |
| hsa-mir-210 | hsa-mir-202 | hsa-mir-99b | hsa-mir-99b | hsa-mir-200b | hsa-mir-99b |
| hsa-mir-212 | hsa-mir-203 | | | hsa-mir-202 | |
| hsa-mir-217 | hsa-mir-205 | | | hsa-mir-203 | |
| hsa-mir-221 | hsa-mir-206 | | | hsa-mir-205 | |
| hsa-mir-222 | hsa-mir-20b | | | hsa-mir-20b | |
| hsa-mir-23a | hsa-mir-21 | | | hsa-mir-21 | |
| hsa-mir-27a | hsa-mir-210 | | | hsa-mir-210 | |
| hsa-mir-29a | hsa-mir-212 | | | hsa-mir-212 | |
| hsa-mir-29c | hsa-mir-221 | | | hsa-mir-216a | |
| hsa-mir-30a | hsa-mir-222 | | | hsa-mir-217 | |
| hsa-mir-30b | hsa-mir-23a | | | hsa-mir-221 | |
| hsa-mir-30c-2 | hsa-mir-24-2 | | | hsa-mir-222 | |
| hsa-mir-30d | hsa-mir-27a | | | hsa-mir-23a | |
| hsa-mir-3178 | hsa-mir-298 | | | hsa-mir-27a | |
| hsa-mir-331 | hsa-mir-29a | | | hsa-mir-298 | |
| hsa-mir-345 | hsa-mir-29c | | | hsa-mir-29a | |
| hsa-mir-34a | hsa-mir-30a | | | hsa-mir-29c | |
| hsa-mir-363 | hsa-mir-30b | | | hsa-mir-301b | |
| hsa-mir-369 | hsa-mir-30d | | | hsa-mir-30a | |
| hsa-mir-371 | hsa-mir-320 | | | hsa-mir-30b | |
| hsa-mir-372 | hsa-mir-331 | | | hsa-mir-30c-2 | |
| hsa-mir-373 | hsa-mir-337 | | | hsa-mir-30d | |
| hsa-mir-374a | hsa-mir-345 | | | hsa-mir-3178 | |
| hsa-mir-377 | hsa-mir-34a | | | hsa-mir-331 | |
| hsa-mir-379 | hsa-mir-369 | | | hsa-mir-345 | |
| hsa-mir-409 | hsa-mir-374a | | | hsa-mir-34a | |
| hsa-mir-422a | hsa-mir-374b | | | hsa-mir-363 | |
| hsa-mir-494 | hsa-mir-377 | | | hsa-mir-369 | |
| hsa-mir-495 | hsa-mir-379 | | | hsa-mir-371 | |
| hsa-mir-497 | hsa-mir-382 | | | hsa-mir-372 | |
| hsa-mir-505 | hsa-mir-409 | | | hsa-mir-373 | |
| hsa-mir-518c | hsa-mir-411 | | | hsa-mir-374a | |
| hsa-mir-519e | hsa-mir-422a | | | hsa-mir-377 | |
| hsa-mir-520a | hsa-mir-429 | | | hsa-mir-379 | |
| hsa-mir-520g | hsa-mir-450b | | | hsa-mir-409 | |
| hsa-mir-522 | hsa-mir-487a | | | hsa-mir-422a | |
| hsa-mir-523 | hsa-mir-493 | | | hsa-mir-485 | |
| hsa-mir-542 | hsa-mir-494 | | | hsa-mir-493 | |
| hsa-mir-572 | hsa-mir-495 | | | hsa-mir-494 | |
| hsa-mir-648 | hsa-mir-505 | | | hsa-mir-495 | |
| hsa-mir-654 | hsa-mir-518d | | | hsa-mir-496 | |
| hsa-mir-665 | hsa-mir-518e | | | hsa-mir-497 | |

TABLE 4-continued

MiRs involved in neonatal and hereditary diseases, respiratory diseases, urogenital diseases in men, urogenital diseases in women, disorders of the immune system and musculoskeletal disorders

| Neonatal and hereditary diseases | Respiratory diseases | Urogenital diseases in men | Urogenital diseases in women | Disorders of the immune system | Musculoskeletal disorders |
|---|---|---|---|---|---|
| hsa-mir-769 | hsa-mir-518f | | | hsa-mir-505 | |
| hsa-mir-92b | hsa-mir-520a | | | hsa-mir-518c | |
| hsa-mir-96 | hsa-mir-520d | | | hsa-mir-519e | |
| hsa-mir-99b | hsa-mir-520e | | | hsa-mir-520a | |
| | hsa-mir-523 | | | hsa-mir-520g | |
| | hsa-mir-542 | | | hsa-mir-520h | |
| | hsa-mir-543 | | | hsa-mir-522 | |
| | hsa-mir-570 | | | hsa-mir-523 | |
| | hsa-mir-572 | | | hsa-mir-525 | |
| | hsa-mir-648 | | | hsa-mir-542 | |
| | hsa-mir-656 | | | hsa-mir-568 | |
| | hsa-mir-668 | | | hsa-mir-570 | |
| | hsa-mir-758 | | | hsa-mir-572 | |
| | hsa-mir-769 | | | hsa-mir-633 | |
| | hsa-mir-96 | | | hsa-mir-648 | |
| | hsa-mir-99b | | | hsa-mir-654 | |
| | | | | hsa-mir-665 | |
| | | | | hsa-mir-769 | |
| | | | | hsa-mir-92b | |
| | | | | hsa-mir-96 | |
| | | | | hsa-mir-99b | |

TABLE 5

The top 10 miRs involved in cancers, bacterial and fungal infections, immune system disorders, cardiovascular diseases, hereditary congenital diseases, skin diseases, musculoskeletal disorders, eye diseases and diseases of the digestive system.

| Cancer | bacterial infections - Mycosis | Immune system disorders | Cardiovascular diseases | Hereditary congenital diseases | Skin diseases | Musculoskeletal disorders | Eye diseases | Diseases of the digestive system |
|---|---|---|---|---|---|---|---|---|
| hsa-mir-21 | hsa-mir-155 | hsa-mir-192 | hsa-mir-192 | hsa-mir-192 | hsa-mir-182 | hsa-mir-192 | hsa-mir-192 | hsa-mir-122 |
| hsa-mir-145 | hsa-mir-21 | hsa-mir-221 | hsa-mir-21 | hsa-mir-221 | hsa-mir-221 | hsa-mir-210 | hsa-mir-145 | hsa-mir-192 |
| hsa-mir-192 | hsa-mir-203 | hsa-mir-141 | hsa-mir-122 | hsa-let-7i | hsa-mir-203 | hsa-mir-182 | hsa-let-7g | hsa-mir-21 |
| hsa-mir-205 | hsa-mir-195 | hsa-mir-145 | hsa-mir-145 | hsa-mir-122 | hsa-mir-106a | hsa-mir-183 | hsa-mir-331 | hsa-mir-210 |
| hsa-mir-143 | hsa-let-7b | hsa-mir-182 | hsa-mir-210 | hsa-mir-141 | hsa-mir-155 | hsa-mir-96 | hsa-mir-99b | hsa-mir-99b |
| hsa-mir-10a | hsa-let-7d | hsa-mir-21 | hsa-mir-29c | hsa-mir-182 | hsa-mir-29a | hsa-mir-106a | hsa-mir-182 | hsa-let-7b |
| hsa-mir-106a | hsa-mir-145 | hsa-mir-203 | hsa-mir-497 | hsa-mir-155 | hsa-mir-210 | hsa-mir-10b | hsa-mir-183 | hsa-let-7d |
| hsa-mir-146a | hsa-mir-1246 | hsa-let-7i | hsa-mir-96 | hsa-mir-145 | hsa-mir-148a | hsa-mir-1246 | hsa-mir-195 | hsa-mir-10a |
| hsa-mir-182 | hsa-mir-192 | hsa-mir-106a | hsa-mir-132 | hsa-mir-222 | hsa-mir-141 | hsa-mir-132 | hsa-mir-106a | hsa-let-7g |
| hsa-mir-221 | hsa-let-7g | hsa-mir-122 | hsa-mir-141 | hsa-mir-20b | hsa-let-7i | hsa-mir-134 | hsa-mir-10a | hsa-let-7i |

TABLE 6

The top 10 miRs involved in diseases of the endocrine system, diseases of the nervous system, diseases related to viruses, diseases related to nutrition and metabolism, lymphatic diseases and hemopathies, neonatal and hereditary diseases, respiratory diseases, urogenital diseases in men, urogenital diseases in women.

| diseases of the endocrine system | diseases of the nervous system | Diseases related to viruses | Diseases related to nutrition and metabolism | Lymphatic diseases and hemopathies | Neonatal and hereditary diseases | Respiratory diseases | Urogenital diseases in men | Urogenital diseases in women |
|---|---|---|---|---|---|---|---|---|
| hsa-mir-145 | hsa-mir-192 | hsa-mir-122 | hsa-mir-192 | hsa-mir-106a | hsa-mir-192 | hsa-mir-21 | hsa-mir-21 | hsa-mir-21 |
| hsa-mir-21 | hsa-mir-122 | hsa-mir-192 | hsa-mir-122 | hsa-mir-205 | hsa-mir-221 | hsa-mir-145 | hsa-let-7b | hsa-let-7b |
| hsa-mir-192 | hsa-mir-145 | hsa-mir-195 | hsa-mir-21 | hsa-mir-145 | hsa-mir-182 | hsa-mir-143 | hsa-mir-145 | hsa-mir-145 |

TABLE 6-continued

The top 10 miRs involved in diseases of the endocrine system, diseases of the nervous system, diseases related to viruses, diseases related to nutrition and metabolism, lymphatic diseases and hemopathies, neonatal and hereditary diseases, respiratory diseases, urogenital diseases in men, urogenital diseases in women.

| diseases of the endocrine system | diseases of the nervous system | Diseases related to viruses | Diseases related to nutrition and metabolism | Lymphatic diseases and hemopathies | Neonatal and hereditary diseases | Respiratory diseases | Urogenital diseases in men | Urogenital diseases in women |
|---|---|---|---|---|---|---|---|---|
| hsa-mir-181c | hsa-mir-141 | hsa-mir-18b | hsa-mir-141 | hsa-mir-125a | hsa-let-7i | hsa-mir-144 | hsa-mir-106a | hsa-mir-181c |
| hsa-mir-182 | hsa-mir-142 | hsa-mir-21 | hsa-mir-145 | hsa-mir-141 | hsa-mir-122 | hsa-mir-182 | hsa-let-7d | hsa-let-7d |
| hsa-mir-183 | hsa-mir-143 | hsa-mir-1246 | hsa-mir-142 | hsa-mir-143 | hsa-mir-141 | hsa-mir-195 | hsa-mir-181c | hsa-mir-106a |
| hsa-mir-96 | hsa-mir-146a | hsa-mir-212 | hsa-mir-143 | hsa-let-7d | hsa-mir-145 | hsa-mir-192 | hsa-mir-192 | hsa-mir-192 |
| hsa-mir-210 | hsa-mir-100 | hsa-mir-34a | hsa-mir-155 | hsa-let-7i | hsa-mir-155 | hsa-mir-221 | hsa-mir-195 | hsa-mir-195 |
| hsa-mir-212 | hsa-mir-155 | hsa-mir-106a | hsa-mir-182 | hsa-mir-331 | hsa-mir-222 | hsa-mir-222 | hsa-mir-200a | hsa-mir-200a |
| hsa-mir-132 | hsa-mir-182 | hsa-mir-10a | hsa-mir-183 | hsa-mir-192 | hsa-mir-20b | hsa-mir-27a | hsa-mir-202 | hsa-mir-202 |

The following examples will better illustrate the invention without limiting its scope.

EXAMPLES

Example 1: miPEP 125a-1 and miPEP 145-2

A transcriptomic analysis carried out by the inventors has revealed that the miR 125a-1 and miR 145-2 are overexpressed during the differentiation of the cells into osteoblasts (unpublished results).

The miPEPs 125a-1 and 145-2 sequences were identified from the primary transcripts of miRs 125a-1 and 145-2.

The respective effects of miPEP 125a-1 and miPEP 145-2 on differentiation of mesenchymal stem cells were analyzed by measuring the expression of the iBSP, PTHR1, STMN2 and OSTERIX genes that correspond to markers of osteogenesis and of osteoblast differentiation (Chiellini et al., Biochem Biophys Res Commun, 374(1):64-8, 2008; Cordonnier et al., Tissue Eng, 17(3): 249-259, 2011).

The experiments were carried out with two fragments of 10 amino acids respectively corresponding to the N-terminal part of the miPEP 125a-1 (=miPEP//125a-1 fragment) and to the N-terminal part of the miPEP 145-2 (=fragment miPEP//145-2).

Mesenchymal stem cells from 4 different donors were cultured for 24 hours in PROLIF medium (αMEM+10% FCS) with or without miPEP//then for 3 days in DIF+BMP4 medium (αMEM+2% FCS+b-Glycerophosphate+Ascorbic acid+BMP4), DIF ΔBMP4 medium (αMEM+2% FCS+b-Glycerophosphate+Ascorbic acid) or PROLIF medium (αMEM+10% FCS), with or without miPEP//.

The expression of the iBSP, PTHR1, STMN2 and OSTERIX genes was then measured in mesenchymal stem cells cultured in the presence or absence of a miPEP*.

1.1—Results

In DIF+BMP4 Medium

The miPEP//125a-1 increases the expression of the iBSP, PTHR1, STMN2 and OSTERIX genes (FIGS. 2, 3, 4 and 5).

The miPEP//145-2 increases the expression of the STMN2 gene (FIG. 6).

In DIF ΔBMP4 Medium

The miPEP//125a-1 increases the expression of the STMN2 and OSTERIX genes (FIGS. 7 and 8).

The miPEP//145-2 increases the expression of the STMN2 and OSTERIX genes (FIGS. 9 and 10).

In PROLIF Medium

The miPEP//145-2 increases the expression STMN2 gene (FIG. 11).

The above results show that miPEP//125a-1 and miPEP//145-2 increase the expression of osteoblast marker genes, indicating that these miPEPs promote osteoblast differentiation of mesenchymal stem cells.

1.2—Materials

MEMα GIBCO (reference 22561-021)⇒"αMEM",
Fetal bovine serum (FBS),
Penicillin/streptomycin GIBCO (reference 15140-122) "P/S",
Dulbecco's PBS GIBCO (reference 14190-169)⇒"PBS",
12-well plate,
βglycerophosphate SIGMA (reference G9422),
Ascorbic acid SIGMA (reference A8960),
BMP4 PEPROTECH (reference 120-05ET)⇒"BMP4",

```
miPEP//125a-1
(MSLCLSPSLT, SEQ ID NO: 11 752), miPEP//145-2
(MVGLNPPLWQ, SEQ ID NO: 11 751),

"scramble" control peptide ScmiPEP//125a
(IQVGHEDETD, SEQ ID NO: 11 758).
```

1.3—Methods a. Composition of Culture Media

Proliferation medium (PROLIF): αMEM+10% FBS+1% P/S

Differentiation medium+BMP4 (DIF+BMP4): αMEM+2% FBS+1% P/S+βglycerophosphate (10 mM)+Ascorbic acid (50 μM)+BMP4 (50 ng/mL)

Differentiation medium without BMP4 (DIF ΔBMP4): αMEM+2% FBS+1% P/S+βglycerophosphate (10 mM)+Ascorbic acid (50 μM)

b. Resuspension of Micropeptides

The miPEP//145-2 was synthesized by Smartbioscience and dissolved at 2 mM in water. The miPEP//125a-1 was synthesized by Smartbioscience and dissolved in water+0.1% ammonium.

c. Seeding of the Cells

The mesenchymal stem cells were seeded in 12-well plates at 70,000 cells/well in 1 mL of PROLIF medium. The cells were then incubated for 72 h at 37° C. in a humid atmosphere with 5% $CO_2$.

d. Cell Treatment with miPEPs

After 72 hours of incubation, the cells were pre-treated with 100 µM of miPEP or "scramble" peptide diluted in PROLIF medium, and then incubated at 37° C. for 24 hours. In parallel, cells treated with PROLIF±water or water+0.1% ammonium medium were used as a negative control.

For 3 days, the cells were treated every 24 h with 100 µM of diluted miPEP either in DIF+BMP4 medium, or in DIF ΔBMP4 medium, or in PROLIF medium. Cells untreated or treated with water or water+0.1% ammonium were used as controls. The cells are incubated at 37° C.

After 3 days of treatment, the culture supernatants were removed, the cell mats were washed once with PBS, and then the plates were frozen at −80° C. until the total RNAs were extracted.

e. Extraction of Total RNA

Total RNAs were extracted according to the supplier's recommendations with the miRNeasy microkit kit (Qiagen).

f. Reverse Transcription Reaction

The RNAs were reverse transcribed with the High Capacity cDNA reverse transcription kit (Applied Biosystem). 600 ng of RNA were added to 2 µL of RT buffer (10×), 2 µL of Random primer (10×), 0.8 µL of dNTPs (25×), 0.5 µL of RNAse OUT (40 U/µL) and 1 µL of multiscribe reverse transcriptase (50 U/µL) in a total volume of 20 µL. The reverse transcription reaction was carried out at 25° C. for 10 min and then 42° C. for 2 h. The activity of the enzyme was stopped by incubating the mixture at 85° C. for 5 min.

g. Evaluation of Gene Expression by Quantitative RT-PCR

The expression of osteoblastic transcription factors iBSP, PTHR1, STMN2 and OSTERIX was evaluated by quantitative RT-PCR with the SsoFast EvagGreen kit. For the RT-PCR reaction, 3 µL of reverse transcriptase diluted 1/8 were added to 1× of SsoFast EvaGreen, 10 µM of each primer and RNase free water in a final volume of 10 µL. The reaction was subjected to the following temperatures: 3 min pre-amplification at 95° C., 40 cycles of 10 sec at 95° C. and sec at 60° C. in a thermal cycler (CFX96 Real-time PCR detection system, Biorad). PPIA was used as a reference gene to normalize quantitative RT-PCR.

For all PCR reactions, two replicates were used for each biological sample.

Example 2: Cell Penetration of miPEPs

The entry of miPEPs into mesenchymal stem cells (MSCs) was analyzed by fluorescence microscopy using fluorescein (FAM)-labeled miPEP//15a-16-1, fused or not to a peptide promoting cell penetration (TAT peptide).

2.1—Results

In a first experiment, undifferentiated MSCs were incubated for 7 h with 5 µM, 10 µM, 50 µM or 100 µM of miPEP//15a-16-1-FAM (FIG. 12).

In a second experiment, undifferentiated MSCs were incubated with 100 µM of miPEP//15a-16-1-FAM for 2 h, 4 h, 6 h, 8 h or 24 h (FIG. 13).

In a third experiment, undifferentiated MSCs were incubated for 7 h with 5 µM, 10 µM, 20 µM, 50 µM or 100 µM of miPEP//15a-16-1-FAM-TAT (FIG. 14).

In a fourth experiment, undifferentiated MSCs were incubated for 2 h, with 10 µM of miPEP//15a-16-1-FAM-TAT (FIG. 15).

The above results indicate, on the one hand, that the miPEP//15a-16-1-FAM homogeneously penetrates the MSCs when the MSCs are treated with at least 50 µM of miPEP, and on the other hand, that the miPEP is captured in the core of the MSCs.

The strongest fluorescence is observed from 4 h to 8 h after the treatment with the miPEP.

These results also indicate that the addition of the TAT peptide to the miPEP promotes cell penetration by a factor of 10 relative to the cellular penetration of the miPEP without the TAT peptide.

2.2—Materials

MEMα GIBCO (reference 22561-021)⇒"αMEM",

Fetal bovine serum (FBS),

Penicillin/streptomycin GIBCO (reference 15140-122) ⇒"P/S",

Dulbecco's PBS GIBCO (reference 14190-169)⇒"PBS", 8-well IBIDI blade (15µ slide 8 well IBIDi; Biovalley), DRAQ5 (5 mM) Biostatus, Formaldehyde solution 37%,

TABLE 7

Sequences of the primers.

|  |  | Forward primer (5'-3') | Reverse primer (5'-3') |
|---|---|---|---|
| Reference gene | PPIA | TCT TTG GGA CCT TGT CTG CAA (SEQ ID NO: 11 759) | GCC GAG GAA AAC CGT GTA CTA T (SEQ ID NO: 11 760) |
| Osteoblastic marker genes | iBSP | GGG CAG TAG TGA CTC ATC CGA AG (SEQ ID NO: 11 761) | CTC CAT AGC CCA GTG TTG TAG CAG (SEQ ID NO: 11762) |
|  | OSX | CTC CTG CGA CTG CCC TAA T (SEQ ID NO: 11 763) | GCC TTG CCA TAC ACC TTG C (SEQ ID NO: 11 764) |
|  | PTHR1 | ACA TCT GCG TCC ACA TCA GG (SEQ ID NO: 11 765) | CCG TTC ACG AGT CTC ATT GGT G (SEQ ID NO: 11766) |
|  | STMN2 | GCG GAG GAA AAG CTG ATC CTG A (SEQ ID NO: 11 767) | TCC GCA GCA TGC CTC TCC TT (SEQ ID NO: 11 768) | miPEP//15a-16-1
(MFKHRFFYMH, SEQ ID NO: 11 753), miPEP//15a-16-1-TAT
(MFKHRFFYMH-YGRKKRRQRRR, SEQ ID NO: 11 757).

2.3—Methods

Undifferentiated MSCs are incubated in ° MEM+10% FBS+1% P/S medium in the presence of fluorescein (FAM) labeled miPEP. After incubation from 2 h to 10 h, the wells are washed 3 times with PBS and then the cells are fixed for 5 min with 3.8% formaldehyde. The nuclei are marked with the Draq5 diluted 1/1 000. The cells are then observed under a confocal microscope in fluorescence.

Example 3: miPEP 15a-16-1

A transcriptomic analysis carried out by the inventors has revealed that the miR 15a and miR 16-1 are overexpressed during the differentiation of the cells into osteoblasts (unpublished results).

The miPEP 15a-16-1 sequence was identified from the primary transcript of 15a-16-1.

The effect of miPEP 15a-16-1 on miR16-1 accumulation was analyzed in mesenchymal stem cells (MSCs). The experiments were carried out with a fragment of 10 amino acids respectively corresponding to the N-terminal portion of the miPEP 15a-16-1 (=fragment miPEP//15 a-16-1).

MSCs from three different patients were treated with 10 μM of miPEP//15a-16-1 fused to TAT peptide (miPEP//15a-16-1-TAT) for 3 h, then the amount of miR16-1 was measured by RT-qPCR.

3.1—Results

Treatment with miPEP//15a-16-1-TAT results in an increase in the amount of miR 16-1 (FIG. 16).

3.2—Materials

MEMα GIBCO (reference 22561-021)⇒"αMEM",
Fetal bovine serum (FBS),
Penicillin/streptomycin GIBCO (reference 15140-122) ⇒"P/S",
Dulbecco's PBS GIBCO (reference 14190-169)⇒"PBS", miPEP//15a-16-1-TAT
(MFKHRFFYMH-YGRKKRRQRRR, SEQ ID NO: 11 757), ScmiPEP//21
(RPHLRMELPV).

3.3—Methods a. Resuspension of Micropeptides

Peptides were synthesized by Smartbioscience and dissolved at 2 mM in water.

b. Seeding of the Cells

The MSCs were seeded in wells of 12-well plates at 72,900 cells per well under 1 mL of PROLIF medium. The cells were then incubated for 72 h at 37° C. in a humid atmosphere with 5% $CO_2$.

c. Cell Treatment with miPEPs

After 24 h of incubation, the cells were treated with 10 μM of miPEP//15a-16-1-TAT or 100 μM of ScmiPEP21 diluted in PROLIF medium and then incubated at 37° C. for 1 h, 2 h, 3 h, 4 h and 6 h. In parallel, cells treated with PROLIF±water medium were used as a negative control.

After treatment from 1 h to 6 h, the culture supernatants were removed and then the cell mats were washed twice with PBS, and then the plates were frozen at −80° C. until miRNA extraction.

d. Total RNA Extraction

The miRNAs were extracted according to the supplier's recommendations with the miRNeasy microkit kit (Qiagen).

e. Reverse Transcription Reaction

The RNAs were reverse transcribed with the High Capacity cDNA reverse transcription kit (Applied Biosystem). 400 ng of RNA were added to 2 μL of RT buffer (10×), 2 μL of Random primer (10×), 0.8 μL of dNTPs (25×), 0.5 μL of RNAse OUT (40 U/μL) and 1 μL of multiscribe reverse transcriptase (50 U/μL) in a total volume of 20 μL. The reverse transcription reaction was carried out at 25° C. for 10 min and then 42° C. for 2 h. The activity of the enzyme was stopped by incubating the mixture at 85° C. for 5 min.

f. Quantification of miRNAs Precursors by Quantitative RT-PCR

The amount of miRNAs precursors in cells treated or not treated with miPEP was evaluated by quantitative RT-PCR with the SsoFast EvagGreen kit. For the RT-PCR reaction, 3 μL of reverse transcriptase diluted 1/5 were added to 1× of SsoFast EvaGreen, 10 μM of each primer and RNase free water in a final volume of 10 μL. The reaction was subjected to the following temperatures: 3 min pre-amplification at 95° C., 40 cycles of 10 sec at 95° C. and 30 sec at 60° C. in a thermal cycler (CFX96 Real-time PCR detection system, Biorad). PPIA was used as a reference gene to normalize quantitative RT-PCR.

For all PCR reactions, two replicates were used for each biological sample.

TABLE 8

Sequences of the primers.

| | | Forward primer (5'-3') | Reverse primer (5'-3') |
|---|---|---|---|
| Reference gene | PPIA | TCT TTG GGA CCT TGT CTG CAA (SEQ ID NO: 11 759) | GCC GAG GAA AAC CGT GTA CTA T (SEQ ID NO: 11 760) |
| miRNA | miR15a | ATAAAAACCTTGGAGT AAAGTAGCAG (SEQ ID NO: 11 769) | GCACAATATGGCCTGC ACC (SEQ ID NO: 11 770) |
| | miR16 | CAGCACGTAAATATTG GCGTTA (SEQ ID NO: 11 771) | TCAACCTTACTTCAGC AGCAC (SEQ ID NO: 11 772) |

Example 4: miPEPs Immunolabeling

The production of polyclonal antibodies specifically recognizing miPEP 125a, miPEP145 and miPEP15a-16-1 is made in mice or rabbits. The animals are treated by repeated injections of miPEP triggering the production of anti-miPEP antibodies.

Mesenchymal stem cells from 6 different donors are cultured for 7 days either in proliferation medium (αMEM+ 10% FCS), or in differentiation medium (αMEM+2% FCS+ β-Glycerophosphate+Ascorbic acid+BMP4). The presence of miPEP is then looked for in the cells by immunolabelings with the polyclonal antibodies anti-miPEP125a, anti-miPEP145 and anti-miPEP 15a-16-1. The cells are incubated for 1 h to 12 h with the primary antibodies. They are then washed 3 times with 0.1% PBS BSA and then treated by adding anti-species secondary antibodies (anti-mouse or anti-rabbit) conjugated to a fluorescent probe. The reading is done under an epifluorescence microscope.

Example 5: In Vivo Bone Formation by Subcutaneous Implantation in Nude Mice

All experiments are done on animals in accordance with the directive 2010/63/EU and after validation of the protocols by the animal ethics committee (Toulouse). A total of 6-8 mice was used per group. The cultured cells are osteo-induced using miPEPs, and then suspended for 1 to 2 hours in the culture medium also containing biomaterial granules in the ratio of $2\times10^6$ cells/50 mg of biomaterial. This biomaterial is biphasic inorganic calcium phosphate (BCP) composed of hydroxyapatite (HA) and beta-tricalcium phosphate ($\beta$-TCP) in a ratio of 20/80, ranging in size from 0.5 to 1 mm (sold by Biomatlante, Vigneux de Bretagne, France). The porosity of this biomaterial (% vol) was 75±5% of pores of which 70% from 0 to 10 µm, 20% from 10 to 100 µm and 10% from 100 to 300 µm. The biomaterial is sterilized by autoclaving.

Female Nude mice (RjOrl: NMRI-Foxnnul/Foxnlnu) (Laboratoires Janvier, Saint-Berthevin, France) are generally anesthetized by inhalationn of isoflurane. The biomaterial alone is implanted as a negative control. Two implants (cells+biomaterials) are subcutaneously placed in the back of the mice on each side of the spine (a mouse may contain different types of implants). After 8 weeks, the treated animals are sacrificed. The implants are then removed and fixed in a buffered 4% formalin solution.

Example 6: Pulmonary Fibrosis miR-29 as Therapeutic Target

The therapeutic benefit of increasing the level of miR-29 has been demonstrated for fibrosis in the heart, kidney, liver, lung and in a context of systemic sclerosis. The ability of a miR-29b analog to directly target the expression of Collagen1a1 (Col1a1), whose deregulation is implicated in the mechanism of fibrosis, has been demonstrated. Thus, an increasing amount of this analog results in a dose-dependent decrease in Col1a1 expression in a cell model (Montgomery et al., MicroRNA mimicry blocks pulmonary fibrosis, EMBO Mol. Med. (2014), 6(10); 1347-1356).

Demonstration of the Therapeutic Effect of a miPEP Encoded by the Primary Transcript of miR-29

NIH 3T3 cells (mouse fibroblast cell line) are cultured on DMEM medium, supplemented with 1-Glutamine (4 mM), Sodium Pyruvate (1 mM) and a 10% BCS of BCS solution. The cells are transfected with Dharmafect I according to the reseller's recommendations and then with increasing amounts of a miPEP encoded by the primary miR-29 transcript. The cells are collected 48 hours after transfection and Col1a1 expression is measured by qPCR.

Example 7: Lung Cancer (Non-Small Cell Lung Cancer)

miR let-7 as a Therapeutic Target miR letR-7 is known to act as a tumor suppressor gene in a variety of human tissues, particularly in the lung, by downregulating the post-transcriptional expression of multiple oncogenes, including RAS, MYC and HMGA2, as well as other genes for cell cycle progression. Increasing amounts of miR let-7 in overexpressing KRAS mutant cells showed a dose-dependent reduction in kras expression (Esquela-Kerscher et al., The let-7 microRNA reduces tumor growth in mouse models of lung cancer, Cell Cycle (2008), 7(6), 759-764).

Demonstration of the Therapeutic Effect of a miPEP Encoded by the Primary Transcript of miR let-7

A549 cells (KRAS overexpressing mutant cell line) were cultured on DMEM medium (90%) supplemented with fetal calf serum (10%) and 1× penicillin/streptomycin solution, then transfected with increasing amount of miPEP encoded by the primary transcript of miR let-7. The next day, the cells are rinsed and incubated for 48 hours with a conventional culture medium. The proliferation tests are carried out with the AlamarBlue kit according to the distributor's recommendations.

Example 8: Ischemia—Reperfusion miR-7 as Therapeutic Target miR-7 is implicated in the deleterious effects of ischemia-reperfusion syndrome (I/R) and is overexpressed in simulated I/R cardiomyocites. In addition, miR-7 has been shown to protect myocardial cells against apoptosis by reducing the expression of poly(ADP-ribose) polymerase (PARP). An increase in miR-7 induces a dose-dependent reduction in PARP expression (Li et al., MicroRNA-7a/b Protects against Cardiac Myocyte Injury in Ischemia/Reperfusion by Targeting Poly(ADP-Ribose) Polymerase, PLoS One (2014), 9(3); e90096).

Demonstration of the Therapeutic Effect of a miPEP Encoded by the Primary Transcript of miR-7

H9c2 cells (rat ventricular cell line) are cultured at 37° C. under 5% $CO_2$ on DMEM medium (90%) supplemented with fetal calf serum (10%) and 100 µg/mL penicillin/streptomycin solution. 48 hours after transfection of a miPEP encoded by the primary miR-7 transcript, the cells are subjected to a simulated I/R episode: the medium is replaced by glucose- and serum-deficient DMEM, and the cells are placed in a hypoxic chamber at 37° C. for 10 h and then reoxygenated for 2 h on DMEM medium containing 10% of fetal calf serum. Quantification of PARP expression is conducted in Western Blot with anti-PARP antibodies.

Example 9: Hepatitis C Virus Infection (HCV)

miR-181c as Therapeutic Target

The expression of Homeobox A1 (HOXA1) is increased in hepatocytes infected with HCV. Exogenous expression of a miR-181c analog inhibits HOXA1 and other cascading agents, including STAT5 and STAT5, involved in the regulation of cell growth. The analog also suppresses HCV replication (Mukherjee et al., Transcriptional Suppression of miR-181c by Hepatitis C Virus Enhances Homeobox A1 Expression, J. Virol. (2014), 88(14); 7929-7940).

Demonstration of the Therapeutic Effect of a miPEP Encoded by the Primary Transcript of miR-181c The human hepatoma cells (Huh7.5) are maintained on DMEM medium (90%) supplemented with fetal calf serum (10%) and antibiotics (100 U penicillin G/mL and 100 µg streptomycin/mL). HCV genotype 2a (clone JFH1) is grown in Huh7.5 cells. The supernatant is filtered on a cellulose acetate membrane. For infection, Huh7.5 cells are incubated with the viral solution for 72 h. The cells reflecting the presence of HCV genotype 2a are cultured on DMEM medium (90%) supplemented with fetal calf serum (10%) and 1% penicillin/streptomycin solution. All cells are maintained at 37° C. under 5% $CO_2$ and transfected with increasing doses of a miPEP encoded by the primary miR-181c transcript. The quantification of HOXA1 is carried out by Western Blot using dedicated antibodies.

Example 10: Evaluation of the Effects of miPEP125a on In Vivo Bone Formation by Subcutaneous Implantation in Nude Mice 10.1—Methods All experiments on animals were done in accordance with directive 2010/63/EU and after validation of protocols by the Animal Ethics Committee (Toulouse, N: 86/809 EEC). A total of 6-8 mice was used per group. The cells cultured osteo-induced or not according to the methods described elsewhere (see Example 1), were then suspended for 1 to 2 h in the culture medium also containing granules of biomaterials in the ratio of $2\times10^6$ cells/50 mg of biomaterial. These biomaterials were biphasic inorganic calcium phosphate (BCP), composed of hydroxyapatite (HA) and beta-tricalcium phosphate (β-TCP) in a ratio of 20/80, ranging in size from 0.5 to 1 mm (sold by Biomatlante, Vigneux de Bretagne, France). The porosity of these biomaterials (% vol) was 75±5% of pores of which 70% (0 to 10 µm), 20% (10 to 100 µm) and 10% (100 to 300 µm). They were sterilized by autoclaving.

The biomaterial alone has been implanted as a negative control. Female Nude mice (RjOrl: NMRI-Foxnnul/Foxnlnu) (Laboratoires Janvier, Saint-Berthevin, France) are generally anesthetized by inhalationn of isoflurane. Two implants (cells+biomaterials) are subcutaneously placed in the back of the mice on each side of the spine. After 4 weeks, the treated animals are sacrificed. The implants are then removed and fixed in a buffered 4% formalin solution. Some groups of mice will also receive regular injections (once a week) during the study either of the miPEP//125a-1 (SEQ ID NO: 11 752) or the control miPEP (scramble ScmiPEP//125a, SEQ ID NO: 11 758).

These implants were then decalcified in a solution of 4.13% EDTA/0.2% PFA in PBS for 96 hours at 50° C. using an automatic microwave for demineralization (KOS Histostation, Milestone Med. Corp. USA). The samples were dehydrated in ethanol and then butanol baths in an automatic dehydration apparatus (MicromMicrotech, Lyon, France). The samples were then immersed in paraphine (Histowax, Histolab, Gottenburg, Sweden). Fine sections (3 mm thick) were made using a microtome (Leica RM2255, Leica Biosystems, Nanterre, France). The sections were stained by the Masson trichrome technique and the collagen in light green.

The photos were obtained by a scan of each cut (NanoZoomer, Hamamatsu, Photonics, Hamamatsu City, Shizuoka, Japan) and observed virtually (NDP view, Hamamatsu). The histomorphometry of the images was done using the ImageJ software and the neoformed bone percentage was calculated by explant area. 3 to 4 sections per explant were analyzed and quantified.

10.2—Materials

Female Nude mice (RjOrl: NMRI-Foxnnul/Foxnlnu), from the approved supplier Janvier (Laboratoires Janvier, Saint-Berthevin, France), Biomaterials: Biphasic inorganic calcium phosphate (BCP), composed of hydroxyapatite (HA) and beta-tricalcium phosphate (β-TCP) in a ratio of 20/80, ranging in size from 0.5 to 1 mm (sold by Biomatlante, Vigneux de Bretagne, France), 1.5 mL Eppendorf tubes, Anesthesia table with Isoflurane, Syringes 19 G, An automatic microwave for demineralization (KOS Histostation, Milestone Med. Corp. USA), Demineralization solution of 4.13% EDTA/0.2% PFA in PBS, Ethanol, Butanol, Automatic dehydration device (MicromMicrotech, Lyon, France), Microtome (Leica RM2255, Leica Biosystems, Nanterre, France), Paraphine (Histowax, Histolab, Gottenburg, Sweden), NanoZoomer (Hamamatsu, Photonics, Hamamatsu City, Shizuoka, Japon), NDPview software (NDP view, Hamamatsu).

10.3—Results

The images in FIG. 17 show that there is no bone formation in the biomaterial control alone (FIG. 17A). In contrast, the addition of MSCs to the biomaterial generated bone formation in all cases (FIG. 17B-F). However, qualitatively it appears that this bone formation is greater when the MSCs have been pre-treated with miPEP125a-1 (FIG. 17C-D) than with the scramble miPEP (FIG. 17E-F).

Quantification of neoformed bone confirms this assessment (FIG. 17G). Indeed, there is significantly more bone formation when the MSCs were pre-treated with miPEP//125a in culture (C) than in the associated control (E: MSC pre-treated with the scramble miPEP, p=0.0499). This quantification also shows that the injection of the miPEP//125a-1 in vivo (D) is without consequence, or even decreases (in a non-significant manner) the induction effect compared to its control (C: MSCs only pre-treated). On the other hand, it is clear that the bone formation of MSCs only pre-treated in vitro (C) or MSCs pre-treated in vitro and then in vivo (D) is significantly higher than the untreated MSCs (B) (p=0.0241 and p=0.0203 respectively).

The treatment of human MSCs with miPEP//125a-1 has therefore increased their ability to form bone in vivo when previously treated in vitro.

The listing of sequences of the present invention is identical to that of the priority document, which corresponds to the French application No. FR16/63245 filed on Dec. 22, 2016.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11607443B2). An electronic copy of the "Sequence Listing" will also be available from the USPTO upon request and payment of the fee set forth in 37 CFR 1.19(b)(3).

The invention claimed is:

1. A pharmaceutical composition comprising:
   a miPEP consisting of SEQ ID NO: 11 745, SEQ ID NO: 11 747, or SEQ ID NO: 11 749, or a fragment of said miPEP consisting of: SEQ ID NO: 11 751, SEQ ID NO: 11 752, or SEQ ID NO: 11 753, said miPEP, or said fragment of said miPEP, being capable of modulating the accumulation of said miR in a eukaryotic cell; or
   a nucleic acid consisting of SEQ ID NO: 11 746, SEQ ID NO: 11 748, or SEQ ID NO: 11 750, said nucleic acid encoding said miPEP, or a nucleic acid encoding said fragment of said miPEP, said miPEP, or said fragment of said miPEP, being capable of modulating the accumulation of said miR in a eukaryotic cell, and
   a pharmaceutically acceptable excipient.

2. The pharmaceutical composition of claim 1, wherein said miPEP is identified, or as identified, by implementing of a process for identifying a miPEP modulating the accumulation of a miR involved in osteoporosis, comprising:
   a) a step of detecting an open reading frame from 12 to 1 503 nucleotides contained in the sequence of the primary transcript of said miR, then
   b) a step of comparison between:
      i. the accumulation of said miR in a specified eukaryotic cell expressing the primary transcript of said miR, in the presence of a peptide encoded by a nucleotide sequence that is identical or degenerate relative to that of said open reading frame, said peptide being present in the cell independently of transcription of the primary transcript of said miR, and
      ii. the accumulation of said miR in a eukaryotic cell of the same type as the aforesaid specified eukaryotic cell expressing the primary transcript of said miR, in the absence of said peptide,
   in which a modulation of the accumulation of said miR in the presence of said peptide relative to the accumulation of said miR in the absence of said peptide indicates the existence of a miPEP, the latter being encoded by said open reading frame and being capable of modulating the accumulation of said miR involved in osteoporosis.

3. The pharmaceutical composition of claim 1, wherein said miPEP, or said fragment of said miPEP, is fused or linked to one or more molecules facilitating the entry of the miPEP, or miPEP fragment, into the cell.

4. The pharmaceutical composition of claim 1, wherein said miPEP, or fragment of said miPEP, is fused in N-ter or in C-ter to the TAT peptide (YGRKKRRQRRR, SEQ ID NO: 11 754).

5. A method of treatment of osteoporosis comprising the administration of a microRNA encoded PEPtides (miPEP), or a fragment of said miPEP, as a drug, wherein said miPEP consists of: SEQ ID NO: 11 745, SEQ ID NO: 11 747 or SEQ ID NO: 11 749, or said fragment of said miPEP consists of: SEQ ID NO: 11 751, SEQ ID NO: 11 752 or SEQ ID NO: 11 753,
   the sequence of which is encoded by a nucleotide sequence contained in the primary transcript of a microRNA (miR), said miPEP or said fragment of said miPEP being capable of modulating the accumulation of said miR in a eukaryotic cell, which miR regulates expression of at least one gene involved in said osteoporosis.

6. The method of claim 5, wherein said miPEP is identified, or as identified, by implementing of a process for identifying a miPEP modulating the accumulation of a miR involved in osteoporosis, comprising:
   a) a step of detecting an open reading frame from 12 to 1 503 nucleotides contained in the sequence of the primary transcript of said miR, then
   b) a step of comparison between:
      i. the accumulation of said miR in a specified eukaryotic cell expressing the primary transcript of said miR, in the presence of a peptide encoded by a nucleotide sequence that is identical or degenerate relative to that of said open reading frame, said peptide being present in the cell independently of transcription of the primary transcript of said miR, and
      ii. the accumulation of said miR in a eukaryotic cell of the same type as the aforesaid specified eukaryotic cell expressing the primary transcript of said miR, in the absence of said peptide,
   in which a modulation of the accumulation of said miR in the presence of said peptide relative to the accumulation of said miR in the absence of said peptide indicates the existence of a miPEP, the latter being encoded by said open reading frame and being capable of modulating the accumulation of said miR involved in said osteoporosis.

7. The method of claim 5, wherein said miPEP is encoded by a nucleotide sequence contained in the primary transcript of a miR selected from the group consisting of: miR15a-16-1, miR125a-1, and miR145-2.

8. The method of claim 5, wherein said miPEP, or said fragment of said miPEP, is fused or linked to one or more molecules facilitating the entry of the miPEP, or miPEP fragment, into the cell.

9. The method of claim 5, wherein said miPEP, or fragment of said miPEP, is fused in N-ter or in C-ter to the TAT peptide (YGRKKRRQRRR, SEQ ID NO: 11 754).

* * * * *